United States Patent [19]

Wissner

[11] 4,297,516

[45] Oct. 27, 1981

[54] 1-SUBSTITUTED-1-OXO-PROSTANE-DERIVATIVES OF THE E, A AND F SERIES

[75] Inventor: Allan Wissner, Ardsley, N.Y.

[73] Assignee: American Cyanamid Company, Stamford, Conn.

[21] Appl. No.: 46,721

[22] Filed: Jun. 7, 1979

Related U.S. Application Data

[63] Continuation-in-part of Ser. No. 3,953, Jan. 16, 1979, Pat. No. 4,254,285, which is a continuation-in-part of Ser. No. 961,032, Nov. 18, 1978, abandoned, which is a continuation-in-part of Ser. No. 858,589, Dec. 8, 1977, Pat. No. 4,202,822, Ser. No. 858,588, Dec. 8, 1977, Pat. No. 4,170,597, Ser. No. 858,580, Dec. 8, 1977, Pat. No. 4,197,245, Ser. No. 858,487, Dec. 8, 1977, abandoned, Ser. No. 858,504, Dec. 8, 1977, Pat. No. 4,172,839, and Ser. No. 858,579, Dec. 8, 1977, Pat. No. 4,212,969.

[51] Int. Cl.³ .......................................... C07C 177/00
[52] U.S. Cl. .................................. 568/330; 542/429; 260/340.9 P; 568/367; 568/376; 568/379; 568/380
[58] Field of Search ..................... 260/586 R, 340.9 P; 542/429; 568/330, 376, 379, 380, 367

[56] References Cited

PUBLICATIONS

Samuelsson, Advances in Prostaglandin & Thromboxone Research V. pp. 483–491 (1977), Raven Press.

Primary Examiner—Robert Gerstl
Attorney, Agent, or Firm—Richard J. Hammond

[57] ABSTRACT

The invention disclosed herein relates to pharmacologically active prostaglandin derivatives of the E, F, or A series having on the terminal methylene carbon of the alpha chain, a substituent selected from the group consisting of:

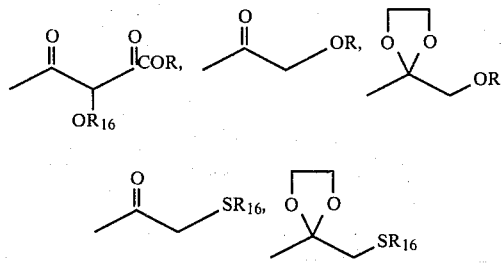

wherein R is $C_1$ to $C_6$ alkyl, and phenyl or phenyl substituted with one or more substituents selected from the group consisting of $C_1$–$C_4$ alkyl, $OR_{16}$, $SR_{16}$, F, or Cl, and $R_{16}$ is $C_1$ to $C_6$ alkyl.

47 Claims, No Drawings

1-SUBSTITUTED-1-OXO-PROSTANE-DERIVATIVES OF THE E, A AND F SERIES

CROSS REFERENCE TO RELATED APPLICATIONS

This application is a continuation-in-part of application Ser. No. 3953 filed Jan. 16, 1979, U.S. Pat. No. 4,254,285 which is in turn a continuation-in-part of application Ser. No. 961,032 filed Nov. 18, 1978 abandoned which is in turn a continuation-in-part of application Ser. Nos. 858,589, 858,588, 858,580, 858,487, 858,504 and 858,579 each of which was filed on Dec. 8, 1977 and now U.S. Pat. Nos. 4,202,822, 4,170,597, 4,197,245, abandoned, U.S. Pat. Nos. 4,172,839 and 4,212,969 respectively.

BRIEF DESCRIPTION OF THE INVENTION

This invention relates to the optically active compound of the formula:

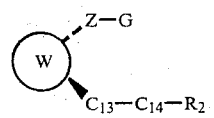

wherein Z is $-(CH_2)_g-$ or

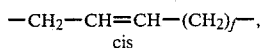

wherein g is an integer from 5 to 7 inclusive, and f is an integer from 2 to 4, inclusive; $C_{13}-C_{14}$ is ethylene or trans-vinylene; W is selected from the group consisting of:

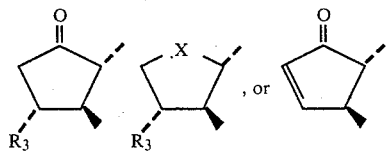

wherein X is:

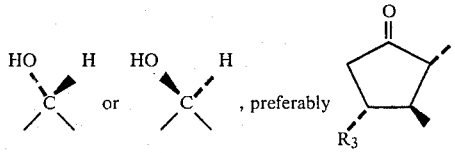

and $R_3$ is hydrogen or hydroxyl; G is selected from the group consisting of:

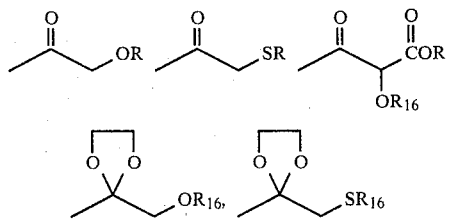

wherein R is $C_1-C_6$ alkyl, and phenyl or phenyl substituted with one or more substituents selected from the group consisting of $C_1-C_4$ alkyl, $-OR_{15}$ or $SR_{15}$, F or CL wherein in $R_{15}$ is $C_1$ to $C_6$ alkyl, preferably R is methyl; $R_{16}$ is $C_1$ to $C_6$ alkyl; and $R_2$ is selected from the group consisting of:

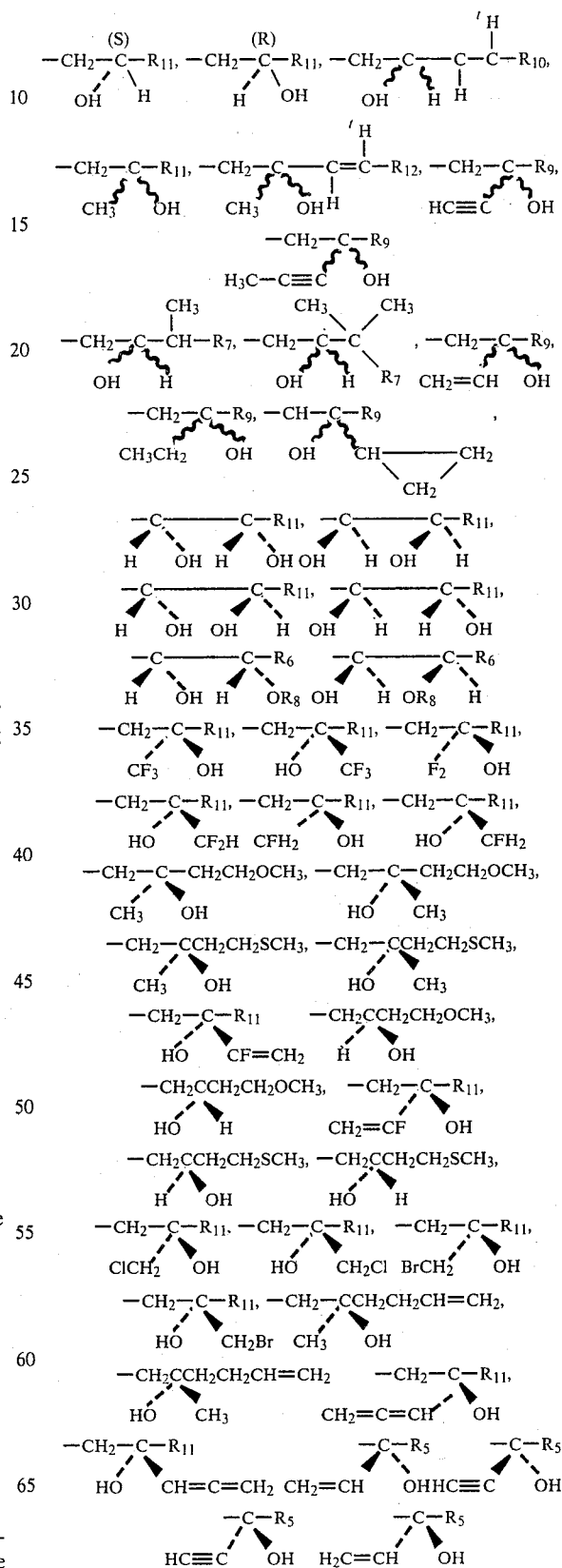

-continued

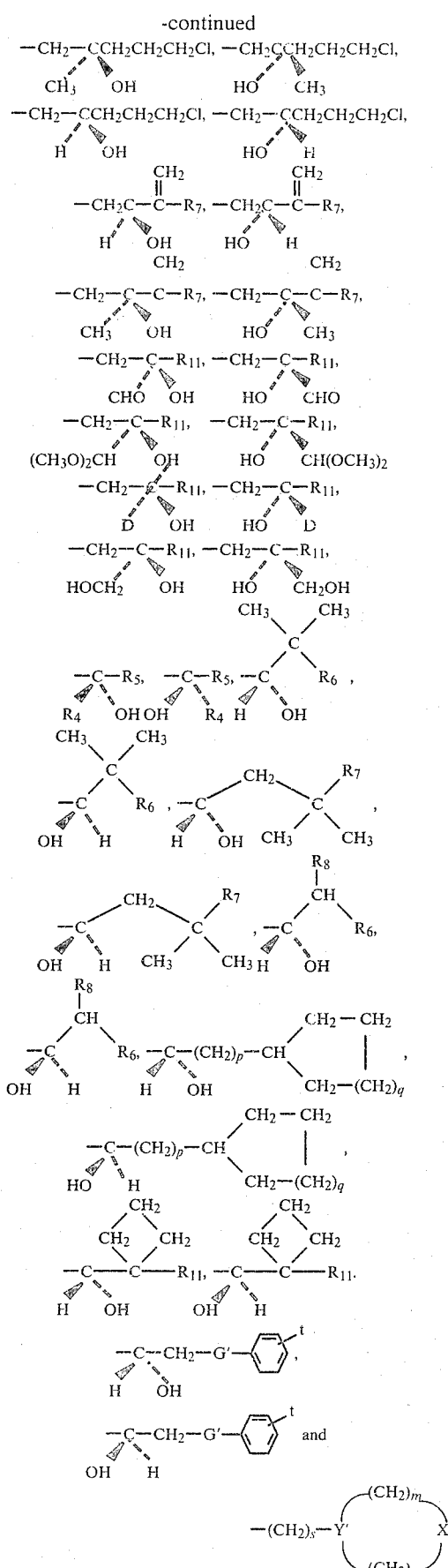

wherein $R_4$ is hydrogen or methyl; $R_5$ is selected from the group consisting of $C_4$-$C_7$ alkyl; $R_6$ is selected from the group consisting of $C_3$-$C_6$ alkyl; $R_7$ is selected from the group consisting of $C_2$-$C_4$ alkyl; $R_8$ is selected from the group consisting of $C_1$-$C_2$ alkyl; $R_9$ is selected from the group consisting of $C_3$-$C_6$ alkyl; $R_{10}$ is selected from the group consisting of $C_1$-$C_4$ alkyl; $R_{11}$ is selected from the group consisting of $C_3$-$C_7$ alkyl; $R_{12}$ is selected from the group consisting of $C_1$-$C_4$ alkyl; p is an integer from 0 to 3; q is 1 or 2; X' is a divalent radical selected from the group consisting of:

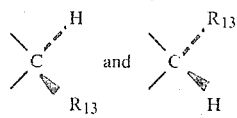

wherein $R_{13}$ is selected from the group consisting of $C_1$-$C_7$ alkyl, hydrogen, and a phenoxy group optionally substituted with a substituent selected from the group consisting of halogen, trifluoromethyl and $C_1$-$C_4$ alkyloxy; Y' is a divalent radical selected from the group consisting of:

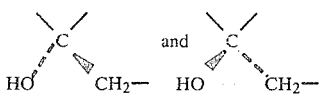

G' is a divalent radical selected from the group consisting of —O— and —$CH_2$—; m is zero or an integer from 1 to 4, inclusive; n is zero or an integer from 1 to 4, inclusive; with the proviso that the sum of m and n has the value of 1 to 4; s is zero or the integer 1; and t is selected from the group consisting of hydrogen, chloro, fluoro, dichloro, trifluoromethyl, methoxy; the racemic mixture thereof; and the mirror image thereof.

This invention also relates to the method of preparing the above-described compounds, as well as to the novel intermediates useful for the preparation of the prostaglandin compounds described herein. The present invention will be fully described with reference to the flowsheets and examples of this application.

DETAILED DESCRIPTION OF THE INVENTION

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic suspensions are preferred. For subcutaneous or intramuscular injection, sterile suspensions of the compounds in aqueous or non-aqueous media are used. Tablets, capules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle,

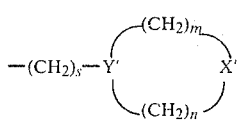

lower arterial blood pressure, antagonize epinephrine-induced mobilization of free fatty acids, and have other pharmacological and autopharmacological effects in mammals. See Bergstom, et al., J. Biol. Chem., 238, 3555 (1963) and Horton, Experientia, 21, 113 (1965) and references cited therein. All of the so-called natural prostaglandins are derivatives of prostanoic acid:

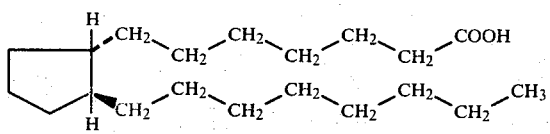

The hydrogen atoms attached to C-8 and C-12 are in trans-configuration. The natural prostaglandins represent only one of the possible optical isomers. The compounds of this invention include all possible optical isomers and racemates.

The configuration of substituents on the prostaglandin molecule are designed to be in the α-configuration if they lie beneath the plane of the molecule as drawn above and are designated with a----bond. Those substituents which lie above the plane of the molecule as drawn above are designated β and are represented by a ▬ bond.

The compounds of this invention which have the structure as shown in formula (A) wherein $R_1$, Z, $R_3$, Y, m, n, s and X are as herein below defined are said to be in the same configuration as the natural prostaglandins with respect to the configurations at $C_8$, $C_{11}$ and $C_{12}$ and are designated by the prefix nat. The enantiomer, represented by formula (B) is said to be in the mirror image or ent configuration. A substituent at $C_{11}$ drawn with a dotted line ($C_{11}$---$R_3$) is said to have an α configuration; a solid line ($C_{11}$—$R_3$) indicates a β configuration. The configuration at Y and X will be expressed in terms of R and S as is understood in the art. For example, the compound represented by formula (C) is named nat-15S,16S-11α,15-dihydroxy-1-(methoxymethyl) -1,9-dioxo-15,16-trimethylene-13-trans-prostene; its enantiomer (formula D) is named ent-15R,16R- 11α,15-dihydroxy-1-(methoxymethyl) -1,9-dioxo-15,16-trimethylene-13-trans-prostene. The racemate (1:1 mixture of (C) and (D) is named nat-15S,16S-(and ent-15R,16R) 11α,15-dihydroxy-1-(methoxymethyl) -1,9-dioxo-15,16-trimethylene-13-trans-prostene. In a similar manner, the compounds represented by formulae (E) to (J) have the configurations shown below.

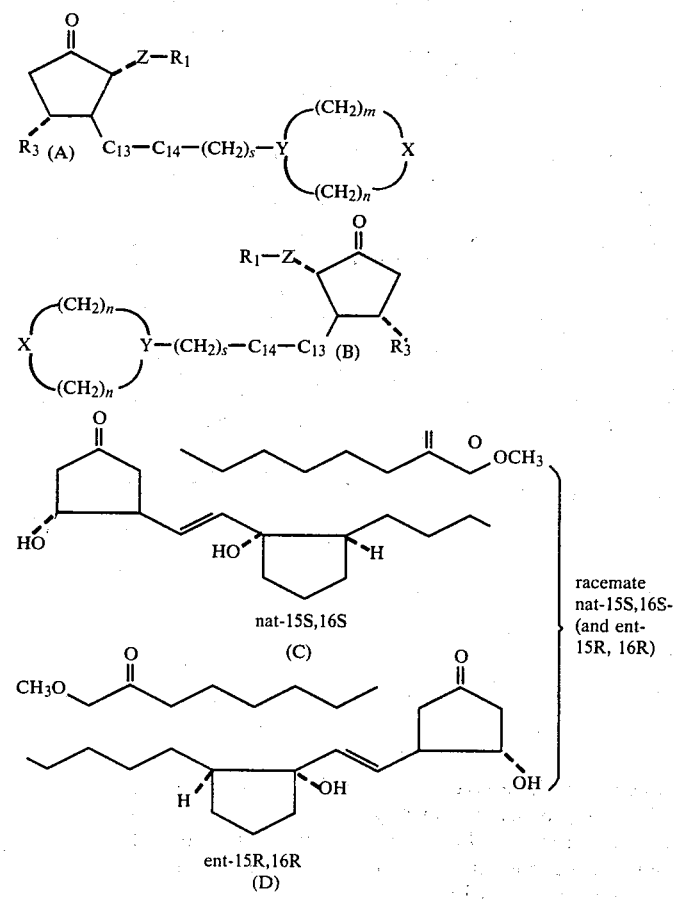

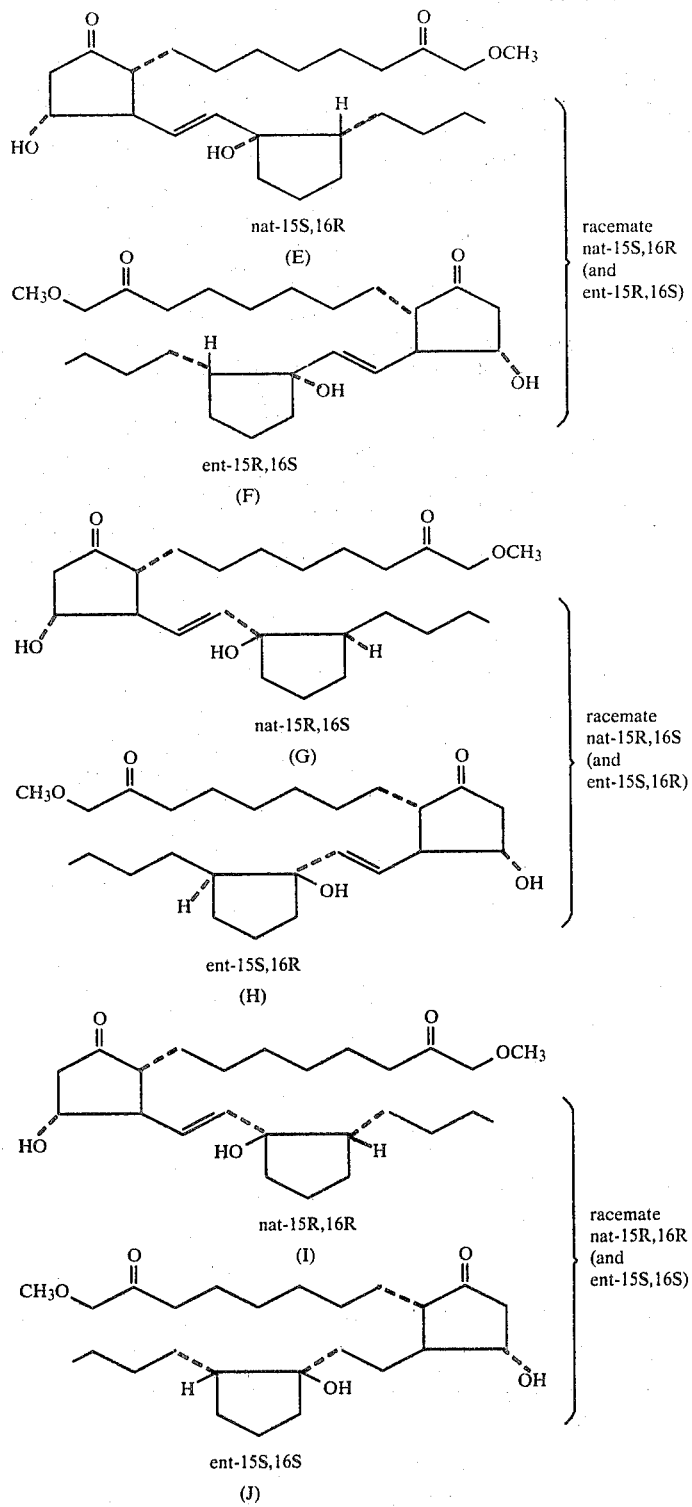

In each of the above formulae (C to J) the hydroxy group at $C_{11}$ is named "11α-hydroxy".

In structures C to J above, m is zero or the integer 1 to 4 inclusive; n is zero or the integer 1 to 4 inclusive; s is zero or one and X is:

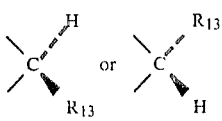

wherein $R_{13}$ is selected from the group consisting of $C_1$ to $C_7$ alkyl, hydrogen, and a phenoxy group optionally substituted with a substituent selected from the group consisting of halogen, trifluoromethyl and $C_1$ to $C_4$ alkoxy.

The novel compounds of this invention can be preprepared by a novel 1,4-conjugate-addition procedure involving treatment of the ether blocked cyclopentenone such as (129) or (111) with a lithio-cuprate reagent such as (117), (118), or (119) prepared as illustrated in Flowsheets A thru N.

The 1,4-conjugate-addition procedure is described hereinbelow in Flowsheet N. The preparation of the various requisite 1-iodo-trans-1-alkenyl or 1-tributyl-stannyl-trans-1-alkenyl derivative is illustrated in Flowsheets A–H and the novel and important methods of preparation of the 4-hydroxycyclopentenones embracing the 1-(alkoxymethyl and phenoxymethyl) -1-oxo α-chain is described in connection with Flowsheets I–M.

vide (4), the ester group of which is reduced to alcohol (5) by reaction with 2 equivalents of diisobutyl aluminum hydride, lithium aluminum hydride or the like. Oxidation of alcohol (5) with dipyridine chromium oxide complex ["Reagents for Organic Synthesis", L. F. Fieser and H. Fieser, John Wiley and Sons, Inc., New York, 4, 215 (1974) ], prepared in situ in methylene chloride solution, provides the corresponding aldehyde (6), which can also be obtained directly from ester (4) by partial reduction with one equivalent of diisobutyl aluminum hydride at $-78°$ C., but the former two-step procedure is preferable. Reaction of aldehyde (6) with lithium acetylide ethylene diamine complex provides the 3-hydroxy-1-alkyne (7), which is converted to its trimethylsilyl ether in the usual manner. The silylated derivative is then treated with disiamylborane (prepared in situ in tetrahydrofuran solution at ice bath

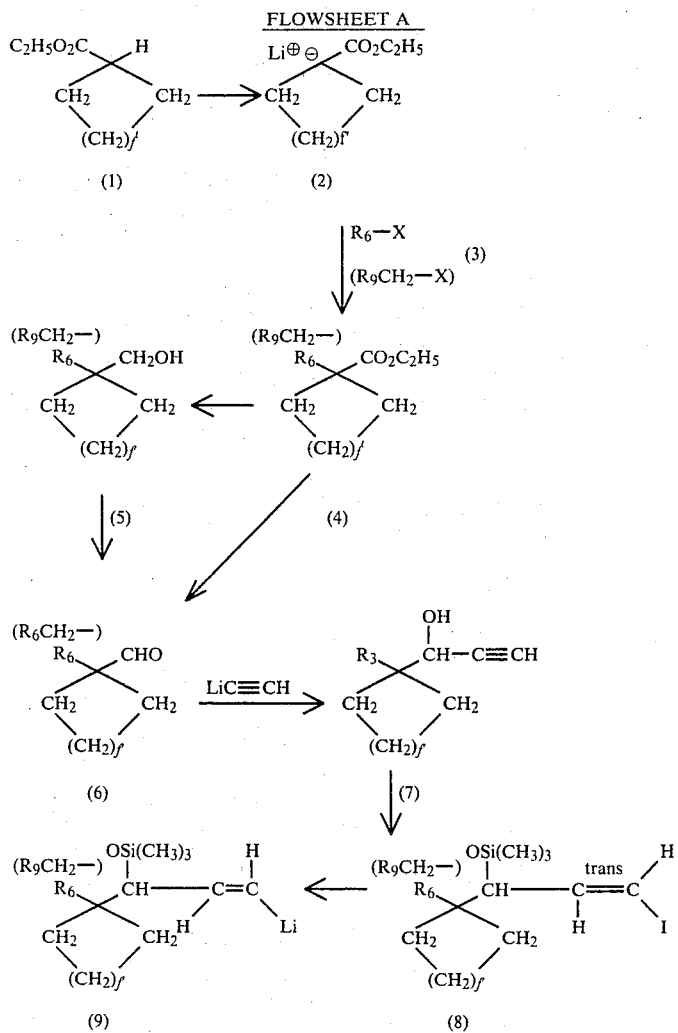

FLOWSHEET A wherein f' is one or two inclusive.

In accordance with the scheme as outlined herein above in Flowsheet A, carbethoxycyclobutane or carbethoxycyclopenane is converted to its enolate anion (2) by treatment with a strong base such as lithium cyclohexylisopropylamide, prepared from the corresponding amine and n-butyl lithium (hexane solution) in a solvent, such as anhydrous tetrahydrofuran, at very low temperatures, such as $-78°$ C. The resulting enolate anion (2) is then alkylated with $R_6$—X (3) to provide temperatures from 2-methyl-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-4,4-methylene-1-alkene (8). Also, the above sequences of reactions can be accomplished, as shown in Flowsheet A, using $R_9CH_2X$ where $R_9$ is a phenyl group.

FLOWSHEET B
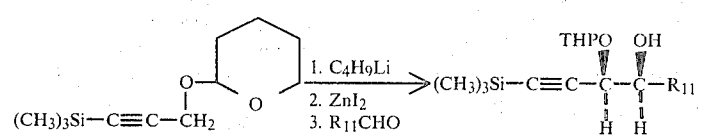
(9)          (10)          (11)
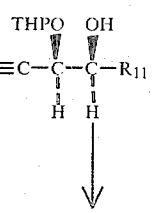
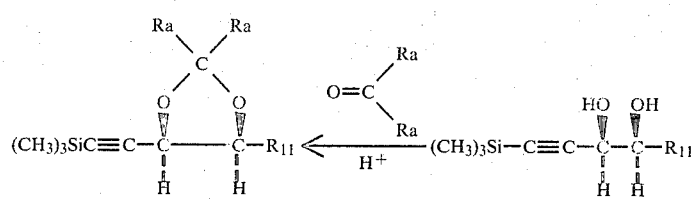
(13)          (12)
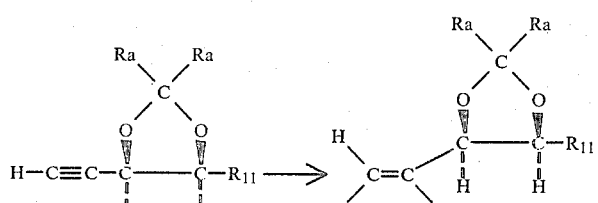
(14)          (15)
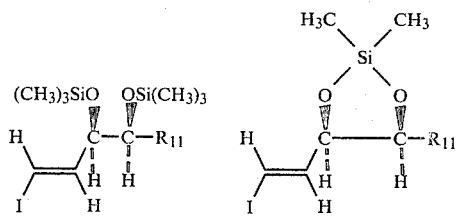
(16)          (17)
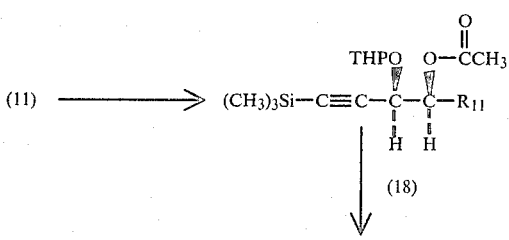
(18)
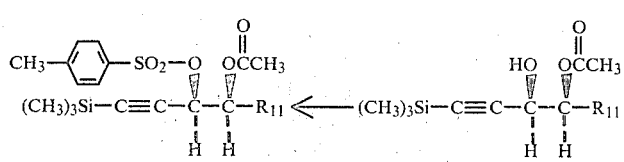
(20)          (19)

FLOWSHEET B

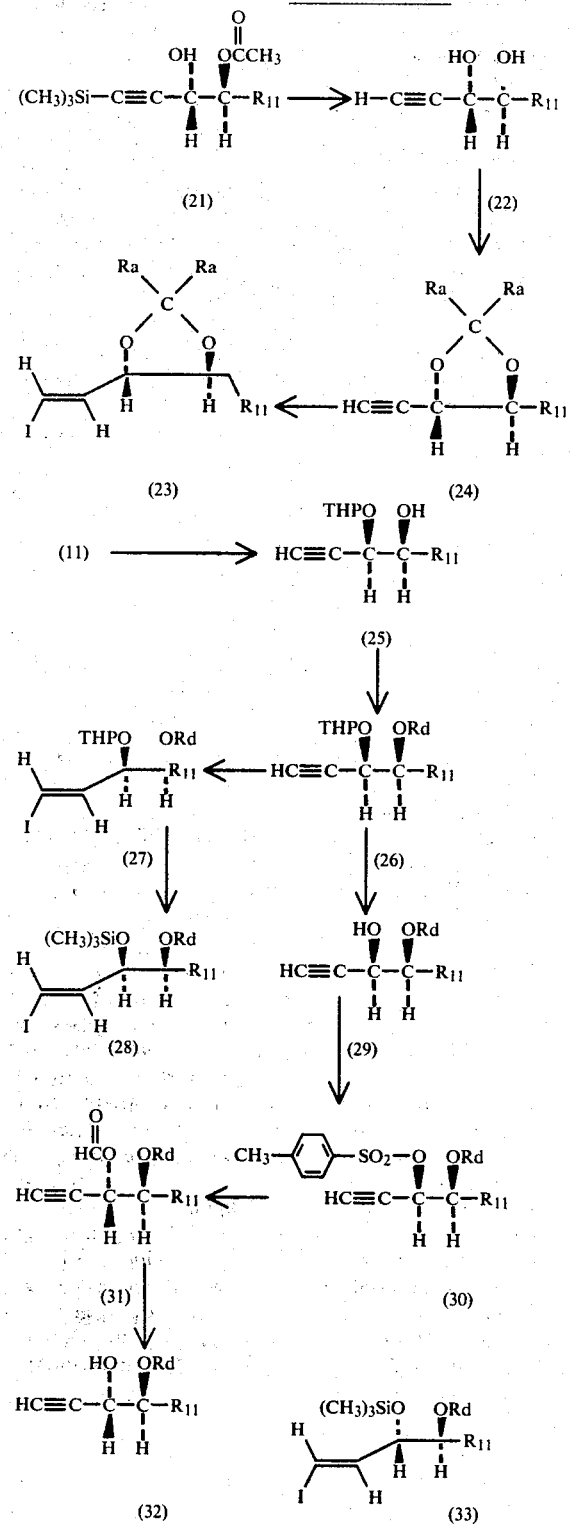

In accordance with the scheme as outlined hereinabove in Flowsheet B, 1-trimethylsilyl-3-tetrahydropyranyloxy-1-propyne (9) is treated with n-butyllithium at −78° C. and then with a freshly prepared solution of zinc iodide in anhydrous tetrahydrofuran, also at −78° C. Reaction of aldehyde (10) with the resulting reagent then provides the 4-hydroxy-3-tetrahydropyranyloxy-1-alkyne (11). This reaction proceeds with great stereoselectivity and the product (11) is in the erythro configuration. [For additional information concerning this reaction see the examples which follow and F. Mercier, R. Epstein and S. Holland, Bull. Soc. Chim. France, 690 (1972). ]

The tetrahydropyranyl group in (11) is removed on weak acid treatment and the resulting erythro diol (12) can be reblocked by treating with an appropriate aldehyde or ketone

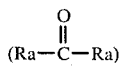

in the presence of strong acid catalyst in the usual way to give the ketal or acetal (13). Acetone is a useful ketone for this purpose and the product (13) is then a 3,4-isopropylidenedioxy-1-alkyne. It is also possible to utilize silyl blocking groups (introduced after removal of the 1-trimethylsilyl group) to ultimately give the vinyl iodides (16) or (17). Weak base treatment of (13), for example heating for about one hour in refluxing methanol with potassium carbonate, results in desilylation to give (14). The 1-alkene (14) is converted to the corresponding 1-iodo-trans-1-alkene (15) by treatment with disiamylborane (prepared in situ in tetrahydrofuran solution at ice bath temperatures from 2-methyl-2-butene, sodium borohydride and boron trifluoride etherate) and then anhydrous trimethylamine oxide. The resulting solution and an iodine solution in tetrahydrofuran are then added simultaneously to an aqueous solution of sodium hydroxide to give (15).

For the preparation of the threo derivatives, the 4-hydroxy-3-tetrahydropyranyloxy-1-alkyne (11) is acetylated to provide the corresponding 4-acetoxy derivative (18). The tetrahydropyranyl group is preferentially hydrolized with weak acid to (19), which is then tosylated in the usual manner to afford the erythro-3-tosyloxy-4-acetoxy-1-alkyne (20). Solvolysis of (20) under essentially neutral conditions by heating in aqueous tetrahydrofuran in the presence of an insoluble acid-acceptor, such as calcium carbonate, results in inversion of $C_3$, furnishing the threo-3-hydroxy-4-acetoxy-1-alkyne (21), which is then deblocked with aqueous base to give the threo-3,4-diol (22). Diol (22) is converted to an acetal or ketal (23) [or silyl derivatives as in (16) or (17)] and thence to the 1-iodo-trans-1-alkene (16) as described hereinabove wherein Ra is lower alkyl ($C_1$ to $C_3$).

For the preparation of the 16-alkoxyprostanoic acids of this invention, the erythro-4-hydroxy-3-tetrahydropyranyloxy-1-alkyne (11) is desilylated by methanol-potassium carbonate treatment and the resulting (25) is alkylated to give the 4-alkoxy-3-tetrahydropyranyloxy-1-alkyne (26). A useful procedure for this last step involves treatment of (25) with a molar equivalent of sodium hydride to give the 4-alkoxide which is then alkylated with the appropriate alkylating agent for example methyl iodide. The 4-alkoxy-1-alkyne (26) is then converted to the corresponding 1-iodo-trans-1-alkene (27) as described hereinabove for the preparation of (15). If desired the tetrahydropyranyl blocking group in (27) can be hydrolyzed (weak acid) and the resulting free 3-ol corresponding to (27) converted to the 3-trimethylsilyloxy derivative (28), all in the usual manner wherein Ra is lower alkyl ($C_1$ to $C_3$).

For the threo series, the tetrahydropyranyl group in erythro-4-alkoxy-1-alkyne (26) is cleaved and the resulting 3-hydroxy-4-alkoxy-1-alkyne (29) is tosylated to give the erythro-3-tosyloxy-4-alkoxy-1-alkyne (30). $Sn_2$ displacement reaction with (30) with reagents such as tetrahydroammonium formate results in inversion to the threo derivative (31) saponification of which provides threo-3-hydroxy-4-alkoxy-1-alkyne (32). Trimethylsilylation followed by the vinyl iodide conversion procedure described hereinabove furnishes the threo-1-iodo-1-alkene (33) wherein Rd is hydrogen or lower alkyl ($C_1$ to $C_3$).

The 15-alkyl and/or 16-alkyl derivatives of this invention can be prepared by substituting

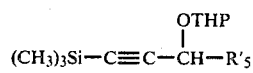

for (9) and/or

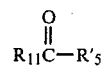

for (10) (R'$_5$=lower alkyl of 1 to 3 carbons) in Flowsheet B.

In accordance with the procedure as outlined in Flowsheet C, an aldehyde (34) is treated with propargylic magnesium halide to form the homopropargylic alcohol (35), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride ethereate) and then anhydrous trimethylamine oxide. The resulting solution and an iodine solution in tetrahydrofuran are added simultaneously to a sodium hydroxide to give the 1-iodo-4-trimethylsilyloxy-trans-1-alkene (36), precursors for 16-hydroxy-prostaglandin.

The trimethylsilyl protecting group is removed with mild acid and the resulting vinyl iodide alcohol is oxidized with pyridinium chlorochromate to provide the 1-iodo-4-oxo-trans-1-alkene (37), which upon treatment with a Grignard reagent ($R_{13}MgX$) provides the 1-iodo-4-hydroxy-trans-1-alkene, which is silylated in the usual manner to provide the silyl ether (38) wherein R'$_{11}$ is lower alkyl ($C_3$ to $C_7$) or lower alkenyl group ($C_3$ to $C_5$) and R'$_{13}$ is vinyl, cyclopropyl or ethyl; X is a chloro or bromo group.

FLOWSHEET C

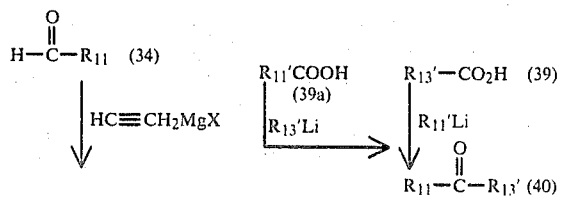

FLOWSHEET C

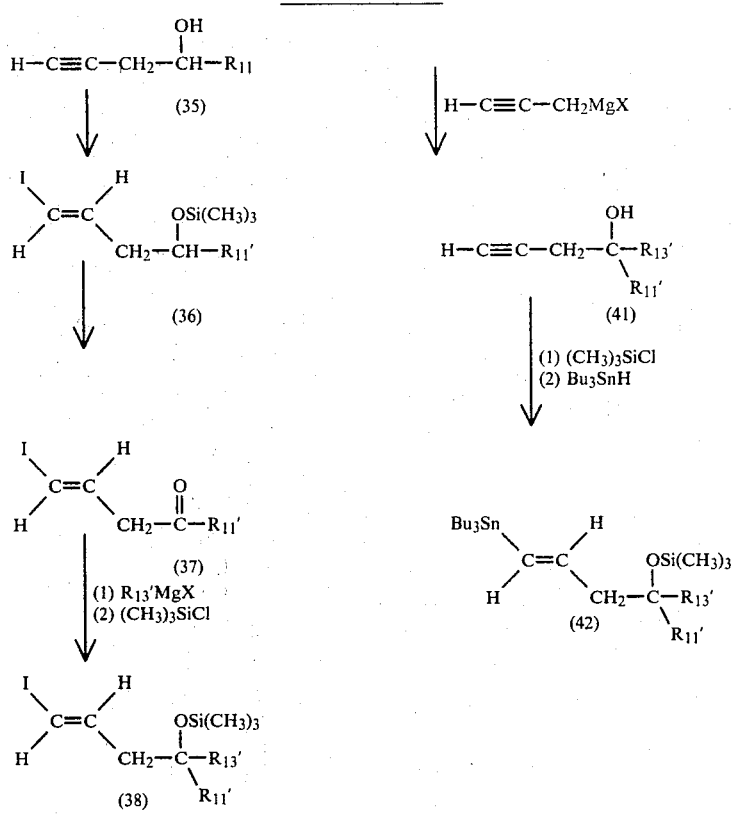

A more preferred method for the preparation of vinyllithium precursor is also described in Flowsheet C. Treatment of the requisite carboxylic acid (39a or 39) with the appropriate organolithium reagent ($R'_{13}Li$ or $R'_{11}Li$ respectively), wherein $R'_{11}$ and $R'_{13}$ are hereinabove defined, give the corresponding ketone (40) which upon treatment with propargylic magnesium halide provides the homopropargylic alcohol (41) which is converted to the trans vinylstannyl derivative by sequential treatment with chlorotrimethylsilane and tri-n-butyltin hydride. Treatment of the vinylstannyl reagent (42) with n-butyllithium at a temperature of $-10°$ C. to $-78°$ C. generates the corresponding vinyllithium reagent.

FLOWSHEET D

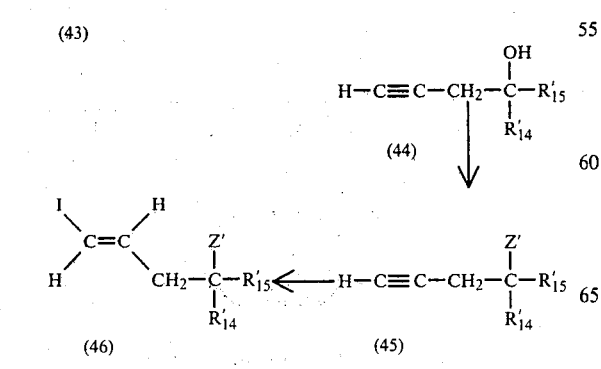

In accordance with Flowsheet D hereinabove, the precursors for other 16-hydroxy prostaglandins are prepared by treating an appropriate aldehyde or ketone (43) with a propargylic magnesium halide to yield the requisite homopropargylic alcohol (44). The alcohol is protected as a tritylether (45) (for secondary alcohols) or as a trimethylsilyl ether (45) (for tertiary alcohols). These ethers are then converted to the appropriate trans-vinyliodide (46) by treatment with disiamylborane generated in situ from 2-methyl-2-butene, sodium borohydride, and boron trifluoride, followed by treatment with trimethylamine oxide and then iodine and sodium hydroxide, wherein $R'_{15}$ is hydrogen, methyl or ethyl; $Z'$ is $O-C(C_6H_5)_3$ when $R'_{15}$ is hydrogen and $Z'$ is $O-Si(CH_3)_3$ when $R'_{15}$ is methyl or ethyl; $R'_{14}$ is selected from the group comprising lower alkyl ($C_3$ to $C_5$), lower 1-alkenyl ($C_3$ to $C_5$),

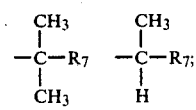

wherein $R_7$ is as described above with the proviso that when $R'_{14}$ is

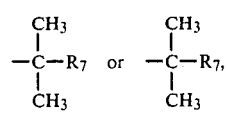

then $R'_{15}$ must be hydrogen.

FLOWHEET E

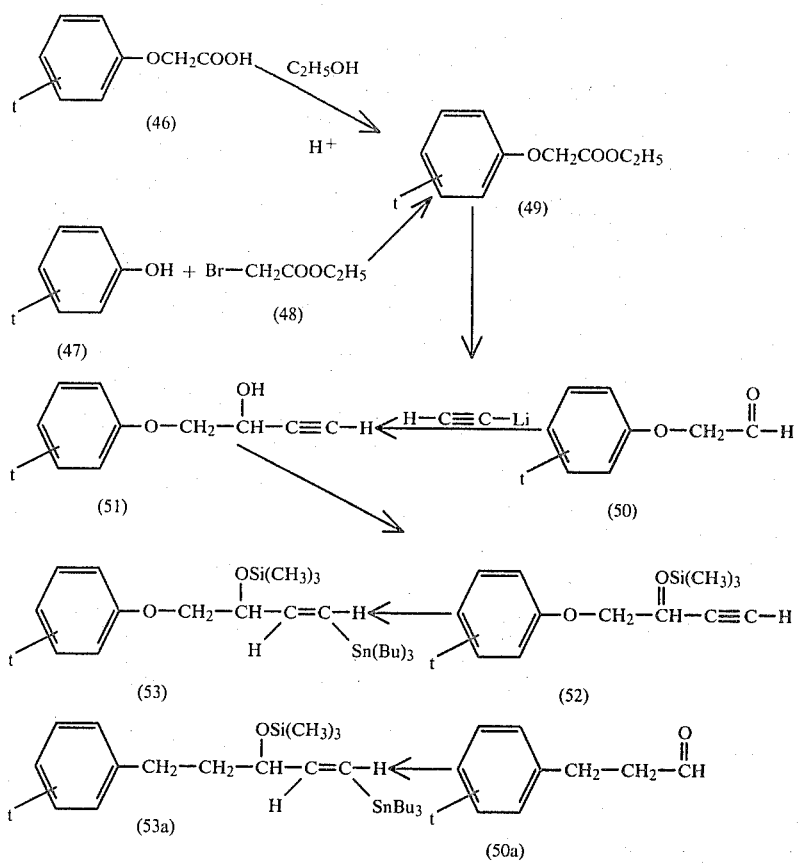

The preparation of the precursors for the synthesis of 16-aryloxy congeners is described in accordance with Flowsheet E hereinabove. The aryl esters (49) are prepared by esterifying the commercially available acids or by treatment of ethyl bromoacetate with the appropriate phenol. The ester (49) is carefully reduced to the aldehyde (50) which upon treatment with lithium acetylide provides the propargylic alcohol (51). Treatment of the alcohol (51) with chlorotrimethylsilane followed by tri-n-butyltin hydride furnishes the requisite vinylstannyl derivative (53). Similar treatment starting with substituted hydrocinnamaldehyde (50a) provides the respective vinylstannyl derivative (53a).

The preparation of the precursors for the synthesis of secondary 15-hydroxy congeners are described in the literature. The preparation of the precursor for 15-methyl-15-hydroxy is described in Flowsheet F hereinbelow. In accordance with Flowsheet F, an acid chloride, wherein $R_5$ is hereinabove defined, is treated with acetylene and aluminum trichloride to provide the vinylchloride (55) which upon treatment with sodium iodide furnishes the vinyliodide (56). Treatment of (56) with methylmagnesium halide followed by chlorotrimethylsilane gives the requisite protected vinyliodide (57).

FLOWHSHEET F

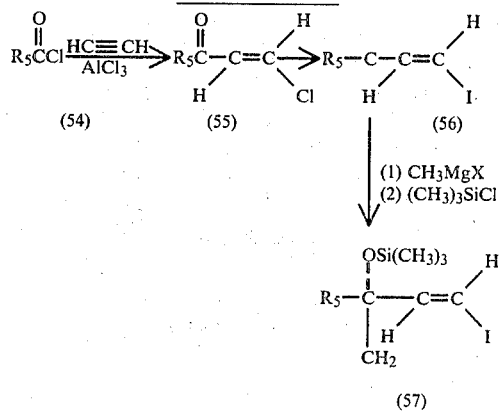

The precursors for the novel compounds of this invention which have a β chain represented by Formula K:

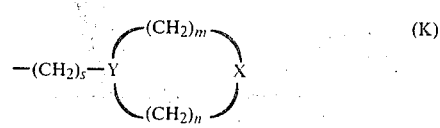

wherein s, y, m, n, and X are hereinabove defined as shown in Flowsheet G and Flowsheet H.

FLOWSHEET G

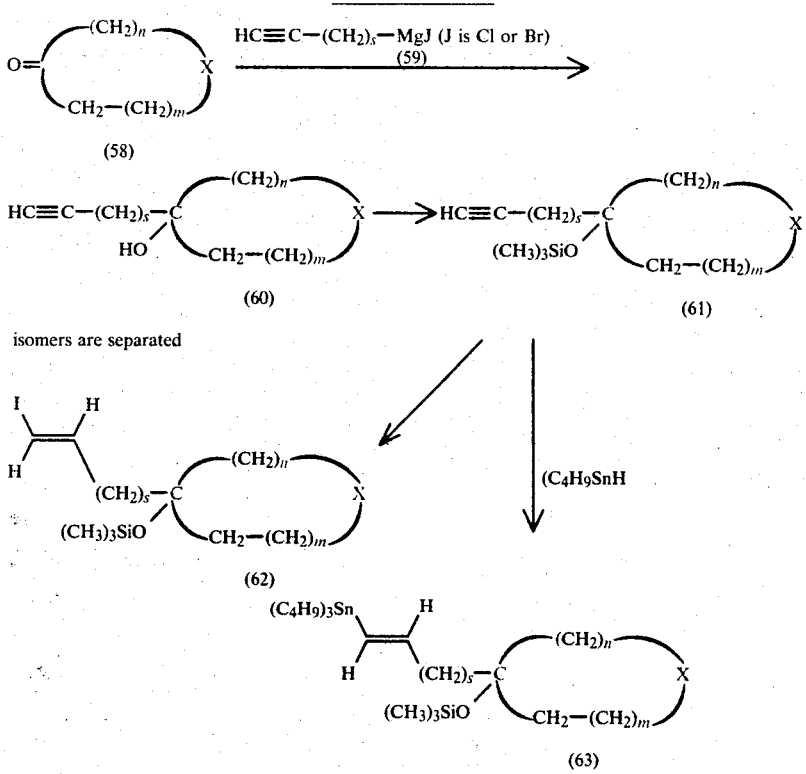

In accordance with the scheme as outlined hereinabove in Flowsheet G a ketone (58) is reacted with a Grignard reagent (59) such as acetylene magnesium chloride (59, s=0) or propargyl magnesium bromide (59, s=1) to give the acetylenic alcohols (60). In those cases where X is not —CH$_2$—, two isomeric acetylenic alcohols are formed. These isomers can be separated by procedures well known to the art including fractional crystallization, fractional distillation and various chromatographic procedures. The individual isomers can then be carried through the remaining reactions outlined in Flowsheet G.

The acetylenic alcohol (60) is converted to its trimethylsilyl ether in the usual manner. The silylated derivative (61) is then treated with diisoamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-trans-1-alkene (62).

(63) in turn is readily prepared by the addition of tri-n-butyl tin hydride to the acetylene (61) in the presence of bisazoisobutyronitrile followed by vacuum distillation at a high enough temperature (about 170° C.) to isomerize any of the cis-vinyl tin compound to the trans-vinyl tin compound.

Certain of the ketones (67) of this invention are prepared as indicated in Flowsheet H below:

FLOWSHEET H

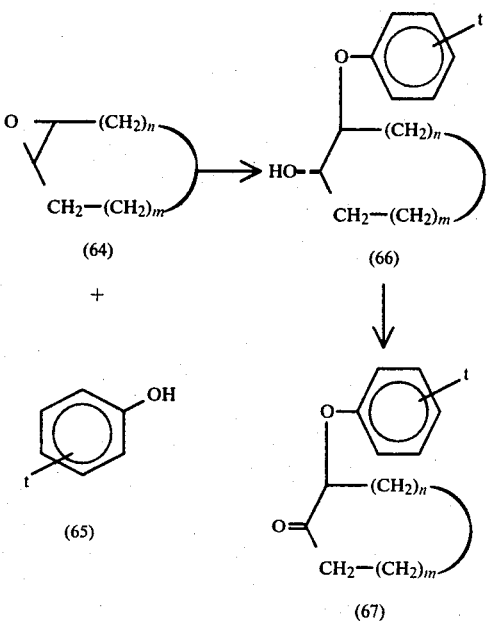

wherein n and m are as hereinabove defined and the moiety

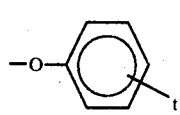

represents a phenoxy group which is optionally substituted with one or more halogen, trifluoromethyl, and lower alkoxy ($C_1$ to $C_4$) groups.

As indicated in Flowsheet H the reaction of an epoxide (64) with a substituted or unsubstituted phenol (65) is the presence of a catalytic amount of aqueous sodium hydroxide and a phase transfer catalyst such as methyl tricapryly ammonium chloride and the like at 70°–80° C. gives the phenoxy substituted alcohol (66) which in turn is oxidized with an oxidizing reagent such as pyridinium chlorochromate in methylene chloride to give the phenoxy substituted ketone (67). This ketone (67) is then carried through the reactions shown in Flowsheet G above.

The 19-unsaturated beta chain precursors are prepared in accordance with the reaction scheme of Flowsheet I. Treatment of the ketone (68) with propargyl magnesium bromide (69) provides the hydroxyalkyne (70) which is silylated to give the ether (71). The TMS ether (71) is heated with tri-n-butylstannane in the presence of azobisisobutylronitrile to afford the trans-vinylstannane (72) which contains from about 10–20% of the corresponding cis-vinylstannane (73). Treatment of the vinylstannane reagents (72), (73) with n-butyllithium at temperatures of $-78°$ C. to $-10°$ C. generates the vinyl lithium reagents (74).

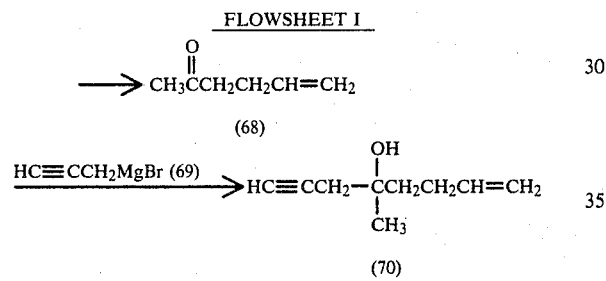

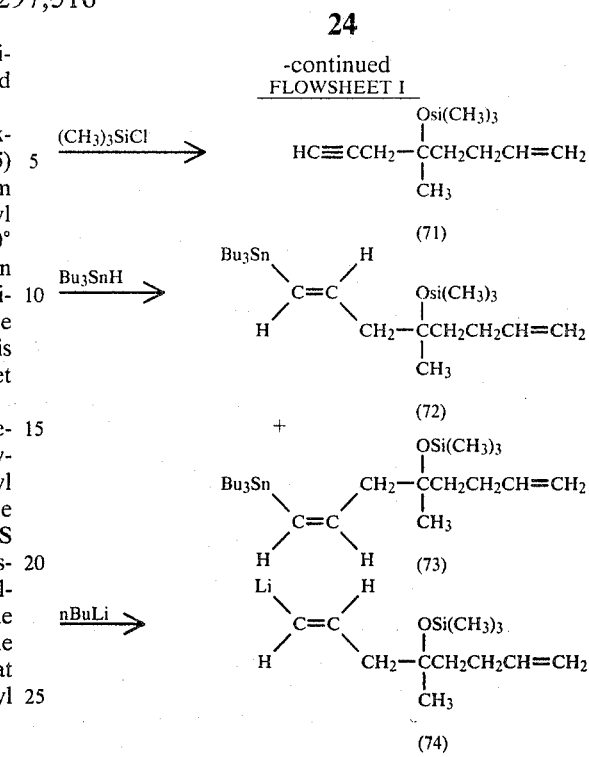

The 17-methylene precursors are prepared in accordance with the procedure outlined in Flowsheet J. Treatment of an aldehyde or ketone such as (75), wherein $R_3$ is hydrogen, methyl or ethyl and $R_4$ is hydrogen, or $C_1$ to $C_3$ alkyl with formalin and dimethylamine hydrochloride, provides the α-methylene aldehyde or ketone (76). Treatment of the carbonyl compound (76) with propargylmagnesium bromide (77) provides the hydroxy alkyne (79) which is silylated to give (78) wherein $R_3$ is as previously defined. The selection of the silylating reagent is determined by the nature of the group at $R_3$. When $R_3$ is hydrogen, then $R_5$ is ethyl; when $R_3$ is methyl or ethyl, then $R_5$ is methyl.

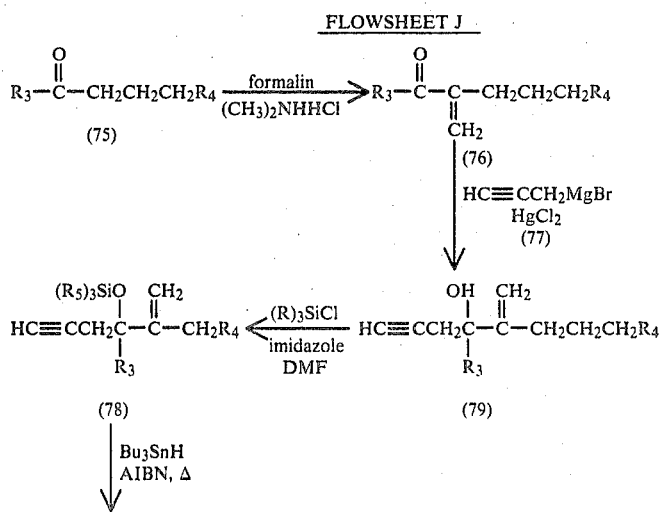

FLOWSHEET J

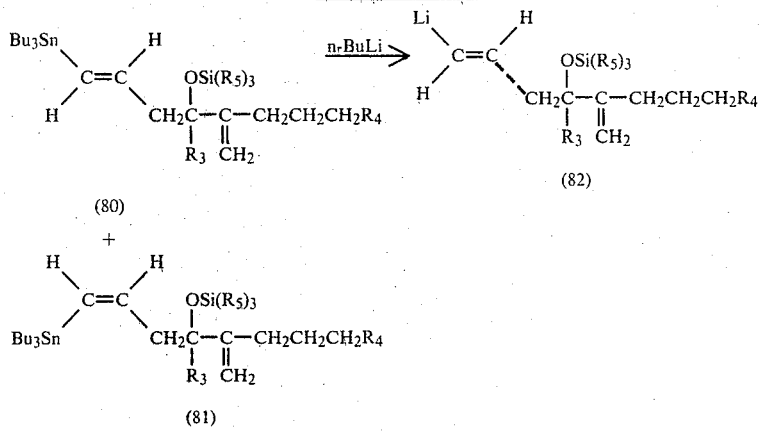

The precursors to the 16 allenyl analogs are prepared in accordance with the procedure outlined in Flowsheet K. Treatment of esters such as (83) with propargyl Grignard (84) (wherein $R_4$ is hydrogen, methyl, ethyl propyl or chloro) provides the dienylketone (85). Treatment of the ketone (85) with propargylmagnesium bromide provides the hydroxyalkyne (86) which is silylated to give the ether (87). The alkyne (87) is converted to the trans vinyliodide (88) by successive treatment with diisoamylborane, triethylamine oxide and $I_2$/NaOH as described by Kluge et al. [J. Amer. Chem. Soc., 94, 7827 (1972)]. Treatment of the vinyliodide (88) with 1 eq. n-BuLi at $-70°$ to $-50°$ C. affords the vinyl lithium (89).

FLOWSHEET K

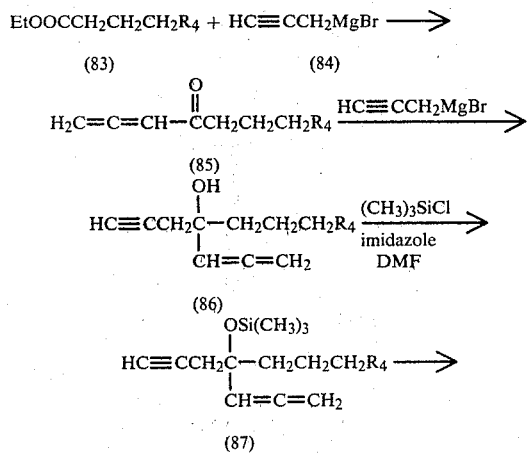

-continued
FLOWSHEET K

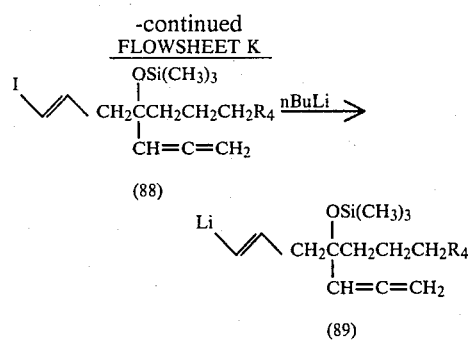

The 16-chloromethyl and 16-bromomethyl analogs are prepared from the precursors shown in Flowsheets L-1 and L-2.

In accordance with the procedure outlined in Flowsheet L-1, treatment of a carboxylic acid halide such as (90) wherein $R_4$ is hydrogen, methyl, ethyl or propyl, with 1,1,2-tris trimethylsilyloxyethylene (91) [Tet. Letters, 2749 (1978)] provides the α-hydroxyketone (92). Treatment of (92) with methansulfonylchloride in dimethylformamide (DMF) provides the α-chloroketone (93).

In accordance with Flowsheet L-2, treatment of the α-haloketones (94) with propargylmagnesium bromide in the presence of mercuric chloride provides the hydroxyalkyne (95) that is treated with a trialkylchlorosilane such as chlorotrimethylsilane to provide the ether (96). The alkyne (96) is treated with tri-n-butylstannane in the presence of azobisisobutryonitrile (AIBN) to provide the trans-vinylstannane (97) containing 10 to 20% of the corresponding cis isomer (98). Lithiation then provides the vinyllithium reagent (99).

FLOWSHEET L-1

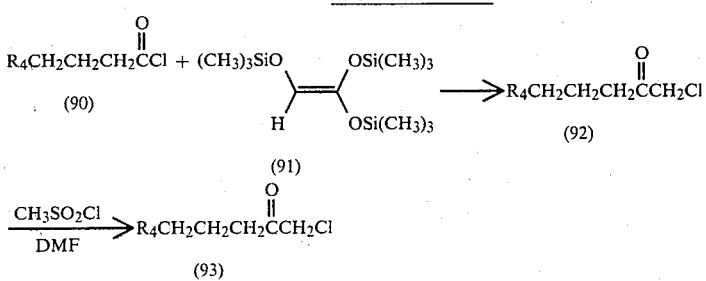

FLOWSHEET L-2

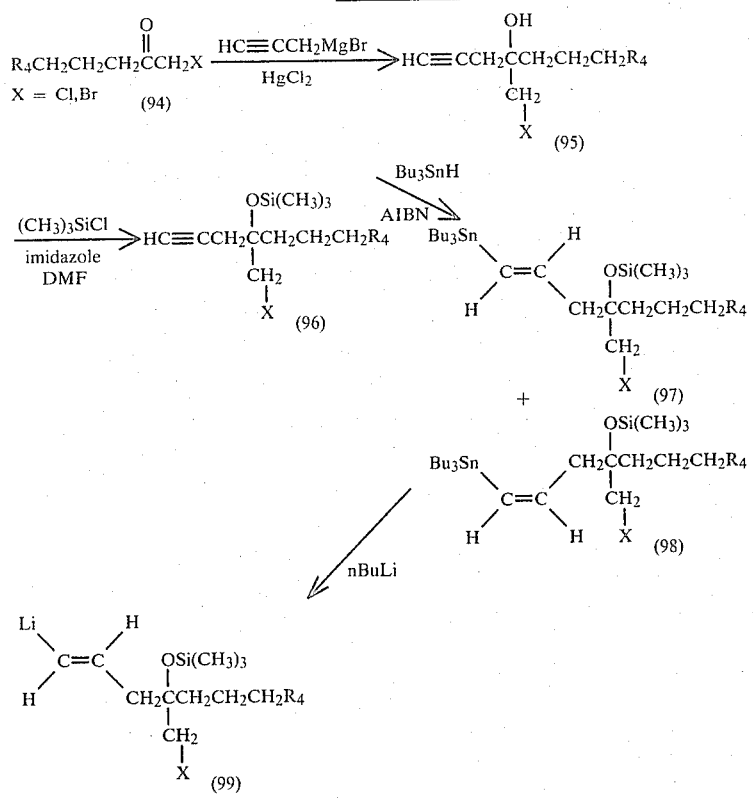

The 19-chloro-20-nor analogs are prepared from the precursors shown in Flowsheet M-1.

In accordance with Flowsheet M-1, wherein $R'_3$ is hydrogen, methyl, vinyl and trimethylsilylethynyl, treatment of the carbonyl compound (100) with propargylmagnesium bromide (101) in the presence of mercuric chloride provides the hydroxyalkyne (102). The hydroxy portion of (102) is protected with a trialkylsilyl group; triethylsilyl when $R'_3$ is hydrogen, and trimethylsilyl when $R'_3$ is methyl, vinyl or trimethylsilylethynyl. The silyl ether (104) is heated with tri-n-butylstannane (105) in the presence of azobisisobutryonitrile (AIBN) to afford the trans-vinylstannane (106) which contains 10 to 20% of the corresponding cis-vinylstannane (107). Treatment of the vinylstannane (106) with n-butyl lithium at temperatures of −78° C. to −10° C. generates the vinyllithium reagents (108).

FLOWSHEET M-1

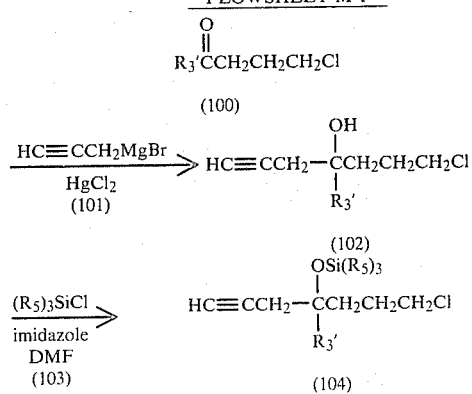

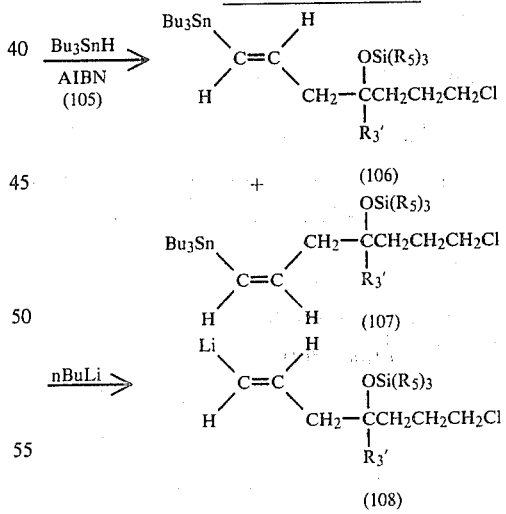

The preparation of the carbonyl compound (110) wherein $R'_3$ is vinyl (7-chloro-hept-1-en-2-one) is shown in Flowsheet M-2. In accordance with Flowsheet M-2, 4-chlorobutrylchloride (109) is treated with vinyltrimethylsilane in the presence of aluminum trichloride at −20° C. to provide, after quenching with NH$_4$Cl the vinylketone (110). A similar sequence for the preparation of the trimethylsilylethynyl ketone (111) is also illustrated in Flowsheet M-2 by utilizing bis-trimethylsilylacetylene.

FLOWSHEET M-2

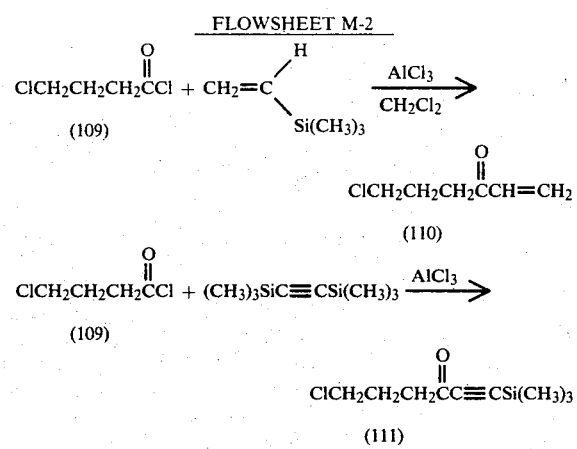

An alternate procedure to prepare precursors to the vinyllithium reagent (108) is shown in Flowsheet M-3. In accordance with Flowsheet M-3, the silylether alkyne (104) is treated with diisoamylborane followed by treatment with trimethylamine oxide and then with I$_2$/NaOH, to provide to 1-iodo-trans-alkenes (113). Treatment of the vinyliodide (113) with two equivalents of t-BuLi according to Untch generates the vinyllithium reagent (108).

FLOWSHEET M-3

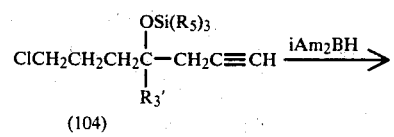

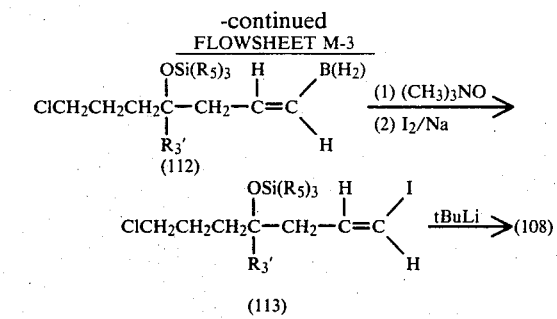

The preparation of 16-formyl and 16-dimethoxy methyl analog precursors is illustrated in Flowsheet N.

In accordance with the procedure outlined in Flowsheet N, treatment of alkyl ester (114) with the sodium salt of dimethylsulfoxide, wherein R$_4$ is hydrogen, methyl, ethyl or propyl, provides the keto sulfoxide (115). Treatment of the ketone with iodine in methanol provides the ketoacetal (116) which upon treatment with propargylmagnesium bromide provides the hydroxyalkyne (117) which is silylated to give the ether (118). The TMS ether (118) is heated with tri-n-butylstannane in the presence of azobisisobutyronitrile (AIBN) to afford the trans vinylstannane (119) which contains 10 to 20% of the corresponding cis vinylstannane (120).

Treatment of the vinylstannyl reagents (119 and 120) with n-butyl lithium at temperatures of $-78°$ C. to $-10°$ C. generates the vinyl lithium reagent (121).

FLOWSHEET N

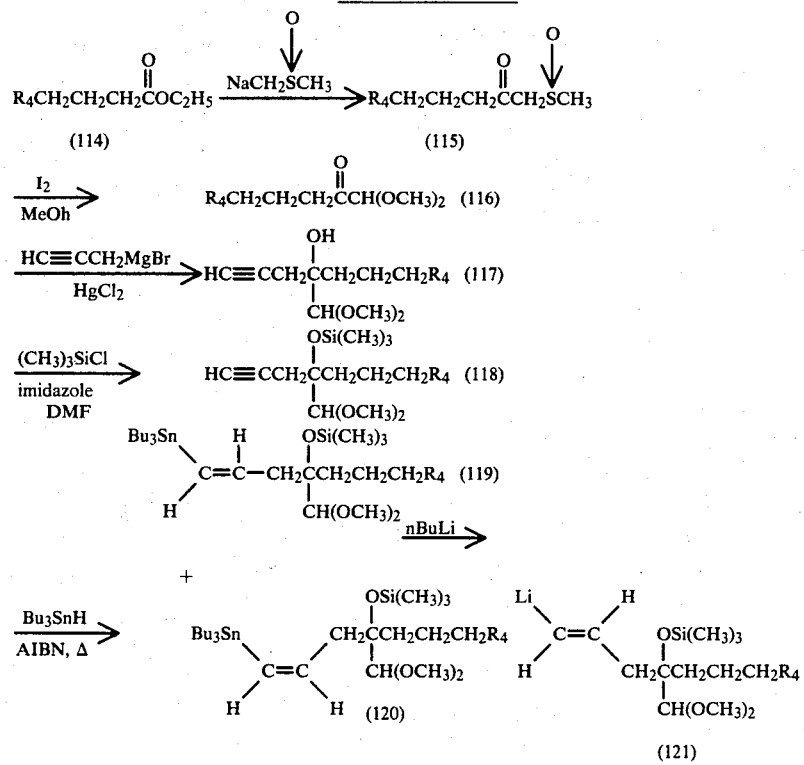

The precursor for the 16-fluoromethyl analogs are prepared as illustrated in Flowsheets O-1 and O-2.

In accordance with the procedure outlined in Flowsheet O-1, treatment of ethyl fluoroacetate (122) with alkyl lithium (123) wherein R$_4$ is hydrogen, methyl, ethyl or propyl, provides the fluoromethyl ketone (124). Treatment of the ketone (124) with propargylmagnesium bromide (125) provides the hydroxyalkyne (126) which is sillyated to give the ether (127). The TMS ether (127) is heated with tri-n-butylstannane in the presence of azobisisobutryonitrile (AIBN) to afford the trans vinylstannane (128) which contains 10 to 20% of the corresponding cis vinylstannane (129).

Treatment of the vinylstannyl reagents (128, 129) with n-butyl lithium at temperatures of −78° C. to −10° C. generates the vinyl lithium reagent (130).

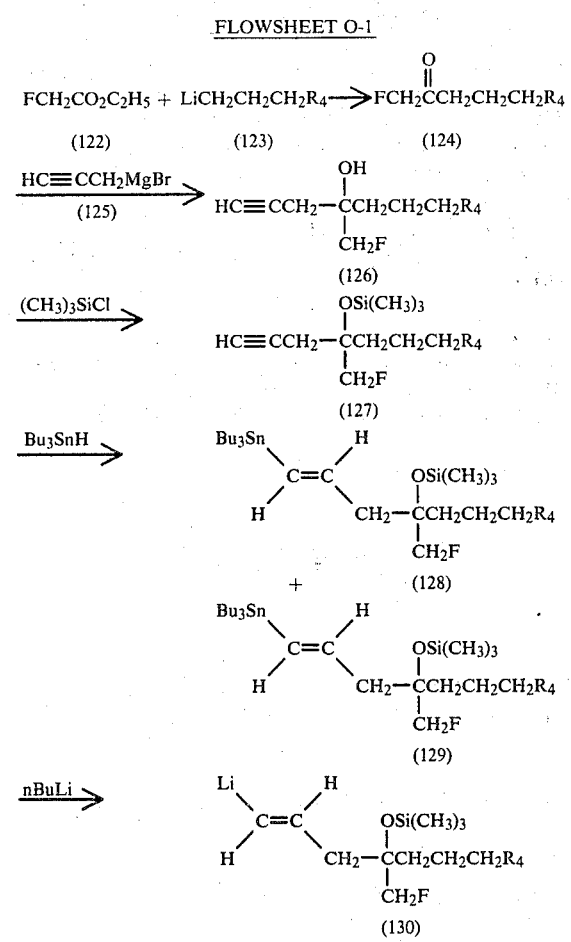

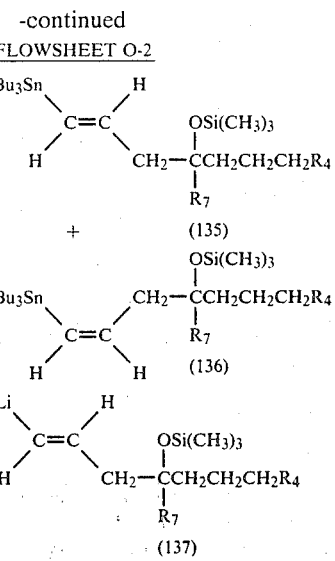

In accordance with Flowsheet O-2, the treatment of acid (131) ($R_7=CF_2H$, $CF_3$) with alkyl lithium (123) wherein $R_4$ is hydrogen, methyl, ethyl or propyl, provides the ketone (132) which upon addition of propargylmagnesium bromide provides the hydroxyalkyne (133). The alcohol (133) is treated with chlorotrimethylsilane to provide the TMS-ether (134) which is heated with tri-n-butylstannane to provide the trans-vinylstannane (135) that contains 10 to 20% of the corresponding cis-vinylstannane (136).

Treatment of the vinylstannane reagent (135, 136) with n-butyl lithium at temperatures of −78° C. to −10° C. generates the vinyl lithium reagents (137).

-continued
FLOWSHEET P-1

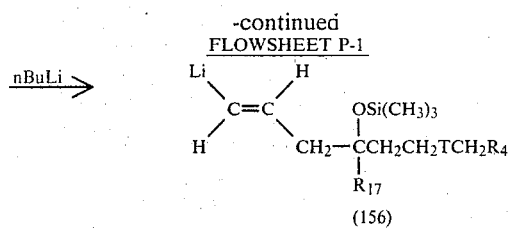

(156)

In accordance with the procedure outlined in Flowsheet P-1, wherein $R_4$ is as defined previously and T is divalent oxygen (—O—) is divalent sulfur (—S—) and $R_{17}$ is hydrogen or methyl, treatment of the unsaturated carbonyl (138) with an alcohol (139) (G=O) with acid (PTSA) catalysis or treatment of (148) with a mercaptan (139) (G=S) with a basic catalysis such as piperidine provides the ketone (140). Treatment of the ketone (140) with propargylmagnesium bromide (151) provides the hydroxyalkyne (152) which is silylated to give the ether (153). The TMS ether (153) is heated with tri-n-butylstannane in the presence of azobisisobutyronitrile (AIBN) to afford the trans vinylstannane (154) which contains 10 to 20% of the corresponding cis vinylstannane (155).

Treatment of the vinylstannyl reagent (154) with n-butyl lithium at temperatures of $-78°$ C. to $-10°$ C., generates the vinyl lithium reagent (156).

propargylic magnesium bromide (158) to form the homopropargylic alcohol (159) which is converted to its trimethylsilyl ether in the usual manner. The silylated ether is then treated with diisoamylborane in tetrahydrofuran, and then with anhydrous trimethylamine oxide. The resulting solution and an iodine solution in tetrahydrofuran are then added simultaneously to an aqueous solution of sodium hydroxide to give the 1-iodo-4-trimethylsilyloxy-7-oxa-trans-1-alkene (160).

The trimethylsilyl protecting group on the alcohol function is removed with mild acid and the resulting vinyliodide alcohol is oxidized with pyridinium chlorochromate to provide the 1-iodo-4-oxo-7-oxa-trans-1-alkene (161), which upon treatment with the appropriate Grignard reagent ($R_6$MgX), provides the 1-iodo-4-hydroxy-7-oxa-trans-1-alkene which is silylated in the usual manner to provide the silyl ether (162) wherein $R_6$ is as defined above, X is Cl or Br.

Lithiation of (162) (1 eq. n-butyl lithium or 2 eq. t-butyl lithium) at $-70°$ C. provides the lithio alkene (163).

The preparation of the precursors for the 1G ethynyl congeners is also shown in Flowsheet P-2.

In accordance with Flowsheet P-2, wherein $R_4$ and T are as previously defined, treatment of the carboxylic acid chloride (164) with bis-trimethylsilylacetylene in the presence of aluminum trichloride provides the acylacetylene (165). Treatment of the acylacetylene (165)

FLOWSHEET P-2

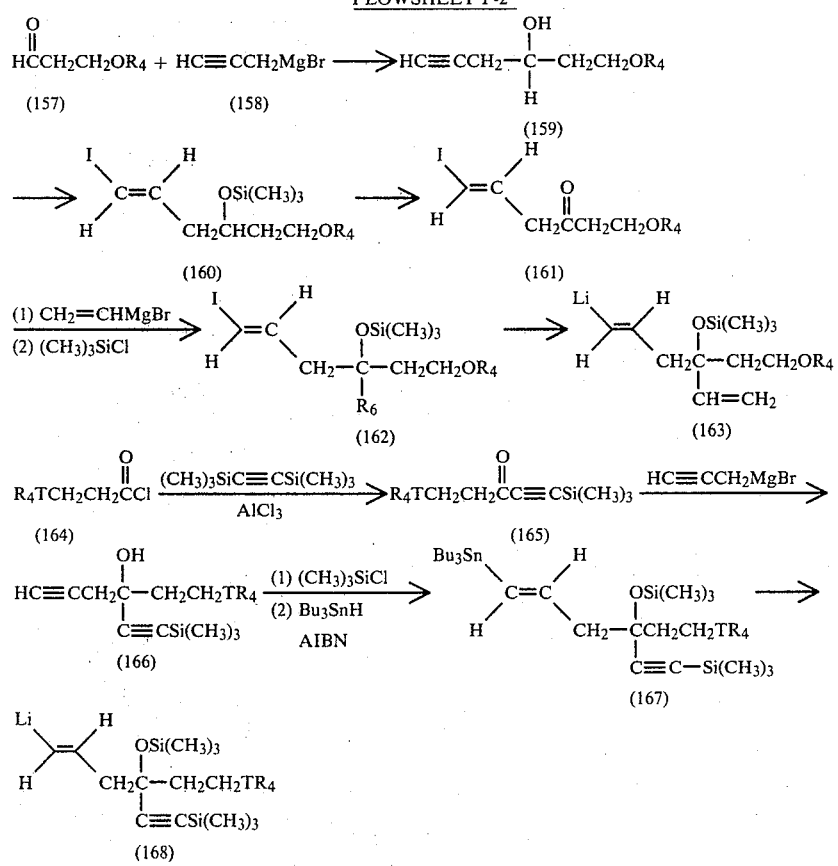

The preparation of the precursors for the 16-vinyl and ethynyl-19-oxa congeners is shown in Flowsheet P-2.

In accordance with Flowsheet P-2, wherein $R_4$ is as hereinabove defined, an aldehyde (157) is treated with with propargyl magnesium bromide forms the diacetylenic alcohol (166) which is silylated to provide the ether. The ether is converted to the vinylstannane (167)

by treatment with tri-n-butylstannane in the presence of azobisisobutryonitrile (AIBN).

The other ketones (58) used in this invention are known in the literature or can be made by procedures well known to the art [G. Lardelli, U. Lamberti, W. T. Walles and A. P. deJonge, *Rec. Trav. Chem. Pays-Bas*, 86, 481 (1967); Ng. Ph. Buu-Hoi, T. B. Loc and Ng. Dat Xuong, *Bull. Soc. Chem. France*, 174 (1958); and G. H. Posner, *Organic Reactions*, 19, 1 (1972)].

FLOWSHEET P-3

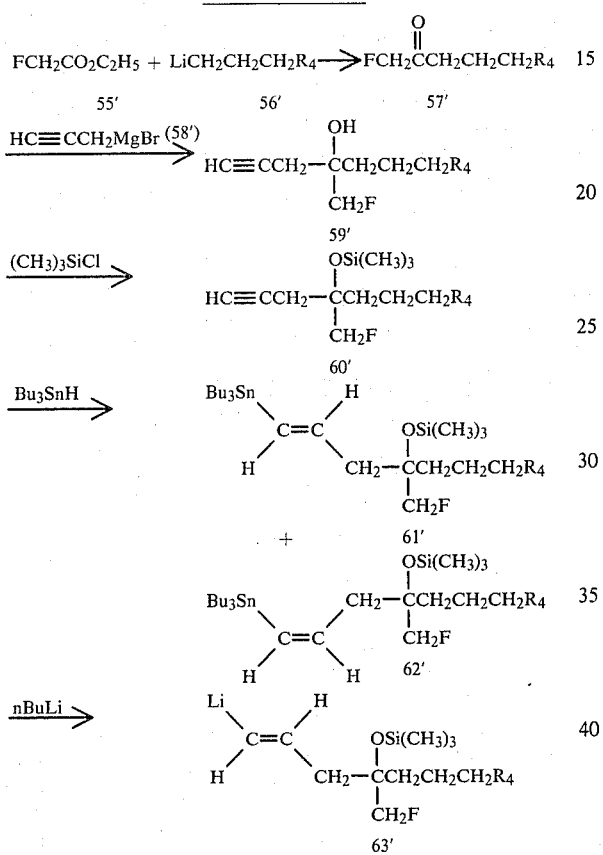

FLOWSHEET P-4

$$R_7COH + LiCH_2CH_2CH_2R_4 \longrightarrow R_7CCH_2CH_2CH_2R_4$$
64'    56'    65'

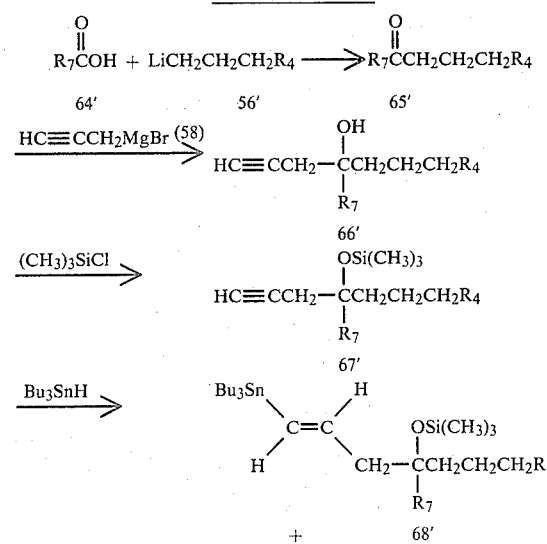

-continued
FLOWSHEET P-4

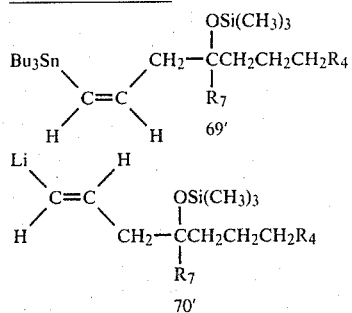

The precursor for the 16-fluoromethyl analogs are prepared as illustrated in Flowsheets P-3 and P-4.

In accordance with the procedure outlined in Flowsheet P-3, treatment of ethyl fluoroacetate with alkyl lithium 56' wherein $R_4$ is hydrogen, methyl, ethyl or propyl provides the fluoromethylketone 57'. Treatment of the ketone 57' with propargylmagnesium bromide 58' provides the hydroxyalkyne 59' which is silylated to give the ether 60'. The TMS ether 60' is heated with tri-n-butylstannane in the presence of azobisisobutyronitrile (AIBN) to afford the trans vinylstannane 61' which contains 10% to 20% of the corresponding cis vinylstannane 62'.

Treatment of the vinylstannyl reagents (61',62') with n-butyl lithium at temperatures of $-78°$ C. to $-10°$ C. generates the vinyl lithium reagent 63'.

In accordance with Flowsheet P-4 the treatment of acid 64' ($R_7 = CF_2H$, CF3) with alkyl lithium 56' wherein $R_4$ is hydrogen, methyl, ethyl or propyl, provides the ketone 65' which upon addition of propargylmagnesium bromide provides the hydroxyalkyne 66'. The alcohol 66' is treated with chlorotrimethylsilane to provide the TMS-ether 67' which is heated with tri-n-butylstannane to provide the trans-vinylstannane 68' that contains 10% to 20% of the corresponding cis-vinylstannane 69'.

Treatment of the vinylstannane reagents 68', 69' with n-butyl lithium at temperatures of $-78°$ C. to $-10°$ C. generates the vinyl lithium reagents 70'.

FLOWSHEET P-5

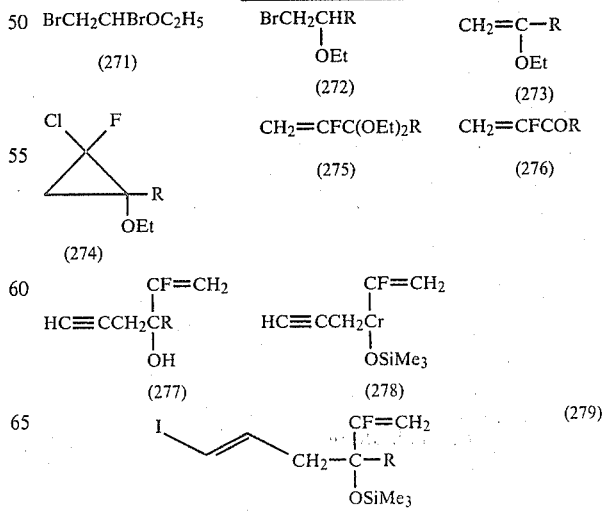

-continued
FLOWSHEET P-5

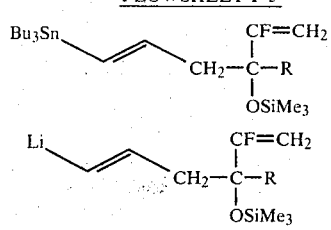

In accordance with the reaction scheme of Flowsheet P-5, the precursors to the novel cuprate reagents and compounds of the present invention are prepared from ethyl 1,2-dibromoethyl ether (271) [*Zhin. Obschei. Khim.*, 2, 1569 (1966)]. Treatment of (271) in ether solution with an alkylmagnesium halide provides a (1-alkyl-2-bromoethyl) ethyl ether (272). Treatment of (272) with strong base, for example, sodium hydride and a catalytic amount of isopropanol, in an inert solvent, for example, dimethylformamide, results in the formation of a (1-alkylvinyl) ethyl ether (273). Reaction of (273) with a source of chlorofluorocarbene, for example, with dichlorofluoromethane in the presence of concentrated aqueous potassium hydroxide [*Helv. Chim. Acta.*, 60, 1739 (1977)] results in the formation of a 2-chloro-2-fluoro-1-ethoxy-1-alkylcyclopropane (274). Conversion of (274) to the desired 2-fluoro-1-alken-3-one (276) is preferably effected by solvolysis of (274) in boiling ethanol in the presence of anhydrous potassium carbonate to provide the intermediate (275); hydrolysis of (275) in dilute aqueous mineral acid in a solvent such as tetrahydrofuran provides the ketone (276). Treatment of (276) with propargylmagnesium halide provides (277), which is converted to its trimethylsilyl derivative (278) in the usual way.

Formation of the vinyllithium reagent (281) from (278) may be carried out by procedures known in the art. For example, reaction of (278) with tri-n-butylstannane in the presence of azobisisobutyronitrile provides the vinylstannane (280), which upon treatment with n-butyllithium at a temperature of −78° C. to −30° C. yields (281). Alternatively, (278) is treated with disiamylborane in tetrahydrofuran solution, followed by sequential treatment with trimethylamine oxide and a mixture of aqueous sodium hydroxide and iodine, to provide the vinyl iodide (279). Reaction of (279) with an alkyllithium, preferably 2 equivalents of t-butyllithium at a temperature of about −75°, provides the vinyllithium (281).

The preparation of the cyclopentenones of this invention containing the hydroxyketone feature (68) wherein Z is hereinabove defined and R₃ is hydrogen or a hydroxy group can be accomplished in several ways, one of which involves the conversion of the corresponding cyclopentenone containing a carboxylate function (168) to the respective alkoxymethyl ketone, phenoxymethyl ketone, alkylthiomethyl ketone, or (alkyl alkoxyacetate) β-ketone derivatives.

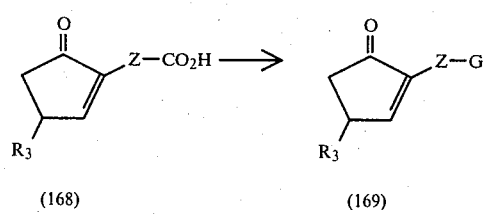

Most of the cyclopentenone carboxylic acids (168) required for the purposes of this invention have been described in the literature or can be prepared by procedures quite analogous to those already described. Appropriate references are provided in the examples which follow. The synthesis of certain non-reference requisite cyclopentenone carboxylic acids (168) is also described herein.

The preparation of the requisite 4-hydroxy-thiacyclopentenones (171) is described in Flowsheet Q. In accordance with Flowsheet Q which is hereinbelow described, treatment of 2-furyllithium (170) with a ω-chloroaldehyde (171) provides the chloroalcohol (172). Treatment of the chloroalcohol (172) with ethylmercaptoacetate furnishes the hydroxyester (173) which upon hydrolysis with sodium formate/formic acid provides the 3-hydroxy-cyclopentenone (174). Treatment of the cyclopentenone (174) with sulfuric acid provides the required 4-hydroxy-cyclopentenone (175).

FLOWSHEET Q

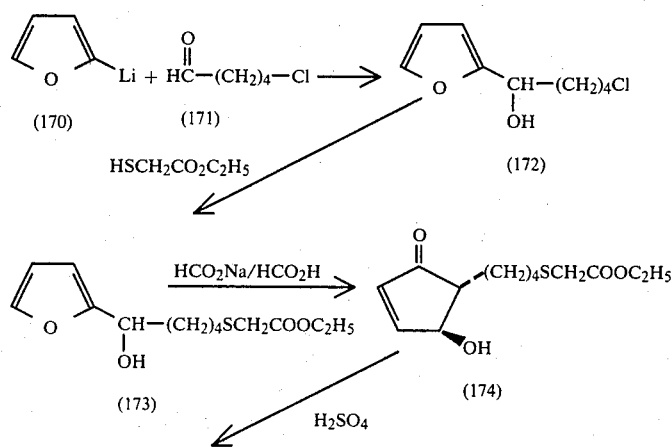

FLOWSHEET Q

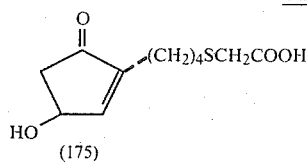

The conversion of the cyclopentenone carboxylic acid (168) to the respective alkoxymethyl and phenoxymethyl analogs (169) and the protection of these compounds for a conjugate addition reaction is described hereinbelow in Flowsheets R-1, R-2, S-1 and S-2.

For the preparation of cyclopentenones of the type (180), wherein Z is hereinabove defined, the carboxylic acid (176) is converted to the acid chloride (177) by first forming the sodium salt with sodium hydride in tetrahydrofuran (THF) and then reacting the resulting suspension with oxalyl chloride in the presence of a catalytic amount of dimethylformamide (DMF) to form the acid chloride (177).

The acid chloride (177) can be heated with two equivalents of 1,1,2-tris-trimethylsilyloxyethylene at 90° to 100° for 2 to 4 hours to produce compound (179). Compound (179) can be readily hydrolyzed and decarboxylated to give the ketone (180) by treatment with dilute hydrochloric acid in tetrahydrofuran (THF).

Derivatization of the ketone function of (180) can be accomplished in two ways. Ketalization of (180) with ethylene glycol is accomplished by refluxing a benzene or toluene solution of (180) and ethylene glycol into a Dean-Stark trap to provide (181).

The preparation of the corresponding cyclopentenones (183) and (184) for preparing 11-deoxy-1-oxo-1-alkylmethylthio prostaglandins is illustrated in Flowsheet R-2 in a fashion similar to that of Flowsheet R-1.

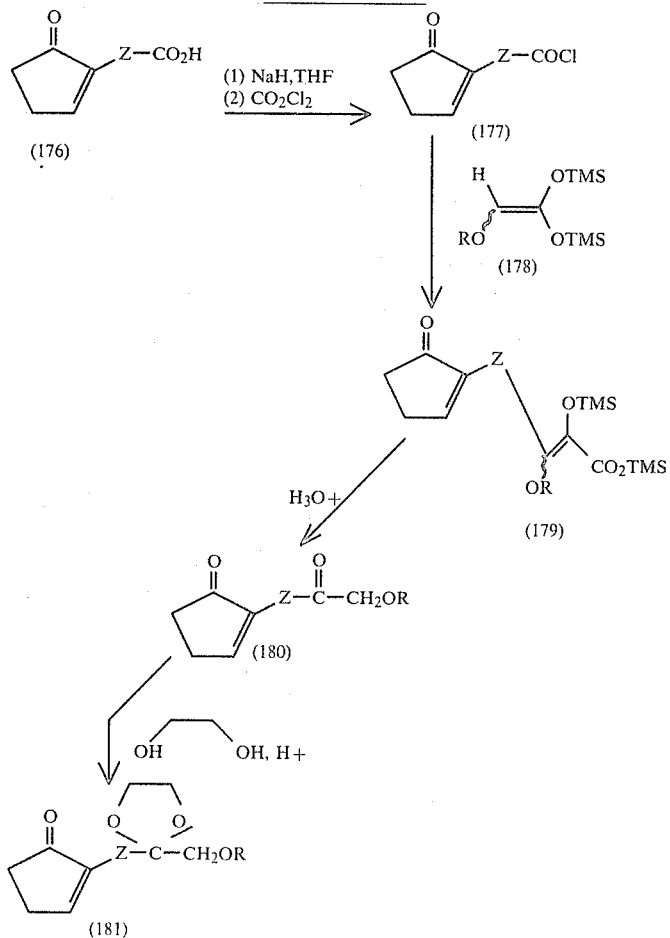

FLOWSHEET R-2

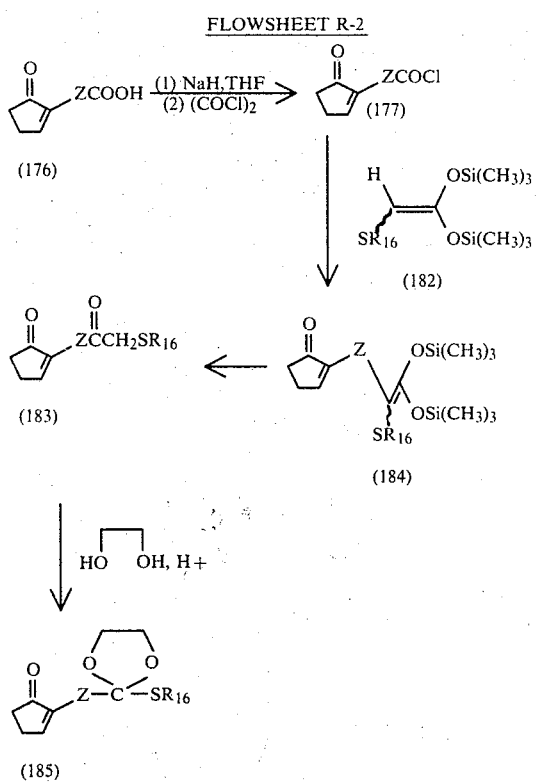

The preparation of the 4-hydroxycyclopentenones of this invention (192–195), wherein Z is hereinabove defined is outlined in Flowsheet S-1 below. The reaction of the hydroxy acid (186) with at least two equivalents of dimethyl-t-butyl-silylchloride in the presence of imidazole in dimethylformamide at 30°–40° C. gives the bis-dimethyl-t-butylsilated compound (187). The carboxylate dimethyl-t-butylsilyl group can be selectively removed by treatment with acetic acid, tetrahydrofuran and water (4:2:1) to give the carboxylic acid (188). The acid chloride (189) is prepared by first treating the acid (188) with sodium hydride in tetrahydrofuran to give the sodium salt. The resulting suspension of the sodium salt is then treated wiht oxalyl chloride in the presence of a catalytic amount of dimethylformamide. Alternatively the acid chloride (189) can be prepared directly by the reaction of the acid (188) or the dimethyl-t-butyl-silyl ester (187) with oxalyl chloride in tetrahydrofuran in the presence of a catalytic amount of dimethylformamide at 0° C.

The acid chloride (189) can be heated with at least two equivalents of 1,1-bis-trimethylsilyl-2-alkoxy (phenoxy) ethylene at 90°–120° C. in the absence of a solvent to give compound (190) which is readily hydrolyzed and decarboxylated to give the 4-hydroxycyclopentenone (191) containing the alkoxymethyl (phenoxymethyl) ketone feature.

The hydroxy ketone (191) is protected as are the silyl ether (192) or the ketals (194) and silyl ether ketal (195).

Alternatively, the hydroxyl moiety may be protected using 1 equivalent of 2-methoxypropene per equivalent of (191) in the presence of a catalyst such as chloroacetic acid to provide compounds such as (193). Other useful protecting groups are dihydro-2H-pyran, ethylvinylether and the like.

Other acid sensitive protecting groups for the hydroxyl group are the triloweralkylsilyls (from silylchlorides), triphenylmethane (from tritylchloride or bromide), mono-p-methoxytriphenylmethane (from mono-p-methoxytriphenylmethylchloride or bromide), methoxymethyl (from chloromethylmethylether) and the like.

The preparation of the alkylthiomethylketone containing cyclopentenones is likewise illustrated in Flowsheet S-2, wherein the reagent 1,1-bis-trimethylsilyloxy-2-alkylthioethylene is utilized.

FLOWSHEET S-1

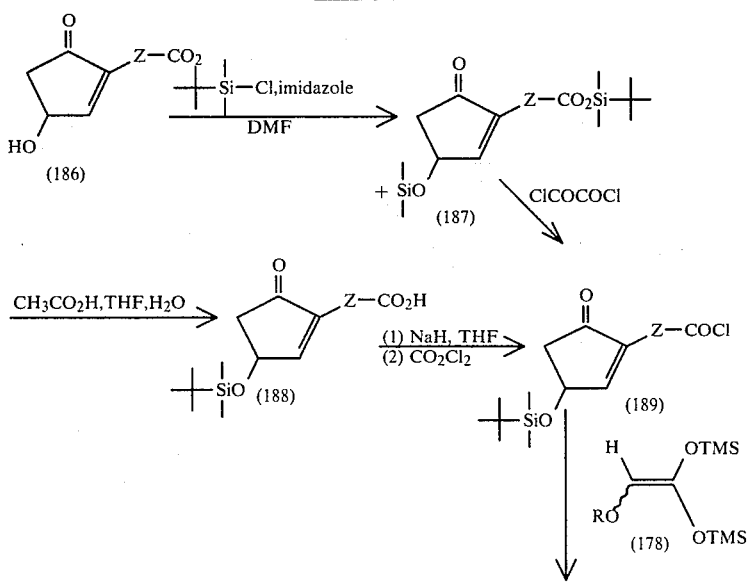

-continued
FLOWSHEET S-1
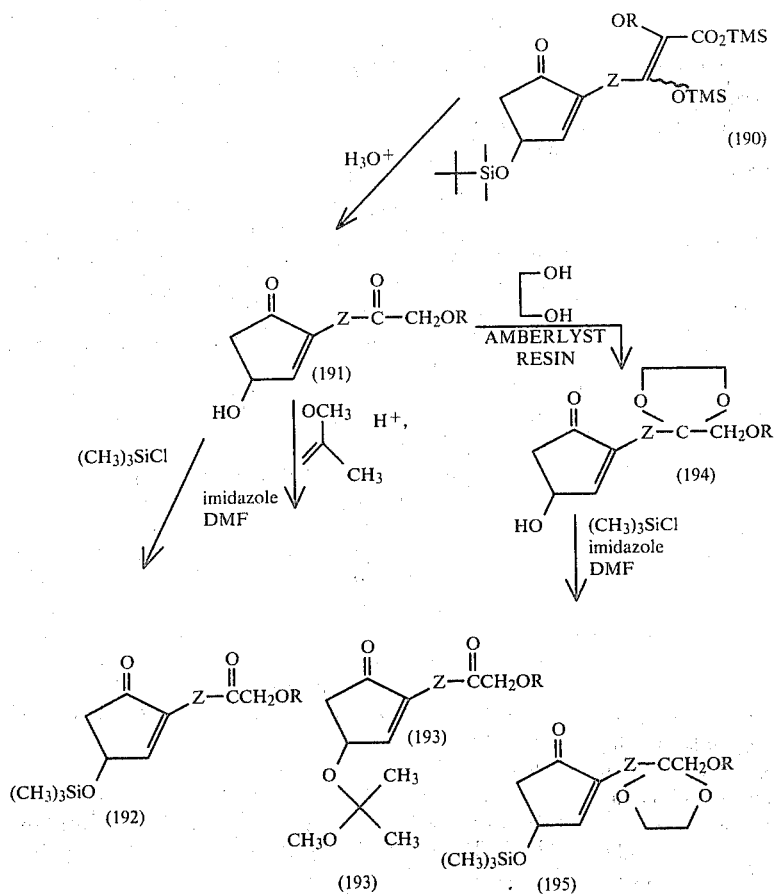
FLOWSHEET S-2
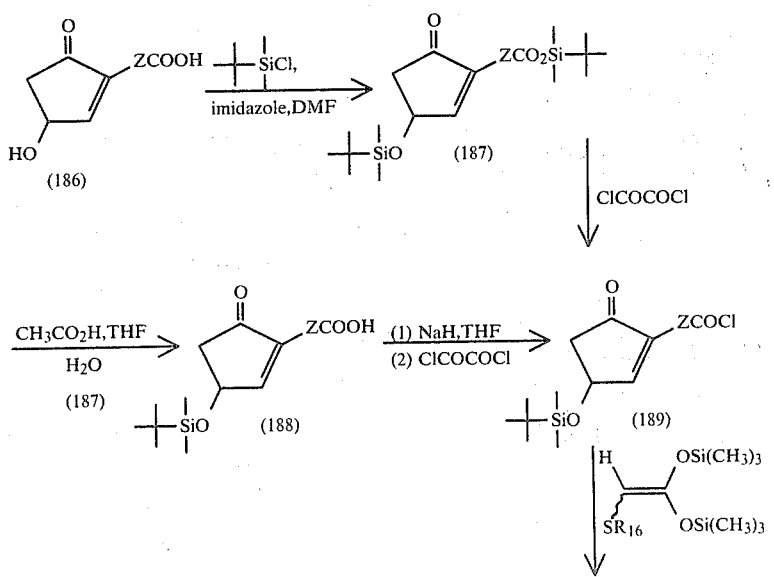

FLOWSHEET S-2

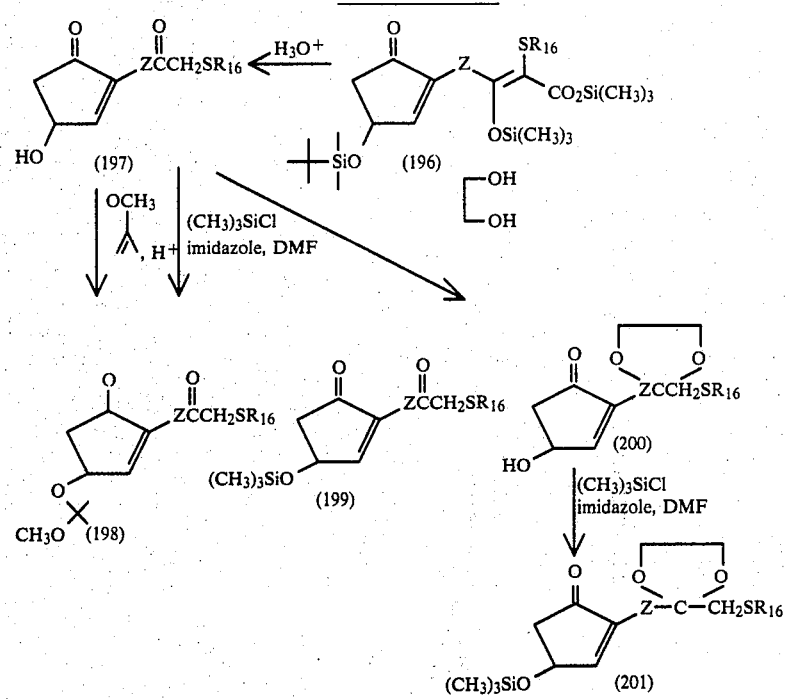

Another preparation of the 4-hydroxycyclopentenones of this invention which contain a cis double bond in the potential α chain (211) is shown hereinbelow in Flowsheet T wherein g is as hereinabove defined. As illustrated in Flowsheet T, there are three methods available to prepare the important intermediate (205). The reaction of the ω-bromo carboxylic acid (202) with oxalyl chloride in an inert solvent such as benzene gives the acid chloride (203). The acid chloride (203) can be treated with an excess of 1,2-bis-trimethylsilyloxy-1-alkoxy (phenoxy)-ethylene in the presence of a catalytic amount of stannic chloride in the absence of solvent to give compound (204) which can readily be hydrolyzed and decarboxylated to the desired alkoxymethyl (phenoxymethyl) ketone (205) using dilute hydrochloric acid in tetrahydrofuran. Protection of the ketone function of (205) is accomplished using ethylene glycol in refluxing toluene using a catalytic amount of p-toluenesulfonic acid. Alternate procedures include the use of a solvent such as chlorobenzene (no catalysts) at reflux and heating with no solvent in the presence of no catalysts. The phosphonium salt (207) is obtained by refluxing a solution of (206) and triphenylphosphine in acetonitrile. Treatment of the phosphonium salt (207) with sodium methylsulfonylmethide in dimethylsulfoxide generates a phosphonium ylid which on reaction with aldehyde (208) gives (209). Refluxing a water-dioxane solution of (209) in the presence of a phosphate buffer (pH 5 to 6) gives the cyclopentenone (210).

Treatment of (210) with chloral and triethylamine in ether gives (211) which on hydrolysis in a mixture of tetrahydrofuran and dilute hydrochloric acid at 50°-70° C. then gives the desired 4-hydroxycyclopentenone (212) which can be protected as described hereinabove in Flowsheet S.

Treatment of (211) with trimethylsilylchloride and imidazole in DMF gives (213) which is also suitably protected for a cojugate addition reaction; similarly, use of (212) provides (214) which is also suitably protected for a conjugate addition. Other useful protecting groups such as 2-methoxypropene, tetrahydropyran, tetrahydrofuran, ethylamylether, triphenylchloromethane and the like may also be employed.

FLOWSHEET T

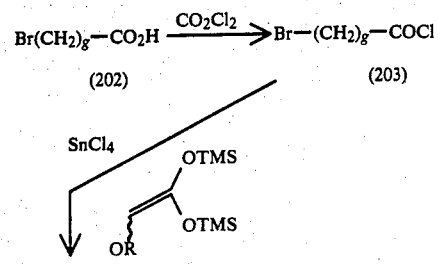

-continued
FLOWSHEET T

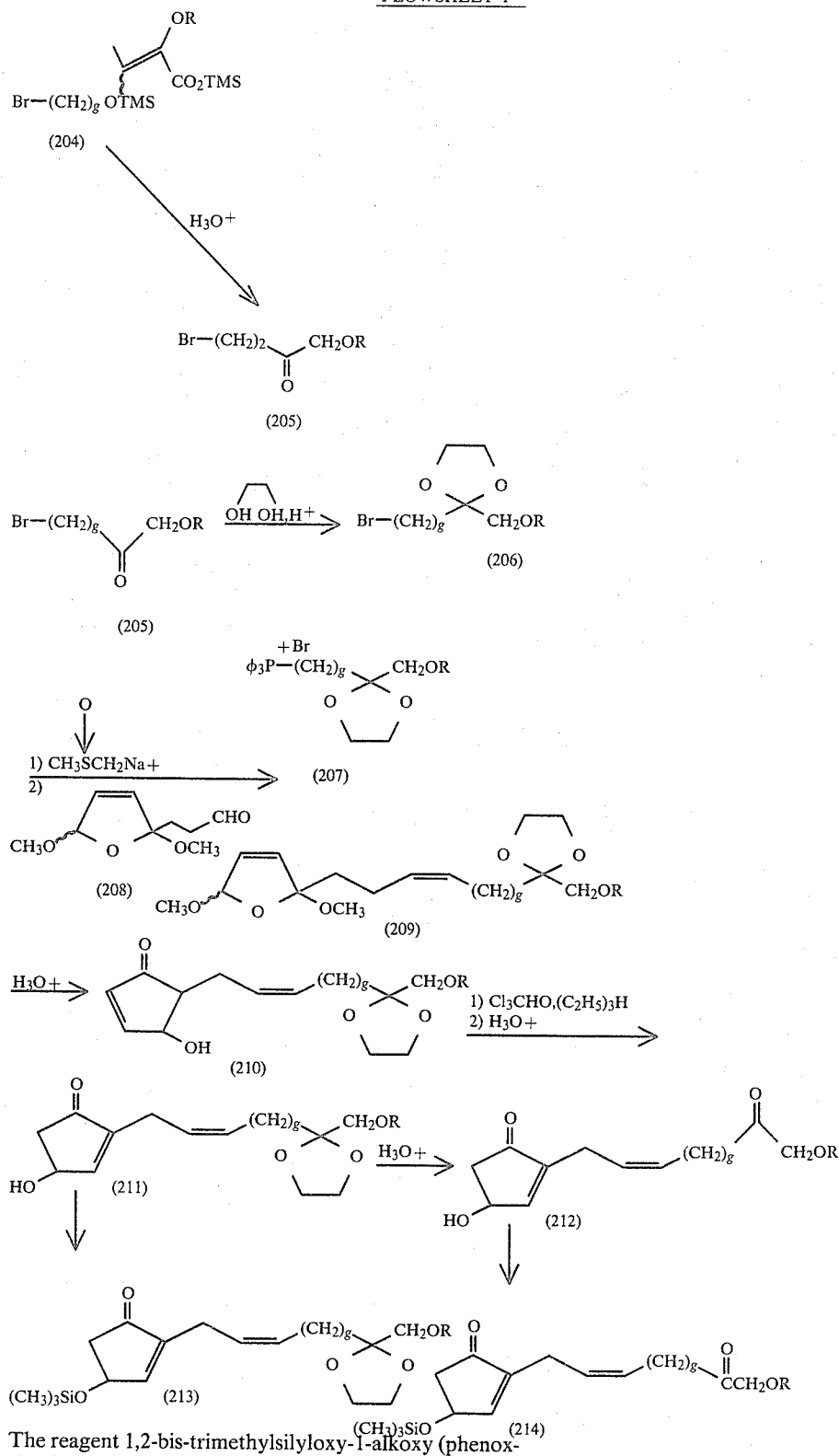

The reagent 1,2-bis-trimethylsilyloxy-1-alkoxy (phenoxy)-ethylene (178) and its use for the conversion of acid chlorides to hydroxyketone (for example 203 to 205 and 189 to 191) are claimed in this invention. The reagent preparation is described hereinbelow in Flowsheet U.

For the preparation of reagents useful for the conversion of carboxylic acid chlorides to alkoxymethyl (phenyl) ketones, an alkoxyacetic acid or phenoxyacetic acid (215) is treated with 1,1,1,3,3,3-hexamethyldisilazane and chlorotrimethylsilane in pyridine to give the trimethylsilyl alkoxy-(phenoxy)-acetate (216). Addition of (216) to a tetrahydrofuran solution of one equivalent of lithium 1,1,1,3,3,3-hexamethyldisilazane amide at −78° C. generates a lithium enolate which is trapped with chlorotrimethylsilane to produce the desired reagent (178).

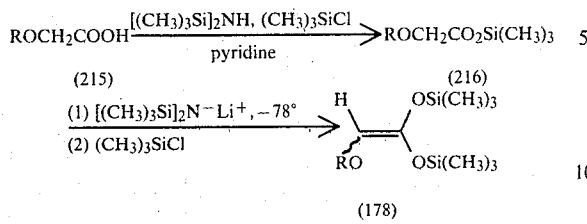

The preparation of reagents useful for the conversion of carboxylic acid chloride to alkylthiomethylketones is shown in Flowsheet U. Mercaptoacetic acid (217) is methylated with NaOH and an alkyl halide such As $R_{16}$-I, wherein $R_{16}$ is as previously defined (preferably an alkyl iodide) to provide the alkylthioacetic acid (218). This acid (218) is trimethylsilylated using 1,1,1,3,3,3-hexamethyldisilazane and chlorotrimethylsilane to provide the TMS-ester (219) which upon lithiation with 1 eq. of 1,1,1,3,3,3-hexamethyldisilazane amide ($-78°$ C.) followed by treatment with chlorotrimethylsilane provides the 1,1-bistrimethylsilyl-2-alkylthioethylene (182).

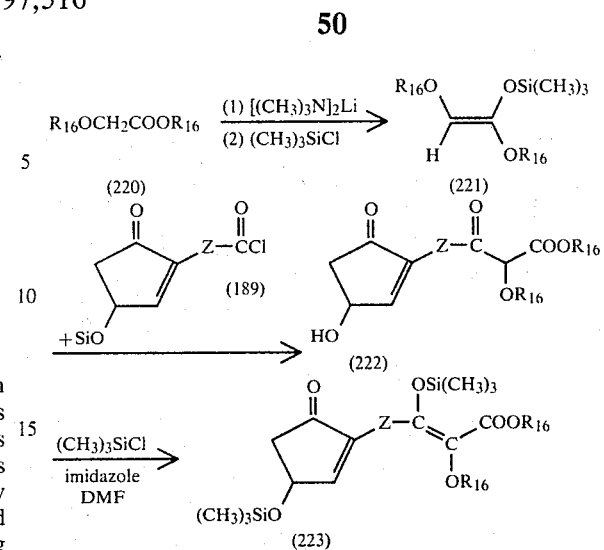

Ketals of the cyclopentenones (191) and (199) may be prepared by exposure of the parent ketones to ethyleneglycol in the presence of amberlyst 15 ® resin, as shown in Flowsheet V.

In accordance with Flowsheet V, wherein G' is

FLOWSHEET U

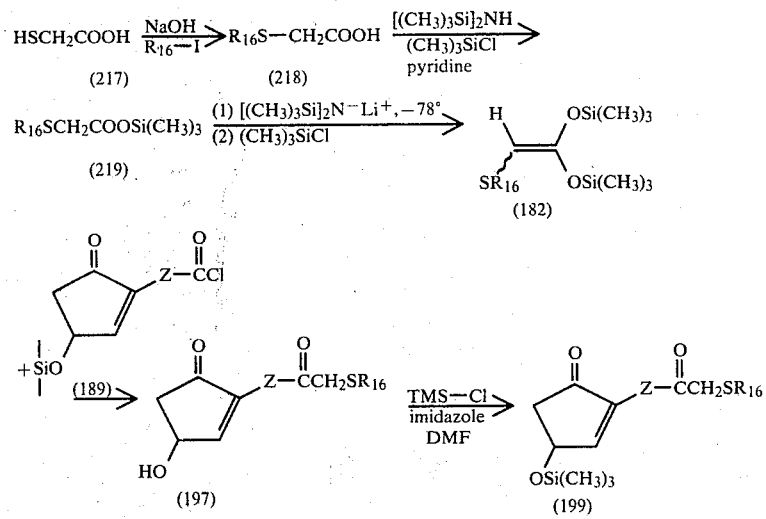

The trisubstituted ethylene is allowed to react with the cyclopentenone (189) to provide the alkylthiomethylketone cyclopentenone (197).

For the preparation of reagents useful for the conversion of carboxylic acid chlorides to α-alkoxy-β-ketoesters, an alkyl alkoxyacetate (220) in tetrahydrofuran is treated with one equivalent of lithium 1,1,1,3,3,3-hexamethyldisilazane amide at $-78°$ C. to generate a lithium enolate which is trapped with chlorotrimethylsilane to produce (221).

The trisubstituted ethylene derivative (221) is allowed to react with the cyclopentenone (189) to provide the α-alkoxy-β-ketoester cyclopentenone (222) which is silylated to provide (223) which is suitably protected for a conjugate addition reaction.

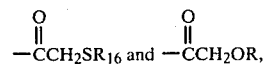

the cyclopentenones are converted to the corresponding ketals (224), wherein G" is

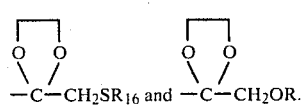

FLOWSHEET V

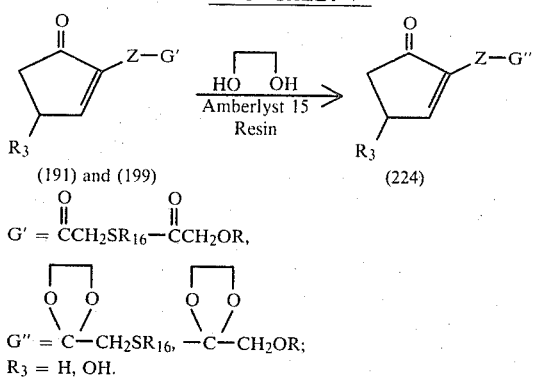

(191) and (199) → (224)

G' = $\overset{O}{\overset{\|}{C}}CH_2SR_{16}$, $\overset{O}{\overset{\|}{C}}CH_2OR$, G'' = $\overset{O\quad O}{\overset{\diagup\ \diagdown}{C}}-CH_2SR_{16}$, $\overset{O\quad O}{\overset{\diagup\ \diagdown}{C}}-CH_2OR$;

$R_3$ = H, OH.

The preparation of the prostaglandin congeners of this invention are described hereinbelow in Flowsheet W wherein Z is as hereinabove defined; $R''_3$ is hydrogen, 2-methoxypropyl-2-oxy ($-OC(CH_3)_2OCH_3$) or trimethylsilyloxy; $R_3$ is hydrogen or hydroxy; and G is the radical

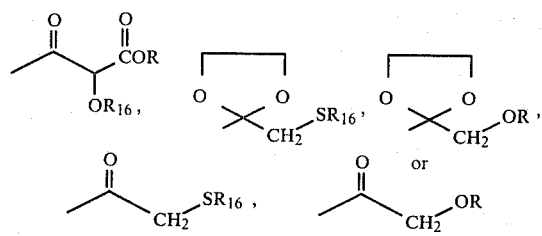

wherein R and $R_{16}$ are as hereinabove defined. R' is selected from the group consisting of:

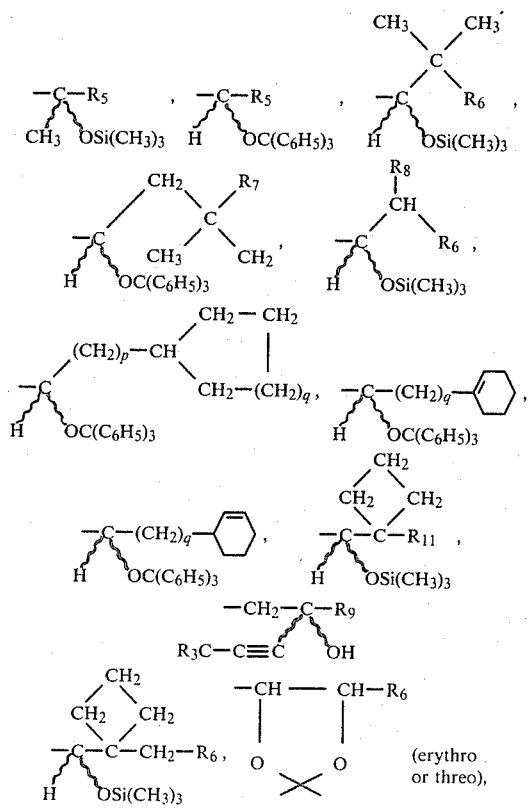

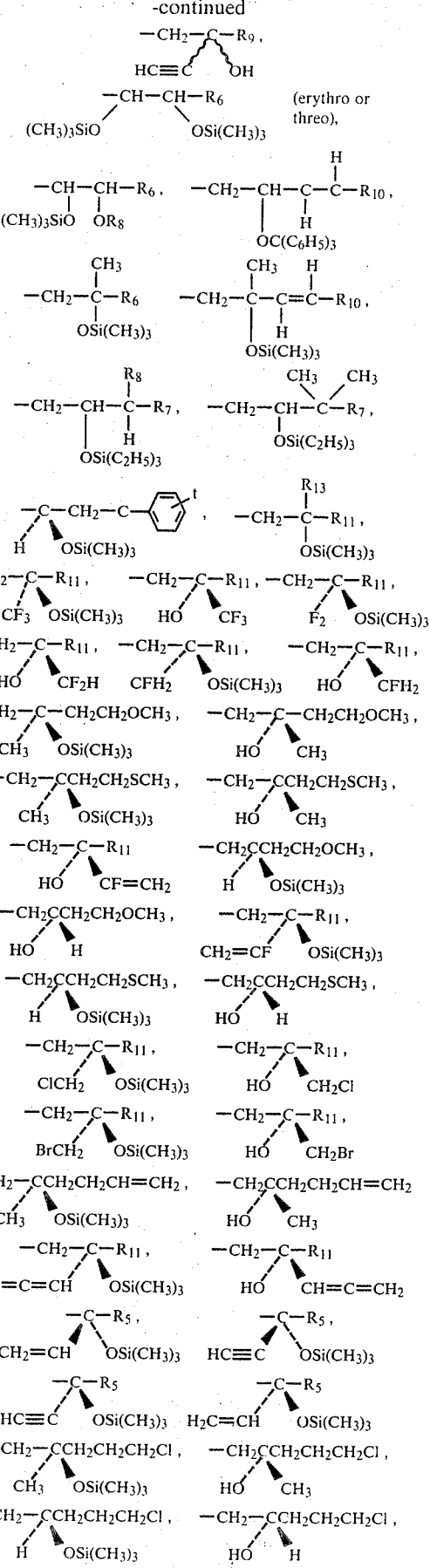

-continued
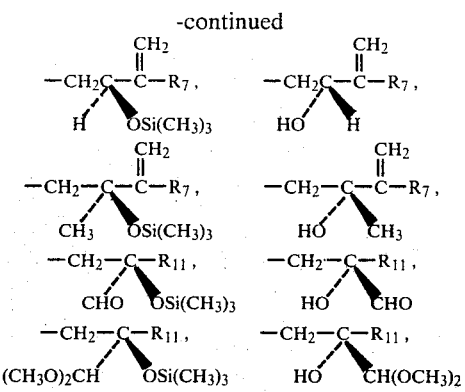
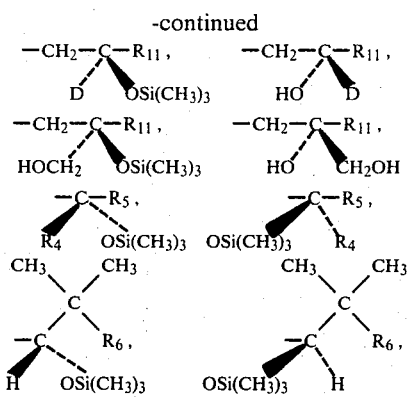
FLOWSHEET W
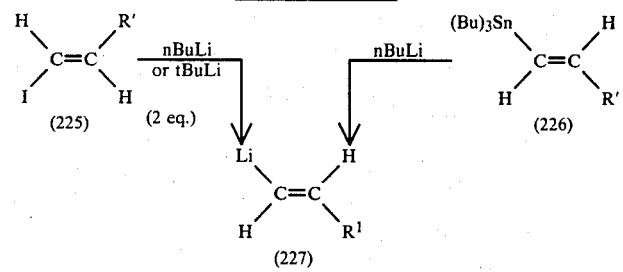
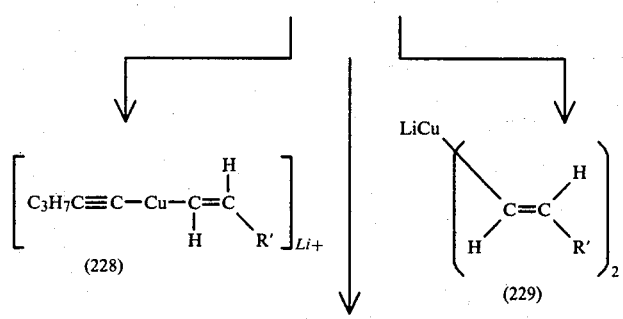
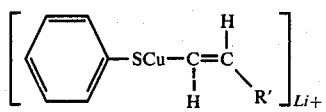
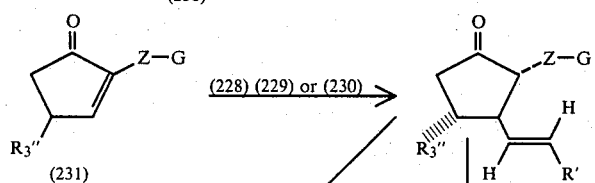
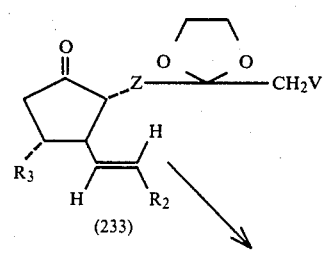
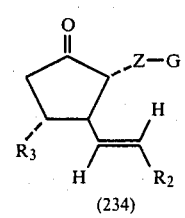

FLOWSHEET W
-continued

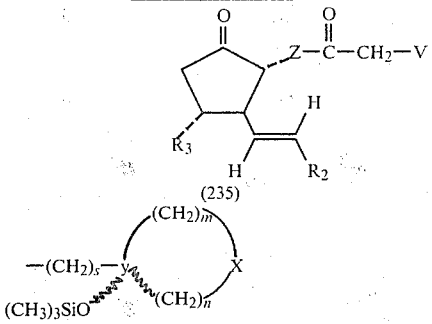

wherein $R_5$, $R_6$, $R_7$, $R_8$, $R_9$, $R_{10}$, $R_{11}$, $R_{13}$, G, p, q, t, s, m, n, y and X are as hereinabove defined.

In accordance with Flowsheet W, the vinyliodide (225) is treated with either one equivalent of n-butyllithium or 2 equivalents of t-butyllithium at low temperature, preferably $-30°$ to $-70°$ C. in an inert solvent, e.g. hexane, ether or toluene to provide the trans alkenyllithium reagent (227).

Alternatively, the vinyllithium reagent (227) can be prepared by treatment of a vinylstannyl derivative such as (226) with n-butyllithium at $-10°$ to $-78°$ C. in ether or THF.

For the preparation of the asymmetrical lithio cuprate (228) or the like, a solution of one molar equivalent of copper (I)-1-alkyne, preferably copper (I)-1-pentyne in anhydrous hexamethylphosphorous triamide preferably one to five molar equivalents, and anhydrous ether is added to one molar equivalent of the aforementioned vinyllithium solution cooled to about $-78°$ C. After about one hour at this temperature, a molar equivalent of the requisite cyclopentenone (231) is added. After several hours at $-78°$ C. to $-20°$ C., the reaction mixture is quenched with aqueous ammonium chloride solution and the blocked product (232) is isolated in the usual manner.

It is also possible to effect conjugate 1,4-addition with the asymmetrical lithio cuprate (230) derived from vinyllithium (227) and cuprous thiophenoxide. A solution of vinyllithium (227) in ether at $-78°$ C. is reacted with an equimolar amount of a reagent prepared by admixture, in ether at a temperature of $0°$ C. to $-78°$ C., of equimolar amounts of cuprous thiophenoxide and copper (I) iodide tributylphosphonium complex. After about 30 minutes at this temperature, the lithio cuprate (230) is treated with the requisite cyclopentenone (231) as described hereinabove for the conjugate addition with 1-alkynyl lithio cuprate (228).

For the preparation of the symmetrical lithio cuprate (229) one molar equivalent of copper (I) iodide tributylphosphine complex, dissolved in anhydrous ether, is added at about $-78°$ C. to two molar equivalents of the aforementioned vinyllithium (227) solution in hexanes, cooled to $-78°$ C. After about one hour at this temperature, the lithio cuprate (229) is treated with the requisite cyclopentenone (231) as described hereinabove for the conjugate addition with the 1-alkynyl lithio cuprate (228).

The procedures for conjugate addition involving organocopper reagents are well known in the art; see for example, C. J. Sih, et al., J.A.C.S., 97, 865 (1975).

All available evidence leads us to believe that the —CH=CH—$R'_2$ function introduced by the cuprate process occupies a position trans to the 11-oxy function.

Similarly, we are led to the conclusion that in the product (232), the two side-chains attached to $C_8$ and $C_{12}$ are trans to each other. However, we are not certain of this configurational relationship in the product as it is obtained directly from the cuprate process. These products may have the side-chains in a trans- and cis-relationship or they may be a mixture containing both the trans and cis-isomers. This is indicated in the nomenclature of the compounds involved by the designation $\xi$. In order to ensure a trans-relationship in (232), these products can be submitted to conditions known in the literature to equilibrate the cis-8-iso-$PGE_1$ to a mixture containing about 90% of the trans product. These conditions involve treatment with potassium acetate in aqueous methanol for 96 hours at room temperature.

When G is

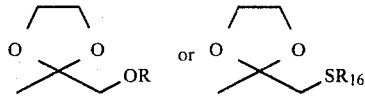

(232) can be partially deblocked to give (233) wherein V is —OR— or —$SR_{16}$—, by treatment of (232) with HOAC, tetrahydrofuran, water (4:2:1) (40° C., 3 to 6 hours).

Treatment of the protected prostaglandin (232) with mild acid (HOAC, THF, $H_2O$, 4:2:1, 25° to 55° C.) provides (234). When G contains the ketal moieties, selective hydrolysis by the above conditions provide the ketal (233). Hydrolysis of the ketal function of (233) is accomplished using HOAC, THF, $H_2O$ (4:2:1, plus cat. HCl, 40° C.) to provide the derivative (235).

When the compounds of this invention are prepared from racemic starting compounds, two racemates are obtained. In appropriate instances, these racemates can be separated from each other by careful application of the usual chromatographic procedures. In the more difficult instances, it may be necessary to apply high pressure liquid chromatography including recycling techniques. [See G. Fallick, American Laboratory, 19–27 (August, 1973) as well as references cited therein. Additional information concerning high speed liquid chromatography and the instruments necessary for its application is available from Waters Associate, Inc., Maple Street, Milford, Mass.]

It is also possible to prepare the compounds of this invention in their optically active forms by the conversion of the optically active 4-hydroxycyclopent-2-en-1-one carboxylic acids (236) to the optically active protected hydroxy ketone analogs (273a, b and c) using the methods outlined hereinabove in Flowsheet X.

FLOWSHEET X

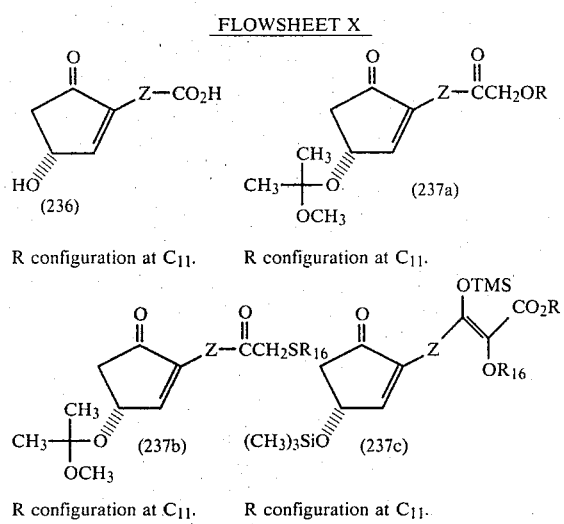

R configuration at $C_{11}$.   R configuration at $C_{11}$.

R configuration at $C_{11}$.   R configuration at $C_{11}$.

When one utilizes a racemic cyclopentenone (231) and a racemic vinyliodide (225) or racemic vinylstannane (226), the conjugate adducts isolated (233–235) consist of a mixture of 4-optical isomers. These four optical isomers are, in the case of the 15-deoxy-16-hydroxyprostaglandins, identified as nat. 16α, nat. 16β, ent. 16α and ent. 16β. Silica gel chromatography of the 4 isomers (233–235) will provide two fractions consisting of nat. 16α and ent. 16β and nat. 16β and ent. 16α.

If one utilizes a resolved cyclopentenone (231) that contains the 4(R) configuration, and a racemic vinyliodide (225) or racemic vinylstannane (226), the conjugate adducts isolated (233–235) consist of a mixture of two optical isomers. These two optical isomers are, in the case of the 15-deoxy-16-hydroxyprostaglandins, identified as nat. 16α and nat. 16β. Silica gel chromatography of the two isomers will provide separated nat. 16α and separated nat. 16β.

If one utilizes an optically active vinyliodide (225) or optically active vinylstannane (226) and a racemic cyclopentenone (231), then the conjugate adducts isolated (233–235) consist of two optical isomers. If the vinyliodide (225) or vinylstannane (226) would provide the nat. 16α as one of the products, the other product will be ent. 16α. Likewise, the products from a vinyliodide (225) or vinylstannane (226) of the opposite optical configuration will be nat. 16β and ent. 16β. Silica gel chromatography will separate nat. 16α from ent. 16β and likewise, nat. 16β is separable from ent. 16β.

If one utilizes a resolved cyclopentenone (231) that contains the 4(R) configuration and an optically active vinyliodide (225) or optically active vinylstannane (226), then the conjugate adducts (233–235) will consist of only one optical isomer, which will be either nat. 16α or nat. 16β, depending upon the configuration of the starting vinyliodide (225) or vinylstannane (226).

In accordance with the following reaction scheme, prostanoids are prepared as described by Stork in J.A.C.S., 97, 4745 (1975) and J.A.C.S. 97 6260 (1975) which are incorporated by reference.

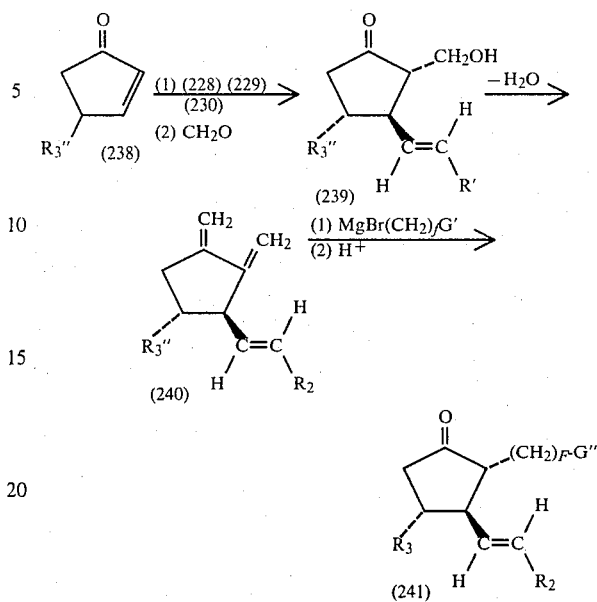

Treatment of the protected 4-oxycyclopentenone (238) with a cuprate such as (228), (229), or (230) is hereinabove defined, followed by quenching with formaldehyde to provide the hydroxymethyl analog (239) which is dehydrated with reagents such as excess methanesulfonyl chloride in pyridine followed by treatment of the crude mesylate with diisopropylethylamine in ether overnight. $R_3''$ and $R'$ are as previously defined. Addition of the methylenecyclopentenone (240) to a solution of the Grignard $MgBr(CH_2)_fG'$, wherein f is as previously defined and $R_1'$ is a substituent selected from the group $R_1$ wherein the hydroxyl group of the substituent is protected by a suitable blocking group such as 2-methoxy-propyl-2-oxy, and a catalytic amount of $Bu_3P.CuI$ ($Bu_3$ is tertiary butyl) followed by mild hydrolysis of the adduct, provides the product prostanoid (241) wherein F, $R_3$ and $R_2$ are as previously defined and G' is:

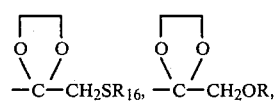

and G'' is:

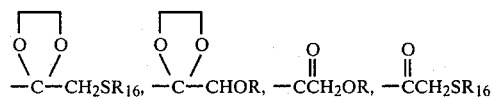

The bromide precursor to the Grignard described above is prepared in accordance with the procedure of Flowsheet T.

Conjugate addition of the vinyl cuprates to (237) followed by deblocking as described hereinabove in Flowsheet W then gives the compounds of this invention in their optically active forms. Although in some cases, two diastereoisomers will be formed, each optically active, they can be separated by chromatographic procedures as described hereinabove.

The preparation of optically active 4-hydroxycyclopent-2-en-1-ones such as (236) is described hereinbelow.

The 4-hydroxycyclopentenone racemates may be resolved into their component enantiomers (242) and (243) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give (244)), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (242) and (243). A useful procedure for the resolution of a 4-hydroxycyclopentenone racemate via an oxime such as (244) is described in the art [R. Pappo, P. Collins and C. Jung, *Tetrahedron Letters*, 943 (1973)] which is herein incorporated by reference. Additional resolutions are described by Bruhn, *Tetrahedron Letters*, 235 (1976) which is herein incorporated by reference.

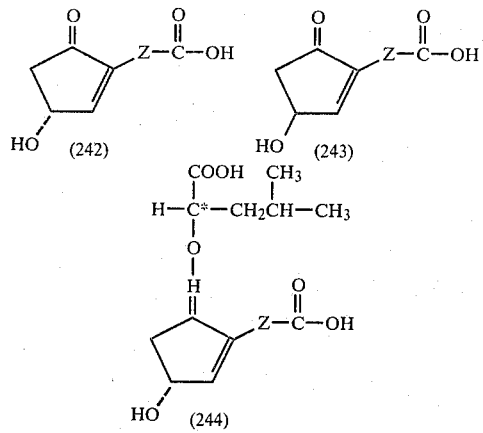

An alternate procedure for the preparation of the 4(R)-hydroxycyclopentenone enantiomers such as (242) involves as a key step the selective microbiological or chemical reduction of trione (245) to the 4(R)-hydroxycyclpentanedione (246). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine) rhodium (I) tetrafluoroborate in the presence of one equivalent of organic base, such as triethylamine.

Conversion of hydroxycyclopentanedione (246) to an enol ether or enol ester (247), E=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (247) with excess sodium bis(2-methoxyethoxy)aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (248). The ester (248) can then be hydrolyzed to acid (242).

For a description of these procedures in the art see: C. J. Sih, et al., J.A.C.S., 95, 1676 (1973); J. B. Heather, et al., *Tetrahedron Letters*, 2213 (1973); R. Pappo and P. W. Collins, *Tetrahedron Letters*, 2627 (1972); and R. Pappo, P. Collins, and C. Jung, *Ann. N.Y. Acad. Sci.*, 180, 64 (1971). The four above citations are incorporated by reference.

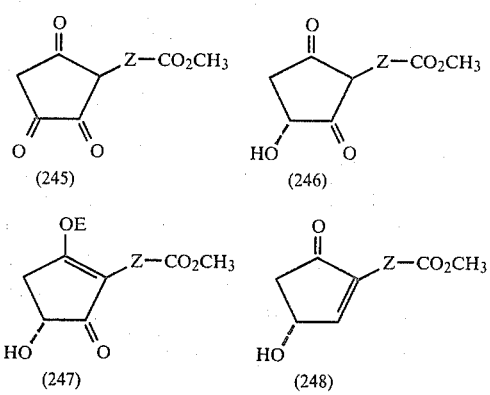

Procedures for the preparation of the requisite cyclopentanetriones (245) are well-established in the art and generally involve the treatment of an ω-1-oxo long chain ester (249) with methyl or ethyl oxalate and a base such as sodium methoxide in methanol, followed by treatment with dilute hydrochloric acid in aqueous methanol to effect the dealkoxalylation of the intermediate (250). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N.Y. Acad. Sci.*, 180, 64 (1971); C. J. Sih, et al., J.A.C.S., 95, 1676 (1973) (see reference 7); and J. B. Heather, et al., *Tetrahedron Letters*, 2313 (1973) for pertinent background literature. The five above citations are incorporated by reference.

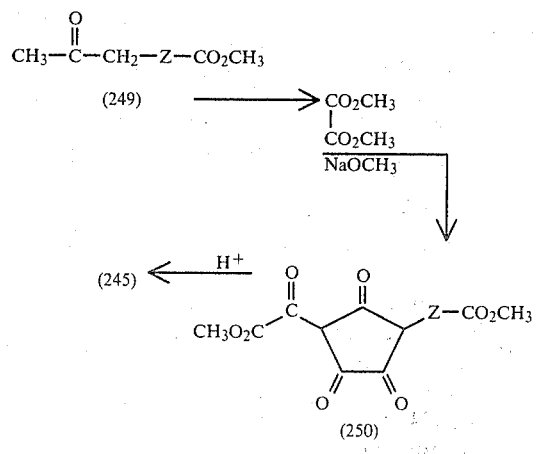

The intermediate keto esters (249) may be prepared by a variety of methods known to the art. One useful procedure is outlined below and involves alkylation of ethyl acetoacetate sodium salt (251) in the usual manner with the appropriate side-chain precursor (252), X=C, Br, I, preferably Br or I, followed by decarbethoxylation and reesterification, all in the usual manner.

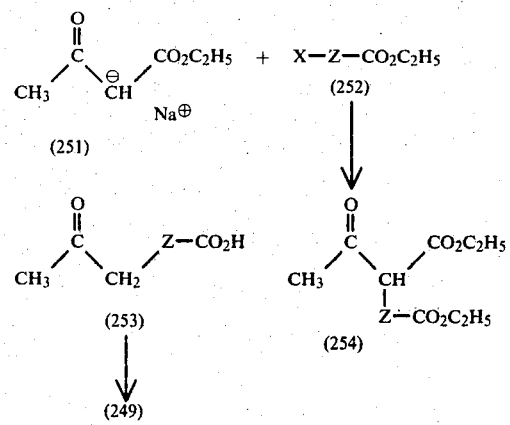

The side-chain precursors (252) are commercially available where Z is —(CH$_2$)$_p$—, and can be prepared as described in Belgian Pat. No. 786,215 (granted and opened to inspection Jan. 15, 1973).

Those precursors wherein Z is —(CH$_2$)$_r$—O—CH$_2$— can be prepared by the transformation shown directly below starting with the mono-tetrahydropyranyl derivative (255). Thus, (255) is converted to the lithium alcoholate by treatment with butyl lithium, the alcoholate is then O-alkylated with ethyl bromoacetate to provide (256), which on de-O-tetrahydropyranylation, mesylation and reaction with lithium bromide gives the required (257). (These and all the above-described transformations can be effected in the usual manner well-established in the art; pertinent examples for most of the reactions can be formed in the above-cited Belgian Pat. No. 786,215, herein incorporated by reference.)

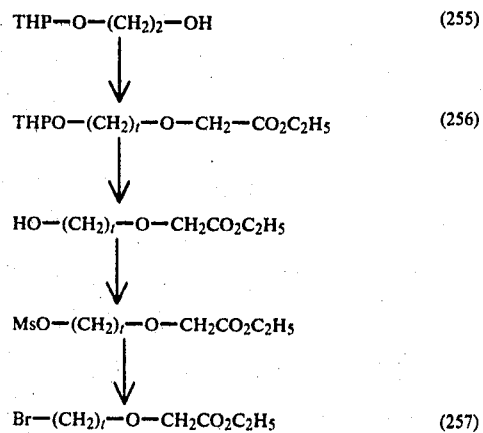

It is also possible to resolve the 4-hydroxycyclopentenone racemate (258) by microbiological means. Thus, treatment of the 4-O-alkanoyl or aroyl derivatives (259), R$_{18}$ aryl or alkyl, of racemate (258) (preferably the 4-O-acetyl and 4-O-propionyl derivatives) with an appropriate microorganism, preferably a Saccharomyces species, e.g., 375-143, affords preferential de-O-acylation of the 4(R)-enantiomer to give (260), which is then separated from the unreacted 4(S)-O-acyl enantiomer (261) by chromatographic procedures. After separation, mild hydrolysis of the 4(S) derivative (261) provides the 4(S)-hydroxycyclopentenone (262). [See N. J. Marsheck and M. Miyano, *Biochima et Biphysica Acta*, 316, 363 (1973) for related examples.]

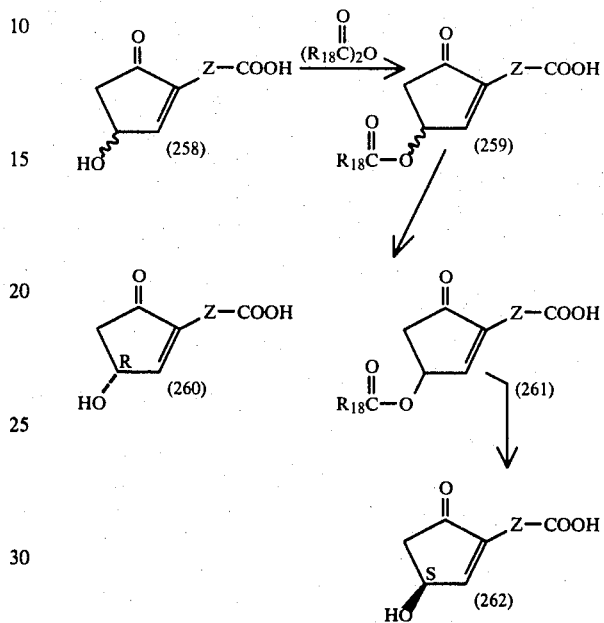

It is also possible to prepare the individual 4-hydroxycyclopentenones (260) and (262) directly by selective microbial hydroxylations of the corresponding 4-unsubstituted cyclopentenone (263). For example, with *Aspergillus niger* ATCC 9142; a selective 4(R)-hydroxylation of (263), Z=(CH$_2$)$_6$, has been reported; see S. Kurozumi, T. Tora and S. Ishimoto, *Tetrahedron Letters*, 4959 (1973), herein incorporated by reference. Other microorganisms can also accomplish this hydroxylation.

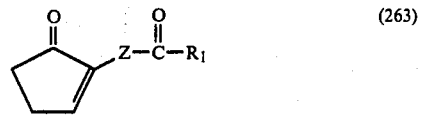

The 9α-hydroxy (PGFα) compounds of the invention (265-266) are prepared by a conjugate addition reaction using the ketal cyclopentenones as described below in Flowsheet Y. With reference to the structures of Flowsheet Y, V is —CH$_2$SR$_{16}$ or —CH$_2$OR; R$_3$ is a hydrogen or hydroxyl group and R' and R$_3$" are as previously defined. The initial conjugate addition product (232) is selectively deblocked to provide the ketal prostaglandin (264) which is dissolved in tetrahydrofuran and treated with an excess of lithium perhydro-9b-boraphenalylhydride or lithium selectride at −78° C. to provide the ketal PGFα analog (266). Hydrolysis of (266) (HOAC, THF, H$_2$O, 4:2:1 (cat. HCl), 40° C.) provide (265).

FLOWSHEET Y

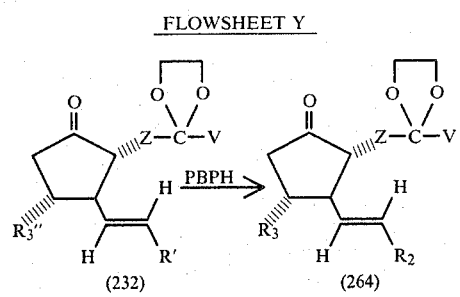

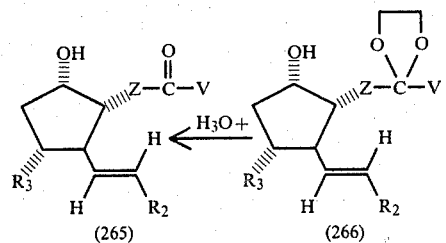

FLOWSHEET Z

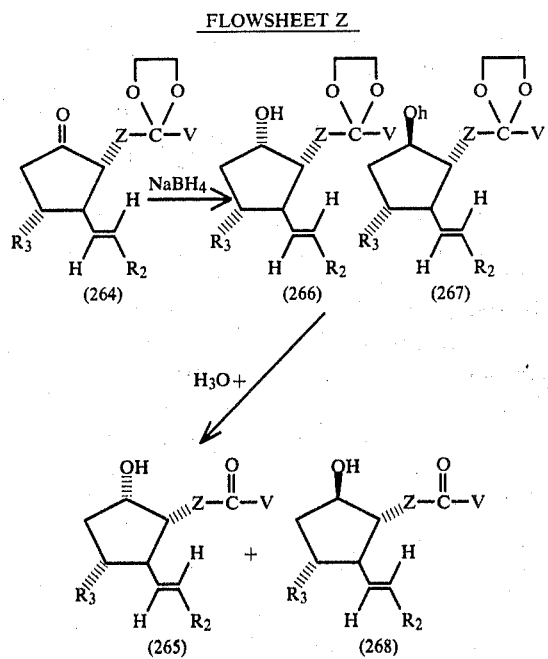

The 9β-hydroxy (PGFβ) compounds of this invention (267, 268) are prepared by performing a conjugate addition as described hereinabove. The partial hydrolyzed conjugate addition product (264) wherein Z, $R_2$ and V are as previously defined is dissolved in ethanol and an excess of sodium borohydride is added. The mixture is stirred for 8 hours, poured into water and the reduced products (266) and (267) are obtained. These can be deblocked with acetic acid-tetrahydrofuran-water 4:2:1 containing catalytic HCl at 40° C. to give the 9α-hydroxy (265) and 9β-hydroxy (268) compounds of this inventions which can be separated by silica gel chromatography. See Flowsheet Y hereinabove, wherein Z, R', $R_2$, $R_3$ and V are as defined hereinabove.

FLOWSHEET AA

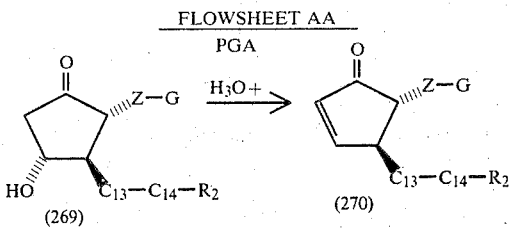

The PGA compounds of this invention (270) are prepared from the corresponding 11α-hydroxy analogs (269) by treatment of (269) with dilute hydrochloric acid in tetrahydrofuran for 2 to 4 days at room temperature as shown hereinabove in Flowsheet AA, wherein $C_{14}C_{14}$, $R_2$ and G are as hereinabove defined.

In accordance with the process of Bundy et al., J.A.C.S. 94, 2123 (1972) or E. J. Corey J.O.C. 38, 3187 (1973) which are incorporated by reference, the $PGA_1$, $PGA_o$ or $PGA_2$ series compounds of this invention may be converted to the corresponding $PGE_o$, $PGE_1$ or $PGE_2$ compound.

This conversion is accomplished by treating either the protected or unprotected PGA compounds (270) with alkaline hydrogen peroxide to provide a mixture of isomeric 10,11-epoxides which, without separation is reduced with chromous acetate in acidic acid or by aluminum amalgum to provide after hydrolysis (if necessary) and silica gel chromatography, the 11α-hydroxy-PGE compounds and a lesser amount of the corresponding 11β-epimer.

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various nonsteroidal anti-inflammatory agents (e.g., indomethacin, aspirin, and phenylbutazone), bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of the other novel compounds of this invention.

The novel compounds of this invention possess the pharmacological activity described below as associated with the appropriate above-described prostaglandin types.

The known PGE, $PGF_\alpha$, $PGF_\beta$, PGA and PGD compounds are all potent in causing multiple biological responses even at low doses. For example, $PGE_1$, $PGE_2$, $PGA_1$ and $PGA_2$ are extremely potent in causing vasodepression and smooth muscle stimulation, and also are potent as antilipolytic agents. For example, the 11-deoxy-PGE compounds of this invention are selective in that they are at most relatively weak stimulants of smooth muscle. A further advantage of these novel compounds should be in their increased stabilities and lengthened self-lives.

Therefore, each of these novel prostaglandin analogs of this invention should be more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, buccally, or rectally, in addition to the usual intravenous, instramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

$PGE_1$, $PGE_2$, $PGE_3$, dihydro-$PGE_1$, $PGF_\alpha$, $PGF_\beta$ and PGA compounds, their esters and pharmacologically acceptable salts, are extremely potent in causing various biological responses. For that reason, these compounds are useful for pharmacological purposes. See, for example, Bergstrome, et al., *Pharmacol. Rev.*, 20, 1 (1968), and references cited herein. A few of those biological responses are systemic arterial blood pressure lowering in the case of the PGA and PGE compounds as measured, for example, in anesthetized (sodium phenobarbital) pentolinium-treated rats with indwelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipoklytic activity as shown by antagonism of epinephrine-induced mobilization of free fatty acids or inhibition of the spontaneous release of glycerol from isolated rat fat pads; inhibition of gastric secretion in the case of PGE compounds, as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen, and in the case of the PGE and PGA compounds, stimulation of epidermal proliferation and keratinization, as shown when they are applied in culture to embryonic chick and rat skin segments.

Because of these biological responses, these known prostaglandins are useful to study, prevent, control, or alleviate a wide variety of disease and undesirable physiological conditions in birds and mammals including humans, useful domestic animals, pets, and zoological specimens, and in laboratory animals, e.g., mice, rats, rabbits, and monkeys.

For example, these compounds are useful in mammals, including man, as nasal decongestants. For this purpose, the compounds are used in a dose range of about 0.01 mg. to about 10 mg per ml of a pharmacologically suitable liquid vehicle or as an aerosol spray, both for topical application.

PGA, $PGF_\beta$ and PGE compounds are useful as hypotensive agents to reduce blood pressure in mammals including man. For this purpose, the $PGF_\beta$ compounds are administered by intravenous infusion at the rate of about 0.01 mg to about 40 mg per Kg of body weight per minute, or in a single dosage or multiple doses of about 25 mg to 2500 mg per Kg of body weight total per day. The PGE and PGA compounds are administered by intravenous infusion at the rate of about 0.01 to about 50 mg per Kg of body weight per minute, or in a single dose or multiple doses of about 25 to 2500 mg per Kg of body weight total per day.

The PGE, $PGF_\alpha$ and $PGF_\beta$ compounds are useful in place of oxytocin to induce labor in pregnant female animals, including humans, cows, sheep and pigs, at or near term or in pregnant animals with intrauterine death of the fetus from about 20 weeks to term. For this purpose, the PGF compound is infused intravenously at a dose of 0.01 mg to 50 mg per Kg of body weight per minute until or near the termination of the second stage of labor, i.e., expulsion of the fetus. Similarly, the PGE compound is infused intravenously at a dose of 0.01 to 50 mg per Kg of body weight per minute until or near the expulsion of the fetus. These compounds are especially useful when the female is one or more weeks postmature and natural labor has not started, or 12 to 60 hours after the membranes have ruptured and natural labor has not yet started.

The PGE, $PGF_\alpha$ and $PGF_\beta$ compounds are useful for controlling the reproductive cycle in ovulating female mammals, including humans and other animals. For that purpose, $PGF_{2\alpha}$, for example, is administered systemically at a dose level in the range of 0.01 mg to about 20 mg per Kg of body weight, advantageously during a span of time starting approxiately at the time of ovulation and ending approximately at the time of menses or just prior to menses. Likewise, a PGE compound is administered in the same fashion at a dose level of 0.01 mg to about 50 mg per Kg of body weight. Additionally, expulsion of an embryo or fetus is accomplished by similar administration of the compound during the first third or the second third of the normal mammalian gestation period. Accordingly, such compounds are useful as abortifacients. They are also useful for induction of menses during approximately the first two weeks of a missed menstrual period and thus, are useful as contraceptive anti-fertility agents.

11α-hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators for example, to relieve the symptoms of paralytic ileus, to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 mg per Kg of body weight per minute until the desired effect is obtained. Subsequent doses are given by intravenous, subcutaneous, or intramuscular injection or infusion during puerperium in the range of 0.01 to 2 mg per Kg of body weight per day, the exact dose depending on the age, weight, and condition of the patient or animal.

The novel PGA, PGE and $PGF_\beta$ of this invention are also useful as bronchodilators for the treatment of asthma and chronic bronchitis. As such they may be conveniently administered by inhalation of aerosol sprays prepared in a dose range of about 10μ g to about 10 mg/ml of a pharmacologically suitable liquid vehicle. Relative to the natural prostaglandins, the PGA and PGE compounds in particular have the significant advantage of inducing prolonged effects.

The PGE and PGA compounds are also useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 mg to about 500 mg per Kg of body weight per minute, or in a total daily dose by injection or infusion in the range of about 0.1 to about 20 mg per Kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE and PGA compounds also stimulate epidermal proliferation and keratinization, and in such a capacity are useful to promote and accelerate healing of skin which has been damaged, for example, by burns, wounds, abrasions or surgery. The Vassopressor action of the PGA compounds makes them particularly useful in speeding the adherence and growth of skin autografts, especially small, deep (Davies) grafts which are intended to cover skinless areas by subsequent outward growth rather than initially, and in retarding rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion cream, or ointment in combination with the usual pharmaceutically acceptable dilutents. In some instances, when there is substantial fluid loss as in the case of extensive burns or skin loss due to other causes, systemic administratin of PGE is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Illustrative of a wet dressing for topical application to second and/or third degree burns of skin area 5 to 25 square centimeters is the use of an isotonic aqueous solution containing one to 500 mg/ml of the PGA compound or several times that concentration of the PGE compound. Especially for topical use, these prostaglandins are useful in combination with antibiotics such as gentamycin, neomycin, polymyxin B, bacitracin, spectinomycin, and oxytetracycline; with other antibacterials such as mafenide hydrochloride, sulfadiazine, furazolium chloride, and nitrofurazone; and with corticoid steroids, such as hydrocortisone, prednisolone, methylprednisolone, and fluoroprednisolone; each of those being used in the combination at the usual concentration suitable for its use alone.

The PGA compounds and derivatives and salts thereof increase the flow of blood in the mammalian kidney, thereby increasing the volume and electrolyte content of the urine. For that reason, PGA compounds are useful in managing cases of renal disfunction, especially in cases of severely impaired renal blood flow, for example, the hepatorena syndrome and early kidney transplant rejection. In case of excessive or inappropriate antidiuretic hormone ADH vasopressin secretion, the diuretic effect of these compounds is even greater. In anephretic states, the vasopressin action of these compounds is especially useful.

The PGE compounds of this invention are also useful as topical vasodilators.

The $PGE_1$ compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The PGE compounds of the present invention exhibit the ability to inhibit platelet aggregation in vitro when tested by the following procedure.

Human protein rich plasma is incubated with modified Tyrode's solution in a proportion of 40–50% human protein rich plasma. The test compounds are added at varying concentrations and after 5 minutes incubation, an aggregating agent such as adenosine diphosphate or collagen is added. The change in optical density (light transmission) is monitored by eye and inhibition is recorded as a (−) or lack of inhibition is recorded as a (+). Test compounds are considered active if they inhibit adenosine diphosphate or collagen induced aggregation at a concentration of 0.025 mg/ml or less within 5–10 minutes.

The PGE compounds of this invention also have bronchodilator activity as determined in a test using dogs anesthetized, artificially ventilated and submitted to a continuous respiratory spasm induced by pilocarpine.

Mongrel dogs of either sex weighing between 5 and 10 kg are used. They are premedicated with morphine HCl by subcutaneous injection at 1.5 mg/Kg. An intravenous perfusion of 5% (W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/minute. The volume is adjusted according to the weight of the animal. [Kleinman and Radford, *J. Appl. Physiol.*, 19, 360 (1964)]. All the measurements are made with the dogs positioned supine in a heated, V-shaped table. Curarization is obtained by succinylcholine chloride using a starting injection of 3 mg/Kg lasting 3 minutes, followed by a continuous perfusion of 0.1 mg/Kg/minute.

The respiratory spasm is induced by a starting injection of 400 μg/Kg of pilocarpine HCl lasting 5 minutes. An increase or decrease in the dose of pilocarpine HCl may occur as a function of the observed effect on the airway's resistance. A 15 minute delay is observed before the start of a continuous perfusion of pilocarpine HCl at a dose of 4 μg/Kg/minute to maintain a constant spasm during the test.

A metallic cannula is inserted and fixed, after tracheotomy, into the upper part of the trachea. The two cephalic veins and the two femoral veins are catheterized to inject the various agents. The femoral artery is catheterized to measure the systemic blood pressure. An esophageal balloon (11 cm × 2.5 cm) is inserted into the lower third of the oesophagus to measure the endothoracic pressure. The measurement of air flow is made with a Fleish pneumotachograph connected to the tracheal tube.

The transpulmonary pressure is measured as follows: The tracheal cannula is equipped with a stainless steel axial tube (1.5 mm) which is closed at its distal end and projected 2.5 cm beyond the end of the cannula. Three holes with a diameter of one mm are pierced on this latter segment. This tube, which is used to measure the tracheal pressure, is connected to one of the two chambers of a Sanborn 267 B/C differential transducer. The other chamber is connected to the esophageal balloon by means of a polyethylene catheter of the same length and characteristics as the balloon's.

The airflow is measured from the Fleish pneumotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by subtracting from the electrical equivalent of the transpulmonary pressure, a voltage proportional to the flow so as to synchronize the pressure and volume signals on the oscilloscope (Mead and Whittenberger, *J. Appl. Physiol.*, 5,779 (1953)].

The value of the pulmonary elastance, expressed in cm of water/liter, is obtained by means of the same principle, i.e., an electrical signal proportioned to the volume is subtracted from the transpulmonary pressure signal, in order to optimize the pressure-flow loop on the oscilloscope.

The details of this method are described by Lulling, et al. [*Med. Pharmacol. Exp.*, 16, 481 (1967)].

The computing operations are carried out with an analogical computer which allows the direct reading, cycle to cycle, of the values of resistance and elastance.

The test compounds are administered by an Aerosol ® route. The micronebulizer of a Bird Mark 7 respirator is fitted on the metallic cannula just after the pneumotachograph. The "puff" of the test compound, in Aerosol ® is driven by a 2 Kg/cm$_2$ pressure, allowed into the micronebulizer just during one inspiration cycle. The micronebulizer is fitted on the respiratory tube only during the "puff." It is weighed just before and just after administration to determine the amount of test compound administered. Approximately 50 mg of the solution is administered to each dog. In accordance with the Pilocarpine Assay described herein, the compounds of this invention should exhibit bronchodilator activity.

The bronchodilator activity for representative compounds of this invention was determined in Guinea Pigs against bronchospasms elicited by intravenous injections of serotonin, histamine, and acetylcholine, by the Konzett procedure the details of which are those discussed by J. Lulling, P. Lievens, F. El Sayed and J. Prignot, *Arzeimittel-Forschung* 18, 995 (1968).

In the table which follows, bronchodilator activity for representative compounds of the invention against spasmogenic agents serotonin, histamine, and acetylcholine is expressed as an $ED_{50}$ determined from the results obtained with three logarithmic cumulative intravenous doses.

| | KONZETT DATA | | | |
|---|---|---|---|---|
| | | $ED_{50}$ Mg/kg | | |
| COMPOUND | POTENCY | SEROTONIN | HISTAMINE | ACETYLCHOLINE |
| dl - 1,9-dioxo-11α,16-dihydroxy-1-methoxymethyl-16α/β-methyl-5-cis,13-trans-prostadiene | 4 | $8 \times 10^{-3}$ | $4.7 \times 10^{-3}$ | $7.7 \times 10^{-3}$ |
| dl - 1,9-dioxo-11α,16-dihydroxy-1-methoxymethyl-16α/β-methyl-13-trans-prostene | 4 | $3.1 \times 10^{-3}$ | $1.2 \times 10^{-3}$ | $4.1 \times 10^{-3}$ |
| dl - 1,9-dioxo-11α,16-dihydroxy-1-methoxymethyl-16α/β-vinyl-13-trans-prostene | 5 | $1.5 \times 10^{-3}$ | $299 \times 10^{-6}$ | $384 \times 10^{-6}$ |
| dl - 1,9-dioxo-11α,16-dihydroxy-1-methoxymethyl-16α/β-ethynyl-13-trans-prostene | 4 | $3.2 \times 10^{-3}$ | $3.8 \times 10^{-3}$ | $16 \times 10^{-3}$ |
| dl - 1,9-dioxo-11α,15-dihydroxy-1-methoxymethyl-15α/β-vinyl-13-trans-prostene | 4 | $0.3 \times 10^{-3}$ | $250 \times 10^{-6}$ | $33 \times 10^{-3}$ |

-continued

KONZETT DATA

| COMPOUND | POTENCY | ED$_{50}$ Mg/kg | | |
|---|---|---|---|---|
| | | SEROTONIN | HISTAMINE | ACETYLCHOLINE |
| dl - 1,9-dioxo-11α,16-dihydroxy-1-phenoxymethyl-16α/β-methyl-13-trans-prostene | 2 | 838 × 10$^{-3}$ | 683 × 10$^{-3}$ | 629 × 10$^{-3}$ |
| dl - 1,9-dioxo-11α,15α-dihydroxy-1-(methyl methoxyacetyl)-13-trans-prostene | 3 | 6.7 × 10$^{-3}$ | 18.7 × 10$^{-3}$ | 12.9 × 10$^{-3}$ |
| dl - 1,9-dioxo-11α,16-dihydroxy-1-(methylthiomethyl)-16α/β vinyl-13-trans-prostene | 3 | 44 × 10$^{-3}$ | 35 × 10$^{-3}$ | 51 × 10$^{-3}$ |
| dl - 1,9-dioxo-11α,16-dihydroxy-1-(methyl methoxyacetyl)-16α/β vinyl-13-trans-prostene | 4 | 4.0 × 10$^{-3}$ | 2.9 × 10$^{-3}$ | 5.0 × 10$^{-3}$ |

DETAILED DESCRIPTION OF THE INVENTION

EXAMPLE 1

Preparation of ethyl 2,2-trimethylenehexanoate

To a stirred solution of 27.6 g of freshly distilled N-isopropylcyclohexylamine in 200 ml of dry tetrahydrofuran cooled to −78° C. is added at a fast rate 96 ml of 2.04 M n-butyllithium in hexane. To the resulting solution is added dropwise 25 g of ethyl cyclobutanecarboxylate. After 30 minutes the resulting solution is allowed to warm to ambient temperature, is transferred to a dropping funnel under nitrogen and is added dropwise over a period of 1¼ hours to a solution of 54 g of n-butyl iodide in 100 ml of dry dimethylsulfoxide maintaining the temperature at 16°–20° C. Stirring is continued for an additional 10 minutes. The separated salts are removed by filtration, the mother liquor is taken to a small volume and the resulting oil is diluted with hexanes. This solution is washed with 2% hydrochloric acid, saturated sodium chloride solution, and dried with anhydrous magnesium sulfate. The solvent is removed and the residual oil is distilled to give 14.6 g (41%) of product, bp 84°–87° C. (10 mm).

EXAMPLE 2

Preparation of ethyl 2,2-tetramethylenehexanoate

In the manner described in Example 1, treatment of the lithium salt of ethyl cyclopentanecarboxylate with n-butyl iodide furnishes the subject product.

EXAMPLE 3

Preparation of 2,2-trimethylenehexan-1-ol

To a stirred solution of 20 g of ethyl 2,2-trimethylenehexaonate (Example 1) in 100 ml of dry toluene, in an argon atmosphere and cooled in an ice bath, is added dropwise 250 ml (2 molar equivalents) of 0.89 M diisobutlaluminum hydride in toluene. The resulting solution is stirred at ambient temperature for 2 hours and then poured into excess iced 5% hydrochloric acid. The organic phase is separated and washed with 5% hydrochloric acid, saturated sodium chloride solution, dried with anhydrous magnesium sulfate and taken to dryness to give 14.8 g (96%) of oil; bp 92°–93° C. (10 mm).

EXAMPLE 4

Preparation of 2,2-tetramethylenehexan-1-ol

In the manner described in Example 3, treatment of ethyl 2,2-tetramethylenehexanoate (Example 2) with 0.89 molar diisobutylaliminum hydride furnishes the subject product.

EXAMPLE 5

Preparation of 2,2-trimethylenehexaldehyde

Chromium trioxide (61.5 g), dried in a vacuum desiccator over phosphorous pentoxide, is added to an ice cold solution of 97 g of dry pyridine in one liter of dry methylene chloride. The deep red suspension is stirred for 15 minutes at 0° C. and then for 45 minutes at ambient temperature. A solution of 14.5 g of 2,2-trimethylenehexanol-1 (Example 3) in 55 ml of methylene chloride is added all at once to the suspension. A black tarry deposit is formed immediately. After stirring at ambient temperature for 15 minutes the solution is decanted from the tarry deposit which is then triturated four times with small portions of methylene chloride. The combined extracts are washed twice with ice cold 5% sodium hydroxide, ice cold 5% hydrochloric acid and finally with saturated sodium chloride solution, dried with magnesium sulfate and taken to dryness. Distillation gives 12.9 g of product; bp 69° C. (11 mm).

EXAMPLE 6

Preparation of 2,2-tetramethylenehexaldehyde

Oxidation of 2,2-tetramethylenehexan-1ol (Example 4) with chromium trioxide-pyridine complex in the manner described in Example 5 furnishes the subject product.

EXAMPLE 7

Preparation of 4,4-trimethylene-1-octyn-3-ol

To a solution of lithium acetylide-ethylenediamine complex (9.4 g) in 90 ml of dry dimethylsulfoxide, cooled in an ice bath, is added 12.94 g of 2,2-trimethylenehexaldehyde (Example 5) in 10 ml of dimethylsulfoxide dropwise, at such at rate that the temperature is maintained at 20°–25° C. The solution is stirred at ambient temperature for 12 hours and then poured into a mixture of ice cold 2% hydrochloric acid and ether. The ether layer is separated and the aqueous phase is extracted with ether. The combined ether extracts are washed with saturated sodium chloride solution, dried with anhydrous magnesium sulfate and taken to dryness. Distillation provides 13.53 g of product; bp 108°–109° C. (13 mm).

EXAMPLE 8

Preparation of 4,4-tetramethylene-1-octyn-3-ol

Treatment of 2,2-tetramethylenehexaldehyde (Example 6) with lithium acetylide-ethylenediamine complex in dimethylsulfoxide in the manner described in Example 4 is productive of the subject compound.

EXAMPLE 9

Preparation of 4,4-trimethylene-3-trimethylsilyloxy-1-octyne

To a stirred solution of 5.3 g of 4,4-trimethylene-1-octyn-3-ol (Example 7) and 5.42 g of imidazole in 32 ml of dry dimethylformamide, cooled in an ice bath under argon atmosphere is added 4.35 g of chlorotrimethylsilane. After stirring at 0° C. for 15 minutes, the solution is stirred at ambient temperature for 18 hours and then poured into 200 ml of hexanes. The solution is washed twice with ice cold water, saturated sodium chloride solution, dried with anhydrous magnesium sulfate and taken to dryness. Distillation furnishes 6.02 g (80%) of colorless oil; bp 110°-112 C. (14 mm).

EXAMPLE 10

Preparation of 4,4-tetramethylene-3-trimethylsilyloxy-1-octyne

Treatment of 4,4-tetramethylene-1-octyn-3-ol (Example 8) with chlorotrimethylsilane in dimethylformamide containing imidazole as described in Example 5 furnishes the subject product.

EXAMPLE 11

Preparation of 1-iodo-4,4-trimethylene-3-trimethylsilyloxy-1-octyne

To a solution of 25 g of 4,4-trimethylene-3-trimethylsilyloxy-1-octyne (Example 9), stirred under argon atmosphere at −78° C., is added dropwise 93 ml of 2.3 M n-butyllithium in hexane at a rate to maintain the temperature below −40° C. After stirring for 40 minutes, a solution of iodine is allowed to warm to ambient temperature and 10% aqueous sodium thiosulfate solution is added until the purple color is removed. The organic phase is washed with dilute aqueous sodium thiosulfate solution, saturated sodium chloride solution, dried with anhydrous sodium sulfate and taken to dryness to afford the subject product as an oil.

EXAMPLE 12

Preparation of 1-iodo-4,4-trimethylene-3-trimethylsilyloxy-1-cis-octene

To a solution of 30 g of 1-iodo-4,4-trimethylene-3-trimethylsilyloxy-1-octyne (Example 10) in 100 ml of methanol, under argon atmosphere is added 54 g of potassium azodicarboxylate [J. Thiele, Annalen der Chemie, 271, 127 (1892)] to this solution is added dropwise 45 ml of acetic acid over a period of about 2 hours. The solids are removed by filtration and the mother liquor is reduced to a small volume; diluted with water and extracted with ether. The ether is evaporated and the residual oil is stirred with 250 ml of 1 M sodium bicarbonate solution. The solution is extracted several times with ether and the combined extracts are washed with saturated sodium chloride solution, dried with anhydrous sodium sulfate and taken to dryness to furnish the subject product as an oil.

EXAMPLE 13

Preparation of 1-iodo-4,4-trimethylene-3-trimethylsilyloxy-1-trans-octene

To a mixture of 4.76 g of sodiumborohydride and 23.6 g of 2-methyl-2-butene in 220 ml of dry tetrahydrofuran at −5° C. is added dropwise 23.8 g of freshly distilled borontrifluoride etherate. The resulting mixture is stirred at −5° C. to −0° C. for 2 hours and to it is added dropwise a solution of 20 g of 4,4-trimethylene-3-trimethylsilyloxy-1-octyne (Example 12) in 20 ml of dry tetrahydrofuran. The resulting mixture is stirred at ambient temperature for 2½ hours. The mixture is then cooled to −5° C. and there is added 44 g of trimethylene oxide portionwise over a period of 20 minutes, maintaining the temperature at 15°-20° C. The mixture is stirred at ambient temperature for 2 hours and then poured simultaneously, with a solution of 119 g of iodine in 290 ml of tetrahydrofuran, into 1490 ml of 15% aqueous sodium hydroxide solution. After stirring for 30 minutes the organic phase is separated and the aqueous phase is extracted with ether. The combined organic phase is washed with 5% aqueous sodium thiosulfate solution, saturated sodium chloride solution, dried with anhydrous magnesium sulfate and taken to dryness to give 27 g of oily material. Chromatography on 135 g of florisil and eluting with 500 ml of hexanes furnishes 24 g of oily product which is shown to be contaminated with starting material and iodoform by infrared and thin layer chromatography. The material is purified by removing the trimethylsilyl group in the following manner. The crude product is dissolved in 350 ml of acetic acid-tetrahydrofuran-water (4:2:1) by stirring at ambient temperature for 5 minutes. The solvent is removed under reduced pressure and the residual oil containing mainly 1-iodo-3-hydroxy-4,4-trimethylene-1-trans-octene is applied to a 2" (flat) dry column containing 1200 g of Woelm silica gel. The column is developed with benzene, cut into one-inch segments and each segment is eluted with chloroform. Combination of the appropriate fractions affords 300 mg of iodomethane, 2.8 g of 4,4-trimethylene-1-octyne-3-ol, and 11.6 g of 1-iodo-3-hydroxy-4,4-trimethylene-1-trans-octene.

Silylation of this material in the manner described above followed by distillation of the residual oil furnishes 13 g of pure product; bp 83°-84° C. (0.2 mm).

EXAMPLE 14

Preparation of 1-iodo-4,4-tetramethylene-3-trimethylsilyloxy-1-trans-octene

Treatment of 4,4-tetramethylene-3-trimethylsilyloxy-1-octene (Example 10) in the manner described in Example 13 furnishes the subject product.

EXAMPLES 15-20

Treatment of the lithium salt of ethyl cyclobutanecarboxylate with the alkyl halides listed in Table 1 below by the procedure described in Example 1 furnishes the 2,2-trimethylene esters of the table.

TABLE 1

| Example | Alkyl Halides | Product 2,2-Trimethylene esters |
|---|---|---|
| 15 | propyl iodide | ethyl 2,2-trimethylenepentanoate |
| 16 | amyl iodide | ethyl 2,2-trimethyleneheptanoate |
| 17 | hexyl iodide | ethyl 2,2-trimethyleneoctanoate |

TABLE 1-continued

| Example | Alkyl Halides | Product 2,2-Trimethylene esters |
|---|---|---|
| 18 | benzyl iodide | ethyl 2,2-trimethylene-3-phenylpropionate |
| 19 | 2-cyclopentyl-1-ethyl bromide | ethyl 2,2-trimethylene-4-cyclopentylbutyrate |
| 20 | 1-chloro-2-butyne | ethyl 2,2-trimethylene-4-hexynoate |

EXAMPLES 21–27

Reduction of the various esters listed in Table 2 below with diisobutylaluminum hydride all in the manner described in Example 3 above is productive of the alcohols of the table.

TABLE 2

| Example | Starting Esters of Example | Product Alcohols |
|---|---|---|
| 21 | 15 | 2,2-trimethylenepentan-1-ol |
| 22 | 16 | 2,2-trimethyleneheptan-1-ol |
| 23 | 17 | 2,2-trimethyleneoctan-1-ol |
| 24 | 18 | 2,2-trimethylene-3-phenylpropan-1-ol |
| 25 | 19 | 2,2-trimethylene-4-cyclopentylbutan-1-ol |
| 26 | 20 | 2,2-trimethylene-4-hexyn-1-ol |
| 27 | 55 | 2,2-trimethylene-4-cis-hexan-1-ol |

EXAMPLES 28–34

Oxidation of the alcohols listed in Table 3 below with chromium trioxide-pyridine complex by the procedure described in Example 5 above furnishes the corresponding aldehydes of the table.

TABLE 3

| Example | Starting Alcohols of Example | Product 2,2-Trimethylenealdehydes |
|---|---|---|
| 28 | 21 | 2,2-trimethylenevaleraldehyde |
| 29 | 22 | 2,2-trimethyleneheptaldehyde |
| 30 | 23 | 2,2-trimethyleneoctaldehyde |
| 31 | 24 | 2,2-trimethylene-3-phenylpropionylaldehyde |
| 32 | 25 | 2,2-trimethylene-4-cyclopentylbutyraldehyde |
| 33 | 26 | 2,2-trimethylenehex-4-yn-1-al |
| 34 | 27 | 2,2-trimethylene-4-cis-hexane-1-al |

EXAMPLES 35–41

Treatment of the various aldehydes listed below in Table 4 with lithium acetylide-ethylenediamine complex in the manner described in Example 7 furnishes the hydroxyacetylenes of the table.

TABLE 4

| Example | Starting Aldehydes of Example | Product Hydroxyacetylenes |
|---|---|---|
| 35 | 28 | 4,4-trimethylene-1-heptyn-3-ol |
| 36 | 29 | 4,4-trimethylene-1-nonyn-3-ol |
| 37 | 30 | 4,4-trimethylene-1-decyn-3-ol |
| 38 | 31 | 4,4-trimethylene-5-phenyl-1-pentyn-3-ol |
| 39 | 32 | 4,4-trimethylene-6-cyclopentyl-1-hexyn-3-ol |
| 40 | 33 | 4,4-trimethylene-1,6-octadiyn-3-ol |
| 41 | 34 | 4,4-trimethylene-4-cis-hexene-3-ol |

EXAMPLES 42–48

Treatment of the various alcohols listed below in Table 5 with chlorotrimethylsilane in the manner described in Example 9 furnishes the corresponding trimethylsilyloxy acetylenes of the table.

TABLE 5

| Example | Starting Alcohols of Example | Product Trimethylsilyloxyacetylenes |
|---|---|---|
| 42 | 35 | 4,4-trimethylene-3-trimethylsilyloxy-1-heptyne |
| 43 | 36 | 4,4-trimethylene-3-trimethylsilyloxy-1-nonyne |
| 44 | 37 | 4,4-trimethylene-3-trimethylsilyloxy-1-decyne |
| 45 | 38 | 4,4-trimethylene-3-trimethylsilyloxy-5-phenyl-1-pentyne |
| 46 | 39 | 4,4-trimethylene-3-trimethylsilyloxy-6-cyclopentyl-1-hexyne |
| 47 | 40 | 4,4-trimethylene-3-trimethylsilyloxy-1,6-octadiyne |
| 48 | 41 | 4-4-trimethylene-3-trimethylsilyloxy-4-cis octene-1-yne |

EXAMPLES 49–54

In the manner described in Example 13 treatment of the various acetylenes of Table 6 below with disiamylborane, made in situ from sodium borohydride and 2-methyl-2-butene, followed by oxidation of the so formed organoborane with trimethylamine oxide followed by treatment of this product with iodine and sodium hydroxide furnishes the trimethylsilyliodovinylcarbinols of the table.

TABLE 6

| Example | Starting Acetylenes of Example | Product Trimethylsilylvinylcarbinols |
|---|---|---|
| 49 | 42 | 1-iodo-4,4-trimethylene-3-trimethylsilyloxy-1-trans-heptene |
| 50 | 43 | 1-iodo-4,4-trimethylene-3-trimethylsilyloxy-1-trans-nonene |
| 51 | 44 | 1-iodo-4,4-trimethylene-3-trimethylsilyloxy-1-trans-decene |
| 52 | 45 | 1-iodo-4,4-trimethylene-3-trimethylsilyloxy-5-phenyl-1-trans-pentene |
| 53 | 46 | 1-iodo-4,4-trimethylene-3-trimethylsilyloxy-6-cyclopentyl-1-trans-hexene |
| 54 | 47 | 1-iodo-4,4-trimethylene-3-trimethylsilyloxy-1-trans-octen-6-yne |

EXAMPLE 55

Preparation of ethyl 2,2-trimethylene-4-cis-hexenoate

A solution of 5 g of ethyl 2,2-trimethylene-4-hexynoate (Example 20) in 40 ml of dry pyridine is hydrogenated in a Parr apparatus using 600 mg of 5% palladium or barium sulfate. After one hour when hydrogen uptake is complete, the solution is filtered through celite and the mother liquor is taken to dryness to furnish 4 g of product as an oil.

EXAMPLE 56

Preparation of 3-tetrahyropyranyloxy-1-propyne

To a stirred solution of 112 g (2.0 mol.) of 3-hydroxy-1-propyne and 260 g (3.0 mol.) of dihydropyran in 1.20 liters of methylene chloride cooled to 0° C. in an ice bath, is added a solution of 20 mg of para-toluenesulfonic acid in 100 ml of methylene chloride, dropwise. The reaction mixture is stirred at 0° C. for one-half hour, and at ambient temperature for one hour. It is then poured into 200 ml of a 5solution of sodium bicarbonate, the organic phase is separated, the aqueousphase extracted with 100 ml of methylene chloride, the combined organic phases washed with 100 ml of a solution of brine, dried over sodium sulfate, and evaporated under vacuum (12 mm) at 45° C. to give 300 g of crude product, which is purified by fractional distillation, bp 71°–73° C. (14 mm) to yield 250 g (89%) of a liquid.

EXAMPLE 57

Preparation of 3-tetrahydropyranyloxy-1-trimethylsilyl-1-propyne

To a stirred −20° C. solution of 125 g (0.89 mol.) of 3-tetrahydropyranyloxy-1-propyne (Example 56) in 450 ml of ether, under a nitrogen atmosphere, is added dropwise, over one hour, a solution of 45 ml (0.89 mol.) of 2.0 N n-butyllithium in hexane. After 150 ml of dry ether is added and the mixture stirred at −20° C. for 30 minutes, a solution of 98 g (0.98 mol.) of trimethylchlorosilane in 73 ml of ether is added dropwise. Stirring is continued for 30 minutes at −20° C. and at ambient temperature for 18 hours. The reaction mixture is again cooled to −20° C., and a solution of 90 ml of acetic acid in 300 ml of ether is added dropwise, followed by 90 ml of water. It is then diluted with 500 ml of water, and extracted 3 times with 300 ml of 5% sodium bicarbonate solution. The organic phase is separated, washed with 500 ml of a saturated brine solution, dried over sodium sulfate, and evaporated at 40° C. under vacuum (12 mm.). The crude product is fractionally distilled, bp 120°–125° C. (18 mm.), to yield 120 g of an oil.

EXAMPLE 58

Preparation of d,l-erythro-3-tetrahydropyranyloxy-4-hydroxy-1-trimethylsilyl-1-octyne To a stirred −78° C. solution of 62 ml (124 mmol.) of a 2.0 M solution of n-butyllithium in hexane and 50 ml of dry tetrahydrofuran, under a nitrogen atmosphere is added dropwise, a solution of 24 g (113 mmol.) of 3-tetrahydropyranyloxy-1-trimethylsilyl-1-propyne (Example 57) in 35 ml of tetrahydrofuran. This red solution is stirred one hour at −78° C., then a freshly prepared solution of zinc iodide (135 mmol.) in 125 ml of tetrahydrofuran [F. Mercier, R. Epstein, and S. Holand, Bull. Soc. Chim. France, 2, 690 (1972)] is added dropwise at −78° C., until the mixture turns yellow. After stirring an additional hour at −78° C., a solution of 21 g (250 mmol.) of n-valeraldehyde in 35 ml of tetrahydrofuran is added dropwise and the reaction mixture stirred for one hour at −78° C. and 18 hours at ambient temperature. It is then cooled to 0° C. and a solution of 12 ml of acetic acid in 65 ml of ether is added dropwise, followed by 75 ml of ice-water. The phases are separated and the aqueous phase is extracted twice with ether. The combined organic phases are washed 3 times with saturated sodium bicarbonate solution, until the last wash is basic, then with a saturated brine solution, dried over sodium sulfate, and evaporated to give 40 g of yellow oil. The crude product may be purified on a 4"×40" dry column of alumina, and eluted with chloroform. I.R.: neat; 3550 (OH), 2200 (C≡C), 840, 750 [(CH$_3$)$_3$Si], cm$^{-1}$.

EXAMPLE 59

Preparation of d,l-erythro-3,4-dihydroxy-1-trimethylsilyl-1-octyne

A solution of 19.6 g (0.066 mol) of d,l-erythro-3-tetrahydropyranyloxy-4-hydroxy-1-trimethylsilyl-1-octyne (Example 58) in 55.5 ml of ethanol, 22.2 ml of acetic acid, and 22.2 ml of water is heated at reflux for 3 hours. The cooled mixture is taken to dryness and evaporated twice with benzene. The residue is taken up in hexane, washed 3 times with saturated potassium bicarbonate solution, dried with magnesium sulfate, and evaporated to give 17.0 g of crude product IR: neat, 3500–3400, broad (two OH).

EXAMPLE 60

Preparation of d,l-erythro-3,4-isopropylidenedioxy-1-trimethylsilyl-1-octyne

To a stirred solution of 17.0 g (79.5 mmol.) of crude d,l-erythro-15,16-dihydroxy-1-trimethylsilyl-1-octyne (Example 59) is 33.6 ml of 2,2-dimethoxy propane at 0° C., is added 0.05 ml of 60% perchloric acid. After 30 minutes at ambient temperature, the mixture is shaken with 50 ml of hexane and 25 ml of saturated sodium bicarbonate solution. The hexane phase is separated, dried with magnesium sulfate, and evaporated to give 19.0 g of crude product.

EXAMPLE 61

Preparation of d,l-erythro-3,4-isopropylidenedioxy-1-octyne

A mixture of 19.0 g (75.0 mmol.) of crude d,l-erythro-3,4-isopropylidenedioxy-1-trimethylsilyl-1-octyne (Example 60) with 95 ml of methanol and 3.0 of potassium carbonate is refluxed for one hour. The mixture is cooled and evaporated at 50° C. (13 mm), taken up in 250 ml of benzene, and washed with 100 ml of water. The water is saturated with salt, the organic phase separated, dried with magnesium sulfate, and evaporated to give 12 g of crude product. Fractional distillation yields 7.0 g of the subject compound as a colorless oil, bp 103°–106° C. (13 mm).

IR: neat; 3300 sharp (H—C≡C), 2100, (C≡C), 780 (erythro configuration) cm$^{-1}$ nmr: $\delta_{TMS}^{CDCl_3}$ is; 4.75 (dd., 1, C≡C—C$\underline{H}$—CH, J=2Hz, J=5Hz), 4.10 (m, 1, C≡C—CH—C$\underline{H}$—CH$_2$, 2.5 (d, 1, $\underline{H}$—C C—CH), 1.9–1.2 (m, 14, alkyl), 0.90 (m, 3H, CH$_2$C$\underline{H}_3$).

EXAMPLE 62

Preparation of d,l-erythro-1-iodo-3,4-isopropylidenedioxy-trans-1-octene

To a stirred 0° C. slurry of 0.852 g (0.023 mol.) of sodium borohydride and 4.21 g (0.060 mol.) of 2-methyl-2-butene in 40 ml of dry tetrahydrofuran, under an argon atmosphere, is added dropwise 4.26 g (0.030 mol.) of boron trifluoride etherate complex. A solution of 2.73 g. (0.015 mol.) of d,l-erythro-3,4-isopropylidenedioxy-1-octyne (Example 61) in 5 ml of tetrahydrofuran is added dropwise, the ice bath removed, and the mixture allowed to stir at ambient temperature for two hours. It is then cooled again to 0° C., and 2.88 g (0.105 mol.) of dry trimethylamine oxide is added in portions over 30 minutes. After stirring 3 hours at room temperature, this mixture is poured simultaneously with a 0° C. solution of 2.13 g of iodine in 53 ml of tetrahydrofuran into 766 ml of a 0° C. 15% solution of sodium hydroxide in water and the whole stirred vigorously at 0° C. for 45 minutes. The organic phase is separated, the aqueous phase is extracted twice with ether, the combined organic phases are washed with a 5% solution of sodium thiosulfate, dried with magnesium sulfate, and evaporated. The crude product is chromatographed on a 2" by 40" dry column of silica gel, be eluting with chloroform, to yield 1.2 g (25%) of a yellow oil.

IR: neat; 1599 sharp, 945 (C=C), cm$^{-1}$.

EXAMPLE 63

Preparation of d,l-erythro-3-tetrahydropyranyloxy-4-acetyloxy-1-trimethylsilyl-1-octyne A solution of 3.0 g (13.2 mmol.) of d,l-erythro-3-tetrahydropyranyloxy-4-hydroxy-1-trimethylsilyl-1-octyne is heated at 100° C. for 15 hours with 3 ml of acetic anhydride and 10 ml of pyridien. The mixture is evaporated to dryness, dissolved in ether, washed with sodium bicarbonate solution and water. The organic phase is dried over magnesium sulfate and evaporated to give 2.5 g of the subject compound as an oil IR: neat; 2200 (C C), 1730 (C=O), 830, 760 [(CH$_3$)$_3$Si], cm$^{-1}$.

EXAMPLE 64

Preparation of d,l-erythro-3-hydroxy-4-acetyloxy-1-trimethylsilyl-1-octyne

In the manner of Example 59, 2.5 g (7.4 mmol.) of d,l-erythro-3-tetrahydropyranyloxy-4-acetyloxy-1-trimethylsilyl-1-octyne (Example 63) in a solution of ethanol, acetic acid, and water is heated at 100° C. for 3 hours. After workup, the crude product is chromatographed on a $\frac{7}{8}''\times 22''$ dry column of silica gel, and eluted with chloroform to give 1.0 g of a yellow oil.

IR: neat; 3500 (OH), 1730 (C=O), cm$^{-1}$.

EXAMPLE 65

Preparation of d,l-erythro-3-paratoluenesulfonyloxy-4-acetyloxy-1-trimethylsilyl-1-octyne To a solution of 7.5 g (41.0 mmol.) of d,l-erythro-3-hydroxy-4-acetyloxy-1-trimethylsilyl-1-octyne (Example 64) in 41 ml of dry pyridine is added 11.0 g (58 mmol.) of paratoluenesulfonyl chloride and the resulting solution is stirred at 25° C. for 15 hours. The mixture is then warmed at 40° C. for one hour, and after cooling, partitioned between 500 ml of diethyl ether and 100 ml of 1.0 N hydrochloric acid. The organic phase is washed three times with 100 ml of 1.0 N hydrochloric acid, once with dilute sodium bicarbonate solution, dried over magnesium sulfate, and evaporated under reduced pressure to give an oil. The crude product is purified on a $2''\times 24''$ dry column of silica gel, and eluted with chloroform to yield a yellow oil.

IR: neat; 1730 (C=O), 1595 (aromatic) cm$^{-1}$.

EXAMPLE 66

Preparation of d,l-threo-3-hydroxy-4-acetyloxy-1-trimethylsilyl-1-octyne

A mixture of 15.5 g (39.0 mmol.) of d,l-erythro-3-para-toluenesulfonyloxy-4-acetyloxy-1-trimethylsilyl-1-octyne (Example 65), 5.0 g of calcium carbonate, 25 ml of water and 250 ml of tetrahydrofuran is refluxed with stirring for 4 days. The mixture is cooled, 100 ml of water added and the organic phase separated. The aqueous phase is extracted with ether, the combined organic phases dried with magnesium sulfate, and evaporated. The crude product is chromatographed on a $3''\times 30''$ dry column of silica gel, and eluted with chloroform to give 7.0 g of an oil.

IR: neat; 3500, (OH), cm$^{-1}$.

EXAMPLE 67

Preparation of d,l-threo-3,4-dihydroxy-1-octyne

A solution of 7.0 g (28 mmol.) of d,l-threo-3-hydroxy-4-acetyloxy-1-trimethylsilyl-1-octyne (Example 66) in 50 ml of methanol is stirred at room temperature for 24 hours with a solution of 6.3 g (112 mmol.) of potassium hydroxide in 50 ml of water. The mixture is extracted twice with hexane, washed with 0.5 M hydrochloric acid, brine, and dried with magnesium sulfate. Afer evaporation, the subject compound is obtained as a yellow oil.

IR: neat, 2500 broad (2-OH), cm$^{-1}$.

EXAMPLE 68

Preparation of d,l-threo-3,4-isopropylidenedioxy-1-octyne

In the manner of Example 60, treatment of a solution of d,l-threo-3,4-dihydroxy-1-octyne (Example 67) in dimethoxypropane with 60% perchloric acid, and fractional distillation (12 mm) is productive of the subject compound as a colorless oil, containing 15% of d,l-erythro-3,4-isopropylidenedioxy-1-octyne (Example 60), as an impurity.

IR: neat; 810 (threo configuration).

nmr: $\delta_{TMS}^{CDCl_3}$ is; 4.2 (dd, 1, —C≡C—C$\underline{H}$—, J's—2H$_z$ 6H$_2$), 4.1-3.9 (m, 1, —C≡C—CH—C$\underline{H}$—CH$_2$—), 2.5 (d, 1, H—C≡C—, J=2H$_z$), 1.9-1.2 (m, 14, alkyl), 0.90 (m, 3H, CH$_2$—C$\underline{H}_3$).

EXAMPLE 69

Preparation of d,l-threo-1-iodo-3,4-isopropylidenedioxy-trans-1-octene

In the manner of Example 62, d,l-threo-3,4-isopropylidenedioxy-trans-1-octyne (Example 68) is treated successively with disiamylborane, trimethylamine oxide, iodine, and sodium hydroxide to give the subject compound.

EXAMPLE 70

Preparation of d,l-erythro-3-tetrahydropyranyloxy-4-hydroxy-1-octyne

Alakline hydrolysis of d,l-erythro-3-tetrahydropyranyloxy-4-hydroxy-1-trimethylsilyl-1-octyne (Example 58) by the procedure of Example 61 is productive of the subject compound.

EXAMPLE 71

Preparation of d,l-erythro-3-tetrahydropyranyloxy-4-methoxy-1-octyne

To a stirred slurry of 6.0 g (150 mmol.) of a 60% oil dispersion of sodium hydride and 96 g of iodomethane, under an argon atmosphere, is added 700 ml of dry tetrahydrofuran. The stirred mixture is cooled to −20° C. and a solution of 30 g (133 mmol.) of d,l-erythro-3-tetrahydropyranyloxy-4-hydroxy-1-octyne (Example 70), is added dropwise, followed by 0.1 ml of methanol.

The mixture is stirred at ambient temperature for 24 hours, 10 ml of methanol is added, and evaporated. The residue is taken up in ether, washed 3 times with water, dried over magnesium sulfate, and evaporated. The crude product is purified by fractional distillation to yield 16.3 g of a colorless oil, bp 137°–140° C. (12 mm).

EXAMPLE 72

Preparation of d,l-erythro-3-tetrahydropyranyloxy-4-methoxy-1-iodo-trans-1-octen In the manner of Example 62, 1.20 g (5.0 mmol.) of d,l-erythro-3-tetrahydropyranyloxy-4-methoxy-1-octyne (Example 71) is treated successively with disiamylborane, trimethylamine oxide, iodine, and sodium hydroxide. Chromatography on a 2"×36" dry column of silica gel and elution with chloroform is productive of 0.80 g (40%) of the subject compound as an oil.

nmr: $\delta_{TMG}^{CDCl_3}$ is; 7.9–6.1 (m, 2, HC=CH), 4.9–4.6 (2m, 2, c=C—CH, O—CH—O), 4.3–4.0 (m, 1, c=c— CH—C$\underline{H}$—CH$_2$), 3.9–3.0 (m, 6, C$\underline{H}_2$—O—C$\underline{H}$, OCH$_3$), 1.8–1.2 (m, 12H, alkyl), 0.9 (m, 3, —CH$_3$).

EXAMPLE 73

Preparation of d,l-erythro-3-hydroxy-4-methoxy-1-iodo-trans-1-octene

A solution of 3.10 g (8.24 mmol.) of d,l-erythro-3-tetrahydropyranyloxy-4-methoxy-1-iodo-trans-1-octene (Example 72) in 60 ml of acetic acid, 30 ml of tetrahydrofuran, and 15 ml of water is stirred at ambient temperature for 18 hours. It is then evaporated at 70° C. under high vacuum (1.0 mm), and three times with 40 ml of toluene to give the crude product as an oil.

EXAMPLE 74

Preparation of d,l-erythro-3-trimethylsilyloxy-4-methoxy-1-iodo-trans-1-octene

To a stirred solution of 3.0 g (10.2 mmol.) of d,l-erythro-3-hydroxy-4-methoxy-1-iodo-trans-1-octene (Example 73) in 11.0 ml of dry dimethylformamide and 1.90 g (28.0 mmol.) of imidazole cooled to 0° C. is added, dropwise, 1.35 g (12.5 mmol.) of trimethylsilyl chloride. The reaction mixture is stirred a further 4 hours at room temperature. It is then poured into a mixture of 100 ml of hexane and 25 ml of water, the organic phase is separated, washed twice with water once with a solution of saturated sodium chloride, dried over magnesium sulfate, and evaporated. The crude product is purified by fractional distillation to yield 2.0 g of a colorless oil, bp 82°–83° C. (0.3 mm).

IR: neat;

H
1602 sharp (C=C),
        H
840, 750 broad [(CH$_3$)$_3$Si—], cm$^{-1}$.

EXAMPLE 75

Preparation of d,l-erythro-1-iodo-3,4-dihydroxy-trans-1-octene

A solution of 1.40 g (4.50 mmol.) of d,l-erythro-1-iodo-3,4-isopropylidenedioxy-trans-1-octene (Example 62) in 30 ml of acetic acid, 10 ml of tetrahydrofuran and 10 ml of water is stirred and heated at 50° C. for five hours. It is then evaporated at 40° C. under high vacuum (1.0 mm), and twice more with 50 ml of benzene. Crystallization from 10 ml of chloroform at 0° C. is productive of 700 mg of the white crystalline subject product.

EXAMPLE 76

Preparation of d,l-erythro-1-iodo-3,4-bis-trimethylsilyloxy-trans-1-octene

To a stirred solution of 700 mg (2.40 mmol.) of d,l-erythro-1-iodo-3,4-dihydroxy-trans-1-octene (Example 75) and 800 mg (12.0 mmol.) of imidazole, in 10 ml of dry dimethylformamide at 0° C. is added dropwise 1.20 g (11.0 mmol.) of trimethylchlorosilane. The ice bath is removed, and the mixture is stirred and heated at 50° C. for five hours. It is then cooled, shaken with 50 ml of hexane and 50 ml of water, the organic layer separated and washed with 15 ml of 0.5 M hydrochloric acid, 15 ml of a saturated solution of sodium bicarbonate, dried with magnesium sulfate, and evaporated. This crude product is fractionally distilled, bp 90°–92° C. (0.40 mm) to yield 250 mg of a colorless oil.

EXAMPLE 77

Preparation of d,l-erythro-3-trimethylsilyloxy-4-ethoxy-1-iodo-trans-1-octene

Following the procedure of Example 71, ethylation using iodo ethane of d,l-erythro-3-tetrahydropyranyloxy-4-hydroxy-1-octyne for a period of 22 hours is productive of the corresponding d,l-erythro-3-tetrahydropyranyloxy-4-ethoxy-1-octyne. This intermediate is converted to d,l-erythro-3-tetrahydropyranyloxy-4-ethoxy-1-iodo-trans-1-octene when treated successively with disiamylborane, trimethylamine oxide iodine, and sodium hydroxide solution after the procedure of Example 72. Acid hydrolysis by the method of Example 18 to d,l-erythro-3-hydroxy-4-ethoxy-1-iodo-trans-1-octene, followed by treatment with chlorotrimethylsilane and imidazole in dimethylformamide using the procedure of Example 74, and subsequent distillation, is productive of the subject compound.

EXAMPLES 78–82

By the method of Example 58 reaction of 1-trimethylsilyl-3-tetrahydropyranyloxy-1-propyne with n-butyllithium and subsequent treatment with the aldehydes listed in Table 7, below, provides the d,l-erythro-1-trimethylsilyl-3-tetrahydropyranyloxy-4-hydroxy-1-alkynes of the table.

TABLE 7

| Example | Starting Aldehyde | Product d,l-erythro-3-tetrahydropyranyloxy-4-hydroxy-1-trimethylsilyl-1-alkyne |
|---|---|---|
| 78 | n-butanal | d,l-erthro-1-trimethylsilyl-3-tetrahydropyranyloxy-4-hydroxy-1-heptyne |
| 79 | n-hexanal | d,l-erythro-1-trimethylsilyl-3-tetrahydropyranyloxy-4-hydroxy-1-nonyne |
| 80 | n-heptanal | d,l-erythro-1-trimethylsilyl-3-tetrahydroxypyranyloxy-4-hydroxy-1-decyne |
| 81 | 4-methyl-n-pentanal | d,l-erythro-1-trimethylsilyl-3-tetrahydropyranyloxy-4-hydroxy-7-methyl-1-octyne |
| 82 | 2-trans-n-pentenal | d,l-erythro-1-trimethylsilyl-3-tetrahydropyranyloxy-4- |

TABLE 7-continued

| Example | Starting Aldehyde | Product d,l-erythro-3-tetrahydropyranyloxy-4-hydroxy-1-trimethylsilyl-1-alkyne |
|---|---|---|
| | | hydroxy-5-trans-en |

EXAMPLES 83–87

Hydrolysis of the 3-tetrahydropyranyloxy group of the d,l-erythro-1-trimethylsilyl-3-tetrahydropyranyloxy-4-hydroxy-1-alkynes listed in Table 8 below by the method described in Example 59, followed by conversion of the resulting d,l-erythro-1-trimethylsilyl-3,4-dihydroxy-1-alkyne to the corresponding d,l-erythro-1-trimethylsilyl-3,4-isopropylidene-dioxy-1-alkyne by treatment with dimethoxypropane in the presence of perchloric acid by the method described in Example 60 followed by desilylation to the corresponding d,l-erythro-3,4-isopropylidenedioxy-1-alkyne by the procedure of Example 61 followed by treatment with disiamylborane, trimethylamine oxide, iodine, and sodium hydroxide solution by the method described in Example 62 provides the product d,l-erythro-1-iodo-3,4-isopropylidenedioxy-trans-1-alkenes of Table 8, below.

TABLE 8

| Example | Starting d,l-erythro-1-trimethylsilyl-3-tetranydropyranyloxy-4-hydroxy-1-alkyne of Example | Product d,l-erythro-1-iodo-3,4-isopropylidenedioxy-trans-1-alkene |
|---|---|---|
| 83 | 78 | d,l-erythro-1-iodo-3,4-isopropylidenedioxy-trans-1-heptene |
| 84 | 79 | d,l-erythro-1-iodo-3,4-isopropylidenedioxy-trans-1-nonene |
| 85 | 80 | d,l-erythro-1-iodo-3,4-isopropylidenedioxy-trans-1-decene |
| 86 | 81 | d,l-eryhtro-1-iodo-3,4-isopropylidenedioxy-7-methyl-trans-1-octene |
| 87 | 82 | d,l-erythro-1-iodo-3,4-isopropylidenedioxy-trans,trans-1,5-octadiene |

EXAMPLES 88–92

Acetylation of the 4-hydroxy group of the d,l-erythro-1-trimethylsilyl-3-tetrahydropyranyloxy-4-hydroxy-1-alkynes listed in Table 9 below by the method described in Example 63, followed by hydrolysis of the resulting d,l-erythro-1-trimethylsilyl-3-tetrahydropyranyloxy-4-acetyloxy-1-alkynes to the corresponding d,l-erythro-1-trimethylsilyl-3-hydroxy-4-acetyloxy-1-alkynes by the method of Example 65, followed by epimerization to d,l-threo-1-trimethylsilyl-3-hydroxy-4-acetyloxy-1-alkynes by the method of Example 66 followed by hydrolysis by the method of Example 67 to give d,l-threo-3,4-dihydroxy-1-alkynes are converted to the corresponding d,l-threo-3,4-isopropylidenedioxy-1-alkynes by treatment with dimethoxypropane in the presence of perchloric acid by the method described in Example 68 followed by treatment with disiamylborane, trimethylamine oxide, iodine, and sodium hydroxide solution by the method described in Example 62 provides the product d,l-threo-3,4-isopropylidenedioxy-trans-1-alkenes of Table 9 below.

TABLE 9

| Example | Starting d,l-erythro-1-trimethylsilyl-3-tetrahydropyranyloxy-4-hydroxy-1-alkyne of Example | Product d,l-threo-1-iodo-3,4-isopropylidenedioxy-trans-1-alkene |
|---|---|---|
| 88 | 78 | d,l-threo-1-iodo-3,4-isopropylidenedioxy-trans-1-heptene |
| 89 | 79 | d,l-threo-1-iodo-3,4-isopropylidenedioxy-trans-1-nonene |
| 90 | 80 | d,l-threo-1-iodo-3,4-isopropylidenedioxy-trans-1-decene |
| 91 | 81 | d,l-threo-1-iodo-3,4-isopropylidenedioxy-trans-1,7-methyl-1-octene |
| 92 | 82 | d,l-threo-1-iodo-3,4-isopropylidenedioxy-trans-1,5-trans-1-octadiene |

EXAMPLE 93

Preparation of 1-octyn-4-ol

A suspension of 24.3 g (1.0 mole) of magnesium in 90 ml of dry ether is stirred at room temperature under nitrogen with 100 mg of mercuric chloride. The reaction is initiated by the addition of 2 ml of propargyl bromide and maintained by the dropwise addition of a solution of 119.5 g (1.0 mole) propargyl bromide and 107.7 g (1.25 mole) of valenaldehyde in 300 ml of dry ether. While the initial reaction is quite vigorous and is maintained at 30° C. only by cooling in an ice bath it may become necessary to heat the mixture to reflux temperature after about a third of the ether solution is added in order to maintain the reaction. After the addition is complete the reaction mixture is refluxed until most of the magnesium is dissolved (several hours) and the reaction mixture is decanted from excess magnesium into 1500 ml of stirred ice-cold ammonium chloride solution. The ether layer is separated and the aqueous layer is extracted three times with 300 ml portions of ether. The combined ether extract is washed with saturated sodium chloride solution, dried over magnesium sulfate and filtered. Evaporation of the ether under vacuum leaves about 115 g of yellow oil, which is distilled through a 15 cm Vigreaux column at 18 mm. The fraction boiling at 81°–82° C. is collected (36 g) and the higher-boiling and lower-boiling distillates may be redistilled to yield additional product. The infrared absorption spectrum shows at most a trace of allene (5.1μ) and gas-liquid partition chromatography shows a purity of about 98% for the main fraction.

EXAMPLES 94–97

The product 1-alkyn-4-ols of Table 10 below are prepared by treatment of the aldehydes listed in Table 10 with propargyl magnesium bromide by the procedure described above in Example 93.

TABLE 10

| Example | Starting Aldehyde | Product 1-alkyn-4-ol |
|---|---|---|
| 94 | n-hexaldehyde | 1-nonyn-4-ol |
| 95 | n-heptaldehyde | 1-decyn-4-ol |
| 96 | n-butyraldehyde | 1-heptyn-4-ol |
| 97 | 3-cis-hexenaldehyde* | 4-hydroxy-6-cis-ene-1-nonyne |

*M. Winter, Helv. Chim. Acta. 46, 1792 (1963).

EXAMPLE 98

Preparation of 4-triphenylmethoxy-1-octyne

A mixture of 10 g (0.08 moles) of 4-hydroxy-1-octyne [1. Crombie and A. G. Jacklin, J. Chem. Soc., 1632 (1957), also Example 93] and 30.75 g (0.09 moles) of triphenylmethyl bromide in 85 ml of dry pyridine is heated on the steam bath for 2 hours. The cooled mixture is treated with water and extracted with ether. The extract is washed successively with ice cold 2% hydrochloric acid, saturated sodium chloride solution, dried with magnesium sulfate, and taken to dryness. Column chromatography of the residue on Florisil affords an oil; λ max 3.01, 4.72 (acetylenic hydrogen), 6.28, 9.65 and 14.25μ (triphenylmethoxy group).

EXAMPLE 99

Preparation of 4-triphenylmethoxy-1-hexyne

A stirred solution of 9.81 g (0.10 moles) of 4-hydroxy-1-hexyne and 33.5 g (0.12 moles) of triphenylmethyl chloride in 100 ml of dry pyridine is heated at reflux for 2 hours. The cooled mixture is treated with water and extracted with a hexane-ether mixture. The extract is washed successively with water and saturated sodium chloride solution, dried over magnesium sulfate, and concentrated. Column chromatography of the residue on Florisil gives an oil, max. 3290 (acetylenic hydrogen), 1600, 1030 and 705 cm$^{-1}$ (triphenylmethoxy group).

EXAMPLES 100-106

The triphenylmethoxy substituted 1-alkynes listed in Table 11 below are prepared by the method of Example 98 from triphenylmethyl bromide and the corresponding hydroxy substituted 1-alkynes, appropriate literature references to which are provided in the table.

TABLE 11

| Example | Reference to Starting Hydroxy Substituted 1-Alkyne | Product Triphenylmethoxy Substituted 1-Alkyne |
|---|---|---|
| 100 | Reference 1 | 4-triphenylmethoxy-1-pentyne |
| 101 | Reference 1 (Example 96) | 4-triphenylmethoxy-1-heptyne |
| 102 | Reference 1 | 4-triphenylmethoxy-5-methyl-1-hexyne |
| 103 | Reference 2 (Example 94) | 4-triphenylmethoxy-1-nonyne |
| 104 | Reference 3 (Example 95) | 4-triphenylmethoxy-1-decyne |
| 105 | Reference 4 | 4-triphenylmethoxy-5-ethyl-1-heptyne |
| 106 | Example 97 | 4-triphenylmethoxy-6-cis-ene-1-nonyne |

References:
1. G. Fontaine, et al., Bull. Soc. Chem. France, 1447 (1963).
2. S. Abe and K. Sato, Bull. Soc. Chem. Japan, 29, 88 (1956); Chem. Abstr., 50, 13737 (1956).
3. L. Crombie and A. G. Jacklin, J. Chem. Soc., 1622 (1957);
4. Nobuharra, Akio, Chem. Abstr., 70, 3219 (1969).

EXAMPLE 107

Preparation of 1-iodo-4-triphenylmethoxy-trans-1-octene

To a stirred suspension of 1.78 g (0.074 mole) of sodium borohydride in 200 ml of dry glyme at −5° C. under nitrogen is added 15.8 g (0.22 mole) of 2-methyl-2-butene and 16.2 g (0.11 mole) of boron trifluoride etherate, and the mixture is stirred for 2 hours at −5° C. to 0° C. A solution of 37.5 g (0.10 mole) of 4-trityloxy-1-octyne (Example 98) in 50 ml of glyme is added to the cold solution during 5–10 minutes, and the solution is allowed to warm to 20° C. during 1.5 hours. The reaction mixture is cooled to 0° C. and 30 g (0.4 mole) of dry trimethylamine-N-oxide is added during 5 minutes. On removing the cooling bath the temperature rises to 40° C. and the mixture is kept between 30°–40° C. for 1.5 hours. The suspension is poured rapidly into one liter of ice cold 15% sodium hydroxide solution during good stirring and a solution of 80 g of iodine in 200 ml of tetrahydrofuran is added immediately. Stirring is continued for 30 minutes without further cooling and the organic layer is separated. The aqueous layer is extracted with three 200 ml portions of ether and the combined organic layers are washed successively with water, 5% sodium thiosulfate solution and saturated sodium chloride, dried over magnesium sulfate, filtered and evaporated to yield 50 g of yellow oil. The bulk of the oil is dissolved in hexane and, after decantation from a gummy solid the hexane solution is percolated through a 5.1 cm diameter column of 1500 g of alumina with additional hexane. Fractions containing the desired product are concentrated to a pale yellow oil (33 g) which has n.m.r. and infrared spectra characteristics of the desired product.

EXAMPLES 108-114

Treatment of the triphenylmethoxy substituted 1-alkynes listed in Table 12 below with disiamylborane, prepared in situ from 2-methyl-2-butene, boron, trifluoride and sodium borohydride, followed by trimethylamine N-oxide, and then sodium hydroxide and iodine—all by the procedure described in Example 107 above furnishes the product triphenylmethoxy substituted 1-iodo-1-trans-alkenes of the table.

TABLE 12

| Example | Starting Triphenylmethoxy Substituted 1-Alkyne of Example | Product 1-Iodo-triphenylmethoxysubstituted-1-trans-alkene |
|---|---|---|
| 108 | 99 | 1-iodo-4-triphenylmethoxy-1-trans-hexene |
| 109 | 100 | 1-iodo-4-triphenylmethoxy-1-trans-pentene |
| 110 | 101 | 1-iodo-4-triphenylmethoxy-1-trans-heptene |
| 111 | 102 | 1-iodo-4-triphenylmethoxy-5-methyl-1-trans-hexene |
| 112 | 103 | 1-iodo-4-triphenylmethoxy-1-trans-nonene |
| 113 | 104 | 1-iodo-4-triphenylmethoxy-1-trans-decene |
| 114 | 106 | 1-iodo-4-triphenylmethoxy-1-trans-6-cis-nonadiene |

EXAMPLES 115-124a

The starting aldehydes or ketones of Table 13 below are converted to the product 1-alkyn-4-ols of the table by the procedure described in Example 93.

TABLE 13

| Example | Starting Aldehyde or Ketone | Product 1-Alkyn-4-ol |
|---|---|---|
| 115 | 2-octanone | 4-methyl-4-hydroxy-1-decyne |
| 116 | trans-2-hexenal | 4-hydroxy-5-trans-nonen-1-yne |
| 117 | 2,2-dimethylhexanal | 5,5-dimethyl-4-hydroxy-1-nonyne |
| 118 | z-heptanone | 4-methyl-4-hydroxy-1-nonyne |
| 119 | 2,2-dimethylpentanal | 5,5-dimethyl-4-hydroxy-1-octyne |
| 120 | 2-methylpentanal | 5-methyl-4-hydroxy-1-octyne |
| 121 | 2-methylhexanal | 5-methyl-4-hydroxy-1-nonyne |
| 122 | 2-hexanone | 4-hydroxy-4-methyl-1-octyne |
| 123 | trans-3-hexen-2-one[a] | 4-hydroxy-4-methyl-5-trans-octen-1-yne |
| 124 | trans-2-pentenal[b] | 4-hydroxy-5-trans-octen-1-yne |
| 124a | trans-2-heptenal[b] | 4-hydroxy-5-trans-decen-1-yne |

[a] G. Sturtz, Bull. Soc. Chim. Fr., 1967, 2477.
[b] R. I. Hoaglin and D. M. Hirsh, U.S. 2,628,257; Chem. Abstr., 48, 1423e (1954).

EXAMPLE 125

Preparation of 4-methyl-4-trimethylsilyloxyl-1-octyne

To a stirred solution of 75.4 g (0.537 moles) of 4-hydroxy-4-methyl-1-octyne (Example 122), 104.9 g (1.54 moles) of imidazole, and 325 ml of dimethylformamide is added 65.2 g (0.60 moles) of chlorotrimethylsilane. After standing overnight the mixture is poured into 800 ml of hexane. The mixture is washed thoroughly with water followed by sodium bicarbonate solution and brine. The solution is dried over magnesium sulfate, filtered, and evaporated to give a liquid, p.m.r. specturm, δ 1.26 (singlet, 3, C$\underline{H}_3$), 1.92 (triplet, 1, $\underline{H}$C), 2.30 (doublet, 2, C$\underline{H}_2$).

EXAMPLES 126–129a

The 1-alkyn-4-ols of Table 14 are converted to the product trimethylsilyl ethers of the table by treatment with chlorotrimethylsilane according to the procedure described in Example 125.

TABLE 14

| Example | Starting 1-Alkyn-4-ol | Product Trimethylsilyl Ether |
|---|---|---|
| 126 | 5,5-dimethyl-4-hydroxy-1-nonyne (Ex. 117) | 5,5-dimethyl-4-trimethyl-silyloxy-1-nonyne |
| 127 | 4-methyl-4-hydroxy-1-nonyne (Ex. 119) | 4-methyl-4-trimethylsilyloxy-1-nonyne |
| 128 | 5,5-dimethyl-4-hydroxy-1-octyne (Ex. 119) | 5,5-dimethyl-4-trimethyl-silyloxy-1-octyne |
| 129 | 4-hydroxy-4-methyl-5-trans-octen-1-yne (Ex. 123) | 4-methyl-4-trimethylsilyloxy-5-trans-octen-1-yne |
| 129a | 4-hydroxy-4-methyl-1-decyne (Ex. 124a) | 4-methyl-4-trimethylsilyloxy-1-decyne |

EXAMPLE 130

Preparation of 1-iodo-4-hydroxy-4-methyl-trans-1octene

To a stirred solution of 400 ml of 0.5 M bis-(3-methyl-2-butyl)borane in glyme, prepared from sodium borohydride, 2-methyl-2-butene, and boronitrifluroide etherate as in Example 107, is added 63.7 g (0.30 moles) of 4-methyl-4-trimethylsilyloxy)-1-octyne (Example 125) at −10° C. The solution is stirred at ambient temperature for 2.5 hours, cooled to −10° C., and treated during 30 minutes with 158 g (2.1 moles) of solid trimethylamine oxide with cooling. The mixture is stirred at ambient temperature for 2 hours and then poured into a stirred, ice-cold solution of 15% aqueous sodium hydroxide; the stirred mixture is treated immediately with a solution of 426 g (1.68 moles) of iodine in 1100 ml of tetrahydrofuran. After 4 hours the mixture is extracted with ether. The extract is washed successively with water, aqueous sodium thiosulfate, and brine and dried over magnesium sulfate. The extract is concentrated, and the residue is subjected to chromatography on silica gel with hexane to provide an oil; p.m.r. (CDCl$_3$): δ1.18 (singlet, 4-C$\underline{H}_3$ group).

EXAMPLES 131–134a

The 4-trimethylsilyloxy-1-alkynes of Table 15 are converted to the 4-hydroxy-1-iodo-trans-1-octenes of the table by the procedure described in Example 130.

TABLE 15

| Example | Starting 4-Trimethylsilyloxy-1-octyne of Example | Product 4-Hydroxy-1-iodo-trans-1-octene |
|---|---|---|
| 131 | 126 | 1-iodo-5,5-dimethyl-4-hydroxy-trans-1-nonene |
| 132 | 127 | 1-iodo-4-methyl-4-hydroxy-trans-1-nonene |
| 133 | 128 | 1-iodo-5,5-dimethyl-4-hydroxy-trans-1-octene |
| 134 | 129 | 1-iodo-4-methyl-4-hydroxy-trans,trans-1,5-octadiene |
| 134a | 129a | 1-iodo-4-methyl-4-hydroxy-trans-1-decene |

EXAMPLE 135

Preparation of 1-iodo-4-methyl-4-trimethylsilyloxy-trans-1-octene

To a stirred mixture of 24.5 g (55.6 mmoles) of 1-iodo-4-hydroxy-4-methyl-trans-octene (Example 130), 13.6 g (200 mmoles) of imidazole, and 75 ml of dimethylformamide is added 10.9 g (100 mmoles) of chlorotrimethylsilane. After standing overnight the mixture is poured into 250 ml of hexane. The mixture is washed thoroughly with water followed by brine and dried over magnesium sulfate. After removal of the solvent, the product is distilled to give a colorless liquid, bp 67.5°–68° C. (0.07 mm).

EXAMPLES 136–139b

The 1-iodo-4-hydroxy-trans-1-alkenes of Table 16 are converted to the product trimethylsilyl ethers of the table according to the procedure described in Example 135.

TABLE 16

| Example | Starting 1-Iodo-4-hydroxy-trans-1-alkene of Example | Product Trimethylsilyl Ether |
|---|---|---|
| 136 | 131 | 1-iodo-5,5-dimethyl-4-trimethylsilyloxy-trans-nonene |
| 137 | 132 | 1-iodo-4-methyl-4-trimethylsilyloxy-trans-1-nonene |
| 138 | 133 | 1-iodo-5,5-dimethyl-4-trimethylsilyloxy-trans-1-octene |
| 139 | 134 | 1-iodo-4-methyl-4-trimethylsilyloxy-trans,trans-1,5-octadiene |
| 139a | 134a | 1-iodo-4-methyl-4-trimethylsilyloxy-trans-1-decene |
| 139b | 134b | 1-iodo-4-methyl-4-trimethylsilyloxy-trans-1-decene |

EXAMPLE 140

Preparation of 4-benzoyloxy-1-octyne

To a stirred solution of 63. g (0.50 moles) of 1-octyn-4-ol (Example 93) in 500 ml of pyridine is added 77 g (0.55 moles) of benzoyl chloride. After stirring for 1.5 hours the mixture is treated with 10 ml of water, allowed to stand for 15 minutes, and concentrated. A solution of the residue in ether is washed successively with ice-cold hydrochloric acid, water, sodium bicarbonate solution, and brine. The solution is dried over magnesium sulfate, filtered through Celite, and concentrated to give an oil, λ max, 3240 (terminal acetylene) and 1730 cm$^{-1}$ (benzyloxy group).

EXAMPLE 141

Stereoselective Hydrolysis of Racemic 4-benzoyloxy-1-octyne by *Rhizopus arrhizus*

An agar slant of *R. arrhizus* (MUMF 1638) is used to inoculate 7 shake flasks (250 ml Erlenmeyer). Each flask contains 50 ml of a medium consisting of 2% Edamine, 2% glucose, and 0.72% corn steep liquor in water with pH adjusted to 7.0. A total of 14 such flasks are incubated on a rotary shaker at 28° C. After 72 hours incubation, 50 mg of racemic 4-benzoyl-oxy-1-octyne (Example 135) in 0.1 ml of acetone is added to each flask. After 28 hours the flasks are harvested and worked up by extraction of the whole mash with an equal volume of chloroform. The combined extracts are dried over magnesium sulfate and concentrated. The resulting oil is chromatographed on a column of silica gel with hexane progressively enriched in ethyl acetate.

From fractions 3–6 is obtained 150 mg of colorless oil, identical to 4-benzoyloxy-1-octyne, $[\alpha]_D^{25} = 5 \pm 1.0°$ (C=0.91, ethyl acetate). This compound has the (S)-configuration.

From fractions 13–20 is obtained 75 mg of colorless oil, identical to 4-hydroxy-1-octyne, $[\alpha]_D^{25} = -17 \pm 1.0°$ (C=0.77, ethyl acetate). This compound has the (R)-configuration.

The strain of *R. arrhizus* utilized in this experiment is a higher fungus which grows steadily on a variety of artificial media at 20°–25° C. In this study of the taxonomic aspects of the culture, Petri dishes of potato-dextrose, malt extract, and cornmeal agars were inoculated and incubated at ambient room temperature for 10 days. Observation of cultural and morphological characteristics are recorded in the description below:

Colonies on Petri dishes of potato-dextrose agar growing rapidly, covering the agar surface in 3–5 days and producing a thick, loose mat of grayish mycelium. Colony surface characterized by abundant black sporangia. Colony reverse grayish white. Colonies on malt extract agar growing rapidly, covering the agar surface in 3–5 days. Mycelial mat thick, grayish-yellow. Colony surface becoming brownish-black from masses of sporangia. Colony reverse yellowish. Colonies on cornmeal agar very thin, whitish; spreading across agar surface. Cultures transparent with relatively few sporangia produced. Visibility of micromorphology is good on this mediu. Rhizoids produced sparingly along stoloniferous hyphae. Generally two to three sporangiophores arose from rhizoids. Walls of sporangiophores olive brown, 14.0–20.0 μm in width at base, tapering slightly to apex; 0.5–1.5 mm in length Sporangiophores terminated by spherical sporangia, 130–225 μm in diameter. Columellae hemispherical, 3–50 μm high by 50–70 μm wide. Spores brownish when mature, 6.0–8.5 μm×4.5–6.0 μm. Spore walls conspicuously marked by longitudinal striations.

EXAMPLE 142

Preparation of (S)-4-hydroxy-1-octyne

A solution of 1.15 g (5.0 mmoles) of (S)-4-benzoyloxy-1-octyne (Example 141) and 1.40 g (25 mmoles) of potassium hydroxide in 50 ml of 10:1 methanol-water is allowed to stand at room temperature for 24 hours. The bulk of the methanol is evaporated at room temperature, and the mixture is extracted with ether. The extract is washed with brine, dried over magnesium sulfate, and evaporated to give a colorless oil, identical to 4-hydroxy-1-octyne $[\alpha]_D^{25} = +17 \pm 1.0°$ (C=0.77, ethyl acetate). This compound has the (S)-configuration.

EXAMPLES 143–148a

The starting 1-alkyn-4-ols of Table 17 below are converted to the triphenylmethoxy substituted 1-alkynes by the method of Example 98.

TABLE 17

| Example | Starting 1-Alkyn-4-ol of Example | Product Triphenylmethoxy Substituted 1-Alkyne |
| --- | --- | --- |
| 143 | 116 | 4-triphenylmethoxy-5-trans-nonen-1-yne |
| 144 | 120 | 5-methyl-4-triphenylmethoxy-1-octyne |
| 145 | 121 | 5-methyl-4-triphenylmethoxy-1-nonyne |
| 146 | 124 | 4-triphenylmethoxy-5-trans-octen-1-yne |
| 147 | 141 | (R)-4-triphenylmethoxy-1-octyne |
| 148 | 142 | (S)-4-triphenylmethoxy-1-octyne |
| 148a | 124a | 4-triphenylmethoxy-5-trans-decen-1-yne |

EXAMPLES 149–154A

The product triphenylmethoxy substituted 1-iodo-1-trans-alkenes of Table 18 below are prepared from the starting triphenylmethoxy substituted 1-alkynes of the table by the procedure described in Example 107.

TABLE 18

| Example | Starting Triphenylmethoxy Substituted 1-Alkyn of Example | Product Triphenylmethoxy Subsituted 1-Iodo-trans-1-alkene |
| --- | --- | --- |
| 149 | 143 | 1-iodo-4-triphenylmethoxy-trans,trans-1,5-nonadiene |
| 150 | 144 | 1-iodo-5-methyl-4-triphenylmethoxy-trans-1-octene |
| 151 | 145 | 1-iodo-5-methyl-4-triphenylmethoxy-trans-1-nonene |
| 152 | 146 | 1-iodo-4-triphenylmethoxy-trans,trans-1,5-octadiene |
| 153 | 147 | (R)-1-iodo-4-triphenylmethoxy-1-trans-octene |
| 154 | 148 | (S)-1-iodo-4-triphenylmethoxy-1-trans-octene |
| 154A | 148a | 1-iodo-4-triphenylmethoxy-trans,trans-1,5-decadiene |

EXAMPLE 154B

Preparation of 4-Trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine, dried over magnesium sulfate, and concentrated. Distillation of the residue gives a colorless liquid, b.p. 38° (0.2 mm).

EXAMPLE 154C

Preparation of 1-Iodo-4-trimethylsiloxy-trans-1-octene

To a stirred solution of 0.20 moles of freshly prepared bis-(3-methyl-2-butyl) borane in 300 ml of tetrahydrofuran at 0°–5° C. is added dropwise a solution of 19.8 g of 4-trimethylsiloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°–40° C. and then poured into 2 liters of 15% sodium hydroxide. The resulting mixture is treated immediately with a solution of 140 g of iodine in 300 ml of tetrahydrofuran. After 0.5 hour the organic phase is separated and the aqueous gas is extracted with ether. The combined organic layers are washed with water, sodium thiosulfate solution, and brine; dried over magnesium sulfate; and concentrated to give an oil, pmr spectrum (CDCl$_3$): 6.2 (d, IC$\underline{H}$=) and 6.7 (quintuplet, =C$\underline{H}$—).

EXAMPLE 154D–E

Preparation of 4-Hydroxy-1-Iodo-trans-1-octene

A 23 g portion of 1-iodo-4-trimethylsiloxy-trans-1-octene is dissolved in a mixture of 200 ml of glacial acetic acid, 100 ml of tetrahydrofuran, and 50 ml of water. After solution occurs, toluene is added and the mixture is evaporated. The resulting oil is chromatographed on silica gel with hexane progressively enriched in benzene followed by acetone to give 16 g of an oil, pmr spectrum (CDCl): 3.69 (m. C$\underline{H}$OH) and 2.3 (s, O$\underline{H}$).

EXAMPLE 154F

Preparation of 4-Oxo-1-iodo-trans-1-octene

To a stirred suspension of 6.15 g of pyridinium chlorochromate (*Tetrahedron Letters*, 1975, 2647) in 20 ml of methylene chloride is added 450 mg of sodium acetate. After 5 minutes, a solution of 3.64 g of 4-hydroxy-1-iodo trans-1-octene in 15 ml of methylene chloride is added in one portion. The dark mixture is stirred at room temperature for 75 minutes, diluted with 50 ml of ether, and decanted. The solid sludge is washed repeatedly with ether and decanted. The combined solutions are percolated through Florisil. The solution is concentrated to give an orange liquid, pmr spectrum (CDCl$_3$): 3.20 (d, j=7 cps, =CHC$\underline{H}_2$CO).

EXAMPLE 154G

Preparation of 4-Hydroxy-4-(1-propynyl)-1-iodo-trans-1-octene

To a stirred solution of propynyllithium at −25° is added a solution of 4-oxo-1-iodo-trans-1-octene in tetrahydrofuran After the addition, the solution is stirred at −20° to −15° C. for 30 minutes. The reaction is quenched with a mixture of hexane and ice. The aqueous phase is separated and extracted with additional hexane. The combined hexane extracts are washed successively with water and brine. The solution is dried over magnesium sulfate and concentrated. The residue is subjected to column chromatography on silica gel with toluene to provide the product as an oil.

EXAMPLE 154H

Preparation of 4-Hydroxy-4-(1-propynyl)-1-iodo-trans-1-decene

Treatment of 4-hydroxy-1-decyne (U.S. Pat. No. 3,950,406) by the procedures of Examples 154B, 154C, 154D, 154F and 154G is productive of the iodo-decene compound.

EXAMPLE 154I–154J

Treatment of the iodoalkenes of Table 4 with chlorotrimethylsilane by the procedure of Example 210H Infra is productive of the trimethylsilylether of the Table.

TABLE 18A

| Example | Starting Iodo Alkene | Product Silylether |
|---------|---------------------|--------------------|
| 154I | 154G | 4-trimethylsilyloxy-4-(1-propynyl)-1-iodo-trans-1-octene |
| 154J | 154H | 4-trimethylsilyloxy-4-(1-propynyl)-1-iodo-trans-1-decene |

EXAMPLE 155

Preparation of ethyl-p-fluorophenoxy-acetate

To a stirred solution of 50 g (0.29 moles) of p-fluorophenoxy acetic acid in one liter of absolute ethanol is added 10 ml of sulfuric acid. The mixture is heated to reflux for 18 hours, cooled to room temperature, and evaporated under vacuum. It is then poured onto 300 g of ice, extracted twice with 500 ml of ether, washed twice with 250 ml of a saturated solution of sodium bicarbonate, 100 ml of saturated sodium chloride solution, dried with magnesium sulfate, filtered and evaporated under vacuum giving 58 g of an oil. This is crystallized from 50 ml of hexane at −25° C. to give 55 g (90%) of the subject product as colorless crystals, mp 32°–33° C.

EXAMPLE 156

Preparation of p-fluorophenoxy acetaldehyde

To a stirred solution of 1.98 g (10 mmoles) of ethyl-p-fluorophenoxy acetate (Example 155) in 15 ml of dry toluene, cooled to −78° C., under argon, is added, dropwise over 30 minutes, 8 ml of a 1.4M solution of diisobutylaluminum hydride in toluene (11 mmoles). The mixture is stirred for 2 hours at −78° C., 1 ml of methanol is added, followed by 5 ml of water, dropwise. The gel formed is filtered through Celite and washed with 100 ml of ether, portionwise. The organic phase is separated, washed twice with 25 ml of a saturated brine solution, dried with magnesium sulfate, filtered, and evaporated. The oil obtained is distilled at 71°–73° C. (0.1 mm) to give 600 mg (45%) of the subject product as a colorless liquid.

EXAMPLE 157

Preparation of 3-hydroxy-4-p-fluorophenoxy-1-butyne

Acetylene gas, dried by passing through a trap containing sulfuric acid, is bubbled at a moderate rate, through 5 ml of vigorously stirred tetrahydrofuran, for 15 minutes. To this acetylenic solution, is then added dropwise, with continued passage of acetylene, 3.5 ml of a 2.4M solution of n-butylmagnesium chloride in tetrahydrofuran (8.4 mmoles) over 45 minutes. The mixture is stirred a further 15 minutes, and a solution of 580 mg (3.9 mmoles) of p-fluorophenoxy acetaldehyde (Example 156) in 3 ml of tetrahydrofuran is added dropwise over 15 minutes. This solution is stirred for 2 more hours, with passage of acetylene, poured into 50 ml of a saturated solution of ammonium chloride, extracted twice with 50 ml of ether, washed with 10 ml of ammonium chloride solution, dried with magnesium sulfate, filtered, and evaporated. The crude subject product is purified by sublimation at 75° C. (0.1 mm) for 5 hours to give 330 mg (48%) of white crystals, mp 46°–47° C.

EXAMPLE 158

Preparation of 4-p-fluorophenoxy-3-trimethylsilyloxy-1-butyne

To a 0° C. solution of 10 g (55 mmoles) of 3-hydroxy-4-p-fluorophenoxy-1-butyne (Example 157) in 75 ml of dry dimethylformamide and 88 g (130 mmoles) of imidazole is added dropwise, with stirring, 7.5 g (68 mmoles) of chlorotrimethylsilane. The mixture, while under an argon atmosphere, is stirred at room temperature for 18 hours, and then poured into 150 ml of hexane and 100 ml of ice-water. The organic phase is separated, washed with 50 ml of a brine solution, dried with magnesium sulfate, and evaporated under vacuum. This crude product is distilled under vacuum at 0.1 mm (bp 73°–75° C.), to give 12.2 g (91%) of the subject compound as a colorless oily liquid.

EXAMPLE 159

Preparation of 1-tri-n-butylstannyl-4-p-fluorophenoxy-3-trimethylsilyloxy-trans-b 1-butene A mixture of 2.52 g (10 mmoles) of 3-trimethylsilyloxy-4-p-fluorophenoxy-1-butyne (Example 158), 2.91 g (10 mmoles) of tri-n-butyl-tin hydride, and 10 mg of azobisisobutyronitrile is heated, under an argon atmosphere, with stirring, for 2 hours at 140° C. After cooling to room temperature, the crude reaction mixture is fractionally distilled at 180°–185° C. (0.05 mm), to give 4.6 g (85%) of the subject product as a colorless liquid.

EXAMPLES 160–162

The product esters of Table 19 below are obtained by the procedure described in Example 155.

TABLE 19

| Example | Starting Aryloxy Acid | Product Aryloxy Ethyl Ester |
|---|---|---|
| 160 | m-chlorophenoxy-acetic acid | ethyl-m-chlorophenoxy-acetate |
| 161 | 3,4-dichlorophenoxyacetic acid | ethyl-3,4-dichlorophenoxyacetate |
| 162 | phenoxyacetic acid | ethyl-phenoxyacetate |

EXAMPLE 163

Preparation of ethyl-m-trifluoromethylphenoxy-acetate

A mixture of 100 g (0.618 mole) of α,α,α-trifluoro-m-cresol, 106 g (0.632 mole) of ethyl bromoacetate, 87.5 g (632 mole) of potassium carbonate, and 1500 ml of acetone is stirred at reflux for 4 hours, and at room temperature for 18 hours. The mixture is filtered, evaporated under vacuum on a rotorary evaporator at 45° C. and at 85° C. (0.1 mm) to remove excess ethyl bromoacetate. The reaction mixture is taken up in 500 ml of ether, washed three times with 100 ml each of 0.1M potassium carbonate, once with 100 ml of water, 100 ml of 0.01M hydrochloric acid, and 100 ml of water. It is then dried with magnesium sulfate, filtered and evaporated, giving 142 g of the crude product. This is fractionally distilled at 73°–75° C. (0.1 mm) to give 124 g of the purified subject product as a colorless liquid.

EXAMPLES 164–166

The product esters of Table 20 are obtained by treating the starting phenols with ethyl bromoacetate by the procedure of Example 162.

TABLE 20

| Example | Starting Phenol | Product Ester |
|---|---|---|
| 164 | p-bromophenol | ethyl p-bromophenoxy-acetate |
| 165 | 4-t-butylphenol | ethyl 4-t-butylphenoxy-acetate |
| 166 | p-methoxyphenol | ethyl p-methoxyphenoxy-acetic acid |

EXAMPLES 167–173

Following the procedure of Example 156, the starting esters of Table 21 are treated with diisobutylaluminum hydride to provide the product aldehydes of the table.

TABLE 21

| Example | Starting Ester | Product Aldehyde |
|---|---|---|
| 167 | 163 | m-trifluoromethylphenoxy acetaldehyde |
| 168 | 164 | p-bromophenoxy acetaldehyde |
| 169 | 165 | 4-t-butylphenoxy acetaldehyde |
| 170 | 166 | p-methoxyphenoxy acetaldehyde |
| 171 | 160 | m-chlorophenoxy acetaldehyde |
| 172 | 161 | 3,4-dichlorophenoxy acetaldehyde |
| 173 | 162 | phenoxyacetaldehyde |

EXAMPLES 174–180d

Following the procedure of Example 156, treatment of the starting aldehyde of Table 22 with acetylene magnesium chloride provides the product alkynes of Table 22.

TABLE 22

| Example | Starting Aldehyde | Product Aryloxy Alkyne |
|---|---|---|
| 174 | 167 | 3-hydroxy-4-m-trifluoromethyl-phenoxy-1-butyne |
| 175 | 168 | 3-hydroxy-4-p-bromophenoxy-1-butyne |
| 176 | 169 | 3-hydroxy-4-t-butylphenoxy-1-butyne |
| 177 | 170 | 3-hydroxy-4-p-methoxyphenoxy-1-butyne |
| 178 | 171 | 3-hydroxy-4-m-chlorophenoxy-1-butyne |
| 179 | 172 | 3-hydroxy-4-(3,4-dichlorophenoxy)-1-butyne |
| 180 | 173 | 3-hydroxy-4-phenoxy-1-butyne |
| 180a | a | 3-hydroxy-5-phenyl-1-pentyne |
| 180b | b | 3-hydroxy-5-(p-chlorophenyl)-1-pentyne |
| 180c | c | 3-hydroxy-5-(p-methoxyphenyl)-1-pentyne |

TABLE 22-continued

| Example | Starting Aldehyde | Product Aryloxy Alkyne |
|---------|-------------------|------------------------|
| 180d | d | 3-hydroxy-5-(m-trifluoromethylphenyl)-1-pentyne | a hydrocinnamaldehyde[1]
b p-chlorohydrocinnamaldehyde[1]
c p-methoxyhydrocinnamaldehyde[1]
d m-trifluoromethylhydrocinnamaldehyde[2]
[1] Billman, et al., Synthetic Communications, 1, 127–131 (1971).
[2] Lednicer, Journ. Med. Chem., 11, 1258 (1968).

EXAMPLES 180e–186e

Treatment of the starting alkynes of Table 23 by the procedure of Example 158 followed by treatment of the procedure of Example 159 provides the product (E) 1-tri-n-butyltin-1-alkenes of the table.

TABLE 23

| Example | Starting Alkyne | Product (E)-1-tri-n-butyltin-1-alkene |
|---------|-----------------|----------------------------------------|
| 180e | 174 | (E)-1-tri-n-butylstannyl-3-trimethylsilyloxy-4-m-trifluoromethylphenoxy-1-butene |
| 181 | 175 | (E)-1-tri-n-butylstannyl-3-trimethylsilyloxy-4-p-bromophenoxy-1-butene |
| 182 | 176 | (E)-1-tri-n-butylstannyl-3-trimethylsilyloxy-4-t-butylphenoxy-1-butene |
| 183 | 177 | (E)-1-tri-n-butylstannyl-3-trimethylsilyloxy-4-p-methoxyphenoxy-1-butene |
| 184 | 178 | (E)-1-tri-n-butylstannyl-3-trimethylsilyloxy-4-m-chlorophenoxy-1-butene |
| 185 | 179 | (E)-1-tri-n-butylstannyl-3-trimethylsilyloxy-3,4-dichlorophenoxy-1-butene |
| 186 | 180 | (E)-1-tri-n-butylstannyl-3-trimethylsilyloxy-4-phenoxy-1-butene |
| 186a | 48 | (E)-1-tri-n-butylstannyl-4,4-trimethylene-3-trimethylsilyloxy-(Z)-6-octadiene |
| 186b | 180a | (E)-1-tri-n-butylstannyl-3-trimethylsilyloxy-5-phenyl-1-pentene |
| 186c | 180b | (E)-1-tri-n-butylstannyl-3-trimethylsilyloxy-5-(p-chlorophenyl)-1-pentene |
| 186d | 180c | (E)-1-tri-n-butylstannyl-3-trimethylsilyloxy-5-(p-methoxyphenyl)-1-pentene |
| 186e | 180d | (E)-1-tri-n-butylstannyl-3-trimethylsilyloxy-5-(m-trifluoromethylphenyl)-1-pentene |

EXAMPLE 187

Preparation of 1-chloro-1-octen-3-one

This compound is prepared according to the procedure of Price and Pappalardo [C. C. Price and J. A. Pappalardo, Org. Syn, 32, 27 (1952)] from hexanoyl chloride, acetylene, and aluminum chloride in 94% yield, bp 51°–52° C. (0.1 mm); λ max 1680, 1595, 941 cm$^{-1}$.

EXAMPLE 188

Preparation of 1-iodo-1-octen-3-one

A mixture of 25 g (0.16 moles) of 1-chloro-1-octen-3-one (Example 187) and 35 g (0.23 moles) of sodium iodide in 200 ml of reagent acetone is stirred at the reflux temprature for 18 hours. The cooled mixture is filtered and the mother liquor taken to dryness. The residual oil is dissolved in benzene and the solution is washed with 5% sodium thiosulfate solution, saturated sodium chloride solution, dried and taken to dryness. The residual oil is crystallized from hexane to give 26 g of a white solid, mp 35°–37° C.; λ max 1670, 950 cm$^{-1}$.

EXAMPLE 189

Preparation of 3-hydroxy-1-iodo-3-methyl-1-octene

To a Grignard solution prepared from 1.05 g (0.41 moles) of magnesium and 6.2 g (0.435 moles) of methyl iodide in 30 ml of dry ether under argon is added dropwise 10 g of 1-iodo-1-octen-3-one (Example 183) in 45 ml of ether. The resulting solution is stirred at ambient temperature for one hour. After the addition of 75 ml of saturated ammonium chloride the ether layer is separated and the aqueous layer is separated and the aqueous layer is extracted several times with ether. The combined ether extracts are washed successively with ammonium chloride and water, dried and taken to dryness to give 9.24 g of produce as an oil; λ max 2.89, 3.23, 6.24 and 10.5.

EXAMPLE 190

Preparation of 1-iodo-3-methyl-3-trimethylsilyloxy-1-octene

To a stirred solution of 11.7 g of 3-hydroxy-1-iodo-3-methyl-1-octene (Example 184) and 7.4 g of imidazole in 45 ml of dry dimethylformamide is added dropwise 5.98 g of trimethylsilylchloride at 0° C. under argon atmosphere. After stirring at 0° C. for an additional 15 minutes, the solution is stirred at ambient temperature for 18 hours. The reaction mixture is poured into 600 ml of hexane and the resulting solution washed with water, saturated sodium chloride solution, dried over anhydrous magnesium sulfate and taken to dryness to furnish 14.7 g of oil. Distillation affords 13.4 g of clear oil; bp 65° C. (0.05 mm); λ max 6.21, 8.00, 9.90, 10.51, 11.90, 13.2μ.

EXAMPLE 190a

Preparation of 1-iodo-3-methyl-3-trimethylsilyloxy-1-decene

Treatment of octanoylchloride by the procedures of Example 187 followed by treatment of the resulting 1-chloro-1-decen-3-one by the procedure of Example 188 followed by treatment according to Examples 189 and 190 is productive of the named compound.

EXAMPLE 191

Preparation of 4-trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine dried over magnesium sulfate, and concentrated. Distillation of the residue gives a colorless liquid, bp 38° C. (0.2 mm).

EXAMPLE 192

Preparation of 1-iodo-4-trimethylsiloxy-trans-1-octene

To a stirred solution of 0.20 moles of freshly prepared bis-(3-methyl-2-butyl)borane in 300 ml of tetrahydrofuran at 0°–5° C. is added dropwise a solution of 19.8 g of 4-trimethylsiloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°–40° C. and then poured into 2 liters of 15% sodium hydroxide. The resulting mixture is treated immediately with a solution of 140 g of iodine in 300 ml of tetrahydrofuran. After 0.5 hour the organic phase is separated and the aqueous phase is extracted with ether. The combined organic layers are washed with water, sodium thiosulfate solution, and brine; dried over magnesium sulfate; and concentrated to give an oil pmr spectrum (CDCl$_3$): 6.2 (d, IC$\underline{H}$=) and 6.7 (quintuplet, =C$\underline{H}$—).

EXAMPLE 193

Preparation of 4-hydroxy-1-iodo-trans-[-octene

A 23 g portion of 1-iodo-4-trimethylsilyloxy-1-octene is dissolved in a mixture of 200 ml of glacial acetic acid, 100 ml of tetrahydrofuran, and 50 ml of water. Concentration provides the named product.

EXAMPLE 194

Preparation of 4-trimethylsiloxy-4-vinyl-1-iodo-trans-1-octene

To a stirred solution of 456 mg of 4-hydroxy-4-vinyl-1-iodo-trans-1-octene and 320 mg of imidazole in 1.0 ml of dimethylformamide is added 0.23 ml of chlorotrimethylsilane during 3 minutes. The mixture is stirred at room temperature for 22 hours and partitioned with a mixture of cold hexane and water. The hexane layer is washed repeatedly with water and then brine, dried over magnesium sulfate, and concentrated to give an oil, pmr spectrum (CDCl$_3$): 0.13 (s, trimethylsiloxy group) and 2.32 (d, =CHC$\underline{H}_2$).

EXAMPLE 195

Preparation of n-butyl cyclopropyl ketone

To a vigorously-stirred solution of 31.0 g of cyclopropanecarboxylic acid in 330 ml of ether is added a solution of n-butyllithium (748 mmoles) in about 750 ml of 2:1 ether-hexane during one hour at 5°–10° C. The resulting suspension is diluted with 300 ml of ether and stirred at room temperature for 2 hours and at reflux for 2 hours. The mixture is cooled and poured into several portions of 1:1 ice:4 N hydrochloric acid. The ethereal phases are combined and washed with brine, sodium carbonate solution, and brine. The extract is dried over magnesium sulfate and concentrated. The residue is distilled to provide a liquid, bp-102°–104° C. (80 mm), pmr spectrum (CDCl$_3$): δ2.55 (triplet, —C$\underline{H}_2$CO—).

EXAMPLE 196

Preparation of 4-cyclopropyl-4-hydroxy-1-octyne

To a stirred, refluxing suspension of amalgam prepared from 6.2 g of magnesium and 50 mg of mercuric chloride suspended in 60 ml of ether is added a solution of a mixture of 30.4 g of n-butyl cyclopropyl ketone (Example 189) and 29.8 g of propargyl bromide in 65 ml of ether during 60 minutes. After reaction at reflux temperature for an additional 30 minutes, the mixture is cooled to 0° C. and treated with 35 ml of saturated ammonium chloride. The mixture is diluted with ether and filtered through Celite. The filtrate is washed with brine, dried over potassium carbonate, and concentrated. The residue is distilled to provide a liquid, δ0.43 (cyclopropyl hydrogens), 2.07 (triplet, HC≡C), and 2.44 (doublet, C≡CC$\underline{H}_2$).

EXAMPLE 197

Preparation of 4-cyclopropyl-4-trimethylsiloxy-1-octyne

To a stirred solution of 27.8 g of 4-cyclopropyl-4-hydroxy-1-octyne (Example 190) and 33.3 g of imidazole in 130 ml of dimethylformamide at 5° C. is added 24 ml of chlorotrimethylsilane during 5 minutes. The solution is stirred at ambient temperature for 17 hours and then partitioned with 600 ml of hexane and 250 ml of ice water. The hexane phase is separated and washed successively with water and brine. The solution is dried over magnesium sulfate and evaporated to give a liquid, pmr spectrum (CDCl$_3$): δ0.12 (singlet, trimethylsiloxy group), 2.02 (triplet, $\underline{H}$C≡C), and 2.45 (doublet, C≡C$\underline{H}_2$).

EXAMPLE 198

Preparation of 4-cyclopropyl-4-trimethylsiloxy-1-(tri-n-butylstannyl)-trans-1-octene A stirred mixture of 23.8 g of 4-cyclopropyl-4-trimethylsiloxy-1-octyne (Example 191), 28 ml of tri-n-butyltin hydride, and 50 mg of azobisisobutyronitrile under nitrogen is heated to 85° C. After the resulting exothermic reaction subsides the mixture is heated at 130° C. for one hour. The crude product is evaporatively distilled to give a liquid, pmr spectrum (CDCl$_3$): δ0.10 (trimethylsiloxy group), 2.33 (doublet, =CHC$\underline{H}_2$), and 6.02 (vinyl hydrogens).

EXAMPLES 199–204a

Treatment of the starting carboxylic acids of Table 24 with the appropriate alkyllithium by the method of Example 190 provides the product ketones of the table.

TABLE 24

| Example | Starting Carboxylic Acid | Alkyl Lithium | Product Ketone |
|---|---|---|---|
| 199 | cyclopropane carboxylic acid | n-hexyllithium | n-hexylcyclopropyl ketone |
| 200 | cyclopropane carboxylic acid | n-propyllithium | n-propylcyclopropyl ketone |
| 201 | acrylic acid | n-hexyllithium | n-hexylvinyl ketone |
| 202 | acrylic acid | n-propyllithium | n-propylvinyl ketone |
| 203 | crotonic acid | n-butyllithium | n-butyl-1-propenyl ketone |
| 204 | crotonic acid | n-hexyllithium | n-hexyl-1-propenyl-ketone |
| 204a | acrylic acid | n-butyllithium | n-butylvinyl ketone |

EXAMPLES 205–210E

Treatment of the starting ketones of Table 25 with propargymagnesium bromide by the procedure of Example 190 followed by treatment with chlorotrimethylsilane by the procedure of Example 191 followed by treatment with tri-n-butyltin hydride by the method of Example 192 is productive of the vinylstannyl derivatives of the table.

TABLE 25

| Example | Starting Ketone | Product Vinylstannyl Derivative |
|---|---|---|
| 205 | 199 | (E)4-trimethylsilyloxy-4-cyclopropyl-1-tri-n-butylstannyldecene |
| 206 | 200 | (E)4-trimethylsilyloxy-4-cyclopropyl-1-tri-n-butylstannylheptene |
| 207 | 201 | (E)4-trimethylsilyloxy-4-vinyl-1-tri-n-butylstannyldecene |
| 208 | 202 | (E)4-trimethylsilyloxy-4-vinyl-1-tri-n-butylstannylheptene |
| 209 | 203 | (E)4-trimethylsilyloxy-4-(1-propenyl)-1-tri-n-butylstannyloctene |
| 210 | 204 | (E)4-trimethylsilyloxy-4-(1-propenyl)-1-tri-n-butylstannyldecene |
| 210A | 204a | (E)4-trimethylsilyloxy-4-vinyl-1-tri-n-butylstannyloctene |
| 210B | 2-hexanone | (E)-4-trimethylsilyloxy-4-methyl-1-tri-n-butylstannyloctene |
| 210C | 3-heptanone | (E)-4-trimethylsilyloxy-4-ethyl-1-tri-n-butylstannyloctene |
| 210D | 3-octanone | (E)-4-trimethylsilyloxy-4-ethyl-1-tri-n-butylstannylnonene |
| 210E | 3-hexanone | (E)-4-trimethylsilyloxy-4-ethyl-1-tri-n-butylstannylheptene |

EXAMPLE 210F n-Butyl trimethylsilylethynyl ketone

To a stirred solution of 14.4 g of valeryl chloride and 20.4 g of bis-trimethylsilylacetylene in 300 ml of dry methylene chloride, cooled in an ice bath, is added powdered anhydrous aluminum chloride, portionwise, over a period of 20 minutes. The mixture is stirred for 5 minutes, then the cooling bath is removed and the mixture is stirred at room temperature for 4 hours. The mixture is poured into 500 ml of ice-water. The organic layer is separated, washed with water and brine, dried over anhydrous sodium sulfate and filtered through diatomaceous earth. The mother liquor is evaporated to dryness giving a brownish residue. This residue is Kugelrohr-distilled to give 16.56 g of colorless liquid at 45° C./0.3 mm which is essentially identical with the authentic product.

EXAMPLE 210G

4-Trimethylsilylethynyl-1-octyn-4-ol

To a stirred suspension of 1.29 g of magnesium and 10 mg of mercuric chloride in 12 ml of ether is added 0.4 ml of propargyl bromide. The reaction is initiated after stirring at room temperature for a few minutes. The stirred mixture is cooled in an ice-water bath and a solution of 9.64 g of n-butyl trimethylsilylethynyl ketone and 3.51 ml of propargyl bromide in 13 ml of ether is added dropwise so that the mixture is very gently boiling during 40 minutes. After addition, the cooling bath is removed and the mixture is stirred at room temperature for 1.5 hours. The mixture is recooled in an ice bath and 10 ml of saturated ammonium chloride solution is added. The resulting white mixture is filtered through diatomaceous earth. The clear mother liquor is washed with saturated sodium chloride solution and dried over anhydrous magnesium sulfate. The solvent is evaporated to dryness giving 10.5 g of a red liquid. This liquid is Kugelrohr-distilled at 60° C./0.25–0.3 mm. The pale yellow liquid distillate which is the desired product weighs 8.5 g.

EXAMPLE 210H

4-Trimethylsilylethynyl-1-octyn-4-ol trimethylsilyl ether

To a stirred mixture of 8.5 g of 4-trimethylsilylethynyl-1-octyn-4-ol and 6.2 g of imidazole in 24 ml of dry dimethylformamide is added, under nitrogen, 5.7 ml of chlorotrimethylsilane, in a slow stream, via a syringe. The mixture is stirred in an ice bath for one hour and then at room temperature overnight. The mixture is poured into hexane, washed with saturated sodium bicarbonate solution, water and then brine and dried over sodium sulfate. The solvents are evaporated to dryness giving 11.1 g of the desired product.

EXAMPLE 210I

4-Trimethylsilylethynyl-4-trimethylsiloxy-1-octen-1-tri-n-butyl stannane

To a mixture of 10 mg of azobisisobutyronitrile and 2.94 g of 4-trimethylsilylethynyl-1-octyn-4-ol trimethylsilyl ether is added 2.65 ml of tri-n-butyl stannane via a syringe. The mixture is stirred and heated under nitrogen in an oil bath at 130° C. for 3 hours and then cooled to room temperature. This mixture is vacuum-distilled through a short-path distillation apparatus to remove a forerun at 40° C./0.4 mm. The yellow oil (pot residue) comprises the desired product.

EXAMPLES 210J–210M

Treatment of the acid chlorides of Table 1 by the procedure of Example 210F with bis-trimethylsilylacetylene is productive of the ketones of Table 25A.

TABLE 25A

| Example | Starting Acid Chloride | Product Alkyl Trimethyl-silylethynyl Ketone |
|---|---|---|
| 210L | butyryl chloride | n-propyl trimethylsilyl-ethynyl ketone |
| 210M | heptanoyl chloride | n-hexyl trimethylsilyl-ethynyl ketone |

EXAMPLES 210N–210O

Treatment of the ketones of Table 25B by the procedure of Example 210G is productive of the 4-trimethylsilylethynyl-1-alkyn-4-ol's of the Table.

TABLE 25B

| Example | Starting Ketone | Product 4-Trimethylsilyl-ethynyl-1-alkyn-4-ol |
|---|---|---|
| 210N | 210L | 4-trimethylsilylethynyl-1-heptyn-4-ol |
| 210O | 210M | 4-trimethylsilylethynyl-1-decyn-4-ol |

EXAMPLES 210P–210O

Treatment of the alkyn-4-ol's of Table 25B with chlorotrimethylsilane by the procedure of Example 210H followed by treatment of the resulting trimethylsilylether with tri-n-butylstannane by the procedure of Example 210I is productive of alkenes of Table 25C.

TABLE 25C

| Example | Starting Alkyn-4-ol | Product Alkene |
|---|---|---|
| 210P | 210N | (E)4-trimethylsilylethynyl-4-trimethylsiloxy-1-tri-n-butylstannane-1-heptene |

TABLE 25C-continued

| Example | Starting Alkyn-4-ol | Product Alkene |
|---------|---------------------|----------------|
| 210Q | 210O | (E)4-trimethylethynyl-4-trimethylsilyloxy-1-tri-n-butylstannane-1-decene |

EXAMPLE 211

Preparation of trans-1-Hydroxy-2-(3-trifluoromethyl)phenoxycyclopentane

A mixture of 88 g of cyclopentene oxide, 150.7 g of 3-trifluoromethylphenol, 5.0 g of sodium hydroxide in 30 ml of water and 4.0 g of methyltricaprylyl ammonium chloride is stirred at 70°–80° C. for 51 hours and at 25° C. for 96 hours. The mixture is then diluted with methylene chloride and poured into water. The organic layer is washed with dilute sodium hydroxide solution and water. The solution is dried over magnesium sulfate. The solvent is removed giving 221.5 g of a liquid which is distilled (bp 110°–113° C. 0.8 mm) giving trans-1-hydroxy-2-(3-trifluoromethyl)phenoxycyclopentane.

EXAMPLE 212

In the manner described above in Example 211 from 4-fluorophenol and cyclopentane epoxide is prepared trans-1-hydroxy-2-(4-fluoro)phenoxycyclopentane.

EXAMPLE 213

In the manner described above in Example 211 from 3-chlorophenol and cyclopentane epoxide is prepared trans-1-hydroxy-2-(3-chloro)phenoxycyclopentane.

EXAMPLE 214

Preparation of 2-(3-Trifluoromethylphenoxy)cyclopentanone

To a suspension of 327.43 g of pyridinium chlorochromate in one liter of methylene chloride is added 220 g of trans-1-hydroxy-2-(3-trifluoromethylphenoxy)cyclopentane in 500 ml of methylene chloride. The mixture is stirred for 2 hours 15 minutes. Another 50 g of the oxidizing agent is added and the mixture is stirred for 4½ hours. The mixture is diluted with ether and decanted from a black residue which is washed with more ether. The combined solutions are filtered through silica gel. The solvent is removed. The residue is dissolved in ether and again filtered through silica-gel. The solvent is removed and the residue is distilled (bp 113°–116° C., 1.5 mm) to give 188 g of 2-(3-trifluoromethylphenoxy)cyclopentanone.

EXAMPLE 215

In the manner described above for Example 214 is prepared from the product of Example 212; 2-(4-fluorophenoxy)cyclopentanone.

EXAMPLE 216

In the manner described above for Example 214 is prepared from the product of Example 213; 2-(3-chlorophenoxy)cyclopentanone.

EXAMPLE 217

Preparation of 1R,2S(and 1S,2R)-1-Ethynyl-1-hydroxy-2-butylcyclopentane and 1R,2R(and 1S,2S)-1-ethynyl-1-hydroxy-2-butylcyclopentane Into 150 ml of dry tetrahydrofuran is bubbled purified acetylene, as a solution of 2.4 M n-butyl magnesium chloride (92 ml) is added dropwise with stirring over a 2 hour period. To the resulting solution of acetylene magnesium chloride is added 21 g of 2-butylcyclopentanone in 50 ml of tetrahydrofuran dropwise over 15 minutes. The solution is stirred for 30 minutes and then is poured into an ice cold solution of saturated ammonium chloride. The mixture is acidified to pH 5 and extracted with ether. The ether solution is washed with brine and dried over magnesium chloride. The ether is removed and the residue is distilled giving 14.8 g of a colorless liquid. This is chromatographed on a dry column of silica-gel eluting with benzene-ethyl acetate (19:1) to separate isomers giving 1R,2S(and 1S,2R)-1-ethynyl-1-hydroxy-2-butylcyclopentane and 1R,2R(and 1S,2S)-1-ethynyl-1-hydroxy-2-butylcyclopentane.

EXAMPLE 218

Preparation of 1-propargyl-1-hydroxycyclohexane

A stirred suspension of 121.6 g (5.0 mol) of magnesium in 1-l of anhydrous ether is treated with 0.6 g of mercuric chloride and about 100 mg of iodine. After several minutes, 3 ml of propargyl bromide is added and if no exotherm is noted, a small amount of reacting propargyl bromide and magnesium in ether is added. When the reaction begins, a mixture of 5.0 mol of cyclohexanone and 595 g (5.0 mol) of propargyl bromide is added dropwise at a rate that produces vigorous refluxing of the solution. (The propargyl bromide must always be present in some excess otherwise the reaction will stop. If this happens, the addition of about 1 ml of propargyl bromide will restart the reaction.) After about half of the propargyl bromide-cyclohexanone mixture has been added, another 500–750 ml of ether is used to dilute the reaction mixture. At the end of the addition, the reaction mixture is refluxed for at least 0.5 hour, cooled and poured into 4 liters of saturated ammonium chloride during good stirring. The ethereal layer is separated and the aqueous layer is washed with ether several times and the combined extract is washed twice with saturated sodium chloride solution and dried over anhydrous magnesium sulfate. Evaporation of the ether yields 583 g (630 g theory) of a dark oil which is distilled giving purified 1-propargyl-1-hydroxycyclohexane.

EXAMPLES 219–238

In the manner of Examples 217 and 218 described above, the following acetylenic alcohols listed in Table 26 were prepared from the acetylenic Grignard reagent and ketone specified.

TABLE 26

| Example | Grignard Reagent | Ketone | Acetylenic Alcohol |
|---------|------------------|--------|---------------------|
| 219 | acetylene magnesium chloride | cyclohexanone | 1-ethynyl-1-hydroxycyclohexane |
| 220 | acetylene magne- | cyclopentanone | 1-ethynyl-1-hydroxycyclopentane |

TABLE 26-continued

| Example | Grignard Reagent | Ketone | Acetylenic Alcohol |
|---|---|---|---|
| 221 | acetylene magnesium chloride | cycloheptanone | 1-ethynyl-1-hydroxycycloheptane |
| 222 | acetylene magnesium chloride | 3-propylcyclopentanone | 1R,3S-(and 1S,3R-) 1-ethynyl-1-hydroxy-3-propylcyclopentane |
| 223 | acetylene magnesium chloride | 3-propylcyclopentanone | 1R,3R-(and 1S,3S-) 1-ethynyl-1-hydroxy-3-propylcyclopentane |
| 224 | acetylene magnesium chloride | 2-butylcyclohexanone | 1R,2S-(and 1S, 2R-) 1-ethynyl-1-hydroxy-2-butylcyclohexane |
| 225 | acetylene magnesium chloride | 2-butylcyclohexanone | 1R,2R-(and 1S,2S-) 1-ethynyl-1-hydroxy-2-butylcyclohexane |
| 226 | acetylene magnesium chloride | 2-(3-trifluoromethylphenoxy)-cyclopentanone | 1R,2S-(and 1S,2R-) 1-ethynyl-1-hydroxy-2-(3-trifluoromethylphenoxy)cyclopentane |
| 227 | acetylene magnesium chloride | 2-(3-trifluoromethylphenoxy)-cyclopentanone | 1R,2R-(and 1S,2S-) 1-ethynyl-1-hydroxy-2-(3-trifluoromethylphenoxy)cyclopentane |
| 228 | acetylene magnesium chloride | 2-(4-fluorophenoxy)cyclopentanone | 1R,2S-(and 1S,2R-) 1-ethynyl-1-hydroxy-2-(4-fluorophenoxy)cyclopentane |
| 229 | acetylene magnesium chloride | 2-(4-fluorophenoxy)cyclopentanone | 1R,2R-(and 1S,2S-) 1-ethynyl-1-hydroxy-2-(4-fluorophenoxy)cyclopentane |
| 230 | acetylene magnesium chloride | 2-(3-chlorphenoxy)-cyclopentanone | 1R,2S-(and 1S,2R-) 1-ethynyl-1-hydroxy-2-(3-chlorophenoxy)cyclopentane |
| 231 | acetylene magnesium chloride | 2-(3-chlorophenoxy)-cyclopentanone | 1R,2R-(and 1S,2S-) 1-ethynyl-1-hydroxy-2-(3-chlorophenoxy)cyclopentane |
| 232 | acetylene magnesium chloride | 3-methylcyclohexanone | 1R,3S-(and 1S,3R-) 1-ethynyl-1-hydroxy-3-methylcyclohexane |
| 233,234 | acetylene magnesium chloride | 3-methylcyclohexanone | 1R,3R(and 1S,3S-) 1-ethynyl-1-hydroxy-3-methylcyclohexane |
| 235 | propargyl magnesium bromide | 2-butylcyclopentanone | 1R,2S-(and 1S,2R-) 1-propargyl-1-hydroxy-2-butylcyclopentane |
| 236 | propargyl magnesium bromide | 2-butylcyclopentanone | 1R,2R-(and 1S,2S-) 1-propargyl-1-hydroxy-2-butylcyclopentane |
| 237 | propargyl magnesium bromide | 2-(3-trifluoromethylphenoxy)-cyclopentanone | 1R,2S-(and 1S,2R-) 1-propargyl-1-hydroxy-2-(3-trifluoromethylphenoxy)cyclopentane |
| 238 | propargyl magnesium bromide | 2-(3-trifluoromethylphenoxy)-cyclopentanone | 1R,2R-(and 1S,2S-) 1-propargyl-1-hydroxy-2-(3-trifluoromethylphenoxy)cyclopentane |

EXAMPLE 239

Preparation of 1R,2S(and 1S,2R)-1-Ethynyl-1-trimethylsilyloxy-2-butylcyclopentane To a solution of 29.4 g of 1R,2S(and 1S,2R)-1-ethynyl-1-hydroxy-2-butylcyclopentane and 30.2 g of imidazole in 180 ml of dimethylformamide is added at 0° C. with stirring 24.1 g of trimethylsilylchloride. The mixture is stirred for 3 hours. The mixture is poured into 700 ml of hexane and washed twice with water and once with brine. The ether solution is dried over magnesium sulfate. The solvent is removed and the residue is distilled (bp 64°–72° C., 0.6 mm) to give 35.8 g of 1R,2S(and 1S,2R)-1-ethynyl-1-trimethylsilyloxy-2-butylcyclopentane.

EXAMPLE 240

Preparation of 1R,2R(and 1S,2S)-1-Ethynyl-1-trimethylsilyloxy-2-butylcyclopentane To a mixture of 45.0 g of 1R,2R(and 1S,2S)-1-ethynyl-1-hydroxy-2-butylcyclopentane and 46.2 g of imidazole in 255 ml of dimethylformamide at 0° C. under nitrogen is added 36.9 g of trimethylsilylchloride. The mixture is stirred at room temperature for 3 hours and then poured into 700 ml of hexane. Water is added, the organic layer is separated and the water layer is extracted with hexane. The combined hexane solutions are washed twice with water and dried over magnesium sulfate. The solvent is removed and the residue is distilled giving the product as 53 g of a colorless oil.

EXAMPLE 241

Preparation of 1-Ethynyl-1-trimethylsilyloxycyclohexane

A 194 g portion of imidazole and 158.2 g of 1-ethynylcyclohexan-1-ol are mixed with 500 g of dimethylformamide with cooling in an ice bath. A 152 g portion of trimethylchlorosilane is added with cooling and stirring in about one minute. The mixture is stirred for one hour and allowed to stand overnight. One liter of hexane is added. The lower layer is separated, diluted with water and extracted with hexane. The hexane layers are washed several times with water and then combined and dried over magnesium sulfate. Filtration and then evaporation of the hexane gives 198.5 g of product which is distilled giving 168 g of the desired product.

EXAMPLE 242

Preparation of 1-Propargyl-1-trimethylsilyloxycyclohexane

To a stirred solution of 55.4 g of 1-(2-propyn-1-yl)cyclohexanol [H. Gutmann, et al., *Helv. Chim. Acta*, 42, 179 (1959)] and 79 g of imidazole in 240 ml of DMF at 10° C. initially is added 56 ml of chlorodimethylsilane during 10 minutes. The cloudy yellow solution is stirred at room temperature for 26 hours. The resulting mixture is partitioned between 1000 ml of hexane and 400 ml of water at 0°–5° C. The hexane phase is washed successively with 6×200 ml of cold water and 200 ml of brine. The extract is dried over magnesium sulfate, filtered, and evaporated to give 85 g of colorless liquid, i.r. (film) :1240 and 830 cm$^{-1}$ (trimethylsilyloxy group).

EXAMPLE 243

Preparation of 1R,2S(and 1S,2R)-1-(trans-2-Iodovinyl)-1-trimethylsilyloxy-2-butylcyclopentane To a mixture of 9.2 g of sodium borohydride and 45.8 g of 2-methyl-2-butene in 350 ml of dry tetrahydrofuran at 0° C. with stirring under nitrogen is added, over 20 minutes, 41.1 ml of boron trifluoride etherate. After 3 hours, to this resulting solution of diisomaylborane is added 38.8 g of 1R,2S(and 1S,2R)-1-ethynyl-1-trimethylsilyloxy-2-butycyclopentane in 40 ml of tetrahydrofuran in 20 minutes. The mixture is stirred 2 hours and then stored at −20° C. overnight. The mixture is allowed to warm to 0° C. and at 0° C. 85 g of dry trimethylamineoxide is added portionwise over 20 minutes. After stirring at 25° C. for one hour, the mixture is filtered through diatomaceous earth. The filtrate is poured simultaneously with a solution of 230 g of iodine in 250 ml of tetrahydrofuran into a stirred, cold solution of 430 g of sodium hydroxide in 1900 ml of water. After stirring for 30 minutes, the organic layer is separated. The aqueous layer is extracted with ether. The combined organic solutions are washed twice with a saturated solution of sodium thiosulfate and once withbrine. The solution is dried over magnesium sulfate, the solvent is removed and the residue is dissolved in hexane. The hexane solution is filtered through diatomaceous earth and silica gel. The hexane is removed and the residue is purified by dry column chromatography on silica gel eluting with hexane: 45.35 g of 1R,2S(and 1S,2R)-1-(trans-2-iodovinyl)-1-trimethylsilyloxy-2-butylcyclopentane is obtained.

EXAMPLE 244

Preparation of 1R,2R(and 1S,2S)-1-(trans-2-Iodovinyl)-1-trimethylsilyloxy-2-butylcyclopentane To a mixture of 12.22 g of sodium borohydride and 60.82 g of 2-methyl-2-butene in 450 ml of tetrahydrofuran under nitrogen at 0° C., is added 54.6 ml of boron trifluoride ehterate, dropwise over a 20 minute period. The solution is stirred at 0° C. for 2 hours and then at room temperature for 30 minutes. This solution is cooled to 0° C. and 55.5 g of 1R,2R(and 1S,2S)-1-ethynyl-1-trimethylsilyloxy-2-butylcyclopentane in 50 ml of tetrahydrofuran is added. The mixture is allowed to stand in a cold room overnight. To this mixture at 0° C. is added with stirring 112.8 g of trimethylamine oxide over a 20 minute period. The mixture is stirred at room temperature for 90 minutes and then filtered. To the filtrate is added simultaneously a solution of 565 g of sodium hydroxide in 2000 ml of water and a solution of 300 g of iodine in 300 ml of tetrahydrofuran. The mixture is stirred 30 minutes, the organic layer is separated and the aqueous layer is extracted with ether. The combined organic solutions are washed with saturated sodium thiosulfate solution and with saturated sodium chloride solution. The solution is dired with magnesium sulfate and filtered through a pad of silica gel. The solution is removed giving an orange liquid which is chromatographed on a dry column of silica gel giving 59.5 g of the product as a yellow liquid.

EXAMPLE 245

Preparation of 1-(3-Tri-n-butylstannyl-2-trans-propenyl)-1-trimethyl-silyloxycyclohexane To a stirred mixture of 31.5 g of 1-propargyl-1-trimethylsilyloxycyclohexane and 150 mg of azobisisobutyronitrile is added 41 ml of tri-n-butyltin hydride. The stirred mixture is heated to about 80° C. The initial exothermic reaction is moderated, and the temperature is subsequently maintained at 130°–135° C. for one hour.

The product is distilled to afford 56 g of colorless liquid, bp 150°–160° C.(0.15–0.3 mm), pmr (CDCl$_3$): 6.0 (multiplet, vinyl protons).

EXAMPLES 246-265

Using the procedure outlined above for Examples 239–242, the acetylenic alcohols listed in Table 27 are converted to their corresponding acetylenic trimethylsilyloxy derivative these in turn using the procedure outlined above for Examples 243 and 244, were converted to their corresponding trans-2-iodovinyl derivatives or using the procedure outlined above for Example 245, were converted to their corresponding trans-2-tri-n-butylstannyl derivatives (Table 27).

TABLE 27

| Example | Acetylene of Example | Method of Example | Vinyl Iodide or Vinyl Tin Compound |
|---|---|---|---|
| 246 | 219 | 244 | 1-(trans-2-iodovinyl)-1-trimethylsilyloxy-cyclohexane |
| 247 | 220 | 244 | 1-(trans-2-iodovinyl)-1-trimethylsilyloxy-cyclopentane |
| 248 | 221 | 245 | 1-(trans-2-tri-n-butylstannylvinyl)-1-trimethylsilyloxycycloheptane |
| 249 | 222 | 244 | 1R,3S-(and 1S,3R-) 1-(trans-2-iodovinyl)-1-trimethylsilyloxy-3-propylcyclopentane |
| 250 | 223 | 244 | 1R,3R-(and 1S,3S-) 1-(trans-2-iodovinyl)-1-trimethylsilyloxy-3-propylcyclopentane |
| 251 | 217 | 244 | 1R,2R-(and 1S,2S-) 1-(trans-2-iodovinyl)-1-trimethylsilyloxy-2-butylcyclopentane |
| 252 | 224 | 244 | 1R,2S-(and 1S,2R-) 1-(trans-2-iodovinyl)-1-trimethylsilyloxy-2-butylcyclohexane |
| 253 | 225 | 244 | 1R,2R-(and 1S,2S-) 1-(trans-2-iodovinyl)-1-trimethylsilyloxy-2-butylcyclohexane |
| 254 | 226 | 245 | 1R,2S-(and 1S,2R-) 1-(trans-2-tri-n-butyl-stannylvinyl-1-trimethylsilyloxy-2-(3-trifluoromethylphenoxy)cyclopentane |
| 255 | 227 | 245 | 1R,2R-(and 1S,2S-) 1-(trans-2-tri-n-butyl-stannylvinyl)-1-trimethylsilyloxy-2-(3-trifluoromethylphenoxy)cyclopentane |
| 256 | 228 | 244 | 1R,2S-(and 1S,2R-) 1-(trans-2-iodovinyl)- |

TABLE 27-continued

| Example | Acetylene of Example | Method of Example | Vinyl Iodide or Vinyl Tin Compound |
|---------|---------------------|-------------------|-------------------------------------|
| | | | 1-trimethylsilyloxy-2-(4-fluorophenoxy)-cyclopentane |
| 257 | 229 | 244 | 1R,2R-(and 1S,2S-) 1-(trans-2-iodovinyl)-1-trimethylsilyloxy-2-(4-fluorophenoxy)-cyclopentane |
| 258 | 230 | 245 | 1R,2S-(and 1S,2R-) 1-(trans-2-tri-n-butyl-stannylvinyl)-1-trimethylsilyloxy-2-(3-chlorophenoxy)cyclopentane |
| 259 | 231 | 245 | 1R,2R-(and 1S,2S-) 1(-trans-2-tri-n-butyl-stannylvinyl-1-trimethylsilyloxy-2-(3-chlorophenoxy)cyclopentane |
| 260 | 232 | 244 | 1R,3S-(and 1S,3R-) 1-(trans-2-iodovinyl)-1-trimethylsilyloxy-2-methylcyclohexane |
| 261 | 234 | 244 | 1R,3R-(and 1S,3S-) 1-(trans-2-iodovinyl)-1-trimethylsilyloxy-3-methylcyclohexane |
| 262 | 235 | 245 | 1R,2S-(and 1S,2R-) 1-(3-tri-n-butylstannyl-2-trans-propenyl)-1-trimethylsilyloxy-2-butylcyclopentane |
| 263 | 236 | 245 | 1R,2R-(and 1S,2S-) 1-(3-tri-n-butylstannyl-2-trans-propenyl)-1-trimethylsilyloxy-butylcyclopentane |
| 264 | 237 | 245 | 1R,2S-(and 1S,2R-) 1-(3-tri-n-butylstannyl-2-trans-propenyl)-1-trimethylsilyloxy-2-(3-trifluoromethylphenoxy)cyclopentane |
| 265 | 238 | 245 | 1R,2R-(and 1S,2S-) 1-(3-tri-n-butylstannyl-2-trans-propenyl)-1-trimethylsilyloxy-2-(3-trifluoromethylphenoxy)cyclopentane |

REFERENCE EXAMPLE 266

2-Methylene Valaraldehyde

A mixture of 200 g. of valaraldehyde. 208.8 g. of 37% formalin and 226.7 g. of dimethylamine hydrochloride is heated with stirring at 90° C. for 24 hours and then steam distilled until no organic material distills over. The distillate is saturated with sodium chloride and the organic layer is separated and dried over magnesium sulfate then distilled, giving the desired product in the fraction boiling at 43°–45° C., 0.52 mm.

REFERENCE EXAMPLE 267

4-Hydroxy-5-methylene-1-octyne

To a stirred mixture of 12.16 g. of magnesium in 120 ml. of ether containing 200 mg. of mercuric chloride is added 2 ml. of propargyl bromide and 0.5 ml. of 1,2-dibromoethane. This mixture is stirred under argon until the reaction begins. To this is added with stirring a solution of 41.57 g. of 2-methylene valaraldehyde and 64.95 g. of propargyl bromide in 90 ml. of ether, dropwise, at a rate to maintain reflux. After addition is complete the mixture is refluxed 15 minutes, stirred at room temperature one hour, cooled to 0° C. and saturated ammonium chloride solution is added dropwise until reflux stops. The mixture is filtered through Celite, dried over magnesium sulfate and the ether is removed giving the product as a light orange oil.

REFERENCE EXAMPLE 268

5-Methylene-4-triethylsilyloxy-1-octyne

To a solution of 30.0 g. of 4-hydroxy-5-methylene-1-octyne and 31.02 g. of imidazole in 80 ml of dimethylformamide at 0° C., is added 40.9 g. of triehtychlorosilane. The mixture is stirred at room temperature for 30 minutes, poured into cold water and extracted with petroleum ether. The petroleum ether is removed and the residue is distilled. The product is recovered in the fraction boiling at 103°–106° C. (1.5 mm.).

REFERENCE EXAMPLE 269

5-Methylene-4-triethylsilyloxy-1-tri-n-butylstannyl-1-octene

A mixture of 20 g. of 5-methylene-4-triethylsilyloxy-1-octyne, 25.36 g. of tri-n-butylstannane and 0.1 g. of azobisisobutyrylnitrile is placed in an oil bath at 100° C. After 10 minutes an exotherm raises the temperature to 150° C. The mixture is then heated at 130°–140° C. for 1.5 hours. The excess tri-n-butylstannane is distilled off at 130° C. (1 mm.) and the residue is distilled in a Kugelrohr at 120°–140° C., 0.15–0.05 mm., giving the product as a colorless liquid.

REFERENCE EXAMPLE 270

3-Methylene-2-hexanone

A mixture of 100 g. of 2-hexanone, 90 g. of 30% formaline and 97.7 g. of dimethylamine hydrochloride is stirred at 85° C. for 24 hours. The mixture is then steam distilled. To the distillate is added 25 g. of potassium carbonate. The mixture is steam distilled. The organic layer is dried over magnesium sulfate and distilled in vacuo. The fraction boiling at 120°–126° C. is saved. To the residue is slowly added 46 g. of methyl iodide. The resulting paste is placed in an oil bath at 170° C. The distillate (120° C.) is collected, combined with the above distillate and redistilled in vacuo giving at 115°–119° C. the desired product.

REFERENCE EXAMPLE 271

4-Hydroxy-4-methyl-5-methylene-1-octyne

To a mixure of 5.0 g. of magnesium and 100 mg. of mercuric chloride in 10 ml. of ether is added with stirring, one ml. of dibromoethane. The mixture is stirred for 10 minutes and 0.5 ml. of propargyl bromide is added. An additional 50 ml. of ether is added, followed by a solution of 17.5 g. of 3-methylene-2-hexanone and 27.8 g. of propargyl bromide in 60 ml. of ether, dropwise at a rate to maintain vigorous reflux. The mixture is refluxed for ½ hour, cooled at 0° C. and saturated ammonium chloride solution is added dropwise. The mixture is filtered through Celite and the solids are washed with ether. The ether solution is dried over magnesium sulfate and the ether is removed giving the desired product.

REFERENCE EXAMPLE 272

4-Methyl-5-methylene-4-trimethylsilyloxy-1-octyne

To a solution of 25.77 g. of 4-hydroxy-4-methyl-5-methylene-1-octyne and 28.6 g. of imidazole in 50 ml. of dimethylformamide is added 22.9 g. of chlorotrimethylsilane. The mixture is stirred at room temperature for 40 minutes, poured into cold water and extracted with petroleum ether. The extract is washed with water and saturated sodium bicarbonate solution, dried over magnesium sulfate and the solvent is removed. The residue is distilled and the desired product recovered at 85°–87° C. (0.45 mm.) as a colorless liquid.

REFERENCE EXAMPLE 273

E-4-Methyl-5-methylene-4-trimethylsilyloxy-1-tri-n-butylstannyl-1-octyne

A mixture of 26 g. of 4-methyl-5-methylene-4-trimethylsilyloxy-1-octyne, 200 mg. of azoisobutyrylnitrile and 41.1 g. of tri-n-butylstannane is stirred under argon in an oil bath at 140° C. The mixture is stirred at 140°–150° C. for one hour under argon, then at 140°–150° C. for 1.5 hours under vacuum to remove excess tri-n-butylstannane. The residue is distilled via a Kugelrohr (150° C., 0.05 mm.) giving the desired product as a colorless liquid.

REFERENCE EXAMPLE 274

Treatment of the starting carbonyls of Table A with formalin by the procedure of Reference Examples 1 or 5 produces the α-methylenecarbonyl derivative which upon condensation with propargylic magnesium bromide by the procedure of Reference Examples 2 or 6 produces the hydroxy alkyne of Table A. Protection of the hydroxy alkynes of Table A with either chlorotriethylsilane according to the procedure of Reference Example 3 or chlorotrimethylsilane by the procedure of Example 6 produces the trialkylsilyloxy alkyne which upon treatment with tri-n-butylstannane by the procedure of Reference Examples 269 or 272 provides the trans-vinylstannanes of Table A.

TABLE A

| STARTING CARBONYL | α-METHYLENE CARBONYL COMPOUND | HYDROXY-ALKANE | TRIALKYLSILYL-OXY ALKYNE | TRANS-VINYL STANNANE |
|---|---|---|---|---|
| butyraldehyde | 2-methylene butryladehyde | 5-methylene-4-hydroxy-1-heptyne | 5-methylene-triethylsiloxy-1-heptyne | 1-trans-tri-n-butyl-stannyl-5-methylene-4-triethylsiloxy-1-heptene |
| 2-pentanone | 3-methylene-2-pentanone | 4-methyl-5-methylene-4-hydroxy-1-heptyne | 4-methyl-5-methylene-4-trimethylsiloxy-1-heptyne | 1-trans-tri-n-butyl-stannyl-4-methyl-5-methylene-siloxy-1-heptene |
| 3-hexanone | 2-methylene-3-hexanone | 4-ethyl-5-methylene-4-hydorxy-1-heptyne | 4-ethyl-5-methylene-4-trimethyl siloxy-1-heptyne | 1-trans-tri-n-butyl-stannyl-4-ethyl-5-methylene-4-trimethylsiloxy-1-heptene |
| Hexaldehyde | 2-methylene-hexaldehyde | 5-methylene-4-hydroxy-1-nonyne | 5-methylene-4-triethylsiloxy-1-nonyne | 1-trans-tri-n-butyl-stannyl-5-methylene-4-triethylsiloxy-1-nonene |
| 2-heptanone | 3-methylene-2-heptanone | 4-methyl-5-methylene-4-hydroxy-1-nonyne | 4-methyl-5-methylene-4-trimethylsiloxy-1-nonyne | 1-trans-tri-n-butyl stannyl-4-methyl-5-methylene-4-trimethyl-siloxy-1-nonene |
| 3-octanone | 4-methylene-3-octanone | 4-ethyl-5-methylene-4-hydroxy-1-nonyne | 4-ethyl-5-methylene-4-trimethyl-siloxy-1-nonyne | 1-trans-tri-n-butyl-stannyl-4-ethyl-5-methylene-4-trimethylsiloxy-1-nonene |
| heptaldehyde | 3-methylene-heptaldehyde | 5-methylene-4-hydroxy-1-decyne | 5-methylene-4-triethylsiloxy-1-decyne | 1-trans-tri-n-butyl stannyl-4-ethyl-5-methylene-4-triethylsiloxy-1-decene |
| 2-octanone | 3-methylene-1-octanone | 4-methyl-5-methylene-4-hydroxy-1-decyne | 4-methyl-5-methylene-4-trimethylsiloxy-1-decyne | 1-trans-tri-n-butyl stannyl-4-methyl-5-methylene-4-trimethylsiloxy-1-decene |
| 3-nonanone | 4-methylene-3-nonanone | 4-methyl-5-methylene-4-hydroxy-1-decyne | 4-ethyl-5-methylene-4-trimethylsiloxy-1-decyne | 1-trans-tri-n-butyl-stannyl-4-ethyl-5-methylene-4-trimethylsiloxy-1-decene |
| 3-heptanone | 4-methylene-3-heptanone | 4-ethyl-5-methylene-4-hydroxy-1-nonyne | 4-ethyl-5-methylene-4-trimethyl-siloxy-1-nonyne | 1-trans-tri-n-butyl stannyl-4-ethyl-5-methylene-4-trimethyl-siloxy-1-octene |

REFERENCE EXAMPLE 275

1,2-Octadien-4-one

To a stirred solution of 0.50 moles of propargylmagnesium bromide in 340 ml. of ether at −78° C. is added a solution of 65.2 g. (0.50 moles) of ethyl valerate in 100 ml. of ether during 60 minutes. The solution is stirred at −78° C. for 30 minutes and then hydrolyzed by pouring onto a mixture of ice and ether. The ether layer is washed with brine, treated with hydroquinone, dried over magnesium sulfate, and concentrated.

To a stirred, ice-cold solution of the liquid concentrate (94 g.) in 1200 ml. of tetrahydrofuran is added 60 ml. of 10% potassium carbonate solution. The resulting mixture is stirred at 0° C. for 2 hours, treated with 15 ml. of 4 N hydrochloric acid, and diluted with ether. The phy on silica gel with heptane solvent to afford the title compound as a liquid.

TABLE B

| STARTING ESTER | DIENONE | HYDROXY ALKYNE | SILOXY ALKYNE | IODOALKENE |
| --- | --- | --- | --- | --- |
| ethyl hexanoate | 1,2-nonadien-4-one | 4-hydroxy-4-propadienyl-1-nonyne | 4-propadienyl-4-trimethylsilyoxy-1-nonyne | 1-iodo-4-propadienyl-4-trimethylsiloxy-trans-1-nonyne |
| ethyl heptanoate | 1,2-decadien-4-one | 4-hydroxy-4-propadienyl-1-decyne | 4-propadienyl-4-trimethylsilyloxy-1-decyne | 1-iodo-4-propadienyl-4-trimethylsilyloxy-trans-1-decene |
| ethyl butyrate | 1,2-heptadien-4-one | 4-hydroxy-4-propadienyl-1-heptyne | 4-propadienyl-4-trimethylsilyoxy-1-heptyne | 1-iodo-4-propadienyl-4-trimethylsilyloxy-trans-1-heptene |
| ethyl-4-chloro-butyrate | 7-chloro-1,2-heptadiene-4-one | 7-chloro-4-hydroxy-4-propadienyl-1-heptyne | 7-chloro-4-propadienyl-4-trimethylsilyoxy-1-heptyne | 1-iodo-7-chloro-4-propadienyl-4-trimethylsilyloxy-trans-1-heptyne | organic layer is washed with brine, dried over magnesium sulfate, treated with hydroquinone and concentrated. The product is distilled to provide the title compound as a colorless liquid, b.p. ca 80° C. (15 mm.).

REFERENCE EXAMPLE 276

4-Hydroxy-propadienyl-1-octyne

To a stirred solution of 125 mmol. of propargylmagnesium bromide in 85 ml. of ether at −20° C. is added a solution of 11.7 g. (95 mmol.) of 1,2-octadien-4-one in 30 ml. of ether during 30 minutes. After the addition, the solution is stirred at 25° C. overnight, cooled to 0° C., and treated dropwise with 18 ml. of saturated ammonium chloride solution. The mixture is filtered, and the filtrate is washed with brine, dried over magnesium sulfate, and concentrated. The product is distilled from anhydrous potassium carbonate to provide the title compound as a colorless liquid, b.p. 84°–87° C. (8 mm.).

REFERENCE EXAMPLE 276a

4-Propadienyl-4-trimethylsilyloxy-1-octyne

To a stirred, ice-cold solution of 10.85 g. (66.1 mmol.) of 4-hydroxy-4-propadienyl-1-octyne and 13.2 g. (194 mmol.) of imidazole in 50 ml. of dimethylformamide at 0° C. is added 9.5 ml. of chlorotrimethylsilane. The solution is kept at 0° C. for 70 hours and diluted with petroleum ether. The resulting mixture is shaken with water at 0° C. The organic layer is washed with water and brine, dried over magnesium sulfate and concentrated to give the title compound as a liquid.

REFERENCE EXAMPLE 277

1-Iodo-4-propadienyl-4-trimethylsilyloxy-trans-1-octene

To a stirred solution of 2.36 g. (10 mmol.) of 4-propadienyl-4-trimethylsilyloxy-1-octyne in 5 ml. of glyme is added a solution of 11 mmol. of bis-(3-methyl-2-butyl)-borane in 15 ml. of glyme at 0° C. The mixture is stirred at 25° C. for 90 minutes, cooled to 0° C., and treated portionwise with 3.0 g. of triethylamine oxide. The stirred mixture is maintained at 25°–30° C. for 45 minutes, diluted with 20 ml. of tetrahydrofuran and poured into 100 ml. of ice-cold 15% sodium hydroxide solution, followed immediately with a solution of 8.0 g. of iodine in 20 ml. of tetrahydrofuran. The mixture is stirred at ambient temperature for 30 minutes and then extracted with ether. The extract is washed successively with water, sodium thiosulfate solution and brine; dried over magnesium sulfate; and filtered. The residue obtained after solvent evaporation is subjected to chromatography on silica gel with heptane solvent to afford the title compound as a liquid.

REFERENCE EXAMPLE 278

Treatment of the ethyl esters of Table A with propargyl magnesium bromide by the procedure of Example 275 followed by treatment with propargyl magnesium bromide by the procedure of Reference Example 276 followed by silyl ether formation by the procedure of Reference Example 277 followed by iodo vinylation by the procedure of Reference Example 269 is productive of the iodoalkenes and intermediates listed in Table B. The terms propadienyl and allenyl are used interchangeably in this application and refer to the —C≡C═CH$_2$ group.

REFERENCE EXAMPLE 279

1-Hydroxy-2-hexanone

To a stirred mixture of 25 g. of valeryl chloride and 122.6 g. of tris(trimethylsilyloxy)ethylene is added 9 drops of anhydrous stannic chloride. After stirring at room temperature for 1.5 hours, the mixture is poured slowly into a stirring mixture of 60 ml. of 0.6 N. hydrochloric acid and 120 ml. of tetrahydrofuran and stirred for one hour. Work up is by diluting with ether, washing with brine, saturated sodium bicarbonate and brine again, and drying over anhydrous sodium sulfate. The ether solution is evaporated to dryness to give 21.5 g. of liquid which is vacuum distilled to give 15.5 g. of colorless liquid at b.p. 70°–77° C./9 mm.; PMRδ 4.28(s), 2.42 (t, J=6).

REFERENCE EXAMPLE 280

1-Chloro-2-hexanone

To a stirred solution of 11.5 g. of 1-hydroxy-2-hexanone in 110 ml. of dimethylformamide is added 35 ml. of methanesulfonyl chloride dropwise during 10 minutes. The mixture is heated and stirred at 85° C. for 3 hours, then cooled in a ice-water bath. To this is added 50 ml. of water dropwise and the mixture is extracted with ether. The ether solution is washed with water and brine, dried, and then distilled to give 10.8 g. of product as a colorless liquid at b.p. 30°–32° C./4 mm.; PMR δ 4.12 (s), 2.60 (t, J=7).

REFERENCE EXAMPLE 281

4-Chloromethyl-4-hydroxy-1-octyne

To a stirred suspension of 2.1 g. of magnesium and 20 mg. of mercuric chloride in 25 ml. of ether is added 0.8 ml. of propargyl bromide. After a few minutes of vigorous stirring, to this is added a mixture of 10.75 g. of 1-chloro-2-hexanone and 7.2 ml. of propargyl bromide in 25 ml. of ether, at such a rate that the reaction mixture is maintained at 25°–28° C. After addition, the mixture is stirred at room temperature one hour, cooled in an ice-water bath and 30 ml. of saturated ammonium chloride is added dropwise. The mixture is filtered through celite and washed with ether. The ether solution is concentrated to give 11.0 g. of a yellow liquid which is vacuum distilled to give 6.9 g. of product as a colorless liquid at b.p. 60°–61° C./−4 mm.; PMR$\delta$ 3.62 (ABq, $CH_2Cl$), 2.53 (d, J=3,C≡C—$CH_2$), 2.06 (t, j=3, HC≡C).

REFERENCE EXAMPLE 282

4-Chloromethyl-4-trimethylsiloxy-1-octyne

To a stirred, ice-cold solution of 7.22 g. of 4-chloromethyl-4-hydroxy-1-octyne and 7.16 g. of imidazole in 28 ml. of dimethylformamide is added 6.5 ml. of trimethylchlorosilane via a syringe during 15 minutes. The resulting mixture is stirred at room temperature overnight, diluted with hexane and poured into a mixture of ice and saturated sodium bicarbonate solution. The hexane solution is separated, washed with saturated sodium bicarbonate, water and brine, dried over ahydrous sodium sulfate and concentrated in vacuo to give 11.8 g. of a colorless liquid which is vacuum distilled at b.p. 50°–57° C./3.5–4 mm. to give 9.7 g. of product as a colorless liquid; PMR $\delta$ 3.58 (s), 2.50 (d), 1.99 (t), 0.87 (s,OTMS).

REFERENCE EXAMPLE 283

1-Tri-n-butylstannyl-4-chloromethyl-4-trimethylsiloxy-trans-1-octene

A mixture of 9.27 g. of 4-chloromethyl-4-trimethylsilyloxy-1-octyne, 40 mg. of azoisobutyronitrile, and 10.0 ml. of tri-n-butyltin hydride is heated and stirred at 125° C. for 1.5 hours, then vacuum distilled through a short path to give, after a forerun, 19.5 g. of product as a colorless liquid at b.p. 140°–160° C./0.1–0.2 mm.; PRM$\delta$5.98 (m, olefin), 3.40 (s, $CH_2Cl$), 2.40 (m, C=C—$CH_2$), 0.14 (s,OTMS).

REFERENCE EXAMPLES 284 and 285

7-Chloro-4-hydroxy-4-methyl-1-heptyne

To a mixture of 6.69 g. of magnesium in 20 ml. of ether under argon, is added 0.1 g. of mercuric chloride and 0.1 g. of dibromoethane. The mixture is stirred for 10 minutes and 0.5 ml. of propargyl bromide is added. A 50 ml. portion of ether is added, followed by a solution of 30 g. of 5-chloro-2-pentanone and 32.55 g. of propargyl bromide in 45 ml. of ether with stirring, at a rate to maintain vigorous reflux. The mixture is stirred an additional 15 minutes, cooled to −5° C. and an ice cold saturated solution of ammonium chloride is added dropwise. The ether layer is decanted and filtered. The solids are washed with ether which is also filtered. The combined ether filtrates are washed with water, dried over magnesium sulfate and the solvent removed giving the product as an orange oil.

REFERENCE EXAMPLE 286

7-Chloro-4-methyl-4-trimethylsilyloxy-1-heptyne

To a solution of 7-chloro-4-hydroxy-4-methyl-1-heptyne in 80 ml. of dimethylformamide at 0° C., is added 43.8 g. (0.644 moles) of imidazole and 35.02 g. (0.322 moles of) chlorotrimethylsilane. The mixture is stirred at room temperature for 45 minutes, poured into water and extracted with hexane. The hexane solution is washed with dilute sodium bicarbonate solution, dried over magnesium sulfate and the solvent removed leaving an orange liquid. This liquid is distilled giving the desired product in the fraction boiling at 83°–88° C., 1.5 mm. as a colorless liquid.

REFERENCE EXAMPLE 287

E/Z-1-tri-n-butylstannyl-7-chloro-4-methyl-4-trimethylsilyloxy-1-heptyne

A stirred mixture of 15 g. of 7-chloro-4-methyl-4-trimethylsilyloxy-1-heptyne, 18.92 g. of tri-n-butylstannane 80 mg. of azobisisobutyrylnitrile, under argon is placed in a bath at 100° C. The mixture is heated at 140° C. for one hour. Excess tri-n-butylstannane is distilled off under vacuum. The residue is distilled via a Kugelrohr (130°–135° C., 0.03 mm.) to give the desired product as a colorless liquid.

REFERENCE EXAMPLE 288

E-7-Chloro-1-iodo-4-methyl-4-trimethylsilyloxy-1-heptene

To a solution of 9.1 g. of sodium borohydride and 44 g. of 2-methyl-2-butene in 390 ml. of tetrahydrofuran, at 0° C. under argon, is added dropwise with stirring 44.56 g. of boron trifluoride etherate. The mixture is stirred 1.5 hours at 0° C., 0.5 hour at room temperature, re-cooled to 0° C. and a mixture of 43 g. of 7-chloro-4-methyl-4-trimethylsilyloxy-1-heptene in 60 ml. of tetrahydrofuran is added over 10 minutes. The mixture is stirred 2 hours at room temperature, then 81.8 g. of trimethylamine oxide is added portionwise over 15 minutes at 0° C. The mixture is stirred 1.5 hours at room temperature, then filtered through Celite. To the filtrate is added simultaneously, a solution of 413.7 g. of sodium hydroxide in 2 liters of water and a solution of 211 g. of iodine in 350 ml. of tetrahydrofuran. The solution is stirred vigorously for 0.5 hour, the organic layer is separated and the aqueous layer is extracted with hexane. Most of the tetrahydrofuran is removed from the initial organic layer and it is combined with the hexane extract. The combined solution is washed twice with saturated sodium thiosulfate solution, brine, dried over magnesium sulfate and filtered through a pad of silica gel. The residue is distilled via a Kugelrohr at 115°–120° C., 0.15 mm. giving the desired product as a yellow oil.

REFERENCE EXAMPLE 289

Preparation of 7-Chloro-hept-1-en-2-one

To a suspension of 28 g. (0.21 mol.) of aluminum trichloride in 75 ml. of $CH_2Cl_2$ at −20° C. is added with stirring a mixture of 20 g. (0.2 mol.) of vinyltrimethylsilane and 28.2 g. (0.2 mol.) of 4-chlorobutrylchloride dropwise over 45 minutes. The mixture is stirred at −20° C. for 4 hours and kept at 0° for 18 hours. The mixture is poured into 300 g. of ice containing 50 g. $NH_4Cl$ and stirred until all solids are dissolved. The mixture is extracted with ether and the combined ether extracts are washed with saturated $NaHCO_3$ and dried ($MgSO_4$). The ether is removed in vacuo and the residue distilled (50°–60°, 0.125 mm.) to give a light yellow liquid (14.9 g.).

REFERENCE EXAMPLE 290

Preparation of 7-Chloro-4-hydroxy-4-vinyl-1-heptyne

To a suspension of 3.0 g. (0.12 mol.) of magnesium metal in 10 ml. ether containing 100 mg. $HgCl_2$ is added with stirring, under argon, 0.3 ml. of $CH_2CH_2B_2$. After 5 minutes a reaction is initiated and 0.5 g. of 80% propargylbromide in toluene is added. Upon evidence of a vigorous reaction, an additional 25 ml. of ether is introduced. A mixture of 13 g. (0.1 mol) of 7-chlorohept-1-en-2-one and 19.5 g. (0.12 mol.) of propargylbromide in 35 ml. ether is added at such a rate to maintain a vigorous reflux. After addition is complete, stirring is continued 10 minutes. The mixture is cooled to 0° C. and satd. $NH_4Cl$ is added slowly. The mixture is filtered through diatomaceous earth and the ether is removed in vacuo to provide the title product as an oil.

REFERENCE EXAMPLE 291

Preparation of 7-Chloro-4-trimethylsilyoxy-4-vinyl-1-heptyne

The alcohol from the previous example is dissolved in DMF (25 ml.) and 16.58 g. of imidazole and 13.3 g. of chlorotrimethylsilane is added. After stirring at ambient temperature for 1 hour, the reaction mixture is poured into ice water and extracted with petroleum ether. The organic extracts are washed with saturated $NaHCO_3$, and dried ($MgSO_4$), and concentrated in vacuo to provide an oil. This residue is distilled (76°–82°, 0.08 mm.) to afford 20.4 g. of the title product as a colorless oil.

REFERENCE EXAMPLE 292

Preparation of E-7-Chloro-4-trimethylsiloxy 4-vinyl-1-tri-n-butylstannyl-1-heptane A mixture of 7-chloro-4-trimethylsilyloxy-4-vinyl-1-heptyne (17 g., 0.07 mol.) and 20.7 g. (0.071 mol.) of tri-n-butylstannane and 150 mg. of azobisisobutrylnitrile (AIBN) is stirred under argon in a 140° oil bath behind a safety shield. After three minutes an exotherm occurs and the mixture is maintained at 140° C. for 1.5 hours. After cooling, air is admitted and the unreacted tri-n-butylstannane is removed by distillation via Kugelrohr (140°, 0.5–0.3 mm.) to give a very light yellow oil (30 g.). This oil consists of a mixture of the E and Z isomers.

REFERENCE EXAMPLE 293

4-Chloropropyl trimethylsilylethynyl ketone

To a stirred solution of 16.8 grams of 4-chlorobutryl chloride and 20.4 grams of bis-trimethylsilylacetylene in 300 ml. of dry methylene chloride, cooled in an ice bath, is added powdered anhydrous aluminum chloride, portionwise over a period of 20 minutes. The mixture is stirred for 5 minutes, then the cooling bath is removed and the mixture stirred at room temperature for 4 hours. The mixture is poured into 500 ml. of ice water. The organic layer is separated, washed with water and brine, dried over anhydrous sodium sulfate and filtered through diatomaceous earth. The clear mother liquor is evaporated to dryness giving a brownish residue. The residue is Kugelrohr-distilled to give a colorless liquid.

REFERENCE EXAMPLE 294

7-Chloro-4-hydroxy-4-trimethylsilylethynyl-1-heptyne

To a stirred suspension of 1.29 grams of magnesium and 10 mg. of mercuric chloride in 12 ml. of ether is added 0.4 ml. of propargyl bromide. The reaction is initiated after stirring at room temperature for a few minutes. The solution of 11.2 grams of 3-chloropropyl trimethylsilylethynyl ketone and 3.51 ml. of propargyl bromide in 13 ml. of ether is added dropwise so that the mixture is very gently boiled during a period of about 40 minutes. After addition is complete, the cooling bath is removed and the mixture is stirred at room temperature for about 1.5 hours. The mixture is recooled in an ice bath and 10 ml. of saturated ammonium chloride solution is added. The resulting white mixture is filtered through diatomaceous earth. The clear mother liquor is washed with saturated sodium chloride solution and dried over anhydrous magnesium sulfate. The solvent is evaporated to dryness giving a red liquid. The liquid is Kugelrohr-distilled to afford the pale yellow liquid distillate which is the desired product.

REFERENCE EXAMPLE 295

7-Chloro-4-trimethylsilyloxy-4-trimethylsilylethynyl-1-heptyne

To a stirred mixture of 8.5 grams of 7-chloro-4-hydroxy-4-trimethylsilylethynyl-1-heptyne (Example 29) and 6.2 grams of imidazole in 24 ml. of dry dimethylformamide is added, under nitrogen, 5.7 ml. of chlorotrimethylsilane, in a slow stream, via a syringe. The mixture is stirred in an ice bath for one hour and then at room temperature overnight. The mixture is poured into hexane, washed with saturated sodium bicarbonate solution, water and then brine and dried over sodium sulfate. The solvents are evaporated to dryness yielding the desired product.

REFERENCE EXAMPLE 296

E-7-Chloro-4-trimethylsilylethynyl-4-trimethylsiloxy-4-trimethylsilylethynyl-1-tributyl stannyl-1-heptene To a mixture of 10 mg. of azobisisobutyronitrile and 2.94 grams of 7-chloro-4-trimethylsilyloxy-4-trimethylsilylethynyl-1-heptene (Example 30) is added 2.65 ml. of tri-n-butyl stannane via a syringe. The mixture is stirred and heated under nitrogen in an oil bath at 130° C. for about 3 hours and then cooled to room temperature. The mixture is vacuum-distilled through a short-path distillation apparatus to remove a forerun of unreacted tri-n-butyl stannane. The yellow oil (pot residue) comprises the desired product as a mixture of E and Z isomers.

REFERENCE EXAMPLE 297

Preparation of E-7-Chloro-4-triethylsilyloxy-1-tri-n-butylstannyl-1-heptene

Treatment of 4-chlorobutyraldehyde by the procedures of Reference Examples 266 to 268 (utilizing chlorotriethylsilane) is productive of the title compound and the intermediates shown in Table D.

TABLE D

| STARTING CARBONYL | HYDROXYALKYNE | SILYLOXYALKYNE | VINYLSTANNANE |
|---|---|---|---|
| 4-chlorobutyraldekyde | 7-chloro-4-hydroxy-1-heptyne | 7-chloro-4-triethylsilyloxy-1-heptyne | E-7-chloro-4-triethylsilyloxy-1-tri-n-butylstannyl-1- |

TABLE D-continued

| STARTING CARBONYL | HYDROXYALKYNE | SILYLOXYALKYNE | VINYLSTANNANE |
|---|---|---|---|
| | | | heptene and the corresponding Z isomer |

REFERENCE EXAMPLE 298

1,1-Dimethoxy-2-hexanone

A mixture of 36.9 g. of washed 50% sodium hydride dispersion (0.77 moles) and 600 ml. of dimethylsulfoxide is heated under argon at 65° C. for 2 hours. At 0° C. is added dropwise, 50 g. (0.38 moles) of ethyl valerate. The solution is stirred at room temperature for 2 hours, then diluted with 1400 ml. of water and 70 ml. of concentrated hydrochloric acid and 75 g. of sodium chloride is added. The mixture is extracted four times with chloroform and the solution is dried (magnesium sulfate charcoal). The solvent is removed. The residue is dissolved in 700 ml. of methanol. A 55.65 g. (0.22 moles) portion of iodine is added and the solution is refluxed 90 minutes. The solvent is removed, the residue is dissolved in chloroform and the solution is washed twice with water and once with saturated sodium thiosulfate. The solution is dried (magnesium sulfate charcoal). The solvent is removed and the residue is distilled twice. The fraction boiling at 64°–72° C., 5 mm. is collected to give 28.3 gm. of the title compound. [T. L. Moore *J. Org. Chem.*, 32 786 (1967).]

REFERENCE EXAMPLE 299

4-Dimethoxymethyl-4-trimethylsiloxy-1-octyne p To a suspension of 5.31 g. (0.22 moles) of magnesium in 15 ml. of ether is added 100 mg. of mercuric chloride and 1.5 ml. of 1,2-dibromoethane. After the reaction begins, another 45 ml. of ether is added followed by the dropwise addition of a solution of 25 g. (0.16 moles of 1,1-dimethoxy-2-hexanone and 27.3 g. (0.2 moles) of 85% propargyl bromide in 45 ml. of ether at a rate which maintains reflux. Midway through the addition 15 ml. of tetrahydrofuran is added. After complete addition of the solution, the mixture is refluxed for 40 minutes. The mixture is cooled to 0° C. and saturated ammonium chloride solution is added followed by magnesium sulfate. The mixture is filtered through Celite and the solvent is removed. The residue is dissolved in 53 ml. of dimethylformamide and at 0° C. is added 24.4 g. (0.36 moles) of imidazole and 21.19 g. (0.20 moles) of trimethylchlorosilane. After stirring at 25° C. for 70 minutes, the solution is poured into water and extracted with hexanes. The organic layer is dried over magnesium sulfate and the solvent is removed. Distillation (75°–95° C., 0.3 mm.) gives 17.4 g. of the title compond.

REFERENCE EXAMPLE 300

E-1-tri-Butylstannyl-4-dimethoxymethyl-4-trimethylsiloxy-1-octene

A mixture of 10.0 g. (36.7 moles) of 4-dimethoxymethyl-4-trimethylsiloxy-1-oxtyne, 12.82 g. (44 moles) of tri-n-butylstannyl hydride and 100 mg. of azobisisobutyronitrile is heated to 140° C. under argon for 2 hours. The excess hydride is distilled off and the residue is purified by molecular distillation (bath temperature = 170°–175° C., 0.2 mm.) to give 20.5 g. of the title compound.

REFERENCE EXAMPLE 301

Treatment of the esters of Table E by the successive procedures of Examples 298-300 is productive of the dimethoxymethyl vinylstannanes of the Table.

TABLE E

| STARTING ESTER | PRODUCT DIMETHOXYMETHYL VINYL STANNANE |
|---|---|
| Ethyl butyrate | E-1-tributylstannyl-4-dimethoxymethyl-4 trimethylsilyloxy-1-heptene |
| Ethyl hexanoate | E-1-tributylstannyl-4-dimethoxymethyl-4-trimethylsilyloxy-1-nonene |
| Ethyl heptanoate | E-1-tributylstannyl-4-dimethoxymethyl-4-trimethylsilyloxy-1-decene |

REFERENCE EXAMPLE 302

1-Fluoro-2-hexanone

A solution of 26.5 g. of ethyl fluoroacetate in 350 ml. of ether is cooled in a dry ice-ethanol bath under nitrogen. To this is added 250 ml. of a solution comprising 110 ml. of 2.67 M n-butylmagnesium chloride in tetrahydrofuran which has been diluted with 140 ml. of ether, dropwise through a dropping funnel over a period of one hour. During this addition, the temperature of the reaction mixture is maintained at −65° C. to −72° C. After complete addition, 100 ml. of 15% aqueous sulfuric acid is added and the mixture is stirred at room temperature for one hour. The ether portion of the mixture is separated, washed with water, then brine, dried and then concentrated on a rotary evaporator at about 15° C. The concentrated solution is di⋯lled through a Vigorox column to remove a forerun (b.p. 40°–80° C./760 mm) and then the product is collected at 30°–35° C./14 mm.

REFERENCE EXAMPLE 303

4-Fluoromethyl-4-hydroxy-1-octyne

A 0.25 ml. of portion of propargyl bromide is added to a stirred suspension of 0.73 g. of magnesium and 6 mg. of mercuric chloride in 7.5 ml. of ether. The reaction is initiated after a few minutes of vigorous stirring at room temperature. A mixture of 3 g. of 80% 1-fluoro-2-hexanone and 3.63 g. of propargyl bromide in 7.5 ml. of ether is added dropwise through a dropping funnel so that the reaction remains gently refluxing (25° C. to 32° C.). Cooling in a water bath is required. The reaction mixture is cooled in an ice bath, quenched with 8 ml. of cold saturated aqueous ammonium chloride, filtered through Celite and washed with ether. The mother liquid is evaporated to dryness giving a reddish oily residue, which is Kugelrohr-distilled at 45° C./−4 mm giving the product as a colorless liquid.

REFERENCE EXAMPLE 304

4-Fluoromethyl-4-trimethylsilyloxy-1-octyne

To a solution of 4.38 g. of 4-fluoromethyl-4-hydroxy-1-octyne and 4.8 g. of imidazole in 19 ml. of dimethylformamide, cooled in an ice bath under nitrogen is added 4.5 ml. of trimethylchlorosilane via a syringe during a few minutes. The mixture is stirred in the ice bath for 30 minutes and then at room temperature under nitrogen overnight. The solution is poured into hexane, washed with saturated aqueous sodium bicarbonate, water, then brine and dried over anhydrous sodium sulfate. The solvents are removed in vacuo giving the product as a colorless liquid.

REFERENCE EXAMPLE 305

4-Fluoromethyl-4-trimethylsilyloxy-1-tri-n-butylstannyl-trans-1-octene

A solution of 6.36 g. of 4-fluoromethyl-4-trimethylsilyloxy-1-octyne, 11.64 g. (10.6 ml.) of tributylstannane and 40 mg. of azobisisobutyronitrile is heated and stirred at 120° C. under nitrogen for 3 hours. The mixture is cooled, filtered through Celite and washed with hexanes. The hexanes are removed in vacuo and the residual liquid in vacuum distilled through a short path. The product is obtained at b.p. 110°–135° C./0.2–0.25 mm. (The product contains a minor amount of cis isomer.)

REFERENCE EXAMPLE 306

1,1-Difluoro-2-hexanone

To a 3 liter, three-neck, round bottom flask, equipped with a magentic stirrer, a dropping funnel filled with 39.9 g. of difluoroacetic acid and 200 ml. of ether, and a rubber septum is added 1350 ml. of ether. After cooling in a dry ice-acetone bath under nitrogen, one mole of n-butyl lithium (2.2 M, hexane) is added via a double tip needle. The difluoroacetic acid solution is slowly added to the cooled n-butyl lithium solution via the dropping funnel over 3 hours. The thick mixture is stirred at $-78°$ C. for one hour and then quenched by pouring into a mixture of one liter of 4 N hydrochloric acid and one liter of ice, divided into three flasks, with stirring. The organic layers are combined and washed with water and brine. The 1500 ml. of solution is distilled at atmospheric pressure in a water bath. After the forerun is collected, the residue is fractionally distilled giving 18.8 g. (b.p. 100°–110° C.) of product that is 75% real.

REFERENCE EXAMPLE 307

4-Difluoromethyl-4-hydroxy-1-octyne

To a stirred suspension of 3.6 g. of magnesium and 30 mg. of mercuric chloride in 0.33 ml. of ether is added 1.5 ml. of propargyl bromide. The mixture is stirred vigorously for several minutes to initiate reaction, then a solution of 15.5 g. of 1,1-difluoro-2-hexanone and 12.1 ml. of propargyl bromide in 33 ml. of ether is added slowly (dropwise) over a 1.5 hour period, so that the mixture remains gently refluxing (25°–30° C.). After addition, the mixture is stirred at room temperature for 30 minutes, then cooled in an ice bath to 0°–5° C. and quenched by adding 35 ml. of saturated ammonium chloride solution dropwise and then stirred for 30 minutes. The mixture is filtered through Celite and washed with ether. The filtrate is concentrated in vacuo giving a yellow oil. This oil is vacuum distilled at 71° C., 12 mm giving the product as 10.54 g. of colorless oil which becomes pale yellow on standing at room temperature.

REFERENCE EXAMPLE 308

4-Difluoromethyl-4-trimethylsiloxy-1-octyne

A solution of 11.5 g. of 4-difluoromethyl-4-hydroxy-1-octyne and 11.32 g. of imidazole in 45 ml. of dimethylformamide is cooled in an ice bath under nitrogen. A 10.3 ml. portion of trimethylchlorosilane is added using a syringe over a 15 minute period. The mixture is stirred in the ice bath for one hour and then overnight at room temperature. The solution is diluted with hexane and then poured into saturated aqueous sodium bicarbonate solution. The hexane solution is separated, washed with aqueous sodium bicarbonate solution and brine, dried over anhydrous sodium sulfate and the solvents are evaporated to dryness giving the desired product as a colorless liquid.

REFERENCE EXAMPLE 309 trans-4-Difluoromethyl-4-trimethylsiloxy-1-tri-n-butylstannyl-1-octene a mixture of 13.0 g. of 4-difluoromethyl-4-trimethylsiloxy-1-octyne, 17.23 ml. of tri-n-butylstannane and 70 mg. of azobisisobutyronitrile is heated under nitrogen in an oil bath at 125°–135° C. for 2 hours. The reaction is cooled to room temperature and vacuum distilled through a short-path apparatus, giving, after a 5 ml. forerun, 35.6 g. of the product as on oil, containing a minor amount of the corresponding cis isomer.

REFERENCE EXAMPLE 310

1,1,1-Trifluoromethyl-2-hexanone

A mechanically stirred solution of 57 g. of trifluoroacetic acid in one liter of anhydrous ether, under argon, is cooled to $-78°$ C. and treated with one mole of n-butyl lithium (2.2 M in hexane) over a $2\frac{1}{4}$ hour period. After an additional $1\frac{1}{4}$ hours, the reaction mixture becomes gelatinous and stirring is discontinued. The reaction mixture, on standing overnight under an argon atmosphere, becomes fluid and stirring is continued for 2 hours. The solution is then syphoned into an agitated mixture of 200 ml. of concentrated hydrochloric acid and approximately one liter of cracked ice. The ether layer is separated, washed with saturated saline solution, then saturated sodium bicarbonate solution and dried over anhydrous magnesium sulfate. The ether is distilled at atmospheric pressure and the residue is fractionally distilled, giving 7.8 g. of the desired product, b.p. 75°–85° C.

REFERENCE EXAMPLE 311

4-Trifluoromethyl-4-hydroxy-1-octyne

To a stirred mixture of 1.78 g. of magnesium and approximately 25 mg. of mercuric chloride in 10 ml. of dry ether is added 0.6 ml. of propargyl bromide. The reaction is initiated by gentle warming. The refluxing solution is cooled in an ice bath and treated with a solution of 4.8 ml. of propargyl bromide and 10.85 g. of 1,1,1-trifluoromethyl-2-hexanone in 7 ml. of dry ether by dropwise addition over an 80 minute period maintaining the reaction temperature between 10° and 15° C. The mixture is stirred for $1\frac{3}{4}$ hours at room temperature, then recooled and terminated with 10 ml. of saturated ammonium chloride solution. The mixture is filtered through Celite and washed copiously with ether. The filtrate is washed with saturated saline solution, dried over anhydrous potassium carbonate-magnesium sulfate and evaporated to an oil. Fractional distillation of the oil at 12 mm pressure afforded 5.5 g. of the desired product, b.p. 65°–70° C.

REFERENCE EXAMPLE 312

4-Trifluoromethyl-4-trimethylsiloxy-1-octyne

A stirred solution of 4.99 g. of 4-trifluoromethyl-4-hydroxy-1-octyne and 5.65 g. of imidazole in 28 ml. of dry dimethylformamide, under argon, is cooled in an ice bath and then treated with 5.2 ml. of trimethylsilyl chloride by dropwise addition over a period of about 20 minutes. After an additional 15 minutes at ice bath temperature, the reaction mixture is stirred at room temperature overnight. The mixture is then poured into approximately 150 ml. of hexane and washed with small portions of ice cold water and saturated saline solution. The solution is dried over anhydrous magnesium sulfate and evaporated under reduced pressure to give the desired product.

REFERENCE EXAMPLE 313 trans-4-Trifluoromethyl-4-trimethylsiloxy-1-tri n-butylstannyl-1-octene

A stirred mixture of 6.66 g. of 4-trifluoromethyl-4-trimethylsiloxy-1-octyne and 26 mg. of azobisisobutyronitrile, under argon, is treated with 6.95 ml. of tri-n-butyl tin hydride, via a syringe. After treatment, a condenser is attached to the reaction vessel and the reaction mixture, under argon, is slowly heated to 130°–135° C. and maintained at this temperature for 1.5 hours. Subsequent fractional distillation of the reaction mixture at approximately 0.07 mm pressure gives the desired product, b.p. 125°–135° C. (containing a minor amount of the corresponding cis isomer).

REFERENCE EXAMPLE 314

Treatment of the starting carbonyl of Table F with the alkyl lithium reagent indicated provides the fluoroketones of the table, which upon subsequent treatment with propargyl magnesium bromide, provides the indicated hydroxy-alkynes, which are treated with trimethylchlorosilane by the procedure indicated to provide the alkyne-trimethylsiloxy ethers which upon treatment with tri-n-butylstannane provide the corresponding trans-vinylstannanes of the table. (Each trans-vinylstannane contains 10–20% of the corresponding cis-vinylstannane.)

TABLE F

| STARTING CARBONYL | ALKYL-LITHIUM | FLUOROKETONE | HYDROXY-ALKYNE | ALKYNE-TRI-METHYLSIL-OXY-ETHER | TRANS-VINYL STANNAN |
|---|---|---|---|---|---|
| trifluoroacetic acid | n-propyl | 1,1,1-trifluoro-2-pentanone | 4-trifluoromethyl-4-hydroxy-1-heptyne | 4-trifluoromethyl-4-trimethylsiloxy-1-heptyne | 1-trans-tri-n-butyl stannyl-4-trifluoromethyl-4-trimethylsiloxy-1-heptene |
| difluoroacetic acid | n-propyl | 1,1-difluoro-2-pentanone | 4-difluoromethyl-4-hydroxy-1-heptyne | 4-difluoromethyl-4-trimethylsiloxy-1-heptyne | 1-trans-tri-n-buty-stannyl-4-difluoromethyl-4-trimethylsiloxy-1-heptene |
| ethyl fluoroacetate | n-propyl | 1-fluoro-2-pentanone | 4-fluoromethyl-4-hydroxy-1-heptyne | 4-fluoromethyl-4-trimethylsiloxy-1-heptyne | 1-trans-tri-n-buty-stannyl-4-fluoromethyl-4-trimethylsiloxy-1-heptene |
| trifluoroacetic acid | n-pentyl | 1,1,1-trifluoro-2-heptanone | 4-trifluoromethyl-4-hydroxy-1-nonyne | 4-trifluoromethyl-4-trimethylsiloxy-1-nonyne | 1-trans-tri-n-buty-stannyl-4-trifluoromethyl-4-trimethylsiloxy-1-nonene |
| difluoroacetic acid | n-pentyl | 1,1-difluoro-2-heptanone | 4-difluoromethyl-4-hydroxy-1-nonyne | 4-difluoromethyl-4-trimethylsiloxy-1-nonyne | 1-trans-tri-n-butyl-stannyl-4-difluoromethyl-4-trimethylsiloxy-1-nonene |
| ethyl fluoroacetate | n-pentyl | 1-fluoro-2-heptanone | 4-fluoromethyl-4-hydroxy-1-nonyne | 4-fluoromethyl-4-trimethylsiloxy-1-nonyne | 1-trans-tri-n-butyl-stannyl-4-fluoromethyl-4-trimethylsiloxy-1-nonene |
| trifluoroacetic acid | n-hexyl | 1,1,1-trifluoro-2-octanone | 4-trifluoromethyl-4-hydroxy-1-decyne | 4-trifluoromethyl-4-trimethylsiloxy-1-decyne | 1-trans-tri-n-butyl-stannyl-4-trifluoromethyl-4-trimethylsiloxy-1-decene |
| difluoroacetic acid | n-hexyl | 1,1-difluoro-2-octanone | 4-difluoromethyl-4-hydroxy-1-decyne | 4-difluoromethyl-4-trimethylsiloxy-1-decyne | 1-trans-tri-n-butyl-stannyl-4-difluoromethyl-4-trimethylsiloxy-1-decene |
| ethyl fluoroacetate | n-hexyl | 1-fluoro-2-octanone | 4-fluoromethyl-4-hydroxy-1-decyne | 4-fluoromethyl-4-trimethylsiloxy-1-decyne | 1-trans-tri-n-butyl stannyl-4-fluoromethyl-4-trimethylsiloxy-1-decene |

REFERENCE EXAMPLE 315

4-hydroxy-4-methyl-7-oxa-1-octyne

To a stirred solution of propargylmagnesium bromide in 35 ml. of ether, prepared from 7.65 g. (0.3 moles) of magnesium, 170 mg. of mercuric chloride and 33.6 g.

(0.28 moles) of propargyl bromide, is added dropwise under argon atmosphere a solution of 25 g. (0.245 moles) of 4-methoxy-2-butanone [L. R. Fedor, *J. Am. Chem. Soc.*, 91:4, 908 (1969)] in 20 ml. of ether at a rate to maintain gentle refluxing. The resulting mixture is stirred at ambient temperature for an additional 30 minutes then quenched at 5° C. by the addition of 140 ml. of saturated ammonium chloride solution. After filtration the ether phase is separated; the aqueous phase is extracted twice with additional ether. The combined ether extracts are washed with saturated sodium chloride solution, dried with anhydrous magnesium sulfate and taken to dryness in vacuo. Distillation of the residual oil provided 13.7 g. (40%) of product; b.p. 84°–85° C. (13 mm.).

REFERENCE EXAMPLE 316

4-Methyl-4-trimethylsilyloxy-7-oxa-1-octyne

To a solution of 13 g. (0.091 moles) of 4-hydroxy-4-methyl-7-oxa-1-octyne and 16 g. (0.235 moles) of imidazole in 80 ml. of dry dimethylformamide is added dropwise, at 5° C. under nitrogen with stirring, 12.5 ml. (0.115 moles) of trimethylchlorosilane. After an additional 15 minutes at 5° C. the solution is stirred at ambient temperature for 18 hours then added to 450 ml. of hexane. The resulting solution is washed with ice-cold water, ice-cold saturated sodium chloride solution, dried with anhydrous magnesium sulfate and taken to dryness in vacuo. Distillation of the residual oil furnishes 16.8 g. (86%) of product; b.p. 87°–88° C. (7 mm.).

REFERENCE EXAMPLE 317

E-1-Tri-n-butylstannyl-4-methyl-4-trimethylsilyloxy-7-oxa-1-octene

To a stirred solution of 15 g. (0.069 moles) of 4-methyl-4-trimethylsilyloxy-7-oxa-1octyne and 75 mg. of azobisisobutyronitrile is added dropwise, under nitrogen atmosphere, 21.1 g. (0.073 moles) of tri-n-butyltin hydride. The solution is stirred at 130°–135° C. for 1½ hours, then cooled to ambient temperature. Distillation provides 29 g. (86%) of product as a colorless oil; b.p. 165°–167° C. (0.25 mm.).

REFERENCE EXAMPLE 318

4-Hydroxy-4-methyl-7-thia-1-octyne

To a stirred mixture of 6.6 g. (0.275 moles) of magnesium and 116 mg. of mercuric chloride in 35 ml. of ether is added, dropwise under argon atmosphere, 35.2 g. of propargyl bromide (80% solution in toluene) and 25 g. (0.21 moles) of methylmercaptobutane-3-one [D. B. Reisner, *J. Am. Chem. Soc.*, 78, 2132 (1956) in 100 ml. of ether at a rate to maintain gentle refluxing. After stirring at the reflux temperature for 35 minutes, the cooled mixture is quenched by dropwise addition of 140 ml. of saturated ammonium chloride solution. The ether phase is separated, washed with saturated sodium chloride solution, dried with anhydrous magnesium sulfate and taken to dryness. Distillation of the residual oil provides 27.4 g. (82%) of product as a colorless oil; b.p 114°–115° C. (7–8 mm.).

REFERENCE EXAMPLE 319 n-butyl trimethylsilylethynyl ketone

To a stirred solution of 14.4 g. of valeryl chloride and 20.4 g. of bis-trimethylsilylacetylene in 300 ml. of dry methylene chloride, cooled in an ice bath, is added powdered anhydrous aluminum chloride, portionwise, over a period of 20 minutes. The mixture is stirred for 5 minutes, then the cooling bath is removed and the mixture is stirred at room temperature for 4 hours. The mixture is poured into 500 ml. of ice-water. The organic layer is separated, washed with water and brine, dried over anhydrous sodium sulfate and filtered through diatomaceous earth. The mother liquor is evaporated to dryness giving a brownish residue. This residue is Kugelrohr-distilled to give 16.56 g. of colorless liquid at 45° C./0.3 mm which is essentially identical with the authentic product.

REFERENCE EXAMPLE 320

4-Trimethylsilylethynyl-1-octyn-4-ol

To a stirred suspension of 1.29 g. of magnesium and 10 mg. of mercuric chloride in 12 ml. of ether is added 0.4 ml. of propargyl bromide. The reaction is initiated after stirring at room temperature for a few minutes. The stirred mixture is cooled in an ice-water bath and a solution of 9.64 g. of n-butyl trimethylsilylethynyl ketone and 3.51 ml. of propargyl bromide in 13 ml. of ether is added, dropwise so that the mixture is very gently boiling during 40 minutes. After addition, the cooling bath is removed and the mixture is stirred at room temperature for 1.5 hours. The mixture is recooled in an ice-bath and 10 ml. of saturated ammonium chloride solution is added. The resulting white mixture is filtered through diatomaceous earth. The clear mother liquid is washed with saturated sodium chloride solution and dried over anhydrous magnesium suflate. The solvent is evaporated to dryness giving 10.5 g. of a red liquid. This liquid is Kugelrohr-distilled at 60° C./0.25–0.3 mm. The pale yellow liquid distillage which is the desired product weights 8.5 g.

REFERENCE EXAMPLE 321

4-Trimethylsilylethynyl-1-octyn-4-ol trimethylsilyl ether

To a stirred mixture of 8.5 g. of 4-trimethylsilylethynyl-1-octyn-4-ol and 6.2 g. of imidazole in 24 ml. of dry dimethylformamide is added,, under nitrogen, 5.7 ml. of chlorotrimethylsilane, in a slow stream, via a syringe. The mixture is stirred in an ice-bath for one hour and then at room temperature overnight. The mixture is poured into hexane, washed with saturated sodium bicarbonate solution, water and then brine and dried over sodium sulfate. The solvents are evaporated to dryness giving 11.1 g. of the desired product.

REFERENCE EXAMPLE 322

4-Trimethylsilylethynyl-4-trimethylsiloxy-1-octen-1-tri-n-butyl stannane

To a mixture of 10 mg. of azobisisobutyronitrile and 2.94 g. of 4-trimethylsilylethynyl-1-octyn-4-ol trimethylsilyl ether is added 2.65 ml. of tri-n-butyl stannane via a syringe. The mixture is stirred and heated under nitrogen in an oil bath at 130° C. for 3 hours and then cooled to room temperature. This mixture is vacuum-distilled through a short-path distillation apparatus to remove a forerun at 40° C./0.4 mm. The yellow oil (pot residue) comprises the desired product.

REFERENCE EXAMPLE 323

Treatment of the acid chlorides in Table G-1 with bistrimethylsilylacetylene, as described in Example 319, provides the trimethylsilylethynyl ketones of Table G, which upon treatment with propargylmagnesium bromide according to Example 320, provides the diacetyleneic ketones of Table G-1, which upon treatment with chlorotrimethylsilane by the procedure of Example 321 followed by treatment with tri-n-butylstannane according to Example 322, provide the vinylstannanes of Table G-1.

TABLE G-1

| STARTING ACID KOLIDE | TRIMETHYLSILYL-ETHYNYL KETONE | DIACETYLENIC KETONE | VINYLSTANNANE |
| --- | --- | --- | --- |
| 4-oxapentanoyl chloride | 3-oxo-6-oxa-1-trimethylsilyl-1-heptyne | 4-hydroxy-4-trimethylsilylethynyl-7-oxa-1-octyne | 4-trimethyl-silyoxy-4-trimethylsilyl-ethynyl-7-oxa-1-tri-n-butyl-stannyl trans-1-octene |
| 4-oxakeptanoyl chloride | 3-oxo-6-oxa-1-trimethylsilyl-1-nonyne | 4-hydroxy-4-trimethylsilylethynyl-7-oxa-1-decyne | 4-trimethyl-silyloxy-4-trimethylsilyl-ethynyl-7-oxa-1-tri-n-butyl-stannyl trans-1-decene |

REFERENCE EXAMPLE 324

Treatment of the aldehydes of Table G-2 with propargyl magnesium bromide by the proceedure described in U.S. Pat. No. 4,061,670, herein incorporated by reference, provides the propargyl alcohol of the Table. Further transformations as illustrated in U.S. Pat. No. 4,061, 670 provides the vinyliodides of Table G-2.

TABLE G-2

| STARTING ALDEHYDE | PROPARGYL ALCOHOL | VINYLIODIDE |
| --- | --- | --- |
| 4-oxapentanol | 4-hydroxy-7-oxa-1-octyne | 4-trimethylsilyloxy-7-oxa-4-vinyl-1-iodo-trans-1-octene |
| 4-oxaheptanal | 4-hydroxy-7-oxa-1-deceyne | 4-trimethylsilyloxy-7-oxa-4-vinyl-1-iodo-trans-1-decene |

REFERENCE EXAMPLE 325 trans-1-Iodo-oct-1-en-4-one

To a solution of 6.4 g. of 4-hydroxy-1-iodo-trans-1-octene (U.S. Pat. No. 4,061,671, Ex. 4) in 25 ml. of ether, cooled in an ice-bath under argon, is added dropwise over 15 minutes, 25 ml. of a solution prepared by dissolving 100 g. of sodium dichromate dihydrate in 300 ml. of water, followed by 136 g. of sulfuric acid with ice-bath cooling and subsequent dilution to 500 ml. After addition, the mixture is stirred at room temperature for 2 hours and diluted with ether. The ether phase is separated and saved. The aqueous phase is extracted with ether. The ether solutions are combined, washed with saturated sodium chloride solution, 5% sodium thiosulfate solution, twice with saturated sodium chloride solution, dried over magnesium sulfate and taken to dryness, giving the product as an orange oil.

REFERENCE EXAMPLE 326

4-Deutero-4-hydroxy-1-iodo-trans-1-octene

To a solution of 5.93 g. of trans-1-iodo-oct-1-en-4-one in 100 ml. of deuterium ethoxide cooled in an ice-salt bath (0° C.)under argon, is added with stirring, 2.0 g. of sodium borodeuteride portionwise over 10 minutes. The mixture is stirred at 0° to 5° C. for 1¾ hours and then diluted with 300 ml. of ice and water. Then 5% hydrochloric acid is slowly added at 0° to 5° C. until the mixture is acidic. Ether is added, the mixture is stirred for 5 minutes and the ether layer is separated and saved. The aqueous layer is extracted with ether. The ether solutions are combined, washed three times with saturated sodium chloride solution, dried over sodium sulfate, refrigerated overnight, filtered and taken to dryness, giving the product as a pale yellow oil.

REFERENCE EXAMPLE 327

4-Deutero-4-triethylsilyloxy-1-iodo-trans-1-octene

To a solution of 5 g. of 4-deutero-4-hydroxy-1-iodo-trans-1-octene in 40 ml. of dry dimethylformamide is added 3.4 g. of imidazole. This solution is cooled in an ice-bath, under argon and to it is added, with stirring, 4 g. of chlorotriethylsilane in a steady stream. The mixture is stirred in the ice-bath for 30 minutes and then at room temperature overnight and poured into a mixture of 80 ml. of hexane and 80 ml. of ice water. The hexane layer is separated, washed with saturated sodium chloride solution, dried over sodium sulfate and taken to dryness giving the desired product.

REFERENCE EXAMPLE 328

Treatment of trans-1-iodo-dec-1-en-4-one (U.S. Pat. No. 4,061,471) by the procedures of Examples 326 and 327 is productive of 4-deutero-4-triethylsilyloxy-1-iodo-trans-1-decene.

REFERENCE EXAMPLE 329

4-Hydroxy-4-methyl-oct-1-yn-7-ene

A mixture of 19.45 g. of magnesium, 0.15 g. of mercuric chloride and 0.5 ml. of 1,2-dibromoethane in 40 ml. of ether, under argon, is stirred for 5 minutes. A 0.5 ml. portion of propargylbromide is added followed by 160 ml. of ether. To the stirred mixture is added dropwise a solution of 60.0 g. of 5-oxo-1-hexane and 87.3 g. of propargyl bromide in 100 ml. of ether, at such a rate as to maintain a vigorous reflux. After addition is complete, the mixture is stirred for 20 minutes, cooled in an ice-bath and a saturated solution of ammonium chloride is added dropwise. The solid is removed by filtration through Celite and washing with water. The solvent is removed from the filtrate giving the product as an orange liquid.

REFERENCE EXAMPLE 330

4-Methyl-4-trimethylsilyloxy-oct-1-yn-7-ene

To a mixture of 50 g. of 4-hydroxy-4-methyl-oct-1-yn-7-ene and 61.3 g. of imidazole in 100 ml. of dimethylformamide at 0° C., is added, with stirring, 49.1 g. of trimethylsilyloxy chloride. The mixture is stirred at room temperature overnight and poured into petroleum ether and water. The organic layer is washed with water and saturated sodium bicarbonate solution and dried over magnesium sulfate. The solvent is removed and the residue distilled (74°–78° C., 1.5 mm.) to give the product as a colorless liquid.

REFERENCE EXAMPLE 331

E-1-Tri-n-butylstannyl-4-methyl-4-trimethylsilyloxy-1,7-octadiene

A mixture of 30 g. of 4-methyl-4-trimethylsilyloxy-oct-1-yn-7-ene, 58.66 g. of tri-n-butylstannane and 200 mg. of azobisisobutyronitrile is placed in a bath at 95° C. and stirred under argon. The mixture is heated at 140° C. for one hour and then at 140° C. under vacuum for 1.5 hours. The mixture is distilled via a Kugelrohr at 140° C., 0.06 mm. to give the product as a colorless liquid.

REFERENCE EXAMPLE 332

1-Hydroxy-hexan-2-one

To a mixture of 25 g. of valeryl chloride and 97.06 g. of tris-trimethylsilyloxyethylene is added 9 drops of stannic chloride. The mixture is stirred until the exotherm reaches 55° C., then placed in an ice-bath. The exotherm continues to about 70° C. When the temperature begins to fall, the mixture is removed from the ice-bath and stirred for 3.5 hours, then slowly poured into a mixture of 50 ml. of 0.6 N hydrochloric acid and 100 ml. of tetrahydrofuran. This mixture is stirred for one hour, then saturated with sodium chloride and extracted with ether. The ether is washed with saturated sodium bicarbonate solution, dried over magnesium sulfate and evaporated, giving the desired product as a light yellow oil.

REFERENCE EXAMPLE 333

1-Triethylsilyloxy-hexan-2-one

To a solution of the crude 1-hydroxy-hexan-2-one (prepared in Example 1) in 80 ml. of dimethylformamide at 0° C. is added with stirring, 40.8 g. of imidazole and 45.21 g. of chlorotriethylsilane. The mixture is stirred at 0° C. for 5 minutes and then at room temperature overnight, then poured into cold water and extracted with petroleum ether. The petroleum ether solution is washed with water, then saturated sodium bicarbonate solution and then dried over magnesium sulfate. The solvent is removed and the residue is distilled. The fraction boiling at 95°–103° C. (0.7 mm.) is collected giving the desired product as a cloudy colorless liquid.

REFERENCE EXAMPLE 334

4-Hydroxy-4-triethylsilyloxymethyl-1-octyne

A mixture of 3.8 g. of magnesium and 50 mg. of mercuric chloride in 40 ml. of ether is stirred under argon. To this is added 10 drops of dibromoethane and 1 ml. of propargyl bromide. This mixture is stirred until the reaction is initiated (15 minutes), then a solution of 30.0 g. of 1-triethylsilyl-oxy-hexan-2-one and 18.55 g. of propargyl bromide in 30 ml. of ether is added dropwise, at a rate to maintain reflux. After addition is complete, the mixture is refluxed ½ hour, then cooled to −5° C. and a saturated solution of ammonium chloride is added. The mixture is filtered through Celite and the solids are washed with ether. The ether is filtered and then evaporated giving the desired product as a yellow oil.

REFERENCE EXAMPLE 335

4-Triethylsilyloxymethyl-4-trimethylsilyloxy-1-octyne

To a solution of the 4-hydroxy-4-triethylsilyloxymethyl-1-octyne (prepared in Example 3) and 23.9 g. of imidazole in 50 ml. of dimethylformamide at 0° C., is added with stirring, 21.2 g. of chlorotrimethylsilane. The mixture is stirred for 75 minutes, then poured into ice water and extracted with hexane. The hexane layer is washed with water, then saturated sodium bicarbonate solution, dried over magnesium sulfate and the hexane is removed. The residue is distilled. The fraction boiling at 133°–136° C. (1.2 mm.) is collected giving the desired product as a colorless liquid.

REFERENCE EXAMPLE 336

E-4-Triethylsilyloxymethyl-4-trimethylsilyloxy-1-tri-n-butylstannyl-1-octene

A mixture of 20.0 g. of 4-triethylsilyloxymethyl-4-trimethylsiloxy-1-octyne, 18.18 g. of tri-n-butylstannane and 70 mg. of azobisisobutyronitrile is stirred under argon and placed in a bath at 100° C. After 5 minutes an exotherm ensues. The mixture is heated at 130°–140° C. for one hour and then the excess tri-n-butylstannane is removed at 130° C. and reduced pressure. The residue is distilled at 130°–140° C., 0.03 mm. in a Kugelrohr apparatus, giving the desired product as a colorless liquid.

REFERENCE EXAMPLE 337

Treatment of the carboxylic acid chlorides of Table H by the procedures of Examples 332, 333, 334 and 335 is productive of the intermediates and vinylstannanes of Table H.

TABLE H

| ACID CHLORIDE | HYDROXYMETHYL KETONE | SILYLOXY KETONE | HYDROXY ALKYNE | SLYLOXY ALKYNE | VINYL STANNANE |
|---|---|---|---|---|---|
| butryl chloride | 1-hydroxy-pentan-2-one | 1-trilethylsilyl-oxy-pentan-2-one | 4-hydroxy-4-triethylsilyl-oxymethyl-1-hyptyne | 4-triethyl-silyloxymethyl-4-trimethyl-silyloxy-1-heptyne | E-4-triethyl-silyloxymethyl-4-trimethyl-silyloxy-1-tributylstannyl-1-heptene |
| hexanoyl chloride | 1-hydroxy-heptan-2-one | 1-triethylsilyloxy-heptan-2-one | 4-hydroxy-4-triethylsilyl-oxymethyl- | 4-triethyl-silyloxymethyl-4-trimethyl- | E-4-triethyl-silyloxymethyl- |

TABLE H-continued

| ACID CHLORIDE | HYDROXYMETHYL KETONE | SILYLOXY KETONE | HYDROXY ALKYNE | SLYLOXY ALKYNE | VINYL STANNANE |
|---|---|---|---|---|---|
| | | | 1-nonyne | silyloxy-1-nonyne | 4-trimethyl-silyloxy-1-tributylstannyl-1-nonene |
| heptanoyl chloride | 1-hydroxy-octan-2-one | 1-triethylsilyloxy-octan-2-one | 4-hydroxy-4-triethylsilyl-oxymethyl-1-decyne | 4-triethyl-silyloxy-methyl-4-trimethyl-silyloxy-1-decyne | E-4-triethyl-silyloxymethyl-4-trimethyl-silyloxy-1-tributylstannyl-1-decene |

REFERENCE EXAMPLE 338

Preparation of trimethylsilyl-2-trimethylsilyloxy acetate

To a solution of 15 g. (0.197 mol) of glycolic acid in 50 ml. of dry pyridine is poured 32.3 g. (0.2 mol) of 1,1,1,3,3,3-hexamethyldisilazine. After stirring 15 minutes, 10.86 g. (0.1 mol) of trimethylsilyl chloride is added dropwise. The mixture is stirred for one hour and then filtered from a white solid which is washed with petroleum ether. The filtrate and washings are concentrated at reduced pressure at 30° C. The residue is distilled (85°-86°, 15 minutes) to give 38 g. of the title compound.

REFERENCE EXAMPLE 339

Preparation of tris-trimethylsilyloxyethylene

To a solution of 50.98 g. (0.316 mol) of 1,1,1,3,3,3-hexamethyldisilazine in 250 ml. of tetrahydrofuran is added with stirring under argon at 0° C. dropwise 133.3 ml. (0.32 mol) of 2.4 M n-butyl lithium in hexane. After addition is complete the solution is maintained at 45° C. for 30 minutes. The solution is cooled to −78° and 58.7 g. of trimethylsilyl-2-trimethylsilyloxy acetate (Example 73) is added dropwise. After stirring 30 minutes, 43.2 g. (0.4 mol) of trimethylsilylchloride is added over 10 over. The solution is allowed to warm to room temperature over 30 minutes. The solvent is removed at reduced pressure. The residue is mixed with an equal volume of petroleum ether and filtered from the suspended lithium chloride. The solvent is removed and the residue is distilled (70°-75° C., 1.4 minutes) to give 64.65 g. of the title compound.

REFERENCE EXAMPLE 340

1,1-Dimethoxy-2-hexanone

A mixture of 36.9 g of washed 50% sodium hydride dispersion (0.77 moles) and 600 ml. of dimethylsulfoxide is heated under argon at 65° C. for 2 hours. At 0° C. is added dropwise, 50 g. (0.38 moles) of ethyl valerate. The solution is stirred at room temperature for 2 hours, then diluted with 1400 ml. of water and 70 ml. of concentrated hydrochloric acid and 75 g. of sodium chloride is added. The mixture is extracted four times with chloroform and the solution is dried (magnesium sulfate charcoal). The solvent is removed. The residue is dissolved in 700 ml. of methanol. A 55.65 g. (0.22 moles) portion of iodine is added and the solution is refluxed 90 minutes. The solvent is removed, the residue is dissolved in chloroform and the solution is washed twice with water and once with saturated sodium thiosulfate. The solution is dried (magnesium sulfate charcoal). The solvent is removed and the residue is distilled twice. The fraction boiling at 64°-72° C., 5 mm. is collected to give 28.3 gm. of the title compound. [T. L. Moore, J. Org. Chem., 32 786 (1967)].

REFERENCE EXAMPLE 341

4-Dimethoxymethyl-4-trimethylsiloxy-1-octyne

To a suspension of 5.31 g. (0.22 moles) of magnesium in 15 ml. of ether is added 100 mg. of mercuric chloride and 1.5 ml. of 1,2-dibromoethane. After the reaction begins, another 45 ml. of ether is added followed by the dropwise addition of a solution of 25 g. (0.16 moles) of 1,1-dimethoxy-2-hexanone and 27.3 g. (0.2 moles) of 85% propargyl bromide in 45 ml. of ether at a rate which maintains reflux. Midway through the addition 15 ml. of tetrahydrofuran is added. After complete addition of the solution, the mixture is refluxed for 40 minutes. The mixture is cooled to 0° C. and saturated ammonium chloride solution is added followed by magnesium sulfate. The mixture is filtered through Celite and the solvent is removed. The residue is dissolved in 53 ml. of dimethylformamide and at 0° C. is added 24.4 g. (0.36 moles) of imidazole and 21.19 g. (0.20 moles) of trimethylchlorosilane. After stirring at 25° C. for 70 minutes, the solution is poured into water and extracted with hexanes. The organic layer is dried over magnesium sulfate and the solvent is removed. Distillation (75°-95° C., 0.3 mm.) gives 17.4 g. of the title compound.

REFERENCE EXAMPLE 342

E-1-tri-n-Butylstannyl-4-dimethoxymethyl-4-trimethylsiloxy-1-octene

A mixture of 10.0 g. (36.7 mmoles) of 4-dimethoxymethyl-4-trimethylsiloxy-1-octyne, 12.82 g. (44 mmoles) of tri-n-butylstannyl hydride 100 mg. of azobisisobutyronitrile is heated to 140° C. under argon for 2 hours. The excess hydride is distilled off and the residue is purified by molecular distillation (bath temperature = 170°-175° C., 0.2 mm.) to give 20.5 g. of the title compound.

REFERENCE EXAMPLE 343

Treatment of the ethyl esters of Table N by the procedure of Reference Example 1 provides the β-ketosulfoxides of the table which are converted to the ketoacetals. Treatment of the ketoacetals of the table with propargyl magnesium bromide, provides the hydroxyalkyne that is protected as the TMS-alkyne of the table by the procedure of Reference 267. Hydrostannation by the procedure of Reference Example 268 provides the trans vinylstannanes of Table N.

orange liquid. Distillation of this crude product gives 21 g. of the desired product, b.p. 83°–85° C., 140 mm.

TABLE N

| Starting Ester | β-keto-sulfonide | ketoacetal | Trimethylsilyloxy alkyne | trans vinyl stannane |
|---|---|---|---|---|
| ethyl butyrate | 4-oxo-2-sulfinyl-neptane | 1,1-dimethoxy-2-pentanone | 4-dimethoxymethyl-4-trimethylsilyloxy-1-heptyne | 1-trans-tri-n-butyl-stannyl-4-dimethoxy-methyl-4-trimethyl-siloxy-1-heptene |
| ethyl hexanoate | 4-oxo-2-sulfinyl-nonane | 1,1-dimethoxy-2-heptane | 4-dimethoxymethyl-4-trimethylsilyloxy-1-nonyne | 1-trans-tri-n-butyl-stannyl-4-dimethoxy-methyl-4-trimethyl-siloxy-1-nonene |
| ethyl heptanoate | 4-oxo-2-sulfinyl-decene | 1,1-dimethoxy-2-octanone | 4-dimethoxymethyl-4-trimethylsilyloxy-1-decyne | 1-trans-tri-n-buty-stannyl-4-dimethoxy-methyl-4-trimethyl-siloxy-1-decene |

REFERENCE EXAMPLE 344

1,2-Dibromo-2-ethoxyethane

To 143 ml. of ethylvinyl ether at −25° C. is added, dropwise with stirring, during 2 hours, 82 ml. of bromine, at such a rate as to maintain the temperature at −10° C. The excess bromine is titrated with a few ml. of ethylvinyl ether. The product is distilled directly from the reaction vessel. After a 30 g. forerun, the main fraction of 266 g. of colorless liquid is collected, b.p. 55°–57° C., 10 mm. Reference: Zhur. Org. Khim., 2, 1569 (1966).

REFERENCE EXAMPLE 345

1-Bromo-2-ethoxyhexane

To a stirred solution of 1.68 moles of n-butylmagnesium bromide, as a 1.7 M solution in ether, is added dropwise a solution of 300 g. of 1,2-dibromo-2-ethoxyethane in 750 ml. of ether during a period of 2 hours at −15° C. The resultingmixture is stirred for one hour while warming to 20° C., then cooled to 0° C., and treated while stirring with 500 ml. of water, followed by 100 ml. of 4 N hydrochloric acid. The organic layer is washed with brine, dried over magnesium sulfate and concentrated. The residue is distilled to provide a colorless liquid, b.p. 83°–84° C., 18 mm.

REFERENCE EXAMPLE 346

2-Ethoxy-1-hexene

A 17.3 g. portion of 50% sodium hydride in mineral oil is washed free of the mineral oil under a nitrogen atmosphere with three 150 ml. portions of petroleum ether. This sodium hydride is then suspended in 300 ml. of dry dimethylformamide. A solution of 62.7 g. of 1-bromo-2-ethoxyhexane in 150 ml. of dimethylformamide is added followed by one ml. of isopropanol. The mixture is stirred and heated cautiously using an oil bath, starting at 25° C. Upon reaching an internal temperature of 82° C., a vigorous exothermic reaction begins. This reaction is maintained by a water bath at 85° C. to 90° C. When the reaction slows, the mixture is heated externally at 85° C. to 90° C. for 45 minutes. The reaction mixture is cooled to 0° C., treated cautiously with a total of 1.5 liters of water and then extracted with three 400 ml. portions of ether. The organic extracts are combined, washed with three 250 ml. portions of water, then two 250 ml. portions of brine and dried over potassium carbonate. To the organic solution is added 6 drops of pyridine and 100 mg. of hydroquinone. This mixture is filtered and concentrated in vacuo, giving an Reference: Chem. Abstr., 54, 8595f.

REFERENCE EXAMPLE 347

2-Butyl-1-chloro-2-ethoxy-1-fluoro cyclopropane

To a solution of 61.0 g. of 2-ethoxy-1-hexene, 135 ml. of 13.5 M potassium hydroxide and 217 g. of "18-crown −6" ether at −15° C. is added dropwise over 30 minutes at 0°, a 90 ml. portion of dichlorofluoromethane. After the addition, the mixture is placed in an ice bath. An exotherm raises the temperature to 20° C., whereupon the mixture is placed in a dry-ice/carbon tetrachloride bath to maintain the temperature at −5° C. to 0° C. After three hours at this temperature, the reaction mixture is diluted with water and extracted with ether. The ether extracts are combined, washed with water, then brine, dried over potassium carbonate and concentrated in vacuo to an oil. This oil is distilled through a 6 inch Vigreux column to provide 82 g. of the desired compound as a colorless liquid, b.p. 70°–71° C., 16 mm.

REFERENCE EXAMPLE 348

3,3-Diethoxy-2-fluoro-1-hexene

A stirred solution of 58.4 g. of 2-butyl-1-chloro-2-ethoxy-1-fluorocyclopropane and 166 g. of anhydrous potassium carbonate in 400 ml. of absolute ethanol is heated at reflux for 18 hours. The solution is cooled and the bulk of the ethanol is removed in vacuo. The residue is partitioned with 500 ml. of water and 750 ml. of ether. The ether phase is washed with three 100 ml. portions of brine, dried over potassium carbonate and concentrated in vacuo to provide 54 g. of a pale yellow oil. A 4.45 g. portion of this oil is distilled through a 6 inch Vigreux column giving 2.5 g. of the desired product as a colorless liquid, b.p. 80°–81° C., 24 mm.

REFERENCE EXAMPLE 349

2-Fluorohex-1-en-2-one

A solution comprising 49 g. of 3,3-diethoxy-2-fluoro-1-hexene, 60 ml. of 4 N hydrochloric acid, 720 ml. of tetrahydrofuran and 0.25 g. of hydroquinone is allowed to stand at room temperature for 17 hours. The solution is then concentrated in vacuo to 150 ml. and diluted with ether and brine. The ether layer is washed with brine, dried over magnesium sulfate and concentrated in vacuo giving 28 g. of a light yellow liquid. This liquid is distilled giving 19 g. of the desired compound. (This ketone should be used immediately in the procedure of Example 272 and hydroquinone should be added to the distillate to prevent polymerization.)

REFERENCE EXAMPLE 350

4-Hydroxy-4-(1'-fluorovinyl)-1-octyne

The grignard reaction is accomplished according to the procedure disclosed in U.S. Pat. No. 4,061,670 which is incorporated herein by reference.

To a stirred suspension of 62 mg. of mercuric chloride and 4.97 g. of magnesium metal shavings in 30 ml. of ether, at room temperature, is added a soluton of 29.1 g. of 80% propargyl bromide in tolune in 90 ml. of ether. After the grignard formation is complete, the grignard soluton is cooled to −20° C. and a solution of 18.9 g. of 2-fluorohex-1-en-2-one in 65 ml. of ether is added. The reaction mixture is stirred at room temperature for 1.5 hours, recooled to 0° C., quenched cautiously with 5 ml. of saturated ammonium chloride and diluted with 50 ml. of ether. The ether phase is wased with brine, filtered through diatomaceous earth, dried over a mixture of potassium carbonate and magnesium sulfate and concentrated in vacuo, giving 30 g. of an oil. A small amount of potassium carbonate is added to this oil which is then distilled through a 6 inch Vigreux column giving 14 g. of the desired product as a colorless liquid, b.p. 70°-73° C., 14 mm.

REFERENCE EXAMPLE 351

4-(1'-Fluorovinyl)-4-trimethylsilyloxy-1-octyne

To a stirred 0° C. solution of 13.7 g. of 4-(1-fluorovinyl)-4-hydroxy-1-octyne and 16.1 g. of imidazole in 60 ml. of anhydrous dimethylformamide is added, via a syringe over a 3 minute period, 11.6 ml. of chlorotrimethylsilane. The resulting solution is stirred at room temperature for 18 hours, cooled to 0° C., diluted with 350 ml. of petroleum ether and shaken with 150 ml. of water. The organic phase is separated, washed with six 50 ml. portions of water, then 50 ml. of brine, dried over magnesium sulfate and concentrated in vacuo giving 18.9 g. of the desired product as a colorless liquid.

REFERENCE EXAMPLE 352

E-4-(1'-Fluorovinyl)-1-tributylstannyl-4-trimethylsilyloxy-1-octene

A mixture of 21.4 ml. of tributylstannane, 18.3 g. of 4-(1'-fluorovinyl)-4-trimethylsilyloxy-1-octyne and azobisisobutyronitrile is heated under an inert atmosphere on an oil bath. Upon reaching 85° C. a rapid exotherm occurs which is moderated to maintain 140° C. using a water bath. After the exotherm the mixture is heated at 135° C. for one hour, then cooled to room temperature. The resulting oil is distilled via a Kugelrohr to give the desired product as 33.68 g. of a light yellow liquid (air bath 160° C., 0.15 mm.).

The residual oil is dissolved in 45 ml. of methanol and the resulting solution is extracted twice with 45 ml. portions of heptane. The extracts are discarded. The methanol solution is taken to dryness leaving 5.64 g. of oil. This oil is applied to a 2 inch flat dry column containing 750 g. of silica gel and developed with ethyl acetate:hexane:acetic acid (60:40:1). The bottom 20 inches of the column is removed and discarded. The remainder of the column is divided into one inch segments. Segments 20-25 are combined to provide 392 mg. of the desired product as an oil.

REFERENCE EXAMPLE 353 dl-11α,16-dihydroxy-9-oxo-16-(1-fluorovinyl)-5-cis,13-trans-prostadiene

To a stirred solution of 8.7 g. of (E)-1-tri-n-butylstannyl)-4-(1'-fluorovinyl)-4-trimethylsilyloxy-1-octene in 10 ml. of dry tetrahydrofuran, cooled to −78° C. under an argon atmosphere, is added dropwise over a period of 15 minutes, 7.7 ml. of 1.92M n-butyllithium. The resulting solution is stirred at −78° C. for 20 minutes, then at −45° C. to −35° C. for 2½ hours. The solution is recooled to −78° C., and a chilled solution of 2.9 g. of pentynylcopper and 9.0 g. of tri-n-butylphosphine in 20 ml. of dry ether is added dropwise over a period of 5 minutes. This turbid solution is stirred at −78° C. for 1½ hours. A solution of 4.0 g. of 4-(trimethylsiloxy)-2-(6'-carbotrimethylsiloxy-2'-(cis)-hexenyl)cyclopent-2-en-1-one in 10 ml. of dry ether is chilled in a dry-ice/acetone bath and added dropwise during a period of 5 minutes. This solution is stirred at −78° C. for 20 minutes, then at −45° C. to 31 35° C. for one hour, then slowly allowed to warm to −23° C. over a period of 45 minutes. The solution is recooled to −78° C. and the reaction is quenched by pouring the solution into an ice cold mixture of 200 ml. of saturated ammonium chloride solution and 200 ml. of ether. The mixture is stirred rapidly for 20 minutes, then stored in a refrigerator overnight.

The layers are separated and the aqueous layer is extracted with two 250 ml. portions of ethyl acetate. The combined organic layers are washed with 250 ml. of cold dilute hydrochloric acid and then twice with 250 ml. of a solution of

REFERENCE EXAMPLE 354

Preparation of 3-vinyl-3-trimethylsilyloxy-1-octyne

Acetylene (dried using $H_2SO_4$ and KOH) was bubbled into 300 ml. of THF at 0° while a solution of the n-butylmagnesium chloride was added dropwise over 1.5 hr. After addition was complete a solution of the 3-oxo-1-octene in 100 ml. of THF was added dropwise over 15 min. The ice in the bath was allowed to melt slowly and the solution was stirred at room temperature overnight.

The mixture was cooled to 0° and 50 ml. of saturated $NH_4Cl$ was added dropwise with stirring. The mixture was filtered through celite, dried over magnesium sulfate and filtered again through Celite. The solvent was removed and the residue was stirred in 75 ml. of DMF containing the imidazole at 0° as the trimethylsilylchloride was slowly poured in. After 10 min. at 0° and 2.5 hr. at room temperature, the mixture was poured into $H_2O$ and extracted with petether. The organic layer was worked with water and $NaHCO_3$ and dried ($MgSO_4$). The solvent was removed and the residue was distilled (0.3 mm 63°-67°) to give the product as a colorless liquid.

REFERENCE EXAMPLE 355

Preparation of 3-vinyl-3-trimethylsilyloxy-1-tri-n-butylstannyl-1-octene

A mixture of the product of reference example 149, tin hydride and azobisisobutyronitrile was stirred under argon and placed in a bath at 100° C. After about 10 minutes an exotherm ensued. The mixture was stirred for 1.5 hours at 140° C. The excess tin hydride was removed by stirring at 130° under vacuum. The residue was distilled via Kugelrohr (0.04 mm 145°-155° ) to provide 24.9 gms of title product as a colorless liquid.

REFERENCE EXAMPLE 356

Trimethylsilyl methoxyacetate

To a solution of 87 g. of methoxyacetic acid in a mixture of 100 ml of tetrahydrofuran and 50 ml. of pyridine at 0° C. is added dropwise 155.8 g. of hexamethyldisilazane followed, dropwise, by 52.5 g. of chlorotrimethylsilane. The mixture is stirred overnight, diluted with petroleum ether and filtered through Celite. The petroleum ether is removed by roto-evaporation at 30° C. and the residue is distilled (aspirator pressure) giving, after a forerun of solvents, a fraction at 54°-55° C. of the desired product.

REFERENCE EXAMPLE 357

1-Methoxy-2,2-bis-trimethylsilyloxyethylene

To a solution of 120.4 g. of hexamethyldisilazane in 400 ml. of tetrahydrofuran at room temperature, under argon, is added with stirring 296.6 ml of 2.4 M n-butyllithium at a rate which maintains the temperature at 30° C. After addition, the solution is stirred for one hour, cooled to −78° C. and 110 g. of trimethylsilyl methoxyacetate is added dropwise so that the temperature remains at −70° C. After addition, the solution is stirred at −78° C. for 20 minutes. An 86.4 g. portion of chlorotrimethylsilane is added dropwise so that the temperature remains at −70° C. The mixture is allowed to warm slowly to room temperature and then stirred overnight. The mixture is diluted with petroleum ether, filtered through Celite; the solvent is removed and the residue is distilled at 66°-69° C., 6 mm. giving the desired product as a colorless liquid.

REFERENCE EXAMPLE 358

Preparation of Trimethylsilyl Methylthioacetate

To a stirred solution of 164.5 g. (1.55 mol) of methylthioacetic acid in 150 ml. of pyridine and 200 ml. of THF was added 187.6 g. (1.16 mol) of HMDS followed by the dropwise addition of 50.5 g. (0.46 mol) of TMS-Cl. The solution was diluted with an equal volume of petroleum ether and filtered through Celite. The solvent was removed and the residue was distilled (54°-57°, 1.55 mm.) to give 207.6 g. (75%) of 10: $^1$H NMR$\delta_{Me4Si}$ (CDCl$_3$) 3.02 (s, 2H, CH$_2$), 2.04 (s, 3H, SCH$_3$), 0.16 (s, 9H, Si(CH$_3$)$_3$); IR (neat) 1718 cm$^{-1}$.

Anal. Calcd for C$_6$H$_{14}$SO$_2$Si: C, 40.41; H, 7.91; S, 17.94.

Found: C, 41.12; H, 8.00; S, 17.25.

REFERENCE EXAMPLE 359

Preparation of 2-methylthia-1,1-bis-trimethylsilyloxyethylene

To a stirred solution of (1.52 mol) of HMDS in 1.2 L. of THF was added over 1.5 h. under nitrogen, at 0° C. 650 ml. of 2.4 M n-butyllithium in hexane. The solution was then maintained at 45° C. for 30 minutes. The solution was cooled to −78° C. and 1.25 mol of trimethylsilyl methylthiaacetate was added dropwise over a 30 minute period. After stirring an additional 30 minutes, 1.9 mol of TMS-Cl was added dropwise. The solution was allowed to warm to room temperature. The solution was poured into 1 L. of petroleum ether and filtered through Celite. The solvent was removed and the residue was redissolved in petroleum ether. The filtration process was repeated. The solvent was removed and the residue was distilled (54°-56° C., 0.1 mm.) to give the desired product.

REFERENCE EXAMPLE 360

Trimethylsilyl phenoxyacetate

To a solution of 75 g. of phenoxyacetic in 60 ml. of tetrahydrofuran and 70 ml. of pyridine is added, in a steady stream, 87.5 g. of hexamethyldisilazane. The mixture is stirred for 10 minutes and 29.45 g. of chlorotrimethylsilane is rapidly added dropwise. The mixture is stirred at room temperature for 2 hours and then the solvents are removed at 55° C. under vacuum. The residue is mixed with petroleum ether, filtered through Celite and the solvents are removed. The residual filtrate is redissolved in petroleum ether and filtered through Celite. The solvent is removed and the residue distilled at 105°-107° C., 2.7 mm. giving the desired product as a colorless liquid.

REFERENCE EXAMPLE 361

1-Phenoxy-2,2-bis-trimethylsilyloxyethylene

To a solution of 74.5 g. of hexamethyldisilazane in 250 ml. of tetrahydrofuran is added 184 ml. of 2.4 M n-butyllithium at a rate which maintains the temperature at 53° C. The mixture is then stirred at 45° C. for 20 minutes, cooled to −78° C. and 90 g. of trimethylsilyl phenoxyacetate in 30 ml. of tetrahydrofuran is added dropwise maintaining the temperature below −70° C. This mixture is stirred for ½ hour and then 54.5 g. of chlorotrimethylsilane is added dropwise maintaining the temperature below −65° C. The mixture is then allowed to warm slowly to room temperature and stirred overnight. The tetrahydrofuran is removed. The residue is dissolved in petroleum ether and filtered through Celite. The solvent is remoed and the residue distilled at 118°-120° C., 1.2 mm. to give the desired product as a colorless liquid.

REFERENCE EXAMPLE 362

1,2-bis-Methoxy-1-trimethylsilyloxyethylene

To a solution of 186 g. (1.2 mol) of 1,1,1,3,3,3-hexamethyldisilazane in 550 ml. of tetrahydrofuran is added under argon with stirring at 0° C. 417.6 ml. of 2.3 M n-butyllithium in hexane. After 0.5 hours the solution is cooled to −78° C. and 100 g. (0.96 mol) methyl methoxyacetate is added dropwise. After 0.5 hours, 104.35 g. (0.96 mol) of trimethylchlorosilane is added dropwise. The solution is allowed to slowly warm to room temperature. The mixture is filtered and the solvent is removed. The residue is dissolved in petroleum ether and the mixture is filtered through Celite. The solvent is removed and the residue is fractionally distilled. The fraction boiling 68°-71°, 35 mm. consists of 83 g. of the title compound.

REFERENCE EXAMPLE 363

4-Dimethyl-t-butylsilyloxy-2-(6-carbodimethyl-t-butylsilyloxyhexyl)cyclopent-2-en-1-one A mixture of 29.3 g. of 4-hydroxy-2-(6-carboxyhexyl)cyclopent-2-en-1-one, 41.95 g. of dimethyl-t-butylchlorosilane and 37.91 g. of imidazole in 130 ml. of dimethylformamide is stirred overnight, poured into water and extracted with petroleum ether. The organic solution is washed with water, then saturated sodium bicarbonate solution and dried over magnesium sulfate. The solvent is removed and the residue distilled via a Kugelrohr giving the desired product as a colorless oil.

REFERENCE EXAMPLE 364

2-(6-Chloroformylhexyl)-4-dimethyl-t-butylsilyloxycyclopent-2-en-1-one

To a mixture of 50.6 g. of 4-dimethyl-t-butylsilyloxy-2-(6-carbodimethyl-t-butylsilyloxyhexyl)cyclopent-2-en-1-one and 0.7 ml. of dimethylformamide in 150 ml. of tetrahydrofuran at 0° C., under argon, is added 16.1 g. of oxalyl chloride. The mixture is stirred at 0° C. for 2 hours and then at room temperature for 2.5 hours. The solvent is removed at 35° C. The residue is dissolved in petroleum ether and filtered through Celite. The petroleum ether is removed, the residue is again dissolved in fresh petroleum ether and filtered through Celite. The solvent is removed giving the desired product as a dark orange oil.

REFERENCE EXAMPLE 365

4-Hydroxy-2-(6-methoxyacetylhexyl)cyclopent-2-en-1-one

A solution of 30 g. of 2-(6-chloroformlhexyl)-4-dimethyl-t-butylsilyloxycyclopent-2-en-1-one and 43 g. of 1-methoxy-2,2-bis-trimethylsilyloxyethylene in 150 ml. of chlorobenzene, under argon, is refluxed for 4¼ hours. The solvent is removed at reduced pressure at 40° C. The residue is refluxed with 300 ml. of tetrahydrofuran and 75 ml. of 0.9 N hydrochloric acid for 1¾ hours. The tetrahydrofuran is removed at reduced pressure. The residue is saturated with sodium chloride and extracted with ethyl acetate. The ethyl acetate solution is washed with saturated sodium bicarbonate solution, dried over magnesium sulfate and filtered through a pad of silica gel. The solvent is removed giving a yellow oil which is chromatographed on a dry silica gel column, eluting with ether to give the desired product.

REFERENCE EXAMPLE 366

4-Trimethylsilyloxy-2-(6-methoxyacetylhexyl)cyclopent-2-en-1-one

To a stirred mixture of 11 g of 4-hydroxy-2-(6-methoxyacetylhexyl)cyclopent-2-en-1-one and 7.33 g. of hexamethyldisilazane in 20 ml. of pyridine is added 2.47 g. of chlorotrimethylsilane. The mixture is stirred at room temperature overnight, the solvent is removed at reduced pressure and the residue is dissolved in petroleum ether and filtered through Celite. The petroleum ether is removed and the residue is distilled via a Kugelrohr at 170°–180° C., 0.05 mm. giving an orange oil. To this oil is added 10 ml. of pyridine, 1.5 ml. of hexamethyldisilazane and 0.7 ml. of chlorotrimethylsilane. After standing for 30 minutes, the mixture is extracted with petroleum ether. The petroleum ether is dried over magnesium sulfate and then the solvent is removed giving the desired product as a yellow oil.

REFERENCE EXAMPLE 367

4-Hydroxy-2-(6-methoxyacetyl-hex-2-cis-enyl)cyclopent-2-en-1-one

A mixture of 10.2 g. of 2-(6-chloroformlhex-2-cis-enyl)-4-dimethyl-t-butylsilyloxycyclopent-2-en-1-one and 16.7 g. of 1-methoxy-2,2-bis-trimethylsilyloxyethylene is stirred at 120° C., under argon, for 7 hours. To this mixture is added 40 ml. of 0.6 N hydrochloric acid, 120 ml. of tetrahydrofuran and 15 ml. of acetic acid and the mixture is stirred at reflux for one hour. The tetrahydrofuran is removed and the residue is mixed with ethyl acetate. The organic layer is washed with saturated sodium bicarbonate solution and dried over magnesium sulfate. The solvent is removed and the residue chromatographed on a silica gel column using ether to elute the desired product.

REFERENCE EXAMPLE 368

4-(1-Methoxy-1-methylethoxy)-2-(6-methoxyacetyl-hex-2-cis-enyl)cyclopent-2-en-1-one To a solution of 1.4 g. of 4-hydroxy-2-(6-methoxyacetylhex-2-cis-enyl) cyclopent-2-en-1-one in 2 ml. of dichloromethane is added one ml. of 2-methoxy propene. After ½ hour, the solvent, is removed giving the desired product.

REFERENCE EXAMPLE 369

4-Hydroxy-2-(6-phenoxyacetylhexyl)cyclopent-2-en-1-one

A mixture of 13.2 g. of 2-(6-chloroformylhexyl)-4-dimethyl-t-butylsilyloxycyclopent-2-en-1-one and 24 g. of 1-phenoxy-2,2-bis-trimethylsilyloxyethylene in 50 ml. of chlorobenzene is stirred at reflux under argon for 5 hours and then at room temperature overnight. The solvent is removed at reduced pressure and 40° C. and the residue is refluxed in a mixture of 100 ml. of tetrahydrofuran and 25 ml. of 1 N hydrochloric acid for 1.5 hours. The tetrahydrofuran is removed and the residue is diluted with water and extracted with ethyl acetate. The organic layer is washed with saturated sodium bicarbonate solution, dried over magnesium sulfate and filtered through a pad of silica gel. The solvent is removed giving a yellow solid which is recrystallized from ethyl acetate-hexane giving the desired product as a tan solid.

REFERENCE EXAMPLE 370

4-Trimethylsilyloxy-2-(6-phenoxyacetylhexyl)cyclopent-2-en-1-one

A mixture of 6.3 g. of 4-hydroxy-2-(6-phenoxyacetylhexyl)cyclopent-2-en-1-one, 3.34 g. of hexamethyldisilizane and 1.12 g. of chlorotrimethylsilane in 20 ml. of pyridine is stirred at room temperature for 2.5 hours. The pyridine is removed. The residue is dissolved in petroleum ether and filtered through Celite. The filtrate is washed with saturated sodium bicarbonate solution, dried over magnesium sulfate and filtered through a pad of silica gel. The pad is washed with ether. The filtrate and washings are combined and the solvent is removed. The resulting yellow oil is crystallized in a freezer giving the desired product.

REFERENCE EXAMPLE 371

2-[8-methoxy-8-methoxycarbonyl-7-(trimethylsilyloxy)-7-octenyl]-4-trimethylsilyloxy cyclopent-2-en-1-one To a solution of 31.6 g. (69.5 mmol) of 2-[6-carbo-t-butyldimethylsilyloxyhexyl]-4-t-butyldimethylsilyloxy cyclopent-2-en-1-one in 80 ml. of tetrahydrofuran at 0° C. with stirring is added 0.4 ml. of dimethylformamide and 10.14 g. (79.9 mmol) of oxalyl chloride. After 2 hours at 0° C. and 2 hours at room temperature, the solvent is removed. The residue is dissolved in petroleum ether and filtered and the solvent is removed. To the residue is added 24.5 g. of 1,2-bis-dimethoxy-1-trimethylsilyloxyethylene and 100 ml. of chlorobenzene. The mixture is refluxed for 6 hours under argon. The solvent is removed and the residue is stirred for one hour in a mixture of 100 ml. of tetrahydrofuran, 20 ml. of acetic acid, and 25 ml. of 0.6 N hydrochloric acid. The solvent is removed and the residue is dissolved in ether. The ether solution is washed with water and saturated sodium bicarbonate. The solution is dried and the ether is removed. The residue is chromatographed on a dry column of silica gel eluting with ether. The major bond is collected and extracted with ethyl acetate. The solvent is removed. To 8.0 g. of the residue is added 30 ml. of dry pyridine, 8.3 g. (51.2 mmol) of 1,1,1,3,3,3-hexamethyldisilazane and 2.8 g. (25.6 mmol) of chlorotrimethylsilane. After stirring 17 hours, the pyridine is removed, the residue is dissolved in petroleum ether and the solution is filtered. The solvent is removed and the residue is subjected to molecular distillation (185°–190° C., 0.04 mm.) to give 10.1 g. of the title compound.

REFERENCE EXAMPLE 372

1,9-Dioxo-11α,15-dihydroxy-1-methoxymethyl-15-vinyl-13-trans-prostene

To a solution of 5.2 g. of E-1-tri-n-butylstannyl-3-trimethylsilyloxy-3-vinyl-1-octene in 7 ml. of tetrahydrofuran under argon at −78° C. is added, with stirring, 4.5 ml. of 2 M n-butyllithium. The solution is stirred for 2 hours and 10 minutes at −20° C. to −15° C. A solution of 1.2 g of pentynyl copper and 3 ml. of hexamethylphosphoramide in 35 ml. of ether is added at −78° C. After one hour a solution of 1.5 g. of 4-trimethylsilyloxy-2-(6-methoxyacetylhexyl)cyclopent-2-en-1-one in 5 ml. of ether is added. The mixture is stirred at 40° C. for ½ hour, then at −40° to −20° C. for ½ hour, recooled to −45° C. and the saturated ammonium chloride solution is added. The mixture is stirred for ½ hour and extracted with ether. The ether solution is washed rapidly with ice cold dilute hydrochloric acid and a saturated sodium bicarbonate-saturated ammonium chloride mixture, and the solvent removed. The residue is stirred in 50 ml. of acetic acid:tetrahydrofuran:water (4:2:1) for one hour. The solvent is removed at reduced pressure and room temperature. The residue is washed with sodium bicarbonate in ether and then partitioned between heptane and methanol. The methanol is removed leaving a yellow oil which is chromatographed on a silica gel, eluting with ether to give the desired product as a yellow oil.

REFERENCE EXAMPLE 373

1,9-Dioxo-11α,16-dihydroxy-16-methyl-1-methoxymethyl-13-trans-prostene

To a solution of 8.4 g. of E-1-tri-n-butylstannyl-4-methyl-4-trimethylsilyloxy-1-octene in 6 ml. of tetrahydrofuran under argon at 78° C. is added, with stirring, 6.4 ml. of 2 M n-butyllithium. The solution is stirred at −22° to −15° C. for 2¼ hours and then recooled to −78° C. A solution of 1.9 g. of pentynyl copper and 1.7 ml. of hexamethylphosphoramide in 30 ml. of ether is added. After 45 minutes, 2.1 g. of 4-trimethylsilyloxy-2-(8-methoxyacetylhexyl)cyclopent-2-en-1-one in 5 ml. of ether is added. The solution is stirred at −50° C. for one hour, at −50° to −20° C. for ½ hour, recooled to −40° C. and saturated ammonium chloride is added. After stirring for 20 minutes, the mixture is extracted with ether. The ether solution is washed with dilute hydrochloric acid and a mixture of saturated ammonium chloride-sodium bicarbonate. The ether is removed and the residue is stirred with 50 ml. of acetic acid:tetrahydrofuran:water (4:2:1) for one hour. The solvents are removed and the residue is partitioned between methanol and heptane. The solvent is removed from the methanol layer and the residue is chromatographed on a dry column of silica gel, eluting with ether to give the desired product as a nearly colorless liquid.

REFERENCE EXAMPLE 374

1,9-Dioxo-11α,16-dihydroxy-1-methoxymethyl-16-vinyl-13-trans-prostene

To a solution of 7.35 g. of E-1-tri-n-butylstannyl-4-vinyl-4-trimethylsilyloxy-1-octene in 7 ml. of tetrahydrofuran at −78° C., under argon, is added with stirring, 6.4 ml. of 2 M n-butyllithium. After stirring at −15° to −10° C. for 2 hours, a solution of 1.8 g. of pentynyl copper and 4.4 ml. of hexamethylphosphoramide in 30 ml. of ether is added at −78° C. After 45 minutes, 2.0 g. of 4-trimethylsilyloxy-2-(6-methoxyacetylhexyl)cyclopent-2-en-1-one in 5 ml. of ether is added. The solution is stirred at −50° C. for ½ hour, then at −50° to −20° C. for ½ hour, cooled to −40° C. and saturated ammonium chloride is added. The recovery procedure of Example 373 is followed, giving the desired product as a yellow oil.

REFERENCE EXAMPLE 375

1,9-Dioxo-11α,16-dihydroxy-16-methyl-1-methoxymethyl-5-cis-13-trans-prostadiene

To a solution of 5.27 g. of E-1-tri-n-butylstannyl-4-methyl-4-trimethylsilyloxy-1-octene in 5 ml. of tetrahydrofuran at −78° C., under argon, is added with stirring, 5.6 ml. of 1.9 M n-butyllithium. The mixture is stirred for 2 hours at −20° to −15° C., recooled to −78° C. and a solution of 1.37 g. of pentynyl copper and 3.5 g. of hexamethylphosphoramide in 25 ml. of ether is added. After 45 minutes 1.4 g. of 4-trimethylsilyloxy-2-(6-methoxyacetylhex-2-cis-enyl)cyclopent-2-en-1-one in 5 ml. of ether is added. The mixture is stirred at −40° C. for one hour, then at −40° to −20° C. for ½ hour, 2 ml. of acetic acid followed by saturated ammonium chloride solution are added and the recovery procedure of Example 373 is employed, giving the desired product as a yellow oil.

REFERENCE EXAMPLE 376

1,9-Dioxo-11α,16-dihydroxy-16-methyl-1-phenoxymethyl-13-trans-prostene

To a solution of 6.69 g. of E-1-tri-n-butylstannyl-4-methyl-4-trimethylsilyloxy-1-octene in tetrahydrofuran at −78° C. is added 5.03 ml. of 2 M n-butyllithium. The mixture is stirred for 2 hours and 10 minutes at −20° to −15° C. and then recooled to −78° C. A solution of 1.6 g. of pentynyl copper and 3.97 g. of hexamethylphosphoramide in 30 ml. of ether is added. After 45 minutes, 2.15 g. of 4-trimethylsilyloxy-2-(6-phenoxyacetylhexyl)cyclopent-2-en-1-one in 5 ml. of ether is added. The solution is stirred at −45° to −20° C. for 45 minutes, saturated ammonium chloride solution is added and the mixture is stirred for 20 minutes and then extracted with ether. The ether layer is treated as described in Example 373 giving the desired product.

REFERENCE EXAMPLE 377

Preparation of
dl-11α,16α/β-dihydroxy-1-(methoxymethoxycarbonyl-methyl)-1,9-dioxo-16-vinyl-13-trans prostene To a solution of 1-trans-tri-n-butylstannyl-4-vinyl-4-trimethylsilyloxy-1-octene (5.64 g., 10.95 mmol) in 5 ml. tetrahydrofuran at −20° C. under argon with stirring is added 3.3 ml. of 2 M n-butyllithium in hexane. The solution is maintained at −20° to −15° C. for 2 hours. The solution is cooled to −78° C. and copper pentyne (0.93 g., 7.12 mmol) and hexamethylphosphorus triamide (2.41 g., 14.78 mmol) in 30 ml. ether is added. After one hour, 2-[8-methoxy-8-carbomethoxy-7-oxo-octyl]-4-trimethylsilyloxy cyclopent-2-en-1-one (2.5 g., 5.47 mmol) in 5 ml. of ether is added. After 0.5 hour at −40° C. and 0.5 hour at −40° to −20° C., a saturated solution of ammonium chloride is added. After stirring for 15 minutes, the mixture is extracted with ether. The ether solution is washed with dilute hydrochloric acid and a mixture of ammonium chloride and sodium bicarbonate solutions. The ether solution is dried over magnesium sulfate and the solvent is removed. The residue is stirred for 40 minutes in a mixture of acetic acid, tetrahydrofuran and water (70 ml.). The solvents are removed and the residue is chromatographed on a dry column of silica gel eluting with ethylacetatehexane 3:1. The major product is collected to give 1.03 g. of the title compound.

REFERENCE EXAMPLE 378 dl-11α,16α/β-dihydroxy-1-(methoxymethyl carbonylmethyl)-1,9-dioxo-16-methyl-13-trans prostene To a solution of 1-trans-tri-n-butylstannyl-4-methyl-trimethylsilyloxy-1-octene (5.51 g., 10.95 mmol) in 5 ml. tetrahydrofuran at −20° C. under argon with stirring is added 3.3 ml. of 2 M n-butyllithium in hexane. The solution is maintained at −20° to −15° C. for 2.5 hours. The solution is cooled to −78° C. and copper pentyne (0.93 g, 7.12 mmol) and hexamethylphosphorous triamide (2.32 g., 7.12 mmol) in 30 ml. of ether is added. After one hour, 2-[8-methoxy-8-carbomethoxy-7-oxo-octyl]-4-trimethylsilyloxy cyclopent-2-en-1-one (2.5 g., 5.47 mmol) in 5 ml. of ether is added. After 0.5 hour at −40° C. and 0.5 hour at −40° to −20° C., a saturated solution of ammonium chloride is added. After stirring for 15 minutes, the mixture is extracted with ether. The ether solution is washed with dilute hydrochloric acid and a mixture of ammonium chloride and sodium bicarbonate solutions. The ether solution is dried over magnesium sulfate and the solvent is removed. The residue is stirred 40 minutes in a mixture of acetic acid, tetrahydrofuran and water (70 ml.). The solvents are removed and the residue is chromatographed on a dry column of silica gel eluting with ether-ethylacetate 3:1–0.1% acetic acid. The major product is collected to give 1.62 g. of the title compound.

REFERENCE EXAMPLE 379

Preparation of
dl-11α,15α-dihydroxy-1-(2'-methoxymethylacetate)-1,9-dioxo-13-trans prostene and
dl-11α,15β-dihydroxy-1-(methoxymethoxy carbonylmethyl)-1,9-dioxo-13-trans prostene To a solution of 1-trans-tri-n-butylstannyl-3-triethyl-silyloxy-1-octene (6.98 g., 13.14 mmol) in 5 ml. tetrahydrofuran at −45° C. under argon with stirring is added 3.3 ml. of 3.94 2 M n-butyllithium in hexanes. The solution is maintained at −45° C. for one hour. The solution is cooled to −78° C. and copper pentyne (1.12 g., 8.54 mmol) and hexamethylphosphorous triamide (2.79 g., 17.08 mmol) in 30 ml. ether is added. After one hour, 2-[8-methoxy-8-methoxycarbonyl-7-oxo-octyl]-4-trimethylsilyloxy cyclopent-2-en-1-one (3.0g., 6.57 mmol) in 5 ml. of ether is added. After 0.5 hour at −40° C. and 0.5 hour at −40° to −20° C., a saturated solution of ammonium chloride is added. After stirring 15 minutes, the mixture is extracted with ether. The ether solution is washed with dilute hydrochloric acid and a mixture of ammonium chloride and sodium bicarbonate solutions. The ether solution is dried over magnesium sulfate and the solvent is removed. The residue is stirred 40 minutes in a mixture of acetic acid, tetrahydrofuran and water (70 ml.). The solvents are removed and the residue is chromatographed on a dry column of silica gel eluting with ether-ethylacetate 7.3–0.2% acetic acid. The major products are collected to give 0.5 g. of the 15α isomer and 0.49 g. of the 15β isomer.

REFERENCE EXAMPLE 380

2-[6-(chloroformyl)hex-2-cis-enyl]-4-bis-dimethyl-t-butylsilyloxy cyclopent-2-en-1-one To an ice-cold solution of 2-(6-carbobis-dimethyl-t-butylsilyloxyhex-2-cis-enyl)-4-bis-dimethyl-t-butyl-silyloxy-cyclopent-2-en-1-one (92.7 g., 204 mmol) in tetrahydrofuran (283 ml.) containing a catalytic amount of dimethylformamide (1.3 ml.) is added freshly distilled oxalylchloride (19.3 ml., 28.0 g., 221 mmol) via syringe (vigorous gas evolution, caution: carbon monoxide). The resulting mixture is stirred at 0° C. for 2 hours and at ambient temperature for 2 hours. The volatile material is removed in vacuo (bath 25° C., dry-ice/acetone cooled received; 0.1 mm. final pressure). The resulting residue is slurried with hexane (900 ml.), filtered through diamataceous earth, followed by 100 ml. hexane washing of the pad. The combined hexane solutions are concentrated in vacuo to give the carboxylic acid chloride as a yellow liquid.

REFERENCE EXAMPLE 381

2-(6-carbobis-dimethyl-t-butylsilyloxyhex-2-cis-enyl)-4-bis-dimethyl-t-butylsilyloxy-cyclopent-2-en-1-one To a stirred, 35° C. solution of 2-(6-carboxyhex-2-cis-enyl)-4-hydroxy-cyclopent-2-en-1-one (33.1 g., 146 mmol) in dimethylformamide (100 ml.) is added imidazole (48 g., 77 mmol) followed immediately by a slurry of t-butyl-chlorodimethylsilane (48.2 g., 321 mmol) in dimethylformamide (45 ml.). The resulting mixture is stirred under nitrogen atmosphere at 55° C. After 4 hours the cooled mixture (2 layers ) is treated with hexane (400 ml.) and water (150 ml.). The hexane layer is separated and washed twice with water (100 ml. each time) and twice with saturated sodium chloride solution (100 ml. each time) and dried over magnesium sulfate. The solvent is removed in vacuo at 50° C. to give mobile amber liquid. Distillation via Kugelrohr (0.4 mm Hg., air bath, 180°–190° C.) gave the title compound as a light yellow liquid.

REFERENCE EXAMPLE 382

The protected cyclopentenone of Table I is prepared by the reaction of the listed acid chloride and the listed ethylene reagent in accordance with the procedure of Examples 363–365, 369 and 371, followed by the protection of the compound in accordance with the procedure of Examples 368 and 370.

REFERENCE EXAMPLE 383

To prepare compounds of the F-Series, the cyclopentenones (191) and (199), the ketone function on the alpha chain is protected with ethylene glycol and a catalytic amount of a mineral acid or acid exchange resin, to give a cyclic dioxalane (Flowsheet V). The remaining hydroxyl functions are trimethylsilated as described hereinabove. The conjugate addition reaction of this protected cyclopentenone described herein and the organocuprates described hereinabove, followed by removal of the TMS groups with acetic acid:-water:THF (4:1:2) (10 minutes, 25° C.) and reduction of the resulting compound with a hindered reducing agent such as lithium tri-sec-butylhydroborate and the like, followed by hydrolytic removal of the ethylene ketal protecting group using THF, acetic and water (2:4:1) containing 1 or 2 drops of concentrated hydrochloric acid is productive of the Fα compound. In order to prepare the PGFβ compounds of this invention, the above-described protected product is reduced with sodium borohydride in ethanol (1 mol per mol of PGE compound). The ethanol is removed and the residue is dissolved in ethylacetate and the resulting solution is washed with water. The solvent is removed and the residue is hydrolized with acetic acid:water:THF (4:1:2) containing 1 to 5 drops of concentrated hydrochloric acid to given a mixture of the PGFα and PGFβ compounds of this invention. The compounds are separated by procedures well-known in the art.

TABLE I

| ACID CHLORIDE | ETHYLENE REAGENT | PROTECTED CYCLOPENT-2-EN-1-ONE |
| --- | --- | --- |
| 2-(5-chloroformylpent-2-cis-enyl)-4-dimethyl-t-butysilyloxycyclopent-2-en-1-one | 2-methoxy-1,1-bis-trimethyl-silyloxyethylene | 2-[5-methoxyacetylpent-2-cis-enyl]-4-trimethylsiloxy cyclopent-2-en-1-one |
| 2-(6-chloroformylhex-2-cis-enyl)-4-dimethyl-t-butysilyloxycyclopent-2-en-1-one | 2-methoxy-1,1-bis-trimethyl-silyloxyethylene | 2-[6-methoxyacetylhex-2-cis-enyl]-4-trimethylsiloxy cyclopent-2-en-1-one |
| 2-(7-chloroformylhept-2-cis-enyl)-4-dimethyl-t-butyl- | 2-methyoxy-1,1-bis-trimethyl-silyloxyethylene | 2-[7-methoxyacetylhept-2-cis-enyl]-4-trimethylsiloxy cyclopent-2-en-1-one |
| 2-(5-chloroformylpentyl)-4-dimethyl-t-butylsilyloxy-cyclopent-2-en-1-one | 2-methoxy-1,1-bis-trimethyl-silyloxyethylene | 2-[5-methoxyacetylpentyl]-4-trimethyl-siloxy cyclopent-2-en-1-one |
| 2-(6-chloroformylhexyl)-4-dimethyl-t-butylsilyloxy-cyclopent-2-en-1-one | 2-methoxy-1,1-bis-trimethyl-silyloxyethylene | 2-[6-methoxyacetylhexyl]-4-trimethyl-siloxy cyclopent-2-en-1-one |
| 2-(7-chloroformylheptyl)-4-dimethyl-t-butylsilyloxy-cyclopent-2-en-1-one | 2-methoxy-1,1-bis-trimethyl-silyloxyethylene | 2-[7-methoxyacetylheptyl]-4-trimethyl-siloxy cyclopent-2-en-1-one |
| 2-(6-chloroformylhex-2-cis enyl)-4R-trimethylsiloxy-cyclopent-2-en-1-one | 2-methoxy-1,1-bis-trimethyl-silyloxyethylene | 2-[6-methoxyacetylhex-2-cis-enyl]-4R-trimethylsiloxy cyclopent-2-en-1-one |
| 2-(6-chloroformylhexyl)-4R-trimethylsiloxycyclopent-2-en-1-one | 2-methoxy-1,1-bis-trimethyl-silyloxyethylene | 2-[6-methoxyacetylhexyl]-4R-trimethyl-siloxy cyclopent-2-en-1-one |
| 2-(5-chloroformylpent-2-cis-enyl)cyclopent-2-en-1-one | 2-methoxy-1,1-bis-trimethyl-silyloxyethylene | 2-[5-methoxyacetylpent-2-cis-enyl] cyclopent-2-en-1-one |
| 2-(6-chloroformylhex-2-cis-enyl)cyclopent-2-en-1-one | 2-methoxy-1,1-bis-trimethyl-silyloxyethylene | 2-[6-methoxyacetylhex-2-cis-enyl] cyclopent-2-en-1-one |
| 2-(7-chloroformylhept-2-cis-enyl)cyclopent-2-en-1-one | 2-methoxy-1,1-bis-trimethyl-silyloxyethylene | 2-[7-methoxyacetylhept-2-cis-enyl] cyclopent-2-en-1-one |
| 2-(5-chloroformypentyl) cyclopent-2-en-1-one | 2-methoxy-1,1-bis-trimethyl-silyloxyethylene | 2-[5-methoxyacetylpentyl] cyclopent-2-en-1-one |
| 2-(6-chloroformylhexyl) cyclopent-2-en-1-one | 2-methoxy-1,1-bis-trimethyl-silyloxyethylene | 2-[6-methoxyacetylhexyl] cyclopent-2-en-1-one |
| 2-(7-chloroformylheptyl) cyclopent-2-en-1-one | 2-methoxy-1,1-bis-trimethyl-silyloxyethylene | 2[7-methoxyacetylheptyl] cyclopent-2-en-1-one |
| 2-(5-chloroformylpent-2-cis-enyl)-4-dimethyl-t-butylsilyl-oxycyclopent-2-en-1-one | 2-phenoxy-1,1-bis-trimethyl-silyloxyethylene | 2-[5-phenoxyacetylpent-2-cis-enyl]-4-trimethylsiloxy cyclopent-2-en-1-one |
| 2-(6-chloroformylhex-2-cis-enyl)-4-dimethyl-t-butylsilyl-oxycyclopent-2-en-1-one | 2-phenoxy-1,1-bis-trimethyl-silyloxyethylene | 2-[6-phenoxyacetylhex-2-cis-enyl]-4-trimethylsiloxy cyclopent-2-en-1-one |
| 2-(7-chloroformylhept-2-cis-enyl)-4-dimethyl-t-butylsilyl-oxycyclopent-2-en-1-one | 2-phenoxy-1,1-bis-trimethyl-silyloxyethylene | 2-[7-phenoxyacetylhept-2-cis-enyl]-4-trimethylsiloxy cyclopent-2-en-1-one |
| 2-(5-chloroformylpentyl)-4-dimethyl-t-butylsilyloxy-cyclopent-2-en-1-one | 2-phenoxy-1,1-bis-trimethyl-silyloxyethylene | 2-[5-phenoxyacetylpentyl]-4-trimethyl-siloxy cyclopent-2-en-1-one |
| 2(6-chloroformylhexyl)-4-dimethyl-t-butylsilyloxy-cyclopent-2-en-1-one | 2-phenoxy-1,1-bis-trimethyl-silyloxyethylene | 2-[6-phenoxyacetylhexyl]-4-trimethyl-siloxy cyclopent-2-en-1-one |
| 2-(7-chloroformylheptyl)-4-dimethyl-t-butylsilyloxy-cyclopent-2-en-1-one | 2-phenoxy-1,1-bis-trimethyl-silyloxyethylene | 2-[7-phenoxyacetylheptyl]-4-trimethyl-siloxy cyclopent-2-en-1-one |
| 2-(6-chloroformylhex-2-cis-enyl)-4R-trimethylsiloxy-cyclopent-2-en-1-one | 2-phenoxy-1,1-bis-trimethyl-silyloxyethylene | 2-[6-phenoxyacetylhex-2-cis-enyl]-4R-trimethylsiloxy cyclopent-2-en-1-one |
| 2-(6-chloroformylhexyl)-4R-trimethylsiloxycyclopent-2-en-1-one | 2-phenoxy-1,1-bis-trimethyl-silyloxyethylene | 2-[6-phenoxyacetylhexyl]-4R-trimethylsiloxy cyclopent-2-en-1-one |
| 2-(5-chloroformylpent-2-cis-enyl)cyclopent-2-en-1-one | 2-phenoxy-1,1-bis-trimethyl-silyloxyethylene | 2-[5-phenoxyacetylpent-2-cis-enyl] cyclopent-2-en-1-one |

TABLE I-continued

| ACID CHLORIDE | ETHYLENE REAGENT | PROTECTED CYCLOPENT-2-EN-1-ONE |
|---|---|---|
| 2-(6-chloroformylhex-2-cis-enyl)cyclopent-2-en-1-one | 2-phenoxy-1,1-bis-trimethyl-silyloxyethylene | 2-[6-phenoxyacetylhex-2-cis-enyl]cyclopent-2-en-1-one |
| 2-(7-chloroformylhept-2-cis-enyl)cyclopent-2-en-1-one | 2-phenoxy-1,1-bis-trimethyl-silyloxyethylene | 2-[7-phenoxyacetylhept-2-cis-enyl]cyclopent-2-en-1-one |
| 2-(5-chloroformylpentyl)cyclopent-2-en-1-one | 2-phenoxy-1,1-bis-trimethyl-silyloxyethylene | 2-[5-phenoxyacetylpentyl]cyclopent-2-en-1-one |
| 2-(6-chloroformylhexyl)cyclopent-2-en-1-one | 2-phenoxy-1,1-bis-trimethyl-silyloxyethylene | 2-[6-phenoxyacetylhexyl]cyclopent-2-en-1-one |
| 2-(7-chloroformylheptyl)cyclopent-2-en-1-one | 2-phenoxy-1,1-bis-trimethyl-silyloxyethylene | 2-[7-phenoxyacetylheptyl]cyclopent-2-en-1-one |
| 2-(5-chloroformylpent-2-cis-enyl)-4-dimethyl-t-butylsilyl-oxycyclopent-2-en-1-one | 2-methylthia-1,1-bis-tri-methylsilyloxyethylene | 2-[5-methylthiaacetylpent-2-cis-enyl]-4-trimethylsiloxy cyclopent-2-en-1-one |
| 2-(6-chloroformylhex-2-cis-enyl-4-dimethyl-t-butyl-silyloxycyclopent-2-en-1-one | 2-methylthia-1,1-bis-tri-methylsilyloxyethylene | 2-[6-methylthiaacetylhex-2-cis-enyl]-4-trimethylsiloxy cyclopent-2-en-1-one |
| 2-(7-chloroformylhept-2-cis-enyl)-4-dimethyl-t-butyl-silyloxycyclopent-2-en-1-one | 2-methylthia-1,1-bis-tri-methylsilyloxyethylene | 2-[7-methylthiaacetylhept-2-cis-enyl]-4-trimethylsiloxy cyclopent-2-en-1-one |
| 2-(5-chloroformylpentyl)-4-dimethyl-t-butylsiloxy-cyclopent-2-en-1-one | 2-methylthia-1,1-bis-tri-methylsilyloxyethylene | 2-[5-methylthiaacetylpentyl]-4-trimethylsiloxy cyclopent-2-en-1-one |
| 2-(6-chloroformylhexyl)-4-dimethyl-t-butylsilyloxy-cyclopent-2-en-1-one | 2-methylthia-1,1-bis-tri-methylsilyloxyethylene | 2-[6-methylthiaacetylhexyl]-4-trimethylsiloxy cyclopent-2-en-1-one |
| 2-(7-chloroformylheptyl)-4-dimethyl-t-butylsilyloxy cyclopent-2-en-1-one | 2-methylthia-1,1-bis-tri-methylsilyloxyethylene | 2-[7-methylthiaacetylheptyl]-4-trimethylsiloxy cyclopent-2-en-1-one |
| 2-(6-chloroformylhex-2-cis-enyl)-4R-trimethylsiloxy-cyclopent-2-en-1-one | 2-methylthia-1,1-bis-tri-methylsilyloxyethylene | 2-[6-methylthiaacetylhex-2-cis-enyl]-4R-trimethylsiloxy cyclopent-2-en-1-one |
| 2-(6-chloroformylhexyl)-4R-trimethylsiloxycyclopent-2-en-1-one | 2-methylthia-1,1-bis-tri-methylsilyloxyethylene | 2-[6-methylthiaacetylhexyl]-4R-trimethylsiloxy cyclopent-2-en-1-one |
| 2-(5-chloroformylpent-2-cis-enyl)cyclopent-2-en-1-one | 2-methylthia-1,1-bis-tri-methylsilyloxyethylene | 2-[5-methylthiaacetylpent-2-cis-enyl]cyclopent-2-en-1-one |
| 2-(6-chloroformylhex-2-cis-enyl(cyclopent-2-en-1-one | 2-methylthia-1,1-bis-tri-methylsilyloxyethylene | 2-[6-methylthiaacetylhex-2-cis-enyl]cyclopent-2-en-1-one |
| 2-(7-chloroformylhept-2-cis-enyl)cyclopent-2-en-1-one | 2-methylthia-1,1-bis-tri-methylsilyloxyethylene | 2-[7-methylthiaacetylhept-2-cis-enyl]cyclopent-2-en-1-one |
| 2-(5-chloformylpentyl)cyclopent-2-en-1-one | 2-methylthia-1,1-bis-tri-methylsilyloxyethylene | 2-[5-methylthiaacetylpentyl]cyclopent-2-en-1-one |
| 2-(6-chloroformylhexyl)cyclopent-2-en-1-one | 2-methylthia-1,1-bis-tri-methylsilyloxyethylene | 2-[6-methylthiaacetylhexyl]cyclopent-2-en-1-one |
| 2-(7-chloroformylheptyl)cyclopent-2-en-1-one | 2-methylthia-1,1-bis-tri-methylsilyloxyethylene | 2-[7-methylthiaacetylheptyl]cyclopent-2-en-1-one |
| 2-(5-chloroformylpent-2-cis-enyl)-4-dimethyl-t-butyl-silyloxycyclopent-2-en-1-one | 1,2-dimethoxy-1-trimethyl-silyloxyethylene | 2-[7-methoxy-7-methoxycarbonyl-6-(trimethylsiloxy)-2-cis,6-heptadienyl]-4-trimethylsiloxy cyclopent-2-en-1-one |
| 2-(6-chloroformylhex-2-cis-enyl)-4-dimethyl-t-butyl-silyloxycyclopent-2-en-1-one | 1,2-dimethoxy-1-trimethyl-silyloxyethylene | 2-[8-methoxy-8-methoxycarbonyl-7-(trimethylsiloxy)-2-cis,7-octadienyl]-4-trimethylsiloxy cyclopent-2-en-1-one |
| 2-(7-chloroformylhept-2-cis-enyl)-4-dimethyl-t-butyl-silyloxycyclopent-2-en-1-one | 1,2-dimethoxy-1-trimethyl-silyloxyethylene | 2-[9-methoxy-9-methoxycarbonyl-8-(trimethylsiloxy)-2-cis,8-nonadienyl]-4-trimethylsiloxy cyclopent-2-en-1-one |
| 2-(5-chloroformylpentyl)-4-dimethyl-t-butylsilyloxy-cyclopent-2-en-1-one | 1,2-dimethoxy-1-trimethyl-silyloxyethylene | 2-[7-methoxy-7-methoxycarbonyl-6-(trimethylsiloxy)-6-heptenyl]-4-trimethylsiloxy cyclopent-2-en-1-one |
| 2-(6-chloroformylhexyl)-4-dimethyl-t-butylsilyloxy-cyclopent-2-en-1-one | 1,2-dimethoxy-1-trimethyl-silyloxyethylene | 2-[8-methoxy-8-methoxycarbonyl-7-(trimethylsiloxy)-7-octenyl]-4-trimethylsiloxy cyclopent-2-en-1-one |
| 2-(7-chloroformylheptyl)-4-dimethyl-t-butylsilyloxy-cyclopent-2-en-1-one | 1,2-dimethoxy-1-trimethyl-silyloxyethylene | 2-[9-methoxy-9-methoxycarbonyl-8-(trimethylsiloxy)-8-nonenyl]-4-trimethylsiloxy cyclopent-2-en-1-one |
| 2-(6-chloroformylhex-2-cis-enyl)-4R-trimethylsiloxy-cyclopent-2-en-1-one | 1,2-dimethoxy-1-trimethyl-silyloxyethylene | 2-[8-methoxy-8-methoxycarbonyl-7-(trimethylsiloxy)-2-cis,7-octadienyl]-4R-trimethylsiloxy cyclopent-2-en-1-one |
| 2-(6-chloroformylhexyl)-4R-trimethylsiloxycyclopent-2-en-1-one | 1,2-dimethoxy-1-trimethyl-silyloxyethylene | 2-[8-methoxy-8-methoxycarbonyl-7-(trimethylsiloxy)-7-octenyl]-4R-trimethylsiloxy cyclopent-2-en-1-one |
| 2-(5-chloroformylpent-2-cis-enyl)cyclopent-2-en-1-one | 1,2-dimethoxy-1-trimethyl-silyloxyethylene | 2-[7-methoxy-7-methoxycarbonyl-6-(trimethylsiloxy)-2-cis,6-hepta-dienyl] cyclopent-2-en-1-one |
| 2-(6-chloroformylhex-2-cis-enyl)cyclopent-2-en-1-one | 1,2-dimethoxy-1-trimethyl-silyloxyethylene | 2-[8-methoxy-8-methoxycarbonyl-7-(trimethylsiloxy)-2-cis,7-octadienyl] cyclopent-2-en-1-one |
| 2-(7-chloroformylhept-2-cis-enyl)cyclopent-2-en-1-one | 1,2-dimethoxy-1-trimethyl-silyloxyethylene | 2-[9-methoxy-9-methoxycarbonyl-8-(trimethylsiloxy)-2-cis,8-nonadienyl] cyclopent-2-en-1-one |
| 2-(5-chloroformylpentyl)cyclopent-2-en-1-one | 1,2-dimethoxy-1-trimethyl-silyloxyethylene | 2-[7-methoxy-7-methoxycarbonyl-6-(trimethylsiloxy)-6-heptenyl] |

TABLE I-continued

| ACID CHLORIDE | ETHYLENE REAGENT | PROTECTED CYCLOPENT-2-EN-1-ONE |
| --- | --- | --- |
| 2-(6-chloroformylhexyl) cyclopent-2-en-1-one | 1,2-dimethoxy-1-trimethyl-silyloxyethylene | cyclopent-2-en-1-one 2-[8-methoxy-8-methoxycarbonyl-7-(trimethylsiloxy)-7-octenyl] cyclopent-2-en-1-one |
| 2-(7-chloroformylheptyl) cyclopent-2-en-1-one | 1,2-dimethoxy-1-trimethyl-silyloxyethylene | 2-[9-methoxy-9-methoxycarbonyl-8-(trimethylsiloxy)-8-nonenyl] cyclopent-2-en-1-one |

DESCRIPTION OF TABLES I-XIV

The product prostaglandins are prepared by the conjugate addition of the listed cyclopentenone and the listed vinyliodide or vinylstannyl beta-chain precursors. For the addition of a vinylstannane, the procedure of Example 379 is followed. For the addition of a vinyliodide, the following procedure is followed:

To a solution of the vinyliodide listed in Tables I-IX, an ether (3 ml. per gm.), at −78° C. under argon is added with stirring 2 equivalents of 1.6 M t-butyllithium in hexane. After one and one-half hours at −78° C. and 30 minutes at −43° C., add 1 equivalent of copperpentyne and hexamethylphosphoroustriamide (HMPTA) (2.7 ml. per gm. of copperpentyne) in ether (20 ml. per gm. of copperpentyne). After stirring for 45 minutes at −78° C., one-half equivalent of the cyclopentenone in ether is added. After stirring for one hour, at −40° C., the solution is allowed to warm to −20° C. over a 30 minute period. To the stirred mixture is added an acetic acid (1 ml. per gm. of vinyltin) followed by a saturated solution of ammoniumchloride).

The mixture is extracted with ether, the ether solution is washed with dilute hydrochloric acid solution followed by saturated sodium bicarbonate solution. The ether layer is separated and the solvent is removed. The residue is stirred in a mixture of THF: $H_2O$: acetic acid (2:1:4) at 40° C. for one hour. The solvents are removed at reduced pressure. The residue is chromatographed on a dry column of silica gel eluting with ether-ethylacetate (4:1) to provide listed products of Tables I-IX.

TABLE I

| EXAMPLE | VINYL IODIDE | CYCLOPENTENONE | PRODUCT PROSTAGLANDIN OF THE PGE1 SERIES |
|---|---|---|---|
| 1 | 1-trans-iodo-3-triphenylmethoxy-1-heptene | 2-[5-methoxyacetyl pentyl]-4-trimethylsiloxy cyclopent-2-en-1-one | dl-11a,15a-dihydroxy-1-methoxymethyl-1,9-dioxo-20-nor-2-nor-13-trans prostene |
| 2 | 1-trans-iodo-3-methyl-3-trimethylsilyloxy-1-heptene | 2-[5-methoxyacetyl pentyl]-4-trimethylsiloxy cyclopent-2-en-1-one | dl-11a,15a-dihydroxy-1-methoxymethyl-1,9-dioxo-15-methyl-20-nor-2-nor-13-trans prostene |
| 3 | 1-trans-iodo-4,4-dimethyl-3-trimethylsilyloxy-1-heptene | 2-[5-methoxyacetyl pentyl]-4-trimethylsiloxy cyclopent-2-en-1-one | dl-11a,15a-dihydroxy-1-methoxymethyl-1,9-dioxo-16,16-dimethyl-20-nor-2-nor-13-trans prostene |
| 4 | 1-trans-iodo-5,5-dimethyl-3-triphenylmethoxy-1-octene | 2-[5-methoxyacetyl pentyl]-4-trimethylsiloxy cyclopent-2-en-1-one | dl-11a,15a-dihydroxy-1-methoxymethyl-1,9-dioxo-17,17-dimethyl-2-nor-13-trans prostene |
| 5 | 1-trans-iodo-4-methyl-3-triphenylmethoxy-1-octene | 2-[5-methoxyacetyl pentyl]-4-trimethylsiloxy cyclopent-2-en-1-one | dl-11a,15a-dihydroxy-1-methoxymethyl-1,9-dioxo-16-methyl-2-nor-13-trans prostene |
| 6 | 1-trans-iodo-4,4,4-trimethylene-3-trimethylsilyloxy-1-heptene | 2-[5-methoxyacetyl pentyl]-4-trimethylsiloxy cyclopent-2-en-1-one | dl-11a,15a-dihydroxy-1-methoxymethyl-1,9-dioxo-16,16-trimethylene-20-nor-2-nor-13-trans prostene |

| EXAMPLE | VINYL TIN | CYCLOPENTENONE | PRODUCT PROSTAGLANDIN OF THE PGE1 SERIES |
|---|---|---|---|
| 7 | 1-trans-tri-n-butylstannyl-3-vinyl-3-trimethylsilyloxy-1-heptene | 2-[5-methoxyacetyl pentyl]-4-trimethylsiloxy cyclopent-2-en-1-one | dl-11a,15a-dihydroxy-1-methoxymethyl-1,9-dioxo-15-vinyl-20-nor-2-nor-13-trans prostene |
| 8 | 1-trans-tri-n-butylstannyl-4-phenoxy-3-triethylsilyloxy-1-butene | 2-[5-methoxyacetyl pentyl]-4-trimethylsiloxy cyclopent-2-en-1-one | dl-11a,15a-dihydroxy-1-methoxymethyl-1,9-dioxo-16-phenoxy-2-nor-17,20-tetranor-13-trans prostene |
| 9 | 1-trans-tri-n-butylstannyl-4-(p-fluorophenoxy)-3-triethylsilyloxy-1-butene | 2-[5-methoxyacetyl pentyl]-4-trimethylsiloxy cyclopent-2-en-1-one | dl-11a,15a-dihydroxy-1-methoxymethyl-1,9-dioxo-16-(p-fluorophenoxy)-2-nor-17,20-tetranor-13-trans prostene |
| 10 | 1-trans-tri-n-butylstannyl-4-(m-chlorophenoxy)-3-triethylsilyloxy-1-butene | 2-[5-methoxyacetyl pentyl]-4-trimethylsiloxy cyclopent-2-en-1-one | dl-11a,15a-dihydroxy-1-methoxymethyl-1,9-dioxo-16-(m-chlorophenoxy)-2-nor-17,20-tetranor-13-trans prostene |
| 11 | 1-trans-tri-n-butylstannyl-4-(m-trifluoromethylphenoxy)-3-triethylsilyloxy-1-butene | 2-[5-methoxyacetyl pentyl]-4-trimethylsiloxy cyclopent-2-en-1-one | dl-11a,15a-dihydroxy-1-methoxymethyl-1,9-dioxo-16-(m-trifluoromethylphenoxy)-2-nor-17,20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 12 | 1-trans-iodo-5-phenyl-3-triethylsilyloxy-1-pentene | 2-[5-methoxyacetyl pentyl]-4-trimethylsiloxy cyclopent-2-en-1-one | dl-11a,15a-dihydroxy-1-methoxymethyl-1,9-dioxo-17-phenyl-2-nor-18,20-trinor-13-trans prostene |
| 13 | 1-trans-iodo-4,4-dimethyl-5-phenyl-3-triethylsilyloxy-1-pentene | 2-[5-methoxyacetyl pentyl]-4-trimethylsiloxy cyclopent-2-en-1-one | dl-11a,15a-dihydroxy-1-methoxymethyl-1,9-dioxo-16,16-dimethyl-17-phenyl-2-nor-18,20-trinor-13-trans prostene |
| 14 | 1-trans-iodo-4-cyclopentyl-3-triphenylmethoxy-1-butene | 2-[5-methoxyacetyl pentyl]-4-trimethylsiloxy cyclopent-2-en-1-one | dl-11a,15a-dihydroxy-1-methoxymethyl-1,9-dioxo-16-cyclopentyl-2-nor-17,20-tetranor-13-trans prostene |
| 15 | 1-trans-iodo-4-cyclohexyl-3-triphenylmethoxy-1-butene | 2-[5-methoxyacetyl pentyl]-4-trimethylsiloxy cyclopent-2-en-1-one | dl-11a,15a-dihydroxy-1-methoxymethyl-1,9-dioxo-16-cyclohexyl-2-nor-17,20-tetranor-13-trans prostene |
| 16 | 1-trans-iodo-4-triphenylmethoxy-1-heptene | 2-[5-methoxyacetyl pentyl]-4-trimethylsiloxy cyclopent-2-en-1-one | dl-11a,16-dihydroxy-1-methoxymethyl-1,9-dioxo-20-nor-2-nor-13-trans prostene |

TABLE I-continued

| EXAMPLE | VINYL TIN | CYCLOPENTENONE | PRODUCT PROSTAGLANDIN OF THE PGE1 SERIES |
|---|---|---|---|
| 17 | 1-trans-tri-n-butylstannyl-4-methyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-methyl-20-nor-2-nor-13-trans prostene |
| 18 | 1-trans-tri-n-butylstannyl-4-ethyl-4-trimethylsilyloxy-1-octene | 2-[5-methoxyacetyl pentyl]-4-trimethylsiloxy cyclopent-2-en-1-one | dl-11a,16-dihydroxy-1-methoxymethyl-1,9-dioxo-16-ethyl-2-nor-13-trans prostene |
| 19 | 1-trans-tri-n-butylstannyl-5-methyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-17-methyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 20 | 1-trans-iodo-5,5-dimethyl 4-trimethylsilyloxy-1-octene | 2-[5-methoxyacetyl pentyl]-4-trimethylsiloxy cyclopent-2-en-1-one | dl-11a,16-dihydroxy-1-methoxymethyl-1,9-dioxo-17,17-dimethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 21 | 1-trans-tri-n-butylstannyl-4-vinyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-vinyl-20-nor-2-nor-13-trans prostene |
| 22 | 1-trans-tri-n-butylstannyl-4-cyclopropyl-4-trimethylsilyloxy-1-octene | 2-[5-methoxyacetyl pentyl]-4-trimethylsiloxy cyclopent-2-en-1-one | dl-11a,16-dihydroxy-1-methoxymethyl-1,9-dioxo-16-cyclopropyl-2-nor-13-trans prostene |
| 23 | 1-trans-tri-n-butylstannyl-4-trimethylsilylethynyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-ethynyl-20-nor-2-nor-13-trans prostene |
| 24 | 1-trans-tri-n-butylstannyl-5-methylene 4-triethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-17-methylene-20-nor-2-nor-13-trans prostene |
| 25 | 1-trans-tri-n-butylstannyl-4-methyl-5-methylene-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-methyl-17-methylene-20-nor-2-nor-13-trans prostene |
| 26 | 1-trans-tri-n-butylstannyl-4-dimethoxymethyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-formyl-20-nor-2-nor-13-trans prostene |
| 27 | 1-trans-tri-n-butylstannyl-4-fluoromethyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-fluoromethyl-20-nor-2-nor-13-trans prostene |
| 28 | 1-trans-tri-n-butylstannyl-4-difluoromethyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-difluoromethyl-20-nor-2-nor-13-trans prostene |
| 29 | 1-trans-tri-n-butylstannyl-4-trifluoromethyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-trifluoromethyl-20-nor-2-nor-13-trans prostene |
| 30 | 1-trans-tri-n-butylstannyl-4-chloromethyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-chloromethyl-20-nor-2-nor-13-trans prostene |
| 31 | 1-trans-tri-n-butylstannyl-4-trimethylsilyloxymethyl-4-trimethylsilyloxy-1-heptene | 2-[5-methoxyacetyl pentyl]-4-trimethylsiloxy cyclopent-2-en-1-one | dl-11a,16-dihydroxy-1-methoxymethyl-1,9-dioxo-16-hydroxymethyl-20-nor-2-nor-13-trans prostene |

TABLE I-continued

| EXAMPLE | VINYL IODIDE | CYCLOPENTENONE | PRODUCT PROSTAGLANDIN OF THE PGE1 SERIES |
|---|---|---|---|
| 32 | 1-trans-iodo-4-methyl-7-chloro 4-trimethylsilyloxy-1-heptene | 2-[5-methoxyacetyl pentyl]-4-trimethylsilyloxy cyclopent-2-en-1-one | dl-11a,16-dihydroxy-1-methoxymethyl-1,9-dioxo-16-methyl-19-chloro-2-nor-20-nor-13-trans prostene |
| 33 | 1-trans-iodo-3-triphenylmethoxy-1-octene | 2-[5-methoxyacetyl pentyl]-4-trimethylsilyloxy cyclopent-2-en-1-one | dl-11a,15a-dihydroxy-1-methoxymethyl-1,9-dioxo-2-nor-13-trans prostene |
| 34 | 1-trans-iodo-3-methyl-3-trimethylsilyloxy-1-octene | 2-[5-methoxyacetyl pentyl]-4-trimethylsilyloxy cyclopent-2-en-1-one | dl-11a,15a-dihydroxy-1-methoxymethyl-1,9-dioxo-15-methyl-2-nor-13-trans prostene |
| 35 | 1-trans-iodo-4,4-dimethyl-3-trimethylsilyloxy-1-octene | 2-[5-methoxyacetyl pentyl]-4-trimethylsilyloxy cyclopent-2-en-1-one | dl-11a,15a-dihydroxy-1-methoxymethyl-1,9-dioxo-16,16-dimethyl-2-nor-13-trans prostene |
| 36 | 1-trans-iodo-4,4-trimethylene-3-trimethylsilyloxy-1-octene | 2-[5-methoxyacetyl pentyl]-4-trimethylsilyloxy cyclopent-2-en-1-one | dl-11a,15a-dihydroxy-1-methoxymethyl-1,9-dioxo-16,16-trimethylene-2-nor-13-trans prostene |

| EXAMPLE | VINYL TIN | CYCLOPENTENONE | PRODUCT PROSTAGLANDIN OF THE PGE1 SERIES |
|---|---|---|---|
| 37 | 1-trans-tri-n-butylstannyl-3-vinyl-3-trimethylsilyloxy-1-octene | 2-[5-methoxyacetyl pentyl]-4-trimethylsilyloxy cyclopent-2-en-1-one | dl-11a,15a-dihydroxy-1-methoxymethyl-1,9-dioxo-15-vinyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 38 | 1-trans-iodo-4-triphenylmethoxy-1-octene | 2-[5-methoxyacetyl pentyl]-4-trimethylsilyloxy cyclopent-2-en-1-one | dl-11a,16-dihydroxy-1-methoxymethyl-1,9-dioxo-2-nor-13-trans prostene |

| EXAMPLE | VINYL TIN | CYCLOPENTENONE | PRODUCT PROSTAGLANDIN OF THE PGE1 SERIES |
|---|---|---|---|
| 39 | 1-trans-tri-n-butylstannyl-4-methyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-methyl-2-nor-13-trans prostene |
| 40 | 1-trans-tri-n-butylstannyl-5-methyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-17-methyl-2-nor-13-trans prostene |
| 41 | 1-trans-tri-n-butylstannyl-4-vinyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-vinyl-2-nor-13-trans prostene |
| 42 | 1-trans-tri-n-butylstannyl-4-trimethylsilylethynyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-ethynyl-2-nor-13-trans prostene |
| 43 | 1-trans-tri-n-butylstannyl-5-methylene-4-triethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-17-methylene-2-nor-13-trans prostene |
| 44 | 1-trans-tri-n-butylstannyl-4-methyl-5-methylene-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-methyl-17-methylene-2-nor-13-trans prostene |
| 45 | 1-trans-tri-n-butylstannyl-4-dimethoxymethyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-formyl-2-nor-13-trans prostene |
| 46 | 1-trans-tri-n-butylstannyl-4-fluoromethyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-fluoromethyl-2-nor-13-trans prostene |
| 47 | 1-trans-tri-n-butylstannyl-4-difluoromethyl- | 2-[5-methoxyacetyl | dl-11a,16-dihydroxy-1-methoxymethyl-1,9-dioxo-16-difluoromethyl- |

TABLE I-continued

| EXAMPLE | VINYL IODIDE / VINYL TIN | CYCLOPENTENONE | PRODUCT PROSTAGLANDIN OF THE PGE1 SERIES |
|---|---|---|---|
| | 4-trimethylsilyloxy-1-octene | pentyl]-4-trimethylsiloxy cyclopent-2-en-1-one | 2-nor-13-trans prostene |
| 48 | 1-trans-tri-n-butylstannyl-4-trifluoromethyl-4-trimethylsilyloxy-1-octene | 2-[5-methoxyacetyl pentyl]-4-trimethylsiloxy cyclopent-2-en-1-one | dl-11a,16-dihydroxy-1-methoxymethyl-1,9-dioxo-16-trifluoromethyl-2-nor-13-trans prostene |
| 49 | 1-trans-tri-n-butylstannyl-4-chloromethyl-4-trimethylsilyloxy-1-octene | 2-[5-methoxyacetyl pentyl]-4-trimethylsiloxy cyclopent-2-en-1-one | dl-11a,16-dihydroxy-1-methoxymethyl-1,9-dioxo-16-chloromethyl-2-nor-13-trans prostene |
| 50 | 1-trans-tri-n-butylstannyl-4-trimethylsilyloxymethyl-4-trimethylsilyloxy-1-octene | 2-[5-methoxyacetyl pentyl]-4-trimethylsiloxy cyclopent-2-en-1-one | dl-11a,16-dihydroxy-1-methoxymethyl-1,9-dioxo-16-hydroxymethyl-2-nor-13-trans prostene |
| EXAMPLE | VINYL IODIDE | CYCLOPENTENONE | PRODUCT PROSTAGLANDIN OF THE PGE1 SERIES |
| 51 | 1-trans-iodo-3-triphenylmethoxy-1-nonene | 2-[5-methoxyacetyl pentyl]-4-trimethylsiloxy cyclopent-2-en-1-one | dl-11a,15a-dihydroxy-1-methoxymethyl-1,9-dioxo-20-methyl-2-nor-13-trans prostene |
| 52 | 1-trans-iodo-3-methyl-3-trimethylsilyloxy-1-nonene | 2-[5-methoxyacetyl pentyl]-4-trimethylsiloxy cyclopent-2-en-1-one | dl-11a,15a-dihydroxy-1-methoxymethyl-1,9-dioxo-15-methyl-20-methyl-2-nor-13-trans prostene |
| 53 | 1-trans-iodo-4,4-dimethyl-3-trimethylsilyloxy-1-nonene | 2-[5-methoxyacetyl pentyl]-4-trimethylsiloxy cyclopent-2-en-1-one | dl-11a,15a-dihydroxy-1-methoxymethyl-1,9-dioxo-16,16-dimethyl-20-methyl-2-nor-13-trans prostene |
| 54 | 1-trans-iodo-4,4-trimethylene-3-trimethylsilyloxy-1-nonene | 2-[5-methoxyacetyl pentyl]-4-trimethylsiloxy cyclopent-2-en-1-one | dl-11a,15a-dihydroxy-1-methoxymethyl-1,9-dioxo-16,16-trimethylene-20-methyl-2-nor-13-trans prostene |
| EXAMPLE | VINYL TIN | CYCLOPENTENONE | PRODUCT PROSTAGLANDIN OF THE PGE1 SERIES |
| 55 | 1-trans-tri-n-butylstannyl-3-vinyl-3-trimethylsilyloxy-1-nonene | 2-[5-methoxyacetyl pentyl]-4-trimethylsiloxy cyclopent-2-en-1-one | dl-11a,15a-dihydroxy-1-methoxymethyl-1,9-dioxo-15-vinyl-20-methyl-2-nor-13-trans prostene |
| EXAMPLE | VINYL IODIDE | CYCLOPENTENONE | PRODUCT PROSTAGLANDIN OF THE PGE1 SERIES |
| 56 | 1-trans-iodo-4-triphenylmethoxy-1-nonene | 2-[5-methoxyacetyl pentyl]-4-trimethylsiloxy cyclopent-2-en-1-one | dl-11a,16-dihydroxy-1-methoxymethyl-1,9-dioxo-20-methyl-2-nor-13-trans prostene |
| EXAMPLE | VINYL TIN | CYCLOPENTENONE | PRODUCT PROSTAGLANDIN OF THE PGE1 SERIES |
| 57 | 1-trans-tri-n-butylstannyl-4-methyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-methyl-20-methyl-2-nor-13-trans prostene |
| 58 | 1-trans-tri-n-butylstannyl-5-methyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-17-methyl-20-methyl-2-nor-13-trans prostene |
| 59 | 1-trans-tri-n-butylstannyl-4-vinyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-vinyl-20-methyl-2-nor-13-trans prostene |
| 60 | 1-trans-tri-n-butylstannyl-4-trimethylsilylethynyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-ethynyl-20-methyl-2-nor-13-trans prostene |
| 61 | 1-trans-tri-n-butylstannyl-5-methylene-4-triethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-17-methylene-20-methyl-2-nor-13-trans prostene |
| 62 | 1-trans-tri-n-butylstannyl-4-methyl-5-methylene | 2-[5-methoxyacetyl pentyl]-4-trimethylsiloxy cyclopent-2-en-1-one | dl-11a,16-dihydroxy-1-methoxymethyl-1,9-dioxo-16-methyl- |

TABLE I-continued

| EXAMPLE | VINYL IODIDE / TIN | CYCLOPENTENONE | PRODUCT PROSTAGLANDIN |
|---|---|---|---|
| | 4-trimethylsilyloxy-1-nonene | pentyl]-4-trimethylsiloxy cyclopent-2-en-1-one | 17-methylene-20-methyl-2-nor-13-trans prostene |
| 63 | 1-trans-tri-n-butylstannyl-4-dimethoxymethyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-formyl-20-methyl-2-nor-13-trans prostene |
| 64 | 1-trans-tri-n-butylstannyl-4-fluoromethyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-fluoromethyl-20-methyl-2-nor-13-trans prostene |
| 65 | 1-trans-tri-n-butylstannyl-4-difluoromethyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-difluoromethyl-20-methyl-2-nor-13-trans prostene |
| 66 | 1-trans-tri-n-butylstannyl-4-trifluoromethyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-trifluoromethyl-20-methyl-2-nor-13-trans prostene |
| 67 | 1-trans-tri-n-butylstannyl-4-chloromethyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-chloromethyl-20-methyl-2-nor-13-trans prostene |
| 68 | 1-trans-tri-n-butylstannyl-4-trimethylsilyloxymethyl-4-trimethylsilyloxy-1-nonene | 2-[5-methoxyacetyl pentyl]-4-trimethylsiloxy cyclopent-2-en-1-one | dl-11a,16-dihydroxy-1-methoxymethyl-1,9-dioxo-16-hydroxymethyl-20-methyl-2-nor-13-trans prostene |
| EXAMPLE | VINYL IODIDE | CYCLOPENTENONE | PRODUCT PROSTAGLANDIN OF THE PGE1 SERIES |
| 69 | 1-trans-iodo-3-triphenylmethoxy-1-decene | 2-[5-methoxyacetyl pentyl]-4-trimethylsiloxy cyclopent-2-en-1-one | dl-11a,15a-dihydroxy-1-methoxymethyl-1,9-dioxo-20-ethyl-2-nor-13-trans prostene |
| 70 | 1-trans-iodo-3-methyl-3-trimethylsilyloxy-1-decene | 2-[5-methoxyacetyl pentyl]-4-trimethylsiloxy cyclopent-2-en-1-one | dl-11a,15a-dihydroxy-1-methoxymethyl-1,9-dioxo-15-methyl-20-ethyl-2-nor-13-trans prostene |
| 71 | 1-trans-iodo-4,4-dimethyl-3-trimethylsilyloxy-1-decene | 2-[5-methoxyacetyl pentyl]-4-trimethylsiloxy cyclopent-2-en-1-one | dl-11a,15a-dihydroxy-1-methoxymethyl-1,9-dioxo-16,16-dimethyl-20-ethyl-2-nor-13-trans prostene |
| 72 | 1-trans-iodo-4,4,4-trimethylene-3-trimethylsilyloxy-1-decene | 2-[5-methoxyacetyl pentyl]-4-trimethylsiloxy cyclopent-2-en-1-one | dl-11a,15a-dihydroxy-1-methoxymethyl-1,9-dioxo-16,16-trimethylene-20-ethyl-2-nor-13-trans prostene |
| EXAMPLE | VINYL TIN | CYCLOPENTENONE | PRODUCT PROSTAGLANDIN OF THE PGE1 SERIES |
| 73 | 1-trans-tri-n-butylstannyl-3-vinyl-3-trimethylsilyloxy-1-decene | 2-[5-methoxyacetyl pentyl]-4-trimethylsiloxy cyclopent-2-en-1-one | dl-11a,15a-dihydroxy-1-methoxymethyl-1,9-dioxo-15-vinyl-20-ethyl-2-nor-13-trans prostene |
| EXAMPLE | VINYL IODIDE | CYCLOPENTENONE | PRODUCT PROSTAGLANDIN OF THE PGE1 SERIES |
| 74 | 1-trans-iodo-4-triphenylmethoxy-1-decene | 2-[5-methoxyacetyl pentyl]-4-trimethylsiloxy cyclopent-2-en-1-one | dl-11a,16-dihydroxy-1-methoxymethyl-1,9-dioxo-20-ethyl-2-nor-13-trans prostene |
| EXAMPLE | VINYL TIN | CYCLOPENTENONE | PRODUCT PROSTAGLANDIN OF THE PGE1 SERIES |
| 75 | 1-trans-tri-n-butylstannyl-4-methyl-4-trimethylsilyloxy-1-decene | 2-[5-methoxyacetyl pentyl]-4-trimethylsiloxy cyclopent-2-en-1-one | dl-11a,16-dihydroxy-1-methoxymethyl-1,9-dioxo-16-methyl-20-ethyl-2-nor-13-trans prostene |
| 76 | 1-trans-tri-n-butylstannyl-5-methyl-4-trimethylsilyloxy-1-decene | 2-[5-methoxyacetyl pentyl]-4-trimethylsiloxy cyclopent-2-en-1-one | dl-11a,16-dihydroxy-1-methoxymethyl-1,9-dioxo-17-methyl-20-ethyl-2-nor-13-trans prostene |
| 77 | 1-trans-tri-n-butylstannyl-4-vinyl-4-trimethylsilyloxy-1-decene | 2-[5-methoxyacetyl pentyl]-4-trimethylsiloxy cyclopent-2-en-1-one | dl-11a,16-dihydroxy-1-methoxymethyl-1,9-dioxo-16-vinyl- |

TABLE I-continued

| EXAMPLE | VINYL IODIDE | CYCLOPENTENONE | PRODUCT PROSTAGLANDIN OF THE PGE1 SERIES |
|---|---|---|---|
| 78 | | 2-[5-methoxyacetyl pentyl]-4-trimethylsilyloxy cyclopent-2-en-1-one 4-trimethylsilyloxy-1-decene | 20-ethyl-2-nor-13-trans prostene |
| 79 | 1-trans-tri-n-butylstannyl-4-trimethylsilylethynyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-ethynyl-20-ethyl-2-nor-13-trans prostene |
| 80 | 1-trans-tri-n-butylstannyl-5-methylene-4-triethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-17-methylene-20-ethyl-2-nor-13-trans prostene |
| 81 | 1-trans-tri-n-butylstannyl-4-methyl-5-methylene-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-methyl-17-methylene-20-ethyl-2-nor-13-trans prostene |
| 82 | 1-trans-tri-n-butylstannyl-4-dimethoxymethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-formyl-20-ethyl-2-nor-13-trans prostene |
| 83 | 1-trans-tri-n-butylstannyl-4-fluoromethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-fluoromethyl-20-ethyl-2-nor-13-trans prostene |
| 84 | 1-trans-tri-n-butylstannyl-4-difluoromethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-difluoromethyl-20-ethyl-2-nor-13-trans prostene |
| 85 | 1-trans-tri-n-butylstannyl-4-trifluoromethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-trifluoromethyl-20-ethyl-2-nor-13-trans prostene |
| 86 | 1-trans-tri-n-butylstannyl-4-chloromethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-chloromethyl-20-ethyl-2-nor-13-trans prostene |
|  | 1-trans-tri-n-butylstannyl-4-trimethylsilyloxymethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-hydroxymethyl-20-ethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 87 | 1-trans-iodo-3-triphenylmethoxy-1-heptene | 2-[6-methoxyacetyl hexyl]-4-trimethylsilyloxy cyclopent-2-en-1-one | dl-11a,15a-dihydroxy-1-methoxymethyl-1,9-dioxo-20-nor-13-trans prostene |
| 88 | 1-trans-iodo-3-methyl-3-trimethylsilyloxy-1-heptene | 2-[6-methoxyacetyl hexyl]-4-trimethylsilyloxy cyclopent-2-en-1-one | dl-11a,15a-dihydroxy-1-methoxymethyl-1,9-dioxo-15-methyl-20-nor-13-trans prostene |
| 89 | 1-trans-iodo-4,4-dimethyl-3-trimethylsilyloxy-1-heptene | 2-[6-methoxyacetyl hexyl]-4-trimethylsilyloxy cyclopent-2-en-1-one | dl-11a,15a-dihydroxy-1-methoxymethyl-1,9-dioxo-16,16-dimethyl-20-nor-13-trans prostene |
| 90 | 1-trans-iodo-5,5-dimethyl-3-triphenylmethoxy-1-octene | 2-[6-methoxyacetyl hexyl]-4-trimethylsilyloxy cyclopent-2-en-1-one | dl-11a,15a-dihydroxy-1-methoxymethyl-1,9-dioxo-17,17-dimethyl-13-trans prostene |
| 91 | 1-trans-iodo-4-methyl-3-triphenylmethoxy-1-octene | 2-[6-methoxyacetyl hexyl]-4-trimethylsilyloxy cyclopent-2-en-1-one | dl-11a,15a-dihydroxy-1-methoxymethyl-1,9-dioxo-16-methyl-13-trans prostene |
| 92 | 1-trans-iodo-4,4-trimethylene-3-trimethylsilyloxy-1-heptene | 2-[6-methoxyacetyl hexyl]-4-trimethylsilyloxy cyclopent-2-en-1-one | dl-11a,15a-dihydroxy-1-methoxymethyl-1,9-dioxo-16,16-trimethylene-20-nor-13-trans prostene |

| EXAMPLE | VINYL TIN | CYCLOPENTENONE | PRODUCT PROSTAGLANDIN OF THE PGE1 SERIES |
|---|---|---|---|
| 93 | 1-trans-tri-n-butylstannyl-3-vinyl-3-trimethylsilyloxy-1-heptene | 2-[6-methoxyacetyl hexyl]-4-trimethylsilyloxy | dl-11a,15a-dihydroxy-1-methoxymethyl-1,9-dioxo-15-vinyl-20-nor-13-trans prostene |

| EXAMPLE | VINYL IODIDE / TIN | CYCLOPENTENONE | PRODUCT |
|---|---|---|---|
| 94 | 1-trans-tri-n-butylstannyl-4-phenoxy-3-triethylsilyloxy-1-butene | 2-[6-methoxyacetyl hexyl]-4-trimethylsilyloxy cyclopent-2-en-1-one | dl-11a,15a-dihydroxy-1-methoxymethyl-1,9-dioxo-16-phenoxy-17-20-tetranor-13-trans prostene |
| 95 | 1-trans-tri-n-butylstannyl-4-(p-fluorophenoxy)-3-triethylsilyloxy-1-butene | 2-[6-methoxyacetyl hexyl]-4-trimethylsilyloxy cyclopent-2-en-1-one | dl-11a,15a-dihydroxy-1-methoxymethyl-1,9-dioxo-16-(p-fluorophenoxy)-17-20-tetranor-13-trans prostene |
| 96 | 1-trans-tri-n-butylstannyl-4-(m-chlorophenoxy)-3-triethylsilyloxy-1-butene | 2-[6-methoxyacetyl hexyl]-4-trimethylsilyloxy cyclopent-2-en-1-one | dl-11a,15a-dihydroxy-1-methoxymethyl-1,9-dioxo-16-(m-chlorophenoxy)-17-20-tetranor-13-trans prostene |
| 97 | 1-trans-tri-n-butylstannyl-4-(m-trifluoromethylphenoxy)-3-triethylsilyloxy-1-butene | 2-[6-methoxyacetyl hexyl]-4-trimethylsilyloxy cyclopent-2-en-1-one | dl-11a,15a-dihydroxy-1-methoxymethyl-1,9-dioxo-16-(m-trifluoromethylphenoxy)-17-20-tetranor-13-trans prostene |
| EXAMPLE | VINYL IODIDE | CYCLOPENTENONE | PRODUCT PROSTAGLANDIN OF THE PGE1 SERIES |
| 98 | 1-trans-iodo-5-phenyl-3-triethylsilyloxy-1-pentene | 2-[6-methoxyacetyl hexyl]-4-trimethylsilyloxy cyclopent-2-en-1-one | dl-11a,15a-dihydroxy-1-methoxymethyl-1,9-dioxo-17-phenyl-18-20-trinor-13-trans prostene |
| 99 | 1-trans-iodo-4,4-dimethyl-5-phenyl-3-triethylsilyloxy-1-pentene | 2-[6-methoxyacetyl hexyl]-4-trimethylsilyloxy cyclopent-2-en-1-one | dl-11a,15a-dihydroxy-1-methoxymethyl-1,9-dioxo-16,16-dimethyl-17-phenyl-18-20-trinor-13-trans prostene |
| 100 | 1-trans-iodo-4-cyclopentyl-3-triphenylmethoxy-1-butene | 2-[6-methoxyacetyl hexyl]-4-trimethylsilyloxy cyclopent-2-en-1-one | dl-11a,15a-dihydroxy-1-methoxymethyl-1,9-dioxo-16-cyclopentyl-17-20-tetranor-13-trans prostene |
| 101 | 1-trans-iodo-4-cyclohexyl-3-triphenylmethoxy-1-butene | 2-[6-methoxyacetyl hexyl]-4-trimethylsilyloxy cyclopent-2-en-1-one | dl-11a,15a-dihydroxy-1-methoxymethyl-1,9-dioxo-16-cyclohexyl-17-20-tetranor-13-trans prostene |
| 102 | 1-trans-iodo-4-triphenylmethoxy-1-heptene | 2-[6-methoxyacetyl hexyl]-4-trimethylsilyloxy cyclopent-2-en-1-one | dl-11a,16-dihydroxy-1-methoxymethyl-1,9-dioxo-20-nor-13-trans prostene |
| EXAMPLE | VINYL TIN | CYCLOPENTENONE | PRODUCT PROSTAGLANDIN OF THE PGE1 SERIES |
| 103 | 1-trans-tri-n-butylstannyl-4-methyl-4-trimethylsilyloxy-1-heptene | 2-[6-methoxyacetyl hexyl]-4-trimethylsilyloxy cyclopent-2-en-1-one | dl-11a,16-dihydroxy-1-methoxymethyl-1,9-dioxo-16-methyl-20-nor-13-trans prostene |
| 104 | 1-trans-tri-n-butylstannyl-4-ethyl-4-trimethylsilyloxy-1-octene | 2-[6-methoxyacetyl hexyl]-4-trimethylsilyloxy cyclopent-2-en-1-one | dl-11a,16-dihydroxy-1-methoxymethyl-1,9-dioxo-16-ethyl-13-trans prostene |
| 105 | 1-trans-tri-n-butylstannyl-5-methyl-4-trimethylsilyloxy-1-heptene | 2-[6-methoxyacetyl hexyl]-4-trimethylsilyloxy cyclopent-2-en-1-one | dl-11a,16-dihydroxy-1-methoxymethyl-1,9-dioxo-17-methyl-20-nor-13-trans prostene |
| EXAMPLE | VINYLE IODIDE | CYCLOPENTENONE | PRODUCT PROSTAGLANDIN OF THE PGE1 SERIES |
| 106 | 1-trans-iodo-5,5-dimethyl-4-trimethylsilyloxy-1-octene | 2-[6-methoxyacetyl hexyl]-4-trimethylsilyloxy cyclopent-2-en-1-one | dl-11a,16-dihydroxy-1-methoxymethyl-1,9-dioxo-17,17-dimethyl-13-trans prostene |
| EXAMPLE | VINYL TIN | CYCLOPENTENONE | PRODUCT PROSTAGLANDIN OF THE PGE1 SERIES |
| 107 | 1-trans-tri-n-butylstannyl-4-vinyl-4-trimethylsilyloxy-1-heptene | 2-[6-methoxyacetyl hexyl]-4-trimethylsilyloxy cyclopent-2-en-1-one | dl-11a,16-dihydroxy-1-methoxymethyl-1,9-dioxo-16-vinyl-20-nor-13-trans prostene |
| 108 | 1-trans-tri-n-butylstannyl-4-cyclopropyl-4-trimethylsilyloxy-1-octene | 2-[6-methoxyacetyl hexyl]-4-trimethylsilyloxy cyclopent-2-en-1-one | dl-11a,16-dihydroxy-1-methoxymethyl-1,9-dioxo-16-cyclopropyl-13-trans prostene |

TABLE I-continued

| | | | |
|---|---|---|---|
| 109 | 1-trans-tri-n-butylstannyl-4-trimethylsilylethynyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-ethynyl-20-nor-13-trans prostene |
| 110 | 1-trans-tri-n-butylstannyl-5-methylene-4-triethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-17-methylene-20-nor-13-trans prostene |
| 111 | 1-trans-tri-n-butylstannyl-4-methyl-5-methylene-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-methyl-17-methylene-20-nor-13-trans prostene |
| 112 | 1-trans-tri-n-butylstannyl-4-dimethoxymethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-formyl-20-nor-13-trans prostene |
| 113 | 1-trans-tri-n-butylstannyl-4-fluoromethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-fluoromethyl-20-nor-13-trans prostene |
| 114 | 1-trans-tri-n-butylstannyl-4-difluoromethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-difluoromethyl-20-nor-13-trans prostene |
| 115 | 1-trans-tri-n-butylstannyl-4-trifluoromethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-trifluoromethyl-20-nor-13-trans prostene |
| 116 | 1-trans-tri-n-butylstannyl-4-chloromethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-chloromethyl-20-nor-13-trans prostene |
| 117 | 1-trans-tri-n-butylstannyl-4-trimethylsilyloxymethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE PGE1 SERIES |
| 118 | 1-trans-iodo-4-methyl-7-chloro-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-methyl-19-chloro-20-nor-13-trans prostene |
| 119 | 1-trans-iodo-3-triphenylmethoxy-1-octene | 2-[6-methoxyacetyl hexyl]-4-trimethylsiloxy cyclopent-2-en-1-one | dl-11a,15a-dihydroxy-1-methoxymethyl-1,9-dioxo-13-trans prostene |
| 120 | 1-trans-iodo-3-methyl-3-trimethylsilyloxy-1-octene | 2-[6-methoxyacetyl hexyl]-4-trimethylsiloxy cyclopent-2-en-1-one | dl-11a,15a-dihydroxy-1-methoxymethyl-1,9-dioxo-15-methyl-13-trans prostene |
| 121 | 1-trans-iodo-4,4-dimethyl-3-trimethylsilyloxy-1-octene | 2-[6-methoxyacetyl hexyl]-4-trimethylsiloxy cyclopent-2-en-1-one | dl-11a,15a-dihydroxy-1-methoxymethyl-1,9-dioxo-16,16-dimethyl-13-trans prostene |
| 122 | 1-trans-iodo-4,4-trimethylene-3-trimethylsilyloxy-1-octene | 2-[6-methoxyacetyl hexyl]-4-trimethylsiloxy cyclopent-2-en-1-one | dl-11a,15a-dihydroxy-1-methoxymethyl-1,9-dioxo-16,16-trimethylene-13-trans prostene |
| EXAMPLE | VINYL TIN | CYCLOPENTENONE | PRODUCT PROSTAGLANDIN OF THE PGE1 SERIES |
| 123 | 1-trans-tri-n-butylstannyl-3-vinyl-3-trimethylsilyloxy-1-octene | 2-[6-methoxyacetyl hexyl]-4-trimethylsiloxy cyclopent-2-en-1-one | dl-11a,15a-dihydroxy-1-methoxymethyl-1,9-dioxo-15-vinyl-13-trans prostene |
| EXAMPLE | VINYL IODIDE | CYCLOPENTENONE | PRODUCT PROSTAGLANDIN OF THE PGE1 SERIES |
| 124 | 1-trans-iodo- | 2-[6-methoxyacetyl | dl-11a,16-dihydroxy-1-methoxymethyl-1,9-dioxo- |

TABLE I-continued

| EXAMPLE | VINYL TIN | CYCLOPENTENONE | PRODUCT PROSTAGLANDIN OF THE PGE1 SERIES |
|---|---|---|---|
| | 4-triphenylmethoxy-1-octene | hexyl]-4-trimethylsiloxy cyclopent-2-en-1-one | 13-trans prostene |
| 125 | 1-trans-tri-n-butylstannyl-4-methyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-methyl-13-trans prostene |
| 126 | 1-trans-tri-n-butylstannyl-5-methyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-17-methyl-13-trans prostene |
| 127 | 1-trans-tri-n-butylstannyl-4-vinyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-vinyl-13-trans prostene |
| 128 | 1-trans-tri-n-butylstannyl-4-trimethylsilylethynyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-ethynyl-13-trans prostene |
| 129 | 1-trans-tri-n-butylstannyl-5-methylene-4-triethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-17-methylene-13-trans prostene |
| 130 | 1-trans-tri-n-butylstannyl-4-methyl-5-methylene-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-methyl-17-methylene-13-trans prostene |
| 131 | 1-trans-tri-n-butylstannyl-4-dimethoxymethyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-formyl-13-trans prostene |
| 132 | 1-trans-tri-n-butylstannyl-4-fluoromethyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-fluoromethyl-13-trans prostene |
| 133 | 1-trans-tri-n-butylstannyl-4-difluoromethyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-difluoromethyl-13-trans prostene |
| 134 | 1-trans-tri-n-butylstannyl-4-trifluoromethyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-trifluoromethyl-13-trans prostene |
| 135 | 1-trans-tri-n-butylstannyl-4-chloromethyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-chloromethyl-13-trans prostene |
| 136 | 1-trans-tri-n-butylstannyl-4-trimethylsilyloxymethyl-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-hydroxymethyl-13-trans prostene |

| EXAMPLE | VINYL IODIDE | CYCLOPENTENONE | PRODUCT PROSTAGLANDIN OF THE PGE1 SERIES |
|---|---|---|---|
| 137 | 1-trans-iodo-3-triphenylmethoxy-1-nonene | 2-[6-methoxyacetyl hexyl]-4-trimethylsiloxy cyclopent-2-en-1-one | dl-11a,15a-dihydroxy-1-methoxymethyl-1,9-dioxo-20-methyl-13-trans prostene |
| 138 | 1-trans-iodo-3-methyl-3-trimethylsilyloxy-1-nonene | 2-[6-methoxyacetyl hexyl]-4-trimethylsiloxy cyclopent-2-en-1-one | dl-11a,15a-dihydroxy-1-methoxymethyl-1,9-dioxo-15-methyl-20-methyl-13-trans prostene |
| 139 | 1-trans-iodo-4,4-dimethyl-3-trimethylsilyloxy-1-nonene | 2-[6-methoxyacetyl hexyl]-4-trimethylsiloxy cyclopent-2-en-1-one | dl-11a,15a-dihydroxy-1-methoxymethyl-1,9-dioxo-16,16-dimethyl-20-methyl-13-trans prostene |
| 140 | 1-trans-iodo-4,4-trimethylene-3-trimethylsilyloxy-1-nonene | 2-[6-methoxyacetyl hexyl]-4-trimethylsiloxy cyclopent-2-en-1-one | dl-11a,15a-dihydroxy-1-methoxymethyl-1,9-dioxo-16,16-trimethylene-20-methyl-13-trans prostene |

4,297,516

TABLE I-continued

| EXAMPLE | VINYL TIN | CYCLOPENTENONE | PRODUCT PROSTAGLANDIN OF THE PGE1 SERIES |
|---|---|---|---|
| 141 | 1-trans-tri-n-butylstannyl-3-vinyl-3-trimethylsilyloxy-1-nonene | 2-[6-methoxyacetyl hexyl]-4-trimethylsiloxy cyclopent-2-en-1-one | dl-11a,15a-dihydroxy-1-methoxymethyl-1,9-dioxo-15-vinyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 142 | 1-trans-iodo-4-triphenylmethoxy-1-nonene | 2-[6-methoxyacetyl hexyl]-4-trimethylsiloxy cyclopent-2-en-1-one | dl-11a,16-dihydroxy-1-methoxymethyl-1,9-dioxo-20-methyl-13-trans prostene |

| EXAMPLE | VINYL TIN | CYCLOPENTENONE | PRODUCT PROSTAGLANDIN OF THE PGE1 SERIES |
|---|---|---|---|
| 143 | 1-trans-tri-n-butylstannyl-4-methyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-methyl-20-methyl-13-trans prostene |
| 144 | 1-trans-tri-n-butylstannyl-5-methyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-17-methyl-20-methyl-13-trans prostene |
| 145 | 1-trans-tri-n-butylstannyl-4-vinyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-vinyl-20-methyl-13-trans prostene |
| 146 | 1-trans-tri-n-butylstannyl-4-trimethylsilylethynyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-ethynyl-20-methyl-13-trans prostene |
| 147 | 1-trans-tri-n-butylstannyl-5-methylene-4-triethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-17-methylene-20-methyl-13-trans prostene |
| 148 | 1-trans-tri-n-butylstannyl-4-methyl-5-methylene-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-methyl-17-methylene-20-methyl-13-trans prostene |
| 149 | 1-trans-tri-n-butylstannyl-4-dimethoxymethyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-formyl-20-methyl-13-trans prostene |
| 150 | 1-trans-tri-n-butylstannyl-4-fluoromethyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-fluoromethyl-20-methyl-13-trans prostene |
| 151 | 1-trans-tri-n-butylstannyl-4-difluoromethyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-difluoromethyl-20-methyl-13-trans prostene |
| 152 | 1-trans-tri-n-butylstannyl-4-trifluoromethyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-trifluoromethyl-20-methyl-13-trans prostene |
| 153 | 1-trans-tri-n-butylstannyl-4-chloromethyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-chloromethyl-20-methyl-13-trans prostene |
| 154 | 1-trans-tri-n-butylstannyl-4-trimethylsilyloxymethyl-4-trimethylsilyloxy-1-nonene | 2-[6-methoxyacetyl hexyl]-4-trimethylsiloxy cyclopent-2-en-1-one | dl-11a,16-dihydroxy-1-methoxymethyl-1,9-dioxo-16-hydroxymethyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 155 | 1-trans-iodo-3-triphenylmethoxy-1-decene | 2-[6-methoxyacetyl hexyl]-4-trimethylsiloxy | dl-11a,15a-dihydroxy-1-methoxymethyl-1,9-dioxo-20-ethyl-13-trans prostene |

TABLE I-continued

| | | | |
|---|---|---|---|
| 156 | 1-trans-iodo-3-methyl-3-trimethylsilyloxy-1-decene | cyclopent-2-en-1-one 2-[6-methoxyacetyl hexyl]-4-trimethylsilyloxy cyclopent-2-en-1-one | dl-11a,15a-dihydroxy-1-methoxymethyl-1,9-dioxo-15-methyl-20-ethyl-13-trans prostene |
| 157 | 1-trans-iodo-4,4-dimethyl-3-trimethylsilyloxy-1-decene | 2-[6-methoxyacetyl hexyl]-4-trimethylsilyloxy cyclopent-2-en-1-one | dl-11a,15a-dihydroxy-1-methoxymethyl-1,9-dioxo-16,16-dimethyl-20-ethyl-13-trans prostene |
| 158 | 1-trans-iodo-4,4-trimethylene-3-trimethylsilyloxy-1-decene | 2-[6-methoxyacetyl hexyl]-4-trimethylsilyloxy cyclopent-2-en-1-one | dl-11a,15a-dihydroxy-1-methoxymethyl-1,9-dioxo-16,16-trimethylene-20-ethyl-13-trans prostene |
| EXAMPLE | VINYL TIN | CYCLOPENTENONE | PRODUCT PROSTAGLANDIN OF THE PGE1 SERIES |
| 159 | 1-trans-tri-n-butylstannyl-3-vinyl-3-trimethylsilyloxy-1-decene | 2-[6-methoxyacetyl hexyl]-4-trimethylsilyloxy cyclopent-2-en-1-one | dl-11a,15a-dihydroxy-1-methoxymethyl-1,9-dioxo-15-vinyl-20-ethyl-13-trans prostene |
| EXAMPLE | VINYL IODIDE | CYCLOPENTENONE | PRODUCT PROSTAGLANDIN OF THE PGE1 SERIES |
| 160 | 1-trans-iodo-4-triphenylmethoxy-1-decene | 2-[6-methoxyacetyl hexyl]-4-trimethylsilyloxy cyclopent-2-en-1-one | dl-11a,16-dihydroxy-1-methoxymethyl-1,9-dioxo-20-ethyl-13-trans prostene |
| EXAMPLE | VINYL TIN | CYCLOPENTENONE | PRODUCT PROSTAGLANDIN OF THE PGE1 SERIES |
| 161 | 1-trans-tri-n-butylstannyl-4-methyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-methyl-20-ethyl-13-trans prostene |
| 162 | 1-trans-tri-n-butylstannyl-5-methyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-17-methyl-20-ethyl-13-trans prostene |
| 163 | 1-trans-tri-n-butylstannyl-4-vinyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-vinyl-20-ethyl-13-trans prostene |
| 164 | 1-trans-tri-n-butylstannyl-4-trimethylsilylethynyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-ethynyl-20-ethyl-13-trans prostene |
| 165 | 1-trans-tri-n-butylstannyl-5-methylene-4-triethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-17-methylene-20-ethyl-13-trans prostene |
| 166 | 1-trans-tri-n-butylstannyl-4-methyl-5-methylene-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-methyl-17-methylene-20-ethyl-13-trans prostene |
| 167 | 1-trans-tri-n-butylstannyl-4-dimethoxymethyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-formyl-20-ethyl-13-trans prostene |
| 168 | 1-trans-tri-n-butylstannyl-4-fluoromethyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-fluoromethyl-20-ethyl-13-trans prostene |
| 169 | 1-trans-tri-n-butylstannyl-4-difluoromethyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-difluoromethyl-20-ethyl-13-trans prostene |
| 170 | 1-trans-tri-n-butylstannyl-4-trifluoromethyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-trifluoromethyl-20-ethyl-13-trans prostene |
| 171 | 1-trans-tri-n-butylstannyl-4-chloromethyl-4-trimethylsilyloxy-1-decene | 2-[6-methoxyacetyl hexyl]-4-trimethylsilyloxy cyclopent-2-en-1-one | dl-11a,16-dihydroxy-1-methoxymethyl-1,9-dioxo-16-chloromethyl-20-ethyl-13-trans prostene |

TABLE I-continued

| | | | |
|---|---|---|---|
| 172 | 1-trans-tri-n-butylstannyl-4-trimethylsilyloxymethyl-4-trimethylsilyloxy-1-decene | hexyl]-4-trimethylsiloxy cyclopent-2-en-1-one 2-[6-methoxyacetyl hexyl]-4-trimethylsiloxy cyclopent-2-en-1-one | 20-ethyl-13-trans prostene dl-11a,16-dihydroxy-1-methoxymethyl-1,9-dioxo-16-hydroxymethyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 173 | 1-trans-iodo-3-triphenylmethoxy-1-heptene | 2-[7-methoxyacetyl heptyl]-4-trimethylsiloxy cyclopent-2-en-1-one | dl-11a,15a-dihydroxy-1-methoxymethyl-1,9-dioxo-20-nor-2-homo-13-trans prostene |
| 174 | 1-trans-iodo-3-methyl-3-trimethylsilyloxy-1-heptene | 2-[7-methoxyacetyl heptyl]-4-trimethylsiloxy cyclopent-2-en-1-one | dl-11a,15a-dihydroxy-1-methoxymethyl-1,9-dioxo-15-methyl-20-nor-2-homo-13-trans prostene |
| 175 | 1-trans-iodo-4,4-dimethyl-3-trimethylsilyloxy-1-heptene | 2-[7-methoxyacetyl heptyl]-4-trimethylsiloxy cyclopent-2-en-1-one | dl-11a,15a-dihydroxy-1-methoxymethyl-1,9-dioxo-16,16-dimethyl-20-nor-2-homo-13-trans prostene |
| 176 | 1-trans-iodo-5,5-dimethyl-3-triphenylmethoxy-1-octene | 2-[7-methoxyacetyl heptyl]-4-trimethylsiloxy cyclopent-2-en-1-one | dl-11a,15a-dihydroxy-1-methoxymethyl-1,9-dioxo-17,17-dimethyl-2-homo-13-trans prostene |
| 177 | 1-trans-iodo-4-methyl-3-triphenylmethoxy-1-octene | 2-[7-methoxyacetyl heptyl]-4-trimethylsiloxy cyclopent-2-en-1-one | dl-11a,15a-dihydroxy-1-methoxymethyl-1,9-dioxo-16-methyl-2-homo-13-trans prostene |
| 178 | 1-trans-iodo-4,4-trimethylene-3-trimethylsilyloxy-1-heptene | 2-[7-methoxyacetyl heptyl]-4-trimethylsiloxy cyclopent-2-en-1-one | dl-11a,15a-dihydroxy-1-methoxymethyl-1,9-dioxo-16,16-trimethylene-20-nor-2-homo-13-trans prostene |

| EXAMPLE | VINYL TIN | CYCLOPENTENONE | PRODUCT PROSTAGLANDIN OF THE PGE1 SERIES |
|---|---|---|---|
| 179 | 1-trans-tri-n-butylstannyl-3-vinyl-3-trimethylsilyloxy-1-heptene | 2-[7-methoxyacetyl heptyl]-4-trimethylsiloxy cyclopent-2-en-1-one | dl-11a,15a-dihydroxy-1-methoxymethyl-1,9-dioxo-15-vinyl-20-nor-2-homo-13-trans prostene |
| 180 | 1-trans-tri-n-butylstannyl-4-phenoxy-3-triethylsilyloxy-1-butene | 2-[7-methoxyacetyl heptyl]-4-trimethylsiloxy cyclopent-2-en-1-one | dl-11a,15a-dihydroxy-1-methoxymethyl-1,9-dioxo-16-phenoxy-2-homo-17-20-tetranor-13-trans prostene |
| 181 | 1-trans-tri-n-butylstannyl-4-(p-fluorophenoxy)-3-triethylsilyloxy-1-butene | 2-[7-methoxyacetyl heptyl]-4-trimethylsiloxy cyclopent-2-en-1-one | dl-11a,15a-dihydroxy-1-methoxymethyl-1,9-dioxo-16-(p-fluorophenoxy)-2-homo-17-20-tetranor-13-trans prostene |
| 182 | 1-trans-tri-n-butylstannyl-4-(m-chlorophenoxy)-3-triethylsilyloxy-1-butene | 2-[7-methoxyacetyl heptyl]-4-trimethylsiloxy cyclopent-2-en-1-one | dl-11a,15a-dihydroxy-1-methoxymethyl-1,9-dioxo-16-(m-chlorophenoxy)-2-homo-17-20-tetranor-13-trans prostene |
| 183 | 1-trans-tri-n-butylstannyl-4-(m-trifluoromethylphenoxy)-3-triethylsilyloxy-1-butene | 2-[7-methoxyacetyl heptyl]-4-trimethylsiloxy cyclopent-2-en-1-one | dl-11a,15a-dihydroxy-1-methoxymethyl-1,9-dioxo-16-(m-trifluoromethylphenoxy)-2-homo-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 184 | 1-trans-iodo-5-phenyl-3-triethylsilyloxy-1-pentene | 2-[7-methoxyacetyl heptyl]-4-trimethylsiloxy cyclopent-2-en-1-one | dl-11a,15a-dihydroxy-1-methoxymethyl-1,9-dioxo-17-phenyl-2-homo-18-20-trinor-13-trans prostene |
| 185 | 1-trans-iodo-4,4-dimethyl-5-phenyl-3-triethylsilyloxy-1-pentene | 2-[7-methoxyacetyl heptyl]-4-trimethylsiloxy cyclopent-2-en-1-one | dl-11a,15a-dihydroxy-1-methoxymethyl-1,9-dioxo-16,16-dimethyl-17-phenyl-2-homo-18-20-trinor-13-trans prostene |
| 186 | 1-trans-iodo-4-cyclopentyl-3-trphenylmethoxy-1-butene | 2-[7-methoxyacetyl heptyl]-4-trimethylsiloxy cyclopent-2-en-1-one | dl-11a,15a-dihydroxy-1-methoxymethyl-1,9-dioxo-16-cyclopentyl-2-homo-17-20-tetranor-13-trans prostene |

TABLE I-continued

| | | | |
|---|---|---|---|
| 187 | 1-trans-iodo-4-cyclohexyl 3-triphenylmethoxy-1-butene | 2-[7-methoxyacetyl heptyl]-4-trimethylsiloxy cyclopent-2-en-1-one | dl-11a,15a-dihydroxy-1-methoxymethyl-1,9-dioxo-16-cyclohexyl-2-homo-17-20-tetranor-13-trans prostene |
| 188 | 1-trans-iodo-4-triphenylmethoxy-1-heptene | 2-[7-methoxyacetyl heptyl]-4-trimethylsiloxy cyclopent-2-en-1-one | dl-11a,16-dihydroxy-1-methoxymethyl-1,9-dioxo-20-nor-2-homo-13-trans prostene |
| EXAMPLE | VINYL TIN | CYCLOPENTENONE | PRODUCT PROSTAGLANDIN OF THE PGE1 SERIES |
| 189 | 1-trans-tri-n-butylstannyl-4-methyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-methyl-20-nor-2-homo-13-trans prostene |
| 190 | 1-trans-tri-n-butylstannyl-4-ethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-ethyl-2-homo-13-trans prostene |
| 191 | 1-trans-tri-n-butylstannyl-5-methyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-17-methyl-20-nor-2-homo-13-trans prostene |
| EXAMPLE | VINYL IODIDE | CYCLOPENTENONE | PRODUCT PROSTAGLANDIN OF THE PGE1 SERIES |
| 192 | 1-trans-iodo-5,5-dimethyl 4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-17,17-dimethyl-2-homo-13-trans prostene |
| EXAMPLE | VINYL TIN | CYCLOPENTENONE | PRODUCT PROSTAGLANDIN OF THE PGE1 SERIES |
| 193 | 1-trans-tri-n-butylstannyl-4-vinyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-vinyl-20-nor-2-homo-13-trans prostene |
| 194 | 1-trans-tri-n-butylstannyl-4-cyclopropyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-cyclopropyl-2-homo-13-trans prostene |
| 195 | 1-trans-tri-n-butylstannyl-4-trimethylsilylethynyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-ethynyl-20-nor-2-homo-13-trans prostene |
| 196 | 1-trans-tri-n-butylstannyl-5-methylene 4-triethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-17-methylene-20-nor-2-homo-13-trans prostene |
| 197 | 1-trans-tri-n-butylstannyl-4-methyl-5-methylene 4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-methyl-17-methylene-20-nor-2-homo-13-trans prostene |
| 198 | 1-trans-tri-n-butylstannyl-4-dimethoxymethyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-formyl-20-nor-2-homo-13-trans prostene |
| 199 | 1-trans-tri-n-butylstannyl-4-fluoromethyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-fluoromethyl-20-nor-2-homo-13-trans prostene |
| 200 | 1-trans-tri-n-butylstannyl-4-difluoromethyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-difluoromethyl-20-nor-2-homo-13-trans prostene |
| 201 | 1-trans-tri-n-butylstannyl-4-trifluoromethyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-trifluoromethyl-20-nor-2-homo-13-trans prostene |
| 202 | 1-trans-tri-n-butylstannyl-4-chloromethyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-chloromethyl-20-nor-2-homo-13-trans prostene |

TABLE I-continued

| | | | |
|---|---|---|---|
| 203 | 1-trans-tri-n-butylstannyl-4-trimethylsilyloxymethyl-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-hydroxymethyl-20-nor-2-homo-13-trans prostene |
| EXAMPLE | VINYL IODIDE | CYCLOPENTENONE | PRODUCT PROSTAGLANDIN OF THE PGE1 SERIES |
| 204 | 1-trans-iodo-4-methyl-7-chloro-4-trimethylsilyloxy-1-heptene | 2-[7-methoxyacetyl heptyl]-4-trimethylsiloxy cyclopent-2-en-1-one | dl-11a,16-dihydroxy-1-methoxymethyl-1,9-dioxo-16-methyl-19-chloro-2-homo-20-nor-13-trans prostene |
| 205 | 1-trans-iodo-3-triphenylmethoxy-1-octene | 2-[7-methoxyacetyl heptyl]-4-trimethylsiloxy cyclopent-2-en-1-one | dl-11a,15a-dihydroxy-1-methoxymethyl-1,9-dioxo-2-homo-13-trans prostene |
| 206 | 1-trans-iodo-3-methyl-3-trimethylsilyloxy-1-octene | 2-[7-methoxyacetyl heptyl]-4-trimethylsiloxy cyclopent-2-en-1-one | dl-11a,15a-dihydroxy-1-methoxymethyl-1,9-dioxo-15-methyl-2-homo-13-trans prostene |
| 207 | 1-trans-iodo-4,4-dimethyl-3-trimethylsilyloxy-1-octene | 2-[7-methoxyacetyl heptyl]-4-trimethylsiloxy cyclopent-2-en-1-one | dl-11a,15a-dihydroxy-1-methoxymethyl-1,9-dioxo-16,16-dimethyl-2-homo-13-trans prostene |
| 208 | 1-trans-iodo-4,4-trimethylene-3-trimethylsilyloxy-1-octene | 2-[7-methoxyacetyl heptyl]-4-trimethylsiloxy cyclopent-2-en-1-one | dl-11a,15a-dihydroxy-1-methoxymethyl-1,9-dioxo-16,16-trimethylene-2-homo-13-trans prostene |
| EXAMPLE | VINYL TIN | CYCLOPENTENONE | PRODUCT PROSTAGLANDIN OF THE PGE1 SERIES |
| 209 | 1-trans-tri-n-butylstannyl-3-vinyl-3-trimethylsilyloxy-1-octene | 2-[7-methoxyacetyl heptyl]-4-trimethylsiloxy cyclopent-2-en-1-one | dl-11a,15a-dihydroxy-1-methoxymethyl-1,9-dioxo-15-vinyl-2-homo-13-trans prostene |
| EXAMPLE | VINYL IODIDE | CYCLOPENTENONE | PRODUCT PROSTAGLANDIN OF THE PGE1 SERIES |
| 210 | 1-trans-iodo-4-triphenylmethoxy-1-octene | 2-[7-methoxyacetyl heptyl]-4-trimethylsiloxy cyclopent-2-en-1-one | dl-11a,16-dihydroxy-1-methoxymethyl-1,9-dioxo-2-homo-13-trans prostene |
| EXAMPLE | VINYL TIN | CYCLOPENTENONE | PRODUCT PROSTAGLANDIN OF THE PGE1 SERIES |
| 211 | 1-trans-tri-n-butylstannyl-4-methyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-methyl-2-homo-13-trans prostene |
| 212 | 1-trans-tri-n-butylstannyl-5-methyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-17-methyl-2-homo-13-trans prostene |
| 213 | 1-trans-tri-n-butylstannyl-4-vinyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-vinyl-2-homo-13-trans prostene |
| 214 | 1-trans-tri-n-butylstannyl-4-trimethylsilylethynyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-ethynyl-2-homo-13-trans prostene |
| 215 | 1-trans-tri-n-butylstannyl-5-methylene-4-triethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-17-methylene-2-homo-13-trans prostene |
| 216 | 1-trans-tri-n-butylstannyl-4-methyl-5-methylene-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-methyl-17-methylene-2-homo-13-trans prostene |
| 217 | 1-trans-tri-n-butylstannyl-4-dimethoxymethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-formyl-2-homo-13-trans prostene |

TABLE I-continued

| | | | |
|---|---|---|---|
| 218 | 1-trans-tri-n-butylstannyl-4-fluoromethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-fluoromethyl-2-homo-13-trans prostene |
| 219 | 1-trans-tri-n-butylstannyl-4-difluoromethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-difluoromethyl-2-homo-13-trans prostene |
| 220 | 1-trans-tri-n-butylstannyl-4-trifluoromethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-trifluoromethyl-2-homo-13-trans prostene |
| 221 | 1-trans-tri-n-butylstannyl-4-chloromethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-chloromethyl-2-homo-13-trans prostene |
| 222 | 1-trans-tri-n-butylstannyl-4-trimethylsilyloxymethyl-4-trimethylsilyloxy-1-octene | 2-[7-methoxyacetyl heptyl]-4-trimethylsiloxy cyclopent-2-en-1-one | dl-11a,16-dihydroxy-1-methoxymethyl-1,9-dioxo-16-hydroxymethyl-2-homo-13-trans prostene |
| EXAMPLE | VINYL IODIDE | CYCLOPENTENONE | PRODUCT PROSTAGLANDIN OF THE PGE1 SERIES |
| 223 | 1-trans-iodo-3-triphenylmethoxy-1-nonene | 2-[7-methoxyacetyl heptyl]-4-trimethylsiloxy cyclopent-2-en-1-one | dl-11a,15a-dihydroxy-1-methoxymethyl-1,9-dioxo-20-methyl-2-homo-13-trans prostene |
| 224 | 1-trans-iodo-3-methyl-3-trimethylsilyloxy-1-nonene | 2-[7-methoxyacetyl heptyl]-4-trimethylsiloxy cyclopent-2-en-1-one | dl-11a,15a-dihydroxy-1-methoxymethyl-1,9-dioxo-15-methyl-20-methyl-2-homo-13-trans prostene |
| 225 | 1-trans-iodo-4,4-dimethyl-3-trimethylsilyloxy-1-nonene | 2-[7-methoxyacetyl heptyl]-4-trimethylsiloxy cyclopent-2-en-1-one | dl-11a,15a-dihydroxy-1-methoxymethyl-1,9-dioxo-16,16-dimethyl-20-methyl-2-homo-13-trans prostene |
| 226 | 1-trans-iodo-4,4-trimethylene-3-trimethylsilyloxy-1-nonene | 2-[7-methoxyacetyl heptyl]-4-trimethylsiloxy cyclopent-2-en-1-one | dl-11a,15a-dihydroxy-1-methoxymethyl-1,9-dioxo-16,16-trimethylene-20-methyl-2-homo-13-trans prostene |
| EXAMPLE | VINYL TIN | CYCLOPENTENONE | PRODUCT PROSTAGLANDIN OF THE PGE1 SERIES |
| 227 | 1-trans-tri-n-butylstannyl-3-vinyl-3-trimethylsilyloxy-1-nonene | 2-[7-methoxyacetyl heptyl]-4-trimethylsiloxy cyclopent-2-en-1-one | dl-11a,15a-dihydroxy-1-methoxymethyl-1,9-dioxo-15-vinyl-20-methyl-2-homo-13-trans prostene |
| EXAMPLE | VINYL IODIDE | CYCLOPENTENONE | PRODUCT PROSTAGLANDIN OF THE PGE1 SERIES |
| 228 | 1-trans-iodo-4-triphenylmethoxy-1-nonene | 2-[7-methoxyacetyl heptyl]-4-trimethylsiloxy cyclopent-2-en-1-one | dl-11a,16-dihydroxy-1-methoxymethyl-1,9-dioxo-20-methyl-2-homo-13-trans prostene |
| EXAMPLE | VINYL TIN | CYCLOPENTENONE | PRODUCT PROSTAGLANDIN OF THE PGE1 SERIES |
| 229 | 1-trans-tri-n-butylstannyl-4-methyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-methyl-20-methyl-2-homo-13-trans prostene |
| 230 | 1-trans-tri-n-butylstannyl-5-methyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-17-methyl-20-methyl-2-homo-13-trans prostene |
| 231 | 1-trans-tri-n-butylstannyl-4-vinyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-vinyl-20-methyl-2-homo-13-trans prostene |
| 232 | 1-trans-tri-n-butylstannyl-4-trimethylsilylethynyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-ethynyl-20-methyl-2-homo-13-trans prostene |

TABLE I-continued

| | | | |
|---|---|---|---|
| 233 | 1-trans-tri-n-butylstannyl-5-methylene 4-triethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-17-methylene-20-methyl-2-homo-13-trans prostene |
| 234 | 1-trans-tri-n-butylstannyl-4-methyl-5-methylene 4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-methyl-17-methylene-20-methyl-2-homo-13-trans prostene |
| 235 | 1-trans-tri-n-butylstannyl-4-dimethoxymethyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-formyl-20-methyl-2-homo-13-trans prostene |
| 236 | 1-trans-tri-n-butylstannyl-4-fluoromethyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-fluoromethyl-20-methyl-2-homo-13-trans prostene |
| 237 | 1-trans-tri-n-butylstannyl-4-difluoromethyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-difluoromethyl-20-methyl-2-homo-13-trans prostene |
| 238 | 1-trans-tri-n-butylstannyl-4-trifluoromethyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-trifluoromethyl-20-methyl-2-homo-13-trans prostene |
| 239 | 1-trans-tri-n-butylstannyl-4-chloromethyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-chloromethyl-20-methyl-2-homo-13-trans prostene |
| 240 | 1-trans-tri-n-butylstannyl-4-trimethylsilyloxymethyl-4-trimethylsilyloxy-1-nonene | 2-[7-methoxyacetyl heptyl]-4-trimethylsiloxy cyclopent-2-en-1-one | dl-11a,16-dihydroxy-1-methoxymethyl-1,9-dioxo-16-hydroxymethyl-20-methyl-2-homo-13-trans prostene |
| EXAMPLE | VINYL IODIDE | CYCLOPENTENONE | PRODUCT PROSTAGLANDIN OF THE PGE1 SERIES |
| 241 | 1-trans-iodo-3-triphenylmethoxy-1-decene | 2-[7-methoxyacetyl heptyl]-4-trimethylsiloxy cyclopent-2-en-1-one | dl-11a,15a-dihydroxy-1-methoxymethyl-1,9-dioxo-20-ethyl-2-homo-13-trans prostene |
| 242 | 1-trans-iodo-3-methyl-3-trimethylsilyloxy-1-decene | 2-[7-methoxyacetyl heptyl]-4-trimethylsiloxy cyclopent-2-en-1-one | dl-11a,15a-dihydroxy-1-methoxymethyl-1,9-dioxo-15-methyl-20-ethyl-2-homo-13-trans prostene |
| 243 | 1-trans-iodo-4,4-dimethyl 3-trimethylsilyloxy-1-decene | 2-[7-methoxyacetyl heptyl]-4-trimethylsiloxy cyclopent-2-en-1-one | dl-11a,15a-dihydroxy-1-methoxymethyl-1,9-dioxo-16,16-dimethyl-20-ethyl-2-homo-13-trans prostene |
| 244 | 1-trans-iodo-4,4-trimethylene 3-trimethylsilyloxy-1-decene | 2-[7-methoxyacetyl heptyl]-4-trimethylsiloxy cyclopent-2-en-1-one | dl-11a,15a-dihydroxy-1-methoxymethyl-1,9-dioxo-16,16-trimethylene-20-ethyl-2-homo-13-trans prostene |
| EXAMPLE | VINYL TIN | CYCLOPENTENONE | PRODUCT PROSTAGLANDIN OF THE PGE1 SERIES |
| 245 | 1-trans-tri-n-butylstannyl-3-vinyl-3-trimethylsilyloxy-1-decene | 2-[7-methoxyacetyl heptyl]-4-trimethylsiloxy cyclopent-2-en-1-one | dl-11a,15a-dihydroxy-1-methoxymethyl-1,9-dioxo-15-vinyl-20-ethyl-2-homo-13-trans prostene |
| EXAMPLE | VINYL IODIDE | CYCLOPENTENONE | PRODUCT PROSTAGLANDIN OF THE PGE1 SERIES |
| 246 | 1-trans-iodo-4-triphenylmethoxy-1-decene | 2-[7-methoxyacetyl heptyl]-4-trimethylsiloxy cyclopent-2-en-1-one | dl-11a,16-dihydroxy-1-methoxymethyl-1,9-dioxo-20-ethyl-2-homo-13-trans prostene |
| EXAMPLE | VINYL TIN | CYCLOPENTENONE | PRODUCT PROSTAGLANDIN OF THE PGE1 SERIES |
| 247 | 1-trans-tri-n-butylstannyl-4-methyl-4-trimethylsilyloxy-1-decene | 2-[7-methoxyacetyl heptyl]-4-trimethylsiloxy | dl-11a,16-dihydroxy-1-methoxymethyl-1,9-dioxo-16-methyl-20-ethyl-2-homo-13-trans prostene |

TABLE I-continued

| | | | |
|---|---|---|---|
| 248 | 1-trans-tri-n-butylstannyl-5-methyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-17-methyl-20-ethyl-2-homo-13-trans prostene |
| 249 | 1-trans-tri-n-butylstannyl-4-vinyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-vinyl-20-ethyl-2-homo-13-trans prostene |
| 250 | 1-trans-tri-n-butylstannyl-4-trimethylsilylethynyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl1,9-dioxo-16-ethynyl-20-ethyl-2-homo-13-trans prostene |
| 251 | 1-trans-tri-n-butylstannyl-5-methylene-4-triethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-17-methylene-20-ethyl-2-homo-13-trans prostene |
| 252 | 1-trans-tri-n-butylstannyl-4-methyl-5-methylene-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-methyl-17-methylene-20-ethyl-2-homo-13-trans prostene |
| 253 | 1-trans-tri-n-butylstannyl-4-dimethoxymethyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-formyl-20-ethyl-2-homo-13-trans prostene |
| 254 | 1-trans-tri-n-butylstannyl-4-fluoromethyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-fluoromethyl-20-ethyl-2-homo-13-trans prostene |
| 255 | 1-trans-tri-n-butylstannyl-4-difluoromethyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-difluoromethyl-20-ethyl-2-homo-13-trans prostene |
| 256 | 1-trans-tri-n-butylstannyl-4-trifluoromethyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-trifluoromethyl-20-ethyl-2-homo-13-trans prostene |
| 257 | 1-trans-tri-n-butylstannyl-4-chloromethyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-chloromethyl-20-ethyl-2-homo-13-trans prostene |
| 258 | 1-trans-tri-n-butylstannyl-4-trimethylsilyloxymethyl-4-trimethylsilyloxy-1-decene | 2-[7-methoxyacetyl heptyl]-4-trimethylsilyloxy cyclopent-2-en-1-one | dl-11a,16-dihydroxy-1-methoxymethyl-1,9-dioxo-16-hydroxymethyl-20-ethyl-2-homo-13-trans prostene |

| EXAMPLE | VINYL IODIDE | CYCLOPENTENONE | PRODUCT PROSTAGLANDIN OF THE PGEI SERIES |
|---|---|---|---|
| 259 | 1-trans-iodo-3-triphenylmethoxy-1-heptene | 2-[6-methoxyacetyl hexyl]-4R-trimethylsilyloxy cyclopent-2-en-1-one | nat-11a,15a-dihydroxy-1-methoxymethyl-1,9-dioxo-20-nor-13-trans prostene |
| 260 | 1-trans -iodo-3-methyl-3-trimethylsilyloxy-1-heptene | 2-[6-methoxyacetyl hexyl]-4R-trimethylsilyloxy cyclopent-2-en-1-one | nat-11a,15a-dihydroxy-1-methoxymethyl-1,9-dioxo-15-methyl-20-nor-13-trans prostene |
| 261 | 1-trans-iodo-4,4-dimethyl-3-trimethylsilyloxy-1-heptene | 2-[6-methoxyacetyl hexyl]-4R-trimethylsilyloxy cyclopent-2-en-1-one | nat-11a,15a-dihydroxy-1-methoxymethyl-1,9-dioxo-16,16-dimethyl-20-nor-13-trans prostene |
| 262 | 1-trans-iodo-5,5-dimethyl-3-triphenylmethoxy-1-octene | 2-[6-methoxyacetyl hexyl]-4R-trimethylsilyloxy cyclopent-2-en-1-one | nat-11a,15a-dihydroxy-1-methoxymethyl-1,9-dioxo-17,17-dimethyl-13-trans prostene |
| 263 | 1-trans-iodo-4-methyl-3-triphenylmethoxy-1-octene | 2-[6-methoxyacetyl hexyl]-4R-trimethylsilyloxy cyclopent-2-en-1-one | nat-11a,15a-dihydroxy-1-methoxymethyl-1,9-dioxo-16-methyl-13-trans prostene |
| 264 | 1-trans-iodo-4,4-trimethylene-3-trimethylsilyloxy-1-heptene | 2-[6-methoxyacetyl hexyl]-4R-trimethylsilyloxy cyclopent-2-en-1-one | nat-11a,15a-dihydroxy-1-methoxymethyl-1,9-dioxo-16,16-trimethylene-20-nor-13-trans prostene |

TABLE I-continued

| EXAMPLE | VINYL TIN | CYCLOPENTENONE | PRODUCT PROSTAGLANDIN OF THE PGE1 SERIES |
|---|---|---|---|
| 265 | 1-trans-tri-n-butylstannyl-3-vinyl-3-trimethylsilyloxy-1-heptene | 2-[6-methoxyacetyl hexyl]-4R-trimethylsilyloxy cyclopent-2-en-1-one | nat-11a,15a-dihydroxy-1-methoxymethyl-1,9-dioxo-15-vinyl-20-nor-13-trans prostene |
| 266 | 1-trans-tri-n-butylstannyl-4-phenoxy-3-triethylsilyloxy-1-butene | 2-[6-methoxyacetyl hexyl]-4R-trimethylsilyloxy cyclopent-2-en-1-one | nat-11a,15a-dihydroxy-1-methoxymethyl-1,9-dioxo-16-phenoxy-17-20-tetranor-13-trans prostene |
| 267 | 1-trans-tri-n-butylstannyl-4-(p-fluorophenoxy)-3-triethylsilyloxy-1-butene | 2-[6-methoxyacetyl hexyl]-4R-trimethylsilyloxy cyclopent-2-en-1-one | nat-11a,15a-dihydroxy-1-methoxymethyl-1,9-dioxo-16-(p-fluorophenoxy)-17-20-tetranor-13-trans prostene |
| 268 | 1-trans-tri-n-butylstannyl-4-(m-chlorophenoxy)-3-triethylsilyloxy-1-butene | 2-[6-methoxyacetyl hexyl]-4R-trimethylsilyloxy cyclopent-2-en-1-one | nat-11a,15a-dihydroxy-1-methoxymethyl-1,9-dioxo-16-(m-chlorophenoxy)-17-20-tetranor-13-trans prostene |
| 269 | 1-trans-tri-n-butylstannyl-4-(m-trifluoromethylphenoxy)-3-triethylsilyloxy-1-butene | 2-[6-methoxyacetyl hexyl]-4R-trimethylsilyloxy cyclopent-2-en-1-one | nat-11a,15a-dihydroxy-1-methoxymethyl-1,9-dioxo-16-(m-trifluoromethylphenoxy)-17-20-tetranor-13-trans prostene |

| EXAMPLE | VINYL IODIDE | CYCLOPENTENONE | PRODUCT PROSTEGLANDIN OF THE PGE1 SERIES |
|---|---|---|---|
| 270 | 1-trans-iodo-5-phenyl-3-triethylsilyloxy-1-pentene | 2-[6-methoxyacetyl hexyl]-4R-trimethylsilyloxy cyclopent-2-en-1-one | nat-11a,15a-dihydroxy-1-methoxymethyl-1,9-dioxo-17-phenyl-18-20-trinor-13-trans prostene |
| 271 | 1-trans-iodo-4,4-dimethyl-5-phenyl-3-triethylsilyloxy-1-pentene | 2-[6-methoxyacetyl hexyl]-4R-trimethylsilyloxy cyclopent-2-en-1-one | nat-11a,15a-dihydroxy-1-methoxymethyl-1,9-dioxo-16,16-dimethyl-17-phenyl-18-20-trinor-13-trans prostene |
| 272 | 1-trans-iodo-4-cyclopentyl-3-triphenylmethoxy-1-butene | 2-[6-methoxyacetyl hexyl]-4R-trimethylsilyloxy cyclopent-2-en-1-one | nat-11a,15a-dihydroxy-1-methoxymethyl-1,9-dioxo-16-cyclopentyl-17-20-tetranor-13-trans prostene |
| 273 | 1-trans-iodo-4-cyclohexyl-3-triphenylmethoxy-1-butene | 2-[6-methoxyacetyl hexyl]-4R-trimethylsilyloxy cyclopent-2-en-1-one | nat-11a,15a-dihydroxy-1-methoxymethyl-1,9-dioxo-16-cyclohexyl-17-20-tetranor-13-trans prostene |
| 274 | 1-trans-iodo-4-triphenylmethoxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-20-nor-13-trans prostene |

| EXAMPLE | VINYL TIN | CYCLOPENTENONE | PRODUCT PROSTAGLANDIN OF THE PGE1 SERIES |
|---|---|---|---|
| 275 | 1-trans-tri-n-butylstannyl-4-methyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-methyl-20-nor-13-trans prostene |
| 276 | 1-trans-tri-n-butylstannyl-4-ethyl-4-trimethylsilyloxy-1-octene | 2-[6-methoxyacetyl hexyl]-4R-trimethylsilyloxy cyclopent-2-en-1-one | nat-11a,16-dihydroxy-1-methoxymethyl-1,9-dioxo-16-ethyl-13-trans prostene |
| 277 | 1-trans-tri-n-butylstannyl-5-methyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-17-methyl-20-nor-13-trans prostene |

| EXAMPLE | VINYL IODIDE | CYCLOPENTENONE | PRODUCT PROSTAGLANDIN OF THE PGE1 SERIES |
|---|---|---|---|
| 278 | 1-trans-iodo-5,5-dimethyl-4-trimethylsilyloxy-1-octene | 2-[6-methoxyacetyl hexyl]-4R-trimethylsilyloxy cyclopent-2-en-1-one | nat-11a,16-dihydroxy-1-methoxymethyl-1,9-dioxo-17,17-dimethyl-13-trans prostene |

| EXAMPLE | VINYL TIN | CYCLOPENTENONE | PRODUCT PROSTAGLANDIN OF THE PGE1 SERIES |
|---|---|---|---|

TABLE I-continued

| | | | |
|---|---|---|---|
| 279 | 1-trans-tri-n-butylstannyl-4-vinyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-vinyl-20-nor-13-trans prostene |
| 280 | 1-trans-tri-n-butylstannyl-4-cyclopropyl-4-trimethylsilyloxy-1-octene | 2-[6-methoxyacetyl hexyl]-4R-trimethylsilyloxy cyclopent-2-en-1-one | nat-11a,16-dihydroxy-1-methoxymethyl-1,9-dioxo-16-cyclopropyl-13-trans prostene |
| 281 | 1-trans-tri-n-butylstannyl-4-trimethylsilylethynyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-ethynyl-20-nor-13-trans prostene |
| 282 | 1-trans-tri-n-butylstannyl-5-methylene-4-triethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-17-methylene-20-nor-13-trans prostene |
| 283 | 1-trans-tri-n-butylstannyl-4-methyl-5-methylene-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-methyl-17-methylene-20-nor-13-trans prostene |
| 284 | 1-trans-tri-n-butylstannyl-4-dimethoxymethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-formyl-20-nor-13-trans prostene |
| 285 | 1-trans-tri-n-butylstannyl-4-fluoromethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-fluoromethyl-20-nor-13-trans prostene |
| 286 | 1-trans-tri-n-butylstannyl-4-difluoromethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-difluoromethyl-20-nor-13-trans prostene |
| 287 | 1-trans-tri-n-butylstannyl-4-trifluoromethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-trifluoromethyl-20-nor-13-trans prostene |
| 288 | 1-trans-tri-n-butylstannyl-4-chloromethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-chloromethyl-20-nor-13-trans prostene |
| 289 | 1-trans-tri-n-butylstannyl-4-trimethylsilyloxymethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE PGE1 SERIES |
| 290 | 1-trans-iodo-4-methyl-7-chloro-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-methyl-19-chloro-20-nor-13-trans prostene |
| 291 | 1-trans-iodo-3-triphenylmethoxy-1-octene | 2-[6-methoxyacetyl hexyl]-4R-trimethylsilyloxy cyclopent-2-en-1-one | nat-11a,15a-dihydroxy-1-methoxymethyl-1,9-dioxo-13-trans prostene |
| 292 | 1-trans-iodo-3-methyl-3-trimethylsilyloxy-1-octene | 2-[6-methoxyacetyl hexyl]-4R-trimethylsilyloxy cyclopent-2-en-1-one | nat-11a,15a-dihydroxy-1-methoxymethyl-1,9-dioxo-15-methyl-13-trans prostene |
| 293 | 1-trans-iodo-4,4-dimethyl-3-trimethylsilyloxy-1-octene | 2-[6-methoxyacetyl hexyl]-4R-trimethylsilyloxy cyclopent-2-en-1-one | nat-11a,15a-dihydroxy-1-methoxymethyl-1,9-dioxo-16,16-dimethyl-13-trans prostene |
| 294 | 1-trans-iodo-4,4-trimethylene-3-trimethylsilyloxy-1-octene | 2-[6-methoxyacetyl hexyl]-4R-trimethylsilyloxy cyclopent-2-en-1-one | nat-11a,15a-dihydroxy-1-methoxymethyl-1,9-dioxo-16,16-trimethylene-13-trans prostene |
| EXAMPLE | VINYL TIN | CYCLOPENTENONE | PRODUCT PROSTAGLANDIN OF THE PGE1 SERIES |
| 295 | 1-trans-tri-n-butylstannyl-3-vinyl- | 2-[6-methoxyacetyl | nat-11a,15a-dihydroxy-1-methoxymethyl-1,9-dioxo-15-vinyl- |

TABLE I-continued

| EXAMPLE | VINYL IODIDE | CYCLOPENTENONE | PRODUCT PROSTAGLANDIN OF THE PGE1 SERIES |
|---|---|---|---|
| 296 | 1-trans-iodo-4-triphenylmethoxy-1-octene | 2-[6-methoxyacetyl hexyl]-4R-trimethylsiloxy cyclopent-2-en-1-one | nat-11a,16-dihydroxy-1-methoxymethyl-1,9-dioxo-13-trans prostene |

| EXAMPLE | VINYL TIN | CYCLOPENTENONE | PRODUCT PROSTAGLANDIN OF THE PGE1 SERIES |
|---|---|---|---|
| 297 | 1-trans-tri-n-butylstannyl-4-methyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-methyl-13-trans prostene |
| 298 | 1-trans-tri-n-butylstannyl-5-methyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-17-methyl-13-trans prostene |
| 299 | 1-trans-tri-n-butylstannyl-4-vinyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-vinyl-13-trans prostene |
| 300 | 1-trans-tri-n-butylstannyl-4-trimethylsilylethynyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-ethynyl-13-trans prostene |
| 301 | 1-trans-tri-n-butylstannyl-5-methylene-4-triethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-17-methylene-13-trans prostene |
| 302 | 1-trans-tri-n-butylstannyl-4-methyl-5-methylene-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-methyl-17-methylene-13-trans prostene |
| 303 | 1-trans-tri-n-butylstannyl-4-dimethoxymethyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-formyl-13-trans prostene |
| 304 | 1-trans-tri-n-butylstannyl-4-fluoromethyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-fluoromethyl-13-trans prostene |
| 305 | 1-trans-tri-n-butylstannyl-4-difluoromethyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-difluoromethyl-13-trans prostene |
| 306 | 1-trans-tri-n-butylstannyl-4-trifluoromethyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-trifluoromethyl-13-trans prostene |
| 307 | 1-trans-tri-n-butylstannyl-4-chloromethyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-chloromethyl-13-trans prostene |
| 308 | 1-trans-tri-n-butylstannyl-4-trimethylsilyloxymethyl-4-trimethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-16-hydroxymethyl-13-trans prostene |

| EXAMPLE | VINYL IODIDE | CYCLOPENTENONE | PRODUCT PROSTAGLANDIN OF THE PGE1 SEREIS |
|---|---|---|---|
| 309 | 1-trans-iodo-3-triphenylmethoxy-1-nonene | 2-[6-methoxyacetyl hexyl]-4R-trimethylsiloxy cyclopent-2-en-1-one | nat-11a,15a-dihydroxy-1-methoxymethyl-1,9-dioxo-20-methyl-13-trans prostene |
| 310 | 1-trans-iodo-3-methyl-3-trimethylsilyloxy-1-nonene | 2-[6-methoxyacetyl hexyl]-4R-trimethylsiloxy cyclopent-2-en-1-one | nat-11a,15a-dihydroxy-1-methoxymethyl-1,9-dioxo-20-methyl-13-trans prostene |

TABLE I-continued

| Example | VINYL TIN / VINYL IODIDE / VINYL TIN | CYCLOPENTENONE | PRODUCT PROSTAGLANDIN OF THE PGE1 SERIES |
|---|---|---|---|
| 311 | 1-trans-iodo-4,4-dimethyl-3-trimethylsilyloxy-1-nonene | 2-[6-methoxyacetyl hexyl]-4R-trimethylsilyloxy cyclopent-2-en-1-one | nat-11a,15a-dihydroxy-1-methoxymethyl-1,9-dioxo-16,16-dimethyl-20-methyl-13-trans prostene |
| 312 | 1-trans-iodo-4,4-trimethylene-3-trimethylsilyloxy-1-nonene | 2-[6-methoxyacetyl hexyl]-4R-trimethylsilyloxy cyclopent-2-en-1-one | nat-11a,15a-dihydroxy-1-methoxymethyl-1,9-dioxo-16,16-trimethylene-20-methyl-13-trans prostene |
| EXAMPLE | VINYL TIN | CYCLOPENTENONE | PRODUCT PROSTAGLANDIN OF THE PGE1 SERIES |
| 313 | 1-trans-tri-n-butylstannyl-3-vinyl-3-trimethylsilyloxy-1-nonene | 2-[6-methoxyacetyl hexyl]-4R-trimethylsilyloxy cyclopent-2-en-1-one | nat-11a,15a,dihydroxy-1-methoxymethyl-1,9-dioxo-15-vinyl-20-methyl-13-trans prostene |
| EXAMPLE | VINYL IODIDE | CYCLOPENTENONE | PRODUCT PROSTAGLANDIN OF THE PGE1 SERIES |
| 314 | 1-trans-iodo-4-triphenylmethoxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-20-methyl-13-trans prostene |
| EXAMPLE | VINYL TIN | CYCLOPENTENONE | PRODUCT PROSTAGLANDIN OF THE PGE1 SERIES |
| 315 | 1-trans-tri-n-butylstannyl-4-methyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-methyl-20-methyl-13-trans prostene |
| 316 | 1-trans-tri-n-butylstannyl-5-methyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-17-methyl-20-methyl-13-trans prostene |
| 317 | 1-trans-tri-n-butylstannyl-4-vinyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-vinyl-20-methyl-13-trans prostene |
| 318 | 1-trans-tri-n-butylstannyl-4-trimethylsilylethynyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-ethynyl-20-methyl-13-trans prostene |
| 319 | 1-trans-tri-n-butylstannyl-5-methylene-4-triethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-17-methylene-20-methyl-13-trans prostene |
| 320 | 1-trans-tri-n-butylstannyl-4-methyl-5-methylene-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-methyl-17-methylene-20-methyl-13-trans prostene |
| 321 | 1-trans-tri-n-butylstannyl-4-dimethoxymethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-formyl-20-methyl-13-trans prostene |
| 322 | 1-trans-tri-n-butylstannyl-4-fluoromethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-fluoromethyl-20-methyl-13-trans prostene |
| 323 | 1-trans-tri-n-butylstannyl-4-difluoromethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-difluoromethyl-20-methyl-13-trans prostene |
| 324 | 1-trans-tri-n-butylstannyl-4-trifluoromethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-trifluoromethyl-20-methyl-13-trans prostene |
| 325 | 1-trans-tri-n-butylstannyl-4-chloromethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-chloromethyl-20-methyl-13-trans prostene |
| 326 | 1-trans-tri-n-butylstannyl-4-trimethylsilyloxymethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-hydroxymethyl-20-methyl-13-trans prostene |

TABLE I-continued

| EXAMPLE | VINYL IODIDE | CYCLOPENTENONE | PRODUCT PROSTAGLANDIN OF THE PGE1 SERIES |
|---|---|---|---|
| 327 | 1-trans-iodo-3-triphenylmethoxy-1-decene | 2-[6-methoxyacetyl hexyl]-4R-trimethylsilyloxy cyclopent-2-en-1-one | nat-11a,15a-dihydroxy-1-methoxymethyl-1,9-dioxo-20-ethyl-13-trans prostene |
| 328 | 1-trans-iodo-3-methyl-3-trimethylsilyloxy-1-decene | 2-[6-methoxyacetyl hexyl]-4R-trimethylsilyloxy cyclopent-2-en-1-one | nat-11a,15a-dihydroxy-1-methoxymethyl-1,9-dioxo-15-methyl-20-ethyl-13-trans prostene |
| 329 | 1-trans-iodo-4,4-dimethyl-3-trimethylsilyloxy-1-decene | 2-[6-methoxyacetyl hexyl]-4R-trimethylsilyloxy cyclopent-2-en-1-one | nat-11a,15a-dihydroxy-1-methoxymethyl-1,9-dioxo-16,16-dimethyl-20-ethyl-13-trans prostene |
| 330 | 1-trans-iodo-4,4-trimethylene-3-trimethylsilyloxy-1-decene | 2-[6-methoxyacetyl hexyl]-4R-trimethylsilyloxy cyclopent-2-en-1-one | nat-11a,15a-dihydroxy-1-methoxymethyl-1,9-dioxo-16,16-trimethylene-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 331 | 1-trans-tri-n-butylstannyl-3-vinyl-3-trimethylsilyloxy-1-decene | 2-[6-methoxyacetyl hexyl]-4R-trimethylsilyloxy cylopent-2-en-1-one | nat-11a,15a-dihydroxy-1-methoxymethyl-1,9-dioxo-15-vinyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 332 | 1-trans-iodo-4-triphenylmethoxy-1-decene | 2-[6-methoxyacetyl hexyl]-4R-trimethylsilyloxy cyclopent-2-en-1-one | nat-11a,16-dihydroxy-1-methoxymethyl-1,9-dioxo-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 333 | 1-trans-tri-n-butylstannyl-4-methyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-methyl-20-ethyl-13-trans prostene |
| 334 | 1-trans-tri-n-butylstannyl-5-methyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-17-methyl-20-ethyl-13-trans prostene |
| 335 | 1-trans-tri-n-butylstannyl-4-vinyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-vinyl-20-ethyl-13-trans prostene |
| 336 | 1-trans-tri-n-butylstannyl-4-trimethylsilylethynyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-ethynyl-20-ethyl-13-trans prostene |
| 337 | 1-trans-tri-n-butylstannyl-4-methyl-5-methylene-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-17-methylene-20-ethyl-13-trans prostene |
| 338 | 1-trans-tri-n-butylstannyl-4-methyl-5-methylene-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-methyl-17-methylene-20-ethyl-13-trans prostene |
| 339 | 1-trans-tri-n-butylstannyl-4-dimethoxymethyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-formyl-20-ethyl-13-trans prostene |
| 340 | 1-trans-tri-n-butylstannyl-4-fluoromethyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-fluoromethyl-20-ethyl-13-trans prostene |
| 341 | 1-trans-tri-n-butylstannyl-4-difluoromethyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-difluoromethyl-20-ethyl-13-trans prostene |

TABLE I-continued

| EXAMPLE | VINYL IODIDE / VINYL TIN | CYCLOPENTENONE | PRODUCT PROSTAGLANDIN |
|---|---|---|---|
| 342 | 1-trans-tri-n-butylstannyl-4-trifluoromethyl-4-trimethylsilyloxy-1-decene | 2-[6-methoxyacetyl hexyl]-4R-trimethylsiloxy cyclopent-2-en-1-one | nat-11a,16-dihydroxy-1-methoxymethyl-1,9-dioxo-16-trifluoromethyl-20-ethyl-13-trans prostene |
| 343 | 1-trans-tri-n-butylstannyl-4-chloromethyl-4-trimethylsilyloxy-1-decene | 2-[6-methoxyacetyl hexyl]-4R-trimethylsiloxy cyclopent-2-en-1-one | nat-11a,16-dihydroxy-1-methoxymethyl-1,9-dioxo-16-chloromethyl-20-ethyl-13-trans prostene |
| 344 | 1-trans-tri-n-butylstannyl-4-trimethylsilyloxymethyl-4-trimethylsilyloxy-1-decene | 2-[6-methoxyacetyl hexyl]-4R-trimethylsiloxy cyclopent-2-en-1-one | nat-11a,16-dihydroxy-1-methoxymethyl-1,9-dioxo-16-hydroxymethyl-20-ethyl-13-trans prostene |

PRODUCT PROSTAGLANDIN OF THE 11-DEOXY PGE1 SERIES

| EXAMPLE | VINYL IODIDE | CYCLOPENTENONE | PRODUCT PROSTAGLANDIN |
|---|---|---|---|
| 345 | 1-trans-iodo-3-triphenylmethoxy-1-heptene | 2-[5-methoxyacetyl pentyl] cyclopent-2-en-1-one | dl-15a-hydroxy-1-methoxymethyl-1,9-dioxo-20-nor-2-nor-13-trans prostene |
| 346 | 1-trans-iodo-3-methyl-3-trimethylsilyloxy-1-heptene | 2-[5-methoxyacetyl pentyl] cyclopent-2-en-1-one | dl-15a-hydroxy-1-methoxymethyl-1,9-dioxo-15-methyl-20-nor-2-nor-13-trans prostene |
| 347 | 1-trans-iodo-4,4-dimethyl-3-trimethylsilyloxy-1-heptene | 2-[5-methoxyacetyl pentyl] cyclopent-2-en-1-one | dl-15a-hydroxy-1-methoxymethyl-1,9-dioxo-16,16-dimethyl-20-nor-2-nor-13-trans prostene |
| 348 | 1-trans-iodo-5,5-dimethyl-3-triphenylmethoxy-1-octene | 2-[5-methoxyacetyl pentyl] cyclopent-2-en-1-one | dl-15a-hydroxy-1-methoxymethyl-1,9-dioxo-17,17-dimethyl-2-nor-13-trans prostene |
| 349 | 1-trans-iodo-4-methyl-3-triphenylmethoxy-1-octene | 2-[5-methoxyacetyl pentyl] cyclopent-2-en-1-one | dl-15a-hydroxy-1-methoxymethyl-1,9-dioxo-16-methyl-2-nor-13-trans prostene |
| 350 | 1-trans-iodo-4,4-trimethylene-3-trimethylsilyloxy-1-heptene | 2-[5-methoxyacetyl pentyl] cyclopent-2-en-1-one | dl-15a-hydroxy-1-methoxymethyl-1,9-dioxo-16,16-trimethylene-20-nor-2-nor-13-trans prostene |

| EXAMPLE | VINYL TIN | CYCLOPENTENONE | PRODUCT PROSTAGLANDIN |
|---|---|---|---|
| 351 | 1-trans-tri-n-butylstannyl-3-vinyl-3-trimethylsilyloxy-1-heptene | 2-[5-methoxyacetyl pentyl] cyclopent-2-en-1-one | dl-15a-hydroxy-1-methoxymethyl-1,9-dioxo-15-vinyl-20-nor-2-nor-13-trans prostene |
| 352 | 1-trans-tri-n-butylstannyl-4-phenoxy-3-triethylsilyloxy-1-butene | 2-[5-methoxyacetyl pentyl] cyclopent-2-en-1-one | dl-15a-hydroxy-1-methoxymethyl-1,9-dioxo-16-phenoxy-2-nor-17-20-tetranor-13-trans prostene |
| 353 | 1-trans-tri-n-butylstannyl-4-(p-fluorophenoxy-3-triethylsilyloxy-1-butene | 2-[5-methoxyacetyl pentyl] cyclopent-2-en-1-one | dl-15a-hydroxy-1-methoxymethyl-1,9-dioxo-16-(p-fluorophenoxy)-2-nor-17-20-tetranor-13-trans prostene |
| 354 | 1-trans-tri-n-butylstannyl-4-(m-chlorophenoxy)-3-triethylsilyloxy-1-butene | 2-[5-methoxyacetyl pentyl] cyclopent-2-en-1-one | dl-15a-hydroxy-1-methoxymethyl-1,9-dioxo-16-(m-chlorophenoxy)-2-nor-17-20-tetranor-13-trans prostene |
| 355 | 1-trans-tri-n-butylstannyl-4-(m-trifluoromethylphenoxy)-3-triethylsilyloxy-1-butene | 2-[5-methoxyacetyl pentyl] cyclopent-2-en-1-one | dl-15a-hydroxy-1-methoxymethyl-1,9-dioxo-16-(m-trifluoromethylphenoxy)-2-nor-17-20-tetranor-13-trans prostene |

PRODUCT PROSTAGLANDIN OF THE 11-DEOXY PGE1 SERIES

| EXAMPLE | VINYL IODIDE | CYCLOPENTENONE | PRODUCT PROSTAGLANDIN |
|---|---|---|---|
| 356 | 1-trans-iodo-5-phenyl-3-triethylsilyloxy-1-pentene | 2-[5-methoxyacetyl pentyl] cyclopent-2-en-1-one | dl-15a-hydroxy-1-methoxymethyl-1,9-dioxo-17-phenyl-2-nor-18-20-trinor-13-trans prostene |
| 357 | 1-trans-iodo-4,4-dimethyl-5-phenyl- | 2-[5-methoxyacetyl pentyl] | dl-15a-hydroxy-1-methoxymethyl-1,9-dioxo- |

TABLE I-continued

| | | | |
|---|---|---|---|
| 358 | 3-triethylsilyloxy-1-butene | pentyl] cyclopent-2-en-1-one | 16,16-dimethyl-17-phenyl-2-nor-18-20-trinor-13-trans prostene |
| | 1-trans-iodo-4-cyclopentyl 3-triphenylmethoxy-1-butene | 2-[5-methoxyacetyl pentyl] cyclopent-2-en-1-one | dl-15a-hydroxy-1-methoxymethyl-1,9-dioxo-16-cyclopentyl-2-nor-17-20-tetranor-13-trans prostene |
| 359 | 1-trans-iodo-4-cyclohexyl 3-triphenylmethoxy-1-butene | 2-[5-methoxyacetyl pentyl] cyclopent-2-en-1-one | dl-15a-hydroxy-1-methoxymethyl-1,9-dioxo-16-cyclohexyl-2-nor-17-20-tetranor-13-trans prostene |
| 360 | 1-trans-iodo-4-triphenylmethoxy-1-heptene | 2-[5-methoxyacetyl pentyl] cyclopent-2-en-1-one | dl-16-hydroxy-1-methoxymethyl-1,9-dioxo-20-nor-2-nor-13-trans prostene |
| EXAMPLE | VINYL TIN | CYCLOPENTENONE | PRODUCT PROSTAGLANDIN OF THE 11-DEOXY PGE1 SERIES |
| 361 | 1-trans-tri-n-butylstannyl-4-methyl-4-trimethylsilyloxy-1-heptene | 2-[5-methoxyacetyl pentyl] cyclopent-2-en-1-one | dl-16-hydroxy-1-methoxymethyl-1,9-dioxo-16-methyl-20-nor-2-nor-13-trans prostene |
| 362 | 1-trans-tri-n-butylstannyl-4-ethyl-4-trimethylsilyloxy-1-octene | 2-[5-methoxyacetyl pentyl] cyclopent-2-en-1-one | dl-16-hydroxy-1-methoxymethyl-1,9-dioxo-16-ethyl-2-nor-13-trans prostene |
| 363 | 1-trans-tri-n-butylstannyl-5-methyl-4-trimethylsilyloxy-1-heptene | 2-[5-methoxyacetyl pentyl] cyclopent-2-en-1-one | dl-16-hydroxy-1-methoxymethyl-1,9-dioxo-17-methyl-20-nor-2-nor-13-trans prostene |
| EXAMPLE | VINYL IODIDE | CYCLOPENTENONE | PRODUCT PROSTAGLANDIN OF THE 11-DEOXY PGE1 SERIES |
| 364 | 1-trans-iodo-5,5-dimethyl-4-trimethylsilyloxy-1-octene | 2-[5-methoxyacetyl pentyl] cyclopent-2-en-1-one | dl-16-hydroxy-1-methoxymethyl-1,9-dioxo-17,17-dimethyl-2-nor-13-trans prostene |
| EXAMPLE | VINYL TIN | CYCLOPENTENONE | PRODUCT PROSTAGLANDIN OF THE 11-DEOXY PGE1 SERIES |
| 365 | 1-trans-tri-n-butylstannyl-4-vinyl-4-trimethylsilyloxy-1-heptene | 2-[5-methoxyacetyl pentyl] cyclopent-2-en-1-one | dl-16-hydroxy-1-methoxymethyl-1,9-dioxo-16-vinyl-20-nor-2-nor-13-trans prostene |
| 366 | 1-trans-tri-n-butylstannyl-4-cyclopropyl-4-trimethylsilyloxy-1-octene | 2-[5-methoxyacetyl pentyl] cyclopent-2-en-1-one | dl-16-hydroxy-1-methoxymethyl-1,9-dioxo-16-cyclopropyl-2-nor-13-trans prostene |
| 367 | 1-trans-tri-n-butylstannyl-4-trimethylsilylethynyl-4-trimethylsilyloxy-1-heptene | 2-[5-methoxyacetyl pentyl] cyclopent-2-en-1-one | dl-16-hydroxy-1-methoxymethyl-1,9-dioxo-16-ethynyl-20-nor-2-nor-13-trans prostene |
| 368 | 1-trans-tri-n-butylstannyl-5-methylene-4-triethylsilyloxy-1-heptene | 2-[5-methoxyacetyl pentyl] cyclopent-2-en-1-one | dl-16-hydroxy-1-methoxymethyl-1,9-dioxo-17-methylene-20-nor-2-nor-13-trans prostene |
| 369 | 1-trans-tri-n-butylstannyl-4-methyl-5-methylene-4-trimethylsilyloxy-1-heptene | 2-[5-methoxyacetyl pentyl] cyclopent-2-en-1-one | dl-16-hydroxy-1-methoxymethyl-1,9-dioxo-16-methyl-17-methylene-20-nor-2-nor-13-trans prostene |
| 370 | 1-trans-tri-n-butylstannyl-4-dimethoxymethyl-4-trimethylsilyloxy-1-heptene | 2-[5-methoxyacetyl pentyl] cyclopent-2-en-1-one | dl-16-hydroxy-1-methoxymethyl-1,9-dioxo-16-formyl-20-nor-2-nor-13-trans prostene |
| 371 | 1-trans-tri-n-butylstannyl-4-fluoromethyl-4-trimethylsilyloxy-1-heptene | 2-[5-methoxyacetyl pentyl] cyclopent-2-en-1-one | dl-16-hydroxy-1-methoxymethyl-1,9-dioxo-16-fluoromethyl-20-nor-2-nor-13-trans prostene |
| 372 | 1-trans-tri-n-butylstannyl-4-difluoromethyl-4-trimethylsilyloxy-1-heptene | 2-[5-methoxyacetyl pentyl] cyclopent-2-en-1-one | dl-16-hydroxy-1-methoxymethyl-1,9-dioxo-16-difluoromethyl-20-nor-2-nor-13-trans prostene |

TABLE I-continued

| | | | |
|---|---|---|---|
| 373 | 1-trans-tri-n-butylstannyl-4-trifluoromethyl-4-trimethylsilyloxy-1-heptene | 2-[5-methoxyacetyl pentyl] cyclopent-2-en-1-one | dl-16-hydroxy-1-methoxymethyl-1,9-dioxo-16-trifluoromethyl-20-nor-2-nor-13-trans prostene |
| 374 | 1-trans-tri-n-butylstannyl-4-chloromethyl-4-trimethylsilyloxy-1-heptene | 2-[5-methoxyacetyl pentyl] cyclopent-2-en-1-one | dl-16-hydroxy-1-methoxymethyl-1,9-dioxo-16-chloromethyl-20-nor-2-nor-13-trans prostene |
| 375 | 1-trans-tri-n-butylstannyl-4-trimethylsilyloxymethyl-4-trimethylsilyloxy-1-heptene | 2-[5-methoxyacetyl pentyl] cyclopent-2-en-1-one | dl-16-hydroxy-1-methoxymethyl-1,9-dioxo-16-hydroxymethyl-20-nor-2-nor-13-trans prostene |
| EXAMPLE | VINYL IODIDE | CYCLOPENTENONE | PRODUCT PROSTAGLANDIN OF THE 11-DEOXY PGE1 SERIES |
| 376 | 1-trans-iodo-4-methyl-7-chloro-4-trimethylsilyloxy-1-heptene | 2-[5-methoxyacetyl pentyl] cyclopent-2-en-1-one | dl-15a-hydroxy-1-methoxymethyl-1,9-dioxo-16-methyl-19-chloro-2-nor-20-nor-13-trans prostene |
| 377 | 1-trans-iodo-3-triphenylmethoxy-1-octene | 2-[5-methoxyacetyl pentyl] cyclopent-2-en-1-one | dl-15a-hydroxy-1-methoxymethyl-1,9-dioxo-2-nor-13-trans prostene |
| 378 | 1-trans-iodo-3-methyl-3-trimethylsilyloxy-1-octene | 2-[5-methoxyacetyl pentyl] cyclopent-2-en-1-one | dl-15a-hydroxy-1-methoxymethyl-1,9-dioxo-15-methyl-2-nor-13-trans prostene |
| 379 | 1-trans-iodo-4,4-dimethyl-3-trimethylsilyloxy-1-octene | 2-[5-methoxyacetyl pentyl] cyclopent-2-en-1-one | dl-15a-hydroxy-1-methoxymethyl-1,9-dioxo-16,16-dimethyl-2-nor-13-trans prostene |
| 380 | 1-trans-iodo-4,4-trimethylene-3-trimethylsilyloxy-1-octene | 2-[5-methoxyacetyl pentyl] cyclopent-2-en-1-one | dl-15a-hydroxy-1-methoxymethyl-1,9-dioxo-16,16-trimethylene-2-nor-13-trans prostene |
| EXAMPLE | VINYL TIN | CYCLOPENTENONE | PRODUCT PROSTAGLANDIN OF THE 11-DEOXY PGE1 SERIES |
| 381 | 1-trans-tri-n-butylstannyl-3-vinyl-3-trimethylsilyloxy-1-octene | 2-[5-methoxyacetyl pentyl] cyclopent-2-en-1-one | dl-15a-hydroxy-1-methoxymethyl-1,9-dioxo-15-vinyl-20-nor-13-trans prostene |
| EXAMPLE | VINYL IODIDE | CYCLOPENTENONE | PRODUCT PROSTAGLANDIN OF THE 11-DEOXY PGE1 SERIES |
| 382 | 1-trans-iodo-4-triphenylmethoxy-1-octene | 2-[5-methoxyacetyl pentyl] cyclopent-2-en-1-one | dl-16-hydroxy-1-methoxymethyl-1,9-dioxo-2-nor-13-trans prostene |
| EXAMPLE | VINYL TIN | CYCLOPENTENONE | PRODUCT PROSTAGLANDIN OF THE 11-DEOXY PGE1 SERIES |
| 383 | 1-trans-tri-n-butylstannyl-4-methyl-4-trimethylsilyloxy-1-octene | 2-[5-methoxyacetyl pentyl] cyclopent-2-en-1-one | dl-16-hydroxy-1-methoxymethyl-1,9-dioxo-16-methyl-2-nor-13-trans prostene |
| 384 | 1-trans-tri-n-butylstannyl-5-methyl-4-trimethylsilyloxy-1-octene | 2-[5-methoxyacetyl pentyl] cyclopent-2-en-1-one | dl-16-hydroxy-1-methoxymethyl-1,9-dioxo-17-methyl-2-nor-13-trans prostene |
| 385 | 1-trans-tri-n-butylstannyl-4-vinyl-4-trimethylsilyloxy-1-octene | 2-[5-methoxyacetyl pentyl] cyclopent-2-en-1-one | dl-16-hydroxy-1-methoxymethyl-1,9-dioxo-16-vinyl-2-nor-13-trans prostene |
| 386 | 1-trans-tri-n-butylstannyl-4-trimethylsilylethynyl-4-trimethylsilyloxy-1-octene | 2-[5-methoxyacetyl pentyl] cyclopent-2-en-1-one | dl-16-hydroxy-1-methoxymethyl-1,9-dioxo-16-ethynyl-2-nor-13-trans prostene |
| 387 | 1-trans-tri-n-butylstannyl-5-methylene-4-triethylsilyloxy-1-octene | 2-[5-methoxyacetyl pentyl] cyclopent-2-en-1-one | dl-16-hydroxy-1-methoxymethyl-1,9-dioxo-17-methylene-2-nor-13-trans prostene |

TABLE I-continued

| | VINYL IODIDE / VINYL TIN | CYCLOPENTENONE | PRODUCT |
|---|---|---|---|
| 388 | 1-trans-tri-n-butylstannyl-4-methyl-5-methylene-4-trimethylsilyloxy-1-octene | 2-[5-methoxyacetyl pentyl] cyclopent-2-en-1-one | dl-16-hydroxy-1-methoxymethyl-1,9-dioxo-16-methyl-17-methylene-2-nor-13-trans prostene |
| 389 | 1-trans-tri-n-butylstannyl-4-dimethoxymethyl-4-trimethylsilyloxy-1-octene | 2-[5-methoxyacetyl pentyl] cyclopent-2-en-1-one | dl-16-hydroxy-1-methoxymethyl-1,9-dioxo-16-formyl-2-nor-13-trans prostene |
| 390 | 1-trans-tri-n-butylstannyl-4-fluoromethyl-4-trimethylsilyloxy-1-octene | 2-[5-methoxyacetyl pentyl] cyclopent-2-en-1-one | dl-16-hydroxy-1-methoxymethyl-1,9-dioxo-16-fluoromethyl-2-nor-13-trans prostene |
| 391 | 1-trans-tri-n-butylstannyl-4-difluoromethyl-4-trimethylsilyloxy-1-octene | 2-[5-methoxyacetyl pentyl] cyclopent-2-en-1-one | dl-16-hydroxy-1-methoxymethyl-1,9-dioxo-16-difluoromethyl-2-nor-13-trans prostene |
| 392 | 1-trans-tri-n-butylstannyl-4-trifluoromethyl-4-trimethylsilyloxy-1-octene | 2-[5-methoxyacetyl pentyl] cyclopent-2-en-1-one | dl-16-hydroxy-1-methoxymethyl-1,9-dioxo-16-trifluoromethyl-2-nor-13-trans prostene |
| 393 | 1-trans-tri-n-butylstannyl-4-chloromethyl-4-trimethylsilyloxy-1-octene | 2-[5-methoxyacetyl pentyl] cyclopent-2-en-1-one | dl-16-hydroxy-1-methoxymethyl-1,9-dioxo-16-chloromethyl-2-nor-13-trans prostene |
| 394 | 1-trans-tri-n-butylstannyl-4-trimethylsilyloxymethyl-4-trimethylsilyloxy-1-octene | 2-[5-methoxyacetyl pentyl] cyclopent-2-en-1-one | dl-16-hydroxy-1-methoxymethyl-1,9-dioxo-16-hydroxymethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 395 | 1-trans-iodo-3-triphenylmethoxy-1-nonene | 2-[5-methoxyacetyl pentyl] cyclopent-2-en-1-one | dl-15a-hydroxy-1-methoxymethyl-1,9-dioxo-20-methyl-2-nor-13-trans prostene |
| 396 | 1-trans-iodo-3-methyl-3-trimethylsilyloxy-1-nonene | 2-[5-methoxyacetyl pentyl] cyclopent-2-en-1-one | dl-15a-hydroxy-1-methoxymethyl-1,9-dioxo-15-methyl-20-methyl-2-nor-13-trans prostene |
| 397 | 1-trans-iodo-4,4-dimethyl-3-trimethylsilyloxy-1-nonene | 2-[5-methoxyacetyl pentyl] cyclopent-2-en-1-one | dl-15a-hydroxy-1-methoxymethyl-1,9-dioxo-16,16-dimethyl-20-methyl-2-nor-13-trans prostene |
| 398 | 1-trans-iodo-4,4-trimethylene-3-trimethylsilyloxy-1-nonene | 2-[5-methoxyacetyl pentyl] cyclopent-2-en-1-one | dl-15a-hydroxy-1-methoxymethyl-1,9-dioxo-16,16-trimethylene-20-methyl-2-nor-13-trans prostene |
| EXAMPLE | VINYL TIN | CYCLOPENTENONE | PRODUCT PROSTAGLANDIN OF THE 11-DEOXY PGE1 SERIES |
| 399 | 1-trans-tri-n-butylstannyl-3-vinyl-3-trimethylsilyloxy-1-nonene | 2-[5-methoxyacetyl pentyl] cyclopent-2-en-1-one | dl-15a-hydroxy-1-methoxymethyl-1,9-dioxo-15-vinyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 400 | 1-trans-iodo-4-triphenylmethoxy-1-nonene | 2-[5-methoxyacetyl pentyl] cyclopent-2-en-1-one | dl-16-hydroxy-1-methoxymethyl-1,9-dioxo-20-methyl-2-nor-13-trans prostene |
| EXAMPLE | VINYL TIN | CYCLOPENTENONE | PRODUCT PROSTAGLANDIN OF THE 11-DEOXY PGE1 SERIES |
| 401 | 1-trans-tri-n-butylstannyl-4-methyl-4-trimethylsilyloxy-1-nonene | 2-[5-methoxyacetyl pentyl] cyclopent-2-en-1-one | dl-16-hydroxy-1-methoxymethyl-1,9-dioxo-16-methyl-20-methyl-2-nor-13-trans prostene |
| 402 | 1-trans-tri-n-butylstannyl-5-methyl-4-trimethylsilyloxy-1-nonene | 2-[5-methoxyacetyl pentyl] cyclopent-2-en-1-one | dl-16-hydroxy-1-methoxymethyl-1,9-dioxo-17-methyl-20-methyl-2-nor-13-trans prostene |

TABLE I-continued

| | | | |
|---|---|---|---|
| 403 | 1-trans-tri-n-butylstannyl-4-vinyl-4-trimethylsilyloxy-1-nonene | 2-[5-methoxyacetyl pentyl] cyclopent-2-en-1-one | dl-16-hydroxy-1-methoxymethyl-1,9-dioxo-16-vinyl-20-methyl-2-nor-13-trans prostene |
| 404 | 1-trans-tri-n-butylstannyl-4-trimethylsilylethynyl-4-trimethylsilyloxy-1-nonene | 2-[5-methoxyacetyl pentyl] cyclopent-2-en-1-one | dl-16-hydroxy-1-methoxymethyl-1,9-dioxo-16-ethynyl-20-methyl-2-nor-13-trans prostene |
| 405 | 1-trans-tri-n-butylstannyl-4-trimethylsilyloxy-5-methylene-1-nonene | 2-[5-methoxyacetyl pentyl] cyclopent-2-en-1-one | dl-16-hydroxy-1-methoxymethyl-1,9-dioxo-17-methylene-20-methyl-2-nor-13-trans prostene |
| 406 | 1-trans-tri-n-butylstannyl-4-methyl-5-methylene-4-trimethylsilyloxy-1-nonene | 2-[5-methoxyacetyl pentyl] cyclopent-2-en-1-one | dl-16-hydroxy-1-methoxymethyl-1,9-dioxo-16-methyl-17-methylene-20-methyl-2-nor-13-trans prostene |
| 407 | 1-trans-tri-n-butylstannyl-4-dimethoxymethyl-4-trimethylsilyloxy-1-nonene | 2-[5-methoxyacetyl pentyl] cyclopent-2-en-1-one | dl-16-hydroxy-1-methoxymethyl-1,9-dioxo-16-formyl-20-methyl-2-nor-13-trans prostene |
| 408 | 1-trans-tri-n-butylstannyl-4-fluoromethyl-4-trimethylsilyloxy-1-nonene | 2-[5-methoxyacetyl pentyl] cyclopent-2-en-1-one | dl-16-hydroxy-1-methoxymethyl-1,9-dioxo-16-fluoromethyl-20-methyl-2-nor-13-trans prostene |
| 409 | 1-trans-tri-n-butylstannyl-4-difluoromethyl-4-trimethylsilyloxy-1-nonene | 2-[5-methoxyacetyl pentyl] cyclopent-2-en-1-one | dl-16-hydroxy-1-methoxymethyl-1,9-dioxo-16-difluoromethyl-20-methyl-2-nor-13-trans prostene |
| 410 | 1-trans-tri-n-butylstannyl-4-trifluoromethyl-4-trimethylsilyloxy-1-nonene | 2-[5-methoxyacetyl pentyl] cyclopent-2-en-1-one | dl-16-hydroxy-1-methoxymethyl-1,9-dioxo-16-trifluoromethyl-20-methyl-2-nor-13-trans prostene |
| 411 | 1-trans-tri-n-butylstannyl-4-chloromethyl-4-trimethylsilyloxy-1-nonene | 2-[5-methoxyacetyl pentyl] cyclopent-2-en-1-one | dl-16-hydroxy-1-methoxymethyl-1,9-dioxo-16-chloromethyl-20-methyl-2-nor-13-trans prostene |
| 412 | 1-trans-tri-n-butylstannyl-4-trimethylsilyloxymethyl-4-trimethylsilyloxy-1-nonene | 2-[5-methoxyacetyl pentyl] cyclopent-2-en-1-one | dl-16-hydroxy-1-methoxymethyl-1,9-dioxo-16-hydroxymethyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 413 | 1-trans-iodo-3-triphenylmethoxy-1-decene | 2-[5-methoxyacetyl pentyl] cyclopent-2-en-1-one | dl-15a-hydroxy-1-methoxymethyl-1,9-dioxo-20-ethyl-2-nor-13-trans prostene |
| 414 | 1-trans-iodo-3-methyl-3-trimethylsilyloxy-1-decene | 2-[5-methoxyacetyl pentyl] cyclopent-2-en-1-one | dl-15a-hydroxy-1-methoxymethyl-1,9-dioxo-15-methyl-20-ethyl-2-nor-13-trans prostene |
| 415 | 1-trans-iodo-4,4-dimethyl-3-trimethylsilyloxy-1-decene | 2-[5-methoxyacetyl pentyl] cyclopent-2-en-1-one | dl-15a-hydroxy-1-methoxymethyl-1,9-dioxo-16,16-dimethyl-20-ethyl-2-nor-13-trans prostene |
| 416 | 1-trans-iodo-4,4-trimethylene-3-trimethylsilyloxy-1-decene | 2-[5-methoxyacetyl pentyl] cyclopent-2-en-1-one | dl-15a-hydroxy-1-methoxymethyl-1,9-dioxo-16,16-trimethylene-20-ethyl-2-nor-13-trans prostene |
| EXAMPLE | VINYL TIN | CYCLOPENTENONE | PRODUCT PROSTAGLANDIN OF THE 11-DEOXY PGE1 SERIES |
| 417 | 1-trans-tri-n-butylstannyl-3-vinyl-3-trimethylsilyloxy-1-decene | 2-[5-methoxyacetyl pentyl] cyclopent-2-en-1-one | dl-15a-hydroxy-1-methoxymethyl-1,9-dioxo-15-vinyl-20-ethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 418 | 1-trans-iodo-4-triphenylmethoxy-1-decene | 2-[5-methoxyacetyl pentyl] cyclopent-2-en-1-one | dl-16-hydroxy-1-methoxymethyl-1,9-dioxo-20-ethyl-20-nor-13-trans prostene |

TABLE I-continued

| EXAMPLE | VINYL TIN | CYCLOPENTENONE | PRODUCT PROSTAGLANDIN OF THE 11-DEOXY PGE1 SERIES |
|---|---|---|---|
| 419 | 1-trans-tri-n-butylstannyl-4-methyl-4-trimethylsilyloxy-1-decene | 2-[5-methoxyacetyl pentyl] cyclopent-2-en-1-one | dl-16-hydroxy-1-methoxymethyl-1,9-dioxo-16-methyl-20-ethyl-2-nor-13-trans prostene |
| 420 | 1-trans-tri-n-butylstannyl-5-methyl-4-trimethylsilyloxy-1-decene | 2-[5-methoxyacetyl pentyl] cyclopent-2-en-1-one | dl-16-hydroxy-1-methoxymethyl-1,9-dioxo-17-methyl-20-ethyl-2-nor-13-trans prostene |
| 421 | 1-trans-tri-n-butylstannyl-4-vinyl-4-trimethylsilyloxy-1-decene | 2-[5-methoxyacetyl pentyl] cyclopent-2-en-1-one | dl-16-hydroxy-1-methoxymethyl-1,9-dioxo-16-vinyl-20-ethyl-2-nor-13-trans prostene |
| 422 | 1-trans-tri-n-butylstannyl-4-trimethylsilylethynyl-4-trimethylsilyloxy-1-decene | 2-[5-methoxyacetyl pentyl] cyclopent-2-en-1-one | dl-16-hydroxy-1-methoxymethyl-1,9-dioxo-16-ethynyl-20-ethyl-2-nor-13-trans prostene |
| 423 | 1-trans-tri-n-butylstannyl-5-methylene-4-triethylsilyloxy-1-decene | 2-[5-methoxyacetyl pentyl] cyclopent-2-en-1-one | dl-16-hydroxy-1-methoxymethyl-1,9-dioxo-17-methylene-20-ethyl-2-nor-13-trans prostene |
| 424 | 1-trans-tri-n-butstannyl-4-methyl-5-methylene-4-trimethylsilyloxy-1-decene | 2-[5-methoxyacetyl pentyl] cyclopent-2-en-1-one | dl-16-hydroxy-1-methoxymethyl-1,9-dioxo-16-methyl-17-methylene-20-ethyl-2-nor-13-trans prostene |
| 425 | 1-trans-tri-n-butstannyl-4-dimethoxymethyl-4-trimethylsilyloxy-1-decene | 2-[5-methoxyacetyl pentyl] cyclopent-2-en-1-one | dl-16-hydroxy-1-methoxymethyl-1,9-dioxo-16-formyl-20-ethyl-2-nor-13-trans prostene |
| 426 | 1-trans-tri-n-butylstannyl-4-fluoromethyl-4-trimethylsilyloxy-1-decene | 2-[5-methoxyacetyl pentyl] cyclopent-2-en-1-one | dl-16-hydroxy-1-methoxymethyl-1,9-dioxo-16-fluoromethyl-20-ethyl-2-nor-13-trans prostene |
| 427 | 1-trans-tri-n-butylstannyl-4-difluoromethyl-4-trimethylsilyloxy-1-decene | 2-[5-methoxyacetyl pentyl] cyclopent-2-en-1-one | dl-16-hydroxy-1-methoxymethyl-1,9-dioxo-16-difluoromethyl-20-ethyl-2-nor-13-trans prostene |
| 428 | 1-trans-tri-n-butylstannyl-4-trifluoromethyl-4-trimethylsilyloxy-1-decene | 2-[5-methoxyacetyl pentyl] cyclopent-2-en-1-one | dl-16-hydroxy-1-methoxymethyl-1,9-dioxo-16-trifluoromethyl-20-ethyl-2-nor-13-trans prostene |
| 429 | 1-trans-tri-n-butylstannyl-4-chloromethyl-4-trimethylsilyloxy-1-decene | 2-[5-methoxyacetyl pentyl] cyclopent-2-en-1-one | dl-16-hydroxy-1-methoxymethyl-1,9-dioxo-16-chloromethyl-20-ethyl-2-nor-13-trans prostene |
| 430 | 1-trans-tri-n-butylstannyl-4-trimethylsilyloxymethyl-4-trimethylsilyloxy-1-decene | 2-[5-methoxyacetyl pentyl] cyclopent-2-en-1-one | dl-16-hydroxy-1-methoxymethyl-1,9-dioxo-16-hydroxymethyl-20-ethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 431 | 1-trans-iodo-3-triphenylmethoxy-1-heptene | 2-[6-methoxyacetyl hexyl] cyclopent-2-en-1-one | dl-15a-hydroxy-1-methoxymethyl-1,9-dioxo-20-ethyl-2-nor-13-trans prostene |
| 432 | 1-trans-iodo-3-methyl-3-trimethylsilyloxy-1-heptene | 2-[6-methoxyacetyl hexyl] cyclopent-2-en-1-one | dl-15a-hydroxy-1-methoxymethyl-1,9-dioxo-15-methyl-20-ethyl-2-nor-13-trans prostene |
| 433 | 1-trans-iodo-4,4-dimethyl-3-trimethylsilyloxy-1-heptene | 2-[6-methoxyacetyl hexyl] cyclopent-2-en-1-one | dl-15a-hydroxy-1-methoxymethyl-1,9-dioxo-16,16-dimethyl-20-nor-13-trans prostene |
| 434 | 1-trans-iodo-5,5-dimethyl-3-triphenylmethoxy-1-octene | 2-[6-methoxyacetyl hexyl] cyclopent-2-en-1-one | dl-15a-hydroxy-1-methoxymethyl-1,9-dioxo-17,17-dimethyl-13-trans prostene |

TABLE I-continued

| | | | |
|---|---|---|---|
| 435 | 1-trans-iodo-4-methyl 3-triphenylmethoxy-1-octene | 2-[6-methoxyacetyl hexyl] cyclopent-2-en-1-one | dl-15a-hydroxy-1-methoxymethyl-1,9-dioxo-16-methyl-13-trans prostene |
| 436 | 1-trans-iodo-4,4-trimethylene 3-trimethylsilyloxy-1-heptene | 2-[6-methoxyacetyl hexyl] cyclopent-2-en-1-one | dl-15a-hydroxy-1-methoxymethyl-1,9-dioxo-16,16-trimethylene-20-nor-13-trans prostene |
| EXAMPLE | VINYL TIN | CYCLOPENTENONE | PRODUCT PROSTAGLANDIN OF THE 11-DEOXY PGE1 SERIES |
| 437 | 1-trans-tri-n-butylstannyl-3-vinyl-3-trimethylsilyloxy-1-heptene | 2-[6-methoxyacetyl hexyl] cyclopent-2-en-1-one | dl-15a-hydroxy-1-methoxymethyl-1,9-dioxo-15-vinyl-20-nor-13-trans prostene |
| 438 | 1-trans-tri-n-butylstannyl-4-phenoxy 3-triethylsilyloxy-1-butene | 2-[6-methoxyacetyl hexyl] cyclopent-2-en-1-one | dl-15a-hydroxy-1-methoxymethyl-1,9-dioxo-16-phenoxy-17-20-tetranor-13-trans prostene |
| 439 | 1-trans-tri-n-butylstannyl-4-(p-fluorophenoxy) 3-triethylsilyloxy-1-butene | 2-[6-methoxyacetyl hexyl] cyclopent-2-en-1-one | dl-15a-hydroxy-1-methoxymethyl-1,9-dioxo-16-(p-fluorophenoxy)-17-20-tetranor-13-trans prostene |
| 440 | 1-trans-tri-n-butylstannyl-4-(m-chlorophenoxy) 3-triethylsilyloxy-1-butene | 2-[6-methoxyacetyl hexyl] cyclopent-2-en-1-one | dl-15a-hydroxy-1-methoxymethyl-1,9-dioxo-16-(m-chlorophenoxy)-17-20-tetranor-13-trans prostene |
| 441 | 1-trans-tri-n-butylstannyl-4-(m-trifluoromethylphenoxy) 3-triethylsilyloxy-1-butene | 2-[6-methoxyacetyl hexyl] cyclopent-2-en-1-one | dl-15a-hydroxy-1-methoxymethyl-1,9-dioxo-16-(m-trifluoromethylphenoxy)-17-20-tetranor-13-trans prostene |
| EXAMPLE | VINYL IODIDE | CYCLOPENTENONE | PRODUCT PROSTAGLANDIN OF THE 11-DEOXY PGE1 SERIES |
| 442 | 1-trans-iodo-5-phenyl 3-triethylsilyloxy-1-pentene | 2-[6-methoxyacetyl hexyl] cyclopent-2-en-1-one | dl-15a-hydroxy-1-methoxymethyl-1,9-dioxo-17-phenyl-18-20-trinor-13-trans prostene |
| 443 | 1-trans-iodo-4,4-dimethyl-5-phenyl 3-triethylsilyloxy-1-pentene | 2-[6-methoxyacetyl hexyl] cyclopent-2-en-1-one | dl-15a-hydroxy-1-methoxymethyl-1,9-dioxo-16,16-dimethyl-17-phenyl-18-20-trinor-13-trans prostene |
| 444 | 1-trans-iodo-4-cyclopental 3-triphenylmethoxy-1-butene | 2-[6-methoxyacetyl hexyl] cyclopent-2-en-1-one | dl-15a-hydroxy-1-methoxymethyl-1,9-dioxo-16-cyclopentyl-17-20-tetranor-13-trans prostene |
| 445 | 1-trans-iodo-4-cyclohexyl 3-triphenylmethoxy-1-butene | 2-[6-methoxyacetyl hexyl] cyclopent-2-en-1-one | dl-15a-hydroxy-1-methoxymethyl-1,9-dioxo-16-cyclohexyl-17-20-tetranor-13-trans prostene |
| 446 | 1-trans-iodo-4-triphenylmethoxy-1-heptene | 2-[6-methoxyacetyl hexyl] cyclopent-2-en-1-one | dl-16a-hydroxy-1-methoxymethyl-1,9-dioxo-20-nor-13-trans prostene |
| EXAMPLE | VINYL TIN | CYCLOPENTENONE | PRODUCT PROSTAGLANDIN OF THE 11-DEOXY PGE1 SERIES |
| 447 | 1-trans-tri-n-butylstannyl-4-methyl-4-trimethylsilyloxy-1-heptene | 2-[6-methoxyacetyl hexyl] cyclopent-2-en-1-one | dl-16-hydroxy-1-methoxymethyl-1,9-dioxo-16-methyl-20-nor-13-trans prostene |
| 448 | 1-trans-tri-n-butylstannyl-4-ethyl-4-trimethylsilyloxy-1-octene | 2-[6-methoxyacetyl hexyl] cyclopent-2-en-1-one | dl-16-hydroxy-1-methoxymethyl-1,9-dioxo-16-ethyl-13-trans prostene |
| 449 | 1-trans-tri-n-butylstannyl-5-methyl-4-trimethylsilyloxy-1-heptene | 2-[6-methoxyacetyl hexyl] cyclopent-2-en-1-one | dl-16-hydroxy-1-methoxymethyl-1,9-dioxo-17-methyl-20-nor-13-trans prostene |
| EXAMPLE | VINYL IODIDE | CYCLOPENTENONE | PRODUCT PROSTAGLANDIN OF THE 11-DEOXY PGE1 SERIES |

TABLE I-continued

| | | | |
|---|---|---|---|
| 450 | 1-trans-iodo-5,5-dimethyl 4-trimethylsilyloxy-1-octene | 2-[6-methoxyacetyl hexyl] cyclopent-2-en-1-one | dl-16-hydroxy-1-methoxymethyl-1,9-dioxo-17,17-dimethyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 451 | 1-trans-tri-n-butylstannyl-4-vinyl-4-trimethylsilyloxy-1-heptene | 2-[6-methoxyacetyl hexyl] cyclopent-2-en-1-one | dl-16-hydroxy-1-methoxymethyl-1,9-dioxo-16-vinyl-20-nor-13-trans prostene |
| 452 | 1-trans-tri-n-butylstannyl-4-cyclopropyl-4-trimethylsilyloxy-1-heptene | 2-[6-methoxyacetyl hexyl] cyclopent-2-en-1-one | dl-16-hydroxy-1-methoxymethyl-1,9-dioxo-16-cyclopropyl-13-trans prostene |
| 453 | 1-trans-tri-n-butylstannyl-4-trimethylsilylethynyl-4-trimethylsilyloxy-1-heptene | 2-[6-methoxyacetyl hexyl] cyclopent-2-en-1-one | dl-16-hydroxy-1-methoxymethyl-1,9-dioxo-16-ethynyl-20-nor-13-trans prostene |
| 454 | 1-trans-tri-n-butylstannyl-5-methylene 4-triethylsilyloxy-1-heptene | 2-[6-methoxyacetyl hexyl] cyclopent-2-en-1-one | dl-16-hydroxy-1-methoxymethyl-1,9-dioxo-17-methylene-20-nor-13-trans prostene |
| 455 | 1-trans-tri-n-butylstannyl-4-methyl-5-methylene 4-trimethylsilyloxy-1-heptene | 2-[6-methoxyacetyl hexyl] cyclopent-2-en-1-one | dl-16-hydroxy-1-methoxymethyl-1,9-dioxo-16-methyl-17-methylene-20-nor-13-trans prostene |
| 456 | 1-trans-tri-n-butylstannyl-4-dimethoxymethyl-4-trimethylsilyloxy-1-heptene | 2-[6-methoxyacetyl hexyl] cyclopent-2-en-1-one | dl-16-hydroxy-1-methoxymethyl-1,9-dioxo-16-formyl-20-nor-13-trans prostene |
| 457 | 1-trans-tri-n-butylstannyl-4-fluoromethyl-4-trimethylsilyloxy-1-heptene | 2-[6-methoxyacetyl hexyl] cyclopent-2-en-1-one | dl-16-hydroxy-1-methoxymethyl-1,9-dioxo-16-fluoromethyl-20-nor-13-trans prostene |
| 458 | 1-trans-tri-n-butylstannyl-4-difluoromethyl-4-trimethylsilyloxy-1-heptene | 2-[6-methoxyacetyl hexyl] cyclopent-2-en-1-one | dl-16-hydroxy-1-methoxymethyl-1,9-dioxo-16-difluoromethyl-20-nor-13-trans prostene |
| 459 | 1-trans-tri-n-butylstannyl-4-trifluoromethyl-4-trimethylsilyloxy-1-heptene | 2-[6-methoxyacetyl hexyl] cyclopent-2-en-1-one | dl-16-hydroxy-1-methoxymethyl-1,9-dioxo-16-trifluoromethyl-20-nor-13-trans prostene |
| 460 | 1-trans-tri-n-butylstannyl-4-chloromethyl-4-trimethylsilyloxy-1-heptene | 2-[6-methoxyacetyl hexyl] cyclopent-2-en-1-one | dl-16-hydroxy-1-methoxymethyl-1,9-dioxo-16-chloromethyl-20-nor-13-trans prostene |
| 461 | 1-trans-tri-n-butylstannyl-4-trimethylsilyloxymethyl-4-trimethylsilyloxy-1-heptene | 2-[6-methoxyacetyl hexyl] cyclopent-2-en-1-one | dl-16-hydroxy-1-methoxymethyl-1,9-dioxo-16-hydroxymethyl-20-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 462 | 1-trans-iodo-4-methyl-7-chloro 4-trimethylsilyloxy-1-heptene | 2-[6-methoxyacetyl hexyl] cyclopent-2-en-1-one | dl-16-hydroxy-1-methoxymethyl-1,9-dioxo-16-methyl-19-chloro-20-nor-13-trans prostene |
| 463 | 1-trans-iodo-3-triphenylmethoxy-1-octene | 2-[6-methoxyacetyl hexyl] cyclopent-2-en-1-one | dl-15a-hydroxy-1-methoxymethyl-1,9-dioxo-13-trans prostene |
| 464 | 1-trans-iodo-3-methyl-3-trimethylsilyloxy-1-octene | 2-[6-methoxyacetyl hexyl] cyclopent-2-en-1-one | dl-15a-hydroxy-1-methoxymethyl-1,9-dioxo-15-methyl-13-trans prostene |
| 465 | 1-trans-iodo-4,4-dimethyl 3-trimethylsilyloxy-1-octene | 2-[6-methoxyacetyl hexyl] cyclopent-2-en-1-one | dl-15a-hydroxy-1-methoxymethyl-1,9-dioxo-16,16-dimethyl-13-trans prostene |
| 466 | 1-trans-iodo-4,4-trimethylene | 2-[6-methoxyacetyl hexyl] cyclopent-2-en-1-one | dl-15a-hydroxy-1-methoxymethyl-1,9-dioxo- |

TABLE I-continued

| EXAMPLE | VINYL TIN / VINYL IODIDE | PRODUCT PROSTAGLANDIN |
|---|---|---|
|  | 3-trimethylsilyloxy-1-octene | hexyl]cyclopent-2-en-1-one | 16,16-trimethylene-13-trans prostene |
| EXAMPLE | VINYL TIN |  | PRODUCT PROSTAGLANDIN OF THE 11-DEOXY PGE1 SERIES |
| 467 | 1-trans-tri-n-butylstannyl-3-vinyl-3-trimethylsilyloxy-1-octene | 2-[6-methoxyacetyl hexyl]cyclopent-2-en-1-one | dl-15a-hydroxy-1-methoxymethyl-1,9-dioxo-15-vinyl-13-trans prostene |
| EXAMPLE | VINYL IODIDE | CYCLOPENTENONE | PRODUCT PROSTAGLANDIN OF THE 11-DEOXY PGE1 SERIES |
| 468 | 1-trans-iodo-4-triphenylmethoxy-1-octene | 2-[6-methoxyacetyl hexyl]cyclopent-2-en-1-one | dl-16-hydroxy-1-methoxymethyl-1,9-dioxo-13-trans prostene |
| EXAMPLE | VINYL TIN | CYCLOPENTENONE | PRODUCT PROSTAGLANDIN OF THE 11-DEOXY PGE1 SERIES |
| 469 | 1-trans-tri-n-butylstannyl-4-methyl-4-trimethylsilyloxy-1-octene | 2-[6-methoxyacetyl hexyl]cyclopent-2-en-1-one | dl-16-hydroxy-1-methoxymethyl-1,9-dioxo-16-methyl-13-trans prostene |
| 470 | 1-trans-tri-n-butylstannyl-5-methyl-4-trimethylsilyloxy-1-octene | 2-[6-methoxyacetyl hexyl]cyclopent-2-en-1-one | dl-16-hydroxy-1-methoxymethyl-1,9-dioxo-17-methyl-13-trans prostene |
| 471 | 1-trans-tri-n-butylstannyl-4-vinyl-4-trimethylsilyloxy-1-octene | 2-[6-methoxyacetyl hexyl]cyclopent-2-en-1-one | dl-16-hydroxy-1-methoxymethyl-1,9-dioxo-16-vinyl-13-trans prostene |
| 472 | 1-trans-tri-n-butylstannyl-4-trimethylsilylethynyl-4-trimethylsilyloxy-1-octene | 2-[6-methoxyacetyl hexyl]cyclopent-2-en-1-one | dl-16-hydroxy-1-methoxymethyl-1,9-dioxo-16-ethynyl-13-trans prostene |
| 473 | 1-trans-tri-n-butylstannyl-5-methylene-4-triethylsilyloxy-1-octene | 2-[6-methoxyacetyl hexyl]cyclopent-2-en-1-one | dl-16-hydroxy-1-methoxymethyl-1,9-dioxo-17-methylene-13-trans prostene |
| 474 | 1-trans-tri-n-butylstannyl-4-methyl-5-methylene-4-trimethylsilyloxy-1-octene | 2-[6-methoxyacetyl hexyl]cyclopent-2-en-1-one | dl-16-hydroxy-1-methoxymethyl-1,9-dioxo-16-methyl-17-methylene-13-trans prostene |
| 475 | 1-trans-tri-n-butylstannyl-4-dimethoxymethyl-4-trimethylsilyloxy-1-octene | 2-[6-methoxyacetyl hexyl]cyclopent-2-en-1-one | dl-16-hydroxy-1-methoxymethyl-1,9-dioxo-16-formyl-13-trans prostene |
| 476 | 1-trans-tri-n-butylstannyl-4-fluoromethyl-4-trimethylsilyloxy-1-octene | 2-[6-methoxyacetyl hexyl]cyclopent-2-en-1-one | dl-16-hydroxy-1-methoxymethyl-1,9-dioxo-16-fluoromethyl-13-trans prostene |
| 477 | 1-trans-tri-n-butylstannyl-4-difluoromethyl-4-trimethylsilyloxy-1-octene | 2-[6-methoxyacetyl hexyl]cyclopent-2-en-1-one | dl-16-hydroxy-1-methoxymethyl-1,9-dioxo-16-difluoromethyl-13-trans prostene |
| 478 | 1-trans-tri-n-butylstannyl-4-trifluoromethyl-4-trimethylsilyloxy-1-octene | 2-[6-methoxyacetyl hexyl]cyclopent-2-en-1-one | dl-16-hydroxy-1-methoxymethyl-1,9-dioxo-16-trifluoromethyl-13-trans prostene |
| 479 | 1-trans-tri-n-butylstannyl-4-chloromethyl-4-trimethylsilyloxy-1-octene | 2-[6-methoxyacetyl hexyl]cyclopent-2-en-1-one | dl-16-hydroxy-1-methoxymethyl-1,9-dioxo-16-chloromethyl-13-trans prostene |
| 480 | 1-trans-tri-n-butylstannyl-4-trimethylsilyloxymethyl-4-trimethylsilyloxy-1-octene | 2-[6-methoxyacetyl hexyl]cyclopent-2-en-1-one | dl-16-hydroxy-1-methoxymethyl-1,9-dioxo-16-hydroxymethyl-13-trans prostene |
| EXAMPLE | VINYL IODIDE | CYCLOPENTENONE | PRODUCT PROSTAGLANDIN OF THE 11-DEOXY PGE1 SERIES |
| 481 | 1-trans-iodo- | 2-[6-methoxyacetyl | dl-15a-hydroxy-1-methoxymethyl-1,9-dioxo- |

TABLE I-continued

| | | | |
|---|---|---|---|
| | 3-triphenylmethoxy-1-nonene | hexyl] cyclopent-2-en-1-one | 20-methyl-13-trans prostene |
| 482 | 1-trans-iodo-3-methyl-3-trimethylsilyloxy-1-nonene | 2-[6-methoxyacetyl hexyl] cyclopent-2-en-1-one | dl-15a-hydroxy-1-methoxymethyl-1,9-dioxo-15-methyl-20-methyl-13-trans prostene |
| 483 | 1-trans-iodo-4,4-dimethyl-3-trimethylsilyloxy-1-nonene | 2-[6-methoxyacetyl hexyl] cyclopent-2-en-1-one | dl-15a-hydroxy-1-methoxymethyl-1,9-dioxo-16,16-dimethyl-20-methyl-13-trans prostene |
| 484 | 1-trans-iodo-4,4-trimethylene-3-trimethylsilyloxy-1-nonene | 2-[6-methoxyacetyl hexyl] cyclopent-2-en-1-one | dl-15a-hydroxy-1-methoxymethyl-1,9-dioxo-16,16-trimethylene-20-methyl-13-trans prostene |
| EXAMPLE | VINYL TIN | CYCLOPENTENONE | PRODUCT PROSTAGLANDIN OF THE 11-DEOXY PGE1 SERIES |
| 485 | 1-trans-tri-n-butylstannyl-3-vinyl-3-trimethylsilyloxy-1-nonene | 2-[6-methoxyacetyl hexyl] cyclopent-2-en-1-one | dl-15a-hydroxy-1-methoxymethyl-1,9-dioxo-15-vinyl-20-methyl-13-trans prostene |
| EXAMPLE | VINYL IODIDE | CYCLOPENTENONE | PRODUCT PROSTAGLANDIN OF THE 11-DEOXY PGE1 SERIES |
| 486 | 1-trans-iodo-4-triphenylmethoxy-1-nonene | 2-[6-methoxyacetyl hexyl] cyclopent-2-en-1-one | dl-16-hydroxy-1-methoxymethyl-1,9-dioxo-20-methyl-13-trans prostene |
| EXAMPLE | VINYL TIN | CYCLOPENTENONE | PRODUCT PROSTAGLANDIN OF THE 11-DEOXY PGE1 SERIES |
| 487 | 1-trans-tri-n-butylstannyl-4-methyl-4-trimethylsilyloxy-1-nonene | 2-[6-methoxyacetyl hexyl] cyclopent-2-en-1-one | dl-16-hydroxy-1-methoxymethyl-1,9-dioxo-16-methyl-20-methyl-13-trans prostene |
| 488 | 1-trans-tri-n-butylstannyl-5-methyl-4-trimethylsilyloxy-1-nonene | 2-[6-methoxyacetyl hexyl] cyclopent-2-en-1-one | dl-16-hydroxy-1-methoxymethyl-1,9-dioxo-17-methyl-20-methyl-13-trans prostene |
| 489 | 1-trans-tri-n-butylstannyl-4-vinyl-4-trimethylsilyloxy-1-nonene | 2-[6-methoxyacetyl hexyl] cyclopent-2-en-1-one | dl-16-hydroxy-1-methoxymethyl-1,9-dioxo-16-vinyl-20-methyl-13-trans prostene |
| 490 | 1-trans-tri-n-butylstannyl-4-trimethylsilylethynyl-4-trimethylsilyloxy-1-nonene | 2-[6-methoxyacetyl hexyl] cyclopent-2-en-1-one | dl-16-hydroxy-1-methoxymethyl-1,9-dioxo-16-ethynyl-20-methyl-13-trans prostene |
| 491 | 1-trans-tri-n-butylstannyl-5-methylene-4-triethylsilyloxy-1-nonene | 2-[6-methoxyacetyl hexyl] cyclopent-2-en-1-one | dl-16-hydroxy-1-methoxymethyl-1,9-dioxo-17-methylene-20-methyl-13-trans prostene |
| 492 | 1-trans-tri-n-butylstannyl-4-methyl-5-methylene-4-trimethylsilyloxy-1-nonene | 2-[6-methoxyacetyl hexyl] cyclopent-2-en-1-one | dl-16-hydroxy-1-methoxymethyl-1,9-dioxo-16-methyl-17-methylene-20-methyl-13-trans prostene |
| 493 | 1-trans-tri-n-butylstannyl-4-dimethoxymethyl-4-trimethylsilyloxy-1-nonene | 2-[6-methoxyacetyl hexyl] cyclopent-2-en-1-one | dl-16-hydroxy-1-methoxymethyl-1,9-dioxo-16-formyl-20-methyl-13-trans prostene |
| 494 | 1-trans-tri-n-butylstannyl-4-fluoromethyl-4-trimethylsilyloxy-1-nonene | 2-[6-methoxyacetyl hexyl] cyclopent-2-en-1-one | dl-16-hydroxy-1-methoxymethyl-1,9-dioxo-16-fluoromethyl-20-methyl-13-trans prostene |
| 495 | 1-trans-tri-n-butylstannyl-4-difluoromethyl-4-trimethylsilyloxy-1-nonene | 2-[6-methoxyacetyl hexyl] cyclopent-2-en-1-one | dl-16-hydroxy-1-methoxymethyl-1,9-dioxo-16-difluoromethyl-20-methyl-13-trans prostene |
| 496 | 1-trans-tri-n-butylstannyl-4-trifluoromethyl-4-trimethylsilyloxy-1-nonene | 2-[6-methoxyacetyl hexyl] cyclopent-2-en-1-one | dl-16-hydroxy-1-methoxymethyl-1,9-dioxo-16-trifluoromethyl-20-methyl-13-trans prostene |

TABLE I-continued

| | | | |
|---|---|---|---|
| 497 | 1-trans-tri-n-butylstannyl-4-chloromethyl-4-trimethylsilyloxy-1-nonene | 2-[6-methoxyacetyl hexyl] cyclopent-2-en-1-one | dl-16-hydroxy-1-methoxymethyl-1,9-dioxo-16-chloromethyl-20-methyl-13-trans prostene |
| 498 | 1-trans-tri-n-butylstannyl-4-trimethylsilyloxymethyl-4-trimethylsilyloxy-1-nonene | 2-[6-methoxyacetyl hexyl] cyclopent-2-en-1-one | dl-16-hydroxy-1-methoxymethyl-1,9-dioxo-16-hydroxymethyl-20-methyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 499 | 1-trans-iodo-3-triphenylmethoxy-1-decene | 2-[6-methoxyacetyl hexyl] cyclopent-2-en-1-one | dl-15a-hydroxy-1-methoxymethyl-1,9-dioxo-20-ethyl-13-trans prostene |
| 500 | 1-trans-iodo-3-methyl-3-trimethylsilyloxy-1-decene | 2-[6-methoxyacetyl hexyl] cyclopent-2-en-1-one | dl-15a-hydroxy-1-methoxymethyl-1,9-dioxo-15-methyl-20-ethyl-13-trans prostene |
| 501 | 1-trans-iodo-4,4-dimethyl-3-trimethylsilyloxy-1-decene | 2-[6-methoxyacetyl hexyl] cyclopent-2-en-1-one | dl-15a-hydroxy-1-methoxymethyl-1,9-dioxo-16,16-dimethyl-20-ethyl-13-trans prostene |
| 502 | 1-trans-iodo-4,4-trimethylene-3-trimethylsilyloxy-1-decene | 2-[6-methoxyacetyl hexyl] cyclopent-2-en-1-one | dl-15a-hydroxy-1-methoxymethyl-1,9-dioxo-16,16-trimethylene-20-ethyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 503 | 1-trans-tri-n-butylstannyl-3-vinyl-3-trimethylsilyloxy-1-decene | 2-[6-methoxyacetyl hexyl] cyclopent-2-en-1-one | dl-15a-hydroxy-1-methoxymethyl-1,9-dioxo-15-vinyl-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 504 | 1-trans-iodo-4-triphenylmethoxy-1-decene | 2-[6-methoxyacetyl hexyl] cyclopent-2-en-1-one | dl-16-hydroxy-1-methoxymethyl-1,9-dioxo-20-ethyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 505 | 1-trans-tri-n-butylstannyl-4-methyl-4-trimethylsilyloxy-1-decene | 2-[6-methoxyacetyl hexyl] cyclopent-2-en-1-one | dl-16-hydroxy-1-methoxymethyl-1,9-dioxo-16-methyl-20-ethyl-13-trans prostene |
| 506 | 1-trans-tri-n-butylstannyl-5-methyl-4-trimethylsilyloxy-1-decene | 2-[6-methoxyacetyl hexyl] cyclopent-2-en-1-one | dl-16-hydroxy-1-methoxymethyl-1,9-dioxo-17-methyl-20-ethyl-13-trans prostene |
| 507 | 1-trans-tri-n-butylstannyl-4-vinyl-4-trimethylsilyloxy-1-decene | 2-[6-methoxyacetyl hexyl] cyclopent-2-en-1-one | dl-16-hydroxy-1-methoxymethyl-1,9-dioxo-16-vinyl-20-ethyl-13-trans prostene |
| 508 | 1-trans-tri-n-butylstannyl-4-trimethylsilylethynyl-4-trimethylsilyloxy-1-decene | 2-[6-methoxyacetyl hexyl] cyclopent-2-en-1-one | dl-16-hydroxy-1-methoxymethyl-1,9-dioxo-16-ethynyl-20-ethyl-13-trans prostene |
| 509 | 1-trans-tri-n-butylstannyl-5-methylene-4-triethylsilyloxy-1-decene | 2-[6-methoxyacetyl hexyl] cyclopent-2-en-1-one | dl-16-hydroxy-1-methoxymethyl-1,9-dioxo-17-methylene-20-ethyl-13-trans prostene |
| 510 | 1-trans-tri-n-butylstannyl-4-methyl-5-methylene-4-trimethylsilyloxy-1-decene | 2-[6-methoxyacetyl hexyl] cyclopent-2-en-1-one | dl-16-hydroxy-1-methoxymethyl-1,9-dioxo-16-methyl-17-methylene-20-ethyl-13-trans prostene |
| 511 | 1-trans-tri-n-butylstannyl-4-dimethoxymethyl-4-trimethylsilyloxy-1-decene | 2-[6-methoxyacetyl hexyl] cyclopent-2-en-1-one | dl-16-hydroxy-1-methoxymethyl-1,9-dioxo-16-formyl-20-ethyl-13-trans prostene |

TABLE I-continued

| 512 | 1-trans-tri-n-butylstannyl-4-fluoromethyl-4-trimethylsilyloxy-1-decene | 2-[6-methoxyacetyl hexyl] cyclopent-2-en-1-one | dl-16-hydroxy-1-methoxymethyl-1,9-dioxo-16-fluoromethyl-20-ethyl-13-trans prostene |
| --- | --- | --- | --- |
| 513 | 1-trans-tri-n-butylstannyl-4-difluoromethyl-4-trimethylsilyloxy-1-decene | 2-[6-methoxyacetyl hexyl] cyclopent-2-en-1-one | dl-16-hydroxy-1-methoxymethyl-1,9-dioxo-16-difluoromethyl-20-ethyl-13-trans prostene |
| 514 | 1-trans-tri-n-butylstannyl-4-trifluoromethyl-4-trimethylsilyloxy-1-decene | 2-[6-methoxyacetyl hexyl] cyclopent-2-en-1-one | dl-16-hydroxy-1-methoxymethyl-1,9-dioxo-16-trifluoromethyl-20-ethyl-13-trans prostene |
| 515 | 1-trans-tri-n-butylstannyl-4-chloromethyl-4-trimethylsilyloxy-1-decene | 2-[6-methoxyacetyl hexyl] cyclopent-2-en-1-one | dl-16-hydroxy-1-methoxymethyl-1,9-dioxo-16-chloromethyl-20-ethyl-13-trans prostene |
| 516 | 1-trans-tri-n-butylstannyl-4-trimethylsilyloxymethyl-4-trimethylsilyloxy-1-decene | 2-[6-methoxyacetyl hexyl] cyclopent-2-en-1-one | dl-16-hydroxy-1-methoxymethyl-1,9-dioxo-16-hydroxymethyl-20-ethyl-13-trans prostene |

| EXAMPLE | VINYL IODIDE | CYCLOPENTENONE | PRODUCT PROSTAGLANDIN OF THE 11-DEOXY PGE1 SERIES |
| --- | --- | --- | --- |
| 517 | 1-trans-iodo-3-triphenylmethoxy-1-heptene | 2-[7-methoxyacetyl heptyl] cyclopent-2-en-1-one | dl-15a-hydroxy-1-methoxymethyl-1,9-dioxo-20-nor-2-homo-13-trans prostene |
| 518 | 1-trans-iodo-3-methyl-3-trimethylsilyloxy-1-heptene | 2-[7-methoxyacetyl heptyl] cyclopent-2-en-1-one | dl-15a-hydroxy-1-methoxymethyl-1,9-dioxo-15-methyl-20-nor-2-homo-13-trans-prostene |
| 519 | 1-trans-iodo-4,4-dimethyl-3-trimethylsilyloxy-1-heptene | 2-[7-methoxyacetyl heptyl] cyclopent-2-en-1-one | dl-15a-hydroxy-1-methoxymethyl-1,9-dioxo-16,16-dimethyl-20-nor-2-homo-13-trans prostene |
| 520 | 1-trans-iodo-5,5-dimethyl-3-triphenylmethoxy-1-octene | 2-[7-methoxyacetyl heptyl] cyclopent-2-en-1-one | dl-15a-hydroxy-1-methoxymethyl-1,9-dioxo-17,17-dimethyl-2-homo-13-trans prostene |
| 521 | 1-trans-iodo-4-methyl-3-triphenylmethoxy-1-octene | 2-[7-methoxyacetyl heptyl] cyclopent-2-en-1-one | dl-15a-hydroxy-1-methoxymethyl-1,9-dioxo-16-methyl-2-homo-13-trans prostene |
| 522 | 1-trans-iodo-4,4-trimethylene-3-trimethylsilyloxy-1-heptene | 2-[7-methoxyacetyl heptyl] cyclopent-2-en-1-one | dl-15a-hydroxy-1-methoxymethyl-1,9-dioxo-16,16-trimethylene-20-nor-2-homo-13-trans prostene |

| EXAMPLE | VINYL TIN | CYCLOPENTENONE | PRODUCT PROSTAGLANDIN OF THE 11-DEOXY PGE1 SERIES |
| --- | --- | --- | --- |
| 523 | 1-trans-tri-n-butylstannyl-3-vinyl-3-trimethylsilyloxy-1-heptene | 2-[7-methoxyacetyl heptyl] cyclopent-2-en-1-one | dl-15a-hydroxy-1-methoxymethyl-1,9-dioxo-15-vinyl-20-nor-2-homo-13-trans prostene |
| 524 | 1-trans-tri-n-butylstannyl-4-phenoxy-3-triethylsilyloxy-1-butene | 2-[7-methoxyacetyl heptyl] cyclopent-2-en-1-one | dl-15a-hydroxy-1-methoxymethyl-1,9-dioxo-16-phenoxy-2-homo-17,20-tetranor-13-trans prostene |
| 525 | 1-trans-tri-n-butylstannyl-4-(p-fluorophenoxy)-3-triethylsilyloxy-1-butene | 2-[7-methoxyacetyl heptyl] cyclopent-2-en-1-one | dl-15a-hydroxy-1-methoxymethyl-1,9-dioxo-16-(p-fluorophenoxy)-2-homo-17-20-tetranor-13-trans prostene |
| 526 | 1-trans-tri-n-butylstannyl-4-(m-chlorophenoxy)-3-triethylsilyloxy-1-butene | 2-[7-methoxyacetyl heptyl] cyclopent-2-en-1-one | dl-15a-hydroxy-1-methoxymethyl-1,9-dioxo-16-(m-chlorophenoxy)-2-homo-17-20-tetranor-13-trans prostene |
| 527 | 1-trans-tri-n-butylstannyl-4-(m-trifluoromethylphenoxy)-3-triethylsilyloxy-1-butene | 2-[7-methoxyacetyl heptyl] cyclopent-2-en-1-one | dl-15a-hydroxy-1-methoxymethyl-1,9-dioxo-16-(m-trifluoromethylphenoxy)-2-homo-17-20-tetranor-13-trans prostene |

TABLE 1-continued

| EXAMPLE | VINYL IODIDE | CYCLOPENTENONE | PRODUCT PROSTAGLANDIN OF THE 11-DEOXY PGE1 SERIES |
|---|---|---|---|
| 528 | 1-trans-iodo-5-phenyl 3-triethylsilyloxy-1-pentene | 2-[7-methoxyacetyl heptyl] cyclopent-2-en-1-one | dl-15a-hydroxy-1-methoxymethyl-1,9-dioxo-17-phenyl-2-homo-18-20-trinor-13-trans prostene |
| 529 | 1-trans-iodo-4,4-dimethyl-5-phenyl 3-triethylsilyloxy-1-pentene | 2-[7-methoxyacetyl heptyl] cyclopent-2-en-1-one | dl-15a-hydroxy-1-methoxymethyl-1,9-dioxo-16,16-dimethyl-17-phenyl-2-homo-18-20-trinor-13-trans prostene |
| 530 | 1-trans-iodo-4-cyclopentyl 3-triphenylmethoxy-1-butene | 2-[7-methoxyacetyl heptyl] cyclopent-2-en-1-one | dl-15a-hydroxy-1-methoxymethyl-1,9-dioxo-16-cyclopentyl-2-homo-17-20-tetranor-13-trans prostene |
| 531 | 1-trans-iodo-4-cyclohexyl 3-triphenylmethoxy-1-butene | 2-[7-methoxyacetyl heptyl] cyclopent-2-en-1-one | dl-16-hydroxy-1-methoxymethyl-1,9-dioxo-16-ethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 535 | 1-trans-tri-n-butylstannyl-5-methyl 4-trimethylsilyloxy-1-heptene | 2-[7-methoxyacetyl heptyl] cyclopent-2-en-1-one | dl-16-hydroxy-1-methoxymethyl-1,9-dioxo-17-methyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 536 | 1-trans-iodo-5,5-dimethyl 4-trimethylsilyloxy-1-octene | 2-[7-methoxyacetyl heptyl] cyclopent-2-en-1-one | dl-16-hydroxy-1-methoxymethyl-1,9-dioxo-17,17-dimethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 537 | 1-trans-tri-n-butylstannyl-4-vinyl-4-trimethylsilyloxy-1-heptene | 2-[7-methoxyacetyl heptyl] cyclopent-2-en-1-one | dl-16-hydroxy-1-methoxymethyl-1,9-dioxo-16-vinyl-20-nor-2-homo-13-trans prostene |
| 538 | 1-trans-tri-n-butylstannyl-4-cyclopropyl-4-trimethylsilyloxy-1-octene | 2-[7-methoxyacetyl heptyl] cyclopent-2-en-1-one | dl-16-hydroxy-1-methoxymethyl-1,9-dioxo-16-cyclopropyl-2-homo-13-trans prostene |
| 539 | 1-trans-tri-n-butylstannyl-4-trimethylsilylethynyl-4-trimethylsilyloxy-1-heptene | 2-[7-methoxyacetyl heptyl] cyclopent-2-en-1-one | dl-16-hydroxy-1-methoxymethyl-1,9-dioxo-16-ethynyl-20-nor-2-homo-13-trans prostene |
| 540 | 1-trans-tri-n-butylstannyl-5-methylene-4-triethylsilyloxy-1-heptene | 2-[7-methoxyacetyl heptyl] cyclopent-2-en-1-one | dl-16-hydroxy-1-methoxymethyl-1,9-dioxo-17-methylene-20-nor-2-homo-13-trans prostene |
| 541 | 1-trans-tri-n-butylstannyl-4-methyl-5-methylene-4-trimethylsilyloxy-1-heptene | 2-[7-methoxyacetyl heptyl] cyclopent-2-en-1-one | dl-16-hydroxy-1-methoxymethyl-1,9-dioxo-16-methyl-17-methylene-20-nor-2-homo-13-trans prostene |
| 542 | 1-trans-tri-n-butylstannyl-4-dimethoxymethyl-4-trimethylsilyloxy-1-heptene | 2-[7-methoxyacetyl heptyl] cyclopent-2-en-1-one | dl-16-hydroxy-1-methoxymethyl-1,9-dioxo-16-formyl-20-nor-2-homo-13-trans prostene |
| 543 | 1-trans-tri-n-butylstannyl-4-fluoromethyl-4-trimethylsilyloxy-1-heptene | 2[7-methoxyacetyl heptyl] cyclopent-2-en-1-one | dl-16-hydroxy-1-methoxymethyl-1,9-dioxo-16-fluoromethyl-20-nor-2-homo-13-trans prostene |
| 544 | 1-trans-tri-n-butylstannyl-4-difluoromethyl-4-trimethylsilyloxy-1-heptene | 2-[7-methoxyacetyl heptyl] cyclopent-2-en-1-one | dl-16-hydroxy-1-methoxymethyl-1,9-dioxo-16-difluoromethyl-20-nor-2-homo-13-trans prostene |
| 545 | 1-trans-tri-n-butylstannyl-4-trifluoromethyl-4-trimethylsilyloxy-1-heptene | 2-[7-methoxyacetyl heptyl] cyclopent-2-en-1-one | dl-16-hydroxy-1-methoxymethyl-1,9-dioxo-16-trifluoromethyl-20-nor-2-homo-13-trans prostene |
| 546 | 1-trans-tri-n-butylstannyl-4-chloromethyl-4-trimethylsilyloxy-1-heptene | 2-[7-methoxyacetyl heptyl] cyclopent-2-en-1-one | dl-16-hydroxy-1-methoxymethyl-1,9-dioxo-16-chloromethyl-20-nor-2-homo-13-trans prostene |

TABLE I-continued

| | | | |
|---|---|---|---|
| 547 | 1-trans-tri-n-butylstannyl-4-trimethylsilyloxymethyl-4-trimethylsilyloxy-1-heptene | cyclopent-2-en-1-one 2-[7-methoxyacetyl heptyl] cyclopent-2-en-1-one | dl-16-hydroxy-1-methoxymethyl-1,9-dioxo-16-hydroxymethyl-20-nor-2-homo-13-trans prostene |
| EXAMPLE | VINYL IODIDE | CYCLOPENTENONE | PRODUCT PROSTAGLANDIN OF THE 11-DEOXY PGE1 SERIES |
| 548 | 1-trans-iodo-4-methyl-7-chloro-4-trimethylsilyloxy-1-heptene | 2-[7-methoxyacetyl heptyl] cyclopent-2-en-1-one | dl-16-hydroxy-1-methoxymethyl-1,9-dioxo-16-methyl-19-chloro-2-homo-20-nor-13-trans prostene |
| 549 | 1-trans-iodo-3-triphenylmethoxy-1-octene | 2-[7-methoxyacetyl heptyl] cyclopent-2-en-1-one | dl-15a-hydroxy-1-methoxymethyl-1,9-dioxo-2-homo-13-trans prostene |
| 550 | 1-trans-iodo-3-methyl-3-trimethylsilyloxy-1-octene | 2-[7-methoxyacetyl heptyl] cyclopent-2-en-1-one | dl-15a-hydroxy-1-methoxymethyl,9-dioxo-15-methyl-2-homo-13-trans prostene |
| 551 | 1-trans-iodo-4,4-dimethyl-3-trimethylsilyloxy-1-octene | 2-[7-methoxyacetyl heptyl] cyclopent-2-en-1-one | dl-15a-hydroxy-1-methoxymethyl-1,9-dioxo-16,16-dimethyl-2-homo-13-trans prostene |
| 552 | 1-trans-iodo-4,4-trimethylene-3-trimethylsilyloxy-1-octene | cyclopent-2-en-1-one 2-[7-methoxyacetyl heptyl] cyclopent-2-en-1-one | dl-15a-hydroxy-1-methoxymethyl-1,9-dioxo-16,16-trimethylene-2-homo-13-trans prostene |
| EXAMPLE | VINYL TIN | CYLOPENTENONE | PRODUCT PROSTAGLANDIN OF THE 11-DEOXY PGE1 SERIES |
| 553 | 1-trans-tri-n-butylstannyl-3-vinyl-3-trimethylsilyloxy-1-octene | 2-[7-methoxyacetyl heptyl] cyclopent-2-en-1-one | dl-15a-hydroxy-1-methoxymethyl-1,9-dioxo-15-vinyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 554 | 1-trans-iodo-4-triphenylmethoxy-1-octene | 2-[7-methoxyacetyl heptyl] cyclopent-2-en-1-one | dl-16-hydroxy-1-methoxymethyl-1,9-dioxo-2-homo-13-trans prostene |
| EXAMPLE | VINYL TIN | CYCLOPENTENONE | PRODUCT PROSTAGLANDIN OF THE 11-DEOXY PGE1 SERIES |
| 555 | 1-trans-tri-n-butylstannyl-4-methyl-4-trimethylsilyloxy-1-octene | 2-[7-methoxyacetyl heptyl] cyclopent-2-en-1-one | dl-16-hydroxy-1-methoxymethyl-1,9-dioxo-16-methyl-2-homo-13-trans prostene |
| 556 | 1-trans-tri-n-butylstannyl-5-methyl-4-trimethylsilyloxy-1-octene | 2-[7-methoxyacetyl heptyl] cyclopent-2-en-1-one | dl-16-hydroxy-1-methoxymethyl-1,9-dioxo-17-methyl-2-homo-13-trans prostene |
| 557 | 1-trans-tri-n-butylstannyl-4-vinyl-4-trimethylsilyloxy-1-octene | 2-[7-methoxyacetyl heptyl] cyclopent-2-en-1-one | dl-16-hydroxy-1-methoxymethyl-1,9-dioxo-16-vinyl-2-homo-13-trans prostene |
| 558 | 1-trans-tri-n-butylstannyl-4-trimethylsilylethynyl-4-trimethylsilyloxy-1-octene | 2-[7-methoxyacetyl heptyl] cyclopent-2-en-1-one | dl-16-hydroxy-1-methoxymethyl-1,9-dioxo-16-ethynyl-2-homo-13-trans prostene |
| 559 | 1-trans-tri-n-butylstannyl-5-methylene-4-triethylsilyloxy-1-octene | 2-[7-methoxyacetyl heptyl] cyclopent-2-en-1-one | dl-16-hydroxy-1-methoxymethyl-1,9-dioxo-17-methylene-2-homo-13-trans prostene |
| 560 | 1-trans-tri-n-butylstannyl-4-methyl-5-methylene-4-trimethylsilyloxy-1-octene | 2-[7-methoxyacetyl heptyl] cyclopent-2-en-1-one | dl-16-hydroxy-1-methoxymethyl-1,9-dioxo-16-methyl-17-methylene-2-homo-13-trans prostene |
| 561 | 1-trans-tri-n-butylstannyl-4-dimethoxymethyl-4-trimethylsilyloxy-1-octene | 2-[7-methoxyacetyl heptyl] cyclopent-2-en-1-one | dl-16-hydroxy-1-methoxymethyl-1,9-dioxo-16-formyl-2-homo-13-trans prostene |

TABLE I-continued

| | | | |
|---|---|---|---|
| 562 | 1-trans-tri-n-butylstannyl-4-fluoromethyl-4-trimethylsilyloxy-1-octene | cyclopent-2-en-1-one 2-[7-methoxyacetyl heptyl] | dl-16-hydroxy-1-methoxymethyl-1,9-dioxo-16-fluoromethyl-2-homo-13-trans prostene |
| 563 | 1-trans-tri-n-butylstannyl-4-difluoromethyl-4-trimethylsilyloxy-1-octene | cyclopent-2-en-1-one 2-[7-methoxyacetyl heptyl] | dl-16-hydroxy-1-methoxymethyl-1,9-dioxo-16-difluoromethyl-2-homo-13-trans prostene |
| 564 | 1-trans-tri-n-butylstannyl-4-trifluoromethyl-4-trimethylsilyloxy-1-octene | cyclopent-2-en-1-one 2-[7-methoxyacetyl heptyl] | dl-16-hydroxy-1-methoxymethyl-1,9-dioxo-16-trifluoromethyl-2-homo-13-trans prostene |
| 565 | 1-trans-tri-n-butylstannyl-4-chloromethyl-4-trimethylsilyloxy-1-octene | cyclopent-2-en-1-one 2-[7-methoxyacetyl heptyl] | dl-16-hydroxy-1-methoxymethyl-1,9-dioxo-16-chloromethyl-2-homo-13-trans prostene |
| 566 | 1-trans-tri-n-butylstannyl-4-trimethylsilyloxymethyl-4-trimethylsilyloxy-1-octene | cyclopent-2-en-1-one 2-[7-methoxyacetyl heptyl] | dl-16-hydroxy-1-methoxymethyl-1,9-dioxo-16-hydroxymethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 567 | 1-trans-iodo-3-triphenylmethoxy-1-nonene | 2-[7-methoxyacetyl heptyl] | dl-15a-hydroxy-1-methoxymethyl-1,9-dioxo-20-methyl-2-homo-13-trans prostene |
| 568 | 1-trans-iodo-3-methyl-3-trimethylsilyloxy-1-nonene | cyclopent-2-en-1-one 2-[7-methoxyacetyl heptyl] | dl-15a-hydroxy-1-methoxymethyl-1,9-dioxo-15-methyl-20-methyl-2-homo-13-trans prostene |
| 569 | 1-trans-iodo-4,4-dimethyl-3-trimethylsilyloxy-1-nonene | cyclopent-2-en-1-one 2-[7-methoxyacetyl heptyl] | dl-15a-hydroxy-1-methoxymethyl-1,9-dioxo-16,16-dimethyl-20-methyl-2-homo-13-trans prostene |
| 570 | 1-trans-iodo-4,4-trimethylene-3-trimethylsilyloxy-1-nonene | cyclopent-2-en-1-one 2-[7-methoxyacetyl heptyl] | dl-15a-hydroxy-1-methoxymethyl-1,9-dioxo-16,16-trimethylene-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 571 | 1-trans-tri-n-butylstannyl-3-vinyl-3-trimethylsilyloxy-1-nonene | 2-[7-methoxyacetyl heptyl] cyclopent-2-en-1-one | dl-15a-hydroxy-1-methoxymethyl-1,9-dioxo-15-vinyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 572 | 1-trans-iodo-4-triphenylmethoxy-1-nonene | 2-[7-methoxyacetyl heptyl] cyclopent-2-en-1-one | dl-16-hydroxy-1-methoxymethyl-1,9-dioxo-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 573 | 1-trans-tri-n-butylstannyl-4-methyl-4-trimethylsilyloxy-1-nonene | 2-[7-methoxyacetyl heptyl] cyclopent-2-en-1-one | dl-16-hydroxy-1-methoxymethyl-1,9-dioxo-16-methyl-20-methyl-2-homo-13-trans prostene |
| 574 | 1-trans-tri-n-butylstannyl-5-methyl-4-trimethylsilyloxy-1-nonene | 2-[7-methoxyacetyl heptyl] cyclopent-2-en-1-one | dl-16-hydroxy-1-methoxymethyl-1,9-dioxo-17-methyl-20-methyl-2-homo-13-trans prostene |
| 575 | 1-trans-tri-n-butylstannyl-4-vinyl-4-trimethylsilyloxy-1-nonene | 2-[7-methoxyacetyl heptyl] cyclopent-2-en-1-one | dl-16-hydroxy-1-methoxymethyl-1,9-dioxo-16-vinyl-20-methyl-2-homo-13-trans prostene |
| 576 | 1-trans-tri-n-butylstannyl-4-trimethylsilylethynyl-4-trimethylsilyloxy-1-nonene | 2-[7-methoxyacetyl heptyl] cyclopent-2-en-1-one | dl-16-hydroxy-1-methoxymethyl-1,9-dioxo-16-ethynyl-20-methyl-2-homo-13-trans prostene |

TABLE I-continued

| | | | |
|---|---|---|---|
| 577 | 1-trans-tri-n-butylstannyl-5-methylene-4-triethylsilyloxy-1-nonene | cyclopent-2-en-1-one 2-[7-methoxyacetyl heptyl] | dl-16-hydroxy-1-methoxymethyl-1,9-dioxo-17-methylene-20-methyl-2-homo-13-trans prostene |
| 578 | 1-trans-tri-n-butylstannyl-4-methyl-5-methylene-4-trimethylsilyloxy-1-nonene | cyclopent-2-en-1-one 2-[7-methoxyacetyl heptyl] | dl-16-hydroxy-1-methoxymethyl-1,9-dioxo-16-methyl-17-methylene-20-methyl-2-homo-13-trans prostene |
| 579 | 1-trans-tri-n-butylstannyl-4-dimethoxymethyl-4-trimethylsilyloxy-1-nonene | cyclopent-2-en-1-one 2-[7-methoxyacetyl heptyl] | dl-16-hydroxy-1-methoxymethyl-1,9-dioxo-16-formyl-20-methyl-2-homo-13-trans prostene |
| 580 | 1-trans-tri-n-butylstannyl-4-fluoromethyl-4-trimethylsilyloxy-1-nonene | cyclopent-2-en-1-one 2-[7-methoxyacetyl heptyl] | dl-16-hydroxy-1-methoxymethyl-1,9-dioxo-16-fluoromethyl-20-methyl-2-homo-13-trans prostene |
| 581 | 1-trans-tri-n-butylstannyl-4-difluoromethyl-4-trimethylsilyloxy-1-nonene | cyclopent-2-en-1-one 2-[7-methoxyacetyl heptyl] | dl-16-hydroxy-1-methoxymethyl-1,9-dioxo-16-difluoromethyl-20-methyl-2-homo-13-trans prostene |
| 582 | 1-trans-tri-n-butylstannyl-4-trifluoromethyl-4-trimethylsilyloxy-1-nonene | cyclopent-2-en-1-one 2-[7-methoxyacetyl heptyl] | dl-16-hydroxy-1-methoxymethyl-1,9-dioxo-16-trifluoromethyl-20-methyl-2-homo-13-trans prostene |
| 583 | 1-trans-tri-n-butylstannyl-4-chloromethyl-4-trimethylsilyloxy-1-nonene | cyclopent-2-en-1-one 2-[7-methoxyacetyl heptyl] | dl-16-hydroxy-1-methoxymethyl-1,9-dioxo-16-chloromethyl-20-methyl-2-homo-13-trans prostene |
| 584 | 1-trans-tri-n-butylstannyl-4-trimethylsilyloxymethyl-4-trimethylsilyloxy-1-nonene | cyclopent-2-en-1-one 2-[7-methoxyacetyl heptyl] | dl-16-hydroxy-1-methoxymethyl-1,9-dioxo-16-hydroxymethyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 585 | 1-trans-iodo-3-triphenylmethoxy-1-decene | 2-[7-methoxyacetyl heptyl] cyclopent-2-en-1-one | dl-15a-hydroxy-1-methoxymethyl-1,9-dioxo-20-ethyl-2-homo-13-trans prostene |
| 586 | 1-trans-iodo-3-methyl-3-trimethylsilyloxy-1-decene | 2-[7-methoxyacetyl heptyl] cyclopent-2-en-1-one | dl-15a-hydroxy-1-methoxymethyl-1,9-dioxo-15-methyl-20-ethyl-2-homo-13-trans prostene |
| 587 | 1-trans-iodo-4,4-dimethyl-3-trimethylsilyloxy-1-decene | 2-[7-methoxyacetyl heptyl] cyclopent-2-en-1-one | dl-15a-hydroxy-1-methoxymethyl-1,9-dioxo-16,16-dimethyl-20-ethyl-2-homo-13-trans prostene |
| 588 | 1-trans-iodo-4,4-trimethylene-3-trimethylsilyloxy-1-decene | 2-[7-methoxyacetyl heptyl] cyclopent-2-en-1-one | dl-15a-hydroxy-1-methoxymethyl-1,9-dioxo-16,16-trimethylene-20-ethyl-2-homo-13-trans prostene |
| EXAMPLE | VINYL TIN | CYCLOPENTENONE | PRODUCT PROSTAGLANDIN OF THE 11-DEOXY PGE1 SERIES |
| 589 | 1-trans-tri-n-butylstannyl-3-vinyl-3-trimethylsilyloxy-1-decene | 2-[7-methoxyacetyl heptyl] cyclopent-2-en-1-one | dl-15a-hydroxy-1-methoxymethyl-1,9-dioxo-15-vinyl-20-ethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 590 | 1-trans-iodo-4-triphenylmethoxy-1-decene | 2-[7-methoxyacetyl heptyl] cyclopent-2-en-1-one | dl-16-hydroxy-1-methoxymethyl-1,9-dioxo-20-ethyl-2-homo-13-trans prostene |
| EXAMPLE | VINYL TIN | CYCLOPENTENONE | PRODUCT PROSTAGLANDIN OF THE 11-DEOXY PGE1 SERIES |
| 591 | 1-trans-tri-n-butylstannyl-4-methyl-4-trimethylsilyloxy-1-decene | 2-[7-methoxyacetyl heptyl] | dl-16-hydroxy-1-methoxymethyl-1,9-dioxo-16-methyl-20-ethyl-2-homo-13-trans prostene |

TABLE I-continued

| | | | |
|---|---|---|---|
| 592 | | 1-trans-tri-n-butylstannyl-5-methyl-4-trimethylsilyloxy-1-decene | cyclopent-2-en-1-one 2-[7-methoxyacetyl heptyl] | dl-16-hydroxy-1-methoxymethyl-1,9-dioxo-17-methyl-20-ethyl-2-homo-13-trans prostene |
| 593 | | 1-trans-tri-n-butylstannyl-4-vinyl-4-trimethylsilyloxy-1-decene | cyclopent-2-en-1-one 2-[7-methoxyacetyl heptyl] | dl-16-hydroxy-1-methoxymethyl-1,9-dioxo-16-vinyl-20-ethyl-2-homo-13-trans prostene |
| 594 | | 1-trans-tri-n-butylstannyl-4-trimethylsilylethynyl-4-trimethylsilyloxy-1-decene | cyclopent-2-en-1-one 2-[7-methoxyacetyl heptyl] | dl-16-hydroxy-1-methoxymethyl-1,9-dioxo-16-ethynyl-20-ethyl-2-homo-13-trans prostene |
| 595 | | 1-trans-tri-n-butylstannyl-5-methylene-4-triethylsilyloxy-1-decene | cyclopent-2-en-1-one 2-[7-methoxyacetyl heptyl] | dl-16-hydroxy-1-methoxymethyl-1,9-dioxo-17-methylene-20-ethyl-2-homo-13-trans prostene |
| 596 | | 1-trans-tri-n-butylstannyl-4-methyl-5-methylene-4-trimethylsilyloxy-1-decene | cyclopent-2-en-1-one 2-[7-methoxyacetyl heptyl] | dl-16-hydroxy-1-methoxymethyl-1,9-dioxo-16-methyl-17-methylene-20-ethyl-2-homo-13-trans prostene |
| 597 | | 1-trans-tri-n-butylstannyl-4-dimethoxymethyl-4-trimethylsilyloxy-1-decene | cyclopent-2-en-1-one 2-[7-methoxyacetyl heptyl] | dl-16-hydroxy-1-methoxymethyl-1,9-dioxo-16-formyl-20-ethyl-2-homo-13-trans prostene |
| 598 | | 1-trans-tri-n-butylstannyl-4-fluoromethyl-4-trimethylsilyloxy-1-decene | cyclopent-2-en-1-one 2-[7-methoxyacetyl heptyl] | dl-16-hydroxy-1-methoxymethyl-1,9-dioxo-16-fluoromethyl-20-ethyl-2-homo-13-trans prostene |
| 599 | | 1-trans-tri-n-butylstannyl-4-difluoromethyl-4-trimethylsilyloxy-1-decene | cyclopent-2-en-1-one 2-[7-methoxyacetyl heptyl] | dl-16-hydroxy-1-methoxymethyl-1,9-dioxo-16-difluoromethyl-20-ethyl-2-homo-13-trans prostene |
| 600 | | 1-trans-tri-n-butylstannyl-4-trifluoromethyl-4-trimethylsilyloxy-1-decene | cyclopent-2-en-1-one 2-[7-methoxyacetyl heptyl] | dl-16-hydroxy-1-methoxymethyl-1,9-dioxo-16-trifluoromethyl-20-ethyl-2-homo-13-trans prostene |
| 601 | | 1-tran-tri-n-butylstannyl-4-chloromethyl-4-trimethylsilyloxy-1-decene | cyclopent-2-en-1-one 2-[7-methoxyacetyl heptyl] | dl-16-hydroxy-1-methoxymethyl-1,9-dioxo-16-chloromethyl-20-ethyl-2-homo-13-trans prostene |
| 602 | | 1-trans-tri-n-butylstannyl-4-trimethylsilyloxymethyl-4-trimethylsilyloxy-1-decene | cyclopent-2-en-1-one 2-[7-methoxyacetyl heptyl] | dl-16-hydroxy-1-methoxymethyl-1,9-dioxo-16-hydroxymethyl-20-ethyl-2-homo-13-trans prostene |
| EXAMPLE | VINYL TIN | | CYCLOPENTENONE | PRODUCT PROSTAGLANDIN OF THE PGE1 SERIES |
| 603 | | 1-trans-tri-n-butylstannyl-4-methyl-4-trimethylsilyloxy-1,7-octadiene | 2-[6-methoxyjacetyl pentyl]-4-trimethylsiloxy cyclopent-2-en-1-one | dl-11a,16-dihydroxy-1-methoxymethyl-1,9-dioxo-16-methyl-2-nor-13-trans-19 prostadiene |
| 604 | | 1-trans-tri-n-butylstannyl-4-methyl-4-trimethylsilyloxy-1,7-octadiene | 2-[6-methoxyacetyl hexyl]-4-trimethylsiloxy cyclopent-2-en-1-one | dl-11a,16-dihydroxy-1-methoxymethyl-1,9-dioxo-16-methyl-13-trans-19 prostadiene |
| 605 | | 1-trans-tri-n-butylstannyl-4-methyl-4-trimethylsilyloxy-1,7-octadiene | 2-[7-methoxyacetyl heptyl]-4-trimethylsiloxy cyclopent-2-en-1-one | dl-11a,16-dihydroxy-1-methoxymethyl-1,9-dioxo-16-methyl-2-homo-13-trans-19 prostadiene |
| 606 | | 1-trans-tri-n-butylstannyl-4-methyl-4-trimethylsilyloxy-1,7-octadiene | 2-[6-methoxyacetyl hexyl]-4R-trimethylsiloxy cyclopent-2-en-1-one | nat-11a,16-dihydroxy-1-methoxymethyl-1,9-dioxo-16-methyl-13-trans-19 prostadiene |
| EXAMPLE | VINYL TIN | | CYCLOPENTENONE | PRODUCT PROSTAGLANDIN OF THE 11-DEOXY PGE1 SERIES |
| 607 | | 1-trans-tri-n-butylstannyl-4-methyl-4-trimethylsilyloxy-1,7-octadiene | 2-[5-methoxyacetyl pentyl] cyclopent-2-en-1-one | dl-16-hydroxy-1-methoxymethyl-1,9-dioxo-16-methyl-2-nor-13-trans-19 prostadiene |

TABLE I-continued

| EXAMPLE | VINYL IODIDE | CYCLOPENTENONE | PRODUCT PROSTAGLANDIN OF THE PGE1 SERIES |
|---|---|---|---|
| 608 | 1-trans-tri-n-butylstannyl-4-methyl-4-trimethylsilyloxy-1,7-octadiene | 2-[6-methoxyacetyl hexyl] cyclopent-2-en-1-one | dl-16-hydroxy-1-methoxymethyl-1,9-dioxo-16-methyl-13-trans-19 prostadiene |
| 609 | 1-trans-tri-n-butylstannyl-4-methyl-4-trimethylsilyloxy-1,7-octadiene | 2-[7-methoxyacetyl heptyl] cyclopent-2-en-1-one | dl-16-hydroxy-1-methoxymethyl-1,9-dioxo-16-methyl-2-homo-13-trans-19 prostadiene |
| 610 | 1-trans-iodo-4-triphenylmethoxy-1,5-heptadiene | 2-[5-methoxyacetyl pentyl]-4-trimethylsiloxy cyclopent-2-en-1-one | dl-11a,16-dihydroxy-1-methoxymethyl-1,9-dioxo-20-nor-2-nor-13-trans-17-trans prostadiene |
| 611 | 1-trans-iodo-4-methyl-4-trimethylsilyloxy-1,5-heptadiene | 2-[5-methoxyacetyl pentyl]-4-trimethylsiloxy cyclopent-2-en-1-one | dl-11a,16-dihydroxy-1-methoxymethyl-1,9-dioxo-16-methyl-20-nor-2-nor-13-trans-17-trans prostadiene |
| 612 | 1-trans-iodo-4-triphenylmethoxy-1,5-octadiene | 2-[5-methoxyacetyl pentyl]-4-trimethylsiloxy cyclopent-2-en-1-one | dl-11a,16-dihydroxy-1-methoxymethyl-1,9-dioxo-2-nor-13-trans-17-trans prostadiene |
| 613 | 1-trans-iodo-4-methyl-4-trimethylsilyloxy-1,5-octadiene | 2-[5-methoxyacetyl pentyl]-4-trimethylsiloxy cyclopent-2-en-1-one | dl-11a,16-dihydroxy-1-methoxymethyl-1,9-dioxo-16-methyl-2-nor-13-trans-17-trans prostadiene |
| 614 | 1-trans-iodo-4-triphenylmethoxy-1,5-nonadiene | 2-[5-methoxyacetyl pentyl]-4-trimethylsiloxy cyclopent-2-en-1-one | dl-11a,16-dihydroxy-1-methoxymethyl-1,9-dioxo-20-methyl-2-nor-13-trans-17-trans prostadiene |
| 615 | 1-trans-iodo-4-methyl-4-trimethylsilyloxy-1,5-nonadiene | 2-[5-methoxyacetyl pentyl]-4-trimethylsiloxy cyclopent-2-en-1-one | dl-11a,16-dihydroxy-1-methoxymethyl-1,9-dioxo-16-methyl-20-methyl-2-nor-13-trans-17-trans prostadiene |
| 616 | 1-trans-iodo-4-triphenylmethoxy-1,5-decadiene | 2-[5-methoxyacetyl pentyl]-4-trimethylsiloxy cyclopent-2-en-1-one | dl-11a,16-dihydroxy-1-methoxymethyl-1,9-dioxo-20-ethyl-2-nor-13-trans-17-trans prostadiene |
| 617 | 1-trans-iodo-4-methyl-4-trimethylsilyloxy-1,5-decadiene | 2-[5-methoxyacetyl pentyl]-4-trimethylsiloxy cyclopent-2-en-1-one | dl-11a,16-dihydroxy-1-methoxymethyl-1,9-dioxo-16-methyl-20-ethyl-2-nor-13-trans-17-trans prostadiene |
| 618 | 1-trans-iodo-4-triphenylmethoxy-1,5-heptadiene | 2-[6-methoxyacetyl hexyl]-4-trimethylsiloxy cyclopent-2-en-1-one | dl-11a,16-dihydroxy-1-methoxymethyl-1,9-dioxo-20-nor-13-trans-17-trans prostadiene |
| 619 | 1-trans-iodo-4-methyl-4-trimethylsilyloxy-1,5-heptadiene | 2-[6-methoxyacetyl hexyl]-4-trimethylsiloxy cyclopent-2-en-1-one | dl-11a,16-dihydroxy-1-methoxymethyl-1,9-dioxo-16-methyl-20-nor-13-trans-17-trans prostadiene |
| 620 | 1-trans-iodo-4-triphenylmethoxy-1,5-octadiene | 2-[6-methoxyacetyl hexyl]-4-trimethylsiloxy cyclopent-2-en-1-one | dl-11a,16-dihydroxy-1-methoxymethyl-1,9-dioxo-13-trans-17-trans prostadiene |
| 621 | 1-trans-iodo-4-methyl-4-trimethylsilyloxy-1,5-octadiene | 2-[6-methoxyacetyl hexyl]-4-trimethylsiloxy cyclopent-2-en-1-one | dl-11a,16-dihydroxy-1-methoxymethyl-1,9-dioxo-16-methyl-13-trans-17-trans prostadiene |
| 622 | 1-trans-iodo-4-triphenylmethoxy-1,5-nonadiene | 2-[6-methoxyacetyl hexyl]-4-trimethylsiloxy cyclopent-2-en-1-one | dl-11a,16-dihydroxy-1-methoxymethyl-1,9-dioxo-20-methyl-13-trans-17-trans prostadiene |
| 623 | 1-trans-iodo-4-methyl-4-trimethylsilyloxy-1,5-nonadiene | 2-[6-methoxyacetyl hexyl]-4-trimethylsiloxy cyclopent-2-en-1-one | dl-11a,16-dihydroxy-1-methoxymethyl-1,9-dioxo-16-methyl-20-methyl-13-trans-17-trans prostadiene |
| 624 | 1-trans-iodo-4-triphenylmethoxy-1,5-decadiene | 2-[6-methoxyacetyl hexyl]-4-trimethylsiloxy cyclopent-2-en-1-one | dl-11a,16-dihydroxy-1-methoxymethyl-1,9-dioxo-20-ethyl-13-trans-17-trans prostadiene |

TABLE I-continued

| EXAMPLE | VINYL IODIDE | CYCLOPENTENONE | PRODUCT PROSTAGLANDIN OF THE 11-DEOXY PGE1 SERIES |
|---|---|---|---|
| 625 | 1-trans-iodo-4-methyl-4-trimethylsilyloxy-1,5-decadiene | 2-[6-methoxyacetyl hexyl]-4-trimethylsiloxy cyclopent-2-en-1-one | dl-11a,16-dihydroxy-1-methoxymethyl-1,9-dioxo-16-methyl-20-ethyl-13-trans-17-trans prostadiene |
| 626 | 1-trans-iodo-4-triphenylmethoxy-1,5-heptadiene | 2-[7-methoxyacetyl heptyl]-4-trimethylsiloxy cyclopent-2-en-1-one | dl-11a,16-dihydroxy-1-methoxymethyl-1,9-dioxo-20-nor-2-homo-13-trans-17-trans prostadiene |
| 627 | 1-trans-iodo-4-methyl-4-trimethylsilyloxy-1,5-heptadiene | 2-[7-methoxyacetyl heptyl]-4-trimethylsiloxy cyclopent-2-en-1-one | dl-11a,16-dihydroxy-1-methoxymethyl-1,9-dioxo-16-methyl-20-nor-2-homo-13-trans-17-trans prostadiene |
| 628 | 1-trans-iodo-4-triphenylmethoxy-1,5-octadiene | 2-[7-methoxyacetyl heptyl]-4-trimethylsiloxy cyclopent-2-en-1-one | dl-11a,16-dihydroxy-1-methoxymethyl-1,9-dioxo-2-homo-13-trans-17-trans prostadiene |
| 629 | 1-trans-iodo-4-methyl-4-trimethylsilyloxy-1,5-octadiene | 2-[7-methoxyacetyl heptyl]-4-trimethylsiloxy cyclopent-2-en-1-one | dl-11a,16-dihydroxy-1-methoxymethyl-1,9-dioxo-16-methyl-2-homo-13-trans-17-trans prostadiene |
| 630 | 1-trans-iodo-4-triphenylmethoxy-1,5-nonadiene | 2-[7-methoxyacetyl heptyl]-4-trimethylsiloxy cyclopent-2-en-1-one | dl-11a,16-dihydroxy-1-methoxymethyl-1,9-dioxo-20-methyl-2-homo-13-trans-17-trans prostadiene |
| 631 | 1-trans-iodo-4-methyl-4-trimethylsilyloxy-1,5-nonadiene | 2-[7-methoxyacetyl heptyl]-4-trimethylsiloxy cyclopent-2-en-1-one | dl-11a,16-dihydroxy-1-methoxymethyl-1,9-dioxo-16-methyl-20-methyl-2-homo-13-trans-17-trans prostadiene |
| 632 | 1-trans-iodo-4-triphenylmethoxy-1,5-decadiene | 2-[7-methoxyacetyl heptyl]-4-trimethylsiloxy cyclopent-2-en-1-one | dl-11a,16-dihydroxy-1-methoxymethyl-1,9-dioxo-20-ethyl-2-homo-13-trans-17-trans prostadiene |
| 633 | 1-trans-iodo-4-methyl-4-trimethylsilyloxy-1,5-decadiene | 2-[7-methoxyacetyl heptyl]-4-trimethylsiloxy cyclopent-2-en-1-one | dl-11a,16-dihydroxy-1-methoxymethyl-1,9-dioxo-16-methyl-20-ethyl-2-homo-13-trans-17-trans prostadiene |
| 634 | 1-trans-iodo-4-triphenylmethoxy-1,5-heptadiene | 2-[6-methoxyacetyl heptyl]-4R-trimethylsiloxy cyclopent-2-en-1-one | nat-11a,16-dihydroxy-1-methoxymethyl-1,9-dioxo-20-nor-13-trans-17-trans prostadiene |
| 635 | 1-trans-iodo-4-methyl-4-trimethylsilyloxy-1,5-heptadiene | 2-[6-methoxyacetyl hexyl]-4R-trimethylsiloxy cyclopent-2-en-1-one | nat-11a,16-dihydroxy-1-methoxymethyl-1,9-dioxo-16-methyl-20-nor-13-trans-17-trans prostadiene |
| 636 | 1-trans-iodo-4-triphenylmethoxy-1,5-octadiene | 2-[6-methoxyacetyl hexyl]-4R-trimethylsiloxy cyclopent-2-en-1-one | nat-11a,16-dihydroxy-1-methoxymethyl-1,9-dioxo-13-trans-17-trans prostadiene |
| 637 | 1-trans-iodo-4-methyl-4-trimethylsilyloxy-1,5-octadiene | 2-[6-methoxyacetyl hexyl]-4R-trimethylsiloxy cyclopent-2-en-1-one | nat-11a,16-dihydroxy-1-methoxymethyl-1,9-dioxo-16-methyl-13-trans-17-trans prostadiene |
| 638 | 1-trans-iodo-4-triphenylmethoxy-1,5-nonadiene | 2-[6-methoxyacetyl hexyl]-4R-trimethylsiloxy cyclopent-2-en-1-one | nat-11a,16-dihydroxy-1-methoxymethyl-1,9-dioxo-20-methyl-13-trans-17-trans prostadiene |
| 639 | 1-trans-iodo-4-methyl-4-trimethylsilyloxy-1,5-nonadiene | 2-[6-methoxyacetyl hexyl]-4R-trimethylsiloxy cyclopent-2-en-1-one | nat-11a,16-dihydroxy-1-methoxymethyl-1,9-dioxo-16-methyl-20-methyl-13-trans-17-trans prostadiene |
| 640 | 1-trans-iodo-4-triphenylmethoxy-1,5-decadiene | 2-[6-methoxylacetyl hexyl]-4R-trimethylsiloxy cyclopent-2-en-1-one | nat-11a,16-dihydroxy-1-methoxymethyl-1,9-dioxo-20-ethyl-13-trans-17-trans prostadiene |
| 641 | 1-trans-iodo-4-methyl-4-trimethylsilyloxy-1,5-decadiene | 2-[6-methoxyacetyl hexyl]-4R-trimethylsiloxy cyclopent-2-en-1-one | nat-11a,16-dihydroxy-1-methoxymethyl-1,9-dioxo-16-methyl-20-ethyl-13-trans-17-trans prostadiene |

TABLE I-continued

| | | |
|---|---|---|
| 642 | 1-trans-iodo-4-triphenylmethoxy-1,5-heptadiene | 2-[5-methoxyacetyl cyclopent-2-en-1-one pentyl] | dl-16-hydroxy-1-methoxymethyl-1,9-dioxo-20-nor-2-nor-13-trans-17-trans prostadiene |
| 643 | 1-trans-iodo-4-methyl-4-trimethylsilyloxy-1,5-heptadiene | 2-[5-methoxyacetyl cyclopent-2-en-1-one pentyl] | dl-16-hydroxy-1-methoxymethyl-1,9-dioxo-16-methyl-20-nor-2-nor-13-trans-17-trans prostadiene |
| 644 | 1-trans-iodo-4-triphenylmethoxy-1,5-octadiene | 2-[5-methoxyacetyl cyclopent-2-en-1-one pentyl] | dl-16-hydroxy-1-methoxymethyl-1,9-dioxo-2-nor-13-trans-17-trans prostadiene |
| 645 | 1-trans-iodo-4-methyl-4-trimethylsilyloxy-1,5-octadiene | 2-[5-methoxyacetyl cyclopent-2-en-1-one pentyl] | dl-16-hydroxy-1-methoxymethyl-1,9-dioxo-16-methyl-2-nor-13-trans-17-trans prostadiene |
| 646 | 1-trans-iodo-4-triphenylmethoxy-1,5-nonadiene | 2-[5-methoxyacetyl cyclopent-2-en-1-one pentyl] | dl-16-hydroxy-1-methoxymethyl-1,9-dioxo-20-methyl-2-nor-13-trans-17-trans prostadiene |
| 647 | 1-trans-iodo-4-methyl-4-trimethylsilyloxy-1,5-nonadiene | 2-[5-methoxyacetyl cyclopent-2-en-1-one pentyl] | dl-16-hydroxy-1-methoxymethyl-1,9-dioxo-16-methyl-20-methyl-2-nor-13-trans-17-trans prostadiene |
| 648 | 1-trans-iodo-4-triphenylmethoxy-1,5-decadiene | 2-[5-methoxyacetyl cyclopent-2-en-1-one pentyl] | dl-16-hydroxy-1-methoxymethyl-1,9-dioxo-2-ethyl-2-nor-13-trans-17-trans prostadiene |
| 649 | 1-trans-iodo-4-methyl-4-trimethylsilyloxy-1,5-decadiene | 2-[5-methoxyacetyl cyclopent-2-en-1-one pentyl] | dl-16-hydroxy-1-methoxymethyl-1,9-dioxo-16-methyl-2-ethyl-2-nor-13-trans-17-trans prostadiene |
| 650 | 1-trans-iodo-4-triphenylmethoxy-1,5-heptadiene | 2-[6-methoxyacetyl cyclopent-2-en-1-one hexyl] | dl-16-hydroxy-1-methoxymethyl-1,9-dioxo-20-nor-13-trans-17-trans prostadiene |
| 651 | 1-trans-iodo-4-methyl-4-trimethylsilyloxy-1,5-heptadiene | 2-[6-methoxyacetyl cyclopent-2-en-1-one hexyl] | dl-16-hydroxy-1-methoxymethyl-1,9-dioxo-16-methyl-20-nor-13-trans-17-trans prostadiene |
| 652 | 1-trans-iodo-4-triphenylmethoxy-1,5-octadiene | 2-[6-methoxyacetyl cyclopent-2-en-1-one hexyl] | dl-16-hydroxy-1-methoxymethyl-1,9-dioxo-13-trans-17-trans prostadiene |
| 653 | 1-trans-iodo-4-methyl-4-trimethylsilyloxy-1,5-octadiene | 2-[6-methoxyacetyl cyclopent-2-en-1-one hexyl] | dl-16-hydroxy-1-methoxymethyl-1,9-dioxo-16-methyl-13-trans-17-trans prostadiene |
| 654 | 1-trans-iodo-4-triphenylmethoxy-1,5-nonadiene | 2-[6-methoxyacetyl cyclopent-2-en-1-one hexyl] | dl-16-hydroxy-1-methoxymethyl-1,9-dioxo-20-methyl-13-trans-17-trans prostadiene |
| 655 | 1-trans-iodo-4-methyl-4-trimethylsilyloxy-1,5-nonadiene | 2-[6-methoxyacetyl cyclopent-2-en-1-one hexyl] | dl-16-hydroxy-1-methoxymethyl-1,9-dioxo-16-methyl-20-methyl-13-trans-17-trans prostadiene |
| 656 | 1-trans-iodo-4-triphenylmethoxy-1,5-decadiene | 2-[6-methoxyacetyl cyclopent-2-en-1-one hexyl] | dl-16-hydroxy-1-methoxymethyl-1,9-dioxo-20-ethyl-13-trans-17-trans prostadiene |
| 657 | 1-trans-iodo-4-methyl-4-trimethylsilyloxy-1,5-decadiene | 2-[6-methoxyacetyl cyclopent-2-en-1-one hexyl] | dl-16-hydroxy-1-methoxymethyl-1,9-dioxo-16-methyl-20-ethyl-13-trans-17-trans prostadiene |
| 658 | 1-trans-iodo-4-triphenylmethoxy-1,5-heptadiene | 2-[7-methoxyacetyl heptyl] cyclopent-2-en-1-one | dl-16-hydroxy-1-methoxymethyl-1,9-dioxo-20-nor-2-homo-13-trans-17-trans prostadiene |
| 659 | 1-trans-iodo-4-methyl-4-trimethylsilyloxy-1,5-heptadiene | 2-[7-methoxyacetyl heptyl] cyclopent-2-en-1-one | dl-16-hydroxy-1-methoxymethyl-1,9-dioxo-16-methyl-20-nor-2-homo-13-trans-17-trans prostadiene |

TABLE I-continued

| EXAMPLE | VINYL IODIDE | CYCLOPENTENONE | PRODUCT PROSTAGLANDIN OF THE PGE1 SERIES |
|---|---|---|---|
| 660 | 1-trans-iodo-4-triphenylmethoxy-1,5-octadiene | 2-[7-methoxyacetyl heptyl] cyclopent-2-en-1-one | dl-16-hydroxy-1-methoxymethyl-1,9-dioxo-2-homo-13-trans-17-trans prostadiene |
| 661 | 1-trans-iodo-4-methyl-4-trimethylsilyloxy-1,5-octadiene | 2-[7-methoxyacetyl heptyl] cyclopent-2-en-1-one | dl-16-hydroxy-1-methoxymethyl-1,9-dioxo-16-methyl-2-homo-13-trans-17-trans prodtadiene |
| 662 | 1-trans-iodo-4-triphenylmethoxy-1,5-nonadiene | 2-[7-methoxyacetyl heptyl] cyclopent-2-en-1-one | dl-16-hydroxy-1-methoxymethyl-1,9-dioxo-20-methyl-2-homo-13-trans-17-trans prostadiene |
| 663 | 1-trans-iodo-4-methyl-4-trimethylsilyloxy-1,5-nonadiene | 2-[7-methoxyacetyl heptyl] cyclopent-2-en-1-one | dl-16-hydroxy-1-methoxymethyl-1,9-dioxo-16-methyl-20-methyl-2-homo-13-trans-17-trans prostadiene |
| 664 | 1-trans-iodo-4-triphenylmethoxy-1,5-decadiene | 2-[7-methoxyacetyl heptyl] cyclopent-2-en-1-one | dl-16-hydroxy-1-methoxymethyl-1,9-dioxo-20-ethyl-2-homo-13-trans-17-trans prostadiene |
| 665 | 1-trans-iodo-4-methyl-4-trimethylsilyloxy-1,5-decadiene | 2-[7-methoxyacetyl heptyl] cyclopent-2-en-1-one | dl-16-hydroxy-1-methoxymethyl-1,9-dioxo-16-methyl-20-ethyl-2-homo-13-trans-17-trans prostadiene |
| EXAMPLE | VINYL IODIDE | CYCLOPENTENONE | PRODUCT PROSTAGLANDIN OF THE PGE1 SERIES |
| 666 | 1-trans ertho-iodo-3,4-isopropylidenedioxy-1-heptene | 2-[5-methoxyacetyl pentyl]-4-trimethylsiloxy cyclopent-2-en-1-one | dl erthro-11a,15a,16-trihydroxy-1-methoxymethyl-1,9-dioxo-20-nor-2-nor-13-trans prostene |
| 667 | 1-trans erthro-iodo-3,4-isopropylidenedioxy-1-octene | 2-[5-methoxyacetyl pentyl]-4-trimethylsiloxy cyclopent-2-en-1-one | dl erthro-11a,15a,16-trihydroxy-1-methoxymethyl-1,9-dioxo-2-nor-13-trans prostene |
| 668 | 1-trans erthro-iodo-3,4-isopropylidenedioxy-1-nonene | 2-[5-methoxyacetyl pentyl]-4-trimethylsiloxy cyclopent-2-en-1-one | dl erthro-11a,15a,16-trihydroxy-1-methoxymethyl-1,9-dioxo-20-methyl-2-nior-13-trans prostene |
| 669 | 1-trans erthro-iodo-3,4-isopropylidenedioxy-1-decene | 2-[5-methoxyacetyl pentyl]-4-trimethylsiloxy cyclopent-2-en-1-one | dl erthro-11a,15a,16-trihydroxy-1-methoxymethyl-1,9-dioxo-20-ethyl-2-nor-13-trans prostene |
| 670 | 1-trans erthro-iodo-3,4-isopropylidenedioxy-1-heptene | 2-[6-methoxyacetyl hexyl]-4-trimethylsiloxy cyclopent-2-en-1-one | dl erthro-11a,15a,16-trihydroxy-1-methoxymethyl-1,9-dioxo-20-nor-13-trans prostene |
| 671 | 1-trans erthro-iodo-3,4-isopropylidenedioxy-1-octene | 2-[6-methoxyacetyl hexyl]-4-trimethylsiloxy cyclopent-2-en-1-one | dl erthro-11a,15a,16-trihydroxy-1-methoxymethyl-1,9-dioxo-13-trans prostene |
| 672 | 1-trans erthro-iodo-3,4-isopropylidenedioxy-1-nonene | 2-[6-methoxyacetyl hexyl]-4-trimethylsiloxy cyclopent-2-en-1-one | dl erthro-11a,15a,16-trihydroxy-1-methoxymethyl-1,9-dioxo-20-methyl-13-trans prostene |
| 673 | 1-trans erthro-iodo-3,4-isopropylidenedioxy-1-decene | 2-[6-methoxyacetyl hexyl]-4-trimethylsiloxy cyclopent-2-en-1-one | dl erthro-11a,15a,16-trihydroxy-1-methoxymethyl-1,9-dioxo-20-ethyl-13-trans prostene |
| 674 | 1-trans erthro-iodo-3,4-isopropylidenedioxy-1-heptene | 2-[7-methoxyacetyl heptyl]-4-trimethylsiloxy cyclopent-2-en-1-one | dl erthro-11a,15a,16-trihydroxy-1-methoxymethyl-1,9-dioxo-20-nor-2-homo-13-trans prostene |
| 675 | 1-trans erthro-iodo-3,4-isopropylidenedioxy-1-octene | 2-[7-methoxyacetyl heptyl]-4-trimethylsiloxy cyclopent-2-en-1-one | dl erthro-11a,15a,16-trihydroxy-1-methoxymethyl-1,9-dioxo-2-homo-13-trans prostene |
| 676 | 1-trans erthro-iodo-3,4-isopropylidenedioxy-1-nonene | 2-[7-methoxyacetyl heptyl]-4-trimethylsiloxy cyclopent-2-en-1-one | dl erthro-11a,15a,16-trihydroxy-1-methoxymethyl-1,9-dioxo-20-methyl-2-homo-13-trans prostene |

TABLE I-continued

| EXAMPLE | VINYL IODIDE | CYCLOPENTENONE | PRODUCT |
|---|---|---|---|
| 677 | 1-trans erthro-iodo-3,4-isopropylidenedioxy-1-decene | 2-[7-methoxyacetyl heptyl]-4-trimethylsiloxy cyclopent-2-en-1-one | dl erthro-11a,15a,16-trihydroxy-1-methoxymethyl-1,9-dioxo-20-ethyl-2-homo-13-trans prostene |
| 678 | 1-trans erthro-iodo-3,4-isopropylidenedioxy-1-heptene | 2-[6-methoxyacetyl hexyl]-4R-trimethylsiloxy cyclopent-2-en-1-one | nat erthro-11a,15a,16-trihydroxy-1-methoxymethyl-1,9-dioxo-20-nor-13-trans prostene |
| 679 | 1-trans erthro-iodo-3,4-isopropylidenedioxy-1-octene | 2-[6-methoxyacetyl hexyl]-4R-trimethylsiloxy cyclopent-2-en-1-one | nat erthro-11a,15a,16-trihydroxy-1-methoxymethyl-1,9-dioxo-13-trans prostene |
| 680 | 1-trans erthro-iodo-3,4-isopropylidenedioxy-1-nonene | 2-[6-methoxyacetyl hexyl]-4R-trimethylsiloxy cyclopent-2-en-1-one | nat erthro-11a,15a,16-trihydroxy-1-methoxymethyl-1,9-dioxo-20-methyl-13-trans prostene |
| 681 | 1-trans erthro-iodo-3,4-isopropylidenedioxy-1-decene | 2-[6-methoxyacetyl hexyl]-4R-trimethylsiloxy cyclopent-2-en-1-one | nat erthro-11a,15a,16-trihydroxy-1-methoxymethyl-1,9-dioxo-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 682 | 1-trans erthro-iodo-3,4-isopropylidenedioxy-1-heptene | 2-[5-methoxyacetyl pentyl] cyclopent-2-en-1-one | dl erthro-15a,16-dihydroxy-1-methoxymethyl-1,9-dioxo-20-nor-2-nor-13-trans prostene |
| 683 | 1-trans erthro-iodo-3,4-isopropylidenedioxy-1-octene | 2-[5-methoxyacetyl pentyl] cyclopent-2-en-1-one | dl erthro-15a,16-dihydroxy-1-methoxymethyl-1,9-dioxo-2-nor-13-trans prostene |
| 684 | 1-trans erthro-iodo-3,4-isopropylidenedioxy-1-nonene | 2-[5-methoxyacetyl pentyl] cyclopent-2-en-1-one | dl erthro-15a,16-dihydroxy-1-methoxymethyl-1,9-dioxo-2-methyl-2-nor-13-trans prostene |
| 685 | 1-trans erthro-iodo-3,4-isopropylidenedioxy-1-decene | 2-[5-methoxyacetyl pentyl] cyclopent-2-en-1-one | dl erthro-15a,16-dihydroxy-1-methoxymethyl-1,9-dioxo-2-ethyl-2-nor-13-trans prostene |
| 686 | 1-trans erthro-iodo-3,4-isopropylidenedioxy-1-heptene | 2-[6-methoxyacetyl hexyl] cyclopent-2-en-1-one | dl erthro-15a,16-dihydroxy-1-methoxymethyl-1,9-dioxo-20-nor-13-trans prostene |
| 687 | 1-trans erthro-iodo-3,4-isopropylidenedioxy-1-octene | 2-[6-methoxyacetyl hexyl] cyclopent-2-en-1-one | dl erthro-15a,16-dihydroxy-1-methoxymethyl-1,9-dioxo-13-trans prostene |
| 688 | 1-trans erthro-iodo-3,4-isopropylidenedioxy-1-nonene | 2-[6-methoxyacetyl hexyl] cyclopent-2-en-1-one | dl erthro-15a,16-dihydroxy-1-methoxymethyl-1,9-dioxo-20-methyl-13-trans prostene |
| 689 | 1-trans erthro-iodo-3,4-isopropylidenedioxy-1-decene | 2-[6-methoxyacetyl hexyl] cyclopent-2-en-1-one | dl erthro-15a,16-dihydroxy-1-methoxymethyl-1,9-dioxo-20-ethyl-13-trans prostene |
| 690 | 1-trans erthro-iodo-3,4-isopropylidenedioxy-1-heptene | 2-[7-methoxyacetyl heptyl] cyclopent-2-en-1-one | dl erthro-15a,16-dihydroxy-1-methoxymethyl-1,9-dioxo-20-nor-2-homo-13-trans prostene |
| 691 | 1-trans erthro-iodo-3,4-isopropylidenedioxy-1-octene | 2-[7-methoxyacetyl heptyl] cyclopent-2-en-1-one | dl erthro-15a,16-dihydroxy-1-methoxymethyl-1,9-dioxo-2-homo-13-trans prostene |
| 692 | 1-trans erthro-iodo-3,4-isopropylidenedioxy-1-nonene | 2-[7-methoxyacetyl heptyl] cyclopent-2-en-1-one | dl erthro-15a,16-dihydroxy-1-methoxymethyl-1,9-dioxo-20-methyl-2-homo-13-trans prostene |
| 693 | 1-trans erthro-iodo-4-methoxy-3-trimethylsilyloxy-1-decene | 2-[7-methoxyacetyl heptyl] cyclopent-2-en-1-one | dl erthro-15a-hydroxy-1-methoxymethyl-1,9-dioxo-16-methoxy-20-ethyl-2-homo-13-trans prostene |

4,297,516

TABLE I-continued

| EXAMPLE | VINYL IODIDE | CYCLOPENTENONE | PRODUCT PROSTAGLANDIN OF THE PGE1 SERIES |
|---|---|---|---|
| 694 | 1-trans three-iodo-3,4-isopropylidenedioxy-1-heptene | 2-[5-methoxyacetyl pentyl]-4-trimethylsiloxy cyclopent-2-en-1-one | dl threo-11a,15a,16-trihydroxy-1-methoxymethyl-1,9-dioxo-20-nor-2-nor-13-trans prostene |
| 695 | 1-trans three-iodo-3,4-isopropylidenedioxy-1-octene | 2-[5-methoxyacetyl pentyl]-4-trimethylsiloxy cyclopent-2-en-1-one | dl threo-11a,15a,16-trihydroxy-1-methoxymethyl-1,9-dioxo-2-nor-13-trans prostene |
| 696 | 1-trans three-iodo-3,4-isopropylidenedioxy-1-nonene | 2-[5-methoxyacetyl pentyl]-4-trimethylsiloxy cyclopent-2-en-1-one | dl threo-11a,15a,16-trihydroxy-1-methoxymethyl-1,9-dioxo-20-methyl-2-nor-13-trans prostene |
| 697 | 1-trans three-iodo-3,4-isopropylidenedioxy-1-decene | 2-[5-methoxyacetyl pentyl]-4-trimethylsiloxy cyclopent-2-en-1-one | dl threo-11a,15a,16-trihydroxy-1-methoxymethyl-1,9-dioxo-20-ethyl-2-nor-13-trans prostene |
| 698 | 1-trans three-iodo-3,4-isopropylidenedioxy-1-heptene | 2-[6-methoxyacetyl hexyl]-4-trimethylsiloxy cyclopent-2-en-1-one | dl threo-11a,15a,16-trihydroxy-1-methoxymethyl-1,9-dioxo-20-nor-13-trans prostene |
| 699 | 1-trans three-iodo-3,4-isopropylidenedioxy-1-octene | 2-[6-methoxyacetyl hexyl]-4-trimethylsiloxy cyclopent-2-en-1-one | dl threo-11a,15a,16-trihydroxy-1-methoxymethyl-1,9-dioxo-13-trans prostene |
| 700 | 1-trans three-iodo-3,4-isopropylidenedioxy-1-nonene | 2-[6-methoxyacetyl hexyl]-4-trimethylsiloxy cyclopent-2-en-1-one | dl threo-11a,15a,16-trihydroxy-1-methoxymethyl-1,9-dioxo-20-methyl-13-trans prostene |
| 701 | 1-trans three-iodo-3,4-isopropylidenedioxy-1-decene | 2-[6-methoxyacetyl hexyl]-4-trimethylsiloxy cyclopent-2-en-1-one | dl threo-11a,15a,16-trihydroxy-1-methoxymethyl-1,9-dioxo-20-ethyl-13-trans prostene |
| 702 | 1-trans three-iodo-3,4-isopropylidenedioxy-1-heptene | 2-[7-methoxyacetyl heptyl]-4-trimethylsiloxy cyclopent-2-en-1-one | dl threo-11a,15a,16-trihydroxy-1-methoxymethyl-1,9-dioxo-20-nor-2-homo-13-trans prostene |
| 703 | 1-trans three-iodo-3,4-isopropylidenedioxy-1-octene | 2-[7-methoxyacetyl heptyl]-4-trimethylsiloxy cyclopent-2-en-1-one | dl threo-11a,15a,16-trihydroxy-1-methoxymethyl-1,9-dioxo-2-homo-13-trans prostene |
| 704 | 1-trans three-iodo-3,4-isopropylidenedioxy-1-nonene | 2-[7-methoxyacetyl heptyl]-4-trimethylsiloxy cyclopent-2-en-1-one | dl threo-11a,15a,16-trihydroxy-1-methoxymethyl-1,9-dioxo-20-methyl-2-homo-13-trans prostene |
| 705 | 1-trans three-iodo-3,4-isopropylidenedioxy-1-decene | 2-[7-methoxyacetyl heptyl]-4-trimethylsiloxy cyclopent-2-en-1-one | dl threo-11a,15a,16-trihydroxy-1-methoxymethyl-1,9-dioxo-20-ethyl-2-homo-13-trans prostene |
| 706 | 1-trans three-iodo-3,4-isopropylidenedioxy-1-heptene | 2-[6-methoxyacetyl hexyl]-4R-trimethylsiloxy cyclopent-2-en-1-one | nat threo-11a,15a,16-trihydroxy-1-methoxymethyl-1,9-dioxo-20-nor-13-trans prostene |
| 707 | 1-trans three-iodo-3,4-isopropylidenedioxy-1-octene | 2-[6-methoxyacetyl hexyl]-4R-trimethylsiloxy cyclopent-2-en-1-one | nat threo-11a,15a,16-trihydroxy-1-methoxymethyl-1,9-dioxo-13-trans prostene |
| 708 | 1-trans three-iodo-3,4-isopropylidenedioxy-1-nonene | 2-[6-methoxyacetyl hexyl]-4R-trimethylsiloxy cyclopent-2-en-1-one | nat threo-11a,15a,16-trihydroxy-1-methoxymethyl-1,9-dioxo-20-methyl-13-trans prostene |
| 709 | 1-trans three-iodo-3,4-isopropylidenedioxy-1-decene | 2-[6-methoxyacetyl hexyl]-4R-trimethylsiloxy cyclopent-2-en-1-one | nat threo-11a,15a,16-trihydroxy-1-methoxymethyl-1,9-dioxo-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 710 | 1-trans three-iodo-3,4-isopropylidenedioxy-1-heptene | 2-[5-methoxyacetyl pentyl] | dl threo-15a,16-dihydroxy-1-methoxymethyl-1,9-dioxo-20-nor-2-nor-13-trans prostene |

TABLE I-continued

| | VINYL IODIDE | CYCLOPENTENONE | PRODUCT PROSTAGLANDIN OF THE PGE1 SERIES |
|---|---|---|---|
| 711 | 1-trans three-iodo-3,4-isopropylidenedioxy-1-octene | 2-[5-methoxyacetyl pentyl]-cyclopent-2-en-1-one | dl threo-15a,16-dihydroxy-1-methoxymethyl-1,9-dioxo-2-nor-13-trans prostene |
| 712 | 1-trans three-iodo-3,4-isopropylidenedioxy-1-nonene | 2-[5-methoxyacetyl pentyl]-cyclopent-2-en-1-one | dl threo-15a,16-dihydroxy-1-methoxymethyl-1,9-dioxo-20-methyl-2-nor-13-trans prostene |
| 713 | 1-trans three-iodo-3,4-isopropylidenedioxy-1-decene | 2-[5-methoxyacetyl pentyl]-cyclopent-2-en-1-one | dl threo-15a,16-dihydroxy-1-methoxymethyl-1,9-dioxo-20-ethyl-2-nor-13-trans prostene |
| 714 | 1-trans three-iodo-3,4-isopropylidenedioxy-1-heptene | 2-[6-methoxyacetyl hexyl]-cyclopent-2-en-1-one | dl threo-15a,16-dihydroxy-1-methoxymethyl-1,9-dioxo-20-nor-13-trans prostene |
| 715 | 1-trans three-iodo-3,4-isopropylidenedioxy-1-octene | 2-[6-methoxyacetyl hexyl]-cyclopent-2-en-1-one | dl threo-15a,16-dihydroxy-1-methoxymethyl-1,9-dioxo-13-trans prostene |
| 716 | 1-trans three-iodo-3,4-isopropylidenedioxy-1-nonene | 2-[6-methoxyacetyl hexyl]-cyclopent-2-en-1-one | dl threo-15a,16-dihydroxy-1-methoxymethyl-1,9-dioxo-20-methyl-2-nor-13-trans prostene |
| 717 | 1-trans three-iodo-3,4-isopropylidenedioxy-1-decene | 2-[6-methoxyacetyl hexyl]-cyclopent-2-en-1-one | dl threo-15a,16-dihydroxy-1-methoxymethyl-1,9-dioxo-20-ethyl-13-trans prostene |
| 718 | 1-trans three-iodo-3,4-isopropylidenedioxy-1-heptene | 2-[7-methoxyacetyl heptyl]-cyclopent-2-en-1-one | dl threo-15a,16-dihydroxy-1-methoxymethyl-1,9-dioxo-20-nor-2-homo-13-trans prostene |
| 719 | 1-trans three-iodo-3,4-isopropylidenedioxy-1-octene | 2-[7-methoxyacetyl heptyl]-cyclopent-2-en-1-one | dl threo-15a,16-dihydroxy-1-methoxymethyl-1,9-dioxo-2-homo-13-trans prostene |
| 720 | 1-trans three-iodo-3,4-isopropylidenedioxy-1-nonene | 2-[7-ethoxyacetyl heptyl]-cyclopent-2-en-1-one | dl threo-15a,16-dihydroxy-1-methoxymethyl-1,9-dioxo-20-methyl-2-homo-13-trans prostene |
| 721 | 1-trans three-iodo-3,4-isopropylidenedioxy-1-decene | 2-[7-methoxyacetyl heptyl]-cyclopent-2-en-1-one | dl threo-15a,16-dihydroxy-1-methoxymethyl-1,9-dioxo-20-ethyl-2-homo-13-trans prostene |
| EXAMPLE | VINYL IODIDE | CYCLOPENTENONE | PRODUCT PROSTAGLANDIN OF THE PGE1 SERIES |
| 722 | 1-trans erthro-iodo-4-methoxy 3-trimethylsilyloxy-1-heptene | 2-[5-methoxyacetyl pentyl]-4-trimethylsilyloxy cyclopent-2-en-1-one | dl erthro-11a,15a-dihydroxy-1-methoxymethyl-1,9-dioxo-16-methoxy-20-nor-2-nor-13-trans prostene |
| 723 | 1-trans erthro-iodo-4-methoxy 3-trimethylsilyloxy-1-octene | 2-[5-methoxyacetyl pentyl]-4-trimethylsilyloxy cyclopent-2-en-1-one | dl erthro-11a,15a-dihydroxy-1-methoxymethyl-1,9-dioxo-16-methoxy-2-nor-13-trans prostene |
| 724 | 1-trans erthro-iodo-4-methoxy 3-trimethylsilyloxy-1-nonene | 2-[5-methoxyacetyl pentyl]-4-trimethylsilyloxy cyclopent-2-en-1-one | dl erthro-11a,15a-dihydroxy-1-methoxymethyl-1,9-dioxo-16-methoxy-20-methyl-2-nor-13-trans prostene |
| 725 | 1-trans erthro-iodo-4-methoxy 3-trimethylsilyloxy-1-decene | 2-[5-methoxyacetyl pentyl]-4-trimethylsilyloxy cyclopent-2-en-1-one | dl erthro-11a,15a-dihydroxy-1-methoxymethyl-1,9-dioxo-16-methoxy-20-ethyl-2-nor-13-trans prostene |
| 726 | 1-trans erthro-iodo-4-methoxy 3-trimethylsilyloxy-1-heptene | 2-[6-methoxyacetyl hexyl]-4-trimethylsiloxy cyclopent-2-en-1-one | dl erthro-11a,15a-dihydroxy-1-methoxymethyl-1,9-dioxo-16-methoxy-20-nor-13-trans prostene |
| 727 | 1-trans erthro-iodo-4-methoxy 3-trimethylsilyloxy-1-octene | 2-[6-methoxyacetyl hexyl]-4-trimethylsilyloxy cyclopent-2-en-1-one | dl erthro-11a,15a-dihydroxy-1-methoxymethyl-1,9-dioxo-16-methoxy-13-trans prostene |

TABLE I-continued

| EXAMPLE | VINYL IODIDE | CYCLOPENTENONE | PRODUCT PROSTAGLANDIN OF THE 11-DEOXY PGE1 SERIES |
|---|---|---|---|
| 728 | 1-trans erthro-iodo-4-methoxy 3-trimethylsilyloxy-1-nonene | 2-[6-methoxyacetyl hexyl]-4-trimethylsiloxy cyclopent-2-en-1-one | dl erthro-11a,15a-dihydroxy-1-methoxymethyl-1,9-dioxo-16-methoxy-20-methyl-13-trans prostene |
| 729 | 1-trans erthro-iodo-4-methoxy 3-trimethylsilyloxy-1-nonene | 2-[6-methoxyacetyl hexyl]-4-trimethylsiloxy cyclopent-2-en-1-one | dl erthro-11a,15a-dihydroxy-1-methoxymethyl-1,9-dioxo-16-methoxy-20-methyl-13-trans prostene |
| 730 | 1-trans erthro-iodo-4-methoxy 3-trimethylsilyloxy-1-heptene | 2-[7-methoxyacetyl heptyl]-4-trimethylsiloxy cyclopent-2-en-1-one | dl erthro-11a,15a-dihydroxy-1-methoxymethyl-1,9-dioxo-16-methoxy-20-nor-2-homo-13-trans prostene |
| 731 | 1-trans erthro-iodo-4-methoxy 3-trimethylsilyloxy-1-octene | 2-[7-methoxyacetyl heptyl]-4-trimethylsiloxy cyclopent-2-en-1-one | dl erthro-11a,15a-dihydroxy-1-methoxymethyl-1,9-dioxo-16-methoxy-2-homo-13-trans prostene |
| 732 | 1-trans erthro-iodo-4-methoxy 3-trimethylsilyloxy-1-nonene | 2-[7-methoxyacetyl heptyl]-4-trimethylsiloxy cyclopent-2-en-1-one | dl erthro-11a,15a-dihydroxy-1-methoxymethyl-1,9-dioxo-16-methoxy-20-methyl-2-homo-13-trans prostene |
| 733 | 1-trans erthro-iodo-4-methoxy 3-trimethylsilyloxy-1-decene | 2-[7-methoxyacetyl heptyl]-4-trimethylsiloxy cyclopent-2-en-1-one | dl erthro-11a,15a-dihydroxy-1-methoxymethyl-1,9-dioxo-16-methoxy-20-methyl-2-homo-13-trans prostene |
| 734 | 1-trans erthro-iodo-4-methoxy 3-trimethylsilyloxy-1-heptene | 2-[6-methoxyacetyl hexyl]-4R-trimethylsiloxy cyclopent-2-en-1-one | nat erthro-11a,15a-dihydroxy-1-methoxymethyl-1,9-dioxo-16-methoxy-20-nor-13-trans prostene |
| 735 | 1-trans erthro-iodo-4-methoxy 3-trimethylsilyloxy-1-octene | 2-[6-methoxyacetyl hexyl]-4R-trimethylsiloxy cyclopent-2-en-1-one | nat erthro-11a,15a-dihydroxy-1-methoxymethyl-1,9-dioxo-16-methoxy-13-trans prostene |
| 736 | 1-trans erthro-iodo-4-methoxy 3-trimethylsilyloxy-1-nonene | 2-[6-methoxyacetyl hexyl]-4R-trimethylsiloxy cyclopent-2-en-1-one | nat erthro-11a,15a-dihydroxy-1-methoxymethyl-1,9-dioxo-16-methoxy-20-methyl-13-trans prostene |
| 737 | 1-trans erthro-iodo-4-methoxy 3-trimethylsilyloxy-1-decene | 2-[6-methoxyacetyl hexyl]-4R-trimethylsiloxy cyclopent-2-en-1-one | nat erthro-11a,15a-dihydroxy-1-methoxymethyl-1,9-dioxo-16-methoxy-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 738 | 1-trans erthro-iodo-4-methoxy 3-trimethylsilyloxy-1-heptene | 2-[5-methoxyacetyl pentyl] cyclopent-2-en-1-one | dl erthro-11a,15a-hydroxy-1-methoxymethyl-1,9-dioxo-16-methoxy-20-nor-2-nor-13-trans prostene |
| 739 | 1-trans erthro-iodo-4-methoxy 3-trimethylsilyloxy-1-octene | 2-[5-methoxyacetyl pentyl]-cyclopent-2-en-1-one | dl erthro-15a-hydroxy-1-methoxymethyl-1,9-dioxo-16-methoxy-2-nor-13-trans prostene |
| 740 | 1-trans erthro-iodo-4-methoxy 3-trimethylsilyloxy-1-nonene | 2-[5-methoxyacetyl pentyl]-cyclopent-2-en-1-one | dl erthro-15a-hydroxy-1-methoxymethyl-1,9-dioxo-16-methoxy-20-methyl-2-nor-13-trans prostene |
| 741 | 1-trans erthro-iodo-4-methoxy 3-trimethylsilyloxy-1-decene | 2-[5-methoxyacetyl pentyl]-cyclopent-2-en-1-one | dl erthro-15a-hydroxy-1-methoxymethyl-1,9-dioxo-16-methoxy-20-ethyl-2-nor-13-trans prostene |
| 742 | 1-trans erthro-iodo-4-methoxy 3-trimethylsilyloxy-1-heptene | 2-[6-methoxyacetyl hexyl]-cyclopent-2-en-1-one | dl erthro-15a-hydroxy-1-methoxymethyl-1,9-dioxo-16-methoxy-20-nor-13-trans prostene |
| 743 | 1-trans erthro-iodo-4-methoxy 3-trimethylsilyloxy-1-octene | 2-[6-methoxyacetyl hexyl]-cyclopent-2-en-1-one | dl erthro-15a-hydroxy-1-methoxymethyl-1,9-dioxo-16-methoxy-13-trans prostene |
| 744 | 1-trans erthro-iodo-4-methoxy 3-trimethylsilyloxy-1-nonene | 2-[6-methoxyacetyl hexyl]-cyclopent-2-en-1-one | dl erthro-15a-hydroxy-1-methoxymethyl-1,9-dioxo-16-methoxy-20-methyl-13-trans prostene |

TABLE I-continued

| | | | |
|---|---|---|---|
| 745 | 1-trans erthro-iodo-4-methoxy 3-trimethylsilyloxy-1-decene | cyclopent-2-en-1-one 2-[6-methoxyacetyl hexyl] | dl erthro-15a-hydroxy-1-methoxymethyl-1,9-dioxo-16-methoxy-20-ethyl-13-trans prostene |
| 746 | 1-trans erthro-iodo-4-methoxy 3-trimethylsilyloxy-1-heptene | cyclopent-2-en-1-one 2-[7-methoxyacetyl heptyl]- | dl erthro-15a-hydroxy-1-methoxymethyl-1,9-dioxo-16-methoxy-20-nor-2-homo-13-trans prostene |
| 747 | 1-trans erthro-iodo-4-methoxy 3-trimethylsilyloxy-1-octene | cyclopent-2-en-1-one 2-[7-methoxyacetyl heptyl]- | dl erthro-15a-hydroxy-1-methoxymethyl-1,9-dioxo-16-methoxy-2-homo-13-trans prostene |
| 748 | 1-trans erthro-iodo-4-methoxy 3-trimethylsilyloxy-1-nonene | cyclopent-2-en-1-one 2-[7-methoxyacetyl heptyl]- | dl erthro-15a-hydroxy-1-methoxymethyl-1,9-dioxo-16-methoxy-20-methyl-2-homo-13-trans prostene |
| 749 | 1-trans erthro-iodo-3,4-isopropylidendioxy-1-decene | cyclopent-2-en-1-one | dl erthro-15a,16-dihydroxy-1-methoxymethyl-1,9-dioxo-20-ethyl-2-homo-13-trans prostene |

TABLE IA

| EXAMPLE | VINYL TIN / VINYL IODIDE | CYCLOPENTENONE | PRODUCT PROSTAGLANDIN OF THE PGE1 SERIES |
|---|---|---|---|
| 1 | VINYL TIN<br>1-trans-tri-n-butylstannyl-7-thia-4-triethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-19-thia-2-nor-13-trans prostene |
| 2 | VINYL TIN<br>1-trans-tri-n-butylstannyl-4-methyl-7-thia-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-19-thia-2-nor-13-trans prostene |
| 3 | VINYL TIN<br>1-trans-tri-n-butylstannyl-7-oxa-4-triethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-19-oxa-2-nor-13-trans prostene |
| 4 | VINYL TIN<br>1-trans-tri-n-butylstannyl-4-methyl-7-oxa-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-19-oxa-2-nor-13-trans prostene |
| 5 | VINYL TIN<br>1-trans-tri-n-butylstannyl-4-bromomethyl-4-trimethylsilyloxy-1-heptene | 2-[5-methoxyacetyl pentyl]-4-trimethylsilyloxy cyclopent-2-en-1-one | dl-11a,16-dihydroxy-1-methoxymethyl-1,9-dioxo-16-bromomethyl-20-nor-2-nor-13-trans prostene |
| EXAMPLE | VINYL IODIDE | CYCLOPENTENONE | PRODUCT PROSTAGLANDIN OF THE PGE1 SERIES |
| 6 | 1-trans-iodo-4-allenyl-4-trimethylsilyloxy-1-heptene | 2-[5-methoxyacetyl pentyl]-4-trimethylsilyloxy cyclopent-2-en-1-one | dl-11a,16-dihydroxy-1-methoxymethyl-1,9-dioxo-16-allenyl-20-nor-2-nor-13-trans prostene |
| EXAMPLE | VINYL TIN | CYCLOPENTENONE | PRODUCT PROSTAGLANDIN OF THE PGE1 SERIES |
| 7 | 1-trans-tri-n-butylstannyl-4-bromomethyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-bromomethyl-2-nor-13-trans prostene |
| EXAMPLE | VINYL IODIDE | CYCLOPENTENONE | PRODUCT PROSTAGLANDIN OF THE PGE1 SERIES |
| 8 | 1-trans-iodo-4-allenyl-4-trimethylsilyloxy-1-octene | 2-[5-methoxyacetyl pentyl]-4-trimethylsilyloxy cyclopent-2-en-1-one | dl-11a,16-dihydroxy-1-methoxymethyl-1,9-dioxo-16-allenyl-2-nor-13-trans prostene |
| EXAMPLE | VINYL TIN | CYCLOPENTENONE | PRODUCT PROSTAGLANDIN OF THE PGE1 SERIES |
| 9 | 1-trans-tri-n-butylstannyl-4-bromomethyl-4-trimethylsilyloxy-1-nonene | 2-[5-methoxyacetyl pentyl]-4-trimethylsilyloxy cyclopent-2-en-1-one | dl-11a,16-dihydroxy-1-methoxymethyl-1,9-dioxo-16-bromomethyl-20-methyl-2-nor-13-trans prostene |
| EXAMPLE | VINYL IODIDE | CYCLOPENTENONE | PRODUCT PROSTAGLANDIN OF THE PGE1 SERIES |
| 10 | 1-trans-iodo-4-allenyl-4-trimethylsilyloxy-1-nonene | 2-[5-methoxyacetyl pentyl]-4-trimethylsilyloxy cyclopent-2-en-1-one | dl-11a,16-dihydroxy-1-methoxymethyl-1,9-dioxo-16-allenyl-2-methyl-2-nor-13-trans prostene |
| EXAMPLE | VINYL TIN | CYCLOPENTENONE | PRODUCT PROSTAGLANDIN OF THE PGE1 SERIES |
| 11 | 1-trans-tri-n-butylstannyl-4-bromomethyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-bromomethyl-20-ethyl-2-nor-13-trans prostene |
| EXAMPLE | VINYL IODIDE | CYCLOPENTENONE | PRODUCT PROSTAGLANDIN OF THE PGE1 SERIES |
| 12 | 1-trans-iodo-4-allenyl-4-trimethylsilyloxy-1-decene | 2-[5-methoxyacetyl pentyl]-4-trimethylsilyloxy cyclopent-2-en-1-one | dl-11a,16-dihydroxy-1-methoxymethyl-1,9-dioxo-16-allenyl-20-ethyl-2-nor-13-trans prostene |
| EXAMPLE | VINYL TIN | CYCLOPENTENONE | PRODUCT PROSTAGLANDIN OF THE PGE1 SERIES |

TABLE IA-continued

| | | | |
|---|---|---|---|
| 13 | 1-trans-tri-n-butylstannyl-7-thia-4-triethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-19-thia-13-trans prostene |
| 14 | 1-trans-tri-n-butylstannyl-4-methyl-7-thia-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-methyl-19-thia-13-trans prostene |
| 15 | 1-trans-tri-n-butylstannyl-7-oxa-4-triethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-19-oxa-13-trans prostene |
| 16 | 1-trans-tri-n-butylstannyl-4-methyl-7-oxa-4-trimethylsilyloxy-1-octene | 2-[6-methoxyacetyl hexyl]-4-trimethylsiloxy cyclopent-2-en-1-one | dl-11a,16-dihydroxy-1-methoxymethyl-1,9-dioxo-16-methyl-19-oxa-13-trans prostene |
| 17 | 1-trans-tri-n-butylstannyl-4-bromomethyl-4-trimethylsilyloxy-1-heptene | 2-[6-methoxyacetyl hexyl]-4-trimethylsiloxy cyclopent-2-en-1-one | dl-11a,16-dihydroxy-1-methoxymethyl-1,9-dioxo-16-bromomethyl-20-nor-13-trans prostene |
| EXAMPLE 18 | VINYL IODIDE 1-trans-iodo-4-allenyl-4-trimethylsilyloxy-1-heptene | CYCLOPENTENONE 2-[6-methoxyacetyl hexyl]-4-trimethylsiloxy cyclopent2-en-1-one | PRODUCT PROSTAGLANDIN OF THE PGE1 SERIES dl-11a,16-dihydroxy-1-methoxymethyl-1,9-dioxo-16-allenyl-20-nor-13-trans prostene |
| EXAMPLE 19 | VINYL TIN 1-trans-tri-n-butylstannyl-4-bromomethyl-4-trimethylsilyloxy-1-octene | CYCLOPENTENONE 2-[6-methoxyacetyl hexyl]-4-trimethylsiloxy cyclopent-2-en-1-one | PRODUCT PROSTAGLANDIN OF THE PGE1 SERIES dl-11a,16-dihydroxy-1-methoxymethyl-1,9-dioxo-16-bromomethyl-13-trans prostene |
| EXAMPLE 20 | VINYL IODIDE 1-trans-iodo-4-allenyl-4-trimethylsilyloxy-1-octene | CYCLOPENTENONE 2-[6-methoxyacetyl hexyl]-4-trimethylsiloxy cyclopent-2-en-1-one | PRODUCT PROSTAGLANDIN OF THE PGE1 SERIES dl-11a,16-dihydroxy-1-methoxymethyl-1,9-dioxo-16-allenyl-13-trans prostene |
| EXAMPLE 21 | VINYL TIN 1-trans-tri-n-butylstannyl-4-bromomethyl-4-trimethylsilyloxy-1-nonene | CYCLOPENTENONE 2-[6-methoxyacetyl hexyl]-4-trimethylsiloxy cyclopent-2-en-1-one | PRODUCT PROSTAGLANDIN OF THE PGE1 SERIES dl-11a,16-dihydroxy-1-methoxymethyl-1,9-dioxo-16-bromomethyl-20-methyl-13-trans prostene |
| EXAMPLE 22 | VINYL IODIDE 1-trans-iodo-4-allenyl-4-trimethylsilyloxy-1-nonene | CYCLOPENTENONE 2-[6-methoxyacetyl hexyl]-4-trimethylsiloxy cyclopent-2-en-1-one | PRODUCT PROSTAGLANDIN OF THE PGE1 SERIES dl-11a,16-dihydroxy-1-methoxymethyl-1,9-dioxo-16-allenyl-20-methyl-13-trans prostene |
| EXAMPLE 23 | VINYL TIN 1-trans-tri-n-butylstannyl-4-bromomethyl-4-trimethylsilyloxy-1-decene | CYCLOPENTENONE 2-[6-methoxyacetyl hexyl]-4-trimethylsiloxy cyclopent-2-en-1-one | PRODUCT PROSTAGLANDIN OF THE PGE1 SERIES dl-11a,16-dihydroxy-1-methoxymethyl-1,9-dioxo-16-bromomethyl-20-ethyl-13-trans prostene |
| EXAMPLE 24 | VINYL IODIDE 1-trans-iodo-4-allenyl-4-trimethylsilyloxy-1-decene | CYCLOPENTENONE 2-[6-methoxyacetyl hexyl]-4-trimethylsiloxy cyclopent-2-en-1-one | PRODUCT PROSTAGLANDIN OF THE PGE1 SERIES dl-11a,16-dihydroxy-1-methoxymethyl-1,9-dioxo-16-allenyl-20-ethyl-13-trans prostene |
| EXAMPLE 25 | VINYL TIN 1-trans-tri-n-butylstannyl-7-thia | CYCLOPENTENONE 2-[7-methoxyacetyl | PRODUCT PROSTAGLANDIN OF THE PGE1 SERIES dl-11a,16-dihydroxy-1-methoxymethyl-1,9-dioxo- |

TABLE IA-continued

| | VINYL IODIDE / VINYL TIN | CYCLOPENTENONE | PRODUCT PROSTAGLANDIN |
|---|---|---|---|
| 26 | 1-trans-tri-n-butylstannyl-4-methyl-7-thia-4-trimethylsilyloxy-1-octene | 4-triethylsilyloxy-1-octene heptyl]-4-trimethylsilyloxy cyclopent-2-en-1-one | 19-thia-2-homo-13-trans prostene |
| 27 | 1-trans-tri-n-butylstannyl-7-oxa-4-triethylsilyloxy-1-octene | 2-[7-methoxyacetyl heptyl]-4-trimethylsilyloxy cyclopent-2-en-1-one | dl-11a,16-dihydroxy-1-methoxymethyl-1,9-dioxo-16-methyl-19-thia-2-homo-13-trans prostene |
| 28 | 1-trans-tri-n-butylstannyl-4-methyl-7-oxa-4-triethylsilyloxy-1-octene | 2-[7-methoxyacetyl heptyl]-4-trimethylsilyloxy cyclopent-2-en-1-one | dl-11a,16-dihydroxy-1-methoxymethyl-1,9-dioxo-19-oxa-2-homo-13-trans prostene |
| 29 | 1-trans-tri-n-butylstannyl-4-bromomethyl-4-trimethylsilyloxy-1-heptene | 2-[7-methoxyacetyl heptyl]-4-trimethylsilyloxy cyclopent-2-en-1-one | dl-11a,16-dihydroxy-1-methoxymethyl-1,9-dioxo-16-methyl-19-oxa-2-homo-13-trans prostene |
| | | 2-[7-methoxyacetyl heptyl]-4-trimethylsilyloxy cyclopent-2-en-1-one | dl-11a,16-dihydroxy-1-methoxymethyl-1,9-dioxo-16-bromomethyl-20-nor-2-homo-13-trans prostene |
| EXAMPLE 30 | VINYL IODIDE 1-trans-iodo-4-allenyl-4-trimethylsilyloxy-1-heptene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-allenyl-20-nor-2-homo-13-trans prostene |
| EXAMPLE 31 | VINYL TIN 1-trans-tri-n-butylstannyl-4-bromomethyl-4-trimethylsilyloxy-1-octene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-bromomethyl-2-homo-13-trans prostene |
| EXAMPLE 32 | VINYL IODIDE 1-trans-iodo-4-allenyl-4-trimethylsilyloxy-1-octene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-allenyl-2-homo-13-trans prostene |
| EXAMPLE 33 | VINYL TIN 1-trans-tri-n-butylstannyl-4-bromomethyl-4-trimethylsilyloxy-1-nonene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-bromomethyl-20-methyl-2-homo-13-trans prostene |
| EXAMPLE 34 | VINYL IODIDE 1-trans-iodo-4-allenyl-4-trimethylsilyloxy-1-nonene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-allenyl-20-methyl-2-homo-13-trans prostene |
| EXAMPLE 35 | VINYL TIN 1-trans-tri-n-butylstannyl-4-bromomethyl-4-trimethylsilyloxy-1-decene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-bromomethyl-20-ethyl-2-homo-13-trans prostene |
| EXAMPLE 36 | VINYL IODIDE 1-trans-iodo-4-allenyl-4-trimethylsilyloxy-1-decene | CYCLOPENTENONE 2-[7-methoxyacetyl heptyl]-4-trimethylsilyloxy cyclopent-2-en-1-one | PRODUCT PROSTAGLANDIN OF THE PGE1 SERIES dl-11a,16-dihydroxy-1-methoxymethyl-1,9-dioxo-16-allenyl-20-ethyl-2-homo-13-trans prostene |
| EXAMPLE 37 | VINYL TIN 1-trans-tri-n-butylstannyl-7-thia-4-triethylsilyloxy-1-octene | CYCLOPENTENONE 2-[6-methoxyacetyl hexyl]-4R-trimethylsilyloxy | PRODUCT PROSTAGLANDIN OF THE PGE1 SERIES nat-11a,16-dihydroxy-1-methoxymethyl-1,9-dioxo-19-thia-13-trans prostene |

TABLE IA-continued

| | | |
|---|---|---|
| 38 | 1-trans-tri-n-butylstannyl-4-methyl-7-thia-4-trimethylsilyloxy-1-octene | cyclopent-2-en-1-one 2-[6-methoxyacetyl hexyl]-4R-trimethylsilyloxy cyclopent-2-en-1-one | nat-11a,16-dihydroxy-1-methoxymethyl-1,9-dioxo-16-methyl-19-thia-13-trans prostene |
| 39 | 1-trans-tri-n-butylstannyl-7-oxa-4-triethylsilyloxy-1-octene | 2-[6-methoxyacetyl hexyl]-4R-trimethylsiloxy cyclopent-2-en-1-one | nat-11a,16-dihydroxy-1-methoxymethyl-1,9-dioxo-19-oxa-13-trans prostene |
| 40 | 1-trans-tri-n-butylstannyl-4-methyl-7-oxa-4-trimethylsilyloxy-1-octene | 2-[6-methoxyacetyl hexyl]-4R-trimethylsilyloxy cyclopent-2-en-1-one | nat-11a,16-dihydroxy-1-methoxymethyl-1,9-dioxo-16-methyl-19-oxa-13-trans prostene |
| 41 | 1-trans-tri-n-butylstannyl-4-bromomethyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-bromomethyl-20-nor-13-trans prostene |
| EXAMPLE | VINYL IODIDE | CYCLOPENTENONE | PRODUCT PROSTAGLANDIN OF THE PGE1 SERIES |
| 42 | 1-trans-iodo-4-allenyl-4-trimethylsilyloxy-1-heptene | 2-[6-methoxyacetyl hexyl]-4R-trimethylsilyloxy cyclopent-2-en-1-one | nat-11a,16-dihydroxy-1-methoxymethyl-1,9-dioxo-16-allenyl-20-nor-13-tran prostene |
| EXAMPLE | VINYL TIN | CYCLOPENTENONE | PRODUCT PROSTAGLANDIN OF THE PGE1 SERIES |
| 43 | 1-trans-tri-n-butylstannyl-4-bromomethyl-4-trimethylsilyloxy-1-octene | 2-[6-methoxyacetyl hexyl]-4R-trimethylsilyloxy cyclopent-2-en-1-one | nat-11a,16-dihydroxy-1-methoxymethyl-1,9-dioxo-16-bromomethyl-13-trans prostene |
| EXAMPLE | VINYL IODIDE | CYCLOPENTENONE | PRODUCT PROSTAGLANDIN OF THE PGE1 SERIES |
| 44 | 1-trans-iodo-4-allenyl-4-trimethylsilyloxy-1-octene | 2-[6-methoxyacetyl hexyl]-4R-trimethylsilyloxy cyclopent-2-en-1-one | nat-11a,16-dihydroxy-1-methoxymethyl-1,9-dioxo-16-allenyl-13-trans prostene |
| EXAMPLE | VINYL TIN | CYCLOPENTENONE | PRODUCT PROSTAGLANDIN OF THE PGE1 SERIES |
| 45 | 1-trans-tri-n-butylstannyl-4-bromomethyl-4-trimethylsilyloxy-1-nonene | 2-[6-methoxyacetyl hexyl]-4R-trimethylsilyloxy cyclopent-2-en-1-one | nat-11a,16-dihydroxy-1-methoxymethyl-1,9-dioxo-16-bromomethyl-20-methyl-13-trans prostene |
| EXAMPLE | VINYL IODIDE | CYCLOPENTENONE | PRODUCT PROSTAGLANDIN OF THE PGE1 SERIES |
| 46 | 1-trans-iodo-4-allenyl-4-trimethylsilyloxy-1-nonene | 2-[6-methoxymethyl hexyl]-4R-trimethylsilyloxy cyclopent-2-en-1-one | nat-11a,16-dihydroxy-1-methoxymethyl-1,9-dioxo-16-allenyl-20-methyl-13-trans prostene |
| EXAMPLE | VINYL TIN | CYCLOPENTENONE | PRODUCT PROSTAGLANDIN OF THE PGE1 SERIES |
| 47 | 1-trans-tri-n-butylstannyl-4-bromomethyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-bromomethyl-20-ethyl-13-trans prostene |
| EXAMPLE | VINYL IODIDE | CYCLOPENTENONE | PRODUCT PROSTAGLANDIN OF THE PGE1 SERIES |
| 48 | 1-trans-iodo-4-allenyl-4-trimethylsilyloxy-1-decene | 2-[6-methoxyacetyl hexyl]-4R-trimethylsilyloxy cyclopent-2-en-1-one | nat-11a,16-dihydroxy-1-methoxymethyl-1,9-dioxo-16-allenyl-20-ethyl-13-trans prostene |
| EXAMPLE | VINYL TIN | CYCLOPENTENONE | PRODUCT PROSTAGLANDIN OF THE PGE1 SERIES |
| 49 | 1-trans-tri-n-butylstannyl-7-thia-4-triethylsilyloxy-1-octene | 2-[5-methoxyacetyl pentyl] cyclopent-2-en-1-one | dl-16-hydroxy-1-methoxymethyl-1,9-dioxo-19-thia-2-nor-13-trans prostene |

TABLE IA-continued

| | | | |
|---|---|---|---|
| 50 | 1-trans-tri-n-butylstannyl-4-methyl-7-thia-4-trimethylsilyloxy-1-octene | 2-[5-methoxyacetyl pentyl] cyclopent-2-en-1-one | dl-16-hydroxy-1-methoxymethyl-1,9-dioxo-16-methyl-19-thia-2-nor-13-trans prostene |
| 51 | 1-trans-tri-n-butylstannyl-7-oxa-4-triethylsilyloxy-1-octene | 2-[5-methoxyacetyl pentyl] cyclopent-2-en-1-one | dl-16-hydroxy-1-methoxymethyl-1,9-dioxo-19-oxa-2-nor-13-trans prostene |
| 52 | 1-trans-tri-n-butylstannyl-4-methyl-7-oxa-4-trimethylsilyloxy-1-octene | 2-[5-methoxyacetyl pentyl] cyclopent-2-en-1-one | dl-16-hydroxy-1-methoxymethyl-1,9-dioxo-16-methyl-19-oxa-2-nor-13-trans prostene |
| 53 | 1-trans-tri-n-butylstannyl-4-bromomethyl-4-trimethylsilyloxy-1-heptene | 2-[5-methoxyacetyl pentyl] cyclopent-2-en-1-one | dl-16-hydroxy-1-methoxymethyl-1,9-dioxo-16-bromomethyl-20-nor-2-nor-13-trans prostene |
| EXAMPLE | VINYL IODIDE | CYCLOPENTENONE | PRODUCT PROSTAGLANDIN OF THE PGE1 SERIES |
| 54 | 1-trans-iodo-4-allenyl-4-trimethylsilyloxy-1-heptene | 2-[5-methoxyacetyl pentyl] cyclopent-2-en-1-one | dl-16-hydroxy-1-methoxymethyl-1,9-dioxo-16-allenyl-20-nor-2-nor-13-trans prostene |
| EXAMPLE | VINYL TIN | CYCLOPENTENONE | PRODUCT PROSTAGLANDIN OF THE PGE1 SERIES |
| 55 | 1-trans-tri-n-butylstannyl-4-bromomethyl-4-trimethylsilyloxy-1-octene | 2-[5-methoxyacetyl pentyl] cyclopent-2-en-1-one | dl-16-hydroxy-1-methoxymethyl-1,9-dioxo-16-bromomethyl-2-nor-13-trans prostene |
| EXAMPLE | VINYL IODIDE | CYCLOPENTENONE | PRODUCT PROSTAGLANDIN OF THE PGE1 SERIES |
| 56 | 1-trans-iodo-4-allenyl-4-trimethylsilyloxy-1-octene | 2-[5-methoxyacetyl pentyl] cyclopent-2-en-1-one | dl-16-hydroxy-1-methoxymethyl-1,9-dioxo-16-allenyl-2-nor-13-trans prostene |
| EXAMPLE | VINYL TIN | CYCLOPENTENONE | PRODUCT PROSTAGLANDIN OF THE PGE1 SERIES |
| 57 | 1-trans-tri-n-butylstannyl-4-bromomethyl-4-trimethylsilyloxy-1-nonene | 2-[5-methoxyacetyl pentyl] cyclopent-2-en-1-one | dl-16-hydroxy-1-methoxymethyl-1,9-dioxo-16-bromomethyl-20-methyl-2-nor-13-trans prostene |
| EXAMPLE | VINYL IODIDE | CYCLOPENTENONE | PRODUCT PROSTAGLANDIN OF THE PGE1 SERIES |
| 58 | 1-trans-iodo-4-allenyl-4-trimethylsilyloxy-1-nonene | 2-[5-methoxyacetyl pentyl] cyclopent-2-en-1-one | dl-16-hydroxy-1-methoxymethyl-1,9-dioxo-16-allenyl-20-methyl-2-nor-13-trans prostene |
| EXAMPLE | VINYL TIN | CYCLOPENTENONE | PRODUCT PROSTAGLANDIN OF THE PGE1 SERIES |
| 59 | 1-trans-tri-n-butylstannyl-4-bromomethyl-4-trimethylsilyloxy-1-decene | 2-[5-methoxyacetyl pentyl] cyclopent-2-en-1-one | dl-16-hydroxy-1-methoxymethyl-1,9-dioxo-16-bromomethyl-20-ethyl-2-nor-13-trans prostene |
| EXAMPLE | VINYL IODIDE | CYCLOPENTENONE | PRODUCT PROSTAGLANDIN OF THE PGE1 SERIES |
| 60 | 1-trans-iodo-4-allenyl-4-trimethylsilyloxy-1-decene | 2-[5-methoxyacetyl pentyl] cyclopent-2-en-1-one | dl-16-hydroxy-1-methoxymethyl-1,9-dioxo-16-allenyl-20-ethyl-2-nor-13-trans prostene |
| EXAMPLE | VINYL TIN | CYCLOPENTENONE | PRODUCT PROSTAGLANDIN OF THE PGE1 SERIES |
| 61 | 1-trans-tri-n-butylstannyl-7-thia-4-triethylsilyloxy-1-octene | 2-[6-methoxyacetyl hexyl] cyclopent-2-en-1-one | dl-16-hydroxy-1-methoxymethyl-1,9-dioxo-19-thia-13-trans prostene |
| 62 | 1-trans-tri-n-butylstannyl-4-methyl-7-thia | 2-[6-methoxyacetyl | dl-16-hydroxy-1-methoxymethyl-1,9-dioxo-16-methyl- |

TABLE IA-continued

| Example | Column 2 | Column 3 | Column 4 |
|---|---|---|---|
| 63 | 4-trimethylsilyloxy-1-octene | hexyl] cyclopent-2-en-1-one | 19-thia-13-trans prostene |
| | 1-trans-tri-n-butylstannyl-7-oxa-4-triethylsilyloxy-1-octene | 2-[6-methoxyacetyl hexyl] cyclopent-2-en-1-one | dl-16-hydroxy-1-methoxymethyl-1,9-dioxo-19-oxa-13-trans prostene |
| 64 | 1-trans-tri-n-butylstannyl-4-methyl-7-oxa-4-trimethylsilyloxy-1-octene | 2-[6-methoxyacetyl hexyl] cyclopent-2-en-1-one | dl-16-hydroxy-1-methoxymethyl-1,9-dioxo-16-methyl-19-oxa-13-trans prostene |
| 65 | 1-trans-tri-n-butylstannyl-4-bromomethyl-4-trimethylsilyloxy-1-heptene | 2-[6-methoxyacetyl hexyl] cyclopent-2-en-1-one | dl-16-hydroxy-1-methoxymethyl-1,9-dioxo-16-bromomethyl-20-nor-13-trans prostene |
| EXAMPLE | VINYL IODIDE | CYCLOPENTENONE | PRODUCT PROSTAGLANDIN OF THE PGE1 SERIES |
| 66 | 1-trans-iodo-4-allenyl-4-trimethylsilyloxy-1-heptene | 2-[6-methoxymethyl hexyl] cyclopent-2-en-1-one | dl-16-hydroxy-1-methoxymethyl-1,9-dioxo-16-allenyl-20-nor-13-trans prostene |
| EXAMPLE | VINYL TIN | CYCLOPENTENONE | PRODUCT PROSTAGLANDIN OF THE PGE1 SERIES |
| 67 | 1-trans-tri-n-butylstannyl-4-bromomethyl-4-trimethylsilyloxy-1-octene | 2-[6-methoxyacetyl hexyl] cyclopent-2-en-1-one | dl-16-hydroxy-1-methoxymethyl-1,9-dioxo-16-bromomethyl-13-trans prostene |
| EXAMPLE | VINYL IODIDE | CYCLOPENTENONE | PRODUCT PROSTAGLANDIN OF THE PGE1 SERIES |
| 68 | 1-trans-iodo-4-allenyl-4-trimethylsilyloxy-1-octene | 2-[6-methoxyacetyl hexyl] cyclopent-2-en-1-one | dl-16-hydroxy-1-methoxymethyl-1,9-dioxo-16-allenyl 13-trans prostene |
| EXAMPLE | VINYL TIN | CYCLOPENTENONE | PRODUCT PROSTAGLANDIN OF THE PGE1 SERIES |
| 69 | 1-trans-tri-n-butylstannyl-4-bromomethyl-4-trimethylsilyloxy-1-nonene | 2-[6-methoxyacetyl hexyl] cyclopent-2-en-1-one | dl-16-hydroxy-1-methoxymethyl-1,9-dioxo-16-bromomethyl-20-methyl-13-trans prostene |
| EXAMPLE | VINYL IODIDE | CYCLOPENTENONE | PRODUCT PROSTAGLANDIN OF THE PGE1 SERIES |
| 70 | 1-trans-iodo-4-allenyl-4-trimethylsilyloxy-1-nonene | 2-[6-methoxyacetyl hexyl] cyclopent-2-en-1-one | dl-16-hydroxy-1-methoxymethyl-1,9-dioxo-16-allenyl-20-methyl-13-trans prostene |
| EXAMPLE | VINYL TIN | CYCLOPENTENONE | PRODUCT PROSTAGLANDIN OF THE PGE1 SERIES |
| 71 | 1-trans-tri-n-butylstannyl-4-bromomethyl-4-trimethylsilyloxy-1-decene | 2-[6-methoxyacetyl hexyl] cyclopent-2-en-1-one | dl-16-hydroxy-1-methoxymethyl-1,9-dioxo-16-bromomethyl-20-ethyl-13-trans prostene |
| EXAMPLE | VINYL IODIDE | CYCLOPENTENONE | PRODUCT PROSTAGLANDIN OF THE PGE1 SERIES |
| 72 | 1-trans-iodo-4-allenyl-4-trimethylsilyloxy-1-decene | 2-[6-methoxyacetyl hexyl] cyclopent-2-en-1-one | dl-16-hydroxy-1-methoxymethyl-1,9-dioxo-16-allenyl-20-ethyl-13-trans prostene |
| EXAMPLE | VINYL TIN | CYCLOPENTENONE | PRODUCT PROSTAGLANDIN OF THE PGE1 SERIES |
| 73 | 1-trans-tri-n-butylstannyl-7-thia-4-triethylsilyloxy-1-octene | 2-[7-methoxyacetyl heptyl] cyclopent-2-en-1-one | dl-16-hydroxy-1-methoxymethyl-1,9-dioxo-19-thia-2-homo-13-trans prostene |
| 74 | 1-trans-tri-n-butylstannyl-4-methyl-7-thia-4-trimethylsilyloxy-1-octene | 2-[7-methoxyacetyl heptyl] cyclopent-2-en-1-one | dl-16-hydroxy-1-methoxymethyl-1,9-dioxo-16-methyl-19-thia-2-homo-13-trans prostene |

TABLE IA-continued

| | | | |
|---|---|---|---|
| 75 | 1-trans-tri-n-butylstannyl-7-oxa-4-triethylsilyloxy-1-octene | cyclopent-2-en-1-one 2-[7-methoxyacetyl heptyl] cyclopent-2-en-1-one | dl-16-hydroxy-1-methoxymethyl-1,9-dioxo-19-oxa-2-homo-13-trans prostene |
| 76 | 1-trans-tri-n-butylstannyl-4-methyl-7-oxa-4-trimethylsilyloxy-1-octene | 2-[7-methoxyacetyl heptyl] cyclopent-2-en-1-one | dl-16-hydroxy-1-methoxymethyl-1,9-dioxo-16-methyl-19-oxa-2-homo-13-trans prostene |
| 77 | 1-trans-tri-n-butylstannyl-4-bromomethyl-4-trimethylsilyloxy-1-heptene | 2-[7-methoxyacetyl heptyl] cyclopent-2-en-1-one | dl-16-hydroxy-1-methoxymethyl-1,9-dioxo-16-bromomethyl-20-nor-2-homo-13-trans prostene |
| EXAMPLE | VINYL IODIDE | CYCLOPENTENONE | PRODUCT PROSTAGLANDIN OF THE PGE1 SERIES |
| 78 | 1-trans-iodo-4-allenyl-4-trimethylsilyloxy-1-heptene | 2-[7-methoxyacetyl heptyl] cyclopent-2-en-1-one | dl-16-hydroxy-1-methoxymethyl-1,9-dioxo-16-allenyl-20-nor-2-homo-13-trans prostene |
| EXAMPLE | VINYL TIN | CYCLOPENTENONE | PRODUCT PROSTAGLANDIN OF THE PGE1 SERIES |
| 79 | 1-trans-tri-n-butylstannyl-4-bromomethyl-4-trimethylsilyloxy-1-octene | 2-[7-methoxyacetyl heptyl] cyclopent-2-en-1-one | dl-16-hydroxy-1-methoxymethyl-1,9-dioxo-16-bromomethyl-2-homo-13-trans prostene |
| EXAMPLE | VINYL IODIDE | CYCLOPENTENONE | PRODUCT PROSTAGLANDIN OF THE PGE1 SERIES |
| 80 | 1-trans-iodo-4-allenyl-4-trimethylsilyloxy-1-octene | 2-[7-methoxyacetyl heptyl] cyclopent-2-en-1-one | dl-16-hydroxy-1-methoxymethyl-1,9-dioxo-16-allenyl-2-homo-13-trans prostene |
| EXAMPLE | VINYL TIN | CYCLOPENTENONE | PRODUCT PROSTAGLANDIN OF THE PGE1 SERIES |
| 81 | 1-trans-tri-n-butylstannyl-4-bromomethyl-4-trimethylsilyloxy-1-nonene | 2-[7-methoxyacetyl heptyl] cyclopent-2-en-1-one | dl-16-hydroxy-1-methoxymethyl-1,9-dioxo-16-bromomethyl-20-methyl-2-homo-13-trans prostene |
| EXAMPLE | VINYL IODIDE | CYCLOPENTENONE | PRODUCT PROSTAGLANDIN OF THE PGE1 SERIES |
| 82 | 1-trans-iodo-4-allenyl-4-trimethylsilyloxy-1-nonene | 2-[7-methoxyacetyl heptyl] cyclopent-2-en-1-one | dl-16-hydroxy-1-methoxymethyl-1,9-dioxo-16-allenyl-20-methyl-2-homo-13-trans prostene |
| EXAMPLE | VINYL TIN | CYCLOPENTENONE | PRODUCT PROSTAGLANDIN OF THE PGE1 SERIES |
| 83 | 1-trans-tri-n-butylstannyl-4-bromomethyl-4-trimethylsilyloxy-1-decene | 2-[7-methoxyacetyl heptyl] cyclopent-2-en-1-one | dl-16-hydroxy-1-methoxymethyl-1,9-dioxo-16-bromomethyl-20-ethyl-2-homo-13-trans prostene |
| EXAMPLE | VINYL IODIDE | CYCLOPENTENONE | PRODUCT PROSTAGLANDIN OF THE PGE1 SERIES |
| 84 | 1-trans-iodo-4-allenyl-4-trimethylsilyloxy-1-decene | 2-[7-methoxyacetyl heptyl] cyclopent-2-en-1-one | dl-16-hydroxy-1-methoxymethyl-1,9-dioxo-16-allenyl-20-ethyl-2-homo-13-trans prostene |

TABLE II

| EXAMPLE | VINYL TIN | CYCLOPENTENONE | PRODUCT PROSTAGLANDIN OF THE PGE2 SERIES |
|---|---|---|---|
| 1 | 1-trans-tri-n-butylstannyl-7-thia 4-triethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-19-thia-2-nor-5-cis-13-trans prostadiene |
| 2 | 1-trans-tri-n-butylstannyl-4-methyl-7-thia 4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-19-thia-2-nor-5-cis-13-trans prostadiene |
| 3 | 1-trans-tri-n-butylstannyl-7-oxa 4-triethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-19-oxa-2-nor-5-cis-13-trans prostadiene |
| 4 | 1-trans-tri-n-butylstannyl-4-methyl-7-oxa 4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-19-oxa-2-nor-5-cis-13-trans prostadiene |
| 5 | 1-trans-tri-n-butylstannyl-4-bromomethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-bromomethyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 6 | 1-trans-iodo-4-allenyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-allenyl-20-nor-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 7 | 1-trans-tri-n-butylstannyl-4-bromomethyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-bromomethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 8 | 1-trans-iodo-4-allenyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-allenyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 9 | 1-trans-tri-n-butylstannyl-4-bromomethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-bromomethyl-20-methyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 10 | 1-trans-iodo-4-allenyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-allenyl-20-methyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 11 | 1-trans-tri-n-butylstannyl-4-bromomethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-bromomethyl-20-ethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 12 | 1-trans-iodo-4-allenyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-allenyl-20-ethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|

TABLE II-continued

| EXAMPLE | VINYL IODIDE / VINYL TIN | CYCLOPENTENONE | PRODUCT PROSTAGLANDIN |
|---|---|---|---|
| 13 | 1-trans-tri-n-butylstannyl-7-thia 4-triethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-19-thia-5-cis-13-trans prostadiene |
| 14 | 1-trans-tri-n-butylstannyl-4-methyl-7-thia 4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-19-thia-5-cis-13-trans prostadiene |
| 15 | 1-trans-tri-n-butylstannyl-7-oxa 4-triethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-19-oxa-5-cis-13-trans prostadiene |
| 16 | 1-trans-tri-n-butylstannyl-4-methyl-7-oxa 4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-19-oxa-5-cis-13-trans prostadiene |
| 17 | 1-trans-tri-n-butylstannyl-4-bromomethyl-4-trimethylsilyloxy-1-heptene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-bromomethyl-20-nor-5-cis-13-trans prostadiene |
| EXAMPLE 18 | VINYL IODIDE 1-trans-iodo-4-allenyl-4-trimethylsilyloxy-1-heptene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-allenyl-20-nor-5-cis-13-trans prostadiene |
| EXAMPLE 19 | VINYL TIN 1-trans-tri-n-butylstannyl-4-bromomethyl-4-trimethylsilyloxy-1-octene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-bromomethyl-5-cis-13-trans prostadiene |
| EXAMPLE 20 | VINYL IODIDE 1-trans-iodo-4-allenyl-4-trimethylsilyloxy-1-octene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-allenyl-5-cis-13-trans prostadiene |
| EXAMPLE 21 | VINYL TIN 1-trans-tri-n-butylstannyl-4-bromomethyl-4-trimethylsilyloxy-1-nonene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-bromomethyl-20-methyl-5-cis-13-trans prostadiene |
| EXAMPLE 22 | VINYL IODIDE 1-trans-iodo-4-allenyl-4-trimethylsilyloxy-1-nonene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-allenyl-20-methyl-5-cis-13-trans prostadiene |
| EXAMPLE 23 | VINYL TIN 1-trans-tri-n-butylstannyl-4-bromomethyl-4-trimethylsilyloxy-1-decene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-bromomethyl-20-ethyl-5-cis-13-trans prostadiene |
| EXAMPLE 24 | VINYL IODIDE 1-trans-iodo-4-allenyl-4-trimethylsilyloxy-1-decene | CYCLOPENTENONE 2-[6-methoxyacetyl hex-2-cis-enyl]-4-trimethylsilyloxy cyclopent-2-en-1-one | PRODUCT PROSTAGLANDIN OF THE PGE2 SERIES dl-11a,16-dihydroxy-1-methoxymethyl-1,9-dioxo-16-allenyl-20-ethyl-5-cis-13-trans prostadiene |
| EXAMPLE 25 | VINYL TIN 1-trans-tri-n-butylstannyl-7-thia | CYCLOPENTENONE 2-[7-methoxyacetyl | PRODUCT PROSTAGLANDIN OF THE PGE2 SERIES dl-11a,16-dihydroxy-1-methoxymethyl-1,9-dioxo- |

TABLE II-continued

| | | | |
|---|---|---|---|
| | 4-triethylsilyloxy-1-octene | hept-2-cis-enyl] 4-trimethylsilyloxy cyclopent-2-en-1-one | 19-thia-2-homo-5-cis-13-trans prostadiene |
| 26 | 1-trans-tri-n-butylstannyl-4-methyl-7-thia 4-trimethylsilyloxy-1-octene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-methyl-19-thia-2-homo-5-cis-13-trans prostadiene |
| 27 | 1-trans-tri-n-butylstannyl-7-oxa 4-triethylsilyloxy-1-octene | 2-[7-methoxyacetyl hept-2-cis-enyl]-4-trimethylsilyloxy cyclopent-2-en-1-one | dl-11a,16-dihydroxy-1-methoxymethyl-1,9-dioxo-19-oxa-2-homo-5-cis-13-trans prostadiene |
| 28 | 1-trans-tri-n-butylstannyl-4-methyl-7-oxa 4-trimethylsilyloxy-1-octene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-methyl-19-oxa-2-homo-5-cis-13-trans prostadiene |
| 29 | 1-trans-tri-n-butylstannyl-4-bromomethyl-4-trimethylsilyloxy-1-heptene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-bromomethyl-20-nor-2-homo-5-cis-13-trans prostadiene |
| EXAMPLE | VINYL IODIDE | CYCLOPENTENONE | PRODUCT PROSTAGLANDIN OF THE PGE2 SERIES |
| 30 | 1-trans-iodo-4-allenyl-4-trimethylsilyloxy-1-heptene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-allenyl-20-nor-2-homo-5-cis-13-trans prostadiene |
| EXAMPLE | VINYL TIN | CYCLOPENTENONE | PRODUCT PROSTAGLANDIN OF THE PGE2 SERIES |
| 31 | 1-trans-tri-n-butylstannyl-4-bromomethyl-4-trimethylsilyloxy-1-octene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-bromomethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 32 | 1-trans-iodo-4-allenyl-4-trimethylsilyloxy-1-octene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-allenyl-2-homo-5-cis-13-trans prostadiene |
| EXAMPLE | VINYL TIN | CYCLOPENTENONE | PRODUCT PROSTAGLANDIN OF THE PGE2 SERIES |
| 33 | 1-trans-tri-n-butylstannyl-4-bromomethyl-4-trimethylsilyloxy-1-nonene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-bromomethyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 34 | 1-trans-iodo-4-allenyl-4-trimethylsilyloxy-1-nonene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-allenyl-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 35 | 1-trans-tri-n-butylstannyl-4-bromomethyl-4-trimethylsilyloxy-1-decene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-bromomethyl-20-ethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 36 | 1-trans-iodo-4-allenyl-4-trimethylsilyloxy-1-decene | 2-[7-methoxyacetyl hept-2-cis-enyl]-4-trimethylsilyloxy cyclopent-2-en-1-one | dl-11a,16-dihydroxy-1-methoxymethyl-1,9-dioxo-16-allenyl-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 37 | 1-trans-tri-n-butylstannyl-7-thia 4-triethylsilyloxy-1-octene | 2-[6-methoxyacetyl hex-2-cis-enyl]-4R-trimethylsilyloxy | nat-11a,16-dihydroxy-1-methoxymethyl-1,9-dioxo-19-thia-5-cis-13-trans prostadiene |

TABLE II-continued

| EXAMPLE | | | |
|---|---|---|---|
| 38 | 1-trans-tri-n-butylstannyl-4-methyl-7-thia 4-trimethylsilyloxy-1-octene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-19-thia-5-cis-13-trans prostadiene |
| 39 | 1-trans-tri-n-butylstannyl-7-oxa 4-triethylsilyloxy-1-octene | 2-[6-methoxyacetyl hex-2-cis-enyl]-4R-trimethylsiloxy cyclopent-2-en-1-one | nat-11a,16-dihydroxy-1-methoxymethyl-1,9-dioxo-19-oxa-5-cis-13-trans prostadiene |
| 40 | 1-trans-tri-n-butylstannyl-4-methyl-7-oxa 4-trimethylsilyloxy-1-octene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-19-oxa-5-cis-13-trans prostadiene |
| 41 | 1-trans-tri-n-butylstannyl-4-bromomethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 42 | 1-trans-iodo-4-allenyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE PGE2 SERIES |
| 43 | 1-trans-tri-n-butylstannyl-4-bromomethyl-4-trimethylsilyloxy-1-octene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-bromomethyl-5-cis-13-trans prostadiene |
| EXAMPLE | VINYL IODIDE | CYCLOPENTENONE | PRODUCT PROSTAGLANDIN OF THE PGE2 SERIES |
| 44 | 1-trans-iodo-4-allenyl-4-trimethylsilyloxy-1-octene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-allenyl-5-cis-13-trans prostadiene |
| EXAMPLE | VINYL TIN | CYCLOPENTENONE | PRODUCT PROSTAGLANDIN OF THE PGE2 SERIES |
| 45 | 1-trans-tri-n-butylstannyl-4-bromomethyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-bromomethyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 46 | 1-trans-iodo-4-allenyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-allenyl-20-methyl-5-cis-13-trans prostadiene |
| EXAMPLE | VINYL TIN | CYCLOPENTENONE | PRODUCT PROSTAGLANDIN OF THE PGE2 SERIES |
| 47 | 1-trans-tri-n-butylstannyl-4-bromomethyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-bromomethyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 48 | 1-trans-iodo-4-allenyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-allenyl-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 49 | 1-trans-tri-n-butylstannyl-7-thia 4-triethylsilyloxy-1-octene | 2-[5-methoxyacetyl pent-2-cis-enyl] cyclopent-2-en-1-one | dl-16-hydroxy-1-methoxymethyl-1,9-dioxo-19-thia-2-nor-5-cis-13-trans prostadiene |

TABLE II-continued

| EXAMPLE | | | PRODUCT PROSTAGLANDIN |
|---|---|---|---|
| 50 | 1-trans-tri-n-butylstannyl-4-methyl-7-thia-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-methyl-19-thia-2-nor-5-cis-13-trans prostadiene |
| 51 | 1-trans-tri-n-butylstannyl-7-oxa-4-triethylsilyloxy-1-octene | 2-[5-methoxyacetyl pent-2-cis-enyl] cyclopent-2-en-1-one | dl-16-hydroxy-1-methoxymethyl-1,9-dioxo-19-oxa-2-nor-5-cis-13-trans prostadiene |
| 52 | 1-trans-tri-n-butylstannyl-4-methyl-7-oxa-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-methyl-19-oxa-2-nor-5-cis-13-trans prostadiene |
| 53 | 1-trans-tri-n-butylstannyl-4-bromomethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-bromomethyl-20-nor-2-nor-5-cis-13-trans prostadiene |
| EXAMPLE 54 | VINYL IODIDE 1-trans-iodo-4-allenyl-4-trimethylsilyloxy-1-heptene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-allenyl-20-nor-2-nor-5-cis-13-trans prostadiene |
| EXAMPLE 55 | VINYL TIN 1-trans-tri-n-butylstannyl-4-bromomethyl-4-trimethylsilyloxy-1-octene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-bromomethyl-2-nor-5-cis-13-trans prostadiene |
| EXAMPLE 56 | VINYL IODIDE 1-trans-iodo-4-allenyl-4-trimethylsilyloxy-1-octene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-allenyl-2-nor-5-cis-13-trans prostadiene |
| EXAMPLE 57 | VINYL TIN 1-trans-tri-n-butylstannyl-4-bromomethyl-4-trimethylsilyloxy-1-nonene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-bromomethyl-20-methyl-2-nor-5-cis-13-trans prostadiene |
| EXAMPLE 58 | VINYL IODIDE 1-trans-iodo-4-allenyl-4-trimethylsilyloxy-1-nonene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-allenyl-20-methyl-2-nor-5-cis-13-trans prostadiene |
| EXAMPLE 59 | VINYL TIN 1-trans-tri-n-butylstannyl-4-bromomethyl-4-trimethylsilyloxy-1-decene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-bromomethyl-20-ethyl-2-nor-5-cis-13-trans prostadiene |
| EXAMPLE 60 | VINYL IODIDE 1-trans-iodo-4-allenyl-4-trimethylsilyloxy-1-decene | CYCLOPENTENONE 2-[5-methoxyacetyl pent-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-16-allenyl-20-ethyl-2-nor-5-cis-13-trans prostadiene |
| EXAMPLE 61 | VINYL TIN 1-trans-tri-n-butylstannyl-7-thia-4-trimethylsilyloxy-1-octene | CYCLOPENTENONE 2-[6-methoxyacetyl hex-2-cis-enyl] cyclopent-2-en-1-one | PRODUCT PROSTAGLANDIN OF THE 11-DEOXY PGE2 SERIES dl-16-hydroxy-1-methoxymethyl-1,9-dioxo-19-thia-5-cis-13-trans prostadiene |
| 62 | 1-trans-tri-n-butylstannyl-4-methyl-7-thia | 2-[6-methoxyacetyl | dl-16-hydroxy-1-methoxymethyl-1,9-dioxo-16-methyl- |

| | | | |
|---|---|---|---|
| 63 | 4-trimethylsilyloxy-1-octene | hex-2-cis-enyl]cyclopent-2-en-1-one | 19-thia-5-cis-13-trans prostadiene |
| | 1-trans-tri-n-butylstannyl-7-oxa-4-triethylsilyloxy-1-octene | 2-[6-methoxyacetyl hex-2-cis-enyl]cyclopent-2-en-1-one | dl-16-hydroxy-1-methoxymethyl-1,9-dioxo-19-oxa-5-cis-13-trans prostadiene |
| 64 | 1-trans-tri-n-butylstannyl-4-methyl-7-oxa-4-trimethylsilyloxy-1-octene | 2-[6-methoxyacetyl hex-2-cis-enyl]cyclopent-2-en-1-one | dl-16-hydroxy-1-methoxymethyl-1,9-dioxo-16-methyl-19-oxa-5-cis-13-trans prostadiene |
| 65 | 1-trans-tri-n-butylstannyl-4-bromomethyl-4-trimethylsilyloxy-1-heptene | 2-[6-methoxyacetyl hex-2-cis-enyl]cyclopent-2-en-1-one | dl-16-hydroxy-1-methoxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 66 | 1-trans-iodo-4-allenyl-4-trimethylsilyloxy-1-heptene | 2-[6-methoxyacetyl hex-2-cis-enyl]cyclopent-2-en-1-one | dl-16-hydroxy-1-methoxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 67 | 1-trans-tri-n-butylstannyl-4-bromomethyl-4-trimethylsilyloxy-1-octene | 2-[6-methoxyacetyl hex-2-cis-enyl]cyclopent-2-en-1-one | dl-16-hydroxy-1-methoxymethyl-1,9-dioxo-16-bromomethyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 68 | 1-trans-iodo-4-allenyl-4-trimethylsilyloxy-1-octene | 2-[6-methoxyacetyl hex-2-cis-enyl]cyclopent-2-en-1-one | dl-16-hydroxy-1-methoxymethyl-1,9-dioxo-16-allenyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 69 | 1-trans-tri-n-butylstannyl-4-bromomethyl-4-trimethylsilyloxy-1-nonene | 2-[6-methoxyacetyl hex-2-cis-enyl]cyclopent-2-en-1-one | dl-16-hydroxy-1-methoxymethyl-1,9-dioxo-16-bromomethyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 70 | 1-trans-iodo-4-allenyl-4-trimethylsilyloxy-1-nonene | 2-[6-methoxyacetyl hex-2-cis-enyl]cyclopent-2-en-1-one | dl-16-hydroxy-1-methoxymethyl-1,9-dioxo-16-allenyl-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 71 | 1-trans-tri-n-butylstannyl-4-bromomethyl-4-trimethylsilyloxy-1-decene | 2-[6-methoxyacetyl hex-2-cis-enyl]cyclopent-2-en-1-one | dl-16-hydroxy-1-methoxymethyl-1,9-dioxo-16-bromomethyl-20-ethyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 72 | 1-trans-iodo-4-allenyl-4-trimethylsilyloxy-1-decene | 2-[6-methoxyacetyl hex-2-cis-enyl]cyclopent-2-en-1-one | dl-16-hydroxy-1-methoxymethyl-1,9-dioxo-16-allenyl-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 73 | 1-trans-tri-n-butylstannyl-7-thia-4-triethylsilyloxy-1-octene | 2-[7-methoxyacetyl hept-2-cis-enyl]cyclopent-2-en-1-one | dl-16-hydroxy-1-methoxymethyl-1,9-dioxo-19-thia-2-homo-5-cis-13-trans prostadiene |
| 74 | 1-trans-tri-n-butylstannyl-4-methyl-7-thia-4-trimethylsilyloxy-1-octene | 2-[7-methoxyacetyl hept-2-cis-enyl] | dl-16-hydroxy-1-methoxymethyl-1,9-dioxo-16-methyl-19-thia-2-homo-5-cis-13-trans prostadiene |

TABLE II-continued

| EXAMPLE | | | PRODUCT PROSTAGLANDIN OF THE 11-DEOXY PGE2 SERIES |
|---|---|---|---|
| 75 | 1-trans-tri-n-butylstannyl-7-oxa-4-triethylsilyloxy-1-octene | cyclopent-2-en-1-one 2-[7-methoxyacetyl hept-2-cis-enyl] cyclopent-2-en-1-one | dl-16-hydroxy-1-methoxymethyl-1,9-dioxo-19-oxa-2-homo-5-cis-13-trans prostadiene |
| 76 | 1-trans-tri-n-butylstannyl-4-methyl-7-oxa-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-methyl-19-oxa-2-homo-5-cis-13-trans prostadiene |
| 77 | 1-trans-tri-n-butylstannyl-4-bromomethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-bromomethyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 78 | 1-trans-iodo-4-allenyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-allenyl-20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 79 | 1-trans-tri-n-butylstannyl-4-bromomethyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-bromomethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 80 | 1-trans-iodo-4-allenyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-allenyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 81 | 1-trans-tri-n-butylstannyl-4-bromomethyl-4-trimethylsilyloxy-1-nonene | 2-[7-methoxyacetyl hept-2-cis-enyl] cyclopent-2-en-1-one | dl-16-hydroxy-1-methoxymethyl-1,9-dioxo-16-bromomethyl-20-methyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 82 | 1-trans-iodo-4-allenyl-4-trimethylsilyloxy-1-nonene | 2-[7-methoxyacetyl hept-2-cis-enyl] cyclopent-2-en-1-one | dl-16-hydroxy-1-methoxymethyl-1,9-dioxo-16-allenyl-20-methyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 83 | 1-trans-tri-n-butylstannyl-4-bromomethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-bromomethyl-20-ethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 84 | 1-trans-iodo-4-allenyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-allenyl-20-ethyl-2-homo-5-cis-13-trans prostadiene |

TABLE III

| EXAMPLE | VINYL IODIDE | CYCLOPENTENONE | PRODUCT PROSTAGLANDIN OF THE PGE2 SERIES |
|---|---|---|---|
| 1 | 1-trans-iodo-3-triphenylmethoxy-1-heptene | 2-[5-methoxyacetyl pent-2-cis-enyl]-4-trimethylsiloxy cyclopent-2-en-1-one | dl-11a,15a-dihydroxy-1-methoxymethyl-1,9-dioxo-20-nor-2-nor-5-cis-13-trans prostadiene |
| 2 | 1-trans-iodo-3-methyl-3-trimethylsilyloxy-1-heptene | 2-[5-methoxyacetyl pent-2-cis-enyl]-4-trimethylsiloxy cyclopent-2-en-1-one | dl-11a,15a-dihydroxy-1-methoxymethyl-1,9-dioxo-15-methyl-20-nor-2-nor-5-cis-13-trans prostadiene |
| 3 | 1-trans-iodo-4,4-dimethyl-3-trimethylsilyloxy-1-heptene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-dimethyl-20-nor-2-nor-5-cis-13-trans prostadiene |
| 4 | 1-trans-iodo-5,5-dimethyl-3-triphenylmethoxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-17,17-dimethyl-2-nor-5-cis-13-trans prostadiene |
| 5 | 1-trans-iodo-4-methyl-3-triphenylmethoxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-methyl-2-nor-5-cis-13-trans prostadiene |
| 6 | 1-trans-iodo-4,4-trimethylene-3-trimethylsilyloxy-1-heptene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 7 | 1-trans-tri-n-butylstannyl-3-vinyl-3-trimethylsilyloxy-1-heptene | 2-[5-methoxyacetyl pent-2-cis-enyl]-4-trimethylsiloxy cyclopent-2-en-1-one | dl-11a,15a-dihydroxy-1-methoxymethyl-1,9-dioxo-15-vinyl-20-nor-2-nor-5-cis-13-trans prostadiene |
| 8 | 1-trans-tri-n-butylstannyl-4-phenoxy-3-triethylsilyloxy-1-butene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-phenoxy-2-nor-17,20-tetranor-5-cis-13-trans prostadiene |
| 9 | 1-trans-tri-n-butylstannyl-4-(p-fluorophenoxy)-3-triethylsilyloxy-1-butene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-(p-fluorophenoxy)-2-nor-17,20-tetranor-5-cis-13-trans prostadiene |
| 10 | 1-trans-tri-n-butylstannyl-4-(m-chlorophenoxy)-3-triethylsilyloxy-1-butene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-(m-chlorophenoxy)-2-nor-17,20-tetranor-5-cis-13-trans prostadiene |
| 11 | 1-trans-tri-n-butylstannyl-4-(m-trifluoromethylphenoxy)-3-triethylsilyloxy-1-butene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-(m-trifluoromethylphenoxy)-2-nor-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 12 | 1-trans-iodo-5-phenyl-3-triethylsilyloxy-1-pentene | 2-[5-methoxyacetyl pent-2-cis-enyl]-4-trimethylsiloxy cyclopent-2-en-1-one | dl-11a,15a-dihydroxy-1-methoxymethyl-1,9-dioxo-17-phenyl-2-nor-18-20-trinor-5-cis-13-trans prostadiene |
| 13 | 1-trans-iodo-4,4-dimethyl-5-phenyl-3-triethylsilyloxy-1-pentene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-dimethyl-17-phenyl-2-nor-18-20-trinor-5-cis-13-trans prostadiene |
| 14 | 1-trans-iodo-4-cyclopentyl-3-triphenylmethoxy-1-butene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-cyclopentyl-2-nor-17,20-tetranor-5-cis-13-trans prostadiene |
| 15 | 1-trans-iodo-4-cyclohexyl-3-triphenylmethoxy-1-butene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16-cyclohexyl-2-nor-17,20-tetranor-5-cis-13-trans prostadiene |
| 16 | 1-trans-iodo-4-triphenylmethoxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-20-nor-2-nor-5-cis-13-trans prostadiene |

TABLE III-continued

| EXAMPLE | VINYL TIN | CYCLOPENTENONE | PRODUCT PROSTAGLANDIN OF THE PGE2 SERIES |
|---|---|---|---|
| 17 | 1-trans-tri-n-butylstannyl-4-methyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-20-nor-2-nor-5-cis-13-trans prostadiene |
| 18 | 1-trans-tri-n-butylstannyl-4-ethyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-ethyl-2-nor-5-cis-13-trans prostadiene |
| 19 | 1-trans-tri-n-butylstannyl-5-methyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-17-methyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 20 | 1-trans-iodo-5,5-dimethyl 4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-17,17-dimethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 21 | 1-trans-tri-n-butylstannyl-4-vinyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-vinyl-20-nor-2-nor-5-cis-13-trans prostadiene |
| 22 | 1-trans-tri-n-butylstannyl-4-cyclopropyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-cyclopropyl-2-nor-5-cis-13-trans prostadiene |
| 23 | 1-trans-tri-n-butylstannyl-4-trimethylsilylethynyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-ethynyl-20-nor-2-nor-5-cis-13-trans prostadiene |
| 24 | 1-trans-tri-n-butylstannyl-4-methylene 4-triethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-17-methylene-20-nor-2-nor-5-cis-13-trans prostadiene |
| 25 | 1-trans-tri-n-butylstannyl-4-methyl-5-methylene 4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-17-methylene-20-nor-2-nor-5-cis-13-trans prostadiene |
| 26 | 1-trans-tri-n-butylstannyl-4-dimethoxymethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-formyl-20-nor-2-nor-5-cis-13-trans prostadiene |
| 27 | 1-trans-tri-n-butylstannyl-4-fluoromethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-fluoromethyl-20-nor-2-nor-5-cis-13-trans prostadiene |
| 28 | 1-trans-tri-n-butylstannyl-4-difluoromethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-difluoromethyl-20-nor-2-nor-5-cis-13-trans prostadiene |
| 29 | 1-trans-tri-n-butylstannyl-4-trifluoromethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-trifluoromethyl-20-nor-2-nor-5-cis-13-trans prostadiene |
| 30 | 1-trans-tri-n-butylstannyl-4-chloromethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-chloromethyl-20-nor-2-nor-5-cis-13-trans prostadiene |
| 31 | 1-trans-tri-n-butylstannyl-4-trimethylsilyloxymethyl-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-hydroxymethyl-20-nor-2-nor-5-cis-13-trans prostadiene |

TABLE III-continued

| EXAMPLE | VINYL IODIDE | CYCLOPENTENONE | PRODUCT PROSTAGLANDIN OF THE PGE2 SERIES |
|---|---|---|---|
| 32 | 1-trans-iodo-4-methyl-7-chloro-4-trimethylsilyloxy-1-heptene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-19-chloro-2-nor-20-nor-5-cis-13-trans prostadiene |
| 33 | 1-trans-iodo-3-triphenylmethoxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-2-nor-5-cis-13-trans prostadiene |
| 34 | 1-trans-iodo-3-methyl-3-trimethylsilyloxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-15-methyl-2-nor-5-cis-13-trans prostadiene |
| 35 | 1-trans-iodo-4,4-dimethyl-3-trimethylsilyloxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-dimethyl-2-nor-5-cis-13-trans prostadiene |
| 36 | 1-trans-iodo-4,4-trimethylene-3-trimethylsilyloxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-trimethylene-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 37 | 1-trans-tri-n-butylstannyl-3-vinyl-3-trimethylsilyloxy-1-octene | 2-[5-methoxyacetyl pent-2-cis-enyl]-4-trimethylsiloxy cyclopent-2-en-1-one | dl-11a,15a-dihydroxy-1-methoxymethyl-1,9-dioxo-15-vinyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 38 | 1-trans-iodo-4-triphenylmethoxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 39 | 1-trans-tri-n-butylstannyl-4-methyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-2-nor-5-cis-13-trans prostadiene |
| 40 | 1-trans-tri-n-butylstannyl-5-methyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-17-methyl-2-nor-5-cis-13-trans prostadiene |
| 41 | 1-trans-tri-n-butylstannyl-4-vinyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-vinyl-2-nor-5-cis-13-trans prostadiene |
| 42 | 1-trans-tri-n-butylstannyl-4-trimethylsilylethynyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-ethynyl-2-nor-5-cis-13-trans prostadiene |
| 43 | 1-trans-tri-n-butylstannyl-5-methylene-4-triethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-17-methylene-2-nor-5-cis-13-trans prostadiene |
| 44 | 1-trans-tri-n-butylstannyl-4-methyl-5-methylene-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-17-methylene-2-nor-5-cis-13-trans prostadiene |
| 45 | 1-trans-tri-n-butylstannyl-4-dimethoxymethyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-formyl-2-nor-5-cis-13-trans prostadiene |
| 46 | 1-trans-tri-n-butylstannyl-4-fluoromethyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-fluoromethyl-2-nor-5-cis-13-trans prostadiene |
| 47 | 1-trans-tri-n-butylstannyl-4-difluoromethyl-4-trimethylsilyloxy-1-octene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-difluoromethyl- |

TABLE III-continued

| EXAMPLE | VINYL IODIDE / VINYL TIN | CYCLOPENTENONE | PRODUCT PROSTAGLANDIN |
|---|---|---|---|
| 48 | 1-trans-tri-n-butylstannyl-4-fluoromethyl-4-trimethylsilyloxy-1-octene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-trifluoromethyl-2-nor-5-cis-13-trans prostadiene |
| 49 | 1-trans-tri-n-butylstannyl-4-chloromethyl-4-trimethylsilyloxy-1-octene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-chloromethyl-2-nor-5-cis-13-trans prostadiene |
| 50 | 1-trans-tri-n-butylstannyl-4-trimethylsilyloxymethyl-4-trimethylsilyloxy-1-octene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-hydroxymethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 51 | 1-trans-iodo-3-triphenylmethoxy-1-nonene | 2-[5-methoxyacetyl pent-2-cis-enyl]-4-trimethylsilyloxy cyclopent-2-en-1-one | dl-11a,15a-dihydroxy-1-methoxymethyl-1,9-dioxo-20-methyl-2-nor-5-cis-13-trans prostadiene |
| 52 | 1-trans-iodo-3-methyl-3-trimethylsilyloxy-1-nonene | 2-[5-methoxyacetyl pent-2-cis-enyl]-4-trimethylsilyloxy cyclopent-2-en-1-one | dl-11a,15a-dihydroxy-1-methoxymethyl-1,9-dioxo-15-methyl-20-methyl-2-nor-5-cis-13-trans prostadiene |
| 53 | 1-trans-iodo-4,4-dimethyl-3-trimethylsilyloxy-1-nonene | 2-[5-methoxyacetyl pent-2-cis-enyl]-4-trimethylsilyloxy cyclopent-2-en-1-one | dl-11a,15a-dihydroxy-1-methoxymethyl-1,9-dioxo-16,16-dimethyl-20-methyl-2-nor-5-cis-13-trans prostadiene |
| 54 | 1-trans-iodo-4,4-trimethylene-3-trimethylsilyloxy-1-nonene | 2-[5-methoxyacetyl pent-2-cis-enyl]-4-trimethylsilyloxy cyclopent-2-en-1-one | dl-11a,15a-dihydroxy-1-methoxymethyl-1,9-dioxo-16,16-trimethylene-20-methyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 55 | 1-trans-tri-n-butylstannyl-3-vinyl-3-trimethylsilyloxy-1-nonene | 2-[5-methoxyacetyl pent-2-cis-enyl]-4-trimethylsilyloxy cyclopent-2-en-1-one | dl-11a,15a-dihydroxy-1-methoxymethyl-1,9-dioxo-15-vinyl-20-methyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 56 | 1-trans-iodo-4-triphenylmethoxy-1-nonene | 2-[5-methoxyacetyl pent-2-cis-enyl]-4-trimethylsilyloxy cyclopent-2-en-1-one | dl-11a,16-dihydroxy-1-methoxymethyl-1,9-dioxo-20-methyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 57 | 1-trans-tri-n-butylstannyl-4-methyl-4-trimethylsilyloxy-1-nonene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-methyl-20-methyl-2-nor-5-cis-13-trans prostadiene |
| 58 | 1-trans-tri-n-butylstannyl-5-methyl-4-trimethylsilyloxy-1-nonene | 2-[5-methoxyacetyl pent-2-cis-enyl]-4-trimethylsilyloxy cyclopent-2-en-1-one | dl-11a,16-dihydroxy-1-methoxymethyl-1,9-dioxo-17-methyl-20-methyl-2-nor-5-cis-13-trans prostadiene |
| 59 | 1-trans-tri-n-butylstannyl-4-vinyl-4-trimethylsilyloxy-1-nonene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-vinyl-20-methyl-2-nor-5-cis-13-trans prostadiene |
| 60 | 1-trans-tri-n-butylstannyl-4-trimethylsilylethynyl-4-trimethylsilyloxy-1-nonene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-ethynyl-20-methyl-2-nor-5-cis-13-trans prostadiene |
| 61 | 1-trans-tri-n-butylstannyl-5-methylene-4-triethylsilyloxy-1-nonene | 2-[5-methoxyacetyl pent-2-cis-enyl]-4-trimethylsilyloxy cyclopent-2-en-1-one | dl-11a,16-dihydroxy-1-methoxymethyl-1,9-dioxo-17-methylene-20-methyl-2-nor-5-cis-13-trans prostadiene |
| 62 | 1-trans-tri-n-butylstannyl-4-methyl-5-methylene | 2-[5-methoxyacetyl | dl-11a,16-dihydroxy-1-methoxymethyl-1,9-dioxo-16-methyl- |

TABLE III-continued

| EXAMPLE | VINYL IODIDE / VINYL TIN | CYCLOPENTENONE | PRODUCT PROSTAGLANDIN |
|---|---|---|---|
| | 4-trimethylsilyloxy-1-nonene | pent-2-cis-enyl]-4-trimethylsilyoxy cyclopent-2-en-1-one | 17-methylene-20-methyl-2-nor-5-cis-13-trans prostadiene |
| 63 | 1-trans-tri-n-butylstannyl-4-dimethoxymethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-formyl-20-methyl-2-nor-5-cis-13-trans prostadiene |
| 64 | 1-trans-tri-n-butylstannyl-4-fluoromethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-fluoromethyl-20-methyl-2-nor-5-cis-13-trans prostadiene |
| 65 | 1-trans-tri-n-butylstannyl-4-difluoromethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-difluoromethyl-20-methyl-2-nor-5-cis-13-trans prostadiene |
| 66 | 1-trans-tri-n-butylstannyl-4-trifluoromethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-trifluoromethyl-20-methyl-2-nor-5-cis-13-trans prostadiene |
| 67 | 1-trans-tri-n-butylstannyl-4-chloromethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-chloromethyl-20-methyl-2-nor-5-cis-13-trans prostadiene |
| 68 | 1-trans-tri-n-butylstannyl-4-trimethylsilyloxymethyl-4-trimethylsilyloxy-1-nonene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-hydroxymethyl-20-methyl-2-nor-5-cis-13-trans prostadiene |
| EXAMPLE | VINYL IODIDE | CYCLOPENTENONE | PRODUCT PROSTAGLANDIN OF THE PGE2 SERIES |
| 69 | 1-trans-iodo-3-triphenylmethoxy-1-decene | 2-[5-methoxyacetyl pent-2-cis-enyl]-4-trimethylsiloxy cyclopent-2-en-1-one | dl-11a,15a-dihydroxy-1-methoxymethyl-1,9-dioxo-20-ethyl-2-nor-5-cis-13-trans prostadiene |
| 70 | 1-trans-iodo-3-methyl-3-trimethylsilyloxy-1-decene | 2-[5-methoxyacetyl pent-2-cis-enyl]-4-trimethylsiloxy cyclopent-2-en-1-one | dl-11a,15a-dihydroxy-1-methoxymethyl-1,9-dioxo-15-methyl-20-ethyl-2-nor-5-cis-13-trans prostadiene |
| 71 | 1-trans-iodo-4,4-dimethyl-3-trimethylsilyloxy-1-decene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-dimethyl-20-ethyl-2-nor-5-cis-13-trans prostadiene |
| 72 | 1-trans-iodo-4,4-trimethylene-3-trimethylsilyloxy-1-decene | 2-[5-methoxyacetyl pent-2-cis-enyl]-4-trimethylsiloxy cyclopent-2-en-1-one | dl-11a,15a-dihydroxy-1-methoxymethyl-1,9-dioxo-16,16-trimethylene-20-ethyl-2-nor-5-cis-13-trans prostadiene |
| EXAMPLE | VINYL TIN | CYCLOPENTENONE | PRODUCT PROSTAGLANDIN OF THE PGE2 SERIES |
| 73 | 1-trans-tri-n-butylstannyl-3-vinyl-3-trimethylsilyloxy-1-decene | 2-[5-methoxyacetyl pent-2-cis-enyl]-4-trimethylsiloxy cyclopent-2-en-1-one | dl-11a,15a-dihydroxy-1-methoxymethyl-1,9-dioxo-15-vinyl-20-ethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 74 | 1-trans-iodo-4-triphenylmethoxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-20-ethyl-2-nor-5-cis-13-trans prostadiene |
| EXAMPLE | VINYL TIN | CYCLOPENTENONE | PRODUCT PROSTAGLANDIN OF THE PGE2 SERIES |
| 75 | 1-trans-tri-n-butylstannyl-4-methyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-20-ethyl-2-nor-5-cis-13-trans prostadiene |
| 76 | 1-trans-tri-n-butylstannyl-5-methyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-17-methyl-20-ethyl-2-nor-5-cis-13-trans prostadiene |
| 77 | 1-trans-tri-n-butylstannyl-4-vinyl- | 2-[5-methoxyacetyl | dl-11a,16-dihydroxy-1-methoxymethyl-1,9-dioxo-16-vinyl- |

TABLE III-continued

| EXAMPLE | VINYL IODIDE | CYCLOPENTENONE | PRODUCT PROSTAGLANDIN OF THE PGE2 SERIES |
|---|---|---|---|
| 78 | 4-trimethylsilyloxy-1-decene | pent-2-cis-enyl]-4-trimethylsiloxy cyclopent-2-en-1-one | 20-ethyl-2-nor-5-cis-13-trans prostadiene |
| | 1-trans-tri-n-butylstannyl-4-trimethylsilylethynyl-4-trimethylsilyloxy-1-decene | 2-[5-methoxyacetyyl pent-2-cis-enyl]-4-trimethylsiloxy cyclopent-2-en-1-one | dl-11a,16-dihydroxy-1-methoxymethyl-1,9-dioxo-16-ethynyl-20-ethyl-2-nor-5-cis-13-trans prostadiene |
| 79 | 1-trans-tri-n-butylstannyl-5-methylene 4-triethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-17-methylene-20-ethyl-2-nor-5-cis-13-trans prostadiene |
| 80 | 1-trans-tri-n-butylstannyl-4-methyl-5-methylene 4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-methyl-17-methylene-20-ethyl-2-nor-5-cis-13-trans prostadiene |
| 81 | 1-trans-tri-n-butylstannyl-4-dimethoxymethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-formyl-20-ethyl-2-nor-5-cis-13-trans prostadiene |
| 82 | 1-trans-tri-n-butylstannyl-4-fluoromethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-fluoromethyl-20-ethyl-2-nor-5-cis-13-trans prostadiene |
| 83 | 1-trans-tri-n-butylstannyl-4-difluoromethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-difluoromethyl-20-ethyl-2-nor-5-cis-13-trans prostadiene |
| 84 | 1-trans-tri-n-butylstannyl-4-trifluoromethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-trifluoromethyl-20-ethyl-2-nor-5-cis-13-trans prostadiene |
| 85 | 1-trans-tri-n-butylstannyl-4-chloromethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-chloromethyl-20-ethyl-2-nor-5-cis-13-trans prostadiene |
| 86 | 1-trans-tri-n-butylstannyl-4-trimethylsilyloxymethyl-4-trimethylsilyloxy-1-decene | 2-[5-methoxyacetyl pent-2-cis-enyl]-4-trimethylsiloxy cyclopent-2-en-1-one | dl-11a,16-dihydroxy-1-methoxymethyl-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 87 | 1-trans-iodo-3-triphenylmethoxy-1-heptene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-20-nor-5-cis-13-trans prostadiene |
| 88 | 1-trans-iodo-3-methyl-3-trimethylsilyloxy-1-heptene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-15-methyl-20-nor-5-cis-13-trans prostadiene |
| 89 | 1-trans-iodo-4,4-dimethyl-3-trimethylsilyloxy-1-heptene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16,16-dimethyl-20-nor-5-cis-13-trans prostadiene |
| 90 | 1-trans-iodo-5,5-dimethyl-3-triphenylmethoxy-1-heptene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-17,17-dimethyl-5-cis-13-trans prostadiene |
| 91 | 1-trans-iodo-4-methyl-3-triphenylmethoxy-1-octene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-methyl-5-cis-13-trans prostadiene |
| 92 | 1-trans-tri-4,4-trimethylene-3-trimethylsilyloxy-1-heptene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16,16-trimethylene-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 93 | 1-trans-tri-n-butylstannyl-3-vinyl-3-trimethylsilyloxy-1-heptene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-15-vinyl-20-nor-5-cis-13-trans prostadiene |

TABLE III-continued

| EXAMPLE | VINYL IODIDE / VINYL TIN | CYCLOPENTENONE | PRODUCT PROSTAGLANDIN |
|---|---|---|---|
| 94 | 1-trans-tri-n-butylstannyl-4-phenoxy-3-triethylsilyloxy-1-butene | cyclopent-2-en-1-one 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-phenoxy-17-20-tetranor-5-cis-13-trans prostadiene |
| 95 | 1-trans-tri-n-butylstannyl-4-(p-fluorophenoxy)-3-triethylsilyloxy-1-butene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-(p-fluorophenoxy)-17-20-tetranor-5-cis-13-trans prostadiene |
| 96 | 1-trans-tri-n-butylstannyl-4-(m-chlorophenoxy)-3-triethylsilyloxy-1-butene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-(m-chlorophenoxy)-17-20-tetranor-5-cis-13-trans prostadiene |
| 97 | 1-trans-tri-n-butylstannyl-4-(m-trifluoromethylphenoxy)-3-triethylsilyloxy-1-butene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-(m-trifluoromethylphenoxy)-17-20-tetranor-5-cis-13-trans prostadiene |
| EXAMPLE | VINYL IODIDE | CYCLOPENTENONE | PRODUCT PROSTAGLANDIN OF THE PGE2 SERIES |
| 98 | 1-trans-iodo-5-phenyl 3-triethylsilyloxy-1-pentene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-17-phenyl-18-20-trinor-5-cis-13-trans prostadiene |
| 99 | 1-trans-iodo-4,4-dimethyl-5-phenyl 3-triethylsilyloxy-1-pentene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16,16-dimethyl-17-phenyl-18-20-trinor-5-cis-13-trans prostadiene |
| 100 | 1-trans-iodo-4-cyclopentyl 3-triphenylmethoxy-1-butene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-cyclopentyl-17-20-tetranor-5-cis-13-trans prostadiene |
| 101 | 1-trans-iodo-4-cyclohexyl 3-triphenylmethoxy-1-butene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16-cyclohexyl-17-20-tetranor-5-cis-13-trans prostadiene |
| 102 | 1-trans-iodo-4-triphenylmethoxy-1-heptene | 2-[6-methoxyacetyl hex-2-cis-enyl]-4-trimethylsilyloxy cyclopent-2-en-1-one | dl-11a,16-dihydroxy-1-methoxymethyl-1,9-dioxo-20-nor-5-cis-13-trans prostadiene |
| EXAMPLE | VINYL TIN | CYCLOPENTENONE | PRODUCT PROSTAGLANDIN OF THE PGE2 SERIES |
| 103 | 1-trans-tri-n-butylstannyl-4-methyl-4-trimethylsilyloxy-1-heptene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-20-nor-5-cis-13-trans prostadiene |
| 104 | 1-trans-tri-n-butylstannyl-4-ethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-ethyl-5-cis-13-trans prostadiene |
| 105 | 1-trans-tri-n-butylstannyl-5-methyl-4-trimethylsilyloxy-1-heptene | 2-[6-methoxyacetyl hex-2-cis-enyl]-4-trimethylsilyloxy cyclopent-2-en-1-one | dl-11a,16-dihydroxy-1-methoxymethyl-1,9-dioxo-17-methyl-20-nor-5-cis-13-trans prostadiene |
| EXAMPLE | VINYL IODIDE | CYCLOPENTENONE | PRODUCT PROSTAGLANDIN OF THE PGE2 SERIES |
| 106 | 1-trans-iodo-5,5-dimethyl 4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-17,17-dimethyl-5-cis-13-trans prostadiene |
| EXAMPLE | VINYL TIN | CYCLOPENTENONE | PRODUCT PROSTAGLANDIN OF THE PGE2 SERIES |
| 107 | 1-trans-tri-n-butylstannyl-4-vinyl-4-trimethylsilyloxy-1-heptene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-vinyl-20-nor-5-cis-13-trans prostadiene |
| 108 | 1-trans-tri-n-butylstannyl-4-cyclopropyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-cyclopropyl-5-cis-13-trans prostadiene |

TABLE III-continued

| | | | |
|---|---|---|---|
| 109 | 1-trans-tri-n-butylstannyl-4-trimethylsilylethynyl-4-trimethylsilyloxy-1-heptene | cyclopent-2-en-1-one 2-[6-methoxyacetyl hex-2-cis-enyl]-4-trimethylsiloxy cyclopent-2-en-1-one | dl-11a,16-dihydroxy-1-methoxymethyl-1,9-dioxo-16-ethynyl-20-nor-5-cis-13-trans prostadiene |
| 110 | 1-trans-tri-n-butylstannyl-5-methylene 4-triethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-17-methylene-20-nor-5-cis-13-trans prostadiene |
| 111 | 1-trans-tri-n-butylstannyl-4-methyl-5-methylene 4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-methyl-17-methylene-20-nor-5-cis-13-trans prostadiene |
| 112 | 1-trans-tri-n-butylstannyl-4-dimethoxymethyl-4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-formyl-20-nor-5-cis-13-trans prostadiene |
| 113 | 1-trans-tri-n-butylstannyl-4-fluoromethyl-4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-fluoromethyl-20-nor-5-cis-13-trans prostadiene |
| 114 | 1-trans-tri-n-butylstannyl-4-difluoromethyl-4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-difluoromethyl-20-nor-5-cis-13-trans prostadiene |
| 115 | 1-trans-tri-n-butylstannyl-4-trifluoromethyl-4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-trifluoromethyl-20-nor-5-cis-13-trans prostadiene |
| 116 | 1-trans-tri-n-butylstannyl-4-chloromethyl-4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-chloromethyl-20-nor-5-cis-13-trans prostadiene |
| 117 | 1-trans-tri-n-butylstannyl-4-trimethylsilyloxymethyl-4-trimethylsilyloxy-1-heptene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-hydroxymethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 118 | 1-trans-iodo-4-methyl-7-chloro 4-trimethylsilyloxy-1-heptene | 2-[6-methoxyacetyl hex-2-cis-enyl]-4-trimethylsiloxy cyclopent-2-en-1-one | dl-11a,15a-dihydroxy-1-methoxymethyl-1,9-dioxo-16-methyl-19-chloro-20-nor-5-cis-13-trans prostadiene |
| 119 | 1-trans-iodo-3-triphenylmethoxy-1-octene | 2-[6-methoxyacetyl hex-2-cis-enyl]-4-trimethylsiloxy cyclopent-2-en-1-one | dl-11a,15a-dihydroxy-1-methoxymethyl-1,9-dioxo-5-cis-13-trans prostadiene |
| 120 | 1-trans-iodo-3-methyl-3-trimethylsilyloxy-1-octene | 2-[6-methoxyacetyl hex-2-cis-enyl]-4-trimethylsiloxy cyclopent-2-en-1-one | dl-11a,15a-dihydroxy-1-methoxymethyl-1,9-dioxo-15-methyl-5-cis-13-trans prostadiene |
| 121 | 1-trans-iodo-4,4-dimethyl 3-trimethylsilyloxy-1-octene | 2-[6-methoxyacetyl hex-2-cis-enyl]-4-trimethylsiloxy cyclopent-2-en-1-one | dl-11a,15a-dihydroxy-1-methoxymethyl-1,9-dioxo-16,16-dimethyl-5-cis-13-trans prostadiene |
| 122 | 1-trans-iodo-4,4-trimethylene 3-trimethylsilyloxy-1-octene | 2-[6-methoxyacetyl hex-2-cis-enyl]-4-trimethylsiloxy cyclopent-2-en-1-one | dl-11a,15a-dihydroxy-1-methoxymethyl-1,9-dioxo-16,16-trimethylene-5-cis-13-trans prostadiene |
| EXAMPLE | VINYL TIN | CYCLOPENTENONE | PRODUCT PROSTAGLANDIN OF THE PGE2 SERIES |
| 123 | 1-trans-tri-n-butylstannyl-3-vinyl-3-trimethylsilyloxy-1-octene | 2-[6-methoxyacetyl hex-2-cis-enyl]-4-trimethylsiloxy cyclopent-2-en-1-one | dl-11a,15a-dihydroxy-1-methoxymethyl-1,9-dioxo-15-vinyl-5-cis-13-trans prostadiene |
| EXAMPLE | VINYL IODIDE | CYCLOPENTENONE | PRODUCT PROSTAGLANDIN OF THE PGE2 SERIES |
| 124 | 1-trans-iodo- | 2-[6-methoxyacetyl | dl-11a,16-dihydroxy-1-methoxymethyl-1,9-dioxo- |

TABLE III-continued

| EXAMPLE | VINYL TIN | CYCLOPENTENONE | PRODUCT PROSTAGLANDIN OF THE PGE2 SERIES |
|---|---|---|---|
| | 4-triphenylmethoxy-1-octene | hex-2-cis-enyl]-4-trimethylsilyloxy cyclopent-2-en-1-one | 5-cis-13-trans prostadiene |
| 125 | 1-trans-tri-n-butylstannyl-4-methyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-5-cis-13-trans prostadiene |
| 126 | 1-trans-tri-n-butylstannyl-4-methyl-5-methyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-17-methyl-5-cis-13-trans prostadiene |
| 127 | 1-trans-tri-n-butylstannyl-4-vinyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-vinyl-5-cis-13-trans prostadiene |
| 128 | 1-trans-tri-n-butylstannyl-4-trimethylsilylethynyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-ethynyl-5-cis-13-trans prostadiene |
| 129 | 1-trans-tri-n-butylstannyl-5-methylene-4-triethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-17-methylene-5-cis-13-trans prostadiene |
| 130 | 1-trans-tri-n-butylstannyl-4-methyl-5-methylene-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-17-methylene-5-cis-13-trans prostadiene |
| 131 | 1-trans-tri-n-butylstannyl-4-dimethoxymethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-formyl-5-cis-13-trans prostadiene |
| 132 | 1-trans-tri-n-butylstannyl-4-fluoromethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-fluoromethyl-5-cis-13-trans prostadiene |
| 133 | 1-trans-tri-n-butylstannyl-4-difluoromethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-difluoromethyl-5-cis-13-trans prostadiene |
| 134 | 1-trans-tri-n-butylstannyl-4-trifluoromethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-trifluoromethyl-5-cis-13-trans prostadiene |
| 135 | 1-trans-tri-n-butylstannyl-4-chloromethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-chloromethyl-5-cis-13-trans prostadiene |
| 136 | 1-trans-tri-n-butylstannyl-4-trimethylsilyloxymethyl-4-trimethylsilyloxy-1-octene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-hydroxymethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 137 | 1-trans-iodo-3-triphenylmethoxy-1-nonene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-20-methyl-5-cis-13-trans prostadiene |
| 138 | 1-trans-iodo-3-methyl-3-trimethylsilyloxy-1-nonene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-15-methyl-20-methyl-5-cis-13-trans prostadiene |
| 139 | 1-trans-iodo-4,4-dimethyl-3-trimethylsilyloxy-1-nonene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16,16-dimethyl-20-methyl-5-cis-13-trans prostadiene |
| 140 | 1-trans-iodo-4,4-trimethylene-3-trimethylsilyloxy-1-nonene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-16,16-trimethylene-20-methyl-5-cis-13-trans prostadiene |

TABLE III-continued

| EXAMPLE | VINYL TIN | CYCLOPENTENONE | PRODUCT PROSTAGLANDIN OF THE PGE2 SERIES |
|---|---|---|---|
| 141 | 1-trans-tri-n-butylstannyl-3-vinyl-3-trimethylsilyloxy-1-nonene | 2-[6-methoxyacetyl hex-2-cis-enyl]-4-trimethylsilyloxy cyclopent-2-en-1-one | dl-11a,15a-dihydroxy-1-methoxymethyl-1,9-dioxo-15-vinyl-20-methyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 142 | 1-trans-iodo-4-triphenylmethoxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-20-methyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 143 | 1-trans-tri-n-butylstannyl-4-methyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-20-methyl-5-cis-13-trans prostadiene |
| 144 | 1-trans-tri-n-butylstannyl-5-methyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-17-methyl-20-methyl-5-cis-13-trans prostadiene |
| 145 | 1-trans-tri-n-butylstannyl-4-vinyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-vinyl-20-methyl-5-cis-13-trans prostadiene |
| 146 | 1-trans-tri-n-butylstannyl-4-trimethylsilylethynyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-ethynyl-20-methyl-5-cis-13-trans prostadiene |
| 147 | 1-trans-tri-n-butylstannyl-5-methylene-4-triethylsilyloxy-1-nonene | 2-[6-methoxyacetyl hex-2-cis-enyl]-4-trimethylsilyloxy cyclopent-2-en-4-one | dl-11a,16-dihydroxy-1-methoxymethyl-1,9-dioxo-17-methylene-20-methyl-5-cis-13-trans prostadiene |
| 148 | 1-trans-tri-n-butylstannyl-4-methyl-5-methylene-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-17-methylene-20-methyl-5-cis-13-trans prostadiene |
| 149 | 1-trans-tri-n-butylstannyl-4-dimethoxymethyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-formyl-20-methyl-5-cis-13-trans prostadiene |
| 150 | 1-trans-tri-n-butylstannyl-4-fluoromethyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-fluoromethyl-20-methyl-5-cis-13-trans prostadiene |
| 151 | 1-trans-tri-n-butylstannyl-4-difluoromethyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-difluoromethyl-20-methyl-5-cis-13-trans prostadiene |
| 152 | 1-trans-tri-n-butylstannyl-4-trifluoromethyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-trifluoromethyl-20-methyl-5-cis-13-trans prostadiene |
| 153 | 1-trans-tri-n-butylstannyl-4-chloromethyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-chloromethyl-20-methyl-5-cis-13-trans prostadiene |
| 154 | 1-trans-tri-n-butylstannyl-4-trimethylsilyloxymethyl-4-trimethylsilyloxy-1-nonene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-hydroxymethyl-20-methyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 155 | 1-trans-iodo-3-triphenylmethoxy-1-decene | 2-[6-methoxyacetyl hex-2-cis-enyl]-4-trimethylsilyloxy | dl-11a,15a-dihydroxy-1-methoxymethyl-1,9-dioxo-20-ethyl-5-cis-13-trans prostadiene |

TABLE III-continued

| | | | |
|---|---|---|---|
| 156 | 1-trans-iodo-3-methyl-3-trimethylsilyloxy-1-decene | 2-[6-methoxyacetyl hex-2-cis-enyl]-4-trimethylsiloxy cyclopent-2-en-1-one | dl-11a,15a-dihydroxy-1-methoxymethyl-1,9-dioxo-15-methyl-20-ethyl-5-cis-13-trans prostadiene |
| 157 | 1-trans-iodo-4,4-dimethyl-3-trimethylsilyloxy-1-decene | 2-[6-methoxyacetyl hex-2-cis-enyl] -4-trimethylsiloxy cyclopent-2-en-1-one | dl-11a,15a-dihydroxy-1-methoxymethyl-1,9-dioxo-16,16-dimethyl-20-ethyl-5-cis-13-trans prostadiene |
| 158 | 1-trans-iodo-4,4-trimethylene-3-trimethylsilyloxy-1-decene | 2-[6-methoxyacetyl hex-2-cis-enyl]-4-trimethylsiloxy cyclopent-2-en-1-one | dl-11a,15a-dihydroxy-1-methoxymethyl-1,9-dioxo-16,16-trimethylene-20-ethyl-5-cis-13-trans prostadiene |
| EXAMPLE | VINYL TIN | CYCLOPENTENONE | PRODUCT PROSTAGLANDIN OF THE PGE2 SERIES |
| 159 | 1-trans-tri-n-butylstannyl-3-vinyl-3-trimethylsilyloxy-1-decene | 2-[6-methoxyacetyl hex-2-cis-enyl]-4-trimethylsiloxy cyclopent-2-en-1-one | dl-11a,15a-dihydroxy-1-methoxymethyl-1,9-dioxo-15-vinyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 160 | 1-trans-iodo-4-triphenylmethoxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-20-ethyl-5-cis-13-trans prostadiene |
| EXAMPLE | VINYL TIN | CYCLOPENTENONE | PRODUCT PROSTAGLANDIN OF THE PGE2 SERIES |
| 161 | 1-trans-tri-n-butylstannyl-4-methyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-methyl-20-ethyl-5-cis-13-trans prostadiene |
| 162 | 1-trans-tri-n-butylstannyl-5-methyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-17-methyl-20-ethyl-5-cis-13-trans prostadiene |
| 163 | 1-trans-tri-n-butylstannyl-4-vinyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-vinyl-20-ethyl-5-cis-13-trans prostadiene |
| 164 | 1-trans-tri-n-butylstannyl-4-trimethylsilyethynyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-ethynyl-20-ethyl-5-cis-13-trans prostadiene |
| 165 | 1-trans-tri-n-butylstannyl-5-methylene-4-triethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-17-methylene-20-ethyl-5-cis-13-trans prostadiene |
| 166 | 1-trans-tri-n-butylstannyl-4-methyl-5-methylene-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-methyl-17-methylene-20-ethyl-5-cis-13-trans prostadiene |
| 167 | 1-trans-tri-n-butylstannyl-4-dimethoxymethyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-formyl-20-ethyl-5-cis-13-trans prostadiene |
| 168 | 1-trans-tri-n-butylstannyl-4-fluoromethyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-fluoromethyl-20-ethyl-5-cis-13-trans prostadiene |
| 169 | 1-trans-tri-n-butylstannyl-4-difluoromethyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-difluoromethyl-20-ethyl-5-cis-13-trans prostadiene |
| 170 | 1-trans-tri-n-butylstannyl-4-trifluoromethyl-4-trimethylsilyloxy-1-decene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-trifluoromethyl-20-ethyl-5-cis-13-trans prostadiene |
| 171 | 1-trans-tri-n-butylstannyl-4-chloromethyl- | 2-[6-methoxyacetyl | dl-11a,16-dihydroxy-1-methoxymethyl-1,9-dioxo-16-chloromethyl- |

TABLE III-continued

| | VINYL IODIDE | CYCLOPENTENONE | PRODUCT PROSTAGLANDIN OF THE PGE 2 SERIES |
|---|---|---|---|
| 172 | 1-trans-tri-n-butylstannyl-4-trimethylsilyloxymethyl-4-trimethylsilyloxy-1-decene | 4-trimethylsilyloxy-1-decene hex-2-cis-enyl]-4-trimethylsilyloxy cyclopent-2-en-1-one 2-[6-methoxyacetyl hex-2-cis-enyl]-4-trimethylsilyloxy cyclopent-2-en-1-one | 20-ethyl-5-cis-13-trans prostadiene dl-11a,16-dihydroxy-1-methyoxymethyl-1,9-dioxo-16-hydroxymethyl-20-ethyl-5-cis-13-trans prostadiene |
| EXAMPLE | VINYL IODIDE | CYCLOPENTENONE | PRODUCT PROSTAGLANDIN OF THE PGE 2 SERIES |
| 173 | 1-trans-iodo-3-triphenylmethoxy-1-heptene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-20-nor-2-homo-5-cis-13-trans prostadiene |
| 174 | 1-trans-iodo-3-methyl-3-trimethylsilyloxy-1-heptene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-15-methyl-20-nor-2-homo-5-cis-13-trans prostadiene |
| 175 | 1-trans-iodo-4,4-dimethyl-3-trimethylsilyloxy-1-heptene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16,16-dimethyl-20-nor-2-homo-5-cis-13-trans prostadiene |
| 176 | 1-trans-iodo-5,5-dimethyl-3-triphenylmethoxy-1-octene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-17,17-dimethyl-2-homo-5-cis-13-trans prostadiene |
| 177 | 1-trans-iodo-4-methyl-3-triphenylmethoxy-1-octene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16-methyl-2-homo-5-cis-13-trans prostadiene |
| 178 | 1-trans-iodo-4,4-trimethylene-3-trimethylsilyloxy-1-heptene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16,16-trimethylene-20-nor-20-homo-5-cis-13-trans prostadiene |
| EXAMPLE | VINYL TIN | CYCLOPENTENONE | PRODUCT PROSTAGLANDIN OF THE PGE2 SERIES |
| 179 | 1-trans-tri-n-butylstannyl-3-vinyl-3-trimethylsilyloxy-1-heptene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-15-vinyl-20-nor-2-homo-5-cis-13-trans prostadiene |
| 180 | 1-trans-tri-n-butylstannyl-4-phenoxy-3-triethylsilyloxy-1-butene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16-phenoxy-2-homo-17-20-tetranor-5-cis-13-trans prostadiene |
| 181 | 1-trans-tri-n-butylstannyl-4-(p-fluorophenoxy)-3-triethylsilyloxy-1-butene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16-(p-fluorophenoxy)-2-homo-17-20-tetranor-5-cis-13-trans prostadiene |
| 182 | 1-trans-tri-n-butylstannyl-4-(m-chlorophenoxy)-3-triethylsilyloxy-1-butene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16-(m-chlorophenoxy)-2-homo-17-20-tetranor-5-cis-13-trans prostadiene |
| 183 | 1-trans-tri-n-butylstannyl-4-(m-trifluoromethylphenoxy)-3-triethylsilyloxy-1-butene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16-(m-trifluoromethylphenoxy)-2-homo-17-20-tetranor-5-cis-13-trans prostadiene |
| EXAMPLE | VINYL IODIDE | CYCLOPENTENONE | PRODUCT PROSTAGLANDIN OF THE PGE2 SERIES |
| 184 | 1-trans-iodo-5-phenyl-3-triethylsilyloxy-1-pentene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-17-phenyl-2-homo-18-20-trinor-5-cis-13-trans prostadiene |
| 185 | 1-trans-iodo-4,4-dimethyl-5-phenyl-3-triethylsilyloxy-1-pentene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16,16-dimethyl-17-phenyl-2-homo-18-20-trinor-5-cis-13-trans prostadiene |
| 186 | 1-trans-iodo-4-cyclopentyl-3-triphenylmethoxy-1-butene | 2-[7-methoxyacetyl hept-2-cis-enyl]-4-trimethylsilyloxy cyclopent-2-en-1-one | dl-11a,15a-dihydroxy-1-methoxymethyl-1,9-dioxo-16-cyclopentyl-2-homo-17-20-tetranor-5-cis-13-trans prostadiene |

TABLE III-continued

| | VINYL IODIDE / VINYL TIN | CYCLOPENTENONE | PRODUCT PROSTAGLANDIN |
|---|---|---|---|
| 187 | 1-trans-iodo-4-cyclohexyl-3-triphenylmethoxy-1-butene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16-cyclohexyl-2-homo-17-20-tetranor-5-cis-13-trans prostadiene |
| 188 | 1-trans-iodo-4-triphenylmethoxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-20-nor-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 189 | 1-trans-tri-n-butylstannyl-4-methyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-20-nor-2-homo-5-cis-13-trans prostadiene |
| 190 | 1-trans-tri-n-butylstannyl-4-ethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-ethyl-2-homo-5-cis-13-trans prostadiene |
| 191 | 1-trans-tri-n-butylstannyl-5-methyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methyl-20-nor-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 192 | 1-trans-iodo-5,5-dimethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-17,17-dimethyl-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 193 | 1-trans-tri-n-butylstannyl-4-vinyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-vinyl-20-nor-2-homo-5-cis-13-trans prostadiene |
| 194 | 1-trans-tri-n-butylstannyl-4-cyclopropyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-cyclopropyl-2-homo-5-cis-13-trans prostadiene |
| 195 | 1-trans-tri-n-butylstannyl-4-trimethylsilylethynyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-ethynyl-20-nor-2-homo-5-cis-13-trans prostadiene |
| 196 | 1-trans-tri-n-butylstannyl-5-methylene-4-triethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methylene-20-nor-2-homo-5-cis-13-trans prostadiene |
| 197 | 1-trans-tri-n-butylstannyl-4-methyl-5-methylene-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-17-methylene-20-nor-2-homo-5-cis-13-trans prostadiene |
| 198 | 1-trans-tri-n-butylstannyl-4-dimethoxymethyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-formyl-20-nor-2-homo-5-cis-13-trans prostadiene |
| 199 | 1-trans-tri-n-butylstannyl-4-fluoromethyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-fluoromethyl-20-nor-2-homo-5-cis-13-trans prostadiene |
| 200 | 1-trans-tri-n-butylstannyl-4-difluoromethyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-difluoromethyl-20-nor-2-homo-5-cis-13-trans prostadiene |
| 201 | 1-trans-tri-n-butylstannyl-4-trifluoromethyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-trifluoromethyl-20-nor-2-homo-5-cis-13-trans prostadiene |
| 202 | 1-trans-tri-n-butylstannyl-4-chloromethyl-4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-chloromethyl-20-nor-2-homo-5-cis-13-trans prostadiene |

TABLE III-continued

| | | | |
|---|---|---|---|
| 203 | 1-trans-tri-n-butylstannyl-4-trimethylsilyloxymethyl-4-trimethylsilyloxy-1-heptene | cyclopent-2-en-1-one 2-[7-methoxyacetyl hept-2-cis-enyl]-4-trimethylsiloxy cyclopent-2-en-1-one | dl-11a,16-dihydroxy-1-methoxymethyl-1,9-dioxo-16-hydroxymethyl-20-nor-2-homo-5-cis-13-trans prostadiene |
| EXAMPLE | VINYL IODIDE | CYCLOPENTENONE | PRODUCT PROSTAGLANDIN OF THE PGE2 SERIES |
| 204 | 1-trans-iodo-4-methyl-7-chloro 4-trimethylsilyloxy-1-heptene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-19-chloro-2-homo-20-nor-5-cis-13-trans prostadiene |
| 205 | 1-trans-iodo-3-triphenylmethoxy-1-octene | 2-[7-methoxyacetyl hept-2-cis-enyl]-4-trimethylsiloxy cyclopent-2-en-1-one | dl-11a,15a-dihydroxy-1-methoxymethyl-1,9-dioxo-2-homo-5-cis-13-trans prostadiene |
| 206 | 1-trans-iodo-3-methyl-3-trimethylsilyloxy-1-octene | 2-[7-methoxyacetyl hept-2-cis-enyl]-4-trimethylsiloxy cyclopent-2-en-1-one | dl-11a,15a-dihydroxy-1-methoxymethyl-1,9-dioxo-15-methyl-2-homo-5-cis-13-trans prostadiene |
| 207 | 1-trans-iodo-4,4-dimethyl-3-trimethylsilyloxy-1-octene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16,16-dimethyl-2-homo-5-cis-13-trans prostadiene |
| 208 | 1-trans-iodo-4,4-trimethyl-3-trimethylsiloxy-1-octene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16,16-trimethylene-2-homo-5-cis-13-trans prostadiene |
| EXAMPLE | VINYL TIN | CYCLOPENTENONE | PRODUCT PROSTAGLANDIN OF THE PGE2 SERIES |
| 209 | 1-trans-tri-n-butylstannyl-3-vinyl-3-trimethylsilyloxy-1-octene | 2-[7-methoxyacetyl hept-2-cis-enyl]-4-trimethylsiloxy cyclopent-2-en-1-one | dl-11a,15a-dihydroxy-1-methoxymethyl-1,9-dioxo-15-vinyl-2-homo-5-cis-13-trans prostadiene |
| EXAMPLE | VINYL IODIDE | CYCLOPENTENONE | PRODUCT PROSTAGLANDIN OF THE PGE2 SERIES |
| 210 | 1-trans-iodo-4-triphenylmethoxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-2-homo-5-cis-13-trans prostadiene |
| EXAMPLE | VINYL TIN | CYCLOPENTENONE | PRODUCT PROSTAGLANDIN OF THE PGE2 SERIES |
| 211 | 1-trans-tri-n-butylstannyl-4-methyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-2-homo-5-cis-13-trans prostadiene |
| 212 | 1-trans-tri-n-butylstannyl-5-methyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methyl-2-homo-5-cis-13-trans prostadiene |
| 213 | 1-trans-tri-n-butylstannyl-4-vinyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-vinyl-2-homo-5-cis-13-trans prostadiene |
| 214 | 1-trans-tri-n-butylstannyl-4-trimethylsilylethynyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-ethynyl-2-homo-5-cis-13-trans prostadiene |
| 215 | 1-trans-tri-n-butylstannyl-5-methylene-4-triethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methylene-2-homo-5-cis-13-trans prostadiene |
| 216 | 1-trans-tri-n-butylstannyl-4-methyl-5-methylene-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-17-methylene-2-homo-5-cis-13-trans prostadiene |
| 217 | 1-trans-tri-n-butylstannyl-4-dimethoxymethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-formyl-2-homo-5-cis-13-trans prostadiene |

TABLE III-continued

| EXAMPLE | VINYL IODIDE / VINYL TIN | CYCLOPENTENONE | PRODUCT PROSTAGLANDIN |
|---|---|---|---|
| 218 | 1-trans-tri-n-butylstannyl-4-fluoromethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-fluoromethyl-2-homo-5-cis-13-trans prostadiene |
| 219 | 1-trans-tri-n-butylstannyl-4-difluoromethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-difluoromethyl-2-homo-5-cis-13-trans prostadiene |
| 220 | 1-trans-tri-n-butylstannyl-4-trifluoromethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-trifluoromethyl-2-homo-5-cis-13-trans prostadiene |
| 221 | 1-trans-tri-n-butylstannyl-4-chloromethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-chloromethyl-2-homo-5-cis-13-trans prostadiene |
| 222 | 1-trans-tri-n-butylstannyl-4-trimethylsilyloxymethyl-4-trimethylsilyloxy-1-octene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-hydroxymethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 223 | 1-trans-iodo-3-triphenylmethoxy-1-nonene | 2-[7-methoxyacetyl hept-2-cis-enyl]-4-trimethylsiloxy cyclopent-2-en-1-one | dl-11a,15a-dihydroxy-1-methoxymethyl-1,9-dioxo-20-methyl-2-homo-5-cis-13-trans prostadiene |
| 224 | 1-trans-iodo-3-methyl-3-trimethylsilyloxy-1-nonene | 2-[7-methoxyacetyl hept-2-cis-enyl]-4-trimethylsiloxy cyclopent-2-en-1-one | dl-11a,15a-dihydroxy-1-methoxymethyl-1,9-dioxo-15-methyl-20-methyl-2-homo-5-cis-13-trans prostadiene |
| 225 | 1-trans-iodo-4,4-dimethyl-3-trimethylsilyloxy-1-nonene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16,16-dimethyl-20-methyl-2-homo-5-cis-13-trans prostadiene |
| 226 | 1-trans-iodo-4,4-trimethylene-3-trimethylsilyloxy-1-nonene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16,16-trimethylene-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 227 | 1-trans-tri-n-butylstannyl-3-vinyl-3-trimethylsilyloxy-1-nonene | 2-[7-methoxyacetyl hept-2-cis-enyl]-4-trimethylsiloxy cyclopent-2-en-1-one | dl-11a,15a-dihydroxy-1-methoxymethyl-1,9-dioxo-15-vinyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 228 | 1-trans-iodo-4-triphenylmethoxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 229 | 1-trans-tri-n-butylstannyl-4-methyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-20-methyl-2-homo-5-cis-13-trans prostadiene |
| 230 | 1-trans-tri-n-butylstannyl-5-methyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methyl-20-methyl-2-homo-5-cis-13-trans prostadiene |
| 231 | 1-trans-tri-n-butylstannyl-4-vinyl-4-trimethylsilyloxy-1-nonene | 2-[7-methoxyacetyl hept-2-cis-enyl]-4-trimethylsiloxy cyclopent-2-en-1-one | dl,11a,16-dihydroxy-1-methoxymethyl-1,9-dioxo-16-vinyl-20-methyl-2-homo-5-cis-13-trans prostadiene |
| 232 | 1-trans-tri-n-butylstannyl-4-trimethylsilylethynyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-ethynyl-20-methyl-2-homo-5-cis-13-trans prostadiene |

TABLE III-continued

| | | | |
|---|---|---|---|
| 233 | 1-trans-tri-n-butylstannyl-5-methylene 4-triethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methylene-20-methyl-2-homo-5-cis-13-trans prostadiene |
| 234 | 1-trans-tri-n-butylstannyl-4-methyl-5-methylene 4-trimethylsilyloxy-1-nonene | 2-[7-methoxyacetyl hept-2-cis-3nyl]-4-trimethylsiloxy cyclopene-2-en-1-one | dl-11a,16-dihydroxy-1-methoxymethyl-1,9-dioxo-16-methyl-17-methylene-20-methyl-2-homo-5-cis-13-trans-prostadiene |
| 235 | 1-trans-tri-n-butylstannyl-4-dimethoxymethyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-formyl-20-methyl-2-homo-5-cis-13-trans prostadiene |
| 236 | 1-trans-tri-n-butylstannyl-4-fluoromethyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-fluoromethyl-20-methyl-2-homo-5-cis-13-trans prostadiene |
| 237 | 1-trans-tri-n-butylstannyl-4-difluoromethyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-difluoromethyl-20-methyl-2-homo-5-cis-13-trans prostadiene |
| 238 | 1-trans-tri-n-butylstannyl-4-trifluoromethyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-trifluoromethyl-20-methyl-2-homo-5-cis-13-trans prostadiene |
| 239 | 1-trans-tri-n-butylstannyl-4-chloromethyl-4-trimethylsilyloxy-1-nonene | 2-[7-methoxyacetyl hept-2-cis-enyl]-4-trimethylsiloxy cyclopent-2-en-1-one | dl-11a,16 dihydroxy-1-methoxymethyl-1,9-dioxo-16-chloromethyl-20-methyl-2-homo-5-cis-13-trans prostadiene |
| 240 | 1-trans-tri-n-butylstannyl-4-trimethylsilyloxymethyl-4-trimethylsilyloxy-1-nonene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-hydroxymethyl-20-methyl-2-homo-5-cis-trans prostadiene |
| EXAMPLE | VINYL IODIDE | CYCLOPENTENONE | PRODUCT PROSTAGLANDIN OF THE PGE2 SERIES |
| 241 | 1-trans-iodo-3-triphenylmethoxy-1-decene | 2-[7-methoxyacetyl hept-2-cis-enyl]-4-trimethylsiloxy cyclopent-2-en-1-one | dl-11a,15a-dihydroxy-1-methoxymethyl-1,9-dioxo-20-ethyl-2-homo-5-cis-13-trans prostadiene |
| 242 | 1-trans-iodo-3-methyl-3-trimethylsilyloxy-1-decene | 2-[7-methoxyacetyl hept-2-cis-enyl]-4-trimethylsiloxy cyclopent-2-en-1-one | dl-11a,15a-dihydroxy-1-methoxymethyl-1,9-dioxo-15-methyl-20-ethyl-2-homo-5-cis-13-trans prostadiene |
| 243 | 1-trans-iodo-4,4-dimethyl 3-trimethylsilyloxy-1-decene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16,16-dimethyl-20-ethyl-2-homo-5-cis-13-trans prostadiene |
| 244 | 1-trans-iodo-4,4-trimethylene 3-trimethylsilyloxy-1-decene | 2-[7-methoxyacetyl hept-2-cis-enyl]-4-trimethylsiloxy cyclopent-2-en-1-one | dl-11a,15a-dihydroxy-1-methoxymethyl-1,9-dioxo-16,16-trimethylene-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 245 | 1-trans-tri-n-butylstannyl-3-vinyl-3-trimethylsilyloxy-1-decene | 2-[7-methoxyacetyl hept-2-cis-enyl]-4-trimethylsiloxy cyclopent-2-en-1-one | dl-11a,15a-dihydroxy-1-methoxymethyl-1,9-dioxo-15-vinyl-20-ethyl-2-home-5-cis-13-trans prostadiene |
| EXAMPLE | VINYL IODIDE | CYCLOPENTENONE | PRODUCT PROSTAGLANDIN OF THE PGE2 SERIES |
| 246 | 1-trans-iodo-4-triphenylmethoxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 247 | 1-trans-tri-n-butylstannyl-4-methyl-4-trimethylsilyloxy-1-decene | 2-[7-methoxyacetyl hept-2-cis-enyl]-4-trimethylsiloxy | dl-11a,16-dihydroxy-1-methoxymethyl-1,9-dioxo-16-methyl-20-ethyl-2-homo-5-cis-13-trans prostadiene |

TABLE III-continued

| | | | |
|---|---|---|---|
| 248 | 1-trans-tri-n-butylstannyl-5-methyl-4-trimethylsilyloxy-1-decene | cyclopent-2-en-1-one 2-[7-methoxyacetyl hept-2-cis-enyl]-4-trimethylsiloxy cyclopent-2-en-1-one | dl-11a,16-dihydroxy-1-methoxymethyl-1,9-dioxo-17-methyl-20-ethyl-2-homo-5-cis-13-trans prostadiene |
| 249 | 1-trans-tri-n-butylstannyl-4-vinyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-vinyl-20-ethyl-2-homo-5-cis-13-trans prostadiene |
| 250 | 1-trans-tri-n-butylstannyl-4-trimethylsilylethynyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-ethynyl-20-ethyl-2-homo-5-cis-13-trans prostadiene |
| 251 | 1-trans-tri-n-butylstannyl-5-methylene-4-triethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-17-methylene-20-ethyl-2-homo-5-cis-13-trans prostadiene |
| 252 | 1-trans-tri-n-butylstannyl-4-methyl-5-methylene-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-17-methylene-20-ethyl-2-homo-5-cis-13-trans prostadiene |
| 253 | 1-trans-tri-n-butylstannyl-4-dimethoxymethyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-formyl-20-ethyl-2-homo-5-cis-13-trans-prostadiene |
| 254 | 1-trans-tri-n-butylstannyl-4-fluoromethyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-fluoromethyl-20-ethyl-2-homo-5-cis-13-trans prostadiene |
| 255 | 1-trans-tri-n-butylstannyl-4-difluoromethyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-difluoromethyl-20-ethyl-2-homo-5-cis-13-trans prostadiene |
| 256 | 1-trans-tri-n-butylstannyl-4-trifluoromethyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-trifluoromethyl-20-ethyl-2-homo-5-cis-13-trans prostadiene |
| 257 | 1-trans-tri-n-butylstannyl-4-chloromethyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-chloromethyl-20-ethyl-2-homo-5-cis-13-trans prostadiene |
| 258 | 1-trans-tri-n-butylstannyl-4-trimethylsilyloxymethyl-4-trimethylsilyloxy-1-decene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-hydroxymethyl-20-ethyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 259 | 1-trans-iodo-3-triphenylmethoxy-1-heptene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-20-nor-5-cis-13-trans prostadiene |
| 260 | 1-trans-iodo-3-methyl-3-trimethylsilyloxy-1-heptene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-15-methyl-20-nor-5-cis-13-trans prostadiene |
| 261 | 1-trans-iodo-4,4-dimethyl-3-trimethylsilyloxy-1-heptene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-dimethyl-20-nor-5-cis-13-trans prostadiene |
| 262 | 1-trans-iodo-5,5-dimethyl-3-triphenylmethoxy-1-octene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-17,17-dimethyl-5-cis-13-trans prostadiene |
| 263 | 1-trans-iodo-4-methyl-3-triphenylmethoxy-1-octene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16-methyl-5-cis-13-trans prostadiene |
| 264 | 1-trans-iodo-4,4-trimethylene-3-trimethylsilyloxy-1-heptene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-trimethylene-20-nor-5-cis-13-trans prostadiene |

TABLE III-continued

| EXAMPLE | VINYL TIN | CYCLOPENTENONE | PRODUCT PROSTAGLANDIN OF THE PGE2 SERIES |
|---|---|---|---|
| 265 | 1-trans-tri-n-butylstannyl-3-vinyl-3-trimethylsilyloxy-1-heptene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-15-vinyl-20-nor-5-cis-13-trans prostadiene |
| 266 | 1-trans-tri-n-butylstannyl-4-phenoxy-3-triethylsilyloxy-1-butene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16-phenoxy-17-20-tetranor-5-cis-13-trans prostadiene |
| 267 | 1-trans-tri-n-butylstannyl-4-(p-fluorophenoxy)-3-triethylsilyloxy-1-butene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16-(p-fluorophenoxy)-17-20-tetranor-5-cis-13-trans prostadiene |
| 268 | 1-trans-tri-n-butylstannyl-4-(m-chlorophenoxy)-3-triethylsilyloxy-1-butene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16-(m-chlorophenoxy)-17-20-tetranor-5-cis-13-trans prostadiene |
| 269 | 1-trans-tri-n-butylstannyl-4-(m-trifluoromethylphenoxy)-3-triethylsilyloxy-1-butene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16-(m-trifluoromethylphenoxy)-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 270 | 1-trans-iodo-5-phenyl-3-triethylsilyloxy-1-pentene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-17-phenyl-18-20-trinor-5-cis-13-trans prostadiene |
| 271 | 1-trans-iodo-4,4-dimethyl-5-phenyl-3-triethylsilyloxy-1-pentene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16,16-dimethyl-17-phenyl-18-20-trinor-5-cis-13-trans prostadiene |
| 272 | 1-trans-iodo-4-cyclopentyl-3-triphenylmethoxy-1-butene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16-cyclopentyl-17-20-tetranor-5-cis-13-trans prostadiene |
| 273 | 1-trans-iodo-4-cyclohexyl-3-triphenylmethoxy-1-butene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-16-cyclohexyl-17-20-tetranor-5-cis-13-trans prostadiene |
| 274 | 1-trans-iodo-4-triphenylmethoxy-1-hpetene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 275 | 1-trans-tri-n-butylstannyl-4-methyl-4-trimethylsilyloxy-1-heptene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-methyl-20-nor-5-cis-13-trans prostadiene |
| 276 | 1-trans-tri-n-butylstannyl-4-ethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-ethyl-5-cis-13-trans prostadiene |
| 277 | 1-trans-tri-n-butylstannyl-5-methyl-4-trimethylsilyloxy-1-heptene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-17-methyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 278 | 1-trans-iodo-5,5-dimethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-17,17-dimethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|

TABLE III-continued

| | | | |
|---|---|---|---|
| 279 | 1-trans-tri-n-butylstannyl-4-vinyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-vinyl-20-nor-5-cis-13-trans prostadiene |
| 280 | 1-trans-tri-n-butylstannyl-4-cyclopropyl-4-trimethylsilyloxy-1-octene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-cyclopropyl-5-cis-13-trans prostadiene |
| 281 | 1-trans-tri-n-butylstannyl-4-trimethylsilylethynyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-ethynyl-20-nor-5-cis-13-trans prostadiene |
| 282 | 1-trans-tri-n-butylstannyl-5-methylene-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-17-methylene-20-nor-5-cis-13-trans prostadiene |
| 283 | 1-trans-tri-n-butylstannyl-4-methyl-5-methylene-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-17-methylene-20-nor-5-cis-13-trans prostadiene |
| 284 | 1-trans-tri-n-butylstannyl-4-dimethoxymethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-formyl-20-nor-5-cis-13-trans prostadiene |
| 285 | 1-trans-tri-n-butylstannyl-4-fluoromethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-fluoromethyl-20-nor-5-cis-13-trans prostadiene |
| 286 | 1-trans-tri-n-butylstannyl-4-difluoromethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-difluoromethyl-20-nor-5-cis-13-trans prostadiene |
| 287 | 1-trans-tri-n-butylstannyl-4-trifluoromethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-trifluoromethyl-20-nor-5-cis-13-trans prostadiene |
| 288 | 1-trans-tri-n-butylstannyl-4-chloromethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-chloromethyl-20-nor-5-cis-13-trans prostadiene |
| 289 | 1-trans-tri-n-butylstannyl-4-trimethylsilyloxymethyl-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-hydroxymethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 290 | 1-trans-iodo-4-methyl-7-chloro-4-trimethylsilyloxy-1-heptene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-19-chloro-20-nor-5-cis-13-trans prostadiene |
| 291 | 1-trans-iodo-3-triphenylmethoxy-1-octene- | 2-[6-methoxyacetyl hex-2-cis-enyl]-4R-trimethylsiloxy cyclopent-2-en-1-one | nat-11a,15a-dihydroxy-1-methoxymethyl-1,9-dioxo-5-cis-13-trans prostadiene |
| 292 | 1-trans-iodo-3-methyl-3-trimethylsilyloxy-1-octene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-15-methyl-5-cis-13-trans prostadiene |
| 293 | 1-trans-iodo-4,4-dimethyl-3-trimethylsilyloxy-1-octene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-dimethyl-5-cis-13-trans prostadiene |
| 294 | 1-trans-iodo-4,4-trimethylene-3-trimethylsilyloxy-1-octene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-trimethylene-5-cis-13-trans prostadiene |
| EXAMPLE | VINYL TIN | CYCLOPENTENONE | PRODUCT PROSTAGLANDIN OF THE PGE2 SERIES |
| 295 | 1-trans-tri-n-butylstannyl-3-vinyl- | 2-[6-methoxyacetyl | nat-11a,15a-dihydroxy-1-methoxymethyl-1,9-dioxo-15-vinyl- |

TABLE III-continued

| EXAMPLE | VINYL IODIDE | CYCLOPENTENONE | PRODUCT PROSTAGLANDIN OF THE PGE2 SERIES |
|---|---|---|---|
| | 3-trimethylsilyloxy-1-octene | hex-2-cis-enyl]-4R-trimethylsilyloxy cyclopent-2-en-1-one | 5-cis-13-trans prostadiene |
| 296 | 1-trans-iodo-4-triphenylmethoxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 297 | 1-trans-tri-n-butylstannyl-4-methyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-methyl-5-cis-13-trans prostadiene |
| 298 | 1-trans-tri-n-butylstannyl-5-methyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-17-methyl-5-cis-13-trans prostadiene |
| 299 | 1-trans-tri-n-butylstannyl-4-vinyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-vinyl-5-cis-13-trans prostadiene |
| 300 | 1-trans-tri-n-butylstannyl-4-trimethylsilylethynyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-ethynyl-5-cis-13-trans prostadiene |
| 301 | 1-trans-tri-n-butylstannyl-5-methylene-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-17-methylene-5-cis-13-trans prostadiene |
| 302 | 1-trans-tri-n-butylstannyl-4-methyl-5-methylene-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-methyl-17-methylene-5-cis-13-trans prostadiene |
| 303 | 1-trans-tri-n-butylstannyl-4-dimethoxymethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-formyl-5-cis-13-trans prostadiene |
| 304 | 1-trans-tri-n-butylstannyl-4-fluoromethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-fluoromethyl-5-cis-13-trans prostadiene |
| 305 | 1-trans-tri-n-butylstannyl-4-difluoromethyl-4-trimethylsilyloxy-1-octene | 2-[6-methoxyacetyl hex-2-cis-enyl] -4R-trimethylsilyloxy cyclopent-2-en-1-one | nat-11a,16-dihydroxy-1-methoxymethyl-1,9-dioxo-16-difluoromethyl-5-cis-13-trans prostadiene |
| 306 | 1-trans-tri-n-butylstannyl-4-trifluoromethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-trifluoromethyl-5-cis-13-trans prostadiene |
| 307 | 1-trans-tri-n-butylstannyl-4-chloromethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-chloromethyl-5-cis-13-trans prostadiene |
| 308 | 1-trans-tri-n-butylstannyl-4-trimethylsilyloxymethyl-4-trimethylsilyloxy-1-octene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-hydroxymethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 309 | 1-trans-iodo-3-triphenylmethoxy-1-nonene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-20-methyl-5-cis-13-trans prostadiene |
| 310 | 1-trans-iodo-3-methyl-3-trimethylsilyloxy-1-nonene | 2-[6-methoxyacetyl hex-2-cis-enyl]-4R-trimethylsilyloxy cyclopent-2-en-1-one | nat-11a,15a-dihydroxy-1-methoxymethyl-1,9-dioxo-20-methyl-5-cis-13-trans prostadiene |

TABLE III-continued

| | | | |
|---|---|---|---|
| 311 | 1-trans-iodo-4,4-dimethyl 3-trimethylsilyloxy-1-nonene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-dimethyl-20-methyl-5-cis-13-trans prostadiene |
| 312 | 1-trans-iodo-4,4-trimethylene 3-trimethylsilyloxy-1-nonene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-trimethylene-20-methyl-5-cis-13-trans prostadiene |
| EXAMPLE | VINYL TIN | CYCLOPENTENONE | PRODUCT PROSTAGLANDIN OF THE PGE2 SERIES |
| 313 | 1-trans-tri-n-butylstannyl-3-vinyl-3-trimethylsilyloxy-1-nonene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 314 | 1-trans-iodo-4-triphenylmethoxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-20-methyl-5-cis-13-trans prostadiene |
| EXAMPLE | VINYL TIN | CYCLOPENTENONE | PRODUCT PROSTAGLANDIN OF THE PGE2 SERIES |
| 315 | 1-trans-tri-n-butylstannyl-4-methyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-20-methyl-5-cis-13-trans prostadiene |
| 316 | 1-trans-tri-n-butylstannyl-5-methyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-17-methyl-20-methyl-5-cis-13-trans prostadiene |
| 317 | 1-trans-tri-n-butylstannyl-4-vinyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-vinyl-20-methyl-5-cis-13-trans prostadiene |
| 318 | 1-trans-tri-n-butylstannyl-4-trimethylsilylethynyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-ethynyl-20-methyl-5-cis-13-trans prostadiene |
| 319 | 1-trans-tri-n-butylstannyl-5-methylene-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-17-methylene-20-methyl-5-cis-13-trans prostadiene |
| 320 | 1-trans-tri-n-butylstannyl-4-methyl-5-methylene-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-17-methylene-20-methyl-5-cis-13-trans prostadiene |
| 321 | 1-trans-tri-n-butylstannyl-4-dimethoxymethyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-formyl-20-methyl-5-cis-13-trans prostadiene |
| 322 | 1-trans-tri-n-butylstannyl-4-fluoromethyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-fluoromethyl-20-methyl-5-cis-13-trans prostadiene |
| 323 | 1-trans-tri-n-butylstannyl-4-difluoromethyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-difluoromethyl-20-methyl-5-cis-13-trans prostadiene |
| 324 | 1-trans-tri-n-butylstannyl-4-trifluoromethyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-trifluoromethyl-20-methyl-5-cis-13-trans prostadiene |
| 325 | 1-trans-tri-n-butylstannyl-4-chloromethyl-4-trimethylsilyloxy-1-nonene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-chloromethyl-20-methyl-5-cis-13-trans prostadiene |
| 326 | 1-trans-tri-n-butylstannyl-4-trimethylsilyloxymethyl-4-trimethylsilyloxy-1-nonene | 2-[6-methoxyacetyl hex-2-cis-enyl]-4R-trimethylsiloxy | nat-11a,16-dihydroxy-1-methoxymethyl-1,9-dioxo-16-hydroxymethyl-20-methyl-5-cis-13-trans prostadiene |

TABLE III-continued

| EXAMPLE | VINYL IODIDE | CYCLOPENTENONE | PRODUCT PROSTAGLANDIN OF THE PGE2 SERIES |
|---|---|---|---|
| 327 | 1-trans-iodo-3-triphenylmethoxy-1-decene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-20-ethyl-5-cis-13-trans prostadiene |
| 328 | 1-trans-iodo-3-methyl-3-trimethylsilyloxy-1-decene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-15-methyl-20-ethyl-5-cis-13-trans prostadiene |
| 329 | 1-trans-iodo-4,4-dimethyl-3-trimethylsilyloxy-1-decene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-dimethyl-20-ethyl-5-cis-13-trans prostadiene |
| 330 | 1-trans-iodo-4,4-trimethylene-3-trimethylsilyloxy-1-decene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-16,16-trimethylene-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 331 | 1-trans-tri-n-butylstannyl-3-vinyl-3-trimethylsilyloxy-1-decene | 2-[6-methoxyacetyl hex-2-cis-enyl]-4R-trimethylsiloxy cyclopent-2-en-1-one | nat-11a,15a-dihydroxy-1-methoxymethyl-1,9-dioxo-15-vinyl-20-ethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 332 | 1-iodo-4-triphenylmethoxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 333 | 1-trans-tri-n-butylstannyl-4-methyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-20-ethyl-5-cis-13-trans prostadiene |
| 334 | 1-trans-tri-n-butylstannyl-5-methyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-17-methyl-20-ethyl-5-cis-13-trans prostadiene |
| 335 | 1-trans-tri-n-butylstannyl-4-vinyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-vinyl-20-ethyl-5-cis-13-trans prostadiene |
| 336 | 1-trans-tri-n-butylstannyl-4-trimethylsilylethynyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-ethynyl-20-ethyl-5-cis-13-trans prostadiene |
| 337 | 1-trans-tri-n-butylstannyl-5-methylene-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-17-methylene-20-ethyl-5-cis-13-trans prostadiene |
| 338 | 1-trans-tri-n-butylstannyl-4-methyl-5-methylene-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-17-methylene-20-ethyl-5-cis-13-trans prostadiene |
| 339 | 1-trans-tri-n-butylstannyl-4-dimethoxymethyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-formyl-20-ethyl-5-cis-13-trans prostadiene |
| 340 | 1-trans-tri-n-butylstannyl-4-fluoromethyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-fluoromethyl-20-ethyl-5-cis-13-trans prostadiene |
| 341 | 1-trans-tri-n-butylstannyl-4-difluoromethyl-4-trimethylsilyloxy-1-decene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-difluoromethyl-20-ethyl-5-cis-13-trans prostadiene |

TABLE III-continued

| EXAMPLE | VINYL IODIDE | CYCLOPENTENONE | PRODUCT PROSTAGLANDIN OF THE 11-DEOXY PGE2 SERIES |
|---|---|---|---|
| 342 | 1-trans-tri-n-butylstannyl-4-trifluoromethyl-4-trimethylsilyloxy-1-decene | cyclopent-2-en-1-one 2-[6-methoxyacetyl hex-2-cis-enyl]-4R-trimethylsiloxy cyclopent-2-en-1-one | nat-11a,16-dihydroxy-1-methoxymethyl-1,9-dioxo-16-trifluoromethyl-20-ethyl-5-cis-13-trans prostadiene |
| 343 | 1-trans-tri-n-butylstannyl-4-chloromethyl-4-trimethylsilyloxy-1-decene | cyclopent-2-en-1-one 2-[6-methoxyacetyl hex-2-cis-enyl]-4R-trimethylsiloxy cyclopent-2-en-1-one | nat-11a,16-dihydroxy-1-methoxymethyl-1,9-dioxo-16-chloromethyl-20-ethyl-5-cis-13-trans prostadiene |
| 344 | 1-trans-tri-n-butylstannyl-4-trimethylsilyloxymethyl-4-trimethylsilyloxy-1-decene | cyclopent-2-en-1-one 2-[6-methoxyacetyl hex-2-cis-enyl]-4R-trimethylsiloxy cyclopent-2-en-1-one | nat-11a,16-dihydroxy-1-methoxymethyl-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 345 | 1-trans-iodo-3-triphenylmethoxy-1-heptene | 2-[5-methoxyacetyl pent-2-cis-enyl] cyclopent-2-en-1-one | dl-15a-hydroxy-1-methoxymethyl-1,9-dioxo-20-nor-2-nor-5-cis-13-trans prostadiene |
| 346 | 1-trans-iodo-3-methyl-3-trimethylsilyloxy-1-heptene | 2-[5-methoxyacetyl pent-2-cis-enyl] cyclopent-2-en-1-one | dl-15a-hydroxy-1-methoxymethyl-1,9-dioxo-15-methyl-20-nor-2-nor-5-cis-13-trans prostadiene |
| 347 | 1-trans-iodo-4,4-dimethyl-3-trimethylsilyloxy-1-heptene | 2-[5-methoxyacetyl pent-2-cis-enyl] cyclopent-2-en-1-one | dl-15a-hydroxy-1-methoxymethyl-1,9-dioxo-16,16-dimethyl-20-nor-2-nor-5-cis-13-trans prostadiene |
| 348 | 1-trans-iodo-5,5-dimethyl-3-triphenylmethoxy-1-octene | 2-[5-methoxyacetyl pent-2-cis-enyl] cyclopent-2-en-1-one | dl-15a-hydroxy-1-methoxymethyl-1,9-dioxo-17,17-dimethyl-2-nor-5-cis-13-trans prostadiene |
| 349 | 1-trans-iodo-4-methyl-3-triphenylmethoxy-1-octene | 2-[5-methoxyacetyl pent-2-cis-enyl] cyclopent-2-en-1-one | dl-15a-hydroxy-1-methoxymethyl-1,9-dioxo-16-methyl-2-nor-5-cis-13-trans prostadiene |
| 350 | 1-trans-iodo-4,4-trimethylene-3-trimethylsilyloxy-1-heptene | 2-[5-methoxyacetyl pent-2-cis-enyl] cyclopent-2-en-1-one | dl-15a-hydroxy-1-methoxymethyl-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 351 | 1-trans-tri-n-butylstannyl-3-vinyl-3-trimethylsilyloxy-1-heptene | 2-[5-methoxyacetyl pent-2-cis-enyl] cyclopent-2-en-1-one | dl-15a-hydroxy-1-methoxymethyl-1,9-dioxo-15-vinyl-20-nor-2-nor-5-cis-13-trans prostadiene |
| 352 | 1-trans-tri-n-butylstannyl-4-phenoxy-3-triethylsilyloxy-1-butene | 2-[5-methoxyacetyl pent-2-cis-enyl] cyclopent-2-en-1-one | dl-15a-hydroxy-1-methoxymethyl-1,9-dioxo-16-phenoxy-2-nor-17-20-tetranor-5-cis-13-trans prostadiene |
| 353 | 1-trans-tri-n-butylstannyl-4-(p-fluorophenoxy)-3-triethylsilyloxy-1-butene | 2-[5-methoxyacetyl pent-2-cis-enyl] cyclopent-2-en-1-one | dl-15a-hydroxy-1-methoxymethyl-1,9-dioxo-16-(p-fluorophenoxy)-2-nor-17-20-tetranor-5-cis-13-trans prostadiene |
| 354 | 1-trans-tri-n-butylstannyl-4-(m-chlorophenoxy)-3-triethylsilyloxy-1-butene | 2-[5-methoxyacetyl pent-2-cis-enyl] cyclopent-2-en-1-one | dl-15a-hydroxy-1-methoxymethyl-1,9-dioxo-16-(m-chlorophenoxy-2-nor-17-20-tetranor-5-cis-13-trans prostadiene |
| 355 | 1-trans-tri-n-butylstannyl-4-(m-trifluoromethylphenoxy)-3-triethylsilyloxy-1-butene | 2-[5-methoxyacetyl pent-2-cis-enyl] cyclopent-2-en-1-one | dl-15a-hydroxy-1-methoxymethyl-1,9-dioxo-16-(m-trifluoromethylphenoxy)-2-nor-17-20-tetranor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 356 | 1-trans-iodo-5-phenyl-3-triethylsilyloxy-1-pentene | 2-[5-methoxyacetyl pent-2-cis-enyl] cyclopent-2-en-1-one | dl-15a-hydroxy-1-methoxymethyl-1,9-dioxo-17-phenyl-2-nor-18-20-trinor-5-cis-13-trans prostadiene |
| 357 | 1-trans-iodo-4,4-dimethyl-5-phenyl | 2-[5-methoxyacetyl pent-2-cis-enyl] cyclopent-2-en-1-one | dl-15a-hydroxy-1-methoxymethyl-1,9-dioxo- |

TABLE III-continued

| | | | |
|---|---|---|---|
| 358 | 3-triethylsilyloxy-1-pentene | 2-[5-methoxyacetyl pent-2-cis-enyl] cyclopent-2-en-1-one | 16,16-dimethyl-17-phenyl-2-nor-18-20-trinor-5-cis-13-trans prostadiene |
| | 1-trans-iodo-4-cyclopentyl 3-triphenylmethoxy-1-butene | 2-[5-methoxyacetyl pent-2-cis-enyl] cyclopent-2-en-1-one | dl-15a-hydroxy-1-methoxymethyl-1,9-dioxo-16-cyclopentyl-2-nor-17-20-tetranor-5-cis-13-trans prostadiene |
| 359 | 1-trans-iodo-4-cyclohexyl 3-triphenylmethoxy-1-butene | 2-[5-methoxyacetyl pent-2-cis-enyl] cyclopent-2-en-1-one | dl-15a-hydroxy-1-methoxymethyl-1,9-dioxo-16-cyclohexyl-2-nor-17-20-tetranor-5-cis-13-trans prostadiene |
| 360 | 1-trans-iodo-4-triphenylmethoxy-1-heptene | 2-[5-methoxyacetyl pent-2-cis-enyl] cyclopent-2-en-1-one | dl-16-hydroxy-1-methoxymethyl-1,9-dioxo-20-nor-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 361 | 1-trans-tri-n-butylstannyl-4-methyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-methyl-20-nor-2-nor-5-cis-13-trans prostadiene |
| 362 | 1-trans-tri-n-butylstannyl-4-ethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-ethyl-2-nor-5-cis-13-trans prostadiene |
| 363 | 1-trans-tri-n-butylstannyl-5-methyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-17-methyl-20-nor-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 364 | 1-trans-iodo-5,5-dimethyl 4-trimethylsilyloxy-1-octene | 2-[5-methoxyacetyl pent-2-cis-enyl] cyclopent-2-en-1-one | dl-16-hydroxy-1-methoxymethyl-1,9-dioxo-17,17-dimethyl-2-nor-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 365 | 1-trans-tri-n-butylstannyl-4-vinyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-vinyl-20-nor-2-nor-5-cis-13-trans prostadiene |
| 366 | 1-trans-tri-n-butylstannyl-4-cyclopropyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-cyclopropyl-2-nor-5-cis-13-trans prostadiene |
| 367 | 1-trans-tri-n-butylstannyl-4-trimethylsilylethynyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-ethynyl-20-nor-2-nor-5-cis-13-trans prostadiene |
| 368 | 1-trans-tri-n-butylstannyl-5-methylene 4-triethylsilyloxy-1-heptene | 2-[5-methoxyacetyl pent-2-cis-enyl] cyclopent-2-en-1-one | dl-16-hydroxy-1-methoxymethyl-1,9-dioxo-17-methylene-20-nor-2-nor-5-cis-13-trans prostadiene |
| 369 | 1-trans-tri-n-butylstannyl-4-methyl-5-methylene 4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-methyl-17-methylene-20-nor-2-nor-5-cis-13-trans prostadiene |
| 370 | 1-trans-tri-n-butylstannyl-4-dimethoxymethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-formyl-20-nor-2-nor-5-cis-13-trans prostadiene |
| 371 | 1-trans-tri-n-butylstannyl-4-fluoromethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-fluoromethyl-20-nor-2-nor-5-cis-13-trans prostadiene |
| 372 | 1-trans-tri-n-butylstannyl-4-difluoromethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-difluoromethyl-20-nor-2-nor-5-cis-13-trans prostadiene |

TABLE III-continued

| | | | |
|---|---|---|---|
| 373 | 1-trans-tri-n-butylstannyl-4-trifluoromethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-trifluoromethyl-20-nor-2-nor-5-cis-13-trans prostadiene |
| 374 | 1-trans-tri-n-butylstannyl-4-chloromethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-chloromethyl-20-nor-2-nor-5-cis-13-trans prostadiene |
| 375 | 1-trans-tri-n-butylstannyl-4-trimethylsilyloxymethyl-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-hydroxymethyl-20-nor-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 376 | 1-trans-iodo-4-methyl-7-chloro-4-trimethylsilyloxy-1-heptene | 2-[5-methoxyacetyl pent-2-cis-enyl] cyclopent-2-en-1-one | dl-16-hydroxy-1-methoxymethyl-1,9-dioxo-16-methyl-19-chloro-2-nor-20-nor-5-cis-13-trans prostadiene |
| 377 | 1-trans-iodo-3-triphenylmethoxy-1-octene | 2-[5-methoxyacetyl pent-2-cis-enyl] cyclopent-2-en-1-one | dl-15a-hydroxy-1-methoxymethyl-1,9-dioxo-2-nor-5-cis-13-trans prostadiene |
| 378 | 1-trans-iodo-3-methyl-3-trimethylsilyloxy-1-octene | 2-[5-methoxyacetyl pent-2-cis-enyl] cyclopent-2-en-1-one | dl-15a-hydroxy-1-methoxymethyl-1,9-dioxo-15-methyl-2-nor-5-cis-13-trans prostadiene |
| 379 | 1-trans-iodo-4,4-dimethyl-3-trimethylsilyloxy-1-octene | 2-[5-methoxyacetyl pent-2-cis-enyl] cyclopent-2-en-1-one | dl-15a-hydroxy-1-methoxymethyl-1,9-dioxo-16,16-dimethyl-2-nor-5-cis-13-trans prostadiene |
| 380 | 1-trans-iodo-4,4-trimethylene-3-trimethylsilyloxy-1-octene | 2-[5-methoxyacetyl pent-2-cis-enyl] cyclopent-2-en-1-one | dl-15a-hydroxy-1-methoxymethyl-1,9-dioxo-16,16-trimethylene-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 381 | 1-trans-tri-n-butylstannyl-3-vinyl-3-trimethylsilyloxy-1-octene | 2-[5-methoxyacetyl pent-2-cis-enyl] cyclopent-2-en-1-one | dl-15a-hydroxy-1-methoxymethyl-1,9-dioxo-15-vinyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 382 | 1-trans-iodo-4-triphenylmethoxy-1-octene | 2-[5-methoxyacetyl pent-2-cis-enyl] cyclopent-2-en-1-one | dl-16-hydroxy-1-methoxymethyl-1,9-dioxo-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 383 | 1-trans-tri-n-butylstannyl-4-methyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-methyl-2-nor-5-cis-13-trans prostadiene |
| 384 | 1-trans-tri-n-butylstannyl-5-methyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-17-methyl-2-nor-5-cis-13-trans prostadiene |
| 385 | 1-trans-tri-n-butylstannyl-4-vinyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-vinyl-2-nor-5-cis-13-trans prostadiene |
| 386 | 1-trans-tri-n-butylstannyl-4-trimethylsilylethynyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-ethynyl-2-nor-5-cis-13-trans prostadiene |
| 387 | 1-trans-tri-n-butylstannyl-5-methylene-4-triethylsilyloxy-1-octene | 2-[5-methoxyacetyl pent-2-cis-enyl] cyclopent-2-en-1-one | dl-16-hydroxy-1-methoxymethyl-1,9-dioxo-17-methylene-2-nor-5-cis-13-trans prostadiene |

TABLE III-continued

| | | | |
|---|---|---|---|
| 388 | 1-trans-tri-n-butylstannyl-4-methyl-5-methylene 4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-methyl-17-methylene-2-nor-5-cis-13-trans prostadiene |
| 389 | 1-trans-tri-n-butylstannyl-4-dimethoxymethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-formyl-2-nor-5-cis-13-trans prostadiene |
| 390 | 1-trans-tri-n-butylstannyl-4-fluoromethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-fluoromethyl-2-nor-5-cis-13-trans prostadiene |
| 391 | 1-trans-tri-n-butylstannyl-4-difluoromethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-difluoromethyl-2-nor-5-cis-13-trans prostadiene |
| 392 | 1-trans-tri-n-butylstannyl-4-trifluoromethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-trifluoromethyl-2-nor-5-cis-13-trans prostadiene |
| 393 | 1-trans-tri-n-butylstannyl-4-chloromethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-chloromethyl-2-nor-5-cis-13-trans prostadiene |
| 394 | 1-trans-tri-n-butylstannyl-4-trimethylsilyloxymethyl-4-trimethylsilyloxy-1-octene | 2-[5-methoxyacetyl pent-2-cis-enyl] cyclopent-2-en-1-one | dl-16-hydroxy-1-methoxymethyl-1,9-dioxo-16-hydroxymethyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 395 | 1-trans-iodo-3-triphenylmethoxy-1-nonene | 2-[5-methoxyacetyl pent-2-cis-enyl] cyclopent-2-en-1-one | dl-15a-hydroxy-1-methoxymethyl-1,9-dioxo-20-methyl-2-nor-5-cis-13-trans prostadiene |
| 396 | 1-trans-iodo-3-methyl-3-trimethylsilyloxy-1-nonene | 2-[5-methoxyacetyl pent-2-cis-enyl] cyclopent-2-en-1-one | dl-15a-hydroxy-1-methoxymethyl-1,9-dioxo-15-methyl-20-methyl-2-nor-5-cis-13-trans prostadiene |
| 397 | 1-trans-iodo-4,4-dimethyl-3-trimethylsilyloxy-1-nonene | 2-[5-methoxyacetyl pent-2-cis-enyl] cyclopent-2-en-1-one | dl-15a-hydroxy-1-methoxymethyl-1,9-dioxo-16,16-dimethyl-20-methyl-2-nor-5-cis-13-trans prostadiene |
| 398 | 1-trans-iodo-4,4-trimethylene-3-trimethylsilyloxy-1-nonene | 2-[5-methoxyacetyl pent-2-cis-enyl] cyclopent-2-en-1-one | dl-15a-hydroxy-1-methoxymethyl-1,9-dioxo-16,16-trimethylene-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 399 | 1-trans-tri-n-butylstannyl-3-vinyl-3-trimethylsilyloxy-1-nonene | 2-[5-methoxyacetyl pent-2-cis-enyl] cyclopent-2-en-1-one | dl-15a-hydroxy-1-methoxymethyl-1,9-dioxo-15-vinyl-20-methyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 400 | 1-trans-iodo-4-triphenylmethoxy-1-nonene | 2-[5-methoxyacetyl pent-2-cis-enyl] cyclopent-2-en-1-one | dl-16-hydroxy-1-methoxymethyl-1,9-dioxo-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 401 | 1-trans-tri-n-butylstannyl-4-methyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-methyl-20-methyl-2-nor-5-cis-13-trans prostadiene |
| 402 | 1-trans-tri-n-butylstannyl-5-methyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-17-methyl-20-methyl-2-nor-5-cis-13-trans prostadiene |

TABLE III-continued

| | VINYL IODIDE / VINYL TIN | 2-[5-methoxyacetyl pent-2-cis-enyl] cyclopent-2-en-1-one | PRODUCT PROSTAGLANDIN |
|---|---|---|---|
| 403 | 1-trans-tri-n-butylstannyl-4-vinyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-vinyl-20-methyl-2-nor-5-cis-13-trans prostadiene |
| 404 | 1-trans-tri-n-butylstannyl-4-trimethylsilylethynyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-ethynyl-20-methyl-2-nor-5-cis-13-trans prostadiene |
| 405 | 1-trans-tri-n-butylstannyl-5-methylene-4-triethylsilyloxy-1-nonene | 2-[5-methoxyacetyl pent-2-cis-enyl] cyclopent-2-en-1-one | dl-16-hydroxy-1-methoxymethyl-1,9-dioxo-17-methylene-20-methyl-2-nor-5-cis-13-trans prostadiene |
| 406 | 1-trans-tri-n-butylstannyl-4-methyl-5-methylene-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-methyl-17-methylene-20-methyl-2-nor-5-cis-13-trans prostadiene |
| 407 | 1-trans-tri-n-butylstannyl-4-dimethoxymethyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-formyl-20-methyl-2-nor-5-cis-13-trans prostadiene |
| 408 | 1-trans-tri-n-butylstannyl-4-fluoromethyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-fluoromethyl-20-methyl-2-nor-5-cis-13-trans prostadiene |
| 409 | 1-trans-tri-n-butylstannyl-4-difluoromethyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-difluoromethyl-20-methyl-2-nor-5-cis-13-trans prostadiene |
| 410 | 1-trans-tri-n-butylstannyl-4-trifluoromethyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-trifluoromethyl-20-methyl-2-nor-5-cis-13-trans prostadiene |
| 411 | 1-trans-tri-n-butylstannyl-4-chloromethyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-chloromethyl-20-methyl-2-nor-5-cis-13-trans prostadiene |
| 412 | 1-trans-tri-n-butylstannyl-4-trimethylsilyloxymethyl-4-trimethylsilyloxy-1-nonene | 2-[5-methoxyacetyl pent-2-cis-enyl] cyclopent-2-en-1-one | dl-16-hydroxy-1-methoxymethyl-1,9-dioxo-16-hydromethyl-20-methyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 413 | 1-trans-iodo-3-triphenylmethoxy-1-decene | 2-[5-methoxyacetyl pent-2-cis-enyl] cyclopent-2-en-1-one | dl-15a-hydroxy-1-methoxymethyl-1,9-dioxo-20-ethyl-2-nor-5-cis-13-trans prostadiene |
| 414 | 1-trans-iodo-3-methyl-3-trimethylsilyloxy-1-decene | 2-[5-methoxyacetyl pent-2-cis-enyl] cyclopent-2-en-1-one | dl-15a-hydroxy-1-methoxymethyl-1,9-dioxo-15-methyl-20-ethyl-2-nor-5-cis-13-trans prostadiene |
| 415 | 1-trans-iodo-4,4-dimethyl-3-trimethylsilyloxy-1-decene | 2-[5-methoxyacetyl pent-2-cis-enyl] cyclopent-2-en-1-one | dl-15a-hydroxy-1-methoxymethyl-1,9-dioxo-16,16-dimethyl-20-ethyl-2-nor-5-cis-13-trans prostadiene |
| 416 | 1-trans-iodo-4,4-trimethylene-3-trimethylsilyloxy-1-decene | 2-[5-methoxyacetyl pent-2-cis-enyl] cyclopent-2-en-1-one | dl-15a-hydroxy-1-methoxymethyl-1,9-dioxo-16,16-trimethylene-20-ethyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 417 | 1-trans-tri-n-butylstannyl-3-vinyl-3-trimethylsilyloxy-1-decene | 2-[5-methoxyacetyl pent-2-cis-enyl] cyclopent-2-en-1-one | dl-15a-hydroxy-1-methoxymethyl-1,9-dioxo-15-vinyl-20-ethyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 418 | 1-trans-iodo-4-triphenylmethoxy-1-decene | 2-[5-methoxyacetyl pent-2-cis-enyl] | dl-16-hydroxy-1-methoxymethyl-1,9-dioxo-20-ethyl-2-nor-5-cis-13-trans prostadiene |

TABLE III-continued

| EXAMPLE | VINYL TIN | CYCLOPENTENONE | PRODUCT PROSTAGLANDIN OF THE 11-DEOXY PGE2 SERIES |
|---|---|---|---|
| 419 | 1-trans-tri-n-butylstannyl-4-methyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-methyl-20-ethyl-2-nor-5-cis-13-trans prostadiene |
| 420 | 1-trans-tri-n-butylstannyl-5-methyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-17-methyl-20-ethyl-2-nor-5-cis-13-trans prostadiene |
| 421 | 1-trans-tri-n-butylstannyl-4-vinyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-vinyl-20-ethyl-2-nor-5-cis-13-trans prostadiene |
| 422 | 1-trans-tri-n-butylstannyl-4-trimethylsilylethynyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-ethynyl-20-ethyl-2-nor-5-cis-13-trans prostadiene |
| 423 | 1-trans-tri-n-butylstannyl-5-methylene-4-triethylsilyloxy-1-decene | 2-[5-methoxyacetyl pent-2-cis-enyl] cyclopent-2-en-1-one | dl-16-hydroxy-1-methoxymethyl-1,9-dioxo-17-methylene-20-ethyl-2-nor-5-cis-13-trans prostadiene |
| 424 | 1-trans-tri-n-butylstannyl-4-methyl-5-methylene-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-methyl-17-methylene-20-ethyl-2-nor-5-cis-13-trans prostadiene |
| 425 | 1-trans-tri-n-butylstannyl-4-dimethoxymethyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-formyl-20-ethyl-2-nor-5-cis-13-trans prostadiene |
| 426 | 1-trans-tri-n-butylstannyl-4-fluoromethyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-fluoromethyl-20-ethyl-2-nor-5-cis-13-trans prostadiene |
| 427 | 1-trans-tri-n-butylstannyl-4-difluoromethyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-difluoromethyl-20-ethyl-2-nor-5-cis-13-trans prostadiene |
| 428 | 1-trans-tri-n-butylstannyl-4-trifluoromethyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-trifluoromethyl-20-ethyl-2-nor-5-cis-13-trans prostadiene |
| 429 | 1-trans-tri-n-butylstannyl-4-chloromethyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-chloromethyl-20-ethyl-2-nor-5-cis-13-trans prostadiene |
| 430 | 1-trans-tri-n-butylstannyl-4-trimethylsilyloxymethyl-4-trimethylsilyloxy-1-decene | 2-[5-methoxyacetyl pent-2-cis-enyl] cyclopent-2-en-1-one | dl-16-hydroxy-1-methoxymethyl-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 431 | 1-trans-iodo-3-triphenylmethoxy-1-heptene | 2-[6-methoxyacetyl hex-2-cis-enyl] cyclopent-2-en-1-one | dl-15a-hydroxy-1-methoxymethyl-1,9-dioxo-20-nor-5-cis-13-trans prostadiene |
| 432 | 1-trans-iodo-3-methyl-3-trimethylsilyloxy-1-heptene | 2-[6-methoxyacetyl hex-2-cis-enyl] cyclopent-2-en-1-one | dl-15a-hydroxy-1-methoxymethyl-1,9-dioxo-15-methyl-20-nor-5-cis-13-trans prostadiene |
| 433 | 1-trans-iodo-4,4-dimethyl-3-trimethylsilyloxy-1-heptene | 2-[6-methoxyacetyl hex-2-cis-enyl] cyclopent-2-en-1-one | dl-15a-hydroxy-1-methoxymethyl-1,9-dioxo-16,16-dimethyl-20-nor-5-cis-13-trans prostadiene |
| 434 | 1-trans-iodo-5,5-dimethyl-3-triphenylmethoxy-1-octene | 2-[6-methoxyacetyl hex-2-cis-enyl] cyclopent-2-en-1-one | dl-15a-hydroxy-1-methoxymethyl-1,9-dioxo-17,17-dimethyl-5-cis-13-trans prostadiene |

TABLE III-continued

| Example | | | Product Prostaglandin |
|---|---|---|---|
| 435 | | 1-trans-iodo-4-methyl 3-triphenylmethoxy-1-octene | 2-[6-methoxyacetyl hex-2-cis-enyl] cyclopent-2-en-1-one | dl-15a-hydroxy-1-methoxymethyl-1,9-dioxo-16-methyl-5-cis-13-trans prostadiene |
| 436 | | 1-trans-iodo-4,4-trimethylene 3-trimethylsilyloxy-1-heptene | 2-[6-methoxyacetyl hex-2-cis-enyl] cyclopent-2-en-1-one | dl-15a-hydroxy-1-methoxymethyl-1,9-dioxo-16,16-trimethylene-20-nor-5-cis-13-trans prostadiene |
| EXAMPLE | VINYL TIN | | CYCLOPENTENONE | PRODUCT PROSTAGLANDIN OF THE 11-DEOXY PGE2 SERIES |
| 437 | | 1-trans-tri-n-butylstannyl-3-vinyl-3-trimethylsilyloxy-1-heptene | 2-[6-methoxyacetyl hex-2-cis-enyl] cyclopent-2-en-1-one | dl-15a-hydroxy-1-methoxymethyl-1,9-dioxo-15-vinyl-20-nor-5-cis-13-trans prostadiene |
| 438 | | 1-trans-tri-n-butylstannyl-4-phenoxy 3-triethylsilyloxy-1-butene | 2-[6-methoxyacetyl hex-2-cis-enyl] cyclopent-2-en-1-one | dl-15a-hydroxy-1-methoxymethyl-1,9-dioxo-16-phenoxy-17-20-tetranor-5-cis-13-trans prostadiene |
| 439 | | 1-trans-tri-n-butylstannyl-4-(p-fluorophenoxy) 3-triethylsilyloxy-1-butene | 2-[6-methoxyacetyl hex-2-cis-enyl] cyclopent-2-en-1-one | dl-15a-hydroxy-1-methoxymethyl-1,9-dioxo-16-(p-fluorophenoxy)-17-20-tetranor-5-cis-13-trans prostadiene |
| 440 | | 1-trans-tri-n-butylstannyl-4-(m-chlorophenoxy) 3-triethylsilyloxy-1-butene | 2-[6-methoxyacetyl hex-2-cis-enyl] cyclopent-2-en-1-one | dl-15a-hydroxy-1-methoxymethyl-1,9-dioxo-16-(m-chlorophenoxy)-17-20-tetranor-5-cis-13-trans prostadiene |
| 441 | | 1-trans-tri-n-butylstannyl-4-(m-trifluoromethylphenoxy) 3-triethylsilyloxy-1-butene | 2-[6-methoxyacetyl hex-2-cis-enyl] cyclopent-2-en-1-one | dl-15a-hydroxy-1-methoxymethyl-1,9-dioxo-16-(m-trifluoromethylphenoxy)-17-20-tetranor-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 442 | | 1-trans-iodo-5-phenyl 3-triethylsilyloxy-1-pentene | 2-[6-methoxyacetyl hex-2-cis-enyl] cyclopent-2-en-1-one | dl-15a-hydroxy-1-methoxymethyl-1,9-dioxo-17-phenyl-18-20-trinor-5-cis-13-trans prostadiene |
| 443 | | 1-trans-iodo-4,4-dimethyl-5-phenyl 3-triethylsilyloxy-1-pentene | 2-[6-methoxyacetyl hex-2-cis-enyl] cyclopent-2-en-1-one | dl-15a-hydroxy-1-methoxymethyl-1,9-dioxo-16,16-dimethyl-17-phenyl-18-20-trinor-5-cis-13-trans prostadiene |
| 444 | | 1-trans-iodo-4-cyclopentyl 3-triphenylmethoxy-1-butene | 2-[6-methoxyacetyl hex-2-cis-enyl] cyclopent-2-en-1-one | dl-15a-hydroxy-1-methoxymethyl-1,9-dioxo-16-cyclopentyl-17-20-tetranor-5-cis-13-trans prostadiene |
| 445 | | 1-trans-iodo-4-cyclohexyl 3-triphenylmethoxy-1-butene | 2-[6-methoxyacetyl hex-2-cis-enyl] cyclopent-2-en-1-one | dl-15a-hydroxy-1-methoxymethyl-1,9-dioxo-16-cyclohexyl-17-20-tetranor-5-cis-13-trans prostadiene |
| 446 | | 1-trans-iodo-4-triphenylmethoxy-1-heptene | 2-[6-methoxyacetyl hex-2-cis-enyl] cyclopent-2-en-1-one | dl-16-hydroxy-1-methoxymethyl-1,9-dioxo-20-nor-5-cis-13-trans prostadiene |
| EXAMPLE | VINYL TIN | | CYCLOPENTENONE | PRODUCT PROSTAGLANDIN OF THE 11-DEOXY PGE2 SERIES |
| 447 | | 1-trans-tri-n-butylstannyl-4-methyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-methyl-20-nor-5-cis-13-trans prostadiene |
| 448 | | 1-trans-tri-n-butylstannyl-4-ethyl-4-trimethylsilyloxy-1-octene | 2-[6-methoxyacetyl hex-2-cis-enyl] cyclopent-2-en-1-one | dl-16-hydroxy-1-methoxymethyl-1,9-dioxo-16-ethyl-5-cis-13-trans prostadiene |
| 449 | | 1-trans-tri-n-butylstannyl-5-methyl 4-trimethylsilyloxy-1-heptene | 2-[6-methoxyacetyl hex-2-cis-enyl] cyclopent-2-en-1-one | dl-16-hydroxy-1-methoxymethyl-1,9-dioxo-17-methyl-20-nor-5-cis-13-trans prostadiene |
| EXAMPLE | VINYL IODIDE | | CYCLOPENTENONE | PRODUCT PROSTAGLANDIN OF THE 11-DEOXY PGE2 SERIES |

TABLE III-continued

| EXAMPLE | VINYL TIN | CYCLOPENTENONE | PRODUCT PROSTAGLANDIN OF THE 11-DEOXY PGE2 SERIES |
|---|---|---|---|
| 450 | 1-trans-iodo-5,5-dimethyl 4-trimethylsilyloxy-1-octene | 2-[6-methoxyacetyl hex-2-cis-enyl] cyclopent-2-en-1-one | dl-16-hydroxy-1-methoxymethyl-1,9-dioxo-17,17-dimethyl-5-cis-13-trans prostadiene |
| 451 | 1-trans-tri-n-butylstannyl-4-vinyl 4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-vinyl-20-nor-5-cis-13-trans prostadiene |
| 452 | 1-trans-tri-n-butylstannyl-4-cyclopropyl-4-trimethylsilyloxy-1-octene | 2-[6-methoxyacetyl hex-2-cis-enyl] cyclopent-2-en-1-one | dl-16-hydroxy-1-methoxymethyl-1,9-dioxo-16-cyclopropyl-5-cis-13-trans prostadiene |
| 453 | 1-trans-tri-n-butylstannyl-4-trimethylsilylethynyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-ethynyl-20-nor-5-cis-13-trans prostadiene |
| 454 | 1-trans-tri-n-butylstannyl-5-methylene 4-triethylsilyloxy-1-heptene | 2-[6-methoxyacetyl hex-2-cis-enyl] cyclopent-2-en-1-one | dl-16-hydroxy-1-methoxymethyl-1,9-dioxo-17-methylene-20-nor-5-cis-13-trans prostadiene |
| 455 | 1-trans-tri-n-butylstannyl-4-methyl-5-methylene 4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-methyl-17-methylene-20-nor-5-cis-13-trans prostadiene |
| 456 | 1-trans-tri-n-butylstannyl-4-dimethoxymethyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-formyl-20-nor-5-cis-13-trans prostadiene |
| 457 | 1-trans-tri-n-butylstannyl-4-fluoromethyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-fluoromethyl-20-nor-5-cis-13-trans prostadiene |
| 458 | 1-trans-tri-n-butylstannyl-4-difluoromethyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-difluoromethyl-20-nor-5-cis-13-trans prostadiene |
| 459 | 1-trans-tri-n-butylstannyl-4-trifluoromethyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-trifluoromethyl-20-nor-5-cis-13-trans prostadiene |
| 460 | 1-trans-tri-n-butylstannyl-4-chloromethyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-chloromethyl-20-nor-5-cis-13-trans prostadiene |
| 461 | 1-trans-tri-n-butylstannyl-4-trimethylsilyloxymethyl-4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 462 | 1-trans-iodo-4-methyl-7-chloro 4-trimethylsilyloxy-1-heptene | 2-[6-methoxyacetyl hex-2-cis-enyl] cyclopent-2-en-1-one | dl-16-hydroxy-1-methoxymethyl-1,9-dioxo-16-methyl-19-chloro-20-nor-5-cis-13-trans prostadiene |
| 463 | 1-trans-iodo-3-triphenylmethoxy-1-octene | 2-[6-methoxyacetyl hex-2-cis-enyl] cyclopent-2-en-1-one | dl-15a-hydroxy-1-methoxymethyl-1,9-dioxo-5-cis-13-trans prostadiene |
| 464 | 1-trans-iodo-3-methyl-3-trimethylsilyloxy-1-octene | 2-[6-methoxyacetyl hex-2-cis-enyl] cyclopent-2-en-1-one | dl-15a-hydroxy-1-methoxymethyl-1,9-dioxo-15-methyl-5-cis-13-trans prostadiene |
| 465 | 1-trans-iodo-4,4-dimethyl 3-trimethylsilyloxy-1-octene | 2-[6-methoxyacetyl hex-2-cis-enyl] cyclopent-2-en-1-one | dl-15a-hydroxy-1-methoxymethyl-1,9-dioxo-16,16-dimethyl-5-cis-13-trans prostadiene |
| 466 | 1-trans-iodo-4,4-trimethylene | 2-[6-methoxyacetyl hex-2-cis-enyl] cyclopent-2-en-1-one | dl-15a-hydroxy-1-methoxymethyl-1,9-dioxo- |

TABLE III-continued

| EXAMPLE | VINYL TIN / VINYL IODIDE | | CYCLOPENTENONE | PRODUCT PROSTAGLANDIN |
|---|---|---|---|---|
| | 3-trimethylsilyloxy-1-octene | | hex-2-cis-enyl] cyclopent-2-en-1-one | 16,16-trimethylene-5-cis-13-trans prostadiene |
| EXAMPLE | VINYL TIN | | CYCLOPENTENONE | PRODUCT PROSTAGLANDIN OF THE 11-DEOXY PGE2 SERIES |
| 467 | 1-trans-tri-n-butylstannyl-3-vinyl-3-trimethylsilyloxy-1-octene | | 2-[6-methoxyacetyl hex-2-cis-enyl] cyclopent-2-en-1-one | dl-15a-hydroxy-1-methoxymethyl-1,9-dioxo-15-vinyl-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 468 | 1-trans-iodo-4-triphenylmethoxy-1-octene | | 2-[6-methoxyacetyl hex-2-cis-enyl] cyclopent-2-en-1-one | dl-16-hydroxy-1-methoxymethyl-1,9-dioxo-5-cis-13-trans prostadiene |
| EXAMPLE | VINYL TIN | | CYCLOPENTENONE | PRODUCT PROSTAGLANDIN OF THE 11-DEOXY PGE2 SERIES |
| 469 | 1-trans-tri-n-butylstannyl-4-methyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-methyl-5-cis-13-trans prostadiene |
| 470 | 1-trans-tri-n-butylstannyl-5-methyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-17-methyl-5-cis-13-trans prostadiene |
| 471 | 1-trans-tri-n-butylstannyl-4-vinyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-vinyl-5-cis-13-trans prostadiene |
| 472 | 1-trans-tri-n-butylstannyl-4-trimethylsilylethynyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-ethynyl-5-cis-13-trans prostadiene |
| 473 | 1-trans-tri-n-butylstannyl-5-methylene-4-triethylsilyloxy-1-octene | | 2-[6-methoxyacetyl hex-2-cis-enyl] cyclopent-2-en-1-one | dl-16-hydroxy-1-methoxymethyl-1,9-dioxo-17-methylene-5-cis-13-trans prostadiene |
| 474 | 1-trans-tri-n-butylstannyl-4-methyl-5-methylene-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-methyl-17-methylene-5-cis-13-trans prostadiene |
| 475 | 1-trans-tri-n-butylstannyl-4-dimethoxymethyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-formyl-5-cis-13-trans prostadiene |
| 476 | 1-trans-tri-n-butylstannyl-4-fluoromethyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-fluoromethyl-5-cis-13-trans prostadiene |
| 477 | 1-trans-tri-n-butylstannyl-4-difluoromethyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-difluoromethyl-5-cis-13-trans prostadiene |
| 478 | 1-trans-tri-n-butylstannyl-4-trifluoromethyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-trifluoromethyl-5-cis-13-trans prostadiene |
| 479 | 1-trans-tri-n-butylstannyl-4-chloromethyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-chloromethyl-5-cis-13-trans prostadiene |
| 480 | 1-trans-tri-n-butylstannyl-4-trimethylsilyloxymethyl-4-trimethylsilyloxy-1-octene | | 2-[6-methoxyacetyl hex-2-cis-enyl] cyclopent-2-en-1-one | dl-16-hydroxy-1-methoxymethyl-1,9-dioxo-16-hydroxymethyl-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 481 | 1-trans-iodo- | | 2-[6-methoxyacetyl | dl-15a-hydroxy-1-methoxymethyl-1,9-dioxo- |

TABLE III-continued

| Example | Vinyl Tin / Iodide | Cyclopentenone | Product Prostaglandin |
|---|---|---|---|
| | 3-triphenylmethoxy-1-nonene | hex-2-cis-enyl] cyclopent-2-en-1-one | 20-methyl-5-cis-13-trans prostadiene |
| 482 | 1-trans-iodo-3-methyl-3-trimethylsilyloxy-1-nonene | 2-[6-methoxyacetyl hex-2-cis-enyl] cyclopent-2-en-1-one | dl-15a-hydroxy-1-methoxymethyl-1,9-dioxo-15-methyl-20-methyl-5-cis-13-trans prostadiene |
| 483 | 1-trans-iodo-4,4-dimethyl-3-trimethylsilyloxy-1-nonene | 2-[6-methoxyacetyl hex-2-cis-enyl] cyclopent-2-en-1-one | dl-15a-hydroxy-1-methoxymethyl-1,9-dioxo-16,16-dimethyl-20-methyl-5-cis-13-trans prostadiene |
| 484 | 1-trans-iodo-4,4-trimethylene-3-trimethylsilyloxy-1-nonene | 2-[6-methoxyacetyl hex-2-cis-enyl] cyclopent-2-en-1-one | dl-15a-hydroxy-1-methoxymethyl-1,9-dioxo-16,16-trimethylene-20-methyl-5-cis-13-trans prostadiene |
| EXAMPLE | VINYL | CYCLOPENTENONE | PRODUCT PROSTAGLANDIN OF THE 11-DEOXY PGE2 SERIES |
| 485 | 1-trans-tri-n-butylstannyl-3-vinyl-3-trimethylsilyloxy-1-nonene | 2-[6-methoxyacetyl hex-2-cis-enyl] cyclopent-2-en-1-one | dl-15a-hydroxy-1-methoxymethyl-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 486 | 1-trans-iodo-4-triphenylmethoxy-1-nonene | 2-[6-methoxyacetyl hex-2-cis-enyl] cyclopent-2-en-1-one | dl-16-hydroxy-1-methoxymethyl-1,9-dioxo-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 487 | 1-trans-tri-n-butylstannyl-4-methyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-methyl-20-methyl-5-cis-13-trans prostadiene |
| 488 | 1-trans-tri-n-butylstannyl-5-methyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-17-methyl-20-methyl-5-cis-13-trans prostadiene |
| 489 | 1-trans-tri-n-butylstannyl-4-vinyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-vinyl-20-methyl-5-cis-13-trans prostadiene |
| 490 | 1-trans-tri-n-butylstannyl-4-trimethylsilylethynyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-ethynyl-20-methyl-5-cis-13-trans prostadiene |
| 491 | 1-trans-tri-n-butylstannyl-5-methylene-4-triethylsilyloxy-1-nonene | 2-[6-methoxyacetyl hex-2-cis-enyl] cyclopent-2-en-1-one | dl-16-hydroxy-1-methoxymethyl-1,9-dioxo-17-methylene-20-methyl-5-cis-13-trans prostadiene |
| 492 | 1-trans-tri-n-butylstannyl-4-methyl-5-methylene-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-methyl-17-methylene-20-methyl-5-cis-13-trans prostadiene |
| 493 | 1-trans-tri-n-butylstannyl-4-dimethoxymethyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-formyl-20-methyl-5-cis-13-trans prostadiene |
| 494 | 1-trans-tri-n-butylstannyl-4-fluoromethyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-fluoromethyl-20-methyl-5-cis-13-trans prostadiene |
| 495 | 1-trans-tri-n-butylstannyl-4-difluoromethyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-difluoromethyl-20-methyl-5-cis-13-trans prostadiene |
| 496 | 1-trans-tri-n-butylstannyl-4-trifluoromethyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-trifluoromethyl-20-methyl-5-cis-13-trans prostadiene |

TABLE III-continued

| EXAMPLE | VINYL IODIDE / VINYL TIN | CYCLOPENTENONE | PRODUCT PROSTAGLANDIN OF THE 11-DEOXY PGE2 SERIES |
|---|---|---|---|
| 497 | 1-trans-tri-n-butylstannyl-4-chloromethyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-chloromethyl-20-methyl-5-cis-13-trans prostadiene |
| 498 | 1-trans-tri-n-butylstannyl-4-trimethylsilyloxymethyl-4-trimethylsilyloxy-1-nonene | 2-[6-methoxyacetyl hex-2-cis-enyl] cyclopent-2-en-1-one | dl-16-hydroxy-1-methoxymethyl-1,9-dioxo-16-hydroxymethyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 499 | 1-trans-iodo-3-triphenylmethoxy-1-decene | 2-[6-methoxyacetyl hex-2-cis-enyl] cyclopent-2-en-1-one | dl-15a-hydroxy-1-methoxymethyl-1,9-dioxo-20-ethyl-5-cis-13-trans prostadiene |
| 500 | 1-trans-iodo-3-methyl-3-trimethylsilyloxy-1-decene | 2-[6-methoxyacetyl hex-2-cis-enyl] cyclopent-2-en-1-one | dl-15a-hydroxy-1-methoxymethyl-1,9-dioxo-15-methyl-20-ethyl-5-cis-13-trans prostadiene |
| 501 | 1-trans-iodo-4,4-dimethyl-3-trimethylsilyloxy-1-decene | 2-[6-methoxyacetyl hex-2-cis-enyl] cyclopent-2-en-1-one | dl-15a-hydroxy-1-methoxymethyl-1,9-dioxo-16,16-dimethyl-20-ethyl-5-cis-13-trans prostadiene |
| 502 | 1-trans-iodo-4,4-trimethylene-3-trimethylsilyloxy-1-decene | 2-[6-methoxyacetyl hex-2-cis-enyl] cyclopent-2-en-1-one | dl-15a-hydroxy-1-methoxymethyl-1,9-dioxo-16,16-trimethylene-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 503 | 1-trans-tri-n-butylstannyl-3-vinyl-3-trimethylsilyloxy-1-decene | 2-[6-methoxyacetyl hex-2-cis-enyl] cyclopent-2-en-1-one | dl-15a-hydroxy-1-methoxymethyl-1,9-dioxo-15-vinyl-20-ethyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 504 | 1-trans-iodo-4-triphenylmethoxy-1-decene | 2-[6-methoxyacetyl hex-2-cis-enyl] cyclopent-2-en-1-one | dl-16-hydroxy-1-methoxymethyl-1,9-dioxo-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 505 | 1-trans-tri-n-butylstannyl-4-methyl-4-trimethylsilyloxy-1-decene | 2-[6-methoxyacetyl hex-2-cis-enyl] cyclopent-2-en-1-one | dl-16-hydroxy-1-methoxymethyl-1,9-dioxo-16-methyl-20-ethyl-5-cis-13-trans prostadiene |
| 506 | 1-trans-tri-n-butylstannyl-5-methyl-4-trimethylsilyloxy-1-decene | 2-[6-methoxyacetyl hex-2-cis-enyl] cyclopent-2-en-1-one | dl-16-hydroxy-1-methoxymethyl-1,9-dioxo-17-methyl-20-ethyl-5-cis-13-trans prostadiene |
| 507 | 1-trans-tri-n-butylstannyl-4-vinyl-4-trimethylsilyloxy-1-decene | 2-[6-methoxyacetyl hex-2-cis-enyl] cyclopent-2-en-1-one | dl-16-hydroxy-1-methoxymethyl-1,9-dioxo-16-vinyl-20-ethyl-5-cis-13-trans prostadiene |
| 508 | 1-trans-tri-n-butylstannyl-4-trimethylsilylethynyl-4-trimethylsilyloxy-1-decene | 2-[6-methoxyacetyl hex-2-cis-enyl] cyclopent-2-en-1-one | dl-16-hydroxy-1-methoxymethyl-1,9-dioxo-16-ethynyl-20-ethyl-5-cis-13-trans prostadiene |
| 509 | 1-trans-tri-n-butylstannyl-5-methylene-4-triethylsilyloxy-1-decene | 2-[6-methoxyacetyl hex-2-cis-enyl] cyclopent-2-en-1-one | dl-16-hydroxy-1-methoxymethyl-1,9-dioxo-17-methylene-20-ethyl-5-cis-13-trans prostadiene |
| 510 | 1-trans-tri-n-butylstannyl-4-methyl-5-methylene-4-trimethylsilyloxy-1-decene | 2-[6-methoxyacetyl hex-2-cis-enyl] cyclopent-2-en-1-one | dl-16-hydroxy-1-methoxymethyl-1,9-dioxo-16-methyl-17-methylene-20-ethyl-5-cis-13-trans prostadiene |
| 511 | 1-trans-tri-n-butylstannyl-4-dimethoxymethyl-4-trimethylsilyloxy-1-decene | 2-[6-methoxyacetyl hex-2-cis-enyl] cyclopent-2-en-1-one | dl-16-hydroxy-1-methoxymethyl-1,9-dioxo-16-formyl-20-ethyl-5-cis-13-trans prostadiene |

TABLE III-continued

| EXAMPLE | VINYL IODIDE | CYCLOPENTENONE | PRODUCT PROSTAGLANDIN OF THE 11-DEOXY PGE2 SERIES |
|---|---|---|---|
| 512 | 1-trans-tri-n-butylstannyl-4-fluoromethyl-4-trimethylsilyloxy-1-decene | 2-[6-methoxyacetyl]cyclopent-2-en-1-one 2-[6-methoxyacetyl]hex-2-cis-enyl] | dl-16-hydroxy-1-methoxymethyl-1,9-dioxo-16-fluoromethyl-20-ethyl-5-cis-13-trans prostadiene |
| 513 | 1-trans-tri-n-butylstannyl-4-difluoromethyl-4-trimethylsilyloxy-1-decene | 2-[6-methoxyacetyl]cyclopent-2-en-1-one 2-[6-methoxyacetyl]hex-2-cis-enyl] | dl-16-hydroxy-1-methoxymethyl-1,9-dioxo-16-difluoromethyl-20-ethyl-5-cis-13-trans prostadiene |
| 514 | 1-trans-tri-n-butylstannyl-4-trifluoromethyl-4-trimethylsilyloxy-1-decene | 2-[6-methoxyacetyl]cyclopent-2-en-1-one 2-[6-methoxyacetyl]hex-2-cis-enyl] | dl-16-hydroxy-1-methoxymethyl-1,9-dioxo-16-trifluoromethyl-20-ethyl-5-cis-13-trans prostadiene |
| 515 | 1-trans-tri-n-butylstannyl-4-chloromethyl-4-trimethylsilyloxy-1-decene | 2-[6-methoxyacetyl]cyclopent-2-en-1-one 2-[6-methoxyacetyl]hex-2-cis-enyl] | dl-16-hydroxy-1-methoxymethyl-1,9-dioxo-16-chloromethyl-20-ethyl-5-cis-13-trans prostadiene |
| 516 | 1-trans-tri-n-butylstannyl-4-trimethylsilyloxymethyl-4-trimethylsilyloxy-1-decene | 2-[6-methoxyacetyl]cyclopent-2-en-1-one 2-[6-methoxyacetyl]hex-2-cis-enyl] | dl-16-hydroxy-1-methoxymethyl-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 517 | 1-trans-iodo-3-triphenylmethoxy-1-heptene | 2-[7-methoxyacetyl]hept-2-cis-enyl] cyclopent-2-en-1-one | dl-15a-hydroxy-1-methoxymethyl-1,9-dioxo-20-nor-2-homo-5-cis-13-trans prostadiene |
| 518 | 1-trans-iodo-3-methyl-3-trimethylsilyloxy-1-heptene | 2-[7-methoxyacetyl]hept-2-cis-enyl] cyclopent-2-en-1-one | dl-15a-hydroxy-1-methoxymethyl-1,9-dioxo-15-methyl-20-nor-2-homo-5-cis-13-trans prostadiene |
| 519 | 1-trans-iodo-4,4-dimethyl-3-trimethylsilyloxy-1-heptene | 2-[7-methoxyacetyl]hept-2-cis-enyl] cyclopent-2-en-1-one | dl-15a-hydroxy-1-methoxymethyl-1,9-dioxo-16,16-dimethyl-20-nor-2-homo-5-cis-13-trans prostadiene |
| 520 | 1-trans-iodo-5,5-dimethyl-3-triphenylmethoxy-1-octene | 2-[7-methoxyacetyl]hept-2-cis-enyl] cyclopent-2-en-1-one | dl-15a-hydroxy-1-methoxymethyl-1,9-dioxo-17,17-dimethyl-2-homo-5-cis-13-trans prostadiene |
| 521 | 1-trans-iodo-4-methyl-3-triphenylmethoxy-1-octene | 2-[7-methoxyacetyl]hept-2-cis-enyl] cyclopent-2-en-1-one | dl-15a-hydroxy-1-methoxymethyl-1,9-dioxo-16-methyl-2-homo-5-cis-13-trans prostadiene |
| 522 | 1-trans-iodo-4,4-trimethylene-3-trimethylsilyloxy-1-heptene | 2-[7-methoxyacetyl]hept-2-cis-enyl] cyclopent-2-en-1-one | dl-15a-hydroxy-1-methoxymethyl-1,9-dioxo-16,16-trimethylene-20-nor-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 523 | 1-trans-tri-n-butylstannyl-3-vinyl-3-trimethylsilyloxy-1-heptene | 2-[7-methoxyacetyl]hept-2-cis-enyl] cyclopent-2-en-1-one | dl-15a-hydroxy-1-methoxymethyl-1,9-dioxo-15-vinyl-20-nor-2-homo-5-cis-13-trans prostadiene |
| 524 | 1-trans-tri-n-butylstannyl-4-phenoxy-3-triethylsilyloxy-1-butene | 2-[7-methoxyacetyl]hept-2-cis-enyl] cyclopent-2-en-1-one | dl-15a-hydroxy-1-methoxymethyl-1,9-dioxo-16-phenoxy-2-homo-17-20-tetranor-5-cis-13-trans prostadiene |
| 525 | 1-trans-tri-n-butylstannyl-4-(p-fluorophenoxy)-3-triethylsilyloxy-1-butene | 2-[7-methoxyacetyl]hept-2-cis-enyl] cyclopent-2-en-1-one | dl-15a-hydroxy-1-methoxymethyl-1,9-dioxo-16-(p-fluorophenoxy)-2-homo-17-20-tetranor-5-cis-13-trans prostadiene |
| 526 | 1-trans-tri-n-butylstannyl-4-(m-chlorophenoxy)-3-triethylsilyloxy-1-butene | 2-[7-methoxyacetyl]hept-2-cis-enyl] cyclopent-2-en-1-one | dl-15a-hydroxy-1-methoxymethyl-1,9-dioxo-16-(m-chlorophenoxy)-2-homo-17-20-tetranor-5-cis-13-trans prostadiene |
| 527 | 1-trans-tri-n-butylstannyl-4-(m-trifluoromethylphenoxy)-3-triethylsilyloxy-1-butene | 2-[7-methoxyacetyl]hept-2-cis-enyl] cyclopent-2-en-1-one | dl-15a-hydroxy-1-methoxymethyl-1,9-dioxo-16-(m-trifluoromethylphenoxy)-2-homo-17-20-tetranor-5-cis-13-trans prostadiene |

TABLE III-continued

| EXAMPLE | VINYL IODIDE | CYCLOPENTENONE | PRODUCT PROSTAGLANDIN OF THE 11-DEOXY PGE2 SERIES |
|---|---|---|---|
| 528 | 1-trans-iodo-5-phenyl-3-triethylsilyloxy-1-pentene | 2-[7-methoxyacetyl hept-2-cis-enyl] cyclopent-2-en-1-one | dl-15a-hydroxy-1-methoxymethyl-1,9-dioxo-17-phenyl-2-homo-18-20-trinor-5-cis-13-trans prostadiene |
| 529 | 1-trans-iodo-4,4-dimethyl-5-phenyl-3-triethylsilyloxy-1-pentene | 2-[7-methoxyacetyl hept-2-cis-enyl] cyclopent-2-en-1-one | dl-15a-hydroxy-1-methoxymethyl-1,9-dioxo-16,16-dimethyl-17-phenyl-2-homo-18-20-trinor-5-cis-13-trans prostadiene |
| 530 | 1-trans-iodo-4-cyclopentyl-3-triphenylmethoxy-1-butene | 2-[7-methoxyacetyl hept-2-cis-enyl] cyclopent-2-en-1-one | dl-15a-hydroxy-1-methoxymethyl-1,9-dioxo-16-cyclopentyl-2-homo-17-20-tetranor-5-cis-13-trans prostadiene |
| 531 | 1-trans-iodo-4-cyclohexyl-3-triphenylmethoxy-1-butene | 2-[7-methoxyacetyl hept-2-cis-enyl] cyclopent-2-en-1-one | dl-15a-hydroxy-1-methoxymethyl-1,9-dioxo-16-cyclohexyl-2-homo-17-20-tetranor-5-cis-13-trans prostadiene |
| 532 | 1-trans-iodo-3-triphenylmethoxy-1-heptene | 2-[7-methoxyacetyl hept-2-cis-enyl] cyclopent-2-en-1-one | dl-16-hydroxy-1-methoxymethyl-1,9-dioxo-20-nor-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 533 | 1-trans-tri-n-butylstannyl-4-methyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-methyl-20-nor-2-homo-5-cis-13-trans prostadiene |
| 534 | 1-trans-tri-n-butylstannyl-4-ethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-ethyl-2-homo-5-cis-13-trans prostadiene |
| 535 | 1-trans-tri-n-butylstannyl-5-methyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-17-methyl-20-nor-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 536 | 1-trans-iodo-5,5-dimethyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-17,17-dimethyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 537 | 1-trans-tri-n-butylstannyl-4-vinyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-vinyl-20-nor-2-homo-5-cis-13-trans prostadiene |
| 538 | 1-trans-tri-n-butylstannyl-4-cyclopropyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-cyclopropyl-2-homo-5-cis-13-trans prostadiene |
| 539 | 1-trans-tri-n-butylstannyl-4-trimethylsilylethynyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-ethynyl-20-nor-2-homo-5-cis-13-trans prostadiene |
| 540 | 1-trans-tri-n-butylstannyl-5-methylene-4-triethylsilyloxy-1-heptene | 2-[7-methoxyacetyl hept-2-cis-enyl] cyclopent-2-en-1-one | dl-16-hydroxy-1-methoxymethyl-1,9-dioxo-17-methylene-20-nor-2-homo-5-cis-13-trans prostadiene |
| 541 | 1-trans-tri-n-butylstannyl-4-methyl-5-methylene-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-methyl-17-methylene-20-nor-2-homo-5-cis-13-trans prostadiene |
| 542 | 1-trans-tri-n-butylstannyl-4-dimethoxymethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-formyl-20-nor-2-homo-5-cis-13-trans prostadiene |
| 543 | 1-trans-tri-n-butylstannyl-4-fluoromethyl- | 2-[7-methoxyacetyl | dl-16-hydroxy-1-methoxymethyl-1,9-dioxo-16-fluoromethyl- |

TABLE III-continued

| | | | |
|---|---|---|---|
| | 4-trimethylsilyloxy-1-heptene | hept-2-cis-enyl] cyclopent-2-en-1-one | 20-nor-2-homo-5-cis-13-trans prostadiene |
| 544 | 1-trans-tri-n-butylstannyl-4-difluoromethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-difluoromethyl-20-nor-2-homo-5-cis-13-trans prostadiene |
| 545 | 1-trans-tri-n-butylstannyl-4-trifluoromethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-trifluoromethyl-20-nor-2-homo-5-cis-13-trans prostadiene |
| 546 | 1-trans-tri-n-butylstannyl-4-chloromethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-chloromethyl-20-nor-2-homo-5-cis-13-trans prostadiene |
| 547 | 1-trans-tri-n-butylstannyl-4-trimethylsilyloxymethyl-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-hydroxymethyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 548 | 1-trans-iodo-4-methyl-7-chloro-4-trimethylsilyloxy-1-heptene | 2-[7-methoxyacetyl hept-2-cis-enyl] cyclopent-2-en-1-one | dl-16-hydroxy-1-methoxymethyl-1,9-dioxo-16-methyl-19-chloro-2-homo-20-nor-5-cis-13-trans prostadiene |
| 549 | 1-trans-iodo-4-triphenylmethoxy-1-octene | 2-[7-methoxyacetyl hept-2-cis-enyl] cyclopent-2-en-1-one | dl-15a-hydroxy-1-methoxymethyl-1,9-dioxo-2-homo-5-cis-13-trans prostadiene |
| 550 | 1-trans-iodo-3-methyl-4-trimethylsilyloxy-1-octene | 2-[7-methoxyacetyl hept-2-cis-enyl] cyclopent-2-en-1-one | dl-15a-hydroxy-1-methoxymethyl-1,9-dioxo-15-methyl-2-homo-5-cis-13-trans prostadiene |
| 551 | 1-trans-iodo-4,4-dimethyl-3-trimethylsilyloxy-1-octene | 2-[7-methoxyacetyl hept-2-cis-enyl] cyclopent-2-en-1-one | dl-15a-hydroxy-1-methoxymethyl-1,9-dioxo-16,16-dimethyl-2-homo-5-cis-13-trans prostadiene |
| 552 | 1-trans-iodo-4,4-trimethylene-3-trimethylsilyloxy-1-octene | 2-[7-methoxyacetyl hept-2-cis-enyl] cyclopent-2-en-1-one | dl-15a-hydroxy-1-methoxymethyl-1,9-dioxo-16,16-trimethylene-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 553 | 1-trans-tri-n-butylstannyl-3-vinyl-3-trimethylsilyloxy-1-octene | 2-[7-methoxyacetyl hept-2-cis-enyl] cyclopent-2-en-1-one | dl-15a-hydroxy-1-methoxymethyl-1,9-dioxo-15-vinyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 554 | 1-trans-iodo-4-triphenylmethoxy-1-octene | 2-[7-methoxyacetyl hept-2-cis-enyl] cyclopent-2-en-1-one | dl-16-hydroxy-1-methoxymethyl-1,9-dioxo-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 555 | 1-trans-tri-n-butylstannyl-4-methyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-methyl-2-homo-5-cis-13-trans prostadiene |
| 556 | 1-trans-tri-n-butylstannyl-5-methyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-17-methyl-2-homo-5-cis-13-trans prostadiene |
| 557 | 1-trans-tri-n-butylstannyl-4-vinyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-vinyl-2-homo-5-cis-13-trans prostadiene |
| 558 | 1-trans-tri-n-butylstannyl-4-trimethylsilylethynyl- | 2-[7-methoxyacetyl | dl-16-hydroxy-1-methoxymethyl-1,9-dioxo-16-ethynyl- |

TABLE III-continued

| | | | |
|---|---|---|---|
| | | 4-trimethylsilyloxy-1-octene | hept-2-cis-enyl] cyclopent-2-en-1-one | 2-homo-5-cis-13-trans prostadiene |
| 559 | | 1-trans-tri-n-butylstannyl-5-methylene-4-triethylsilyloxy-1-octene | 2-[7-methoxyacetyl hept-2-cis-enyl] cyclopent-2-en-1-one | dl-16-hydroxy-1-methoxymethyl-1,9-dioxo-17-methylene-2-homo-5-cis-13-trans prostadiene |
| 560 | | 1-trans-tri-n-butylstannyl-4-methyl-5-methylene-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-methyl-17-methylene-2-homo-5-cis-13-trans prostadiene |
| 561 | | 1-trans-tri-n-butylstannyl-4-dimethoxymethyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-formyl-2-homo-5-cis-13-trans prostadiene |
| 562 | | 1-trans-tri-n-butylstannyl-4-fluoromethyl-4-trimethysilyloxy-1-octene | 2-[7-methoxyacetyl hept-2-cis-enyl] cyclopent-2-en-1-one | dl-16-hydroxy-1-methoxymethyl-1,9-dioxo-16-fluoromethyl-2-homo-5-cis-13-trans prostadiene |
| 563 | | 1-trans-tri-n-butylstannyl-4-difluoromethyl-4-trimethylsilyloxy-1-octene | 2-[7-methoxyacetyl hept-2-cis-enyl] cyclopent-2-en-1-one | dl-16-hydroxy-1-methoxymethyl-1,9-dioxo-16-difluoromethyl-2-homo-5-cis-13-trans-prostadiene |
| 564 | | 1-trans-tri-n-butylstannyl-4-trifluoromethyl-4-trimethylsilyloxy-1-octene | 2-[7-methoxyacetyl hept-2 cis enyl] cyclopent-2-en-1-one | dl-16-hydroxy-1-methoxymethyl-1,9-dioxo-16-trifluoromethyl-2-homo-5-cis-13-trans prostadiene |
| 565 | | 1-trans-tri-n-butylstannyl-4-chloromethyl-4-trimethylsilyloxy-1-octene | 2-[7-methoxyacetyl hept-2-cis enyl] cyclopent-2-en-1-one | dl-16-hydroxy-1-methoxymethyl-1,9-dioxo-16-chloromethyl-2-homo-5-cis-13-trans prostadiene |
| 566 | | 1-trans-tri-n-butylstannyl-4-trimethylsilyloxymethyl-4-trimethylsilyloxy-1-octene | 2-[7-methoxyacetyl hept-2-cis enyl] cyclopent-2-en-1-one | dl-16-hydroxy-1-methoxymethyl-1,9-dioxo-16-hydroxymethyl-2-homo-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 567 | 1-trans-iodo-3-triphenylmethoxy-1-nonene | | 2-[7-methoxyacetyl hept-2-cis-enyl] cyclopent-2-en-1-one | dl-15a-hydroxy-1-methoxymethyl-1,9-dioxo-20-methyl-2-homo-5-cis-13-trans prostadiene |
| 568 | 1-trans-iodo-3-methyl-3-trimethylsilyloxy-1-nonene | | 2-[7-methoxyacetyl hept-2 cis enyl] cyclopent-2-en-1-one | dl-15a-hydroxy-1-methoxymethyl-1,9-dioxo-15-methyl-20-methyl-2-homo-5-cis-13-trans prostadiene |
| 569 | 1-trans-iodo-4,4-dimethyl-3-trimethylsilyloxy-1-nonene | | 2-[7-methoxyacetyl hept-2 cis enyl] cyclopent-2-en-1-one | dl-15a-hydroxy-1-methoxymethyl-1,9-dioxo-16,16-dimethyl-20-methyl-2-homo-5-cis-13-trans prostadiene |
| 570 | 1-trans-iodo-4,4-trimethylene-3-trimethylsilyloxy-1-nonene | | 2-[7-methoxyacetyl hept-2-cis enyl] cyclopent-2-en-1-one | dl-15a-hydroxy-1-methoxymethyl-1,9-dioxo-16,16-trimethylene-20-methyl-2-homo-5-cis-13-trans prostadiene |
| EXAMPLE | VINYL TIN | | CYCLOPENTENONE | PRODUCT PROSTAGLANDIN OF THE 11-DEOXY PGE2 SERIES |
| 571 | 1-trans-tri-n-butylstannyl-3-vinyl-3-trimethylsilyloxy-1-nonene | | 2-[7-methoxyacetyl hept-2-cis enyl] cyclopent-2-en-1-one | dl-15a-hydroxy-1-methoxymethyl-1,9-dioxo-15-vinyl-20-methyl-2-homo-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 572 | 1-trans-iodo-4-triphenylmethoxy-1-nonene | | 2-[7-methoxyacetyl hept-2-cis enyl] cyclopent-2-en-1-one | dl-16-hydroxy-1-methoxymethyl-1,9-dioxo-20-methyl-2-homo-5-cis-13-trans prostadiene |
| EXAMPLE | VINYL TIN | | CYCLOPENTENONE | PRODUCT PROSTAGLANDIN OF THE 11-DEOXY PGE2 SERIES |
| 573 | 1-trans-tri-n-butylstannyl-4-methyl | | 2-[7-methoxyacetyl | dl-16-hydroxy-1-methoxymethyl-1,9-dioxo-16-methyl- |

TABLE III-continued

| | | | |
|---|---|---|---|
| | 4-trimethylsilyloxy-1-nonene | hept-2-cis-enyl] | 20-methyl-2-homo-5-cis-13-trans prostadiene |
| 574 | 1-trans-tri-n-butylstannyl-5-methyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-17-methyl-20-methyl-2-homo-5-cis-13-trans prostadiene |
| 575 | 1-trans-tri-n-butylstannyl-4-vinyl-4-trimethylsiloxy-1-nonene | cyclopent-2-en-1-one 2-[7-methoxyacetyl hept-2-cis-enyl] | dl-16-hydroxy-1-methoxymethyl-1,9-dioxo-16-vinyl-20-methyl-2-homo-5-cis-13-trans prostadiene |
| 576 | 1-trans-tri-n-butylstannyl-4-trimethylsilylethynyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-ethynyl-20-methyl-2-homo-5-cis-13-trans prostadiene |
| 577 | 1-trans-tri-butylstannyl-5-methylene-4-triethylsilyloxy-1-nonene | cyclopent-2-en-1-one 2-[7-methoxyacetyl hept-2-cis-enyl] | dl-16-hydroxy-1-methoxymethyl-1,9-dioxo-17-methylene-20-methyl-2-homo-5-cis-13-trans prostadiene |
| 578 | 1-trans-tri-n-butylstannyl-4-methyl-5-methylene-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-methyl-17-methylene-20-methyl-2-homo-5-cis-13-trans prostadiene |
| 579 | 1-trans-tri-n-butylstannyl-4-dimethoxymethyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-formyl-20-methyl-2-homo-5-cis-13-trans prostadiene |
| 580 | 1-trans-tri-n-butylstannyl-4-fluoromethyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-fluoromethyl-20-methyl-2-homo-5-cis-13-trans prostadiene |
| 581 | 1-trans-tri-n-butylstannyl-4-difluoromethyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-difluoromethyl-20-methyl-2-homo-5-cis-13-trans prostadiene |
| 582 | 1-trans-tri-n-butylstannyl-4-trifluoromethyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-trifluoromethyl-20-methyl-2-homo-5-cis-13-trans prostadiene |
| 583 | 1-trans-tri-n-butylstannyl-4-chloromethyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-chloromethyl-20-methyl-2-homo-5-cis-13-trans prostadiene |
| 584 | 1-trans-tri-n-butylstannyl-4-trimethylsilyloxymethyl-4-trimethylsilyloxy-1-nonene | cyclopent-2-en-1-one 2-[7-methoxyacetyl hept-2-cis-enyl] | dl-16-hydroxy-1-methoxymethyl-1,9-dioxo-16-hydroxymethyl-20-methyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 585 | 1-trans-iodo-3-triphenylmethoxy-1-decene | 2-[7-methoxyacetyl hept-2-cis-enyl] cyclopent-2-en-1-one | dl-15a-hydroxy-1-methoxymethyl-1,9-dioxo-20-ethyl-2-homo-5-cis-13-trans prostadiene |
| 586 | 1-trans-iodo-3-methyl-3-trimethylsilyloxy-1-decene | 2-[7-methoxyacetyl hept-2-cis-enyl] cyclopent-2-en-1-one | dl-15a-hydroxy-1-methoxymethyl-1,9-dioxo-15-methyl-20-ethyl-2-homo-5-cis-13-trans prostadiene |
| 587 | 1-trans-iodo-4,4-dimethyl-3-trimethylsilyloxy-1-decene | 2-[7-methoxyacetyl hep-2-cis-enyl] cyclopent-2-en-1-one | dl-15a-hydroxy-1-methoxymethyl-1,9-dioxo-16,16-dimethyl-20-ethyl-2-homo-5-cis-13-trans prostadiene |
| 588 | 1-trans-iodo-4,4-trimethylene-3-trimethylsilyloxy-1-decene | 2-[7-methoxyacetyl hept-2-cis-enyl] cyclopent-2-en-1-one | dl-15a-hydroxy-1-methoxymethyl-1,9-dioxo-16,16-trimethylene-20-ethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 589 | 1-trans-tri-n-butylstannyl-3-vinyl-3-trimethylsilyxoy-1-decene | 2-[7-methoxyacetyl hept-2-cis-enyl] | dl-15a-hydroxy-1-methoxymethyl-1,9-dioxo-15-vinyl-20-ethyl-2-homo-5-cis-13-trans prostadiene |

TABLE III-continued

| EXAMPLE | VINYL IODIDE | CYCLOPENTENONE | PRODUCT PROSTAGLANDIN OF THE 11-DEOXY PGE2 SERIES |
|---|---|---|---|
| 590 | 1-trans-iodo-4-triphenylmethoxy-1-decene | 2-[7-methoxyacetyl hept-2-cis-enyl] cyclopent-2-en-1-one | dl-16-hydroxy-1-methoxymethyl-1,9-dioxo-20-ethyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 591 | 1-trans-tri-n-butylstannyl-4-methyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-methyl-20-ethyl-2-homo-5-cis-13-trans prostadiene |
| 592 | 1-trans-tri-n-butylstannyl-4-methyl-5-methyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-17-methyl-20-ethyl-2-homo-5-cis-13-trans prostadiene |
| 593 | 1-trans-tri-n-butylstannyl-4-vinyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-vinyl-20-ethyl-2-homo-5-cis-13-trans prostadiene |
| 594 | 1-trans-tri-n-butylstannyl-4-trimethylsilylethynyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-ethynyl-20-ethyl-2-homo-5-cis-13-trans prostadiene |
| 595 | 1-trans-tri-n-butylstannyl-5-methylene-4-trimethylsilyloxy-1-decene | 2-[7-methoxyacetyl hept-2-cis-enyl] cyclopent-2-en-1-one | dl-16-hydroxy-1-methoxymethyl-1,9-dioxo-17-methylene-20-ethyl-2-homo-5-cis-13-trans prostadiene |
| 596 | 1-trans-tri-n-butylstannyl-4-methyl-5-methylene-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-methyl-17-methylene-20-ethyl-2-homo-5-cis-13-trans prostadiene |
| 597 | 1-trans-tri-n-butylstannyl-4-dimethoxymethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-formyl-20-ethyl-2-homo-5-cis-13-trans prostadiene |
| 598 | 1-trans-tri-n-butylstannyl-4-methyl-4-fluoromethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-fluoromethyl-20-ethyl-2-homo-5-cis-13-trans prostadiene |
| 599 | 1-trans-tri-n-butylstannyl-4-difluoromethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-difluoromethyl-20-ethyl-2-homo-5-cis-13-trans prostadiene |
| 600 | 1-trans-tri-n-butylstannyl-4-trifluoromethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-trifluoromethyl-20-ethyl-2-homo-5-cis-13-trans prostadiene |
| 601 | 1-trans-tri-n-butylstannyl-4-chloromethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-chloromethyl-20-ethyl-2-homo-5-cis-13-trans prostadiene |
| 602 | 1-trans-tri-n-butylstannyl-4-trimethylsilyloxymethyl-4-trimethylsilyloxy-1-decene | 2-[7-methoxyacetyl hept-2-cis-enyl] cyclopent-2-en-1-one | dl-16-hydroxy-1-methoxymethyl-1,9-dioxo-16-hydroxymethyl-20-ethyl-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 603 | 1-trans-tri-n-butylstannyl-4-methyl-4-trimethylsilyloxy-1,7-octadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-methyl-2-nor-5-cis-13-trans-19 prostatriene |
| 604 | 1-trans-tri-n-butylstannyl-4-methyl-4-trimethylsilyloxy-1,7-octadiene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-5-cis-13-trans-19 prostatriene |
| 605 | 1-trans-tri-n-butylstannyl-4-methyl- | 2-[7-methoxyacetyl | dl-11a,16-dihydroxy-1-methoxymethyl-1,9-dioxo-16-methyl- |

TABLE III-continued

| | | | |
|---|---|---|---|
| | | 4-trimethylsilyloxy-1,7-octadiene | hept-2-cis-enyl]-4-trimethylsilyloxy cyclopent-2-en-1-one | 2-homo-5-cis-13-trans-19 prostatriene |
| 606 | | 1-trans-tri-n-butylstannyl-4-methyl-4-trimethylsilyloxy-1,7-octadiene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-methyl-5-cis-13-trans-19 prostatriene |
| EXAMPLE | VINYL TIN | | CYCLOPENTENTONE | PRODUCT PROSTAGLANDIN OF THE 11-DEOXY PGE2 SERIES |
| 607 | | 1-trans-tri-n-butylstannyl-4-methyl-4-trimethylsilyloxy-1,7-octadiene | 2-[5-methoxyacetyl pent-2-cis-enyl] cyclopent-2-en-1-one | dl-16-hydroxy-1-methoxymethyl-1,9-dioxo-16-methyl-2-nor-5-cis-13-trans-19 prostatriene |
| 608 | | 1-trans-tri-n-butylstannyl-4-methyl-4-trimethylsilyloxy-1,7-octadiene | 2-[6-methoxyacetyl hex-2-cis-enyl] cyclopent-2-en-1-one | dl-16-hydroxy-1-methoxymethyl-1,9-dioxo-16-methyl-5-cis-13-trans-19 prostatriene |
| 609 | | 1-trans-tri-n-butylstannyl-4-methyl-4-trimethylsilyloxy-1,7-octadiene | 2-[7-methoxyacetyl hept-2-cis-enyl] cyclopent-2-en-1-one | dl-16-hydroxy-1-methoxymethyl-1,9-dioxo-16-methyl-2-homo-5-cis-13-trans-19 prostatriene |
| EXAMPLE | VINYL IODIDE | | CYCLOPENTENONE | PRODUCT PROSTAGLANDIN OF THE PGE2 SERIES |
| 610 | | 1-trans-iodo-4-triphenylmethoxy-1,5-heptadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-20-nor-2-nor-5-cis-13-trans-17-trans prostatriene |
| 611 | | 1-trans-iodo-4-methyl-4-trimethylsilyloxy-1,5-heptadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-methyl-20-nor-2-nor-5-cis-13-trans-17-trans prostatriene |
| 612 | | 1-trans-iodo-4-triphenylmethoxy-1,5-octadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-2-nor-5-cis-13-trans-17-trans prostatriene |
| 613 | | 1-trans-iodo-4-methyl-4-trimethylsilyloxy-1,5-octadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-methyl-2-nor-5-cis-13-trans-17-trans prostatriene |
| 614 | | 1-trans-iodo-4-triphenylmethoxy-1,5-nonadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-20-methyl-2-nor-5-cis-13-trans-17-trans prostatriene |
| 615 | | 1-trans-iodo-4-methyl-4-trimethylsilyloxy-1,5-nonadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-methyl-20-methyl-2-nor-5-cis-13-trans-17-trans prostatriene |
| 616 | | 1-trans-iodo-4-triphenylmethoxy-1,5-decadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-20-ethyl-2-nor-5-cis-13-trans-17-trans prostatriene |
| 617 | | 1-trans-iodo-4-methyl-4-trimethylsilyloxy-1,5-decadiene | 2-[5-methoxyacetyl pent-2-cis-enyl]-4-trimethylsilyloxy cyclopent-2-en-1-one | dl-11a,16-dihydroxy-1-methoxymethyl-1,9-dioxo-16-methyl-20-ethyl-2-nor-5-cis-13-trans-17-trans prostatriene |
| 618 | | 1-trans-iodo-4-triphenylmethoxy-1,5-heptadiene | 2-[6-methoxyacetyl hex-2-cis-enyl]-4-trimethylsilyloxy cyclopent-2-en-1-one | dl-11a,16-dihydroxy-1-methoxymethyl-1,9-dioxo-20-nor-5-cis-13-trans-17-trans prostatriene |
| 619 | | 1-trans-iodo-4-methyl-4-trimethylsilyloxy-1,5-heptadiene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-20-nor-5-cis-13-trans-17-trans prostatriene |
| 620 | | 1-trans-iodo-4-triphenylmethoxy-1,5-octadiene | 2-[6-methoxyacetyl hex-2-cis-enyl]-4-trimethylsilyloxy cyclopent-2-en-1-one | dl-11a,16-dihydroxy-1-methoxymethyl-1,9-dioxo-5-cis-13-trans-17-trans prostatriene |
| 621 | | 1-trans-iodo-4-methyl-4-trimethylsilyloxy-1,5-octadiene | 2-[6-methoxyacetyl hex-2-cis-enyl]-4-trimethylsilyloxy cyclopent-2-en-1-one | dl-11a,16-dihydroxy-1-methoxymethyl-1,9-dioxo-16-methyl-5-cis-13-trans-17-trans prostatriene |

TABLE III-continued

| | | | |
|---|---|---|---|
| 622 | 1-trans-iodo-4-triphenylmethoxy-1,5-nonadiene | cyclopent-2-en-1-one 2-[6-methoxyacetyl hex-2-cis-enyl]-4-trimethylsiloxy cyclopent-2-en-1-one | dl-11a,16-dihydroxy-1-methoxymethyl-1,9-dioxo-20-methyl-5-cis-13-trans-17-trans prostatriene |
| 623 | 1-trans-iodo-4-methyl-4-trimethylsilyloxy-1,5-nonadiene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-methyl-20-methyl-5-cis-13-trans-17-trans prostatriene |
| 624 | 1-trans-iodo-4-triphenylmethoxy-1,5-decadiene | 2-[6-methoxyacetyl hex-2-cis-enyl]-4-trimethylsiloxy cyclopent-2-en-1-one | dl-11a,16-dihydroxy-1-methoxymethyl-1,9-dioxo-20-ethyl-5-cis-13-trans-17-trans prostatriene |
| 625 | 1-trans-iodo-4-methyl-4-trimethylsilyloxy-1,5-decadiene | 2-[6-methoxyacetyl hex-2-cis-enyl]-4-trimethylsiloxy cyclopent-2-en-1-one | dl-11a,16-dihydroxy-1-methoxymethyl-1,9-dioxo-16-methyl-20-ethyl-5-cis-13-trans-17-trans prostatriene |
| 626 | 1-trans-iodo-4-triphenylmethoxy-1,5-heptadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-20-nor-2-homo-5-cis-13-trans-17-trans prostatriene |
| 627 | 1-trans-iodo-4-methyl-4-trimethylsilyloxy-1,5-heptadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-20-nor-2-homo-5-cis-13-trans-17-trans prostatriene |
| 628 | 1-trans-iodo-4-triphenylmethoxy-1,5-octadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-2-homo-5-cis-13-trans-17-trans prostatriene |
| 629 | 1-trans-iodo-4-methyl-4-trimethylsilyloxy-1,5-octadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-2-homo-5-cis-13-trans-17-trans prostatriene |
| 630 | 1-trans-iodo-4-triphenylmethoxy-1,5-nonadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-20-methyl-2-homo-5-cis-13-trans-17-trans prostatriene |
| 631 | 1-trans-iodo-4-methyl-4-trimethylsilyloxy-1,5-nonadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-20-methyl-2-homo-5-cis-13-trans-17-trans prostatriene |
| 632 | 1-trans-iodo-4-triphenylmethoxy-1,5-decadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-20-ethyl-2-homo-5-cis-13-trans-17-trans prostatriene |
| 633 | 1-trans-iodo-4-methyl-4-trimethylsilyloxy-1,5-decadiene | 2-[7-methoxyacetyl hept-2-cis-enyl]-4-trimethylsiloxy cyclopent-2-en-1-one | dl-11a,16-dihydroxy-1-methoxymethyl-1,9-dioxo-16-methyl-20-ethyl-2-homo-5-cis-13-trans-17-trans prostatriene |
| 634 | 1-trans-iodo-4-triphenylmethoxy-1,5-heptadiene | 2-[6-methoxyacetyl hex-2-cis-enyl]-4R-trimethylsiloxy cyclopent-2-en-1-one | nat-11a,16-dihydroxy-1-methoxymethyl-1,9-dioxo-20-nor-5-cis-13-trans-17-trans prostatriene |
| 635 | 1-trans-iodo-4-methyl-4-trimethylsilyloxy-1,5-heptadiene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-20-nor-5-cis-13-trans-17-trans prostatriene |
| 636 | 1-trans-iodo-4-triphenylmethoxy-1,5-octadiene | 2-[6-methoxyacetyl hex-2-cis-enyl]-4R-trimethylsiloxy cyclopent-2-en-1-one | nat-11a,16-dihydroxy-1-methoxymethyl-1,9-dioxo-5-cis-13-trans-17-trans prostatriene |
| 637 | 1-trans-iodo-4-methyl-4-trimethylsilyloxy-1,5-octadiene | 2-[6-methoxyacetyl hex-2-cis-enyl]-4R-trimethylsiloxy cyclopent-2-en-1-one | nat-11a,16-dihydroxy-1-methoxymethyl-1,9-dioxo-16-methyl-5-cis-13-trans-17-trans prostatriene |
| 638 | 1-trans-iodo-4-triphenylmethoxy-1,5-nonadiene | 2-[6-methoxyacetyl hex-2-cis-enyl]-4R-trimethylsiloxy cyclopent-2-en-1-one | nat-11a,16-dihydroxy-1-methoxymethyl-1,9-dioxo-20-methyl-5-cis-13-trans-17-trans prostatriene |
| 639 | 1-trans-iodo-4-methyl- | 2-[6-methoxyacetyl | nat-11a,16-dihydroxy-1-methoxymethyl-1,9-dioxo-16-methyl- |

TABLE III-continued

| | VINYL IODIDE | CYCLOPENTENONE | PRODUCT PROSTAGLANDIN OF THE 11-DEOXY PGE2 SERIES |
|---|---|---|---|
| 640 | 1-trans-iodo-4-trimethylsilyloxy-1,5-nonadiene | hex-2-cis-enyl]-4R-trimethylsilyloxy cyclopent-2-en-1-one | 20-methyl-5-cis-13-trans-17-trans prostatriene |
| | 1-trans-iodo-4-triphenylmethoxy-1,5-decadiene | hex-2-cis-enyl]-4R-trimethylsilyloxy cyclopent-2-en-1-one | nat-11a,16-dihydroxy-1-methoxymethyl-1,9-dioxo-20-ethyl-5-cis-13-trans-17-trans prostatriene |
| 641 | 1-trans-iodo-4-methyl-4-trimethylsilyloxy-1,5-decadiene | 2-[6-methoxyacetyl hex-2-cis-enyl]-4R-trimethylsilyloxy cyclopent-2-en-1-one | nat-11a,16-dihydroxy-1-methoxymethyl-1,9-dioxo-16-methyl-20-ethyl-5-cis-13-trans-17-trans prostatriene |

| EXAMPLE | VINYL IODIDE | CYCLOPENTENONE | PRODUCT PROSTAGLANDIN OF THE 11-DEOXY PGE2 SERIES |
|---|---|---|---|
| 642 | 1-trans-iodo-4-triphenylmethoxy-1,5-heptadiene | 2-[5-methoxyacetyl pent-2-cis-enyl] cyclopent-2-en-1-one | dl-16-hydroxy-1-methoxymethyl-1,9-dioxo-20-nor-2-nor-5-cis-13-trans-17-trans prostatriene |
| 643 | 1-trans-iodo-4-methyl-4-trimethylsilyloxy-1,5-heptadiene | 2-[5-methoxyacetyl pent-2-cis-enyl] cyclopent-2-en-1-one | dl-16-hydroxy-1-methoxymethyl-1,9-dioxo-16-methyl-20-nor-2-nor-5-cis-13-trans-17-trans prostatriene |
| 644 | 1-trans-iodo-4-triphenylmethoxy-1,5-octadiene | 2-[5-methoxyacetyl pent-2-cis-enyl] cyclopent-2-en-1-one | dl-16-hydroxy-1-methoxymethyl-1,9-dioxo-2-nor-5-cis-13-trans-17-trans prostatriene |
| 645 | 1-trans-iodo-4-methyl-4-trimethylsilyloxy-1,5-octadiene | 2-[5-methoxyacetyl pent-2-cis-enyl] cyclopent-2-en-1-one | dl-16-hydroxy-1-methoxymethyl-1,9-dioxo-16-methyl-2-nor-5-cis-13-trans-17-trans prostatriene |
| 646 | 1-trans-iodo-4-triphenylmethoxy-1,5-nonadiene | 2-[5-methoxyacetyl pent-2-cis-enyl] cyclopent-2-en-1-one | dl-16-hydroxy-1-methoxymethyl-1,9-dioxo-20-methyl-2-nor-5-cis-13-trans-17-trans prostatriene |
| 647 | 1-trans-iodo-4-methyl-4-trimethylsilyloxy-1,5-nonadiene | 2-[5-methoxyacetyl pent-2-cis-enyl] cyclopent-2-en-1-one | dl-16-hydroxy-1-methoxymethyl-1,9-dioxo-16-methyl-20-methyl-2-nor-5-cis-13-trans-17-trans prostatriene |
| 648 | 1-trans-iodo-4-triphenylmethoxy-1,5-decadiene | 2-[5-methoxyacetyl pent-2-cis-enyl] cyclopent-2-en-1-one | dl-16-hydroxy-1-methoxymethyl-1,9-dioxo-20-ethyl-2-nor-5-cis-13-trans-17-trans prostatriene |
| 649 | 1-trans-iodo-4-methyl-4-trimethylsilyloxy-1,5-decadiene | 2-[5-methoxyacetyl pent-2-cis-enyl] cyclopent-2-en-1-one | dl-16-hydroxy-1-methoxymethyl-1,9-dioxo-16-methyl-20-ethyl-2-nor-5-cis-13-trans-17-trans prostatriene |
| 650 | 1-trans-iodo-4-triphenylmethoxy-1,5-heptadiene | 2-[6-methoxyacetyl hex-2-cis-enyl] cyclopent-2-en-1-one | dl-16-hydroxy-1-methoxymethyl-1,9-dioxo-20-nor-5-cis-13-trans-17-trans prostatriene |
| 651 | 1-trans-iodo-4-methyl-4-trimethylsilyloxy-1,5-heptadiene | 2-[6-methoxyacetyl hex-2-cis-enyl] cyclopent-2-en-1-one | dl-16-hydroxy-1-methoxymethyl-1,9-dioxo-16-methyl-20-nor-5-cis-13-trans-17-trans prostatriene |
| 652 | 1-trans-iodo-4-triphenylmethoxy-1,5-octadiene | 2-[6-methoxyacetyl hex-2-cis-enyl] cyclopent-2-en-1-one | dl-16-hydroxy-1-methoxymethyl-1,9-dioxo-5-cis-13-trans-17-trans prostatriene |
| 653 | 1-trans-iodo-4-methyl-4-trimethylsilyloxy-1,5-octadiene | 2-[6-methoxyacetyl hex-2-cis-enyl] cyclopent-2-en-1-one | dl-16-hydroxy-1-methoxymethyl-1,9-dioxo-16-methyl-5-cis-13-trans-17-trans prostatriene |
| 654 | 1-trans-iodo-4-triphenylmethoxy-1,5-nonadiene | 2-[6-methoxyacetyl hex-2-cis-enyl] cyclopent-2-en-1-one | dl-16-hydroxy-1-methoxymethyl-1,9-dioxo-20-methyl-5-cis-13-trans-17-trans prostatriene |
| 655 | 1-trans-iodo-4-methyl-4-trimethylsilyloxy-1,5-nonadiene | 2-[6-methoxyacetyl hex-2-cis-enyl] cyclopent-2-en-1-one | dl-16-hydroxy-1-methoxymethyl-1,9-dioxo-16-methyl-20-methyl-5-cis-13-trans-17-trans prostatriene |
| 656 | 1-trans-iodo- | 2-[6-methoxyacetyl | dl-16-hydroxy-1-methoxymethyl-1,9-dioxo- |

TABLE III-continued

| | VINYL IODIDE | CYCLOPENTENONE | PRODUCT PROSTAGLANDIN OF THE PGE2 SERIES |
|---|---|---|---|
| 657 | 1-trans erthro-iodo-4-methyl-4-triphenylmethoxy-1,5-decadiene | [2-[6-methoxyacetyl cyclopent-2-en-1-one hex-2-cis-enyl] | 20-ethyl-5-cis-13-trans-17-trans prostatriene |
| 657 | 1-trans-iodo-4-methyl-4-trimethylsilyloxy-1,5-decadiene | [2-[6-methoxyacetyl cyclopent-2-en-1-one hex-2-cis-enyl] | dl-16-hydroxy-1-methoxymethyl-1,9-dioxo-16-methyl-20-ethyl-5-cis-13-trans-17-trans prostatriene |
| 658 | 1-trans-iodo-4-triphenylmethoxy-1,5-heptadiene | 2-[7-methoxyacetyl cyclopent-2-en-1-one hept-2-cis-enyl] | dl-16-hydroxy-1-methoxymethyl-1,9-dioxo-20-nor-2-homo-5-cis-13-trans-17-trans prostatriene |
| 659 | 1-trans-iodo-4-methyl-4-trimethylsilyloxy-1,5-heptadiene | 2-[7-methoxyacetyl cyclopent-2-en-1-one hept-2-cis-enyl] | dl-16-hydroxy-1-methoxymethyl-1,9-dioxo-16-methyl-20-nor-2-homo-5-cis-13-trans-17-trans prostatriene |
| 660 | 1-trans-iodo-4-triphenylmethoxy-1,5-octadiene | 2-[7-methoxyacetyl cyclopent-2-en-1-one hept-2-cis-enyl] | dl-16-hydroxy-1-methoxymethyl-1,9-dioxo-2-homo-5-cis-13-trans-17-trans prostatriene |
| 661 | 1-trans-iodo-4-methyl-4-trimethylsilyloxy-1,5-octadiene | 2-[7-methoxyacetyl cyclopent-2-en-1-one hept-2-cis-enyl] | dl-16-hydroxy-1-methoxymethyl-1,9-dioxo-16-methyl-2-homo-5-cis-13-trans-17-trans prostatriene |
| 662 | 1-trans-iodo-4-triphenylmethoxy-1,5-nonadiene | 2-[7-methoxyacetyl cyclopent-2-en-1-one hept-2-cis-enyl] | dl-16-hydroxy-1-methoxymethyl-1,9-dioxo-20-methyl-2-homo-5-cis-13-trans-17-trans prostatriene |
| 663 | 1-trans-iodo-4-methyl-4-trimethylsilyloxy-1,5-nonadiene | 2-[7-methoxyacetyl cyclopent-2-en-1-one hept-2-cis-enyl] | dl-16-hydroxy-1-methoxymethyl-1,9-dioxo-16-methyl-20-methyl-2-homo-5-cis-13-trans-17-trans prostatriene |
| 664 | 1-trans-iodo-4-triphenylmethoxy-1,5-decadiene | 2-[7-methoxyacetyl cyclopent-2-en-1-one hept-2-cis-enyl] | dl-16-hydroxy-1-methoxymethyl-1,9-dioxo-20-ethyl-2-homo-5-cis-13-trans-17-trans prostatriene |
| 665 | 1-trans-iodo-4-methyl-4-trimethylsilyloxy-1,5-decadiene | 2-[7-methoxyacetyl cyclopent-2-en-1-one hept-2-cis-enyl] | dl-16-hydroxy-1-methoxymethyl-1,9-dioxo-16-methyl-20-ethyl-2-homo-5-cis-13-trans-17-trans prostatriene |

| EXAMPLE | VINYL IODIDE | CYCLOPENTENONE | PRODUCT PROSTAGLANDIN OF THE PGE2 SERIES |
|---|---|---|---|
| 666 | 1-trans erthro-iodo-3,4-isopropylidenedioxy-1-heptene | 2-[5-methoxyacetyl pent-2-cis-enyl]-4-trimethylsiloxy cyclopent-2-en-1-one | dl erthro-11a,15a,16-trihydroxy-1-methoxymethyl-1,9-dioxo-20-nor-2-nor-5-cis-13-trans prostadiene |
| 667 | 1-trans erthro-iodo-3,4-isopropylidenedioxy-1-octene | 2-[5-methoxyacetyl pent-2-cis-enyl]-4-trimethylsiloxy cyclopent-2-en-1-one | dl erthro-11a,15a,16-trihydroxy-1-methoxymethyl-1,9-dioxo-2-nor-5-cis-13-trans prostadiene |
| 668 | 1-trans erthro-iodo-3,4-isopropylidenedioxy-1-nonene | 2-[5-methoxyacetyl pent-2-cis-enyl]-4-trimethylsiloxy cyclopent-2-en-1-one | dl erthro-11a,15a,16-trihydroxy-1-methoxymethyl-1,9-dioxo-20-methyl-2-nor-5-cis-13-trans prostadiene |
| 669 | 1-trans erthro-iodo-3,4-isopropylidenedioxy-1-decene | 2-[5-methoxyacetyl pent-2-cis-enyl]-4-trimethylsiloxy cyclopent-2-en-1-one | dl erthro-11a,15a,16-trihydroxy-1-methoxymethyl-1,9-dioxo-20-ethyl-2-nor-5-cis-13-trans prostadiene |
| 670 | 1-trans erthro-iodo-3,4-isopropylidenedioxy-1-heptene | 2-[6-methoxyacetyl hex-2-cis-enyl]-4-trimethylsiloxy cyclopent-2-en-1-one | dl erthro-11a,15a,16-trihydroxy-1-methoxymethyl-1,9-dioxo-20-nor-5-cis-13-trans prostadiene |
| 671 | 1-trans erthro-iodo-3,4-isopropylidenedioxy-1-octene | 2-[6-methoxyacetyl hex-2-cis-enyl]-4-trimethylsiloxy cyclopent-2-en-1-one | dl erthro-11a,15a,16-trihydroxy-1-methoxymethyl-1,9-dioxo-5-cis-13-trans prostadiene |
| 672 | 1-trans erthro-iodo-3,4-isopropylidenedioxy-1-nonene | 2-[6-methoxyacetyl hex-2-cis-enyl]-4-trimethylsiloxy cyclopent-2-en-1-one | dl erthro-11a,15a,16-trihydroxy-1-methoxymethyl-1,9-dioxo-20-methyl-5-cis-13-trans prostadiene |
| 673 | 1-trans erthro-iodo- | 2-[6-methoxyacetyl | dl erthro-11a,15a,16-trihydroxy-1-methoxymethyl-1,9-dioxo- |

TABLE III-continued

| | VINYL IODIDE | CYCLOPENTENONE | PRODUCT |
|---|---|---|---|
| | 3,4-isopropylidenedioxy-1-decene | hex-2-cis-enyl]-4-trimethylsiloxy cyclopent-2-en-1-one | 20-ethyl-5-cis-13-trans prostadiene |
| 674 | 1-trans erthro-iodo-3,4-isopropylidenedioxy-1-heptene | 2-[7-methoxyacetyl hept-2-cis-enyl]-4-trimethylsiloxy cyclopent-2-en-1-one | dl erthro-11a,15a,16-trihydroxy-1-methoxymethyl-1,9-dioxo-20-nor-2-homo-5-cis-13-trans prostadiene |
| 675 | 1-trans erthro-iodo-3,4-isopropylidenedioxy-1-octene | 2-[7-methoxyacetyl hept-2-cis-enyl] -4-trimethylsiloxy cyclopent-2-en-1-one | dl erthro-11a,15a,16-trihydroxy-1-methoxymethyl-1,9-dioxo-2-homo-5-cis-13-trans prostadiene |
| 676 | 1-trans erthro-iodo-3,4-isopropylidenedioxy-1-nonene | 2-[7-methoxyacetyl hept-2-cis-enyl]-4-trimethylsiloxy cyclopent-2-en-1-one | dl erthro-11a,15a,16-trihydroxy-1-methoxymethyl-1,9-dioxo-20-methyl-2-homo-5-cis-13-trans prostadiene |
| 677 | 1-trans erthro-iodo-3,4-isopropylidenedioxy-1-decene | 2-[7-methoxyacetyl hept-2-cis-enyl]-4-trimethylsiloxy cyclopent-2-en-1-one | dl erthro-11a,15a,16-trihydroxy-1-methoxymethyl-1,9-dioxo-20-ethyl-2-homo-5-cis-13-trans prostadiene |
| 678 | 1-trans erthro-iodo-3,4-isopropylidenedioxy-1-heptene | 2-[6-methoxyacetyl hex-2-cis-enyl]-4R-trimethylsiloxy cyclopent-2-en-1-one | nat erthro-11a,15a,16-trihydroxy-1-methoxymethyl-1,9-dioxo-20-nor-5-cis-13-trans prostadiene |
| 679 | 1-trans erthro-iodo-3,4-isopropylidenedioxy-1-octene | 2-[6-methoxyacetyl hex-2-cis-enyl]-4R-trimethylsiloxy cyclopent-2-en-1-one | nat erthro-11a,15a,16-trihydroxy-1-methoxymethyl-1,9-dioxo-5-cis-13-trans prostadiene |
| 680 | 1-trans erthro-iodo-3,4-isopropylidenedioxy-1-nonene | 2-[6-methoxyacetyl hex-2-cis-enyl]-4R-trimethylsiloxy cyclopent-2-en-1-one | nat erthro-11a,15a,16-trihydroxy-1-methoxymethyl-1,9-dioxo-20-methyl-5-cis-13-trans prostadiene |
| 681 | 1-trans erthro-iodo-3,4-isopropylidenedioxy-1-decene | 2-[6-methoxyacetyl hex-2-cis-enyl]-4R-trimethylsiloxy cyclopent-2-en-1-one | nat erthro-11a,15a,16-trihydroxy-1-methoxymethyl-1,9-dioxo-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 682 | 1-trans erthro-iodo-3,4-isopropylidenedioxy-1-heptene | 2-[5-methoxyacetyl pent-2-cis-enyl] cyclopent-2-en-1-one | dl erthro-15a,16-dihydroxy-1-methoxymethyl-1,9-dioxo-20-nor-2-nor-5-cis-13-trans prostadiene |
| 683 | 1-trans erthro-iodo-3,4-isopropylidenedioxy-1-octene | 2-[5-methoxyacetyl pent-2-cis-enyl] cyclopent-2-en-1-one | dl erthro-15a,16-dihydroxy-1-methoxymethyl-1,9-dioxo-2-nor-5-cis-13-trans prostadiene |
| 684 | 1-trans erthro-iodo-3,4-isopropylidenedioxy-1-nonene | 2-[5-methoxyacetyl pent-2-cis-enyl] cyclopent-2-en-1-one | dl erthro-15a,16-dihydroxy-1-methoxymethyl-1,9-dioxo-20-methyl-2-nor-5-cis-13-trans prostadiene |
| 685 | 1-trans erthro-iodo-3,4-isopropylidenedioxy-1-decene | 2-[5-methoxyacetyl pent-2-cis-enyl] cyclopent-2-en-1-one | dl erthro-15a,16-dihydroxy-1-methoxymethyl-1,9-dioxo-20-ethyl-2-nor-5-cis-13-trans prostadiene |
| 686 | 1-trans erthro-iodo-3,4-isopropylidenedioxy-1-heptene | 2-[6-methoxyacetyl hex-2-cis-enyl] cyclopent-2-en-1-one | dl erthro-15a,16-dihydroxy-1-methoxymethyl-1,9-dioxo-20-nor-5-cis-13-trans prostadiene |
| 687 | 1-trans erthro-iodo-3,4-isopropylidenedioxy-1-octene | 2-[6-methoxyacetyl hex-2-cis-enyl] cyclopent-2-en-1-one | dl erthro-15a,16-dihydroxy-1-methoxymethyl-1,9-dioxo-5-cis-13-trans prostadiene |
| 688 | 1-trans erthro-iodo-3,4-isopropylidenedioxy-1-nonene | 2-[6-methoxyacetyl hex-2-cis-enyl] cyclopent-2-en-1-one | dl erthro-15a,16-dihydroxy-1-methoxymethyl-1,9-dioxo-20-methyl-5-cis-13-trans prostadiene |
| 689 | 1-trans erthro-iodo-3,4-isopropylidenedioxy-1-decene | 2-[6-methoxyacetyl hex-2-cis-enyl] cyclopent-2-en-1-one | dl erthro-15a,16-dihydroxy-1-methoxymethyl-1,9-dioxo-20-ethyl-5-cis-13-trans prostadiene |
| 690 | 1-trans erthro-iodo- | 2-[7-methoxyacetyl | dl erthro-15a,16-dihydroxy-1-methoxymethyl-1,9-dioxo- |

TABLE III-continued

| EXAMPLE | VINYL IODIDE | CYCLOPENTENONE | PRODUCT PROSTAGLANDIN OF THE PGE2 SERIES |
|---|---|---|---|
| | 1-trans erthro-iodo-3,4-isopropylidenedioxy-1-heptene | hept-2-cis-enyl]cyclopent-2-en-1-one | 20-nor-2-homo-5-cis-13-trans prostadiene |
| 691 | 1-trans erthro-iodo-3,4-isopropylidenedioxy-1-octene | 2-[7-methoxyacetyl hept-2-cis-enyl]cyclopent-2-en-1-one | dl erthro-15a,16-dihydroxy-1-methoxymethyl-1,9-dioxo-2-homo-5-cis-13-trans prostadiene |
| 692 | 1-trans erthro-iodo-3,4-isopropylidenedioxy-1-nonene | 2-[7-methoxyacetyl hept-2-cis-enyl]cyclopent-2-en-1-one | dl erthro-15a,16-dihydroxy-1-methoxymethyl-1,9-dioxo-20-methyl-5-cis-13-trans prostadiene |
| 693 | 1-trans erthro-iodo-3,4-isopropylidenedioxy-1-decene | 2-[7-methoxyacetyl hept-2-cis-enyl]cyclopent-2-en-1-one | dl erthro-15a,16-dihydroxy-1-methoxymethyl-1,9-dioxo-20-ethyl-2-homo-5-cis-13-trans prostadiene |
| 694 | 1-trans threo-iodo-3,4-isopropylidenedioxy-1-heptene | 2-[5-methoxyacetyl pent-2-cis-enyl]-4-trimethylsiloxy cyclopent-2-en-1-one | dl threo-11a,15a,16-trihydroxy-1-methoxymethyl-1,9-dioxo-20-nor-2-nor-5-cis-13-trans prostadiene |
| 695 | 1-trans threo-iodo-3,4-isopropylidenedioxy-1-octene | 2-[5-methoxyacetyl pent-2-cis-enyl]-4-trimethylsiloxy cyclopent-2-en-1-one | dl threo-11a,15a,16-trihydroxy-1-methoxymethyl-1,9-dioxo-2-nor-5-cis-13-trans prostadiene |
| 696 | 1-trans threo-iodo-3,4-isopropylidenedioxy-1-nonene | 2-[5-methoxyacetyl pent-2-cis-enyl]-4-trimethylsiloxy cyclopent-2-en-1-one | dl threo-11a,15a,16-trihydroxy-1-methoxymethyl-1,9-dioxo-20-methyl-2-nor-5-cis-13-trans prostadiene |
| 697 | 1-trans threo-iodo-3,4-isopropylidenedioxy-1-decene | 2-[5-methoxyacetyl pent-2-cis-enyl]-4-trimethylsiloxy cyclopent-2-en-1-one | dl threo-11a,15a,16-trihydroxy-1-methoxymethyl-1,9-dioxo-20-ethyl-2-nor-5-cis-13-trans prostadiene |
| 698 | 1-trans threo-iodo-3,4-isopropylidenedioxy-1-heptene | 2-[6-methoxyacetyl hex-2-cis-enyl]-4-trimethylsiloxy cyclopent-2-en-1-one | dl threo-11a,15a,16-trihydroxy-1-methoxymethyl-1,9-dioxo-20-nor-5-cis-13-trans prostadiene |
| 699 | 1-trans threo-iodo-3,4-isopropylidenedioxy-1-octene | 2-[6-methoxyacetyl hex-2-cis-enyl]-4-trimethylsiloxy cyclopent-2-en-1-one | dl threo-11a,15a,16-trihydroxy-1-methoxymethyl-1,9-dioxo-5-cis-13-trans prostadiene |
| 700 | 1-trans threo-iodo-3,4-isopropylidenedioxy-1-nonene | 2-[6-methoxyacetyl hex-2-cis-enyl]-4-trimethylsiloxy cyclopent-2-en-1-one | dl threo-11a,15a,16-trihydroxy-1-methoxymethyl-1,9-dioxo-20-methyl-5-cis-13-trans prostadiene |
| 701 | 1-trans threo-iodo-3,4-isopropylidenedioxy-1-decene | 2-[6-methoxyacetyl hex-2-cis-enyl]-4-trimethylsiloxy cyclopent-2-en-1-one | dl threo-11a,15a,16-trihydroxy-1-methoxymethyl-1,9-dioxo-20-ethyl-5-cis-13-trans prostadiene |
| 702 | 1-trans threo-iodo-3,4-isopropylidenedioxy-1-heptene | 2-[7-methoxyacetyl hept-2-cis-enyl]-4-trimethylsiloxy cyclopent-2-en-1-one | dl threo-11a,15a,16-trihydroxy-1-methoxymethyl-1,9-dioxo-20-nor-2-homo-5-cis-13-trans prostadiene |
| 703 | 1-trans threo-iodo-3,4-isopropylidenedioxy-1-octene | 2-[7-methoxyacetyl hept-2-cis-enyl]-4-trimethylsiloxy cyclopent-2-en-1-one | dl threo-11a,15a,16-trihydroxy-1-methoxymethyl-1,9-dioxo-2-homo-5-cis-13-trans prostadiene |
| 704 | 1-trans threo-iodo-3,4-isopropylidenedioxy-1-nonene | 2-[7-methoxyacetyl hept-2-cis-enyl]-4-trimethylsiloxy cyclopent-2-en-1-one | dl threo-11a,15a,16-trihydroxy-1-methoxymethyl-1,9-dioxo-20-methyl-2-homo-5-cis-13-trans prostadiene |
| 705 | 1-trans threo-iodo-3,4-isopropylidenedioxy-1-decene | 2-[7-methoxyacetyl hept-2-cis-enyl]-4-trimethylsiloxy cyclopent-2-en-1-one | dl threo-11a,15a,16-trihydroxy-1-methoxymethyl-1,9-dioxo-2-ethyl-2-homo-5-cis-13-trans prostadiene |
| 706 | 1-trans threo-iodo-3,4-isopropylidenedioxy-1-heptene | 2-[6-methoxyacetyl hex-2-cis-enyl]-4R-trimethylsiloxy cyclopent-2-en-1-one | nat threo-11a,15a,16-trihydroxy-1-methoxymethyl-1,9-dioxo-20-nor-5-cis-13-trans prostadiene |
| 707 | 1-trans threo-iodo- | 2-[6-methoxyacetyl | nat threo-11a,15a,16-trihydroxy-1-methoxymethyl-1,9-dioxo- |

TABLE III-continued

| EXAMPLE | VINYL IODIDE | CYCLOPENTENONE | PRODUCT PROSTAGLANDIN OF THE 11-DEOXY PGE2 SERIES |
|---|---|---|---|
| | 3,4-isopropylidenedioxy-1-octene | hex-2-cis-enyl]-4R-trimethylsiloxy cyclopent-2-en-1-one | 5-cis-13-trans prostadiene |
| 708 | 1-trans threo-iodo-3,4-isopropylidenedioxy-1-nonene | hex-2-cis-enyl]-4R-trimethylsiloxy cyclopent-2-en-1-one 2-[6-methoxyacetyl | nat threo-11a,15a,16-trihydroxy-1-methoxymethyl-1,9-dioxo-20-methyl-5-cis-13-trans prostadiene |
| 709 | 1-trans threo-iodo-3,4-isopropylidenedioxy-1-decene | 2-[6-methoxyacetyl hex-2-cis-enyl]-4R-trimethylsiloxy cyclopent-2-en-1-one | nat threo-11a,15a,16-trihydroxy-1-methoxymethyl-1,9-dioxo-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 710 | 1-trans threo-iodo-3,4-isopropylidenedioxy-1-heptene | 2-[5-methoxyacetyl pent-2-cis-enyl] cyclopent-2-en-1-one | dl threo-15a,16-dihydroxy-1-methoxymethyl-1,9-dioxo-20-nor-2-nor-5-cis-13-trans prostadiene |
| 711 | 1-trans threo-iodo-3,4-isopropylidenedioxy-1-octene | 2-[5-methoxyacetyl pent-2-cis-enyl] cyclopent-2-en-1-one | dl threo-15a,16-dihydroxy-1-methoxymethyl-1,9-dioxo-2-nor-5-cis-13-trans prostadiene |
| 712 | 1-trans threo-iodo-3,4-isopropylidenedioxy-1-nonene | 2-[5-methoxyacetyl pent-2-cis-enyl] cyclopent-2-en-1-one | dl threo-15a,16-dihydroxy-1-methoxymethyl-1,9-dioxo-20-methyl-2-nor-5-cis-13-trans prostadiene |
| 713 | 1-trans threo-iodo-3,4-isopropylidenedioxy-1-decene | 2-[5-methoxyacetyl pent-2-cis-enyl] cyclopent-2-en-1-one | dl threo-15a,16-dihydroxy-1-methoxymethyl-1,9-dioxo-20-ethyl-2-nor-5-cis-13-trans prostadiene |
| 714 | 1-trans threo-iodo-3,4-isopropylidenedioxy-1-heptene | 2-[6-methoxyacetyl hex-2-cis-enyl] cyclopent-2-en-1-one | dl threo-15a,16-dihydroxy-1-methoxymethyl-1,9-dioxo-20-nor-5-cis-13-trans prostadiene |
| 715 | 1-trans threo-iodo-3,4-isopropylidenedioxy-1-octene | 2-[6-methoxyacetyl hex-2-cis-enyl] cyclopent-2-en-1-one | dl threo-15a,16-dihydroxy-1-methoxymethyl-1,9-dioxo-5-cis-13-trans prostadiene |
| 716 | 1-trans threo-iodo-3,4-isopropylidenedioxy-1-nonene | 2-[6-methoxyacetyl hex-2-cis-enyl] cyclopent-2-en-1-one | dl threo-15a,16-dihydroxy-1-methoxymethyl-1,9-dioxo-20-methyl-5-cis-13-trans prostadiene |
| 717 | 1-trans threo-iodo-3,4-isopropylidenedioxy-1-decene | 2-[6-methoxyacetyl hex-2-cis-enyl] cyclopent-2-en-1-one | dl threo-15a,16-dihydroxy-1-methoxymethyl-1,9-dioxo-20-ethyl-5-cis-13-trans prostadiene |
| 718 | 1-trans threo-iodo-3,4-isopropylidenedioxy-1-heptene | 2-[7-methoxyacetyl hept-2-cis-enyl] cyclopent-2-en-1-one | dl threo-15a,16-dihydroxy-1-methoxymethyl-1,9-dioxo-20-nor-2-homo-5-cis-13-trans prostadiene |
| 719 | 1-trans threo-iodo-3,4-isopropylidenedioxy-1-octene | 2-[7-methoxyacetyl hept-2-cis-enyl] cyclopent-2-en-1-one | dl threo-15a,16-dihydroxy-1-methoxymethyl-1,9-dioxo-2-homo-5-cis-13-trans prostadiene |
| 720 | 1-trans threo-iodo-3,4-isopropylidenedioxy-1-nonene | 2-[7-methoxyacetyl hept-2-cis-enyl] cyclopent-2-en-1-one | dl threo-15a,16-dihydroxy-1-methoxymethyl-1,9-dioxo-20-methyl-2-homo-5-cis-13-trans prostadiene |
| 721 | 1-trans threo-iodo-3,4-isopropylidenedioxy-1-decene | 2-[7-methoxyacetyl hept-2-cis-enyl] cyclopent-2-en-1-one | dl-threo-15a,16-dihydroxy-1-methoxymethyl-1,9-dioxo-20-ethyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 722 | 1-trans erthro-iodo-4-methoxy 3-trimethylsilyloxy-1-heptene | 2-[5-methoxyacetyl pent-2-cis-enyl]-4-trimethylsiloxy cyclopent-2-en-1-one | dl ertho-11a,15a-dihydroxy-1-methoxymethyl-1,9-dioxo-16-methoxy-20-nor-2-nor-5-cis-13-trans prostadiene |
| 723 | 1-trans erthro-iodo-4-methoxy 3-trimethylsilyloxy-1-octene | 2-[5-methoxyacetyl pent-2-cis-enyl]-4-trimethylsiloxy | dl erthro-11a,15a-dihydroxy-1-methoxymethyl-1,9-dioxo-16-methoxy-2-nor-5-cis-13-trans prostadiene |

TABLE III-continued

| EXAMPLE | VINYL IODIDE | CYCLOPENTENONE | PRODUCT |
|---|---|---|---|
| 724 | 1-trans erthro-iodo-4-methoxy 3-trimethylsilyloxy-1-nonene | cyclopent-2-en-1-one 2-[5-methoxyacetyl pent-2-cis-enyl]-4-trimethylsilyloxy cyclopent-2-en-1-one | dl erthro-11a,15a-dihydroxy-1-methoxymethyl-1,9-dioxo-16-methoxy-20-methyl-2-nor-5-cis-13-trans prostadiene |
| 725 | 1-trans erthro-iodo-4-methoxy 3-trimethylsilyloxy-1-decene | 2-[5-methoxyacetyl pent-2-cis-enyl]-4-trimethylsilyloxy cyclopent-2-en-1-one | dl erthro-11a,15a-dihydroxy-1-methoxymethyl-1,9-dioxo-16-methoxy-20-ethyl-2-nor-5-cis-13-trans prostadiene |
| 726 | 1-trans erthro-iodo-4-methoxy 3-trimethylsilyloxy-1-heptene | 2-[6-methoxyacetyl hex-2-cis-enyl]-4-trimethylsilyloxy cyclopent-2-en-1-one | dl erthro-11a,15a-dihydroxy-1-methoxymethyl-1,9-dioxo-16-methoxy-20-nor-5-cis-13-trans prostadiene |
| 727 | 1-trans erthro-iodo-4-methoxy 3-trimethylsilyloxy-1-octene | 2-[6-methoxyacetyl hex-2-cis-enyl]-4-trimethylsilyloxy cyclopent-2-en-1-one | dl erthro-11a,15a-dihydroxy-1-methoxymethyl-1,9-dioxo-16-methoxy-5-cis-13-trans prostadiene |
| 728 | 1-trans erthro-iodo-4-methoxy 3-trimethylsilyloxy-1-nonene | 2-[6-methoxyacetyl hex-2-cis-enyl]-4-trimethylsilyloxy cyclopent-2-en-1-one | dl erthro-11a,15a-dihydroxy-1-methoxymethyl-1,9-dioxo-16-methoxy-20-methyl-5-cis-13-trans prostadiene |
| 729 | 1-trans erthro-iodo-4-methoxy 3-trimethylsilyloxy-1-decene | 2-[6-methoxyacetyl hex-2-cis-enyl]-4-trimethylsilyloxy cyclopent-2-en-1-one | dl erthro-11a,15a-dihydroxy-1-methoxymethyl-1,9-dioxo-16-methoxy-20-ethyl-5-cis-13-trans prostadiene |
| 730 | 1-trans erthro-iodo-4-methoxy 3-trimethylsilyloxy-1-heptene | 2-[7-methoxyacetyl hept-2-cis-enyl]-4-trimethylsilyloxy cyclopent-2-en-1-one | dl erthro-11a,15a-dihydroxy-1-methoxymethyl-1,9-dioxo-16-methoxy-20-nor-2-homo-5-cis-13-trans prostadiene |
| 731 | 1-trans erthro-iodo-4-methoxy 3-trimethylsilyloxy-1-octene | 2-[7-methoxyacetyl hept-2-cis-enyl]-4-trimethylsilyloxy cyclopent-2-en-1-one | dl erthro-11a,15a-dihydroxy-1-methoxymethyl-1,9-dioxo-16-methoxy-2-homo-5-cis-13-trans prostadiene |
| 732 | 1-trans erthro-iodo-4-methoxy 3-trimethylsilyloxy-1-nonene | 2-[7-methoxyacetyl hept-2-cis-enyl]-4-trimethylsilyloxy cyclopent-2-en-1-one | dl erthro-11a,15a-dihydroxy-1-methoxymethyl-1,9-dioxo-16-methoxy-20-methyl-2-homo-5-cis-13-trans prostadiene |
| 733 | 1-trans erthro-iodo-4-methoxy 3-trimethylsilyloxy-1-decene | 2-[7-methoxyacetyl hept-2-cis-enyl]-4-trimethylsilyloxy cyclopent-2-en-1-one | dl erthro-11a,15a-dihydroxy-1-methoxymethyl-1,9-dioxo-16-methoxy-20-ethyl-2-homo-5-cis-13-trans prostadiene |
| 734 | 1-trans erthro-iodo-4-methoxy 3-trimethylsilyloxy-1-heptene | 2-[6-methoxyacetyl hex-2-cis-enyl]-4R-trimethylsilyloxy cyclopent-2-en-1-one | nat erthro-11a,15a-dihydroxy-1-methoxymethyl-1,9-dioxo-16-methoxy-20-nor-5-cis-13-trans prostadiene |
| 735 | 1-trans erthro-iodo-4-methoxy 3-trimethylsilyloxy-1-octene | 2-[6-methoxyacetyl hex-2-cis-enyl]-4R-trimethylsilyloxy cyclopent-2-en-1-one | nat erthro-11a,15a-dihydroxy-1-methoxymethyl-1,9-dioxo-16-methoxy-5-cis-13-trans prostadiene |
| 736 | 1-trans erthro-iodo-4-methoxy 3-trimethylsilyloxy-1-nonene | 2-[6-methoxyacetyl hex-2-cis-enyl]-4R-trimethylsilyloxy cyclopent-2-en-1-one | nat erthro-11a,15a-dihydroxy-1-methoxymethyl-1,9-dioxo-16-methoxy-20-methyl-5-cis-13-trans prostadiene |
| 737 | 1-trans erthro-iodo-4-methoxy 3-trimethylsilyloxy-1-decene | 2-[6-methoxyacetyl hex-2-cis-enyl]-4R-trimethylsilyloxy cyclopent-2-en-1-one | nat erthro-11a,15a-dihydroxy-1-methoxymethyl-1,9-dioxo-16-methoxy-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 738 | 1-trans erthro-iodo-4-methoxy 3-trimethylsilyloxy-1-heptene | 2-[5-methoxyacetyl pent-2-cis-enyl] cyclopent-2-en-1-one | dl erthro-15a-hydroxy-1-methoxymethyl-1,9-dioxo-16-methoxy-20-nor-2-nor-5-cis-13-trans prostadiene |
| 739 | 1-trans erthro-iodo-4-methoxy 3-trimethylsilyloxy-1-octene | 2-[5-methoxyacetyl pent-2-cis-enyl] cyclopent-2-en-1-one | dl erthro-15a-hydroxy-1-methoxymethyl-1,9-dioxo-16-methoxy-2-nor-5-cis-13-trans prostadiene |
| 740 | 1-trans erthro-iodo-4-methoxy 3-trimethylsilyloxy-1-nonene | 2-[5-methoxyacetyl pent-2-cis-enyl] cyclopent-2-en-1-one | dl erthro-15a-hydroxy-1-methoxymethyl-1,9-dioxo-16-methoxy-20-methyl-2-nor-5-cis-13-trans prostadiene |

TABLE III-continued

| | | | |
|---|---|---|---|
| 741 | 1-trans erthro-iodo-4-methoxy 3-trimethylsilyloxy-1-decene | cyclopent-2-en-1-one 2-[5-methoxyacetyl pent-2-cis-enyl] | dl erthro-15a-hydroxy-1-methoxymethyl-1,9-dioxo-16-methoxy-20-ethyl-2-nor-5-cis-13-trans prostadiene |
| 742 | 1-trans erthro-iodo-4-methoxy 3-trimethylsilyloxy-1-heptene | cyclopent-2-en-1-one 2-[6-methoxyacetyl hex-2-cis-enyl]- | dl erthro-15a-hydroxy-1-methoxymethyl-1,9-dioxo-16-methoxy-20-nor-5-cis-13-trans prostadiene |
| 743 | 1-trans erthro-iodo-4-methoxy 3-trimethylsilyloxy-1-octene | cyclopent-2-en-1-one 2-[6-methoxyacetyl hex-2-cis-enyl]- | dl erthro-15a-hydroxy-1-methoxymethyl-1,9-dioxo-16-methoxy-5-cis-13-trans prostadiene |
| 744 | 1-trans erthro-iodo-4-methoxy 3-trimethylsilyloxy-1-nonene | cyclopent-2-en-1-one 2-[6-methoxyacetyl hex-2-cis-enyl]- | dl erthro-15a-hydroxy-1-methoxymethyl-1,9-dioxo-16-methoxy-20-methyl-5-cis-13-trans prostadiene |
| 745 | 1-trans erthro-iodo-4-methoxy 3-trimethylsilyloxy-1-decene | cyclopent-2-en-1-one 2-[6-methoxyacetyl hex-2-cis-enyl]- | dl erthro-15a-hydroxy-1-methoxymethyl-1,9-dioxo-16-methoxy-20-ethyl-5-cis-13-trans prostadiene |
| 746 | 1-trans erthro-iodo-4-methoxy 3-trimethylsilyloxy-1-heptene | cyclopent-2-en-1-one 2-[7-methoxyacetyl hept-2-cis-enyl] | dl erthro-15a-hydroxy-1-methoxymethyl-1,9-dioxo-16-methoxy-20-nor-2-homo-5-cis-13-trans prostadiene |
| 747 | 1-trans erthro-iodo-4-methoxy 3-trimethylsilyloxy-1-octene | cyclopent-2-en-1-one 2-[7-methoxyacetyl hept-2-cis-enyl] | dl erthro-15a-hydroxy-1-methoxymethyl-1,9-dioxo-16-methoxy-2-homo-5-cis-13-trans prostadiene |
| 748 | 1-trans erthro-iodo-4-methoxy 3-trimethylsilyloxy-1-nonene | cyclopent-2-en-1-one 2-[7-methoxyacetyl hept-2-cis-enyl] | dl erthro-15a-hydroxy-1-methoxymethyl-1,9-dioxo-16-methoxy-20-methyl-2-homo-5-cis-13-trans prostadiene |
| 749 | 1-trans erthro-iodo-4-methoxy 3-trimethylsilyloxy-1-decene | cyclopent-2-en-1-one 2-[7-methoxyacetyl hept-2-cis-enyl] cyclopent-2-en-1-one | dl erthro-15a-hydroxy-1-methoxymethyl-1,9-dioxo-16-methoxy-20-ethyl-2-homo-5-cis-13-trans prostadiene |

TABLE IV

| EXAMPLE | VINYL IODIDE | CYCLOPENTENONE | PRODUCT PROSTAGLANDIN OF THE PGE2 SERIES |
|---|---|---|---|
| 1 | 1-trans-iodo-3-triphenylmethoxy-1-heptene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-20-nor-2-nor-5-cis-13-trans prostadiene |
| 2 | 1-trans-iodo-3-methyl-3-trimethylsiloxy-1-heptene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-15-methyl-20-nor-2-nor-5-cis-13-trans prostadiene |
| 3 | 1-trans-iodo-4,4-dimethyl-3-trimethylsilyloxy-1-heptene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-dimethyl-20-nor-2-nor-5-cis-13-trans prostadiene |
| 4 | 1-trans-iodo-5,5-dimethyl-3-triphenylmethoxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-17,17-dimethyl-2-nor-5-cis-13-trans prostadiene |
| 5 | 1-trans-iodo-4-methyl-3-triphenylmethoxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-methyl-2-nor-5-cis-13-trans prostadiene |
| 6 | 1-trans-iodo-4,4-trimethylene-3-trimethylsilyloxy-1-heptene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 7 | 1-trans-tri-n-butylstannyl-3-vinyl-3-trimethylsilyloxy-1-heptene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-15-vinyl-20-nor-2-nor-5-cis-13-trans prostadiene |
| 8 | 1-trans-tri-n-butylstannyl-4-phenoxy-3-trimethylsilyloxy-1-butene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-phenoxy-2-nor-17-20-tetranor-5-cis-13-trans prostadiene |
| 9 | 1-trans-tri-n-butylstannyl-4-(p-fluorophenoxy)-3-triethylsilyloxy-1-butene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-(p-fluorophenoxy)-2-nor-17-20-tetranor-5-cis-13-trans prostadiene |
| 10 | 1-trans-tri-n-butylstannyl-4-(m-chlorophenoxy)-3-triethylsilyloxy-1-butene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-(m-chlorophenoxy)-2-nor-17-20-tetranor-5-cis-13-trans prostadiene |
| 11 | 1-trans-tri-n-butylstannyl-4-(m-trifluoromethylphenoxy)-3-triethylsilyloxy-1-butene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-(m-trifluoromethylphenoxy)-2-nor-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 12 | 1-trans-iodo-5-phenyl-3-triethylsilyloxy-1-pentene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-17-phenyl-2-nor-18-20-trinor-5-cis-13-trans prostadiene |
| 13 | 1-trans-iodo-4,4-dimethyl-5-phenyl-3-triethylsilyloxy-1-pentene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-dimethyl-17-phenyl-2-nor-18-20-trinor-5-cis-13-trans prostadiene |
| 14 | 1-trans-iodo-4-cyclopentyl-3-triphenylmethoxy-1-butene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-cyclopentyl-2-nor-17-20-tetranor-5-cis-13-trans prostadiene |
| 15 | 1-trans-iodo-4-cyclohexyl-3-triphenylmethoxy-1-butene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16-cyclohexyl-2-nor-17-20-tetranor-5-cis-13-trans prostadiene |
| 16 | 1-trans-iodo-4-triphenylmethoxy-1-heptene | 2-[5-methylthiaacetyl pent-2-cis-enyl]-4-trimethylsiloxy cyclopent-2-en-1-one | dl-11a,16-dihydoxy-1-methylthiamethyl-1,9-dioxo-20-nor-2-nor-5-cis-13-trans prostadiene |

TABLE IV-continued

| EXAMPLE | VINYL TIN | CYCLOPENTENONE | PRODUCT PROSTAGLANDIN OF THE PGE2 SERIES |
|---|---|---|---|
| 17 | 1-trans-tri-n-butylstannyl-4-methyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-20-nor-2-nor-5-cis-13-trans prostadiene |
| 18 | 1-trans-tri-n-butylstannyl-4-ethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-ethyl-2-nor-5-cis-13-trans prostadiene |
| 19 | 1-trans-tri-n-butylstannyl-5-methyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 20 | 1-trans-iodo-5,5-dimethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17,17-dimethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 21 | 1-trans-tri-n-butylstannyl-4-vinyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-vinyl-20-nor-2-nor-5-cis-13-trans prostadiene |
| 22 | 1-trans-tri-n-butylstannyl-4-cyclopropyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-cyclopropyl-2-nor-5-cis-13-trans prostadiene |
| 23 | 1-trans-tri-n-butylstannyl-4-trimethylsilylethynyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-ethynyl-20-nor-2-nor-5-cis-13-trans prostadiene |
| 24 | 1-trans-tri-n-butylstannyl-5-methylene-4-triethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methylene-20-nor-2-nor-5-cis-13-trans prostadiene |
| 25 | 1-trans-tri-n-butylstannyl-4-methyl-5-methylene-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-17-methylene-20-nor-2-nor-5-cis-13-trans prostadiene |
| 26 | 1-trans-tri-n-butylstannyl-4-dimethoxymethyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-formyl-20-nor-2-nor-5-cis-13-trans prostadiene |
| 27 | 1-trans-tri-n-butylstannyl-4-fluoromethyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-fluoromethyl-20-nor-2-nor-5-cis-13-trans prostadiene |
| 28 | 1-trans-tri-n-butylstannyl-4-difluoromethyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-difluoromethyl-20-nor-2-nor-5-cis-13-trans prostadiene |
| 29 | 1-trans-tri-n-butylstannyl-4-trifluoromethyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-trifluoromethyl-20-nor-2-nor-5-cis-13-trans prostadiene |
| 30 | 1-trans-tri-n-butylstannyl-4-chloromethyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-chloromethyl-20-nor-2-nor-5-cis-13-trans prostadiene |
| 31 | 1-trans-tri-n-butylstannyl-4-trimethylsilyloxymethyl-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-hydroxymethyl-20-nor-2-nor-5-cos-13-trans prostadiene |

TABLE IV-continued

| EXAMPLE | VINYL IODIDE | CYCLOPENTENONE | PRODUCT PROSTAGLANDIN OF THE PGE2 SERIES |
|---|---|---|---|
| 32 | 1-trans-iodo-4-methyl-7-chloro-4-trimethylsilyloxy-1-heptene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-19-chloro-2-nor-20-nor-5-cis-13-trans prostadiene |
| 33 | 1-trans-iodo-3-triphenylmethoxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-2-nor-5-cis-13-trans prostadiene |
| 34 | 1-trans-iodo-3-methyl-3-trimethylsilyloxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-15-methyl-2-nor-5-cis-13-trans prostadiene |
| 35 | 1-trans-iodo-4,4-dimethyl-3-trimethylsilyloxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-dimethyl-2-nor-5-cis-13-trans prostadiene |
| 36 | 1-trans-iodo-4,4-trimethylene-3-trimethylsilyloxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-trimethylene-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 37 | 1-trans-tri-n-butylstannyl-3-vinyl-3-trimethylsilyloxy-1-octene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-15-vinyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 38 | 1-trans-iodo-4-triphenylmethoxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 39 | 1-trans-tri-n-butylstannyl-4-methyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-2-nor-5-cis-13-trans prostadiene |
| 40 | 1-trans-tri-n-butylstannyl-5-methyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methyl-2-nor-5-cis-13-trans prostadiene |
| 41 | 1-trans-tri-n-butylstannyl-4-vinyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-vinyl-2-nor-5-cis-13-trans prostadiene |
| 42 | 1-trans-tri-n-butylstannyl-4-trimethylsilylethynyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-ethynyl-2-nor-5-cis-13-trans prostadiene |
| 43 | 1-trans-tri-n-butylstannyl-5-methylene-4-triethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methylene-2-nor-5-cis-13-trans prostadiene |
| 44 | 1-trans-tri-n-butylstannyl-4-methyl-5-methylene-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-17-methylene-2-nor-5-cis-13-trans prostadiene |
| 45 | 1-trans-tri-n-butylstannyl-4-dimethoxymethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-formyl-2-nor-5-cis-13-trans prostadiene |
| 46 | 1-trans-tri-n-butylstannyl-4-fluoromethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-fluoromethyl-2-nor-5-cis-13-trans prostadiene |
| 47 | 1-trans-tri-n-butylstannyl-4-difluoromethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-difluoromethyl- |

TABLE IV-continued

| EXAMPLE | VINYL IODIDE / VINYL TIN | CYCLOPENTENONE | PRODUCT PROSTAGLANDIN OF THE PGE2 SERIES |
|---|---|---|---|
| | 4-trimethylsilyloxy-1-octene | pent-2-cis-enyl]-4-trimethylsiloxy cyclopent-2-en-1-one | 2-nor-5-cis-13-trans prostadiene |
| 48 | 1-trans-tri-n-butylstannyl-4-trifluoromethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-trifluoromethyl-2-nor-5-cis-13-trans prostadiene |
| 49 | 1-trans-tri-n-butylstannyl-4-chloromethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-chloromethyl-2-nor-5-cis-13-trans prostadiene |
| 50 | 1-trans-tri-n-butylstannyl-4-trimethylsilyloxymethyl-4-trimethylsilyloxy-1-octene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-hydroxymethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 51 | 1-trans-iodo-3-triphenylmethoxy-1-nonene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-20-methyl-2-nor-5-cis-13-trans prostadiene |
| 52 | 1-trans-iodo-3-methyl-3-trimethylsilyloxy-1-nonene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-15-methyl-20-methyl-2-nor-5-cis-13-trans prostadiene |
| 53 | 1-trans-iodo-4,4-dimethyl-3-trimethylsilyloxy-1-nonene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-dimethyl-20-methyl-2-nor-5-cis-13-trans prostadiene |
| 54 | 1-trans-iodo-4,4-trimethylene-3-trimethylsiloxy-1-nonene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-16,16-trimethylene-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 55 | 1-trans-tri-n-butylstannyl-3-vinyl-3-trimethylsilyloxy-1-nonene | 2-[5-methylthiaacetyl pent-2-cis-enyl]-4-trimethylsiloxy cyclopent-2-en-1-one | dl-11a,15a-dihydroxy-1-methylthiamethyl-1,9-dioxo-15-vinyl-20-methyl-nor-5-cis-13-trans prostadiene |
| EXAMPLE | VINYL IODIDE | CYCLOPENTENONE | PRODUCT PROSGAGLANDIN OF THE PGE2 SERIES |
| 56 | 1-trans-iodo-4-triphenylmethoxy-1-nonene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 57 | 1-trans-tri-n-butylstannyl-4-methyl-4-trimethylsilyloxy-1-nonene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-20-methyl-nor-5-cis-13-trans prostadiene |
| 58 | 1-trans-tri-n-butylstannyl-4-methyl-5-methyl-4-trimethylsilyloxy-1-nonene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methyl-20-methyl-2-nor-5-cis-13-trans prostadiene |
| 59 | 1-trans-tri-n-butylstannyl-4-vinyl-4-trimethylsilyloxy-1-nonene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-vinyl-20-methyl-2-nor-5-cis-13-trans prostadiene |
| 60 | 1-trans-tri-n-butylstannyl-4-trimethylsilylethynyl-4-trimethylsilyloxy-1-nonene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-ethynyl-20-methyl-2-nor-5-cis-13-trans prostadiene |
| 61 | 1-trans-tri-n-butylstannyl-5-methylene-4-triethylsilyloxy-1-nonene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methylene-20-methyl-2-nor-5-cis-13-trans prostadiene |
| 62 | 1-trans-tri-n-butylstannyl-4-methyl-5-methylene | 2-[5-methylthiaacetyl | dl-11a,16-dihydroxy-1-methylthiamethyl-1,9-dioxo-16-methyl- |

TABLE IV-continued

| EXAMPLE | VINYL IODIDE / VINYL TIN | CYCLOPENTENONE | PRODUCT PROSTAGLANDIN |
|---|---|---|---|
| | 4-trimethylsilyloxy-1-nonene | pent-2-cis-enyl]-4-trimethylsilyloxy cyclopent-2-en-1-one | 17-methylene-20-methyl-2-nor-5-cis-13-trans prostadiene |
| 63 | 1-trans-tri-n-butylstannyl-4-dimethoxymethyl-4-trimethylsilyloxy-1-nonene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-formyl-20-methyl-2-nor-5-cis-13-trans prostadiene |
| 64 | 1-trans-tri-n-butylstannyl-4-fluoromethyl-4-trimethylsilyloxy-1-nonene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-fluoromethyl-20-methyl-2-nor-5-cis-13-trans prostadiene |
| 65 | 1-trans-tri-n-butylstannyl-4-difluoromethyl-4-trimethylsilyloxy-1-nonene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-difluoromethyl-20-methyl-2-nor-5-cis-13-trans prostadiene |
| 66 | 1-trans-tri-n-butylstannyl-4-trifluoromethyl-4-trimethylsilyloxy-1-nonene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-trifluoromethyl-20-methyl-2-nor-5-cis-13-trans prostadiene |
| 67 | 1-trans-tri-n-butylstannyl-4-chloromethyl-4-trimethylsilyloxy-1-nonene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-chloromethyl-20-methyl-2-nor-5-cis-13-trans prostadiene |
| 68 | 1-trans-tri-n-butylstannyl-4-trimethylsilyloxymethyl-4-trimethylsilyloxy-1-nonene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-hydroxymethyl-20-methyl-2-nor-5-cis-13-trans prostadiene |
| EXAMPLE | VINYL IODIDE | CYCLOPENTENONE | PRODUCT PROSTAGLANDIN OF THE PGE2 SERIES |
| 69 | 1-trans-iodo-3-triphenylmethoxy-1-decene | 2-[5-methylthiaacetyl pent-2-cis-enyl]-4-trimethylsilyloxy cyclopent-2-en-1-one | dl-11a,15a-dihydroxy-1-methylthiamethyl-1,9-dioxo-20-ethyl-2-nor-5-cis-13-trans prostadiene |
| 70 | 1-trans-iodo-3-methyl-3-trimethylsilyloxy-1-decene | 2-[5-methylthiaacetyl pent-2-cis-enyl]-4-trimethylsilyloxy cyclopent-2-en-1-one | dl-11a,15a-dihydroxy-1-methylthiamethyl-1,9-dioxo-15-methyl-20-ethyl-2-nor-5-cis-13-trans prostadiene |
| | | 2-[5-methylthiaacetyl pent-2-cis-enyl]-4-trimethylsilyloxy cyclopent-2-en-1-one | dl-11a,15a-dihydroxy-1-methylthiamethyl-1,9-dioxo-15-methyl-20-ethyl-2-nor-5-cis-13-trans prostadiene |
| 71 | 1-trans-iodo-4,4-dimethyl-3-trimethylsilyloxy-1-decene | 2-[5-methylthiaacetyl pent-2-cis-enyl]-4-trimethylsilyloxy cyclopent-2-en-1-one | dl-11a,15a-dihydroxy-1-methylthiamethyl-1,9-dioxo-16,16-dimethyl-20-ethyl-2-nor-5-cis-13-trans prostadiene |
| 72 | 1-trans-iodo-4,4-trimethylene-3-trimethylsilyloxy-1-decene | 2-[5-methylthiaacetyl pent-2-cis-enyl]-4-trimethylsilyloxy cyclopent-2-en-1-one | dl-11a,15a-dihydroxy-1-methylthiamethyl-1,9-dioxo-16,16-trimethylene-20-ethyl-2-nor-5-cis-13-trans prostadiene |
| EXAMPLE | VINYL TIN | CYCLOPENTENONE | PRODUCT PROSTAGLANDIN OF THE PGE2 SERIES |
| 73 | 1-trans-tri-n-butylstannyl-3-vinyl-3-trimethylsilyloxy-1-decene | 2-[5-methylthiaacetyl pent-2-cis-enyl]-4-trimethylsilyloxy cyclopent-2-en-1-one | dl-11a,15a-dihydroxy-1-methylthiamethyl-1,9-dioxo-15-vinyl-20-ethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 74 | 1-trans-iodo-4-triphenylmethoxy-1-decene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-20-ethyl-2-nor-5-cis-13-trans prostadiene |
| EXAMPLE | VINYL TIN | CYCLOPENTENONE | PRODUCT PROSTAGLANDIN OF THE PGE2 SERIES |
| 75 | 1-trans-tri-n-butylstannyl-4-methyl-4-trimethylsilyloxy-1-decene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-16-methyl-20-ethyl-2-nor-5-cis-13-trans prostadiene |
| 76 | 1-trans-tri-n-butylstannyl-5-methyl-4-trimethylsilyloxy-1-decene | 2-[5-methylthiaacetyl pent-2-cis-enyl]-4-trimethylsilyloxy cyclopent-2-en-1-one | dl-11a,16-dihydroxy-1-methylthiamethyl-1,9-dioxo-17-methyl-20-ethyl-2-nor-5-cis-13-trans prostadiene |

TABLE IV-continued

| | VINYL TIN | CYCLOPENTENONE | PRODUCT PROSTAGLANDIN OF THE PGE2 SERIES |
|---|---|---|---|
| 77 | 1-trans-tri-n-butylstannyl-4-vinyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-vinyl-20-ethyl-2-nor-5-cis-13-trans prostadiene |
| 78 | 1-trans-tri-n-butylstannyl-4-trimethylsilylethynyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-ethynyl-20-ethyl-2-nor-5-cis-13-trans prostadiene |
| 79 | 1-trans-tri-n-butylstannyl-5-methylene-4-triethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-17-methylene-20-ethyl-2-nor-5-cis-13-trans prostadiene |
| 80 | 1-trans-tri-n-butylstannyl-4-methyl-5-methylene-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-methyl-17-methylene-20-ethyl-2-nor-5-cis-13-trans prostadiene |
| 81 | 1-trans-tri-n-butylstannyl-4-dimethoxymethyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-formyl-20-ethyl-2-nor-5-cis-13-trans prostadiene |
| 82 | 1-trans-tri-n-butylstannyl-4-fluoromethyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-fluoromethyl-20-ethyl-2-nor-5-cis-13-trans prostadiene |
| 83 | 1-trans-tri-n-butylstannyl-4-difluoromethyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-difluoromethyl-20-ethyl-2-nor-5-cis-13-trans prostadiene |
| 84 | 1-trans-tri-n-butylstannyl-4-trifluoromethyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-trifluoromethyl-20-ethyl-2-nor-5-cis-13-trans prostadiene |
| 85 | 1-trans-tri-n-butylstannyl-4-chloromethyl-4-trimethylsilyloxy-1-decene | 2-[5-methylthiaacetyl pent-2-cis-enyl]-4-trimethylsiloxy cyclopent-2-en-1-one | dl-11a,16-dihydroxy-1-methylthiamethyl-1,9-dioxo-16-chloromethyl-20-ethyl-2-nor-5-cis-13-trans prostadiene |
| 86 | 1-trans-tri-n-butylstannyl-4-trimethylsilyloxymethyl-4-trimethylsilyloxy-1-decene | 2-[5-methylthiaacetyl pent-2-cis-enyl]-4-trimethylsiloxy cyclopent-2-en-1-oen | dl-11a,16-dihydroxy-1-methylthiamethyl-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 87 | 1-trans-iodo-3-triphenylmethoxy-1-heptene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-20-nor-5-cis-13-trans prostadiene |
| 88 | 1-trans-iodo-3-methyl-3-trimethylsilyloxy-1-heptene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-15-methyl-20-nor-5-cis-13-trans prostadiene |
| 89 | 1-trans-iodo-4,4-dimethyl-3-trimethylsilyloxy-1-heptene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16,16-dimethyl-20-nor-5-cis-13-trans prostadiene |
| 90 | 1-trans-iodo-5,5-dimethyl-3-triphenylmethoxy-1-octene | 2-[6-methylthiaacetyl hex-2-cis-enyl]-4-trimethylsiloxy cyclopent-2-en-1-one | dl-11a,15a-dihydroxy-1 -methylthiamethyl-1,9-dioxo-17,17-dimethyl-5-cis-13-trans prostadiene |
| 91 | 1-trans-iodo-4-methyl-3-trimethylsilyloxy-1-octene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16-methyl-5-cis-13-trans prostadiene |
| 92 | 1-trans-iodo-4,4-trimethylene-3-trimethylsilyloxy-1-heptene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16,16-trimethylene-20-nor-5-cis-13-trans prostadiene |

| EXAMPLE | VINYL TIN | CYCLOPENTENEONE | PRODUCT PROSTAGLANDIN OF THE PGE2 SERIES |
|---|---|---|---|
| 93 | 1-trans-tri-n-butylstannyl-3-vinyl- | 2-[6-methylthiaacetyl | dl-11a,15a-dihydroxy-1-methylthiamethyl-1,9-dioxo-15-vinyl- |

TABLE IV-continued

| EXAMPLE | VINYL IODIDE | CYCLOPENTENONE | PRODUCT PROSTAGLANDIN OF THE PGE2 SERIES |
|---|---|---|---|
| | 3-trimethylsilyloxy-1-heptene | hex-2-cis-enyl]-4-trimethylsiloxy cyclopent-2-en-1-one | 20-nor-5-cis-13-trans prostadiene |
| 94 | 1-trans-tri-n-butylstannyl-4-phenoxy 3-triethylsilyloxy-1-butene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16-phenoxy-17-20-tetranor-5-cis-13-trans prostadiene |
| 95 | 1-trans-tri-n-butylstannyl-4-(p-fluorophenoxy) 3-triethylsilyloxy-1-butene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16-(p-flourophenoxy)-17-20-tetranor-5-cis-13-trans prostadiene |
| 96 | 1-trans-tri-n-butylstannyl-4-(m-chlorophenoxy) 3-triethylsilyloxy-1-butene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo 16-(m-chlorophenoxy)-17-20-tetranor-5-cis-13-trans prostadiene |
| 97 | 1-trans-tri-n-butylstannyl-4-(m-trifluoromethylphenoxy) 3-triethylsilyloxy-1-butene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16-(m-trifluoromethylphenoxy)-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 98 | 1-iodo-5-penyl 3-triethylsilyloxy-1-pentene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-17-phenyl-18-20-trinor-5-cis-13-trans prostadiene |
| 99 | 1-iodo-4,4-dimethyl-5-phenyl 3-triethylsilyloxy-1-pentene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16,16-dimethyl-17-phenyl-18-20-trinor-5-cis-13-trans prostadiene |
| 100 | 1-iodo-4-cyclopentyl 3-triphenylmethyloxy-1-butene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16-cyclopentyl-17-20-tetranor-5-cis-13-trans prostadiene |
| 101 | 1-iodo-4-cyclohexyl 3-triphenylmethoxy-1-butene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16-cyclohexyl-17-20-tetranor-5-cis-13-trans prostadiene |
| 102 | 1-iodo-4-triphenylmethyoxy-1-heptene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 103 | 1-trans-tri-n-butylstannyl-4-methyl-4-trimethylsilyloxy-1-heptene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-methyl-20-nor-5-cis-13-trans prostadiene |
| 104 | 1-trans-tri-n-butylstannyl-4-ethyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-ethyl-5-cis-13-trans prostadiene |
| 105 | 1-trans-tri-n-butylstannyl-5-methyl 4-trimethylsilyloxy-1-heptene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-17-methyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 106 | 1-iodo-5,5-dimethyl 4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-17,17-dimethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 107 | 1-trans-tri-n-butylstannyl-4-vinyl-4-trimethylsilyloxy-1-heptene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-vinyl 20-nor-5-cis-13-trans prostadiene |
| 108 | 1-trans-tri-n-butylstannyl-4-cyclopropyl | 2-[6-methylthiaacetyl | dl-11a,16-dihydroxy-1-methylthiamethyl-1,9-dioxo-16-cyclopropyl- |

TABLE IV-continued

| Example | Vinyl Iodide | Cyclopentenone | Product Prostaglandin of the PGE2 Series |
|---|---|---|---|
| | 4-trimethylsilyloxy-1-octene | hex-2-cis-enyl]-4-trimethylsilyloxy cyclopent-2-en-1-one | 5-cis-13-trans prostadiene |
| 109 | 1-trans-tri-n-butylstannyl-4-trimethylsilylethynyl-4-trimethylsilyloxy-1-heptne | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-ethynyl-20-nor-5-cis-13-trans prostadiene |
| 110 | 1-trans-tri-n-butylstannyl-5-methylene 4-triethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-17-methylene-20-nor-5-cis-13-trans prostadiene |
| 111 | 1-trans-tri-n-butylstannyl-4-methyl-5-methylene 4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-methyl-17-methylene-20-nor-5-cis-13-trans prostadiene |
| 112 | 1-trans-tri-n-butylstannyl-4-dimethoxymethyl-4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-formyl-20-nor-5-cis-13-trans prostadiene |
| 113 | 1-trans-tri-n-butylstannyl-4-fluoromethyl-4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-fluoromethyl-20-nor-5-cis-13-trans prostadiene |
| 114 | 1-trans-tri-n-butylstannyl-4-difluoromethyl-4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-difluoromethyl-20-nor-5-cis-13-trans prostadiene |
| 115 | 1-trans-tri-n-butylstannyl-4-trifluoromethyl-4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-trifluoromethyl-20-nor-5-cis-13-trans prostadiene |
| 116 | 1-trans-tri-n-butylstannyl-4-chloromethyl-4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-chloromethyl-20-nor-5-cis-13-trans prostadiene |
| 117 | 1-trans-tri-n-butylstannyl-4-trimethylsilyloxymethyl-4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-hydroxymethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 118 | 1-trans-iodo-4-methyl-7-chloro 4-trimethylsilyloxy-1-heptene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-methyl-19-chloro-20-nor-5-cis-13-trans prostadiene |
| 119 | 1-trans-iodo-3-triphenylmethoxy-1-octene | 2-[6-methylthiaacetyl hex-2-cis-enyl]-4-trimethylsilyloxy cyclopent-2-en-1-one | dl-11a,15a-dihydroxy-1-methylthiamethyl-1,9-dioxo-5-cis-13-trans prostadiene |
| 120 | 1-trans-iodo-3-methyl-3-trimethylsilyloxy-1-octene | 2-[6-methylthiaacetyl hex-2-cis-enyl]-4-trimethylsilyloxy cuclopent-2-en-1-one | dl-11a,15a-dihydroxy-1-methylthiamethyl-1,9-dioxo-15-methyl-5-cis-13-trans prostadiene |
| 121 | 1-trans-iodo-4,4-dimethyl 3-trimethylsilyloxy-1-octene | 2-[6-methylthiaacetyl hex-2-cis-enyl]-4-trimethylsilyloxy cyclopent-2-en-1-one | dl-11a,15a-dihydroxy-1-methylthiamethyl-1,9-dioxo-16,16-dimethyl-5-cis-13-trans prostadiene |
| 122 | 1-trans-iodo-4,4-trimethylene 3-trimethylsilyloxy-1-octene | 2-[6-methylthiaacetyl hex-2-cis-enyl]-4-trimethylsilyloxy cyclopent-2-en-1-one | dl-11a,15a-dihydroxy-1-methylthiamethyl-1,9-dioxo-16,16-trimethylene-5-cis-13-trans prostadiene |
| EXAMPLE | VINYL TIN | CYCLOPENTENONE | PROSTAGLANDIN OF THE PGE2 SERIES |
| 123 | 1-trans-tri-n-butylstannyl-3-vinyl-3-trimethylsilyloxy-1-octene | 2-[6-methylthiaacetyl hex-2-cis-enyl]-4-trimethylsilyloxy cyclopent-2-en-1-one | dl-11a,15a-dihydroxy-1-methylthiamethyl-1,9-dioxo-15-vinyl-5-cis-13-trans prostadiene |
| EXAMPLE | VINYL ODIDE | CYCLOPENTENONE | PRODUCT PROSTAGLANDIN OF THE PGE2 SERIES |

TABLE IV-continued

| EXAMPLE | VINYL TIN | CYCLOPENTENONE | PRODUCT PROSTAGLANDIN OF THE PGE2 SERIES |
|---|---|---|---|
| 124 | 1-trans-iodo-4-triphenylmethoxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-5-cis-13-trans prostadiene |
| EXAMPLE | VINYL TIN | CYCLOPENTENONE | PRODUCT PROSTAGLANDIN OF THE PGE2 SERIES |
| 125 | 1-trans-tri-n-butylstannyl-4-methyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-methyl-5-cis-13-trans prostadiene |
| 126 | 1-trans-tri-n-butylstannyl-5-methyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-17-methyl-5-cis-13-trans prostadiene |
| 127 | 1-trans-tri-n-butylstannyl-4-vinyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-vinyl-5-cis-13-trans prostadiene |
| 128 | 1-trans-tri-n-butylstannyl-4-trimethylsilylethynyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-ethynyl-5-cis-13-trans prostadiene |
| 129 | 1-trans-tri-n-butylstannyl-5-methylene-4-triethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-17-methylene-5-cis-13-trans prostadiene |
| 130 | 1-trans-tri-n-butylstannyl-4-methyl-5-methylene-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-methyl-17-methylene-5-cis-13-trans prostadiene |
| 131 | 1-trans-tri-n-butylstannyl-4-dimethoxymethyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-formyl-5-cis-13-trans prostadiene |
| 132 | 1-trans-tri-n-butylstannyl-4-fluoromethyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-fluoromethyl-5-cis-13-trans prostadiene |
| 133 | 1-trans-tri-n-butylstannyl-4-difluoromethyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-difluoromethyl-5-cis-13-trans prostadiene |
| 134 | 1-trans-tri-n-butylstannyl-4-trifluoromethyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-trifluoromethyl-5-cis-13-trans prostadiene |
| 135 | 1-trans-tri-n-butylstannyl-4-chloromethyl-4-trimethylsilyloxy-1-octene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-chloromethyl-5-cis-13-trans prostadiene |
| 136 | 1-trans-tri-n-butylstannyl-4-trimethylsilyloxymethyl-4-trimethylsilyloxy-1-octene | 2-[6-methylthiaacetyl hex-2-cis-enyl]-4-trimethylsiloxy cyclopene-2-en-1-one | dl-11a,16-dihydroxy-1-methylthiamethyl-1,9-dioxo-16-hydroxymethyl-5-cis-13-trans prostadiene |
| EXAMPLE | VINYL IODIDE | CYCLOPENTENONE | PRODUCT PROSTAGLANDIN OF THE PGE2 SERIES |
| 137 | 1-trans-iodo-3-triphenylmethoxy-1-nonene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-20-methyl-5-cis-13-trans prostadiene |
| 138 | 1-trans-iodo-3-methyl-3-trimethylsilyloxy-1-nonene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-15-methyl-20-methyl-5-cis-13-trans prostadiene |
| 139 | 1-trans-iodo-4,4-dimethyl-3-trimethylsilyloxy-1-nonene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-16,16-dimethyl-20-methyl-5-cis-13-trans prostadiene |
| 140 | 1-trans-iodo-4,4-trimethylene | 2-[6-methylthiaacetyl | dl-11a,15a-dihydroxy-1-methylthiamethyl-1,9-dioxo- |

TABLE IV-continued

| EXAMPLE | VINYL TIN / VINYL IODIDE | CYCLOPENTENONE | PRODUCT PROSTAGLANDIN OF THE PGE2 SERIES |
|---|---|---|---|
| | 3-trimethylsilyloxy-1-nonene | hex-2-cis-enyl]-4-trimethylsilyloxy cyclopent-2-en-1-one | 16,16-trimethylene-20-methyl-5-cis-13-trans prostadiene |
| EXAMPLE | VINYL TIN | CYCLOPENTENONE | PRODUCT PROSTAGLANDIN OF THE PGE2 SERIES |
| 141 | 1-trans-tri-n-butylstannyl-3-vinyl-3-trimethylsilyloxy-1-nonene | 2-[6-methylthiaacetyl hex-2-cis-enyl]-4-trimethylsilyloxy cyclopent-2-en-1-one | dl-11a,15a-dihydroxy-1-methylthiamethyl-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 142 | 1-trans-iodo-4-triphenylmethoxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-20-methyl-5-cis-13-trans prostadiene |
| EXAMPLE | VINYL TIN | CYCLOPENTENONE | PRODUCT PROSTAGLANDIN OF THE PGE2 SERIES |
| 143 | 1-trans-tri-n-butylstannyl-4-methyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-methyl-20-methyl-5-cis-13-trans prostadiene |
| 144 | 1-trans-tri-n-butylstannyl-5-methyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-17-methyl-20-methyl-5-cis-13-trans prostadiene |
| 145 | 1-trans-tri-n-butylstannyl-4-vinyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-vinyl-20-methyl-5-cis-13-trans prostadiene |
| 146 | 1-trans-tri-n-butylstannyl-4-trimethylsilylethynyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-ethynyl-20-methyl-5-cis-13-trans prostadiene |
| 147 | 1-trans-tri-n-butylstannyl-5-methylene-4-triethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-17-methylene-20-methyl-5-cis-13-trans prostadiene |
| 148 | 1-trans-tri-n-butylstannyl-4-methyl-5-methylene-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-methyl-17-methylene-20-methyl-5-cis-13-trans prostadiene |
| 149 | 1-trans-tri-n-butylstannyl-4-dimethoxymethyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-formyl-20-methyl-5-cis-13-trans prostadiene |
| 150 | 1-trans-tri-n-butylstannyl-4-fluoromethyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-fluoromethyl-20-methyl-5-cis-13-trans prostadiene |
| 151 | 1-trans-tri-n-butylstannyl-4-difluoromethyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-difluoromethyl-20-methyl-5-cis-13-trans prostadiene |
| 152 | 1-trans-tri-n-butylstannyl-4-trifluoromethyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-trifluoromethyl-20-methyl-5-cis-13-trans prostadiene |
| 153 | 1-trans-tri-n-butylstannyl-4-chloromethyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-chloromethyl-20-methyl-5-cis-13-trans-prostadiene |
| 154 | 1-trans-tri-n-butylstannyl-4-trimethylsilyloxymethyl-4-trimethylsilyloxy-1-nonene | 2-[6-methylthiaacetyl hex-2-cis-enyl]-4-trimethylsilyloxy cyclopent-2-en-1-one | dl-11a,16-dihydroxy-1-methylthiamethyl-1,9-dioxo-16-hydroxymethyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 155 | 1-trans-iodo- | 2-[6-methylthiaacetyl | dl-11a,15a-dihydroxy-1-methylthiamethyl-1,9-dioxo- |

TABLE IV-continued

| EXAMPLE | | | PRODUCT PROSTAGLANDIN |
|---|---|---|---|
| | | 3-triphenylmethoxy-1-decene | hex-2-cis-enyl]-4-trimethylsiloxy cyclopent-2-en-1-one | 20-ethyl-5-cis-13-trans prostadiene |
| 156 | | 1-trans-iodo-3-methyl-3-trimethylsilyloxy-1-decene | 2[6-methylthiaacetyl hex-2-cis-enyl]-4-trimethylsiloxy cyclopent-2-en-1-one | dl-11a,15a-dihydroxy-1-methylthiamethyl-1,9-dioxo-15-methyl-20-ethyl-5-cis-13-trans prostadiene |
| 157 | | 1-trans-iodo-4,4-dimethyl-3-trimethylsilyloxy-1-decene | 2[6-methylthiaacetyl hex-2-cis-enyl]-4-trimethylsiloxy cyclopent-2-en-1-one | dl-11a,15a-dihydroxy-1-methylthiamethyl-1,9-dioxo-16,16-dimethyl-20-ethyl-5-cis-13-trans prostadiene |
| 158 | | 1-trans-iodo-4,4-trimethylene-3-trimethylsilyloxy-1-decene | 2[6-methylthiaacetyl hex-2-cis-enyl]-4-trimethylsiloxy cyclopent-2-en-1-one | dl-11a,15a-dihydroxy-1-methylthiamethyl-1,9-dioxo-16,16-trimethylene-20-ethyl-5-cis-13-trans prostadiene |
| EXAMPLE | VINYL TIN | | CYCLOPENTENONE | PRODUCT PROSTAGLANDIN OF THE PGE2 SERIES |
| 159 | | 1-trans-tri-n-butylstannyl-3-vinyl-3-trimethylsilyloxy-1-decene | 2-[6-methylthiaacetyl hex-2-cis-enyl]-4-trimethylsiloxy cyclopent-2-en-1-one | dl-11a,15a-dihydroxy-1-methylthiamethyl-1,9-dioxo-15-vinyl-20-ethyl-5-cis-13-trans prostadiene |
| EXAMPLE | VINYL IODIDE | | CYCLOPENTENONE | PRODUCT PROSTAGLANDIN OF THE PGE2 SERIES |
| 160 | | 1-trans-iodo-4-triphenylmethoxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo 20-ethyl-5-cis-13-trans prostadiene |
| EXAMPLE | VINYL TIN | | CYCLOPENTENONE | PRODUCT PROSTAGLANDIN OF THE PGE2 SERIES |
| 161 | | 1-trans-tri-n-butylstannyl-4-methyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-ethynyl-20-ethyl-5-cis-13-trans prostadiene |
| 165 | | 1-trans-tri-n-butylstannyl-5-methylene-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-17-methylene-20-ethyl-5-cis-13-trans prostadiene |
| 166 | | 1-trans-tri-n-butylstannyl-4-methyl-5-methylene-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-methyl-17-methylene-20-ethyl-5-cis-13-trans prostadiene |
| 167 | | 1-trans-tri-n-butylstannyl-4-dimethoxymethyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-formyl-20-ethyl-5-cis-13-trans prostadiene |
| 168 | | 1-trans-tri-n-butylstannyl-4-fluoromethyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-fluoromethyl-20-ethyl-5-cis-13-trans prostadiene |
| 169 | | 1-trans-tri-n-butylstannyl-4-difluoromethyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-difluoromethyl-20-ethyl-5-cis-13-trans prostadiene |
| 170 | | 1-trans-tri-n-butylstannyl-4-triflouromethyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-trifluoromethyl-20-ethyl-5-cis-13-trans prostadiene |
| 171 | | 1-trans-tri-n-butylstannyl-4-chloromethyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-chloromethyl-20-ethyl-5-cis-13-trans prostadiene |
| 172 | | 1-trans-tri-n-butylstannyl-4-trimethylsilyloxymethyl-4-trimethylsilyloxy-1-decene | 2-[6-methylthiaacetyl hex-2-cis-enyl]-4-trimethylsiloxy cyclopent-2-en-1-one | dl-11a,16-dihydroxy-1-methylthiamethyl-1,9-dioxo-16-hydroxymethyl-20-ethyl-5-cis-13-trans prostadiene |

TABLE IV-continued

| EXAMPLE | VINYL IODIDE | CYCLOPENTENONE | PRODUCT PROSTAGLANDIN OF THE PGE2 SERIES |
|---|---|---|---|
| 173 | 1-trans-iodo-3-triphenylmethoxy-1-heptene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-20-nor-2-homo-5-cis-13-trans prostadiene |
| 174 | 1-trans-iodo-3-methyl 3-trimethylsilyloxy-1-heptene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-15-methyl-20-nor-2-homo-5-cis-13-trans prostadiene |
| 175 | 1-trans-iodo-4,4-dimethyl 3-trimethylsilyloxy-1-heptene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-dimethyl-20-nor-2-homo-5-cis-13-trans prostadiene |
| 176 | 1-trans-iodo-5,5-dimethyl 3-triphenylmethoxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-17,17-dimethyl-2-homo-5-cis-13-trans prostadiene |
| 177 | 1-trans-iodo-4-methyl 3-triphenylmethoxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-methyl-2-homo-5-cis-13-trans prostadiene |
| 178 | 1-trans-iodo-4,4-trimethylene 3-trimethylsilyloxy-1-heptene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-trimethylene-20-nor-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 179 | 1-trans-tri-n-butylstannyl-3-vinyl 3-trimethylsilyloxy-1-heptene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-15 vinyl-20-nor-2-homo-5-cis-13-trans prostadiene |
| 180 | 1-trans-tri-n-butylstannyl-4-phenoxy 3-triethylsilyloxy-1-butene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-phenoxy-2-homo-17-20-tetranor-5-cis-13-trans prostadiene |
| 181 | 1-trans-tri-n-butylstannyl-4-(p-fluorophenoxy) 3-triethylsilyloxy-1-butene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-(m-fluorophenoxy)-2-homo-17-20-tetranor-5-cis-13-trans prostadiene |
| 182 | 1-trans-tri-n-butylstannyl-4-(m-chlorophenoxy) 3-triethylsilyloxy-1-butene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-(m-chlorophenoxy)-2-homo-17-20-tetranor-5-cis-13-trans prostadiene |
| 183 | 1-trans-tri-n-butylstannyl-4-(m-trifluoromethylphenoxy) 3-triethylsilyloxy-1-butene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-(m-trifluoromethylphenoxy)-2-homo-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 184 | 1-trans-iodo-5-phenyl 3-triethylsilyloxy-1-pentene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-17-phenyl-2-homo-18-20-trinor-5-cis-13-trans prostadiene |
| 185 | 1-trans-iodo-4,4-dimethyl-5-phenyl 3-triethylsilyloxy-1-pentene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-dimethyl-17-phenyl-18-20-trinor-5-cis-13-trans prostadiene |
| 186 | 1-trans-iodo-4-cyclopentyl 3-triethylsilyloxy-1-butene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-cyclopentyl-2-homo-17-20-tetranor-5-cis-13-trans prostadiene |
| 187 | 1-trans-iodo-4-cyclohexyl 3-triethylsilyloxy-1-butene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-cyclohexyl-2-homo-17-20-tetranor-5-cis-13-trans prostadiene |
| 188 | 1-trans-iodo-4-triphenylmethoxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-20-nor-2-homo-5-cis-13-trans prostadiene |

TABLE IV-continued

| EXAMPLE | VINYL TIN | CYCLOPENTENONE | PRODUCT PROSTAGLANDIN OF THE PGE2 SERIES |
|---|---|---|---|
| 189 | 1-trans-tri-n-butylstannyl-4-methyl 4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo,16-methyl-20-nor-2-homo-5-cis-13-trans prostadiene |
| 190 | 1-trans-tri-n-butylstannyl-4-ethyl 4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-ethyl-2-homo-5-cis-13-trans prostadiene |
| 191 | 1-trans-tri-n-butylstannyl-5-methyl 4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17-methyl-20-nor-2-homo-5-cis-13-trans prostadiene |

| EXAMPLE | VINYLIODIDE | CYCLOPENTENONE | PRODUCT PROSTAGLANDIN OF THE PGE2 SERIES |
|---|---|---|---|
| 192 | 1-trans-iodo-5,5-dimethyl 4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17,17-dimethyl-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 193 | 1-trans-tri-n-butylstannyl-4-vinyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-vinyl-20-nor-2-homo-5-cis-13-trans prostadiene |
| 194 | 1-trans-tri-n-butylstannyl-4-cyclopropyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-chloropropyl-2-homo-5-cis-13-trans prostadiene |
| 195 | 1-trans-tri-n-butylstannyl-4-trimethylsilyethynyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-ethynyl-20-nor-2-homo-5-cis-13-trans prostadiene |
| 196 | 1-trans-tri-n-butylstannyl-4-methylene 4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo 17-methylene-20-nor-2-homo-5-cis-13-trans prostadiene |
| 197 | 1-trans-tri-n-butylstannyl-4-methyl-5-methylene 4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-methyl-17-methylene-20-nor-2-homo-5-cis-13-trans prostadiene |
| 198 | 1-trans-tri-n-butylstannyl-4-dimethoxymethyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-formyl-20-nor-2-homo-5-cis-13-trans prostadiene |
| 199 | 1-trans-tri-n-butylstannyl-4-fluoromethyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-fluoromethyl-20-nor-2-homo-5-cis-13-trans prostadiene |
| 200 | 1-trans-tri-n-butylstannyl-4-difluoromethyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-difluoromethyl-20-nor-2-homo-5-cis-13-trans prostadiene |
| 201 | 1-trans-tri-n-butylstannyl-4-trifluoromethyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-trifluoromethyl-20-nor-2-homo-5-cis-13-trans prostadiene |
| 202 | 1-trans-tri-n-butylstannyl-4-chloromethyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-chloromethyl-20-nor-2-homo-5-cis-13-trans prostadiene |
| 203 | 1-trans-tri-n-butylstannyl-4-trimethylsilyloxymethyl-4-trimethylsilyloxy-1-heptene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-hydroxymethyl-20-nor-2-homo-5-cis-13-trans prostadiene |

TABLE IV-continued

| EXAMPLE | VINYL IODIDE | CYCLOPENTENONE | PRODUCT PROSTAGLANDIN OF THE PGE2 SERIES |
|---|---|---|---|
| 204 | 1-trans-iodo-4-methyl-7-chloro-4-trimethylsilyloxy-1-heptene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16-methyl-19-chloro-2-homo-20-nor-5-cis-13-trans prostadiene |
| 205 | 1-trans-iodo-3-triphenylmethoxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-2-homo-5-cis-13-trans prostadiene |
| 206 | 1-trans-iodo-3-methyl-3-trimethylsilyloxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-15-methyl-2-homo-5-cis-13-trans prostadiene |
| 207 | 1-trans-iodo-4,4-dimethyl-3-trimethylsilyloxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-dimethyl-2-homo-5-cis-13-trans prostadiene |
| 208 | 1-trans-iodo-4,4-trimethylene-3-trimethylsilyloxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-trimethylene-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 209 | 1-trans-tri-n-butylstannyl-3-vinyl-3-trimethylsilyloxy-1-octene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-15-vinyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 210 | 1-trans-iodo-4-triphenylmethoxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 211 | 1-trans-tri-n-butylstannyl-4-methyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-methyl-2-homo-5-cis-13-trans prostadiene |
| 212 | 1-trans-tri-n-butylstannyl-5-methyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17-methyl-2-homo-5-cis-13-trans prostadiene |
| 213 | 1-trans-tri-n-butylstannyl-4-vinyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-vinyl-2-homo-5-cis-13-trans prostadiene |
| 214 | 1-trans-tri-n-butylstannyl-4-trimethylsilylethynyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-ethynyl-2-homo-5-cis-13-trans prostadiene |
| 215 | 1-trans-tri-n-butylstannyl-5-methylene-4-triethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17-methylene-2-homo-5-cis-13-trans prostadiene |
| 216 | 1-trans-tri-n-butylstannyl-4-methyl-5-methylene-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-methyl-17-methylene-2-homo-5-cis-13-trans prostadiene |
| 217 | 1-trans-tri-n-butylstannyl-4-dimethoxymethyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-formyl-2-homo-5-cis-13-trans prostadiene |
| 218 | 1-trans-tri-n-butylstannyl-4-fluoromethyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-fluoromethyl-2-homo-5-cis-13-trans prostadiene |
| 219 | 1-trans-tri-n-butylstannyl-4-difluoromethyl- | 2-[7-methylthiaacetyl | dl-11a,16-dihydroxy-1-methylthiamethyl-1,9-dioxo-16-difluoromethyl- |

TABLE IV-continued

| EXAMPLE | VINYL IODIDE / VINYL TIN | CYCLOPENTENONE | PRODUCT PROSTAGLANDIN OF THE PGE2 SERIES |
|---|---|---|---|
| | 4-trimethylsilyloxy-1-octene | hept-2-cis-enyl]-4-trimethylsiloxy cyclopent-2-en-1-one | 2-homo-5-cis-13-trans prostadiene |
| 220 | 1-trans-tri-n-butylstannyl-4-trifluoromethyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-triflouromethyl-2-homo-5-cis-13-trans prostadiene |
| 221 | 1-trans-tri-n-butylstannyl-4-chloromethyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-chloromethyl-2-homo-5-cis-13-trans prostadiene |
| 222 | 1-trans-tri-n-butylstannyl-4-trimethylsilyloxymethyl-4-trimethylsilyloxy-1-octene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-hydroxymethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 223 | 1-trans-iodo-4-triphenylmethoxy-1-nonene | 2-[7-methylthiaacetyl]-4-trimethylsiloxy cyclopent-2-en-1-one | dl-11a,15a-dihydroxy-1-methylthiamethyl-1,9-dioxo-20-methyl-2-homo-5-cis-13-trans prostadiene |
| 224 | 1-trans-iodo-3-methyl-3-trimethylsilyloxy-1-nonene | 2-[7-methylthiaacetyl hept-2-cis-enyl] -4-trimethylsiloxy cyclopent-2-en-1-one | dl-11a,15a-dihydroxy-1-methylthiamethyl-1,9-dioxo-15-methyl-20-methyl-2-homo-5-cis-13-trans prostadiene |
| 225 | 1-trans-iodo-4,4-dimethyl 3-trimethylsilyloxy-1-nonene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-dimethyl-20-methyl-2-homo-5-cis-13-trans prostadiene |
| 226 | 1-trans-iodo-4,4-trimethylene 3-trimethylsilyloxy-1-nonene | 2-[7-methylthiaacetyl hept-2-cis-enyl]-4-trimethylsiloxy cyclopent-2-en-1-one | dl-11a,15a-dihydroxy-1-methylthiamethyl-1,9-dioxo-16,16-trimethylene-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 227 | 1-trans-tri n-butylstannyl-3-vinyl-3-trimethylsilyloxy-1-nonene | 2-[7-methylthiaacetyl]-4-trimethylsiloxy cyclopent-2-en-1-one | dl-11a,15a-dihydroxy-1-methylthiamethyl-1,9-dioxo-15-vinyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 228 | 1-trans-iodo-4-triphenylmethoxy-1-nonene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 229 | 1-trans-tri-n-butylstannyl-4-methyl-4-trimethylsilyloxy-1-nonene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-methyl-20-methyl-2-homo-5-cis-13-trans prostadiene |
| 230 | 1-trans-tri-n-butylstannyl-5- methyl-4-trimethylsilyloxy-1-nonene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17-methyl-20-methyl-2-homo-5-cis-13-trans prostadiene |
| 231 | 1-trans-tri-n-butylstannyl-4-vinyl-4-trimethylsilyloxy-1-nonene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-vinyl-20-methyl-2-homo-5-cis-13-trans prostadiene |
| 232 | 1-trans-tri-n-butylstannyl-4-trimethylsilylethynyl-4-trimethylsilyloxy-1-nonene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-ethynyl-20-methyl-2-homo-5-cis-13-trans prostadiene |
| 233 | 1-trans-tri-n-butylstannyl-5-methylene-4-trimethylsilyloxy-1-nonene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17-methylene-20-methyl-2-homo-5-cis-13-trans prostadiene |
| 234 | 1-trans-tri-n-butylstannyl-4-methyl-5-methylene | 2-[7-methylthiaacetyl | dl-11a,16-dihydroxy-1-methylthiamethyl-1,9-dioxo-16-methyl- |

TABLE IV-continued

| Example | Vinyl Iodide / Vinyl Tin | Cyclopentenone | Product Prostaglandin |
|---|---|---|---|
| | 4-trimethylsilyloxy-1-nonene | hept-2-cis-enyl]-4-trimethylsilyloxy cyclopent-2-en-1-one | 17-methylene-20-methyl-2-homo-5-cis-13-trans prostadiene |
| 235 | 1-trans-tri-n-butylstannyl-4-dimethoxymethyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-formyl-20-methyl-2-homo-5-cis-13-trans prostadiene |
| 236 | 1-trans-tri-n-butylstannyl-4-fluoromethyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-fluoromethyl-20-methyl-2-homo-5-cis-13-trans prostadiene |
| 237 | 1-trans-tri-n-butylstannyl-4-difluoromethyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-difluoromethyl-20-methyl-2-homo-5-cis-13-trans prostadiene |
| 238 | 1-trans-tri-n-butylstannyl-4-trifluoromethyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-trifluoromethyl-20-methyl-2-homo-5-cis-13-trans prostadiene |
| 239 | 1-trans-tri-n-butylstannyl-4-chloromethyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-chloromethyl-20-methyl-2-homo-5-cis-13-trans prostadiene |
| 240 | 1-trans-tri-n-butylstannyl-4-trimethylsilyloxymethyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-hydroxymethyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 241 | 1-trans-iodo-3-triphenylmethoxy-1-decene | 2-[7-methylthiaacetyl hept-2-cis-enyl]-4-trimethylsilyloxy cyclopent-2-en-1-one | dl-11a,15a-dihydroxy-1-methylthiamethyl-1,9-dioxo-20-ethyl-2-homo-5-cis-13-trans prostadiene |
| 242 | 1-trans-iodo-3-methyl-3-trimethylsilyloxy-1-decene | 2-[7-methylthiaacetyl hept-2-cis-enyl]-4-trimethylsilyloxy cyclopent-2-en-1-one | dl-11a,15a-dihydroxy-1-methylthiamethyl-1,9-dioxo-16-methyl-20-ethyl-2-homo-5-cis-13-trans prostadiene |
| 243 | 1-trans-iodo-4,4dimethyl-3-trimethylsilyloxy-1-decene | 2-[7-methylthiaacetyl hept-2-cis-enyl]-4-trimethylsilyloxy cyclopent-2-en-1-one | dl-11a,15a-dihydroxy-1-methylthiamethyl-1,9-dioxo-16,16-dimethyl-20-ethyl-2-homo-5-cis-13-trans prostadiene |
| 244 | 1-trans-iodo-4,4-trimethylene-3-trimethylsilyloxy-1-decene | 2-[7-methylthiaacetyl hept-2-cis-enyl]-4-trimethylsilyloxy cyclopent-2-en-1-one | dl-11a,15a-dihydroxy-1-methylthiamethyl-1,9-dioxo-16,16-trimethylene-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 245 | 1-trans-tri-n-butylstannyl-3-vinyl-3-trimethylsilyloxy-1-decene | 2-[7-methylthiaacetyl hept-2-cis-enyl]-4-trimethylsilyloxy cyclopent-2-en-1-one | dl-11a,15a-dihydroxy-1-methylthiamethyl-1,9-dioxo-15-vinyl-20-ethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 246 | 1-trans-iodo-4-triphenylmethoxy-1-decene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 247 | 1-trans-tri-n-butylstannyl-4-methyl-4-trimethylsilyloxy-1-decene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-methyl-20-ethyl-2-homo-5-cis-13-trans prostadiene |
| 248 | 1-trans-tri-n-butylstannyl-5-methyl-4-trimethylsilyloxy-1-decene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-17-methyl-20-ethyl-2-homo-5-cis-13-trans prostadiene |
| 249 | 1-trans-tri-n-butylstannyl-4-vinyl-4-trimethylsilyloxy-1-nonene | 2-[7-methylthiaacetyl hept-2-cis-enyl]-4-trimethylsilyloxy cyclopent-2-en-1-one | dl-11a,16-dihydroxy-1-methylthiamethyl-1,9-dioxo-16-vinyl- |

TABLE IV-continued

| EXAMPLE | VINYL IODIDE | CYCLOPENTENONE | PRODUCT PROSTAGLANDIN OF THE PGE2 SERIES |
|---|---|---|---|
| | 4-trimethylsilyloxy-1-decene | hept-2-cis-enyl]-4-trimethylsiloxy cyclopent-2-en-1-one | 20-ethyl-2-homo-5-cis-13-trans prostadiene |
| 250 | 1-trans-tri-n-butylstannyl-4-trimethylsilylethynyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-ethynyl-20-ethyl-2-homo-5-cis-13-trans prostadiene |
| 251 | 1-trans-tri-n-butylstannyl-5-methylene-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-17-methylene-20-ethyl-2-homo-5-cis-13-trans prostadiene |
| 252 | 1-trans-tri-n-butylstannyl-4-methyl-5-methylene-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-methyl-17-methylene-20-ethyl-2-homo-5-cis-13-trans prostadiene |
| 253 | 1-trans-tri-n-butylstannyl-4-dimethoxymethyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-formyl-20-ethyl-2-homo-5-cis-13-trans prostadiene |
| 254 | 1-trans-tri-n-butylstannyl-4-fluoromethyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-fluoromethyl-20-ethyl-2-homo-5-cis-13-trans prostadiene |
| 255 | 1-trans-tri-n-butylstannyl-4-difluoromethyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-difluoromethyl-20-ethyl-2-homo-5-cis-13-trans prostadiene |
| 256 | 1-trans-tri-n-butylstannyl-4-trifluoromethyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-trifluoromethyl-20-ethyl-2-homo-5-cis-13-trans prostadiene |
| 257 | 1-trans-tri-n-butylstannyl-4-chloromethyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-chloromethyl-20-ethyl-2-homo-5-cis-13-trans prostadiene |
| 258 | 1-trans-tri-n-butylstannyl-4-trimethylsilyloxymethyl-4-trimethylsilyloxy-1-decene | 2-[7-methylthiaacetyl hept-2-cis-enyl]-4-trimethylsiloxy cyclopent-2-en-1-one | dl-11a,16-dihydroxy-1-methylthiamethyl-1,9-dioxo-16-hydroxymethyl-20-ethyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 259 | 1-trans-iodo-3-triphenylmethoxy-1-heptene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-20-nor-5-cis-13-trans prostadiene |
| 260 | 1-trans-iodo-3-methyl-3-trimethylsilyloxy-1-heptene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-15-methyl-20-nor-5-cis-13-trans prostadiene |
| 261 | 1-trans-iodo-4,4-dimethyl-3-trimethylsilyloxy-1-heptene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-dimethyl-20-nor-5-cis-13-trans prostadiene |
| 262 | 1-trans-iodo-5,5-dimethyl-3-triphenylmethoxy-1-octene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-17,17-dimethyl-5-cis-13-trans prostadiene |
| 263 | 1-trans-iodo-4-methyl-3-triphenylmethoxy-1-octene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-methyl-5-cis-13-trans prostadiene |
| 264 | 1-trans-iodo-4,4-trimethylene-3-trimethylsilyloxy-1-heptene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-trimethylene-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 265 | 1-trans-tri-n-butylstannyl-3-vinyl-3-trimethylsilyloxy-1-heptene | 2-[6-methylthiaacetyl hex-2-cis-enyl]-4R-trimethylsiloxy | nat-11a,15a-dihydroxy-1-methylthiamethyl-1,9-dioxo-15-vinyl-20-nor-5-cis-13-trans prostadiene |

TABLE IV-continued

| | | | |
|---|---|---|---|
| 266 | 1-trans-tri-n-butylstannyl-4-phenoxy 3-trimethylsilyloxy-1-butene | cyclopent-2-en-1-one 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-phenoxy-17-20-tetranor-5-cis-13-trans prostadiene |
| 267 | 1-trans-tri-n-butylstannyl-4-(p-fluorophenoxy) 3-trimethylsilyloxy-1-butene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-(p-fluorophenoxy)-17-20-tetranor-5-cis-13-trans prostadiene |
| 268 | 1-trans-tri-n-butylstannyl-4-(m-chlorophenoxy) 3-triethylsilyloxy-1-butene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-(m-chlorophenoxy)-17-20-tetranor-5-cis-13-trans prostadiene |
| 269 | 1-trans-tri-n-butylstannyl-4-(m-trifluoromethylphenoxy) 3-triethylsilyloxy-1-butene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-(m-trifluoromethylphenoxy)-17-20-tetranor-5-cis-13-trans prostadiene |
| EXAMPLE | VINYL IODIDE | CYCLOPENTENONE | PRODUCT PROSTAGLANDIN OF THE PGE2 SERIES |
| 270 | 1-trans-iodo-5-phenyl 3-triethylsilyloxy-1-pentene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-17-phenyl-18-20-trinor-5-cis-13-trans prostadiene |
| 271 | 1-trans-iodo-4,4-dimethyl-5-phenyl 3-triethylsilyloxy-1-pentene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-dimethyl-17-phenyl-18-20-trinor-5-cis-13-trans prostadiene |
| 272 | 1-trans-iodo-4-cyclopentyl 3-triphenylmethoxy-1-butene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-cyclopentyl-17-20-tetranor-5-cis-13-trans prostadiene |
| 273 | 1-trans-iodo-4-cyclohexyl 3-triphenylmethoxy-1-butene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16-cyclohexyl-17-20-tetranor-5-cis-13-trans prostadiene |
| 274 | 1-trans-iodo-4-triphenylmethoxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-20-nor-5-cis-13-trans prostadiene |
| EXAMPLE | VINYL TIN | CYCLOPENTENONE | PRODUCT PROSTAGLADIN OF THE PGE2 SERIES |
| 275 | 1-trans-tri-n-butylstannyl-4-methyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-20-nor-5-cis-13-trans prostadiene |
| 276 | 1-trans-tri-n-butylstannyl-4-ethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-ethyl-5-cis-13-trans prostadiene |
| 277 | 1-trans-tri-n-butylstannyl-5-methyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methyl-20-nor-5-cis-13-trans prostadiene |
| EXAMPLE | VINYL IODIDE | CYCLOPENTENONE | PRODUCT PROSTAGLANDIN OF THE PGE2 SERIES |
| 278 | 1-trans-iodo-5,5-dimethyl 4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17,17-dimethyl-5-cis-13-trans prostadiene |
| EXAMPLE | VINYL TIN | CYCLOPENTENONE | PRODUCT PROSTAGLANDIN OF THE PGE2 SERIES |
| 279 | 1-trans-tri-n-butylstannyl-4-vinyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-vinyl-20-nor-5-cis-13-trans prostadiene |
| 280 | 1-trans-tri-n-butylstannyl-4-cyclopropyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-cyclopropyl-5-cis-13-trans prostadiene |

TABLE IV-continued

| | | | |
|---|---|---|---|
| 281 | 1-trans-tri-n-butylstannyl-4-trimethylsilylethynyl-4-trimethylsilyloxy-1-heptene | cyclopent-2-en-1-one 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-ethynyl-20-nor-5-cis-13-trans prostadiene |
| 282 | 1-trans-tri-n-butylstannyl-5-methylene-4-triethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methylene-20-nor-5-cis-13-trans prostadiene |
| 283 | 1-trans-tri-n-butylstannyl-4-methyl-5-methylene-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-17-methylene-20-nor-5-cis-13-trans prostadiene |
| 284 | 1-trans-tri-n-butylstannyl-4-dimethoxymethyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-20-nor-5-cis-13-trans prostadiene |
| 285 | 1-trans-tri-n-butylstannyl-4-fluoromethyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-fluoromethyl-20-nor-5-cis-13-trans prostadiene |
| 286 | 1-trans-tri-n-butylstannyl-4-difluoromethyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-difluoromethyl-20-nor-5-cis-13-trans prostadiene |
| 287 | 1-trans-tri-n-butylstannyl-4-trifluoromethyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-trifluoromethyl-20-nor-5-cis-13-trans prostadiene |
| 288 | 1-trans-tri-n-butylstannyl-4-chloromethyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-chloromethyl-20-nor-5-cis-13-trans prostadiene |
| 289 | 1-trans-tri-n-butylstannyl-4-trimethylsilyloxymethyl-4-trimethylsilyloxy-1-heptene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 293 | 1-trans-iodo-4,4-dimethyl 3-trimethylsilyloxy-1-octene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-dimethyl-5-cis-13-trans prostadiene |
| 294 | 1-trans-iodo-4,4-trimethylene 3-trimethylsilyloxy-1-octene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-trimethylene-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 295 | 1-trans-tri-n-butylstannyl-3-vinyl-3-trimethylsilyloxy-1-octene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-15-vinyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 296 | 1-trans-iodo-4-triphenylmethoxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 297 | 1-trans-tri-n-butylstannyl-4-methyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-5-cis-13-trans prostadiene |

TABLE IV-continued

| | | | |
|---|---|---|---|
| 298 | 1-trans-tri-n-butylstannyl-5-methyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methyl-5-cis-13-trans prostadiene |
| 299 | 1-trans-tri-n-butylstannyl-4-vinyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-vinyl-5-cis-13-trans prostadiene |
| 300 | 1-trans-tri-n-butylstannyl-4-trimethylsilylethynyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-ethnyl-5-cis-13-trans prostadiene |
| 301 | 1-trans-tri-n-butylstannyl-5-methylene-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methylene-5-cis-13-trans prostadiene |
| 302 | 1-trans-tri-n-butylstannyl-4-methyl-5-methylene-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-17-methylene-5-cis-13-trans prostadiene |
| 303 | 1-trans-tri-n-butylstannyl-4-dimethoxymethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-formyl-5-cis-13-trans prostadiene |
| 304 | 1-trans-tri-n-butylstannyl-4-fluoromethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-fluoromethyl-5-cis-13-trans prostadiene |
| 305 | 1-trans-tri-n-butylstannyl-4-difluoromethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-difluoromethyl-5-cis-13-trans prostadiene |
| 306 | 1-trans-tri-n-butylstannyl-4-trifluooromethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-trifluoromethyl-5-cis-13-trans prostadiene |
| 307 | 1-trans-tri-n-butylstannyl-4-chloromethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-chloromethyl-5-cis-13-trans prostadiene |
| 308 | 1-trans-tri-n-butylstannyl-4-trimethylsilyloxymethyl-4-trimethylsilyloxy-1-octene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-hydroxymethyl-5-cis-13-trans prostadiene |
| EXAMPLE | VINYL IODIDE | CYCLOPENTENONE | PRODUCT PROSTAGLANDIN OF THE PGE2 SERIES |
| 309 | 1-trans-iodo-3-triphenylmethoxy-1-nonene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-20-methyl-5-cis-13-trans prostadiene |
| 310 | 1-trans-iodo-3-methyl-3-trimethylsilyloxy-1-nonene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-20-methyl-5-cis-13-trans prostadiene |
| 311 | 1-trans-iodo-4,4-dimethyl-3-trimethylsilyloxy-1-nonene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-dimethyl-20-methyl-5-cis-13-trans prostadiene |
| 312 | 1-trans-iodo-4,4-trimethylene-3-trimethylsilyloxy-1-nonene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-trimethylene-20-methyl-5-cis-13-trans prostadiene |
| EXAMPLE | VINYL TIN | CYCLOPENTENONE | PRODUCT PROSTAGLANDIN OF THE PGE2 SERIES |
| 313 | 1-trans-tri-n-butylstannyl-3-vinyl-3-trimethylsilyloxy-1-nonene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-15-vinyl-20-methyl-5-cis-13-trans prostadiene |

TABLE IV-continued

| EXAMPLE | VINYL IODIDE | CYCLOPENTENONE | PRODUCT PROSTAGLANDIN OF THE PGE2 SERIES |
|---|---|---|---|
| 314 | 1-trans-iodo-4-triphenylmethoxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-vinyl-20-methyl-5-cis-13-trans prostadiene |

| EXAMPLE | VINYL TIN | CYCLOPENTENONE | PROUCT PROSTAGLANDIN OF THE PGE2 SERIES |
|---|---|---|---|
| 318 | 1-trans-tri-n-butylstannyl-4-trimethylsilylethynyl-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-ethynyl-20-methyl-5-cis-13-trans prostadiene |
| 319 | 1-trans-tri-n-butylstannyl-4-trimethylsilyloxy-1-nonene-5-methylene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methylene-20-methyl-5-cis-13-trans prostadiene |
| 320 | 1-trans-tri-n-butylstannyl-4-methyl-5-methylene-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-17-methylene-20-methyl-5-cis-13-trans prostadiene |
| 321 | 1-trans-tri-n-butylstannyl-4-methyl-dimethoxymethyl-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-formyl-20-methyl-5-cis-13-trans prostadiene |
| 322 | 1-trans-tri-n-butylstannyl-4-methyl-4-fluoromethyl-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-fluoromethyl-20-methyl-5-cis-13-trans prostadiene |
| 323 | 1-trans-tri-n-butylstannyl-4-difluoromethyl-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-difluoromethyl-20-methyl-5-cis-13-trans prostadiene |
| 324 | 1-trans-tri-n-butylstannyl-4-trifluoromethyl-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-trifluoromethyl-20-methyl-5-cis-13-trans prostadiene |
| 325 | 1-trans-tri-n-butylstannyl-4-chloromethyl-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-chloromethyl-20-methyl-5-cis-13-trans prostadiene |
| 326 | 1-trans-tri-n-butylstannyl-4-trimethylsilyloxymethyl-4-trimethylsilyloxy-1-nonene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-hydroxymethyl-20-methyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 327 | 1-trans-iodo-3-trimethylsilyloxy-1-decene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-20-ethyl-5-cis-13-trans prostadiene |
| 328 | 1-trans-iodo-3-methyl-3-trimethylsilyloxy-1-decene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-15-methyl-20-ethyl-5-cis-13-trans prostadiene |
| 329 | 1-trans-iodo-4,4-dimethyl-3-trimethylsilyloxy-1-decene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-dimethyl-20-ethyl-5-cis-13-trans prostadiene |
| 330 | 1-trans-iodo-4,4-trimethylene-3-trimethylsilyloxy-1-decene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-16,16-trimethylene-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 331 | 1-trans-tri-n-butylstannyl-3-vinyl-3-trimethylsilyloxy-1-decene | 2-[6-methylthiaacetyl hex-2-cis-enyl]-4R-trimethylsiloxy cyclopent-2-en-1-one | nat-11a,15a-dihydroxy-1-methylthiamethyl-1,9-dioxo-15-vinyl-20-ethyl-5-cis-13-trans prostadiene |

TABLE IV-continued

| EXAMPLE | VINYL IODIDE | CYCLOPENTENONE | PRODUCT PROSTAGLANDIN OF THE PGE2 SERIES |
|---|---|---|---|
| 332 | 1-trans-iodo-4-triphenylmethoxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 333 | 1-trans-tri-n-butylstannyl-4-methyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-20-ethyl-5-cis-13-trans prostadiene |
| 334 | 1-trans-tri-n-butylstannyl-5-methyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methyl-20-ethyl-5-cis-13-trans prostadiene |
| 335 | 1-trans-tri-n-butylstannyl-4-vinyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-vinyl-20-ethyl-5-cis-13-trans prostadiene |
| 336 | 1-trans-tri-n-butylstannyl-4-trimethylsilylethynyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-ethynyl-20-ethyl-5-cis-13-trans prostadiene |
| 337 | 1-trans-tri-n-butylstannyl-5-methylene-4-triethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-17-methylene-20-ethyl-5-cis-13-trans prostadiene |
| 338 | 1-trans-tri-n-butylstannyl-4-methyl-5-methylene-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-methyl-17-methylene-20-ethyl-5-cis-13-trans prostadiene |
| 339 | 1-trans-tri-n-butylstannyl-4-dimethoxymethyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-formyl-20-ethyl-5-cis-13-trans prostadiene |
| 340 | 1-trans-tri-n-butylstannyl-4-fluoromethyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-fluoromethyl-20-ethyl-5-cis-13-trans prostadiene |
| 341 | 1-trans-tri-n-butylstannyl-4-difluoromethyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-difluoromethyl-20-ethyl-5-cis-13-trans prostadiene |
| 342 | 1-trans-tri-n-butylstannyl-4-trifluoromethyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-trifluoromethyl-20-ethyl-5-cis-13-trans prostadiene |
| 343 | 1-trans-tri-n-butylstannyl-4-chloromethyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-chloromethyl-20-ethyl-5-cis-13-trans prostadiene |
| 344 | 1-trans-tri-n-butylstannyl-4-trimethylsilyloxymethyl-4-trimethylsilyloxy-1-decene | 2-[6-methylthiaacetyl hex-2-cis-enyl]-4R-trimethylsiloxy cyclopent-2-en-1-one | nat-11a,16-dihydroxy-1-methylthiamethyl-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 345 | 1-trans-iodo-3-triphenylmethoxy-1-heptene | 2-[5-methylthiaacetyl pent-2-cis-enyl] cyclopent-2-en-1-one | dl-15a-hydroxy-1-methylthiamethyl-1,9-dioxo-20-nor-2-nor-5-cis-13-trans prostadiene |
| 346 | 1-trans-iodo-3-methyl-3-trimethylsilyloxy-1-heptene | 2-[5-methylthiaacetyl pent-2-cis-enyl] cyclopent-2-en-1-one | dl-15a-hydroxy-1-methylthiamethyl-1,9-dioxo-20-nor-2-nor-5-cis-13-trans prostadiene |
| 347 | 1-trans-iodo-4,4-dimethyl-3-trimethylsilyloxy-1-heptene | 2-[5-methylthiaacetyl pent-2-cis-enyl] cyclopent-2-en-1-one | dl-15a-hydroxy-1-methylthiamethyl-1,9-dioxo-16,16-dimethyl-20-nor-2-nor-5-cis-13-trans prostadiene |

TABLE IV-continued

| EXAMPLE | VINYL TIN / VINYL IODIDE | CYCLOPENTENONE | PRODUCT PROSTAGLANDIN |
|---|---|---|---|
| 348 | 1-trans-iodo-5,5-dimethyl 3-triphenylmethoxy-1-octene | 2-[5-methylthiaacetyl pent-2-cis-enyl] cyclopent-2-en-1-one | dl-15a-hydroxy-1-methylthiamethyl-1,9-dioxo-17,17-dimethyl-2-nor-5-cis-13-trans prostadiene |
| 349 | 1-trans-iodo-4-methyl-3-triphenylmethoxy-1-octene | 2-[5-methylthiaacetyl pent-2-cis-enyl] cyclopent-2-en-1-one | dl-15a-hydroxy-1-methylthiamethyl-1,9-dioxo-16-methyl-2-nor-5-cis-13-trans prostadiene |
| 350 | 1-trans-iodo-4,4-trimethylene 3-trimethylsilyloxy-1-heptene | 2-[5-methylthiaacetyl pent-2-cis-enyl] cyclopent-2-en-1-one | dl-15a-hydroxy-1-methylthiamethyl-1,9-dioxo-16,16-trimethylene-20-nor-2-nor-5-cis-13-trans prostadiene |

PRODUCT PROSTAGLANDIN OF THE 11-DEOXY PGE2 SERIES

| EXAMPLE | VINYL TIN | CYCLOPENTENONE | PRODUCT PROSTAGLANDIN |
|---|---|---|---|
| 351 | 1-trans-tri-n-butylstannyl-3-vinyl-3-trimethylsilyloxy-1-heptene | 2-[5-methylthiaacetyl pent-2-cis-enyl] cyclopent-2-en-1-one | dl-15a-hydroxy-1-methylthiamethyl-1,9-dioxo-15-vinyl-20-nor-2-nor-5-cis-13-trans prostadiene |
| 352 | 1-trans-tri-n-butylstannyl-4-phenoxy 3-triethylsilyloxy-1-butene | 2-[5-methylthiaacetyl pent-2-cis-enyl] cyclopent-2-en-1-one | dl-15a-hydroxy-1-methylthiamethyl-1,9-dioxo-16-phenoxy-2-nor-17-20-tetranor-5-cis-13-trans prostadiene |
| 353 | 1-trans-tri-n-butylstannyl-4-(p-fluorophenoxy) 3-triethylsilyloxy-1-butene | 2-[5-methylthiaacetyl pent-2-cis-enyl] cyclopent-2-en-1-one | dl-15a-hydroxy-1-methylthiamethyl-1,9-dioxo-16-(p-fluorophenoxy)-2-nor-17-20-tetranor-5-cis-13-trans prostadiene |
| 354 | 1-trans-tri-n-butylstannyl-4-(m-chlorophenoxy) 3-triethylsilyloxy-1-butene | 2-[5-methylthiaacetyl pent-2-cis-enyl] cyclopent-2-en-1-one | dl-15a-hydroxy-1-methylthiamethyl-1,9-dioxo-16-(m-chlorophenoxy)-2-nor-17-20-tetranor-5-cis-13-trans prostadiene |
| 355 | 1-trans-tri-n-butylstannyl-4-(m-trifluoromethylphenoxy) 3-triethylsilyloxy-1-butene | 2-[5-methylthiaacetyl pent-2-cis-enyl] cyclopent-2-en-1-one | dl-15a-hydroxy-1-methylthiamethyl-1,9-dioxo-16-(m-trifluoromethylphenoxy)-2-nor-17-20-tetranor-5-cis-13-trans prostadiene |

PRODUCT PROSTAGLANDIN OF THE 11-DEOXY PGE2 SERIES

| EXAMPLE | VINYL IODIDE | CYCLOPENTENONE | PRODUCT PROSTAGLANDIN |
|---|---|---|---|
| 356 | 1-trans-iodo-5-phenyl 3-trimethylsilyloxy-1-pentene | 2-[5-methylthiaacetyl pent-2-cis-enyl] cyclopent-2-en-1-one | dl-15a-hydroxy-1-methylthiamethyl-1,9-dioxo-17-phenyl-2-nor-18-20-trinor-5-cis-13-trans prostadiene |
| 357 | 1-trans-iodo-4,4-dimethyl-5-phenyl 3-trimethylsilyloxy-1-pentene | 2-[5-methylthiaacetyl pent-2-cis-enyl] cyclopent-2-en-1-one | dl-15a-hydroxy-1-methylthiamethyl-1,9-dioxo-16,16-dimethyl-17-phenyl-20-trinor-5-cis-13-trans prostadiene |
| 358 | 1-trans-iodo-4-cyclopentyl 3-triphenylmethoxy-1-butene | 2-[5-methylthiaacetyl pent-2-cis-enyl] cyclopent-2-en-1-one | dl-15a-hydroxy-1-methylthiamethyl-1,9-dioxo-16-cyclopentyl-2-nor-17-20-tetranor-5-cis-13-trans prostadiene |
| 359 | 1-trans-iodo-4-cyclohexal 3-triphenylmethoxy-1-butene | 2-[5-methylthiaacetyl pent-2-cis-enyl] cyclopent-2-en-1-one | dl-15a-hydroxy-1-methylthiamethyl-1,9-dioxo-16-cyclohexyl-2-nor-17-20-tetranor-5-cis-13-trans prostadiene |
| 360 | 1-trans-iodo-4-triphenylmethoxy-1-heptene | 2-[5-methylthiaacetyl pent-2-cis-enyl] cyclopent-2-en-1-one | dl-16-hydroxy-1-methylthiamethyl-1,9-dioxo-20-nor-2-nor-5-cis-13-trans prostadiene |

PRODUCT PROSTAGLANDIN OF THE 11-DEOXY PGE2 SERIES

| EXAMPLE | VINYL TIN | CYCLOPENTENONE | PRODUCT PROSTAGLANDIN |
|---|---|---|---|
| 361 | 1-trans-tri-n-butylstannyl-5-methyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-methyl-20-nor-2-nor-5-cis-13-trans prostadiene |
| 362 | 1-trans-tri-n-butylstannyl-4-ethyl-4-trimethylsilyloxy-1-octene | 2-[5-methylthiaacetyl pent-2-cis-enyl] cyclopent-2-en-1-one | dl-16-hydroxy-1-methylthiamethyl-1,9-dioxo-16-ethyl-2-nor-5-cis-13-trans prostadiene |
| 363 | 1-trans-tri-n-butylstannyl-5-methyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-17-methyl-20-nor-2-nor-5-cis-13-trans prostadiene |

TABLE IV-continued

| EXAMPLE | VINYL IODIDE | cyclopent-2-en-1-one | PRODUCT PROSTAGLANDIN OF THE 11-DEOXY PGE2 SERIES |
|---|---|---|---|
| 364 | 1-trans-iodo-5,5-dimethyl-4-trimethylsilyloxy-1-octene | 2-[5-methylthiaacetyl pent-2-cis-enyl] cyclopent-2-en-1-one | dl-16-hydroxy-1-methylthiamethyl-1,9-dioxo-17,17-dimethyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 365 | 1-trans-tri-n-butylstannyl-4-vinyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-vinyl-20-nor-2-nor-5-cis-13-trans prostadiene |
| 366 | 1-trans-tri-n-butylstannyl-4-cyclopropyl-4-trimethylsilyloxy-1-octene | 2-[5-methylthiaacetyl pent-2-cis-enyl] cyclopent-2-en-1-one | dl-16-hydroxy-1-methylthiamethyl-1,9-dioxo-16-cyclopropyl-2-nor-5-cis-13-trans prostadiene |
| 367 | 1-trans-tri-n-butylstannyl-4-trimethylsilylethynyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-ethylyl-20-nor-2-nor-5-cis-13-trans prostadiene |
| 368 | 1-trans-tri-n-butylstannyl-5-methylene-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-17-methylene-20-nor-2-nor-5-cis-13-trans prostadiene |
| 369 | 1-trans-tri-n-butylstannyl-4-methyl-5-methylene-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-methyl-17-methylene-20-nor-2-nor-5-cis-13-trans prostadiene |
| 370 | 1-trans-tri-n-butylstannyl-4-dimethoxymethyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-formyl-20-nor-2-nor-5-cis-13-trans prostadiene |
| 371 | 1-trans-tri-n-butylstannyl-4-fluoromethyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-fluoromethyl-20-nor-2-nor-5-cis-13-trans prostadiene |
| 372 | 1-trans-tri-n-butylstannyl-4-difluoromethyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-difluoromethyl-20-nor-2-nor-5-cis-13-trans prostadiene |
| 373 | 1-trans-tri-n-butylstannyl-4-trifluoromethyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-trifluoromethyl-20-nor-2-nor-5-cis-13-trans prostadiene |
| 374 | 1-trans-tri-n-butylstannyl-4-chloromethyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-chloromethyl-20-nor-2-nor-5-cis-13-trans prostadiene |
| 375 | 1-trans-tri-n-butylstannyl-4-trimethylsilyloxymethyl-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-hydroxymethyl-20-nor-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 376 | 1-trans-iodo-4-methyl-7-chloro-4-trimethylsilyloxy-1-heptene | 2-[5-methylthiaacetyl pent-2-cis-enyl] cyclopent-2-en-1-one | dl-16-hydroxy-1-methylthiamethyl-1,9-dioxo-16-methyl-19-chloro-2-nor-20-nor-5-cis-13-trans prostadiene |
| 377 | 1-trans-iodo-3-triphenylmethoxy-1-octene | 2-[5-methylthiaacetyl pent-2-cis-enyl] cyclopent-2-en-1-one | dl-15a-hydroxy-1-methylthiamethyl-1,9-dioxo-2-nor-5-cis-13-trans prostadiene |
| 378 | 1-trans-iodo-3-methyl-3-trimethylsilyloxy-1-octene | 2-[5-methylthiaacetyl pent-2-cis-enyl] cyclopent-2-en-1-one | dl-15a-hydroxy-1-methylthiamethyl-1,9-dioxo-15-methyl-2-nor-5-cis-13-trans prostadiene |
| 379 | 1-trans-iodo-4,4-dimethyl | 2-[5-methylthiaacetyl pent-2-cis-enyl] | dl-15a-hydroxy-1-methylthiamethyl-1,9-dioxo- |

TABLE IV-continued

| | VINYL TIN | | |
|---|---|---|---|
| | 3-trimethylsilyloxy-1-octene | pent-2-cis-enyl]cyclopent-2-en-1-one | 16,16-dimethyl-2-nor-5-cis-13-trans prostadiene |
| 380 | 1-trans-iodo-4,4-trimethylene 3-trimethylsilyloxy-1-octene | 2-[5-methylthiaacetyl pent-2-cis-enyl]cyclopent-2-en-1-one | dl-15a-hydroxy-1-methylthiamethyl-1,9-dioxo-16,16-trimethylene-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 381 | 1-trans-tri-n-butylstannyl-3-vinyl-3-trimethylsilyloxy-1-octene | 2-[5-methylthiaacetyl pent-2-cis-enyl]cyclopent-2-en-1-one | dl-15a-hydroxy-1-methylthiamethyl-1,9-dioxo-15-vinyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 382 | 1-trans-iodo-4-triphenylmethoxy-1-octene | 2-[5-methylthiaacetyl pent-2-cis-enyl]cyclopent-2-en-1-one | dl-16-hydroxy-1-methylthiamethyl-1,9-dioxo-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 383 | 1-trans-tri-n-butylstannyl-4-methyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-methyl-2-nor-5-cis-13-trans prostadiene |
| 384 | 1-trans-tri-n-butylstannyl-5-methyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-17-methyl-2-nor-5-cis-13-trans prostadiene |
| 385 | 1-trans-tri-n-butylstannyl-4-vinyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-vinyl-2-nor-5-cis-13-trans prostadiene |
| 386 | 1-trans-tri-n-butylstannyl-4-trimethylsilylethynyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-ethynyl-2-nor-5-cis-13-trans prostadiene |
| 387 | 1-trans-tri-n-butylstannyl-5-methylene-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-17-methylene-2-nor-5-cis-13-trans prostadiene |
| 388 | 1-trans-tri-n-butylstannyl-4-methyl-5-methylene-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-methyl-17-methylene-2-nor-5-cis-13-trans prostadiene |
| 389 | 1-trans-tri-n-butylstannyl-4-dimethoxymethyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-formyl-2-nor-5-cis-13-trans prostadiene |
| 390 | 1-trans-tri-n-butylstannyl-4-fluoromethyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-fluoromethyl-2-nor-5-cis-13-trans prostadiene |
| 391 | 1-trans-tri-n-butylstannyl-4-difluoromethyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-difluoromethyl-2-nor-5-cis-13-trans prostadiene |
| 392 | 1-trans-tri-n-butylstannyl-4-trifluoromethyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-trifluoromethyl-2-nor-5-cis-13-trans prostadiene |
| 393 | 1-trans-tri-n-butylstannyl-4-chloromethyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-chloromethyl-2-nor-5-cis-13-trans prostadiene |
| 394 | 1-trans-tri-n-butylstannyl-4-trimethylsilyloxymethyl-4-trimethylsilyloxy-1-octene | 2-[5-methylthiaacetyl pent-2-cis-enyl]cyclopent-2-en-1-one | dl-16-hydroxy-1-methylthiamethyl-1,9-dioxo-16-hydroxymethyl-2-nor-5-cis-13-trans prostadiene |

TABLE IV-continued

| EXAMPLE | VINYL IODIDE | CYCLOPENTENONE | PRODUCT PROSTAGLANDIN OF THE 11-DEOXY PGE2 SERIES |
|---|---|---|---|
| 395 | 1-trans-iodo-3-triphenylmethoxy-1-nonene | 2-[5-methylthiaacetyl pent-2-cis-enyl] cyclopent-2-en-1-one | dl-15a-hydroxy-1-methylthiamethyl-1,9-dioxo-20-methyl-2-nor-5-cis-13-trans prostadiene |
| 396 | 1-trans-iodo-3-methyl-3-trimethylsilyloxy-1-nonene | 2-[5-methylthiaacetyl pent-2-cis-enyl] cyclopent-2-en-1-one | dl-15a-hydroxy-1-methylthiamethyl-1,9-dioxo-15-methyl-20-methyl-2-nor-5-cis-13-trans prostadiene |
| 397 | 1-trans-iodo-4,4-dimethyl-3-trimethylsilyloxy-1-nonene | 2-[5-methylthiaacetyl pent-2-cis-enyl] cyclopent-2-en-1-one | dl-15a-hydroxy-1-methylthiamethyl-1,9-dioxo-16,16-dimethyl-20-methyl-2-nor-5-cis-13-trans prostadiene |
| 398 | 1-trans-iodo-4,4-trimethylene-3-trimethylsilyloxy-1-nonene | 2-[5-methylthiaacetyl pent-2-cis-enyl] cyclopent-2-en-1-one | dl-15a-hydroxy-1-methylthiamethyl-1,9-dioxo-16,16-trimethylene-20-methyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 399 | 1-trans-tri-n-butylstannyl-3-vinyl-3-trimethylsilyloxy-1-nonene | 2-[5-methylthiaacetyl pent-2-cis-enyl] cyclopent-2-en-1-one | dl-15a-hydroxy-1-methylthiamethyl-1,9-dioxo-15-vinyl-20-methyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 400 | 1-trans-iodo-4-triphenylmethoxy-1-nonene | 2-[5-methylthiaacetyl pent-2-cis-enyl] cyclopent-2-en-1-one | dl-16-hydroxy-1-methylthiamethyl-1,9-dioxo-20-methyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 401 | 1-trans-tri-n-butylstannyl-4-methyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-methyl-20-methyl-2-nor-5-cis-13-trans prostadiene |
| 402 | 1-trans-tri-n-butylstannyl-4-methyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-17-methyl-20-methyl-2-nor-5-cis-13-trans prostadiene |
| 403 | 1-trans-tri-n-butylstannyl-4-methyl-4-vinyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-vinyl-20-methyl-2-nor-5-cis-13-trans prostadiene |
| 404 | 1-trans-tri-n-butylstannyl-4-trimethylsilylethynyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-ethynyl-20-methyl-2-nor-5-cis-13-trans prostadiene |
| 405 | 1-trans-tri-n-butylstannyl-5-methylene-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-17-methylene-20-methyl-2-nor-5-cis-13-trans prostadiene |
| 406 | 1-trans-tri-n-butylstannyl-4-methyl-5-methylene-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-methyl-17-methylene-20-methyl-2-nor-5-cis-13-trans prostadiene |
| 407 | 1-trans-tri-n-butylstannyl-4-dimethoxymethyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-formyl-20-methyl-2-nor-5-cis-13-trans prostadiene |
| 408 | 1-trans-tri-n-butylstannyl-4-fluoromethyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-fluoromethyl-20-methyl-2-nor-5-cis-13-trans prostadiene |
| 409 | 1-trans-tri-n-butylstannyl-4-difluoromethyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-difluoromethyl-20-methyl-2-nor-5-cis-13-trans prostadiene |
| 410 | 1-trans-tri-n-butylstannyl-4-trifluoromethyl- | 2-[5-methylthiaacetyl | dl-16-hydroxy-1-methylthiamethyl-1,9-dioxo-16-trifluoromethyl- |

TABLE IV-continued

| EXAMPLE | VINYL IODIDE / VINYL TIN | CYCLOPENTENONE | PRODUCT PROSTAGLANDIN |
|---|---|---|---|
| | 4-trimethylsilyloxy-1-nonene | pent-2-cis-enyl] cyclopent-2-en-1-one | 20-methyl-2-nor-5-cis-13-trans prostadiene |
| 411 | 1-trans-tri-n-butylstannyl-4-chloromethyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-chloromethyl-20-methyl-2-nor-5-cis-13-trans prostadiene |
| 412 | 1-trans-tri-n-butylstannyl-4-trimethylsilyloxymethyl-4-trimethylsilyloxy-1-nonene | 2-[5-methylthiaacetyl pent-2-cis-enyl] cyclopent-2-en-1-one | dl-16-hydroxy-1-methylthiamethyl-1,9-dioxo-16-hydroxymethyl-20-methyl-2-nor-5-cis-13-trans prostadiene |

PRODUCT PROSTAGLANDIN OF THE 11-DEOXY PGE2 SERIES

| EXAMPLE | VINYL IODIDE | CYCLOPENTENONE | PRODUCT |
|---|---|---|---|
| 413 | 1-trans-iodo-4-triphenylmethoxy-1-decene | 2-[5-methylthiaacetyl pent-2-cis-enyl] cyclopent-2-en-1-one | dl-15a-hydroxy-1-methylthiamethyl-1,9-dioxo-20-ethyl-2-nor-5-cis-13-trans prostadiene |
| 414 | 1-trans-iodo-3-methyl-3-trimethylsilyloxy-1-decene | 2-[5-methylthiaacetyl pent-2-cisenyl] cyclopent-2-en-1-one | dl-15a-hydroxy-1-methylthiamethyl-1,9-dioxo-15-methyl-20-ethyl-2-nor-5-cis-13-trans prostadiene |
| 415 | 1-trans-iodo-4,4-dimethyl-3-trimethylsilyloxy-1-decene | 2-[5-methylthiaacetyl pent-2-cis-enyl] cyclopent-2-en-1-one | dl-15a-hydroxy-1-methylthiamethyl-1,9-dioxo-16,16-dimethyl-20-ethyl-2-nor-5-cis-13-trans prostadiene |
| 416 | 1-trans-iodo-4,4-trimethylene-3-trimethylsilyloxy-1-decene | 2-[5-methylthiaacetyl pent-2-cis-enyl] cyclopent-2-en-1-one | dl-15a-hydroxy-1-methylthiamethyl-1,9-dioxo-16,16-trimethylene-20-ethyl-2-nor-5-cis-13-trans prostadiene |

PRODUCT PROSTAGLANDIN OF THE 11-DEOXY PGE2 SERIES

| EXAMPLE | VINYL TIN | CYCLOPENTENONE | PRODUCT |
|---|---|---|---|
| 417 | 1-trans-tri-n-butylstannyl-3-vinyl-3-trimethylsilyloxy-1-decene | 2-[5-methylthiaacetyl pent-2-cis-enyl] cyclopent-2-en-1-one | dl-15a-hydroxy-1-methylthiamethyl-1,9-dioxo-15-vinyl-20-ethyl-2-nor-5-cis-13-trans prostadiene |

PRODUCT PROSTAGLANDIN OF THE 11-DEOXY PGE2 SERIES

| EXAMPLE | VINYL IODIDE | CYCLOPENTENONE | PRODUCT |
|---|---|---|---|
| 418 | 1-trans-iodo-4-triphenylmethoxy-1-decene | 2-[5-methylthiaacetyl pent-2-cis-enyl] cyclopent-2-en-1-one | dl-16-hydroxy-1-methylthiamethyl-1,9-dioxo-20-ethyl-2-nor-5-cis-13-trans prostadiene |

PRODUCT PROSTAGLANDIN OF THE 11-DEOXY PGE2 SERIES

| EXAMPLE | VINYL TIN | CYCLOPENTENONE | PRODUCT |
|---|---|---|---|
| 419 | 1-trans-tri-n-butylstannyl-4-methyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-methyl-20-ethyl-2-nor-5-cis-13-trans prostadiene |
| 420 | 1-trans-tri-n-butylstannyl-5-methyl-4-trimethylsilyloxy-1-decene | 2-[5-methylthiaacetyl pent-2-cis-enyl] cyclopene-2-en-1-one | dl-16-hydroxy-1-methylthiamethyl-1,9-dioxo-17-methyl-20-ethyl-2-nor-5-cis-13-trans prostadiene |
| 421 | 1-trans-tri-n-butylstannyl-4-vinyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-vinyl-20-ethyl-2-nor-5-cis-13-trans prostadiene |
| 422 | 1-trans-tri-n-butylstannyl-4-trimethylsilylethynyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-ethynyl-20-ethyl-2-nor-5-cis-13-trans prostadiene |
| 423 | 1-trans-tri-n-butylstannyl-5-methylene-4-triethylsilyloxy-1-decene | 2-[5-methylthiaacetyl pent-2-cis-enyl] cyclopent-2-en-1-one | dl-16-hydroxy-1-methylthiamethyl-1,9-dioxo-17-methylene-20-ethyl-2-nor-5-cis-13-trans prostadiene |
| 424 | 1-trans-tri-n-butylstannyl-4-methyl-5-methylene-4-trimethylsilyloxy-1-decene | 2-[5-methylthiaacetyl pent-2-cis-enyl] cyclopent-2-en-..-one | dl-16-hydroxy-1-methylthiamethyl-1,9-dioxo-16-methyl-17-methylene-20-ethyl-2-nor-5-cis-13-trans prostadiene |
| 425 | 1-trans-tri-n-butylstannyl-4-dimethoxymethyl- | 2-[5-methylthiaacetyl | dl-16-hydroxy-1-methylthiamethyl-1,9-dioxo-16-formyl- |

TABLE IV-continued

| | | | |
|---|---|---|---|
| | 4-trimethylsilyloxy-1-decene | pent-2-cis-enyl] cyclopent-2-en-1-one | 20-ethyl-2-nor-5-cis-13-trans prostadiene |
| 426 | 1-trans-tri-n-butylstannyl-4-fluoromethyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-fluoromethyl-20-ethyl-2-nor-5-cis-13-trans prostadiene |
| 427 | 1-trans-tri-n-butylstannyl-4-difluoromethyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-difluoromethyl-20-ethyl-2-nor-5-cis-13-trans prostadiene |
| 428 | 1-trans-tri-n-butylstannyl-4-trifluoromethyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-trifluoromethyl-20-ethyl-2-nor-5-cis-13-trans prostadiene |
| 429 | 1-trans-tri-n-butylstannyl-4-chloromethyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-chloromethyl-20-ethyl-2-nor-5-cis-13-trans prostadiene |
| 430 | 1-trans-tri-n-butylstannyl-4-trimethylsilyloxymethyl-4-trimethylsilyloxy-1-decene | 2-[5-methylthiaacetyl pent-2-cis-enyl] cyclopent-2-en-1-one | dl-16-hydroxy-1-methylthiamethyl-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 431 | 1-trans-iodo-3-triphenylmethoxy-1-heptene | 2-[6-methylthiaacetyl hex-2-cis-enyl] cyclopent-2-en-1-one | dl-15a-hydroxy-1-methylthiamethyl-1,9-dioxo-20-nor-5-cis-13-trans prostadiene |
| 432 | 1-trans-iodo-3-methyl-3-trimethylsilyloxy-1-heptene | 2-[6-methylthiaacetyl hex-2-cis-enyl] cyclopent-2-en-1-one | dl-15a-hydroxy-1-methylthiamethyl-1,9-dioxo-15-methyl-20-nor-5-cis-13-trans prostadiene |
| 433 | 1-trans-iodo-4,4-dimethyl-3-trimethylsilyloxy-1-heptene | 2-[6-methylthiaacetyl hex-2-cis-enyl] cyclopent-2-en-1-one | dl-15a-hydroxy-1-methylthiamethyl-1,9-dioxo-16,16-dimethyl-20-nor-5-cis-13-trans prostadiene |
| 434 | 1-trans-iodo-5,5-dimethyl-3-triphenylmethoxy-1-octene | 2-[6-methylthiaacetyl hex-2-cis-enyl] cyclopent-2-en-1-one | dl-15a-hydroxy-1-methylthiamethyl-1,9-dioxo-17,17-dimethyl-5-cis-13-trans prostadiene |
| 435 | 1-trans-iodo-4-methyl-3-triphehylmethoxy-1-octene | 2-[6-methylthiaacetyl hex-2-cis-enyl] cyclopent-2-en-1-one | dl-15a-hydroxy-1-methylthiamethyl-1,9-dioxo-16-methyl-5-cis-13-trans prostadiene |
| 436 | 1-trans-iodo-4,4,4-trimethylene-3-trimethylsilyloxy-1-heptene | 2-[6-methylthiaacetyl hex-2-cis-enyl] cyclopent-2-en-1-one | dl-15a-hydroxy-1-methylthiamethyl-1,9-dioxo-16,16-trimethylene-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 437 | 1-trans-tri-n-butylstannyl-3-vinyl-3-trimethylsilyloxy-1-heptene | 2-[6-methylthiaacetyl hex-2-cis-enyl] cyclopent-2-en-1-one | dl-15a-hydroxy-1-methylthiamethyl-1,9-dioxo-15-vinyl-20-nor-5-cis-13-trans prostadiene |
| 438 | 1-trans-tri-n-butylstannyl-4-phenoxy-3-triethylsilyloxy-1-butene | 2-[6-methylthiaacetyl hex-2-cis-enyl] cyclopent-2-en-1-one | dl-15a-hydroxy-1-methylthiamethyl-1,9-dioxo-16-phenoxy-17-20-tetranor-5-cis-13-trans prostadiene |
| 439 | 1-trans-tri-n-butylstannyl-4-(p-fluorophenoxy)-3-triethylsilyloxy-1-butene | 2-[6-methylthiaacetyl hex-2-cis-enyl] cyclopent-2-en-1-one | dl-15a-hydroxy-1-methylthiamethyl-1,9-dioxo-16-(p-fluorophenoxy)-17-20-tetranor-5-cis-13-trans prostadiene |
| 440 | 1-trans-tri-n-butylstannyl-4-(m-chlorophenoxy)-3-triethylsilyloxy-1-butene | 2-[6-methylthiaacetyl hex-2-cis-enyl] cyclopent-2-en-1-one | dl-15a-hydroxy-1-methylthiamethyl-1,9-dioxo-16-(m-chlorophenoxy)-17-20-tetranor-5-cis-13-trans prostadiene |
| 441 | 1-trans-tri-n-butylstannyl-4-(m-trifluoromethylphenoxy)-3-triethylsilyloxy-1-butene | 2-[6-methylthiaacetyl hex-2-cis-enyl] cyclopent-2-en-1-one | dl-16a-hydroxy-1-methylthiamethyl-1,9-dioxo-16-(m-trifluoromethylphenoxy)-17-20-tetranor-5-cis-13-trans prostadiene |

TABLE IV-continued

| EXAMPLE | VINYL IODIDE | CYCLOPENTENONE | PRODUCT PROSTAGLANDIN OF THE 11-DEOXY PGE2 SERIES |
|---|---|---|---|
| | | cyclopent-2-en-1-one | |
| 442 | 1-trans-iodo-5-phenyl 3-triethylsilyloxy-1-pentene | 2-[6-methylthiaacetyl hex-2-cis-enyl] cyclopent-2-en-1-one | dl-15a-hydroxy-1-methylthiamethyl-1,9-dioxo-17-phenyl-18-20-trinor-5-cis-13-trans prostadiene |
| 443 | 1-trans-iodo-4,4-dimethyl-5-phenyl 3-triethylsilyloxy-1-pentene | 2-[6-methylthiaacetyl hex-2-cis-enyl] cyclopent-2-en-1-one | dl-15a-hydroxy-1-methylthiamethyl-1,9-dioxo-16,16-dimethyl-17-phenyl-18-20-trinor-5-cis-13-trans prostadiene |
| 444 | 1-trans-iodo-4-cyclopentyl 3-triphenylmethoxy-1-butene | 2-[6-methylthiaacetyl hex-2-cis-enyl] cyclopent-2-en-1-one | dl-15a-hydroxy-1-methylthiamethyl-1,9-dioxo-16-cyclopentyl-17-20-tetranor-5-cis-13-trans prostadiene |
| 445 | 1-trans-iodo-4-cyclohexyl 3-triphenymethoxy-1-butene | 2-[6-methylthiaacetyl hex-2-cis-enyl] cyclopent-2-en-1-one | dl-15a-hydroxy-1-methylthiamethyl-1,9-dioxo-16-cyclohexyl-17-20-tetranor-5-cis-13-trans prostadiene |
| 446 | 1-trans-iodo-4-triphenylmethoxy-1-heptene | 2-[6-methylthiaacetyl hex-2-cis-enyl] cyclopent-2-en-1-one | dl-16-hydroxy-1-methylthiamethyl-1,9-dioxo-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 447 | 1-1-trans-tri-n-butylstannyl-4-methyl-4-trimethylsilyloxy-1-heptene | 2-[6-methylthiaacetyl hex-2-cis-enyl] cyclopent-2-en-1-one | dl-16-hydroxy-1-methylthiamethyl-1,9-dioxo-16-methyl-20-nor-5-cis-13-trans prostadiene |
| 448 | 1-trans-tri-n-butylstannyl-4-ethyl-4-trimethylsilyloxy-1-octene | 2-[6-methylthiaacetyl hex-2-cis-enyl] cyclopent-2-en-1-one | dl-16-hydroxy-1-methylthiamethyl-1,9-dioxo-16-ethyl-5-cis-13-trans prostadiene |
| 449 | 1-trans-tri-n-butylstannyl-5-methyl-4-trimethylsilyloxy-1-heptene | 2-[6-methylthiaacetyl hex-2-cis-enyl] cyclopent-2-en-1-one | dl-16-hydroxy-1-methylthiamethyl-1,9-dioxo-17-methyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 450 | 1-trans-iodo-5,5-dimethyl 4-trimethylsilyloxy-1-octene | 2-[6-methylthiaacetyl hex-2-cis-enyl] cyclopent-2-en-1-one | dl-16-hydroxy-1-methylthiamethyl-1,9-dioxo-17,17-dimethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 451 | 1-trans-tri-n-butylstannyl-4-vinyl-4-trimethylsilyloxy-1-heptene | 2-[6-methylthiaacetyl hex-2-cis-enyl] cyclopent-2-cis-en-1-one | dl-16-hydroxy-1-methylthiamethyl-1,9-dioxo-16-vinyl-20-nor-5-cis-13-trans prostadiene |
| 452 | 1-trans-tri-n-butylstannyl-4-cyclopropyl-4-trimethylsilyloxy-1-octene | 2-[6-methylthiaacetyl hex-2-cis-enyl] cyclopent-2-en-1-one | dl-16-hydroxy-1-methylthiamethyl-1,9-dioxo-16-cyclopropyl-5-cis-13-trans prostadiene |
| 453 | 1-trans-tri-n-butylstannyl-4-trimethylsilylethynyl-4-trimethylsilyloxy-1-heptene | 2-[6-methylthiaacetyl hex-2-cis-enyl] cyclopent-2-en-1-one | dl-16-hydroxy-1-methylthiamethyl-1,9-dioxo-16-ethynyl-20-nor-5-cis-13-trans prostadiene |
| 454 | 1-trans-tri-n-butylstannyl-5-methylene-4-triethylsilyloxy-1-heptene | 2-[6-methylthiaacetyl hex-2-cis-enyl] cyclopent-2-en-1-one | dl-16-hydroxy-1-methylthiamethyl-1,9-dioxo-17-methylene-20-nor-5-cis-13-trans prostadiene |
| 455 | 1-trans-tri-n-butlstannyl-4-methyl-5-methylene 4-trimethylsilyloxy-1-heptene | 2-[6-methylthiaacetyl hex-2-cis-enyl] cyclopent-2-en-1-one | dl-16-hydroxy-1-methylthiamethyl-1,9-dioxo-16-methyl-17-methylene-20-nor-5-cis-13-trans prostadiene |
| 456 | 1-trans-tri-n-butylstannyl-4-dimethoxymethyl-4-trimethylsilyloxy-1-heptene | 2-[6-methylthiaacetyl hex-2-cis-enyl] cyclopent-2-en-1-one | dl-16-hydroxy-1-methylthiamethyl-1,9-dioxo-16-formyl-20-nor-5-cis-13-trans prostadiene |

TABLE IV-continued

| | | | |
|---|---|---|---|
| 457 | 1-trans-tri-n-butylstannyl-4-fluoromethyl-4-trimethylsilyloxy-1-heptene | cyclopent-2-en-1-one 2-[6-methylthiaacetyl hex-2-cis-enyl] | dl-16-hydroxy-1-methylthiamethyl-1,9-dioxo-16-fluoromethyl-20-nor-5-cis-13-trans prostadiene |
| 458 | 1-trans-tri-n-butylstannyl-4-difluoromethyl-4-trimethylsilyloxy-1-heptene | cyclopent-2-en-1-one 2-[6-methylthiaacetyl hex-2-cis-enyl] | dl-16-hydroxy-1-methylthiamethyl-1,9-dioxo-16-difluoromethyl-20-nor-5-cis-13-trans prostadiene |
| 459 | 1-trans-tri-n-butylstannyl-4-trifluoromethyl-4-trimethylsilyloxy-1-heptene | cyclopent-2-en-1-one 2-[6-methylthiaacetyl hex-2-cis-enyl] | dl-16-hydroxy-1-methylthiamethyl-1,9-dioxo-16-trifluoromethyl-20-nor-5-cis-13-trans prostadiene |
| 460 | 1-trans-tri-n-butylstannyl-4-chloromethyl-4-trimethylsilyloxy-1-heptene | cyclopent-2-en-1-one 2-[6-methylthiaacetyl hex-2-cis-enyl] | dl-16-hydroxy-1-methylthiamethyl-1,9-dioxo-16-chloromethyl-20-nor-5-cis-13-trans prostadiene |
| 461 | 1-trans-tri-n-butylstannyl-4-trimethylsilyloxymethyl-4-trimethylsilyloxy-1-heptene | 2[6-methylthiaacetyl hex-2-cis-enyl] cyclopent-2-en-1-one | dl-16-hydroxy-1-methylthiamethyl-1,9-dioxo-16-hydroxymethyl-20-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 462 | 1-trans-iodo-4-methyl-7-chloro 4-trimethylsilyloxy-1-heptene | 2-[6-methylthiaacetyl hex-2-cis-enyl] cyclopent-2-en-1-one | dl-16-hydroxy-1-methylthiamethyl-1,9-dioxo-16-methyl-19-chloro-20-nor-5-cis-13-trans prostadiene |
| 463 | 1-trans-iodo-3-triphenylmethoxy-1-octene | 2-[6-methylthiaacetyl hex-2-cis-enyl] cyclopent-2-en-1-one | dl-15a-hydroxy-1-methylthiamethyl-1,9-dioxo-5-cis-13-trans prostadiene |
| 464 | 1-trans-iodo-3-methyl-3-trimethylsilyloxy-1-octene | 2-[6-methylthiaacetyl hex-2-cis-enyl] cyclopent-2-en-1-one | dl-15a-hydroxy-1-methylthiamethyl-1,9-dioxo-15-methyl-5-cis-13-trans prostadiene |
| 465 | 1-trans-iodo-4,4-dimethyl-3-trimethylsilyloxy-1-octene | 2-[6-methylthiaacetyl hex-2-cis-enyl] cyclopent-2-en-1-one | dl-15a-hydroxy-1-methylthiamethyl-1,9-dioxo-16,16-dimethyl-5-cis-13-trans prostadiene |
| 466 | 1-trans-iodo-4,4-trimethylene-3-trimethylsilyloxy-1-octene | 2-[6-methylthiaacetyl hex-2-cis-enyl] cyclopent-2-en-1-one | dl-15a-hydroxy-1-methylthiamethyl-1,9-dioxo-16,16-trimethylene-5-cis-13-prostadiene |
| EXAMPLE | VINYL TIN | CYCLOPENTENONE | PRODUCT PROSTAGLANDIN OF THE 11-DEOXY PGE2 SERIES |
| 467 | 1-trans-tri-n-butylstannyl-3-vinyl-3-trimethylsilyloxy-1-octene | 2-[6-methylthiaacetyl hex-2-cis-enyl] cyclopent-2-en-1-one | dl-15a-hydroxy-1-methylthiamethyl-1,9-dioxo-15-vinyl-5-cis-13-trans prostadiene |
| EXAMPLE | VINYL IODIDE | CYCLOPENYENONE | PRODUCT PROSTAGLANDIN OF THE 11-DEOXY PGE2 SERIES |
| 468 | 1-trans-iodo-4-triphenylmethoxy-1-octene | 2-[6-methylthiaacetyl hex-2-cis-enyl] dcyclopent-2-en-1-one | dl-16-hydroxy-1-methylthiamethyl-1,9-dioxo-5-cis-13-trans prostadiene |
| EXAMPLE | VINYL TIN | CYCLOPENTENONE | PRODUCT PROSTAGLANDIN OF THE 11-DEOXY PGE2 SERIES |
| 469 | 1-trans-tri-n-butylstannyl-4-methyl-4-trimethylsilyloxy-1-octene | 2-[6-methylthiaacetyl hex-2-cis-enyl] | dl-16-hydroxy-1-methylthiamethyl-1,9-dioxo-16-methyl-5-cis-13-trans prostadiene |
| 470 | 1-trans-tri-n-butylstannyl-5-methyl-4-trimethylsilyloxy-1-octene | 2-[6-methylthiaacetyl hex-2-cis-enyl] cyclopent-2-en-1-one | dl-16-hydroxy-1-methylthiamethyl-1,9-dioxo-17-methyl-5-cis-13-trans prostadiene |
| 471 | 1-trans-tri-n-butylstannyl-4-vinyl-4-trimethylsilyloxy-1-octene | 2-[6-methylthiaacetyl hex-2-cis-enyl] | dl-16-hydroxy-1-methylthiamethyl-1,9-dioxo-16-vinyl-5-cis-13-trans prostadiene |

TABLE IV-continued

| EXAMPLE | VINYL TIN | | PRODUCT PROSTAGLANDIN OF THE 11-DEOXY PGE2 SERIES |
|---|---|---|---|
| 472 | 1-trans-tri-n-butylstannyl-4-trimethylsilylethynyl-4-trimethylsilyloxy-1-octene | cyclopent-2-en-1-one 2-[6-methylthiaacetyl hex-2-cis-enyl] | dl,16-hydroxy-1-methylthiamethyl-1,9-dioxo-16-ethynyl-5-cis-13-trans prostadiene |
| 473 | 1-trans-tri-n-butylstannyl-5-methylene-4-triethylsilyloxy-1-octene | cyclopent-2-en-1-one 2-[6-methylthiaacetyl hex-2-cis-enyl] | dl-16-hydroxy-1-methylthiamethyl-1,9-dioxo-17-methylene-5-cis-13-trans prostadiene |
| 474 | 1-trans-tri-n-butylstannyl-4-methyl-5-methylene-4-trimethylsilyloxy-1-octene | cyclopent-2-en-1-one 2-[6-methylthiaacetyl hex-2-cis-enyl] | dl-16-hydroxy-1-methylthiamethyl-1,9-dioxo-16-methyl-17-methylene-5-cis-13-trans prostadiene |
| 475 | 1-trans-tri-n-butylstannyl-4-dimethoxymethyl-4-trimethylsilyloxy-1-octene | cyclopent-2-en-1-one 2-[6-methylthiaacetyl hex-2-cis-enyl] | dl-16-hydroxy-1-methylthiamethyl-1,9-dioxo-16-formyl-5-cis-13-trans prostadiene |
| 476 | 1-trans-tri-n-butylstannyl-4-fluoromethyl-4-trimethylsilyloxy-1-octene | cyclopent-2-en-1-one 2-[6-methylthiaacetyl hex-2-cis-enyl] | dl-16-hydroxy-1-methylthiamethyl-1,9-dioxo-16-fluoromethyl-5-cis-13-trans prostadiene |
| 477 | 1-trans-tri-n-butylstannyl-4-difluoromethyl-4-trimethylsilyloxy-1-octene | cyclopent-2-en-1-one 2-[6-methylthiaacetyl hex-2-cis-enyl] | dl-16-hydroxy-1-methylthiamethyl-1,9-dioxo-16-difluoromethyl-5-cis-13-trans prostadiene |
| 478 | 1-trans-tri-n-butylstannyl-4-trifluoromethyl-4-trimethylsilyloxy-1-octene | cyclopent-2-en-1-one 2-[6-methylthiaacetyl hex-2-cis-enyl] | dl-16-hydroxy-1-methylthiamethyl-1,9-dioxo-16-trifluoromethyl-5-cis-13-trans prostadiene |
| 479 | 1-trans-tri-n-butylstannyl-4-chloromethyl-4-trimethylsilyloxy-1-octene | cyclopent-2-en-1-one 2-[6-methylthiaacetyl hex-2-cis-enyl] | dl-16-hydroxy-1-methylthiamethyl-1,9-sioxo-16-chloromethyl-5-cis-13-trans prostadiene |
| 480 | 1-trans-tri-n-butylstannyl-4-trimethylsilyloxymethyl-4-trimethylsilyloxy-1-octene | cyclopent-2-en-1-one 2-[6-methylthiaacetyl hex-2-cis-enyl] | dl-16-hydroxy-1-methylthiamethyl-1,9-dioxo-16-hydroxymethyl-5-cis-13-trans prostadiene |
| 481 | 1-trans-iodo-3-triphenylmethoxy-1-nonene | cyclopent-2-en-1-one 2-[6-methylthiaacetyl hex-2-cis-enyl] | dl-15a-hydroxy-1-methylthiamethyl-1,9-dioxo-20-methyl-5-cis-13-trans prostadiene |
| 482 | 1-trans-iodo-3-methyl-3-trimethylsilyloxy-1-nonene | cyclopent-2-en-1-one 2-[6-methylthiaacetyl hex-2-cis-enyl] | dl-15a-hydroxy-1-methylthiamethyl-1,9-dioxo-15-methyl-20-methyl-5-cis-13-trans prostadiene |
| 483 | 1-trans-iodo-4,4-dimethyl-3-triphenylmethoxy-1-nonene | cyclopent-2-en-1-one 2-[6-methylthiaacetyl hex-2-cis-enyl] | dl-15a-hydroxy-1-methylthiamethyl-1,9-dioxo-16,16-dimethyl-20-methyl-5-cis-13-trans prostadiene |
| 484 | 1-trans-iodo-4,4-trimethylene-3-trimethylsilyloxy-1-nonene | cyclopent-2-en-1-one 2-[6-methylthiaacetyl hex-2-cis-enyl] | dl-15a-hydroxy-1-methylthiamethyl-1,9-dioxo-16,16-trimethylene-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 485 | 1-trans-tri-n-butylstannyl-3-vinyl-3-trimethylsilyloxy-1-nonene | 2-[6-methylthiaacetyl hex-2-cis-enyl] cyclopent-2-en-1-one | dl-15a-hydroxy-1-methylthiamethyl-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 486 | 1-trans-iodo-4-triphenylmethoxy-1-nonene | 2-[6-methylthiaacetyl hex-2-cis-enyl] cyclopent-2-en-1-one | dl-16-hydroxy-1-methylthiamethyl-1,9-dioxo-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 487 | 1-trans-tri-n-butylstannyl-4-methyl- | 2-[6-methylthiaacetyl | dl-16-hydroxy-1-methylthiamethyl-1,9-dioxo-16-methyl- |

TABLE IV-continued

| | | | |
|---|---|---|---|
| | 4-trimethylsilyloxy-1-nonene | hex-2-cis-enyl] | 20-methyl-5-cis-13-trans prostadiene |
| 488 | 1-trans-tri-n-butylstannyl-5-methyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-17-methyl-20-methyl-5-cis-13-trans prostadiene |
| 489 | 1-trans-tri-n-butylstannyl-4-vinyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-vinyl-20-methyl-5-cis-13-trans prostadiene |
| 490 | 1-trans-tri-n-butylstannyl-4-trimethylsilylethynyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-ethynyl-20-methyl-5-cis-13-trans prostadiene |
| 491 | 1-trans-tri-n-butylstannyl-5-methylene-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-17-methylene-20-methyl-5-cis-13-trans prostadiene |
| 492 | 1-trans-tri-n-butylstannyl-4-methyl-5-methylene-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-methyl-17-methylene-20-methyl-5-cis-13-trans prostadiene |
| 493 | 1-trans-tri-n-butylstannyl-4-dimethoxymethyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-formyl-20-methyl-5-cis-13-trans prostadiene |
| 494 | 1-trans-tri-n-butylstannyl-4-fluoromethyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-fluoromethyl-20-methyl-5-cis-13-trans prostadiene |
| 495 | 1-trans-tri-n-butylstannyl-4-difluoromethyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-difluoromethyl-20-methyl-5-cis-13-trans prostadiene |
| 496 | 1-trans-tri-n-butylstannyl-4-trifluoromethyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-trifluoromethyl-20-methyl-5-cis-13-trans prostadiene |
| 497 | 1-trans-tri-n-butylstannyl-4-chloromethyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-chloromethyl-20-methyl-5-cis-13-trans prostadiene |
| 498 | 1-trans-tri-n-butylstannyl-4-trimethylsilyloxymethyl-4-trimethylsilyloxy-1-nonene | cyclopent-2-en-1-one 2-[6-methylthiaacetyl hex-2-cis-enyl] | dl-16-hydroxy-1-methylthiamethyl-1,9-dioxo-16-hydroxymethyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 499 | 1-trans-iodo-3-triphenylmethoxy-1-decene | 2-[6-methylthiaacetyl hex-2-cis-enyl] | dl-15a-hydroxy-1-methylthiamethyl-1,9-dioxo-20-ethyl-5-cis-13-trans prostadiene |
| 500 | 1-trans-iodo-3-methyl-3-trimethylsilyloxy-1-decene | 2-[6-methylthiaacetyl hex-2-cis-enyl] | dl-15a-hydroxy-1-methylthiamethyl-1,9-dioxo-15-methyl-20-ethyl-5-cis-13-trans prostadiene |
| 501 | 1-trans-iodo-4,4-dimethyl-3-trimethylsilyloxy-1-decene | 2-[6-methylthiaacetyl hex-2-cis-enyl] | dl-15a-hydroxy-1-methylthiamethyl-1,9-dioxo-16,16-dimethyl-20-ethyl-5-cis-13-trans prostadiene |
| 502 | 1-trans-iodo-4,4-trimethylene-3-trimethylsilyloxy-1-decene | 2-[6-methylthiaacetyl hex-2-cis-enyl] | dl-15a-hydroxy-1-methylthiamethyl-1,9-dioxo-16,16-trimethylene-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 503 | 1-trans-tri-n-butylstannyl-3-vinyl-3-trimethylsilyloxy-1-decene | 2-[6-methylthiaacetyl hex-2-cis-enyl] | dl-15a-hydroxy-1-methylthiamethyl-1,9-dioxo-15-vinyl-20-ethyl-5-cis-13-trans prostadiene |

TABLE IV-continued

| EXAMPLE | VINYL IODIDE | CYCLOPENTENONE | PRODUCT PROSTAGLANDIN OF THE 11-DEOXY PGE2 SERIES |
|---|---|---|---|
| 504 | 1-trans-iodo-4-triphenylmethoxy-1-decene | 2-[6-methylthiaacetyl hex-2-cis-enyl] cyclopent-2-en-1-one | dl-16-hydroxy-1-methylthiamethyl-1,9-dioxo-20-ethyl-5-cis-13-trans prostadiene |

| EXAMPLE | VINYL TIN | CYCLOPENTENONE | PRODUCT PROSTAGLANDIN OF THE 11 DEOXY PGE2 SERIES |
|---|---|---|---|
| 505 | 1-trans-tri-n-butylstannyl-4-methyl-4-trimethylsilyloxy-1-decene | 2-[6-methylthiaacetyl hex-2-cis-enyl] cyclopent-2-en-1-one | dl-16-hydoxy-1-methylthiamethyl-1,9-dioxo-16-methyl-20-ethyl-5-cis-13-trans prostadiene |
| 506 | 1-trans-tri-n-butylstannyl-5-methyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-17-methyl-20-ethyl-5-cis-13-trans prostadiene |
| 507 | 1-trans-tri-n-butylstannyl-4-vinyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-vinyl-20-ethyl-5-cis-13-trans prostadiene |
| 508 | 1-trans-tri-n-butylstannyl-4-trimethylsilylethynyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-ethynyl-20-ethyl-5-cis-13-trans prostadiene |
| 509 | 1-trans-tri-n-butylstannyl-5-methylene-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-17-methylene-20-ethyl-5-cis-13-trans prostadiene |
| 510 | 1-trans-tri-n-butylstannyl-4-methyl-5-methylene-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-methyl-17-methylene-20-ethyl-5-cis-13-trans prostadiene |
| 511 | 1-trans-tri-n-butylstannyl-4-dimethoxymethyl-4-trimethylsilyloxy-1-decene | 2-[6-methylthiaacetyl hex-2-cis-enyl] cyclopent-2-en-1-one | dl-16-hydoxy-1-methylthiamethyl-1,9-dioxo-16-formyl-20-ethyl-5-cis-13-trans prostadiene |
| 512 | 1-trans-tri-n-butylstannyl-4-fluoromethyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-fluoromethyl-20-ethyl-5-cis-13-trans prostadiene |
| 513 | 1-trans-tri-n-butylstannyl-4-difluoromethyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-difluoromethyl-20-ethyl-5-cis-13-trans prostadiene |
| 514 | trans-tri-n-butylstannyl-4-trifluoromethyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-trifluoromethyl-20-ethyl-5-cis-13-trans prostadiene |
| 515 | 1-trans-tri-n-butylstannyl-4-chloromethyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-chloromethyl-20-ethyl-5-cis-13-trans prostadiene |
| 516 | 1-trans-tri-n-butylstannyl-4-trimethylsilyloxymethyl-4-trimethylsilyloxy-1-decene | 2-[6-methylthiaacetyl hex-2-cis-enyl] cyclopent-2-en-1-one | dl-16-hydroxy-1-methylthiamethyl-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 517 | 1-trans-iodo-3-triphenylmethoxy-1-heptene | 2-[7-methylthiaacetyl hept-2-cis-enyl] cyclopent-2-en-1-one | dl-15a-hydroxy-1-methylthiamethyl-1,9-dioxo-20-nor-2-homo-5-cis-13-trans prostadiene |
| 518 | 1-trans-iodo-3-methyl-3-trimethylsilyloxy-1-heptene | 2-[7-methylthiaacetyl hept-2-cis-enyl] cyclopent-2-en-1-one | dl-15a-hydroxy-1-methylthiamethyl-1,9-dioxo-15-methyl-20-nor-2-homo-5-cis-13-trans prostadiene |
| 519 | 1-trans-iodo-4,4-dimethyl | 2-[7-methylthiaacetyl | dl-15a-hydroxy-1-methylthiamethyl-1,9-dioxo- |

TABLE IV-continued

| EXAMPLE | VINYL TIN / VINYL IODIDE | CYCLOPENTENONE | PRODUCT PROSTAGLANDIN OF THE 11-DEOXY PGE2 SERIES |
|---|---|---|---|
| | 3-trimethylsilyloxy-1-heptene | hept-2-cis-enyl]cyclopent-2-en-1-one | 16,16-dimethyl-20-nor-2-homo-5-cis-13-trans prostadiene |
| 520 | 1-trans-iodo-5,5-dimethyl-3-triphenylmethoxy-1-octene | 2-[7-methylthiaacetyl hept-2-cis-enyl]cyclopent-2-en-1-one | dl-15a-hydroxy-1-methylthiamethyl-1,9-dioxo-17,17-dimethyl-2-homo-5-cis-13-trans prostadiene |
| 521 | 1-trans-iodo-4-methyl-3-triphenylmethoxy-1-octene | 2-[7-methylthiaacetyl hept-2-cis-enyl]cyclopent-2-en-1-one | dl-15a-hydroxy-1-methylthiamethyl-1,9-dioxo-16-methyl-2-homo-5-cis-13-trans prostadiene |
| 522 | 1-trans-iodo-4,4-trimethylene-3-trimethylsilyloxy-1-heptene | 2-[7-methylthiaacetyl hept-2-cis-enyl]cyclopent-2-en-1-one | dl-15a-hydroxy-1-methylthiamethyl-1,9-dioxo-16,16-trimethylene-20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 523 | 1-trans-tri-n-butylstannyl-3-vinyl-3-trimethylsilyloxy-1-heptene | 2-[7-methylthiaacetyl hept-2-cis-enyl]cyclopent-2-en-1-one | dl-15a-hydroxy-1-methylthiamethyl-1,9-dioxo-15-vinyl-20-nor-2-homo-5-cis-13-trans prostadiene |
| 524 | 1-trans-tri-n-butylstannyl-4-phenoxy-3-triethylsilyloxy-1-butene | 2-[7-methylthiaacetyl hept-2-cis-enyl]cyclopent-2-en-1-one | dl-15a-hydroxy-1-methylthiamethyl-1,9-dioxo-16-phenoxy-2-homo-17-20-tetranor-5-cis-13-trans prostadiene |
| 525 | 1-trans-tri-n-butylstannyl-4-(p-fluorophenoxy)-3-triethylsilyloxy-1-butene | 2-[7-methylthiaacetyl hept-2-cis-enyl]cyclopent-2-en-1-one | dl-15a-hydroxy-1-methylthiamethyl-1,9-dioxo-16-(p-fluorophenoxy)-2-homo-17-20-tetranor-5-cis-13-trans prostadiene |
| 526 | 1-trans-tri-n-butylstannyl-4-(m-chlorophenoxy)-3-triethylsilyloxy-1-butene | 2-[7-methylthiaacetyl hept-2-cis-enyl]cyclopent-2-en-1-one | dl-15a-hydroxy-1-methylthiamethyl-1,9-dioxo-16-(m-chlorophenoxy)-2-homo-17-20-tetranor-5-cis-13-trans prostadiene |
| 527 | 1-trans-tri-n-butylstannyl-4-(m-trifluoromethylphenoxy)-3-triethylsilyloxy-1-butene | dl-15a-hydroxy-1-methylthiamethyl-1,9-dioxo-hept-2-cis-enyl]cyclopent-2-en-1-one | 16-(m-trifluoromethylphenoxy)-2-homo-17-20-tetranor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 528 | 1-trans-iodo-5-phenyl-3-triethylsilyloxy-1-pentene | 2-[7-methylthiaacetyl hept-2-cis-enyl]cyclopent-2-en-1-one | dl-15a-hydroxy-1-methylthiamethyl-1,9-dioxo-17-phenyl-2-homo-18-20-trinor-5-cis-13-trans prostadiene |
| 529 | 1-trans-iodo-4,4-dimethyl-5-phenyl-3-triethylsilyloxy-1-pentene | 2-[methylthiaacetyl hept-2-cis-enyl]cyclopent-2-en-1-one | dl-15a-hydroxy-1-methylthiamethyl-1,9-dioxo-16,16-dimethyl-17-phenyl-2-homo-18-20-trinor-5-cis-13-trans prostadiene |
| 530 | 1-trans-iodo-4-cyclopentyl-3-triphenylmethoxy-1-butene | 2-[7-methylthiaacetyl hept-2-cis-enyl]cyclopent-2-en-1-one | dl-15a-hydroxy-1-methylthiamethyl-1,9-dioxo-16-cyclopentyl-2-homo-17-20-tetranor-5-cis-13-trans prostadiene |
| 531 | 1-trans-iodo-4-cyclohexyl-3-triphenylmethoxy-1-butene | 2-[7-methylthiaacetyl hept-2-cis-enyl]cyclopent-2-en-1-one | dl-15a-hydroxy-1-methylthiamethyl-1,9-dioxo-16-cyclohexyl-2-homo-17-20-tetranor-5-cis-13-trans prostadiene |
| 532 | 1-trans-iodo-4-triphenylmethoxy-1-heptene | 2-[7-methylthiaacetyl hept-2-cis-enyl]cyclopent-2-en-1-one | dl-16-hydroxy-1-methylthiamethyl-1,9-dioxo-20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 533 | 1-trans-tri-n-butylstannyl-4-methyl-4-trimethylsilyloxy-1-heptene | 2-[7-methylthiaacetyl hept-2-cis-enyl]cyclopent-2-en-1-one | dl-16-hydroxy-1-methylthiamethyl-1,9-dioxo-16-methyl-20-nor-2-homo-5-cis-13-trans prostadiene |
| 534 | 1-trans-tri-n-butylstannyl-4-ethyl-4-trimethylsilyloxy-1-octene | 2-[7-methylthiaacetyl hept-2-cis-enyl]cyclopent-2-en-1-one | dl-16-hydroxy-1-methylthiamethyl-1,9-dioxo-16-ethyl-2-homo-5-cis-13-trans prostadiene |

TABLE IV-continued

| EXAMPLE | VINYL IODIDE / VINYL TIN | CYCLOPENTENONE | PRODUCT PROSTAGLANDIN |
|---|---|---|---|
| 535 | 1-trans-tri-n-butylstannyl-5-methyl 4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-17-methyl-20-nor-2-homo-5-cis-13-trans prostadiene |

PRODUCT PROSTAGLANDIN OF THE 11-DEOXY PGE2 SERIES

| EXAMPLE | VINYL IODIDE | CYCLOPENTENONE | PRODUCT PROSTAGLANDIN |
|---|---|---|---|
| 536 | 1-trans-iodo-5,5-dimethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-17,17-dimethyl-2-homo-5-cis-13-trans prostadiene |

PRODUCT PROSTAGLANDIN OF THE 11 DEOXY PGE2 SERIES

| EXAMPLE | VINYL TIN | CYCLOPENTENONE | PRODUCT PROSTAGLANDIN |
|---|---|---|---|
| 537 | 1-trans-tri-n-butylstannyl-4-vinyl- | 2-[7-methylthiaacetyl hept-2-cis-enyl] cyclopent-2-en-1-one | dl-16-hydroxy-1-methylthiamethyl-1,9-dioxo-16-vinyl- |
| 538 | 1-trans-tri-n-butylstannyl-4-cyclopropyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-cyclopropyl-2-homo-5-cis-13-trans prostadiene |
| 539 | 1-trans-tri-n-butylstannyl-4-trimethylsilylethynyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-ethynyl-20-nor-2-homo-5-cis-13-trans prostadiene |
| 540 | 1-trans-tri-n-butylstannyl-5-methylene-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-17-methylene-20-nor-2-homo-5-cis-13-trans prostadiene |
| 541 | 1-trans-tri-n-butylstannyl-4-methyl-5-methylene-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-methyl-17-methylene-20-nor-2-homo-5-cis-13-trans prostadiene |
| 542 | 1-trans-tri-n-butylstannyl-4-dimethyoxymethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-formyl-20-nor-2-homo-5-cis-13-trans prostadiene |
| 543 | 1-trans-tri-n-butylstannyl-4-fluoromethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-fluoromethyl-20-nor-2-homo-5-cis-13-trans prostadiene |
| 544 | 1-trans-tri-n-butylstannyl-4-difluoromethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-difluoromethyl-20-nor-2-homo-5-cis-13-trans prostadiene |
| 545 | 1-trans-tri-n-butylstannyl-4-trifluoromethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-trifluoromethyl-20-nor-2-homo-5-cis-13-trans prostadiene |
| 546 | 1-trans-tri-n-butylstannyl-4-chloromethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-chloromethyl-20-nor-2-homo-5-cis-13-trans prostadiene |
| 547 | 1-trans-tri-n-butylstannyl-4-trimethylsilyloxymethyl-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-hydroxymethyl-20-nor-2-homo-5-cis-13-trans prostadiene |

PRODUCT PROSTAGLANDIN OF THE 11-DEOXY PGE2 SERIES

| EXAMPLE | VINYL IODIDE | CYCLOPENTENONE | PRODUCT PROSTAGLANDIN |
|---|---|---|---|
| 548 | 1-trans-iodo-4-methyl-7-chloro-4-trimethylsilyloxy-1-heptene | 2-[7-methylthiaacetyl hept-2-cis-enyl] cyclopent-2-en-1-one | dl-16-hydroxy-1-methylthiamethyl-1,9-dioxo-16-methyl-19-chloro-2-homo-20-nor-5-cis-13-trans prostadiene |
| 549 | 1-trans-iodo-3-triphenylmethoxy-1-octene | 2-[7-methylthiaacetyl hept-2-cis-enyl] cyclopent-2-en-1-one | dl-15a-hydroxy-1-methylthiamethyl-1,9-dioxo-2-homo-5-cis-13-trans prostadiene |
| 550 | 1-trans-iodo-3-methyl-3-trimethylsilyloxy-1-octene | 2-[7-methylthiaacetyl hept-2-cis-enyl] cyclopent-2-en-1-one | dl-15a-hydroxy-1-methylthiamethyl-1,9-dioxo-15-methyl-2-homo-5-cis-13-trans prostadiene |
| 551 | 1-trans-iodo-4,4-dimethyl | 2-[7-methylthiaacetyl | dl-15a-hydroxy-1-methylthiamethyl-1,9-dioxo- |

TABLE IV-continued

| Example | | | Product |
|---|---|---|---|
| | 3-trimethylsilyloxy-1-octene | hept-2-cis-enyl] cyclopent-2-en-1-one | 16,16-dimethyl-2-homo-5-cis-13-trans prostadiene |
| 552 | 1-trans-iodo-4,4-trimethylene-3-trimethylsilyloxy-1-octene | 2-[7-methylthiaacetyl hept-2-cis-enyl] cyclopent-2-en-1-one | dl-15a-hydroxy-1-methylthiamethyl-1,9-dioxo-16,16-trimethylene-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 553 | 1-trans-tri-n-butylstannyl-3-vinyl-3-trimethylsilyloxy-1-octene | 2-[7-methylthiaacetyl hept-2-cis-enyl] cyclopent-2-en-1-one | dl-15a-hydroxy-1-methylthiamethyl-1,9-dioxo-15-vinyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 554 | 1-trans-iodo-4-triphenylmethoxy-1-octene | 2-[7-methylthiaacetyl hept-2-cis-enyl] cyclopent-2-en-1-one | dl-16-hydroxy-1-methylthiamethyl-1,9-dioxo-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 555 | 1-trans-tri-n-butylstannyl-4-methyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-methyl-2-homo-5-cis-13-trans prostadiene |
| 556 | 1-trans-tri-n-butylstannyl-5-methyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-17-methyl-2-homo-5-cis-13-trans prostadiene |
| 557 | 1-trans-tri-n-butylstannyl-4-vinyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-vinyl-2-homo-5-cis-13-trans prostadiene |
| 558 | 1-trans-tri-n-butylstannyl-4-trimethylsilylethynyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-ethynyl-2-homo-5-cis-13-trans prostadiene |
| 559 | 1-trans-tri-n-butylstannyl-5-methylene-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-17-methylene-2-homo-5-cis-13-trans prostadiene |
| 560 | 1-trans-tri-n-butylstannyl-4-methyl-5-methylene-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-methyl-17-methylene-2-homo-5-cis-13-trans prostadiene |
| 561 | 1-trans-tri-n-butylstannyl-4-dimethoxymethyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-formyl-2-homo-5-cis-13-trans prostadiene |
| 562 | 1-trans-tri-n-butylstannyl-4-fluoromethyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-fluoromethyl-2-homo-5-cis-13-trans prostadiene |
| 563 | 1-trans-tri-n-butylstannyl-4-difluoromethyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-difluoromethyl-2-homo-5-cis-13-trans prostadiene |
| 564 | 1-trans-tri-n-butylstannyl-4-trifluoromethyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-trifluoromethyl-2-homo-5-cis-13-trans prostadiene |
| 565 | 1-trans-tri-n-butylstannyl-4-chloromethyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-chloromethyl-2-homo-5-cis-13-trans prostadiene |
| 566 | 1-trans-tri-n-butylstannyl-4-trimethylsilyloxymethyl-4-trimethylsilyloxy-1-octene | 2-[7-methylthiaacetyl hept-2-cis-enyl] cyclopent-2-en-1-one | dl-16-hydroxy-1-methylthiamethyl-1,9-dioxo-16-hydroxymethyl-2-homo-5-cis-13-trans prostadiene |

TABLE IV-continued

| EXAMPLE | VINYL IODIDE | CYCLOPENTENONE | PRODUCT PROSTAGLANDIN OF THE 11-DEOXY PGE2 SERIES |
|---|---|---|---|
| 567 | 1-trans-iodo-3-triphenylmethoxy-1-nonene | 2-[7-methylthiaacetyl hept-2-cis-enyl] cyclopent-2-en-1-one | dl-15a-hydroxy-1-methylthiamethyl-1,9-dioxo-20-methyl-2-homo-5-cis-13-trans prostadiene |
| 568 | 1-trans-iodo-3-methyl-3-trimethylsilyloxy-1-nonene | 2-[7-methylthiaacetyl hept-2-cis-enyl] cyclopent-2-en-1-one | dl-15a-hydroxy-1-methylthiamethyl-1,9-dioxo-15-methyl-20-methyl-2-homo-5-cis-13-trans prostadiene |
| 569 | 1-trans-iodo-4,4-dimethyl-3-trimethylsilyloxy-1-nonene | 2-[7-methylthiaacetyl hept-2-cis-enyl] cyclopent-2-en-1-one | dl-15a-hydroxy-1-methylthiamethyl-1,9-dioxo-16,16-dimethyl-20-methyl-2-homo-5-cis-13-trans prostadiene |
| 570 | 1-trans-iodo-4,4-trimethylene-3-trimethylsilyloxy-1-nonene | 2-[7-methylthiaacetyl hept-2-cis-enyl] cyclopent-2-en-1-one | dl-15a-hydroxy-1-methylthiamethyl-1,9-dioxo-16,16-trimethylene-20-methyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 571 | 1-trans-tri-n-butylstannyl-3-vinyl-3-trimethylsilyloxy-1-nonene | 2-[7-methylthiaacetyl hept-2-cis-enyl] cyclopent-2-en-1-one | dl-15a-hydroxy-1-methylthiamethyl-1,9-dioxo-15-vinyl-20-methyl-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 572 | 1-trans-iodo-4-triphenylmethoxy-1-nonene | 2-[7-methylthiaacetyl hept-2-cis-enyl] cyclopent-2-en-1-one | dl-16-hydroxy-1-methylthiamethyl-1,9-dioxo-20-methyl-2-homo-5-cis-13-trans prostadiene |

| EXAMPLE | VINYL TIN | CYCLOPENTENONE | PODUCT PROSTAGLANDIN OF THE 11-DEOXY PGE2 SERIES |
|---|---|---|---|
| 573 | 1-trans-tri-n-butylstannyl-4-methyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-methyl-20-methyl-2-homo-5-cis-13-trans prostadiene |
| 574 | 1-trans-tri-n-butylstannyl-5-methyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-17-methyl-20-methyl-2-homo-5-cis-13-trans prostadiene |
| 575 | 1-trans-tri-n-butylstannyl-4-vinyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-vinyl-20-methyl-2-homo-5-cis-13-trans prostadiene |
| 576 | 1-trans-tri-n-butylstannyl-4-trimethylsilylethynyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-ethynyl-20-methyl-2-homo-5-cis-13-trans prostadiene |
| 577 | 1-trans-tri-n-butylstannyl-5-methylene-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-17-methylene-20-methyl-2-homo-5-cis-13-trans prostadiene |
| 578 | 1-trans-tri-n-butylstannyl-4-methyl-5-methylene-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-methyl-17-methylene-20-methyl-2-homo-5-cis-13-trans prostadiene |
| 579 | 1-trans-tri-n-butylstannyl-4-dimethoxymethyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-formyl-20-methyl-2-homo-5-cis-13-trans prostadiene |
| 580 | 1-trans-tri-n-butylstannyl-4-fluoromethyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-fluoromethyl-20-methyl-2-homo-5-cis-13-trans prostadiene |
| 581 | 1-trans-tri-n-butylstannyl-4-difluoromethyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-difluoromethyl-20-methyl-2-homo-5-cis-13-trans prostadiene |
| 582 | 1-trans-tri-n-butylstannyl-4-trifluoromethyl- | 2-[7-methylthiaacetyl hept-2-cis-enyl] | dl-16-hydroxy-1-methylthiamethyl-1,9-dioxo-16-trifluoromethyl- |

TABLE IV-continued

| EXAMPLE | VINYL IODIDE / VINYL TIN | | PRODUCT |
|---|---|---|---|
| | 4-trimethylsilyloxy-1-nonene | hept-2-cis-enyl] cyclopent-2-en-1-one | 20-methyl-2-homo-5-cis-13-trans prostadiene |
| 583 | 1-trans-tri-n-butylstannyl-4-chloromethyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-chloromethyl-20-methyl-2-homo-5-cis-13-trans prostadiene |
| 584 | 1-trans-tri-n-butylstannyl-4-trimethylsilyloxymethyl-4-trimethylsilyloxy-1-nonene | 2-[7-methylthiaacetyl hept-2-cis-enyl] cyclopent-2-en-1-one | dl-16-hydroxy-1-methylthiamethyl-1,9-dioxo-16-hydroxymethyl-20-methyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 585 | 1-trans-iodo-3-triphenylmethoxy-1-decene | 2-[7-methylthiaacetyl hept-2-cis-enyl] cyclopent-2-en-1-one | dl-15a-hydroxy-1-methylthiamethyl-1,9-dioxo-20-ethyl-2-homo-5-cis-13-trans prostadiene |
| 586 | 1-trans-iodo-3-methyl-3-trimethylsilyloxy-1-decene | 2-[7-methylthiaacetyl hept-2-cis-enyl] cyclopent-2-en-1-one | dl-15a-hydroxy-1-methylthiamethyl-1,9-dioxo-15-methyl-20-ethyl-2-homo-5-cis-13-trans prostadiene |
| 587 | 1-trans-iodo-4,4-dimethyl-3-trimethylsilyloxy-1-decene | 2-[7-methylthiaacetyl hept-2-cis-enyl] cyclopent-2-en-1-one | dl-15a-hydroxy-1-methylthiamethyl-1,9-dioxo-16,16-dimethyl-20-ethyl-2-homo-5-cis-13-trans prostadiene |
| 588 | 1-trans-iodo-4,4-trimethylene-3-trimethylsilyloxy-1-decene | 2-[7-methylthiaacetyl hept-2-cis-enyl] cyclopent-2-en-1-one | dl-15a-hydroxy-1-methylthiamethyl-1,9-dioxo-16,16-trimethylene-20-ethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 589 | 1-trans-tri-n-butylstannyl-3-vinyl-3-trimethylsilyloxy-1-decene | 2-[7-methylthiaacetyl hept-2-cis-enyl] cyclopent-2-en-1-one | dl-15a-hydroxy-1-methylthiamethyl-1,9-dioxo-15-vinyl-20-ethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 590 | 1-trans-iodo-4-triphenylmethoxy-1-decene | 2-[7-methylthiaacetyl hept-2-cis-enyl] cyclopent-2-en-1-one | dl-16-hydroxy-1-methylthiamethyl-1,9-dioxo-20-ethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 591 | 1-trans-tri-n-butylstannyl-4-methyl-4-trimethylsilyloxy-1-decene | 2-[7-methylthiaacetyl hept-2-cis-enyl] cyclopent-2-en-1-one | dl-16-hydroxy-1-methylthiamethyl-1,9-dioxo-16-methyl-20-ethyl-2-homo-5-cis-13-trans prostadiene |
| 592 | 1-trans-tri-n-butylstannyl-5-methyl-4-trimethylsilyloxy-1-decene | 2-[7-methylthiaacetyl hept-2-cis-enyl] cyclopent-2-en-1-one | dl-16-hydroxy-1-methylthiamethyl-1,9-dioxo-17-methyl-20-ethyl-2-homo-5-cis-13-trans prostadiene |
| 593 | 1-trans-tri-n-butylstannyl-4-vinyl-4-trimethylsilyloxy-1-decene | 2-[7-methylthiaacetyl hept-2-cis-enyl] cyclopent-2-en-1-one | dl-16-hydroxy-1-methylthiamethyl-1,9-dioxo-16-vinyl-20-ethyl-2-homo-5-cis-13-trans prostadiene |
| 594 | 1-trans-tri-n-butylstannyl-4-trimethylsilylethynyl-4-trimethylsilyloxy-1-decene | 2-[7-methylthiaacetyl hept-2-cis-enyl] cyclopent-2-en-1-one | dl-16-hydroxy-1-methylthiamethyl-1,9-dioxo-16-ethynyl-20-ethyl-2-homo-5-cis-13-trans prostadiene |
| 595 | 1-trans-tri-n-butylstannyl-5-methylene-4-trimethylsilyloxy-1-decene | 2-[7-methylthiaacetyl hept-2-cis-enyl] cyclopent-2-en-1-one | dl-16-hydroxy-1-methylthiamethyl-1,9-dioxo-17-methylene-20-ethyl-2-homo-5-cis-13-trans prostadiene |
| 596 | 1-trans-tri-n-butylstannyl-4-methyl-5-methylene-4-trimethylsilyloxy-1-decene | 2-[7-methylthiaacetyl hept-2-cis-enyl] cyclopent-2-en-1-one | dl-16-hydroxy-1-methylthiamethyl-1,9-dioxo-16-methyl-17-methylene-20-ethyl-2-homo-5-cis-13-trans prostadiene |
| 597 | 1-trans-tri-n-butylstannyl-4-dimethoxymethyl- | 2-[7-methylthiaacetyl hept-2-cis-enyl] cyclopent-2-en-1-one | dl-16-hydroxy-1-methylthiamethyl-1,9-dioxo-16-formyl- |

TABLE IV-continued

| | | |
|---|---|---|
| | 4-trimethylsilyloxy-1-decene hept-2-cis-enyl] | 20-ethyl-2-homo-5-cis-13-trans prostadiene |
| 598 | 1-trans-tri-n-butylstannyl-4-fluoromethyl-4-trimethylsilyloxy-1-decene 2-[7-methylthiaacetyl cyclopent-2-en-1-one hept-2-cis-enyl] | dl-16-hydroxy-1-methylthiamethyl-1,9-dioxo-16-fluormethyl-20-ethyl-2-homo-5-cis-13-trans prostadiene |
| 599 | 1-trans-tri-n-butylstannyl-4-difluoromethyl-4-trimethylsilyloxy-1-decene 2-[7-methylthiaacetyl cyclopent-2-en-1-one hept-2-cis-enyl] | dl-16-hydroxy-1-methylthiamethyl-1,9-dioxo-16-difluoromethyl-20-ethyl-2-homo-5-cis-13-trans prostadiene |
| 600 | 1-trans-tri-n-butylstannyl-4-trifluoromethyl-4-trimethylsilyloxy-1-decene 2-[7-methylthiaacetyl cyclopent-2-en-1-one hept-2-cis-enyl] | dl-16-hydroxy-1-methylthiamethyl-1,9-dioxo-16-trifluoromethyl-20-ethyl-2-homo-5-cis-13-trans prostadiene |
| 601 | 1-trans-tri-n-butylstannyl-4-chloromethyl-4-trimethylsilyloxy-1-decene 2-[7-methylthiaacetyl cyclopent-2-en-1-one hept-2-cis-enyl] | dl-16-hydroxy-1-methylthiamethyl-1,9-dioxo-16-chloromethyl-20-ethyl-2-homo-5-cis-13-trans prostadiene |
| 602 | 1-trans-tri-n-butylstannyl-4-trimethylsilyloxymethyl-4-trimethylsilyloxy-1-decene 2-[7-methylthiaacetyl cyclopent-2-en-1-one hept-2-cis-enyl] | dl-16-hydroxy-1-methylthiamethyl-1,9-dioxo-16-hydroxymethyl-20-ethyl-2-homo-5-cis-13-trans prostadiene |

TABLE V

| EXAMPLE | VINYL TIN | CYCLOPENTENONE | PRODUCT PROSTAGLANDIN OF THE PGE2 SERIES |
|---|---|---|---|
| 1 | 1-trans-tri-n-butylstannyl-7-thia 4-triethylsilyloxy-1-octene | 2-[5-methylthioacetyl pent-2-cis-enyl]-4-trimethylsiloxy cyclopent-2-en-1-one | dl-11a,16-dihydroxy-1-methylthiomethyl-1,9-dioxo-19-thia-2-nor-cis-5-cis-13-trans prostadiene |
| 2 | 1-trans-tri-n-butylstannyl-4-methyl-7-thia 4-trimethylsilyloxy-1-octene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-methyl-19-thia-2-nor-cis-5-cis-13-trans prostadiene |
| 3 | 1-trans-tri-n-butylstannyl-7-oxa 4-triethylsilyloxy-1-octene | 2-[5-methylthioacetyl pent-2-cis-enyl]-4-trimethylsiloxy cyclopent-2-en-1-one | dl-11a,16-dihydroxy-1-methylthiomethyl-1,9-dioxo-19-oxa-2-nor-5-cis-13-trans prostadiene |
| 4 | 1-trans-tri-n-butylstannyl-4-methyl-7-oxa 4-trimethylsilyloxy-1-octene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-methyl-19-oxa-2-nor-5-cis-13-trans prostadiene |
| 5 | 1-trans-tri-n-butylstannyl-4-bromomethyl-4-trimethylsilyloxy-1-heptene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-bromomethyl-20-nor-2-nor-5-cis-13-trans prostadiene |
| EXAMPLE | VINYL IODIDE | CYCLOPENTENONE | PRODUCT PROSTAGLANDIN OF THE PGE2 SERIES |
| 6 | 1-trans-iodo-4-allenyl-4-trimethylsilyloxy-1-heptene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-allenyl-20-nor-2-nor-5-cis-13-trans prostadiene |
| EXAMPLE | VINYL TIN | CYCLOPENTENONE | PRODUCT PROSTAGLANDIN OF THE PGE2 SERIES |
| 7 | 1-trans-tri-n-butylstannyl-4-bromomethyl-4-trimethylsilyloxy-1-octene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-bromomethyl-2-nor-2-nor-5-cis-13-trans prostadiene |
| EXAMPLE | VINYL IODIDE | CYCLOPENTENONE | PRODUCT PROSTAGLANDIN OF THE PGE2 SERIES |
| 8 | 1-trans-iodo-4-allenyl-4-trimethylsilyloxy-1-octene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-allenyl-2-nor-5-cis-13-trans prostadiene |
| EXAMPLE | VINYL TIN | CYCLOPENTENONE | PRODUCT PROSTAGLANDIN OF THE PGE2 SERIES |
| 9 | 1-trans-tri-n-butylstannyl-4-bromomethyl-4-trimethylsilyloxy-1-nonene | 2-[5-methylthioacetyl pent-2-cis-enyl]-4-trimethylsiloxy cyclopent-2-en-1-one | dl,11a,16-dihydroxy-1-methylthiomethyl-1,9-dioxo-16-bromomethyl-20-methyl-2-nor-2-nor-5-cis-13-trans prostadiene |
| EXAMPLE | VINYL IODIDE | CYCLOPENTENONE | PRODUCT PROSTAGLANDIN OF THE PGE2 SERIES |
| 10 | 1-trans-iodo-4-allenyl-4-trimethylsilyloxy-1-nonene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-allenyl-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 11 | 1-trans-tri-n-butylstannyl-4-bromomethyl-4-trimethylsilyloxy-1-decene | 2-[5-methylthioacetyl pent-2-cis-enyl]-4-trimethylsiloxy cyclopent-2-en-1-one | dl,11a,16-dihydroxy-1-methylthiomethyl-1,9-dioxo-16-bromomethyl-20-ethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 12 | 1-trans-iodo-4-allenyl-4-trimethylsilyloxy-1-decene | 2-[5-methylthioacetyl pent-2-cis-enyl]-4-trimethylsiloxy cyclopent-2-en-1-one | dl-11a,16-dihydroxy-1-methylthiomethyl-1,9-dioxo-16-allenyl-20-ethyl-2-nor-5-cis-13-trans prostadiene |
| EXAMPLE | VINYL TIN | CYCLOPENTENONE | PRODUCT PROSTAGLANDIN OF THE PGE2 SERIES |

TABLE V-continued

| EXAMPLE | VINYL TIN / VINYL IODIDE | CYCLOPENTENONE | PRODUCT PROSTAGLANDIN OF THE PGE2 SERIES |
|---|---|---|---|
| 13 | 1-trans-tri-n-butylstannyl-7-thia-4-triethylsilyloxy-1-octene | 2-[6-methylthioacetyl hex-2-cis-enyl]-4-trimethylsiloxy cyclopent-2-en-1-one | dl-11a,16-dihydroxy-1-methylthiomethyl-1,9-dioxo-19-thia-5-cis-13-trans prostadiene |
| 14 | 1-trans-tri-n-butylstannyl-4-methyl-7-thia-4-trimethylsilyloxy-1-octene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-methyl-19-thia-5-cis-13-trans prostadiene |
| 15 | 1-trans-tri-n-butylstannyl-7-oxa-4-triethylsilyloxy-1-octene | 2-[6-methylthioacetyl hex-2-cis-enyl]-4-trimethylsiloxy cyclopent-2-en-1-one | dl-11a,16-dihydroxy-1-methylthiomethyl-1,9-dioxo-19-oxa-5-cis-13-trans prostadiene |
| 16 | 1-trans-tri-n-butylstannyl-4-methyl-7-oxa-4-trimethylsilyloxy-1-octene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-methyl-19-oxa-5-cis-13-trans prostadiene |
| 17 | 1-trans-tri-n-butylstannyl-4-bromomethyl-4-trimethylsilyloxy-1-heptene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 18 | 1-trans-iodo-4-allenyl-4-trimethylsilyloxy-1-heptene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE PGE2 SERIES |
| 19 | 1-trans-tri-n-butylstannyl-4-bromomethyl-4-trimethylsilyloxy-1-octene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-bromomethyl-5-cis-13-trans prostadiene |
| EXAMPLE | VINYL IODIDE | CYCLOPENTENONE | PRODUCT PROSTAGLANDIN OF THE PGE2 SERIES |
| 20 | 1-iodo-4-allenyl-4-trimethylsilyloxy-1-octene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-allenyl-5-cis-13-trans prostadiene |
| EXAMPLE | VINYL TIN | CYCLOPENTENONE | PRODUCT PROSTAGLANDIN OF THE PGE2 SERIES |
| 21 | 1-trans-tri-n-butylstannyl-4-bromomethyl-4-trimethylsilyloxy-1-nonene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-bromomethyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 22 | 1-iodo-4-allenyl-4-trimethylsilyloxy-1-nonene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-allenyl-20-methyl-5-cis-13-trans prostadiene |
| EXAMPLE | VINYL TIN | CYCLOPENTENONE | PRODUCT PROSTAGLANDIN OF THE PGE2 SERIES |
| 23 | 1-trans-tri-n-butylstannyl-4-bromomethyl-4-trimethylsilyloxy-1-decene | 2-[6-methylthioacetyl hex-2-cis-enyl]-4-trimethylsiloxy cyclopent-2-en-1-one | dl-11a,16-dihydroxy-1-methylthiomethyl-1,9-dioxo-16-bromomethyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 24 | 1-iodo-4-allenyl-4-trimethylsilyloxy-1-decene | 2[6-methylthioacetyl hex-2-cis-enyl]-4-trimethylsiloxy cyclopent-2-en-1-one | dl-11a,16-dihydroxy-1-methylthiomethyl-1,9-dioxo-16-allenyl-20-ethyl-5-cis-13-trans prostadiene |
| EXAMPLE | VINYL TIN | CYCLOPENTENONE | PRODUCT PROSTAGLANDIN OF THE PGE2 SERIES |
| 25 | 1-trans-tri-n-butylstannyl-7-thia | 2-[7-methylthioacetyl | dl-11a,16-dihydroxy-1-methylthiomethyl-1,9-dioxo- |

TABLE V-continued

| EXAMPLE | VINYL | CYCLOPENTENONE | PRODUCT PROSTAGLANDIN |
|---|---|---|---|
| 26 | 1-trans-tri-n-butylstannyl-4-methyl-7-thia-4-trimethylsilyloxy-1-octene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-methyl-19-thia-2-homo-5-cis-13-trans prostadiene |
| 27 | 1-trans-tri-n-butylstannyl-7-oxa-4-triethylsilyloxy-1-octene | 2-[7-methylthioacetyl hept-2-cis-enyl]-4-trimethylsiloxy cyclopent-2-en-1-one | dl-11a,16-dihydroxy-1-methylthiomethyl-1,9-dioxo-19-oxa-2-homo-5-cis-13-trans prostadiene |
| 28 | 1-trans-tri-n-butylstannyl-4-methyl-7-oxa-4-trimethylsilyloxy-1-octene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-methyl-19-oxa-2-homo-5-cis-13-trans prostadiene |
| 29 | 1-trans-tri-n-butylstannyl-4-bromomethyl-4-trimethylsilyloxy-1-heptene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-bromomethyl-20-nor-2-homo-5-cis-13-trans prostadiene |
| EXAMPLE | VINYL IODIDE | CYCLOPENTENONE | PRODUCT PROSTAGLANDIN OF THE PGE2 SERIES |
| 30 | 1-trans-iodo-4-allenyl-4-trimethylsilyloxy-1-heptene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-allenyl-20-nor-2-homo-5-cis-13-trans prostadiene |
| EXAMPLE | VINYL TIN | CYCLOPENTENONE | PRODUCT PROSTAGLANDIN OF THE PGE2 SERIES |
| 31 | 1-trans-tri-n-butylstannyl-4-bromomethyl-4-trimethylsilyloxy-1-octene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-bromomethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 32 | 1-trans-iodo-4-allenyl-4-trimethylsilyloxy-1-octene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-allenyl-2-homo-5-cis-13-trans prostadiene |
| EXAMPLE | VINYL TIN | CYCLOPENTENONE | PRODUCT PROSTAGLANDIN OF THE PGE2 SERIES |
| 33 | 1-trans-tri-n-butylstannyl-4-bromomethyl-4-trimethylsilyloxy-1-nonene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-bromomethyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 34 | 1-trans-iodo-4-allenyl-4-trimethylsilyloxy-1-nonene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-allenyl-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 35 | 1-trans-tri-n-butylstannyl-4-bromomethyl-4-trimethylsilyloxy-1-decene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-bromomethyl-20-ethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 36 | 1-trans-iodo-4-allenyl-4-trimethylsilyloxy-1-decene | 2-[7-methylthioacetyl hept-2-cis-enyl]-4-trimethylsiloxy cyclopent-2-en-1-one | dl-11a,16-dihydroxy-1-methylthiomethyl-1,9-dioxo-16-allenyl-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 37 | 1-trans-tri-n-butylstannyl-7-thia-4-triethylsilyloxy-1-octene | 2-[6-methylthioacetyl hex-2-cis-enyl]-4R-trimethylsiloxy | nat-11a,16-dihydroxy-1-methylthiomethyl-1,9-dioxo-19-thia-5-cis-13-trans prostadiene |

| | | | |
|---|---|---|---|
| 38 | 1-trans-tri-n-butylstannyl-4-methyl-7-thia-4-trimethylsilyloxy-1-octene | cyclopent-2-en-1-one 2-[6-methylthioacetyl hex-2-cis-enyl]-4R-trimethylsiloxy cyclopent-2-en-1-one | nat-11a,16-dihydroxy-1-methylthiomethyl-1,9-dioxo-16-methyl-19-thia-5-cis-13-trans prostadiene |
| 39 | 1-trans-tri-n-butylstannyl-7-oxa-4-triethylsilyloxy-1-octene | 2-[6-methylthioacetyl hex-2-cis-enyl]-4R-trimethylsiloxy cyclopent-2-en-1-one | nat-11a,16-dihydroxy-1-methylthiomethyl-1,9-dioxo-19-oxa-5-cis-13-trans prostadiene |
| 40 | 1-trans-tri-n-butylstannyl-4-methyl-7-oxa-4-trimethylsilyloxy-1-octene | 2-[6-methylthioacetyl hex-2-cis-enyl]-4R-trimethylsiloxy cyclopent-2-en-1-one | nat-11a,16-dihydroxy-1-methylthiomethyl-1,9-dioxo-16-methyl-19-oxa-5-cis-13-trans prostadiene |
| 41 | 1-trans-tri-n-butylstannyl-4-bromomethyl-4-trimethylsilyloxy-1-heptene | 2-[6-methylthioacetyl hex-2-cis-enyl]-4R-trimethylsiloxy cyclopent-2-en-1-one | nat-11a,16-dihydroxy-1-methylthiomethyl-1,9-dioxo-16-bromomethyl-20-nor-5-cis-13-trans prostadiene |
| EXAMPLE 42 | VINYL IODIDE 1-trans-iodo-4-allenyl-4-trimethylsilyloxy-1-heptene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-allenyl-20-nor-5-cis-13-trans prostadiene |
| EXAMPLE 43 | VINYL TIN 1-trans-tri-n-butylstannyl-4-bromomethyl-4-trimethylsilyloxy-1-octene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-bromomethyl-5-cis-13-trans prostadiene |
| EXAMPLE 44 | VINYL IODIDE 1-trans-iodo-4-allenyl-4-trimethylsilyloxy-1-octene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-allenyl-5-cis-13-trans prostadiene |
| EXAMPLE 45 | VINYL TIN 1-trans-tri-n-butylstannyl-4-bromomethyl-4-trimethylsilyloxy-1-nonene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-bromomethyl-20-methyl-5-cis-13-trans prostadiene |
| EXAMPLE 46 | VINYL IODIDE 1-trans-iodo-4-allenyl-4-trimethylsilyloxy-1-nonene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-allenyl-20-methyl-5-cis-13-trans prostadiene |
| EXAMPLE 47 | VINYL TIN 1-trans-tri-n-butylstannyl-4-bromomethyl-4-trimethylsilyloxy-1-decene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-bromomethyl-20-ethyl-5-cis-13-trans prostadiene |
| EXAMPLE 48 | VINYL IODIDE 1-trans-iodo-4-allenyl-4-trimethylsilyloxy-1-decene | CYCLOPENTENONE 2-[6-methylthioacetyl hex-2-cis-enyl]-4R-trimethylsiloxy cyclopent-2-en-1-one | PRODUCT PROSTAGLANDIN OF THE PGE2 SERIES nat-11a,16-dihydroxy-1-methylthiomethyl-1,9-dioxo-16-allenyl-20-ethyl-5-cis-13-trans prostadiene |
| EXAMPLE 49 | VINYL TIN 1-trans-tri-n-butylstannyl-7-thia-4-triethylsilyloxy-1-octene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-19-thia-2-nor-5-cis-13-trans prostadiene |

TABLE V-continued

| EXAMPLE | VINYL IODIDE / VINYL TIN | CYCLOPENTENONE | PRODUCT PROSTAGLANDIN |
|---|---|---|---|
| 50 | 1-trans-tri-n-butylstannyl-4-methyl-7-thia 4-trimethylsilyloxy-1-octene | 2-[5-methylthioacetyl pent-2-cis-enyl] cyclopent-2-en-1-one | dl-16-hydroxy-1-methylthiomethyl-1,9-dioxo-16-methyl-19-thia-2-nor-5-cis-13-trans prostadiene |
| 51 | 1-trans-tri-n-butylstannyl-7-oxa 4-triethylsilyloxy-1-octene | 2-[5-methylthioacetyl pent-2-cis-enyl] cyclopent-2-en-1-one | dl-16-hydroxy-1-methylthiomethyl-1,9-dioxo-19-oxa-2-nor-5-cis-13-trans prostadiene |
| 52 | 1-trans-tri-n-butylstannyl-4-methyl-7-oxa 4-trimethylsilyloxy-1-octene | 2-[5-methylthioacetyl pent-2-cis-enyl] cyclopent-2-en-1-one | dl-16-hydroxy-1-methylthiomethyl-1,9-dioxo-16-methyl-19-oxa-2-nor-5-cis-13-trans prostadiene |
| 53 | 1-trans-tri-n-butylstannyl-4-bromomethyl-4-trimethylsilyloxy-1-heptene | 2-[5-methylthioacetyl pent-2-cis-enyl] cyclopent-2-en-1-one | dl-16-hydroxy-1-methylthiomethyl-1,9-dioxo-16-bromomethyl-20-nor-2-nor-5-cis-13-trans prostadiene |
| EXAMPLE 54 | VINYL IODIDE 1-trans-iodo-4-allenyl-4-trimethylsilyloxy-1-heptene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-nor-2-nor-5-cis-13-trans prostadiene |
| EXAMPLE 55 | VINYL TIN 1-trans-tri-n-butylstannyl-4-bromomethyl-4-trimethylsilyloxy-1-octene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-2-nor-5-cis-13-trans prostadiene |
| EXAMPLE 56 | VINYL IODIDE 1-trans-iodo-4-allenyl-4-trimethylsilyloxy-1-octene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-2-nor-5-cis-13-trans prostadiene |
| EXAMPLE 57 | VINYL TIN 1-trans-tri-n-butylstannyl-4-bromomethyl-4-trimethylsilyloxy-1-nonene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-20-methyl-2-nor-5-cis-13-trans prostadiene |
| EXAMPLE 58 | VINYL IODIDE 1-trans-iodo-4-allenyl-4-trimethylsilyloxy-1-nonene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-methyl-2-nor-5-cis-13-trans prostadiene |
| EXAMPLE 59 | VINYL TIN 1-trans-tri-n-butylstannyl-4-bromomethyl-4-trimethylsilyloxy-1-decene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-20-ethyl-2-nor-5-cis-13-trans prostadiene |
| EXAMPLE 60 | VINYL IODIDE 1-trans-iodo-4-allenyl-4-trimethylsilyloxy-1-decene | CYCLOPENTENONE 2-[5-methylthioacetyl pent-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-ethyl-2-nor-5-cis-13-trans prostadiene |
| EXAMPLE 61 | VINYL TIN 1-trans-tri-n-butylstannyl-7-thia 4-triethylsilyloxy-1-octene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-19-thia-5-cis-13-trans prostadiene |
| 62 | 1-trans-tri-n-butylstannyl-4-methyl-7-thia | 2-[6-methylthioacetyl | dl-16-hydroxy-1-methylthiomethyl-1,9-dioxo-16-methyl- |

TABLE V-continued

| | | | |
|---|---|---|---|
| 63 | 4-trimethylsilyloxy-1-octene | hex-2-cis-enyl] cyclopent-2-en-1-one | 19-thia-5-cis-13-trans prostadiene |
| 64 | 1-trans-tri-n-butylstannyl-7-oxa-4-triethylsilyloxy-1-octene | 2-[6-methylthioacetyl hex-2-cis-enyl] cyclopent-2-en-1-one | dl-16-hydroxy-1-methylthiomethyl-1,9-dioxo-19-oxa-5-cis-13-trans prostadiene |
| 65 | 1-trans-tri-n-butylstannyl-4-methyl-7-oxa-4-trimethylsilyloxy-1-octene | 2-[6-methylthioacetyl hex-2-cis-enyl] cyclopent-2-en-1-one | dl-16-hydroxy-1-methylthiomethyl-1,9-dioxo-16-methyl-19-oxa-5-cis-13-trans prostadiene |
| | 1-trans-tri-n-butylstannyl-4-bromomethyl-4-trimethylsilyloxy-1-heptene | 2-[6-methylthioacetyl hex-2-cis-enyl] cyclopent-2-en-1-one | dl-16-hydroxy-1-methylthiomethyl-1,9-dioxo-16-bromomethyl-20-nor-5-cis-13-trans prostadiene |
| EXAMPLE 66 | VINYL IODIDE 1-trans-iodo-4-allenyl-4-trimethylsilyloxy-1-heptene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-nor-5-cis-13-trans prostadiene |
| EXAMPLE 67 | VINYL TIN 1-trans-tri-n-butylstannyl-4-bromomethyl-4-trimethylsilyloxy-1-octene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-5-cis-13-trans prostadiene |
| EXAMPLE 68 | VINYL IODIDE 1-trans-iodo-4-allenyl-4-trimethylsilyloxy-1-octene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-5-cis-13-trans prostadiene |
| EXAMPLE 69 | VINYL TIN 1-trans-tri-n-butylstannyl-4-bromomethyl-4-trimethylsilyloxy-1-nonene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-20-methyl-5-cis-13-trans prostadiene |
| EXAMPLE 70 | VINYL IODIDE 1-trans-iodo-4-allenyl-4-trimethylsilyloxy-1-nonene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-methyl-5-cis-13-trans prostadiene |
| EXAMPLE 71 | VINYL TIN 1-trans-tri-n-butylstannyl-4-bromomethyl-4-trimethylsilyloxy-1-decene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-20-ethyl-5-cis-13-trans prostadiene |
| EXAMPLE 72 | VINYL IODIDE 1-trans-iodo-4-allenyl-4-trimethylsilyloxy-1-decene | CYCLOPENTENONE 2-[6-methylthioacetyl hex-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-ethyl-5-cis-13-trans prostadiene |
| EXAMPLE 73 | VINYL TIN 1-trans-tri-n-butylstannyl-7-thia-4-triethylsilyloxy-1-octene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-19-thia-2-homo-5-cis-13-trans prostadiene |
| 74 | 1-trans-tri-n-butylstannyl-4-methyl-7-thia-4-trimethylsilyloxy-1-octene | 2-[7-methylthioacetyl hept-2-cis-enyl] | dl-16-hydroxy-1-methylthiomethyl-1,9-dioxo-16-methyl-19-thia-2-homo-5-cis-13-trans prostadiene |

TABLE V-continued

| | VINYL IODIDE | CYCLOPENTENONE | PRODUCT PROSTAGLANDIN OF THE 11-DEOXY PGE2 SERIES |
|---|---|---|---|
| 75 | 1-trans-tri-n-butylstannyl-7-oxa-4-triethylsilyloxy-1-octene | 2-[7-methylthioacetyl hept-2-cis-enyl] cyclopent-2-en-1-one | dl-16-hydroxy-1-methylthiomethyl-1,9-dioxo-19-oxa-2-homo-5-cis-13-trans prostadiene |
| 76 | 1-trans-tri-n-butylstannyl-4-methyl-7-oxa-4-trimethylsilyloxy-1-octene | 2-[7-methylthioacetyl hept-2-cis-enyl] cyclopent-2-en-1-one | dl-16-hydroxy-1-methylthiomethyl-1,9-dioxo-16-methyl-19-oxa-2-homo-5-cis-13-trans prostadiene |
| 77 | 1-trans-tri-n-butylstannyl-4-bromomethyl-4-trimethylsilyloxy-1-heptene | 2-[7-methylthioacetyl hept-2-cis-enyl] cyclopent-2-en-1-one | dl-16-hydroxy-1-methylthiomethyl-1,9-dioxo-16-bromomethyl-20-nor-2-homo-5-cis-13-trans prostadiene |
| EXAMPLE 78 | VINYL IODIDE 1-trans-iodo-4-allenyl-4-trimethylsilyloxy-1-heptene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-nor-2-homo-5-cis-13-trans prostadiene |
| EXAMPLE 79 | VINYL TIN 1-trans-tri-n-butylstannyl-4-bromomethyl-4-trimethylsilyloxy-1-octene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-2-homo-5-cis-13-trans prostadiene |
| EXAMPLE 80 | VINYL IODIDE 1-trans-iodo-4-allenyl-4-trimethylsilyloxy-1-octene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-2-homo-5-cis-13-trans prostadiene |
| EXAMPLE 81 | VINYL TIN 1-trans-tri-n-butylstannyl-4-bromomethyl-4-trimethylsilyloxy-1-nonene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-20-methyl-2-homo-5-cis-13-trans prostadiene |
| EXAMPLE 82 | VINYL IODIDE 1-trans-iodo-4-allenyl-4-trimethylsilyloxy-1-nonene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-methyl-2-homo-5-cis-13-trans prostadiene |
| EXAMPLE 83 | VINYL TIN 1-trans-tri-n-butylstannyl-4-bromomethyl-4-trimethylsilyloxy-1-decene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-bromomethyl-20-ethyl-2-homo-5-cis-13-trans prostadiene |
| EXAMPLE 84 | VINYL IODIDE 1-trans-iodo-4-allenyl-4-trimethylsilyloxy-1-decene | CYCLOPENTENONE 2-[7-methylthioacetyl hept-2-cis-enyl] cyclopent-2-en-1-one | PRODUCT PROSTAGLANDIN OF THE 11-DEOXY PGE2 SERIES dl-16-hydroxy-1-methylthiomethyl-1,9-dioxo-16-allenyl-20-ethyl-2-homo-5-cis-13-trans prostadiene |

TABLE VI

| EXAMPLE | VINYL IODIDE | CYCLOPENTENONE | PROSTAGLANDIN OF THE PGE1 SERIES |
|---|---|---|---|
| 1 | 1-trans-iodo-3-triphenylmethoxy-1-heptene | 2-[5-methylthiaacetyl pentyl]-4-trimethylsilyloxy cyclopent-2-en-1-one | dl-11a,15a-dihydroxy-1-methylthiamethyl-1,9-dioxo-20-nor-2-nor-13-trans prostene |
| 2 | 1-trans-iodo-3-methyl-3-trimethylsilyloxy-1-heptene | 2-[5-methylthiaacetyl pentyl]-4-trimethylsilyloxy cyclopent-2-en-1-one | dl-11a,15a-dihydroxy-1-methylthiamethyl-1,9-dioxo-15-methyl-20-nor-2-nor-13-trans prostene |
| 3 | 1-trans-iodo-4,4-dimethyl-3-trimethylsilyloxy-1-heptene | 2-[5-methylthiaacetyl pentyl]-4-trimethylsilyloxy cyclopent-2-en-1-one | dl-11a,15a-dihydroxy-1-methylthiamethyl-1,9-dioxo-16,16-dimethyl-20-nor-2-nor-13-trans prostene |
| 4 | 1-trans-iodo-5,5-dimethyl-3-triphenylmethoxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-17,17-dimethyl-2-nor-13-trans prostene |
| 5 | 1-trans-iodo-4-methyl-3-triphenylmethoxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-16-methyl-2-nor-13-trans prostene |
| 6 | 1-trans-iodo-4,4-trimethylene-3-trimethylsilyloxy-1-heptene | 2-[5-methylthiaacetyl pentyl]-4-trimethylsilyloxy cyclopent-2-en-1-one | dl-11a,15a-dihydroxy-1-methylthiamethyl-1,9-dioxo-16,16-trimethylene-20-nor-2-nor-13-trans prostene |

| EXAMPLE | VINYL TIN | CYCLOPENTENONE | PRODUCT PROSTAGLANDIN OF THE PGE1 SERIES |
|---|---|---|---|
| 7 | 1-trans-tri-n-butylstannyl-3-vinyl-3-trimethylsilyloxy-1-heptene | 2-[5-methylthiaacetyl pentyl]-4-trimethylsilyloxy cyclopent-2-en-1-one | dl-11a,15a-dihydroxy-1-methylthiamethyl-1,9-dioxo-15-vinyl-20-nor-2-nor-13-trans prostene |
| 8 | 1-trans-tri-n-butylstannyl-4-phenoxy-3-triethylsilyloxy-1-butene | 2-[5-methylthiaacetyl pentyl]-4-trimethylsilyloxy cyclopent-2-en-1-one | dl-11a,15a-dihydroxy-1-methylthiamethyl-1,9-dioxo-16-phenoxy-2-nor-17-20-tetranor-13-trans prostene |
| 9 | 1-trans-tri-n-butylstannyl-4-(p-fluorophenoxy)-3-triethylsilyloxy-1-butene | 2-[5-methylthiaacetyl pentyl]-4-trimethylsilyloxy cyclopent-2-en-1-one | dl-11a,15a-dihydroxy-1-methylthiamethyl-1,9-dioxo-16(p-fluorophenoxy)-2-nor-17-20-tetranor-13-trans prostene |
| 10 | 1-trans-tri-n-butylstannyl-4-(m-chlorophenoxy)-3-triethylsilyloxy-1-butene | 2-[5-methylthiaacetyl pentyl]-4-trimethylsilyloxy cyclopent-2-en-1-one | dl-11a,15a-dihydroxy-1-methylthiamethyl-1,9-dioxo-16(m-chlorophenoxy)-2-nor-17-20-tetranor-13-trans prostene |
| 11 | 1-trans-tri-n-butylstannyl-4-(m-trifluoromethylphenoxy)-3-triethylsilyloxy-1-butene | 2-[5-methylthiaacetyl pentyl]-4-trimethylsilyloxy cyclopent-2-en-1-one | dl-11a,15a-dihydroxy-1-methylthiamethyl-1,9-dioxo-16-(m-trifluoromethylphenoxy)-2-nor-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 12 | 1-trans-iodo-5-phenyl-3-triethylsilyloxy-1-pentene | 2-[5-methylthiaacetyl pentyl]-4-trimethylsilyloxy cyclopent-2-en-1-one | dl-11a,15a-dihydroxy-1-methylthiamethyl-1,9-dioxo-17-phenyl-2-nor-18-20-trinor-13-trans prostene |
| 13 | 1-trans-iodo-4,4-dimethyl-5-phenyl-3-triethylsilyloxy-1-pentene | 2-[5-methylthiaacetyl pentyl]-4-trimethylsilyloxy cyclopent-2-en-1-one | dl-11a,15a-dihydroxy-1-methylthiamethyl-1,9-dioxo-16,16-dimethyl-17-phenyl-2-nor-18-20-trinor-13-trans prostene |
| 14 | 1-trans-iodo-4-cyclopentyl-3-triphenylmethoxy-1-butene | 2-[5-methylthiaacetyl pentyl]-4-trimethylsilyloxy cyclopent-2-en-1-one | dl-11a,15a-dihydroxy-1-methylthiamethyl-1,9-dioxo-16-cyclopentyl-2-nor-17-20-tetranor-13-trans prostene |
| 15 | 1-trans-iodo-4-cyclohexyl-3-triphenylmethoxy-1-butene | 2-[5-methylthiaacetyl pentyl]-4-trimethylsilyloxy cyclopent-2-en-1-one | dl-11a,15a-dihydroxy-1-methylthiamethyl-1,9-dioxo-16-cyclohexyl-2-nor-17-20-tetranor-13-trans prostene |
| 16 | 1-trans-iodo-4-triphenylmethoxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-20-nor-2-nor-13-trans prostene |

TABLE VI-continued

| EXAMPLE | VINYL TIN | CYCLOPENTENONE | PRODUCT PROSTAGLANDIN OF THE PGE1 SERIES |
|---|---|---|---|
| 17 | 1-trans-tri-n-butylstannyl-4-methyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-20-nor-2-nor-13-trans prostene |
| 18 | 1-trans-tri-n-butylstannyl-4-ethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-ethyl-2-nor-13-trans prostene |
| 19 | 1-trans-tri-n-butylstannyl-5-methyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-17-methyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 20 | 1-trans-iodo-5,5-dimethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-17,17-dimethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 21 | 1-trans-tri-n-butylstannyl-4-vinyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-vinyl-20-nor-2-nor-13-trans prostene |
| 22 | 1-trans-tri-n-butylstannyl-4-cyclopropyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-cyclopropyl-2-nor-13-trans prostene |
| 23 | 1-trans-tri-n-butylstannyl-4-trimethylsilylethynyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-ethynyl-20-nor-2-nor-13-trans prostene |
| 24 | 1-trans-tri-n-butylstannyl-5-methylene-4-triethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-17-methylene-20-nor-2-nor-13-trans prostene |
| 25 | 1-trans-tri-n-butylstannyl-4-methyl-5-methylene-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-17-methylene-20-nor-2-nor-13-trans prostene |
| 26 | 1-trans-tri-n-butylstannyl-4-dimethoxymethyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-formyl-20-nor-2-nor-13-trans prostene |
| 27 | 1-trans-tri-n-butylstannyl-4-fluoromethyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-fluoromethyl-20-nor-2-nor-13-trans prostene |
| 28 | 1-trans-tri-n-butylstannyl-4-difluoromethyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-difluoromethyl-20-nor-2-nor-13-trans prostene |
| 29 | 1-trans-tri-n-butylstannyl-4-trifluoromethyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-trifluoromethyl-20-nor-2-nor-13-trans prostene |
| 30 | 1-trans-tri-n-butylstannyl-4-chloromethyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-chloromethyl-20-nor-2-nor-13-trans prostene |
| 31 | 1-trans-tri-n-butylstannyl-4-trimethylsilyloxymethyl-4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-hydroxymethyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|

TABLE VI-continued

| | | | |
|---|---|---|---|
| 32 | 1-trans-iodo-4-methyl-7-chloro 4-trimethylsilyloxy-1-heptene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-19-chloro-2-nor-20-nor-13-trans prostene |
| 33 | 1-trans-iodo-3-triphenylmethoxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-2-nor-13-trans prostene |
| 34 | 1-trans-iodo-3-methyl-3-trimethylsilyloxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-15-methyl-2-nor-13-trans prostene |
| 35 | 1-trans-iodo-4,4-dimethyl 3-trimethylsilyloxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-16,16-dimethyl-2-nor-13-trans prostene |
| 36 | 1-trans-iodo-4,4-trimethylene 3-trimethylsilyloxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-16,16-trimethylene-2-nor-13-trans prostene |
| EXAMPLE | VINYL TIN | CYCLOPENTENONE | PRODUCT PROSTAGLANDIN OF THE PGE1 SERIES |
| 37 | 1-trans-tri-n-butylstannyl-3-vinyl-3-trimethylsilyloxy-1-octene | 2-[5-methylthiaacetyl pentyl]-4-trimethylsilyloxy cyclopent-2-en-1-one | dl-11a,15a-dihydroxy-1-methylthiamethyl-1,9-dioxo-15-vinyl-2-nor-13-trans prostene |
| EXAMPLE | VINYL IODIDE | CYCLOPENTENONE | PRODUCT PROSTAGLANDIN OF THE PGE1 SERIES |
| 38 | 1-trans-iodo-4-triphenylmethoxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-2-nor-13-trans prostene |
| EXAMPLE | VINYL TIN | CYCLOPENTENONE | PRODUCT PROSTAGLANDIN OF THE PGE1 SERIES |
| 39 | 1-trans-tri-n-butylstannyl-4-methyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-2-nor-13-trans prostene |
| 40 | 1-trans-tri-n-butylstannyl-5-methyl 4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-17-methyl-2-nor-13-trans prostene |
| 41 | 1-trans-tri-n-butylstannyl-4-vinyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-vinyl-2-nor-13-trans prostene |
| 42 | 1-trans-tri-n-butylstannyl-4-trimethylsilylethynyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-ethynyl-2-nor-13-trans prostene |
| 43 | 1-trans-tri-n-butylstannyl-5-methylene 4-triethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-17-methylene-2-nor-13-trans prostene |
| 44 | 1-trans-tri-n-butylstannyl-4-methyl-5-methylene 4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-17-methylene-2-nor-13-trans prostene |
| 45 | 1-trans-tri-n-butylstannyl-4-dimethoxymethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-formyl-2-nor-13-trans prostene |
| 46 | 1-trans-tri-n-butylstannyl-4-fluoromethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-fluoromethyl-2-nor-13-trans prostene |
| 47 | 1-trans-tri-n-butylstannyl-4-difluoromethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-difluoromethyl-2-nor-13-trans prostene |

TABLE VI-continued

| | | | |
|---|---|---|---|
| 48 | 1-trans-tri-n-butylstannyl-4-trifluoromethyl-4-trimethylsilyloxy-1-octene | cyclopent-2-en-1-one 2-[5-methylthiaacetyl pentyl]-4-trimethylsilyloxy cyclopent-2-en-1-one | dl-11a,16-dihydroxy-1-methylthiamethyl-1,9-dioxo-16-trifluoromethyl-2-nor-13-trans prostene |
| 49 | 1-trans-tri-n-butylstannyl-4-chloromethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-chloromethyl-2-nor-13-trans prostene |
| 50 | 1-trans-tri-n-butylstannyl-4-trimethylsilyloxymethyl-4-trimethylsilyloxy-1-octene | 2-[5-methylthiaacetyl pentyl]-4-trimethylsilyloxy cyclopent-2-en-1-one | dl-11a,16-dihydroxy-1-methylthiamethyl-1,9-dioxo-16-hydroxymethyl-2-nor-13-trans prostene |
| EXAMPLE | VINYL IODIDE | CYCLOPENTENONE | PRODUCT PROSTAGLANDIN OF THE PGE1 SERIES |
| 51 | 1-trans-iodo-3-triphenylmethoxy-1-nonene | 2-[5-methylthiaacetyl pentyl]-4-trimethylsilyloxy cyclopent-2-en-1-one | dl-11a,15a-dihydroxy-1-methylthiamethyl-1,9-dioxo-20-methyl-2-nor-13-trans prostene |
| 52 | 1-trans-iodo-3-methyl-3-trimethylsilyloxy-1-nonene | 2-[5-methylthiaacetyl pentyl]-4-trimethylsilyloxy cyclopent-2-en-1-one | dl-11a,15a-dihydroxy-1-methylthiamethyl-1,9-dioxo-15-methyl-20-methyl-2-nor-3-trans prostene |
| 53 | 1-trans-iodo-4,4-dimethyl-3-trimethylsilyloxy-1-nonene | 2-[5-methylthiaacetyl pentyl]-4-trimethylsilyloxy cyclopent-2-en-1-one | dl-11a,15a-dihydroxy-1-methylthiamethyl-1,9-dioxo-16,16-dimethyl-20-methyl-2-nor-13-trans prostene |
| 54 | 1-trans-iodo-4,4-trimethylene-3-trimethylsilyloxy-1-nonene | 2-[5-methylthiaacetyl pentyl]-4-trimethylsilyloxy cyclopent-2-en-1-one | dl-11a,15a-dihydroxy-1-methylthiamethyl-1,9-dioxo-16,16-trimethylene-20-methyl-2-nor-13-trans prostene |
| EXAMPLE | VINYL TIN | CYCLOPENTENONE | PRODUCT PROSTAGLANDIN OF THE PGE1 SERIES |
| 55 | 1-trans-tri-n-butylstannyl-3-vinyl-3-trimethylsilyloxy-1-nonene | 2-[5-methylthiaacetyl pentyl]-4-trimethylsilyloxy cyclopent-2-en-1-one | dl-11a,15a-dihydroxy-1-methylthiamethyl-1,9-dioxo-15-vinyl-20-methyl-2-nor-13-trans prostene |
| EXAMPLE | VINYL IODIDE | CYCLOPENTENONE | PRODUCT PROSTAGLANDIN OF THE PGE1 SERIES |
| 56 | 1-trans-iodo-4-triphenylmethoxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-20-methyl-2-nor-13-trans prostene |
| EXAMPLE | VINYL TIN | CYCLOPENTENONE | PRODUCT PROSTAGLANDIN OF THE PGE1 SERIES |
| 57 | 1-trans-tri-n-butylstannyl-4-methyl-4-trimethylsilyloxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-20-methyl-2-nor-13-trans prostene |
| 58 | 1-trans-tri-n-butylstannyl-5-methyl-4-trimethylsilyloxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-17-methyl-20-methyl-2-nor-13-trans prostene |
| 59 | 1-trans-tri-n-butylstannyl-4-vinyl-4-trimethylsilyloxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-16-vinyl-20-methyl-2-nor-13-trans prostene |
| 60 | 1-trans-tri-n-butylstannyl-4-trimethylsilylethynyl-4-trimethylsilyloxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-16-ethynyl-20-methyl-2-nor-13-trans prostene |
| 61 | 1-trans-tri-n-butylstannyl-5-methylene-4-triethylsilyloxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-17-methylene-20-methyl-2-nor-13-trans prostene |
| 62 | 1-trans-tri-n-butylstannyl-4-methyl-5-methylene-4-trimethylsilyloxy-1-nonene | 2-[5-methylthiaacetyl pentyl]-4-trimethylsilyloxy cyclopent-2-en-1-one | dl-11a,16-dihydroxy-1-methylthiamethyl-1,9-dioxo-16-methyl-17-methylene-20-methyl-2-nor-13-trans prostene |

TABLE VI-continued

| | | | |
|---|---|---|---|
| 63 | 1-trans-tri-n-butylstannyl-4-dimethoxymethyl-4-trimethylsilyloxy-1-nonene | 2-[5-methylthioacetyl pentyl]-4-trimethylsiloxy cyclopent-2-en-1-one | dl-11a,16-dihydroxy-1-methylthiamethyl-1,9-dioxo-16-formyl-20-methyl-2-nor-13-trans prostene |
| 64 | 1-trans-tri-n-butylstannyl-4-fluoromethyl-4-trimethylsilyloxy-1-nonene | 2-[5-methylthioacetyl pentyl]-4-trimethylsiloxy cyclopent-2-en-1-one | dl-11a,16-dihydroxy-1-methylthiamethyl-1,9-dioxo-16-fluoromethyl-20-methyl-2-nor-13-trans prostene |
| 65 | 1-trans-tri-n-butylstannyl-4-difluoromethyl-4-trimethylsilyloxy-1-nonene | 2-[5-methylthioacetyl pentyl]-4-trimethylsiloxy cyclopent-2-en-1-one | dl-11a,16-dihydroxy-1-methylthiamethyl-1,9-dioxo-16-difluoromethyl-20-methyl-2-nor-13-trans prostene |
| 66 | 1-trans-tri-n-butylstannyl-4-trifluoromethyl-4-trimethylsilyloxy-1-nonene | 2-[5-methylthioacetyl pentyl]-4-trimethylsiloxy cyclopent-2-en-1-one | dl-11a,16-dihydroxy-1-methylthiamethyl-1,9-dioxo-16-trifluoromethyl-20-methyl-2-nor-13-trans prostene |
| 67 | 1-trans-tri-n-butylstannyl-4-chloromethyl-4-trimethylsilyloxy-1-nonene | 2-[5-methylthioacetyl pentyl]-4-trimethylsiloxy cyclopent-2-en-1-one | dl-11a,16-dihydroxy-1-methylthiamethyl-1,9-dioxo-16-chloromethyl-20-methyl-2-nor-13-trans prostene |
| 68 | 1-trans-tri-n-butylstannyl-4-trimethylsilyloxymethyl-4-trimethylsilyloxy-1-nonene | 2-[5-methylthioacetyl pentyl]-4-trimethylsiloxy cyclopent-2-en-1-one | dl-11a,16-dihydroxy-1-methylthiamethyl-1,9-dioxo-16-hydroxymethyl-20-methyl-2-nor-13-trans prostene |
| EXAMPLE | VINYL IODIDE | CYCLOPENTENONE | PRODUCT PROSTAGLANDIN OF THE PGE1 SERIES |
| 69 | 1-trans-iodo-3-triphenylmethoxy-1-decene | 2-[5-methylthioacetyl pentyl]-4-trimethylsiloxy cyclopent-2-en-1-one | dl-11a,15a-dihydroxy-1-methylthiamethyl-1,9-dioxo-20-ethyl-2-nor-13-trans prostene |
| 70 | 1-trans-iodo-3-methyl-3-trimethylsilyloxy-1-decene | 2-[5-methylthioacetyl pentyl]-4-trimethylsiloxy cyclopent-2-en-1-one | dl-11a,15a-dihydroxy-1-methylthiamethyl-1,9-dioxo-15-methyl-20-ethyl-2-nor-13-trans prostene |
| 71 | 1-trans-iodo-4,4-dimethyl-3-trimethylsilyloxy-1-decene | 2-[5-methylthioacetyl pentyl]-4-trimethylsiloxy cyclopent-2-en-1-one | dl-11a,15a-dihydroxy-1-methylthiamethyl-1,9-dioxo-16,16-dimethyl-20-ethyl-2-nor-13-trans prostene |
| 72 | 1-trans-iodo-4,4-trimethylene-3-trimethylsilyloxy-1-decene | 2-[5-methylthioacetyl pentyl]-4-trimethylsiloxy cyclopent-2-en-1-one | dl-11a,15a-dihydroxy-1-methylthiamethyl-1,9-dioxo-16,16-trimethylene-20-ethyl-2-nor-13-trans prostene |
| EXAMPLE | VINYL TIN | CYCLOPENTENONE | PRODUCT PROSTAGLANDIN OF THE PGE1 SERIES |
| 73 | 1-trans-tri-n-butylstannyl-3-vinyl-3-trimethylsilyloxy-1-decene | 2-[5-methylthioacetyl pentyl]-4-trimethylsiloxy cyclopent-2-en-1-one | dl-11a,15a-dihydroxy-1-methylthiamethyl-1,9-dioxo-15-vinyl-20-ethyl-2-nor-13-trans prostene |
| EXAMPLE | VINYL IODIDE | CYCLOPENTENONE | PRODUCT PROSTAGLANDIN OF THE PGE1 SERIES |
| 74 | 1-trans-iodo-4-triphenylmethoxy-1-decene | 2-[5-methylthioacetyl pentyl]-4-trimethylsiloxy cyclopent-2-en-1-one | dl-11a,16-dihydroxy-1-methylthiamethyl-1,9-dioxo-20-ethyl-2-nor-13-trans prostene |
| EXAMPLE | VINYL TIN | CYCLOPENTENONE | PRODUCT PROSTAGLANDIN OF THE PGE1 SERIES |
| 75 | 1-trans-tri-n-butylstannyl-4-methyl-4-trimethylsilyloxy-1-decene | 2-[5-methylthioacetyl pentyl]-4-trimethylsiloxy cyclopent-2-en-1-one | dl-11a,16-dihydroxy-1-methylthiamethyl-1,9-dioxo-16-methyl-20-ethyl-2-nor-13-trans prostene |
| 76 | 1-trans-tri-n-butylstannyl-5-methyl-4-trimethylsilyloxy-1-decene | 2-[5-methylthioacetyl pentyl]-4-trimethylsiloxy cyclopent-2-en-1-one | dl-11a,16-dihydroxy-1-methylthiamethyl-1,9-dioxo-17-methyl-20-ethyl-2-nor-13-trans prostene |
| 77 | 1-trans-tri-n-butylstannyl-4-vinyl-4-trimethylsilyloxy-1-decene | 2-[5-methylthioacetyl pentyl]-4-trimethylsiloxy cyclopent-2-en-1-one | dl-11a,16-dihydroxy-1-methylthiamethyl-1,9-dioxo-16-vinyl-20-ethyl-2-nor-13-trans prostene |

TABLE VI-continued

| | | | |
|---|---|---|---|
| 78 | 1-trans-tri-n-butylstannyl-4-trimethylsilylethynyl-4-trimethylsilyloxy-1-decene | cyclopent-2-en-1-one 2-[5-methylthiaacetyl pentyl]-4-trimethylsilyloxy cyclopent-2-en-1-one | dl-11a,16-dihydroxy-1-methylthiamethyl-1,9-dioxo-16-ethynyl-20-ethyl-2-nor-13-trans prostene |
| 79 | 1-trans-tri-n-butylstannyl-5-methylene-4-triethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-17-methylene-20-ethyl-2-nor-13-trans prostene |
| 80 | 1-trans-tri-n-butylstannyl-4-methyl-5-methylene-4-trimethylsilyloxy-1-decene | 2-[5-methylthiaacetyl pentyl]-4-trimethylsilyloxy cyclopent-2-en-1-one | dl-11a,16-hihydroxy-1-methylthiamethyl-1,9-dioxo-16-methyl-17-methylene-20-ethyl-2-nor-13-trans prostene |
| 81 | 1-trans-tri-n-butylstannyl-4-dimethoxymethyl-4-trimethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-16-formyl-20-ethyl-2-nor-13-trans prostene |
| 82 | 1-trans-tri-n-butylstannyl-4-fluoromethyl-4-trimethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-16-fluoromethyl-20-ethyl-2-nor-13-trans-prostene |
| 83 | 1-trans-tri-n-butylstannyl-4-difluoromethyl-4-trimethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-16-difluoromethyl-20-ethyl-2-nor-13-trans prostene |
| 84 | 1-trans-tri-n-butylstannyl-4-trifluoromethyl-4-trimethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-16-trifluoromethyl-20-ethyl-2-nor-13-trans prostene |
| 85 | 1-trans-tri-n-butylstannyl-4-chloromethyl-4-trimethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-16-chloromethyl-20-ethyl-2-nor-13-trans prostene |
| 86 | 1-trans-tri-n-butylstannyl-4-trimethylsilyloxymethyl-4-trimethylsilyloxy-1-decene | 2-[5-methylthiaacetyl pentyl]-4-trimethylsilyloxy cyclopent-2-en-1-one | dl-11a,16-dihydroxy-1-methylthiamethyl-1,9-dioxo-16-hydroxymethyl-20-ethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 87 | 1-trans-iodo-3-triphenylmethoxy-1-heptene | 2-[6-methylthiaacetyl hexyl]-4-trimethylsilyloxy cyclopent-2-en-1-one | dl-11a,15a-dihydroxy-1-methylthiamethyl-1,9-dioxo-20-nor-13-trans prostene |
| 88 | 1-trans-iodo-3-methyl-3-trimethylsilyloxy-1-heptene | 2-[6-methylthiaacetyl hexyl]-4-trimethylsilyloxy cyclopent-2-en-1-one | dl,11a,15a-dihydroxy-1-methylthiamethyl-1,9-dioxo-15-methyl-20-nor-13-trans prostene |
| 89 | 1-trans-iodo-4,4-dimethyl-3-trimethylsilyloxy-1-heptene | 2-[6-methylthiaacetyl hexyl]-4-trimethylsilyloxy cyclopent-2-en-1-one | dl-11a,15a-dihydroxy-1-methylthiamethyl-1,9-dioxo-16,16-dimethyl-20-nor-13-trans prostene |
| 90 | 1-trans-iodo-5,5-dimethyl-3-triphenylmethoxy-1-octene | 2-[6-methylthiaacetyl hexyl]-4-trimethylsilyloxy cyclopent-2-en-1-one | dl-11a,15a-dihydroxy-1-methylthiamethyl-1,9-dioxo-17,17-dimethyl-13-trans prostene |
| 91 | 1-trans-iodo-4-methyl-3-triphenylmethoxy-1-octene | 2-[6-methylthiaacetyl hexyl]-4-trimethylsilyloxy cyclopent-2-en-1-one | dl-11a,15a-dihydroxy-1-methylthiamethyl-1,9-dioxo-16-methyl-13-trans prostene |
| 92 | 1-trans-iodo-4,4-trimethylene-3-trimethylsilyloxy-1-heptene | 2-[6-methylthiaacetyl hexyl]-4-trimethylsilyloxy cyclopent-2-en-1-one | dl-11a,15a-dihydroxy-1-methylthiamethyl-1,9-dioxo-16,16-trimethylene-20-nor-13-trans prostene |

| EXAMPLE | VINYL TIN | CYCLOPENTENONE | PRODUCT PROSTAGLANDIN OF THE PGE1 SERIES |
|---|---|---|---|
| 93 | 1-trans-tri-n-butylstannyl-3-vinyl-3-trimethylsilyloxy-1-heptene | 2-[6-methylthiaacetyl hexyl]-4-trimethylsilyloxy cyclopent-2-en-1-one | dl-11a,15a-dihydroxy-1-methylthiamethyl-1,9-dioxo-15-vinyl-20-nor-13-trans prostene |

TABLE VI-continued

| | | | |
|---|---|---|---|
| 94 | 1-trans-tri-n-butylstannyl-4-phenoxy-3-triethylsilyloxy-1-butene | 2-[6-methylthiaacetyl hexyl]-4-trimethylsilyloxy cyclopent-2-en-1-one | dl-11a,15a-dihydroxy-1-methylthiamethyl-1,9-dioxo-16-phenoxy-17-20-tetranor-13-trans prostene |
| 95 | 1-trans-tri-n-butylstannyl-4-(p-fluorophenoxy)-3-triethylsilyloxy-1-butene | 2-[6-methylthiaacetyl hexyl]-4-trimethylsilyloxy cyclopent-2-en-1-one | dl-11a,15a-dihydroxy-1-methylthiamethyl-1,9-dioxo-16-(p-fluorophenoxy)-17-20-tetranor-13-trans prostene |
| 96 | 1-trans-tri-n-butylstannyl-4-(m-chlorophenoxy)-3-triethylsilyloxy-1-butene | 2-[6-methylthiaacetyl hexyl]-4-trimethylsilyloxy cyclopent-2-en-1-one | dl-11a,15a-dihydroxy-1-methylthiamethyl-1,9-dioxo-16-(m-chlorophenoxy)-17-20-tetranor-13-trans prostene |
| 97 | 1-trans-tri-n-butylstannyl-4-(m-trifluoromethylphenoxy)-3-treithylsilyloxy-1-butene | 2-[6-methylthiaacetyl hexyl]-4-trimethylsilyloxy cyclopent-2-en-1-one | dl-11a,15a-dihydroxy-1-methylthiamethyl-1,9-dioxo-16-(m-trifluoromethylphenoxy)-17-20-tetranor-13-trans prostene |
| EXAMPLE | VINYL IODIDE | CYCLOPENTENONE | PRODUCT PROSTAGLANDIN OF THE PGE1 SERIES |
| 98 | 1-trans-iodo-5-phenyl-3-triethylsilyloxy-1-pentene | 2-[6-methylthiaacetyl hexyl]-4-trimethylsilyloxy cyclopent-2-en-1-one | dl-11a,15a-dihydroxy-1-methylthiamethyl-1,9-dioxo-17-phenyl-18-20-trinor-13-trans prostene |
| 99 | 1-trans-iodo-4,4-dimethyl-5-phenyl-3-triethylsilyloxy-1-pentene | 2-[6-methylthiaacetyl hexyl]-4-trimethylsilyloxy cyclopent-2-en-1-one | dl-11a,15a-dihydroxy-1-methylthiamethyl-1,9-dioxo-16,16-dimethyl-17-phenyl-18-20-trinor-13-trans prostene |
| 100 | 1-iodo-4-cyclopentyl-3-triphenylmethoxy-1-butene | 2-[6-methylthiaacetyl hexyl]-4-trimethylsilyloxy cyclopent-2-en-1-one | dl-11a,15a-dihydroxy-1-methylthiamethyl-1,9-dioxo-16-cyclopentyl-17-20-tetranor-13-trans prostene |
| 101 | 1-iodo-4-cyclohexyl-3-triphenylmethoxy-1-butene | 2-[6-methylthiaacetyl hexyl]-4-trimethylsilyloxy cyclopent-2-en-1-one | dl-11a,15a-dihydroxy-1-methylthiamethyl-1,9-dioxo-16-cyclohexyl-17-20-tetranor-13-trans prostene |
| 102 | 1-trans-iodo-3-triphenylmethoxy-1-heptene | 2-[6-methylthiaacetyl hexyl]-4-trimethylsilyloxy cyclopent-2-en-1-one | dl-11a,15a-dihydroxy-1-methylthiamethyl-1,9-dioxo-20-nor-13-trans prostene |
| EXAMPLE | VINYL TIN | CYCLOPENTENONE | PRODUCT PROSTAGLANDIN OF THE PGE1 SERIES |
| 103 | 1-trans-tri-n-butylstannyl-4-methyl-4-trimethylsilyloxy-1-heptene | 2-[6-methylthiaacetyl hexyl]-4-trimethylsilyloxy cyclopent-2-en-1-one | dl-11a,16-dihydroxy-1-methylthiamethyl-1,9-dioxo-16-methyl-20-nor-13-trans prostene |
| 104 | 1-trans-tri-n-butylstannyl-4-ethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-ethyl 13-trans prostene |
| 105 | 1-trans-tri-n-butylstannyl-5-methyl-4-trimethylsilyloxy-1-heptene | 2-[6-methylthiaacetyl hexyl]-4-trimethylsilyloxy cyclopent-2-en-1-one | dl-11a,16-dihydroxy-1-methylthiamethyl-1,9-dioxo-17-methyl-20-nor-13-trans prostene |
| EXAMPLE | VINYL IODIDE | CYCLOPENTENONE | PRODUCT PROSTAGALNDIN OF THE PGE1 SERIES |
| 106 | 1-trans-iodo-5,5-dimethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-17,17-dimethyl-13-trans prostene |
| EXAMPLE | VINYL TIN | CYCLOPENTENONE | PRODUCT PROSTAGLANDIN OF THE PGE1 SERIES |
| 107 | 1-trans-tri-n-butylstannyl-4-vinyl-4-trimethylsilyloxy-1-heptene | 2-[6-methylthiaacetyl hexyl]-4-trimethylsilyloxy cyclopent-2-en-1-one | dl-11a,16-dihydroxy-1-methylthiamethyl-1,9-dioxo-16-vinyl 20-nor-13-trans prostene |
| 108 | 1-trans-tri-n-butylstannyl-4-cyclopropyl-4-trimethylsilyloxy-1-heptene | 2-[6-methylthiaacetyl hexyl]-4-trimethylsilyloxy cyclopent-2-en-1-one | dl-11a,16-dihydroxy-1-methylthiamethyl-1,9-dioxo-16-cyclopropyl-13-trans prostene |

TABLE VI-continued

| | | | PRODUCT PROSTAGLANDIN OF THE PGE1 SERIES |
|---|---|---|---|
| 109 | 1-trans-tri-n-butylstannyl-4-trimethylsilylethynyl-4-trimethylsilyloxy-1-heptene | 2-[6-methylthiaacetyl hexyl]-4-trimethylsiloxy cyclopent-2-en-1-one | dl-11a,16-dihydroxy-1-methylthiamethyl-1,9-dioxo-16-ethynyl 20-nor-13-trans prostene |
| 110 | 1-trans-tri-n-butylstannyl-5-methylene 4-trimethylsilyloxy-1-heptene | 2-[6-methylthiaacetyl hexyl]-4-trimethylsiloxy cyclopent-2-en-1-one | dl-11a,16-dihydroxy-1-methylthiamethyl-1,9-dioxo-17-methylene-20-nor-13-trans prostene |
| 111 | 1-trans-tri-n-butylstannyl-4-methyl-5-methylene 4-trimethylsilyloxy-1-heptene | 2-[6-methylthiaacetyl hexyl]-4-trimethylsiloxy cyclopent-2-en-1-one | dl-11a,16-dihydroxy-1-methylthiamethyl-1,9-dioxo-16-methyl-17-methylene-20-nor-13-trans prostene |
| 112 | 1-trans-tri-n-butylstannyl-4-dimethoxymethyl-4-trimethylsilyloxy-1-heptene | 2-[6-methylthiaacetyl hexyl]-4-trimethylsiloxy cyclopent-2-en-1-one | dl-11a,16-dihydroxy-1-methylthiamethyl-1,9-dioxo-16-trifluoromethyl-20-nor-13-trans prostene |
| 116 | 1-trans-tri-n-butylstannyl-4-chloromethyl-4-trimethylsilyloxy-1-heptene | 2-[6-methylthiaacetyl hexyl]-4-trimethylsiloxy cyclopent-2-en-1-one | dl-11a,16-dihydroxy-1-methylthiamethyl-1,9-dioxo-16-chloromethyl-20-nor-13-trans prostene |
| 117 | 1-trans-tri-n-butylstannyl-4-trimethylsilyloxymethyl-4-trimethylsilyloxy-1-heptene | 2-[6-methylthiaacetyl hexyl]-4-trimethylsiloxy cyclopent-2-en-1-one | dl-11a,16-dihydroxy-1-methylthiamethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE PGE1 SERIES |
| 118 | 1-trans-iodo-4-methyl-7-chloro 4-trimethylsilyloxy-1-heptene | 2-[6-methylthiaacetyl hexyl]-4-trimethylsiloxy cyclopent-2-en-1-one | dl-11a,15a-dihydroxy-1-methylthiamethyl-1,9-dioxo-16-methyl 19-chloro-20-nor-13-trans prostene |
| 119 | 1-trans-iodo-3-triphenylmethoxy-1-octene | 2-[6-methylthiaacetyl hexyl]-4-trimethylsiloxy cyclopent-2-en-1-one | dl-11a,15a-dihydroxy-1-methylthiamethyl-1,9-dioxo-13-trans prostene |
| 120 | 1-trans-iodo-3-methyl-3-trimethylsilyloxy-1-octene | 2-[6-methylthiaacetyl hexyl]-4-trimethylsiloxy cyclopent-2-en-1-one | dl-11a,15a-dihydroxy-1-methylthiamethyl-1,9-dioxo-15-methyl-13-trans prostene |
| 121 | 1-trans-iodo-4,4-dimethyl 3-trimethylsilyloxy-1-octene | 2-[6-methylthiaacetyl hexyl]-4-trimethylsiloxy cyclopent-2-en-1-one | dl-11a,15a-dihydroxy-1-methylthiamethyl-1,9-dioxo-16,16-dimethyl-13-trans prostene |
| 122 | 1-trans-iodo-4,4-trimethylene 3-trimethylsilyloxy-1-octene | 2-[6-methylthiaacetyl hexyl]-4-trimethylsiloxy cyclopent-2-en-1-one | dl-11a,15a-dihydroxy-1-methylthiamethyl-1,9-dioxo-16,16-trimethylene-13-trans prostene |
| EXAMPLE | VINYL TIN | CYCLOPENTENONE | PRODUCT PROSTAGLANDIN OF THE PGE1 SERIES |
| 123 | 1-trans-tri-n-butylstannyl-3-vinyl-3-trimethylsilyloxy-1-octene | 2-[6-methylthiaacetyl hexyl]-4-trimethylsiloxy cyclopent-2-en-1-one | dl-11a,15a-dihydroxy-1-methylthiamethyl-1,9-dioxo-15-vinyl-13-trans prostene |
| EXAMPLE | VINYL IODIDE | CYCLOPENTENONE | PRODUCT PROSTAGLANDIN OF THE PGE1 SERIES |
| 124 | 1-trans-iodo-4-triphenylkmethoxy-1-octene | 2-[6-methylthiaacetyl hexyl]-4-trimethylsiloxy cyclopent-2-en-1-one | dl-11a,16-dihydroxy-1-methylthiamethyl-1,9-dioxo-13-trans prostene |
| EXAMPLE | VINYL TIN | CYCLOPENTENONE | PRODUCT PROSTAGLANDIN OF THE PGE1 SERIES |
| 125 | 1-trans-tri-n-butylstannyl-4-methyl-4-trimethylsilyloxy-1-octene | 2-[6-methylthiaacetyl hexyl]-4-trimethylsiloxy cyclopent-2-en-1-one | dl-11a,16-dihydroxy-1-methylthiamethyl-1,9-dioxo-16-methyl 13-trans prostene |
| 126 | 1-trans-tri-n-butylstannyl-5-methyl-4-trimethylsilyloxy-1-octene | 2-[6-methylthiaacetyl hexyl]-4-trimethylsiloxy cyclopent-2-en-1-one | dl-11a,16-dihydroxy-1-methylthiamethyl-1,9-dioxo-17-methyl-13-trans prostene |

TABLE VI-continued

| | VINYL TIN | CYCLOPENTENONE | PRODUCT PROSTAGLANDIN OF THE PGE1 SERIES |
|---|---|---|---|
| 127 | 1-trans-tri-n-butylstannyl-4-vinyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-vinyl-13-trans prostene |
| 128 | 1-trans-tri-n-butylstannyl-4-trimethylsilylethynyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-ethynyl-13-trans prostene |
| 129 | 1-trans-tri-n-butylstannyl-5-methylene 4-triethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-17-methylene-13-trans prostene |
| 130 | 1-trans-tri-n-butylstannyl-4-methyl-5-methylene 4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-methyl-17-methylene-13-trans prostene |
| 131 | 1-trans-tri-n-butylstannyl-4-dimethoxymethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-formyl-13-trans prostene |
| 132 | 1-trans-tri-n-butylstannyl-4-fluoromethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-fluoromethyl-13-trans prostene |
| 133 | 1-trans-tri-n-butylstannyl-4-difluoromethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-difluoromethyl-13-trans prostene |
| 134 | 1-trans-tri-n-butylstannyl-4-trifluoromethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-trifluoromethyl-13-trans prostene |
| 135 | 1-trans-tri-n-butylstannyl-4-chloromethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-chloromethyl-13-trans prostene |
| 136 | 1-trans-tri-n-butylstannyl-4-trimethylsilyloxymethyl-4-trimethylsilyloxy-1-octene | 2-[6-methylthiaacetyl hexyl]-4-trimethylsilyloxy cyclopent-2-en-1-one | dl-11a,16-dihydroxy-1-methylthiamethyl-1,9-dioxo-16-hydroxymethyl-13-trans prostene |
| EXAMPLE | VINYL IODIDE | CYCLOPENTENONE | PRODUCT PROSTAGLANDIN OF THE PGE1 SERIES |
| 137 | 1-trans-iodo-3-triphenylmethoxy-1-nonene | 2-[6-methylthiaacetyl hexyl]-4-trimethylsilyloxy cyclopent-2-en-1-one | dl-11a,15a-dihydroxy-1-methylthiamethyl-1,9-dioxo-20-methyl-13-trans prostene |
| 138 | 1-trans-iodo-3-methyl-3-trimethylsilyloxy-1-nonene | 2-[6-methylthiaacetyl hexyl]-4-trimethylsilyloxy cyclopent-2-en-1-one | dl-11a,15a-dihydroxy-1-methylthiamethyl-1,9-dioxo-15-methyl-20-methyl-13-trans prostene |
| 139 | 1-trans-iodo-4,4-dimethyl-3-trimethylsilyloxy-1-nonene | 2-[6-methylthiaacetyl hexyl]-4-trimethylsilyloxy cyclopent-2-en-1-one | dl-11a,15a-dihydroxy-1-methylthiamethyl-1,9-dioxo-16,16-dimethyl-20-methyl-13-trans prostene |
| 140 | 1-trans-iodo-4,4-trimethylene 3-trimethylsilyloxy-1-nonene | 2-[6-methylthiaacetyl hexyl]-4-trimethylsilyloxy cyclopent-2-en-1-one | dl-11a,15a-dihydroxy-1-methylthiamethyl-1,9-dioxo-16,16-trimethylene-20-methyl-13-trans prostene |
| EXAMPLE | VINYL IODIDE | CYCLOPENTENONE | PRODUCT PROSTAGLANDIN OF THE PGE1 SERIES |
| 141 | 1-trans-tri-n-butylstannyl-3-vinyl-3-trimethylsilyloxy-1-nonene | 2-[6-methylthiaacetyl hexyl]-4-trimethylsilyloxy cyclopent-2-en-1-one | dl-11a,15a-dihydroxy-1-methylthiamethyl-1,9-dioxo-15-vinyl-20-methyl-13-trans prostene |
| EXAMPLE | VINYL IODIDE | CYCLOPENTENONE | PRODUCT PROSTAGLANDIN OF THE PGE1 SERIES |
| 142 | 1-trans-iodo-4-triphenylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-20-methyl-13-trans prostene |

TABLE VI-continued

| EXAMPLE | VINYL TIN | CYCLOPENTENONE | PRODUCT PROSTAGLANDIN OF THE PGE1 SERIES |
|---|---|---|---|
| 143 | 1-trans-tri-n-butylstannyl-4-methyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-methyl-20-methyl-13-trans prostene |
| 144 | 1-trans-tri-n-butylstannyl-4-methyl-5-methyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-17-methyl-20-methyl-13-trans prostene |
| 145 | 1-trans-tri-n-butylstannyl-4-vinyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-vinyl-20-methyl-13-trans prostene |
| 146 | 1-trans-tri-n-butylstannyl-4-trimethylsilylethynyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-ethynyl-20-methyl-13-trans prostene |
| 147 | 1-trans-tri-n-butylstannyl-5-methylene-4-triethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-17-methylene-20-methyl-13-trans prostene |
| 148 | 1-trans-tri-n-butylstannyl-4-methyl-5-methylene-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-methyl-17-methylene-20-methyl-13-trans prostene |
| 149 | 1-trans-tri-n-butylstannyl-4-dimethoxymethyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-formyl-20-methyl-13-trans prostene |
| 150 | 1-trans-tri-n-butylstannyl-4-fluoromethyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-fluoromethyl-20-methyl-13-trans prostene |
| 151 | 1-trans-tri-n-butylstannyl-4-difluoromethyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-difluoromethyl-20-methyl-13-trans prostene |
| 152 | 1-trans-tri-n-butylstannyl-4-trifluoromethyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-trifluoromethyl-20-methyl-13-trans prostene |
| 153 | 1-trans-tri-n-butylstannyl-4-chloromethyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-chloromethyl-20-methyl-13-trans prostene |
| 154 | 1-trans-tri-n-butylstannyl-4-trimethylsilyloxymethyl-4-trimethylsilyloxy-1-nonene | 2-[6-methylthiaacetyl hexyl]-4-trimethylsilyloxy cyclopent-2-en-1-one | dl-11a,16-dihydroxy-1-methylthiamethyl-1,9-dioxo-16-hydroxymethyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 155 | 1-trans-iodo-3-triphenylmethoxy-1-decene | 2-[6-methylthiaacetyl hexyl]-4-trimethylsilyloxy cyclopent-2-en-1-one | dl-11a,15a-dihydroxy-1-methylthiamethyl-1,9-dioxo-20-ethyl-13-trans prostene |
| 156 | 1-trans-iodo-3-methyl-3-trimethylsilyloxy-1-decene | 2-[6-methylthiaacetyl hexyl]-4-trimethylsilyloxy cyclopent-2-en-1-one | dl-11a,15a-dihydroxy-1-methylthiamethyl-1,9-dioxo-15-methyl-20-ethyl-13-trans prostene |
| 157 | 1-trans-iodo-4,4-dimethyl-3-trimethylsilyloxy-1-decene | 2-[6-methylthiaacetyl hexyl]-4-trimethylsilyloxy cyclopent-2-en-1-one | dl-11a,15a-dihydroxy-1-methylthiamethyl-1,9-dioxo-16,16-dimethyl-20-ethyl-13-trans prostene |
| 158 | 1-trans-iodo-4,4-trimethylene-3-trimethylsilyloxy-1-decene | 2-[6-methylthiaacetyl hexyl]-4-trimethylsilyloxy cyclopent-2-en-1-one | dl-11a,15a-dihydroxy-1-methylthiamethyl-1,9-dioxo-16,16-trimethylene-20-ethyl-13-trans prostene |

TABLE VI-continued

| EXAMPLE | VINYL TIN | CYCLOPENTENONE | PRODUCT PROSTAGLANDIN OF THE PGE1 SERIES |
|---|---|---|---|
| 159 | 1-trans-tri-n-butylstannyl-3-vinyl-3-trimethylsilyloxy-1-decene | 2-[6-methylthiaacetyl hexyl]-4-trimethylsiloxy cyclopent-2-en-1-one | dl-11a,15a-dihydroxy-1-methylthiamethyl-1,9-dioxo-15-vinyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 160 | 1-trans-iodo-4-triphenylmethoxy-1-decene | 2-[ 6-methylthiaacetyl hexyl]-4-trimethylsiloxy cyclopent-2-en-1-one | dl-11a,16-dihydroxy-1-methylthiamethyl-1,9-dioxo-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 161 | 1-trans-tri-n-butylstannyl-4-methyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-methyl-20-ethyl-13-trans prostene |
| 162 | 1-trans-tri-n-butylstannyl-5-methyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-17-methyl-20-ethyl-13-trans prostene |
| 163 | 1-trans-tri-n-butylstannyl-4-vinyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-vinyl-20-ethyl-13-trans prostene |
| 164 | 1-trans-tri-n-butylstannyl-4-trimethylsilylethynyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-ethynyl-20-ethyl-13-trans prostene |
| 165 | 1-trans-tri-n-butylstannyl-5-methylene-4-triethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-17-methylene-20-ethyl-13-trans prostene |
| 166 | 1-trans-tri-n-butylstannyl-4-methyl-5-methylene-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-methyl-17-methylene-20-ethyl-13-trans prostene |
| 167 | 1-trans-tri-n-butylstannyl-4-dimethoxymethyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-formyl-20-ethyl-13-trans prostene |
| 168 | 1-trans-tri-n-butylstannyl-4-fluoromethyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-fluoromethyl-20-ethyl-13-trans prostene |
| 169 | 1-trans-tri-n-butylstannyl-4-difluoromethyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-difluoromethyl-20-ethyl-13-trans prostene |
| 170 | 1-trans-tri-n-butylstannyl-4-trifluoromethyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-trifluoromethyl-20-ethyl-13-trans prostene |
| 171 | 1-trans-tri-n-butylstannyl-4-chloromethyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-chloromethyl-20-ethyl-13-trans prostene |
| 172 | 1-trans-tri-n-butylstannyl-4-trimethylsilyloxymethyl-4-trimethylsilyloxy-1-decene | 2-[6-methylthiaacetyl hexyl]-4-trimethylsiloxy cyclopent-2-en-1-one | dl-11a,16-dihydroxy-1-methylthiamethyl-1,9-dioxo-16-hydroxymethyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 173 | 1-trans-iodo-3-triphenymethoxy-1-heptene | 2-[7-methylthiaacetyl heptyl]-4-trimethylsilyloxy cyclopent-2-en-1-one | dl-11a,15a-dihydroxy-1-methyithiamethyl-1,9-dioxo-20-nor-2-homo-13-trans prostene |
| 174 | 1-trans-iodo-3-methyl- | 2-[7-methylthiaacetyl | dl-11a,15a-dihydroxy-1-methylthiamethyl-1,9-dioxo-15-methyl- |

TABLE VI-continued

| | | | |
|---|---|---|---|
| 175 | 3-trimethylsilyloxy-1-heptene | heptyl]-4-trimethylsilyloxy cyclopent-2-en-1-one | 20-nor-2-homo-13-trans prostene |
| | 1-trans-iodo-4,4-dimethyl 3-trimethylsilyloxy-1-heptene | 2-[7-methylthiaacetyl heptyl]-4-trimethylsilyloxy cyclopent-2-en-1-one | dl-11a,15a-dihydroxy-1-methylthiamethyl-1,9-dioxo-16,16-dimethyl-20-nor-2-homo-13-trans prostene |
| 176 | 1-trans-iodo-5,5-dimethyl 3-triphenylmethoxy-1-octene | 2-[7-methylthiaacetyl heptyl]-4-trimethylsilyloxy cyclopent-2-en-1-one | dl-11a,15a-dihydroxy-1-methylthiamethyl-1,9-dioxo-17,17-dimethyl-2-homo-13-trans prostene |
| 177 | 1-trans-iodo-4-methyl 3-triphenylmethoxy-1-octene | 2-[7-methylthiaacetyl heptyl]-4-trimethylsilyloxy cyclopent-2-en-1-one | dl-11a,15a-dihydroxy-1-methylthiamethyl-1,9-dioxo-16-methyl-2-homo-13-trans prostene |
| 178 | 1-trans-iodo-4,4-trimethylene 3-trimethylsilyloxy-1-heptene | 2-[7-methylthiaacetyl heptyl]-4-trimethylsilyloxy cyclopent-2-en-1-one | dl-11a,15a-dihydroxy-1-methylthiamethyl-1,9-dioxo-16,16-trimethylene-20-nor-2-homo-13-trans prostene |
| EXAMPLE | VINYL TIN | CYCLOPENTENONE | PRODUCT PROSTAGLANDIN OF THE PGE1 SERIES |
| 179 | 1-trans-tri-n-butylstannyl-3-vinyl-3-trimethylsilyloxy-1-heptene | 2-[7-methylthiaacetyl heptyl]-4-trimethylsilyloxy cyclopent-2-en-1-one | dl-11a,15a-dihydroxy-1-methylthiamethyl-1,9-dioxo-15-vinyl-20-nor-2-homo-13-trans prostene |
| 180 | 1-trans-tri-n-butylstannyl-4-phenoxy 3-triethylsilyloxy-1-butene | 2-[7-methylthiaacetyl heptyl]-4-trimethylsilyloxy cyclopent-2-en-1-one | dl-11a,15a-dihydroxy-1-methylthiamethyl-1,9-dioxo-16-phenoxy-2-homo-17-20-tetranor-13-trans prostene |
| 181 | 1-trans-tri-n-butylstannyl-4-(p-fluorophenoxy) 3-triethylsilyloxy-1-butene | 2-[7-methylthiaacetyl heptyl]-4-trimethylsilyloxy cyclopent-2-en-1-one | dl-11a,15a-dihydroxy-1-methylthiamethyl-1,9-dioxo-16-(p-fluorophenoxy)-2-homo-17-20-tetranor-13-trans prostene |
| 182 | 1-trans-tri-n-butylstannyl-4-(m-chlorophenoxy) 3-triethylsilyloxy-1-butene | 2-[7-methylthiaacetyl heptyl]-4-trimethylsilyloxy cyclopent-2-en-1-one | dl-11a,15a-dihydroxy-1-methylthiamethyl-1,9-dioxo-16-(m-chlorophenoxy)-2-homo-17-20-tetranor-13-trans prostene |
| 183 | 1-trans-tri-n-butylstannyl-4-(m-trifluoromethylphenoxy) 3-triethylsilyloxy-1-butene | 2-[7-methylthiaacetyl heptyl]-4-trimethylsilyloxy cyclopent-2-en-1-one | dl-11a,15a-dihydroxy-1-methylthiamethyl-1,9-dioxo-16-(m-trifluoromethylphenoxy)-2-homo-17-20-tetranor-13-trans prostene |
| EXAMPLE | VINYL IODIDE | CYCLOPENTENONE | PRODUCT PROSTAGLANDIN OF THE PGE1 SERIES |
| 184 | 1-trans-iodo-5-phenyl 3-triethylsilyloxy-1-pentene | 2-[7-methylthiaacetyl heptyl]-4-trimethylsilyloxy cyclopent-2-en-1-one | dl-11a,15a-dihydroxy-1-methylthiamethyl-1,9-dioxo-17-phenyl-2-homo-18-20-trinor-13-trans prostene |
| 185 | 1-trans-iodo-4,4-dimethyl-5-phenyl 3-triethylsilyloxy-1-pentene | 2-[7-methylthiaacetyl heptyl]-4-trimethylsilyloxy cyclopent-2-en-1-one | dl-11a,15a-dihydroxy-1-methylthiamethyl-1,9-dioxo-16,16-dimethyl-17-phenyl-2-homo-18-20-trinor-13-trans prostene |
| 186 | 1-trans-iodo-4-cyclopentyl 3-triphenylmethoxy-1-butene | 2-[7-methylthiaacetyl heptyl]-4-trimethylsilyloxy cyclopent-2-en-1-one | dl-11a,15a-dihydroxy-1-methylthiamethyl-1,9-dioxo-16-cyclopentyl-2-homo-17-20-tetranor-13-trans prostene |
| 187 | 1-trans-iodo-4-cyclohexyl 3-triphenylmethoxy-1-butene | 2-[7-methylthiaacetyl heptyl]-4-trimethylsilyloxy cyclopent-2-en-1-one | dl-11a,15a-dihydroxy-1-methylthiamethyl-1,9-dioxo-16-cyclohexyl-2-homo-17-20-tetranor-13-trans prostene |
| 188 | 1-trans-iodo-4-triphenylmethoxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-20-nor-2-homo-13-trans prostene |
| EXAMPLE | VINYL TIN | CYCLOPENTENONE | PRODUCT PROSTAGLANDIN OF THE PGE1 SERIES |
| 189 | 1-trans-tri-n-butylstannyl-4-methyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-20-nor-2-homo-13-trans prostene |

TABLE VI-continued

| EXAMPLE | VINYL IODIDE | CYCLOPENTENONE | PRODUCT PROSTAGLANDIN OF THE PGE1 SERIES |
|---|---|---|---|
| 190 | 1-trans-tri-n-butylstannyloxy-1-octene-4-ethyl-4-trimethylsilyloxy | 2-[methylthiaacetyl heptyl]-4-trimethylsilyloxy cyclopent-2-en-1-one | dl-11a,16-dihydroxy-1-methylthiamethyl-1,9-dioxo-16-ethyl-2-homo-13-trans prostene |
| 191 | 1-trans-tri-n-butylstannyloxy-1-heptene-4-trimethylsilyloxy-5-methyl | 2-[7-methylthiaacetyl heptyl]-4-trimethylsilyloxy cyclopent-2-en-1-one | dl-11a,16-dihydroxy-1-methylthiamethyl-1,9-dioxo-17-methyl-20-nor-2-homo-13-trans prostene |
| EXAMPLE | VINYL IODIDE | CYCLOPENTENONE | PRODUCT PROSTAGLANDIN OF THE PGE1 SERIES |
| 192 | 1-trans-iodo-5,5-dimethyl-4-trimethylsilyloxy-1-octene | 2-[7-methylthiaacetyl heptyl]-4-trimethylsilyloxy cyclopent-2-en-1-one | dl-11a,16-dihydroxy-1-methylthiamethyl-1,9-dioxo-17,17-dimethyl-2-homo-13-trans prostene |
| EXAMPLE | VINYL TIN | CYCLOPENTENONE | PRODUCT PROSTAGLANDIN OF THE PGE1 SERIES |
| 193 | 1-trans-tri-n-butylstannyl-4-vinyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-vinyl-20-nor-2-homo-13-trans prostene |
| 194 | 1-trans-tri-n-butylstannyl-4-cyclopropyl-4-trimethylsilyloxy-1-octene | 2-[7-methylthiaacetyl heptyl]-4-trimethylsilyloxy cyclopent-2-en-1-one | dl-11a,16-dihydroxy-1-methylthiamethyl-1,9-dioxo-16-cyclopropyl-2-homo-13-trans prostene |
| 195 | 1-trans-tri-n-butylstannyl-4-trimethylsilylethynyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-ethynyl-20-nor-2-homo-13-trans prostene |
| 196 | 1-trans-tri-n-butylstannyl-5-methylene-4-triethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-17-methylene-20-nor-2-homo-13-trans prostene |
| 197 | 1-trans-tri-n-butylstannyl-4-methyl-5-methylene-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-17-methylene-20-nor-2-homo-13-trans prostene |
| 198 | 1-trans-tri-n-butylstannyl-4-dimethoxymethyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-formyl-20-nor-2-homo-13-trans prostene |
| 199 | 1-trans-tri-n-butylstannyl-4-fluoromethyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-fluoromethyl-20-nor-2-homo-13-trans prostene |
| 200 | 1-trans-tri-n-butylstannyl-4-difluoromethyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-difluoromethyl-20-nor-2-homo-13-trans prostene |
| 201 | 1-trans-tri-n-butylstannyl-4-trifluoromethyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-trifluoromethyl-20-nor-2-homo-13-trans prostene |
| 202 | 1-trans-tri-n-butylstannyl-4-chloromethyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-chloromethyl-20-nor-2-homo-13-trans prostene |
| 203 | 1-trans-tri-n-butylstannyl-4-trimethylsilyloxymethyl-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-hydroxymethyl-20-nor-2-homo-13-trans prostene |
| EXAMPLE | VINYL IODIDE | CYCLOPENTENONE | PRODUCT PROSTAGLANDIN OF THE PGE1 SERIES |
| 204 | 1-trans-iodo-4-methyl-7-chloro-4-trimethylsilyloxy-1-heptene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-19-chloro-2-homo-20-nor-13-trans prostene |
| 205 | 1-trans-iodo-3-triphenylmethoxy-1-octene | 2-[7-meth.thiaacetyl heptyl]-4-trimethylsilyloxy cyclopent-2-en-1-one | dl-11a,15a-dihydroxy-1-methylthiamethyl-1,9-dioxo-2-homo-13-trans prostene |

TABLE VI-continued

| EXAMPLE | | | PRODUCT PROSTAGLANDIN |
|---|---|---|---|
| 206 | 1-trans-iodo-3-methyl-3-trimethylsilyloxy-1-octene | 2-[7-methylthiaacetyl heptyl]-4-trimethylsiloxy cyclopent-2-en-1-one | dl-11a,15a-dihydroxy-1-methylthiamethyl-1,9-dioxo-15-methyl-2-homo-13-trans prostene |
| 207 | 1-trans-iodo-4,4-dimethyl-3-trimethylsilyloxy-1-octene | 2-[7-methylthiaacetyl heptyl]-4-trimethylsiloxy cyclopent-2-en-1-one | dl-11a,15a-dihydroxy-1-methylthiamethyl-1,9-dioxo-16,16-dimethyl-2-homo-13-trans prostene |
| 208 | 1-trans-iodo-4,4-trimethylene-3-trimethylsilyloxy-1-octene | 2-[7-methylthiaacetyl heptyl]-4-trimethylsiloxy cyclopent-2-en-1-one | dl-11a,15a-dihydroxy-1-methylthiamethyl-1,9-dioxo-16,16-trimethylene-2-homo-13-trans prostene |
| EXAMPLE | VINYL TIN | CYCLOPENTENONE | PRODUCT PROSTAGLANDIN OF THE PGE1 SERIES |
| 209 | 1-trans-tri-n-butylstannyl-3-vinyl-3-trimethylsilyloxy-1-octene | 2-[7-methylthiaacetyl heptyl]-4-trimethylsiloxy cyclopent-2-en-1-one | dl-11a,15a-dihydroxy-1-methylthiamethyl-1,9-dioxo-15-vinyl-2-homo-13-trans prostene |
| EXAMPLE | VINYL IODIDE | CYCLOPENTENONE | PRODUCT PROSTAGLANDIN OF THE PGE1 SERIES |
| 210 | 1-trans-iodo-4-triphenylmethoxy-1-octene | 2-[7-methylthiaacetyl heptyl]-4-trimethylsiloxy cyclopent-2-en-1-one | dl-11a,16-dihydroxy-1-methylthiamethyl-1,9-dioxo-2-homo-13-trans prostene |
| EXAMPLE | VINYL TIN | CYCLOPENTENONE | PRODUCT PROSTAGLANDIN OF THE PGE1 SERIES |
| 211 | 1-trans-tri-n-butylstannyl-4-methyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-methyl-2-homo-13-trans prostene |
| 212 | 1-trans-tri-n-butylstannyl-5-methyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-17-methyl-2-homo-13-trans prostene |
| 213 | 1-trans-tri-n-butylstannyl-4-vinyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-vinyl-2-homo-13-trans prostene |
| 214 | 1-trans-tri-n-butylstannyl-4-trimethylsilylethynyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-ethynyl-2-homo-13-trans prostene |
| 215 | 1-trans-tri-n-butylstannyl-5-methylene-4-triethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-17-methylene-2-homo-13-trans prostene |
| 216 | 1-trans-tri-n-butylstannyl-4-methyl-5-methylene-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-methyl-17-methylene-2-homo-13-trans prostene |
| 217 | 1-trans-tri-n-butylstannyl-4-dimethoxymethyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-formyl-2-homo-13-trans prostene |
| 218 | 1-trans-tri-n-butylstannyl-4-fluoromethyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-fluoromethyl-2-homo-13-trans prostene |
| 219 | 1-trans-tri-n-butylstannyl-4-difluoromethyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-difluoromethyl-2-homo-13-trans prostene |
| 220 | 1-trans-tri-n-butylstannyl-4-trifluoromethyl-4-trimethylsilyloxy-1-octene | 2-[7-methylthiaacetyl heptyl]-4-trimethylsiloxy cyclopent-2-en-1-one | dl-11a,16-dihydroxy-1-methylthiamethyl-1,9-dioxo-16-trifluoromethyl-2-homo-13-trans prostene |
| 221 | 1-trans-tri-n-butylstannyl-4-chloromethyl- | 2-[7-methylthiaacetyl | dl-11a,16-dihydroxy-1-methylthiamethyl-1,9-dioxo-16-chloromethyl- |

TABLE VI-continued

| EXAMPLE | VINYL IODIDE | CYCLOPENTENONE | PRODUCT PROSTAGLANDIN OF THE PGE1 SERIES |
|---|---|---|---|
| 222 | 1-trans-tri-n-butylstannyl-4-trimethylsilyloxymethyl-4-trimethylsilyloxy-1-octene | 2-[7-methylthiaacetyl heptyl]-4-trimethylsilyloxy cyclopent-2-en-1-one | dl-11a,16-dihydroxy-1-methylthiamethyl-1,9-dioxo-16-hydroxymethyl-2-homo-13-trans prostene |
| EXAMPLE | VINYL IODIDE | CYCLOPENTENONE | PRODUCT PROSTAGLANDIN OF THE PGE1 SERIES |
| 223 | 1-trans-iodo-3-triphenylmethoxy-1-nonene | 2-[7-methylthiaacetyl heptyl]-4-trimethylsilyloxy cyclopent-2-en-1-one | dl-11a,15a-dihydroxy-1-methylthiamethyl-1,9-dioxo-20-methyl-2-homo-13-trans prostene |
| 224 | 1-trans-iodo-3-methyl-3-trimethylsilyloxy-1-nonene | 2-[7-methylthiaacetyl heptyl]-4-trimethylsilyloxy cyclopent-2-en-1-one | dl-11a,15a-dihydroxy-1-methylthiamethyl-1,9-dioxo-15-methyl-20-methyl-2-homo-13-trans prostene |
| 225 | 1-trans-iodo-4,4-dimethyl-3-trimethylsilyloxy-1-nonene | 2-[7-methylthiaacetyl heptyl]-4-trimethylsilyloxy cyclopent-2-en-1-one | dl-11a,15a-dihydroxy-1-methylthiamethyl-1,9-dioxo-16,16-dimethyl-20-methyl-2-homo-13-trans prostene |
| 226 | 1-trans-iodo-4,4-trimethylene-3-trimethylsilyloxy-1-nonene | 2-[7-methylthiaacetyl heptyl]-4-trimethylsilyloxy cyclopent-2-en-1-one | dl-11a,15a-dihydroxy-1-methylthiamethyl-1,9-dioxo-16,16-trimethylene-20-methyl-2-homo-13-trans prostene |
| EXAMPLE | VINYL TIN | CYCLOPENTENONE | PRODUCT PROSTAGLANDIN OF THE PGE1 SERIES |
| 227 | 1-trans-tri-n-butylstannyl-3-vinyl-3-trimethylsilyloxy-1-nonene | 2-[7-methylthiaacetyl heptyl]-4-trimethylsilyloxy cyclopent-2-en-1-one | dl-11a,15a-dihydroxy-1-methylthiamethyl-1,9-dioxo-15-vinyl-20-methyl-2-homo-13-trans prostene |
| EXAMPLE | VINYL IODIDE | CYCLOPENTENONE | PRODUCT PROSTAGLANDIN OF THE PGE1 SERIES |
| 228 | 1-trans-iodo-4-triphenylmethoxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-20-methyl-2-homo-13-trans prostene |
| EXAMPLE | VINYL TIN | CYCLOPENTENONE | PRODUCT PROSTAGLANDIN OF THE PGE1 SERIES |
| 229 | 1-trans-tri-n-butylstannyl-4-methyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-20-methyl-2-homo-13-trans prostene |
| 230 | 1-trans-tri-n-butylstannyl-5-methyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-17-methyl-20-methyl-2-homo-13-trans prostene |
| 231 | 1-trans-tri-n-butylstannyl-4-vinyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-vinyl-20-methyl-2-homo-13-trans prostene |
| 232 | 1-trans-tri-n-butylstannyl-4-trimethylsilylethynyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-ethynyl-20-methyl-2-homo-13-trans prostene |
| 233 | 1-trans-tri-n-butylstannyl-5-methylene-4-triethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-17-methylene-20-methyl-2-homo-13-trans prostene |
| 234 | 1-trans-tri-n-butylstannyl-4-methyl-5-methylene-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-17-methylene-20-methyl-2-homo-13-trans prostene |
| 235 | 1-trans-tri-n-butylstannyl-4-dimethoxymethyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-formyl-20-methyl-2-homo-13-trans prostene |
| 236 | 1-trans-tri-n-butylstannyl-4-fluoromethyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-fluoromethyl- |

TABLE VI-continued

| EXAMPLE | VINYL IODIDE / VINYL TIN | CYCLOPENTENONE | PRODUCT PROSTAGLANDIN OF THE PGE1 SERIES |
|---|---|---|---|
| | 4-trimethylsilyloxy-1-nonene | heptyl]-4-trimethylsilyloxy cyclopent-2-en-1-one | 20-methyl-2-homo-13-trans prostene |
| 237 | 1-trans-tri-n-butylstannyl-4-difluoromethyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-difluoromethyl-20-methyl-2-homo-13-trans prostene |
| 238 | 1-trans-tri-n-butylstannyl-4-trifluoromethyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-trifluoromethyl-20-methyl-2-homo-13-trans prostene |
| 239 | 1-trans-tri-n-butylstannyl-4-chloromethyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-chloromethyl-20-methyl-2-homo-13-trans prostene |
| 240 | 1-trans-tri-n-butylstannyl-4-trimethylsilyloxymethyl-4-trimethylsilyloxy-1-nonene | 2-[7-methylthiaacetyl heptyl]-4-trimethylsilyloxy cyclopent-2-en-1-one | dl-11a,16-dihydroxy-1-methylthiamethyl-1,9-dioxo-16-hydroxymethyl-20-methyl-2-homo-13-trans prostene |
| EXAMPLE | VINYL IODIDE | CYCLOPENTENONE | PRODUCT PROSTAGLANDIN OF THE PGE1 SERIES |
| 241 | 1-trans-iodo-3-triphenylmethoxy-1-decene | 2-[7-methylthiaacetyl heptyl]-4-trimethylsilyloxy cyclopent-2-en-1-one | dl-11a,15a-dihydroxy-1-methylthiamethyl-1,9-dioxo-20-ethyl-2-homo-13-trans prostene |
| 242 | 1-trans-iodo-3-methyl-3-trimethylsilyloxy-1-decene | 2-[7-methylthiaacetyl heptyl]-4-trimethylsilyloxy cyclopent-2-en-1-one | dl-11a,15a-dihydroxy-1-methylthiamethyl-1,9-dioxo-15-methyl-20-ethyl-2-homo-13-trans prostene |
| 243 | 1-trans-iodo-4,4-dimethyl-3-trimethylsilyloxy-1-decene | 2-[7-methylthiaacetyl heptyl]-4-trimethylsilyloxy cyclopent-2-en-1-one | dl-11a,15a-dihydroxy-1-methylthiamethyl-1,9-dioxo-16,16-dimethyl-20-ethyl-2-homo-13-trans prostene |
| 244 | 1-trans-iodo-4,4-trimethylene-3-trimethylsilyloxy-1-decene | 2-[7-methylthiaacetyl heptyl]-4-trimethylsilyloxy cyclopent-2-en-1-one | dl-11a,15a-dihydroxy-1-methylthiamethyl-1,9-dioxo-16,16-trimethylene-20-ethyl-2-homo-13-transprostene |
| EXAMPLE | VINYL TIN | CYCLOPENTENONE | PRODUCT PROSTAGLANDIN OF THE PGE1 SERIES |
| 245 | 1-trans-tri-n-butylstannyl-3-vinyl-3-trimethylsilyloxy-1-decene | 2-[7-methylthiaacetyl heptyl]-4-trimethylsilyloxy cyclopent-2-en-1-one | dl-11a,15a-dihydroxy-1-methylthiamethyl-1,9-dioxo-15-vinyl-20-ethyl-2-homo-13-trans prostene |
| EXAMPLE | VINYL IODIDE | CYCLOPENTENONE | PRODUCT PROSTAGLANDIN OF THE PGE1 SERIES |
| 246 | 1-trans-iodo-4-triphenylmethoxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-20-ethyl-2-homo-13-trans prostene |
| EXAMPLE | VINYL TIN | CYCLOPENTENONE | PRODUCT PROSTAGLANDIN OF THE PGE1 SERIES |
| 247 | 1-trans-tri-n-butylstannyl-4-methyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-20-ethyl-2-homo-13-trans prostene |
| 248 | 1-trans-tri-n-butylstannyl-5-methyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-17-methyl-20-ethyl-2-homo-13-trans prostene |
| 249 | 1-trans-tri-n-butylstannyl-4-vinyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-vinyl-20-ethyl-2-homo-13-trans prostene |
| 250 | 1-trans-tri-n-butylstannyl-4-trimethylsilylethynyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-ethynyl-20-ethyl-2-homo-13-trans prostene |
| 251 | 1-trans-tri-n-butylstannyl-5-methylene | 2-[7-methylthiaacetyl | dl-11a,16-dihydroxy-1-methylthiamethyl-1,9-dioxo- |

TABLE VI-continued

| EXAMPLE | VINYL IODIDE | CYCLOPENTENONE | PRODUCT PROSTAGLANDIN OF THE PGE1 SERIES |
|---|---|---|---|
| 252 | 1-trans-tri-n-butylstannyl-4-methyl-5-methylene 4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-methyl-17-methylene-20-ethyl-2-homo-13-trans prostene |
| 253 | 1-trans-tri-n-butylstannyl-4-dimethoxymethyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-formyl-20-ethyl-2-homo-13-trans prostene |
| 254 | 1-trans-tri-n-butylstannyl-4-fluoromethyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-fluoromethyl-20-ethyl-2-homo-13-trans prostene |
| 255 | 1-trans-tri-n-butylstannyl-4-difluoromethyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-difluoromethyl-20-ethyl-2-homo-13-trans prostene |
| 256 | 1-trans-tri-n-butylstannyl-4-trifluoromethyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-trifluoromethyl-20-ethyl-2-homo-13-trans prostene |
| 257 | 1-trans-tri-n-butylstannyl-4-chloromethyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-chloromethyl-20-ethyl-2-homo-13-trans prostene |
| 258 | 1-trans-tri-n-butylstannyl-4-trimethylsilyloxymethyl-4-trimethylsilyloxy-1-decene | 2-[7-methylthiaacetyl heptyl]-4-trimethylsilyloxy cyclopent-2-en-1-one | dl-11a,16-dihydroxy-1-methylthiamethyl-1,9-dioxo-16-hydroxymethyl-20-ethyl-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 259 | 1-trans-iodo-3-triphenylmethoxy-1-heptene | 2-[6-methylthiaacetyl hexyl]-4R-trimethylsilyloxy cyclopent-2-en-1-one | nat-11a,15a-dihydroxy-1-methylthiamethyl-1,9-dioxo-20-nor-13-trans prostene |
| 260 | 1-trans-iodo-methyl-3-trimethylsilyloxy-1-heptene | 2-[6-methylthiaacetyl hexyl]-4R-trimethylsilyloxy cyclopent-2-en-1-one | nat-11a,15a-dihydroxy-1-methylthiamethyl-1,9-dioxo-15-methyl-20-nor-13-trans prostene |
| 261 | 1-trans-iodo-4,4-dimethyl-3-trimethylsilyloxy-1-heptene | 2-[6-methylthiaacetyl hexyl]-4R-trimethylsilyloxy cyclopent-2-en-1-one | nat-11a,15a-dihydroxy-1-methylthiamethyl-1,9-dioxo-16,16-dimethyl-20-nor-13-trans prostene |
| 262 | 1-trans-iodo-5,5-dimethyl-3-triphenylmethoxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-17,17-dimethyl-13-trans prostene |
| 263 | 1-trans-iodo-methyl-3-triphenylmethoxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-16-methyl-13-trans prostene |
| 264 | 1-trans-iodo-4,4-trimethylene-3-trimethylsilyloxy-1-heptene | 2-[6-methylthiaacetyl hexyl]-4R-trimethylsilyloxy cyclopent-2-en-1-one | nat-11a,15a-dihydroxy-1-methylthiamethyl-1,9-dioxo-16,16-trimethylene-20-nor-13-trans prostene |

| EXAMPLE | VINYL TIN | CYCLOPENTENONE | PRODUCT PROSTAGLANDIN OF THE PGE1 SERIES |
|---|---|---|---|
| 265 | 1-trans-tri-n-butylstannyl-3-vinyl-3-trimethylsilyloxy-1-heptene | 2-[6-methylthiaacetyl hexyl]-4R-trimethylsilyloxy cyclopent-2-en-1-one | nat-11a,15a-dihydroxy-1-methylthiamethyl-1,9-dioxo-15-vinyl-20-nor-13-trans prostene |
| 266 | 1-trans-tri-n-butylstannyl-4-phenoxy-3-triethylsilyloxy-1-butene | 2-[6-methylthiaacetyl hexyl]-4R-trimethylsilyloxy cyclopent-2-en-1-one | nat-11a,15a-dihydroxy-1-methylthiamethyl-1,9-dioxo-16-phenoxy-17,20-tetranor-13-trans prostene |
| 267 | 1-trans-tri-n-butylstannyl-4-(p-fluorophenoxy)-3-triethylsilyloxy-1-butene | 2-[6-methylthiaacetyl hexyl]-4R-trimethylsilyloxy cyclopent-2-en-1-one | nat-11a,15a-dihydroxy-1-methylthiamethyl-1,9-dioxo-16-(p-fluorophenoxy)-17-20-tetranor-13-trans prostene |

TABLE VI-continued

| EXAMPLE | VINYL IODIDE | CYCLOPENTENONE | PRODUCT PROSTAGLANDIN OF THE PGE1 SERIES |
|---|---|---|---|
| 268 | 1-trans-tri-n-butylstannyl-4-(m-chlorophenoxy)-3-triethylsilyloxy-1-butene | 2-[6-methylthiaacetyl hexyl]-4R-trimethylsiloxy cyclopent-2-en-1-one | nat-11a,15a-dihydroxy-1-methylthiamethyl-1,9-dioxo-16-(m-chlorophenoxy)-17-20-tetranor-13-trans prostene |
| 269 | 1-trans-tri-n-butylstannyl-4-(m-trifluoromethylphenoxy)-3-triethylsilyloxy-1-butene | 2-[6-methylthiaacetyl hexyl]-4R-trimethylsiloxy cyclopent-2-en-1-one | nat-11a,15a-dihydroxy-1-methylthiamethyl-1,9-dioxo-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 270 | 1-trans-iodo-5-phenyl-3-triethylsilyloxy-1-pentene | 2-[6-methylthiaacetyl hexyl]-4R-trimethylsiloxy cyclopent-2-en-1-one | nat-11a,15a-dihydroxy-1-methylthiamethyl-1,9-dioxo-17-phenyl-18-20-trinor-13-trans prostene |
| 271 | 1-trans-iodo-4,4-dimethyl-5-phenyl-3-triethylsilyloxy-1-pentene | 2-[6-methylthiaacetyl hexyl]-4R-trimethylsiloxy cyclopent-2-en-1-one | nat-11a,15a-dihydroxy-1-methylthiamethyl-1,9-dioxo-16,16-dimethyl-17-phenyl-18-20-trinor-13-trans prostene |
| 272 | 1-trans-iodo-4-cyclopentyl-3-triphenylmethoxy-1-butene | 2-[6-methylthiaacetyl hexyl]-4R-trimethylsiloxy cyclopent-2-en-1-one | nat-11a,15a-dihydroxy-1-methylthiamethyl-1,9-dioxo-16-cyclopentyl-17-20-tetranor-13-trans prostene |
| 273 | 1-trans-iodo-4-cyclohexyl-3-triphenylmethoxy-1-butene | 2-[6-methylthiaacetyl hexyl]-4R-trimethylsiloxy cyclopent-2-en-1-one | nat-11a,15a-dihydroxy-1-methylthiamethyl-1,9-dioxo-16-cyclohexyl-17-20-tetranor-13-trans prostene |
| 274 | 1-trans-iodo-4-triphenylmethoxy-1-heptene | 2-[6-methylthiaacetyl hexyl]-4R-trimethylsiloxy cyclopent-2-en-1-one | nat-11a,15-dihydroxy-1-methylthiamethyl-1,9-dioxo-20-nor-13-trans prostene |

| EXAMPLE | VINYL TIN | CYCLOPENTENONE | PRODUCT PROSTAGLANDIN OF THE PGE1 SERIES |
|---|---|---|---|
| 275 | 1-trans-tri-n-butylstannyl-4-methyl-4-trimethylsilyloxy-1-heptene | 2-[6-methylthiaacetyl hexyl]-4R-trimethylsiloxy cyclopent-2-en-1-one | nat-11a,16-dihydroxy-1-methylthiamethyl-1,9-dioxo-16-methyl-20-nor-13-trans prostene |
| 276 | 1-trans-tri-n-butylstannyl-4-ethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-ethyl-13-trans prostene |
| 277 | 1-trans-tri-n-butylstannyl-5-methyl-4-trimethylsilyloxy-1-heptene | 2-[6-methylthiaacetyl hexyl]-4R-trimethylsiloxy cyclopent-2-en-1-one | nat-11a,16-dihydroxy-1-methylthiamethyl-1,9-dioxo-17-methyl-20-nor-13-trans prostene |

| EXAMPLE | VINYL IODIDE | CYCLOPENTENONE | PRODUCT PROSTAGLANDIN OF THE PGE1 SERIES |
|---|---|---|---|
| 278 | 1-trans-iodo-5,5-dimethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-17,17-dimethyl-13-trans prostene |

| EXAMPLE | VINYL TIN | CYCLOPENTENONE | PROUCT PROSTAGLANDIN OF THE PGE1 SERIES |
|---|---|---|---|
| 279 | 1-trans-tri-n-butylstannyl-4-vinyl-4-trimethylsilyloxy-1-heptene | 2-[6-methylthiaacetyl hexyl]-4R-trimethylsiloxy cyclopent-2-en-1-one | nat-11a,16-dihydroxy-1-methylthiamethyl-1,9-dioxo-16-vinyl-20-nor-13-trans prostene |
| 280 | 1-trans-tri-n-butylstannyl-4-cyclopropyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-cyclopropyl-13-trans prostene |
| 281 | 1-trans-tri-n-butylstannyl-4-trimethylsilylethynyl-4-trimethylsilyloxy-1-heptene | 2-[6-methylthiaacetyl hexyl]-4R-trimethylsiloxy cyclopent-2-en-1-one | nat-11a,16-dihydroxy-1-methylthiamethyl-1,9-dioxo-16-ethynyl-20-nor-13-trans prostene |
| 282 | 1-trans-tri-n-butylstannyl-5-methylene-4-triethylsilyloxy-1-heptene | 2-[6-methylthiaacetyl hexyl]-4R-trimethylsiloxy cyclopent-2-en-1-one | nat-11a,16-dihydroxy-1-methylthiamethyl-1,9-dioxo-17-methylene-20-nor-13-trans prostene |

TABLE VI-continued

| EXAMPLE | VINYL IODIDE / VINYL TIN | CYCLOPENTENONE | PRODUCT PROSTAGLANDIN OF THE PGE1 SERIES |
|---|---|---|---|
| 283 | 1-trans-tri-n-butylstannyl-4-methyl-5-methylene 4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-methyl-17-methylene-20-nor-13-trans prostene |
| 284 | 1-trans-tri-n-butylstannyl-4-dimethoxymethyl-4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-formyl-20-nor-13-trans prostene |
| 285 | 1-trans-tri-n-butylstannyl-4-fluoromethyl-4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-fluoromethyl-20-nor-13-trans prostene |
| 286 | 1-trans-tri-n-butylstannyl-4-difluoromethyl-4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-difluoromethyl-20-nor-13-trans prostene |
| 287 | 1-trans-tri-n-butylstannyl-4-trifluoromethyl-4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-trifluoromethyl-20-nor-13-trans prostene |
| 288 | 1-trans-tri-n-butylstannyl-4-chloromethyl-4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-chloromethyl-20-nor-13-trans prostene |
| 289 | 1-trans-tri-n-butylstannyl-4-trimethylsilyloxymethyl-4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE PGE1 SERIES |
| 290 | 1-trans-iodo-4-methyl-7-chloro 4-trimethylsilyloxy-1-heptene | 2-[6-methylthiaacetyl hexyl]-4R-trimethylsilyloxy cyclopent-2-en-1-one | nat-11a,16-dihydroxy-1-methylthiamethyl-1,9-dioxo-16-methyl-19-chloro-20-nor-13-trans prostene |
| 291 | 1-trans-iodo-3-triphenylmethoxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-13-trans prostene |
| 292 | 1-trans-iodo-3-methyl-3-trimethylsilyloxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-15-methyl-13-trans prostene |
| 293 | 1-trans-iodo-4,4-dimethyl 3-trimethylsilyloxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-16,16-dimethyl-13-trans prostene |
| 294 | 1-trans-iodo-4,4-trimethylene 3-trimethylsilyloxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-16,16-trimethylene-13-trans prostene |
| EXAMPLE | VINYL TIN | CYCLOPENTENONE | PRODUCT PROSTAGLANDIN OF THE PGE1 SERIES |
| 295 | 1-trans-tri-n-butylstannyl-3-vinyl-3-trimethylsilyloxy-1-octene | 2-[6-methylthiaacetyl hexyl]-4R-trimethylsilyloxy cyclopent-2-en-1-one | nat-11a,15a-dihydroxy-1-methylthiamethyl-1,9-dioxo-15-vinyl-13-trans prostene |
| EXAMPLE | VINYL IODIDE | CYCLOPENTENONE | PROSUCT PROSTAGLANDIN OF THE PGE1 SERIES |
| 296 | 1-trans-iodo-4-triphenylmethoxy-1-octene | 2-[6-methylthiaacetyl hexyl]-4R-trimethylsilyloxy cyclopent-2-en-1-one | nat-11a,16-dihydroxy-1-methylthiamethyl-1,9-dioxo-13-trans prostene |
| EXAMPLE | VINYL TIN | CYCLOPENTENONE | PRODUCT PROSTAGLANDIN OF THE PGE1 SERIES |
| 297 | 1-trans-tri-n-butylstannyl-4-methyl-4-trimethylsilyloxy-1-octene | 2-[6-methylthiaacetyl hexyl]-4R-trimethylsilyloxy | nat-11a,16-dihydroxy-1-methylthiamethyl-1,9-dioxo-16-methyl-13-trans prostene |

TABLE VI-continued

| | VINYL TIN | CYCLOPENTENONE | PRODUCT PROSTAGLANDIN OF THE PGE1 SERIES |
|---|---|---|---|
| 298 | 1-trans-tri-n-butylstannyl-5-methyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-17-methyl-13-trans prostene |
| 299 | 1-trans-tri-n-butylstannyl-4-vinyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-vinyl-13-trans prostene |
| 300 | 1-trans-tri-n-butylstannyl-4-trimethylsilylethynyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-ethynyl-13-trans prostene |
| 301 | 1-trans-tri-n-butylstannyl-5-methylene-4-triethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-17-methylene-13-trans prostene |
| 302 | 1-trans-tri-n-butylstannyl-4-methyl-5-methylene-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-methyl-17-methylene-13-trans prostene |
| 303 | 1-trans-tri-n-butylstannyl-4-dimethoxymethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-formyl-13-trans prostene |
| 304 | 1-trans-tri-n-butylstannyl-4-fluoromethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-fluoromethyl-13-trans prostene |
| 305 | 1-trans-tri-n-butylstannyl-4-difluoromethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-difluoromethyl-13-trans prostene |
| 306 | 1-trans-tri-n-butylstannyl-4-trifluoromethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-trifluoromethyl-13-trans prostene |
| 307 | 1-trans-tri-n-butylstannyl-4-chloromethyl-4-trimethylsilyloxy-1-octene | 2-[6-methylthiaacetyl hexyl]-4R-trimethylsiloxy cyclopent-2-en-1-one | nat-11a,16-dihydroxy-1-methylthiamethyl-1,9-dioxo-16-chloromethyl-13-trans prostene |
| 308 | 1-trans-tri-n-butylstannyl-4-trimethylsilyloxymethyl-4-trimethylsilyloxy-1-octene | 2-[6-methylthiaacetyl hexyl]-4R-trimethylsiloxy cyclopent-2-en-1-one | nat-11a,16-dihydroy-1-methylthiamethyl-1,9-dioxo-16-hydroxymethyl-13-trans prostene |

| EXAMPLE | VINYL IODIDE | CYCLOPENTENONE | PRODUCT PROSTAGLANDIN OF THE PGE1 SERIES |
|---|---|---|---|
| 309 | 1-trans-iodo-3-triphenylmethoxy-1-nonene | 2-[6-methylthiaacetyl hexyl]-4R-trimethylsiloxy cyclopent-2-en-1-one | nat-11a,15a-dihydroxy-1-methylthiamethyl-1,9-dioxo-20-methyl-13-trans prostene |
| 310 | 1-trans-iodo-3-methyl-3-trimethylsilyloxy-1-nonene | 2-[6-methylthiaacetyl hexyl]-4R-trimethylsiloxy cyclopent-2-en-1-one | nat-11a,15a-dihydroxy-1-methylthiamethyl-1,9-dioxo-15-methyl-20-methyl-13-trans prostene |
| 311 | 1-trans-iodo-4,4-dimethyl-3-trimethylsilyloxy-1-nonene | 2-[6-methylthiaacetyl hexyl]-4R-trimethylsiloxy cyclopent-2-en-1-one | nat-11a,15a-dihydroxy-1-methylthiamethyl-1,9-dioxo-16,16-dimethyl-20-methyl-13-trans prostene |
| 312 | 1-trans-iodo-4,4-trimethylene-3-trimethylsilyloxy-1-nonene | 2-[6-methylthiaacetyl hexyl]-4R-trimethylsiloxy cyclopent-2-en-1-one | nat-11a,15a-dihydroxy-1-methylthiamethyl-1,9-dioxo-16,16-trimethylene-20-methyl-13-trans prostene |

| EXAMPLE | VINYL TIN | CYCLOPENTENONE | PRODUCT PROSTAGLANDIN OF THE PGE1 SERIES |
|---|---|---|---|
| 313 | 1-trans-tri-n-butylstannyl-3-vinyl-3-trimethylsilyloxy-1-nonene | 2-[6-methylthiaacetyl hexyl]-4R-trimethylsiloxy cyclopent-2-en-1-one | nat-11a,15a-dihydroxy-1-methylthiamethyl-1,9-dioxo-15-vinyl-20-methyl-13-trans prostene |

TABLE VI-continued

| EXAMPLE | VINYL IODIDE | CYCLOPENTENONE | PRODUCT PROSTAGLANDIN OF THE PGE1 SERIES |
|---|---|---|---|
| 314 | 1-trans-iodo-4-triphenylmethoxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-20-methyl-13-trans prostene |

| EXAMPLE | VINYL TIN | CYCLOPENTENONE | PRODUCT PROSTAGLANDIN OF THE PGE1 SERIES |
|---|---|---|---|
| 315 | 1-trans-tri-n-butylstannyl-4-methyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-methyl-20-methyl-13-trans prostene |
| 316 | 1-trans-tri-n-butylstannyl-4-methyl-5-methyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-17-methyl-20-methyl-13-trans prostene |
| 317 | 1-trans-tri-n-butylstannyl-4-vinyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-vinyl-20-methyl-13-trans prostene |
| 318 | 1-trans-tri-n-butylstannyl-4-trimethylsilylethynyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-ethynyl-20-methyl-13-trans prostene |
| 319 | 1-trans-tri-n-butylstannyl-5-methylene-4-triethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-17-methylene-20-methyl-13-trans prostene |
| 320 | 1-trans-tri-n-butylstannyl-4-methyl-5-methylene-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-methyl-17-methylene-20-methyl-13-trans prostene |
| 321 | 1-trans-tri-n-butylstannyl-4-dimethoxymethyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-formyl-20-methyl-13-trans prostene |
| 322 | 1-trans-tri-n-butylstannyl-4-fluoromethyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-fluoromethyl-20-methyl-13-trans prostene |
| 323 | 1-trans-tri-n-butylstannyl-4-difluoromethyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-difluoromethyl-20-methyl-13-trans prostene |
| 324 | 1-trans-tri-n-butylstannyl-4-trifluoromethyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-trifluoromethyl-20-methyl-13-trans prostene |
| 325 | 1-trans-tri-n-butylstannyl-4-chloromethyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-chloromethyl-20-methyl-13-trans prostene |
| 326 | 1-trans-tri-n-butylstannyl-4-trimethylsilyloxymethyl-4-trimethylsilyloxy-1-nonene | 2-[6-methylthiaacetyl hexyl]-4R-trimethylsiloxy cyclopent-2-en-1-one | nat-11a,16-dihydroxy-1-methylthiamethyl-1,9-dioxo-16-hydroxymethyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 327 | 1-trans-iodo-3-triphenylmethoxy-1-decene | 2-[6-methylthiaacetyl hexyl]-4R-trimethylsiloxy cyclopent-2-en-1-one | nat-11a,15a-dihydroxy-1-methylthiamethyl-1,9-dioxo-20-ethyl-13-trans prostene |
| 328 | 1-trans-iodo-3-methyl-3-trimethylsilyloxy-1-decene | 2-[6-methylthiaacetyl hexyl]-4R-trimethylsiloxy cyclopent-2-en-1-one | nat-11a,15a-dihydroxy-1-methylthiamethyl-1,9-dioxo-15-methyl-20-ethyl-13-trans prostene |
| 329 | 1-trans-iodo-4,4-dimethyl-3-trimethylsilyloxy-1-decene | 2-[6-methylthiaacetyl hexyl]-4R-trimethylsiloxy cyclopent-2-en-1-one | nat-11a,15a-dihydroxy-1-methylthiamethyl-1,9-dioxo-16,16-dimethyl-20-ethyl-13-trans prostene |

TABLE VI-continued

| | | | |
|---|---|---|---|
| 330 | 1-trans-iodo-4,4-trimethylene 3-trimethylsilyloxy-1-decene | 2-[6-methylthiaacetyl hexyl]-4R-trimethylsiloxy cyclopent-2-en-1-one | nat-11a,15a-dihydroxy-1-methylthiamethyl-1,9-dioxo-16,16-trimethylene-20-ethyl-13-trans prostene |
| EXAMPLE | VINYL TIN | CYCLOPENTENONE | PRODUCT PROSTAGLANDIN OF THE PGE1 SERIES |
| 331 | 1-trans-tri-n-butylstannyl-3-vinyl-3-trimethylsilyloxy-1-decene | 2-[6-methylthiaacetyl hexyl]-4R-trimethylsiloxy cyclopent-2-en-1-one | nat-11a,15a-dihydroxy-1-methylthiamethyl-1,9-dioxo-15-vinyl-20-ethyl-13-trans prostene |
| EXAMPLE | VINYL IODIDE | CYCLOPENTENONE | PRODUCT PROSTAGLANDIN OF THE PGE1 SERIES |
| 332 | 1-trans-iodo-4-triphenylmethoxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-20-ethyl-13-trans prostene |
| EXAMPLE | VINYL TIN | CYCLOPENTENONE | PRODUCT PROSTAGLANDIN OF THE PGE1 SERIES |
| 333 | 1-trans-tri-n-butylstannyl-4-methyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-methyl-20-ethyl-13-trans prostene |
| 334 | 1-trans-tri-n-butylstannyl-5-methyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-17-methyl-20-ethyl-13-trans prostene |
| 335 | 1-trans-tri-n-butylstannyl-4-vinyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-vinyl-20-ethyl-13-trans prostene |
| 336 | 1-trans-tri-n-butylstannyl-4-trimethylsilylethynyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-ethynyl-20-ethyl-13-trans prostene |
| 337 | 1-trans-tri-n-butylstannyl-5-methylene-4-triethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-17-methylene-20-ethyl-13-trans prostene |
| 338 | 1-trans-tri-n-butylstannyl-4-methyl-5-methylene-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-methyl-17-methylene-20-ethyl-13-trans prostene |
| 339 | 1-trans-tri-n-butylstannyl-4-dimethoxymethyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-formyl-20-ethyl-13-trans prostene |
| 340 | 1-trans-tri-n-butylstannyl-4-fluoromethyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-fluoromethyl-20-ethyl-13-trans prostene |
| 341 | 1-trans-tri-n-butylstannyl-4-difluoromethyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-difluoromethyl-20-ethyl-13-trans prostene |
| 342 | 1-trans-tri-n-butylstannyl-4-trifluoromethyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-trifluoromethyl-20-ethyl-13-trans prostene |
| 343 | 1-trans-tri-n-butylstannyl-4-chloromethyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-chloromethyl-20-ethyl-13-trans prostene |
| 344 | 1-trans-tri-n-butylstannyl-4-trimethylsilyloxymethyl-4-trimethylsilyloxy-1-decene | 2-[6-methylthiaacetyl hexyl]-4R-trimethylsiloxy cyclopent-2-en-1-one | nat-11a,16-dihydroxy-1-methylthiamethyl-1,9-dioxo-16-hydroxymethyl-20-ethyl-13-trans prostene |
| EXAMPLE | VINYL IODIDE | CYCLOPENTENONE | PRODUCT PROSTAGLANDIN OF THE 11-DEOXY PGE1 SERIES |

TABLE VI-continued

| EXAMPLE | | | PRODUCT PROSTAGLANDIN OF THE 11-DEOXY PGE1 SERIES |
|---|---|---|---|
| 345 | 1-trans-iodo-3-triphenylmethoxy-1-heptene | 2-[5-methylthiaacetyl pentyl] cyclopent-2-en-1-one | dl-15a-hydroxy-1-methylthiamethyl-1,9-dioxo-20-nor-2-nor-13-trans prostene |
| 346 | 1-trans-iodo-3-methyl-3-trimethylsilyloxy-1-heptene | 2-[5-methylthiaacetyl pentyl] cyclopent-2-en-1-one | dl-15a-hydroxy-1-methylthiamethyl-1,9-dioxo-15-methyl-20-nor-2-nor-13-trans prostene |
| 347 | 1-trans-iodo-4,4-dimethyl-3-trimethylsilyloxy-1-heptene | 2-[5-methylthiaacetyl pentyl] cyclopent-2-en-1-one | dl-15a-hydroxy-1-methylthiamethyl-1,9-dioxo-16,16-dimethyl-20-nor-2-nor-13-trans prostene |
| 348 | 1-trans-iodo-5,5-dimethyl-3-triphenylmethoxy-1-octene | 2-[5-methylthiaacetyl pentyl] cyclopent-2-en-one | dl-15a-hydroxy-1-methylthiamethyl-1,9-dioxo-17,17-dimethyl-2-nor-13-trans prostene |
| 349 | 1-trans-iodo-4-methyl-3-triphenylmethoxy-1-octene | 2-[5-methylthiaacetyl pentyl] cyclopent-2-en-1-one | dl-15a-hydroxy-1-methylthiamethyl-1,9-dioxo-16-methyl-2-nor-13-trans prostene |
| 350 | 1-trans-iodo-4,4-trimethylene-3-trimethylsilyloxy-1-heptene | 2-[5-methylthiaacetyl pentyl] cyclopent-2-en-1-one | dl-15a-hydroxy-1-methylthiamethyl-1,9-dioxo-16,16-trimethylene-20-nor-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 351 | 1-trans-tri-n-butylstannyl-3-vinyl-3-trimethylsilyloxy-1-heptene | 2-[5-methylthiaacetyl pentyl] cyclopent-2-en-1-one | dl-15a-hydroxy-1-methylthiamethyl-1,9-dioxo-15-vinyl-20-nor-2-nor-13-trans prostene |
| 352 | 1-trans-tri-n-butylstannyl-4-phenoxy-3-triethylsilyloxy-1-butene | 2-[5-methylthiaacetyl pentyl] cyclopent-2-en-1-one | dl-15a-hydroxy-1-methylthiamethyl-1,9-dioxo-16-phenoxy-2-nor-17-20-tetranor-13-trans prostene |
| 353 | 1-trans-tri-n-butylstannyl-4-(p-fluorophenoxy)-3-triethylsilyloxy-1-butene | 2-[5-methylthiaacetyl pentyl] cyclopent-2-en-1-one | dl-15a-hydroxy-1-methylthiamethyl-1,9-dioxo-16-(p-fluorophenoxy)-2-nor-17-20-tetranor-13-trans prostene |
| 354 | 1-trans-tri-n-butylstannyl-4-(m-chlorophenoxy)-3-triethylsilyloxy-1-butene | 2-[5-methylthiaacetyl pentyl] cyclopent-2-en-1-one | dl-15a-hydroxy-1-methylthiamethyl-1,9-dioxo-16-(m-chlorophenoxy)-2-nor-17-20-tetranor-13-trans prostene |
| 355 | 1-trans-tri-n-butylstannyl-4-(m-trifluoromethylphenoxy)-3-triethylsilyloxy-1-butene | 2-[5-methylthiaacetyl pentyl] cyclopent-2-en-1-one | dl-15a-hydroxy-1-methylthiamethyl-1,9-dioxo-16-(m-trifluoromethylphenoxy)-2-nor-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 356 | 1-trans-iodo-5-phenyl-3-triethylsilyloxy-1-butene | 2-[5-methylthiaacetyl pentyl] cyclopent-2-en-1-one | dl-15a-hydroxy-1-methylthiamethyl-1,9-dioxo-17-phenyl-2-nor-18-20-trinor-13-trans prostene |
| 357 | 1-trans-iodo-4,4-dimethyl-5-phenyl-3-triethylsilyloxy-1-pentene | 2-[5-methylthiaacetyl pentyl] cyclopent-2-en-1-one | dl-15a-hydroxy-1-methylthiamethyl-1,9-dioxo-16,16-dimethyl-17-phenyl-2-nor-18-20-trinor-13-trans prostene |
| 358 | 1-trans-iodo-4-cyclopentyl-3-triphenylmethoxy-1-butene | 2-[5-methylthiaacetyl pentyl] cyclopent-2-en-1-one | dl-15a-hydroxy-1-methylthiamethyl-1,9-dioxo-16-cyclopentyl-2-nor-17-20-tetranor-13-trans prostene |
| 359 | 1-trans-iodo-4-cyclohexyl-3-triphenylmethoxy-1-butene | 2-[5-methylthiaacetyl pentyl] cyclopent-2-en-1-one | dl-15a-hydroxy-1-methylthiamethyl-1,9-dioxo-16-cyclohexyl-2-nor-17-20-tetranor-13-trans prostene |
| 360 | 1-trans-iodo-4-triphenylmethoxy-1-heptene | 2-[5-methylthiaacetyl pentyl] cyclopent-2-en-1-one | dl-16-hydroxy-1-methylthiamethyl-1,9-dioxo-20-nor-2-nor-13-trans prostene |

TABLE VI-continued

| EXAMPLE | VINYL TIN | CYCLOPENTENONE | PRODUCT PROSTAGLANDIN OF THE 11-DEOXY PGE1 SERIES |
|---|---|---|---|
| 361 | 1-trans-tri-n-butylstannyl-4-methyl-4-trimethylsilyloxy-1-heptene | 2-[5-methylthiaacetyl pentyl]cyclopent-2-en-1-one | dl-16-hydroxy-1-methylthiamethyl-1,9-dioxo-16-methyl-20-nor-2-nor-13-trans prostene |
| 362 | 1-trans-tri-n-butylstannyl-4-ethyl-4-trimethylsilyloxy-1-octene | 2-[5-methylthiaacetyl pentyl]cyclopent-2-en-1-one | dl-16-hydroxy-1-methylthiamethyl-1,9-dioxo-16-ethyl-2-nor-13-trans prostene |
| 363 | 1-trans-tri-n-butylstannyl-5-methyl-4-trimethylsilyloxy-1-heptene | 2-[5-methylthiaacetyl pentyl]cyclopent-2-en-1-one | dl-16-hydroxy-1-methylthiamethyl-1,9-dioxo-17-methyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 364 | 1-trans-iodo-5,5-dimethyl-4-trimethylsilyloxy-1-octene | 2-[5-methylthiaacetyl pentyl]cyclopent-2-en-1-one | dl-16-hydroxy-1-methylthiamethyl-1,9-dioxo-17,17-dimethyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 365 | 1-trans-tri-n-butylstannyl-4-vinyl-4-trimethylsilyloxy-1-heptene | 2-[5-methylthiaacetyl pentyl]cyclopent-2-en-1-one | dl-16-hydroxy-1-methylthiamethyl-1,9-dioxo-16-vinyl-20-nor-2-nor-13-trans prostene |
| 366 | 1-trans-tri-n-butylstannyl-4-cyclopropyl-4-trimethylsilyloxy-1-octene | 2-[5-methylthiaacetyl pentyl]cyclopent-2-en-1-one | dl-16-hydroxy-1-methylthiamethyl-1,9-dioxo-16-cyclopropyl-2-nor-13-trans prostene |
| 367 | 1-trans-tri-n-butylstannyl-4-trimethylsilylethynyl-4-trimethylsilyloxy-1-heptene | 2-[5-methylthiaacetyl pentyl]cyclopent-2-en-1-one | dl-16-hydroxy-1-methylthiamethyl-1,9-dioxo-16-ethynyl-20-nor-2-nor-13-trans prostene |
| 368 | 1-trans-tri-n-butylstannyl-5-methylene-4-triethylsilyloxy-1-heptene | 2-[5-methylthiaacetyl pentyl]cyclopent-2-en-1-one | dl-16-hydroxy-1-methylthiamethyl-1,9-dioxo-17-Methylene-20-nor-2-nor-13-trans prostene |
| 369 | 1-trans-tri-n-butylstannyl-4-methyl-5-methylene-4-trimethylsilyloxy-1-heptene | 2-[5-methylthiaacetyl pentyl]cyclopent-2-en-1-one | dl-16-hydroxy-1-methylthiamethyl-1,9-dioxo-16-methyl-17-methylene-20-nor-2-nor-13-trans prostene |
| 370 | 1-trans-tri-n-butylstannyl-4-dimethoxymethyl-4-trimethylsilyloxy-1-heptene | 2-[5-methylthiaacetyl pentyl]cyclopent-2-en-1-one | dl-16-hydroxy-1-methylthiamethyl-1,9-dioxo-16-formyl-20-nor-2-nor-13-trans prostene |
| 371 | 1-trans-tri-n-butylstannyl-4-fluoromethyl-4-trimethylsilyloxy-1-heptene | 2-[5-methylthiaacetyl pentyl]cyclopent-2-en-1-one | dl-16-hydroxy-1-methylthiamethyl-1,9-dioxo-16-fluoromethyl-20-nor-2-nor-13-trans prostene |
| 372 | 1-trans-tri-n-butylstannyl-4-trifluoromethyl-4-trimethylsilyloxy-1-heptene | 2-[5-methylthiaacetyl pentyl]cyclopent-2-en-1-one | dl-16-hydroxy-1-methylthiamethyl-1,9-dioxo-16-trifluoromethyl-20-nor-2-nor-13-trans prostene |
| 373 | 1-trans-tri-n-butylstannyl-4-trifluoromethyl-4-trimethylsilyloxy-1-heptene | 2-[5-methylthiaacetyl pentyl]cyclopent-2-en-1-one | dl-16-hydroxy-1-methylthiamethyl-1,9-dioxo-16-trifluoromethyl-20-nor-2-nor-13-trans prostene |
| 374 | 1-trans-tri-n-butylstannyl-4-chloromethyl-4-trimethylsilyloxy-1-heptene | 2-[5-methylthiaacetyl pentyl]cyclopent-2-en-1-one | dl-16-hydroxy-1-methylthiamethyl-1,9-dioxo-16-chloromethyl-20-nor-2-nor-13-trans prostene |
| 375 | 1-trans-tri-n-butylstannyl-4-trimethylsilyloxymethyl-4-trimethylsilyloxy-1-heptene | 2-[5-methylthiaacetyl pentyl]cyclopent-2-en-1-one | dl-16-hydroxy-1-methylthiamethyl-1,9-dioxo-16-hydroxymethyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 376 | 1-trans-iodo-4-methyl-7-chloro | 2-[5-methylthiaacetyl | dl-16-hydroxy-1-methylthiamethyl-1,9-dioxo-16-methyl- |

TABLE VI-continued

| | | | |
|---|---|---|---|
| 377 | | 4-trimethylsilyloxy-1-heptene | pentyl]cyclopent-2-en-1-one | 19-chloro-2-nor-20-nor-13-trans prostene |
| 378 | | 1-trans-iodo-3-triphenylmethoxy-1-octene | 2-[5-methylthiaacetyl pentyl]cyclopent-2-en-1-one | dl-15a-hydroxy-1-methylthiamethyl-1,9-dioxo-2-nor-13-trans prostene |
| | | 1-trans-iodo-3-methyl-3-trimethylsilyloxy-1-octene | 2-[5-methylthiaacetyl pentyl]cyclopent-2-en-1-one | dl-15a-hydroxy-1-methylthiamethyl-1,9-dioxo-15-methyl-2-nor-13-trans prostene |
| 379 | | 1-trans-iodo-4,4-dimethyl-3-trimethylsilyloxy-1-octene | 2-[5-methylthiaacetyl pentyl]cyclopent-2-en-1-one | dl-16a-hydroxy-1-methylthiamethyl-1,9-dioxo-16,16-dimethyl-2-nor-13-trans prostene |
| 380 | | 1-trans-iodo-4,4-trimethylene-3-trimethylsilyloxy-1-octene | 2-[5-methylthiaacetyl pentyl]cyclopent-2-en-1-one | dl-15a-hydroxy-1-methylthiamethyl-1,9-dioxo-16,16-trimethylene-2-nor-13-trans prostene |
| EXAMPLE | VINYL TIN | | CYCLOPENTENONE | PRODUCT PROSTAGLANDIN OF THE 11-DEOXY PGE1 SERIES |
| 381 | | 1-trans-tri-n-butylstannyl-3-vinyl-3-trimethylsilyloxy-1-octene | 2-[5-methylthiaacetyl pentyl]cyclopent-2-en-1-one | dl-15a-hydroxy-1-methylthiamethyl-1,9-dioxo-15-vinyl-2-nor-13-trans prostene |
| EXAMPLE | VINYL IODIDE | | CYCLOPENTENONE | PRODUCT PROSTAGLANDIN OF THE 11-DEOXY PGE1 SERIES |
| 382 | | 1-trans-iodo-4-triphenylmethoxy-1-octene | 2-[5-methylthiaacetyl pentyl]cyclopent-2-en-1-one | dl-16-hydroxy-1-methylthiamethyl-1,9-dioxo-2-nor-13-trans prostene |
| EXAMPLE | VINYL TIN | | CYCLOPENTENONE | PRODUCT PROSTAGLANDIN OF THE 11-DEOXY PGE1 SERIES |
| 383 | | 1-trans-tri-n-butylstannyl-1-methyl-4-trimethylsilyloxy-1-octene | 2-[5-methylthiaacetyl pentyl]cyclopent-2-en-1-one | dl-16-hydroxy-1-methylthiamethyl-1,9-dioxo-16-methyl-2-nor-13-trans prostene |
| 384 | | 1-trans-tri-n-butylstannyl-5-methyl-4-trimethylsilyloxy-1-octene | 2-[5-methylthiaacetyl pentyl]cyclopent-2-en-1-one | dl-16-hydroxy-1-methylthiamethyl-1,9-dioxo-17-methyl-2-nor-13-trans prostene |
| 385 | | 1-trans-tri-n-butylstannyl-4-vinyl-4-trimethylsilyloxy-1-octene | 2-[5-methylthiaacetyl pentyl]cyclopent-2-en-1-one | dl-16-hydroxy-1-methylthiamethyl-1,9-dioxo-16-vinyl-2-nor-13-trans prostene |
| 386 | | 1-trans-tri-n-butylstannyl-4-trimethylsilylethynyl-4-trimethylsilyloxy-1-octene | 2-[5-methylthiaacetyl pentyl]cyclopent-2-en-1-one | dl-16-hydroxy-1-methylthiamethyl-1,9-dioxo-16-ethynyl-2-nor-13-trans prostene |
| 387 | | 1-trans-tri-n-butylstannyl-5-methylene-4-triethylsilyloxy-1-octene | 2-[5-methylthiaacetyl pentyl]cyclopent-2-en-1-one | dl-16-hydroxy-1-methylthiamethyl-1,9-dioxo-17-methylene-2-nor-13-trans prostene |
| 388 | | 1-trans-tri-n-butylstannyl-4-methyl-5-methylene-4-trimethylsilyloxy-1-octene | 2-[5-methylthiaacetyl pentyl]cyclopent-2-en-1-one | dl-16-hydroxy-1-methylthiamethyl-1,9-dioxo-16-methyl-17-methylene-2-nor-13-trans prostene |
| 389 | | 1-trans-tri-n-butylstannyl-4-dimethoxymethyl-4-trimethylsilyloxy-1-octene | 2-[5-methylthiaacetyl pentyl]cyclopent-2-en-1-one | dl-16-hydroxy-1-methylthiamethyl-1,9-dioxo-16-formyl-2-nor-13-trans prostene |
| 390 | | 1-trans-tri-n-butylstannyl-4-fluoromethyl-4-trimethylsilyloxy-1-octene | 2-[5-methylthiaacetyl pentyl]cyclopent-2-en-1-one | dl-16-hydroxy-1-methylthiamethyl-1,9-dioxo-16-fluoromethyl-2-nor-13-trans prostene |
| 391 | | 1-trans-tri-n-butylstannyl-4-difluoromethyl-4-trimethylsilyloxy-1-octene | 2-[5-methylthiaacetyl pentyl]cyclopent-2-en-1-one | dl-16-hydroxy-1-methylthiamethyl-1,9-dioxo-16-difluoromethyl-2-nor-13-trans prostene |

TABLE VI-continued

| EXAMPLE | VINYL IODIDE | CYCLOPENTENONE | PRODUCT PROSTAGLANDIN OF THE 11-DEOXY PGE1 SERIES |
|---|---|---|---|
| 392 | 1-trans-tri-n-butylstannyl-4-trifluoromethyl-4-trimethylsilyloxy-1-octene | 2-[5-methylthiaacetyl pentyl] cyclopent-2-en-1-one | dl-16-hydroxy-1-methylthiamethyl-1,9-dioxo-16-trifluoromethyl-2-nor-13-trans prostene |
| 393 | 1-trans-tri-n-butylstannyl-4-chloromethyl-4-trimethylsilyloxy-1-octene | 2-[5-methylthiaacetyl pentyl] cyclopent-2-en-1-one | dl-16-hydroxy-1-methylthiamethyl-1,9-dioxo-16-chloromethyl-2-nor-13-trans prostene |
| 394 | 1-trans-tri-n-butylstannyl-4-trimethylsilyloxymethyl-4-trimethylsilyloxy-1-octene | 2-[5-methylthiaacetyl pentyl] cyclopent-2-en-1-one | dl-16-hydroxy-1-methylthiamethyl-1,9-dioxo-16-hydroxymethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 395 | 1-trans-iodo-3-triphenylmethyl-1-nonene | 2-[5-methylthiaacetyl pentyl] cyclopent-2-en-1-one | dl-15a-hydroxy-1-methylthiamethyl-1,9-dioxo-20-methyl-2-nor-13-trans prostene |
| 396 | 1-trans-iodo-3-methyl-3-trimethylsilyloxy-1-nonene | 2-[5-methylthiaacetyl pentyl] cyclopent-2-en-1-one | dl-15a-hydroxy-1-methylthiamethyl-1,9-dioxo-15-methyl-20-methyl-2-nor-13-trans prostene |
| 397 | 1-trans-iodo-4,4-dimethyl-3-trimethylsilyloxy-1-nonene | 2-[5-methylthiaacetyl pentyl] cyclopent-2-en-1-one | dl-15a-hydroxy-1-methylthiamethyl-1,9-dioxo-16,16-dimethyl-20-methyl-2-nor-13-trans prostene |
| 398 | 1-trans-iodo-4,4-trimethylene-3-trimethylsilyloxy-1-nonene | 2-[5-methylthiaacetyl pentyl] cyclopent-2-en-1-one | dl-15a-hydroxy-1-methylthiamethyl-1,9-dioxo-16,16-trimethylene-20-methyl-2-nor-13-trans prostene |

| EXAMPLE | VINYL TIN | CYCLOPENTENONE | PROSTAGLANDIN OF THE PGE1 SERIES |
|---|---|---|---|
| 399 | 1-trans-tri-n-butylstannyl-3-vinyl-3-trimethylsilyloxy-1-nonene | 2-[5-methylthiaacetyl pentyl] cyclopent-2-en-1-one | dl-15a-hydroxy-1-methylthiamethyl-1,9-dioxo-15-vinyl-20-methyl-2-nor-13-trans prostene |
| 400 | 1-trans-iodo-4-triphenylmethoxy-1-nonene | 2-[5-methylthiaacetyl pentyl] cyclopent-2-en-1-one | dl-16-hydroxy-1-methylthiamethyl-1,9-dioxo-2-methyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 401 | 1-trans-tri-n-butylstannyl-4-methyl-4-trimethylsilyloxy-1-nonene | 2-[5-methylthiaacetyl pentyl] cyclopent-2-en-1-one | dl-16-hydroxy-1-methylthiamethyl-1,9-dioxo-16-methyl-20-methyl-2-nor-13-trans prostene |
| 402 | 1-trans-tri-n-butylstannyl-5-methyl-4-trimethylsilyloxy-1-nonene | 2-[5-methylthiaacetyl pentyl] cyclopent-2-en-1-one | dl-16-hydroxy-1-methylthiamethyl-1,9-dioxo-17-methyl-20-methyl-2-nor-13-trans prostene |
| 403 | 1-trans-tri-n-butylstannyl-4-vinyl-4-trimethylsilyloxy-1-nonene | 2-[5-methylthiaacetyl pentyl] cyclopent-2-en-1-one | dl-16-hydroxy-1-methylthiamethyl-1,9-dioxo-16-vinyl-20-methyl-2-nor-13-trans prostene |
| 404 | 1-trans-tri-n-butylstannyl-4-trimethylsilylethynyl-4-trimethylsilyloxy-1-nonene | 2-[5-methylthiaacetyl pentyl] cyclopent-2-en-1-one | dl-16-hydroxy-1-methylthiamethyl-1,9-dioxo-16-ethynyl-20-methyl-2-nor-13-trans prostene |
| 405 | 1-trans-tri-n-butylstannyl-5-methylene-4-triethylsilyloxy-nonene | 2-[5-methylthiaacetyl pentyl] cyclopent-2-en-1-one | dl-16-hydroxy-1-methylthiamethyl-1,9-dioxo-17-methylene-20-methyl-2-nor-13-trans prostene |
| 406 | 1-trans-tri-n-butylstannyl-4-methyl-5-methylene-4-trimethylsilyloxy-1-nonene | 2-[5-methylthiaacetyl pentyl] cyclopent-2-en-1-one | dl-16-hydroxy-1-methylthiamethyl-1,9-dioxo-16-methyl-17-methylene-20-methyl-2-nor-13-trans prostene |
| 407 | 1-trans-tri-n-butylstannyl-4-dimethoxymethyl-4-trimethylsilyloxy-1-nonene | 2-[5-methylthiaacetyl pentyl] cyclopent-2-en-1-one | dl-16-hydroxy-1-methylthiamethyl-1,9-dioxo-16-formyl-20-methyl-2-nor-13-trans prostene |

TABLE VI-continued

| | | | PRODUCT PROSTAGLANDIN |
|---|---|---|---|
| 408 | 1-trans-tri-n-butylstannyl-4-fluoromethyl-4-trimethylsilyloxy-1-nonene | cyclopent-2-en-1-one 2-[5-methylthiaacetyl pentyl] | dl-16-hydroxy-1-methylthiamethyl-1,9-dioxo-16-fluoromethyl-20-methyl-2-nor-13-trans prostene |
| 409 | 1-trans-tri-n-butylstannyl-4-difluoromethyl-4-trimethylsilyloxy-1-nonene | cyclopent-2-en-1-one 2-[5-methylthiaacetyl pentyl] | dl-16-hydroxy-1-methylthiamethyl-1,9-dioxo-16-difluoromethyl-20-methyl-2-nor-13-trans prostene |
| 410 | 1-trans-tri-n-butylstannyl-4-trifluoromethyl-4-trimethylsilyloxy-1-nonene | cyclopent-2-en-1-one 2-[5-methylthiaacetyl pentyl] | dl-16-hydroxy-1-methylthiamethyl-1,9-dioxo-16-trifluoromethyl-20-methyl-2-nor-13-trans prostene |
| 411 | 1-trans-tri-n-butylstannyl-4-chloromethyl-4-trimethylsilyloxy-1-nonene | cyclopent-2-en-1-one 2-[5-methylthiaacetyl pentyl] | dl-16-hydroxy-1-methylthiamethyl-1,9-dioxo-16-chloromethyl-20-methyl-2-nor-13-trans prostene |
| 412 | 1-trans-tri-n-butylstannyl-4-trimethylsilyloxymethyl-4-trimethylsilyloxy-1-nonene | cyclopent-2-en-1-one 2-[5-methylthiaacetyl pentyl] | dl-16-hydroxy-1-methylthiamethyl-1,9-dioxo-16-hydroxymethyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 413 | 1-trans-iodo-3-triphenylmethoxy-1-decene | cyclopent-2-en-1-one 2-[5-methylthiaacetyl pentyl] | dl-15a-hydroxy-1-methylthiamethyl-1,9-dioxo-20-ethyl-2-nor-13-trans prostene |
| 414 | 1-trans-iodo-3-methyl-3-trimethylsilyloxy-1-decene | cyclopent-2-en-1-one 2-[5-methylthiaacetyl pentyl] | dl-15a-hydroxy-1-methylthiamethyl-1,9-dioxo-15-methyl-20-ethyl-2-nor-13-trans prostene |
| 415 | 1-trans-iodo-4,4-dimethyl-3-trimethylsilyloxy-1-decene | cyclopent-2-en-1-one 2-[5-methylthiaacetyl pentyl] | dl-15a-hydroxy-1-methylthiamethyl-1,9-dioxo-16,16-dimethyl-20-ethyl-2-nor-13-trans prostene |
| 416 | 1-trans-iodo-4,4-trimethylene-3-trimethylsilyloxy-1-decene | cyclopent-2-en-1-one 2-[5-methylthiaacetyl pentyl] | dl-15a-hydroxy-1-methylthiamethyl-1,9-dioxo-16,16-trimethylene-20-ethyl-2-nor-13-trans prostene |
| EXAMPLE | VINYL TIN | CYCLOPENTENONE | PRODUCT PROSTAGLANDIN OF THE 11-DEOXY PGE1 SERIES |
| 417 | 1-trans-tri-n-butylstannyl-3-vinyl-3-trimethylsilyloxy-1-decene | 2-[5-methylthiaacetyl pentyl] cyclopent-2-en-1-one | dl-15a-hydroxy-1-methylthiamethyl-1,9-dioxo-15-vinyl-20-ethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 418 | 1-trans-iodo-4-triphenylmethoxy-1-decene | 2-[5-methylthiaacetyl pentyl] cyclopent-2-en-1-one | dl-16-hydroxy-1-methylthiamethyl-1,9-dioxo-20-ethyl-2-nor-13-trans prostene |
| EXAMPLE | VINYL TIN | CYCLOPENTENEONE | PRODUCT PROSTAGLANDIN OF THE 11-DEOXY PGE1 SERIES |
| 419 | 1-trans-tri-n-butylstannyl-4-methyl-4-trimethylsilyloxy-1-decene | 2-[5-methylthiaacetyl pentyl] cyclopent-2-en-1-one | dl-16-hydroxy-1-methylthiamethyl-1,9-dioxo-16-methyl-20-ethyl-2-nor-13-trans prostene |
| 420 | 1-trans-tri-n-butylstannyl-5-methyl-4-trimethylsilyloxy-1-decene | 2-[5-methylthiaacetyl pentyl] cyclopent-2-en-1-one | dl-16-hydroxy-1-methylthiamethyl-1,9-dioxo-17-methyl-20-ethyl-2-nor-13-trans prostene |
| 421 | 1-trans-tri-n-butylstannyl-4-vinyl-4-trimethylsilyloxy-1-decene | 2-[5-methylthiaacetyl pentyl] cyclopent-2-en-1-one | dl-16-hydroxy-1-methylthiamethyl-1,9-dioxo-16-vinyl-20-ethyl-2-nor-13-trans prostene |
| 422 | 1-trans-tri-n-butylstannyl-4-trimethylsilylethynyl-4-trimethylsilyloxy-1-decene | 2-[5-methylthiaacetyl pentyl] cyclopent-2-en-1-one | dl-16-hydroxy-1-methylthiamethyl-1,9-dioxo-16-ethynyl-20-ethyl-2-nor-13-trans prostene |

TABLE VI-continued

| | VINYL IODIDE | CYCLOPENTENONE | PRODUCT PROSTAGLANDIN OF THE 11-DEOXY PGE1 SERIES |
|---|---|---|---|
| 423 | 1-trans-tri-n-butylstannyl-5-methylene 4-triethylsilyloxy-1-decene | cyclopent-2-en-1-one 2-[5-methylthiaacetyl pentyl] | dl-16-hydroxy-1-methylthiamethyl-1,9-dioxo-17-methylene-20-ethyl-2-nor-13-trans prostene |
| 424 | 1-trans-tri-n-butylstannyl-4-methyl-5-methylene 4-trimethylsilyloxy-1-decene | cyclopent-2-en-1-one 2-[5-methylthiaacetyl pentyl] | dl-16-hydroxy-1-methylthiamethyl-1,9-dioxo-16-methyl-17-methylene-20-ethyl-2-nor-13-trans prostene |
| 425 | 1-trans-tri-n-butylstannyl-4-dimethoxymethyl-4-trimethylsilyloxy-1-decene | cyclopent-2-en-1-one 2-[5-methylthiaacetyl pentyl] | dl-16-hydroxy-1-methylthiamethyl-1,9-dioxo-16-formyl-20-ethyl-2-nor-13-trans prostene |
| 426 | 1-trans-tri-n-butylstannyl-4-fluoromethyl-4-trimethylsilyloxy-1-decene | cyclopent-2-en-1-one 2-[5-methylthiaacetyl pentyl] | dl-16-hydroxy-1-methylthiamethyl-1,9-dioxo-16-fluoromethyl-20-ethyl-2-nor-13-trans prostene |
| 427 | 1-trans-tri-n-butylstannyl-4-difluoromethyl-4-trimethylsilyloxy-1-decene | cyclopent-2-en-1-one 2-[5-methylthiaacetyl pentyl] | dl-16-hydroxy-1-methylthiamethyl-1,9-dioxo-16-difluoromethyl-20-ethyl-2-nor-13-trans prostene |
| 428 | 1-trans-tri-n-butylstannyl-4-trifluoromethyl-4-trimethylsilyloxy-1-decene | cyclopent-2-en-1-one 2-[5-methylthiaacetyl pentyl] | dl-16-hydroxy-1-methylthiamethyl-1,9-dioxo-16-trifluoromethyl-20-ethyl-2-nor-13-trans prostene |
| 429 | 1-trans-tri-n-butylstannyl-4-chloromethyl-4-trimethylsilyloxy-1-decene | cyclopent-2-en-1-one 2-[5-methylthiaacetyl pentyl] | dl-16-hydroxy-1-methylthiamethyl-1,9-dioxo-16-chloromethyl-20-ethyl-2-nor-13-trans prostene |
| 430 | 1-trans-tri-n-butylstannyl-4-trimethylsilyloxymethyl-4-trimethylsilyloxy-1-decene | cyclopent-2-en-1-one 2-[5-methylthiaacetyl pentyl] | dl-16-hydroxy-1-methylthiamethyl-1,9-dioxo-16-hydroxymethyl-20-ethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 431 | 1-trans-iodo-3-triphenylmethoxy-1-heptene | 2-[6-methylthiaacetyl hexyl] cyclopent-2-en-1-one | dl-15a-hydroxy-1-methylthiamethyl-1,9-dioxo-20-nor-13-trans prostene |
| 432 | 1-trans-iodo-3-methyl-3-trimethylsilyloxy-1-heptene | 2-[6-methylthiaacetyl hexyl] cyclopent-2-en-1-one | dl-15a-hydroxy-1-methylthiamethyl-1,9-dioxo-15-methyl-20-nor-13-trans prostene |
| 433 | 1-trans-iodo-4,4-dimethyl-3-trimethylsilyloxy-1-heptene | 2-[6-methylthiaacety hexyl] cyclopent-2-en-1-one | dl-15a-hydroxy-1-methylthiamethyl-1,9-dioxo-16,16-dimethyl-20-nor-13-trans prostene |
| 434 | 1-trans-iodo-5,5-dimethyl-3-triphenylmethoxy-1-octene | 2-[6-methylthiaacetyl hexyl] cyclopent-2-en-1-one | dl-15a-hydroxy-1-methylthiamethyl-1,9-dioxo-17,17-dimethyl-13-trans prostene |
| 435 | 1-trans-iodo-4-methyl-3-triphenylmethoxy-1-octene | 2-[6-methylthiaacetyl hexyl] cyclopent-2-en-1-one | dl-15a-hydroxy-1-methylthiamethyl-1,9-dioxo-16-methyl-13-trans prostene |
| 436 | 1-trans-iodo-4,4-trimethylene-3-trimethylsilyloxy-1-heptene | 2-[6-methylthiaacetyl hexyl] cyclopent-2-en-1-one | dl-15a-hydroxy-1-methylthiamethyl-1,9-dioxo-16,16-trimethylene-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 437 | 1-trans-tri-n-butylstannyl-3-vinyl-3-trimethylsilyloxy-1-heptene | 2-[6-methylthiaacetyl hexyl] cyclopent-2-en-1-one | dl-15a-hydroxy-1-methylthiamethyl-1,9-dioxo-15-vinyl-20-nor-13-trans prostene |
| 438 | 1-trans-tri-n-butylstannyl-4-phenoxy-3-triethylsilyloxy-1-butene | 2-[6-methylthiaacetyl hexyl] cyclopent-2-en-1-one | dl-15a-hydroxy-1-methylthiamethyl-1,9-dioxo-16-phenoxy-17,20-tetranor-13-trans prostene |

TABLE VI-continued

| EXAMPLE | VINYL IODIDE / VINYL TIN | CYCLOPENTENONE | PRODUCT PROSTAGLANDIN |
|---|---|---|---|
| 439 | 1-trans-tri-n-butylstannyl-4-(p-fluorophenoxy)-3-triethylsilyloxy-1-butene | 2-[6-methylthiaacetyl hexyl]cyclopent-2-en-1-one | dl-15a-hydroxy-1-methylthiamethyl-1,9-dioxo-16-(p-fluorophenoxy)-17-20-tetranor-13-trans prostene |
| 440 | 1-trans-tri-n-butylstannyl-4-(m-chlorophenoxy)-3-triethylsilyloxy-1-butene | 2-[6-methylthiaacetyl hexyl]cyclopent-2-en-1-one | dl-15a-hydroxy-1-methylthiamethyl-1,9-dioxo-16-(m-chlorophenoxy)-17-20-tetranor-13-trans prostene |
| 441 | 1-trans-tri-n-butylstannyl-4-(m-trifluoromethylphenoxy)-3-triethylsilyloxy-1-butene | 2-[6-methylthiaacetyl hexyl]cyclopent-2-en-1-one | dl-15a-hydroxy-1-methylthiamethyl-1,9-dioxo-16-(m-trifluoromethylphenoxy)-17-20-tetranor-13-trans prostene |
| EXAMPLE | VINYL IODIDE | CYCLOPENTENONE | PRODUCT PROSTAGLANDIN OF THE 11-DEOXY PGE1 SERIES |
| 442 | 1-trans-iodo-5-phenyl-3-triethylsilyloxy-1-pentene | 2-[6-methylthiaacetyl hexyl]cyclopent-2-en-1-one | dl-15a-hydroxy-1-methylthiamethyl-1,9-dioxo-17-phenyl-18-20-trinor-13-trans prostene |
| 443 | 1-trans-iodo-4,4-dimethyl-5-phenyl-3-triethylsilyloxy-1-pentene | 2-[6-methylthiaacetyl hexyl]cyclopent-2-en-1-one | dl-15a-hydroxy-1-methylthiamethyl-1,9-dioxo-16,16-dimethyl-17-phenyl-18-20-trinor-13-trans prostene |
| 444 | 1-trans-iodo-4-cyclopentyl-3-triphenylmethoxy-1-butene | 2-[6-methylthiaacetyl hexyl]cyclopent-2-en-1-one | dl-15a-hydroxy-1-methylthiamethyl-1,9-dioxo-16-cyclopentyl-17-20-tetranor-13-trans prostene |
| 445 | 1-trans-iodo-4-cyclohexyl-3-triphenylmethoxy-1-butene | 2-[6-methylthiaacetyl hexyl]cyclopent-2-en-1-one | dl-15a-hydroxy-1-methylthiamethyl-1,9-dioxo-16-cyclohexyl-17-20-tetranor-13-trans prostene |
| 446 | 1-trans-iodo-4-triphenylmethoxy-1-heptene | 2-[6-methylthiaacetyl hexyl]cyclopent-2-en-1-one | dl-16-hydroxy-1-methylthiamethyl-1,9-dioxo-20-nor-13-trans prostene |
| EXAMPLE | VINYL TIN | CYCLOPENTENONE | PRODUCT PROSTAGLANDIN OF THE 11-DEOXY PGE1 SERIES |
| 447 | 1-trans-tri-n-butylstannyl-4-methyl-4-trimethylsilyloxy-1-heptene | 2-[6-methylthiaacetyl hexyl]cyclopent-2-en-1-one | dl-16-hydroxy-1-methylthiamethyl-1,9-dioxo-16-methyl-20-nor-13-trans prostene |
| 448 | 1-trans-tri-n-butylstannyl-4-ethyl-4-trimethylsilyloxy-1-octene | 2-[6-methylthiaacetyl hexyl]cyclopent-2-en-1-one | dl-16-hydroxy-1-methylthiamethyl-1,9-dioxo-16-ethyl-13-trans prostene |
| 449 | 1-trans-tri-n-butylstannyl-5-methyl-4-trimethylsilyloxy-1-heptene | 2-[6-methylthiaacetyl hexyl]cyclopent-2-en-1-one | dl-16-hydroxy-1-methylthiamethyl-1,9-dioxo-17-methyl-20-nor-13-trans prostene |
| EXAMPLE | VINYL IODIDE | CYCLOPENTENONE | PRODUCT PROSTAGLANDIN OF THE 11-DEOXY PGE1 SERIES |
| 450 | 1-trans-iodo-5,5-dimethyl-4-trimethylsilyloxy-1-octene | 2-[6-methylthiaacetyl hexyl]cyclopent-2-en-1-one | dl-16-hydroxy-1-methylthiamethyl-1,9-dioxo-17,17-dimethyl-13-trans prostene |
| EXAMPLE | VINYL TIN | CYCLOPENTENONE | PRODUCT PROSTAGLANDIN OF THE 11-DEOXY PGE1 SERIES |
| 451 | 1-trans-tri-n-butylstannyl-4-vinyl-4-trimethylsilyloxy-1-heptene | 2-[6-methylthiaacetyl hexyl]cyclopent-2-en-1-one | dl-16-hydroxy-1-methylthiamethyl-1,9-dioxo-16-vinyl-20-nor-13-trans prostene |
| 452 | 1-trans-tri-n-butylstannyl-4-cyclopropyl-4-trimethylsilyloxy-1-octene | 2-[6-methylthiaacetyl hexyl]cyclopent-2-en-1-one | dl-16-hydroxy-1-methylthiamethyl-1,9-dioxo-16-cyclopropyl-13-trans prostene |
| 453 | 1-trans-tri-n-butylstannyl-4-trimethylsilylethynyl-4-trimethylsilyloxy-1-heptene | 2-[6-methylthiaacetyl hexyl]cyclopent-2-en-1-one | dl-16-hydroxy-1-methylthiamethyl-1,9-dioxo-16-ethynyl-20-nor-13-trans prostene |

TABLE VI-continued

| | | | |
|---|---|---|---|
| 454 | 1-trans-tri-n-butylstannyl-5-methylene 4-triethylsilyloxy-1-heptene | 2-[6-methylthiaacetyl hexyl] cyclopent-2-en-1-one | dl-16-hydroxy-1-methylthiamethyl-1,9-dioxo-17-methylene-20-nor-13-trans prostene |
| 455 | 1-trans-tri-n-butylstannyl-4-methyl-5-methylene 4-trimethylsilyloxy-1-heptene | 2-[6-methylthiaacetyl hexyl] cyclopent-2-en-1-one | dl-16-hydroxy-1-methylthiamethyl-1,9-dioxo-16-methyl-17-methylene-20-nor-13-trans prostene |
| 456 | 1-trans-tri-n-butylstannyl-4-dimethoxymethyl-4-trimethylsilyloxy-1-heptene | 2-[6-methylthiaacetyl hexyl] cyclopent-2-en-1-one | dl-16-hydroxy-1-methylthiamethyl-1,9-dioxo-16-formyl-20-nor-13-trans prostene |
| 457 | 1-trans-tri-n-butylstannyl-4-fluoromethyl-4-trimethylsilyloxy-1-heptene | 2-[6-methylthiaacetyl hexyl] cyclopent-2-en-1-one | dl-16-hydroxy-1-methylthiamethyl-1,9-dioxo-16-fluoromethyl-20-nor-13-trans prostene |
| 458 | 1-trans-tri-n-butylstannyl-4-difluoromethyl-4-trimethylsilyloxy-1-heptene | 2-[6-methylthiaacetyl hexyl] cyclopent-2-en-1-one | dl-16-hydroxy-1-methylthiamethyl-1,9-dioxo-16-difluoromethyl-20-nor-13-trans prostene |
| 459 | 1-trans-tri-n-butylstannyl-4-trifluoromethyl-4-trimethylsilyloxy-1-heptene | 2-[6-methylthiaacetyl hexyl] cyclopent-2-en-1-one | dl-16-hydroxy-1-methylthiamethyl-1,9-dioxo-16-trifluoromethyl-20-nor-13-trans prostene |
| 460 | 1-trans-tri-n-butylstannyl-4-chloromethyl-4-trimethylsilyloxy-1-heptene | 2-[6-methylthiaacetyl hexyl] cyclopent-2-en-1-one | dl-16-hydroxy-1-methylthiamethyl-1,9-dioxo-16-chloromethyl-20-nor-13-trans prostene |
| 461 | 1-trans-tri-n-butylstannyl-4-trimethylsilyloxymethyl-4-trimethylsilyloxy-1-heptene | 2-[6-methylthiaacetyl hexyl] cyclopent-2-en-1-one | dl-16-hydroxy-1-methylthiamethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE 11-DEOXY PGE1 SERIES |
| 462 | 1-trans-iodo-4-methyl-7-chloro 4-trimethylsilyloxy-1-heptene | 2-[6-methylthiaacetyl hexyl] cyclopent-2-en-1-one | dl-16-hydroxy-1-methylthiamethyl-1,9-dioxo-16-methyl-19-chloro-20-nor-13-trans prostene |
| 463 | 1-trans-iodo-3-triphenylmethoxy-1-octene | 2-[6-methylthiaacetyl hexyl] cyclopent-2-en-1-one | dl-15a-hydroxy-1-methylthiamethyl-1,9-dioxo-13-trans prostene |
| 464 | 1-trans-iodo-3-methyl-3-trimethylsilyloxy-1-octene | 2-[6-methylthiaacetyl hexyl] cyclopent-2-en-1-one | dl-15a-hydroxy-1-methylthiamethyl-1,9-dioxo-15-methyl-13-trans prostene |
| 465 | 1-trans-iodo-4,4-dimethyl 3-trimethylsilyloxy-1-octene | 2-[6-methylthiaacetyl hexyl] cyclopent-2-en-1-one | dl-15a-hydroxy-1-methylthiamethyl-1,9-dioxo-16,16-dimethyl-13-trans prostene |
| 466 | 1-trans-iodo-4,4-trimethylene 3-trimethylsilyloxy-1-octene | 2-[6-methylthiaacetyl hexyl] cyclopent-2-en-1-one | dl-15a-hydroxy-1-methylthiamethyl-1,9-dioxo-16,16-trimethylene-13-trans prostene |
| EXAMPLE | VINYL TIN | CYCLOPENTENONE | PRODUCT PROSTAGLANDIN OF THE 11-DEOXY PGE1 SERIES |
| 467 | 1-trans-tri-n-butylstannyl-3-vinyl-3-trimethylsilyloxy-1-octene | 2-[6-methylthiaacetyl hexyl] cyclopent-2-en-1-one | dl-15a-hydroxy-1-methylthiamethyl-1,9-dioxo-15-vinyl-13-trans prostene |
| EXAMPLE | VINYL IODIDE | CYCLOPENTENONE | PRODUCT PROSTAGLANDIN OF THE 11-DEOXY PGE1 SERIES |
| 468 | 1-trans-iodo-4-triphenylmethoxy-1-octene | 2-[6-methylthiaacetyl hexyl] cyclopent-2-en-1-one | dl-16-hydroxy-1-methylthiamethyl-1,9-dioxo-13-trans prostene |
| 469 | 1-trans-tri-n-butylstannyl-4-methyl-4-trimethylsilyloxy-1-octene | 2-[6-methylthiaacetyl hexyl] cyclopent-2-en-1-one | dl-16-hydroxy-1-methylthiamethyl-1,9-dioxo-16-methyl-13-trans prostene |

TABLE VI-continued

| | | | |
|---|---|---|---|
| 470 | 1-trans-tri-n-butylstannyl-5-methyl-4-trimethylsilyloxy-1-octene | cyclopent-2-en-1-one 2-[6-methylthiaacetyl hexyl] | dl-16-hydroxy-1-methylthiamethyl-1,9-dioxo-17-methyl-13-trans prostene |
| 471 | 1-trans-tri-n-butylstannyl-4-vinyl-4-trimethylsilyloxy-1-octene | cyclopent-2-en-1-one 2-[6-methylthiaacetyl hexyl] | dl-16-hydroxy-1-methylthiamethyl-1,9-dioxo-16-vinyl-13-trans prostene |
| 472 | 1-trans-tri-n-butylstannyl-4-trimethylsilylethynyl-4-trimethylsilyloxy-1-octene | cyclopent-2-en-1-one 2-[6-methylthiaacetyl hexyl] | dl-16-hydroxy-1-methylthiamethyl-1,9-dioxo-16-ethynyl-13-trans prostene |
| 473 | 1-trans-tri-n-butylstannyl-5-methylene-4-triethylsilyloxy-1-octene | cyclopent-2-en-1-one 2-[6-methylthiaacetyl hexyl] | dl-16-hydroxy-1-methylthiamethyl-1,9-dioxo-17-methylene-13-trans prostene |
| 474 | 1-trans-tri-n-butylstannyl-4-methyl-5-methylene-4-trimethylsilyloxy-1-octene | cyclopent-2-en-1-one 2-[6-methylthiaacetyl hexyl] | dl-16-hydroxy-1-methylthiamethyl-1,9-dioxo-16-methyl-17-methylene-13-trans prostene |
| 475 | 1-trans-tri-n-butylstannyl-4-dimethoxymethyl-4-trimethylsilyloxy-1-octene | cyclopent-2-en-1-one 2-[6-methylthiaacetyl hexyl] | dl-16-hydroxy-1-methylthiamethyl-1,9-dioxo-16-formyl-13-trans prostene |
| 476 | 1-trans-tri-n-butylstannyl-4-fluoromethyl-4-trimethylsilyloxy-1-octene | cyclopent-2-en-1-one 2-[6-methylthiaacetyl hexyl] | dl-16-hydroxy-1-methylthiamethyl-1,9-dioxo-16-fluoromethyl-13-trans prostene |
| 477 | 1-trans-tri-n-butylstannyl-4-difluoromethyl-4-trimethylsilyloxy-1-octene | cyclopent-2-en-1-one 2-[6-methylthiaacetyl hexyl] | dl-16-hydroxy-1-methylthiamethyl-1,9-dioxo-16-difluoromethyl-13-trans prostene |
| 478 | 1-trans-tri-n-butylstannyl-4-trifluoromethyl-4-trimethylsilyloxy-1-octene | cyclopent-2-en-1-one 2-[6-methylthiaacetyl hexyl] | dl-16-hydroxy-1-methylthiamethyl-1,9-dioxo-16-trifluoromethyl-13-trans prostene |
| 479 | 1-trans-tri-n-butylstannyl-4-chloromethyl-4-trimethylsilyloxy-1-octene | cyclopent-2-en-1-one 2-[6-methylthiaacetyl hexyl] | dl-16-hydroxy-1-methylthiamethyl-1,9-dioxo-16-chloromethyl-13-trans prostene |
| 480 | 1-trans-tri-n-butylstannyl-4-trimethylsilyloxymethyl-4-trimethylsilyloxy-1-octene | cyclopent-2-en-1-one 2-[6-methylthiaacetyl hexyl] | dl-16-hydroxy-1-methylthiamethyl-1,9-dioxo-16-hydroxymethyl-13-trans prostene |
| EXAMPLE | VINYL IODIDE | CYCLOPENTENONE | PRODUCT PROSTAGLANDIN OF THE 11-DEOXY PGE1 SERIES |
| 481 | 1-trans-iodo-3-triphenylmethoxy-1-nonene | 2-[6-methylthiaacetyl hexyl] cyclopent-2-en-1-one | dl-15a-hydroxy-1-methylthiamethyl-1,9-dioxo-20-methyl-13-trans prostene |
| 482 | 1-trans-iodo-3-methyl-3-trimethylsilyloxy-1-nonene | 2-[6-methylthiaacetyl hexyl] cyclopent-2-en-1-one | dl-15a-hydroxy-1-methylthiamethyl-1,9-dioxo-15-methyl-20-methyl-13-trans prostene |
| 483 | 1-trans-iodo-4,4-dimethyl-3-trimethylsilyloxy-1-nonene | 2-[6-methylthiaacetyl hexyl] cyclopent-2-en-1-one | dl-15a-hydroxy-1-methylthiamethyl-1,9-dioxo-16,16-dimethyl-20-methyl-13-trans prostene |
| 484 | 1-trans-iodo-4,4-trimethylene-3-trimethylsilyloxy-1-nonene | 2-[6-methylthiaacetyl hexyl] cyclopent-2-en-1-one | dl-15a-hydroxy-1-methylthiamethyl-1,9-dioxo-16,16-trimethylene-20-methyl-13-trans prostene |
| EXAMPLE | VINYL TIN | CYCLOPENTENONE | PRODUCT PROSTAGLANDIN OF THE DEOXY PGE1 SERIES |
| 485 | 1-trans-tri-n-butylstannyl-3-vinyl-3-trimethylsilyloxy-1- | 2-[6-methylthiaacetyl hexyl] cyclopent-2-en-1-one | dl-15a-hydroxy-1-methylthiamethyl-1,9-dioxo-15-vinyl-20-methyl-13-trans prostene |

TABLE VI-continued

| EXAMPLE | VINYL IODIDE | CYCLOPENTENONE | PRODUCT PROSTAGLANDIN OF THE 11-DEOXY PGE1 SERIES |
|---|---|---|---|
| 486 | 1-trans-iodo-4-triphenylmethoxy-1-nonene | 2-[6-methylthiaacetyl hexyl] cyclopent-2-en-1-one | dl-16-hydroxy-1-methylthiamethyl-1,9-dioxo-20-methyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 487 | 1-trans-tri-n-butylstannyl-4-methyl-4-trimethylsilyloxy-1-nonene | 2-[6-methylthiaacetyl hexyl] cyclopent-2-en-1-one | dl-16-hydroxy-1-methylthiamethyl-1,9-dioxo-16-methyl-20-methyl-13-trans prostene |
| 488 | 1-trans-tri-n-butylstannyl-5-methyl-4-trimethylsilyloxy-1-nonene | 2-[6-methylthiaacetyl hexyl] cyclopent-2-en-1-one | dl-16-hydroxy-1-methylthiamethyl-1,9-dioxo-17-methyl-20-methyl-13-trans prostene |
| 489 | 1-trans-tri-n-butylstannyl-4-vinyl-4-trimethylsilyloxy-1-nonene | 2-[6-methylthiaacetyl hexyl] cyclopent-2-en-1-one | dl-16-hydroxy-1-methylthiamethyl-1,9-dioxo-16-vinyl-20-methyl-13-trans prostene |
| 490 | 1-trans-tri-n-butylstannyl-4-trimethylsilylethynyl-4-trimethylsilyloxy-1-nonene | 2-[6-methylthiaacetyl hexyl] cyclopent-2-en-1-one | dl-16-hydroxy-1-methylthiamethyl-1,9-dioxo-16-ethynyl-20-methyl-13-trans prostene |
| 491 | 1-trans-tri-n-butylstannyl-5-methylene-4-triethylsilyloxy-1-nonene | 2-[6-methylthiaacetyl hexyl] cyclopent-2-en-1-one | dl-16-hydroxy-1-methylthiamethyl-1,9-dioxo-17-methylene-20-methyl-13-trans prostene |
| 492 | 1-trans-tri-n-butylstannyl-4-methyl-5-methylene-4-trimethylsilyloxy-1-nonene | 2-[6-methylthiaacetyl hexyl] cyclopent-2-en-1-one | dl-16-hydroxy-1-methylthiamethyl-1,9-dioxo-16-methyl-17-methylene-20-methyl-13-trans prostene |
| 493 | 1-trans-tri-n-butylstannyl-4-dimethoxymethyl-4-trimethylsilyloxy-1-nonene | 2-[6-methylthiaacetyl hexyl] cyclopent-2-en-1-one | dl-16-hydroxy-1-methylthiamethyl-1,9-dioxo-16-formyl-20-methyl-13-trans prostene |
| 494 | 1-trans-tri-n-butylstannyl-4-fluoromethyl-4-trimethylsilyloxy-1-nonene | 2-[6-methylthiaacetyl hexyl] cyclopent-2-en-1-one | dl-16-hydroxy-1-methylthiamethyl-1,9-dioxo-16-fluoromethyl-20-methyl-13-trans prostene |
| 495 | 1-trans-tri-n-butylstannyl-4-difluoromethyl-4-trimethylsilyloxy-1-nonene | 2-[6-methylthiaacetyl hexyl] cyclopent-2-en-1-one | dl-16-hydroxy-1-methylthiamethyl-1,9-dioxo-16-difluoromethyl-20-methyl-13-trans prostene |
| 496 | 1-trans-tri-n-butylstannyl-4-trifluoromethyl-4-trimethylsilyloxy-1-nonene | 2-[6-methylthiaacetyl hexyl] cyclopent-2-en-1-one | dl-16-hydroxy-1-methylthiamethyl-1,9-dioxo-16-trifluoromethyl-20-methyl-13-trans prostene |
| 497 | 1-trans-tri-n-butylstannyl-4-chloromethyl-4-trimethylsilyloxy-1-nonene | 2-[6-methylthiaacetyl hexyl] cyclopent-2-en-1-one | dl-16-hydroxy-1-methylthiamethyl-1,9-dioxo-16-chloromethyl-20-methyl-13-trans prostene |
| 498 | 1-trans-tri-n-butylstannyl-4-trimethylsilyloxymethyl-4-trimethylsilyloxy-1-nonene | 2-[6-methylthiaacetyl hexyl] cyclopent-2-en-1-one | dl-16-hydroxy-1-methylthiamethyl-1,9-dioxo-16-hydroxymethyl-20-methyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 499 | 1-trans-iodo-3-triphenylmethoxy-1-decene | 2-[6-methylthiaacetyl hexyl] cyclopent-2-en-1-one | dl-15a-hydroxy-1-methylthiamethyl-1,9-dioxo-20-ethyl-13-trans prostene |
| 500 | 1-trans-iodo-3-methyl-3-trimethylsilyloxy-1-decene | 2-[6-methylthiaacetyl hexyl] cyclopent-2-en-1-one | dl-15a-hydroxy-1-methylthiamethyl-1,9-dioxo-15-methyl-20-ethyl-13-trans prostene |
| 501 | 1-trans-iodo-4,4-dimethyl-3-trimethylsilyloxy-1-decene | 2-[6-methylthiaacetyl hexyl] cyclopent-2-en-1-one | dl-15a-hydroxy-1-methylthiamethyl-1,9-dioxo-16,16-dimethyl-20-ethyl-13-trans prostene |

TABLE VI-continued

| | | | |
|---|---|---|---|
| 502 | 1-trans-iodo-4,4-trimethylene 3-trimethylsilyloxy-1-decene | 2-[6-methylthiaacetyl hexyl] cyclopent-2-en-1-one | dl-15a-hydroxy-1-methylthiamethyl-1,9-dioxo-16,16-trimethylene-20-ethyl-13-trans prostene |
| EXAMPLE | VINYL TIN | CYCLOPENTENONE | PRODUCT PROSTAGLANDIN OF THE 11-DEOXY PGE1 SERIES |
| 503 | 1-trans-tri-n-butylstannyl-4-vinyl-3-trimethylsilyloxy-1-decene | 2-[6-methylthiaacetyl hexyl] cyclopent-2-en-1-one | dl-15a-hydroxy-1-methylthiamethyl-1,9-dioxo-15-vinyl-20-ethyl-13-trans prostene |
| EXAMPLE | VINYL IODIDE | CYCLOPENTENONE | PRODUCT PROSTAGLANDIN OF THE 11-DEOXY PGE1 SERIES |
| 504 | 1-trans-iodo-4-triphenylmethoxy-1-decene | 2-[6-methylthiaacetyl hexyl] cyclopent-2-en-1-one | dl-16-hydroxy-1-methylthiamethyl-1,9-dioxo-20-ethyl-13-trans prostene |
| EXAMPLE | VINYL TIN | CYCLOPENTENONE | PRODUCT PROSTAGLANDIN OF THE 11-DEOXY PGE1 SERIES |
| 505 | 1-trans-tri-n-butylstannyl-4-methyl-4-trimethylsilyloxy-1-decene | 2-[6-methylthiaacetyl hexyl] cyclopent-2-en-1-one | dl-16-hydroxy-1-methylthiamethyl-1,9-dioxo-16-methyl-20-ethyl-13-trans prostene |
| 506 | 1-trans-tri-n-butylstannyl-5-methyl-4-trimethylsilyloxy-1-decene | 2-[6-methylthiaacetyl hexyl] cyclopent-2-en-1-one | dl-16-hydroxy-1-methylthiamethyl-1,9-dioxo-17-methyl-20-ethyl-13-trans prostene |
| 507 | 1-trans-tri-n-butylstannyl-4-vinyl-4-trimethylsilyloxy-1-decene | 2-[6-methylthiaacetyl hexyl] cyclopent-2-en-1-one | dl-16-hydroxy-1-methylthiamethyl-1,9-dioxo-16-vinyl-20-ethyl-13-trans prostene |
| 508 | 1-trans-tri-n-butylstannyl-4-trimethylsilylethynyl-4-trimethylsilyloxy-1-decene | 2-[6-methylthiaacetyl hexyl] cyclopent-2-en-1-one | dl-16-hydroxy-1-methylthiamethyl-1,9-dioxo-16-ethynyl-20-ethyl-13-trans prostene |
| 509 | 1-trans-tri-n-butylstannyl-5-methylene-4-triethylsilyloxy-1-decene | 2-[6-methylthiaacetyl hexyl] cyclopent-2-en-1-one | dl-16-hydroxy-1-methylthiamethyl-1,9-dioxo-17-methylene-20-ethyl-13-trans prostene |
| 510 | 1-trans-tri-n-butylstannyl-4-methyl-5-methylene 4-trimethylsilyloxy-1-decene | 2-[6-methylthiaacetyl hexyl] cyclopent-2-en-1-one | dl-16-hydroxy-1-methylthiamethyl-1,9-dioxo-16-methyl-17-methylene-20-ethyl-13-trans prostene |
| 511 | 1-trans-tri-n-butylstannyl-4-dimethoxymethyl-4-trimethylsilyloxy-1-decene | 2-[6-methylthiaacetyl hexyl] cyclopent-2-en-1-one | dl-16-hydroxy-1-methylthiamethyl-1,9-dioxo-16-formyl-20-ethyl-13-trans prostene |
| 512 | 1-trans-tri-n-butylstannyl-4-fluoromethyl-4-trimethylsilyloxy-1-decene | 2-[6-methylthiaacetyl hexyl] cyclopent-2-en-1-one | dl-16-hydroxy-1-methylthiamethyl-1,9-dioxo-16-fluoromethyl-20-ethyl-13-trans prostene |
| 513 | 1-trans-tri-n-butylstannyl-4-difluoromethyl-4-trimethylsilyloxy-1-decene | 2-[6-methylthiaacetyl hexyl] cyclopent-2-en-1-one | dl-16-hydroxy-1-methylthiamethyl-1,9-dioxo-16-difluoromethyl-20-ethyl-13-trans prostene |
| 514 | 1-trans-tri-n-butylstannyl-4-trifluoromethyl-4-trimethylsilyloxy-1-decene | 2-[6-methylthiaacetyl hexyl] cyclopent-2-en-1-one | dl-16-hydroxy-1-methylthiamethyl-1,9-dioxo-16-trifluoromethyl-20-ethyl-13-trans prostene |
| 515 | 1-trans-tri-n-butylstannyl-4-chloromethyl-4-trimethylsilyloxy-1-decene | 2-[6-methylthiaacetyl hexyl] cyclopent-2-en-1-one | dl-16-hydroxy-1-methylthiamethyl-1,9-dioxo-16-chloromethyl-20-ethyl-13-trans prostene |
| 516 | 1-trans-tri-n-butylstannyl-4-trimethylsilyloxymethyl-4-trimethylsilyloxy-1-decene | 2-[6-methylthiaacetyl hexyl] cyclopent-2-en-1-one | dl-16-hydroxy-1-methylthiamethyl-1,9-dioxo-16-hydroxymethyl-20-ethyl-13-trans prostene |
| EXAMPLE | VINYLE IODIDE | CYCLOPENTENONE | PRODUCT PROSTAGLANDIN OF THE 11-DEOXY PGE1 SERIES |

TABLE VI-continued

| | VINYL TIN | | |
|---|---|---|---|
| 517 | 1-trans-iodo-3-triphenylmethoxy-1-heptene | 2-[7-methylthiaacetyl cyclopent-2-en-1-one | dl-15a-hydroxy-1-methylthiamethyl-1,9-dioxo-20-nor-2-homo-13-trans prostene |
| 518 | 1-trans-iodo-3-methyl-3-trimethylsilyloxy-1-heptene | 2-[7-methylthiaacetyl cyclopent-2-en-1-one | dl-15a-hydroxy-1-methylthiamethyl-1,9-dioxo-15-methyl-20-nor-2-homo-13-transprostene |
| 519 | 1-trans-iodo-4,4-dimethyl-3-trimethylsilyloxy-1-heptene | 2-[7-methylthiaacetyl cyclopent-2-en-1-one | dl-15a-hydroxy-1-methylthiamethyl-1,9-dioxo-16,16-dimethyl-20-nor-2-homo-13-trans prostene |
| 520 | 1-trans-iodo-5,5-dimethyl-3-triphenylmethoxy-1-octene | 2-[7-methylthiaacetyl cyclopent-2-en-1-one | dl-15a-hydroxy-1-methylthiamethyl-1,9-dioxo-17,17-dimethyl-2-homo-13-trans prostene |
| 521 | 1-trans-iodo-4-methyl-3-triphenylmethoxy-1-octene | 2-[7-methylthiaacetyl cyclopent-2-en-1-one | dl-15a-hydroxy-1-methylthiamethyl-1,9-dioxo-16-methyl-2-homo-13-trans prostene |
| 522 | 1-trans-iodo-4,4-trimethylene-3-trimethylsilyloxy-1-heptene | 2-[7-methylthiaacetyl cyclopent-2-en-1-one | dl-15a-hydroxy-1-methylthiamethyl-1,9-dioxo-16,16-trimethylene-20-nor-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 523 | 1-trans-tri-n-butylstannyl-3-vinyl-3-trimethylsilyloxy-1-heptene | 2-[7-methylthiaacetyl cyclopent-2-en-1-one | dl-15a-hydroxy-1-methylthiamethyl-1,9-dioxo-15-vinyl-20-nor-2-homo-13-trans prostene |
| 524 | 1-trans-tri-n-butylstannyl-4-phenoxy-3-triethylsilyloxy-1-butene | 2-[7-methylthiaacetyl cyclopent-2-en-1-one | dl-15a-hydroxy-1-methylthiamethyl-1,9-dioxo-16-phenoxy-2-homo-17-20-tetranor-13-trans prostene |
| 525 | 1-trans-tri-n-butylstannyl-4-(p-fluorophenoxy)-3-triethylsilyloxy-1-butene | 2-[7-methylthiaacetyl cyclopent-2-en-1-one | dl-15a-hydroxy-1-methylthiamethyl-1,9-dioxo-16-(p-fluorophenoxy)-2-homo-17-20-tetranor-13-trans prostene |
| 526 | 1-trans-tri-n-butylstannyl-4-(m-chlorophenoxy)-3-triethylsilyloxy-1-butene | 2-[7-methylthiaacetyl cyclopent-2-en-1-one | dl-15a-hydroxy-1-methylthiamethyl-1,9-dioxo-16-(m-chlorophenoxy)-2-homo-17-20-tetranor-13-trans prostene |
| 527 | 1-trans-tri-n-butylstannyl-4-(m-trifluoromethylphenoxy)-3-triethylsilyloxy-1-butene | 2-[7-methylthiaacetyl cyclopent-2-en-1-one | dl-15a-hydroxy-1-methylthiamethyl-1,9-dioxo-16-(m-trifluoromethylphenoxy)-2-homo-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 528 | 1-trans-iodo-5-phenyl-3-triethylsilyloxy-1-pentene | 2-[7-methylthiaacetyl cyclopent-2-en-1-one | dl-15a-hydroxy-1-methylthiamethyl-1,9-dioxo-17-phenyl-2-homo-18-20-trinor-13-trans prostene |
| 529 | 1-trans-iodo-4,4-dimethyl-5-phenyl-3-triethylsilyloxy-1-pentene | 2-[7-methylthiaacetyl cyclopent-2-en-1-one | dl-15a-hydroxy-1-methylthiamethyl-1,9-dioxo-16,16-dimethyl-17-phenyl-2-homo-18-20-trinor-13-trans prostene |
| 530 | 1-trans-iodo-4-cyclopentyl-3-triphenylmethoxy-1-butene | 2-[7-methylthiaacetyl cyclopent-2-en-1-one | dl-15a-hydroxy-1-methylthiamethyl-1,9-dioxo-16-cyclopentyl-2-homo-17-20-tetranor-13-trans prostene |
| 531 | 1-trans-iodo-4-cyclohexyl-3-triphenylmethoxy-1-butene | 2-[7-methylthiaacetyl cyclopent-2-en-1-one | dl-15a-hydroxy-1-methylthiamethyl-1,9-dioxo-16-cyclohexyl-2-homo-17-20-tetranor-13-trans prostene |
| 532 | 1-trans-iodo-4-triphenylmethoxy-1-heptene | 2-[7-methylthiaacetyl cyclopent-2-en-1-one | dl-16-hydroxy-1-methylthiamethyl-1,9-dioxo-20-nor-2-homo-13-trans prostene |

TABLE VI-continued

| EXAMPLE | VINYL TIN | CYCLOPENTENONE | PRODUCT PROSTAGLANDIN OF THE 11-DEOXY PGE1 SERIES |
|---|---|---|---|
| 533 | 1-trans-tri-n-butylstannyl-4-methyl-4-trimethylsilyloxy-1-heptene | 2-[7-methylthiaacetyl heptyl] cyclopent-2-en-1-one | dl-16-hydroxy-1-methylthiamethyl-1,9-dioxo-16-methyl-20-nor-2-homo-13-trans prostene |
| 534 | 1-trans-tri-n-butylstannyl-4-ethyl-4-trimethylsilyloxy-1-octene | 2-[7-methylthiaacetyl heptyl] cyclopent-2-en-1-one | dl-16-hydroxy-1-methylthiamethyl-1,9-dioxo-16-ethyl-2-homo-13-trans prostene |
| 535 | 1-trans-tri-n-butylstannyl-5-methyl-4-trimethylsilyloxy-1-heptene | 2-[7-methylthiaacetyl heptyl] cyclopent-2-en-1-one | dl-16-hydroxy-1-methylthiamethyl-1,9-dioxo-17-methyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 536 | 1-trans-iodo-5,5-dimethyl-4-trimethylsilyloxy-1-octene | 2-[7-methylthiaacetyl heptyl] cyclopent-2-en-1-one | dl-16-hydroxy-1-methylthiamethyl-1,9-dioxo-17,17-dimethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 537 | 1-trans-tri-n-butylstannyl-4-vinyl-4-trimethylsilyloxy-1-heptene | 2-[7-methylthiaacetyl heptyl] cyclopent-2-en-1-one | dl-16-hydroxy-1-methylthiamethyl-1,9-dioxo-16-vinyl-20-nor-2-homo-13-trans prostene |
| 538 | 1-trans-tri-n-butylstannyl-4-cyclopropyl-4-trimethylsilyloxy-1-octene | 2-[7-methylthiaacetyl heptyl] cyclopent-2-en-1-one | dl-16-hydroxy-1-methylthiamethyl-1,9-dioxo-16-cyclopropyl-2-homo-13-trans prostene |
| 539 | 1-trans-tri-n-butylstannyl-4-trimethylsilylethynyl-4-trimethylsilyloxy-1-heptene | 2-[7-methylthiaacetyl heptyl] cyclopent-2-en-1-one | dl-16-hydroxy-1-methylthiamethyl-1,9-dioxo-16-ethynyl-20-nor-2-homo-13-trans prostene |
| 540 | 1-trans-tri-n-butylstannyl-5-methylene-4-triethylsilyloxy-1-heptene | 2-[7-methylthiaacetyl heptyl] cyclopent-2-en-1-one | dl-16-hydroxy-1-methylthiamethyl-1,9-dioxo-17-methylene-20-nor-2-homo-13-trans prostene |
| 541 | 1-trans-tri-n-butylstannyl-4-methyl-5-methylene-4-trimethylsilyloxy-1-heptene | 2-[7-methylthiaacetyl heptyl] cyclopent-2-en-1-one | dl-16-hydroxy-1-methylthiamethyl-1,9-dioxo-16-methyl-17-methylene-20-nor-2-homo-13-trans prostene |
| 542 | 1-trans-tri-n-butylstannyl-4-dimethoxymethyl-4-trimethylsilyloxy-1-heptene | 2-[7-methylthiaacetyl heptyl] cyclopent-2-en-1-one | dl-16-hydroxy-1-methylthiamethyl-1,9-dioxo-16-formyl-20-nor-2-homo-13-trans prostene |
| 543 | 1-trans-tri-n-butylstannyl-4-fluoromethyl-4-trimethylsilyloxy-1-heptene | 2-[7-methylthiaacetyl heptyl] cyclopent-2-en-1-one | dl-16-hydroxy-1-methylthiamethyl-1,9-dioxo-16-fluoromethyl-20-nor-2-homo-13-trans prostene |
| 544 | 1-trans-tri-n-butylstannyl-4-difluoromethyl-4-trimethylsilyloxy-1-heptene | 2-[7-methylthiaacetyl heptyl] cyclopent-2-en-1-one | dl-16-hydroxy-1-methylthiamethyl-1,9-dioxo-16-difluoromethyl-20-nor-2-homo-13-trans prostene |
| 545 | 1-trans-tri-n-butylstannyl-4-trifluoromethyl-4-trimethylsilyloxy-1-heptene | 2-[7-methylthiaacetyl heptyl] cyclopent-2-en-1-one | dl-16-hydroxy-1-methylthiamethyl-1,9-dioxo-16-trifluoromethyl-20-nor-2-homo-13-trans prostene |
| 546 | 1-trans-tri-n-butylstannyl-4-chloromethyl-4-trimethylsilyloxy-1-heptene | 2-[7-methylthiaacetyl heptyl] cyclopent-2-en-1-one | dl-16-hydroxy-1-methylthiamethyl-1,9-dioxo-16-chloromethyl-20-nor-2-homo-13-trans prostene |
| 547 | 1-trans-tri-n-butylstannyl-4-trimethylsilyloxymethyl-4-trimethylsilyloxy-1-heptene | 2-[7-methylthiaacetyl heptyl] cyclopent-2-en-1-one | dl-16-hydroxy-1-methylthiamethyl-1,9-dioxo-16-hydroxymethyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 548 | 1-trans-iodo-4-methyl-7-chloro | 2-[7-methylthiaacetyl heptyl] cyclopent-2-en-1-one | dl-16-hydroxy-1-methylthiamethyl-1,9-dioxo-16-methyl- |

TABLE VI-continued

| | | | |
|---|---|---|---|
| | 4-trimethylsilyloxy-1-heptene | heptyl] cyclopent-2-en-1-one | 19-chloro-2-homo-20-nor-13-trans prostene |
| 549 | 1-trans-iodo-3-triphenylmethoxy-1-octene | 2-[7-methylthiaacetyl heptyl] cyclopent-2-en-1-one | dl-15a-hydroxy-1-methylthiamethyl-1,9-dioxo-2-homo-13-trans prostene |
| 550 | 1-trans-iodo-3-methyl-3-trimethylsilyloxy-1-octene | 2-[7-methylthiaacetyl heptyl] cyclopent-2-en-1-one | dl-15a-hydroxy-1-methylthiamethyl-1,9-dioxo-15-methyl-2-homo-13-trans prostene |
| 551 | 1-trans-iodo-4,4-dimethyl-3-trimethylsilyloxy-1-octene | 2-[7-methylthiaacetyl heptyl] cyclopent-2-en-1-one | dl-15a-hydroxy-1-methylthiamethyl-1,9-dioxo-16,16-dimethyl-2-homo-13-trans prostene |
| 552 | 1-trans-iodo-4,4-trimethylene-3-trimethylsilyloxy-1-octene | 2-[7-methylthiaacetyl heptyl] cyclopent-2-en-1-one | dl-15a-hydroxy-1-methylthiamethyl-1,9-dioxo-16,16-trimethylene-2-homo-13-trans prostene |
| EXAMPLE | VINYL TIN | CYCLOPENTENONE | PRODUCT PROSTAGLANDIN OF THE 11-DEOXY PGE1 SERIES |
| 553 | 1-trans-tri-n-butylstannyl-3-vinyl-3-trimethylsilyloxy-1-octene | 2-[7-methylthiaacetyl heptyl] cyclopent-2-en-1-one | dl-15a-hydroxy-1-methylthiamethyl-1,9-dioxo-15-vinyl-2-homo-13-trans prostene |
| EXAMPLE | VINYL IODIDE | CYCLOPENTENONE | PRODUCT PROSTAGLANDIN OF THE PGE1 SERIES |
| 554 | 1-trans-iodo-4-triphenylmethoxy-1-octene | 2-[7-methylthiaacetyl heptyl] cyclopent-2-en-1-one | dl-16-hydroxy-1-methylthiamethyl-1,9-dioxo-2-homo-13-trans prostene |
| EXAMPLE | VINYL TIN | CYCLOPENTENONE | PRODUCT PROSTAGLANDIN OF THE 11-DEOXY PGE1 SERIES |
| 555 | 1-trans-tri-n-butylstannyl-4-methyl-4-trimethylsilyloxy-1-octene | 2-[7-methylthiaacetyl heptyl] cyclopent-2-en-1-one | dl-16-hydroxy-1-methylthiamethyl-1,9-dioxo-16-methyl-2-homo-13-trans prostene |
| 556 | 1-trans-tri-n-butylstannyl-5-methyl-4-trimethylsilyloxy-1-octene | 2-[7-methylthiaacetyl heptyl] cyclopent-2-en-1-one | dl-16-hydroxy-1-methylthiamethyl-1,9-dioxo-17-methyl-2-homo-13-trans prostene |
| 557 | 1-trans-tri-n-butylstannyl-4-vinyl-4-trimethylsilyloxy-1-octene | 2-[7-methylthiaacetyl heptyl] cyclopent-2-en-1-one | dl-16-hydroxy-1-methylthiamethyl-1,9-dioxo-16-vinyl-2-homo-13-trans prostene |
| 558 | 1-trans-tri-n-butylstannyl-4-trimethylsilylethynyl-4-trimethylsilyloxy-1-octene | 2-[7-methylthiaacetyl heptyl] cyclopent-2-en-1-one | dl-16-hydroxy-1-methylthiamethyl-1,9-dioxo-16-ethynyl-2-homo-13-trans prostene |
| 559 | 1-trans-tri-n-butylstannyl-5-methylene-4-triethylsilyloxy-1-octene | 2-[7-methylthiaacetyl heptyl] cyclopent-2-en-1-one | dl-16-hydroxy-1-methylthiamethyl-1,9-dioxo-17-methylene-2-homo-13-trans prostene |
| 560 | 1-trans-tri-n-butylstannyl-4-methyl-5-methylene-4-trimethylsilyloxy-1-octene | 2-[7-methylthiaacetyl heptyl] cyclopent-2-en-1-one | dl-16-hydroxy-1-methylthiamethyl-1,9-dioxo-16-methyl-17-methylene-homo-13-trans prostene |
| 561 | 1-trans-tri-n-butylstannyl-4-dimethoxymethyl-4-trimethylsilyloxy-1-octene | 2-[7-methylthiaacetyl heptyl] cyclopent-2-en-1-one | dl-16-hydroxy-1-methylthiamethyl-1,9-dioxo-16-formyl-2-homo-13-trans prostene |
| 562 | 1-trans-tri-n-butylstannyl-4-fluoromethyl-4-trimethylsilyloxy-1-octene | 2-[7-methylthiaacetyl heptyl] cyclopent-2-en-1-one | dl-16-hydroxy-1-methylthiamethyl-1,9-dioxo-16-fluoromethyl-2-homo-13-trans prostene |
| 563 | 1-trans-tri-n-butylstannyl-4-difluoromethyl-4-trimethylsilyloxy-1-octene | 2-[7-methylthiaacetyl heptyl] cyclopent-2-en-1-one | dl-16-hydroxy-1-methylthiamethyl-1,9-dioxo-16-difluoromethyl-2-homo-13-trans prostene |

TABLE VI-continued

| | | | |
|---|---|---|---|
| 564 | 1-trans-tri-n-butylstannyl-4-trifluoromethyl-4-trimethylsilyloxy-1-octene | 2-[7-methylthiaacetyl heptyl] cyclopent-2-en-1-one | dl-16-hydroxy-1-methylthiamethyl-1,9-dioxo-16-trifluoromethyl-2-homo-13-trans prostene |
| 565 | 1-trans-tri-n-butylstannyl-4-chloromethyl-4-trimethylsilyloxy-1-octene | 2-[7-methylthiaacetyl heptyl] cyclopent-2-en-1-one | dl-16-hydroxy-1-methylthiamethyl-1,9-dioxo-16-chloromethyl-2-homo-13-trans prostene |
| 566 | 1-trans-tri-n-butylstannyl-4-trimethylsilyloxymethyl-4-trimethylsilyloxy-1-octene | 2-[7-methylthiaacetyl heptyl] cyclopent-2-en-1-one | dl-16-hydroxy-1-methylthiamethyl-1,9-dioxo-16-hydromethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 567 | 1-trans-iodo-3-triphenylmethoxy-1-nonene | 2-[7-methylthiaacetyl heptyl] cyclopent-2-en-1-one | dl-15a-hydroxy-1-methylthiamethyl-1,9-dioxo-20-methyl-2-homo-13-trans prostene |
| 568 | 1-trans-iodo-3-methyl-3-trimethylsilyloxy-1-nonene | 2-[7-methylthiaacetyl heptyl] cyclopent-2-en-1-one | dl-15a-hydroxy-1-methylthiamethyl-1,9-dioxo-15-methyl-20-methyl-2-homo-13-trans prostene |
| 569 | 1-trans-iodo-4,4-dimethyl-3-trimethylsilyloxy-1-nonene | 2-[7-methylthiaacetyl heptyl] cyclopent-2-en-1-one | dl-15a-hydroxy-1-methylthiamethyl-1,9-dioxo-16,16-dimethyl-20-methyl-2-homo-13-trans prostene |
| 570 | 1-trans-iodo-4,4-trimethylene-3-trimethylsilyloxy-1-nonene | 2-[7-methylthiaacetyl heptyl] cyclopent-2-en-1-one | dl-15a-hydroxy-1-methylthiamethyl-1,9-dioxo-16,16-trimethylene-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 571 | 1-trans-tri-n-butylstannyl-3-vinyl-3-trimethylsilyloxy-1-nonene | 2-[7-methylthiaacetyl heptyl] cyclopent-2-en-1-one | dl-15a-hydroxy-1-methylthiamethyl-1,9-dioxo-15-vinyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 572 | 1-trans-iodo-4-triphenylmethoxy-1-nonene | 2-[7-methylthiaacetyl heptyl] cyclopent-2-en-1-one | dl-16-hydroxy-1-methylthiamethyl-1,9-dioxo-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 573 | 1-trans-tri-n-butylstannyl-4-methyl-4-trimethylsilyloxy-1-nonene | 2-[7-methylthiaacetyl heptyl] cyclopent-2-en-1-one | dl-16-hydroxy-1-methylthiamethyl-1,9-dioxo-16-methyl-20-methyl-2-homo-13-trans prostene |
| 574 | 1-trans-tri-n-butylstannyl-5-methyl-4-trimethylsilyloxy-1-nonene | 2-[7-methylthiaacetyl heptyl] cyclopent-2-en-1-one | dl-16-hydroxy-1-methylthiamethyl-1,9-dioxo-17-methyl-20-methyl-2-homo-13-trans prostene |
| 575 | 1-trans-tri-n-butylstannyl-4-vinyl-4-trimethylsilyloxy-1-nonene | 2-[7-methylthiaacetyl heptyl] cyclopent-2-en-1-one | dl-16-hydroxy-1-methylthiamethyl-1,9-dioxo-16-vinyl-20-methyl-2-homo-13-trans prostene |
| 576 | 1-trans-tri-n-butylstannyl-4-trimethylsilylethynyl-4-trimethylsilyloxy-1-nonene | 2-[7-methylthiaacetyl heptyl] cyclopent-2-en-1-one | dl-16-hydroxy-1-methylthiamethyl-1,9-dioxo-16-ethynyl-20-methyl-2-homo-13-trans prostene |
| 577 | 1-trans-tri-n-butylstannyl-5-methylene-4-triethylsilyloxy-1-nonene | 2-[7-methylthiaacetyl heptyl] cyclopent-2-en-1-one | dl-16-hydroxy-1-methylthiamethyl-1,9-dioxo-17-methylene-20-methyl-2-homo-13-trans prostene |
| 578 | 1-trans-tri-n-butylstannyl-4-methyl-5-methylene-4-trimethylsilyloxy-1-nonene | 2-[7-methylthiaacetyl heptyl] cyclopent-2-en-1-one | dl-16-hydroxy-1-methylthiamethyl-1,9-dioxo-16-methyl-17-methylene-20-methyl-2-homo-13-trans prostene |

TABLE VI-continued

| | | | |
|---|---|---|---|
| 579 | 1-trans-tri-n-butylstannyl-4-dimethoxymethyl-4-trimethylsilyloxy-1-nonene | 2-[7-methylthiaacetyl heptyl] cyclopent-2-en-1-one | dl-16-hydroxy-1-methylthiamethyl-1,9-dioxo-16-formyl-20-methyl-2-homo-13-trans prostene |
| 580 | 1-trans-tri-n-butylstannyl-4-fluoromethyl-4-trimethylsilyloxy-1-nonene | 2-[7-methylthiaacetyl heptyl] cyclopent-2-en-1-one | dl-16-hydroxy-1-methylthiamethyl-1,9-dioxo-16-fluoromethyl-20-methyl-2-homo-13-trans prostene |
| 581 | 1-trans-tri-n-butylstannyl-4-difluoromethyl-4-trimethylsilyloxy-1-nonene | 2-[7-methylthiaacetyl heptyl] cyclopent-2-en-1-one | dl-16-hydroxy-1-methylthiamethyl-1,9-dioxo-16-difluoromethyl-20-methyl-2-homo-13-trans prostene |
| 582 | 1-trans-tri-n-butylstannyl-4-trifluoromethyl-4-trimethylsilyloxy-1-nonene | 2-[7-methylthiaacetyl heptyl] cyclopent-2-en-1-one | dl-16-hydroxy-1-methylthiamethyl-1,9-dioxo-16-trifluoromethyl-20-methyl-2-homo-13-trans prostene |
| 583 | 1-trans-tri-n-butylstannyl-4-chloromethyl-4-trimethylsilyloxy-1-nonene | 2-[7-methylthiaacetyl heptyl] cyclopent-2-en-1-one | dl-16-hydroxy-1-methylthiamethyl-1,9-dioxo-16-chloromethyl-20-methyl-2-homo-13-trans prostene |
| 584 | 1-trans-tri-n-butylstannyl-4-trimethylsilyloxymethyl-4-trimethylsilyloxy-1-nonene | 2-[7-methylthiaacetyl heptyl] cyclopent-2-en-1-one | dl-16-hydroxy-1-methylthiamethyl-1,9-dioxo-16-hydroxymethyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 585 | 1-trans-iodo-3-triphenylmethoxy-1-decene | 2-[7-methylthiaacetyl heptyl] cyclopent-2-en-1-one | dl-15a-hydroxy-1-methylthiamethyl-1,9-dioxo-20-ethyl-2-homo-13-trans prostene |
| 586 | 1-trans-iodo-3-methyl-3-trimethylsilyloxy-1-decene | 2-[7-methylthiaacetyl heptyl] cyclopent-2-en-1-one | dl-15a-hydroxy-1-methylthiamethyl-1,9-dioxo-15-methyl-20-ethyl-2-homo-13-trans prostene |
| 587 | 1-trans-iodo-4,4-dimethyl-3-trimethylsilyloxy-1-decene | 2-[7-methylthiaacetyl heptyl] cyclopent-2-err-1-one | dl-15a-hydroxy-1-methylthiamethyl-1,9-dioxo-16,16-dimethyl-20-ethyl-2-homo-13-trans prostene |
| 588 | 1-trans-iodo-4,4-trimethylene-3-trimethylsilyloxy-1-decene | 2-[7-methylthiaacetyl heptyl] cyclopent-2-en-1-one | dl-15a-hydroxy-1-methylthiamethyl-1,9-dioxo-16,16-trimethylene-20-ethyl-2-homo-13-trans prostene |
| EXAMPLE | VINYL TIN | CYCLOPENTENONE | PRODUCT PROSTAGLANDIN OF THE 11-DEOXY PGE1 SERIES |
| 589 | 1-trans-tri-n-butylstannyl-3-vinyl-3-trimethylsilyloxy-1-decene | 2-[7-methylthiaacetyl heptyl] cyclopent-2-en-1-one | dl-15a-hydroxy-1-methylthiamethyl-1,9-dioxo-15-vinyl-20-ethyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 590 | 1-trans-iodo-4-triphenylmethoxy-1-decene | 2-[7-methylthiaacetyl heptyl] cyclopent-2-en-1-one | dl-16-hydroxy-1-methylthiamethyl-1,9-dioxo-20-ethyl-2-homo-13-trans prostene |
| EXAMPLE | VINYL TIN | CYCLOPENTENONE | PRODUCT PROSTAGLANDIN OF THE 11-DEOXY PGE1 SERIES |
| 591 | 1-trans-tri-n-butylstannyl-4-methyl-4-trimethylsilyloxy-1-decene | 2-[7-methylthiaacetyl heptyl] cyclopent-2-en-1-one | dl-16-hydroxy-1-methylthiamethyl-1,9-dioxo-16-methyl-20-ethyl-2-homo-13-trans prostene |
| 592 | 1-trans-tri-n-butylstannyl-5-methyl-4-trimethylsilyloxy-1-decene | 2-[7-methylthiaacetyl heptyl] cyclopent-2-en-1-one | dl-16-hydroxy-1-methylthiamethyl-1,9-dioxo-17-methyl-20-ethyl-2-homo-13-trans prostene |
| 593 | 1-trans-tri-n-butylstannyl-4-vinyl-4-trimethylsilyloxy-1-decene | 2-[7-methylthiaacetyl heptyl] cyclopent-2-en-1-one | dl-16-hydroxy-1-methylthiamethyl-1,9-dioxo-16-vinyl-20-ethyl-2-homo-13-trans prostene |

TABLE VI-continued

| | | |
|---|---|---|
| 594 | 1-trans-tri-n-butylstannyl-4-trimethylsilylethynyl-4-trimethylsilyloxy-1-decene | 2-[7-methylthiaacetyl heptyl] cyclopent-2-en-1-one | dl-16-hydroxy-1-methylthiamethyl-1,9-dioxo-16-ethynyl-20-ethyl-2-homo-13-trans prostene |
| 595 | 1-trans-tri-n-butylstannyl-5-methylene 4-triethylsilyloxy-1-decene | 2-[7-methylthiaacetyl heptyl] cyclopent-2-en-1-one | dl-16-hydroxy-1-methylthiamethyl-1,9-dioxo-17-methylene-20-ethyl-2-homo-13-trans prostene |
| 596 | 1-trans-tri-n-butylstannyl-4-methyl-5-methylene-4-trimethylsilyloxy-1-decene | 2-[7-methylthiaacetyl heptyl] cyclopent-2-en-1-one | dl-16-hydroxy-1-methylthiamethyl-1,9-dioxo-16-methyl-17-methylene-20-ethyl-2-homo-13-trans prostene |
| 597 | 1-trans-tri-n-butylstannyl-4-dimethoxymethyl-4-trimethylsilyloxy-1-decene | 2-[7-methylthiaacetyl heptyl] cyclopent-2-en-1-one | dl-16-hydroxy-1-methylthiamethyl-1,9-dioxo-16-formyl-20-ethyl-2-homo-13-trans prostene |
| 598 | 1-trans-tri-n-butylstannyl-4-fluoromethyl-4-trimethylsilyloxy-1-decene | 2-[7-methylthiaacetyl heptyl] cyclopent-2-en-1-one | dl-16-hydroxy-1-methylthiamethyl-1,9-dioxo-16-fluoromethyl-20-ethyl-2-homo-13-trans prostene |
| 599 | 1-trans-tri-n-butylstannyl-4-difluoromethyl-4-trimethylsilyloxy-1-decene | 2-[7-methylthiaacetyl heptyl] cyclopent-2-en-1-one | dl-16-hydroxy-1-methylthiamethyl-1,9-dioxo-16-difluoromethyl-20-ethyl-2-homo-13-trans prostene |
| 600 | 1-trans-tri-n-butylstannyl-4-trifluoromethyl-4-trimethylsilyloxy-1-decene | 2-[7-methylthiaacetyl heptyl] cyclopent-2-en-1-one | dl-16-hydroxy-1-methylthiamethyl-1,9-dioxo-16-trifluoromethyl-20-ethyl-2-homo-13-trans prostene |
| 601 | 1-trans-tri-n-butylstannyl-4-chloromethyl-4-trimethylsilyloxy-1-decene | 2-[7-methylthiaacetyl heptyl] cyclopent-2-en-1-one | dl-16-hydroxy-1-methylthiamethyl-1,9-dioxo-16-chloromethyl-20-ethyl-2-homo-13-trans prostene |
| 602 | 1-trans-tri-n-butylstannyl-4-trimethylsilyloxymethyl-4-trimethylsilyloxy-1-decene | 2-[7-methylthiaacetyl heptyl] cyclopent-2-en-1-one | dl-16-hydroxy-1-methylthiamethyl-1,9-dioxo-16-hydroxymethyl-20-ethyl-2-mono-13-trans prostene |

TABLE VII

| EXAMPLE | VINYL TIN | CYCLOPENTENONE | PRODUCT PROSTAGLANDIN OF THE PGE1 SERIES |
|---|---|---|---|
| 1 | 1-trans-tri-n-butylstannyl-7-thia 4-triethylsilyloxy-1-octene | 2-[5-methylthioacetyl pentyl]-4-trimethylsilyloxy cyclopent-2-en-1-one | dl-11a,16-dihydroxy-1-methylthiomethyl-1,9-dioxo-19-thia-2-nor-13-trans prostene |
| 2 | 1-trans-tri-n-butylstannyl-4-methyl-7-thia 4-trimethylsilyloxy-1-octene | 2-[5-methylthioacetyl pentyl]-4-trimethylsilyloxy cyclopent-2-en-1-one | dl-11a,16-dihydroxy-1-methylthiomethyl-1,9-dioxo-16-methyl-19-thia-2-nor-13-trans prostene |
| 3 | 1-trans-tri-n-butylstannyl-7-oxa 4-triethylsilyloxy-1-octene | 2-[5-methylthioacetyl pentyl]-4-trimethylsilyloxy cyclopent-2-en-1-one | dl-11a,16-dihydroxy-1-methylthiomethyl-1,9-dioxo-19-oxa-2-nor-13-trans prostene |
| 4 | 1-trans-tri-n-butylstannyl-4-methyl-7-oxa 4-trimethylsilyloxy-1-octene | 2-[5-methylthioacetyl pentyl]-4-trimethylsilyloxy cyclopent-2-en-1-one | dl-11a,16-dihydroxy-1-methylthiomethyl-1,9-dioxo-16-methyl-19-oxa-2-nor-13-trans prostene |
| 5 | 1-trans-tri-n-butylstannyl-4-bromomethyl-4-trimethylsilyloxy-1-heptene | 2-[5-methylthioacetyl pentyl]-4-trimethylsilyloxy cyclopent-2-en-1-one | dl-11a,16-dihydroxy-1-methylthiomethyl-1,9-dioxo-16-bromomethyl-20-nor-2-nor-13-trans prostene |
| EXAMPLE | VINYL IODIDE | CYCLOPENTENONE | PRODUCT PROSTAGLANDIN OF THE PGE1 SERIES |
| 6 | 1-trans-iodo-4-allenyl-4-trimethylsilyloxy-1-heptene | 2-[5-methylthioacetyl pentyl]-4-trimethylsilyloxy cyclopent-2-en-1-one | dl-11a,16-dihydroxy-1-methylthiomethyl-1,9-dioxo-16-allenyl-20-nor-2-nor-13-trans prostene |
| EXAMPLE | VINYL TIN | CYCLOPENTENONE | PRODUCT PROSTAGLANDIN OF THE PGE1 SERIES |
| 7 | 1-trans-tri-n-butylstannyl-4-bromomethyl-4-trimethylsilyloxy-1-octene | 2-[5-methylthioacetyl pentyl]-4-trimethylsilyloxy cyclopent-2-en-1-one | dl-11a,16-dihydroxy-1-methylthiomethyl-1,9-dioxo-16-bromomethyl-2-nor-13-trans prostene |
| EXAMPLE | VINYL IODIDE | CYCLOPENTENONE | PRODUCT PROSTAGLANDIN OF THE PGE1 SERIES |
| 8 | 1-trans-iodo-4-allenyl-4-trimethylsilyloxy-1-octene | 2-[5-methylthioacetyl pentyl]-4-trimethylsilyloxy cyclopent-2-en-1-one | dl-11a,16-dihydroxy-1-methylthiomethyl-1,9-dioxo-16-allenyl-2-nor-13-trans prostene |
| EXAMPLE | VINYL TIN | CYCLOPENTENONE | PRODUCT PROSTAGLANDIN OF THE PGE1 SERIES |
| 9 | 1-trans-tri-n-butylstannyl-4-bromomethyl-4-trimethylsilyloxy-1-nonene | 2-[5-methylthioacetyl pentyl]-4-trimethylsilyloxy cyclopent-2-en-1-one | dl-11a,16-dihydroxy-1-methylthiomethyl-1,9-dioxo-16-bromomethyl-20-methyl-2-nor-13-trans prostene |
| EXAMPLE | VINYL IODIDE | CYCLOPENTENONE | PRODUCT PROSTAGLANDIN OF THE PGE1 SERIES |
| 10 | 1-trans-iodo-4-allenyl-4-trimethylsilyloxy-1-nonene | 2-[5-methylthioacetyl pentyl]-4-trimethylsilyloxy cyclopent-2-en-1-one | dl-11a,16-dihydroxy-1-methylthiomethyl-1,9-dioxo-16-allenyl-20-methyl-2-nor-13-trans prostene |
| EXAMPLE | VINYL TIN | CYCLOPENTENONE | PRODUCT PROSTAGLANDIN OF THE PGE1 SERIES |
| 11 | 1-trans-tri-n-butylstannyl-4-bromomethyl-4-trimethylsilyloxy-1-decene | 2-[5-methylthioacetyl pentyl]-4-trimethylsilyloxy cyclopent-2-en-1-one | dl-11a,16-dihydroxy-1-methylthiomethyl-1,9-dioxo-16-bromomethyl-20-ethyl-2-nor-13-trans prostene |
| EXAMPLE | VINYL IODIDE | CYCLOPENTENONE | PRODUCT PROSTAGLANDIN OF THE PGE1 SERIES |
| 12 | 1-trans-iodo-4-allenyl-4-trimethylsilyloxy-1-decene | 2-[5-methylthioacetyl pentyl]-4-trimethylsilyloxy cyclopent-2-en-1-one | dl-11a,16-dihydroxy-1-methylthiomethyl-1,9-dioxo-16-allenyl-20-ethyl-2-nor-13-trans prostene |
| EXAMPLE | VINYL TIN | CYCLOPENTENONE | PRODUCT PROSTAGLANDIN OF THE PGE1 SERIES |

TABLE VII-continued

| | VINYL IODIDE / VINYL TIN | CYCLOPENTENONE | PRODUCT PROSTAGLANDIN OF THE PGE1 SERIES |
|---|---|---|---|
| 13 | 1-trans-tri-n-butylstannyl-7-thia 4-triethylsilyloxy-1-octene | 2-[6-methylthioacetyl hexyl]-4-trimethylsilyloxy cyclopent-2-en-1-one | dl-11a,16-dihydroxy-1-methylthiomethyl-1,9-dioxo-19-thia-13-trans prostene |
| 14 | 1-trans-tri-n-butylstannyl-4-methyl-7-thia 4-trimethylsilyloxy-1-octene | 2-[6-methylthioacetyl hexyl]-4-trimethylsilyloxy cyclopent-2-en-1-one | dl-11a,16-dihydroxy-1-methylthiomethyl-1,9-dioxo-19-thia-13-trans prostene |
| 15 | 1-trans-tri-n-butylstannyl-7-oxa 4-triethylsilyloxy-1-octene | 2-[6-methylthioacetyl hexyl]-4-trimethylsilyloxy cyclopent-2-en-1-one | dl-11a,16-dihydroxy-1-methylthiomethyl-1,9-dioxo-19-oxa-13-trans prostene |
| 16 | 1-trans-tri-n-butylstannyl-4-methyl-7-oxa 4-trimethylsilyloxy-1-octene | 2-[6-methylthioacetyl hexyl]-4-trimethylsilyloxy cyclopent-2-en-1-one | dl-11a,16-dihydroxy-1-methylthiomethyl-1,9-dioxo-16-methyl-19-oxa-13-trans prostene |
| 17 | 1-trans-tri-n-butylstannyl-4-bromomethyl-4-trimethylsilyloxy-1-heptene | 2-[6-methylthioacetyl hexyl]-4-trimethylsilyloxy cyclopent-2-en-1-one | dl-11a,16-dihydroxy-1-methylthiomethyl-1,9-dioxo-16-bromomethyl-20-nor-13-trans prostene |
| EXAMPLE 18 | VINYL IODIDE 1-trans-iodo-4-allenyl-4-trimethylsilyloxy-1-heptene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-allenyl-20-nor-13-trans prostene |
| EXAMPLE 19 | VINYL TIN 1-trans-tri-n-butylstannyl-4-bromomethyl-4-trimethylsilyloxy-1-octene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-bromomethyl-13-trans prostene |
| EXAMPLE 20 | VINYL IODIDE 1-trans-iodo-4-allenyl-4-trimethylsilyloxy-1-octene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-allenyl-13-trans prostene |
| EXAMPLE 21 | VINYL TIN 1-trans-tri-n-butylstannyl-4-bromomethyl-4-trimethylsilyloxy-1-nonene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-bromomethyl-20-methyl-13-trans prostene |
| EXAMPLE 22 | VINYL IODIDE 1-trans-iodo-4-allenyl-4-trimethylsilyloxy-1-nonene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-allenyl-20-methyl-13-trans prostene |
| EXAMPLE 23 | VINYL TIN 1-trans-tri-n-butylstannyl-4-bromomethyl-4-trimethylsilyloxy-1-decene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-bromomethyl-20-ethyl-13-trans prostene |
| EXAMPLE 24 | VINYL IODIDE 1-trans-iodo-4-allenyl-4-trimethylsilyloxy-1-decene | CYCLOPENTENONE 2-[6-methylthioacetyl hexyl]-4-trimethylsilyloxy cyclopent-2-en-1-one | PRODUCT PROSTAGLANDIN OF THE PGE1 SERIES dl-11a,16-dihydroxy-1-methylthiomethyl-1,9-dioxo-16-allenyl-20-ethyl-13-trans prostene |
| EXAMPLE 25 | VINYL TIN 1-trans-tri-n-butylstannyl-7-thia | CYCLOPENTENONE 2-[7-methylthioacetyl | PRODUCT PROSTAGLANDIN OF THE PGE1 SERIES dl-11a,16-dihydroxy-1-methylthiomethyl-1,9-dioxo- |

TABLE VII-continued

| | | | |
|---|---|---|---|
| 26 | 1-trans-tri-n-butylstannyl-4-methyl-7-thia-4-trimethylsilyloxy-1-octene | 2-[7-methylthioacetyl heptyl]-4-trimethylsilyloxy cyclopent-2-en-1-one | dl-11a,16-dihydroxy-1-methylthiomethyl-1,9-dioxo-16-methyl-19-thia-2-homo-13-trans prostene |
| 27 | 1-trans-tri-n-butylstannyl-7-oxa-4-triethylsilyloxy-1-octene | 2-[7-methylthioacetyl heptyl]-4-trimethylsilyloxy cyclopent-2-en-1-one | dl-11a,16-dihydroxy-1-methylthiomethyl-1,9-dioxo-19-oxa-2-homo-13-trans prostene |
| 28 | 1-trans-tri-n-butylstannyl-4-methyl-7-oxa-4-trimethylsilyloxy-1-octene | 2-[7-methylthioacetyl heptyl]-4-trimethylsilyloxy cyclopent-2-en-1-one | dl-11a,16-dihydroxy-1-methylthiomethyl-1,9-dioxo-16-methyl-19-oxa-2-homo-13-trans prostene |
| 29 | 1-trans-tri-n-butylstannyl-4-bromomethyl-4-trimethylsilyloxy-1-heptene | 2-[7-methylthioacetyl heptyl]-4-trimethylsilyloxy cyclopent-2-en-1-one | dl-11a,16-dihydroxy-1-methylthiomethyl-1,9-dioxo-16-bromomethyl-20-nor-2-homo-13-trans prostene |
| EXAMPLE | VINYL IODIDE | CYCLOPENTENONE | PRODUCT PROSTAGLANDIN OF THE PGE1 SERIES |
| 30 | 1-trans-iodo-4-allenyl-4-trimethylsilyloxy-1-heptene | 2-[7-methylthioacetyl heptyl]-4-trimethylsilyloxy cyclopent-2-en-1-one | dl-11a,16-dihydroxy-1-methylthiomethyl-1,9-dioxo-16-allenyl-20-nor-2-homo-13-trans prostene |
| EXAMPLE | VINYL TIN | CYCLOPENTENONE | PRODUCT PROSTAGLANDIN OF THE PGE1 SERIES |
| 31 | 1-trans-tri-n-butylstannyl-4-bromomethyl-4-trimethylsilyloxy-1-octene | 2-[7-methylthioacetyl heptyl]-4-trimethylsilyloxy cyclopent-2-en-1-one | dl-11a,16-dihydroxy-1-methylthiomethyl-1,9-dioxo-16-bromomethyl-2-homo-13-trans prostene |
| EXAMPLE | VINYL IODIDE | CYCLOPENTENONE | PRODUCT PROSTAGLANDIN OF THE PGE1 SERIES |
| 32 | 1-iodo-4-allenyl-4-trimethylsilyloxy-1-octene | 2-[7-methylthioacetyl heptyl]-4-trimethylsilyloxy cyclopent-2-en-1-one | dl-11a,16-dihydroxy-1-methylthiomethyl-1,9-dioxo-16-allenyl-2-homo-13-trans prostene |
| EXAMPLE | VINYL TIN | CYCLOPENTENONE | PRODUCT PROSTAGLANDIN OF THE PGE1 SERIES |
| 33 | 1-trans-tri-n-butylstannyl-4-bromomethyl-4-trimethylsilyloxy-1-nonene | 2-[7-methylthioacetyl heptyl]-4-trimethylsilyloxy cyclopent-2-en-1-one | dl-11a,16-dihydroxy-1-methylthiomethyl-1,9-dioxo-16-bromomethyl-20-methyl-2-homo-13-trans prostene |
| EXAMPLE | VINYL IODIDE | CYCLOPENTENONE | PRODUCT PROSTAGLANDIN OF THE PGE1 SERIES |
| 34 | 1-iodo-4-allenyl-4-trimethylsilyloxy-1-nonene | 2-[7-methylthioacetyl]-4-trimethylsilyloxy cyclopent-2-en-1-one | dl-11a,16-dihydroxy-1-methylthiomethyl-1,9-dioxo-16-allenyl-20-methyl-2-homo-13-trans prostene |
| EXAMPLE | VINYL TIN | CYCLOPENTENONE | PRODUCT PROSTAGLANDIN OF THE PGE1 SERIES |
| 35 | 1-trans-tri-n-butylstannyl-4-bromomethyl-4-trimethylsilyloxy-1-decene | 2-[7-methylthioacetyl heptyl]-4-trimethylsilyloxy cyclopent-2-en-1-one | dl-11a,16-dihydroxy-1-methylthiomethyl-1,9-dioxo-16-bromomethyl-20-ethyl-2-homo-13-trans prostene |
| EXAMPLE | VINYL IODIDE | CYCLOPENTENONE | PRODUCT PROSTAGLANDIN OF THE PGE1 SERIES |
| 36 | 1-iodo-4-allenyl-4-trimethylsilyloxy-1-decene | 2-[7-methylthioacetyl heptyl]-4-trimethylsilyloxy cyclopent-2-en-1-one | dl-11a,16-dihydroxy-1-methylthiomethyl-1,9-dioxo-16-allenyl-20-ethyl-2-homo-13-trans prostene |
| EXAMPLE | VINYL TIN | CYCLOPENTENONE | PRODUCT PROSTAGLANDIN OF THE PGE1 SERIES |
| 37 | 1-trans-tri-n-butylstannyl-7-thia-4-triethylsilyloxy-1-octene | 2-[6-methylthioacetyl hexyl]-4R-trimethylsiloxy | nat-11a,16-dihydroxy-1-methylthiomethyl-1,9-dioxo-19-thia-13-trans prostene |

TABLE VII-continued

| | | | PRODUCT |
|---|---|---|---|
| 38 | 1-trans-tri-n-butylstannyl-4-methyl-7-thia 4-trimethylsilyloxy-1-octene | 2-[6-methylthioacetyl hexyl]-4R-trimethylsilyloxy cyclopent-2-en-1-one | nat-11a,16-dihydroxy-1-methylthiomethyl-1,9-dioxo-16-methyl-19-thia-13-trans prostene |
| 39 | 1-trans-tri-n-butylstannyl-7-oxa 4-triethylsilyloxy-1-octene | 2-[6-methylthioacetyl hexyl]-4R-trimethylsilyloxy cyclopent-2-en-1-one | nat-11a,16-dihydroxy-1-methylthiomethyl-1,9-dioxo-19-oxa-13-trans prostene |
| 40 | 1-trans-tri-n-butylstannyl-4-methyl-7-oxa 4-trimethylsilyloxy-1-octene | 2-[6-methylthioacetyl hexyl]-4R-trimethylsilyloxy cyclopent-2-en-1-one | nat-11a,16-dihydroxy-1-methylthiomethyl-1,9-dioxo-16-methyl-19-oxa-13-trans prostene |
| 41 | 1-trans-tri-n-butylstannyl-4-bromomethyl-4-trimethylsilyloxy-1-heptene | 2-[6-methylthioacetyl hexyl]-4R-trimethylsilyloxy cyclopent-2-en-1-one | nat-11a,16-dihydroxy-1-methylthiomethyl-1,9-dioxo-16-bromomethyl-20-nor-13-trans prostene |
| EXAMPLE | VINYL IODIDE | CYCLOPENTENONE | PRODUCT PROSTAGLANDIN OF THE PGE1 SERIES |
| 42 | 1-trans-iodo-4-allenyl-4-trimethylsilyloxy-1-heptene | 2-[6-methylthioacetyl hexyl]-4R-trimethylsilyloxy cyclopent-2-en-1-one | nat-11a,16-dihydroxy-1-methylthiomethyl-1,9-dioxo-16-allenyl-20-nor-13-trans prostene |
| EXAMPLE | VINYL TIN | CYCLOPENTENONE | PRODUCT PROSTAGLANDIN OF THE PGE1 SERIES |
| 43 | 1-trans-tri-n-butylstannyl-4-bromomethyl-4-trimethylsilyloxy-1-octene | 2-[6-methylthioacetyl hexyl]-4R-trimethylsilyloxy cyclopent-2-en-1-one | nat-11a,16-dihydroxy-1-methylthiomethyl-1,9-dioxo-16-bromomethyl-13-trans prostene |
| EXAMPLE | VINYL IODIDE | CYCLOPENTENONE | PRODUCT PROSTAGLANDIN OF THE PGE1 SERIES |
| 44 | 1-trans-iodo-4-allenyl-4-trimethylsilyloxy-1-octene | 2-[6-methylthioacetyl hexyl]-4R-trimethylsilyloxy cyclopent-2-en-1-one | nat-11a,16-dihydroxy-1-methylthiomethyl-1,9-dioxo-16-allenyl-13-trans prostene |
| EXAMPLE | VINYL TIN | CYCLOPENTENONE | PRODUCT PROSTAGLANDIN OF THE PGE1 SERIES |
| 45 | 1-trans-tri-n-butylstannyl-4-bromomethyl-4-trimethylsilyloxy-1-nonene | 2-[6-methylthioacetyl hexyl]-4R-trimethylsilyloxy cyclopent-2-en-1-one | nat-11a,16-dihydroxy-1-methylthiomethyl-1,9-dioxo-16-bromomethyl-20-methyl-13-trans prostene |
| EXAMPLE | VINYL IODIDE | CYCLOPENTENONE | PRODUCT PROSTAGLANDIN OF THE PGE1 SERIES |
| 46 | 1-trans-iodo-4-allenyl-4-trimethylsilyloxy-1-nonene | 2-[6-methylthioacetyl hexyl]-4R-trimethylsilyloxy cyclopent-2-en-1-one | nat-11a,16-dihydroxy-1-methylthiomethyl-1,9-dioxo-16-allenyl-20-methyl-13-trans prostene |
| EXAMPLE | VINYL TIN | CYCLOPENTENONE | PRODUCT PROSTAGLANDIN OF THE PGE1 SERIES |
| 47 | 1-trans-tri-n-butylstannyl-4-bromomethyl-4-trimethylsilyloxy-1-decene | 2-[6-methylthioacetyl hexyl]-4R-trimethylsilyloxy cyclopent-2-en-1-one | nat-11a,16-dihydroxy-1-methylthiomethyl-1,9-dioxo-16-bromomethyl-20-ethyl-13-trans prostene |
| EXAMPLE | VINYL IODIDE | CYCLOPENTENONE | PRODUCT PROSTAGLANDIN OF THE PGE1 SERIES |
| 48 | 1-trans-iodo-4-allenyl-4-trimethylsilyloxy-1-decene | 2-[6-methylthioacetyl hexyl]-4R-trimethylsilyloxy cyclopent-2-en-1-one | nat-11a,16-dihydroxy-1-methylthiomethyl-1,9-dioxo-16-allenyl-20-ethyl-13-trans prostene |
| EXAMPLE | VINYL TIN | CYCLOPENTENONE | PRODUCT PROSTAGLANDIN OF THE 11-DEOXY PGE1 SERIES |
| 49 | 1-trans-tri-n-butylstannyl-7-thia 4-triethylsilyloxy-1-octene | 2-[6-methylthioacetyl pentyl] cyclopent-2-en-1-one | dl-16-hydroxy-1-methylthiomethyl-1,9-dioxo-19-thia-2-nor-13-trans prostene |

TABLE VII-continued

| | | | |
|---|---|---|---|
| 50 | 1-trans-tri-n-butylstannyl-4-methyl-7-thia-4-trimethylsilyloxy-1-octene | 2-[5-methylthioacetyl pentyl] cyclopent-2-en-1-one | dl-16-hydroxy-1-methylthiomethyl-1,9-dioxo-16-methyl-19-thia-2-nor-13-trans prostene |
| 51 | 1-trans-tri-n-butylstannyl-7-oxa-4-triethylsilyloxy-1-octene | 2-[5-methylthioacetyl pentyl] cyclopent-2-en-1-one | dl-16-hydroxy-1-methylthiomethyl-1,9-dioxo-19-oxa-2-nor-13-trans prostene |
| 52 | 1-trans-tri-n-butylstannyl-4-methyl-7-oxa-4-trimethylsilyloxy-1-octene | 2-[5-methylthioacetyl pentyl] cyclopent-2-en-1-one | dl-16-hydroxy-1-methylthiomethyl-1,9-dioxo-16-methyl-19-oxa-2-nor-13-trans prostene |
| 53 | 1-trans-tri-n-butylstannyl-4-bromomethyl-4-trimethylsilyloxy-1-heptene | 2-[5-methylthioacetyl pentyl] cyclopent-2-en-1-one | dl-16-hydroxy-1-methylthiomethyl-1,9-dioxo-16-bromomethyl-20-nor-2-nor-13-trans prostene |
| EXAMPLE 54 | VINYL IODIDE 1-trans-iodo-4-allenyl-4-trimethylsilyloxy-1-heptene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-20-nor-2-nor-13-trans prostene |
| EXAMPLE 55 | VINYL TIN 1-trans-tri-n-butylstannyl-4-bromomethyl-4-trimethylsilyloxy-1-octene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-bromomethyl-2-nor-13-trans prostene |
| EXAMPLE 56 | VINYL IODIDE 1-trans-iodo-4-allenyl-4-trimethylsilyloxy-1-octene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-2-nor-13-trans prostene |
| EXAMPLE 57 | VINYL TIN 1-trans-tri-n-butylstannyl-4-bromomethyl-4-trimethylsilyloxy-1-nonene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-bromomethyl-20-methyl-2-nor-13-trans prostene |
| EXAMPLE 58 | VINYL IODIDE 1-trans-iodo-4-allenyl-4-trimethylsilyloxy-1-nonene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-20-methyl-2-nor-13-trans prostene |
| EXAMPLE 59 | VINYL TIN 1-trans-tri-n-butylstannyl-4-bromomethyl-4-trimethylsilyloxy-1-decene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-bromomethyl-20-ethyl-2-nor-13-trans prostene |
| EXAMPLE 60 | VINYL IODIDE 1-trans-iodo-4-allenyl-4-trimethylsilyloxy-1-decene | CYCLOPENTENONE 2-[5-methylthioacetyl pentyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-20-ethyl-2-nor-13-trans prostene |
| EXAMPLE 61 | VINYL TIN 1-trans-tri-n-butylstannyl-7-thia-4-triethylsilyloxy-1-octene | CYCLOPENTENONE 2-[6-methylthioacetyl hexyl] cyclopent-2-en-1-one | PRODUCT PROSTAGLANDIN OF THE 11-DEOXY PGE1 SERIES dl-16-hydroxy-1-methylthiomethyl-1,9-dioxo-19-thia-13-trans prostene |
| 62 | 1-trans-tri-n-butylstannyl-4-methyl-7-thia | 2-[6-methylthioacetyl | dl-16-hydroxy-1-methylthiomethyl-1,9-dioxo-16-methyl- |

TABLE VII-continued

| | | | | |
|---|---|---|---|---|
| | 4-trimethylsilyloxy-1-octene | hexyl] cyclopent-2-en-1-one | | 19-thia-13-trans prostene |
| 63 | 1-trans-tri-n-butylstannyl-7-oxa-4-triethylsilyloxy-1-octene | 2-[6-methylthioacetyl hexyl] cyclopent-2-en-1-one | | dl-16-hydroxy-1-methylthiomethyl-1,9-dioxo-19-oxa-13-trans prostene |
| 64 | 1-trans-tri-n-butylstannyl-4-methyl-7-oxa-4-trimethylsilyloxy-1-octene | 2-[6-methylthioacetyl hexyl] cyclopent-2-en-1-one | | dl-16-hydroxy-1-methylthiomethyl-1,9-dioxo-16-methyl-19-oxa-13-trans prostene |
| 65 | 1-trans-tri-n-butylstannyl-4-bromomethyl-4-trimethylsilyloxy-1-heptene | 2-[6-methylthioacetyl hexyl] cyclopent-2-en-1-one | | dl-16-hydroxy-1-methylthiomethyl-1,9-dioxo-16-bromomethyl-2-nor-13-trans prostene |
| EXAMPLE | VINYL IODIDE | CYCLOPENTENONE | | PRODUCT PROSTAGLANDIN OF THE 11-DEOXY PGE1 SERIES |
| 66 | 1-trans-iodo-4-allenyl-4-trimethylsilyloxy-1-heptene | 2-[6-methylthioacetyl hexyl] cyclopent-2-en-1-one | | dl-16-hydroxy-1-methylthiomethyl-1,9-dioxo-16-allenyl-2-nor-13-trans prostene |
| EXAMPLE | VINYL TIN | CYCLOPENTENONE | | PRODUCT PROSTAGLANDIN OF THE 11-DEOXY PGE1 SERIES |
| 67 | 1-trans-tri-n-butylstannyl-4-bromomethyl-4-trimethylsilyloxy-1-octene | 2-[6-methylthioacetyl hexyl] cyclopent-2-en-1-one | | dl-16-hydroxy-1-methylthiomethyl-1,9-dioxo-16-bromomethyl-13-trans prostene |
| EXAMPLE | VINYL IODIDE | CYCLOPENTENONE | | PRODUCT PROSTAGLANDIN OF THE 11-DEOXY PGE1 SERIES |
| 68 | 1-trans-iodo-4-allenyl-4-trimethylsilyloxy-1-octene | 2-[6-methylthioacetyl hexyl] cyclopent-2-en-1-one | | dl-16-hydroxy-1-methylthiomethyl-1,9-dioxo-16-allenyl-13-trans prostene |
| EXAMPLE | VINYL TIN | CYCLOPENTENONE | | PRODUCT PROSTAGLANDIN OF THE 11-DEOXY PGE1 SERIES |
| 69 | 1-trans-tri-n-butylstannyl-4-bromomethyl-4-trimethylsilyloxy-1-nonene | 2-[6-methylthioacetyl hexyl] cyclopent-2-en-1-one | | dl-16-hydroxy-1-methylthiomethyl-1,9-dioxo-16-bromomethyl-20-methyl-13-trans prostene |
| EXAMPLE | VINYL IODIDE | CYCLOPENTENONE | | PRODUCT PROSTAGLANDIN OF THE 11-DEOXY PGE1 SERIES |
| 70 | 1-trans-iodo-4-allenyl-4-trimethylsilyloxy-1-nonene | 2-[6-methylthioacetyl hexyl] cyclopent-2-en-1-one | | dl-16-hydroxy-1-methylthiomethyl-1,9-dioxo-16-allenyl-20-methyl-13-trans prostene |
| EXAMPLE | VINYL TIN | CYCLOPENTENONE | | PRODUCT PROSTAGLANDIN OF THE 11-DEOXY PGE1 SERIES |
| 71 | 1-trans-tri-n-butylstannyl-4-bromomethyl-4-trimethylsilyloxy-1-decene | 2-[6-methylthioacetyl hexyl] cyclopent-2-en-1-one | | dl-16-hydroxy-1-methylthiomethyl-1,9-dioxo-16-bromomethyl-20-ethyl-13-trans prostene |
| EXAMPLE | VINYL IODIDE | CYCLOPENTENONE | | PRODUCT PROSTAGLANDIN OF THE 11-DEOXY PGE1 SERIES |
| 72 | 1-trans-iodo-4-allenyl-4-trimethylsilyloxy-1-decene | 2-[6-methylthioacetyl hexyl] cyclopent-2-en-1-one | | dl-16-hydroxy-1-methylthiomethyl-1,9-dioxo-16-allenyl-20-ethyl-13-trans prostene |
| EXAMPLE | VINYL TIN | CYCLOPENTENONE | | PRODUCT PROSTAGLANDIN OF THE 11-DEOXY PGE1 SERIES |
| 73 | 1-trans-tri-n-butylstannyl-7-thia-4-triethylsilyloxy-1-octene | 2-[7-methylthioacetyl heptyl] cyclopent-2-en-1-one | | dl-16-hydroxy-1-methylthiomethyl-1,9-dioxo-19-thia-2-homo-13-trans prostene |
| 74 | 1-trans-tri-n-butylstannyl-4-methyl-7-thia-4-trimethylsilyloxy-1-octene | 2-[7-methylthioacetyl heptyl] | | dl-16-hydroxy-1-methylthiomethyl-1,9-dioxo-16-methyl-19-thia-2-homo-13-trans prostene |

TABLE VII-continued

| | | | PRODUCT PROSTAGLANDIN OF THE 11-DEOXY PGE1 SERIES |
|---|---|---|---|
| 75 | 1-trans-tri-n-butylstannyl-7-oxa-4-triethylsilyloxy-1-octene | cyclopent-2-en-1-one 2-[7-methylthioacetyl heptyl] cyclopent-2-en-1-one | dl-16-hydroxy-1-methylthiomethyl-1,9-dioxo-19-oxa-2-homo-13-trans prostene |
| 76 | 1-trans-tri-n-butylstannyl-4-methyl-7-oxa-4-trimethylsilyloxy-1-octene | 2-[7-methylthioacetyl heptyl] cyclopent-2-en-1-one | dl-16-hydroxy-1-methylthiomethyl-1,9-dioxo-16-methyl-19-oxa-2-homo-13-trans prostene |
| 77 | 1-trans-tri-n-butylstannyl-4-bromomethyl-4-trimethylsilyloxy-1-heptene | 2-[7-methylthioacetyl heptyl] cyclopent-2-en-1-one | dl-16-hydroxy-1-methylthiomethyl-1,9-dioxo-16-bromomethyl-20-nor-2-homo-13-trans prostene |
| EXAMPLE 78 | VINYL IODIDE 1-trans-iodo-4-allenyl-4-trimethylsilyloxy-1-heptene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-20-nor-2-homo-13-trans prostene |
| EXAMPLE 79 | VINYL TIN 1-trans-tri-n-butylstannyl-4-bromomethyl-4-trimethylsilyloxy-1-octene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-bromomethyl-2-homo-13-trans prostene |
| EXAMPLE 80 | VINYL IODIDE 1-trans-iodo-4-allenyl-4-trimethylsilyloxy-1-octene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-2-homo-13-trans prostene |
| EXAMPLE 81 | VINYL TIN 1-trans-tri-n-butylstannyl-4-bromomethyl-4-trimethylsilyloxy-1-nonene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-bromomethyl-20-methyl-2-homo-13-trans prostene |
| EXAMPLE 82 | VINYL IODIDE 1-trans-iodo-4-allenyl-4-trimethylsilyloxy-1-nonene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-20-methyl-2-homo-13-trans prostene |
| EXAMPLE 83 | VINYL TIN 1-trans-tri-n-butylstannyl-4-bromomethyl-4-trimethylsilyloxy-1-decene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-bromomethyl-20-ethyl-2-homo-13-trans prostene |
| EXAMPLE 84 | VINYL IODIDE 1-trans-iodo-4-allenyl-4-trimethylsilyloxy-1-decene | CYCLOPENTENONE 2-[7-methylthioacetyl heptyl] cyclopent-2-en-1-one | PRODUCT PROSTAGLANDIN OF THE 11-DEOXY PGE1 SERIES dl-16-hydroxy-1-methylthiomethyl-1,9-dioxo-16-allenyl-20-ethyl-2-homo-13-trans prostene |

TABLE VIII

| EXAMPLE | VINYL IODIDE | CYCLOPENTENONE | PRODUCT PROSTAGLANDIN OF THE PGE1 SERIES |
|---|---|---|---|
| 1 | 1-trans-iodo-3-triphenylmethoxy-1-heptene | 2-[5-phenoxyacetyl pentyl]-4-trimethylsiloxy cyclopent-2-en-1-one | dl-11a,15a-dihydroxy-1-phenoxymethyl-1,9-dioxo-20-nor-2-nor-13-trans prostene |
| 2 | 1-trans-iodo-3-methyl-3-trimethylsilyloxy-1-heptene | 2-[5-phenoxyacetyl pentyl]-4-trimethylsiloxy cyclopent-2-en-1-one | dl-11a,15a-dihydroxy-1-phenoxymethyl-1,9-dioxo-15-methyl-20-nor-2-nor-13-trans prostene |
| 3 | 1-trans-iodo-4,4-dimethyl-3-trimethylsilyloxy-1-heptene | 2-[5-phenoxyacetyl pentyl]-4-trimethylsiloxy cyclopent-2-en-1-one | dl-11a,15a-dihydroxy-1-phenoxymethyl-1,9-dioxo-16,16-dimethyl-20-nor-2-nor-13-trans prostene |
| 4 | 1-trans-iodo-5,5-dimethyl-3-triphenylmethoxy-1-octene | 2-[5-phenoxyacetyl pentyl]-4-trimethylsiloxy cyclopent-2-en-1-one | dl-11a,15a-dihydroxy-1-phenoxymethyl-1,9-dioxo-17,17-dimethyl-2-nor-13-trans prostene |
| 5 | 1-trans-iodo-4-methyl-3-triphenylmethoxy-1-octene | 2-[5-phenoxyacetyl pentyl]-4-trimethylsiloxy cyclopent-2-en-1-one | dl-11a,15a-dihydroxy-1-phenoxymethyl-1,9-dioxo-16-methyl-2-nor-13-trans prostene |
| 6 | 1-trans-iodo-4,4-trimethylene-3-trimethylsilyloxy-1-heptene | 2-[5-phenoxyacetyl pentyl]-4-trimethylsiloxy cyclopent-2-en-1-one | dl-11a,15a-dihydroxy-1-phenoxymethyl-1,9-dioxo-16,16-trimethylene-20-nor-2-nor-13-trans prostene |

| EXAMPLE | VINYL TIN | CYCLOPENTENONE | PRODUCT PROSTAGLANDIN OF THE PGE1 SERIES |
|---|---|---|---|
| 7 | 1-trans-tri-n-butylstannyl-3-vinyl-3-triethylsilyloxy-1-heptene | 2-[5-phenoxyacetyl pentyl]-4-trimethylsiloxy cyclopent-2-en-1-one | dl-11a,15a-dihydroxy-1-phenoxymethyl-1,9-dioxo-15-vinyl-20-nor-2-nor-13-trans prostene |
| 8 | 1-trans-tri-n-butylstannyl-4-phenoxy-3-triethylsilyloxy-1-butene | 2-[5-phenoxyacetyl pentyl]-4-trimethylsiloxy cyclopent-2-en-1-one | dl-11a,15a-dihydroxy-1-phenoxymethyl-1,9-dioxo-16-phenoxy-2-nor-17-20-tetranor-13-trans prostene |
| 9 | 1-trans-tri-n-butylstannyl-4-(p-fluorophenoxy)-3-triethylsilyloxy-1-butene | 2-[5-phenoxyacetyl pentyl]-4-trimethylsiloxy cyclopent-2-en-1-one | dl-11a,15a-dihydroxy-1-phenoxymethyl-1,9-dioxo-16-(p-fluorophenoxy)-2-nor-17-20-tetranor-13-trans prostene |
| 10 | 1-trans-tri-n-butylstannyl-4-(m-chlorophenoxy)-3-triethylsilyloxy-1-butene | 2-[5-phenoxyacetyl pentyl]-4-trimethylsiloxy cyclopent-2-en-1-one | dl-11a,15a-dihydroxy-1-phenoxymethyl-1,9-dioxo-16-(m-chlorophenoxy)-2-nor-17-20-tetranor-13-trans prostene |
| 11 | 1-trans-tri-n-butylstannyl-4-(m-trifluoromethylphenoxy)-3-triethylsilyloxy-1-butene | 2-[5-phenoxyacetyl pentyl]-4-trimethylsiloxy cyclopent-2-en-1-one | dl-11a,15a-dihydroxy-1-phenoxymethyl-1,9-dioxo-16-(m-trifluoromethylphenoxy)-2-nor-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 12 | 1-trans-iodo-5-phenyl-3-triethylsilyloxy-1-pentene | 2-[5-phenoxyacetyl pentyl]-4-trimethylsiloxy cyclopent-2-en-1-one | dl-11a,15a-dihydroxy-1-phenoxymethyl-1,9-dioxo-17-phenyl-2-nor-18-20-trinor-13-trans prostene |
| 13 | 1-trans-iodo-4,4-dimethyl-5-phenyl-3-triethylsilyloxy-1-pentene | 2-[5-phenoxyacetyl pentyl]-4-trimethylsiloxy cyclopent-2-en-1-one | dl-11a,15a-dihydroxy-1-phenoxymethyl-1,9-dioxo-16,16-dimethyl-17-phenyl-2-nor-18-20-trinor-13-trans prostene |
| 14 | 1-trans-iodo-4-cyclopentyl-3-triphenylmethoxy-1-butene | 2-[5-phenoxyacetyl pentyl]-4-trimethylsiloxy cyclopent-2-en-1-one | dl-11a,15a-dihydroxy-1-phenoxymethyl-1,9-dioxo-16-cyclopentyl-2-nor-17-20-tetranor-13-trans prostene |
| 15 | 1-trans-iodo-4-cyclohexyl-3-triphenylmethoxy-1-butene | 2-[5-phenoxyacetyl pentyl]-4-trimethylsiloxy cyclopent-2-en-1-one | dl-11a,15a-dihydroxy-1-phenoxymethyl-1,9-dioxo-16-cyclohexyl-2-nor-17-20-tetranor-13-trans prostene |
| 16 | 1-trans-iodo-4-triphenylmethoxy-1-heptene | 2-[5-phenoxyacetyl pentyl]-4-trimethylsiloxy cyclopent-2-en-1-one | dl-11a,16-dihydroxy-1-phenoxymethyl-1,9-dioxo-20-nor-2-nor-13-trans prostene |

TABLE VIII-continued

| EXAMPLE | VINYL TIN | CYCLOPENTENONE | PRODUCT PROSTAGLANDIN OF THE PGE1 SERIES |
|---|---|---|---|
| 17 | 1-trans-tri-n-butylstannyl-4-methyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-methyl-20-nor-2-nor-13-trans prostene |
| 18 | 1-trans-tri-n-butylstannyl-4-ethyl-4-trimethylsilyloxy-1-octene | 2-[5-phenoxyacetyl pentyl]-4-trimethylsilyloxy cyclopent-2-en-1-one | dl-11a,16-dihydroxy-1-phenoxymethyl-1,9-dioxo-16-ethyl-2-nor-13-trans prostene |
| 19 | 1-trans-tri-n-butylstannyl-5-methyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-17-methyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 20 | 1-trans-iodo-5,5-dimethyl-4-trimethylsilyloxy-1-octene | 2-[5-phenoxyacetyl pentyl]-4-trimethylsilyloxy cyclopent-2-en-1-one | dl-11a,16-dihydroxy-1-phenoxymethyl-1,9-dioxo-17,17-dimethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 21 | 1-trans-tri-n-butylstannyl-4-vinyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-vinyl-20-nor-2-nor-13-trans prostene |
| 22 | 1-trans-tri-n-butylstannyl-4-cyclopropyl-4-trimethylsilyloxy-1-octene | 2-[5-phenoxyacetyl pentyl]-4-trimethylsilyloxy cyclopent-2-en-1-one | dl-11a,16-dihydroxy-1-phenoxymethyl-1,9-dioxo-16-cyclopropyl-2-nor-13-trans prostene |
| 23 | 1-trans-tri-n-butylstannyl-4-trimethylsilylethynyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-ethynyl-20-nor-2-nor-13-trans prostene |
| 24 | 1-trans-tri-n-butylstannyl-5-methylene-4-triethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-17-methylene-20-nor-2-nor-13-trans prostene |
| 25 | 1-trans-tri-n-butylstannyl-4-methyl-5-methylene-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-17-methylene-20-nor-2-nor-13-trans prostene |
| 26 | 1-trans-tri-n-butylstannyl-4-dimethoxymethyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-formyl-20-nor-2-nor-13-trans prostene |
| 27 | 1-trans-tri-n-butylstannyl-4-fluoromethyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-fluoromethyl-20-nor-2-nor-13-trans prostene |
| 28 | 1-trans-tri-n-butylstannyl-4-difluoromethyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-difluoromethyl-20-nor-2-nor-13-trans prostene |
| 29 | 1-trans-tri-n-butylstannyl-4-trifluoromethyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-trifluoromethyl-20-nor-2-nor-13-trans prostene |
| 30 | 1-trans-tri-n-butylstannyl-4-chloromethyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-chloromethyl-20-nor-2-nor-13-trans prostene |
| 31 | 1-trans-tri-n-butylstannyl-4-trimethylsilyloxymethyl-4-trimethylsilyloxy-1-heptene | 2-[5-phenoxyacetyl pentyl]-4-trimethylsilyloxy cyclopent-2-en-1-one | dl-11a,16-dihydroxy-1-phenoxymethyl-1,9-dioxo-16-hydroxymethyl-20-nor-2-nor-13-trans prostene |

TABLE VIII-continued

| EXAMPLE | VINYL IODIDE | CYCLOPENTENONE | PRODUCT PROSTAGLANDIN OF THE PGE1 SERIES |
|---|---|---|---|
| 32 | 1-trans-iodo-4-methyl-7-chloro-4-trimethylsilyloxy-1-heptene | 2-[5-phenoxyacetyl pentyl]-4-trimethylsiloxy cyclopent-2-en-1-one | dl-11a,16-dihydroxy-1-phenoxymethyl-1,9-dioxo-16-methyl-19-chloro-2-nor-20-nor-13-trans prostene |
| 33 | 1-trans-iodo-3-triphenylmethoxy-1-octene | 2-[5-phenoxyacetyl pentyl]-4-trimethylsiloxy cyclopent-2-en-1-one | dl-11a,15-dihydroxy-1-phenoxymethyl-1,9-dioxo-2-nor-13-trans prostene |
| 34 | 1-trans-iodo-3-methyl-3-trimethylsilyloxy-1-octene | 2-[5-phenoxyacetyl pentyl]-4-trimethylsiloxy cyclopent-2-en-1-one | dl-11a,15a-dihydroxy-1-phenoxymethyl-1,9-dioxo-15-methyl-2-nor-13-trans prostene |
| 35 | 1-trans-iodo-4,4-dimethyl-3-trimethylsilyloxy-1-octene | 2-[5-phenoxyacetyl pentyl]-4-trimethylsiloxy cyclopent-2-en-1-one | dl-11a,15a-dihydroxy-1-phenoxymethyl-1,9-dioxo-16,16-dimethyl-2-nor-13-trans prostene |
| 36 | 1-trans-iodo-4,4-trimethylene-3-trimethylsilyloxy-1-octene | 2-[5-phenoxyacetyl pentyl]-4-trimethylsiloxy cyclopent-2-en-1-one | dl-11a,15a-dihydroxy-1-phenoxymethyl-1,9-dioxo-16,16-trimethylene-2-nor-13-trans prostene |

| EXAMPLE | VINYL TIN | CYCLOPENTENONE | PRODUCT PROSTAGLANDIN OF THE PGE1 SERIES |
|---|---|---|---|
| 37 | 1-trans-tri-n-butylstannyl-3-vinyl-3-trimethylsilyloxy-1-octene | 2-[5-phenoxyacetyl pentyl]-4-trimethylsiloxy cyclopent-2-en-1-one | dl-11a,15a-dihydroxy-1-phenoxymethyl-1,9-dioxo-15-vinyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 38 | 1-trans-iodo-4-triphenylmethoxy-1-octene | 2-[5-phenoxyacetyl pentyl]-4-trimethylsiloxy cyclopent-2-en-1-one | dl-11a,16-dihydroxy-1-phenoxymethyl-1,9-dioxo-2-nor-13-trans prostene |

| EXAMPLE | VINYL TIN | CYCLOPENTENONE | PRODUCT PROSTAGLANDIN OF THE PGE1 SERIES |
|---|---|---|---|
| 39 | 1-trans-tri-n-butylstannyl-4-methyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-methyl-2-nor-13-trans prostene |
| 40 | 1-trans-tri-n-butylstannyl-5-methyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-17-methyl-2-nor-13-trans prostene |
| 41 | 1-trans-tri-n-butylstannyl-4-vinyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-vinyl-2-nor-13-trans prostene |
| 42 | 1-trans-tri-n-butylstannyl-4-trimethylsilylethynyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-ethynyl-2-nor-13-trans prostene |
| 43 | 1-trans-tri-n-butylstannyl-5-methylene-4-triethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-17-methylene-2-nor-13-trans prostene |
| 44 | 1-trans-tri-n-butylstannyl-4-methyl-5-methylene-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-methyl-17-methylene-2-nor-13-trans prostene |
| 45 | 1-trans-tri-n-butylstannyl-4-dimethoxymethyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-formyl-2-nor-13-trans prostene |
| 46 | 1-trans-tri-n-butylstannyl-4-fluoromethyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-fluoromethyl-2-nor-13-trans prostene |
| 47 | 1-trans-tri-n-butylstannyl-4-difluoromethyl- | 2-[5-phenoxyacetyl | dl-11a,16-dihydroxy-1-phenoxymethyl-1,9-dioxo-16-difluoromethyl- |

TABLE VIII-continued

| | | | PRODUCT PROSTAGLANDIN OF THE PGE1 SERIES |
|---|---|---|---|
| 48 | 1-trans-tri-n-butylstannyl-4-trifluoromethyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-trifluoromethyl-2-nor-13-trans prostene |
| 49 | 1-trans-tri-n-butylstannyl-4-chloromethyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-chloromethyl-2-nor-13-trans prostene |
| 50 | 1-trans-tri-n-butylstannyl-4-trimethylsilyloxymethyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-hydroxymethyl-2-nor-13-trans prostene |
| EXAMPLE | VINYL IODIDE | CYCLOPENTENONE | PRODUCT PROSTAGLANDIN OF THE PGE1 SERIES |
| 51 | 1-trans-iodo-3-triphenylmethoxy-1-nonene | 2-[5-phenoxyacetyl pentyl]-4-trimethylsiloxy cyclopent-2-en-1-one | dl-11a,15a-dihydroxy-1-phenoxymethyl-1,9-dioxo-20-methyl-2-nor-13-trans prostene |
| 52 | 1-trans-iodo-3-methyl-3-trimethylsilyloxy-1-nonene | 2-[5-phenoxyacetyl pentyl]-4-trimethylsiloxy cyclopent-2-en-1-one | dl-11a,15a-dihydroxy-1-phenoxymethyl-1,9-dioxo-15-methyl-20-methyl-2-nor-13-trans prostene |
| 53 | 1-trans-iodo-4,4-dimethyl-3-trimethylsilyloxy-1-nonene | 2-[5-phenoxyacetyl pentyl]-4-trimethylsiloxy cyclopent-2-en-1-one | dl-11a,15a-dihydroxy-1-phenoxymethyl-1,9-dioxo-16,16-dimethyl-20-methyl-2-nor-13-trans prostene |
| 54 | 1-trans-iodo-4,4-trimethylene-3-trimethylsilyloxy-1-nonene | 2-[5-phenoxyacetyl pentyl]-4-trimethylsiloxy cyclopent-2-en-1-one | dl-11a,15a-dihydroxy-1-phenoxymethyl-1,9-dioxo-16,16-trimethylene-20-methyl-2-nor-13-trans prostene |
| EXAMPLE | VINYL TIN | CYCLOPENTENONE | PRODUCT PROSTAGLANDIN OF THE PGE1 SERIES |
| 55 | 1-trans-tri-n-butylstannyl-3-vinyl-3-trimethylsilyloxy-1-nonene | 2-[5-phenoxyacetyl pentyl]-4-trimethylsiloxy cyclopent-2-en-1-one | dl-11a,15a-dihydroxy-1-phenoxymethyl-1,9-dioxo-15-vinyl-20-methyl-2-nor-13-trans prostene |
| EXAMPLE | VINYL IODIDE | CYCLOPENTENONE | PRODUCT PROSTAGLANDIN OF THE PGE1 SERIES |
| 56 | 1-trans-iodo-4-triphenylmethoxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-20-methyl-2-nor-13-trans prostene |
| EXAMPLE | VINYL TIN | CYCLOPENTENONE | PRODUCT PROSTAGLANDIN OF THE PGE1 SERIES |
| 57 | 1-trans-tri-n-butylstannyl-4-methyl-4-trimethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-16-methyl-20-methyl-2-nor-13-trans prostene |
| 58 | 1-trans-tri-n-butylstannyl-5-methyl-4-trimethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-17-methyl-20-methyl-2-nor-13-trans prostene |
| 59 | 1-trans-tri-n-butylstannyl-4-vinyl-4-trimethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-16-vinyl-20-methyl-2-nor-13-trans prostene |
| 60 | 1-trans-tri-n-butylstannyl-4-trimethylsilylethynyl-4-trimethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-16-ethynyl-20-methyl-2-nor-13-trans prostene |
| 61 | 1-trans-tri-n-butylstannyl-5-methylene-4-triethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-17-methylene-20-methyl-2-nor-13-trans prostene |
| 62 | 1-trans-tri-n-butylstannyl-4-methyl-5-methylene | 2-[5-phenoxyacetyl pentyl]-4-trimethylsiloxy cyclopent-2-en-1-one | dl-11a,16-dihydroxy-1-phenoxymethyl-1,9-dioxo-16-methyl- |

TABLE VIII-continued

| EXAMPLE | VINYL IODIDE / VINYL TIN | CYCLOPENTENONE | PRODUCT PROSTAGLANDIN |
|---|---|---|---|
| 63 | 1-trans-tri-n-butylstannyl-4-dimethoxymethyl-4-trimethylsilyloxy-1-nonene | 2-[5-phenoxyacetyl pentyl]-4-trimethylsilyloxy cyclopent-2-en-1-one | dl-11a,16-dihydroxy-1-phenoxymethyl-1,9-dioxo-16-formyl-20-methyl-2-nor-13-trans prostene |
| 64 | 1-trans-tri-n-butylstannyl-4-fluoromethyl-4-trimethylsilyloxy-1-nonene | 2-[5-phenoxyacetyl pentyl]-4-trimethylsilyloxy cyclopent-2-en-1-one | dl-11a,16-dihydroxy-1-phenoxymethyl-1,9-dioxo-16-fluoromethyl-20-methyl-2-nor-13-trans prostene |
| 65 | 1-trans-tri-n-butylstannyl-4-difluoromethyl-4-trimethylsilyloxy-1-nonene | 2-[5-phenoxyacetyl pentyl]-4-trimethylsilyloxy cyclopent-2-en-1-one | dl-11a,16-dihydroxy-1-phenoxymethyl-1,9-dioxo-16-difluoromethyl-20-methyl-2-nor-13-trans prostene |
| 66 | 1-trans-tri-n-butylstannyl-4-trifluoromethyl-4-trimethylsilyloxy-1-nonene | 2-[5-phenoxyacetyl pentyl]-4-trimethylsilyloxy cyclopent-2-en-1-one | dl-11a,16-dihydroxy-1-phenoxymethyl-1,9-dioxo-16-trifluoromethyl-20-methyl-2-nor-13-trans prostene |
| 67 | 1-trans-tri-n-butylstannyl-4-chloromethyl-4-trimethylsilyloxy-1-nonene | 2-[5-phenoxyacetyl pentyl]-4-trimethylsilyloxy cyclopent-2-en-1-one | dl-11a,16-dihydroxy-1-phenoxymethyl-1,9-dioxo-16-chloromethyl-20-methyl-2-nor-13-trans prostene |
| 68 | 1-trans-tri-n-butylstannyl-4-trimethylsilyloxymethyl-4-trimethylsilyloxy-1-nonene | 2-[5-phenoxyacetyl pentyl]-4-trimethylsilyloxy cyclopent-2-en-1-one | dl-11a,16-dihydroxy-1-phenoxymethyl-1,9-dioxo-16-hydroxymethyl-20-methyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 69 | 1-trans-iodo-3-triphenylmethoxy-1-decene | 2-[5-phenoxyacetyl pentyl]-4-trimethylsilyloxy cyclopent-2-en-1-one | dl-11a,15a-dihydroxy-1-phenoxymethyl-1,9-dioxo-20-ethyl-2-nor-13-trans prostene |
| 70 | 1-trans-iodo-3-methyl-3-trimethylsilyloxy-1-decene | 2-[5-phenoxyacetyl pentyl]-4-trimethylsilyloxy cyclopent-2-en-1-one | dl-11a,15a-dihydroxy-1-phenoxymethyl-1,9-dioxo-15-methyl-20-ethyl-2-nor-13-trans prostene |
| 71 | 1-trans-iodo-4,4-dimethyl-3-trimethylsilyloxy-1-decene | 2-[5-phenoxyacetyl pentyl]-4-trimethylsilyloxy cyclopent-2-en-1-one | dl-11a,15a-dihydroxy-1-phenoxymethyl-1,9-dioxo-16,16-dimethyl-20-ethyl-2-nor-13-trans prostene |
| 72 | 1-trans-iodo-4,4-trimethylene-3-trimethylsilyloxy-1-decene | 2-[5-phenoxyacetyl pentyl]-4-trimethylsilyloxy cyclopent-2-en-1-one | dl-11a,15a-dihydroxy-1-phenoxymethyl-1,9-dioxo-16,16-trimethylene-20-ethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 73 | 1-trans-tri-n-butylstannyl-3-vinyl-3-trimethylsilyloxy-1-decene | 2-[5-phenoxyacetyl pentyl]-4-trimethylsilyloxy cyclopent-2-en-1-one | dl-11a,15a-dihydroxy-1-phenoxymethyl-1,9-dioxo-15-vinyl-20-ethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 74 | 1-trans-iodo-4-triphenylmethoxy-1-decene | 2-[5-phenoxyacetyl pentyl]-4-trimethylsilyloxy cyclopent-2-en-1-one | dl-11a,16-dihydroxy-1-phenoxymethyl-1,9-dioxo-20-ethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 75 | 1-trans-tri-n-butylstannyl-4-methyl-4-trimethylsilyloxy-1-decene | 2-[5-phenoxyacetyl pentyl]-4-trimethylsilyloxy cyclopent-2-en-1-one | dl-11a,16-dihydroxy-1-phenoxymethyl-1,9-dioxo-16-methyl-20-ethyl-2-nor-13-trans prostene |
| 76 | 1-trans-tri-n-butylstannyl-5-methyl-4-trimethylsilyloxy-1-decene | 2-[5-phenoxyacetyl pentyl]-4-trimethylsilyloxy cyclopent-2-en-1-one | dl-11a,16-dihydroxy-1-phenoxymethyl-1,9-dioxo-17-methyl-20-ethyl-2-nor-13-trans prostene |
| 77 | 1-trans-tri-n-butylstannyl-4-vinyl- | 2-[5-phenoxyacetyl | dl-11a,16-dihydroxy-1-phenoxymethyl-1,9-dioxo-16-vinyl- |

TABLE VIII-continued

| | CYCLOPENTENONE | VINYL IODIDE | PRODUCT PROSTAGLANDIN OF THE PGE1 SERIES |
|---|---|---|---|
| 78 | 2-[5-phenoxyacetyl pentyl]-4-trimethylsilyloxy cyclopent-2-en-1-one | 4-trimethylsilyloxy-1-decene | 20-ethyl-2-nor-13-trans prostene |
| 79 | 2-[5-phenoxyacetyl pentyl]-4-trimethylsilyloxy cyclopent-2-en-1-one | 1-trans-tri-n-butylstannyl-4-trimethylsilylethynyl-4-trimethylsilyloxy-1-decene | dl-11a,16-dihydroxy-1-phenoxymethyl-1,9-dioxo-16-ethynyl-20-ethyl-2-nor-13-trans prostene |
| 80 | 2-[5-phenoxyacetyl pentyl]-4-trimethylsilyloxy cyclopent-2-en-1-one | 1-trans-tri-n-butylstannyl-5-methylene-4-triethylsilyloxy-1-decene | dl-11a,16-dihydroxy-1-phenoxymethyl-1,9-dioxo-17-methylene-20-ethyl-2-nor-13-trans prostene |
| 81 | 2-[5-phenoxyacetyl pentyl]-4-trimethylsilyloxy cyclopent-2-en-1-one | 1-trans-tri-n-butylstannyl-4-methyl-5-methylene-4-trimethylsilyloxy-1-decene | dl-11a,16-dihydroxy-1-phenoxymethyl-1,9-dioxo-16-methyl-17-methylene-20-ethyl-2-nor-13-trans prostene |
| 82 | 2-[5-phenoxyacetyl pentyl]-4-trimethylsilyloxy cyclopent-2-en-1-one | 1-trans-tri-n-butylstannyl-4-dimethoxymethyl-4-trimethylsilyloxy-1-decene | dl-11a,16-dihydroxy-1-phenoxymethyl-1,9-dioxo-16-formyl-20-ethyl-2-nor-13-trans prostene |
| 83 | 2-[5-phenoxyacetyl pentyl]-4-trimethylsilyloxy cyclopent-2-en-1-one | 1-trans-tri-n-butylstannyl-4-fluoromethyl-4-trimethylsilyloxy-1-decene | dl-11a,16-dihydroxy-1-phenoxymethyl-1,9-dioxo-16-fluoromethyl-20-ethyl-2-nor-13-trans prostene |
| 84 | 2-[5-phenoxyacetyl pentyl]-4-trimethylsilyloxy cyclopent-2-en-1-one | 1-trans-tri-n-butylstannyl-4-difluoromethyl-4-trimethylsilyloxy-1-decene | dl-11a,16-dihydroxy-1-phenoxymethyl-1,9-dioxo-16-difluoromethyl-20-ethyl-2-nor-13-trans prostene |
| 85 | 2-[5-phenoxyacetyl pentyl]-4-trimethylsilyloxy cyclopent-2-en-1-one | 1-trans-tri-n-butylstannyl-4-trifluoromethyl-4-trimethylsilyloxy-1-decene | dl-11a,16-dihydroxy-1-phenoxymethyl-1,9-dioxo-16-trifluoromethyl-20-ethyl-2-nor-13-trans prostene |
| 86 | 2-[5-phenoxyacetyl pentyl]-4-trimethylsilyloxy cyclopent-2-en-1-one | 1-trans-tri-n-butylstannyl-4-chloromethyl-4-trimethylsilyloxy-1-decene | dl-11a,16-dihydroxy-1-phenoxymethyl-1,9-dioxo-16-chloromethyl-20-ethyl-2-nor-13-trans prostene |
| | | 1-trans-tri-n-butylstannyl-4-trimethylsilyloxymethyl-4-trimethylsilyloxy-1-decene | dl-11a,16-dihydroxy-1-phenoxymethyl-1,9-dioxo-16-hydroxymethyl-20-ethyl-2-nor-13-trans prostene |

| EXAMPLE | CYCLOPENTENONE | VINYL IODIDE | PRODUCT PROSTAGLANDIN OF THE PGE1 SERIES |
|---|---|---|---|
| 87 | 2-[6-phenoxyacetyl hexyl]-4-trimethylsiloxy cyclopent-2-en-1-one | 1-trans-iodo-3-triphenylmethoxy-1-heptene | dl-11a,15a-dihydroxy-1-phenoxymethyl-1,9-dioxo-20-nor-13-trans prostene |
| 88 | 2-[6-phenoxyacetyl hexyl]-4-trimethylsiloxy cyclopent-2-en-1-one | 1-trans-iodo-3-methyl-3-trimethylsilyloxy-1-heptene | dl-11a,15a-dihydroxy-1-phenoxymethyl-1,9-dioxo-15-methyl-20-nor-13-trans prostene |
| 89 | 2-[6-phenoxyacetyl hexyl]-4-trimethylsiloxy cyclopent-2-en-1-one | 1-trans-iodo-4,4-dimethyl-3-trimethylsilyloxy-1-heptene | dl-11a,15a-dihydroxy-1-phenoxymethyl-1,9-dioxo-16,16-dimethyl-20-nor-13-trans prostene |
| 90 | 2-[6-phenoxyacetyl hexyl]-4-trimethylsiloxy cyclopent-2-en-1-one | 1-trans-iodo-5,5-dimethyl-3-triphenylmethoxy-1-octene | dl-11a,15a-dihydroxy-1-phenoxymethyl-1,9-dioxo-17,17-dimethyl-13-trans prostene |
| 91 | 2-[6-phenoxyacetyl hexyl]-4-trimethylsiloxy cyclopent-2-en-1-one | 1-trans-iodo-4-methyl-3-triphenylmethoxy-1-octene | dl-11a,15a-dihydroxy-1-phenoxymethyl-1,9-dioxo-16-methyl-13-trans prostene |
| 92 | 2-[6-phenoxyacetyl hexyl]-4-trimethylsiloxy cyclopent-2-en-1-one | 1-trans-iodo-4,4-trimethylene-3-trimethylsilyloxy-1-heptene | dl-11a,15a-dihydroxy-1-phenoxymethyl-1,9-dioxo-16,16-trimethylene-20-nor-13-trans prostene |

| EXAMPLE | CYCLOPENTENONE | VINYL TIN | PRODUCT PROSTAGLANDIN OF THE PGE1 SERIES |
|---|---|---|---|
| 93 | 2-[6-phenoxyacetyl hexyl]-4-trimethylsilyloxy cyclopent-2-en-1-one | 1-trans-tri-n-butylstannyl-3-vinyl-3-trimethylsilyloxy-1-heptene | dl-11a,15a-dihydroxy-1-phenoxymethyl-1,9-dioxo-15-vinyl-20-nor-13-trans prostene |

TABLE VIII-continued

| EXAMPLE | VINYL IODIDE | CYCLOPENTENONE | PRODUCT PROSTAGLANDIN OF THE PGE1 SERIES |
|---|---|---|---|
| 94 | 1-trans-tri-n-butylstannyl-4-phenoxy-3-triethylsilyloxy-1-butene | 2-[6-phenoxyacetyl hexyl]-4-trimethylsilyloxy cyclopent-2-en-1-one | dl-11a,15a-dihydroxy-1-phenoxymethyl-1,9-dioxo-16-phenoxy-17-20-tetranor-13-trans prostene |
| 95 | 1-trans-tri-n-butylstannyl-4-(p-fluorophenoxy)-3-triethylsilyloxy-1-butene | 2-[6-phenoxyacetyl hexyl]-4-trimethylsilyloxy cyclopent-2-en-1-one | dl-11a,15a-dihydroxy-1-phenoxymethyl-1,9-dioxo-16-(p-fluorophenoxy)-17-20-tetranor-13-trans prostene |
| 96 | 1-trans-tri-n-butylstannyl-4-(m-chlorophenoxy)-3-triethylsilyloxy-1-butene | 2-[6-phenoxyacetyl hexyl]-4-trimethylsilyloxy cyclopent-2-en-1-one | dl-11a,15a-dihydroxy-1-phenoxymethyl-1,9-dioxo-16-(m-chlorophenoxy)-17-20-tetranor-13-trans prostene |
| 97 | 1-trans-tri-n-butylstannyl-4-(m-trifluoromethylphenoxy)-3-triethylsilyloxy-1-butene | 2-[6-phenoxyacetyl hexyl]-4-trimethylsilyloxy cyclopent-2-en-1-one | dl-11a,15a-dihydroxy-1-phenoxymethyl-1,9-dioxo-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 98 | 1-trans-iodo-5-phenyl-3-triethylsilyloxy-1-pentene | 2-[6-phenoxyacetyl hexyl]-4-trimethylsilyloxy cyclopent-2-en-1-one | dl-11a,15a-dihydroxy-1-phenoxymethyl-1,9-dioxo-17-phenyl-18-20-trinor-13-trans prostene |
| 99 | 1-trans-iodo-4,4-dimethyl-5-phenyl-3-triethylsilyloxy-1-pentene | 2-[6-phenoxyacetyl hexyl]-4-trimethylsilyloxy cyclopent-2-en-1-one | dl-11a,15a-dihydroxy-1-phenoxymethyl-1,9-dioxo-16,16-dimethyl-17-phenyl-18-20-trinor-13-trans prostene |
| 100 | 1-trans-iodo-4-cyclopentyl-3-triphenylmethoxy-1-butene | 2-[6-phenoxyacetyl hexyl]-4-trimethylsilyloxy cyclopent-2-en-1-one | dl-11a,15a-dihydroxy-1-phenoxymethyl-1,9-dioxo-16-cyclopentyl-17-20-tetanor-13-trans prostene |
| 101 | 1-trans-iodo-4-cyclohexyl-3-triphenylmethoxy-1-butene | 2-[6-phenoxyacetyl hexyl]-4-trimethylsilyloxy cyclopent-2-en-1-one | dl-11a,15a-dihydroxy-1-phenoxymethyl-1,9-dioxo-16-cyclopentyl-17-20-tetanor-13-trans prostene |
| 102 | 1-trans-iodo-4-triphenylmethoxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-20-nor-13-trans prostene |

| EXAMPLE | VINYL TIN | CYCLOPENTENONE | PRODUCT PROSTAGLANDIN OF THE PGE1 SERIES |
|---|---|---|---|
| 103 | 1-trans-tri-n-butylstannyl-4-methyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-methyl-20-nor-13-trans prostene |
| 104 | 1-trans-tri-n-butylstannyl-4-ethyl-4-trimethylsilyloxy-1-octene | 2-[6-phenoxyacetyl hexyl]-4-trimethylsilyloxy cyclopent-2-en-1-one | dl-11a,16-dihydroxy-1-phenoxymethyl-1,9-dioxo-16-ethyl-13-trans prostene |
| 105 | 1-trans-tri-n-butylstannyl-5-methyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-17-methyl-20-nor-13-trans prostene |

| EXAMPLE | VINYL IODIDE | CYCLOPENTENONE | PRODUCT PROSTAGLANDIN OF THE PGE1 SERIES |
|---|---|---|---|
| 106 | 1-trans-iodo-5,5-dimethyl-4-trimethylsilyloxy-1-octene | 2-[6-phenoxyacetyl hexyl]-4-trimethylsilyloxy cyclopent-2-en-1-one | dl-11a,16-dihydroxy-1-phenoxymethyl-1,9-dioxo-17,17-dimethyl-13-trans prostene |

| EXAMPLE | VINYL TIN | CYCLOPENTENONE | PRODUCT PROSTAGLANDIN OF THE PGE1 SERIES |
|---|---|---|---|
| 107 | 1-trans-tri-n-butylstannyl-4-vinyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-vinyl-20-nor-13-trans prostene |
| 108 | 1-trans-tri-n-butylstannyl-4-cyclopropyl-4-trimethylsilyloxy-1-octene | 2-[6-phenoxyacetyl hexyl]-4-trimethylsilyloxy cyclopent-2-en-1-one | dl-11a,16-dihydroxy-1-phenoxymethyl-1,9-dioxo-16-cyclopropyl-13-trans prostene |

TABLE VIII-continued

| | VINYL IODIDE | CYCLOPENTENONE | PRODUCT PROSTAGLANDIN OF THE PGE1 SERIES |
|---|---|---|---|
| 109 | 1-trans-tri-n-butylstannyl-4-trimethylsilylethynyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxy-1,9-dioxo-16-ethynyl-20-nor-13-trans prostene |
| 110 | 1-trans-tri-n-butylstannyl-5-methylene 4-triethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-17-methylene-20-nor-13-trans prostene |
| 111 | 1-trans-tri-n-butylstannyl-4-methyl-5-methylene 4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-methyl-17-methylene-20-nor-13-trans prostene |
| 112 | 1-trans-tri-n-butylstannyl-4-dimethoxymethyl-4-trimethylxilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-formyl-20-nor-13-trans prostene |
| 113 | 1-trans-tri-n-butylstannyl-4-fluoromethyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-fluoromethyl-20-nor-13-trans prostene |
| 114 | 1-trans-tri-n-butylstannyl-4-difluoromethyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-difluoromethyl-20-nor-13-trans prostene |
| 115 | 1-trans-tri-n-butylstannyl-4-trifluoromethyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-trifluoromethyl-20-nor-13-trans prostene |
| 116 | 1-trans-tri-n-butylstannyl-4-chloromethyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-chloromethyl-20-nor-13-trans prostene |
| 117 | 1-trans-tri-n-butylstannyl-4-trimethylsilyloxymethyl-4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE PGE1 SERIES |
| 118 | 1-trans-iodo-4-methyl-7-chloro 4-trimethylsilyloxy-1-heptene | 2-[6-phenoxyacetyl hexyl]-4-trimethylsilyloxy cyclopent-2-en-1-one | dl-11a,16-dihydroxy-1-phenoxymethyl-1,9-dioxo-16-methyl-19-chloro-20-nor-13-trans prostene |
| 119 | 1-trans-iodo-3-triphenylmethoxy-1-octene | 2-[6-phenoxyacetyl hexyl]-4-trimethylsilyloxy cyclopent-2-en-1-one | dl-11a,15a-dihydroxy-1-phenoxymethyl-1,9-dioxo-13-trans prostene |
| 120 | 1-trans-iodo-2-methyl-3-trimethylsilyloxy-1-octene | 2-[6-phenoxyacetyl hexyl]-4-trimethylsilyloxy cyclopent-2-en-1-one | dl-11a,15a-dihydroxy-1-phenoxymethyl-1,9-dioxo-15-methyl-13-trans prostene |
| 121 | 1-trans-iodo-4,4-dimethyl-3-trimethylsilyloxy-1-octene | 2-[6-phenoxyacetyl hexyl]-4-trimethylsilyloxy cyclopent-2-en-1-one | dl-11a,15a-dihydroxy-1-phenoxymethyl-1,9-dioxo-16,16-dimethyl-13-trans prostene |
| 122 | 1-trans-iodo-4,4-trimethylene 3-trimethylsilyloxy-1-octene | 2-[6-phenoxyacetyl hexyl]-4-trimethylsilyloxy cyclopent-2-en-1-one | dl-11a,15a-dihydroxy-1-phenoxymethyl-1,9-dioxo-16,16-trimethylene-13-trans prostene |
| EXAMPLE | VINYL TIN | CYCLOPENTENONE | PRODUCT PROSTAGLANDIN OF THE PGE1 SERIES |
| 123 | 1-trans-tri-n-butylstannyl-3-vinyl-3-trimethylsilyloxy-1-octene | 2-[6-phenoxyacetyl hexyl]-4-trimethylsilyloxy cyclopent-2-en-1-one | dl-11a,15a-dihydroxy-1-phenoxymethyl-1,9-dioxo-15-vinyl-13-trans prostene |
| EXAMPLE | VINYL IODIDE | CYCLOPENTENONE | PRODUCT PROSTAGLANDIN OF THE PGE1 SERIES |
| 124 | 1-trans-iodo- | 2-[6-phenoxyacetyl | dl-11a,16-dihydroxy-1-phenoxymethyl-1,9-dioxo- |

TABLE VIII-continued

| EXAMPLE | VINYL TIN | CYCLOPENTENONE | PRODUCT PROSTAGLANDIN OF THE PGE1 SERIES |
|---|---|---|---|
| | 4-triphenylmethoxy-1-octene | hexyl]-4-trimethylsiloxy cyclopent-2-en-1-one | 13-trans prostene |
| 125 | 1-trans-tri-n-butylstannyl-4-methyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-methyl-13-trans prostene |
| 126 | 1-trans-tri-n-butylstannyl-5-methyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-17-methyl-13-trans prostene |
| 127 | 1-trans-tri-n-butylstannyl-4-vinyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-vinyl-13-trans prostene |
| 128 | 1-trans-tri-n-butylstannyl-4-trimethylsilylethynyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-ethynyl-13-trans prostene |
| 129 | 1-trans-tri-n-butylstannyl-5-methylene-4-triethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-17-methylene-13-trans prostene |
| 130 | 1-trans-tri-n-butylstannyl-4-methyl-5-methylene-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-methyl-17-methylene-13-trans prostene |
| 131 | 1-trans-tri-n-butylstannyl-4-dimethoxymethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-formyl-13-trans prostene |
| 132 | 1-trans-tri-n-butylstannyl-4-fluoromethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-fluoromethyl-13-trans prostene |
| 133 | 1-trans-tri-n-butylstannyl-4-difluoromethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-difluoromethyl-13-trans prostene |
| 134 | 1-trans-tri-n-butylstannyl-4-trifluoromethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-trifluoromethyl-13-trans prostene |
| 135 | 1-trans-tri-n-butylstannyl-4-chloromethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-chloromethyl-13-trans prostene |
| 136 | 1-trans-tri-n-butylstannyl-4-trimethylsilyloxymethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-hydroxymethyl-13-trans prostene |

| EXAMPLE | VINYL IODIDE | CYCLOPENTENONE | PRODUCT PROSTAGLANDIN OF THE PGE1 SERIES |
|---|---|---|---|
| 137 | 1-trans-iodo-3-triphenylmethoxy-1-nonene | 2-[6-phenoxyacetyl hexyl]-4-trimethylsiloxy cyclopent-2-en-1-one | dl-11a,15a-dihydroxy-1-phenoxymethyl-1,9-dioxo-20-methyl-13-trans prostene |
| 138 | 1-trans-iodo-3-methyl-3-trimethylsilyloxy-1-nonene | 2-[6-phenoxyacetyl hexyl]-4-trimethylsiloxy cyclopent-2-en-1-one | dl-11a,15a-dihydroxy-1-phenoxymethyl-1,9-dioxo-16-methyl-20-methyl-13-trans prostene |
| 139 | 1-trans-iodo-4,4-dimethyl-3-trimethylsilyloxy-1-nonene | 2-[6-phenoxyacetyl hexyl]-4-trimethylsiloxy cyclopent-2-en-1-one | dl-11a,15a-dihydroxy-1-phenoxymethyl-1,9-dioxo-16,16-dimethyl-20-methyl-13-trans prostene |
| 140 | 1-trans-iodo-4,4-trimethylene-3-trimethylsilyloxy-1-nonene | 2-[6-phenoxyacetyl hexyl]-4-trimethylsiloxy cyclopent-2-en-1-one | dl-11a,15a-dihydroxy-1-phenoxymethyl-1,9-dioxo-16,16-trimethylene-20-methyl-13-trans prostene |

TABLE VIII-continued

| EXAMPLE | VINYL TIN | CYCLOPENTENONE | PRODUCT PROSTAGLANDIN OF THE PGE1 SERIES |
|---|---|---|---|
| 141 | 1-trans-tri-n-butylstannyl-3-vinyl-3-trimethylsilyloxy-1-nonene | 2-[6-phenoxyacetyl hexyl]-4-trimethylsiloxy cyclopent-2-en-1-one | dl-11a,15a-dihydroxy-1-phenoxymethyl-1,9-dioxo-15-vinyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 142 | 1-trans-iodo-4-triphenylmethoxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-20-methyl-13-trans prostene |

| EXAMPLE | VINYL TIN | CYCLOPENTENONE | PRODUCT PROSTAGLANDIN OF THE PGE1 SERIES |
|---|---|---|---|
| 143 | 1-trans-tri-n-butylstannyl-4-methyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-methyl-20-methyl-13-trans prostene |
| 144 | 1-trans-tri-n-butylstannyl-5-methyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-17-methyl-20-methyl-13-trans prostene |
| 145 | 1-trans-tri-n-butylstannyl-4-vinyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-vinyl-20-methyl-13-trans prostene |
| 146 | 1-trans-tri-n-butylstannyl-4-trimethylsilylethynyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-ethynyl-20-methyl-13-trans prostene |
| 147 | 1-trans-tri-n-butylstannyl-5-methylene-4-triethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-17-methylene-20-methyl-13-trans prostene |
| 148 | 1-trans-tri-n-butylstannyl-4-methyl-5-methylene-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-methyl-17-methylene-20-methyl-13-trans prostene |
| 149 | 1-trans-tri-n-butylstannyl-4-dimethoxymethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-formyl-20-methyl-13-trans prostene |
| 150 | 1-trans-tri-n-butylstannyl-4-fluoromethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-fluoromethyl-20-methyl-13-trans prostene |
| 151 | 1-trans-tri-n-butylstannyl-4-difluoromethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-difluoromethyl-20-methyl-13-trans prostene |
| 152 | 1-trans-tri-n-butylstannyl-4-trifluoromethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-trifluoromethyl-20-methyl-13-trans prostene |
| 153 | 1-trans-tri-n-butylstannyl-4-chloromethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-chloromethyl-20-methyl-13-trans prostene |
| 154 | 1-trans-tri-n-butylstannyl-4-trimethylsilyloxymethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-hydroxymethyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 155 | 1-trans-iodo-4-triphenylmethoxy-1-decene | 2-[6-phenoxyacetyl hexyl]-4-trimethylsiloxy | dl-11a,15a-dihydroxy-1-phenoxymethyl-1,9-dioxo-20-ethyl-13-trans prostene |

TABLE VIII-continued

| | | | |
|---|---|---|---|
| 156 | | 1-trans-iodo-3-methyl-3-trimethylsilyloxy-1-decene | 2-[6-phenoxyacetyl hexyl]-4-trimethylsiloxy cyclopent-2-en-1-one | dl-11a,15a-dihydroxy-1-phenoxymethyl-1,9-dioxo-15-methyl-20-ethyl-13-trans prostene |
| 157 | | 1-trans-iodo-4,4-dimethyl-3-trimethylsilyloxy-1-decene | 2-[6-phenoxyacetyl hexyl]-4-trimethylsiloxy cyclopent-2-en-1-one | dl-11a,15a-dihydroxy-1-phenoxymethyl-1,9-dioxo-16,16-dimethyl-20-ethyl-13-trans prostene |
| 158 | | 1-trans-iodo-4,4-trimethylene-3-trimethylsilyloxy-1-decene | 2-[6-phenoxyacetyl hexyl]-4-trimethylsiloxy cyclopent-2-en-1-one | dl-11a,15a-dihydroxy-1-phenoxymethyl-1,9-dioxo-16,16-trimethylene-20-ethyl-13-trans prostene |
| EXAMPLE | VINYL TIN | | CYCLOPENTENONE | PRODUCT PROSTAGLANDIN OF THE PGE1 SERIES |
| 159 | | 1-trans-tri-n-butylstannyl-3-vinyl-3-trimethylsilyloxy-1-decene | 2-[6-phenoxyacetyl hexyl]-4-trimethylsiloxy cyclopent-2-en-1-one | dl-11a,15a-dihydroxy-1-phenoxymethyl-1,9-dioxo-15-vinyl-20-ethyl-13-trans prostene |
| EXAMPLE | VINYL IODIDE | | CYCLOPENTENONE | PRODUCT PROSTAGLANDIN OF THE PGE1 SERIES |
| 160 | | 1-trans-iodo-4-triphenylmethoxy-1-decene | 2-[6-phenoxyacetyl hexyl]-4-trimethylsiloxy cyclopent-2-en-1-one | dl-11a,16-dihydroxy-1-phenoxymethyl-1,9-dioxo-20-ethyl-13-trans prostene |
| EXAMPLE | VINYL TIN | | CYCLOPENTENONE | PRODUCT PROSTAGLANDIN OF THE PGE1 SERIES |
| 161 | | 1-trans-tri-n-butylstannyl-4-methyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-methyl-20-ethyl-13-trans prostene |
| 162 | | 1-trans-tri-n-butylstannyl-5-methyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-17-methyl-20-ethyl-13-trans prostene |
| 163 | | 1-trans-tri-n-butylstannyl-4-vinyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-vinyl-20-ethyl-13-trans prostene |
| 164 | | 1-trans-tri-n-butylstannyl-4-trimethylsilylethynyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-ethynyl-20-ethyl-13-trans prostene |
| 165 | | 1-trans-tri-n-butylstannyl-5-methylene-4-triethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-17-methylene-20-ethyl-13-trans prostene |
| 166 | | 1-trans-tri-n-butylstannyl-4-methyl-5-methylene-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-methyl-17-methylene-20-ethyl-13-trans prostene |
| 167 | | 1-trans-tri-n-butylstannyl-4-dimethoxymethyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-formyl-20-ethyl-13-trans prostene |
| 168 | | 1-trans-tri-n-butylstannyl-4-fluoromethyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-fluoromethyl-20-ethyl-13-trans prostene |
| 169 | | 1-trans-tri-n-butylstannyl-4-difluoromethyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-difluoromethyl-20-ethyl-13-trans prostene |
| 170 | | 1-trans-tri-n-butylstannyl-4-trifluoromethyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-trifluoromethyl-20-ethyl-13-trans prostene |
| 171 | | 1-trans-tri-n-butylstannyl-4-chloromethyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-chloromethyl |

TABLE VIII-continued

| | | | |
|---|---|---|---|
| 172 | 4-trimethylsilyloxy-1-decene | hexyl]-4-trimethylsiloxy cyclopent-2-en-1-one | 20-ethyl-13-trans prostene |
| | 1-trans-tri-n-butylstannyl-4-trimethylsilyloxymethyl-4-trimethylsilyloxy-1-decene | 2-[6-phenoxyacetyl hexyl]-4-trimethylsiloxy cyclopent-2-en-1-one | dl-11a,16-dihydroxy-1-phenoxymethyl-1,9-dioxo-16-hydroxymethyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 173 | 1-trans-iodo-3-triphenylmethoxy-1-heptene | 2-[7-phenoxyacetyl heptyl]-4-trimethylsiloxy cyclopent-2-en-1-one | dl-11a,15a-dihydroxy-1-phenoxymethyl-1,9-dioxo-20-nor-2-homo-13-trans prostene |
| 174 | 1-trans-iodo-3-methyl-3-trimethylsilyloxy-1-heptene | 2-[7-phenoxyacetyl heptyl]-4-trimethylsiloxy cyclopent-2-en-1-one | dl-11a,15a-dihydroxy-1-phenoxymethyl-1,9-dioxo-15-methyl-20-nor-2-homo-13-trans prostene |
| 175 | 1-trans-iodo-4,4-dimethyl-3-trimethylsilyloxy-1-heptene | 2-[7-phenoxyacetyl heptyl]-4-trimethylsiloxy cyclopent-2-en-1-one | dl-11a,15a-dihydroxy-1-phenoxymethyl-1,9-dioxo-16,16-dimethyl-20-nor-2-homo-13-trans prostene |
| 176 | 1-trans-iodo-5,5-dimethyl-3-triphenylmethoxy-1-octene | 2-[7-phenoxyacetyl heptyl]-4-trimethylsiloxy cyclopent-2-en-1-one | dl-11a,15a-dihydroxy-1-phenoxymethyl-1,9-dioxo-17,17-dimethyl-2-homo-13-trans prostene |
| 177 | 1-trans-iodo-4-methyl-3-triphenylmethoxy-1-octene | 2-[7-phenoxyacetyl heptyl]-4-trimethylsiloxy cyclopent-2-en-1-one | dl-11a,15a-dihydroxy-1-phenoxymethyl-1,9-dioxo-16-methyl-2-homo-13-trans prostene |
| 178 | 1-trans-iodo-4,4-trimethylene-3-trimethylsilyloxy-1-heptene | 2-[7-phenoxyacetyl heptyl]-4-trimethylsiloxy cyclopent-2-en-1-one | dl-11a,15a-dihydroxy-1-phenoxymethyl-1,9-dioxo-16,16-trimethylene-20-nor-2-homo-13-trans prostene |

| EXAMPLE | VINYL TIN | CYCLOPENTENONE | PRODUCT PROSTAGLANDID OF THE PGE1 SERIES |
|---|---|---|---|
| 179 | 1-trans-tri-n-butylstannyl-3-vinyl-3-trimethylsilyloxy-1-heptene | 2-[7-phenoxyacetyl heptyl]-4-trimethylsiloxy cyclopent-2-en-1-one | dl-11a,15a-dihydroxy-1-phenoxymethyl-1,9-dioxo-15-vinyl-20-nor-2-homo-13-trans prostene |
| 180 | 1-trans-tri-n-butylstannyl-4-phenoxy-3-triethylsilyloxy-1-butene | 2-[7-phenoxyacetyl heptyl]-4-trimethylsiloxy cyclopent-2-en-1-one | dl-11a,15a-dihydroxy-1-phenoxymethyl-1,9-dioxo-16-phenoxy-2-homo-17-20-tetranor-13-trans prostene |
| 181 | 1-trans-tri-n-butylstannyl-4-(p-fluorophenoxy)-3-triethylsilyloxy-1-butene | 2-[7-phenoxyacetyl heptyl]-4-trimethylsiloxy cyclopent-2-en-1-one | dl-11a,15a-dihydroxy-1-phenoxymethyl-1,9-dioxo-16-(p-fluorophenoxy)-2-homo-17-20-tetranor-13-trans prostene |
| 182 | 1-trans-tri-n-butylstannyl-4-(m-chlorophenoxy)-3-triethylsilyloxy-1-butene | 2-[7-phenoxyacetyl heptyl]-4-trimethylsiloxy cyclopent-2-en-1-one | dl-11a,15a-dihydroxy-1-phenoxymethyl-1,9-dioxo-16-(m-chlorophenoxy)-2-homo-17-20-tetranor-13-trans prostene |
| 183 | 1-trans-tri-n-butylstannyl-4-(m-trifluoromethylphenoxy)-3-triethylsilyloxy-1-butene | 2-[7-phenoxyacetyl]-4-phenoxyacetyl cyclopent-2-en-1-one | dl-11a,15a-dihydroxy-1-phenoxymethyl-1,9-dioxo-16-(m-trifluoromethylphenoxy)-2-homo-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 184 | 1-trans-iodo-5-phenyl-3-triethylsilyloxy-1-pentene | 2-[7-phenoxyacetyl heptyl]-4-trimethylsiloxy cyclopent-2-en-1-one | dl-11a,15a-dihydroxy-1-phenoxymethyl-1,9-dioxo-17-phenyl-2-homo-18-20-trinor-13-trans prostene |
| 185 | 1-trans-iodo-4,4-dimethyl-5-phenyl-3-triethylsilyloxy-1-pentene | 2-[7-phenoxyacetyl heptyl]-4-trimethylsiloxy cyclopent-2-en-1-one | dl-11a,15a-dihydroxy-1-phenoxymethyl-1,9-dioxo-16,16-dimethyl-17-phenyl-2-homo-18-20-trinor-13-trans prostene |
| 186 | 1-trans-iodo-4-cyclopentyl-3-triphenylmethoxy-1-butene | 2-[7-phenoxyacetyl heptyl]-4-trimethylsiloxy cyclopent-2-en-1-one | dl-11a,15a-dihydroxy-1-phenoxymethyl-1,9-dioxo-16-cyclopentyl-2-homo-17-20-tetranor-13-trans prostene |

TABLE VIII-continued

| | | | |
|---|---|---|---|
| 187 | 1-trans-iodo-4-cyclohexyl-3-triphenylmethoxy-1-butene | 2-[7-phenoxyacetyl heptyl]-4-trimethylsiloxy cyclopent-2-en-1-one | dl-11a,15a-dihydroxy-1-phenoxymethyl-1,9-dioxo-16-cyclohexyl-2-homo-17,20-tetranor-13-trans prostene |
| 188 | 1-trans-iodo-4-triphenylmethoxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-20-nor-2-homo-13-trans prostene |
| EXAMPLE | VINYL TIN | CYCLOPENTENONE | PRODUCT PROSTAGLANDIN OF THE PGE 1 SERIES |
| 189 | 1-trans-tri-n-butylstannyl-4-methyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-methyl-20-nor-2-homo-13-trans prostene |
| 190 | 1-trans-tri-n-butylstannyl-4-ethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-16-ethyl-2-homo-13-trans prostene |
| 191 | 1-trans-tri-n-butylstannyl-5-methyl-4-triethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-17-methyl-20-nor-2-homo-13-trans prostene |
| EXAMPLE | VINYL IODIDE | CYCLOPENTENONE | PRODUCT PROSTAGLANDIN OF THE PGE1 SERIES |
| 192 | 1-trans-iodo-5,5-dimethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-17,17-dimethyl-2-homo-13-trans prostene |
| EXAMPLE | VINYL TIN | CYCLOPENTENONE | PRODUCT PROSTAGLANDIN OF THE PGE1 SERIES |
| 193 | 1-trans-tri-n-butylstannyl-4-vinyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-vinyl-20-nor-2-homo-13-trans prostene |
| 194 | 1-trans-tri-n-butylstannyl-4-cyclopropyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-cyclopropyl-2-homo-13-trans prostene |
| 195 | 1-trans-tri-n-butylstannyl-4-trimethylsilylethynyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-ethynyl-20-nor-2-homo-13-trans prostene |
| 196 | 1-trans-tri-n-butylstannyl-5-methylene-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-17-methylene-20-nor-2-homo-13-trans prostene |
| 197 | 1-trans-tri-n-butylstannyl-4-methyl-5-methylene-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-methyl-17-methylene-20-nor-2-homo-13-trans prostene |
| 198 | 1-trans-tri-n-butylstannyl-4-dimethoxymethyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-formyl-20-nor-2-homo-13-trans prostene |
| 199 | 1-trans-tri-n-butylstannyl-4-fluoromethyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-fluoromethyl-20-nor-2-homo-13-trans prostene |
| 200 | 1-trans-tri-n-butylstannyl-4-difluoromethyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-difluoromethyl-20-nor-2-homo-13-trans prostene |
| 201 | 1-trans-tri-n-butylstannyl-4-trifluoromethyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-trifluoromethyl-20-nor-2-homo-13-trans prostene |
| 202 | 1-trans-tri-n-butystannyl-4-chloromethyl-4-trimethylsilyloxy-1-heptene | 2-[7-phenoxyacetyl heptyl]-4-trimethylsiloxy cyclopent-2-en-1-one | dl-11a,16-dihydroxy-1-phenoxymethyl-1,9-dioxo-16-chloromethyl-20-nor-2-homo-13-trans prostene |

TABLE VIII-continued

| | | | |
|---|---|---|---|
| 203 | 1-trans-tri-n-butylstannyl-4-trimethylsilyloxymethyl-4-trimethylsilyloxy-1-heptene | 2-[7-phenoxyacetyl heptyl]-4-trimethylsilyloxy cyclopent-2-en-1-one | dl-11a,16-dihydroxy-1-phenoxymethyl-1,9-dioxo-16-hydroxymethyl-20-nor-2-homo-13-trans prostene |
| EXAMPLE | VINYL IODIDE | CYCLOPENTENONE | PRODUCT PROSTAGLANDIN OF THE PGE1 SERIES |
| 204 | 1-trans-iodo-4-methyl-7-chloro-4-trimethylsilyloxy-1-heptene | 2-[7-phenoxyacetyl heptyl]-4-trimethylsilyloxy cyclopent-2-en-1-one | dl-11a,16-dihydroxy-1-phenoxymethyl-1,9-dioxo-16-methyl-19-chloro-2-homo-20-nor-13-trans prostene |
| 205 | 1-trans-iodo-3-triphenylmethoxy-1-octene | 2-[7-phenoxyacetyl heptyl]-4-trimethylsilyloxy cyclopent-2-en-1-one | dl-11a,15a-dihydroxy-1-phenoxymethyl-1,9-dioxo-2-homo-13-trans prostene |
| 206 | 1-trans-iodo-3-methyl-3-trimethylsilyloxy-1-octene | 2-[7-phenoxyacetyl heptyl]-4-trimethylsilyloxy cyclopent-2-en-1-one | dl-11a,15a-dihydroxy-1-phenoxymethyl-1,9-dioxo-15-methyl-2-homo-13-trans prostene |
| 207 | 1-trans-iodo-4,4-dimethyl-3-trimethylsilyloxy-1-octene | 2-[7-phenoxyacetyl heptyl]-4-trimethylsilyloxy cyclopent-2-en-1-one | dl-11a,15a-dihydroxy-1-phenoxymethyl-1,9-dioxo-16,16-dimethyl-2-homo-13-trans prostene |
| 208 | 1-trans-iodo-4,4-trimethylene-3-trimethylsilyloxy-1-octene | 2-[7-phenoxyacetyl heptyl]-4-trimethylsilyloxy cyclopent-2-en-1-one | dl-11a,15a-dihydroxy-1-phenoxymethyl-1,9-dioxo-16,16-trimethylene-2-homo-13-trans prostene |
| EXAMPLE | VINYL TIN | CYCLOPENTENONE | PRODUCT PROSTAGLANDIN OF THE PGE1 SERIES |
| 209 | 1-trans-tri-n-butylstannyl-3-vinyl-3-trimethylsilyloxy-1-octene | 2-[7-phenoxyacetyl heptyl]-4-trimethylsilyloxy cyclopent-2-en-1-one | dl-11a,15a-dihydroxy-1-phenoxymethyl-1,9-dioxo-15-vinyl-2-homo-13-trans prostene |
| EXAMPLE | VINYL IODIDE | CYCLOPENTENONE | PRODUCT PROSTAGLANDIN OF THE PGE1 SERIES |
| 210 | 1-trans-iodo-4-triphenylmethoxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-2-homo-13-trans prostene |
| EXAMPLE | VINYL TIN | CYCLOPENTENONE | PRODUCT PROSTAGLANDIN OF THE PGE1 SERIES |
| 211 | 1-trans-tri-n-butylstannyl-4-methyl-4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-16-methyl-2-homo-13-trans prostene |
| 212 | 1-trans-tri-n-butylstannyl-5-methyl-4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-17-methyl-2-homo-13-trans prostene |
| 213 | 1-trans-tri-n-butylstannyl-4-vinyl-4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-16-vinyl-2-homo-13-trans prostene |
| 214 | 1-trans-tri-n-butylstannyl-4-trimethylsilylethynyl-4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-16-ethynyl-2-homo-13-trans prostene |
| 215 | 1-trans-tri-n-butylstannyl-5-methylene-4-triethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-17-methylene-2-homo-13-trans prostene |
| 216 | 1-trans-tri-n-butylstannyl-4-methyl-5-methylene-4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-16-methyl-17-methylene-2-homo-13-trans prostene |
| 217 | 1-trans-tri-n-butylstannyl-4-dimethoxymethyl-4-trimethylsilyloxy-1-octene | 2-[7-phenoxyacetyl heptyl]-4-trimethylsilyloxy | dl-11a,16-dihydroxy-1-phenoxymethyl-1,9-dioxo-16-formyl-2-homo-13-trans prostene |

TABLE VIII-continued

| | VINYL TIN | CYCLOPENTENONE | PRODUCT PROSTAGLANDIN |
|---|---|---|---|
| 218 | 1-trans-tri-n-butylstannyl-4-fluoromethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-16-fluoromethyl-2-homo-13-trans prostene |
| 219 | 1-trans-tri-n-butylstannyl-4-difluoromethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-16-difluoromethyl-2-homo-13-trans prostene |
| 220 | 1-trans-tri-n-butylstannyl-4-trifluoromethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-16-trifluoromethyl-2-homo-13-trans prostene |
| 221 | 1-trans-tri-n-butylstannyl-4-chloromethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-16-chloromethyl-2-homo-13-trans prostene |
| 222 | 1-trans-tri-n-butylstannyl-4-trimethylsilyloxymethyl-4-trimethylsilyloxy-1-octene | 2-[7-phenoxyacetyl heptyl]-4-trimethylsiloxy cyclopent-2-en-1-one | dl-11a,16-dihydroxy-1-phenoxymethyl-1,9-dioxo-16-hydroxymethyl-2-homo-13-trans prostene |
| EXAMPLE | VINYL IODIDE | CYCLOPENTENONE | PRODUCT PROSTAGLANDIN OF THE PGE1 SERIES |
| 223 | 1-trans-iodo-3-triphenylmethoxy-1-nonene | 2-[7-phenoxyacetyl heptyl]-4-trimethylsiloxy cyclopent-2-en-1-one | dl-11a,15a-dihydroxy-1-phenoxymethyl-1,9-dioxo-20-methyl-2-homo-13-trans prostene |
| 224 | 1-trans-iodo-3-methyl-3-trimethylsilyloxy-1-nonene | 2-[7-phenoxyacetyl heptyl]-4-trimethylsiloxy cyclopent-2-en-1-one | dl-11a,15a-dihydroxy-1-phenoxymethyl-1,9-dioxo-15-methyl-20-methyl-2-homo-13-trans prostene |
| 225 | 1-trans-iodo-4,4-dimethyl-3-trimethylsilyloxy-1-nonene | 2-[7-phenoxyacetyl heptyl]-4-trimethylsiloxy cyclopent-2-en-1-one | dl-11a,15a-dihydroxy-1-phenoxymethyl-1,9-dioxo-16,16-dimethyl-20-methyl-2-homo-13-trans prostene |
| 226 | 1-trans-iodo-4,4-trimethylene-3-trimethylsilyloxy-1-nonene | 2-[7-phenoxyacetyl heptyl]-4-trimethylsiloxy cyclopent-2-en-1-one | dl-11a,15a-dihydroxy-1-phenoxymethyl-1,9-dioxo-16,16-trimethylene-20-methyl-2-homo-13-trans prostene |
| EXAMPLE | VINYL TIN | CYCLOPENTENONE | PRODUCT PROSTAGLANDIN OF THE PGE1 SERIES |
| 227 | 1-trans-tri-n-butylstannyl-3-vinyl-3-trimethylsilyloxy-1-nonene | 2-[7-phenoxyacetyl heptyl]-4-trimethylsiloxy cyclopent-2-en-1-one | dl-11a,15a-dihydroxy-1-phenoxymethyl-1,9-dioxo-15-vinyl-20-methyl-2-homo-13-trans prostene |
| EXAMPLE | VINYL IODIDE | CYCLOPENTENONE | PRODUCT PROSTAGLANDIN OF THE PGE1 SERIES |
| 228 | 1-trans-iodo-4-triphenylmethoxy-1-nonene | 2-[7-phenoxyacetyl heptyl]-4-trimethylsiloxy cyclopent-2-en-1-one | dl-11a,16-dihydroxy-1-phenoxymethyl-1,9-dioxo-20-methyl-2-homo-13-trans prostene |
| EXAMPLE | VINYL TIN | CYCLOPENTENONE | PRODUCT PROSTAGLANDIN OF THE PGE1 SERIES |
| 229 | 1-trans-tri-n-butylstannyl-4-methyl-4-trimethylsilyloxy-1-nonene | 2-[7-phenoxyacetyl heptyl]-4-trimethylsiloxy cyclopent-2-en-1-one | dl-11a,16-dihydroxy-1-phenoxymethyl-1,9-dioxo-16-methyl-20-methyl-2-homo-13-trans prostene |
| 230 | 1-trans-tri-n-butylstannyl-5-methyl-4-trimethylsilyloxy-1-nonene | 2-[7-phenoxyacetyl heptyl]-4-trimethylsiloxy cyclopent-2-en-1-one | dl-11a,16-dihydroxy-1-phenoxymethyl-1,9-dioxo-17-methyl-20-methyl-2-homo-13-trans prostene |
| 231 | 1-trans-tri-n-butylstannyl-4-vinyl-4-trimethylsilyloxy-1-nonene | 2-[7-phenoxyacetyl heptyl]-4-trimethylsiloxy cyclopent-2-en-1-one | dl-11a,16-dihydroxy-1-phenoxymethyl-1,9-dioxo-16-vinyl-20-methyl-2-homo-13-trans prostene |
| 232 | 1-trans-tri-n-butylstannyl-4-trimethylsilylethynyl-4-trimethylsilyloxy-1-nonene | 2-[7-phenoxyacetyl heptyl]-4-trimethylsiloxy cyclopent-2-en-1-one | dl-11a,16-dihydroxy-1-phenoxymethyl-1,9-dioxo-16-ethynyl-20-methyl-2-homo-13-trans prostene |

TABLE VIII-continued

| | | | |
|---|---|---|---|
| 233 | 1-trans-tri-n-butylstannyl-5-methylene 4-triethylsilyloxy-1-nonene | cyclopent-2-en-1-one 2-[7-phenoxyacetyl heptyl]-4-trimethylsilyloxy cyclopent-2-en-1-one | dl-11a,16-dihydroxy-1-phenoxymethyl-1,9-dioxo-17-methylene-20-methyl-2-homo-13-trans prostene |
| 234 | 1-trans-tri-n-butylstannyl-4-methyl-5-methylene 4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-methyl-17-methylene-20-methyl-2-homo-13-trans prostene |
| 235 | 1-trans-tri-n-butylstannyl-4-dimethoxymethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-formyl-20-methyl-2-homo-13-trans prostene |
| 236 | 1-trans-tri-n-butylstannyl-4-fluoromethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-fluoromethyl-20-methyl-2-homo-13-trans prostene |
| 237 | 1-trans-tri-n-butylstannyl-4-difluoromethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-difluoromethyl-20-methyl-2-homo-13-trans prostene |
| 238 | 1-trans-tri-n-butylstannyl-4-trifluoromethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-trifluoromethyl-20-methyl-2-homo-13-trans prostene |
| 239 | 1-trans-tri-n-butylstannyl-4-chloromethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-chloromethyl-20-methyl-2-homo-13-trans prostene |
| 240 | 1-trans-tri-n-butylstannyl-4-trimethylsilyloxymethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-hydroxymethyl-20-methyl-2-homo-13-trans prostene |
| EXAMPLE | VINYL IODIDE | CYCLOPENTENONE | PRODUCT PROSTAGLANDIN OF THE PGE1 SERIES |
| 241 | 1-trans-iodo-3-triphenylmethoxy-1-decene | 2-[7-phenoxyacetyl heptyl]-4-trimethylsiloxy cyclopent-2-en-1-one | dl-11a,15a-dihydroxy-1-phenoxymethyl-1,9-dioxo-20-ethyl-2-homo-13-trans prostene |
| 242 | 1-trans-iodo-3-methyl-3-trimethylsilyloxy-1-decene | 2-[7-phenoxyacetyl heptyl]-4-trimethylsiloxy cyclopent-2-en-1-one | dl-11a,15a-dihydroxy-1-phenoxymethyl-1,9-dioxo-15-methyl-20-ethyl-2-homo-13-trans prostene |
| 243 | 1-trans-iodo-4,4-dimethyl-3-trimethylsilyloxy-1-decene | 2-[7-phenoxyacetyl heptyl]-4-trimethylsiloxy cyclopent-2-en-1-one | dl-11a,15a-dihydroxy-1-phenoxymethyl-1,9-dioxo-16,16-dimethyl-20-ethyl-2-homo-13-trans prostene |
| 244 | 1-trans-iodo-4,4-trimethylene-3-trimethylsilyloxy-1-decene | 2-[7-phenoxyacetyl heptyl]-4-trimethylsiloxy cyclopent-2-en-1-one | dl-11a,15a-dihydroxy-1-phenoxymethyl-1,9-dioxo-16,16-trimethylene-20-ethyl-2-homo-13-trans prostene |
| EXAMPLE | VINYL TIN | CYCLOPENTENONE | PRODUCT PROSTAGLANDIN OF THE PGE1 SERIES |
| 245 | 1-trans-tri-n-butylstannyl-3-vinyl-3-trimethylsilyloxy-1-decene | 2-[7-phenoxyacetyl heptyl]-4-trimethylsiloxy cyclopent-2-en-1-one | dl-11a,15a-dihydroxy-1-phenoxymethyl-1,9-dioxo-15-vinyl-20-ethyl-2-homo-13-trans prostene |
| EXAMPLE | VINYL IODIDE | CYCLOPENTENONE | PRODUCT PROSTAGLANDIN OF THE PGE1 SERIES |
| 246 | 1-trans-iodo-4-triphenylmethoxy-1-decene | 2-[7-phenoxyacetyl heptyl]-4-trimethylsiloxy cyclopent-2-en-1-one | dl-11a,16-dihydroxy-1-phenoxymethyl-1,9-dioxo-20-ethyl-2-homo-13-trans prostene |
| EXAMPLE | VINYL TIN | CYCLOPENTENONE | PRODUCT PROSTAGLANDIN OF THE PGE1 SERIES |
| 247 | 1-trans-tri-n-butylstannyl-4-methyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-methyl-20-ethyl-2-homo-13-trans prostene |

TABLE VIII-continued

| | VINYL IODIDE | CYCLOPENTENONE | PRODUCT |
|---|---|---|---|
| 248 | 1-trans-tri-n-butylstannyl-5-methyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-17-methyl-20-ethyl-2-homo-13-trans prostene |
| 249 | 1-trans-tri-n-butylstannyl-4-vinyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-vinyl-20-ethyl-2-homo-13-trans prostene |
| 250 | 1-trans-tri-n-butylstannyl-4-trimethylsilylethynyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-ethynyl-20-ethyl-2-homo-13-trans prostene |
| 251 | 1-trans-tri-n-butylstannyl-5-methylene-4-triethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-17-methylene-20-ethyl-2-homo-13-trans prostene |
| 252 | 1-trans-tri-n-butylstannyl-4-methyl-5-methylene-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-methyl-17-methylene-20-ethyl-2-homo-13-trans prostene |
| 253 | 1-trans-tri-n-butylstannyl-4-dimethoxymethyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-formyl-20-ethyl-2-homo-13-trans prostene |
| 254 | 1-trans-tri-n-butylstannyl-4-fluoromethyl-4-trimethylsilyloxy-1-decene | 2-[7-phenoxyacetyl heptyl]-4-trimethylsiloxy cyclopent-2-en-1-one | dl-11a,16-dihydroxy-phenoxymethyl-1,9-dioxo-16-fluoromethyl-20-ethyl-2-homo-13-trans prostene |
| 255 | 1-trans-tri-n-butylstannyl-4-difluoromethyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-difluoromethyl-20-ethyl-2-homo-13-trans prostene |
| 256 | 1-trans-tri-n-butylstannyl-4-trifluoromethyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-trifluoromethyl-20-ethyl-2-homo-13-trans prostene |
| 257 | 1-trans-tri-n-butylstannyl-4-chloromethyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-chloromethyl-20-ethyl-2-homo-13-trans prostene |
| 258 | 1-trans-tri-n-butylstannyl-4-trimethylsilyloxymethyl-4-trimethylsilyloxy-1-decene | 2-[7-phenoxyacetyl heptyl]-4-trimethylsiloxy cyclopent-2-en-1-one | dl-11a,16-dihydroxy-1-phenoxymethyl-1,9-dioxo-16-hydroxymethyl-20-ethyl-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 259 | 1-trans-iodo-3-triphenylmethoxy-1-heptene | 2-[6-phenoxyacetyl hexyl]-4R-trimethylsiloxy cyclopent-2-en-1-one | nat-11a,15a-dihydroxy-1-phenoxymethyl-1,9-dioxo-20-nor-13-trans prostene |
| 260 | 1-trans-iodo-3-methyl-3-trimethylsilyloxy-1-heptene | 2-[6-phenoxyacetyl hexyl]-4R-trimethylsiloxy cyclopent-2-en-1-one | nat-11a,15a-dihydroxy-1-phenoxymethyl-1,9-dioxo-15-methyl-20-nor-13-trans prostene |
| 261 | 1-trans-iodo-4,4-dimethyl-3-trimethylsilyloxy-1-heptene | 2-[6-phenoxyacetyl hexyl]-4R-trimethylsiloxy cyclopent-2-en-1-one | nat-11a,15a-dihydroxy-1-phenoxymethyl-1,9-dioxo-16,16-dimethyl-20-nor-13-trans prostene |
| 262 | 1-trans-iodo-5,5-dimethyl-3-triphenylmethoxy-1-octene | 2-[6-phenoxyacetyl hexyl]-4R-trimethylsiloxy cyclopent-2-en-1-one | nat-11a,15a-dihydroxy-1-phenoxymethyl-1,9-dioxo-17,17-dimethyl-13-trans prostene |
| 263 | 1-trans-iodo-4-methyl-3-triphenylmethoxy-1-octene | 2-[6-phenoxyacetyl hexyl]-4R-trimethylsiloxy cyclopent-2-en-1-one | nat-11a,15a-dihydroxy-1-phenoxymethyl-1,9-dioxo-16-methyl-13-trans prostene |
| 264 | 1-trans-iodo-4,4-trimethylene-3-trimethylsilyloxy-1-heptene | 2-[6-phenoxyacetyl hexyl]-4R-trimethylsiloxy cyclopent-2-en-1-one | nat-11a,15a-dihydroxy-1-phenoxymethyl-1,9-dioxo-16,16-trimethylene-20-nor-13-trans prostene |

TABLE VIII-continued

| EXAMPLE | VINYL TIN | CYCLOPENTENONE | PRODUCT PROSTAGLANDIN OF THE PGE1 SERIES |
|---|---|---|---|
| 265 | 1-trans-tri-n-butylstannyl-3-vinyl-3-trimethylsilyloxy-1-heptene | 2-[6-phenoxyacetyl hexyl]-4R-trimethylsiloxy cyclopent-2-en-1-one | nat-11a,15a-dihydroxy-1-phenoxymethyl-1,9-dioxo-15-vinyl-20-nor-13-trans prostene |
| 266 | 1-trans-tri-n-butylstannyl-4-phenoxy 3-triethylsilyloxy-1-butene | 2-[6-phenoxyacetyl hexyl]-4R-trimethylsiloxy cyclopent-2-en-1-one | nat-11a,15a-dihydroxy-1-phenoxymethyl-1,9-dioxo-16-phenoxy-17-20-tetranor-13-trans prostene |
| 267 | 1-trans-tri-n-butylstannyl-4-(p-fluorophenoxy) 3-triethylsilyloxy-1-butene | 2-[6-phenoxyacetyl hexyl]-4R-trimethylsiloxy cyclopent-2-en-1-one | nat-11a,15a-dihydroxy-1-phenoxymethyl-1,9-dioxo-16-(p-fluorophenoxy)-17-20-tetranor-13-trans prostene |
| 268 | 1-trans-tri-n-butylstannyl-4-(m-chlorophenoxy) 3-triethylsilyloxy-1-butene | 2-[6-phenoxyacetyl hexyl]-4R-trimethylsiloxy cyclopent-2-en-1-one | nat-11a,15a-dihydroxy-1-phenoxymethyl-1,9-dioxo-16-(m-chlorophenoxy)-17-20-tetranor-13-trans prostene |
| 269 | 1-trans-tri-n-butylstannyl-4-(m-trifluoromethylphenoxy) 3-triethylsilyloxy-1-butene | 2-[6-phenoxyacetyl hexyl]-4R-trimethylsiloxy cyclopent-2-en-1-one | nat-11a,15a-dihydroxy-1-phenoxymethyl-1,9-dioxo-16-(m-trifluoromethylphenoxy)-17-20-tetranor-13-trans prostene |
| EXAMPLE | VINYL IODIDE | CYCLOPENTENONE | PRODUCT PROSTAGLANDIN OF THE PGE1 SERIES |
| 270 | 1-trans-iodo-5-phenyl 3-triethylsilyloxy-1-pentene | 2-[6-phenoxyacetyl hexyl]-4R-trimethylsiloxy cyclopent-2-en-1-one | nat-11a,15a-dihydroxy-1-phenoxymethyl-1,9-dioxo-17-phenyl-18-20-trinor-13-trans prostene |
| 271 | 1-trans-iodo-4,4-dimethyl-5-phenyl 3-triethylsilyloxy-1-pentene | 2-[6-phenoxyacetyl hexyl]-4R-trimethylsiloxy cyclopent-2-en-1-one | nat-11a,15a-dihydroxy-1-phenoxymethyl-1,9-dioxo-16,16-dimethyl-17-phenyl-18-20-trinor-13-trans prostene |
| 272 | 1-trans-iodo-4-cyclopentyl 3-triphenylmethoxy-1-butene | 2-[6-phenoxyacetyl hexyl]-4R-trimethylsiloxy cyclopent-2-en-1-one | nat-11a,15a-dihydroxy-1-phenoxymethyl-1,9-dioxo-16-cyclopentyl-17-20-tetranor-13-trans prostene |
| 273 | 1-trans-iodo-4-cyclohexyl 3-triphenylmethoxy-1-butene | 2-[6-phenoxyacetyl hexyl]-4R-trimethylsiloxy cyclopent-2-en-1-one | nat-11a,15a-dihydroxy-1-phenoxymethyl-1,9-dioxo-16-cyclohexyl-17-20-tetranor-13-trans prostene |
| 274 | 1-trans-iodo-4-triphenylmethoxy-1-heptene | 2[6-phenoxy hexyl]-4R-trimethylsiloxy cyclopent-2-en-1-one | nat-11a,15a-dihydroxy-1-phenoxymethyl-1,9-dioxo-20-nor-13-trans prostene |
| EXAMPLE | VINYL TIN | CYCLOPENTENONE | PRODUCT PROSTAGLANDIN OF THE PGE1 SERIES |
| 275 | 1-trans-tri-n-butylstannyl-4-methyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-20-nor-13-trans prostene |
| 276 | 1-trans-tri-n-butylstannyl-4-ethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-ethyl-13-trans prostene |
| 277 | 1-trans-tri-n-butylstannyl-5-methyl 4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-17-methyl-20-nor-13-trans prostene |
| EXAMPLE | VINYL IODIDE | CYCLOPENTENONE | PRODUCT PROSTAGLANDIN OF THE PGE1 SERIES |
| 278 | 1-trans-iodo-5,5-dimethyl 4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-17,17-dimethyl-13-trans prostene |
| EXAMPLE | VINYL TIN | CYCLOPENTENONE | PRODUCT PROSTAGLANDIN OF THE PGE1 SERIES |

TABLE VIII-continued

| | | | |
|---|---|---|---|
| 279 | 1-trans-tri-n-butylstannyl-4-vinyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-vinyl-20-nor-13-trans prostene |
| 280 | 1-trans-tri-n-butylstannyl-4-cyclopropyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-cyclopropyl-13-trans prostene |
| 281 | 1-trans-tri-n-butylstannyl-4-trimethylsilylethynyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-ethynyl-20-nor-13-trans prostene |
| 282 | 1-trans-tri-n-butylstannyl-5-methylene-4-triethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-17-methylene-20-nor-13-trans prostene |
| 283 | 1-trans-tri-n-butylstannyl-4-methyl-5-methylene-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-17-methylene-20-nor-13-trans prostene |
| 284 | 1-trans-tri-n-butylstannyl-4-dimethoxymethyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-formyl-20-nor-13-trans prostene |
| 285 | 1-trans-tri-n-butylstannyl-4-fluoromethyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-fluoromethyl-20-nor-13-trans prostene |
| 286 | 1-trans-tri-n-butylstannyl-4-difluoromethyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-difluoromethyl-20-nor-13-trans prostene |
| 287 | 1-trans-tri-n-butylstannyl-4-trifluoromethyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-trifluoromethyl-20-nor-13-trans prostene |
| 288 | 1-trans-tri-n-butylstannyl-4-chloromethyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-chloromethyl-20-nor-13-trans prostene |
| 289 | 1-trans-tri-n-butylstannyl-4-trimethylsilyloxymethyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-hydroxymethyl-20-nor-13-trans prostene |
| EXAMPLE | VINYL IODIDE | CYCLOPENTENONE | PRODUCT PROSTAGLANDIN OF THE PGE1 SERIES |
| 290 | 1-trans-iodo-4-methyl-7-chloro 4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-19-chloro-20-nor-13-trans prostene |
| 291 | 1-trans-iodo-3-triphenylmethoxy-1-octene | 2-[6-phenoxyacetyl hexyl]-4R-trimethylsiloxy cyclopent-2-en-1-one | nat-11a,15a-dihydroxy-1-phenoxymethyl-1,9-dioxo-13-trans prostene |
| 292 | 1-trans-iodo-3-methyl-3-trimethylsilyloxy-1-octene | 2-[6-phenoxyacetyl hexyl]-4R-trimethylsiloxy cyclopent-2-en-1-one | nat-11a,15a-dihydroxy-1-phenoxymethyl-1,9-dioxo-15-methyl-13-trans prostene |
| 293 | 1-trans-iodo-4,4-dimethyl-3-trimethylsilyloxy-1-octene | 2-[6-phenoxyacetyl hexyl]-4R-trimethylsiloxy cyclopent-2-en-1-one | nat-11a,15a-dihydroxy-1-phenoxymethyl-1,9-dioxo-16,16-dimethyl-13-trans prostene |
| 294 | 1-trans-iodo-4,4-trimethylene-3-trimethylsilyloxy-1-octene | 2-[6-phenoxyacetyl hexyl]-4R-trimethylsiloxy cyclopent-2-en-1-one | nat-11a,15a-dihydroxy-1-phenoxymethyl-1,9-dioxo-16,16-trimethylene-13-trans prostene |
| EXAMPLE | VINYL TIN | CYCLOPENTENONE | PRODUCT PROSTAGLANDIN OF THE PGE1 SERIES |
| 295 | 1-trans-tri-n-butylstannyl-3-vinyl- | 2-[6-phenoxyacetyl | nat-11a,15a-dihydroxy-1-phenoxymethyl-1,9-dioxo-15-vinyl- |

TABLE VIII-continued

| EXAMPLE | VINYL IODIDE | CYCLOPENTENONE | PRODUCT PROSTAGLANDIN OF THE PGE1 SERIES |
|---|---|---|---|
| 296 | 1-trans-iodo-4-triphenylmethoxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-13-trans prostene |

| EXAMPLE | VINYL TIN | CYCLOPENTENONE | PRODUCT PROSTAGLANDIN OF THE PGE1 SERIES |
|---|---|---|---|
| 297 | 1-trans-tri-n-butylstannyl-4-methyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-13-trans prostene |
| 298 | 1-trans-tri-n-butylstannyl-5-methyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-17-methyl-13-trans prostene |
| 299 | 1-trans-tri-n-butylstannyl-4-vinyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-vinyl-13-trans prostene |
| 300 | 1-trans-tri-n-butylstannyl-4-trimethylsilylethynyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-ethynyl-13-trans prostene |
| 301 | 1-trans-tri-n-butylstannyl-5-methylene-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-17-methylene-13-trans prostene |
| 302 | 1-trans-tri-n-butylstannyl-4-methyl-5-methylene-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-17-methylene-13-trans prostene |
| 303 | 1-trans-tri-n-butylstannyl-4-dimethoxymethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-formyl-13-trans prostene |
| 304 | 1-trans-tri-n-butylstannyl-4-fluoromethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-fluoromethyl-13-trans prostene |
| 305 | 1-trans-tri-n-butylstannyl-4-difluoromethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-difluoromethyl-13-trans prostene |
| 306 | 1-trans-tri-n-butylstannyl-4-trifluoromethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-trifluoromethyl-13-trans prostene |
| 307 | 1-trans-tri-n-butylstannyl-4-chloromethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-chloromethyl-13-trans prostene |
| 308 | 1-trans-tri-n-butylstannyl-4-trimethylsilyloxymethyl-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-hydroxymethyl-13-trans prostene |

| EXAMPLE | VINYL IODIDE | CYCLOPENTENONE | PRODUCT PROSTAGLANDIN OF THE PGE1 SERIES |
|---|---|---|---|
| 309 | 1-trans-iodo-3-triphenylmethoxy-1-nonene | 2-[6-phenoxyacetyl hexyl]-4R-trimethylsiloxy cyclopent-2-en-1-one | nat-11a,15a-dihydroxy-1-phenoxymethyl-1,9-dioxo-20-methyl-13-trans prostene |
| 310 | 1-trans-iodo-3-methyl-3-trimethylsilyloxy-1-nonene | 2-[6-phenoxyacetyl hexyl]-4R-trimethylsiloxy cyclopent-2-en-1-one | nat-11a,15a-dihydroxy-1-phenoxymethyl-1,9-dioxo-20-methyl-13-trans prostene |

TABLE VIII-continued

| EXAMPLE | | | PRODUCT |
|---|---|---|---|
| 311 | 1-trans-iodo-4,4-dimethyl-3-trimethylsilyloxy-1-nonene | 2-[6-phenoxyacetyl hexyl]-4R-trimethylsilyloxy cyclopent-2-en-1-one | nat-11a,15a-dihydroxy-1-phenoxymethyl-1,9-dioxo-16,16-dimethyl-20-methyl-13-trans prostene |
| 312 | 1-trans-iodo-4,4-trimethylene-3-trimethylsilyloxy-1-nonene | 2-[6-phenoxyacetyl hexyl]-4R-trimethylsilyloxy cyclopent-2-en-1-one | nat-11a,15a-dihydroxy-1-phenoxymethyl-1,9-dioxo-16,16-trimethylene-20-methyl-13-trans prostene |

| EXAMPLE | VINYL TIN | CYCLOPENTENONE | PRODUCT PROSTAGLANDIN OF THE PGE1 SERIES |
|---|---|---|---|
| 313 | 1-trans-tri-n-butylstannyl-3-vinyl-3-trimethylsilyloxy-1-nonene | 2-[6-phenoxyacetyl hexyl]-4R-trimethylsilyloxy cyclopent-2-en-1-one | nat-11a,15a-dihydroxy-1-phenoxymethyl-1,9-dioxo-15-vinyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 314 | 1-trans-iodo-3-triphenylmethoxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-20-methyl-13-trans prostene |

| EXAMPLE | VINYL TIN | CYCLOPENTENONE | PRODUCT PROSTAGLANDIN OF THE PGE1 SERIES |
|---|---|---|---|
| 315 | 1-trans-tri-n-butylstannyl-4-methyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-methyl-20-methyl-13-trans prostene |
| 316 | 1-trans-tri-n-butylstannyl-5-methyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-17-methyl-20-methyl-13-trans prostene |
| 317 | 1-trans-tri-n-butylstannyl-4-vinyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-vinyl-20-methyl-13-trans prostene |
| 318 | 1-trans-tri-n-butylstannyl-4-trimethylsilylethynyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-ethynyl-20-methyl-13-trans prostene |
| 319 | 1-trans-tri-n-butylstannyl-5-methylene-4-triethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-17-methylene-20-methyl-13-trans prostene |
| 320 | 1-trans-tri-n-butylstannyl-4-methyl-5-methylene-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-methyl-17-methylene-20-methyl-13-trans prostene |
| 321 | 1-trans-tri-n-butylstannyl-4-dimethoxymethyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-formyl-20-methyl-13-trans prostene |
| 322 | 1-trans-tri-n-butylstannyl-4-fluoromethyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-fluoromethyl-20-methyl-13-trans prostene |
| 323 | 1-trans-tri-n-butylstannyl-4-difluoromethyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-difluoromethyl-20-methyl-13-trans prostene |
| 324 | 1-trans-tri-n-butylstannyl-4-trifluoromethyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-trifluoromethyl-20-methyl-13-trans prostene |
| 325 | 1-trans-tri-n-butylstannyl-4-chloromethyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-chloromethyl-20-methyl-13-trans prostene |
| 326 | 1-trans-tri-n-butylstannyl-4-trimethylsilyloxymethyl-4-trimethylsilyloxy-1-nonene | 2-[6-phenoxyacetyl hexyl]-4R-trimethylsilyloxy cyclopent-2-en-1-one | nat-11a,16-dihydroxy-1-phenoxymethyl-1,9-dioxo-16-hydroxymethyl-20-methyl-13-trans prostene |

TABLE VIII-continued

| EXAMPLE | VINYL IODIDE | CYCLOPENTENONE | PRODUCT PROSTAGLANDIN OF THE PGE1 SERIES |
|---|---|---|---|
| 327 | 1-trans-iodo-3-triphenylmethoxy-1-decene | 2-[6-phenoxyacetyl hexyl]-4R-trimethylsiloxy cyclopent-2-en-1-one | nat-11a,15a-dihydroxy-1-phenoxymethyl-1,9-dioxo-20-ethyl-13-trans prostene |
| 328 | 1-trans-iodo-3-methyl-3-trimethylsilyloxy-1-decene | 2-[6-phenoxyacetyl hexyl]-4R-trimethylsiloxy cyclopent-2-en-1-one | nat-11a,15a-dihydroxy-1-phenoxymethyl-1,9-dioxo-15-methyl-20-ethyl-13-trans prostene |
| 329 | 1-trans-iodo-4,4-dimethyl 3-trimethylsilyloxy-1-decene | 2-[6-phenoxyacetyl hexyl]-4R-trimethylsiloxy cyclopent-2-en-1-one | nat-11a,15a-dihydroxy-1-phenoxymethyl-1,9-dioxo-16,16-dimethyl-20-ethyl-13-trans prostene |
| 330 | 1-trans-iodo-4,4-trimethylene 3-trimethylsilyloxy-1-decene | 2-[6-phenoxyacetyl hexyl]-4R-trimethylsiloxy cyclopent-2-en-1-one | nat-11a,15a-dihydroxy-1-phenoxymethyl-1,9-dioxo-16,16-trimethylene-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 331 | 1-trans-tri-n-butylstannyl-3-vinyl-3-trimethylsilyloxy-1-decene | 2-[6-phenoxyacetyl hexyl]-4R-trimethylsiloxy cyclopent-2-en-1-one | nat-11a,15a-dihydroxy-1-phenoxymethyl-1,9-dioxo-15-vinyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 332 | 1-trans-iodo-4-triphenylmethoxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 333 | 1-trans-tri-n-butylstannyl-4-methyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-20-ethyl-13-trans prostene |
| 334 | 1-trans-tri-n-butylstannyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-17-methyl-20-ethyl-13-trans prostene |
| 335 | 1-trans-tri-n-butylstannyl-4-vinyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-vinyl-20-ethyl-13-trans prostene |
| 336 | 1-trans-tri-n-butylstannyl-4-trimethylsilylethynyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-ethynyl-20-ethyl-13-trans prostene |
| 337 | 1-trans-tri-n-butylstannyl-5-methylene-4-triethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-17-methylene-20-ethyl-13-trans prostene |
| 338 | 1-trans-tri-n-butylstannyl-4-methyl-5-methylene-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-17-methylene-20-ethyl-13-trans prostene |
| 339 | 1-trans-tri-n-butylstannyl-4-dimethoxymethyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-formyl-20-ethyl-13-trans prostene |
| 340 | 1-trans-tri-n-butylstannyl-4-fluoromethyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-fluoromethyl-20-ethyl-13-trans prostene |
| 341 | 1-trans-tri-n-butylstannyl-4-difluoromethyl-4-trimethylsilyloxy-1-decene | 2-[6-phenoxyacetyl hexyl]-4R-trimethylsiloxy cyclopent-2-en-1-one | nat-11a,16-dihydroxy-1-phenoxymethyl-1,9-dioxo-16-difluoromethyl-20-ethyl-13-trans prostene |

TABLE VIII-continued

| | | | |
|---|---|---|---|
| 342 | 1-trans-tri-n-butylstannyl-4-trifluoromethyl-4-trimethylsilyloxy-1-decene | cyclopent-2-en-1-one 2-[6-phenoxyacetyl hexyl]-4R-trimethylsilyloxy cyclopent-2-en-1-one | nat-11a,16-dihydroxy-1-phenoxymethyl-1,9-dioxo-16-trifluoromethyl-20-ethyl-13-trans prostene |
| 343 | 1-trans-tri-n-butylstannyl-4-chloromethyl-4-trimethylsilyloxy-1-decene | 2-[6-phenoxyacetyl hexyl]-4R-trimethylsilyloxy cyclopent-2-en-1-one | nat-11a,16-dihydroxy-1-phenoxymethyl-1,9-dioxo-16-chloromethyl-20-ethyl-13-trans prostene |
| 344 | 1-trans-tri-n-butylstannyl-4-trimethylsilyloxymethyl-4-trimethylsilyloxy-1-decene | 2-[6-phenoxyacetyl hexyl]-4R-trimethylsilyloxy cyclopent-2-en-1-one | nat-11a,16-dihydroxy-1-phenoxymethyl-1,9-dioxo-16-hydroxymethyl-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 345 | 1-trans-iodo-3-triphenylmethoxy-1-heptene | 2-[5-phenoxyacetyl pentyl] cyclopent-2-en-1-one | dl-15a-hydroxy-1-phenoxymethyl-1,9-dioxo-20-nor-2-nor-13-trans prostene |
| 346 | 1-trans-iodo-3-methyl-3-trimethylsilyloxy-1-heptene | 2-[5-phenoxyacetyl pentyl] cyclopent-2-en-1-one | dl-15a-hydroxy-1-phenoxymethyl-1,9-dioxo-15-methyl-20-nor-2-nor-13-trans prostene |
| 347 | 1-trans-iodo-4,4-dimethyl-3-trimethylsilyloxy-1-heptene | 2-[5-phenoxyacetyl pentyl] cyclopent-2-en-1-one | dl-15a-hydroxy-1-phenoxymethyl-1,9-dioxo-16,16-dimethyl-20-nor-2-nor-13-trans prostene |
| 348 | 1-trans-iodo-5,5-dimethyl-3-triphenylmethoxy-1-octene | 2-[5-phenoxyacetyl pentyl] cyclopent-2-en-1-one | dl-15a-hydroxy-1-phenoxymethyl-1,9-dioxo-17,17-dimethyl-2-nor-13-trans prostene |
| 349 | 1-trans-iodo-4-methyl-3-triphenylmethoxy-1-octene | 2-[5-phenoxyacetyl pentyl] cyclopent-2-en-1-one | dl-15a-hydroxy-1-phenoxymethyl-1,9-dioxo-16-methyl-2-nor-13-trans prostene |
| 350 | 1-trans-iodo-4,4-trimethylene-3-trimethylsilyloxy-1-heptene | 2-[5-phenoxyacetyl pentyl] cyclopent-2-en-1-one | dl-15a-hydroxy-1-phenoxymethyl-1,9-dioxo-16,16-trimethylene-20-nor-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 351 | 1-trans-tri-n-butylstannyl-3-vinyl-3-trimethylsilyloxy-1-heptene | 2-[5-phenoxyacetyl pentyl] cyclopent-2-en-1-one | dl-15a-hydroxy-1-phenoxymethyl-1,9-dioxo-15-vinyl-20-nor-2-nor-13-trans prostene |
| 352 | 1-trans-tri-n-butylstannyl-4-phenoxy-3-triethylsilyloxy-1-butene | 2-[5-phenoxyacetyl pentyl] cyclopent-2-en-1-one | dl-15a-hydroxy-1-phenoxymethyl-1,9-dioxo-16-phenoxy-2-nor-17-20-tetranor-13-trans prostene |
| 353 | 1-trans-tri-n-butylstannyl-4-(p-fluorophenoxy)-3-triethylsilyloxy-1-butene | 2-[5-phenoxyacetyl pentyl] cyclopent-2-en-1-one | dl-15a-hydroxy-1-phenoxymethyl-1,9-dioxo-16-(p-fluorophenoxy)-2-nor-17-20-tetranor-13-trans prostene |
| 354 | 1-trans-tri-n-butylstannyl-4-(m-chlorophenoxy)-3-triethylsilyloxy-1-butene | 2-[5-phenoxyacetyl pentyl] cyclopent-2-en-1-one | dl-15a-hydroxy-1-phenoxymethyl-1,9-dioxo-16-(m-chlorophenoxy)-2-nor-17-20-tetranor-13-trans prostene |
| 355 | 1-trans-tri-n-butylstannyl-4-(m-trifluoromethylphenoxy)-3-triethylsilyloxy-1-butene | 2-[5-phenoxyacetyl pentyl] cyclopent-2-en-1-one | dl-15a-hydroxy-1-phenoxymethyl-1,9-dioxo-16-(m-trifluoromethylphenoxy)-2-nor-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 356 | 1-trans-iodo-5-phenyl-3-triethylsilyloxy-1-pentene | 2-[5-phenoxyacetyl pentyl] cyclopent-2-en-1-one | dl-15a-hydroxy-1-phenoxymethyl-1,9-dioxo-17-phenyl-2-nor-18-20-trinor-13-trans prostene |
| 357 | 1-trans-iodo-4,4-dimethyl-5-phenyl | 2-[5-phenoxyacetyl pentyl] cyclopent-2-en-1-one | dl-15a-hydroxy-1-phenoxymethyl-1,9-dioxo- |

TABLE VIII-continued

| | | | |
|---|---|---|---|
| | 3-triethylsilyloxy-1-pentene | pentyl]cyclopent-2-en-1-one | 16,16-dimethyl-17-phenyl-2-nor-18-20-trinor-13-trans prostene |
| 358 | 1-trans-iodo-4-cyclopentyl-3-triphenylmethoxy-1-butene | 2-[5-phenoxyacetyl pentyl]cyclopent-2-en-1-one | dl-15a-hydroxy-1-phenoxymethyl-1,9-dioxo-16-cyclopentyl-2-nor-17-20-tetranor-13-trans prostene |
| 359 | 1-trans-iodo-4-cyclohexyl-3-triphenylmethoxy-1-butene | 2-[5-phenoxyacetyl pentyl]cyclopent-2-en-1-one | dl-15a-hydroxy-1-phenoxymethyl-1,9-dioxo-16-cyclohexyl-2-nor-17-20-tetranor-13-trans prostene |
| 360 | 1-trans-iodo-4-triphenylmethoxy-1-heptene | 2-[5-phenoxyacetyl pentyl]cyclopent-2-en-1-one | dl-16-hydroxy-1-phenoxymethyl-1,9-dioxo-20-nor-2-nor-13-trans prostene |
| EXAMPLE | VINYL TIN | CYCLOPENTENONE | PRODUCT PROSTAGLANDIN OF THE 11-DEOXY PGE1 SERIES |
| 361 | 1-trans-tri-n-butylstannyl-4-methyl-4-trimethylsilyloxy-1-heptene | 2-[5-phenoxyacetyl pentyl]cyclopent-2-en-1-one | dl-16-hydroxy-1-phenoxymethyl-1,9-dioxo-16-methyl-20-nor-2-nor-13-trans prostene |
| 362 | 1-trans-tri-n-butylstannyl-4-ethyl-4-trimethylsilyloxy-1-octene | 2-[5-phenoxyacetyl pentyl]cyclopent-2-en-1-one | dl-16-hydroxy-1-phenoxymethyl-1,9-dioxo-16-ethyl-2-nor-13-trans prostene |
| 363 | 1-trans-tri-n-butylstannyl-5-methyl-4-trimethylsilyloxy-1-heptene | 2-[5-phenoxyacetyl pentyl]cyclopent-2-en-1-one | dl-16-hydroxy-1-phenoxymethyl-1,9-dioxo-17-methyl-20-nor-2-nor-13-trans prostene |
| EXAMPLE | VINYL IODIDE | CYCLOPENTENONE | PRODUCT PROSTAGLANDIN OF THE 11-DEOXY PGE1 SERIES |
| 364 | 1-trans-iodo-5,5-dimethyl-4-trimethylsilyloxy-1-octene | 2-[5-phenoxyacetyl pentyl]cyclopent-2-en-1-one | dl-16-hydroxy-1-phenoxymethyl-1,9-dioxo-17,17-dimethyl-2-nor-13-trans prostene |
| EXAMPLE | VINYL TIN | CYCLOPENTENONE | PRODUCT PROSTAGLANDIN OF THE 11-DEOXY PGE1 SERIES |
| 365 | 1-trans-tri-n-butylstannyl-4-vinyl-4-trimethylsilyloxy-1-heptene | 2-[5-phenoxyacetyl pentyl]cyclopent-2-en-1-one | dl-16-hydroxy-1-phenoxymethyl-1,9-dioxo-16-vinyl-20-nor-2-nor-13-trans prostene |
| 366 | 1-trans-tri-n-butylstannyl-4-cyclopropyl-4-trimethylsilyloxy-1-octene | 2-[5-phenoxyacetyl pentyl]cyclopent-2-en-1-one | dl-16-hydroxy-1-phenoxymethyl-1,9-dioxo-16-cyclopropyl-2-nor-13-trans prostene |
| 367 | 1-trans-tri-n-butylstannyl-4-trimethylsilylethynyl-4-trimethylsilyloxy-1-heptene | 2-[5-phenoxyacetyl pentyl]cyclopent-2-en-1-one | dl-16-hydroxy-1-phenoxymethyl-1,9-dioxo-16-ethynyl-20-nor-2-nor-13-trans prostene |
| 368 | 1-trans-tri-n-butylstannyl-5-methylene-4-triethylsilyloxy-1-heptene | 2-[5-phenoxyacetyl pentyl]cyclopent-2-en-1-one | dl-16-hydroxy-1-phenoxymethyl-1,9-dioxo-17-methylene-20-nor-2-nor-13-trans prostene |
| 369 | 1-trans-tri-n-butylstannyl-4-methyl-5-methylene-4-trimethylsilyloxy-1-heptene | 2-[5-phenoxyacetyl pentyl]cyclopent-2-en-1-one | dl-16-hydroxy-1-phenoxymethyl-1,9-dioxo-16-methyl-17-methylene-20-nor-2-nor-13-trans prostene |
| 370 | 1-trans-tri-n-butylstannyl-4-dimethoxymethyl-4-trimethylsilyloxy-1-heptene | 2-[5-phenoxyacetyl pentyl]cyclopent-2-en-1-one | dl-16-hydroxy-1-phenoxymethyl-1,9-dioxo-16-formyl-20-nor-2-nor-13-trans prostene |
| 371 | 1-trans-tri-n-butylstannyl-4-fluoromethyl-4-trimethylsilyloxy-1-heptene | 2-[5-phenoxyacetyl pentyl]cyclopent-2-en-1-one | dl-16-hydroxy-1-phenoxymethyl-1,9-dioxo-16-fluoromethyl-20-nor-2-nor-13-trans prostene |
| 372 | 1-trans-tri-n-butylstannyl-4-difluoromethyl-4-trimethylsilyloxy-1-heptene | 2-[5-phenoxyacetyl pentyl]cyclopent-2-en-1-one | dl-16-hydroxy-1-phenoxymethyl-1,9-dioxo-16-difluoromethyl-20-nor-2-nor-13-trans prostene |

| EXAMPLE | | | |
|---|---|---|---|
| 373 | 1-trans-tri-n-butylstannyl-4-trifluoromethyl-4-trimethylsilyloxy-1-heptene | 2-[5-phenoxyacetyl pentyl] cyclopent-2-en-1-one | dl-16-hydroxy-1-phenoxymethyl-1,9-dioxo-16-trifluoromethyl-20-nor-2-nor-13-trans prostene |
| 374 | 1-trans-tri-n-butylstannyl-4-chloromethyl-4-trimethylsilyloxy-1-heptene | 2-[5-phenoxyacetyl pentyl] cyclopent-2-en-1-one | dl-16-hydroxy-1-phenoxymethyl-1,9-dioxo-16-chloromethyl-20-nor-2-nor-13-trans prostene |
| 375 | 1-trans-tri-n-butylstannyl-4-trimethylsilyloxymethyl-4-trimethylsilyloxy-1-heptene | 2-[5-phenoxyacetyl pentyl] cyclopent-2-en-1-one | dl-16-hydroxy-1-phenoxymethyl-1,9-dioxo-16-hydroxymethyl-20-nor-2-nor-13-trans prostene |
| EXAMPLE | VINYL IODIDE | CYCLOPENTENONE | PRODUCT PROSTAGLANDIN OF THE 11-DEOXY PGE1 SERIES |
| 376 | 1-trans-iodo-4-methyl-7-chloro-4-trimethylsilyloxy-1-heptene | 2-[5-phenoxyacetyl pentyl] cyclopent-2-en-1-one | dl-16-hydroxy-1-phenoxymethyl-1,9-dioxo-16-methyl-19-chloro-2-nor-20-nor-13-trans prostene |
| 377 | 1-trans-iodo-3-triphenylmethoxy-1-octene | 2-[5-phenoxyacetyl pentyl] cyclopent-2-en-1-one | dl-15a-hydroxy-1-phenoxymethyl-1,9-dioxo-2-nor-13-trans prostene |
| 378 | 1-trans-iodo-3-methyl-3-trimethylsilyloxy-1-octene | 2-[5-phenoxyacetyl pentyl] cyclopent-2-en-1-one | dl-15a-hydroxy-1-phenoxymethyl-1,9-dioxo-15-methyl-2-nor-13-trans prostene |
| 379 | 1-trans-iodo-4,4-dimethyl-3-trimethylsilyloxy-1-octene | 2-[5-phenoxyacetyl pentyl] cyclopent-2-en-1-one | dl-15a-hydroxy-1-phenoxymethyl-1,9-dioxo-16,16-dimethyl-2-nor-13-trans prostene |
| 380 | 1-trans-iodo-4,4-trimethylene-3-trimethylsilyloxy-1-octene | 2-[5-phenoxyacetyl pentyl] cyclopent-2-en-1-one | dl-15a-hydroxy-1-phenoxymethyl-1,9-dioxo-16,16-trimethylene-2-nor-13-trans prostene |
| EXAMPLE | VINYL TIN | CYCLOPENTENONE | PRODUCT PROSTAGLANDIN OF THE 11-DEOXY PGE1 SERIES |
| 381 | 1-trans-tri-n-butylstannyl-3-vinyl-3-trimethylsilyloxy-1-octene | 2-[5-phenoxyacetyl pentyl] cyclopent-2-en-1-one | dl-15a-hydroxy-1-phenoxymethyl-1,9-dioxo-15-vinyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 382 | 1-trans-iodo-4-triphenylmethoxy-1-octene | 2-[5-phenoxyacetyl pentyl] cyclopent-2-en-1-one | dl-16-hydroxy-1-phenoxymethyl-1,9-dioxo-2-nor-13-trans prostene |
| EXAMPLE | VINYL TIN | CYCLOPENTENONE | PRODUCT PROSTAGLANDIN OF THE 11-DEOXY PGE1 SERIES |
| 383 | 1-trans-tri-n-butylstannyl-4-methyl-4-trimethylsilyloxy-1-octene | 2-[5-phenoxyacetyl pentyl] cyclopent-2-en-1-one | dl-16-hydroxy-1-phenoxymethyl-1,9-dioxo-16-methyl-2-nor-13-trans prostene |
| 384 | 1-trans-tri-n-butylstannyl-5-methyl-4-trimethylsilyloxy-1-octene | 2-[5-phenoxyacetyl pentyl] cyclopent-2-en-1-one | dl-16-hydroxy-1-phenoxymethyl-1,9-dioxo-17-methyl-2-nor-13-trans prostene |
| 385 | 1-trans-tri-n-butylstannyl-4-vinyl-4-trimethylsilyloxy-1-octene | 2-[5-phenoxyacetyl pentyl] cyclopent-2-en-1-one | dl-16-hydroxy-1-phenoxymethyl-1,9-dioxo-16-vinyl-2-nor-13-trans prostene |
| 386 | 1-trans-tri-n-butylstannyl-4-trimethylsilylethynyl-4-trimethylsilyloxy-1-octene | 2-[5-phenoxyacetyl pentyl] cyclopent-2-en-1-one | dl-16-hydroxy-1-phenoxymethyl-1,9-dioxo-16-ethynyl-2-nor-13-trans prostene |
| 387 | 1-trans-tri-n-butylstannyl-5-methylene-4-triethylsilyloxy-1-octene | 2-[5-phenoxyacetyl pentyl] cyclopent-2-en-1-one | dl-16-hydroxy-1-phenoxymethyl-1,9-dioxo-17-methylene-2-nor-13-trans prostene |

TABLE VIII-continued

| | | | |
|---|---|---|---|
| 388 | 1-trans-tri-n-butylstannyl-4-methyl-5-methylene-4-trimethylsilyloxy-1-octene | 2-[5-phenoxyacetyl pentyl] cyclopent-2-en-1-one | dl-16-hydroxy-1-phenoxymethyl-1,9-dioxo-16-methyl-17-methylene-2-nor-13-trans prostene |
| 389 | 1-trans-tri-n-butylstannyl-4-dimethoxymethyl-4-trimethylsilyloxy-1-octene | 2-[5-phenoxyacetyl pentyl] cyclopent-2-en-1-one | dl-16-hydroxy-1-phenoxymethyl-1,9-dioxo-16-formyl-2-nor-13-trans prostene |
| 390 | 1-trans-tri-n-butylstannyl-4-fluoromethyl-4-trimethylsilyloxy-1-octene | 2-[5-phenoxyacetyl pentyl] cyclopent-2-en-1-one | dl-16-hydroxy-1-phenoxymethyl-1,9-dioxo-16-fluoromethyl-2-nor-13-trans prostene |
| 391 | 1-trans-tri-n-butylstannyl-4-difluoromethyl-4-trimethylsilyloxy-1-octene | 2-[5-phenoxyacetyl pentyl] cyclopent-2-en-1-one | dl-16-hydroxy-1-phenoxymethyl-1,9-dioxo-16-difluoromethyl-2-nor-13-trans prostene |
| 392 | 1-trans-tri-n-butylstannyl-4-trifluoromethyl-4-trimethylsilyloxy-1-octene | 2-[5-phenoxyacetyl pentyl] cyclopent-2-en-1-one | dl-16-hydroxy-1-phenoxymethyl-1,9-dioxo-16-trifluoromethyl-2-nor-13-trans prostene |
| 393 | 1-trans-tri-n-butylstannyl-4-chloromethyl-4-trimethylsilyloxy-1-octene | 2-[5-phenoxyacetyl pentyl] cyclopent-2-en-1-one | dl-16-hydroxy-1-phenoxymethyl-1,9-dioxo-16-chloromethyl-2-nor-13-trans prostene |
| 394 | 1-trans-tri-n-butylstannyl-4-trimethylsilyloxymethyl-4-trimethylsilyloxy-1-octene | 2-[5-phenoxyacetyl pentyl] cyclopent-2-en-1-one | dl-16-hydroxy-1-phenoxymethyl-1,9-dioxo-16-hydroxymethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 395 | 1-trans-iodo-3-triphenylmethoxy-1-nonene | 2-[5-phenoxyacetyl pentyl] cyclopent-2-en-1-one | dl-15a-hydroxy-1-phenoxymethyl-1,9-dioxo-20-methyl-2-nor-13-trans prostene |
| 396 | 1-trans-iodo-3-methyl-3-trimethylsilyloxy-1-nonene | 2-[5-phenoxyacetyl pentyl] cyclopent-2-en-1-one | dl-15a-hydroxy-1-phenoxymethyl-1,9-dioxo-15-methyl-20-methyl-2-nor-13-trans prostene |
| 397 | 1-trans-iodo-4,4-dimethyl-3-trimethylsilyloxy-1-nonene | 2-[5-phenoxyacetyl pentyl] cyclopent-2-en-1-one | dl-15a-hydroxy-1-phenoxymethyl-1,9-dioxo-16,16-dimethyl-20-methyl-2-nor-13-trans prostene |
| 398 | 1-trans-iodo-4,4-trimethylene-3-trimethylsilyloxy-1-nonene | 2-[5-phenoxyacetyl pentyl] cyclopent-2-en-1-one | dl-15a-hydroxy-1-phenoxymethyl-1,9-dioxo-16,16-trimethylene-20-methyl-2-nor-13-trans prostene |
| EXAMPLE | VINYL TIN | CYCLOPENTENONE | PRODUCT PROSTAGLANDIN OF THE 11-DEOXY PGE1 SERIES |
| 399 | 1-trans-tri-n-butylstannyl-3-vinyl-3-trimethylsilyloxy-1-nonene | 2-[5-phenoxyacetyl pentyl] cyclopent-2-en-1-one | dl-15a-hydroxy-1-phenoxymethyl-1,9-dioxo-15-vinyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 400 | 1-trans-iodo-4-triphenylmethoxy-1-nonene | 2-[5-phenoxyacetyl pentyl] cyclopent-2-en-1-one | dl-16-hydroxy-1-phenoxymethyl-1,9-dioxo-20-methyl-2-nor-13-trans prostene |
| EXAMPLE | VINYL TIN | CYCLOPENTENONE | PRODUCT PROSTAGLANDIN OF THE 11-DEOXY PGE1 SERIES |
| 401 | 1-trans-tri-n-butylstannyl-4-methyl-4-trimethylsilyloxy-1-nonene | 2-[5-phenoxyacetyl pentyl] cyclopent-2-en-1-one | dl-16-hydroxy-1-phenoxymethyl-1,9-dioxo-16-methyl-20-methyl-2-nor-13-trans prostene |
| 402 | 1-trans-tri-n-butylstannyl-5-methyl-4-trimethylsilyloxy-1-nonene | 2-[5-phenoxyacetyl pentyl] cyclopent-2-en-1-one | dl-16-hydroxy-1-phenoxymethyl-1,9-dioxo-17-methyl-20-methyl-2-nor-13-trans prostene |

TABLE VIII-continued

| | | | |
|---|---|---|---|
| 403 | 1-trans-tri-n-butylstannyl-4-vinyl-4-trimethylsilyloxy-1-nonene | 2-[5-phenoxyacetyl pentyl] cyclopent-2-en-1-one | dl-16-hydroxy-1-phenoxymethyl-1,9-dioxo-16-vinyl-20-methyl-2-nor-13-trans prostene |
| 404 | 1-trans-tri-n-butylstannyl-4-trimethylsilylethynyl-4-trimethylsilyloxy-1-nonene | 2-[5-phenoxyacetyl pentyl] cyclopent-2-en-1-one | dl-16-hydroxy-1-phenoxymethyl-1,9-dioxo-16-ethynyl-20-methyl-2-nor-13-trans prostene |
| 405 | 1-trans-tri-n-butylstannyl-5-methylene-4-triethylsilyloxy-1-nonene | 2-[5-phenoxyacetyl pentyl] cyclopent-2-en-1-one | dl-16-hydroxy-1-phenoxymethyl-1,9-dioxo-17-methylene-20-methyl-2-nor-13-trans prostene |
| 406 | 1-trans-tri-n-butylstannyl-4-methyl-5-methylene-4-trimethylsilyloxy-1-nonene | 2-[5-phenoxyacetyl pentyl] cyclopent-2-en-1-one | dl-16-hydroxy-1-phenoxymethyl-1,9-dioxo-16-methyl-17-methylene-20-methyl-2-nor-13-trans prostene |
| 407 | 1-trans-tri-n-butylstannyl-4-dimethoxymethyl-4-trimethylsilyloxy-1-nonene | 2-[5-phenoxyacetyl pentyl] cyclopent-2-en-1-one | dl-16-hydroxy-1-phenoxymethyl-1,9-dioxo-16-formyl-20-methyl-2-nor-13-trans prostene |
| 408 | 1-trans-tri-n-butylstannyl-4-fluoromethyl-4-trimethylsilyloxy-1-nonene | 2-[5-phenoxyacetyl pentyl] cyclopent-2-en-1-one | dl-16-hydroxy-1-phenoxymethyl-1,9-dioxo-16-fluoromethyl-20-methyl-2-nor-13-trans prostene |
| 409 | 1-trans-tri-n-butylstannyl-4-difluoromethyl-4-trimethylsilyloxy-1-nonene | 2-[5-phenoxyacetyl pentyl] cyclopent-2-en-1-one | dl-16-hydroxy-1-phenoxymethyl-1,9-dioxo-16-difluoromethyl-20-methyl-2-nor-13-trans prostene |
| 410 | 1-trans-tri-n-butylstannyl-4-trifluoromethyl-4-trimethylsilyloxy-1-nonene | 2-[5-phenoxyacetyl pentyl] cyclopent-2-en-1-one | dl-16-hydroxy-1-phenoxymethyl-1,9-dioxo-16-trifluoromethyl-20-methyl-2-nor-13-trans prostene |
| 411 | 1-trans-tri-n-butylstannyl-4-chloromethyl-4-trimethylsilyloxy-1-nonene | 2-[5-phenoxyacetyl pentyl] cyclopent-2-en-1-one | dl-16-hydroxy-1-phenoxymethyl-1,9-dioxo-16-chloromethyl-20-methyl-2-nor-13-trans prostene |
| 412 | 1-trans-tri-n-butylstannyl-4-trimethylsilyloxymethyl-4-trimethylsilyloxy-1-nonene | 2-[5-phenoxyacetyl pentyl] cyclopent-2-en-1-one | dl-16-hydroxy-1-phenoxymethyl-1,9-dioxo-16-hydroxymethyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 413 | 1-trans-iodo-3-triphenylmethoxy-1-decene | 2-[5-phenoxyacetyl pentyl] cyclopent-2-en-1-one | dl-15a-hydroxy-1-phenoxymethyl-1,9-dioxo-20-ethyl-2-nor-13-trans prostene |
| 414 | 1-trans-iodo-3-methyl-3-trimethylsilyloxy-1-decene | 2-[5-phenoxyacetyl pentyl] cyclopent-2-en-1-one | dl-15a-hydroxy-1-phenoxymethyl-1,9-dioxo-15-methyl-20-ethyl-2-nor-13-trans prostene |
| 415 | 1-trans-iodo-4,4-dimethyl-3-trimethylsilyloxy-1-decene | 2-[5-phenoxyacetyl pentyl] cyclopent-2-en-1-one | dl-15a-hydroxy-1-phenoxymethyl-1,9-dioxo-16,16-dimethyl-20-ethyl-2-nor-13-trans prostene |
| 416 | 1-trans-iodo-4,4-trimethylene-3-trimethylsilyloxy-1-decene | 2-[5-phenoxyacetyl pentyl] cyclopent-2-en-1-one | dl-15a-hydroxy-1-phenoxymethyl-1,9-dioxo-16,16-trimethylene-20-ethyl-2-nor-13-trans prostene |
| EXAMPLE | VINYL TIN | CYCLOPENTENONE | PRODUCT PROSTAGLANDIN OF THE 11-DEOXY PGE1 SERIES |
| 417 | 1-trans-tri-n-butylstannyl-3-vinyl-3-trimethylsilyloxy-1-decene | 2-[5-phenoxyacetyl pentyl] cyclopent-2-en-1-one | dl-15a-hydroxy-1-phenoxymethyl-1,9-dioxo-15-vinyl-20-ethyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 418 | 1-trans-iodo-4-triphenylmethoxy-1-decene | 2-[5-phenoxyacetyl pentyl] cyclopent-2-en-1-one | dl-16-hydroxy-1-phenoxymethyl-1,9-dioxo-20-ethyl-2-nor-13-trans prostene |

TABLE VIII-continued

| EXAMPLE | VINYL TIN | CYCLOPENTENONE | PRODUCT PROSTAGLANDIN OF THE 11-DEOXY PGE1 SERIES |
|---|---|---|---|
| 419 | 1-trans-tri-n-butylstannyl-4-methyl-4-trimethylsilyloxy-1-decene | 2-[5-phenoxyacetyl pentyl] cyclopent-2-en-1-one | dl-16-hydroxy-1-phenoxymethyl-1,9-dioxo-16-methyl-20-ethyl-2-nor-13-trans prostene |
| 420 | 1-trans-tri-n-butylstannyl-5-methyl-4-trimethylsilyloxy-1-decene | 2-[5-phenoxyacetyl pentyl] cyclopent-2-en-1-one | dl-16-hydroxy-1-phenoxymethyl-1,9-dioxo-17-methyl-20-ethyl-2-nor-13-trans prostene |
| 421 | 1-trans-tri-n-butylstannyl-4-vinyl-4-trimethylsilyloxy-1-decene | 2-[5-phenoxyacetyl pentyl] cyclopent-2-en-1-one | dl-16-hydroxy-1-phenoxymethyl-1,9-dioxo-16-vinyl-20-ethyl-2-nor-13-trans prostene |
| 422 | 1-trans-tri-n-butylstannyl-4-trimethylsilylethynyl-4-trimethylsilyloxy-1-decene | 2-[5-phenoxyacetyl pentyl] cyclopent-2-en-1-one | dl-16-hydroxy-1-phenoxymethyl-1,9-dioxo-16-ethynyl-20-ethyl-2-nor-13-trans prostene |
| 423 | 1-trans-tri-n-butylstannyl-5-methylene-4-triethylsilyloxy-1-decene | 2-[5-phenoxyacetyl pentyl] cyclopent-2-en-1-one | dl-16-hydroxy-1-phenoxymethyl-1,9-dioxo-17-methylene-20-ethyl-2-nor-13-trans prostene |
| 424 | 1-trans-tri-n-butylstannyl-4-methyl-5-methylene-4-trimethylsilyloxy-1-decene | 2-[5-phenoxyacetyl pentyl] cyclopent-2-en-1-one | dl-16-hydroxy-1-phenoxymethyl-1,9-dioxo-16-methyl-17-methylene-20-ethyl-2-nor-13-trans prostene |
| 425 | 1-trans-tri-n-butylstannyl-4-dimethoxymethyl-4-trimethylsilyloxy-1-decene | 2-[5-phenoxyacetyl pentyl] cyclopent-2-en-1-one | dl-16-hydroxy-1-phenoxymethyl-1,9-dioxo-16-formyl-20-ethyl-2-nor-13-trans prostene |
| 426 | 1-trans-tri-n-butylstannyl-4-fluoromethyl-4-trimethylsilyloxy-1-decene | 2-[5-phenoxyacetyl pentyl] cyclopent-2-en-1-one | dl-16-hydroxy-1-phenoxymethyl-1,9-dioxo-16-fluoromethyl-20-ethyl-2-nor-13-trans prostene |
| 427 | 1-trans-tri-n-butylstannyl-4-difluoromethyl-4-trimethylsilyloxy-1-decene | 2-[5-phenoxyacetyl pentyl] cyclopent-2-en-1-one | dl-16-hydroxy-1-phenoxymethyl-1,9-dioxo-16-difluoromethyl-20-ethyl-2-nor-13-trans prostene |
| 428 | 1-trans-tri-n-butylstannyl-4-trifluoromethyl-4-trimethylsilyloxy-1-decene | 2-[5-phenoxyacetyl pentyl] cyclopent-2-en-1-one | dl-16-hydroxy-1-phenoxymethyl-1,9-dioxo-16-trifluoromethyl-20-ethyl-2-nor-13-trans prostene |
| 429 | 1-trans-tri-n-butylstannyl-4-chloromethyl-4-trimethylsilyloxy-1-decene | 2-[5-phenoxyacetyl pentyl] cyclopent-2-en-1-one | dl-16-hydroxy-1-phenoxymethyl-1,9-dioxo-16-chloromethyl-20-ethyl-2-nor-13-trans prostene |
| 430 | 1-trans-tri-n-butylstannyl-4-trimethylsilyloxymethyl-4-trimethylsilyloxy-1-decene | 2-[5-phenoxyacetyl pentyl] cyclopent-2-en-1-one | dl-16-hydroxy-1-phenoxymethyl-1,9-dioxo-16-hydroxymethyl-20-ethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 431 | 1-trans-iodo-3-triphenylmethoxy-1-heptene | 2-[6-phenoxyacetyl hexyl] cyclopent-2-en-1-one | dl-15a-hydroxy-1-phenoxymethyl-1,9-dioxo-20-nor-13-trans prostene |
| 432 | 1-trans-iodo-3-methyl-3-trimethylsilyloxy-1-heptene | 2-[6-phenoxyacetyl hexyl] cyclopent-2-en-1-one | dl-15a-hydroxy-1-phenoxymethyl-1,9-dioxo-15-methyl-20-nor-13-trans prostene |
| 433 | 1-trans-iodo-4,4-dimethyl-3-trimethylsilyloxy-1-heptene | 2-[6-phenoxyacetyl hexyl] cyclopent-2-en-1-one | dl-15a-hydroxy-1-phenoxymethyl-1,9-dioxo-16,16-dimethyl-20-nor-13-trans prostene |
| 434 | 1-trans-iodo-5,5-dimethyl-3-triphenylmethoxy-1-octene | 2-[6-phenoxyacetyl hexyl] cyclopent-2-en-1-one | dl-15a-hydroxy-1-phenoxymethyl-1,9-dioxo-17,17-dimethyl-13-trans prostene |

TABLE VIII-continued

| EXAMPLE | VINYL TIN / VINYL IODIDE | CYCLOPENTENONE | PRODUCT PROSTAGLANDIN |
|---|---|---|---|
| 435 | 1-trans-iodo-4-methyl 3-triphenylmethoxy-1-octene | 2-[6-phenoxyacetyl hexyl] cyclopent-2-en-1-one | dl-15a-hydroxy-1-phenoxymethyl-1,9-dioxo-16-methyl-13-trans prostene |
| 436 | 1-trans-iodo-4,4-trimethylene 3-trimethylsilyloxy-1-heptene | 2-[6-phenoxyacetyl hexyl] cyclopent-2-en-1-one | dl-15a-hydroxy-1-phenoxymethyl-1,9-dioxo-16,16-trimethylene-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 437 | 1-trans-tri-n-butylstannyl-3-vinyl-3-trimethylsilyloxy-1-heptene | 2-[6-phenoxyacetyl hexyl] cyclopent-2-en-1-one | dl-15a-hydroxy-1-phenoxymethyl-1,9-dioxo-15-vinyl-20-nor-13-trans prostene |
| 438 | 1-trans-tri-n-butylstannyl-4-phenoxy 3-triethylsilyloxy-1-butene | 2-[6-phenoxyacetyl hexyl] cyclopent-2-en-1-one | dl-15a-hydroxy-1-phenoxymethyl-1,9-dioxo-16-phenoxy-17-20-tetranor-13-trans prostene |
| 439 | 1-trans-tri-n-butylstannyl-4-(p-fluorophenoxy) 3-triethylsilyloxy-1-butene | 2-[6-phenoxyacetyl hexyl] cyclopent-2-en-1-one | dl-15a-hydroxy-1-phenoxymethyl-1,9-dioxo-16-(p-fluorophenoxy)-17-20-tetranor-13-trans prostene |
| 440 | 1-trans-tri-n-butylstannyl-4-(m-chlorophenoxy) 3-triethylsilyloxy-1-butene | 2-[6-phenoxyacetyl hexyl] cyclopent-2-en-1-one | dl-15a-hydroxy-1-phenoxymethyl-1,9-dioxo-16-(m-chlorophenoxy)-17-20-tetranor-13-trans prostene |
| 441 | 1-trans-tri-n-butylstannyl-4-(m-trifluoromethylphenoxy) 3-triethylsilyloxy-1-butene | 2-[6-phenoxyacetyl hexyl] cyclopent-2-en-1-one | dl-15a-hydroxy-1-phenoxymethyl-1,9-dioxo-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 442 | 1-trans-iodo-5-phenyl 3-triethylsilyloxy-1-pentene | 2-[6-phenoxyacetyl hexyl] cyclopent-2-en-1-one | dl-15a-hydroxy-1-phenoxymethyl-1,9-dioxo-17-phenyl-18-20-trinor-13-trans prostene |
| 443 | 1-trans-iodo-4,4-dimethyl-5-phenyl 3-triethylsilyloxy-1-pentene | 2-[6-phenoxyacetyl hexyl] cyclopent-2-en-1-one | dl-15a-hydroxy-1-phenoxymethyl-1,9-dioxo-16,16-dimethyl-17-phenyl-18-20-trinor-13-trans prostene |
| 444 | 1-trans-iodo-4-cyclopentyl 3-triphenylmethoxy-1-butene | 2-[6-phenoxyacetyl hexyl] cyclopent-2-en-1-one | dl-15a-hydroxy-1-phenoxymethyl-1,9-dioxo-16-cyclopentyl-17-20-tetranor-13-trans prostene |
| 445 | 1-trans-iodo-4-cyclohexyl 3-triphenylmethoxy-1-butene | 2-[6-phenoxyacetyl hexyl] cyclopent-2-en-1-one | dl-15a-hydroxy-1-phenoxymethyl-1,9-dioxo-16-cyclohexyl-17-20-tetranor-13-trans prostene |
| 446 | 1-trans-iodo-4-triphenylmethoxy-1-heptene | 2-[6-phenoxyacetyl hexyl] cyclopent-2-en-1-one | dl-16-hydroxy-1-phenoxymethyl-1,9-dioxo-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 447 | 1-trans-tri-n-butylstannyl-4-methyl-4-trimethylsilyloxy-1-heptene | 2-[6-phenoxyacetyl hexyl] cyclopent-2-en-1-one | dl-16-hydroxy-1-phenoxymethyl-1,9-dioxo-16-methyl-20-nor-13-trans prostene |
| 448 | 1-trans-tri-n-butylstannyl-4-ethyl-4-trimethylsilyloxy-1-octene | 2-[6-phenoxyacetyl hexyl] cyclopent-2-en-1-one | dl-16-hydroxy-1-phenoxymethyl-1,9-dioxo-16-ethyl-13-trans prostene |
| 449 | 1-trans-tri-n-butylstannyl-5-methyl-4-trimethylsilyloxy-1-heptene | 2-[6-phenoxyacetyl hexyl] cyclopent-2-en-1-one | dl-16-hydroxy-1-phenoxymethyl-1,9-dioxo-17-methyl-20-nor-13-trans prostene |

| EXAMPLE | VINYL IODIDE | CYCLOPENTENONE | PRODUCT PROSTAGLANDIN OF THE 11-DEOXY PGE1 SERIES |

TABLE VIII-continued

| EXAMPLE | VINYL TIN | CYCLOPENTENONE | PRODUCT PROSTAGLANDIN OF THE 11-DEOXY PGE1 SERIES |
|---|---|---|---|
| 450 | 1-trans-iodo-5,5-dimethyl 4-trimethylsilyloxy-1-octene | 2-[6-phenoxyacetyl hexyl] cyclopent-2-en-1-one | dl-16-hydroxy-1-phenoxymethyl-1,9-dioxo-17,17-dimethyl-13-trans prostene |
| 451 | 1-trans-tri-n-butylstannyl-4-vinyl-4-trimethylsilyloxy-1-heptene | 2-[6-phenoxyacetyl hexyl] cyclopent-2-en-1-one | dl-16-hydroxy-1-phenoxymethyl-1,9-dioxo-16-vinyl-20-nor-13-trans prostene |
| 452 | 1-trans-tri-n-butylstannyl-4-cyclopropyl-4-trimethylsilyloxy-1-octene | 2-[6-phenoxyacetyl hexyl] cyclopent-2-en-1-one | dl-16-hydroxy-1-phenoxymethyl-1,9-dioxo-16-cyclopropyl-13-trans prostene |
| 453 | 1-trans-tri-n-butylstannyl-4-trimethylsilylethynyl-4-trimethylsilyloxy-1-heptene | 2-[6-phenoxyacetyl hexyl] cyclopent-2-en-1-one | dl-16-hydroxy-1-phenoxymethyl-1,9-dioxo-16-ethynyl-20-nor-13-trans prostene |
| 454 | 1-trans-tri-n-butylstannyl-5-methylene 4-triethylsilyloxy-1-heptene | 2-[6-phenoxyacetyl hexyl] cyclopent-2-en-1-one | dl-16-hydroxy-1-phenoxymethyl-1,9-dioxo-17-methylene-20-nor-13-trans prostene |
| 455 | 1-trans-tri-n-butylstannyl-4-methyl-5-methylene 4-trimethylsilyloxy-1-heptene | 2-[6-phenoxyacetyl hexyl] cyclopent-2-en-1-one | dl-16-hydroxy-1-phenoxymethyl-1,9-dioxo-16-methyl-17-methylene-20-nor-13-trans prostene |
| 456 | 1-trans-tri-n-butylstannyl-4-dimethoxymethyl-4-trimethylsilyloxy-1-heptene | 2-[6-phenoxyacetyl hexyl] cyclopent-2-en-1-one | dl-16-hydroxy-1-phenoxymethyl-1,9-dioxo-16-formyl-20-nor-13-trans prostene |
| 457 | 1-trans-tri-n-butylstannyl-4-fluoromethyl-4-trimethylsilyloxy-1-heptene | 2-[6-phenoxyacetyl hexyl] cyclopent-2-en-1-one | dl-16-hydroxy-1-phenoxymethyl-1,9-dioxo-16-fluoromethyl-20-nor-13-trans prostene |
| 458 | 1-trans-tri-n-butylstannyl-4-difluoromethyl-4-trimethylsilyloxy-1-heptene | 2-[6-phenoxyacetyl hexyl] cyclopent-2-en-1-one | dl-16-hydroxy-1-phenoxymethyl-1,9-dioxo-16-difluoromethyl-20-nor-13-trans prostene |
| 459 | 1-trans-tri-n-butylstannyl-4-trifluoromethyl-4-trimethylsilyloxy-1-heptene | 2-[6-phenoxyacetyl hexyl] cyclopent-2-en-1-one | dl-16-hydroxy-1-phenoxymethyl-1,9-dioxo-16-trifluoromethyl-20-nor-13-trans prostene |
| 460 | 1-trans-tri-n-butylstannyl-4-chloromethyl-4-trimethylsilyloxy-1-heptene | 2-[6-phenoxyacetyl hexyl] cyclopent-2-en-1-one | dl-16-hydroxy-1-phenoxymethyl-1,9-dioxo-16-chloromethyl-20-nor-13-trans prostene |
| 461 | 1-trans-tri-n-butylstannyl-4-trimethylsilyloxymethyl-4-trimethylsilyloxy-1-heptene | 2-[6-phenoxyacetyl hexyl] cyclopent-2-en-1-one | dl-16-hydroxy-1-phenoxymethyl-1,9-dioxo-16-hydroxymethyl-20-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 462 | 1-trans-iodo-4-methyl-7-chloro-4-trimethylsilyloxy-1-heptene | 2-[6-phenoxyacetyl hexyl] cyclopent-2-en-1-one | dl-16-hydroxy-1-phenoxymethyl-1,9-dioxo-16-methyl-19-chloro-20-nor-13-trans prostene |
| 463 | 1-trans-iodo-3-triphenylmethoxy-1-octene | 2-[6-phenoxyacetyl hexyl] cyclopent-2-en-1-one | dl-15a-hydroxy-1-phenoxymethyl-1,9-dioxo-13-trans prostene |
| 464 | 1-trans-iodo-3-methyl-3-trimethylsilyloxy-1-octene | 2-[6-phenoxyacetyl hexyl] cyclopent-2-en-1-one | dl-15a-hydroxy-1-phenoxymethyl-1,9-dioxo-15-methyl-13-trans prostene |
| 465 | 1-trans-iodo-4,4-dimethyl 3-trimethylsilyloxy-1-octene | 2-[6-phenoxyacetyl hexyl] cyclopent-2-en-1-one | dl-15a-hydroxy-1-phenoxymethyl-1,9-dioxo-16,16-dimethyl-13-trans prostene |
| 466 | 1-trans-iodo-4,4-trimethylene | 2-[6-phenoxyacetyl | dl-15a-hydroxy-1-phenoxymethyl-1,9-dioxo- |

TABLE VIII-continued

| EXAMPLE | VINYL TIN / VINYL IODIDE | CYCLOPENTENONE | PRODUCT PROSTAGLANDIN OF THE 11-DEOXY PGE1 SERIES |
|---|---|---|---|
| | 3-trimethylsilyloxy-1-octene | hexyl]cyclopent-2-en-1-one | 16,16-trimethylene-13-trans prostene |
| EXAMPLE | VINYL TIN | CYCLOPENTENONE | PRODUCT PROSTAGLANDIN OF THE 11-DEOXY PGE1 SERIES |
| 467 | 1-trans-tri-n-butylstannyl-3-vinyl-3-trimethylsilyloxy-1-octene | 2-[6-phenoxyacetyl hexyl]cyclopent-2-en-1-one | dl-15a-hydroxy-1-phenoxymethyl-1,9-dioxo-15-vinyl-13-trans prostene |
| EXAMPLE | VINYL IODIDE | CYCLOPENTENONE | PRODUCT PROSTAGLANDIN OF THE 11-DEOXY PGE1 SERIES |
| 468 | 1-trans-iodo-4-triphenylmethoxy-1-octene | 2-[6-phenoxyacetyl hexyl]cyclopent-2-en-1-one | dl-16-hydroxy-1-phenoxymethyl-1,9-dioxo-13-trans prostene |
| EXAMPLE | VINYL TIN | CYCLOPENTENONE | PRODUCT PROSTAGLANDIN OF THE 11-DEOXY PGE1 SERIES |
| 469 | 1-trans-tri-n-butylstannyl-4-methyl-4-trimethylsilyloxy-1-octene | 2-[6-phenoxyacetyl hexyl]cyclopent-2-en-1-one | dl-16-hydroxy-1-phenoxymethyl-1,9-dioxo-16-methyl-13-trans prostene |
| 470 | 1-trans-tri-n-butylstannyl-5-methyl-4-trimethylsilyloxy-1-octene | 2-[6-phenoxyacetyl hexyl]cyclopent-2-en-1-one | dl-16-hydroxy-1-phenoxymethyl-1,9-dioxo-17-methyl-13-trans prostene |
| 471 | 1-trans-tri-n-butylstannyl-4-vinyl-4-trimethylsilyloxy-1-octene | 2-[6-phenoxyacetyl hexyl]cyclopent-2-en-1-one | dl-16-hydroxy-1-phenoxymethyl-1,9-dioxo-16-vinyl-13-trans prostene |
| 472 | 1-trans-tri-n-butylstannyl-4-trimethylsilylethynyl-4-trimethylsilyloxy-1-octene | 2-[6-phenoxyacetyl hexyl]cyclopent-2-en-1-one | dl-16-hydroxy-1-phenoxymethyl-1,9-dioxo-16-ethynyl-13-trans prostene |
| 473 | 1-trans-tri-n-butylstannyl-5-methylene-4-triethylsilyloxy-1-octene | 2-[6-phenoxyacetyl hexyl]cyclopent-2-en-1-one | dl-16-hydroxy-1-phenoxymethyl-1,9-dioxo-17-methylene-13-trans prostene |
| 474 | 1-trans-tri-n-butylstannyl-4-methyl-5-methylene-4-trimethylsilyloxy-1-octene | 2-[6-phenoxyacetyl hexyl]cyclopent-2-en-1-one | dl-16-hydroxy-1-phenoxymethyl-1,9-dioxo-16-methyl-17-methylene-13-trans prostene |
| 475 | 1-trans-tri-n-butylstannyl-4-dimethoxymethyl-4-trimethylsilyloxy-1-octene | 2-[6-phenoxyacetyl hexyl]cyclopent-2-en-1-one | dl-16-hydroxy-1-phenoxymethyl-1,9-dioxo-16-formyl-13-trans prostene |
| 476 | 1-trans-tri-n-butylstannyl-4-fluoromethyl-4-trimethylsilyloxy-1-octene | 2-[6-phenoxyacetyl hexyl]cyclopent-2-en-1-one | dl-16-hydroxy-1-phenoxymethyl-1,9-dioxo-16-fluoromethyl-13-trans prostene |
| 477 | 1-trans-tri-n-butylstannyl-4-difluoromethyl-4-trimethylsilyloxy-1-octene | 2-[6-phenoxyacetyl hexyl]cyclopent-2-en-1-one | dl-16-hydroxy-1-phenoxymethyl-1,9-dioxo-16-difluoromethyl-13-trans prostene |
| 478 | 1-trans-tri-n-butylstannyl-4-trifluoromethyl-4-trimethylsilyloxy-1-octene | 2-[6-phenoxyacetyl hexyl]cyclopent-2-en-1-one | dl-16-hydroxy-1-phenoxymethyl-1,9-dioxo-16-trifluoromethyl-13-trans prostene |
| 479 | 1-trans-tri-n-butylstannyl-4-chloromethyl-4-trimethylsilyloxy-1-octene | 2-[6-phenoxyacetyl hexyl]cyclopent-2-en-1-one | dl-16-hydroxy-1-phenoxymethyl-1,9-dioxo-16-chloromethyl-13-trans prostene |
| 480 | 1-trans-tri-n-butylstannyl-4-trimethylsilyloxymethyl-4-trimethylsilyloxy-1-octene | 2-[6-phenoxyacetyl hexyl]cyclopent-2-en-1-one | dl-16-hydroxy-1-phenoxymethyl-1,9-dioxo-16-hydroxymethyl-13-trans prostene |
| EXAMPLE | VINYL IODIDE | CYCLOPENTENONE | PRODUCT PROSTAGLANDIN OF THE 11-DEOXY PGE1 SERIES |
| 481 | 1-trans-iodo- | 2-[6-phenoxyacetyl | dl-15a-hydroxy-1-phenoxymethyl-1,9-dioxo- |

TABLE VIII-continued

| | | | |
|---|---|---|---|
| 482 | 3-triphenylmethoxy-1-nonene | 2-[6-phenoxyacetyl hexyl] cyclopent-2-en-1-one | 20-methyl-13-trans prostene |
| | 1-trans-iodo-3-methyl-3-trimethylsilyloxy-1-nonene | 2-[6-phenoxyacetyl hexyl] cyclopent-2-en-1-one | dl-15a-hydroxy-1-phenoxymethyl-1,9-dioxo-15-methyl-20-methyl-13-trans prostene |
| 483 | 1-trans-iodo-4,4-dimethyl-3-trimethylsilyloxy-1-nonene | 2-[6-phenoxyacetyl hexyl] cyclopent-2-en-1-one | dl-15a-hydroxy-1-phenoxymethyl-1,9-dioxo-16,16-dimethyl-20-methyl-13-trans prostene |
| 484 | 1-trans-iodo-4,4-trimethylene-3-trimethylsilyloxy-1-nonene | 2-[6-phenoxyacetyl hexyl] cyclopent-2-en-1-one | dl-15a-hydroxy-1-phenoxymethyl-1,9-dioxo-16,16-trimethylene-20-methyl-13-trans prostene |
| EXAMPLE | VINYL TIN | CYCLOPENTENONE | PRODUCT PROSTAGLANDIN OF THE 11-DEOXY PGE1 SERIES |
| 485 | 1-trans-tri-n-butylstannyl-3-vinyl-3-trimethylsilyloxy-1-nonene | 2-[6-phenoxyacetyl hexyl] cyclopent-2-en-1-one | dl-15a-hydroxy-1-phenoxymethyl-1,9-dioxo-15-vinyl-20-methyl-13-trans prostene |
| EXAMPLE | VINYL IODIDE | CYCLOPENTENONE | PRODUCT PROSTAGLANDIN OF THE 11-DEOXY PGE1 SERIES |
| 486 | 1-trans-iodo-4-triphenylmethoxy-1-nonene | 2-[6-phenoxyacetyl hexyl] cyclopent-2-en-1-one | dl-16-hydroxy-1-phenoxymethyl-1,9-dioxo-20-methyl-13-trans prostene |
| EXAMPLE | VINYL TIN | CYCLOPENTENONE | PRODUCT PROSTAGLANDIN OF THE 11-DEOXY PGE1 SERIES |
| 487 | 1-trans-tri-n-butylstannyl-4-methyl-4-trimethylsilyloxy-1-nonene | 2-[6-phenoxyacetyl hexyl] cyclopent-2-en-1-one | dl-16-hydroxy-1-phenoxymethyl-1,9-dioxo-16-methyl-20-methyl-13-trans prostene |
| 488 | 1-trans-tri-n-butylstannyl-5-methyl-4-trimethylsilyloxy-1-nonene | 2-[6-phenoxyacetyl hexyl] cyclopent-2-en-1-one | dl-16-hydroxy-1-phenoxymethyl-1,9-dioxo-17-methyl-20-methyl-13-trans prostene |
| 489 | 1-trans-tri-n-butylstannyl-4-vinyl-4-trimethylsilyloxy-1-nonene | 2-[6-phenoxyacetyl hexyl] cyclopent-2-en-1-one | dl-16-hydroxy-1-phenoxymethyl-1,9-dioxo-16-vinyl-20-methyl-13-trans prostene |
| 490 | 1-trans-tri-n-butylstannyl-4-trimethylsilylethynyl-4-trimethylsilyloxy-1-nonene | 2-[6-phenoxyacetyl hexyl] cyclopent-2-en-1-one | dl-16-hydroxy-1-phenoxymethyl-1,9-dioxo-16-ethynyl-20-methyl-13-trans prostene |
| 491 | 1-trans-tri-n-butylstannyl-5-methylene-4-triethylsilyloxy-1-nonene | 2-[6-phenoxyacetyl hexyl] cyclopent-2-en-1-one | dl-16-hydroxy-1-phenoxymethyl-1,9-dioxo-17-methylene-20-methyl-13-trans prostene |
| 492 | 1-trans-tri-n-butylstannyl-4-methyl-5-methylene-4-trimethylsilyloxy-1-nonene | 2-[6-phenoxyacetyl hexyl] cyclopent-2-en-1-one | dl-16-hydroxy-1-phenoxymethyl-1,9-dioxo-16-methyl-17-methylene-20-methyl-13-trans prostene |
| 493 | 1-trans-tri-n-butylstannyl-4-dimethoxymethyl-4-trimethylsilyloxy-1-nonene | 2-[6-phenoxyacetyl hexyl] cyclopent-2-en-1-one | dl-16-hydroxy-1-phenoxymethyl-1,9-dioxo-16-formyl-20-methyl-13-trans prostene |
| 494 | 1-trans-tri-n-butylstannyl-4-fluoromethyl-4-trimethylsilyloxy-1-nonene | 2-[6-phenoxyacetyl hexyl] cyclopent-2-en-1-one | dl-16-hydroxy-1-phenoxymethyl-1,9-dioxo-16-fluoromethyl-20-methyl-13-trans prostene |
| 495 | 1-trans-tri-n-butylstannyl-4-difluoromethyl-4-trimethylsilyloxy-1-nonene | 2-[6-phenoxyacetyl hexyl] cyclopent-2-en-1-one | dl-16-hydroxy-1-phenoxymethyl-1,9-dioxo-16-difluoromethyl-20-methyl-13-trans prostene |
| 496 | 1-trans-tri-n-butylstannyl-4-trifluoromethyl-4-trimethylsilyloxy-1-nonene | 2-[6-phenoxyacetyl hexyl] cyclopent-2-en-1-one | dl-16-hydroxy-1-phenoxymethyl-1,9-dioxo-16-trifluoromethyl-20-methyl-13-trans prostene |

TABLE VIII-continued

| | | | |
|---|---|---|---|
| 497 | 1-trans-tri-n-butylstannyl-4-chloromethyl-4-trimethylsilyloxy-1-nonene | 2-[6-phenoxyacetyl hexyl] cyclopent-2-en-1-one | dl-16-hydroxy-1-phenoxymethyl-1,9-dioxo-16-chloromethyl-20-methyl-13-trans prostene |
| 498 | 1-trans-tri-n-butylstannyl-4-trimethylsilyloxymethyl-4-trimethylsilyloxy-1-nonene | 2-[6-phenoxyacetyl hexyl] cyclopent-2-en-1-one | dl-16-hydroxy-1-phenoxymethyl-1,9-dioxo-16-hydroxymethyl-20-methyl-13-trans prostene |
| EXAMPLE | VINYL IODIDE | CYCLOPENTENONE | PRODUCT PROSTAGLANDIN OF THE 11-DEOXY PGE1 SERIES |
| 499 | 1-trans-iodo-3-triphenylmethoxy-1-decene | 2-[6-phenoxyacetyl hexyl] cyclopent-2-en-1-one | dl-15a-hydroxy-1-phenoxymethyl-1,9-dioxo-20-ethyl-13-trans prostene |
| 500 | 1-trans-iodo-3-methyl-3-trimethylsilyloxy-1-decene | 2-[6-phenoxyacetyl hexyl] cyclopent-2-en-1-one | dl-15a-hydroxy-1-phenoxymethyl-1,9-dioxo-15-methyl-20-ethyl-13-trans prostene |
| 501 | 1-trans-iodo-4,4-dimethyl-3-trimethylsilyloxy-1-decene | 2-[6-phenoxyacetyl hexyl] cyclopent-2-en-1-one | dl-15a-hydroxy-1-phenoxymethyl-1,9-dioxo-16,16-dimethyl-20-ethyl-13-trans prostene |
| 502 | 1-trans-iodo-4,4-trimethylene-3-trimethylsilyloxy-1-decene | 2-[6-phenoxyacetyl hexyl] cyclopent-2-en-1-one | dl-15a-hydroxy-1-phenoxymethyl-1,9-dioxo-16,16-trimethylene-20-ethyl-13-trans prostene |
| EXAMPLE | VINYL TIN | CYCLOPENTENONE | PRODUCT PROSTAGLANDIN OF THE 11-DEOXY PGE1 SERIES |
| 503 | 1-trans-tri-n-butylstannyl-3-vinyl-3-trimethylsilyloxy-1-decene | 2-[6-phenoxyacetyl hexyl] cyclopent-2-en-1-one | dl-15a-hydroxy-1-phenoxymethyl-1,9-dioxo-15-vinyl-20-ethyl-13-trans prostene |
| EXAMPLE | VINYL IODIDE | CYCLOPENTENONE | PRODUCT PROSTAGLANDIN OF THE 11-DEOXY PGE1 SERIES |
| 504 | 1-trans-iodo-4-triphenylmethoxy-1-decene | 2-[6-phenoxyacetyl hexyl] cyclopent-2-en-1-one | dl-16-hydroxy-1-phenoxymethyl-1,9-dioxo-20-ethyl-13-trans prostene |
| EXAMPLE | VINYL TIN | CYCLOPENTENONE | PRODUCT PROSTAGLANDIN OF THE 11-DEOXY PGE1 SERIES |
| 505 | 1-trans-tri-n-butylstannyl-4-methyl-4-trimethylsilyloxy-1-decene | 2-[6-phenoxyacetyl hexyl] cyclopent-2-en-1-one | dl-16-hydroxy-1-phenoxymethyl-1,9-dioxo-16-methyl-20-ethyl-13-trans prostene |
| 506 | 1-trans-tri-n-butylstannyl-5-methyl-4-trimethylsilyloxy-1-decene | 2-[6-phenoxyacetyl hexyl] cyclopent-2-en-1-one | dl-16-hydroxy-1-phenoxymethyl-1,9-dioxo-17-methyl-20-ethyl-13-trans prostene |
| 507 | 1-trans-tri-n-butylstannyl-4-vinyl-4-trimethylsilyloxy-1-decene | 2-[6-phenoxyacetyl hexyl] cyclopent-2-en-1-one | dl-16-hydroxy-1-phenoxymethyl-1,9-dioxo-16-vinyl-20-ethyl-13-trans prostene |
| 508 | 1-trans-tri-n-butylstannyl-4-trimethylsilylethynyl-4-trimethylsilyloxy-1-decene | 2-[6-phenoxyacetyl hexyl] cyclopent-2-en-1-one | dl-16-hydroxy-1-phenoxymethyl-1,9-dioxo-16-ethynyl-20-ethyl-13-trans prostene |
| 509 | 1-trans-tri-n-butylstannyl-5-methylene-4-triethylsilyloxy-1-decene | 2-[6-phenoxyacetyl hexyl] cyclopent-2-en-1-one | dl-16-hydroxy-1-phenoxymethyl-1,9-dioxo-17-methylene-20-ethyl-13-trans prostene |
| 510 | 1-trans-tri-n-butylstannyl-4-methyl-5-methylene-4-trimethylsilyloxy-1-decene | 2-[6-phenoxyacetyl hexyl] cyclopent-2-en-1-one | dl-16-hydroxy-1-phenoxymethyl-1,9-dioxo-16-methyl-17-methylene-20-ethyl-13-trans prostene |
| 511 | 1-trans-tri-n-butylstannyl-4-dimethoxymethyl-4-trimethylsilyloxy-1-decene | 2-[6-phenoxyacetyl hexyl] cyclopent-2-en-1-one | dl-16-hydroxy-1-phenoxymethyl-1,9-dioxo-16-formyl-20-ethyl-13-trans prostene |

TABLE VIII-continued

| Example | | | |
|---|---|---|---|
| 512 | 1-trans-tri-n-butylstannyl-4-fluoromethyl-4-trimethylsilyloxy-1-decene | 2-[6-phenoxyacetyl hexyl] cyclopent-2-en-1-one | dl-16-hydroxy-1-phenoxymethyl-1,9-dioxo-16-fluoromethyl-20-ethyl-13-trans prostene |
| 513 | 1-trans-tri-n-butylstannyl-4-difluoromethyl-4-trimethylsilyloxy-1-decene | 2-[6-phenoxyacetyl hexyl] cyclopent-2-en-1-one | dl-16-hydroxy-1-phenoxymethyl-1,9-dioxo-16-difluoromethyl-20-ethyl-13-trans prostene |
| 514 | 1-trans-tri-n-butylstannyl-4-trifluoromethyl-4-trimethylsilyloxy-1-decene | 2-[6-phenoxyacetyl hexyl] cyclopent-2-en-1-one | dl-16-hydroxy-1-phenoxymethyl-1,9-dioxo-16-trifluoromethyl-20-ethyl-13-trans prostene |
| 515 | 1-trans-tri-n-butylstannyl-4-chloromethyl-4-trimethylsilyloxy-1-decene | 2-[6-phenoxyacetyl hexyl] cyclopent-2-en-1-one | dl-16-hydroxy-1-phenoxymethyl-1,9-dioxo-16-chloromethyl-20-ethyl-13-trans prostene |
| 516 | 1-trans-tri-n-butylstannyl-4-trimethylsilyloxymethyl-4-trimethylsilyloxy-1-decene | 2-[60 6-phenoxyacetyl hexyl] cyclopent-2-en-1-one | trimethylsilyloxy-1-heptene 20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 517 | 1-trans-iodo-3-triphenylmethoxy-1-heptene | 2-[7-phenoxyacetyl heptyl] cyclopent-2-en-1-one | dl-15a-hydroxy-1-phenoxymethyl-1,9-dioxo-20-nor-2-homo-13-trans prostene |
| 518 | 1-trans-iodo-3-methyl-3-trimethylsilyloxy-1-heptene | 2-[7-phenoxyacetyl heptyl] cyclopent-2-en-1-one | dl-15a-hydroxy-1-phenoxymethyl-1,9-dioxo-15-methyl-20-nor-2-homo-13-trans prostene |
| 519 | 1-trans-iodo-4,4-dimethyl-3-trimethylsiloxy-1-heptene | 2-[7-phenoxyacetyl heptyl] cyclopent-2-en-1-one | dl-15a-hydroxy-1-phenoxymethyl-1,9-dioxo-16,16-dimethyl-20-nor-2-homo-13-trans prostene |
| 520 | 1-trans-iodo-5,5-dimethyl-3-triphenylmethoxy-1-octene | 2-[7-phenoxyacetyl heptyl] cyclopent-2-en-1-one | dl-15a-hydroxy-1-phenoxymethyl-1,9-dioxo-17,17-dimethyl-2-homo-13-trans prostene |
| 521 | 1-trans-iodo-4-methyl-3-triphenylmethoxy-1-octene | 2-[7-phenoxyacetyl heptyl] cyclopent-2-en-1-one | dl-15a-hydroxy-1-phenoxymethyl-1,9-dioxo-16-methyl-2-homo-13-trans prostene |
| 522 | 1-trans-iodo-4,4-trimethylene-3-trimethylsilyloxy-1-heptene | 2-[7-phenoxyacetyl heptyl] cyclopent-2-en-1-one | dl-15a-hydroxy-1-phenoxymethyl-1,9-dioxo-16,16-trimethylene-20-nor-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 523 | 1-trans-tri-n-butylstannyl-3-vinyl-3-trimethylsilyloxy-1-heptene | 2-[7-phenoxyacetyl heptyl] cyclopent-2-en-1-one | dl-15a-hydroxy-1-phenoxymethyl-1,9-dioxo-15-vinyl-20-nor-2-homo-13-trans prostene |
| 524 | 1-trans-tri-n-butylstannyl-4-phenoxy-3-triethylsilyloxy-1-butene | 2-[7-phenoxyacetyl heptyl] cyclopent-2-en-1-one | dl-15a-hydroxy-1-phenoxymethyl-1,9-dioxo-16-phenoxy-2-homo-17-20-tetranor-13-trans prostene |
| 525 | 1-trans-tri-n-butylstannyl-4-(p-fluorophenoxy)-3-triethylsilyloxy-1-butene | 2-[7-phenoxyacetyl heptyl] cyclopent-2-en-1-one | dl-15a-hydroxy-1-phenoxymethyl-1,9-dioxo-16-(p-fluorophenoxy)-2-homo-17-20-tetranor-13-trans prostene |
| 526 | 1-trans-tri-n-butylstannyl-4-(m-chlorophenoxy)-3-triethylsilyloxy-1-butene | 2-[7-phenoxyacetyl heptyl] cyclopent-2-en-1-one | dl-15a-hydroxy-1-phenoxymethyl-1,9-dioxo-16-(m-chlorophenoxy)-2-homo-17-20-tetranor-13-trans prostene |
| 527 | 1-trans-tri-n-butylstannyl-4-(m-trifluoromethylphenoxy)-3-triethylsilyloxy-1-butene | 2-[7-phenoxyacetyl heptyl] cyclopent-2-en-1-one | dl-15a-hydroxy-1-phenoxymethyl-1,9-dioxo-16-(m-trifluoromethylphenoxy)-2-homo-17-20-tetranor-13-trans prostene |

TABLE VIII-continued

| EXAMPLE | VINYL IODIDE | CYCLOPENTENONE | PRODUCT PROSTAGLANDIN OF THE 11-DEOXY PGE1 SERIES |
|---|---|---|---|
| 528 | 1-trans-iodo-5-phenyl 3-triethylsilyloxy-1-pentene | 2-[7-phenoxyacetyl cyclopent-2-en-1-one heptyl] | dl-15a-hydroxy-1-phenoxymethyl-1,9-dioxo-17-phenyl-2-homo-18-20-trinor-13-trans prostene |
| 529 | 1-trans-iodo-4,4-dimethyl-5-phenyl 3-triethylsilyloxy-1-pentene | 2-[7-phenoxyacetyl cyclopent-2-en-1-one heptyl] | dl-15a-hydroxy-1-phenoxymethyl-1,9-dioxo-16,16-dimethyl-17-phenyl-2-homo-18-20-trinor-13-trans prostene |
| 530 | 1-trans-iodo-4-cyclopentyl 3-triphenylmethoxy-1-butene | 2-[7-phenoxyacetyl cyclopent-2-en-1-one heptyl] | dl-15a-hydroxy-1-phenoxymethyl-1,9-dioxo-16-cyclopentyl-2-homo-17-20-tetranor-13-trans prostene |
| 531 | 1-trans-iodo-4-cyclohexyl 3-triphenylmethoxy-1-butene | 2-[7-phenoxyacetyl cyclopent-2-en-1-one heptyl] | dl-15a-hydroxy-1-phenoxymethyl-1,9-dioxo-16-cyclohexyl-2-homo-17-20-tetranor-13-trans prostene |
| 532 | 1-trans-iodo-4-triphenylmethoxy-1-heptene | 2-[7-phenoxyacetyl cyclopent-2-en-1-one heptyl] | dl-16-hydroxy-1-phenoxymethyl-1,9-dioxo-20-nor-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 533 | 1-trans-tri-n-butylstannyl-4-methyl-4-trimethylsilyloxy-1-heptene | 2-[7-phenoxyacetyl cyclopent-2-en-1-one heptyl] | dl-16-hydroxy-1-phenoxymethyl-1,9-dioxo-16-methyl-20-nor-2-homo-13-trans prostene |
| 534 | 1-trans-tri-n-butylstannyl-4-ethyl-4-trimethylsilyloxy-1-octene | 2-[7-phenoxyacetyl cyclopent-2-en-1-one heptyl] | dl-16-hydroxy-1-phenoxymethyl-1,9-dioxo-16-ethyl-2-homo-13-trans prostene |
| 535 | 1-trans-tri-n-butylstannyl-5-methyl-4-trimethylsilyloxy-1-heptene | 2-[7-phenoxyacetyl cyclopent-2-en-1-one heptyl] | dl-16-hydroxy-1-phenoxymethyl-1,9-dioxo-17-methyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 536 | 1-trans-iodo-5,5-dimethyl 4-trimethylsilyloxy-1-octene | 2-[7-phenoxyacetyl cyclopent-2-en-1-one heptyl] | dl-16-hydroxy-1-phenoxymethyl-1,9-dioxo-17,17-dimethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 537 | 1-trans-tri-n-butylstannyl-4-vinyl-4-trimethylsilyloxy-1-heptene | 2-[7-phenoxyacetyl cyclopent-2-en-1-one heptyl] | dl-16-hydroxy-1-phenoxymethyl-1,9-dioxo-16-vinyl-20-nor-2-homo-13-trans prostene |
| 538 | 1-trans-tri-n-butylstannyl-4-cyclopropyl-4-trimethylsilyloxy-1-heptene | 2-[7-phenoxyacetyl cyclopent-2-en-1-one heptyl] | dl-16-hydroxy-1-phenoxymethyl-1,9-dioxo-16-cyclopropyl-2-homo-13-trans prostene |
| 539 | 1-trans-tri-n-butylstannyl-4-trimethylsilylethynyl-4-trimethylsilyloxy-1-heptene | 2-[7-phenoxyacetyl cyclopent-2-en-1-one heptyl] | dl-16-hydroxy-1-phenoxymethyl-1,9-dioxo-16-ethynyl-20-nor-2-homo-13-trans prostene |
| 540 | 1-trans-tri-n-butylstannyl-5-methylene 4-triethylsilyloxy-1-heptene | 2-[7-phenoxyacetyl cyclopent-2-en-1-one heptyl] | dl-16-hydroxy-1-phenoxymethyl-1,9-dioxo-17-methylene-20-nor-2-homo-13-trans prostene |
| 541 | 1-trans-tri-n-butylstannyl-4-methyl-5-methylene 4-trimethylsilyloxy-1-heptene | 2-[7-phenoxyacetyl cyclopent-2-en-1-one heptyl] | dl-16-hydroxy-1-phenoxymethyl-1,9-dioxo-16-methyl-17-methylene-20-nor-2-homo-13-trans prostene |
| 542 | 1-trans-tri-n-butylstannyl-4-dimethoxymethyl-4-trimethylsilyloxy-1-heptene | 2-[7-phenoxyacetyl cyclopent-2-en-1-one heptyl] | dl-16-hydroxy-1-phenoxymethyl-1,9-dioxo-16-formyl-20-nor-2-homo-13-trans prostene |
| 543 | 1-trans-tri-n-butylstannyl-4-fluoromethyl- | 2-[7-phenoxyacetyl | dl-16-hydroxy-1-phenoxymethyl-1,9-dioxo-16-fluoromethyl- |

TABLE VIII-continued

| Example | Vinyl Iodide/Tin | Cyclopentenone | Product |
|---|---|---|---|
| | 4-trimethylsilyloxy-1-heptene | heptyl] cyclopent-2-en-1-one | 20-nor-2-homo-13-trans prostene |
| 544 | 1-trans-tri-n-butylstannyl-4-difluoromethyl-4-trimethylsilyloxy-1-heptene | 2-[7-phenoxyacetyl heptyl] cyclopent-2-en-1-one | dl-16-hydroxy-1-phenoxymethyl-1,9-dioxo-16-difluoromethyl-20-nor-2-homo-13-trans prostene |
| 545 | 1-trans-tri-n-butylstannyl-4-trifluoromethyl-4-trimethylsilyloxy-1-heptene | 2-[7-phenoxyacetyl heptyl] cyclopent-2-en-1-one | dl-16-hydroxy-1-phenoxymethyl-1,9-dioxo-16-trifluoromethyl-20-nor-2-homo-13-trans prostene |
| 546 | 1-trans-tri-n-butylstannyl-4-chloromethyl-4-trimethylsilyloxy-1-heptene | 2-[7-phenoxyacetyl heptyl] cyclopent-2-en-1-one | dl-16-hydroxy-1-phenoxymethyl-1,9-dioxo-16-chloromethyl-20-nor-2-homo-13-trans prostene |
| 547 | 1-trans-tri-n-butylstannyl-4-trimethylsilyloxymethyl-4-trimethylsilyloxy-1-heptene | 2-[7-phenoxyacetyl heptyl] cyclopent-2-en-1-one | dl-16-hydroxy-1-phenoxymethyl-1,9-dioxo-16-hydroxymethyl-20-nor-2-homo-13-trans prostene |
| EXAMPLE | VINYL IODIDE | CYCLOPENTENONE | PRODUCT PROSTAGLANDIN OF THE 11-DEOXY PGE1 SERIES |
| 548 | 1-trans-iodo-4-methyl-7-chloro-4-trimethylsilyloxy-1-heptene | 2-[7-phenoxyacetyl heptyl] cyclopent-2-en-1-one | dl-15a-hydroxy-1-phenoxymethyl-1,9-dioxo-16-methyl-19-chloro-2-homo-20-nor-13-trans prostene |
| 549 | 1-trans-iodo-3-triphenylmethoxy-1-octene | 2-[7-phenoxyacetyl heptyl] cyclopent-2-en-1-one | dl-15a-hydroxy-1-phenoxymethyl-1,9-dioxo-2-homo-13-trans prostene |
| 550 | 1-trans-iodo-3-methyl-3-trimethylsilyloxy-1-octene | 2-[7-phenoxyacetyl heptyl] cyclopent-2-en-1-one | dl-15a-hydroxy-1-phenoxymethyl-1,9-dioxo-15-methyl-2-homo-13-trans prostene |
| 551 | 1-trans-iodo-4,4-dimethyl-3-trimethylsilyloxy-1-octene | 2-[7-phenoxyacetyl heptyl] cyclopent-2-en-1-one | dl-15a-hydroxy-1-phenoxymethyl-1,9-dioxo-16,16-dimethyl-2-homo-13-trans prostene |
| 552 | 1-trans-iodo-4,4-trimethylene-3-trimethylsilyloxy-1-octene | 2-[7-phenoxyacetyl heptyl] cyclopent-2-en-1-one | dl-15a-hydroxy-1-phenoxymethyl-1,9-dioxo-16,16-trimethylene-2-homo-13-trans prostene |
| EXAMPLE | VINYL TIN | CYCLOPENTENONE | PRODUCT PROSTAGLANDIN OF THE 11-DEOXY PGE1 SERIES |
| 553 | 1-trans-tri-n-butylstannyl-3-vinyl-3-trimethylsilyloxy-1-octene | 2-[7-phenoxyacetyl heptyl] cyclopent-2-en-1-one | dl-15a-hydroxy-1-phenoxymethyl-1,9-dioxo-15-vinyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 554 | 1-trans-iodo-4-triphenylmethoxy-1-octene | 2-[7-phenoxyacetyl heptyl] cyclopent-2-en-1-one | dl-16-hydroxy-1-phenoxymethyl-1,9-dioxo-2-homo-13-trans prostene |
| EXAMPLE | VINYL TIN | CYCLOPENTENONE | PRODUCT PROSTAGLANDIN OF THE 11-DEOXY PGE1 SERIES |
| 555 | 1-trans-tri-n-butylstannyl-4-methyl-4-trimethylsilyloxy-1-octene | 2-[7-phenoxyacetyl heptyl] cyclopent-2-en-1-one | dl-16-hydroxy-1-phenoxymethyl-1,9-dioxo-16-methyl-2-homo-13-trans prostene |
| 556 | 1-trans-tri-n-butylstannyl-5-methyl-4-trimethylsilyloxy-1-octene | 2-[7-phenoxyacetyl heptyl] cyclopent-2-en-1-one | dl-16-hydroxy-1-phenoxymethyl-1,9-dioxo-17-methyl-2-homo-13-trans prostene |
| 557 | 1-trans-tri-n-butylstannyl-4-vinyl-4-trimethylsilyloxy-1-octene | 2-[7-phenoxyacetyl heptyl] cyclopent-2-en-1-one | dl-16-hydroxy-1-phenoxymethyl-1,9-dioxo-16-vinyl-2-homo-13-trans prostene |
| 558 | 1-trans-tri-n-butylstannyl-4-trimethylsilylethynyl- | 2-[7-phenoxyacetyl | dl-16-hydroxy-1-phenoxymethyl-1,9-dioxo-16-ethynyl- |

TABLE VIII-continued

| | | | |
|---|---|---|---|
| 559 | 4-trimethylsilyloxy-1-octene | heptyl]<br>cyclopent-2-en-1-one | 2-homo-13-trans prostene |
| 559 | 1-trans-tri-n-butylstannyl-5-methylene<br>4-triethylsilyloxy-1-octene | 2-[7-phenoxyacetyl<br>heptyl]<br>cyclopent-2-en-1-one | dl-16-hydroxy-1-phenoxymethyl-1,9-dioxo-<br>17-methylene-2-homo-13-trans prostene |
| 560 | 1-trans-tri-n-butylstannyl-4-methyl-5-methylene<br>4-trimethylsilyloxy-1-octene. | 2-[7-phenoxyacetyl<br>heptyl]<br>cyclopent-2-en-1-one | dl-16-hydroxy-1-phenoxymethyl-1,9-dioxo-16-methyl-<br>17-methylene-2-homo-13-trans prostene |
| 561 | 1-trans-tri-n-butylstannyl-4-dimethoxymethyl-<br>4-trimethylsilyloxy-1-octene | 2-[7-phenoxyacetyl<br>heptyl]<br>cyclopent-2-en-1-one | dl-16-hydroxy-1-phenoxymethyl-1,9-dioxo-16-formyl-<br>2-homo-13-trans prostene |
| 562 | 1-trans-tri-n-butylstannyl-4-fluoromethyl-<br>4-trimethylsilyloxy-1-octene | 2-[7-phenoxyacetyl<br>heptyl]<br>cyclopent-2-en-1-one | dl-16-hydroxy-1-phenoxymethyl-1,9-dioxo-16-fluoromethyl-<br>2-homo-13-trans prostene |
| 563 | 1-trans-tri-n-butylstannyl-4-difluoromethyl-<br>4-trimethylsilyloxy-1-octene | 2-[7-phenoxyacetyl<br>heptyl]<br>cyclopent-2-en-1-one | dl-16-hydroxy-1-phenoxymethyl-1,9-dioxo-16-difluoromethyl-<br>2-homo-13-trans prostene |
| 564 | 1-trans-tri-n-butylstannyl-4-trifluoromethyl-<br>4-trimethylsilyloxy-1-octene | 2-[7-phenoxyacetyl<br>heptyl]<br>cyclopent-2-en-1-one | dl-16-hydroxy-1-phenoxymethyl-1,9-dioxo-16-trifluoromethyl-<br>2-homo-13-trans prostene |
| 565 | 1-trans-tri-n-butylstannyl-4-chloromethyl-<br>4-trimethylsilyloxy-1-octene | 2-[7-phenoxyacetyl<br>heptyl]<br>cyclopent-2-en-1-one | dl-16-hydroxy-1-phenoxymethyl-1,9-dioxo-16-chloromethyl-<br>2-homo-13-trans prostene |
| 566 | 1-trans-tri-n-butylstannyl-4-trimethylsilyloxymethyl-<br>4-trimethylsilyloxy-1-octene | 2-[7-phenoxyacetyl<br>heptyl]<br>cyclopent-2-en-1-one | dl-16-hydroxy-1-phenoxymethyl-1,9-dioxo-16-hydroxymethyl-<br>2-homo-13-trans prostene |
| EXAMPLE | VINYL IODIDE | CYCLOPENTENONE | PRODUCT PROSTAGLANDIN OF THE 11-DEOXY PGE1 SERIES |
| 567 | 1-trans-iodo-<br>3-triphenylmethoxy-1-nonene | 2-[7-phenoxyacetyl<br>heptyl]<br>cyclopent-2-en-1-one | dl-15a-hydroxy-1-phenoxymethyl-1,9-dioxo-<br>20-methyl-2-homo-13-trans prostene |
| 568 | 1-trans-iodo-3-methyl-<br>3-trimethylsilyloxy-1-nonene | 2-[7-phenoxyacetyl<br>heptyl]<br>cyclopent-2-en-1-one | dl-15a-hydroxy-1-phenoxymethyl-1,9-dioxo-15-methyl-<br>20-methyl-2-homo-13-trans prostene |
| 569 | 1-trans-iodo-4,4-dimethyl<br>3-trimethylsilyloxy-1-nonene | 2-[7-phenoxyacetyl<br>heptyl]<br>cyclopent-2-en-1-one | dl-15a-hydroxy-1-phenoxymethyl-1,9-dioxo-<br>16,16-dimethyl-20-methyl-2-homo-13-trans prostene |
| 570 | 1-trans-iodo-4,4-trimethylene<br>3-trimethylsilyloxy-1-nonene | 2-[7-phenoxyacetyl<br>heptyl]<br>cyclopent-2-en-1-one | dl-15a-hydroxy-1-phenoxymethyl-1,9-dioxo-<br>16,16-trimethylene-20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 571 | 1-trans-tri-n-butylstannyl-3-vinyl-<br>3-trimethylsilyloxy-1-nonene | 2-[7-phenoxyacetyl<br>heptyl]<br>cyclopent-2-en-1-one | dl-15a-hydroxy-1-phenoxymethyl-1,9-dioxo-15-vinyl-<br>20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 572 | 1-trans-iodo-<br>4-triphenylmethoxy-1-nonene | 2-[7-phenoxyacetyl<br>heptyl]<br>cyclopent-2-en-1-one | dl-16-hydroxy-1-phenoxymethyl-1,9-dioxo-<br>20-methyl-2-homo-13-trans prostene |
| EXAMPLE | VINYL TIN | CYCLOPENTENONE | PRODUCT PROSTAGLANDIN OF THE 11-DEOXY PGE1 SERIES |
| 573 | 1-trans-tri-n-butylstannyl-4-methyl- | 2-[7-phenoxyacetyl | dl-16-hydroxy-1-phenoxymethyl-1,9-dioxo-16-methyl- |

TABLE VIII-continued

| | | | |
|---|---|---|---|
| 574 | 4-trimethylsilyloxy-1-nonene | [7-phenoxyacetyl heptyl] cyclopent-2-en-1-one | 20-methyl-2-homo-13-trans prostene |
| 575 | 1-trans-tri-n-butylstannyl-5-methyl-4-trimethylsilyloxy-1-nonene | 2-[7-phenoxyacetyl heptyl] cyclopent-2-en-1-one | dl-16-hydroxy-1-phenoxymethyl-1,9-dioxo-17-methyl-20-methyl-2-homo-13-trans prostene |
| 576 | 1-trans-tri-n-butylstannyl-4-vinyl-4-trimethylsilyloxy-1-nonene | 2-[7-phenoxyacetyl heptyl] cyclopent-2-en-1-one | dl-16-hydroxy-1-phenoxymethyl-1,9-dioxo-16-vinyl-20-methyl-2-homo-13-trans prostene |
| 577 | 1-trans-tri-n-butylstannyl-4-trimethylsilylethynyl-4-trimethylsilyloxy-1-nonene | 2-[7-phenoxyacetyl heptyl] cyclopent-2-en-1-one | dl-16-hydroxy-1-phenoxymethyl-1,9-dioxo-16-ethynyl-20-methyl-2-homo-13-trans prostene |
| 578 | 1-trans-tri-n-butylstannyl-5-methylene-4-triethylsilyloxy-1-nonene | 2-[7-phenoxyacetyl heptyl] cyclopent-2-en-1-one | dl-16-hydroxy-1-phenoxymethyl-1,9-dioxo-17-methylene-20-methyl-2-homo-13-trans prostene |
| 579 | 1-trans-tri-n-butylstannyl-4-methyl-5-methylene-4-trimethylsilyloxy-1-nonene | 2-[7-phenoxyacetyl heptyl] cyclopent-2-en-1-one | dl-16-hydroxy-1-phenoxymethyl-1,9-dioxo-16-methyl-17-methylene-20-methyl-2-homo-13-trans prostene |
| 580 | 1-trans-tri-n-butylstannyl-4-dimethoxymethyl-4-trimethylsilyloxy-1-nonene | 2-[7-phenoxyacetyl heptyl] cyclopent-2-en-1-one | dl-16-hydroxy-1-phenoxymethyl-1,9-dioxo-16-formyl-20-methyl-2-homo-13-trans prostene |
| 581 | 1-trans-tri-n-butylstannyl-4-fluoromethyl-4-trimethylsilyloxy-1-nonene | 2-[7-phenoxyacetyl heptyl] cyclopent-2-en-1-one | dl-16-hydroxy-1-phenoxymethyl-1,9-dioxo-16-fluoromethyl-20-methyl-2-homo-13-trans prostene |
| 582 | 1-trans-tri-n-butylstannyl-4-difluoromethyl-4-trimethylsilyloxy-1-nonene | 2-[7-phenoxyacetyl heptyl] cyclopent-2-en-1-one | dl-16-hydroxy-1-phenoxymethyl-1,9-dioxo-16-difluoromethyl-20-methyl-2-homo-13-trans prostene |
| 583 | 1-trans-tri-n-butylstannyl-4-trifluoromethyl-4-trimethylsilyloxy-1-nonene | 2-[7-phenoxyacetyl heptyl] cyclopent-2-en-1-one | dl-16-hydroxy-1-phenoxymethyl-1,9-dioxo-16-trifluoromethyl-20-methyl-2-homo-13-trans prostene |
| 584 | 1-trans-tri-n-butylstannyl-4-chloromethyl-4-trimethylsilyloxy-1-nonene | 2-[7-phenoxyacetyl heptyl] cyclopent-2-en-1-one | dl-16-hydroxy-1-phenoxymethyl-1,9-dioxo-16-chloromethyl-20-methyl-2-homo-13-trans prostene |
| | 1-trans-tri-n-butylstannyl-4-trimethylsilyloxymethyl-4-trimethylsilyloxy-1-nonene | 2-[7-phenoxyacetyl heptyl] cyclopent-2-en-1-one | dl-16-hydroxy-1-phenoxymethyl-1,9-dioxo-16-hydroxymethyl-20-methyl-2-homo-13-trans prostene |
| EXAMPLE | VINYL IODIDE | CYCLOPENTENONE | PRODUCT PROSTAGLANDIN OF THE 11-DEOXY PGE1 SERIES |
| 585 | 1-trans-iodo-3-triphenylmethoxy-1-decene | 2-[7-phenoxyacetyl heptyl] cyclopent-2-en-1-one | dl-15a-hydroxy-1-phenoxymethyl-1,9-dioxo-20-ethyl-2-homo-13-trans prostene |
| 586 | 1-trans-iodo-3-methyl-3-trimethylsilyloxy-1-decene | 2-[7-phenoxyacetyl heptyl] cyclopent-2-en-1-one | dl-15a-hydroxy-1-phenoxymethyl-1,9-dioxo-15-methyl-20-ethyl-2-homo-13-trans prostene |
| 587 | 1-trans-iodo-4,4-dimethyl-3-trimethylsilyloxy-1-decene | 2-[7-phenoxyacetyl heptyl] cyclopent-2-en-1-one | dl-15a-hydroxy-1-phenoxymethyl-1,9-dioxo-16,16-dimethyl-20-ethyl-2-homo-13-trans prostene |
| 588 | 1-trans-iodo-4,4-trimethylene-3-trimethylsilyloxy-1-decene | 2-[7-phenoxyacetyl heptyl] cyclopent-2-en-1-one | dl-15a-hydroxy-1-phenoxymethyl-1,9-dioxo-16,16-trimethylene-20-ethyl-2-homo-13-trans prostene |
| EXAMPLE | VINYL TIN | CYCLOPENTENONE | PRODUCT PROSTAGLANDIN OF THE 11-DEOXY PGE1 SERIES |
| 589 | 1-trans-tri-n-butylstannyl-3-vinyl-3-trimethylsilyloxy-1-decene | 2-[7-phenoxyacetyl heptyl] | dl-15a-hydroxy-1-phenoxymethyl-1,9-dioxo-15-vinyl-20-ethyl-2-homo-13-trans prostene |

TABLE VIII-continued

| EXAMPLE | VINYL IODIDE | CYCLOPENTENONE | PRODUCT PROSTAGLANDIN OF THE 11-DEOXY PGE1 SERIES |
|---|---|---|---|
| 590 | 1-trans-iodo-4-triphenylmethoxy-1-decene | 2-[7-phenoxyacetyl heptyl] cyclopent-2-en-1-one | dl-16-hydroxy-1-phenoxymethyl-1,9-dioxo-20-ethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 591 | 1-trans-tri-n-butylstannyl-4-methyl-4-trimethylsilyloxy-1-decene | 2-[7-phenoxyacetyl heptyl] cyclopent-2-en-1-one | dl-16-hydroxy-1-phenoxymethyl-1,9-dioxo-16-methyl-20-ethyl-2-homo-13-trans prostene |
| 592 | 1-trans-tri-n-butylstannyl-5-methyl-4-trimethylsilyloxy-1-decene | 2-[7-phenoxyacetyl heptyl] cyclopent-2-en-1-one | dl-16-hydroxy-1-phenoxymethyl-1,9-dioxo-17-methyl-20-ethyl-2-homo-13-trans prostene |
| 593 | 1-trans-tri-n-butylstannyl-4-vinyl-4-trimethylsilyloxy-1-decene | 2-[7-phenoxyacetyl heptyl] cyclopent-2-en-1-one | dl-16-hydroxy-1-phenoxymethyl-1,9-dioxo-16-vinyl-20-ethyl-2-homo-13-trans prostene |
| 594 | 1-trans-tri-n-butylstannyl-4-trimethylsilylethynyl-4-trimethylsilyloxy-1-decene | 2-[7-phenoxyacetyl heptyl] cyclopent-2-en-1-one | dl-16-hydroxy-1-phenoxymethyl-1,9-dioxo-16-ethynyl-20-ethyl-2-homo-13-trans prostene |
| 595 | 1-trans-tri-n-butylstannyl-5-methylene-4-triethylsilyloxy-1-decene | 2-[7-phenoxyacetyl heptyl] cyclopent-2-en-1-one | dl-16-hydroxy-1-phenoxymethyl-1,9-dioxo-17-methylene-20-ethyl-2-homo-13-trans prostene |
| 596 | 1-trans-tri-n-butylstannyl-4-methyl-5-methylene-4-trimethylsilyloxy-1-decene | 2-[7-phenoxyacetyl heptyl] cyclopent-2-en-1-one | dl-16-hydroxy-1-phenoxymethyl-1,9-dioxo-16-methyl-17-methylene-20-ethyl-2-homo-13-trans prostene |
| 597 | 1-trans-tri-n-butylstannyl-4-dimethoxymethyl-4-trimethylsilyloxy-1-decene | 2-[7-phenoxyacetyl heptyl] cyclopent-2-en-1-one | dl-16-hydroxy-1-phenoxymethyl-1,9-dioxo-16-formyl-20-ethyl-2-homo-13-trans prostene |
| 598 | 1-trans-tri-n-butylstannyl-4-fluoromethyl-4-trimethylsilyloxy-1-decene | 2-[7-phenoxyacetyl heptyl] cyclopent-2-en-1-one | dl-16-hydroxy-1-phenoxymethyl-1,9-dioxo-16-fluoromethyl-20-ethyl-2-homo-13-trans prostene |
| 599 | 1-trans-tri-n-butylstannyl-4-difluoromethyl-4-trimethylsilyloxy-1-decene | 2-[7-phenoxyacetyl heptyl] cyclopent-2-en-1-one | dl-16-hydroxy-1-phenoxymethyl-1,9-dioxo-16-difluoromethyl-20-ethyl-2-homo-13-trans prostene |
| 600 | 1-trans-tri-n-butylstannyl-4-trifluoromethyl-4-trimethylsilyloxy-1-decene | 2-[7-phenoxyacetyl heptyl] cyclopent-2-en-1-one | dl-16-hydroxy-1-phenoxymethyl-1,9-dioxo-16-trifluoromethyl-20-ethyl-2-homo-13-trans prostene |
| 601 | 1-trans-tri-n-butylstannyl-4-chloromethyl-4-trimethylsilyloxy-1-decene | 2-[7-phenoxyacetyl heptyl] cyclopent-2-en-1-one | dl-16-hydroxy-1-phenoxymethyl-1,9-dioxo-16-chloromethyl-20-ethyl-2-homo-13-trans prostene |
| 602 | 1-trans-tri-n-butylstannyl-4-trimethylsilyloxymethyl-4-trimethylsilyloxy-1-decene | 2-[7-phenoxyacetyl heptyl] cyclopent-2-en-1-one | dl-16-hydroxy-1-phenoxymethyl-1,9-dioxo-16-hydroxymethyl-20-ethyl-2-homo-13-trans prostene |

TABLE IX

| EXAMPLE | VINYL TIN | CYCLOPENTENONE | PRODUCT PROSTAGLANDIN OF THE PGE1 SERIES |
|---|---|---|---|
| 1 | 1-trans-tri-n-butylstannyl-7-thia-4-triethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-19-thia-2-nor-13-trans prostene |
| 2 | 1-trans-tri-n-butylstannyl-4-methyl-7-thia-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-methyl-19-thia-2-nor-13-trans prostene |
| 3 | 1-trans-tri-n-butylstannyl-7-oxa-4-triethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-19-oxa-2-nor-13-trans prostene |
| 4 | 1-trans-tri-n-butylstannyl-4-methyl-7-oxa-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-methyl-19-oxa-2-nor-13-trans prostene |
| 5 | 1-trans-tri-n-butylstannyl-4-bromomethyl-4-trimethylsilyloxy-1-heptene | 2-[5-phenoxyacetyl pentyl]-4-trimethylsiloxy cyclopent-2-en-1-one | dl-11a,16-dihydroxy-1-phenoxymethyl-1,9-dioxo-16-bromomethyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 6 | 1-trans-iodo-4-allenyl-4-trimethylsilyloxy-1-heptene | 2-[5-phenoxyacetyl pentyl]-4-trimethylsiloxy cyclopent-2-en-1-one | dl-11a,16-dihydroxy-1-phenoxymethyl-1,9-dioxo-16-allenyl-20-nor-2-nor-13-trans prostene |

| EXAMPLE | VINYL TIN | CYCLOPENTENONE | PRODUCT PROSTAGLANDIN OF THE PGE1 SERIES |
|---|---|---|---|
| 7 | 1-trans-tri-n-butylstannyl-4-bromomethyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-bromomethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 8 | 1-trans-iodo-4-allenyl-4-trimethylsilyloxy-1-octene | 2-[5-phenoxyacetyl pentyl]-4-trimethylsiloxy cyclopent-2-en-1-one | dl-11a,16-dihydroxy-1-phenoxymethyl-1,9-dioxo-16-allenyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 9 | 1-trans-tri-n-butylstannyl-4-bromomethyl-4-trimethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-16-bromomethyl-20-methyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 10 | 1-trans-iodo-4-allenyl-4-trimethylsilyloxy-1-nonene | 2-[5-phenoxyacetyl pentyl]-4-trimethylsiloxy cyclopent-2-en-1-one | dl-11a,16-dihydroxy-1-phenoxymethyl-1,9-dioxo-16-allenyl-20-methyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 11 | 1-trans-tri-n-butylstannyl-4-bromomethyl-4-trimethylsilyloxy-1-decene | 2-[5-phenoxyacetyl pentyl]-4-trimethylsiloxy | dl-11a,16-dihydroxy-1-phenoxymethyl-1,9-dioxo-16-bromomethyl-20-ethyl-2-nor-13-trans prostene |

TABLE IX-continued

| EXAMPLE | VINYL IODIDE | CYCLOPENTENONE | PRODUCT PROSTAGLANDIN OF THE PGE1 SERIES |
|---|---|---|---|
| | | cyclopent-2-en-1-one | |
| 12 | 1-trans-iodo-4-allenyl-4-trimethylsilyloxy-1-decene | 2-[5-phenoxyacetyl pentyl]-4-trimethylsilyloxy cyclopent-2-en-1-one | dl-11a,16-dihydroxy-1-phenoxymethyl-1,9-dioxo-16-allenyl-20-ethyl-2-nor-13-trans prostene |
| EXAMPLE | VINYL TIN | CYCLOPENTENONE | PRODUCT PROSTAGLANDIN OF THE PGE1 SERIES |
| 13 | 1-trans-tri-n-butylstannyl-7-thia-4-triethylsilyloxy-1-octene | 2-[6-phenoxyacetyl hexyl]-9 -4-trimethylsiloxy cyclopent-2-en-1-one | dl-11a,16-dihydroxy-1-phenoxymethyl-1,9-dioxo-19-thia-13-trans prostene |
| 14 | 1-trans-tri-n-butylstannyl-4-methyl-7-thia-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-methyl-19-thia-13-trans prostene |
| 15 | 1-trans-tri-n-butylstannyl-7-oxa-4-triethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-19-oxa-13-trans prostene |
| 16 | 1-trans-tri-n-butylstannyl-4-methyl-7-oxa-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-methyl-19-oxa-13-trans prostene |
| 17 | 1-trans-tri-n-butylstannyl-4-bromomethyl-4-trimethylsilyloxy-1-heptene | 2-[6-phenoxyacetyl hexyl]-4-trimethylsiloxy cyclopent-2-en-1-one | dl-11a,16-dihydroxy-1-phenoxymethyl-1,9-dioxo-16-bromomethyl-20-nor-13-trans prostene |
| EXAMPLE | VINYL IODIDE | CYCLOPENTENONE | PRODUCT PROSTAGLANDIN OF THE PGE1 SERIES |
| 18 | 1-trans-iodo-4-allenyl-4-trimethylsilyloxy-1-heptene | 2-[6-phenoxyacetyl hexyl]-4-trimethylsiloxy cyclopent-2-en-1-one | dl-11a,16-dihydroxy-1-phenoxymethyl-1,9-dioxo-16-allenyl-20-nor-13-trans prostene |
| EXAMPLE | VINYL TIN | CYCLOPENTENONE | PRODUCT PROSTAGLANDIN OF THE PGE1 SERIES |
| 19 | 1-trans-tri-n-butylstannyl-4-bromomethyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-bromomethyl-13-trans prostene |
| EXAMPLE | VINYL IODIDE | CYCLOPENTENONE | PRODUCT PROSTAGLANDIN OF THE PGE1 SERIES |
| 20 | 1-trans-iodo-4-allenyl-4-trimethylsilyloxy-1-octene | 2-[6-phenoxyacetyl hexyl]-4-trimethylsiloxy cyclopent-2-en-1-one | dl-11a,16-dihydroxy-1-phenoxymethyl-1,9-dioxo-16-allenyl-13-trans prostene |
| EXAMPLE | VINYL TIN | CYCLOPENTENONE | PRODUCT PROSTAGLANDIN OF THE PGE1 SERIES |
| 21 | 1-trans-tri-n-butylstannyl-4-bromomethyl-4-trimethylsilyloxy-1-nonene | 2-[6-phenoxyacetyl hexyl]-4-trimethylsiloxy cyclopent-2-en-1-one | dl-11a,16-dihydroxy-1-phenoxymethyl-1,9-dioxo-16-bromomethyl-20-methyl-13-trans prostene |
| EXAMPLE | VINYL IODIDE | CYCLOPENTENONE | PRODUCT PROSTAGLANDIN OF THE PGE1 SERIES |
| 22 | 1-trans-iodo-4-allenyl- | 2-[6-phenoxyacetyl | dl-11a,16-dihydroxy-1-phenoxymethyl-1,9-dioxo-16-allenyl- |

TABLE IX-continued

| | | | |
|---|---|---|---|
| | | 4-trimethylsilyloxy-1-nonene | hexyl]-4-trimethylsilyloxy cyclopent-2-en-1-one | 20-methyl-13-trans prostene |
| EXAMPLE 23 | VINYL TIN | 1-trans-tri-n-butylstannyl-4-bromomethyl-4-trimethylsilyloxy-1-decene | CYCLOPENTENONE 2-[6-phenoxyacetyl hexyl]-4-trimethylsilyloxy cyclopent-2-en-1-one | PRODUCT PROSTAGLANDIN OF THE PGE1 SERIES dl-11a,16-dihydroxy-1-phenoxymethyl-1,9-dioxo-16-bromomethyl-20-ethyl-13-trans prostene |
| EXAMPLE 24 | VINYL IODIDE | 1-trans-iodo-4-allenyl-4-trimethylsilyloxy-1-decene | CYCLOPENTENONE 2-[6-phenoxyacetyl hexyl]-4-trimethylsilyloxy cyclopent-2-en-1-one | PRODUCT PROSTAGLANDIN OF THE PGE1 SERIES dl-11a,16-dihydroxy-1-phenoxymethyl-1,9-dioxo-16-allenyl-20-ethyl-13-trans prostene |
| EXAMPLE 25 | VINYL TIN | 1-trans-tri-n-butylstannyl-7-thia 4-triethylsilyloxy-1-octene | CYCLOPENTENONE 2-[7-phenoxyacetyl heptyl]-4-trimethylsilyloxy cyclopent-2-en-1-one | PRODUCT PROSTAGLANDIN OF THE PGE1 SERIES dl-11a,16-dihydroxy-1-phenoxymethyl-1,9-dioxo-19-thia-2-homo-13-trans prostene |
| 26 | | 1-trans-tri-n-butylstannyl-4-methyl-7-thia 4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-16-methyl-19-thia-2-homo-13-trans prostene |
| 27 | | 1-trans-tri-n-butylstannyl-7-oxa 4-triethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-19-oxa-2-homo-13-trans prostene |
| 28 | | 1-trans-tri-n-butylstannyl-4-methyl-7-oxa 4-trimethylsilyloxy-1-octene | 2-[7-phenoxyacetyl heptyl]-4-trimethylsilyloxy cyclopent-2-en-1-one | dl-11a,16-dihydroxy-1-phenoxymethyl-1,9-dioxo-16-methyl-19-oxa-2-homo-13-trans prostene |
| 29 | | 1-trans-tri-n-butylstannyl-4-bromomethyl-4-trimethylsilyloxy-1-heptene | 2-[7-phenoxyacetyl heptyl]-4-trimethylsilyloxy cyclopent-2-en-1-one | dl-11a,16-dihydroxy-1-phenoxymethyl-1,9-dioxo-16-bromomethyl-20-nor-2-homo-13-trans prostene |
| EXAMPLE 30 | VINYL IODIDE | 1-trans-iodo-4-allenyl-4-trimethylsilyloxy-1-heptene | CYCLOPENTENONE 2-[7-phenoxyacetyl heptyl]-4-trimethylsilyloxy cyclopent-2-en-1-one | PRODUCT PROSTAGLANDIN OF THE PGE1 SERIES dl-11a,16-dihydroxy-1-phenoxymethyl-1,9-dioxo-16-allenyl-20-nor-2-homo-13-trans prostene |
| EXAMPLE 31 | VINYL TIN | 1-trans-tri-n-butylstannyl-4-bromomethyl-4-trimethylsilyloxy-1-octene | CYCLOPENTENONE 2-[7-phenoxyacetyl heptyl]-4-trimethylsilyloxy cyclopent-2-en-1-one | PRODUCT PROSTAGLANDIN OF THE PGE1 SERIES dl-11a,16-dihydroxy-1-phenoxymethyl-1,9-dioxo-16-bromomethyl-2-homo-13-trans prostene |
| EXAMPLE 32 | VINYL IODIDE | 1-trans-iodo-4-allenyl-4-trimethylsilyloxy-1-octene | CYCLOPENTENONE 2-[7-phenoxyacetyl heptyl]-4-trimethylsilyloxy cyclopent-2-en-1-one | PRODUCT PROSTAGLANDIN OF THE PGE1 SERIES dl-11a,16-dihydroxy-1-phenoxymethyl-1,9-dioxo-16-allenyl-2-homo-13-trans prostene |
| EXAMPLE | VINYL TIN | | CYCLOPENTENONE | PRODUCT PROSTAGLANDIN OF THE PGE1 SERIES |

TABLE IX-continued

| | | | |
|---|---|---|---|
| 33 | 1-trans-tri-n-butylstannyl-4-bromomethyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-bromomethyl-20-methyl-2-homo-13-trans prostene |
| EXAMPLE | VINYL IODIDE | | PRODUCT PROSTAGLANDIN OF THE PGE1 SERIES |
| 34 | 1-trans-iodo-4-allenyl-4-trimethylsilyloxy-1-nonene | 2-[7-phenoxyacetyl heptyl]-4-trimethylsilyloxy cyclopent-2-en-1-one | dl-11a,16-dihydroxy-1-phenoxymethyl-1,9-dioxo-16-allenyl-20-methyl-2-homo-13-trans prostene |
| EXAMPLE | VINYL TIN | | PRODUCT PROSTAGLANDIN OF THE PGE1 SERIES |
| 35 | 1-trans-tri-n-butylstannyl-4-bromomethyl-4-trimethylsilyloxy-1-decene | 2-[7-phenoxyacetyl heptyl]-4-trimethylsilyloxy cyclopent-2-en-1-one | dl-11a,16-dihydroxy-1-phenoxymethyl-1,9-dioxo-16-bromomethyl-20-ethyl-2-homo-13-trans prostene |
| EXAMPLE | VINYL IODIDE | | PRODUCT PROSTAGLANDIN OF THE PGE1 SERIES |
| 36 | 1-trans-iodo-4-allenyl-4-trimethylsilyloxy-1-decene | 2-[7-phenoxyacetyl heptyl]-4-trimethylsilyloxy cyclopent-2-en-1-one | dl-11a,16-dihydroxy-1-phenoxymethyl-1,9-dioxo-16-allenyl-20-ethyl-2-homo-13-trans prostene |
| EXAMPLE | VINYL TIN | | PRODUCT PROSTAGLANDIN OF THE PGE1 SERIES |
| 37 | 1-trans-tri-n-butylstannyl-7-thia-4-triethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-19-thia-13-trans prostene |
| 38 | 1-trans-tri-n-butylstannyl-4-methyl-7-thia-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-19-thia-13-trans prostene |
| 39 | 1-trans-tri-n-butylstannyl-7-oxa-4-triethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-19-oxa-13-trans prostene |
| 40 | 1-trans-tri-n-butylstannyl-4-methyl-7-oxa-4-trimethylsilyloxy-1-octene | 2-[6-phenoxyacetyl hexyl]-4R-trimethylsiloxy cyclopent-2-en-1-one | nat-11a,16-dihydroxy-1-phenoxymethyl-1,9-dioxo-16-methyl-19-oxa-13-trans prostene |
| 41 | 1-trans-tri-n-butylstannyl-4-bromomethyl-4-trimethylsilyloxy-1-heptene | 2-[6-phenoxyacetyl hexyl]4R-trimethylsiloxy cyclopent-2-en-1-one | nat-11a,16-dihydroxy-1-phenoxymethyl-1,9-dioxo-16-bromomethyl-20-nor-13-trans prostene |
| EXAMPLE | VINYL IODIDE | | PRODUCT PROSTAGLANDIN OF THE PGE1 SERIES |
| 42 | 1-trans-iodo-4-allenyl-4-trimethylsilyloxy-1-heptene | 2-[6-phenoxyacetyl hexyl]-4R-trimethylsiloxy cyclopent-2-en-1-one | nat-11a,16-dihydroxy-1-phenoxymethyl-1,9-dioxo-16-allenyl-20-nor-13-trans prostene |
| EXAMPLE | VINYL TIN | | PRODUCT PROSTAGLANDIN OF THE PGE1 SERIES |
| 43 | 1-trans-tri-n-butylstannyl-4-bromomethyl-4-trimethylsilyloxy-1-octene | 2-[6-phenoxyacetyl hexyl]4R-trimethylsiloxy cyclopent-2-en-1-one | nat-11a,16-dihydroxy-1-phenoxymethyl-1,9-dioxo-16-bromomethyl-13-trans prostene |
| | | | PRODUCT PROSTAGLANDIN OF |

TABLE IX-continued

| EXAMPLE | VINYL IODIDE / VINYL TIN | CYCLOPENTENONE | PRODUCT PROSTAGLANDIN OF THE PGE1 SERIES |
|---|---|---|---|
| EXAMPLE 44 | VINYL IODIDE<br>1-trans-iodo-4-allenyl-4-trimethylsilyloxy-1-octene | 2-[6-phenoxyacetyl hexyl]4R-trimethylsiloxy cyclopent-2-en-1-one | THE PGE1 SERIES<br>nat-11a,16-dihydroxy-1-phenoxymethyl-1,9-dioxo-16-allenyl-13-trans prostene |
| EXAMPLE 45 | VINYL TIN<br>1-trans-tri-n-butylstannyl-4-bromomethyl-4-trimethylsilyloxy-1-nonene | 2-[6-phenoxyacetyl hexyl]-4R-trimethylsiloxy cyclopent-2-en-1-one | PRODUCT PROSTAGLANDIN OF THE PGE1 SERIES<br>nat-11a,16-dihydroxy-1-phenoxymethyl-1,9-dioxo-16-bromomethyl-20-methyl-13-trans prostene |
| EXAMPLE 46 | VINYL IODIDE<br>1-trans-iodo-4-allenyl-4-trimethylsilyloxy-1-nonene | 2-[6-phenoxyacetyl hexyl]-4R-trimethylsiloxy cyclopent-2-en-1-one | PRODUCT PROSTAGLANDIN OF THE PGE1 SERIES<br>nat-11a,16-dihydroxy-1-phenoxymethyl-1,9-dioxo-16-allenyl-20-methyl-13-trans prostene |
| EXAMPLE 47 | VINYL TIN<br>1-trans-tri-n-butylstannyl-4-bromomethyl-4-trimethylsilyloxy-1-decene | 2-[6-phenoxyacetyl hexyl]-4R-trimethylsiloxy cyclopent-2-en-1-one | PRODUCT PROSTAGLANDIN OF THE PGE1 SERIES<br>nat-11a,16-dihydroxy-1-phenoxymethyl-1,9-dioxo-16-bromomethyl-20-ethyl-13-trans prostene |
| EXAMPLE 48 | VINYL IODIDE<br>1-trans-iodo-4-allenyl-4-trimethylsilyloxy-1-decene | 2-[6-phenoxyacetyl hexyl]-4R-trimethylsiloxy cyclopent-2-en-1-one | PRODUCT PROSTAGLANDIN OF THE PGE1 SERIES<br>nat-11a,16-dihydroxy-1-phenoxymethyl-1,9-dioxo-16-allenyl-20-ethyl-13-trans prostene |
| EXAMPLE 49 | VINYL TIN<br>1-trans-tri-n-butylstannyl-7-thia 4-triethylsilyloxy-1-octene | 2-[5-phenoxyacetyl phenyl] cyclopent-2-en-1-one | PRODUCT PROSTAGLANDIN OF THE PGE1 SERIES<br>dl-16-hydroxy-1-phenoxymethyl-1,9-dioxo-19-thia-2-nor-13-trans prostene |
| EXAMPLE 50 | VINYL TIN<br>1-trans-tri-n-butylstannyl-4-methyl-7-thia 4-trimethylsilyloxy-1-octene | 2-[5-phenoxyacetyl phenyl] cyclopent-2-en-1-one | PRODUCT PROSTAGLANDIN OF THE 11-DEOXY PGE1 SERIES<br>dl-16-hydroxy-1-phenoxymethyl-1,9-dioxo-16-methyl-19-thia-2-nor-13-trans prostene |
| EXAMPLE 51 | 1-trans-tri-n-butylstannyl-7-oxa 4-triethylsilyloxy-1-octene | 2-[5-phenoxyacetyl phenyl] cyclopent-2-en-1-one | dl-16-hydroxy-1-phenoxymethyl-1,9-dioxo-19-oxa-2-nor-13-trans prostene |
| EXAMPLE 52 | 1-trans-tri-n-butylstannyl-4-methyl-7-oxa 4-trimethylsilyloxy-1-octene | 2-[5-phenoxyacetyl phenyl] cyclopent-2-en-1-one | dl-16-hydroxy-1-phenoxymethyl-1,9-dioxo-16-methyl-19-oxa-2-nor-13-trans prostene |
| EXAMPLE 53 | 1-trans-tri-n-butylstannyl-4-bromomethyl-4-trimethylsilyloxy-1-heptene | 2-[5-phenoxyacetyl phenyl] cyclopent-2-en-1-one | dl-16-hydroxy-1-phenoxymethyl-1,9-dioxo-16-bromomethyl-20-nor-2-nor-13-trans prostene |
| EXAMPLE 54 | VINYL IODIDE<br>1-trans-iodo-4-allenyl- | 2-[5-phenoxyacetyl | PRODUCT PROSTAGLANDIN OF THE 11-DEOXY PGE1 SERIES<br>dl-16-hydroxy-1-phenoxymethyl-1,9-dioxo-16-allenyl- |

TABLE IX-continued

| EXAMPLE | | | PRODUCT |
|---|---|---|---|
| | | phenyl] cyclopent-2-en-1-one | 20-nor-2-nor-13-trans prostene |
| | | | PRODUCT PROSTAGLANDIN OF THE 11-DEOXY PGE1 SERIES |
| EXAMPLE 55 | VINYL TIN | 2-[5-phenoxyacetyl phenyl] cyclopent-2-en-1-one | dl-16-hydroxy-1-phenoxymethyl-1,9-dioxo-16-bromomethyl-2-nor-13-trans prostene |
| | 1-trans-tri-n-butylstannyl-4-bromomethyl-4-trimethylsilyloxy-1-ocetene | | PRODUCT PROSTAGLANDIN OF THE 11-DEOXY PGE1 SERIES |
| EXAMPLE 56 | VINYL IODIDE | 2-[5-phenoxyacetyl phenyl] cyclopent-2-en-1-one | dl-16-hydroxy-1-phenoxymethyl-1,9-dioxo-16-allenyl-2-nor-13-trans prostene |
| | 1-trans-iodo-4-allenyl-4-trimethylsilyloxy-1-ocetene | | PRODUCT PROSTAGLANDIN OF THE 11-DEOXY PGE1 SERIES |
| EXAMPLE 57 | VINYL TIN | 2-[5-phenoxyacetyl phenyl] cyclopent-2-en-1-one | dl-16-hydroxy-1-phenoxymethyl-1,9-dioxo-16-bromomethyl-20-methyl-2-nor-13-trans prostene |
| | 1-trans-tri-n-butylstannyl-4-bromomethyl-4-trimethylsilyloxy-1-nonene | | PRODUCT PROSTAGLANDIN OF THE 11-DEOXY PGE1 SERIES |
| EXAMPLE 58 | VINYL IODIDE | 2-[5-phenoxyacetyl phenyl] cyclopent-2-en-1-one | dl-16-hydroxy-1-phenoxymethyl-1,9-dioxo-16-allenyl-20-methyl-2-nor-13-trans prostene |
| | 1-trans-iodo-4-allenyl-4-trimethylsilyloxy-1-nonene | | PRODUCT PROSTAGLANDIN OF THE 11-DEOXY PGE1 SERIES |
| EXAMPLE 59 | VINYL TIN | 2-[5-phenoxyacetyl phenyl] cyclopent-2-en-1-one | dl-16-hydroxy-1-phenoxymethyl-1,9-dioxo-16-bromomethyl-20-ethyl-2-nor-13-trans prostene |
| | 1-trans-tri-n-butylstannyl-4-bromomethyl-4-trimethylsilyloxy-1-decene | | PRODUCT PROSTAGLANDIN OF THE 11-DEOXY PGE1 SERIES |
| EXAMPLE 60 | VINYL IODODE | 2-[5-phenoxyacetyl phenyl] cyclopent-2-en-1-one | dl-16-hydroxy-1-phenoxymethyl-1,9-dioxo-16-allenyl-20-etyyl-2-nor-13-trans prostene |
| | 1-trans-iodo-4-allenyl-4-trimethylsilyloxy-1-decene | | PRODUCT PROSTAGLANDIN OF THE 11-DEOXY PGE1 SERIES |
| EXAMPLE 61 | VINYL TIN | 2-[6-phenoxyacetyl hexyl] cyclopent-2-en-1-one | dl-16-hydroxy-1-phenoxymethyl-1,9-dioxo-19-thia-13-trans prostene |
| | 1-trans-tri-n-butylstannyl-7-thia-4-triethylsiloxy-1-octene | | |
| EXAMPLE 62 | | 2-[6-phenoxyacetyl hexyl] cyclopent-2-en-1-one | dl-16-hydroxy-1-phenoxymethyl-1,9-dioxo-16-methyl-19-thia-13-trans prostene |
| | 1-trans-tri-n-butylstannyl-4-methyl-7-thia-4-trimethylsilyloxy-1-ocetene | | |
| EXAMPLE 63 | | 2-[6-phenoxyacetyl hexyl] cyclopent-2-en-1-one | dl-16-hydroxy-1-phenoxymethyl-1,9-dioxo-19-oxa-13-trans prostene |
| | 1-trans-tri-n-butylstannyl-7-oxa-4-triethylsilyloxy-1-octene | | |
| EXAMPLE 64 | | 2-[6-phenoxyacetyl hexyl] cyclopent-2-en-1-one | dl-16-hydroxy-1-phenoxymethyl-1,9-dioxo-16-methyl-19-oxa-13-trans prostene |
| | 1-trans-tri-n-butylstannyl-4-methyl-7-oxa-4-trimethylsilyloxy-1-ocetene | | |

TABLE IX-continued

| | | | | |
|---|---|---|---|---|
| 65 | 1-trans-tri-n-butylstannyl-4-bromomethyl-4-trimethylsilyloxy-1-heptene | 2-[6-phenoxyacetyl hexyl] cyclopent-2-en-1-one | | dl-16-hydroxy-1-phenoxymethyl-1,9-dioxo-16-bromomethyl-20-nor-13-trans prostene |
| EXAMPLE | VINYL IODIDE | CYCLOPENTENONE | | PRODUCT PROSTAGLANDIN OF THE 11-DEOXY PGE1 SERIES |
| 66 | 1-trans-iodo-4-allenyl-4-trimethylsilyloxy-1-heptene | 2-[6-phenoxyacetyl hexyl] cyclopent-2-en-1-one | | dl-16-hydroxy-1-phenoxymethyl-1,9-dioxo-16-allenyl-20-nor-13-trans prostene |
| EXAMPLE | VINYL TIN | CYCLOPENTENONE | | PRODUCT PROSTAGLANDIN OF THE 11-DEOXY PGE1 SERIES |
| 67 | 1-trans-tri-n-butylstannyl-4-bromomethyl-4-trimethylsilyloxy-1-octene | 2-[6-phenoxyacetyl hexyl] cyclopent-2-en-1-one | | dl-16-hydroxy-1-phenoxymethyl-1,9-dioxo-16-bromomethyl-13-trans prostene |
| EXAMPLE | VINYL IODIDE | CYCLOPENTENONE | | PRODUCT PROSTAGLANDIN OF THE 11-DEOXY PGE1 SERIES |
| 68 | 1-trans-iodo-4-allenyl-4-trimethylsilyloxy-1-octene | 2-[6-phenoxyacetyl hexyl] cyclopent-2-en-1-one | | dl-16-hydroxy-1-phenoxymethyl-1,9-dioxo-16-allenyl-13-trans prostene |
| EXAMPLE | VINYL TIN | CYCLOPENTENONE | | PRODUCT PROSTAGLANDIN OF THE 11-DEOXY PGE1 SERIES |
| 69 | 1-trans-tri-n-butylstannyl-4-bromomethyl-4-trimethylsilyloxy-1-nonene | 2-[6-phenoxyacetyl hexyl] cyclopent-2-en-1-one | | dl-16-hydroxy-1-phenoxymethyl-1,9-dioxo-16-bromomethyl-20-methyl-13-trans prostene |
| EXAMPLE | VINYL IODIDE | CYCLOPENTENONE | | PRODUCT PROSTAGLANDIN OF THE 11-DEOXY PGE1 SERIES |
| 70 | 1-trans-iodo-4-allenyl-4-trimethylsilyloxy-1-nonene | 2-[6-phenoxyacetyl hexyl] cyclopent-2-en-1-one | | dl-16-hydroxy-1-phenoxymethyl-1,9-dioxo-16-allenyl-20-methyl-13-trans prostene |
| EXAMPLE | VINYL TIN | CYCLOPENTENONE | | PRODUCT PROSTAGLANDIN OF THE 11-DEOXY PGE1 SERIES |
| 71 | 1-trans-tri-n-butylstannyl-4-bromomethyl-4-trimethylsilyloxy-1-decene | 2-[6-phenoxyacetyl hexyl] cyclopent-2-en-1-one | | dl-16-hydroxy-1-phenoxymethyl-1,9-dioxo-16-bromomethyl-20-ethyl-13-trans prostene |
| EXAMPLE | VINYL IODIDE | CYCLOPENTENONE | | PRODUCT PROSTAGLANDIN OF THE 11-DEOXY PGE1 SERIES |
| 72 | 1-trans-iodo-4-allenyl-4-trimethylsilyloxy-1-decene | 2-[6-phenoxyacetyl hexyl] cyclopent-2-en-1-one | | dl-16-hydroxy-1-phenoxymethyl-1,9-dioxo-16-allenyl-20-ethyl-13-trans prostene |
| EXAMPLE | VINYL TIN | CYCLOPENTENONE | | PRODUCT PROSTAGLANDIN OF THE 11-DEOXY PGE1 SERIES |
| 73 | 1-trans-tri-n-butylstannyl-7-thia-4-trimethylsilyloxy-1-octene | 2-[7-phenoxyacetyl heptyl] cyclopent-2-en-1-one | | dl-16-hydroxy-1-phenoxymethyl-1,9-dioxo-19-thia-2-homo-13-trans prostene |
| 74 | 1-trans-tri-n-butylstannyl-4-methyl-7-thia-4-trimethylsilyloxy-1-octene | 2-[7-phenoxyacetyl heptyl] | | dl-16-hydroxy-1-phenoxymethyl-1,9-dioxo-16-methyl-19-thia-2-homo-13-trans prostene |

TABLE IX-continued

| | | | |
|---|---|---|---|
| 75 | 1-trans-tri-n-butylstannyl-7-oxa-4-trimethylsilyloxy-1-octene | cyclopent-2-en-1-one 2-[7-phenoxyacetyl heptyl] | dl-16-hydroxy-1-phenoxymethyl-1,9-dioxo-19-oxa-2-homo-13-trans prostene |
| 76 | 1-trans-tri-n-butylstannyl-4-methyl-7-oxa-4-trimethylsilyloxy-1-octene | cyclopent-2-en-1-one 2-[7-phenoxyacetyl heptyl] | dl-16-hydroxy-1-phenoxymethyl-1,9-dioxo-16-methyl-19-oxa-2-homo-13-trans prostene |
| 77 | 1-trans-tri-n-butylstannyl-4-bromomethyl-4-trimethylsilyloxy-1-heptene | cyclopent-2-en-1-one 2-[7-phenoxyacetyl heptyl] | dl-16-hydroxy-1-phenoxymethyl-1,9-dioxo-16-bromomethyl-20-nor-2-homo-13-trans prostene |
| EXAMPLE 78 | VINYL IODIDE 1-trans-iodo-4-allenyl-4-trimethylsilyloxy-1-heptene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-allenyl-20-nor-2-homo-13-trans prostene |
| EXAMPLE 79 | VINYL TIN 1-trans-tri-n-butylstannyl-4-bromomethyl-4-trimethylsilyloxy-1-octene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-bromomethyl-2-homo-13-trans prostene |
| EXAMPLE 80 | VINYL IODIDE 1-trans-iodo-4-allenyl-4-trimethylsilyloxy-1-octene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-allenyl-2-homo-13-trans prostene |
| EXAMPLE 81 | VINYL TIN 1-trans-tri-n-butylstannyl-4-bromomethyl-4-trimethylsilyloxy-1-nonene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-bromomethyl-20-methyl-2-homo-13-trans prostene |
| EXAMPLE 82 | VINYL IODIDE 1-trans-iodo-4-allenyl-4-trimethylsilyloxy-1-nonene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-allenyl-20-methyl-2-homo-13-trans prostene |
| EXAMPLE 83 | VINYYL TIN 1-trans-tri-n-butylstannyl-4-bromomethyl-4-trimethylsilyloxy-1-decene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-bromomethyl-20-ethyl-2-homo-13-trans prostene |
| EXAMPLE 84 | VINYL IODIDE 1-trans-iodo-4-allenyl-4-trimethylsilyloxy-1-decene | CYCLOPENTENONE 2-[7-phenoxyacetyl heptyl] cyclopent-2-en-1-one | PRODUCT PROSTAGLANDIN OF THE 11-DEOXY PGE1 SERIES dl-16-hydroxy-1-phenoxymethyl-1,9-dioxo-16-allenyl-20-ethyl-2-homo-13-trans prostene |

TABLE X

| EXAMPLE | VINYL TIN | CYCLOPENTENONE | PRODUCT PROSTAGLANDIN OF THE PGE2 SERIES |
|---|---|---|---|
| 1 | 1-trans-tri-n-butylstannyl-7-thia 4-triethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-19-thia-2-nor-5-cis-13-trans prostadiene |
| 2 | 1-trans-tri-n-butylstannyl-4-methyl-7-thia 4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-19-thia-2-nor-5-cis-13-trans prostadiene |
| 3 | 1-trans-tri-n-butylstannyl-7-oxa 4-triethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-19-oxa-2-nor-5-cis-13-trans prostadiene |
| 4 | 1-trans-tri-n-butylstannyl-4-methyl-7-oxa 4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-19-oxa-2-nor-5-cis-13-trans prostadiene |
| 5 | 1-trans-tri-n-butylstannyl-4-bromomethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-bromomethyl-20-nor-2-nor-5-cis-13-trans prostadiene |
| EXAMPLE | VINYL IODIDE | CYCLOPENTENONE | PRODUCT PROSTAGLANDIN OF THE PGE2 SERIES |
| 6 | 1-trans-iodo-4-allenyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-allenyl-20-nor-2-nor-5-cis-13-trans prostadiene |
| EXAMPLE | VINYL TIN | CYCLOPENTENONE | PRODUCT PROSTAGLANDIN OF THE PGE2 SERIES |
| 7 | 1-trans-tri-n-butylstannyl-4-bromomethyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-bromomethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 8 | 1-trans-iodo-4-allenyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-allenyl-2-nor-5-cis-13-trans prostadiene |
| EXAMPLE | VINYL TIN | CYCLOPENTENONE | PRODUCT PROSTAGLANDIN OF THE PGE2 SERIES |
| 9 | 1-trans-tri-n-butylstannyl-4-bromomethyl-4-trimethylsilyloxy-1-nonene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-bromomethyl-20-methyl-2-nor-5-cis-13-trans prostadiene |
| EXAMPLE | VINYL IODIDE | CYCLOPENTENONE | PRODUCT PROSTAGLANDIN OF THE PGE2 SERIES |
| 10 | 1-trans-iodo-4-allenyl-4-trimethylsilyloxy-1-nonene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-allenyl-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 11 | 1-trans-tri-n-butylstannyl-4-bromomethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-bromomethyl-20-ethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 12 | 1-trans-iodo-4-allenyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-allenyl-20-ethyl-2-nor-5-cis-13-trans prostadiene |
| EXAMPLE | VINYL TIN | CYCLOPENTENONE | PRODUCT PROSTAGLANDIN OF THE PGE2 SERIES |

TABLE X-continued

| EXAMPLE | | | PRODUCT PROSTAGLANDIN OF THE PGE2 SERIES |
|---|---|---|---|
| 13 | 1-trans-tri-n-butylstannyl-7-thia 4-triethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-19-thia-5-cis-13-trans prostadiene |
| 14 | 1-trans-tri-n-butylstannyl-4-methyl-7-thia 4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-19-thia-5-cis-13-trans prostadiene |
| 15 | 1-trans-tri-n-butylstannyl-7-oxa 4-triethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-19-oxa-5-cis-13-trans prostadiene |
| 16 | 1-trans-tri-n-butylstannyl-4-methyl-7-oxa 4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-19-oxa-5-cis-13-trans prostadiene |
| 17 | 1-trans-tri-n-butylstannyl-4-bromomethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 18 | 1-trans-iodo-4-allenyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE PGE2 SERIES |
| 19 | 1-trans-tri-n-butylstannyl-4-bromomethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-bromomethyl-5-cis-13-trans prostadiene |
| EXAMPLE | VINYL IODIDE | CYCLOPENTENONE | PRODUCT PROSTAGLANDIN OF THE PGE2 SERIES |
| 20 | 1-trans-iodo-4-allenyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-allenyl-5-cis-13-trans prostadiene |
| EXAMPLE | VINYL TIN | CYCLOPENTENONE | PRODUCT PROSTAGLANDIN OF THE PGE2 SERIES |
| 21 | 1-trans-tri-n-butylstannyl-4-bromomethyl-4-trimethylsilyloxy-1-nonene | 2-[6-phenoxyacetyl-hex-2-cis-enyl-]-4-trimethylsiloxy cyclopent-2-en-1-one | dl-11a,16-dihydroxy-1-phenoxymethyl-1,9-dioxo-16-bromomethyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 22 | 1-trans-iodo-4-allenyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-allenyl-20-methyl-5-cis-13-trans prostadiene |
| EXAMPLE | VINYL TIN | CYCLOPENTENONE | PRODUCT PROSTAGLANDIN OF THE PGE2 SERIES |
| 23 | 1-trans-tri-n-butylstannyl-4-bromomethyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-bromomethyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 24 | 1-trans-iodo-4-allenyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-allenyl-20-ethyl-5-cis-13-trans prostadiene |
| EXAMPLE | VINYL TIN | CYCLOPENTENONE | PRODUCT PROSTAGLANDIN OF THE PGE2 SERIES |
| 25 | 1-trans-tri-n-butylstannyl-7-thia | 2-[7-phenoxyacetyl | dl-11a,16-dihydroxy-1-phenoxymethyl-1,9-dioxo- |

TABLE X-continued

| EXAMPLE | | | PRODUCT |
|---|---|---|---|
| 26 | 1-trans-tri-n-butylstannyl-4-methyl-7-thia-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-19-thia-2-homo-5-cis-13-trans prostadiene |
| 27 | 1-trans-tri-n-butylstannyl-7-oxa-4-triethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-19-oxa-2-homo-5-cis-13-trans prostadiene |
| 28 | 1-trans-tri-n-butylstannyl-4-methyl-7-oxa-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-19-oxa-2-homo-5-cis-13-trans prostadiene |
| 29 | 1-trans-tri-n-butylstannyl-4-bromomethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-bromomethyl-20-nor-2-homo-5-cis-13-trans prostadiene |
| EXAMPLE 30 | VINYL IODIDE 1-trans-iodo-4-allenyl-4-trimethylsilyloxy-1-heptene | CYCLOPENTENONE 2-[7-phenoxyacetyl hept-2-cis-enyl]-4-trimethylsiloxy cyclopent-2-en-1-one | PRODUCT PROSTAGLANDIN OF THE PGE2 SERIES dl-11a,16-dihydroxy-1-phenoxymethyl-1,9-dioxo-16-allenyl-20-nor-2-homo-5-cis-13-trans prostadiene |
| EXAMPLE 31 | VINYL TIN 1-trans-tri-n-butylstannyl-4-bromomethyl-4-trimethylsilyloxy-1-octene | CYCLOPENTENONE 2-[7-phenoxyacetyl hept-2-cis-enyl]-4-trimethylsiloxy cyclopent-2-en-1-one | PRODUCT PROSTAGLANDIN OF THE PGE2 SERIES dl-11a,16-dihydroxy-1-phenoxymethyl-1,9-dioxo-16-bromomethyl-2-homo-5-cis-13-trans prostadiene |
| EXAMPLE 32 | VINYL IODIDE 1-iodo-4-allenyl-4-trimethylsilyloxy-1-octene | CYCLOPENTENONE 2-[7-phenoxyacetyl-hept-2-cis-enyl]-4-trimethylsiloxy cyclopent-2-en-1-one | PRODUCT PROSTAGLANDIN OF THE PGE2 SERIES dl-11a,16-dihydroxy-1-phenoxymethyl-1,9-dioxo-16-allenyl-2-homo-5-cis-13-trans prostadiene |
| EXAMPLE 33 | VINYL TIN 1-trans-tri-n-butylstannyl-4-bromomethyl-4-trimethylsilyloxy-1-nonene | CYCLOPENTENONE 2-[7-phenoxyacetyl hept-2-cis-enyl]-4-trimethylsiloxy cyclopent-2-en-1-one | PRODUCT PROSTAGLANDIN OF THE PGE2 SERIES dl-11a,16-dihydroxy-1-phenoxymethyl-1,9-dioxo-16-bromomethyl-20-methyl-2-homo-5-cis-13-trans prostadiene |
| EXAMPLE 34 | VINYL IODIDE 1-iodo-4-allenyl-4-trimethylsilyloxy-1-nonene | CYCLOPENTENONE 2-[7-phenoxyacetyl hept-2-cis-enyl]-4-trimethylsiloxy cyclopent-2-en-1-one | PRODUCT PROSTAGLANDIN OF THE PGE2 SERIES dl-11a,16-dihydroxy-1-phenoxymethyl-1,9-dioxo-16-allenyl-20-methyl-2-homo-5-cis-13-trans prostadiene |
| EXAMPLE 35 | VINYL TIN 1-trans-tri-n-butylstannyl-4-bromomethyl-4-trimethylsilyloxy-1-decene | CYCLOPENTENONE 2-[7-phenoxyacetyl hept-2-cis-enyl]-4-trimethylsiloxy cyclopent-2-en-1-one | PRODUCT PROSTAGLANDIN OF THE PGE2 SERIES dl-11a,16-dihydroxy-1-phenoxymethyl-1,9-dioxo-16-bromomethyl-20-ethyl-2-homo-5-cis-13-trans prostadiene |
| EXAMPLE 36 | VINYL IODIDE 1-iodo-4-allenyl-4-trimethylsilyloxy-1-decene | CYCLOPENTENONE 2-[6-phenoxyacetyl hex-2-cis-enyl]-4-trimethylsiloxy | PRODUCT PROSTAGLANDIN OF THE PGE2 SERIES dl-11a,16-dihydroxy-1-phenoxymethyl-1,9-dioxo-16-allenyl-20-ethyl-2-homo-5-cis-13-trans prostadiene |
| EXAMPLE 37 | VINYL TIN 1-trans-tri-n-butylstannyl-7-thia-4-triethylsilyloxy-1-octene | CYCLOPENTENONE 2-[6-phenoxyacetyl hex-2-cis-enyl]-4R-trimethylsiloxy | PRODUCT PROSTAGLANDIN OF THE PGE2 SERIES nat-11a,16-dihydroxy-1-phenoxymethyl-1,9-dioxo-19-thia-5-cis-13-trans prostadiene |

TABLE X-continued

| EXAMPLE | | | PRODUCT |
|---|---|---|---|
| 38 | 1-trans-tri-n-butylstannyl-4-methyl-7-thia-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-19-thia-5-cis-13-trans prostadiene |
| 39 | 1-trans-tri-n-butylstannyl-7-oxa-4-triethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-19-oxa-5-cis-13-trans prostadiene |
| 40 | 1-trans-tri-n-butylstannyl-4-methyl-7-oxa-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-19-oxa-5-cis-13-trans prostadiene |
| 41 | 1-trans-tri-n-butylstannyl-4-bromomethyl-4-trimethylsilyloxy-1-heptene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-bromomethyl-20-nor-5-cis-13-trans prostadiene |

| EXAMPLE | | | PRODUCT PROSTAGLANDIN OF THE PGE2 SERIES |
|---|---|---|---|
| 42 | VINYL IODIDE 1-iodo-4-allenyl-4-trimethylsilyloxy-1-heptene | CYCLOPENTENONE 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-allenyl-20-nor-5-cis-13-trans prostadiene |

| EXAMPLE | | | PRODUCT PROSTAGLANDIN OF THE PGE2 SERIES |
|---|---|---|---|
| 43 | VINYL TIN 1-trans-tri-n-butylstannyl-4-bromomethyl-4-trimethylsilyloxy-1-octene | CYCLOPENTENONE 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-bromomethyl-5-cis-13-trans prostadiene |

| EXAMPLE | | | PRODUCT PROSTAGLANDIN OF THE PGE2 SERIES |
|---|---|---|---|
| 44 | VINYL IODIDE 1-iodo-4-allenyl-4-trimethylsilyloxy-1-octene | CYCLOPENTENONE 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-allenyl-5-cis-13-trans prostadiene |

| EXAMPLE | | | PRODUCT PROSTAGLANDIN OF THE PGE2 SERIES |
|---|---|---|---|
| 45 | VINYL TIN 1-trans-tri-n-butylstannyl-4-bromomethyl-4-trimethylsilyloxy-1-nonene | CYCLOPENTENONE 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-bromomethyl-20-methyl-5-cis-13-trans prostadiene |

| EXAMPLE | | | PRODUCT PROSTAGLANDIN OF THE PGE2 SERIES |
|---|---|---|---|
| 46 | VINYL IODIDE 1-iodo-4-allenyl-4-trimethylsilyloxy-1-nonene 1-trans-tri-n-butylstannyl-7-thia-4-triethylsilyloxy-1-octene | CYCLOPENTENONE 2-[5-phenoxyacetyl pent-2-cis-enyl] cyclopent-2-en-1-one | dl-16-hydroxy-1-phenoxymethyl-1,9-dioxo-19-thia-2-nor-5-cis-13-trans prostadiene |

| EXAMPLE | | | PRODUCT PROSTAGLANDIN OF THE 11-DEOXY PGE2 SERIES |
|---|---|---|---|
| 50 | VINYL TIN 1-trans-tri-n-butylstannyl-4-methyl-7-thia-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-methyl-19-thia-2-nor-5-cis-13-trans prostadiene |
| 51 | 1-trans-tri-n-butylstannyl-7-oxa-4-triethylsilyloxy-1-octene | 2-[5-phenoxyacetyl pent-2-cis-enyl] cyclopent-2-en-1-one | dl-16-hydroxy-1-phenoxymethyl-1,9-dioxo-19-oxa-2-nor-5-cis-13-trans prostadiene |
| 52 | 1-trans-tri-n-butylstannyl-4-methyl-7-oxa-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-methyl-19-oxa-2-nor-5-cis-13-trans prostadiene |
| 53 | 1-trans-tri-n-butylstannyl-4-bromomethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-bromomethyl-20-nor-2-nor-5-cis-13-trans prostadiene |

TABLE X-continued

| EXAMPLE | VINYL IODIDE / VINYL TIN | CYCLOPENTENONE | PRODUCT PROSTAGLANDIN OF THE 11-DEOXY PGE2 SERIES |
|---|---|---|---|
| EXAMPLE 54 | VINYL IODIDE 1-trans-iodo-4-allenyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-allenyl-20-nor-2-cis-13-trans prostadiene |
| EXAMPLE 55 | VINYL TIN 1-trans-tri-n-butylstannyl-4-bromomethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-bromomethyl-2-nor-5-cis-13-trans prostadiene |
| EXAMPLE 56 | VINYL IODIDE 1-trans-iodo-4-allenyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-allenyl-2-nor-5-cis-13-trans prostadiene |
| EXAMPLE 57 | VINYL TIN 1-trans-tri-n-butylstannyl-4-bromomethyl-4-trimethylsilyloxy-1-nonene | 2-[5 phenoxyacetyl pent-2-cis-enyl] cyclopent-2-en-1-one | dl-16-hydroxy-1-phenoxymethyl-1,9-dioxo-16-bromomethyl-20-methyl-2-nor-5-cis-13-trans prostadiene |
| EXAMPLE 58 | VINYL IODIDE 1-trans-iodo-4-allenyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-allenyl-20-methyl-2-nor-5-cis-13-trans prostadiene |
| EXAMPLE 59 | VINYL TIN 1-trans-tri-n-butylstannyl-4-bromomethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-bromomethyl-20-ethyl-2-nor-5-cis-13-trans prostadiene |
| EXAMPLE 60 | VINYL IODIDE 1-trans-iodo-4-allenyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-allenyl-20-ethyl-2-nor-5-cis-13-trans prostadiene |
| EXAMPLE 61 | VINYL TIN 1-trans-tri-n-butylstannyl-7-thia-4-triethylsilyloxy-1-octene | 2-[6-phenoxyacetyl hex-2-cis-enyl] cyclopent-2-en-1-one | dl-16-hydroxy-1-phenoxymethyl-1,9-dioxo-19-thia-5-cis-13-trans prostadiene |
| EXAMPLE 62 | 1-trans-tri-n-butylstannyl-4-methyl-7-thia-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-methyl-19-thia-5-cis-13-trans prostadiene |
| EXAMPLE 63 | 1-trans-tri-n-butylstannyl-7-oxa-4-triethylsilyloxy-1-octene | 2-[6-phenoxyacetyl hex-2-cis-enyl] cyclopent-2-en-1-one | dl-16-hydroxy-1-phenoxymethyl-1,9-dioxo-19-oxa-5-cis-13-trans prostadiene |
| EXAMPLE 64 | 1-trans-tri-n-butylstannyl-4-methyl-7-oxa-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-methyl-19-oxa-5-cis-13-trans prostadiene |
| EXAMPLE 65 | 1-trans-tri-n-butylstannyl-4-bromomethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-bromomethyl-20-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |

TABLE X-continued

| EXAMPLE | | | |
|---|---|---|---|
| 66 | 1-trans-iodo-4-allenyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-allenyl-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 67 | 1-trans-tri-n-butylstannyl-4-bromomethyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-bromomethyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 68 | 1-trans-iodo-4-allenyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-allenyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 69 | 1-trans-tri-n-butylstannyl-4-bromomethyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-bromomethyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 70 | 1-trans-iodo-4-allenyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-allenyl-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 71 | 1-trans-tri-n-butylstannyl-4-bromomethyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-bromomethyl-20-ethyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 72 | 1-trans-iodo-4-allenyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-allenyl-20-ethyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 73 | 1-trans-tri-n-butylstannyl-7-thia-4-triethylsilyloxy-1-octene | 2-[7-phenoxyacetyl hept-2-cis-enyl] cyclopent-2-en-1-one | dl-16-hydroxy-1-phenoxymethyl-1,9-dioxo-19-thia-2-homo-5-cis-13-trans prostadiene |
| 74 | 1-trans-tri-n-butylstannyl-4-methyl-7-thia-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-methyl-19-thia-2-homo-5-cis-13-trans prostadiene |
| 75 | 1-trans-tri-n-butylstannyl-7-oxa-4-triethylsilyloxy-1-octene | 2-[7-phenoxyacetyl hept-2-cis-enyl] cyclopent-2-en-1-one | dl-16-hydroxy-1-phenoxymethyl-1,9-dioxo-19-oxa-2-homo-5-cis-13-trans prostadiene |
| 76 | 1-trans-tri-n-butylstannyl-4-methyl-7-oxa-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-methyl-19-oxa-2-homo-5-cis-13-trans prostadiene |
| 77 | 1-trans-tri-n-butylstannyl-4-bromomethyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-bromomethyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 78 | 1-trans-iodo-4-allenyl- | 2-[7-phenoxyacetyl | dl-16-hydroxy-1-phenoxymethyl-1,9-dioxo-16-allenyl- |

TABLE X-continued

| | | | |
|---|---|---|---|
| | 4-trimethylsilyloxy-1-heptene | hept-2-cis-enyl]<br>cyclopent-2-en-1-one | 20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 79 | 1-trans-tri-n-butylstannyl-4-bromomethyl-<br>4-trimethylsilyloxy-1-octene | 2-[7-phenoxyacetyl<br>hept-2-cis-enyl]<br>cyclopent-2-en-1-one | dl-16-hydroxy-1-phenoxymethyl-1,9-dioxo-16-bromomethyl-<br>2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 80 | 1-trans-iodo-4-allenyl-<br>4-trimethylsilyloxy-1-octene | 2-[7-phenoxyacetyl<br>hept-2-cis-enyl]<br>cyclopent-2-en-1-one | dl-16-hydroxy-1-phenoxymethyl-1,9-dioxo-16-allenyl-<br>2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 81 | 1-trans-tri-n-butylstannyl-4-bromomethyl-<br>4-trimethylsilyloxy-1-nonene | 2-[7-phenoxyacetyl<br>hept-2-cis-enyl]<br>cyclopent-2-en-1-one | dl-16-hydroxy-1-phenoxymethyl-1,9-dioxo-16-bromomethyl-<br>20-methyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 82 | 1-trans-iodo-4-allenyl-<br>4-trimethylsilyloxy-1-nonene | 2-[7-phenoxyacetyl<br>hept-2-cis-enyl]<br>cyclopent-2-en-1-one | dl-16-hydroxy-1-phenoxymethyl-1,9-dioxo-16-allenyl-<br>20-methyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 83 | 1-trans-tri-n-butylstannyl-4-bromomethyl-<br>4-trimethylsilyloxy-1-decene | 2-[7-phenoxyacetyl<br>hept-2-cis-enyl]<br>cyclopent-2-en-1-one | dl-16-hydroxy-1-phenoxymethyl-1,9-dioxo-16-bromomethyl-<br>20-ethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 84 | 1-trans-iodo-4-allenyl-<br>4-trimethylsilyloxy-1-decene | 2-[7-phenoxyacetyl<br>hept-2-cis-enyl]<br>cyclopent-2-en-1-one | dl-16-hydroxy-1-phenoxymethyl-1,9-dioxo-16-allenyl-<br>20-ethyl-2-homo-5-cis-13-trans prostadiene |

TABLE XI

| EXAMPLE | VINYL IODIDE | CYCLOPENTENONE | PRODUCT PROSTAGLANDIN OF THE PGE2 SERIES |
|---------|--------------|----------------|------------------------------------------|
| 1 | 1-trans-iodo-3-triphenylmethoxy-1-heptene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-20-nor-2-nor-5-cis-13-trans prostadiene |
| 2 | 1-trans-iodo-3-methyl-3-trimethylsilyloxy-1-heptene | 2-[5-phenoxyacetyl]-4-trimethylsiloxy cyclopent-2-en-1-one | dl-11a,15a-dihydroxy-1-phenoxymethyl-1,9-dioxo-15-methyl-20-nor-2-nor-5-cis-13-trans prostadiene |
| 3 | 1-trans-iodo-4,4-dimethyl-3-trimethylsilyloxy-1-heptene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-16,16-dimethyl-20-nor-2-nor-5-cis-13-trans prostadiene |
| 4 | 1-trans-iodo-5,5-dimethyl-3-triphenylmethoxy-1-octene | 2-[5-phenoxyacetyl]-4-trimethylsiloxy cyclopent-2-en-1-one | dl,11a,15a-dihydroxy-1-phenoxymethyl-1,9-dioxo-17,17-dimethyl-2-nor-5-cis-13-trans prostadiene |
| 5 | 1-trans-iodo-4-methyl-3-triphenylmethoxy-1-octene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-16-methyl-2-nor-5-cis-13-trans prostadiene |
| 6 | 1-trans-iodo-4,4-trimethylene-3-trimethylsilyloxy-1-heptene | 2-[5-phenoxyacetyl]-4-trimethylsiloxy cyclopent-2-en-1-one | dl-11a,15a-dihydroxy-1-phenoxymethyl-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE PGE2 SERIES |
|---------|-----------|----------------|------------------------------------------|
| 7 | 1-trans-tri-n-butylstannyl-3-vinyl-3-trimethylsilyloxy-1-heptene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-15-vinyl-20-nor-2-nor-5-cis-13-trans prostadiene |
| 8 | 1-trans-tri-n-butylstannyl-4-phenoxy-3-triethylsilyloxy-1-butene | 2-[5-phenoxyacetyl]-4-trimethylsiloxy cyclopent-2-en-1-one | dl-11a,15a-dihydroxy-1-phenoxymethyl-1,9-dioxo-16-phenoxy-2-nor-17-20-tetranor-5-cis-13-trans prostadiene |
| 9 | 1-trans-tri-n-butylstannyl-4-(p-fluorophenoxy)-3-triethylsilyloxy-1-butene | 2-[5-phenoxyacetyl]-4-trimethylsiloxy cyclopent-2-en-1-one | dl-11a,15a-dihydroxy-1-phenoxymethyl-1,9-dioxo-16-(p-fluorophenoxy)-2-nor-17-20-tetranor-5-cis-13-trans prostadiene |
| 10 | 1-trans-tri-n-butylstannyl-4-(m-chlorophenoxy)-3-triethylsilyloxy-1-butene | 2-[5-phenoxyacetyl]-4-trimethylsiloxy cyclopent-2-en-1-one | dl-11a,15a-dihydroxy-1-phenoxymethyl-1,9-dioxo-16-(m-chlorophenoxy)-2-nor-17-20-tetranor-5-cis-13-trans prostadiene |
| 11 | 1-trans-tri-n-butylstannyl-4-(m-trifluoromethylphenoxy)-3-triethylsilyloxy-1-butene | 2-[5-phenoxyacetyl]-4-trimethylsiloxy cyclopent-2-en-1-one | dl-11a,15a-dihydroxy-1-phenoxymethyl-1,9-dioxo-16-(m-trifluoromethylphenoxy)-2-nor-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---------|--------------|----------------|------------------------------------------|
| 12 | 1-trans-iodo-5-phenyl-3-triethylsilyloxy-1-pentene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-17-phenyl-2-nor-18-20-trinor-5-cis-13-trans prostadiene |
| 13 | 1-trans-iodo-4,4-dimethyl-5-phenyl-3-triethylsilyloxy-1-pentene | 2-[5-phenoxyacetyl]-4-trimethylsiloxy cyclopent-2-en-1-one | dl-11a,15a-dihydroxy-1-phenoxymethyl-1,9-dioxo-16,16-dimethyl-17-phenyl-2-nor-18-20-trinor-5-cis-13-trans prostadiene |
| 14 | 1-trans-iodo-4-cyclopentyl-3-triphenylmethoxy-1-butene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-16-cyclopentyl-2-nor-17-20-tetranor-5-cis-13-trans prostadiene |
| 15 | 1-trans-iodo-4-cyclohexyl-3-triphenylmethoxy-1-butene | 2-[5-phenoxyacetyl]-4-trimethylsiloxy cyclopent-2-en-1-one | dl-11a,15a-dihydroxy-1-phenoxymethyl-1,9-dioxo-16-cyclohexyl-2-nor-17-20-tetranor-5-cis-13-trans prostadiene |
| 16 | 1-trans-iodo-4-triphenylmethoxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-20-nor-2-nor-5-cis-13-trans prostadiene |

TABLE XI-continued

| EXAMPLE | VINYL TIN | CYCLOPENTENONE | PRODUCT PROSTAGLANDIN OF THE PGE2 SERIES |
|---|---|---|---|
| 17 | 1-trans-tri-n-butylstannyl-4-methyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-20-nor-2-cis-5-cis-13-trans prostadiene |
| 18 | 1-trans-tri-n-butylstannyl-4-ethyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-ethyl-2-nor-5-cis-13-trans prostadiene |
| 19 | 1-trans-tri-n-butylstannyl-5-methyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-17-methyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 20 | 1-trans-iodo-5,5-dimethyl 4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-17,17-dimethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 21 | 1-trans-tri-n-butylstannyl-4-vinyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-vinyl-20-nor-2-nor-5-cis-13-trans prostadiene |
| 22 | 1-trans-tri-n-butylstannyl-4-cyclopropyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-cyclopropyl-2-nor-5-cis-13-trans prostadiene |
| 23 | 1-trans-tri-n-butylstannyl-4-trimethylsilylethynyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-ethynyl-20-nor-2-nor-5-cis-13-trans prostadiene |
| 24 | 1-trans-tri-n-butylstannyl-5-methylene 4-triethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-17-methylene-20-nor-2-nor-5-cis-13-trans prostadiene |
| 25 | 1-trans-tri-n-butylstannyl-4-methyl-5-methylene 4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-17-methylene-20-nor-2-nor-5-cis-13-trans prostadiene |
| 26 | 1-trans-tri-n-butylstannyl-4-dimethoxymethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-formyl-20-nor-2-nor-5-cis-13-trans prostadiene |
| 27 | 1-trans-tri-n-butylstannyl-4-fluoromethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-fluoromethyl-20-nor-2-nor-5-cis-13-trans prostadiene |
| 28 | 1-trans-tri-n-butylstannyl-4-difluoromethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-difluoromethyl-20-nor-2-nor-5-cis-13-trans prostadiene |
| 29 | 1-trans-tri-n-butylstannyl-4-trifluoromethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-trifluoromethyl-20-nor-2-nor-5-cis-13-trans prostadiene |
| 30 | 1-trans-tri-n-butylstannyl-4-chloromethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-chloromethyl-20-nor-2-nor-5-cis-13-trans prostadiene |
| 31 | 1-trans-tri-n-butylstannyl-4-trimethylsilyloxymethyl-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-hydroxymethyl-20-nor-2-nor-5-cis-13-trans prostadiene |

TABLE XI-continued

| EXAMPLE | VINYL IODIDE | CYCLOPENTENONE | PRODUCT PROSTAGLANDIN OF THE PGE2 SERIES |
|---|---|---|---|
| 32 | 1-trans-iodo-4-methyl-7-chloro-4-trimethylsilyloxy-1-heptene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-19-chloro-2-nor-20-nor-5-cis-13-trans prostadiene |
| 33 | 1-trans-iodo-3-triphenylmethoxy-1-octene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-2-nor-5-cis-13-trans prostadiene |
| 34 | 1-trans-iodo-3-methyl-3-trimethylsilyloxy-1-octene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-15-methyl-2-nor-5-cis-13-trans prostadiene |
| 35 | 1-trans-iodo-4,4-dimethyl-3-trimethylsilyloxy-1-octene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-16,16-dimethyl-2-nor-5-cis-13-trans prostadiene |
| 36 | 1-trans-iodo-4,4-trimethylene-3-trimethylsilyloxy-1-octene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-16,16-trimethylene-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 37 | 1-trans-tri-n-butylstannyl-3-vinyl-3-trimethylsilyloxy-1-octene | 2-[5-phenoxyacetyl pent-2-cis-enyl]-4-trimethylsiloxy cyclopent-2-en-1-one | dl-11a,15a-dihydroxy-1-phenoxymethyl-1,9-dioxo-15-vinyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 38 | 1-trans-iodo-4-triphenylmethoxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 39 | 1-trans-tri-n-butylstannyl-4-methyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-2-nor-5-cis-13-trans prostadiene |
| 40 | 1-trans-tri-n-butylstannyl-5-methyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-17-methyl-2-nor-5-cis-13-trans prostadiene |
| 41 | 1-trans-tri-n-butylstannyl-4-vinyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-vinyl-2-nor-5-cis-13-trans prostadiene |
| 42 | 1-trans-tri-n-butylstannyl-4-trimethylsilylethynyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-ethynyl-2-nor-5-cis-13-trans prostadiene |
| 43 | 1-trans-tri-n-butylstannyl-5-methylene-4-triethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-17-methylene-2-nor-5-cis-13-trans prostadiene |
| 44 | 1-trans-tri-n-butylstannyl-4-methyl-5-methylene-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-17-methylene-2-nor-5-cis-13-trans prostadiene |
| 45 | 1-trans-tri-n-butylstannyl-4-dimethoxymethyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-formyl-2-nor-5-cis-13-trans prostadiene |
| 46 | 1-trans-tri-n-butylstannyl-4-fluoromethyl-4-trimethylsilyloxy-1-octene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-fluoromethyl-2-nor-5-cis-13-trans prostadiene |
| 47 | 1-trans-tri-n-butylstannyl-4-difluoromethyl- | 2-[5-phenoxyacetyl | dl-11a,16-dihydroxy-1-phenoxymethyl-1,9-dioxo-16-difluoromethyl- |

TABLE XI-continued

| | | | |
|---|---|---|---|
| 48 | 4-trimethylsilyloxy-1-octene | pent-2-cis-enyl]-4-trimethylsilyloxy cyclopent-2-en-1-one | 2-nor-5-cis-13-trans prostadiene |
| | 1-trans-tri-n-butylstannyl-4-trifluoromethyl-4-trimethylsilyloxy-1-octene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-trifluoromethyl-2-nor-5-cis-13-trans prostadiene |
| 49 | 1-trans-tri-n-butylstannyl-4-chloromethyl-4-trimethylsilyloxy-1-octene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-chloromethyl-2-nor-5-cis-13-trans prostadiene |
| 50 | 1-trans-tri-n-butylstannyl-4-trimethylsilyloxymethyl-4-trimethylsilyloxy-1-octene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-hyroxymethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 51 | 1-trans-iodo-3-triphenylmethoxy-1-nonene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-20-methyl-2-nor-5-cis-13-trans prostadiene |
| 52 | 1-trans-iodo-3-methyl-3-trimethylsilyloxy-1-nonene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-15-methyl-20-methyl-2-nor-5-cis-13-trans prostadiene |
| 53 | 1-trans-iodo-4,4-dimethyl-3-trimethylsilyloxy-1-nonene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-16,16-dimethyl-20-methyl-2-nor-5-cis-13-trans prostadiene |
| 54 | 1-trans-iodo-4,4-trimethylene-3-trimethylsilyloxy-1-nonene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-16,16-trimethylene-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 55 | 1-trans-tri-n-butylstannyl-3-vinyl-3-trimethylsilyloxy-1-nonene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-15-vinyl-20-methyl-2-nor-5-cis-13-trans prostadiene |
| EXAMPLE | VINYL IODIDE | CYCLOPENTENONE | PRODUCT PROSTAGLANDIN OF THE PGE2 SERIES |
| 56 | 1-trans-iodo-4-triphenylmethoxy-1-nonene | 2-[5-phenoxyacetyl pent-2-cis-enyl] -4-trimethylsilyloxy cyclopent-2-en-1-one | dl-11a,16-dihydroxy-1-phenoxymethyl-1,9-dioxo-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 57 | 1-trans-tri-n-butylstannyl-4-methyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-methyl-20-methyl-2-nor-5-cis-13-trans prostadiene |
| 58 | 1-trans-tri-n-butylstannyl-4-methyl-5-methyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-17-methyl-20-methyl-2-nor-5-cis-13-trans prostadiene |
| 59 | 1-trans-tri-n-butylstannyl-4-vinyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-vinyl-20-methyl-2-nor-5-cis-13-trans prostadiene |
| 60 | 1-trans-tri-n-butylstannyl-4-trimethylsilylethynyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-ethynyl-20-methyl-2-nor-5-cis-13-trans prostadiene |
| 61 | 1-trans-tri-n-butylstannyl-4-methyl-5-methylene-4-triethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-17-methylene-20-methyl-2-nor-5-cis-13-trans prostadiene |
| 62 | 1-trans-tri-n-butylstannyl-4-methyl-5-methylene | 2-[5-phenoxyacetyl | dl-11a,16-dihydroxy-1-phenoxymethyl-1,9-dioxo-16-methyl- |

TABLE XI-continued

| EXAMPLE | VINYL IODIDE | CYCLOPENTENONE | PRODUCT PROSTAGLANDIN OF THE PGE2 SERIES |
|---|---|---|---|
| | 4-trimethylsilyloxy-1-nonene | pent-2-cis-enyl]-4-trimethylsilyloxy cyclopent-2-en-1-one | 17-methylene-20-methyl-2-nor-5-cis-13-trans prostadiene |
| 63 | 1-trans-tri-n-butylstannyl-4-dimethoxymethyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-formyl-20-methyl-2-nor-5-cis-13-trans prostadiene |
| 64 | 1-trans-tri-n-butylstannyl-4-fluoromethyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-fluoromethyl-20-methyl-2-nor-5-cis-13-trans prostadiene |
| 65 | 1-trans-tri-n-butylstannyl-4-difluoromethyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-difluoromethyl-20-methyl-2-nor-5-cis-13-trans prostadiene |
| 66 | 1-trans-tri-n-butylstannyl-4-trifluoromethyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-trifluoromethyl-20-methyl-2-nor-5-cis-13-trans prostadiene |
| 67 | 1-trans-tri-n-butylstannyl-4-chloromethyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-chloromethyl-20-methyl-2-nor-5-cis-13-trans prostadiene |
| 68 | 1-trans-tri-n-butylstannyl-4-trimethylsilyloxymethyl-4-trimethylsilyloxy-1-nonene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-hydroxymethyl-20-methyl-2-nor-5-cis-13-trans prostadiene |
| EXAMPLE | VINYL IODIDE | CYCLOPENTENONE | PRODUCT PROSTAGLANDIN OF THE PGE2 SERIES |
| 69 | 1-trans-iodo-3-triphenylmethoxy-1-decene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-20-ethyl-2-nor-5-cis-13-trans prostadiene |
| 70 | 1-trans-iodo-3-methyl-3-trimethylsilyloxy-1-decene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-15-methyl-20-ethyl-2-nor-5-cis-13-trans prostadiene |
| 71 | 1-trans-iodo-4,4-dimethyl-3-trimethylsilyloxy-1-decene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-16,16-dimethyl-20-ethyl-2-nor-5-cis-13-trans prostadiene |
| 72 | 1-trans-iodo-4,4-trimethylene-3-trimethylsilyloxy-1-decene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-16,16-trimethylene-20-ethyl-2-nor-5-cis-13-trans prostadiene |
| EXAMPLE | VINYL TIN | CYCLOPENTENONE | PRODUCT PROSTAGLANDIN OF THE PGE2 SERIES |
| 73 | 1-trans-tri-n-butylstannyl-3-vinyl-3-trimethylsilyloxy-1-decene | 2-[5-phenoxyacetyl pent-2-cis-enyl]-4-trimethylsilyloxy cyclopent-2-en-1-one | dl-11a,15a-dihydroxy-1-phenoxymethyl-1,9-dioxo-15-vinyl-20-ethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 74 | 1-trans-iodo-4-triphenylmethoxy-1-decene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-20-ethyl-2-nor-5-cis-13-trans prostadiene |
| EXAMPLE | VINYL TIN | CYCLOPENTENONE | PRODUCT PROSTAGLANDIN OF THE PGE2 SERIES |
| 75 | 1-trans-tri-n-butylstannyl-4-methyl-4-trimethylsilyloxy-1-decene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-16-methyl-20-ethyl-2-nor-5-cis-13-trans prostadiene |
| 76 | 1-trans-tri-n-butylstannyl-5-methyl-4-trimethylsilyloxy-1-decene | 2-[5-phenoxyacetyl pent-2-cis-enyl]-4-trimethylsilyloxy cyclopent-2-en-1-one | dl-11a,16-dihydroxy-1-phenoxymethyl-1,9-dioxo-17-methyl-20-ethyl-2-nor-5-cis-13-trans prostadiene |
| 77 | 1-trans-tri-n-butylstannyl-4-vinyl- | 2-[5-phenoxyacetyl | dl-11a,16-dihydroxy-1-phenoxymethyl-1,9-dioxo-16-vinyl- |

TABLE XI-continued

| | VINYL IODIDE | CYCLOPENTENONE | PRODUCT PROSTAGLANDIN OF THE PGE2 SERIES |
|---|---|---|---|
| | 4-trimethylsilyloxy-1-decene | pent-2-cis-enyl]-4-trimethylsiloxy cyclopent-2-en-1-one | 20-ethyl-2-nor-5-cis-13-trans prostadiene |
| 78 | 1-trans-tri-n-butylstannyl-4-trimethylsilylethynyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-ethynyl-20-ethyl-2-nor-5-cis-13-trans prostadiene |
| 79 | 1-trans-tri-n-butylstannyl-5-methylene-4-triethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-17-methylene-20-ethyl-2-nor-5-cis-13-trans prostadiene |
| 80 | 1-trans-tri-n-butylstannyl-4-methyl-5-methylene-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-methyl-17-methylene-20-ethyl-2-nor-5-cis-13-trans prostadiene |
| 81 | 1-trans-tri-n-butylstannyl-4-dimethoxymethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-formyl-20-ethyl-2-nor-5-cis-13-trans prostadiene |
| 82 | 1-trans-tri-n-butylstannyl-4-fluoromethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-fluoromethyl-20-ethyl-2-nor-5-cis-13-trans prostadiene |
| 83 | 1-trans-tri-n-butylstannyl-4-difluoromethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-difluoromethyl-20-ethyl-2-nor-5-cis-13-trans prostadiene |
| 84 | 1-trans-tri-n-butylstannyl-4-trifluoromethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-trifluoromethyl-20-ethyl-2-nor-5-cis-13-trans prostadiene |
| 85 | 1-trans-tri-n-butylstannyl-4-chloromethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-chloromethyl-20-ethyl-2-nor-5-cis-13-trans prostadiene |
| 86 | 1-trans-tri-n-butylstannyl-4-trimethylsilyloxymethyl-4-trimethylsilyloxy-1-decene | 2-[5-phenoxyacetyl pent-2-cis-enyl]-4-trimethylsiloxy cyclopent-2-en-1-one | dl-11a,16-dihydroxy-1-phenoxymethyl-1,9-dioxo-16-hydroxymethyl-20-ethyl-2-nor-5-cis-13-trans prostadiene |
| EXAMPLE | VINYL IODIDE | CYCLOPENTENONE | PRODUCT PROSTAGLANDIN OF THE PGE2 SERIES |
| 87 | 1-trans-iodo-3-triphenylmethoxy-1-heptene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-20-nor-5-cis-13-trans prostadiene |
| 88 | 1-trans-iodo-3-methyl-3-trimethylsilyloxy-1-heptene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-methyl-20-nor-5-cis-13-trans prostadiene |
| 89 | 1-trans-iodo-4,4-dimethyl-3-trimethylsilyloxy-1-heptene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-dimethyl-20-nor-5-cis-13-trans prostadiene |
| 90 | 1-trans-iodo-5,5-dimethyl-3-triphenylmethoxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-17,17-dimethyl-5-cis-13-trans prostadiene |
| 91 | 1-trans-iodo-4-methyl-3-triphenylmethoxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-methyl-5-cis-13-trans prostadiene |
| 92 | 1-trans-iodo-4,4-trimethylene-3-trimethylsilyloxy-1-heptene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-trimethylene-20-nor-5-cis-13-trans prostadiene |
| EXAMPLE | VINYL TIN | CYCLOPENTENONE | PRODUCT PROSTAGLANDIN OF THE PGE2 SERIES |
| 93 | 1-trans-tri-n-butylstannyl-3-vinyl-3-trimethylsilyloxy-1-heptene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-vinyl-20-nor-5-cis-13-trans prostadiene |

TABLE XI-continued

| | | | |
|---|---|---|---|
| 94 | 1-trans-tri-n-butylstannyl-4-phenoxy-3-triethylsilyloxy-1-butene | cyclopent-2-en-1-one 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-phenoxy-17,20-tetranor-5-cis-13-trans prostadiene |
| 95 | 1-trans-tri-n-butylstannyl-4-(p-fluorophenoxy)-3-triethylsilyloxy-1-butene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-(p-fluorophenoxy)-17-20-tetranor-5-cis-13-trans prostadiene |
| 96 | 1-trans-tri-n-butylstannyl-4-(m-chlorophenoxy)-3-triethylsilyloxy-1-butene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-(m-chlorophenoxy)-17-20-tetranor-5-cis-13-trans prostadiene |
| 97 | 1-trans-tri-n-butylstannyl-4-(m-trifluoromethylphenoxy)-3-triethylsilyloxy-1-butene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-(m-trifluoromethylphenoxy)-17-20-tetranor-5-cis-13-trans prostadiene |
| EXAMPLE | VINYL IODIDE | CYCLOPENTENONE | PRODUCT PROSTAGLANDIN OF THE PGE2 SERIES |
| 98 | 1-trans-iodo-5-phenyl 3-triethylsilyloxy-1-pentene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-17-phenyl-18-20-trinor-5-cis-13-trans prostadiene |
| 99 | 1-trans-iodo-4,4-dimethyl-5-phenyl 3-triethylsilyloxy-1-pentene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-dimethyl-17-phenyl-18-20-trinor-5-cis-13-trans prostadiene |
| 100 | 1-trans-iodo-4-cyclopentyl 3-triphenylmethoxy-1-butene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-cyclopentyl-17-20-tetranor-5-cis-13-trans prostadiene |
| 101 | 1-trans-iodo-4-cyclohexyl 3-triphenylmethoxy-1-butene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16-cyclohexyl-17-20-tetranor-5-cis-13-trans prostadiene |
| 102 | 1-trans-iodo-4-triphenylmethoxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-20-nor-5-cis-13-trans prostadiene |
| EXAMPLE | VINYL TIN | CYCLOPENTENONE | PRODUCT PROSTAGLANDIN OF THE PGE2 SERIES |
| 103 | 1-trans-tri-n-butylstannyl-4-methyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-20-nor-5-cis-13-trans prostadiene |
| 104 | 1-trans-tri-n-butylstannyl-4-ethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-ethyl-5-cis-13-trans prostadiene |
| 105 | 1-trans-tri-n-butylstannyl-5-methyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methyl-20-nor-5-cis-13-trans prostadiene |
| EXAMPLE | VINYL IODIDE | CYCLOPENTENONE | PRODUCT PROSTAGLANDIN OF THE PGE2 SERIES |
| 106 | 1-trans-iodo-5,5-dimethyl 4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17,17-dimethyl-5-cis-13-trans prostadiene |
| EXAMPLE | VINYL TIN | CYCLOPENTENONE | PRODUCT PROSTAGLANDIN OF THE PGE2 SERIES |
| 107 | 1-trans-tri-n-butylstannyl-4-vinyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-vinyl-20-nor-5-cis-13-trans prostadiene |
| 108 | 1-trans-tri-n-butylstannyl-4-cyclopropyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-cyclopropyl-5-cis-13-trans prostadiene |

TABLE XI-continued

| | | | |
|---|---|---|---|
| 109 | 1-trans-tri-n-butylstannyl-4-trimethylsilylethynyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-ethynyl-20-nor-5-cis-13-trans prostadiene |
| 110 | 1-trans-tri-n-butylstannyl-5-methylene-4-triethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methylene-20-nor-5-cis-13-trans prostadiene |
| 111 | 1-trans-tri-n-butylstannyl-4-methyl-5-methylene-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-17-methylene-20-nor-5-cis-13-trans prostadiene |
| 112 | 1-trans-tri-n-butylstannyl-4-dimethoxymethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-formyl-20-nor-5-cis-13-trans prostadiene |
| 113 | 1-trans-tri-n-butylstannyl-4-fluoromethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-fluoromethyl-20-nor-5-cis-13-trans prostadiene |
| 114 | 1-trans-tri-n-butylstannyl-4-difluoromethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-difluoromethyl-20-nor-5-cis-13-trans prostadiene |
| 115 | 1-trans-tri-n-butylstannyl-4-trifluoromethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-trifluoromethyl-20-nor-5-cis-13-trans prostadiene |
| 116 | 1-trans-tri-n-butylstannyl-4-chloromethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-chloromethyl-20-nor-5-cis-13-trans prostadiene |
| 117 | 1-trans-tri-n-butylstannyl-4-trimethylsilyloxymethyl-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-hydroxymethyl-20-nor-5-cis-13-trans prostadiene |
| EXAMPLE | VINYL IODIDE | CYCLOPENTENONE | PRODUCT PROSTAGLANDIN OF THE PGE2 SERIES |
| 118 | 1-trans-iodo-4-methyl-7-chloro-4-trimethylsilyloxy-1-heptene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-19-chloro-20-nor-5-cis-13-trans prostadiene |
| 119 | 1-trans-iodo-3-triphenylmethoxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-5-cis-13-trans prostadiene |
| 120 | 1-trans-iodo-3-methyl-3-trimethylsilyloxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-methyl-5-cis-13-trans prostadiene |
| 121 | 1-trans-iodo-4,4-dimethyl-3-trimethylsilyloxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-dimethyl-5-cis-13-trans prostadiene |
| 122 | 1-trans-iodo-4,4-trimethylene-3-trimethylsilyloxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-trimethylene-5-cis-13-trans prostadiene |
| EXAMPLE | VINYL TIN | CYCLOPENTENONE | PRODUCT PROSTAGLANDIN OF THE PGE2 SERIES |
| 123 | 1-trans-tri-n-butylstannyl-3-vinyl-3-trimethylsilyloxy-1-octene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-vinyl-5-cis-13-trans prostadiene |
| EXAMPLE | VINYL IODIDE | CYCLOPENTENONE | PRODUCT PROSTAGLANDIN OF THE PGE2 SERIES |
| 124 | 1-trans-iodo- | 2-[6-phenoxyacetyl | dl-11a,16-dihydroxy-1-phenoxymethyl-1,9-dioxo- |

TABLE XI-continued

| EXAMPLE | VINYL TIN | CYCLOPENTENONE | PRODUCT PROSTAGLANDIN OF THE PGE2 SERIES |
|---|---|---|---|
| | 4-triphenylmethoxy-1-octene | hex-2-cis-enyl]-4-trimethylsiloxy cyclopent-2-en-1-one | 5-cis-13-trans prostadiene |
| 125 | 1-trans-tri-n-butylstannyl-4-methyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-5-cis-13-trans prostadiene |
| 126 | 1-trans-tri-n-butylstannyl-5-methyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methyl-5-cis-13-trans prostadiene |
| 127 | 1-trans-tri-n-butylstannyl-4-vinyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-vinyl-5-cis-13-trans prostadiene |
| 128 | 1-trans-tri-n-butylstannyl-4-trimethylsilylethynyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-ethynyl-5-cis-13-trans prostadiene |
| 129 | 1-trans-tri-n-butylstannyl-5-methylene-4-triethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methylene-5-cis-13-trans prostadiene |
| 130 | 1-trans-tri-n-butylstannyl-4-methyl-5-methylene-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-17-methylene-5-cis-13-trans prostadiene |
| 131 | 1-trans-tri-n-butylstannyl-4-dimethoxymethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-formyl-5-cis-13-trans prostadiene |
| 132 | 1-trans-tri-n-butylstannyl-4-fluoromethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-fluoromethyl-5-cis-13-trans prostadiene |
| 133 | 1-trans-tri-n-butylstannyl-4-difluoromethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-difluoromethyl-5-cis-13-trans prostadiene |
| 134 | 1-trans-tri-n-butylstannyl-4-trifluoromethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-trifluoromethyl-5-cis-13-trans prostadiene |
| 135 | 1-trans-tri-n-butylstannyl-4-chloromethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-chloromethyl-5-cis-13-trans prostadiene |
| 136 | 1-trans-tri-n-butylstannyl-4-trimethylsilyloxymethyl-4-trimethylsilyloxy-1-octene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-hydroxymethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 137 | 1-trans-iodo-3-triphenylmethoxy-1-nonene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-20-methyl-5-cis-13-trans prostadiene |
| 138 | 1-trans-iodo-3-methyl-3-trimethylsilyloxy-1-nonene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-methyl-20-methyl-5-cis-13-trans prostadiene |
| 139 | 1-trans-iodo-4,4-dimethyl-3-trimethylsilyloxy-1-nonene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-dimethyl-20-methyl-5-cis-13-trans prostadiene |
| 140 | 1-trans-iodo-4,4-trimethylene-3-trimethylsilyloxy-1-nonene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-trimethylene-20-methyl-5-cis-13-trans prostadiene |

TABLE XI-continued

| EXAMPLE | VINYL TIN | CYCLOPENTENONE | PRODUCT PROSTAGLANDIN OF THE PGE2 SERIES |
|---|---|---|---|
| 141 | 1-trans-tri-n-butylstannyl-3-vinyl-3-trimethylsilyloxy-1-nonene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-vinyl-20-methyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 142 | 1-trans-iodo-4-triphenylmethoxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-20-methyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 143 | 1-trans-tri-n-butylstannyl-4-methyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-20-methyl-5-cis-13-trans prostadiene |
| 144 | 1-trans-tri-n-butylstannyl-5-methyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methyl-20-methyl-5-cis-13-trans prostadiene |
| 145 | 1-trans-tri-n-butylstannyl-4-vinyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-vinyl-20-methyl-5-cis-13-trans prostadiene |
| 146 | 1-trans-tri-n-butylstannyl-4-trimethylsilylethynyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-ethynyl-20-methyl-5-cis-13-trans prostadiene |
| 147 | 1-trans-tri-n-butylstannyl-5-methylene-4-triethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methylene-20-methyl-5-cis-13-trans prostadiene |
| 148 | 1-trans-tri-n-butylstannyl-4-methyl-5-methylene-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-17-methylene-20-methyl-5-cis-13-trans prostadiene |
| 149 | 1-trans-tri-n-butylstannyl-4-dimethoxymethyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-formyl-20-methyl-5-cis-13-trans prostadiene |
| 150 | 1-trans-tri-n-butylstannyl-4-fluoromethyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-fluoromethyl-20-methyl-5-cis-13-trans prostadiene |
| 151 | 1-trans-tri-n-butylstannyl-4-difluoromethyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-difluoromethyl-20-methyl-5-cis-13-trans prostadiene |
| 152 | 1-trans-tri-n-butylstannyl-4-trifluoromethyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-trifluoromethyl-20-methyl-5-cis-13-trans prostadiene |
| 153 | 1-trans-tri-n-butylstannyl-4-chloromethyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-chloromethyl-20-methyl-5-cis-13-trans prostadiene |
| 154 | 1-trans-tri-n-butylstannyl-4-trimethylsilyloxymethyl-4-trimethylsilyloxy-1-nonene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-hydroxymethyl-20-methyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 155 | 1-trans-iodo-3-triphenylmethoxy-1-decene | 2-[6-phenoxyacetyl hex-2-cis-enyl]-4-trimethylsiloxy | dl-11a,15a-dihydroxy-1-phenoxymethyl-1,9-dioxo-20-ethyl-5-cis-13-trans prostadiene |

TABLE XI-continued

| | VINYL TIN | CYCLOPENTENONE | PRODUCT PROSTAGLANDIN OF THE PGE2 SERIES |
|---|---|---|---|
| 156 | 1-trans-iodo-3-methyl-3-trimethylsilyloxy-1-decene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-methyl-20-ethyl-5-cis-13-trans prostadiene |
| 157 | 1-trans-iodo-4,4-dimethyl-3-trimethylsilyloxy-1-decene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-dimethyl-20-ethyl-5-cis-13-trans prostadiene |
| 158 | 1-trans-iodo-4,4-trimethylene-3-trimethylsilyloxy-1-decene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-16,16-trimethylene-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 159 | 1-trans-tri-n-butylstannyl-3-vinyl-3-trimethylsilyloxy-1-decene | 2-[6-phenoxyacetyl hex-2-cis-enyl]-4-trimethylsiloxy cyclopent-2-en-1-one | dl-11a,15a-dihydroxy-1-phenoxymethyl-1,9-dioxo-15-vinyl-20-ethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 160 | 1-trans-iodo-4-triphenylmethoxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 161 | 1-trans-tri-n-butylstannyl-4-methyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-20-ethyl-5-cis-13-trans prostadiene |
| 162 | 1-trans-tri-n-butylstannyl-5-methyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methyl-20-ethyl-5-cis-13-trans prostadiene |
| 163 | 1-trans-tri-n-butylstannyl-4-vinyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-vinyl-20-ethyl-5-cis-13-trans prostadiene |
| 164 | 1-trans-tri-n-butylstannyl-4-trimethylsilylethynyl-4-trimethylsilyloxy-1-decene | 2-[6-phenoxyacetyl hex-2-cis-enyl]-4-trimethylsiloxy cyclopent-2-en-1-one | -dl-11a,16-dihydroxy-1-phenoxymethyl-1,9-dioxo-16-ethynyl-20-ethyl-5-cis-13-trans protadiene |
| 165 | 1-trans-tri-n-butylstannyl-5-methylene-4-triethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-17-methylene-20-ethyl-5-cis-13-trans prostadiene |
| 166 | 1-trans-tri-n-butylstannyl-4-methyl-5-methylene-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-methyl-17-methylene-20-ethyl-5-cis-13-trans prostadiene |
| 167 | 1-trans-tri-n-butylstannyl-4-dimethoxymethyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-formyl-20-ethyl-5-cis-13-trans prostadiene |
| 168 | 1-trans-tri-n-butylstannyl-4-fluoromethyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-fluoromethyl-20-ethyl-5-cis-13-trans prostadiene |
| 169 | 1-trans-tri-n-butylstannyl-4-difluoromethyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-difluoromethyl-20-ethyl-5-cis-13-trans prostadiene |
| 170 | 1-trans-tri-n-butylstannyl-4-trifluoromethyl-4-trimethylsilyloxy-1-decene | 2-[6-phenoxyacetyl hex-2-cis-enyl]-4-trimethylsiloxy cyclopent-2-en-1-one | dl-11a,16-dihydroxy-1-phenoxymethyl-1,9-dioxo-16-trifluoromethyl-20-ethyl-5-cis-13-trans prostadiene |
| 171 | 1-trans-tri-n-butylstannyl-4-chloromethyl- | 2-[6-phenoxyacetyl | dl-11a,16-dihydroxy-1-phenoxymethyl-1,9-dioxo-16-chloromethyl- |

TABLE XI-continued

| Example | Vinyl Iodide | Cyclopentenone | Product Prostaglandin of the PGE2 Series |
|---|---|---|---|
| 172 | 1-trans-tri-n-butylstannyl-4-trimethylsilyloxymethyl-4-trimethylsilyloxy-1-decene | 2-[6-phenoxyacetyl hex-2-cis-enyl]-4-trimethylsilyloxy cyclopent-2-en-1-one | dl-11a,16-dihydroxy-1-phenoxymethyl-1,9-dioxo-16-hydroxymethyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 173 | 1-trans-iodo-3-triphenylmethoxy-1-heptene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-20-nor-2-homo-5-cis-13-trans prostadiene |
| 174 | 1-trans-iodo-3-methyl-3-trimethylsilyloxy-1-heptene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-15-methyl-20-nor-2-homo-5-cis-13-trans prostadiene |
| 175 | 1-trans-iodo-4,4-dimethyl-3-trimethylsilyloxy-1-heptene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16,16-dimethyl-20-nor-2-homo-5-cis-13-trans prostadiene |
| 176 | 1-trans-iodo-5,5-dimethyl-3-triphenylmethoxy-1-octene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-17,17-dimethyl-2-homo-5-cis-13-trans prostadiene |
| 177 | 1-trans-iodo-4-methyl-3-triphenylmethoxy-1-octene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16-methyl-2-homo-5-cis-13-trans prostadiene |
| 178 | 1-trans-iodo-4,4-trimethylene-3-trimethylsilyloxy-1-heptene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16,16-trimethylene-20-nor-2-homo-5-cis-13-trans prostadiene |
| EXAMPLE | VINYL TIN | CYCLOPENTENONE | PRODUCT PROSTAGLANDIN OF THE PGE2 SERIES |
| 179 | 1-trans-tri-n-butylstannyl-3-vinyl-3-trimethylsilyloxy-1-heptene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-15-vinyl-20-nor-2-homo-5-cis-13-trans prostadiene |
| 180 | 1-trans-tri-n-butylstannyl-4-phenoxy-3-triethylsilyloxy-1-butene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16-phenoxy-2-homo-17,20-tetranor-5-cis-13-trans prostadiene |
| 181 | 1-trans-tri-n-butylstannyl-4-(p-fluorophenoxy)-3-triethylsilyloxy-1-butene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16-(p-fluorophenoxy)-2-homo-17,20-tetranor-5-cis-13-trans prostadiene |
| 182 | 1-trans-tri-n-butylstannyl-4-(m-chlorophenoxy)-3-triethylsilyloxy-1-butene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16-(m-chlorophenoxy)-2-homo-17,20-tetranor-5-cis-13-trans prostadiene |
| 183 | 1-trans-tri-n-butylstannyl-4-(m-trifluoromethylphenoxy)-3-triethylsilyloxy-1-butene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16-(m-trifluoromethylphenoxy)-2-homo-17,20-tetranor-5-cis-13-trans prostadiene |
| EXAMPLE | VINYL IODIDE | CYCLOPENTENONE | PRODUCT PROSTAGLANDIN OF THE PGE2 SERIES |
| 184 | 1-trans-iodo-5-phenyl-3-triethylsilyloxy-1-pentene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-17-phenyl-2-homo-18-20-trinor-5-cis-13-trans prostadiene |
| 185 | 1-trans-iodo-4,4-dimethyl-5-phenyl-3-triethylsilyloxy-1-pentene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16,16-dimethyl-17-phenyl-2-homo-18-20-trinor-5-cis-13-trans prostadiene |
| 186 | 1-trans-iodo-4-cyclopentyl-3-triphenylmethoxy-1-butene | 2-[7-phenoxyacetyl hept-2-cis-enyl]-4-trimethylsilyloxy cyclopent-2-en-1-one | dl-11a,15a-dihydroxy-1-phenoxymethyl-1,9-dioxo-16-cyclopentyl-2-homo-17,20-tetranor-5-cis-13-trans prostadiene |

TABLE XI-continued

| EXAMPLE | VINYL TIN / VINYL IODIDE | CYCLOPENTENONE | PRODUCT PROSTAGLANDIN |
|---|---|---|---|
| 187 | 1-trans-iodo-4-cyclohexyl 3-triphenylmethoxy-1-butene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-16-cyclohexyl-2-homo-17-20-tetranor-5-cis-13-trans prostadiene |
| 188 | 1-trans-iodo-4-triphenylmethoxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-20-homo-2-homo-5-cis-13-trans prostadiene |
| EXAMPLE | VINYL TIN | CYCLOPENTENONE | PRODUCT PROSTAGLANDIN OF THE PGE2 SERIES |
| 189 | 1-trans-tri-n-butylstannyl-4-methyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-20-nor-2-homo-5-cis-13-trans prostadiene |
| 190 | 1-trans-tri-n-butylstannyl-4-ethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-ethyl-2-homo-5-cis-13-trans prostadiene |
| 191 | 1-trans-tri-n-butylstannyl-5-methyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methyl-20-nor-2-homo-5-cis-13-trans prostadiene |
| EXAMPLE | VINYL IODIDE | CYCLOPENTENONE | PRODUCT PROSTAGLANDIN OF THE PGE2 SERIES |
| 192 | 1-trans-iodo-5,5-dimethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17,17-dimethyl-2-homo-5-cis-13-trans prostadiene |
| EXAMPLE | VINYL TIN | CYCLOPENTENONE | PRODUCT PROSTAGLANDIN OF THE PGE2 SERIES |
| 193 | 1-trans-tri-n-butylstannyl-4-vinyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-vinyl-20-nor-2-homo-5-cis-13-trans prostadiene |
| 194 | 1-trans-tri-n-butylstannyl-4-cyclopropyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-cyclopropyl-2-homo-5-cis-13-trans prostadiene |
| 195 | 1-trans-tri-n-butylstannyl-4-trimethylsilylethynyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-ethynyl-20-nor-2-homo-5-cis-13-trans prostadiene |
| 196 | 1-trans-tri-n-butylstannyl-5-methylene-4-triethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methylene-20-nor-2-homo-5-cis-13-trans prostadiene |
| 197 | 1-trans-tri-n-butylstannyl-4-methyl-5-methylene-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-17-methylene-20-nor-2-homo-5-cis-13-trans prostadiene |
| 198 | 1-trans-tri-n-butylstannyl-4-dimethoxymethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-formyl-20-nor-2-homo-5-cis-13-trans prostadiene |
| 199 | 1-trans-tri-n-butylstannyl-4-fluoromethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-fluoromethyl-20-nor-2-homo-5-cis-13-trans prostadiene |
| 200 | 1-trans-tri-n-butylstannyl-4-difluoromethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-difluoromethyl-20-nor-2-homo-5-cis-13-trans prostadiene |
| 201 | 1-trans-tri-n-butylstannyl-4-trifluoromethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-trifluoromethyl-20-nor-2-homo-5-cis-13-trans prostadiene |
| 202 | 1-trans-tri-n-butylstannyl-4-chloromethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-chloromethyl-20-nor-2-homo-5-cis-13-trans prostadiene |

TABLE XI-continued

| | VINYL IODIDE / VINYL TIN | CYCLOPENTENONE | PRODUCT PROSTAGLANDIN |
|---|---|---|---|
| 203 | 1-trans-tri-n-butylstannyl-4-trimethylsilyloxymethyl-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-hydroxymethyl-20-nor-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 204 | 1-trans-iodo-4-methyl-7-chloro-4-trimethylsilyloxy-1-heptene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-19-chloro-2-homo-20-nor-5-cis-13-trans prostadiene |
| 205 | 1-trans-iodo-3-triphenylmethoxy-1-octene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-2-homo-5-cis-13-trans prostadiene |
| 206 | 1-trans-iodo-3-methyl-3-trimethylsilyloxy-1-octene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-15-methyl-2-homo-5-cis-13-trans prostadiene |
| 207 | 1-trans-iodo-4,4-dimethyl-3-trimethylsilyloxy-1-octene | 2-[7-phenoxyacetyl hept-2-cis-enyl]-4-trimethylsiloxy cyclopent-2-en-1-one | dl-11a,15-dihydroxy-1-phenoxymethyl-1,9-dioxo-16,16-dimethyl-2-homo-5-cis-13-trans prostadiene |
| 208 | 1-trans-iodo-4,4-trimethylene-3-trimethylsilyloxy-1-octene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-16,16-trimethylene-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 209 | 1-trans-tri-n-butylstannyl-3-vinyl-3-trimethylsilyloxy-1-octene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-15-vinyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 210 | 1-trans-iodo-4-triphenylmethoxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 211 | 1-trans-tri-n-butylstannyl-4-methyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-2-homo-5-cis-13-trans prostadiene |
| 212 | 1-trans-tri-n-butylstannyl-5-methyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methyl-2-homo-5-cis-13-trans prostadiene |
| 213 | 1-trans-tri-n-butylstannyl-4-vinyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-vinyl-2-homo-5-cis-13-trans prostadiene |
| 214 | 1-trans-tri-n-butylstannyl-4-trimethylsilylethynyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-ethynyl-2-homo-5-cis-13-trans prostadiene |
| 215 | 1-trans-tri-n-butylstannyl-5-methylene-4-triethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methylene-2-homo-5-cis-13-trans prostadiene |
| 216 | 1-trans-tri-n-butylstannyl-4-methyl-5-methylene-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-17-methylene-2-homo-5-cis-13-trans prostadiene |
| 217 | 1-trans-tri-n-butylstannyl-4-dimethoxymethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-formyl-2-homo-5-cis-13-trans prostadiene |

TABLE XI-continued

| | | | |
|---|---|---|---|
| 218 | 1-trans-tri-n-butylstannyl-4-fluoromethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-fluoromethyl-2-homo-5-cis-13-trans prostadiene |
| 219 | 1-trans-tri-n-butylstannyl-4-difluoromethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-difluoromethyl-2-homo-5-cis-13-trans prostadiene |
| 220 | 1-trans-tri-n-butylstannyl-4-trifluoromethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-trifluoromethyl-2-homo-5-cis-13-trans prostadiene |
| 221 | 1-trans-tri-n-butylstannyl-4-chloromethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-chloromethyl-2-homo-5-cis-13-trans prostadiene |
| 222 | 1-trans-tri-n-butylstannyl-4-trimethylsilyloxymethyl-4-trimethylsilyloxy-1-octene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-hydroxymethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 223 | 1-trans-iodo-3-triphenylmethoxy-1-nonene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-20-methyl-2-homo-5-cis-13-trans prostadiene |
| 224 | 1-trans-iodo-3-methyl-3-trimethylsilyloxy-1-nonene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-15-methyl-20-methyl-2-homo-5-cis-13-trans prostadiene |
| 225 | 1-trans-iodo-4,4-dimethyl-3-trimethylsilyloxy-1-nonene | 2-[7-phenoxyacetyl hept-2-cis-enyl]-4-trimethylsiloxy cyclopent-2-en-1-one | dl-11a,15a-dihydroxy-20-methyl-2-homo-5-cis-13-trans prostadiene 16,16-dimethyl-1-phenoxymethyl-1,9-dioxo- |
| 226 | 1-trans-iodo-4,4-trimethylene-3-trimethylsilyloxy-1-nonene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-16,16-trimethylene-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 227 | 1-trans-tri-n-butylstannyl-3-vinyl-3-trimethylsilyloxy-1-nonene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-15-vinyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 228 | 1-trans-iodo-4-triphenylmethoxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 229 | 1-trans-tri-n-butylstannyl-4-methyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-20-methyl-2-homo-5-cis-13-trans prostadiene |
| 230 | 1-trans-tri-n-butylstannyl-5-methyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methyl-20-methyl-2-homo-5-cis-13-trans prostadiene |
| 231 | 1-trans-tri-n-butylstannyl-4-vinyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-vinyl-20-methyl-2-homo-5-cis-13-trans prostadiene |
| 232 | 1-trans-tri-n-butylstannyl-4-trimethylsilylethynyl-4-trimethylsilyloxy-1-nonene | 2-[7-phenoxyacetyl hept-2-cis-enyl]-4-trimethylsiloxy | dl-11a,16-dihydroxy-1-phenoxymethyl-1,9-dioxo-16-ethynyl-20-methyl-2-homo-5-cis-13-trans prostadiene |

TABLE XI-continued

| | | | |
|---|---|---|---|
| 233 | | 1-trans-tri-n-butylstannyl-5-methylene 4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methylene-20-methyl-2-homo-5-cis-13-trans prostadiene |
| 234 | | 1-trans-tri-n-butylstannyl-4-methyl-5-methylene-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-17-methylene-20-methyl-2-homo-5-cis-13-trans prostadiene |
| 235 | | 1-trans-tri-n-butylstannyl-4-dimethoxymethyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-formyl-20-methyl-2-homo-5-cis-13-trans prostadiene |
| 236 | | 1-trans-tri-n-butylstannyl-4-fluoromethyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-fluoromethyl-20-methyl-2-homo-5-cis-13-trans prostadiene |
| 237 | | 1-trans-tri-n-butylstannyl-4-difluoromethyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-difluoromethyl-20-methyl-2-homo-5-cis-13-trans prostadiene |
| 238 | | 1-trans-tri-n-butylstannyl-4-trifluoromethyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-trifluoromethyl-20-methyl-2-homo-5-cis-13-trans prostadiene |
| 239 | | 1-trans-tri-n-butylstannyl-4-chloromethyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-chloromethyl-20-methyl-2-homo-5-cis-13-trans prostadiene |
| 240 | | 1-trans-tri-n-butylstannyl-4-trimethylsilyloxymethyl-4-trimethylsilyloxy-1-nonene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-hydroxymethyl-20-methyl-2-homo-5-cis-13-trans prostadiene |
| EXAMPLE | VINYL IODIDE | | CYCLOPENTENONE | PRODUCT PROSTAGLANDIN OF THE PGE2 SERIES |
| 241 | | 1-trans-iodo-3-triphenylmethoxy-1-decene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-20-ethyl-2-homo-5-cis-13-trans prostadiene |
| 242 | | 1-trans-iodo-3-methyl-3-trimethylsilyloxy-1-decene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-15-methyl-20-ethyl-2-homo-5-cis-13-trans prostadiene |
| 243 | | 1-trans-iodo-4,4-dimethyl-3-trimethylsilyloxy-1-decene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-16,16-dimethyl-20-ethyl-2-homo-5-cis-13-trans prostadiene |
| 244 | | 1-trans-iodo-4,4-trimethylene-3-trimethylsilyloxy-1-decene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-16,16-trimethylene-20-ethyl-2-homo-5-cis-13-trans prostadiene |
| EXAMPLE | VINYL TIN | | CYCLOPENTENONE | PRODUCT PROSTAGLANDIN OF THE PGE2 SERIES |
| 245 | | 1-trans-tri-n-butylstannyl-3-vinyl-3-trimethylsilyloxy-1-decene | 2-[7-phenoxyacetyl hept-2-cis-enyl]-4-trimethylsiloxy cyclopent-2-en-1-one | dl-11a,15a-dihydroxy-1-phenoxymethyl-1,9-dioxo-15-vinyl-20-ethyl-2-homo-5-cis-13-trans prostadiene |
| EXAMPLE | VINYL IODIDE | | CYCLOPENTENONE | PRODUCT PROSTAGLANDIN OF THE PGE2 SERIES |
| 246 | | 1-trans-iodo-4-triphenylmethoxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-20-ethyl-2-homo-5-cis-13-trans prostadiene |
| EXAMPLE | VINYL TIN | | CYCLOPENTENONE | PRODUCT PROSTAGLANDIN OF THE PGE2 SERIES |
| 247 | | 1-trans-tri-n-butylstannyl-4-methyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-20-ethyl-2-homo-5-cis-13-trans prostadiene |

TABLE XI-continued

| | VINYL IODIDE | CYCLOPENTENONE | PRODUCT PROSTAGLANDIN OF THE PGE2 SERIES |
|---|---|---|---|
| 248 | 1-trans-tri-n-butylstannyl-5-methyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methyl-20-ethyl-2-homo-5-cis-13-trans prostadiene |
| 249 | 1-trans-tri-n-butylstannyl-4-vinyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-vinyl-20-ethyl-2-homo-5-cis-13-trans prostadiene |
| 250 | 1-trans-tri-n-butylstannyl-4-trimethylsilylethynyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-ethynyl-20-ethyl-2-homo-5-cis-13-trans prostadiene |
| 251 | 1-trans-tri-n-butylstannyl-5-methylene-4-triethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-17-methylene-20-ethyl-2-homo-5-cis-13-trans prostadiene |
| 252 | 1-trans-tri-n-butylstannyl-4-methyl-5-methylene-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-methyl-17-methylene-20-ethyl-2-homo-5-cis-13-trans prostadiene |
| 253 | 1-trans-tri-n-butylstannyl-4-dimethoxymethyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-formyl-20-ethyl-2-homo-5-cis-13-trans prostadiene |
| 254 | 1-trans-tri-n-butylstannyl-4-fluoromethyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-fluoromethyl-20-ethyl-2-homo-5-cis-13-trans prostadiene |
| 255 | 1-trans-tri-n-butylstannyl-4-difluoromethyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-difluoromethyl-20-ethyl-2-homo-5-cis-13-trans prostadiene |
| 256 | 1-trans-tri-n-butylstannyl-4-trifluoromethyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-trifluoromethyl-20-ethyl-2-homo-5-cis-13-trans prostadiene |
| 257 | 1-trans-tri-n-butylstannyl-4-chloromethyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-chloromethyl-20-ethyl-2-homo-5-cis-13-trans prostadiene |
| 258 | 1-trans-tri-n-butylstannyl-4-trimethylsilyloxymethyl-4-trimethylsilyloxy-1-decene | 2-[7-phenoxyacetyl hept-2-cis-enyl]-4-trimethylsiloxy cyclopent-2-en-1-one | dl-11a,16-dihydroxy-1-phenoxymethyl-1,9-dioxo-16-hydroxymethyl-20-ethyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 259 | 1-trans-iodo-3-triphenylmethoxy-1-heptene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-20-nor-5-cis-13-trans prostadiene |
| 260 | 1-trans-iodo-3-methyl-3-trimethylsilyloxy-1-heptene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-15-methyl-20-nor-5-cis-13-trans prostadiene |
| 261 | 1-trans-iodo-4,4-dimethyl-3-trimethylsilyloxy-1-heptene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16,16-dimethyl-20-nor-5-cis-13-trans prostadiene |
| 262 | 1-trans-iodo-5,5-dimethyl-3-triphenylmethoxy-1-octene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-17,17-dimethyl-5-cis-13-trans prostadiene |
| 263 | 1-trans-iodo-4-methyl-3-triphenylmethoxy-1-octene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16-methyl-5-cis-13-trans prostadiene |
| 264 | 1-trans-iodo-4,4-trimethylene-3-trimethylsilyloxy-1-heptene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16,16-trimethylene-20-nor-5-cis-13-trans prostadiene |

TABLE XI-continued

| EXAMPLE | VINYL TIN | CYCLOPENTENONE | PRODUCT PROSTAGLANDIN OF THE PGE2 SERIES |
|---|---|---|---|
| 265 | 1-trans-tri-n-butylstannyl-3-vinyl-3-trimethylsilyloxy-1-heptene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-15-vinyl-20-nor-5-cis-13-trans prostadiene |
| 266 | 1-trans-tri-n-butylstannyl-4-phenoxy-3-triethylsilyloxy-1-butene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-phenoxy-17-20-tetranor-5-cis-13-trans prostadiene |
| 267 | 1-trans-tri-n-butylstannyl-4-(p-fluorophenoxy)-3-triethylsilyloxy-1-butene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-(p-fluorophenoxy)-17-20-tetranor-5-cis-13-trans prostadiene |
| 268 | 1-trans-tri-n-butylstannyl-4-(m-chlorophenoxy)-3-triethylsilyloxy-1-butene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-(m-chlorophenoxy)-17-20-tetranor-5-cis-13-trans prostadiene |
| 269 | 1-trans-tri-n-butylstannyl-4-(m-trifluoromethylphenoxy)-3-triethylsilyloxy-1-butene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-(m-trifluoromethylphenoxy)-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 270 | 1-trans-iodo-5-phenyl-3-triethylsilyloxy-1-pentene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-17-phenyl-18-20-trinor-5-cis-13-trans prostadiene |
| 271 | 1-trans-iodo-4,4-dimethyl-5-phenyl-3-triethylsilyloxy-1-pentene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16,16-dimethyl-17-phenyl-18-20-trinor-5-cis-13-trans prostadiene |
| 272 | 1-trans-iodo-4-cyclopentyl-3-triphenylmethoxy-1-butene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-cyclopentyl-17-20-tetranor-5-cis-13-trans prostadiene |
| 273 | 1-trans-iodo-4-cyclohexyl-3-triphenylmethoxy-1-butene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-cyclohexyl-17-20-tetranor-5-cis-13-trans prostadiene |
| 274 | 1-trans-iodo-4-triphenylmethoxy-1-heptene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 275 | 1-trans-tri-n-butylstannyl-4-methyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-methyl-20-nor-5-cis-13-trans prostadiene |
| 276 | 1-trans-tri-n-butylstannyl-4-ethyl-4-trimethylsilyloxy-1-octene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-ethyl-5-cis-13-trans prostadiene |
| 277 | 1-trans-tri-n-butylstannyl-5-methyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-17-methyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 278 | 1-trans-iodo-5,5-dimethyl-4-trimethylsilyloxy-1-octene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-17,17-dimethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|

TABLE XI-continued

| EXAMPLE | VINYL IODIDE | CYCLOPENTENONE | PRODUCT PROSTAGLANDIN OF THE PGE2 SERIES |
|---|---|---|---|
| 279 | 1-trans-tri-n-butylstannyl-4-vinyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-vinyl-20-nor-5-cis-13-trans prostadiene |
| 280 | 1-trans-tri-n-butylstannyl-4-cyclopropyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-cyclopropyl-5-cis-13-trans prostadiene |
| 281 | 1-trans-tri-n-butylstannyl-4-trimethylsilylethynyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-ethynyl-20-nor-5-cis-13-trans prostadiene |
| 282 | 1-trans-tri-n-butylstannyl-5-methylene-4-triethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-17-methylene-20-nor-5-cis-13-trans prostadiene |
| 283 | 1-trans-tri-n-butylstannyl-4-methyl-5-methylene-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-methyl-17-methylene-20-nor-5-cis-13-trans prostadiene |
| 284 | 1-trans-tri-n-butylstannyl-4-dimethoxymethyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-formyl-20-nor-5-cis-13-trans prostadiene |
| 285 | 1-trans-tri-n-butylstannyl-4-fluoromethyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-fluoromethyl-20-nor-5-cis-13-trans prostadiene |
| 286 | 1-trans-tri-n-butylstannyl-4-difluoromethyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-difluoromethyl-20-nor-5-cis-13-trans prostadiene |
| 287 | 1-trans-tri-n-butylstannyl-4-trifluoromethyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-trifluoromethyl-20-nor-5-cis-13-trans prostadiene |
| 288 | 1-trans-tri-n-butylstannyl-4-chloromethyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-chloromethyl-20-nor-5-cis-13-trans prostadiene |
| 289 | 1-trans-tri-n-butylstannyl-4-trimethylsilyloxymethyl-4-trimethylsilyloxy-1-heptene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 290 | 1-trans-iodo-4-methyl-7-chloro-4-trimethylsilyloxy-1-heptene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16-methyl-19-chloro-20-nor-5-cis-13-trans prostadiene |
| 291 | 1-trans-iodo-3-triphenylmethoxy-1-octene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-5-cis-13-trans prostadiene |
| 292 | 1-trans-iodo-3-methyl-3-trimethylsilyloxy-1-octene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-15-methyl-5-cis-13-trans prostadiene |
| 293 | 1-trans-iodo-4,4-dimethyl-3-trimethylsilyloxy-1-octene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16,16-dimethyl-5-cis-13-trans prostadiene |
| 294 | 1-trans-iodo-4,4-trimethylene-3-trimethylsilyloxy-1-octene | 2-[6-phenoxyacetyl hex-2-cis-enyl]-4R-trimethylsilyloxy cyclopent-2-en-1-one | nat-11a,15a-dihydroxy-1-phenoxymethyl-1,9-dioxo-16,16-trimethylene-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 295 | 1-trans-tri-n-butylstannyl-3-vinyl- | 2-[6-phenoxyacetyl | nat-11a,15a-dihydroxy-1-phenoxymethyl-1,9-dioxo-15-vinyl- |

TABLE XI-continued

| EXAMPLE | VINYL IODIDE | CYCLOPENTENONE | PRODUCT PROSTAGLANDIN OF THE PGE2 SERIES |
|---|---|---|---|
| | 3-trimethylsilyloxy-1-octene | hex-2-cis-enyl]-4R-trimethylsilyloxy cyclopent-2-en-1-one | 5-cis-13-trans prostadiene |
| 296 | 1-trans-iodo-4-triphenylmethoxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 297 | 1-trans-tri-n-butylstannyl-4-methyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-5-cis-13-trans prostadiene |
| 298 | 1-trans-tri-n-butylstannyl-5-methyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-17-methyl-5-cis-13-trans prostadiene |
| 299 | 1-trans-tri-n-butylstannyl-4-vinyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-vinyl-5-cis-13-trans prostadiene |
| 300 | 1-trans-tri-n-butylstannyl-4-trimethylsilylethynyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-ethynyl-5-cis-13-trans prostadiene |
| 301 | 1-trans-tri-n-butylstannyl-5-methylene-4-triethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-17-methylene-5-cis-13-trans prostadiene |
| 302 | 1-trans-tri-n-butylstannyl-4-methyl-5-methylene-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-17-methylene-5-cis-13-trans prostadiene |
| 303 | 1-trans-tri-n-butylstannyl-4-dimethoxymethyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-formyl-5-cis-13-trans prostadiene |
| 304 | 1-trans-tri-n-butylstannyl-4-fluoromethyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-fluoromethyl-5-cis-13-trans prostadiene |
| 305 | 1-trans-tri-n-butylstannyl-4-difluoromethyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-difluoromethyl-5-cis-13-trans prostadiene |
| 306 | 1-trans-tri-n-butylstannyl-4-trifluoromethyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-trifluoromethyl-5-cis-13-trans prostadiene |
| 307 | 1-trans-tri-n-butylstannyl-4-chloromethyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-chloromethyl-5-cis-13-trans prostadiene |
| 308 | 1-trans-tri-n-butylstannyl-4-trimethylsilyloxymethyl-4-trimethylsilyloxy-1-octene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-hydroxymethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 309 | 1-trans-iodo-3-triphenylmethoxy-1-nonene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-20-methyl-5-cis-13-trans prostadiene |
| 310 | 1-trans-iodo-3-methyl-3-trimethylsilyloxy-1-nonene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-20-methyl-5-cis-13-trans prostadiene-15-methyl |

TABLE XI-continued

| | | | |
|---|---|---|---|
| 311 | 1-trans-iodo-4,4-dimethyl-3-trimethylsilyloxy-1-nonene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16,16-dimethyl-20-methyl-5-cis-13-trans prostadiene |
| 312 | 1-trans-iodo-4,4-trimethylene-3-trimethylsilyloxy-1-nonene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16,16-trimethylene-20-methyl-5-cis-13-trans prostadiene |
| EXAMPLE | VINYL TIN | CYCLOPENTENONE | PRODUCT PROSTAGLANDIN OF THE PGE2 SERIES |
| 313 | 1-trans-tri-n-butylstannyl-3-vinyl-3-trimethylsilyloxy-1-nonene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 314 | 1-trans-iodo-4-triphenylmethoxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-20-methyl-5-cis-13-trans prostadiene |
| EXAMPLE | VINYL TIN | CYCLOPENTENONE | PRODUCT PROSTAGLANDIN OF THE PGE2 SERIES |
| 315 | 1-trans-tri-n-butylstannyl-4-methyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-20-methyl-5-cis-13-trans prostadiene |
| 316 | 1-trans-tri-n-butylstannyl-4-methyl-5-methyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-17-methyl-20-methyl-5-cis-13-trans prostadiene |
| 317 | 1-trans-tri-n-butylstannyl-4-vinyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-vinyl-20-methyl-5-cis-13-trans prostadiene |
| 318 | 1-trans-tri-n-butylstannyl-4-trimethylsilylethynyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-ethynyl-20-methyl-5-cis-13-trans prostadiene |
| 319 | 1-trans-tri-n-butylstannyl-5-methylene-4-triethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-17-methylene-20-methyl-5-cis-13-trans prostadiene |
| 320 | 1-trans-tri-n-butylstannyl-4-methyl-5-methylene-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-17-methylene-20-methyl-5-cis-13-trans prostadiene |
| 321 | 1-trans-tri-n-butylstannyl-4-dimethoxymethyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-formyl-20-methyl-5-cis-13-trans prostadiene |
| 322 | 1-trans-tri-n-butylstannyl-4-fluoromethyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-fluoromethyl-20-methyl-5-cis-13-trans prostadiene |
| 323 | 1-trans-tri-n-butylstannyl-4-difluoromethyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-difluoromethyl-20-methyl-5-cis-13-trans prostadiene |
| 324 | 1-trans-tri-n-butylstannyl-4-trifluoromethyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-trifluoromethyl-20-methyl-5-cis-13-trans prostadiene |
| 325 | 1-trans-tri-n-butylstannyl-4-chloromethyl-4-trimethylsilyloxy-1-nonene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-chloromethyl-20-methyl-5-cis-13-trans prostadiene |
| 326 | 1-trans-tri-n-butylstannyl-4-trimethylsilyloxymethyl-4-trimethylsilyloxy-1-nonene | 2-[6-phenoxyac.tyl hex-2-cis-enyl]-4R-trimethylsiloxy cyclopent-2-en-1-one | nat-11a,16-dihydroxy-1-phenoxymethyl-1,9-dioxo-16-hydroxymethyl-20-methyl-5-cis-13-trans prostadiene |

TABLE XI-continued

| EXAMPLE | VINYL IODIDE | CYCLOPENTENONE | PRODUCT PROSTAGLANDIN OF THE PGE2 SERIES |
|---|---|---|---|
| 327 | 1-trans-iodo-3-triphenylmethoxy-1-decene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-20-ethyl-5-cis-13-trans prostadiene |
| 328 | 1-trans-iodo-3-methyl-3-trimethylsilyloxy-1-decene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-15-methyl-20-ethyl-5-cis-13-trans prostadiene |
| 329 | 1-trans-iodo-4,4-dimethyl-3-trimethylsilyloxy-1-decene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16,16-dimethyl-20-ethyl-5-cis-13-trans prostadiene |
| 330 | 1-trans-iodo-4,4-trimethylene-3-trimethylsilyloxy-1-decene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-16,16-trimethylene-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 331 | 1-trans-tri-n-butylstannyl-3-vinyl-3-trimethylsilyloxy-1-decene | 2-[6-phenoxyacetyl hex-2-cis-enyl]-4R-trimethylsiloxy cyclopent-2-en-1-one | nat-11a,15a-dihydroxy-1-phenoxymethyl-1,9-dioxo-15-vinyl-20-ethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 332 | 1-trans-iodo-4-triphenylmethoxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-20-ethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 333 | 1-trans-tri-n-butylstannyl-4-methyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-20-ethyl-5-cis-13-trans prostadiene |
| 334 | 1-trans-tri-n-butylstannyl-5-methyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-17-methyl-20-ethyl-5-cis-13-transprostadiene |
| 335 | 1-trans-tri-n-butylstannyl-4-vinyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-vinyl-20-ethyl-5-cis-13-trans prostadiene |
| 336 | 1-trans-tri-n-butylstannyl-4-trimethylsilylethynyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-ethynyl-20-ethyl-5-cis-13-trans prostadiene |
| 337 | 1-trans-tri-n-butylstannyl-5-methylene-4-triethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-17-methylene-20-ethyl-5-cis-13-trans prostadiene |
| 338 | 1-trans-tri-n-butylstannyl-4-methyl-5-methylene-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-methyl-17-methylene-20-ethyl-5-cis-13-trans prostadiene |
| 339 | 1-trans-tri-n-butylstannyl-4-dimethoxymethyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-formyl-20-ethyl-5-cis-13-trans prostadiene |
| 340 | 1-trans-tri-n-butylstannyl-4-fluoromethyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-fluoromethyl-20-ethyl-5-cis-13-trans prostadiene |
| 341 | 1-trans-tri-n-butylstannyl-4-difluoromethyl-4-trimethylsilyloxy-1-decene | 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-difluoromethyl-20-ethyl-5-cis-13-trans prostadiene |

TABLE XI-continued

| EXAMPLE | VINYL IODIDE | CYCLOPENTENONE | PRODUCT PROSTAGLANDIN OF THE 11-DEOXY PGE2 SERIES |
|---|---|---|---|
| 342 | 1-trans-tri-n-butylstannyl-4-trifluoromethyl-4-trimethylsilyloxy-1-decene | cyclopent-2-en-1-one 2-[6-phenoxyacetyl hex-2-cis-enyl]-4R-trimethylsiloxy cyclopent-2-en-1-one | nat-11a,16-dihydroxy-1-phenoxymethyl-1,9-dioxo-16-trifluoromethyl-20-ethyl-5-cis-13-trans prostadiene |
| 343 | 1-trans-tri-n-butylstannyl-4-chloromethyl-4-trimethylsilyloxy-1-decene | 2-[6-phenoxyacetyl hex-2-cis-enyl-]-4R-trimethylsiloxy cyclopent-2-en-1-one | nat-11a,16-dihydroxy-1-phenoxymethyl-1,9-dioxo-16-chloromethyl-20-ethyl-5-cis-13-trans prostadiene |
| 344 | 1-trans-tri-n-butylstannyl-4-trimethylsilyloxymethyl-4-trimethylsilyloxy-1-decene | 2-[6-phenoxyacetyl hex-2-cis-enyl]-4R-trimethylsilyloxy cyclopent-2-en-1-one | nat-11a,16-dihydroxy-1-phenoxymethyl-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 345 | 1-trans-iodo-3-triphenylmethoxy-1-heptene | 2-[5-phenoxyacetyl pent-2-cis-enyl] cyclopent-2-en-1-one | dl-15a-hydroxy-1-phenoxymethyl-1,9-dioxo-20-nor-2-nor-5-cis-13-trans prostadiene |
| 346 | 1-trans-iodo-3-methyl-3-trimethylsilyloxy-1-heptene | 2-[5-phenoxyacetyl pent-2-cis-enyl] cyclopent-2-en-1-one | dl-15a-hydroxy-1-phenoxymethyl-1,9-dioxo-15-methyl-20-nor-2-nor-5-cis-13-trans prostadiene |
| 347 | 1-trans-iodo-4,4-dimethyl-3-trimethylsilyloxy-1-heptene | 2-[5-phenoxyacetyl pent-2-cis-enyl] cyclopent-2-en-1-one | dl-15a-hydroxy-1-phenoxymethyl-1,9-dioxo-16,16-dimethyl-20-nor-2-nor-5-cis-13-trans prostadiene |
| 348 | 1-trans-iodo-5,5-dimethyl-3-triphenylmethoxy-1-octene | 2-[5-phenoxyacetyl pent-2-cis-enyl] cyclopent-2-en-1-one | dl-15a-hydroxy-1-phenoxymethyl-1,9-dioxo-17,17-dimethyl-2-nor-5-cis-13-trans prostadiene |
| 349 | 1-trans-iodo-4-methyl-3-triphenylmethoxy-1-octene | 2-[5-phenoxyacetyl pent-2-cis-enyl] cyclopent-2-en-1-one | dl-15a-hydroxy-1-phenoxymethyl-1,9-dioxo-16-methyl-2-nor-5-cis-13-trans prostadiene |
| 350 | 1-trans-iodo-4,4-trimethylene-3-trimethylsilyloxy-1-heptene | 2-[5-phenoxyacetyl pent-2-cis-enyl] cyclopent-2-en-1-one | dl-15a-hydroxy-1-phenoxymethyl-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 351 | 1-trans-tri-n-butylstannyl-3-vinyl-3-trimethylsilyloxy-1-heptene | 2-[5-phenoxyacetyl pent-2-cis-enyl] cyclopent-2-en-1-one | dl-15a-hydroxy-1-phenoxymethyl-1,9-dioxo-15-vinyl-20-nor-2-nor-5-cis-13-trans prostadiene |
| 352 | 1-trans-tri-n-butylstannyl-4-phenoxy-3-triethylsilyloxy-1-butene | 2-[5-phenoxyacetyl pent-2-cis-enyl] cyclopent-2-en-1-one | dl-15a-hydroxy-1-phenoxymethyl-1,9-dioxo-16-phenoxy-2-nor-17-20-tetranor-5-cis-13-trans prostadiene |
| 353 | 1-trans-tri-n-butylstannyl-4-(p-fluorophenoxy)-3-triethylsilyloxy-1-butene | 2-[5-phenoxyacetyl pent-2-cis-enyl] cyclopent-2-en-1-one | dl-15a-hydroxy-1-phenoxymethyl-1,9-dioxo-16-(p-fluorophenoxy)-2-nor-17-20-tetranor-5-cis-13-trans prostadiene |
| 354 | 1-trans-tri-n-butylstannyl-4-(m-chlorophenoxy)-3-triethylsilyloxy-1-butene | 2-[5-phenoxyacetyl pent-2-cis-enyl] cyclopent-2-en-1-one | dl-15a-hydroxy-1-phenoxymethyl-1,9-dioxo-16-(m-chlorophenoxy)-2-nor-17-20-tetranor-5-cis-13-trans prostadiene |
| 355 | 1-trans-tri-n-butylstannyl-4-(m-trifluoromethylphenoxy)-3-triethylsilyloxy-1-butene | 2-[5-phenoxyacetyl pent-2-cis-enyl] cyclopent-2-en-1-one | dl-15a-hydroxy-1-phenoxymethyl-1,9-dioxo-16-(m-trifluoromethylphenoxy)-2-nor-17-20-tetranor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 356 | 1-trans-iodo-5-phenyl-3-triethylsilyloxy-1-pentene | 2-[5-phenoxyacetyl pent-2-cis-enyl] cyclopent-2-en-1-one | dl-15a-hydroxy-1-phenoxymethyl-1,9-dioxo-17-phenyl-2-nor-18-20-trinor-5-cis-13-trans prostadiene |
| 357 | 1-trans-iodo-4,4-dimethyl-5-phenyl | 2-[5-phenoxyacetyl | dl-15a-hydroxy-1-phenoxymethyl-1,9-dioxo- |

TABLE XI-continued

| | | | |
|---|---|---|---|
| 358 | 3-triethylsilyloxy-1-pentene | 2-[5-phenoxyacetyl pent-2-cis-enyl] cyclopent-2-en-1-one | 16,16-dimethyl-17-phenyl-2-nor-18-20-trinor-5-cis-13-trans prostadiene |
| 358 | 1-trans-iodo-4-cyclopentyl 3-triphenylmethoxy-1-butene | 2-[5-phenoxyacetyl pent-2-cis-enyl] cyclopent-2-en-1-one | dl-15a-hydroxy-1-phenoxymethyl-1,9-dioxo-16-cyclopentyl-2-nor-17-20-tetranor-5-cis-13-trans prostadiene |
| 359 | 1-trans-iodo-4-cyclohexyl 3-triphenylmethoxy-1-butene | 2-[5-phenoxyacetyl pent-2-cis-enyl] cyclopent-2-en-1-one | dl-15a-hydroxy-1-phenoxymethyl-1,9-dioxo-16-cyclohexyl-2-nor-17-20-tetranor-5-cis-13-trans prostadiene |
| 360 | 1-trans-iodo-4-triphenylmethoxy-1-heptene | 2-[5-phenoxyacetyl pent-2-cis-enyl] cyclopent-2-en-1-one | dl-16-hydroxy-1-phenoxymethyl-1,9-dioxo-20-nor-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 361 | 1-trans-tri-n-butylstannyl-4-methyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-methyl-20-nor-2-nor-5-cis-13-trans prostadiene |
| 362 | 1-trans-tri-n-butylstannyl-4-ethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-ethyl-2-nor-5-cis-13-trans prostadiene |
| 363 | 1-trans-tri-n-butylstannyl-5-methyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-17-methyl-20-nor-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 364 | 1-trans-iodo-5,5-dimethyl 4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-17,17-dimethyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 365 | 1-trans-tri-n-butylstannyl-4-vinyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-vinyl-20-nor-2-nor-5-cis-13-trans prostadiene |
| 366 | 1-trans-tri-n-butylstannyl-4-cyclopropyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-cyclopropyl-2-nor-5-cis-13-trans prostadiene |
| 367 | 1-trans-tri-n-butylstannyl-4-trimethylsilylethynyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-ethynyl-20-nor-2-nor-5-cis-13-trans prostadiene |
| 368 | 1-trans-tri-n-butylstannyl-4-methylene 4-triethylsilyloxy-1-heptene | 2-[5-phenoxyacetyl pent-2-cis-enyl] cyclopent-2-en-1-one | dl-16-hydroxy-1-phenoxymethyl-1,9-dioxo-17-methylene-20-nor-2-nor-5-cis-13-trans prostadiene |
| 369 | 1-trans-tri-n-butylstannyl-4-methyl-5-methylene 4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-methyl-17-methylene-20-nor-2-nor-5-cis-13-trans prostadiene |
| 370 | 1-trans-tri-n-butylstannyl-4-dimethoxymethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-formyl-20-nor-2-nor-5-cis-13-trans prostadiene |
| 371 | 1-trans-tri-n-butylstannyl-4-fluoromethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-fluoromethyl-20-nor-2-nor-5-cis-13-trans prostadiene |
| 372 | 1-trans-tri-n-butylstannyl-4-difluoromethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-difluoromethyl-20-nor-2-nor-5-cis-13-trans prostadiene |

TABLE XI-continued

| | | | |
|---|---|---|---|
| 373 | 1-trans-tri-n-butylstannyl-4-trifluoromethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-trifluoromethyl-20-nor-2-nor-5-cis-13-trans prostadiene |
| 374 | 1-trans-tri-n-butylstannyl-4-chloromethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-chloromethyl-20-nor-2-nor-5-cis-13-trans prostadiene |
| 375 | 1-trans-tri-n-butylstannyl-4-trimethylsilyloxymethyl-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-hydroxymethyl-20-nor-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 376 | 1-trans-iodo-4-methyl-7-chloro-4-trimethylsilyloxy-1-heptene | 2-[5-phenoxyacetyl pent-2-cis-enyl] cyclopent-2-en-1-one | dl-16-hydroxy-1-phenoxymethyl-1,9-dioxo-16-methyl-19-chloro-2-nor-20-nor-5-cis-13-trans prostadiene |
| 377 | 1-trans-iodo-3-triphenylmethoxy-1-octene | 2-[5-phenoxyacetyl pent-2-cis-enyl] cyclopent-2-en-1-one | dl-15a-hydroxy-1-phenoxymethyl-1,9-dioxo-2-nor-5-cis-13-trans prostadiene |
| 378 | 1-trans-iodo-3-methyl-3-trimethylsilyloxy-1-octene | 2-[5-phenoxyacetyl pent-2-cis-enyl] cyclopent-2-en-1-one | dl-15a-hydroxy-1-phenoxymethyl-1,9-dioxo-15-methyl-2-nor-5-cis-13-trans prostadiene |
| 379 | 1-trans-iodo-4,4-dimethyl-3-trimethylsilyloxy-1-octene | 2-[5-phenoxyacetyl pent-2-cis-enyl] cyclopent-2-en-1-one | dl-15a-hydroxy-1-phenoxymethyl-1,9-dioxo-16,16-dimethyl-2-nor-5-cis-13-trans prostadiene |
| 380 | 1-trans-iodo-4,4-trimethylene-3-trimethylsilyloxy-1-octene | 2-[5-phenoxyacetyl pent-2-cis-enyl] cyclopent-2-en-1-one | dl-15a-hydroxy-1-phenoxymethyl-1,9-dioxo-16,16-trimethylene-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 381 | 1-trans-tri-n-butylstannyl-3-vinyl-3-trimethylsilyloxy-1-octene | 2-[5-phenoxyacetyl pent-2-cis-enyl] cyclopent-2-en-1-one | dl-15a-hydroxy-1-phenoxymethyl-1,9-dioxo-15-vinyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 382 | 1-trans-iodo-4-triphenylmethoxy-1-octene | 2-[5-phenoxyacetyl pent-2-cis-enyl] cyclopent-2-en-1-one | dl-16-hydroxy-1-phenoxymethyl-1,9-dioxo-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 383 | 1-trans-tri-n-butylstannyl-4-methyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-methyl-2-nor-5-cis-13-trans prostadiene |
| 384 | 1-trans-tri-n-butylstannyl-5-methyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-17-methyl-2-nor-5-cis-13-trans prostadiene |
| 385 | 1-trans-tri-n-butylstannyl-4-vinyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-vinyl-2-nor-5-cis-13-trans prostadiene |
| 386 | 1-trans-tri-n-butylstannyl-5-trimethylsilylethynyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-ethynyl-2-nor-5-cis-13-trans prostadiene |
| 387 | 1-trans-tri-n-butylstannyl-5-methylene-4-triethylsilyloxy-1-octene | 2-[5-phenoxyacetyl pent-2-cis-enyl] cyclopent-2-en-1-one | dl-16-hydroxy-1-phenoxymethyl-1,9-dioxo-17-methylene-2-nor-5-cis-13-trans prostadiene |

TABLE XI-continued

| | | | |
|---|---|---|---|
| 388 | 1-trans-tri-n-butylstannyl-5-methyl-5-methylene-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-methyl-17-methylene-2-nor-5-cis-13-trans prostadiene |
| 389 | 1-trans-tri-n-butylstannyl-4-dimethoxymethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-formyl-2-nor-5-cis-13-trans prostadiene |
| 390 | 1-trans-tri-n-butylstannyl-4-fluoromethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-fluoromethyl-2-nor-5-cis-13-trans prostadiene |
| 391 | 1-trans-tri-n-butylstannyl-4-difluoromethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-difluoromethyl-2-nor-5-cis-13-trans prostadiene |
| 392 | 1-trans-tri-n-butylstannyl-4-trifluoromethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-trifluoromethyl-2-nor-5-cis-13-trans prostadiene |
| 393 | 1-trans-tri-n-butylstannyl-4-chloromethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-chloromethyl-2-nor-5-cis-13-trans prostadiene |
| 394 | 1-trans-tri-n-butylstannyl-4-trimethylsilyloxymethyl-4-trimethylsilyloxy-1-octene | 2-[5-phenoxyacetyl pent-2-cis-enyl] cyclopent-2-en-1-one | dl-16-hydroxy-1-phenoxymethyl-1,9-dioxo-16-hydroxymethyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 395 | 1-trans-iodo-3-triphenylmethoxy-1-nonene | 2-[5-phenoxyacetyl pent-2-cis-enyl] cyclopent-2-en-1-one | dl-15a-hydroxy-1-phenoxymethyl-1,9-dioxo-20-methyl-2-nor-5-cis-13-trans prostadiene |
| 396 | 1-trans-iodo-3-methyl-3-trimethylsilyloxy-1-nonene | 2-[5-phenoxyacetyl pent-2-cis-enyl] cyclopent-2-en-1-one | dl-15a-hydroxy-1-phenoxymethyl-1,9-dioxo-15-methyl-20-methyl-2-nor-5-cis-13-trans prostadiene |
| 397 | 1-trans-iodo-4,4-dimethyl-3-trimethylsilyloxy-1-nonene | 2-[5-phenoxyacetyl pent-2-cis-enyl] cyclopent-2-en-1-one | dl-15a-hydroxy-1-phenoxymethyl-1,9-dioxo-16,16-dimethyl-20-methyl-2-nor-5-cis-13-trans prostadiene |
| 398 | 1-trans-iodo-4,4-trimethylene-3-trimethylsilyloxy-1-nonene | 2-[5-phenoxyacetyl pent-2-cis-enyl] cyclopent-2-en-1-one | dl-15a-hydroxy-1-phenoxymethyl-1,9-dioxo-16,16-trimethylene-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 399 | 1-trans-tri-n-butylstannyl-3-vinyl-3-trimethylsilyloxy-1-nonene | 2-[5-phenoxyacetyl pent-2-cis-enyl] cyclopent-2-en-1-one | dl-15a-hydroxy-1-phenoxymethyl-1,9-dioxo-15-vinyl-20-methyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 400 | 1-trans-iodo-4-triphenylmethoxy-1-nonene | 2-[5-phenoxyacetyl pent-2-cis-enyl] cyclopent-2-en-1-one | dl-16-hydroxy-1-phenoxymethyl-1,9-dioxo-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 401 | 1-trans-tri-n-butylstannyl-4-methyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-methyl-20-methyl-2-nor-5-cis-13-trans prostadiene |
| 402 | 1-trans-tri-n-butylstannyl-5-methyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-17-methyl-20-methyl-2-nor-5-cis-13-trans prostadiene |

TABLE XI-continued

| | | | |
|---|---|---|---|
| 403 | | 1-trans-tri-n-butylstannyl-4-vinyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-vinyl-20-methyl-2-nor-5-cis-13-trans prostadiene |
| 404 | | 1-trans-tri-n-butylstannyl-4-trimethylsilylethynyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-ethynyl-20-methyl-2-nor-5-cis-13-trans prostadiene |
| 405 | | 1-trans-tri-n-butylstannyl-5-methylene-4-triethylsilyloxy-1-nonene | 2-[5-phenoxyacetyl pent-2-cis-enyl] cyclopent-2-en-1-one | dl-16-hydroxy-1-phenoxymethyl-1,9-dioxo-17-methylene-20-methyl-2-nor-5-cis-13-trans prostadiene |
| 406 | | 1-trans-tri-n-butylstannyl-4-methyl-5-methylene-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-methyl-17-methylene-20-methyl-2-nor-5-cis-13-trans prostadiene |
| 407 | | 1-trans-tri-n-butylstannyl-4-dimethoxymethyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-formyl-20-methyl-2-nor-5-cis-13-trans prostadiene |
| 408 | | 1-trans-tri-n-butylstannyl-4-fluoromethyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-fluoromethyl-20-methyl-2-nor-5-cis-13-trans prostadiene |
| 409 | | 1-trans-tri-n-butylstannyl-4-difluoromethyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-difluoromethyl-20-methyl-2-nor-5-cis-13-trans prostadiene |
| 410 | | 1-trans-tri-n-butylstannyl-4-trifluoromethyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-trifluoromethyl-20-methyl-2-nor-5-cis-13-trans prostadiene |
| 411 | | 1-trans-tri-n-butylstannyl-4-chloromethyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-chloromethyl-20-methyl-2-nor-5-cis-13-trans prostadiene |
| 412 | | 1-trans-tri-n-butylstannyl-4-trimethylsilyloxymethyl-4-trimethylsilyloxy-1-nonene | 2-[5-phenoxyacetyl pent-2-cis-enyl] cyclopent-2-en-1-one | dl-16-hydroxy-1-phenoxymethyl-1,9-dioxo-16-hydroxymethyl-20-methyl-2-nor-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 413 | 1-trans-iodo-3-triphenylmethoxy-1-decene | | 2-[5-phenoxyacetyl pent-2-cis-enyl] cyclopent-2-en-1-one | dl-15a-hydroxy-1-phenoxymethyl-1,9-dioxo-20-ethyl-2-nor-5-cis-13-trans prostadiene |
| 414 | 1-trans-iodo-3-methyl-3-trimethylsilyloxy-1-decene | | 2-[5-phenoxyacetyl pent-2-cis-enyl] cyclopent-2-en-1-one | dl-15a-hydroxy-1-phenoxymethyl-1,9-dioxo-15-methyl-20-ethyl-2-nor-5-cis-13-trans prostadiene |
| 415 | 1-trans-iodo-4,4-dimethyl-3-trimethylsilyloxy-1-decene | | 2-[5-phenoxyacetyl pent-2-cis-enyl] cyclopent-2-en-1-one | dl-15a-hydroxy-1-phenoxymethyl-1,9-dioxo-16,16-dimethyl-20-ethyl-2-nor-5-cis-13-trans prostadiene |
| 416 | 1-trans-iodo-4,4-trimethylene-3-trimethylsilyloxy-1-decene | | 2-[5-phenoxyacetyl pent-2-cis-enyl] cyclopent-2-en-1-one | dl-15a-hydroxy-1-phenoxymethyl-1,9-dioxo-16,16-trimethylene-20-ethyl-2-nor-5-cis-13-trans prostadiene |
| EXAMPLE | VINYL TIN | | CYCLOPENTENONE | PRODUCT PROSTAGLANDIN OF THE 11-DEOXY PGE2 SERIES |
| 417 | 1-trans-tri-n-butylstannyl-3-vinyl-3-trimethylsilyloxy-1-decene | | 2-[5-phenoxyacetyl pent-2-cis-enyl] cyclopent-2-en-1-one | dl-15a-hydroxy-1-phenoxymethyl-1,9-dioxo-15-vinyl-20-ethyl-2-nor-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 418 | 1-trans-iodo-4-triphenylmethoxy-1-decene | | 2-[5-phenoxyacetyl pent-2-cis-enyl] | dl-16-hydroxy-1-phenoxymethyl-1,9-dioxo-20-ethyl-2-nor-5-cis-13-trans prostadiene |

TABLE XI-continued

| EXAMPLE | VINYL TIN | CYCLOPENTENONE | PRODUCT PROSTAGLANDIN OF THE 11-DEOXY PGE2 SERIES |
|---|---|---|---|
| 419 | 1-trans-tri-n-butylstannyl-4-methyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-methyl-20-ethyl-2-nor-5-cis-13-trans prostadiene |
| 420 | 1-trans-tri-n-butylstannyl-5-methyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-17-methyl-20-ethyl-2-nor-5-cis-13-trans prostadiene |
| 421 | 1-trans-tri-n-butylstannyl-4-vinyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-vinyl-20-ethyl-2-nor-5-cis-13-trans prostadiene |
| 422 | 1-trans-tri-n-butylstannyl-4-trimethylsilylethynyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-ethynyl-20-ethyl-2-nor-5-cis-13-trans prostadiene |
| 423 | 1-trans-tri-n-butylstannyl-5-methylene-4-triethylsilyloxy-1-decene | 2-[5-phenoxyacetyl pent-2-cis-enyl] cyclopent-2-en-1-one | dl-16-hydroxy-1-phenoxymethyl-1,9-dioxo-17-methylene-20-ethyl-2-nor-5-cis-13-trans prostadiene |
| 424 | 1-trans-tri-n-butylstannyl-4-methyl-5-methylene-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-methyl-17-methylene-20-ethyl-2-nor-5-cis-13-trans prostadiene |
| 425 | 1-trans-tri-n-butylstannyl-4-dimethoxymethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-formyl-20-ethyl-2-nor-5-cis-13-trans prostadiene |
| 426 | 1-trans-tri-n-butylstannyl-4-fluoromethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-fluoromethyl-20-ethyl-2-nor-5-cis-13-trans prostadiene |
| 427 | 1-trans-tri-n-butylstannyl-4-difluoromethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-difluoromethyl-20-ethyl-2-nor-5-cis-13-trans prostadiene |
| 428 | 1-trans-tri-n-butylstannyl-4-trifluoromethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-trifluoromethyl-20-ethyl-2-nor-5-cis-13-trans prostadiene |
| 429 | 1-trans-tri-n-butylstannyl-4-chloromethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-chloromethyl-20-ethyl-2-nor-5-cis-13-trans prostadiene |
| 430 | 1-trans-tri-n-butylstannyl-4-trimethylsilyloxymethyl-4-trimethylsilyloxy-1-decene | 2-[5-phenoxyacetyl pent-2-cis-enyl] cyclopent-2-en-1-one | dl-16-hydroxy-1-phenoxymethyl-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 431 | 1-trans-iodo-3-triphenylmethoxy-1-heptene | 2-[6-phenoxyacetyl hex-2-cis-enyl] cyclopent-2-en-1-one | dl-15a-hydroxy-1-phenoxymethyl-1,9-dioxo-20-nor-5-cis-13-trans prostadiene |
| 432 | 1-trans-iodo-3-methyl-3-trimethylsilyloxy-1-heptene | 2-[6-phenoxyacetyl hex-2-cis-enyl] cyclopent-2-en-1-one | dl-15a-hydroxy-1-phenoxymethyl-1,9-dioxo-15-methyl-20-nor-5-cis-13-trans prostadiene |
| 433 | 1-trans-iodo-4,4-dimethyl-3-trimethylsilyloxy-1-heptene | 2-[6-phenoxyacetyl hex-2-cis-enyl] cyclopent-2-en-1-one | dl-15a-hydroxy-1-phenoxymethyl-1,9-dioxo-16,16-dimethyl-20-nor-5-cis-13-trans prostadiene |
| 434 | 1-trans-iodo-5,5-dimethyl-3-triphenylmethoxy-1-octene | 2-[6-phenoxyacetyl hex-2-cis-enyl] cyclopent-2-en-1-one | dl-15a-hydroxy-1-phenoxymethyl-1,9-dioxo-17,17-dimethyl-5-cis-13-trans prostadiene |

TABLE XI-continued

| EXAMPLE | VINYL IODIDE / VINYL TIN | | PRODUCT |
|---|---|---|---|
| 435 | 1-trans-iodo-4-methyl-3-triphenylmethoxy-1-octene | 2-[6-phenoxyacetyl hex-2-cis-enyl] cyclopent-2-en-1-one | dl-15a-hydroxy-1-phenoxymethyl-1,9-dioxo-16-methyl-5-cis-13-trans prostadiene |
| 436 | 1-trans-iodo-4,4-trimethylene-3-trimethylsilyloxy-1-heptene | 2-[6-phenoxyacetyl hex-2-cis-enyl] cyclopent-2-en-1-one | dl-15a-hydroxy-1-phenoxymethyl-1,9-dioxo-16,16-trimethylene-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 437 | 1-trans-tri-n-butylstannyl-3-vinyl-3-trimethylsilyloxy-1-heptene | 2-[6-phenoxyacetyl hex-2-cis-enyl] cyclopent-2-en-1-one | dl-15a-hydroxy-1-phenoxymethyl-1,9-dioxo-15-vinyl-20-nor-5-cis-13-trans prostadiene |
| 438 | 1-trans-tri-n-butylstannyl-4-phenoxy-3-triethylsilyloxy-1-butene | 2-[6-phenoxyacetyl hex-2-cis-enyl] cyclopent-2-en-1-one | dl-15a-hydroxy-1-phenoxymethyl-1,9-dioxo-16-phenoxy-17-20-tetranor-5-cis-13-trans prostadiene |
| 439 | 1-trans-tri-n-butylstannyl-4-(p-fluorophenoxy)-3-triethylsilyloxy-1-butene | 2-[6-phenoxyacetyl hex-2-cis-enyl] cyclopent-2-en-1-one | dl-15a-hydroxy-1-phenoxymethyl-1,9-dioxo-16-(p-fluorophenoxy)-17-20-tetranor-5-cis-13-trans prostadiene |
| 440 | 1-trans-tri-n-butylstannyl-4-(m-chlorophenoxy)-3-triethylsilyloxy-1-butene | 2-[6-phenoxyacetyl hex-2-cis-enyl] cyclopent-2-en-1-one | dl-15a-hydroxy-1-phenoxymethyl-1,9-dioxo-16-(m-chlorophenoxy)-17-20-tetranor-5-cis-13-trans prostadiene |
| 441 | 1-trans-tri-n-butylstannyl-4-(m-trifluoromethylphenoxy)-3-triethylsilyloxy-1-butene | 2-[6-phenoxyacetyl hex-2-cis-enyl] cyclopent-2-en-1-one | dl-15a-hydroxy-1-phenoxymethyl-1,9-dioxo-16-(m-trifluoromethylphenoxy)-17-20-tetranor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 442 | 1-trans-iodo-5-phenyl-3-triethylsilyloxy-1-pentene | 2-[6-phenoxyacetyl hex-2-cis-enyl] cyclopent-2-en-1-one | dl-15a-hydroxy-1-phenoxymethyl-1,9-dioxo-17-phenyl-18-20-trinor-5-cis-13-trans prostadiene |
| 443 | 1-trans-iodo-4,4-dimethyl-5-phenyl-3-triethylsilyloxy-1-pentene | 2-[6-phenoxyacetyl hex-2-cis-enyl] cyclopent-2-en-1-one | dl-15a-hydroxy-1-phenoxymethyl-1,9-dioxo-16,16-dimethyl-17-phenyl-18-20-trinor-5-cis-13-trans prostadiene |
| 444 | 1-trans-iodo-4-cyclopentyl-3-triphenylmethoxy-1-butene | 2-[6-phenoxyacetyl hex-2-cis-enyl] cyclopent-2-en-1-one | dl-15a-hydroxy-1-phenoxymethyl-1,9-dioxo-16-cyclopentyl-17-20-tetranor-5-cis-13-trans prostadiene |
| 445 | 1-trans-iodo-4-cyclohexyl-3-triphenylmethoxy-1-butene | 2-[6-phenoxyacetyl hex-2-cis-enyl] cyclopent-2-en-1-one | dl-15a-hydroxy-1-phenoxymethyl-1,9-dioxo-16-cyclohexyl-17-20-tetranor-5-cis-13-trans prostadiene |
| 446 | 1-trans-iodo-4-triphenylmethoxy-1-heptene | 2-[6-phenoxyacetyl hex-2-cis-enyl] cyclopent-2-en-1-one | dl-16-hydroxy-1-phenoxymethyl-1,9-dioxo-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 447 | 1-trans-tri-n-butylstannyl-4-methyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-methyl-20-nor-5-cis-13-trans prostadiene |
| 448 | 1-trans-tri-n-butylstannyl-4-ethyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-ethyl-5-cis-13-trans prostadiene |
| 449 | 1-trans-tri-n-butylstannyl-5-methyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-17-methyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|

TABLE XI-continued

| | VINYL TIN | CYCLOPENTENONE | PRODUCT PROSTAGLANDIN OF THE 11-DEOXY PGE2 SERIES |
|---|---|---|---|
| 450 | 1-trans-iodo-5,5-dimethyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-17,17-dimethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 451 | 1-trans-tri-n-butylstannyl-4-vinyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-vinyl-20-nor-5-cis-13-trans prostadiene |
| 452 | 1-trans-tri-n-butylstannyl-4-cyclopropyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-cyclopropyl-5-cis-13-trans prostadiene |
| 453 | 1-trans-tri-n-butylstannyl-4-trimethylsilylethynyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-ethynyl-20-nor-5-cis-13-trans prostadiene |
| 454 | 1-trans-tri-n-butylstannyl-5-methylene-4-triethylsilyloxy-1-heptene | 2-[6-phenoxyacetyl hex-2-cis-enyl] cyclopent-2-en-1-one | dl-16-hydroxy-1-phenoxymethyl-1,9-dioxo-17-methylene-20-nor-5-cis-13-trans prostadiene |
| 455 | 1-trans-tri-n-butylstannyl-4-methyl-5-methylene-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-methyl-17-methylene-20-nor-5-cis-13-trans prostadiene |
| 456 | 1-trans-tri-n-butylstannyl-4-dimethoxymethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-formyl-20-nor-5-cis-13-trans prostadiene |
| 457 | 1-trans-tri-n-butylstannyl-4-fluoromethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-fluoromethyl-20-nor-5-cis-13-trans prostadiene |
| 458 | 1-trans-tri-n-butylstannyl-4-difluoromethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-difluoromethyl-20-nor-5-cis-13-trans prostadiene |
| 459 | 1-trans-tri-n-butylstannyl-4-trifluoromethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-trifluoromethyl-20-nor-5-cis-13-trans prostadiene |
| 460 | 1-trans-tri-n-butylstannyl-4-chloromethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-chloromethyl-20-nor-5-cis-13-trans prostadiene |
| 461 | 1-trans-tri-n-butylstannyl-4-trimethylsilyloxymethyl-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 462 | 1-trans-iodo-4-methyl-7-chloro-4-trimethylsilyloxy-1-heptene | 2-[6-phenoxyacetyl hex-2-cis-enyl] cyclopent-2-en-1-one | dl-16-hydroxy-1-phenoxymethyl-1,9-dioxo-16-methyl-19-chloro-20-nor-5-cis-13-trans prostadiene |
| 463 | 1-trans-iodo-3-triphenylmethoxy-1-octene | 2-[6-phenoxyacetyl hex-2-cis-enyl] cyclopent-2-en-1-one | dl-15a-hydroxy-1-phenoxymethyl-1,9-dioxo-5-cis-13-trans prostadiene |
| 464 | 1-trans-iodo-3-methyl-3-trimethylsilyloxy-1-octene | 2-[6-phenoxyacetyl hex-2-cis-enyl] cyclopent-2-en-1-one | dl-15a-hydroxy-1-phenoxymethyl-1,9-dioxo-15-methyl-5-cis-13-trans prostadiene |
| 465 | 1-trans-iodo-4,4-dimethyl-3-trimethylsilyloxy-1-octene | 2-[6-phenoxyacetyl hex-2-cis-enyl] cyclopent-2-en-1-one | dl-15a-hydroxy-1-phenoxymethyl-1,9-dioxo-16,16-dimethyl-5-cis-13-trans prostadiene |
| 466 | 1-trans-iodo-4,4-trimethylene | 2-[6-phenoxyacetyl cyclopent-2-en-1-one | dl-15a-hydroxy-1-phenoxymethyl-1,9-dioxo- |

TABLE XI-continued

| EXAMPLE | | | |
|---|---|---|---|
| 467 | 1-trans-tri-n-butylstannyl-3-vinyl-3-trimethylsilyloxy-1-octene | 2-[6-phenoxyacetyl hex-2-cis-enyl] cyclopent-2-en-1-one | dl-15a-hydroxy-1-phenoxymethyl-1,9-dioxo-15-vinyl-5-cis-13-trans prostadiene |
| | 3-trimethylsilyloxy-1-octene | hex-2-cis-enyl] cyclopent-2-en-1-one | 16,16-trimethylene-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 468 | 1-trans-iodo-4-triphenylmethoxy-1-octene | 2-[6-phenoxyacetyl hex-2-cis-enyl] cyclopent-2-en-1-one | dl-16-hydroxy-1-phenoxymethyl-1,9-dioxo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 469 | 1-trans-tri-n-butylstannyl-4-methyl-4-trimethylsilyloxy-1-octene | 2-[6-phenoxyacetyl cyclopent-2-en-1-one | dl-16-hydroxy-1-phenoxymethyl-1,9-dioxo-16-methyl-5-cis-13-trans prostadiene |
| 470 | 1-trans-tri-n-butylstannyl-5-methyl-4-trimethylsilyloxy-1-octene | 2-[6-phenoxyacetyl cyclopent-2-en-1-one | dl-16-hydroxy-1-phenoxymethyl-1,9-dioxo-17-methyl-5-cis-13-trans prostadiene |
| 471 | 1-trans-tri-n-butylstannyl-4-vinyl-4-trimethylsilyloxy-1-octene | 2-[6-phenoxyacetyl cyclopent-2-en-1-one | dl-16-hydroxy-1-phenoxymethyl-1,9-dioxo-16-vinyl-5-cis-13-trans prostadiene |
| 472 | 1-trans-tri-n-butylstannyl-4-trimethylsilylethynyl-4-trimethylsilyloxy-1-octene | 2-[6-phenoxyacetyl cyclopent-2-en-1-one | dl-16-hydroxy-1-phenoxymethyl-1,9-dioxo-16-ethynyl-5-cis-13-trans prostadiene |
| 473 | 1-trans-tri-n-butylstannyl-5-methylene-4-triethylsilyloxy-1-octene | 2-[6-phenoxyacetyl hex-2-cis-enyl] | dl-16-hydroxy-1-phenoxymethyl-1,9-dioxo-17-methylene-5-cis-13-trans prostadiene |
| 474 | 1-trans-tri-n-butylstannyl-4-methyl-5-methylene-4-trimethylsilyloxy-1-octene | 2-[6-phenoxyacetyl hex-2-cis-enyl] | dl-16-hydroxy-1-phenoxymethyl-1,9-dioxo-16-methyl-17-methylene-5-cis-13-trans prostadiene |
| 475 | 1-trans-tri-n-butylstannyl-4-dimethoxymethyl-4-trimethylsilyloxy-1-octene | 2-[6-phenoxyacetyl hex-2-cis-enyl] | dl-16-hydroxy-1-phenoxymethyl-1,9-dioxo-16-formyl-5-cis-13-trans prostadiene |
| 476 | 1-trans-tri-n-butylstannyl-4-fluoromethyl-4-trimethylsilyloxy-1-octene | 2-[6-phenoxyacetyl hex-2-cis-enyl] | dl-16-hydroxy-1-phenoxymethyl-1,9-dioxo-16-fluoromethyl-5-cis-13-trans prostadiene |
| 477 | 1-trans-tri-n-butylstannyl-4-difluoromethyl-4-trimethylsilyloxy-1-octene | 2-[6-phenoxyacetyl hex-2-cis-enyl] | dl-16-hydroxy-1-phenoxymethyl-1,9-dioxo-16-difluoromethyl-5-cis-13-trans prostadiene |
| 478 | 1-trans-tri-n-butylstannyl-4-trifluoromethyl-4-trimethylsilyloxy-1-octene | 2-[6-phenoxyacetyl hex-2-cis-enyl] | dl-16-hydroxy-1-phenoxymethyl-1,9-dioxo-16-trifluoromethyl-5-cis-13-trans prostadiene |
| 479 | 1-trans-tri-n-butylstannyl-4-chloromethyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-chloromethyl-5-cis-13-trans prostadiene |
| 480 | 1-trans-tri-n-butylstannyl-4-trimethylsilyloxymethyl-4-trimethylsilyloxy-1-octene | 2-[6-phenoxyacetyl hex-2-cis-enyl] cyclopent-2-en-1-one | dl-16-hydroxy-1-phenoxymethyl-1,9-dioxo-16-hydroxymethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 481 | 1-trans-iodo- | 2-[6-phenoxyacetyl | dl-15a-hydroxy-1-phenoxymethyl-1,9-dioxo- |

TABLE XI-continued

| EXAMPLE | VINYL TIN | CYCLOPENTENONE | PRODUCT PROSTAGLANDIN OF THE 11-DEOXY PGE2 SERIES |
|---|---|---|---|
| | 3-triphenylmethoxy-1-nonene | hex-2-cis-enyl] cyclopent-2-en-1-one | 20-methyl-5-cis-13-trans prostadiene |
| 482 | 1-trans-iodo-3-methyl-3-trimethylsilyloxy-1-nonene | 2-[6-phenoxyacetyl hex-2-cis-enyl] cyclopent-2-en-1-one | dl-15a-hydroxy-1-phenoxymethyl-1,9-dioxo-15-methyl-20-methyl-5-cis-13-trans prostadiene |
| 483 | 1-trans-iodo-4,4-dimethyl-3-trimethylsilyloxy-1-nonene | 2-[6-phenoxyacetyl hex-2-cis-enyl] cyclopent-2-en-1-one | dl-15a-hydroxy-1-phenoxymethyl-1,9-dioxo-16,16-dimethyl-20-methyl-5-cis-13-trans prostadiene |
| 484 | 1-trans-iodo-4,4-trimethylene-3-trimethylsilyloxy-1-nonene | 2-[6-phenoxyacetyl hex-2-cis-enyl] cyclopent-2-en-1-one | dl-15a-hydroxy-1-phenoxymethyl-1,9-dioxo-16,16-trimethylene-20-methyl-5-cis-13-trans prostadiene |
| 485 | 1-trans-tri-n-butylstannyl-3-vinyl-3-trimethylsilyloxy-1-nonene | 2-[6-phenoxyacetyl hex-2-cis-enyl] cyclopent-2-en-1-one | dl-15a-hydroxy-1-phenoxymethyl-1,9-dioxo-15-vinyl-20-methyl-5-cis-13-trans prostadiene |
| 486 | 1-trans-iodo-4-triphenylmethoxy-1-nonene | 2-[6-phenoxyacetyl hex-2-cis-enyl] cyclopent-2-en-1-one | dl-16-hydroxy-1-phenoxymethyl-1,9-dioxo-20-methyl-5-cis-13-trans prostadiene |
| 487 | 1-trans-tri-n-butylstannyl-4-methyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-methyl-20-methyl-5-cis-13-trans prostadiene |
| 488 | 1-trans-tri-n-butylstannyl-5-methyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-17-methyl-20-methyl-5-cis-13-trans prostadiene |
| 489 | 1-trans-tri-n-butylstannyl-4-vinyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-vinyl-20-methyl-5-cis-13-trans prostadiene |
| 490 | 1-trans-tri-n-butylstannyl-4-trimethylsilylethynyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-ethynyl-20-methyl-5-cis-13-trans prostadiene |
| 491 | 1-trans-tri-n-butylstannyl-5-methylene-4-triethylsilyloxy-1-nonene | 2-[6-phenoxyacetyl hex-2-cis-enyl] cyclopent-2-en-1-one | dl-16-hydroxy-1-phenoxymethyl-1,9-dioxo-17-methylene-20-methyl-5-cis-13-trans prostadiene |
| 492 | 1-trans-tri-n-butylstannyl-4-methyl-5-methylene-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-methyl-17-methylene-20-methyl-5-cis-13-trans prostadiene |
| 493 | 1-trans-tri-n-butylstannyl-4-dimethoxymethyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-formyl-20-methyl-5-cis-13-trans prostadiene |
| 494 | 1-trans-tri-n-butylstannyl-4-fluoromethyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-fluoromethyl-20-methyl-5-cis-13-trans prostadiene |
| 495 | 1-trans-tri-n-butylstannyl-4-difluoromethyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-difluoromethyl-20-methyl-5-cis-13-trans prostadiene |
| 496 | 1-trans-tri-n-butylstannyl-4-trifluoromethyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-trifluoromethyl-20-methyl-5-cis-13-trans prostadiene |
| 497 | 1-trans-tri-n-butylstannyl-4-chloromethyl-4-trimethylsilyloxy-1-nonene | 2-[6-phenoxyacetyl hex-2-cis-enyl] cyclopent-2-en-1-one | dl-16-hydroxy-1-phenoxymethyl-1,9-dioxo-16-chloromethyl-20-methyl-5-cis-13-trans prostadiene |
| 498 | 1-trans-tri-n-butylstannyl-4-trimethylsilyloxymethyl- | 2-[6-phenoxyacetyl | dl-16-hydroxy-1-phenoxymethyl-1,9-dioxo-16-hydroxymethyl- |

TABLE XI-continued

| EXAMPLE | VINYL IODIDE | CYCLOPENTENONE | PRODUCT PROSTAGLANDIN OF THE 11-DEOXY PGE2 SERIES |
|---|---|---|---|
| | 4-trimethylsilyloxy-1-nonene | hex-2-cis-enyl] cyclopent-2-en-1-one | 20-methyl-5-cis-13-trans prostadiene |
| 499 | 1-trans-iodo-3-triphenylmethoxy-1-decene | 2-[6-phenoxyacetyl hex-2-cis-enyl] cyclopent-2-en-1-one | dl-15a-hydroxy-1-phenoxymethyl-1,9-dioxo-20-ethyl-5-cis-13-trans prostadiene |
| 500 | 1-trans-iodo-3-methyl-3-trimethylsilyloxy-1-decene | 2-[6-phenoxyacetyl hex-2-cis-enyl] cyclopent-2-en-1-one | dl-15a-hydroxy-1-phenoxymethyl-1,9-dioxo-15-methyl-20-ethyl-5-cis-13-trans prostadiene |
| 501 | 1-trans-iodo-4,4-dimethyl-3-trimethylsilyloxy-1-decene | 2-[6-phenoxyacetyl hex-2-cis-enyl] cyclopent-2-en-1-one | dl-15a-hydroxy-1-phenoxymethyl-1,9-dioxo-16,16-dimethyl-20-ethyl-5-cis-13-trans prostadiene |
| 502 | 1-trans-iodo-4,4-trimethylene-3-trimethylsilyloxy-1-decene | 2-[6-phenoxyacetyl hex-2-cis-enyl] cyclopent-2-en-1-one | dl-15a-hydroxy-1-phenoxymethyl-1,9-dioxo-16,16-trimethylene-20-ethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 503 | 1-trans-tri-n-butylstannyl-3-vinyl-3-trimethylsilyloxy-1-decene | 2-[6-phenoxyacetyl hex-2-cis-enyl] cyclopent-2-en-1-one | dl-15a-hydroxy-1-phenoxymethyl-1,9-dioxo-15-vinyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 504 | 1-trans-iodo-4-triphenylmethoxy-1-decene | 2-[6-phenoxyacetyl hex-2-cis-enyl] cyclopent-2-en-1-one | dl-16-hydroxy-1-phenoxymethyl-1,9-dioxo-20-ethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 505 | 1-trans-tri-n-butylstannyl-4-methyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-methyl-20-ethyl-5-cis-13-trans prostadiene |
| 506 | 1-trans-tri-n-butylstannyl-5-methyl-4-triethylsilyloxy-1-decene | 2-[6-phenoxyacetyl hex-2-cis-enyl] cyclopent-2-en-1-one | dl-16-hydroxy-1-phenoxymethyl-1,9-dioxo-17-methyl-20-ethyl-5-cis-13-trans prostadiene |
| 507 | 1-trans-tri-n-butylstannyl-4-vinyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-vinyl-20-ethyl-5-cis-13-trans prostadiene |
| 508 | 1-trans-tri-n-butylstannyl-4-trimethylsilylethynyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-ethynyl-20-ethyl-5-cis-13-trans prostadiene |
| 509 | 1-trans-tri-n-butylstannyl-5-methylene-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-17-methylene-20-ethyl-5-cis-13-trans prostadiene |
| 510 | 1-trans-tri-n-butylstannyl-4-methyl-5-methylene-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-methyl-17-methylene-20-ethyl-5-cis-13-trans prostadiene |
| 511 | 1-trans-tri-n-butylstannyl-4-dimethoxymethyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-formyl-20-ethyl-5-cis-13-trans prostadiene |
| 512 | 1-trans-tri-n-butylstannyl-4-fluoromethyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-fluoromethyl-20-ethyl-5-cis-13-trans prostadiene |
| 513 | 1-trans-tri-n-butylstannyl-4-difluoromethyl- | 2-[6-phenoxyacetyl | dl-16-hydroxy-1-phenoxymethyl-1,9-dioxo-16-difluoromethyl- |

TABLE XI-continued

| | | | |
|---|---|---|---|
| 514 | 4-trimethylsilyloxy-1-decene | hex-2-cis-enyl] cyclopent-2-en-1-one | 20-ethyl-5-cis-13-trans prostadiene |
| 515 | 1-trans-tri-n-butylstannyl-4-trifluoromethyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-trifluoromethyl-20-ethyl-5-cis-13-trans prostadiene |
| 516 | 1-trans-tri-n-butylstannyl-4-chloromethyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-chloromethyl-20-ethyl-5-cis-13-trans prostadiene |
| 516 | 1-trans-tri-n-butylstannyl-4-trimethylsilyloxymethyl-4-trimethylsilyloxy-1-decene | 2-[6-phenoxyacetyl hex-2-cis-enyl] cyclopent-2-en-1-one | dl-16-hydroxy-1-phenoxymethyl-1,9-dioxo-16-hydroxymethyl-20-ethyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 517 | 1-trans-iodo-3-triphenylmethoxy-1-heptene | 2-[7-phenoxyacetyl hept-2-cis-enyl] cyclopent-2-en-1-one | dl-15a-hydroxy-1-phenoxymethyl-1,9-dioxo-20-nor-2-homo-5-cis-13-trans prostadiene |
| 518 | 1-trans-iodo-3-methyl-3-trimethylsilyloxy-1-heptene | 2-[7-phenoxyacetyl hept-2-cis-enyl] cyclopent-2-en-1-one | dl-15a-hydroxy-1-phenoxymethyl-1,9-dioxo-15-methyl-20-nor-2-homo-5-cis-13-trans prostadiene |
| 519 | 1-trans-iodo-4,4-dimethyl-3-triphenylmethoxy-1-heptene | 2-[7-phenoxyacetyl hept-2-cis-enyl] cyclopent-2-en-1-one | dl-15a-hydroxy-1-phenoxymethyl-1,9-dioxo-16,16-dimethyl-20-nor-2-homo-5-cis-13-trans prostadiene |
| 520 | 1-trans-iodo-5,5-dimethyl-3-triphenylmethoxy-1-octene | 2-[7-phenoxyacetyl hept-2-cis-enyl] cyclopent-2-en-1-one | dl-15a-hydroxy-1-phenoxymethyl-1,9-dioxo-17,17-dimethyl-2-homo-5-cis-13-trans prostadiene |
| 521 | 1-trans-iodo-4-methyl-3-triphenylmethoxy-1-octene | 2-[7-phenoxyacetyl hept-2-cis-enyl] cyclopent-2-en-1-one | dl-15a-hydroxy-1-phenoxymethyl-1,9-dioxo-16-methyl-2-homo-5-cis-13-trans prostadiene |
| 522 | 1-trans-iodo-4,4-trimethylene-3-trimethylsilyloxy-1-heptene | 2-[7-phenoxyacetyl hept-2-cis-enyl] cyclopent-2-en-1-one | dl-15a-hydroxy-1-phenoxymethyl-1,9-dioxo-16,16-trimethylene-20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 523 | 1-trans-tri-n-butylstannyl-3-vinyl-3-trimethylsilyloxy-1-heptene | 2-[7-phenoxyacetyl hept-2-cis-enyl] cyclopent-2-en-1-one | dl-15a-hydroxy-1-phenoxymethyl-1,9-dioxo-15-vinyl-20-nor-2-homo-5-cis-13-trans prostadiene |
| 524 | 1-trans-tri-n-butylstannyl-4-phenoxy-3-triethylsilyloxy-1-butene | 2-[7-phenoxyacetyl hept-2-cis-enyl] cyclopent-2-en-1-one | dl-15a-hydroxy-1-phenoxymethyl-1,9-dioxo-16-phenoxy-2-homo-17-20-tetranor-5-cis-13-trans prostadiene |
| 525 | 1-trans-tri-n-butylstannyl-4-(p-fluorophenoxy)-3-triethylsilyloxy-1-butene | 2-[7-phenoxyacetyl hept-2-cis-enyl] cyclopent-2-en-1-one | dl-15a-hydroxy-1-phenoxymethyl-1,9-dioxo-16-(p-fluorophenoxy)-2-homo-17-20-tetranor-5-cis-13-trans prostadiene |
| 526 | 1-trans-tri-n-butylstannyl-4-(m-chlorophenoxy)-3-triethylsilyloxy-1-butene | 2-[7-phenoxyacetyl hept-2-cis-enyl] cyclopent-2-en-1-one | dl-15a-hydroxy-1-phenoxymethyl-1,9-dioxo-16-(m-chlorophenoxy)-2-homo-17-20-tetranor-5-cis-13-trans prostadiene |
| 527 | 1-trans-tri-n-butylstannyl-4-(m-trifluoromethylphenoxy)-3-triethylsilyloxy-1-butene | 2-[7-phenoxyacetyl hept-2-cis-enyl] cyclopent-2-en-1-one | dl-15a-hydroxy-1-phenoxymethyl-1,9-dioxo-16-(m-trifluoromethylphenoxy)-2-homo-17-20-tetranor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 528 | 1-trans-iodo-5-phenyl-3-triethylsilyloxy-1-pentene | 2-[7-phenoxyacetyl hept-2-cis-enyl] cyclopent-2-en-1-one | dl-15a-hydroxy-1-phenoxymethyl-1,9-dioxo-17-phenyl-2-homo-18-20-trinor-5-cis-13-trans prostadiene |

TABLE XI-continued

| | | | |
|---|---|---|---|
| 529 | 1-trans-iodo-4,4-dimethyl-5-phenyl-3-triethylsilyloxy-1-pentene | 2-[7-phenoxyacetyl hept-2-cis-enyl] cyclopent-2-en-1-one | dl-15a-hydroxy-1-phenoxymethyl-1,9-dioxo-16,16-dimethyl-17-phenyl-2-homo-18-20-trinor-5-cis-13-trans prostadiene |
| 530 | 1-trans-iodo-4-cyclopentyl-3-triphenylmethoxy-1-butene | 2-[7-phenoxyacetyl hept-2-cis-enyl] cyclopent-2-en-1-one | dl-15a-hydroxy-1-phenoxymethyl-1,9-dioxo-16-cyclopentyl-2-homo-17-20-tetranor-5-cis-13-trans prostadiene |
| 531 | 1-trans-iodo-4-cyclohexyl-3-triphenylmethoxy-1-butene | 2-[7-phenoxyacetyl hept-2-cis-enyl] cyclopent-2-en-1-one | dl-15a-hydroxy-1-phenoxymethyl-1,9-dioxo-16-cyclohexyl-2-homo-17-20-tetranor-5-cis-13-trans prostadiene |
| 532 | 1-trans-iodo-4-triphenylmethoxy-1-heptene | 2-[7-phenoxyacetyl hept-2-cis-enyl] cyclopent-2-en-1-one | dl-16-hydroxy-1-phenoxymethyl-1,9-dioxo-20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 533 | 1-trans-tri-n-butylstannyl-4-methyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-methyl-20-nor-2-homo-5-cis-13-trans prostadiene |
| 534 | 1-trans-tri-n-butylstannyl-4-ethyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-ethyl-2-homo-5-cis-13-trans prostadiene |
| 535 | 1-trans-tri-n-butylstannyl-5-methyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-17-methyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 536 | 1-trans-iodo-5,5-dimethyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-17,17-dimethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 537 | 1-trans-tri-n-butylstannyl-4-vinyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-vinyl-20-nor-2-homo-5-cis-13-trans prostadiene |
| 538 | 1-trans-tri-n-butylstannyl-4-cyclopropyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-cyclopropyl-2-homo-5-cis-13-trans prostadiene |
| 539 | 1-trans-tri-n-butylstannyl-4-trimethylsilylethynyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-ethynyl-20-nor-2-homo-5-cis-13-trans prostadiene |
| 540 | 1-trans-tri-n-butylstannyl-5-methylene-4-triethylsilyloxy-1-heptene | 2-[7-phenoxyacetyl hept-2-cis-enyl] cyclopent-2-en-1-one | dl-16-hydroxy-1-phenoxymethyl-1,9-dioxo-17-methylene-20-nor-2-homo-5-cis-13-trans prostadiene |
| 541 | 1-trans-tri-n-butylstannyl-4-methyl-5-methylene-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-methyl-17-methylene-20-nor-2-homo-5-cis-13-trans prostadiene |
| 542 | 1-trans-tri-n-butylstannyl-4-dimethoxymethyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-formyl-20-nor-2-homo-5-cis-13-trans prostadiene |
| 543 | 1-trans-tri-n-butylstannyl-4-fluoromethyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-fluoromethyl-20-nor-2-homo-5-cis-13-trans prostadiene |
| 544 | 1-trans-tri-n-butylstannyl-4-difluoromethyl-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-difluoromethyl-20-nor-2-homo-5-cis-13-trans prostadiene |

TABLE XI-continued

| | | | |
|---|---|---|---|
| 545 | 1-trans-tri-n-butylstannyl-4-trifluoromethyl-4-trimethylsilyloxy-1-heptene | cyclopent-2-en-1-one 2-[7-phenoxyacetyl hept-2-cis-enyl] | dl-16-hydroxy-1-phenoxymethyl-1,9-dioxo-16-trifluoromethyl-20-nor-2-homo-5-cis-13-trans prostadiene |
| 546 | 1-trans-tri-n-butylstannyl-4-chloromethyl-4-trimethylsilyloxy-1-heptene | cyclopent-2-en-1-one 2-[7-phenoxyacetyl hept-2-cis-enyl] | dl-16-hydroxy-1-phenoxymethyl-1,9-dioxo-16-chloromethyl-20-nor-2-homo-5-cis-13-trans prostadiene |
| 547 | 1-trans-tri-n-butylstannyl-4-trimethylsilyloxymethyl-4-trimethylsilyloxy-1-heptene | cyclopent-2-en-1-one 2-[7-phenoxyacetyl hept-2-cis-enyl] | dl-16-hydroxy-1-phenoxymethyl-1,9-dioxo-16-hydroxymethyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 548 | 1-trans-iodo-4-methyl-7-chloro-4-trimethylsilyloxy-1-heptene | 2-[7-phenoxyacetyl hept-2-cis-enyl] cyclopent-2-en-1-one | dl-16-hydroxy-1-phenoxymethyl-1,9-dioxo-16-methyl-19-chloro-2-homo-20-nor-5-cis-13-trans prostadiene |
| 549 | 1-trans-iodo-3-triphenylmethoxy-1-octene | 2-[7-phenoxyacetyl hept-2-cis-enyl] cyclopent-2-en-1-one | dl-15a-hydroxy-1-phenoxymethyl-1,9-dioxo-2-homo-5-cis-13-trans prostadiene |
| 550 | 1-trans-iodo-3-methyl-3-trimethylsilyloxy-1-octene | 2-[7-phenoxyacetyl hept-2-cis-enyl] cyclopent-2-en-1-one | dl-15a-hydroxy-1-phenoxymethyl-1,9-dioxo-15-methyl-2-homo-5-cis-13-trans prostadiene |
| 551 | 1-trans-iodo-4,4-dimethyl-3-trimethylsilyloxy-1-octene | 2-[7-phenoxyacetyl hept-2-cis-enyl] cyclopent-2-en-1-one | dl-15a-hydroxy-1-phenoxymethyl-1,9-dioxo-16,16-dimethyl-2-homo-5-cis-13-trans prostadiene |
| 552 | 1-trans-iodo-4,4-trimethylene-3-trimethylsilyloxy-1-octene | 2-[7-phenoxyacetyl hept-2-cis-enyl] cyclopent-2-en-1-one | dl-15a-hydroxy-1-phenoxymethyl-1,9-dioxo-16,16-trimethylene-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 553 | 1-trans-tri-n-butylstannyl-3-vinyl-3-trimethylsilyloxy-1-octene | 2-[7-phenoxyacetyl hept-2-cis-enyl] cyclopent-2-en-1-one | dl-15a-hydroxy-1-phenoxymethyl-1,9-dioxo-15-vinyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 554 | 1-trans-iodo-4-triphenylmethoxy-1-octene | 2-[7-phenoxyacetyl hept-2-cis-enyl] cyclopent-2-en-1-one | dl-16-hydroxy-1-phenoxymethyl-1,9-dioxo-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 555 | 1-trans-tri-n-butylstannyl-4-methyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-methyl-2-homo-5-cis-13-trans prostadiene |
| 556 | 1-trans-tri-n-butylstannyl-5-methyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-17-methyl-2-homo-5-cis-13-trans prostadiene |
| 557 | 1-trans-tri-n-butylstannyl-4-vinyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-vinyl-2-homo-5-cis-13-trans prostadiene |
| 558 | 1-trans-tri-n-butylstannyl-4-trimethylsilylethynyl-4-trimethylsilyloxy-1-octene | 2-[7-phenoxyacetyl hept-2-cis-enyl] cyclopent-2-en-1-one | dl-16-hydroxy-1-phenoxymethyl-1,9-dioxo-16-ethynyl-2-homo-5-cis-13-trans prostadiene |
| 559 | 1-trans-tri-n-butylstannyl-5-methylene-4-triethylsilyloxy-1-octene | 2-[7-phenoxyacetyl hept-2-cis-enyl] cyclopent-2-en-1-one | dl-16-hydroxy-1-phenoxymethyl-1,9-dioxo-17-methylene-2-homo-5-cis-13-trans prostadiene |

TABLE XI-continued

| | | |
|---|---|---|
| 560 | 1-trans-tri-n-butylstannyl-4-methyl-5-methylene 4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-methyl-17-methylene-2-homo-5-cis-13-trans prostadiene |
| 561 | 1-trans-tri-n-butylstannyl-4-dimethoxymethyl-4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-formyl-2-homo-5-cis-13-trans prostadiene |
| 562 | 1-trans-tri-n-butylstannyl-4-fluoromethyl-4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-fluoromethyl-2-homo-5-cis-13-trans prostadiene |
| 563 | 1-trans-tri-n-butylstannyl-4-difluoromethyl-4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-difluoromethyl-2-homo-5-cis-13-trans prostadiene |
| 564 | 1-trans-tri-n-butylstannyl-4-trifluoromethyl-4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-trifluoromethyl-2-homo-5-cis-13-trans prostadiene |
| 565 | 1-trans-tri-n-butylstannyl-4-chloromethyl-4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-chloromethyl-2-homo-5-cis-13-trans prostadiene |
| 566 | 1-trans-tri-n-butylstannyl-4-trimethylsilyloxymethyl-4-trimethylsilyloxy-1-octene | cyclopent-2-en-1-one 2-[7-phenoxyacetyl hept-2-cis-enyl] | dl-16-hydroxy-1-phenoxymethyl-1,9-dioxo-16-hydroxymethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 567 | 1-trans-iodo-3-triphenylmethoxy-1-nonene | cyclopent-2-en-1-one 2-[7-phenoxyacetyl hept-2-cis-enyl] | dl-15a-hydroxy-1-phenoxymethyl-1,9-dioxo-20-methyl-2-homo-5-cis-13-trans prostadiene |
| 568 | 1-trans-iodo-3-methyl-3-trimethylsilyloxy-1-nonene | cyclopent-2-en-1-one 2-[7-phenoxyacetyl hept-2-cis-enyl] | dl-15a-hydroxy-1-phenoxymethyl-1,9-dioxo-15-methyl-20-methyl-2-homo-5-cis-13-trans prostadiene |
| 569 | 1-trans-iodo-4,4-dimethyl 3-trimethylsilyloxy-1-nonene | cyclopent-2-en-1-one 2-[7-phenoxyacetyl hept-2-cis-enyl] | dl-15a-hydroxy-1-phenoxymethyl-1,9-dioxo-16,16-dimethyl-20-methyl-2-homo-5-cis-13-trans prostadiene |
| 570 | 1-trans-iodo-4,4-trimethylene 3-trimethylsilyloxy-1-nonene | cyclopent-2-en-1-one 2-[7-phenoxyacetyl hept-2-cis-enyl] | dl-15a-hydroxy-1-phenoxymethyl-1,9-dioxo-16,16-trimethylene-20-methyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 571 | 1-trans-tri-n-butylstannyl-3-vinyl-3-trimethylsilyloxy-1-nonene | cyclopent-2-en-1-one 2-[7-phenoxyacetyl hept-2-cis-enyl] | dl-15a-hydroxy-1-phenoxymethyl-1,9-dioxo-15-vinyl-20-methyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 572 | 1-trans-iodo-4-triphenylmethoxy-1-nonene | cyclopent-2-en-1-one 2-[7-phenoxyacetyl hept-2-cis-enyl] | dl-16-hydroxy-1-phenoxymethyl-1,9-dioxo-20-methyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 573 | 1-trans-tri-n-butylstannyl-4-methyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-methyl-20-methyl-2-homo-5-cis-13-trans prostadiene |
| 574 | 1-trans-tri-n-butylstannyl-4-methyl-5-methyl 4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-17-methyl-20-methyl-2-homo-5-cis-13-trans prostadiene |

TABLE XI-continued

| | | | |
|---|---|---|---|
| 575 | | 1-trans-tri-n-butylstannyl-4-vinyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-vinyl-20-methyl-2-homo-5-cis-13-trans prostadiene |
| 576 | | 1-trans-tri-n-butylstannyl-4-trimethylsilylethynyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-ethynyl-20-methyl-2-homo-5-cis-13-trans prostadiene |
| 577 | | 1-trans-tri-n-butylstannyl-5-methylene 4-triethylsilyloxy-1-nonene | cyclopent-2-en-1-one 2-[7-phenoxyacetyl hept-2-cis-enyl] | dl-16-hydroxy-1-phenoxymethyl-1,9-dioxo-17-methylene-20-methyl-2-homo-5-cis-13-trans prostadiene |
| 578 | | 1-trans-tri-n-butylstannyl-4-methyl-5-methylene 4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-methyl-17-methylene-20-methyl-2-homo-5-cis-13-trans prostadiene |
| 579 | | 1-trans-tri-n-butylstannyl-4-dimethoxymethyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-formyl-20-methyl-2-homo-5-cis-13-trans prostadiene |
| 580 | | 1-trans-tri-n-butylstannyl-4-fluoromethyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-fluoromethyl-20-methyl-2-homo-5-cis-13-trans prostadiene |
| 581 | | 1-trans-tri-n-butylstannyl-4-difluoromethyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-difluoromethyl-20-methyl-2-homo-5-cis-13-trans prostadiene |
| 582 | | 1-trans-tri-n-butylstannyl-4-trifluoromethyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-trifluoromethyl-20-methyl-2-homo-5-cis-13-trans prostadiene |
| 583 | | 1-trans-tri-n-butylstannyl-4-chloromethyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-chloromethyl-20-methyl-2-homo-5-cis-13-trans prostadiene |
| 584 | | 1-trans-tri-n-butylstannyl-4-trimethylsilyloxymethyl-4-trimethylsilyloxy-1-nonene | cyclopent-2-en-1-one 2-[7-phenoxyacetyl hept-2-cis-enyl] | dl-16-hydroxy-1-phenoxymethyl-1,9-dioxo-16-hydroxymethyl-20-methyl-2-homo-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 585 | 1-trans-iodo-3-triphenylmethoxy-1-decene | | 2-[7-phenoxyacetyl hept-2-cis-enyl] cyclopent-2-en-1-one | dl-15a-hydroxy-1-phenoxymethyl-1,9-dioxo-20-ethyl-2-homo-5-cis-13-trans prostadiene |
| 586 | 1-trans-iodo-3-methyl-3-trimethylsilyloxy-1-decene | | 2-[7-phenoxyacetyl hept-2-cis-enyl] cyclopent-2-en-1-one | dl-15a-hydroxy-1-phenoxymethyl-1,9-dioxo-15-methyl-20-ethyl-2-homo-5-cis-13-trans prostadiene |
| 587 | 1-trans-iodo-4,4-dimethyl-3-trimethylsilyloxy-1-decene | | 2-[7-phenoxyacetyl hept-2-cis-enyl] cyclopent-2-en-1-one | dl-15a-hydroxy-1-phenoxymethyl-1,9-dioxo-16,16-dimethyl-20-ethyl-2-homo-5-cis-13-trans prostadiene |
| 588 | 1-trans-iodo-4,4-trimethylene 3-trimethylsilyloxy-1-decene | | 2-[7-phenoxyacetyl hept-2-cis-enyl] cyclopent-2-en-1-one | dl-15a-hydroxy-1-phenoxymethyl-1,9-dioxo-16,16-trimethylene-20-ethyl-2-homo-5-cis-13-trans prostadiene |
| EXAMPLE | VINYL TIN | | CYCLOPENTENONE | PRODUCT PROSTAGLANDIN OF THE 11-DEOXY PGE2 SERIES |
| 589 | 1-trans-tri-n-butylstannyl-3-vinyl-3-trimethylsilyloxy-1-decene | | 2-[7-phenoxyacetyl hept-2-cis-enyl] cyclopent-2-en-1-one | dl-15a-hydroxy-1-phenoxymethyl-1,9-dioxo-15-vinyl-20-ethyl-2-homo-5-cis-13-trans prostadiene |
| EXAMPLE | VINYL IODIDE | | CYCLOPENTENONE | PRODUCT PROSTAGLANDIN OF THE 11-DEOXY PGE2 SERIES |
| 590 | 1-trans-iodo- | | 2-[7-phenoxyacetyl | dl-16-hydroxy-1-phenoxymethyl-1,9-dioxo- |

TABLE XI-continued

| | | 4-triphenylmethoxy-1-decene | hept-2-cis-enyl]<br>cyclopent-2-en-1-one | 20-ethyl-2-homo-5-cis-13-trans prostadiene |
|---|---|---|---|---|
| EXAMPLE | VINYL TIN | | CYCLOPENTENONE | PRODUCT PROSTAGLANDIN OF THE 11-DEOXY PGE2 SERIES |
| 591 | 1-trans-tri-n-butylstannyl-4-methyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-methyl-20-ethyl-2-homo-5-cis-13-trans prostadiene |
| 592 | 1-trans-tri-n-butylstannyl-5-methyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-17-methyl-20-ethyl-2-homo-5-cis-13-trans prostadiene |
| 593 | 1-trans-tri-n-butylstannyl-4-vinyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-vinyl-20-ethyl-2-homo-5-cis-13-trans prostadiene |
| 594 | 1-trans-tri-n-butylstannyl-4-trimethylsilylethynyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-ethynyl-20-ethyl-2-homo-5-cis-13-trans prostadiene |
| 595 | 1-trans-tri-n-butylstannyl-5-methylene-4-triethylsilyloxy-1-decene | | 2-[7-phenoxyacetyl hept-2-cis-enyl] cyclopent-2-en-1-one | dl-16-hydroxy-1-phenoxymethyl-1,9-dioxo-17-methylene-20-ethyl-2-homo-5-cis-13-trans prostadiene |
| 596 | 1-trans-tri-n-butylstannyl-4-methyl-5-methylene-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-methyl-17-methylene-20-ethyl-2-homo-5-cis-13-trans prostadiene |
| 597 | 1-trans-tri-n-butylstannyl-4-dimethoxymethyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-formyl-20-ethyl-2-homo-5-cis-13-trans prostadiene |
| 598 | 1-trans-tri-n-butylstannyl-4-fluoromethyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-fluoromethyl-20-ethyl-2-homo-5-cis-13-trans prostadiene |
| 599 | 1-trans-tri-n-butylstannyl-4-difluoromethyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-difluoromethyl-20-ethyl-2-homo-5-cis-13-trans prostadiene |
| 600 | 1-trans-tri-n-butylstannyl-4-trifluoromethyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-trifluoromethyl-20-ethyl-2-homo-5-cis-13-trans prostadiene |
| 601 | 1-trans-tri-n-butylstannyl-4-chloromethyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-chloromethyl-20-ethyl-2-homo-5-cis-13-trans prostadiene |
| 602 | 1-trans-tri-n-butylstannyl-4-trimethylsilyloxymethyl-4-trimethylsilyloxy-1-decene | | 2-[7-phenoxyacetyl hept-2-cis-enyl] cyclopent-2-en-1-one | dl-16-hydroxy-1-phenoxymethyl-1,9-dioxo-16-hydroxymethyl-20-ethyl-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 1 | 1-trans-iodo-3-triphenylmethoxy-1-heptene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-20-nor-2-nor-5-cis-13-trans prostadiene |
| 2 | 1-trans-iodo-3-methyl-3-trimethylsilyloxy-1-heptene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-15-methyl-20-nor-2-nor-5-cis-13-trans prostadiene |
| 3 | 1-trans-iodo-4,4-dimethyl-3-trimethylsilyloxy-1-heptene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16,16-dimethyl-20-nor-2-nor-5-cis-13-trans prostadiene |
| 4 | 1-trans-iodo-5,5-dimethyl-3-triphenylmethoxy-1-octene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-17,17-dimethyl-2-nor-5-cis-13-trans prostadiene |
| 5 | 1-trans-iodo-4-methyl-3-triphenylmethoxy-1-octene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-methyl-2-nor-17-20-tetranor-5-cis-13-trans prostadiene |
| 6 | 1-trans-iodo-4,4-trimethylene-3-trimethylsilyloxy-1-heptene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 7 | 1-trans-tri-n-butylstannyl-3-vinyl-3-trimethylsilyloxy-1-heptene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-15-vinyl-20-nor-2-nor-5-cis-13-trans prostadiene |
| 8 | 1-trans-tri-n-butylstannyl-4-phenoxy-3-triethylsilyloxy-1-butene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-phenoxy-2-nor-17-20-tetranor-5-cis-13-trans prostadiene |
| 9 | 1-trans-tri-n-butylstannyl-4-(p-fluorophenoxy)-3-triethylsilyloxy-1-butene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-(p-fluorophenoxy)-2-nor-17-20-tetranor-5-cis-13-trans prostadiene |
| 10 | 1-trans-tri-n-butylstannyl-4-(m-chlorophenoxy)-3-triethylsilyloxy-1-butene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-(m-chlorophenoxy)-2-nor-17-20-tetranor-5-cis-13-trans prostadiene |
| 11 | 1-trans-tri-n-butylstannyl-4-(m-trifluoromethylphenoxy)-3-triethylsilyloxy-1-butene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-(m-trifluoromethylphenoxy)-2-nor-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 12 | 1-trans-iodo-5-phenyl-3-triethylsilyloxy-1-pentene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-17-phenyl-2-nor-18-20-trinor-5-cis-13-trans prostadiene |
| 13 | 1-trans-iodo-4,4-dimethyl-5-phenyl-3-triethylsilyloxy-1-pentene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16,16-dimethyl-17-phenyl-2-nor-18-20-trinor-5-cis-13-trans prostadiene |
| 14 | 1-trans-iodo-4-cyclopentyl-3-triphenylmethoxy-1-butene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-cyclopentyl-2-nor-17-20-tetranor-5-cis-13-trans prostadiene |
| 15 | 1-trans-iodo-4-cyclohexyl-3-triphenylmethoxy-1-butene | 2-[7-methoxy-7-methoxycabonyl-6-(trimethylsilyloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16-cyclohexyl-2-nor-17-20-tetranor-5-cis-13-trans prostadiene |
| 16 | 1-trans-iodo-4-triphenylmethoxy-1-heptene | 2-[7-methoxy-7-methoxycabonyl-6-(trimethylsilyloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-20-nor-2-nor-5-cis-13-trans prostadiene |

-continued

| EXAMPLE | VINYL TIN | CYCLOPENTENONE | PRODUCT PROSTAGLANDIN OF THE PGE2 SERIES |
|---|---|---|---|
| 17 | 1-trans-tri-n-butylstannyl-4-methyl-4-trimethylsilyloxy-1-heptene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-20-nor-2-nor-5-cis-13-trans prostadiene |
| 18 | 1-trans-tri-n-butylstannyl-4-ethyl-4-trimethylsilyloxy-1-octene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-ethyl-2-nor-5-cis-13-trans prostadiene |
| 19 | 1-trans-tri-n-butylstannyl-5-methyl-4-trimethylsilyloxy-1-heptene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-17-methyl-20-nor-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 20 | 1-trans-iodo-5,5-dimethyl-4-trimethylsilyloxy-1-octene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-17,17-dimethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 21 | 1-trans-tri-n-butylstannyl-4-vinyl-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-vinyl-20-nor-2-nor-5-cis-13-trans prostadiene |
| 22 | 1-trans-tri-n-butylstannyl-4-cyclopropyyl-4-trimethylsilyloxy-1-octene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-cyclopropyl-2-nor-5-cis-13-trans prostadiene |
| 23 | 1-trans-tri-n-butylstannyl-4-trimethylsilylethynyl-4-trimethylsilyloxy-1-heptene | 2-[7-methoxy-7-methoxycarbonyl-6-(trimethylsiloxy)-2-cis,6 heptadienyl]-4-trimethylsiloxy cyclopent-2-en-1-one | dl-11a,16-dihydroxy-1-(methoxymethoxycarbonylmethyl)-1,9-dioxo-16-ethynyl-20-nor-2-nor-5-cis-13-trans prostadiene |
| 24 | 1-trans-tri-n-butylstannyl-5-methylene-4-triethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-17-methylene-20-nor-2-nor-5-cis-13-trans prostadiene |
| 25 | 1-trans-tri-n-butylstannyl-4-methyl-5-methylene-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-nor-2-nor-5-cis-13-trans prostadiene |
| 26 | 1-trans-tri-n-butylstannyl-4-dimethoxymethyl-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-formyl-20-nor-2-nor-5-cis-13-trans prostadiene |
| 27 | 1-trans-tri-n-butylstannyl-4-fluoromethyl-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-fluoromethyl-20-nor-2-nor-5-cis-13-trans prostadiene |
| 28 | 1-trans-tri-n-butylstannyl-4-difluoromethyl-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-difluoromethyl-20-nor-2-nor-5-cis-13-trans prostadiene |
| 29 | 1-trans-tri-n-butylstannyl-4-trifluoromethyl-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-trifluoromethyl-20-nor-2-nor-5-cis-13-trans prostadiene |
| 30 | 1-trans-tri-n-butylstannyl-4-chloromethyl-4-trimethylsilyloxy-1-heptene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-chloromethyl-20-nor-2-nor-5-cis-13-trans prostadiene |
| 31 | 1-trans-tri-n-butylstannyl-4-trimethylsilyloxymethyl- | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-hydroxymethyl- |

| EXAMPLE | VINYL IODIDE | CYCLOPENTENONE | PRODUCT PROSTAGLANDIN OF THE PGE2 SERIES |
|---|---|---|---|
| | 4-trimethylsilyloxy-1-heptene | 6-(trimethylsiloxy)-2-cis,6-heptadienyl]-4-trimethylsilyoxy-cyclopent-2-en-1-one | 20-nor-2-nor-5-cis-13-trans prostadiene |
| 32 | 1-trans-iodo-4-methyl-7-chloro 4-trimethylsilyloxy-1-heptene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-16-methyl-19-chloro-2-nor-20-nor-5-cis-13-trans prostadiene |
| 33 | 1-trans-iodo-3-triphenylmethoxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,15a-dihydroxy-1-(methoxymethoxycarbonylmethyl)-1,9-dioxo-2-nor-5-cis-13-trans prostadiene |
| 34 | 1-trans-iodo-3-methyl-3-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,15a-dihydroxy-1-(methoxymethoxycarbonylmethyl)-1,9-dioxo-15-methyl-2-nor-5-cis-13-trans prostadiene |
| 35 | 1-trans-iodo-4,4-dimethyl 3-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,15a-dihydroxy-1-(methoxymethoxycarbonylmethyl)-1,9-dioxo-16,16-dimethyl-2-nor-5-cis-13-trans prostadiene |
| 36 | 1-trans-iodo-4,4-trimethylene 3-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,15a-dihydroxy-1-(methoxymethoxycarbonylmethyl)-1,9-dioxo-16,16-trimethylene-2-nor-5-cis-13-trans prostadiene |
| EXAMPLE | VINYL TIN | CYCLOPENTENONE | PRODUCT PROSTAGLANDIN OF THE PGE2 SERIES |
| 37 | 1-trans-tri-n-butylstannyl-3-vinyl-3-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,15a-dihydroxy-1-(methoxymethoxycarbonylmethyl)-1,9-dioxo-15-vinyl-2-nor-5-cis-13-trans prostadiene |
| EXAMPLE | VINYL IODIDE | CYCLOPENTENONE | PRODUCT PROSTAGLANDIN OF THE PGE2 SERIES |
| 38 | 1-trans-iodo-4-triphenylmethoxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-2-nor-5-cis-13-trans prostadiene |
| EXAMPLE | VINYL TIN | CYCLOPENTENONE | PRODUCT PROSTAGLANDIN OF THE PGE2 SERIES |
| 39 | 1-trans-tri-n-butylstannyl-4-methyl-4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-16-methyl-2-nor-5-cis-13-trans prostadiene |
| 40 | 1-trans-tri-n-butylstannyl-5-methyl 4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-17-methyl-2-nor-5-cis-13-trans prostadiene |
| 41 | 1-trans-tri-n-butylstannyl-4-vinyl-4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-16-vinyl-2-nor-5-cis-13-trans prostadiene |
| 42 | 1-trans-tri-n-butylstannyl-4-trimethylsilylethynyl-4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-16-ethynl-2-nor-5-cis-13-trans prostadiene |
| 43 | 1-trans-tri-n-butylstannyl-4-methyl-5-methylene 4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-17-methylene-2-nor-5-cis-13-trans prostadiene |
| 44 | 1-trans-tri-n-butylstannyl-4-methyl-5-methylene 4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-16-methyl-17-methylene-2-nor-5-cis-13-trans prostadiene |
| 45 | 1-trans-tri-n-butylstannyl-4-dimethoxymethyl-4-trimethylsilyloxy-1-octene | 2-[7-methoxy-7-methoxycarbonyl-6-(trimethylsiloxy)-2-cis,6-heptadienyl]-4-trimethylsilyoxy cyclopent-2-en-1-one | dl-11a,16-dihydroxy-1-(methoxymethoxycarbonylmethyl)-1,9-dioxo-16-formyl-2-nor-5-cis-13-trans prostadiene |
| 46 | 1-trans-tri-n-butylstannyl-4-fluoromethyl- | 2-[7-methoxy-7-methoxycarbonyl- | dl-11a,16-dihydroxy-1-(methoxymethoxycarbonylmethyl)-1,9-dioxo-16- |

-continued

| | | | |
|---|---|---|---|
| | | | 4-trimethylsilyloxy-1-octene | 6-(trimethylsilyloxy)-2-cis,6-heptadienyl]-4-trimethylsilyloxy cyclopent-2-en-1-one | fluoromethyl-2-nor-5-cis-13-trans prostadiene |
| 47 | 1-trans-tri-n-butylstannyl-4-difluoromethyl-4-trimethylsilyloxy-1-octene | 2-[7-methoxy-7-methoxycarbonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-16-difluoromethyl-2-nor-5-cis-13-trans prostadiene |
| 48 | 1-trans-tri-n-butylstannyl-4-trifluoromethyl-4-trimethylsilyloxy-1-octene | 2-[7-methoxy-7-methoxycarbonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-16-trifluoromethyl-2-nor-5-cis-13-trans prostadiene |
| 49 | 1-trans-tri-n-butylstannyl-4-chloromethyl-4-trimethylsilyloxy-1-octene | 2-[7-methoxy-7-methoxycarbonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-16-chloromethyl-2-nor-5-cis-13-trans prostadiene |
| 50 | 1-trans-tri-n-butylstannyl-4-trimethylsilyloxymethyl-4-trimethylsilyloxy-1-octene | 2-[7-methoxy-7-methoxycarbonyl-6-(trimethylsilyloxy)-2-cis,6-heptadienyl]-4-trimethylsilyloxy cyclopent-2-en-1-one | dl-11a,16-dihydroxy-16-(methoxymethoxycarbonylmethyl)-1,9-dioxo-4-trimethylsilyloxy hydroxymethyl-2-nor-5-cis-13-trans prostadiene |
| | | dl-11a,16-dihydroxy-16-(methoxymethoxycarbonylmethyl)-1,9-dioxo-16- | | |
| EXAMPLE | VINYL IODIDE | CYCLOPENTENONE | PRODUCT PROSTAGLANDIN OF THE PGE2 SERIES |
| 51 | 1-trans-iodo-3-triphenylmethoxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,15-dihydroxy-1-(methoxymethoxycarbonylmethyl)-1,9-dioxo-20-methyl-2-nor-5-cis-13-trans prostadiene |
| 52 | 1-trans-iodo-3-methyl-3-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,15a-dihydroxy-1-(methoxymethoxycarbonylmethyl)-1,9-dioxo-20-methyl-2-nor-5-cis-13-trans prostadiene |
| 53 | 1-trans-iodo-4,4-dimethyl-3-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,15a-dihydroxy-1-(methoxymethoxycarbonylmethyl)-1,9-dioxo-16,16-dimethyl-20-methyl-2-nor-5-cis-13-trans prostadiene |
| 54 | 1-trans-iodo-4,4-trimethylene-3-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,15a-dihydroxy-1-(methoxymethoxycarbonylmethyl)-1,9-dioxo-16,16-trimethylene-20-methyl-2-nor-5-cis-13-trans prostadient |
| EXAMPLE | VINYL TIN | CYCLOPENTENONE | PRODUCT PROSTAGLANDIN OF THE PGE2 SERIES |
| 55 | 1-trans-tri-n-butylstannyl-3-vinyl-3-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,15a-dihydroxy-1-(methoxymethoxycarbonylmethyl)-1,9-dioxo-15-vinyl-20-methyl-2-nor-5-cis-13-trans prostadiene |
| EXAMPLE | VINYL IODIDE | CYCLOPENTENONE | PROSTAGLANDIN OF THE PGE2 SERIES |
| 56 | 1-trans-iodo-4-triphenylmethoxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-20-methyl-2-nor-5-cis-13-trans prostadiene |
| EXAMPLE | VINYL TIN | CYCLOPENTENONE | PRODUCT PROSTAGLANDIN OF THE PGE2 SERIES |
| 57 | 1-trans-tri-n-butylstannyl-4-methyl-4-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-16-methyl-20-methyl-2-nor-5-cis-13-trans prostadiene |
| 58 | 1-trans-tri-n-butylstannyl-5-methyl-4-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-17-methyl-20-methyl-2-nor-5-cis-13-trans prostadiene |
| 59 | 1-trans-tri-n-butylstannyl-4-vinyl-4-trimethylsilyloxy-1-nonene | 2-[7-methoxy-7-methoxycabonyl-6-(trimethylsilyloxy)-2-cis,6-heptadienyl]-4-trimethylsilyloxy cyclopent-2-en-1-one | dl-11a,16-dihydroxy-1-(methoxymethoxycarbonylmethyl)-1,9-dioxo-16-vinyl-20-methyl-2-nor-5-cis-13-trans prostadiene |

| EXAMPLE | VINYL TIN | CYCLOPENTENONE | PROSTAGLANDIN OF THE PGE2 SERIES |
|---|---|---|---|
| 60 | 1-trans-tri-n-butylstannyl-4-trimethylsilylethynyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-ethynyl-20-methyl-2-nor-5-cis-13-trans prostadiene |
| 61 | 1-trans-tri-n-butylstannyl-5-methylene 4-triethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-17-methylene-20-methyl-2-nor-5-cis-13-trans prostadiene |
| 62 | 1-trans-tri-n-butylstannyl-4-methyl-5-methylene 4-trimethylsilyloxy-1-nonene | 2-[7-methoxy-7-methyoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-methyl-2-nor-5-cis-13-trans prostadiene |
| 63 | 1-trans-tri-n-butylstannyl-4-dimethoxymethyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-formyl-20-methyl-2-nor-5-cis-13-trans prostadiene |
| 64 | 1-trans-tri-n-butylstannyl-4-fluoromethyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-fluoromethyl-20-methyl-2-nor-5-cis-13-trans prostadiene |
| 65 | 1-trans-tri-n-butylstannyl-4-difluoromethyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-difluoromethyl-20-methyl-2-nor-5-cis-13-trans prostadiene |
| 66 | 1-trans-tri-n-butylstannyl-4-trifluoromethyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-trifluoromethyl-20-methyl-2-nor-5-cis-13-trans prostadiene |
| 67 | 1-trans-tri-n-butylstannyl-4-chloromethyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)0-1,9-dioxo-16-chloromethyl-20-methyl-2-nor-5-cis-13-trans prostadiene |
| 68 | 1-trans-tri-n-butylstannyl-4-trimethylsilyloxymethyl-4-trimethylsilyloxy-1-nonene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)0-1,9-dioxo-16-hydroxymethyl-20-methyl-2-ethyl-2-nor-5-cis-13-trans prostadiene |

| EXAMPLE | VINYL IODIDE | CYCLOPENTENONE | PROSTAGLANDIN OF THE PGE2 SERIES |
|---|---|---|---|
| 69 | 1-trans-iodo-3-triphenylmethoxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-20-ethyl-2-nor-5-cis-13-trans prostadiene |
| 70 | 1-trans-iodo-3-methyl-3-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-15-methyl-20-ethyl-2-nor-5-cis-13-trans prostadiene |
| 71 | 1-trans-iodo-4,4-dimethyl-3-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16,16-dimethyl-20-ethyl-2-nor-5-cis-13-trans prostadiene |
| 72 | 1-trans-iodo-4,4-trimethylene-3-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,15a-dihydroxy-1-(methoxymethoxycarbonylmethyl)-1,9-dioxo-16,16-trimethylene-20-ethyl-2-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 73 | 1-trans-tri-n-butylstannyl-3-vinyl-3-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,15a-dihydroxy-1-(methoxymethoxycarbonylmethyl)-1,9-cioxo-15-vinyl-20-ethyl-2-nor-5-cis-13-trans prostadiene |

| EXAMPLE | VINYL IODIDE | CYCLOPENTENONE | PRODUCT PRPSTAGLANDIN OF THE PGE2 SERIES |
|---|---|---|---|
| 74 | 1-trans-iodo-4-triphenylmethoxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-20-ethyl-2-nor-5-cis-13-trans prostadiene |

| EXAMPLE | VINYL TIN | CYCLOPENTINONE | PRODUCT PROSTAGLANDIN OF THE PGE2 SERIES |
|---|---|---|---|

-continued

| | | | |
|---|---|---|---|
| 75 | 1-trans-tri-n-butylstannyl-4-methyl-4-trimethylsilyloxy-1-decene | 2-[7-methoxycabonyl-6-(trimethylsiloxy)-2-cis,6-heptadeinyl]-4-trimethylsiloxy cyclopent-2-en-1-one | dl-11a,16-dihydroxy-1-(methoxymethoxycarbonylmethyl)-1,9-dioxo-16-methyl-20-ethyl-2-nor-5-cis-13-trans prostadiene |
| 76 | 1-trans-tri-n-butylstannyl-5-methyl-4-trimethylsilyloxy-1-decene | 2-[7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarmonylmethyl)-1,9-dioxo-17-methyl-20-ethyl-2-nor-5-cis-13-trans prostadiene |
| 77 | 1-trans-tri-n-butylstannyl-4-vinyl-4-trimethylsilyloxy-1-decene | 2-[ 7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-vinyl-20-ethyl-2-nor-5-cis-13-trans prostadiene |
| 78 | 1-trans-tri-n-butylstannyl-4-trimethylsilylethynyl-4-(trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-ethynyl-20-ethyl-2-nor-5-cis-13-trans prostadiene |
| 79 | 1-trans-tri-n-butylstannyl-5-methylene-4-triethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-17-methylene-20-ethyl-2-nor-5-cis-13-trans prostadiene |
| 80 | 1-trans-tri-n-butylstannyl-4-methyl-5-methylene-4-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-ethyl-2-nor-5-cis-13-trans prostadiene |
| 81 | 1-trans-tri-n-butylstannyl-4-dimethoxymethyl-4-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methyoxymethoxycarbonylmethyl)-1,9-dioxo-16-formyl-20-ethyl-2-nor-5-cis-13-trans prostadiene |
| 82 | 1-trans-tri-n-butylstannyl-4-fluoromethyl-4-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-fluoromethyl-2-ethyl-2-nor-5-cis-13-trans prostadiene |
| 83 | 1-trans-tri-n-butylstannyl-4-difouoromethyl-4-trimethylsilyloxy-1-decene | 2-[ 7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-difluoromethyl-20-ethyl-2-nor-5-cis-13-trans prostadiene |
| 84 | 1-trans-tri-n-butylstannyl-4-trifluoromethyl-4-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-trifluoromethyl-20-ethyl-2-nor-5-cis-13-trans prostadiene |
| 85 | 1-trans-tri-n-butylstanyl-4-chloromethyl-4-trans-tri-n-butylstannyl-4-chloromethyl-4-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-chloromethyl-20-ethyl-2-nor-5-cis-13-trans prostadiene |
| 86 | 1-trans-tri-n-butylstannyl-4-trimethylsilyloxymethyl-4-trimethylsilyloxy-1-decene | 2-[7-methoxy-7-methoxycabonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 87 | 1-trans-iodo-3-triphenylmethoxy-1-heptene | 2-[8-methoxy-8-methoxycarbonyl-7-(trimethylsiloxy)-2-cis,7-octadienyl]4-trimethylsiloxy cuyclopent-2-en-1-one | dl-11a,15a-dihydroxy-1-(methoxymethoxycarbonylmethyl)-1,9-dioxo-20-nor-5-cis-13-trans prostadiene |
| 88 | 1-trans-iodo-3-methyl-3-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-15-methyl-16,16-dimethyl-20-nor-5-cis-13-trans prostadiene |
| 89 | 1-trans-iodo-4,4-dimethyl-3-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16,16-dimethyl-20-nor-5-cis-13-trans prostadiene |
| 90 | 1-trans-iodo-5,5-dimethyl-3-triphenylmethoxy-1-octene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-17-17-dimethyl-5-cis-13-trans prostadiene |
| 91 | 1-trans-iodo-4-methyl-3-triphenylmethoxy-1-octene | 2-[8-methoxy-8-meth‥xycarbonyl-2-‥s,7-octadienyl]-4-trimethylsiloxy cyclopent-2-en-1-one | dl-11a,15a-dihydroxy-1-(methoxymethoxycarbonylmethyl)-1,9-dioxo-16-methyl-5-cis-13-trans prostadiene |

| EXAMPLE | VINYL IODIDE / VINYL TIN | CYCLOPENTENONE | PRODUCT PROSTAGLANDIN OF THE PGE2 SERIES |
|---|---|---|---|
| 92 | 1-trans-iodo-4,4-trimethylene-3-trimethylsilyloxy-1-heptene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16,16-trimethylene-20-nor-5-cis-13-trans prostadiene |
| EXAMPLE | VINYL TIN | CYCLOPENTENONE | PRODUCT PROSTAGLANDIN OF THE PGE2 SERIES |
| 93 | 1-trans-tri-n-butylstannyl-3-vinyl-3-triethylsilyloxy-1-heptene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-15-vinyl-20-nor-5-cis-13-trans prostadiene |
| 94 | 1-trans-tri-n-butylstannyl-4-phenoxy-3-triethylsilyloxy-1-butene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16-phenoxy-17-20-tetranor-5-cis-13-trans prostadiene |
| 95 | 1-trans-tri-n-butylstannyl-4-(p-fluorophenoxy)-3-triethylsilyloxy-1-butene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16-(p-fluorophenoxy)-17-20-tetranor-5-cis-13-trans prostadiene |
| 96 | 1-trans-tri-n-butylstannyl-4-(m-chlorophenoxy)-3-triethylsilyloxy-1-butene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16-(m-chlorophenoxy)-17-20-tetranor-5-cis-13-trans prostadiene |
| 97 | 1-trans-tri-n-butylstannyl-4-(m-trifluoromethylphenoxy)-3-triethylsilyloxy-1-butene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16-(m-trifluoromethylphenoxy)-17-20-tetranor-5-cis-13-trans prostadiene |
| EXAMPLE | VINYL IODIDE | CYCLOPENTENONE | PRODUCT PROSTAGLANDIN OF THE PGE2 SERIES |
| 98 | 1-trans-iodo-5-phenyl-3-triethylsilyloxy-1-pentene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-17-phenyl-18-20-trinor-5-cis-13-trans prostadiene |
| 99 | 1-trans-iodo-4,4-dimethyl-5-phenyl-3-triethylsilyloxy-1-pentene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16,16-dimethyl-17-phenyl-13-20-trinor-5-cis-13-trans prostadiene |
| 100 | 1-trans-iodo-4-cyclopentyl-3-triphenylmethoxy-1-butene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16-cyclopentyl-17-20-tetranor-5-cis-13-trans prostadiene |
| 101 | 1-trans-iodo-4-cyclohexyl-3-triphenylmethoxy-1-butene | 2-[8-methoxy-8-methoxycarbonyl-7-(trimethylsiloxy)-2-cis,7-octadienyl]-4-trimethylsiloxy-cyclopent-2-en-1-one | dl-11a,15a-dihydroxy-1-(methoxymethoxycarbonylmethyl)-1,9-dioxo-16-cyclohexyl-17-20-tetranor-5-cis-13-trans prostadiene |
| 102 | 1-trans-iodo-3-triphenylmethoxy-1-heptene | 2-[8-methoxy-8-methoxycarbonyl-7-(trimethylsiloxy)-2-cis,7-octadienyl]-4-trimethylsiloxy-cyclopent-2-en-1-one | dl-11a,16-dihydroxy-1-(methoxymethoxycarbonylmethyl)-1,9-dioxo-20-nor-5-cis-13-trans prostadiene |
| EXAMPLE | VINYL TIN | CYCLOPENTENONE | PRODUCT PROSTAGLANDIN OF THE PGE2 SERIES |
| 103 | 1-trans-tri-n-butylstannyl-4-methyl-4-trimethylsilyloxy-1-heptene | 2-[8-methoxy-8-methoxycarbonyl-7-(trimethylsiloxy)-2-cis,7-octadienyl]-4-trimethylsiloxy-cyclopent-2-en-1-one | dl-11a,16a-dihydroxy-1-(methoxymethoxycarbonylmethyl)-1,9-dioxo-16-methyl-20-nor-5-cis-13-trans prostadiene |
| 104 | 1-trans-tri-n-butylstannyl-4-ethyl-4-trimethylsilyloxy-1-octene | 2-[8-methoxy-8-methoxycarbonyl-7-(trimethylsiloxy)-2-cis,7-octadienyl]-4-trimethylsiloxy-cyclopent-2-en-1-one | dl-11a,16a-dihydroxy-1-(methoxymethoxycarbonylmethyl)-1,9-dioxo-16-ethyl-5-cis-13-trans prostadiene |
| 105 | 1-trans-tri-n-butylstannyl-5-methyl-4-trimethylsilyloxy-1-heptene | 2-[8-methoxy-8-methoxycarbonyl-7-(trimethylsiloxy)-2-cis,7-octadienyl]-4-trimethylsiloxy-cyclopent-2-en-1-one | dl-11a,16-dihydroxy-1-(methoxymethoxycarbonylmethyl)-1,9-dioxo-17-methyl-20-nor-5-cis-13-trans prostadiene |
| EXAMPLE | VINYL IODIDE | CYCLOPENTENONE | PRODUCT PROSTAGLANDIN OF THE PGE2 SERIES |
| 106 | 1-trans-iodo-5,5-dimethyl-4-trimethylsilyloxy-1-octene | 2-[8-methoxy-8-methoxycarbonyl-7-(trimethylsiloxy)-2-cis,7-octadienyl]-4-trimethylsiloxy-cyclopent-2-en-1-one | dl-11a,16-dihydroxy-1-(methoxymethoxycarbonylmethyl)-1,9-dioxo-17,17-dimethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 107 | 1-trans-tri-n-butylstannyl-4-vinyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-vinyl-20-nor-5-cis-13-trans prostadiene |
| 108 | 1-trans-tri-n-butylstannyl-4-cyclopropyl-4-trimethylsilyloxy-1-octene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-5-cis-13-trans prostadiene |
| 109 | 1-trans-tri-n-butylstannyl-4-trimethylsilylethynyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | cyclopropyl-5-cis-13-trans 20-nor-5-cis-13-trans prostadiene |
| 110 | 1-trans-tri-n-butylstannyl-5-methylene-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methylene-20-nor-5-cis-13-trans prostadiene |
| 111 | 1-trans-tri-n-butylstannyl-4-methyl-5-methylene-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-nor-5-cis-13-trans prostadiene |
| 112 | 1-trans-tri-n-butylstannyl-4-dimethoxymethyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-formyl-20-nor-5-cis-13-trans prostadiene |
| 113 | 1-trans-tri-n-butylstannyl-4-fluoromethyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-fluoromethyl-20-nor-5-cis-13-trans prostadiene |
| 114 | 1-trans-tri-n-butylstannyl-4-difluoromethyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-difluoromethyl-20-nor-5-cis-13-trans prostadiene |
| 115 | 1-trans-tri-n-butylstannyl-4-trifluoromethyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-trifluoromethyl-20-nor-5-cis-13-trans prostadiene |
| 116 | 1-trans-tri-n-butylstannyl-4-chloromethyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-chloromethyl-20-nor-5-cis-13-trans prostadiene |
| 117 | 1-trans-tri-n-butylstannyl-4-trimethylsilyloxymethyl-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 118 | 1-trans-iodo-4-methyl-7-chloro-4-trimethylsilyloxy-1-heptene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16-methyl-19-chloro-20-nor-5-cis-13-trans prostadiene |
| 119 | 1-trans-iodo-3-triphenylmethoxy-1-octene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-5-cis-13-trans prostadiene |
| 120 | 1-trans-iodo-3-methyl-3-trimethylsilyloxy-1-octene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-15-methyl-5-cis-13-trans prostadiene |
| 121 | 1-trans-iodo-4,4-dimethyl-3-trimethylsilyloxy-1-octene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16,16-dimethyl-5-cis-13-trans prostadiene |
| 122 | 1-trans-iodo-4,4-trimethylene-3-trimethylsilyloxy-1-octene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16,16-trimethylene-5-cis-13-trans prostadiene |

| EXAMPLE | VINYL TIN | CYCLOPENTENONE | PRODUCT PROSTAGLANDIN OF THE PGE2 SERIES |
|---|---|---|---|

| | | -continued | |
|---|---|---|---|
| 123 | | 1-trans-tri-n-butylstannyl-3-vinyl-3-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-15-vinyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 124 | 1-trans-iodo-4-triphenylmethoxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-5-cis-13-trans prostadiene |

| EXAMPLE | VINYL TIN | CYCLOPENTENONE | PRODUCT POSTAGLANDIN OF THE PGE2 SEIRES |
|---|---|---|---|
| 125 | 1-trans-tri-n-butylstannyl-4-methyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-5-cis-13-trans prostadiene |
| 126 | 1-trans-tri-n-butylstannyl-5-methyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methyl-5-cis-13-trans prostadiene |
| 127 | 1-trans-tri-n-butylstannyl-4-vinyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-vinyl-5-cis-13-trans prostadiene |
| 128 | 1-trans-tri-n-butylstannyl-4-trimethylsilylethynyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-ethynyl-5-cis-13-trans prostadiene |
| 129 | 1-trans-tri-n-butylstannyl-3-methylene-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methylene-5-cis-13-trans prostadiene |
| 130 | 1-trans-tri-n-butylstannyl-4-methyl-5-methylene-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methylene-5-cis-13-trans prostadiene |
| 131 | 1-trans-tri-n-butylstannyl-4-dimethoxymethyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-formyl-5-cis-13-trans prostadiene |
| 132 | 1-trans-tri-n-butylstannyl-4-fluoromethyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-fluoromethyl-5-cis-13-trans prostadiene |
| 133 | 1-trans-tri-n-butylstannyl-4-difluoromethyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-difluoromethyl-5-cis-13-trans prostadiene |
| 134 | 1-trans-tri-n-butylstannyl-4-trifluoromethyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-trifluoromethyl-5-cis-13-trans prostadiene |
| 135 | 1-trans-tri-n-butylstannyl-4-chloromethyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-chloromethyl-5-cis-13-trans prostadiene |
| 136 | 1-trans-tri-n-butylstannyl-4-trimethylsilyloxymethyl-4-trimethylsilyloxy-1-octene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-hydroxymethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 137 | 1-trans-iodo-3-triphenylmethoxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-20-methyl-5-cis-13-trans prostadiene |
| 138 | 1-trans-iodo-3-methyl- | 2-[8-methoxy-8-methoxycarbonyl- | dl-11a,15a-dihydroxy-1-(methoxymethoxycarbonylmethyl)-1,9-dioxo-15-methyl- |

| | | -continued | |
|---|---|---|---|
| | | 3-trimethylsilyloxy-1-nonene | 7-(trimethylsilyloxy)-2-cis,7-octadienyl]-4-trimethylsilyloxy cyclopent-2-en-1-one | 20-methyl-5-cis-13-trans prostadiene |
| 139 | | 1-trans-iodo-4,4-dimethyl-3-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16,16-dimethyl-20-methyl-5-cis-13-trans prostadiene |
| 140 | | 1-trans-iodo-4,4-trimethylene-3-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16,16-trimethylene-20-methyl-5-cis-13-trans prostadiene |
| EXAMPLE | VINYL IODIDE | CYCLOPENTENONE | | PRODUCT PROSTAGLANDIN OF THE PGE2 SERIES |
| 141 | | 1-trans-tri-n-butylstannyl-3-vinyl-3-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-15-vinyl-20-methyl-5-cis-13-trans prostadiene |
| EXAMPLE | VINYL IODIDE | CYCLOPENTENONE | | PRODUCT PROSTAGLANDIN OF THE PGE2 SERIES |
| 142 | | 1-trans-iodo-4-triphenylmethoxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-20-methyl-5-cis-13-trans prostadiene |
| EXAMPLE | VINYL TIN | CYCLOPENTENONE | | PRODUCT PROSTAGLANDIN OF THE PGE2 SEIRES |
| 143 | | 1-trans-tri-n-butylstannyl-4-methyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-20-methyl-5-cis-13-trans prostadiene |
| 144 | | 1-trans-tri-n-butylstannyl-5-methyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methyl-20-methyl-5-cis-13-trans prostadiene |
| 145 | | 1-trans-tri-n-butylstannyl-4-vinyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-vinyl-20-methyl-5-cis-13-trans prostadiene |
| 146 | | 1-trans-tri-n-butylstannyl-4-trimethylsilylethynyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-ethynyl-20-methyl-5-cis-13-trans prostadiene |
| 147 | | 1-trans-tri-n-butylstannyl-5-methylene-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methylene-20-methyl-5-cis-13-trans prostadiene |
| 148 | | 1-trans-tri-n-butylstannyl-4-methyl-5-methylene-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-methyl-5-cis-13-trans prostadiene |
| 149 | | 1-trans-tri-n-butylstannyl-4-dimethoxymethyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-formyl-20-methyl-5-cis-13-trans prostadiene |
| 150 | | 1-trans-tri-n-butylstannyl-4-fluoromethyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-fluoromethyl-20-methyl-5-cis-13-trans prostadiene |
| 151 | | 1-trans-tri-n-butylstannyl-4-difluoromethyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-difluoromethyl-20-methyl-5-cis-13-trans prostadiene |
| 152 | | 1-trans-tri-n-butylstannyl-4-trifluoromethyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-trifluoromethyl-20-methyl-5-cis-13-trans prostadiene |
| 153 | | 1-trans-tri-n-butylstannyl-4-chloromethyl-4-trimethylsilyloxy-1-nonene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-chloromethyl-20-methyl-5-cis-13-trans prostadiene |

| | -continued | | |
|---|---|---|---|
| 154 | 1-trans-tri-n-butylstannyl-4-trimethylsilyloxymethyl-4-trimethylsilyloxy-1-nonene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-hydroxymethyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 155 | 1-trans-iodo-3-triphenylmethoxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-20-ethyl-5-cis-13-trans prostadiene |
| 156 | 1-trans-iodo-3-methyl-3-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-15-methyl-20-ethyl-5-cis-13-trans prostadiene |
| 157 | 1-trans-iodo-4,4-dimethyl-3-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-16,16-dimethyl-20-ethyl-5-cis-13-trans prostadiene |
| 158 | 1-trans-iodo-4,4-trimethylene-3-trimethylsilyloxy-1-decene | 2-[8-methoxy-8-methoxycarbonyl-7-(trimethylsiloxy)-2-cis,7 octadienyl]-4-trimethylsiloxy cyclopent-2-en-1-one | dl-11a,15a-dihydroxy-1-(methoxymethoxycarbonylmethyl)-1,9-dioxo-16,16-trimethylene-20-ethyl-5-cis-13-trans prostadiene |
| EXAMPLE | VINYL TIN | CYCLOPENTENONE | PRODUCT PROSTAGLANDIN OF THE PGE2 SEIES |
| 159 | 1-trans-tri-n-butylstannyl-3-vinyl-3-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,15a-dihydroxy-1-(methoxymethoxycarbonylmethyl)-1,9-dioxo-15-vinyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 160 | 1-trans-iodo-4-triphenylmethoxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-vinyl-20-ethyl-5-cis-13-trans prostadiene |
| EXAMPLE | VINYL TIN | CYCLOPENTENONE | PRODUCT PROSTAGLANDIN OF THE PGE2 SERIES |
| 161 | 1-trans-tri-n-butylstannyl-4-methyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-20-ethyl-5-cis-13-trans prostadiene |
| 162 | 1-trans-tri-n-butylstannyl-5-methyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methyl-20-ethyl-5-cis-13-trans prostadiene |
| 163 | 1-trans-tri-n-butylstannyl-4-vinyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-vinyl-20-ethyl-5-cis-13-trans prostadiene |
| 164 | 1-trans-tri-n-butylstannyl-4-trimethylsilylethynyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-ethynyl-20-ethyl-5-cis-13-trans prostadiene |
| 165 | 1-trans-tri-n-butylstannyl-5-methylene-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-17-methylene-20-ethyl-5-cis-13-trans prostadiene |
| 166 | 1-trans-tri-n-butylstannyl-4-methyl-5-methylene-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-ethyl-5-cis-13-trans prostadiene |
| 167 | 1-trans-tri-n-butylstannyl-4-dimethoxymethyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-formyl-20-ethyl-5-cis-13-trans prostadiene |
| 168 | 1-trans-tri-n-butylstannyl-4-fluoromethyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-fluoromethyl-20-ethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 169 | 1-trans-tri-n-butylstannyl-4-difluoromethyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-difluoromethyl-20-ethyl-5-cis-13-trans prostadiene |
| 170 | 1-trans-tri-n-butylstannyl-4-trifluoromethyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-trifluoromethyl-20-ethyl-5-cis-13-trans prostadiene |
| 171 | 1-trans-tri-n-butylstannyl-4-chloromethyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-chloromethyl-20-ethyl-5-cis-13-trans prostadiene |
| 172 | 1-trans-tri-n-butylstannyl-4-trimethylsilyloxymethyl-4-trimethylsilyloxy-1-decene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 173 | 1-trans-iodo-3-triphenylmethoxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-20-nor-2-homo-5-cis-13-trans prostadiene |
| 174 | 1-trans-iodo-3-methyl-3-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-15-methyl-20-nor-2-homo-5-cis-13-trans prostadiene |
| 175 | 1-trans-iodo-4,4-dimethyl-3-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16,16-dimethyl-20-nor-2-homo-5-cis-13-trans prostadiene |
| 176 | 1-trans-iodo-5,5-dimethyl-3-triphenylmethoxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-17,17-dimethyl-2-homo-5-cis-13-trans prostadiene |
| 177 | 1-trans-iodo-4-methyl-3-triphenylmethoxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16-methyl-2-homo-5-cis-13-trans prostadiene |
| 178 | 1-trans-iodo-4,4-trimethylene-3-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16,16-trimethylene-20-nor-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 179 | 1-trans-tri-n-butylstannyl-3-vinyl-3-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-15-vinyl-20-nor-2-homo-5-cis-13-trans prostadiene |
| 180 | 1-trans-tri-n-butylstannyl-4-phenoxy-3-triethylsilyloxy-1-butene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16-phenoxy-2-homo-17-20-tetranor-5-cis-13-trans prostadiene |
| 181 | 1-trans-tri-n-butylstannyl-4-(p-fluorophenoxy)-3-triethylsilyloxy-1-butene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16-(p-fluorophenoxy)-2-homo-17-20-tetranor-5-cis-13-trans prostadiene |
| 182 | 1-trans-tri-n-butylstannyl-4-(m-chlorophenoxy)-3-triethylsilyloxy-1-butene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16-(m-chlorophenoxy)-2-homo-17-20-tetranor-5-cis-13-trans prostadiene |
| 183 | 1-trans-tri-n-butylstannyl-4-(m-fluoromethylphenoxy)-3-triethylsilyloxy-1-butene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16-(m-trifluoromethylphenoxy)-2-homo-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 184 | 1-trans-iodo-5-phenyl-3-triethylsilyloxy-1-pentene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-17-phenyl-2-homo-18-20-trinor-5-cis-13-trans prostadiene |

-continued

| EXAMPLE | | | PRODUCT PROSTAGLANDIN |
|---|---|---|---|
| 185 | 1-trans-iodo-4,4-dimethyl-5-phenyl-3-triethylsilyloxy-1-pentene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16,16-dimethyl-17-phenyl-2-homo-18,20-trinor-5-cis-13-trans prostadiene |
| 186 | 1-trans-iodo-4-cyclopentyl-3-triphenylmethoxy-1-butene | 2-[9-methoxy-9-methoxycarbonyl-8-(trimethylsiloxy)-2-cis,8-nonadienyl]-4-trimethylsiloxy cyclopent-2-en-one | dl-11a,15a-dihydroxy-1-(methoxymethoxycarbonylmethyl)-1,9-dioxo-16-cyclopentyl-2-homo-17,20-tetranor-5-cis-13-trans prostadiene |
| 187 | 1-trans-iodo-4-cyclohexyl-3-triphenylmethoxy-1-butene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16-cyclohexyl-2-homo-17,20-tetranor-5-cis-13-trans prostadiene |
| 188 | 1-trans-iodo-4-triphenylmethoxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-20-nor-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 189 | 1-trans-tri-n-butylstannyl-4-methyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-20-nor-2-homo-5-cis-13-trans prostadiene |
| 190 | 1-trans-tri-n-butylstannyl-4-ethyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-ethyl-2-homo-5-cis-13-trans prostadiene |
| 191 | 1-trans-tri-n-butylstannyl-5-methyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-17-methyl-20-nor-2-homo-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 192 | 1-trans-iodo-5,5-dimethyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-17,17-dimethyl-2-homo-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 193 | 1-trans-tri-n-butylstannyl-4-vinyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-vinyl-20-nor-2-homo-5-cis-13-trans prostadiene |
| 194 | 1-trans-tri-n-butylstannyl-4-cyclopropyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-cyclopropyl-2-homo-5-cis-13-trans prostadiene |
| 195 | 1-trans-tri-n-butylstannyl-4-trimethylsilylethynyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-ethynyl-20-nor-2-homo-5-cis-13-trans prostadiene |
| 196 | 1-trans-tri-n-butylstannyl-5-methylene-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-17-methylene-20-nor-2-homo-5-cis-13-trans prostadiene |
| 197 | 1-trans-tri-n-butylstannyl-4-methyl-5-methylene-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-17-methylene-20-nor-2-homo-5-cis-13-trans prostadiene |
| 198 | 1-trans-tri-n-butylstannyl-4-dimethoxymethyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-formyl-20-nor-2-homo-5-cis-13-trans prostadiene |
| 199 | 1-trans-tri-n-butylstannyl-4-fluoromethyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-fluoromethyl-20-nor-2-homo-5-cis-13-trans prostadiene |
| 200 | 1-trans-tri-n-butylstannyl-4-difluoromethyl- | 2-[9-methoxy-9-methoxycarbonyl- | dl-11a,16-dihydroxy-1-(methoxymethoxycarbonylmethyl)-1,9-dioxo-16- |

| EXAMPLE | VINYL IODIDE / VINYL TIN | CYCLOPENTENONE | PRODUCT PROSTAGLANDIN |
|---|---|---|---|
| | 4-trimethylsilyloxy-1-heptene | 8-(trimethylsiloxy)-2-cis,8-nonadienyl]-4-trimethylsiloxy cyclopent-2-en-1-one | difluoromethyl-20-nor-2-homo-5-cis,8-nonadienyl]-4-trimethylsiloxy-1,9-dioxo-13-trans prostadiene |
| 201 | 1-trans-tri-n-butylstannyl-4-trifluoromethyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-trifluoromethyl-20-nor-2-homo-5-cis-13-trans prostadiene |
| 202 | 1-trans-tri-n-butylstannyl-4-choromethyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-chloromethyl-20-nor-2-homo-5-cis-13-trans prostadiene |
| 203 | 1-trans-tri-n-butylstannyl-4-trimethylsilyloxymethyl-4-trimethylsilyloxy-1-heptene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-hydroxymethyl-20-nor-2-homo-5-cis-13-trans prostadiene |
| EXAMPLE | VINYL IODIDE | CYCLOPENTENONE | PRODUCT PROSTAGLANDIN OF THE PGE2 SERIES |
| 204 | 1-trans-iodo-4-methyl-7-chloro-4-trimethylsilyloxy-1-heptene | 2-[9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-19-chloro-2-homo-20-nor-5-cis-13-trans prostadiene |
| 205 | 1-trans-iodo-3-triphenylmethoxy-1-octene | 2-[9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-2-homo-5-cis-13-trans prostadiene |
| 206 | 1-trans-iodo-3-methyl-3-trimethylsilyloxy-1-octene | 2-[9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-15-methyl-2-homo-5-cis-13-trans prostadiene |
| 207 | 1-trans-iodo-4,4-dimethyl-3-trimethylsilyloxy-1-octene | 2-[9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16,16-dimethyl-2-homo-5-cis-13-trans prostadiene |
| 208 | 1-trans-iodo-4,4-trimethylene-3-trimethylsilyloxy-1-octene | 2-[9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-16,16-trimethylene-2-homo-5-cis-13-trans prostadiene |
| EXAMPLE | VINYL TIN | CYCLOPENTENONE | PRODUCT PROSTAGLANDIN OF THE PGE2 SERIES |
| 209 | 1-trans-tri-n-butylstannyl-3-vinyl-3-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,15a-dihydroxy-1-(methoxymethoxycarbonylmethyl)-1,9-dioxo-15-vinyl-2-homo-5-cis-13-trans prostadiene |
| EXAMPLE | VINYL IODIDE | CYCLOPENTENONE | PRODUCT PROSTAGLANDIN OF THE PGE2 SERIES |
| 210 | 1-trans-iodo-4-triphenylmethoxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-2-homo-5-cis-13-trans prostadiene |
| EXAMPLE | VINYL TIN | CYCLOPENTENONE | PRODUCT PROSTAGLANDIN OF THE PGE2 SERIES |
| 211 | 1-trans-tri-n-butylstannyl-4-methyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-2-homo-5-cis-13-trans prostadiene |
| 212 | 1-trans-tri-n-butylstannyl-5-methyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-17-methyl-2-homo-5-cis-13-trans prostadiene |
| 213 | 1-trans-tri-n-butylstannyl-4-vinyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-vinyl-2-homo-5-cis-13-trans prostadiene |
| 214 | 1-trans-tri-n-butylstannyl-4-trimethylsilylethynyl-4-trimethylsilyloxy-1-octene | 2-[9-methoxy-9-methoxycarbonyl-8-(trimethylsiloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-ethynyl-2-homo-5-cis-13-trans prostadiene |
| 215 | 1-trans-tri-n-butylstannyl-5-methylene | 2-[9-methoxy-9-methoxycarbonyl- | dl-11a,16-dihydroxyl-1-(methoxymethoxycarbonylmethyl)-1,9-dioxo- |

-continued

| EXAMPLE | VINYL IODIDE | CYCLOPENTENONE | PRODUCT PROSTAGLANDIN OF THE PGE2 SERIES |
|---|---|---|---|
| 216 | 1-trans-tri-n-butylstannyl-4-methyl-5-methylene-4-trimethylsilyloxy-1-octene | 2-[8-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-methyl-17-methylene-2-homo-5-cis-13-trans prostadiene |
| 217 | 1-trans-tri-n-butylstannyl-4-dimethoxymethyl-4-trimethylsilyloxy-1-octene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-formyl-2-homo-5-cis-13-trans prostadient |
| 218 | 1-trans-tri-n-butylstannyl-4-fluoromethyl-4-trimethylsilyloxy-1-octene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-fluoromethyl-2-homo-5-cis-13-trans prostadiene |
| 219 | 1-trans-tri-n-butylstannyl-4-difluoromethyl-4-trimethylsilyloxy-1-octene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-difluoromethyl-2-homo-5-cis-13-trans prostadiene |
| 220 | 1-trans-tri-n-butylstannyl-4-trifluoromethyl-4-trimethylsilyloxy-1-octene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-trifluoromethyl-2-homo-5-cis-13-trans prostadiene |
| 221 | 1-trans-tri-n-butylstannyl-4-chloromethyl-4-trimethylsilyloxy-1-octene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-chloromethyl-2-homo-5-cis-13-trans prostadiene |
| 222 | 1-trans-tri-n-butylstannyl-4-trimethylsilyloxymethyl-4-trimethylsilyloxy-1-octene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-hydroxymethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 223 | 1-trans-iodo-3-triphenylmethoxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-20-methyl-2-homo-5-cis-13-trans prostadiene |
| 224 | 1-trans-iodo-3-methyl-3-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-15-methyl-20-methyl-2-homo-5-cis-13-trans prostadiene |
| 225 | 1-trans-iodo-4,4-dimethyl-3-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-16,16-dimethyl-20-methyl-2-homo-5-cis-13-trans prostadiene |
| 226 | 1-trans-iodo-4,4-trimethylene-3-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-16,16-trimethylene-20-methyl-2-homo-2-cis-13-trans prostadiene |
| EXAMPLE | VINYL TIN | CYCLOPENTENONE | PRODUCT PROSTAGLANDIN OF THE PGE2 SERIES |
| 227 | 1-trans-tri-n-butylstannyl-3-vinyl-3-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-15-vinyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 228 | 1-trans-iodo-4-triphenylmethoxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-20-methyl-2-homo-5-cis-13-trans prostadiene |
| EXAMPLE | VINYL TIN | CYCLOPENTENONE | PRODUCT PROSTAGLANDIN OF THE PGE2 SERIES |
| 229 | 1-trans-tri-n-butylstannyl-4-methyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-methyl-20-methyl-2-homo-5-cis-13-trans prostadiene |
| 230 | 1-trans-tri-n-butylstannyl-5-methyl | 2-[9-methoxy-9-methoxycarbonyl- | dl-11a,16-dihydroxy-1-(methoxymethoxycarbonylmethyl)-1,9-dioxo- |

-continued

| EXAMPLE | VINYL IODIDE | CYCLOPENTENONE | PRODUCT PROSTAGLANDIN OF THE PGE2 SERIES |
|---|---|---|---|
| 231 | | 8-(trimethylsilyloxy)-2-cis,8-nonadienyl]-4-trimethylsilyloxy cyclopent-2-en-1-one | 17-methyl-20-methyl-2-homo-5-cis-13-trans prostadiene |
| | 4-trimethylsilyloxy-1-nonene | | |
| 232 | 1-trans-tri-n-butylstannyl-4-vinyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-vinyl-20-methyl-2-homo-5-cis-13-trans prostadiene |
| 233 | 1-trans-tri-n-butylstannyl-4-trimethylsilylethynyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-ethynyl-20-methyl-2-homo-5-cis-13-trans prostadiene |
| 234 | 1-trans-tri-n-butylstannyl-5-methylene-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-17-methylene-20-methyl-2-homo-5-cis-13-trans prostadiene |
| 235 | 1-trans-tri-n-butylstannyl-4-methyl-5-methylene-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-methyl-17-methylene-20-methyl-2-homo-5-cis-13-trans prostadiene |
| 236 | 1-trans-tri-n-butylstannyl-4-dimethoxymethyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-formyl-20-methyl-2-homo-5-cis-13-trans prostadiene |
| 237 | 1-trans-tri-n-butylstannyl-4-fluoromethyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-fluoromethyl-20-methyl-2-homo-5-cis-13-trans prostadiene |
| 238 | 1-trans-tri-n-butylstannyl-4-difluoromethyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-difluoromethyl-20-methyl-2-homo-5-cis-13-trans prostadiene |
| 239 | 1-trans-tri-n-butylstannyl-4-trifluoromethyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-trifluoromethyl-20-methyl-2-homo-5-cis-13-trans prostadiene |
| 240 | 1-trans-tri-n-butylstannyl-4-chloromethyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-chloromethyl-20-methyl-2-homo-5-cis-13-trans prostadiene |
| | 1-trans-tri-n-butylstannyl-4-trimethylsilyloxymethyl-4-trimethylsilyloxy-1-nonene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-hydroxymethyl-20-methyl-2-homo-5-cis-13-trans prostadiene |
| EXAMPLE | VINYL IODIDE | CYCLOPENTENONE | PRODUCT PROSTAGLANDIN OF THE PGE2 SERIES |
| 241 | 1-trans-iodo-3-triphenylmethoxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-20-ethyl-2-homo-5-cis-13-trans prostadiene |
| 242 | 1-trans-iodo-3-methyl-3-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-15-methyl-20-ethyl-2-homo-5-cis-13-trans prostadiene |
| 243 | 1-trans-iodo-4,4-dimethyl-3-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-16,16-dimethyl-20-ethyl-2-homo-5-cis-13-trans prostadiene |
| 244 | 1-trans-iodo-4,4-trimethylene-3-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-16,16-trimethylene-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 245 | 1-trans-tri-n-butylstannyl-3-vinyl-3-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,15a-dihydroxy-1-(methoxymethoxycarbonylmethyl)-1,9-dioxo-15-vinyl-20-ethyl-2-homo-5-cis-13-trans prostadiene |
| EXAMPLE | VINYL IODIDE | CYCLOPENTENONE | PRODUCT PROSTAGLANDIN OF THE PGE2 SERIES |

| | -continued | |
|---|---|---|
| 246 | 1-trans-iodo-4-triphenylmethoxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-20-ethyl-2-homo-5-cis-13-trans prostadiene |
| EXAMPLE | VINYL TIN | CYCLOPENTENONE | PRODUCT PROSTAGLANDIN OF THE PGE2 SERIES |
| 247 | 1-trans-tri-n-butylstannyl-4-methyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-methyl-20-ethyl-2-homo-5-cis-13-trans prostadiene |
| 248 | 1-trans-tri-n-butylstannyl-5-methyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-17-methyl-20-ethyl-2-homo-5-cis-13-trans prostadiene |
| 249 | 1-trans-tri-n-butylstannyl-4-vinyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-vinyl-20-ethyl-2-homo-5-cis-13-trans prostadiene |
| 250 | 1-trans-tri-n-butylstannyl-4-trimethylsilylethynyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-ethynyl-20-ethyl-2-homo-5-cis-13-trans prostadiene |
| 251 | 1-trans-tri-n-butylstannyl-5-methylene-4-triethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-17-methylene-20-ethyl-2-homo-5-cis-13-trans prostadiene |
| 252 | 1-trans-tri-n-butylstannyl-4-methyl-5-methylene-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-methyl-17-methylene-20-ethyl-2-homo-5-cis-13-trans prostadiene |
| 253 | 1-trans-tri-n-butylstannyl-4-dimethoxymethyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-formyl-20-ethyl-2-homo-5-cis-13-trans prostadiene |
| 254 | 1-trans-tri-n-butylstannyl-4-fluoromethyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-fluoromethyl-20-ethyl-2-homo-5-cis-13-trans prostadiene |
| 255 | 1-trans-tri-n-butylstannyl-4-difluoromethyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-difluoromethyl-20-ethyl-2-homo-5-cis-13-trans prostadiene |
| 256 | 1-trans-tri-n-butylstannyl-4-trifluoromethyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-trifluoromethyl-20-ethyl-2-homo-5-cis-13-trans prostadiene |
| 257 | 1-trans-tri-n-butylstannyl-4-chloromethyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-chloromethyl-20-ethyl-2-homo-5-cis-13-trans prostadiene |
| 258 | 1-trans-tri-n-butylstannyl-4-trimethylsilyloxymethyl-4-trimethylsilyloxy-1-decene | 2-[9-methoxy-9-methoxycarbonyl-8-(trimethylsilyloxy)-2-cis,8-nonadienyl]-4-trimethylsilyloxy cyclopent-2-en-1-one | dl-11a,16-dihydroxy-1-(methoxymethoxycarbonylmethyl)-1,9-dioxo-16-hydroxymethyl-20-ethyl-2-homo-5-cis-13-trans prostadiene |
| EXAMPLE | VINYL IODIDE | CYCLOPENTENONE | PRODUCT PROSTAGLANDIN OF THE PGE2 SERIES |
| 259 | 1-trans-iodo-3-triphenylmethoxy-1-heptene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-20-nor-5-cis-13-trans prostadiene |
| 260 | 1-trans-iodo-3-methyl-3-trimethylsilyloxy-1-heptene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-15-methyl-20-nor-5-cis-13-trans prostadiene |
| 261 | 1-trans-iodo-4,4-dimethyl-3-trimethylsilyloxy-1-heptene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16,16-dimethyl-20-nor-5-cis-13-trans prostadiene |
| 262 | 1-trans-iodo-5,5-dimethyl | 2-[8-methoxy-8-methoxycarbonyl | nat-11a,15-dihydroxy-1-(methoxymethoxycarbonylmethyl)-1,9-dioxo- |

| EXAMPLE | VINYL TIN | CYCLOPENTENONE | PRODUCT PROSTAGLANDIN OF THE PGE2 SERIES |
|---|---|---|---|
| 263 | 1-trans-iodo-4-methyl-3-triphenylmethoxy-1-octene | 7-(trimethylsiloxy)-2-cis,7-octadienyl]-4R-trimethylsilyloxy cyclopent-2-en-1-one | 17,17-dimethyl-5-cis-13-trans prostadiene |
| 264 | 1-trans-iodo-4,4-trimethylene-3-trimethylsilyloxy-1-heptene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16,16-trimethylene-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 265 | 1-trans-tri-n-butylstannyl-3-vinyl-3-trimethylsilyloxy-1-heptene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-15-vinyl-20-nor-5-cis-13-trans prostadiene |
| 266 | 1-trans-tri-n-butylstannyl-4-phenoxy-3-triethylsilyloxy-1-butene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16-phenoxy-17-20-tetranor-5-cis-13-trans prostadiene |
| 267 | 1-trans-tri-n-butylstannyl-4-(p-fluorophenoxy)-3-triethylsilyloxy-1-butene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16-(p-fluorophenoxy)-17-20-tetranor-5-cis-13-trans prostadiene |
| 268 | 1-trans-tri-n-butylstannyl-4-(m-chlorophenoxy)-3-triethylsilyloxy-1-butene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16-(m-chlorophenoxy)-17-20-tetranor-5-cis-13-trans prostadiene |
| 269 | 1-trans-tri-n-butylstannyl-4-(m-trifluoromethylphenoxy)-3-triethylsilyloxy-1-butene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16-(m-trifluoromethylphenoxy)-17-20-tetranor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 270 | 1-trans-iodo-5-phenyl-3-triethylsilyloxy-1-pentene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-17-phenyl-18-20-trinor-5-cis-13-trans prostadiene |
| 271 | 1-trans-iodo-4,4-dimethyl-5-phenyl-3-triethylsilyloxy-1-pentene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16,16-dimethyl-17-phenyl-18-20-trinor-5-cis-13-trans prostadiene |
| 272 | 1-trans-iodo-4-cyclopentyl-3-triphenylmethoxy-1-butene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16-cyclopentyl-17-20-tetranor-5-cis-13-trans prostadiene |
| 273 | 1-trans-iodo-4-cyclohexyl-3-triphenylmethoxy-1-butene | 2-[8-methoxy-8-methoxycarbonyl-7-(trimethylsiloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16-cyclohexyl-17-20-tetranor-5-cis-13-trans prostadiene |
| 274 | 1-trans-iodo-4-triphenylmethoxy-1-heptene | 2-[8-methoxy-8-methoxycarbonyl-7-(trimethylsiloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-20-nor-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 275 | 1-trans-tri-n-butylstannyl-4-methyl-4-trimethylsilyloxy-1-heptene | 2-[8-methoxy-8-methoxycarbonyl-7-(trimethylsiloxy)-2-cis,7-octadienyl] 9 4R-trimethylsilyloxy cyclopent-2-en-1-one | nat-11a,16-dihydroxy-1-(methoxymethoxycarbonylmethyl)-1,9-dioxo-16-methyl-20-nor-5-cis-13-trans prostadiene |
| 276 | 1-trans-tri-n-butylstannyl-4-ethyl-4-trimethylsilyloxy-1-octene | 2-[8-methoxy-8-methoxycarbonyl-7-(trimethylsiloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-ethyl-5-cis-13-trans prostadiene |
| 277 | 1-trans-tri-n-butylstannyl-5-methyl-4-trimethylsilyloxy-1-heptene | 2-[8-methoxy-8-methoxycarbonyl-7-(trimethylsiloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-17-methyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 278 | 1-trans-iodo-5,5-dimethyl 4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-17,17-dimethyl-5-cis-13-trans prostadiene |

| EXAMPLE | VINYL TIN | CYCLOPENTENONE | PRODUCT PROSTAGLANDIN OF THE PGE2 SERIES |
|---|---|---|---|
| 279 | 1-trans-tri-n-butylstannyl-4-vinyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-vinyl-20-nor-5-cis-13-trans prostadiene |
| 280 | 1-trans-tri-n-butylstannyl-4-cyclopropyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-cyclopropyl-5-cis-13-trans prostadiene |
| 281 | 1-trans-tri-n-butylstannyl-4-trimethylsilylethynyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-ethynyl-20-nor-5-cis-13-trans prostadiene |
| 282 | 1-trans-tri-n-butylstannyl-5-methylene 4-triethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-17-methylene-20-nor-5-cis-13-trans prostadiene |
| 283 | 1-trans-tri-n-butylstannyl-4-methyl-5-methylene 4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-methyl-17-methylene-20-nor-5-cis-13-trans prostadiene |
| 284 | 1-trans-tri-n-butylstannyl-4-dimethoxymethyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-formyl-20-nor-5-cis-13-trans prostadiene |
| 285 | 1-trans-tri-n-butylstannyl-4-fluoromethyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-fluoromethyl-20-nor-5-cis-13-trans prostadiene |
| 286 | 1-trans-tri-n-butylstannyl-4-difluoromethyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-difluoromethyl-20-nor-5-cis-13-trans prostadiene |
| 287 | 1-trans-tri-n-butylstannyl-4-trifluoromethyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-trifluoromethyl-20-nor-5-cis-13-trans prostadiene |
| 288 | 1-trans-tri-n-butylstannyl-4-chloromethyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-chloromethyl-20-nor-5-cis-13-trans prostadiene |
| 289 | 1-trans-tri-n-butylstannyl-4-trimethylsilyloxymethyl-4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE PGE2 SERIES |
|---|---|---|---|
| 290 | 1-trans-iodo-4-methyl-7-chloro 4-trimethylsilyloxy-1-heptene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-methyl-19-chloro-20-nor-5-cis-13-trans prostadiene |
| 291 | 1-trans-iodo-3-triphenylmethoxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,15a-dihydroxy-1-(methoxymethoxycarbonylmethyl)-1,9-dioxo-5-cis-13-trans prostadiene |
| 292 | 1-trans-iodo-3-methyl-3-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,15a-dihydroxy-1-(methoxymethoxycarbonylmethyl)-1,9-dioxo-15-methyl-5-cis-13-trans prostadiene |
| 293 | 1-trans-iodo-4,4-dimethyl 3-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,15a-dihydroxy-1-(methoxymethoxycarbonylmethyl)-1,9-dioxo-16,16-dimethyl-5-cis-13-trans prostadiene |

-continued

| EXAMPLE | VINYL TIN / VINYL IODIDE | CYCLOPENTENONE | PRODUCT PROSTAGLANDIN OF THE PGE2 SERIES |
|---|---|---|---|
| 294 | 1-trans-iodo-4,4-trimethylene 3-trimethylsilyloxy-1-octene | 2-[8-methoxy-8-methoxycarbonyl 7-(trimethylsiloxy)-2-cis,7-octadienyl]-4R-trimethylsiloxy cyclopent-2-en-1-one | nat-11a,15a,dihydroxy-1-(methoxymethoxycarbonylmethyl)-1,9-dioxo-16,16-trimethylene-5-cis-13-trans prostadiene |
| EXAMPLE | VINYL TIN | CYCLOPENTENONE | PRODUCT PROSTAGLANDIN OF THE PGE2 SERIES |
| 295 | 1-trans-tri-n-butylstannyl-3-vinyl-3-trimethylsilyloxy-1-octene | 2-[8-methoxycarbonyl-7-(trimethylsiloxy)-2-cis,7-octadienyl]-4R-trimethylsiloxy cyclopent-2-en-1-one | nat-11a,15a-dihydroxy-1-(methoxymethoxycarbonylmethyl)-1,9-dioxo-15-vinyl-5-cis-13-trans prostadiene |
| EXAMPLE | VINYL IODIDE | CYCLOPENTENONE | PRODUCT PROSTAGLANDIN OF THE PGE2 SERIES |
| 296 | 1-trans-iodo-4-triphenylmethoxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-5-cis-13-trans prostadiene |
| EXAMPLE | VINYL TIN | CYCLOPENTENONE | PRODUCT PROSTAGLANDIN OF THE PGE2 SERIES |
| 297 | 1-trans-tri-n-butylstannyl-4-methyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-methyl-5-cis-13-trans prostadiene |
| 298 | 1-trans-tri-n-butylstannyl-5-methyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-17-methyl-5-cis-13-trans prostadiene |
| 299 | 1-trans-tri-n-butylstannyl-4-vinyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-vinyl-5-cis-13-trans-prostadiene |
| 300 | 1-trans-tri-n-butylstannyl-4-trimethylsilylethynyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-ethynyl-5-cis-13-trans prostadiene |
| 301 | 1-trans-tri-n-butylstannyl-5-methylene 4-triethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-17-methylene-5-cis-13-trans prostadiene |
| 302 | 1-trans-tri-n-butylstannyl-4-methyl-5-methylene 4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-methyl-17-methylene-5-cis-13-trans prostadiene |
| 303 | 1-trans-tri-n-butylstannyl-4-dimethoxymethyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-formyl-5-cis-13-trans prostadiene |
| 304 | 1-trans-tri-n-butylstannyl-4-fluoromethyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-fluoromethyl-5-cis-13-trans prostadiene |
| 305 | 1-trans-tri-n-butylstannyl-4-difluoromethyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-difluoromethyl-5-cis-13-trans prostadiene |
| 306 | 1-trans-tri-n-butylstannyl-4-trifluoromethyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-trifluoromethyl-5-cis-13-trans prostadiene |
| 307 | 1-trans-tri-n-butylstannyl-4-chloromethyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-chloromethyl-5-cis-13-trans prostadiene |
| 308 | 1-trans-tri-n-butylstannyl-4-trimethylsilyloxymethyl-4-trimethylsilyloxy-1-octene | 2-[8-methoxy-8-methoxycarbonyl-7-(trimethylsiloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-hydroxymethyl-5-cis-13-trans prostadiene |
| EXAMPLE | VINYL IODIDE | CYCLOPENTENONE | PRODUCT PROSTAGLANDIN OF THE PGE2 SERIES |

| | -continued | | |
|---|---|---|---|
| 309 | 1-trans-iodo-3-triphenylmethoxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,15a-dihydroxy-1-(methoxymethoxycarbonylmethyl)-1,9-dioxo-20-methyl-5-cis-13-trans prostadiene |
| 310 | 1-trans-iodo-3-methyl-3-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,15a-dihydroxy-1-(methoxymethoxycarbonylmethyl)-1,9-dioxo-15-methyl-20-methyl-5-cis-13-trans prostadiene |
| 311 | 1-trans-iodo-4,4-dimethyl-3-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,15a-dihydroxy-1-(methoxymethoxycarbonylmethyl)-1,9-dioxo-16,16-dimethyl-20-methyl-5-cis-13-trans prostadiene |
| 312 | 1-trans-iodo-4,4-trimethylene-3-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,15a-dihydroxy-1-(methoxymethoxycarbonylmethyl)-1,9-dioxo-16,16-trimethylene-20-methyl-5-cis-13-trans prostadiene |
| EXAMPLE | VINYL TIN | CYCLOPENTENONE | PRODUCT PROSTAGLANDIN OF THE PGE2 SERIES |
| 313 | 1-trans-tri-n-butylstannyl-3-vinyl-3-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,15a-dihydroxy-1-(methoxymethoxycarbonylmethyl)-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 314 | 1-trans-iodo-4-triphenylmethoxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-20-methyl-5-cis-13-trans prostadiene |
| EXAMPLE | VINYL TIN | CYCLOPENTENONE | PRODUCT PROSTAGLANDIN OF THE PGE2 SERIES |
| 315 | 1-trans-tri-n-butylstannyl-4-methyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-methyl-20-methyl-5-cis-13-trans prostadiene |
| 316 | 1-trans-tri-n-butylstannyl-5-methyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-17-methyl-20-methyl-5-cis-13-trans prostadiene |
| 317 | 1-trans-tri-n-butylstannyl-4-vinyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-vinyl-20-methyl-5-cis-13-trans prostadiene |
| 318 | 1-trans-tri-n-butylstannyl-4-trimethylsilylethynyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-ethynyl-20-methyl-5-cis-13-trans prostadiene |
| 319 | 1-trans-tri-n-butylstannyl-5-methylene-4-triethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-17-methylene-20-methyl-5-cis-13-trans prostadiene |
| 320 | 1-trans-tri-n-butylstannyl-4-methyl-5-methylene-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-methyl-17-methylene-20-methyl-5-cis-13-trans prostadiene |
| 321 | 1-trans-tri-n-butylstannyl-4-dimethoxymethyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-formyl-20-methyl-5-cis-13-trans prostadiene |
| 322 | 1-trans-tri-n-butylstannyl-4-fluoromethyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-fluoromethyl-20-methyl-5-cis-13-trans prostadiene |
| 323 | 1-trans-tri-n-butylstannyl-4-difluoromethyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-difluoromethyl-20-methyl-5-cis-13-trans prostadiene |
| 324 | 1-trans-tri-n-butylstannyl-4-trifluoromethyl-4-trimethylsilyloxy-1-nonene | 2-[8-methoxy-8-methoxycarbonyl-7-(trimethylsilyloxy)-2-cis,7-octadienyl]-4R-trimethylsilyoxy cyclopent-2-en-1-one | nat-11a,16-dihydroxy-1-(methoxymethoxycarbonylmethyl)-1,9-dioxo-16-trifluoromethyl-20-methyl-5-cis-13-trans prostadiene |

| | | | |
|---|---|---|---|
| 325 | 1-trans-tri-n-butylstannyl-4-chloromethyl-4-trimethylsilyloxy-1-nonene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-chloromethyl-20-methyl-5-cis-13-trans prostadiene |
| 326 | 1-trans-tri-n-butylstannyl-4-trimethylsilyloxymethyl-4-trimethylsilyloxy-1-nonene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-hydroxymethyl-20-methyl-5-cis-13-trans prostadiene |
| EXAMPLE | VINYL IODIDE | CYCLOPENTENONE | PRODUCT PROSTAGLANDIN OF THE PGE2 SERIES |
| 327 | 1-trans-iodo-3-triphenylmethoxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-20-ethyl-5-cis-13-trans prostadiene |
| 328 | 1-trans-iodo-3-methyl-3-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-15-methyl-20-ethyl-5-cis-13-trans prostadiene |
| 329 | 1-trans-iodo-4,4-dimethyl-3-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16,16-dimethyl-20-ethyl-5-cis-13-trans prostadiene |
| 330 | 1-trans-iodo-4,4-trimethylene-3-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,15a-dihydroxy-1-(methoxymethoxycarbonylmethyl)-1,9-dioxo-16,16-trimethylene-20-ethyl-5-cis-13-trans prostadiene |
| EXAMPLE | VINYL TIN | CYCLOPENTENONE | PRODUCT PROSTAGLANDIN OF THE PGE2 SERIES |
| 331 | 1-trans-tri-n-butylstannyl-3-vinyl-3-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,15a,dihydroxy-1-(methoxymethoxycarbonylmethyl)-1,9-dioxo-15-vinyl-20-ethyl-5-cis-13-trans prostadiene |
| EXAMPLE | VINYL IODIDE | CYCLOPENTENONE | PRODUCT PROSTAGLANDIN OF THE PGE2 SERIES |
| 332 | 1-trans-iodo-4-triphenylmethoxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-20-ethyl-5-cis-13-trans prostadiene |
| EXAMPLE | VINYL TIN | CYCLOPENTENONE | PRODUCT PROSTAGLANDIN OF THE PGE2 SERIES |
| 333 | 1-trans-tri-n-butylstannyl-4-methyl-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-methyl-20-ethyl-5-cis-13-trans prostadiene |
| 334 | 1-trans-tri-n-butylstannyl-5-methyl-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-17-methyl-20-ethyl-5-cis-13-trans prostadiene |
| 335 | 1-trans-tri-n-butylstannyl-4-vinyl-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-vinyl-20-ethyl-5-cis-13-trans prostadiene |
| 336 | 1-trans-tri-n-butylstannyl-4-trimethylsilylethynyl-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-ethyl-20-ethyl-5-cis-13-trans prostadiene |
| 337 | 1-trans-tri-n-butylstannyl-5-methylene-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-17-methylene-20-ethyl-5-cis-13-trans prostadiene |
| 338 | 1-trans-tri-n-butylstannyl-4-methyl-5-methylene-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-17-methylene-20-ethyl-5-cis-13-trans prostadiene |
| 339 | 1-trans-tri-n-butylstannyl-4-dimethoxymethyl-4-trimethylsilyloxy-1-decene | 2-[8-methoxy-8-methoxycarbonyl-7-(trimethylsilyloxy)-2-cis,7-octadienyl]-4R-trimethylsilyloxy cyclopent-2-en-1-one | nat-11a,16-dihydroxy-1-(methoxymethoxycarbonylmethyl)-1,9-dioxo-16-formyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 340 | 1-trans-tri-n-butylstannyl-4-fluoromethyl-4-trimethylsilyloxy-1-decene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-fluoromethyl-20-ethyl-5-cis-13-trans prostadiene |
| 341 | 1-trans-tri-n-butylstannyl-4-difluoromethyl-4-trimethylsilyloxy-1-decene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-difluoromethyl-20-ethyl-5-cis-13-trans prostadiene |
| 342 | 1-trans-tri-n-butylstannyl-4-trifluoromethyl-4-trimethylsilyloxy-1-decene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-trifluoromethyl-20-ethyl-5-cis-13-trans prostadiene |
| 343 | 1-trans-tri-n-butylstannyl-4-chloromethyl-4-trimethylsilyloxy-1-decene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-chloromethyl-20-ethyl-5-cis-13-trans prostadiene |
| 344 | 1-trans-tri-n-butylstannyl-4-trimethylsilyloxymethyl-4-trimethylsilyloxy-1-decene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 345 | 1-trans-iodo-3-triphenylmethoxy-1-heptene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-20-nor-2-nor-5-cis-13-trans prostadiene |
| 346 | 1-trans-iodo-3-methyl-3-trimethylsilyloxy-1-heptene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-15-methyl-20-nor-2-nor-5-cis-13-trans prostadiene |
| 347 | 1-trans-iodo-4,4-dimethyl-3-trimethylsilyloxy-1-heptene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16,16-dimethyl-20-nor-2-nor-5-cis-13-trans prostadiene |
| 348 | 1-trans-iodo-5,5-dimethyl-3-triphenylmethoxy-1-octene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-17,17-dimethyl-2-nor-5-cis-13-trans prostadiene |
| 349 | 1-trans-iodo-4-methyl-3-triphenylmethoxy-1-octene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16-methyl-2-nor-5-cis-13-trans prostadiene |
| 350 | 1-trans-iodo-4,4-trimethylene-3-trimethylsilyloxy-1-heptene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16,16-trimethylene-20-nor-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 351 | 1-trans-tri-n-butylstannyl-3-vinyl-3-trimethylsilyloxy-1-heptene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-15-vinyl-20-nor-2-nor-5-cis-13-trans prostadiene |
| 352 | 1-trans-tri-n-butylstannyl-4-phenoxy-3-trimethylsilyloxy-1-butene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16-phenoxy-2-nor-17-20-tetranor-5-cis-13-trans prostadiene |
| 353 | 1-trans-tri-n-butylstannyl-4-(p-fluorophenoxy)-3-trimethylsilyloxy-1-butene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16-(p-fluorophenoxy)-2-nor-17-20-tetranor-5-cis-13-trans prostadiene |
| 354 | 1-trans-tri-n-butylstannyl-4-(m-chlorophenoxy)-3-triethylsilyloxy-1-butene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16-(m-chlorophenoxy)-2-nor-17-20-tetranor-5-cis-13-trans prostadiene |
| 355 | 1-trans-tri-n-butylstannyl-4-(m-trifluoromethylphenoxy)-3-triethylsilyloxy-1-butene | 2-[7-methoxy-7-methoxycarbonyl-6-(trimethylsilyloxy)-2-cis,6-heptadienyl] cyclopent-2-en-1-one | dl-15a-hydroxy-1-(methoxymethoxycarbonylmethyl)-1,9-dioxo-16-(m-trifluoromethylphenoxy)-2-nor-17-20-tetranor-5-cis-13-trans prostadiene |

-continued

| EXAMPLE | VINYL IODIDE | CYCLOPENTENONE | PRODUCT PROSTAGLANDIN OF THE 11-DEOXY PGE2 SERIES |
|---|---|---|---|
| 356 | 1-trans-iodo-5-phenyl 3-triethylsilyloxy-1-pentene | 2-[7-methoxy-7-methoxycarbonyl-6-(trimethylsilyloxy)-2-cis,6-heptadienyl]cyclopent-2-en-1-one | dl-15a-hydroxy-1-(methoxymethoxycarbonylmethyl)-1,9-dioxo-17-phenyl-2-nor-18-20-trinor-5-cis-13-trans prostadiene |
| 357 | 1-trans-iodo-4,4-dimethyl-5-phenyl 3-triethylsilyloxy-1-pentene | 2-[7-methoxy-7-methoxycarbonyl-6-(trimethylsilyloxy)-2-cis,6-heptadienyl]cyclopent-2-en-1-one | dl-15a-hydroxy-1-(methoxymethoxycarbonylmethyl)-1,9-dioxo-16,16-dimethyl-17-phenyl-2-nor-18-20-trinor-5-cis-13-trans prostadiene |
| 358 | 1-trans-iodo-4-cyclopentyl 3-triphenylmethoxy-1-butene | 2-[7-methoxy-7-methoxycarbonyl-6-(trimethylsilyloxy)-2-cis,6-heptadienyl]cyclopent-2-en-1-one | dl-15a-hydroxy-1-(methoxymethoxycarbonylmethyl)-1,9-dioxo-16-cyclopentyl-2-nor-17-20-tetranor-5-cis-13-trans prostadiene |
| 359 | 1-trans-iodo-4-cyclohexyl 3-triphenylmethoxy-1-butene | 2-[7-methoxy-7-methoxycarbonyl-6-(trimethylsilyloxy)-2-cis,6-heptadienyl]cyclopent-2-en-1-one | dl-15a-hydroxy-1-(methoxymethoxycarbonylmethyl)-1,9-dioxo-16-cyclohexyl-2-nor-17-20-tetranor-5-cis-13-trans prostadiene |
| 360 | 1-trans-iodo-4-triphenylmethoxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-20-nor-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 361 | 1-trans-tri-n-butylstannyl-4-methyl-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-methyl-20-nor-2-nor-5-cis-13-trans prostadiene |
| 362 | 1-trans-tri-n-butylstannyl-4-ethyl-4-trimethylsilyloxy-1-octene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-ethyl-2-nor-5-cis-13-trans prostadiene |
| 363 | 1-trans-tri-n-butylstannyl-5-methyl-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-17-methyl-20-nor-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 364 | 1-trans-iodo-5,5-dimethyl 4-trimethylsilyloxy-1-octene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-17,17-dimethyl-2-nor-5-cis-13-trans prostadiene |

| EXAMPLE | VINYL TIN | CYCLOPENTENONE | PROUCT PROSTAGLANDIN OF THE 11-DEOXY PGE2 SERIES |
|---|---|---|---|
| 365 | 1-trans-tri-n-butylstannyl-4-vinyl-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-vinyl-20-nor-2-nor-5-cis-13-trans prostadiene |
| 366 | 1-trans-tri-n-butylstannyl-4-cyclopropyl-4-trimethylsilyloxy-1-octene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-cyclopropyl-2-nor-5-cis-13-trans prostadiene |
| 367 | 1-trans-tri-n-butylstannyl-4-trimethylsilylethynyl-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-ethynyl-20-nor-2-nor-5-cis-13-trans prostadiene |
| 368 | 1-trans-tri-n-butylstannyl-5-methylene-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-17-methylene-20-nor-2-nor-5-cis-13-trans prostadiene |
| 369 | 1-trans-tri-n-butylstannyl-4-methyl-5-methylene-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-methyl-17-methylene-20-nor-2-nor-5-cis-13-trans prostadiene |
| 370 | 1-trans-tri-n-butylstannyl-4-dimethoxymethyl-4-trimethylsilyloxy-1-heptene | 2-[7-methoxy-7-methoxycarbonyl-6-(trimethylsilyloxy)-2-cis,6-heptadienyl]cyclopent-2-en-1-one | dl-16-hydroxy-1-(methoxymethoxycarbonylmethyl)-1,9-dioxo-16-formyl-20-nor-2-nor-5-cis-13-trans prostadiene |
| 371 | 1-trans-tri-n-butylstannyl-4-fluoromethyl- | 2-[7-methoxy-7-methoxycarbonyl- | dl-16-hydroxy-1-(methoxymethoxycarbonylmethyl)-1,9-dioxo-16-fluoromethyl- |

|  |  | -continued |  |
|---|---|---|---|
| | | 4-trimethylsilyloxy-1-heptene | 6-(trimethylsiloxy)-2-cis,6-heptadienyl]cyclopent-2-en-1-one | 20-nor-2-nor-5-cis-13-trans prostadiene |
| 372 | | 1-trans-tri-n-butylstannyl-4-difluoromethyl-4-trimethylsilyloxy-1-heptene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-16-difluoromethyl-20-nor-2-nor-5-cis-13-trans prostadiene |
| 373 | | 1-trans-tri-n-butylstannyl-4-trifluoromethyl-4-trimethylsilyloxy-1-heptene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-16-trifluoromethyl-20-nor-2-nor-5-cis-13-trans prostadiene |
| 374 | | 1-trans-tri-n-butylstannyl-4-chloromethyl-4-trimethylsilyloxy-1-heptene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-16-chloromethyl-20-nor-2-nor-5-cis-13-trans prostadiene |
| 375 | | 1-trans-tri-n-butylstannyl-4-trimethylsilyloxymethyl-4-trimethylsilyloxy-1-heptene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-16-hydroxymethyl-20-nor-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 376 | | 1-trans-iodo-4-methyl-7-chloro-4-trimethylsilyloxy-1-heptene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-19-chloro-2-nor-20-nor-5-cis-13-trans prostadiene |
| 377 | | 1-trans-iodo-3-triphenylmethoxy-1-octene | 2-[7-methoxy-7-methoxycarbonyl-6-(trimethylsiloxy)-2-cis,6-heptadienyl]cyclopent-2-en-1-one | dl-15a-hydroxy-1-(methoxymethoxycarbonylmethyl)-1,9-dioxo-2-nor-5-cis-13-trans prostadiene |
| 378 | | 1-trans-iodo-3-methyl-3-trimethylsilyloxy-1-octene | 2-[7-methoxy-7-methoxycarbonyl-6-(trimethylsiloxy)-2-cis,6-heptadienyl]cyclopent-2-en-1-one | dl-15a-hydroxy-1-(methoxymethoxycarbonylmethyl)-1,9-dioxo-15-methyl-2-nor-5-cis-13-trans prostadiene |
| 379 | | 1-trans-iodo-4,4-dimethyl-3-trimethylsilyloxy-1-octene | 2-[7-methoxy-7-methoxycarbonyl-6-(trimethylsiloxy)-2-cis,6-heptadienyl]cyclopent-2-en-1-one | dl-15a-hydroxy-1-(methoxymethoxycarbonylmethyl)-1,9-dioxo-16,16-dimethyl-2-nor-5-cis-13-trans prostadiene |
| 380 | | 1-trans-iodo-4,4,4-trimethylene-3-trimethylsilyloxy-1-octene | 2-[7-methoxy-7-methoxycarbonyl-6-(trimethylsiloxy)-2-cis,6-heptadienyl]cyclopent-2-en-1-one | dl-15a-hydroxy-1-(methoxymethoxycarbonylmethyl)-1,9-dioxo-16,16-trimethylene-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 381 | | 1-trans-tri-n-butylstannyl-3-vinyl-3-trimethylsilyloxy-1-octene | 2-[7-methoxy-7-methoxycaronyl-6-(trimethylsiloxy)-2-cis,6-heptadienyl]cyclopent-2-en-1-one | dl-15a-hydroxy-1-(methoxymethoxycarbonylmethyl)-1,9-dioxo-15-vinyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 382 | | 1-trans-iodo-4-triphenylmethoxy-1-octene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 383 | | 1-trans-tri-n-butylstannyl-4-methyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-2-nor-5-cis-13-trans prostadiene |
| 384 | | 1-trans-tri-n-butylstannyl-5-methyl-4-trimethylsilyloxy-1-octene | 2-[7-methoxy-7-methoxycaronyl-6-(trimethylsiloxy)-2-cis,6-heptadienyl]cyclopent-2-en-1-one | dl-16-hydroxy-1-(methoxymethoxycarbonylmethyl)-1,9-dioxo-17-methyl-2-nor-5-cis-13-trans prostadiene |
| 385 | | 1-trans-tri-n-butylstannyl-4-vinyl-4-trimethylsilyloxy-1-octene | 2-[7-methoxy-7-methoxycarbonyl-6-(trimethylsiloxy)-2-cis,6-heptadienyl]cyclopent-2-en-1-one | dl-16-hydroxy-1-(methoxymethoxycarbonylmethyl)-1,9-dioxo-16-vinyl-2-nor-5-cis-13-trans prostadiene |

-continued

| EXAMPLE | | | |
|---|---|---|---|
| 386 | 1-trans-tri-n-butylstannyl-4-trimethylsilylethynyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-ethynyl-2-nor-5-cis-13-trans prostadiene |
| 387 | 1-trans-tri-n-butylstannyl-5-methylene-4-triethylsilyloxy-1-octene | 2-[7-methoxy-7-methoxycaronyl-6-(trimethylsiloxy)-2-cis,6-heptadienyl]cyclopent-2-en-1-one | dl-16-hydroxy-1-(methoxymethoxycarbonylmethyl)-1,9-dioxo-17-methylene-2-nor-5-cis-13-trans prostadiene |
| 388 | 1-trans-tri-n-butylstannyl-4-methyl-5-methylene-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-17-methylene-2-nor-5-cis-13-trans prostadiene |
| 389 | 1-trans-tri-n-butylstannyl-4-dimethoxymethyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-formyl-2-nor-5-cis-13-trans prostadiene |
| 390 | 1-trans-tri-n-butylstannyl-4-fluoromethyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-fluoromethyl-2-nor-5-cis-13-trans prostadiene |
| 391 | 1-trans-tri-n-butylstannyl-4-difluoromethyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-difluoromethyl-2-nor-5-cis-13-trans prostadiene |
| 392 | 1-trans-tri-n-butylstannyl-4-trifluoromethyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-trifluoromethyl-2-nor-5-cis-13-trans prostadiene |
| 393 | 1-trans-tri-n-butylstannyl-4-chloromethyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-chloromethyl-2-nor-5-cis-13-trans prostadiene |
| 394 | 1-trans-tri-n-butylstannyl-4-trimethylsilyloxymethyl-4-trimethylsilyloxy-1-octene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-hydroxymethyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 395 | 1-trans-iodo-3-triphenylmethoxy-1-nonene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-20-methyl-2-nor-5-cis-13-trans prostadiene |
| 396 | 1-trans-iodo-3-methyl-3-trimethylsilyloxy-1-nonene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-20-methyl-2-nor-5-cis-13-trans prostadiene |
| 397 | 1-trans-iodo-4,4-dimethyl-3-trimethylsilyloxy-1-nonene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-16,16-dimethyl-20-methyl-2-nor-5-cis-13-trans prostadiene |
| 398 | 1-trans-iodo-4,4-trimethylene-3-trimethylsilyloxy-1-nonene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-16,16-trimethylene-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 399 | 1-trans-tri-n-butylstannyl-3-vinyl-3-trimethylsilyloxy-1-nonene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-15-vinyl-20-methyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 400 | 1-trans-iodo-4-triphenylmethoxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-20-methyl-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |

| EXAMPLE | VINYL IODIDE | -continued | PRODUCT PROSTAGLANDIN OF THE 11-PGE2 SERIES |
|---|---|---|---|
| 401 | 1-trans-tri-n-butylstannyl-4-methyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-20-methyl-2-nor-5-cis-13-trans prostadiene |
| 402 | 1-trans-tri-n-butylstannyl-5-methyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-17-methyl-20-methyl-2-nor-5-cis-13-trans prostadiene |
| 403 | 1-trans-tri-n-butylstannyl-4-vinyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-vinyl-20-methyl-2-nor-5-cis-13-trans prostadiene |
| 404 | 1-trans-tri-n-butylstannyl-4-trimethylsilylethynyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-ethynyl-20-methyl-2-nor-5-cis-13-trans prostadiene |
| 405 | 1-trans-tri-n-butylstannyl-5-methylene-4-triethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-17-methylene-20-methyl-2-nor-5-cis-13-trans prostadiene |
| 406 | 1-trans-tri-n-butylstannyl-4-methyl-5-methylene-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-17-methylene-20-methyl-2-nor-5-cis-13-trans prostadiene |
| 407 | 1-trans-tri-n-butylstannyl-4-dimethoxymethyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-formyl-20-methyl-2-nor-5-cis-13-trans prostadiene |
| 408 | 1-trans-tri-n-butylstannyl-4-fluoromethyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-fluoromethyl-20-methyl-2-nor-5-cis-13-trans prostadiene |
| 409 | 1-trans-tri-n-butylstannyl-4-difluoromethyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-difluoromethyl-20-methyl-2-nor-5-cis-13-trans prostadiene |
| 410 | 1-trans-tri-n-butylstannyl-4-trifluoromethyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-trifluoromethyl-20-methyl-2-nor-5-cis-13-trans prostadiene |
| 411 | 1-trans-tri-n-butylstannyl-4-chloromethyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-chloromethyl-20-methyl-2-nor-5-cis-13-trans prostadiene |
| 412 | 1-trans-tri-n-butylstannyl-4-trimethylsilyloxymethyl-4-trimethylsilyloxy-1-nonene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-hydroxymethyl-20-methyl-2-nor-5-cis-13-trans prostadiene |

| EXAMPLE | VINYL IODIDE | CYCLOPENTENONE | PRODUCT PROSTAGLANDIN OF THE 11-PGE2 SERIES |
|---|---|---|---|
| 413 | 1-trans-3-triphenylmethoxy-1-decene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-20-ethyl-2-nor-5-cis-13-trans prostadiene |
| 414 | 1-trans-iodo-3-methyl-3-trimethylsilyloxy-1-decene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-15-methyl-20-ethyl-2-nor-5-cis-13-trans prostadiene |
| 415 | 1-trans-iodo-4,4-dimethyl-3-trimethylsilyloxy-1-decene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-16,16-dimethyl-20-ethyl-2-nor-5-cis-13-trans prostadiene |
| 416 | 1-trans-iodo-4,4-trimethylene-3-trimethylsilyloxy-1-decene | 2-[7-methoxy-7-methoxycabonyl-6-(trimethylsiloxy)-2-cis,6-heptadienyl]cyclopent-2-en-1-one | dl-15a-hydroxy-1-(methoxymethoxycarbonylmethyl)-1,9-dioxo-16,16-trimethylene-20-ethyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 417 | 1-trans-tri-n-butylstannyl-3-vinyl- | 2-[7-methoxy-7-methoxycabonyl- | dl-15a-hydroxy-1-(methoxymethoxycarbonylmethyl)-1,9-dioxo-15-vinyl- |

| EXAMPLE | VINYL IODIDE | CYCLOPENTENONE | PRODUCT PROSTAGLANDIN OF THE 11-DEOXY PGE2 SERIES |
|---|---|---|---|
| 418 | 1-trans-iodo-4-triphenylmethoxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-20-ethyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 419 | 1-trans-tri-n-butylstannyl-4-methyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-20-ethyl-2-nor-5-cis-13-trans prostadiene |
| 420 | 1-trans-tri-n-butylstannyl-5-methyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-17-methyl-20-ethyl-2-nor-5-cis-13-trans prostadiene |
| 421 | 1-trans-tri-n-butylstannyl-4-vinyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-vinyl-20-ethyl-2-nor-5-cis-13-trans prostadiene |
| 422 | 1-trans-tri-n-butylstannyl-4-trimethylsilylethynyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-ethynyl-20-ethyl-2-nor-5-cis-13-trans prostadiene |
| 423 | 1-trans-tri-n-butylstannyl-5-methylene-4-triethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-17-methylene-20-ethyl-2-nor-5-cis-13-trans prostadiene |
| 424 | 1-trans-tri-n-butylstannyl-4-methyl-5-methylene-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-methyl-17-methylene-20-ethyl-2-nor-5-cis-13-trans prostadiene |
| 425 | 1-trans-tri-n-butylstannyl-4-dimethoxymethyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-formyl-20-ethyl-2-nor-5-cis-13-trans prostadiene |
| 426 | 1-trans-tri-n-butylstannyl-4-fluoromethyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-fluoromethyl-20-ethyl-2-nor-5-cis-13-trans prostadiene |
| 427 | 1-trans-tri-n-butylstannyl-4-difluoromethyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-difluoromethyl-20-ethyl-2-nor-5-cis-13-trans prostadiene |
| 428 | 1-trans-tri-n-butylstannyl-4-trifluoromethyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-trifluoromethyl-20-ethyl-2-nor-5-cis-13-trans prostadiene |
| 429 | 1-trans-tri-n-butylstannyl-4-chloromethyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-chloromethyl-20-ethyl-2-nor-5-cis-13-trans prostadiene |
| 430 | 1-trans-tri-n-butylstannyl-4-trimethylsilyloxymethyl-4-trimethylsilyloxy-1-decene | 2-[7-methoxy-7-methoxycabonyl-6-(trimethylsiloxy)-2-cis,6-heptadienyl]cyclopent-2-en-1-one | dl-16-hydroxy-1-(methoxymethoxycarbonylmethyl)-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 431 | 1-trans-iodo-3-triphenylmethoxy-1-heptene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-20-nor-5-cis-13-trans prostadiene |
| 432 | 1-trans-iodo-3-methyl-3-trimethylsilyloxy-1-heptene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-15-methyl-20-nor-5-cis-13-trans prostadiene |

| | -continued | | |
|---|---|---|---|
| 433 | 1-trans-iodo-4,4-dimethyl 3-trimethylsilyloxy-1-heptene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16,16-dimethyl-20-nor-5-cis-13-trans prostadiene |
| 434 | 1-trans-iodo-5,5-dimethyl 3-triphenylmethoxy-1-octene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-17,17-dimethyl-5-cis-13-trans prostadiene |
| 435 | 1-trans-iodo-4-methyl 3-triphenylmethoxy-1-octene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16-methyl-5-cis-13-trans prostadiene |
| 436 | 1-trans-iodo-4,4-trimethylene 3-trimethylsilyloxy-1-heptene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16,16-trimethylene-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 437 | 1-trans-tri-n-butylstannyl-3-vinyl-3-trimethylsilyloxy-1-heptene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-15-vinyl-20-nor-5-cis-13-trans prostadiene |
| 438 | 1-trans-tri-n-butylstannyl-4-phenoxy 3-triethylsilyloxy-1-butene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16-phenoxy-17-20-tetranor-5-cis-13-trans prostadiene |
| 439 | 1-trans-tri-n-butylstannyl-4-(p-fluorophenoxy) 3-triethylsilyloxy-1-butene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16-(p-fluorophenoxy)-17-20-tetranor-5-cis-13-trans prostadiene |
| 440 | 1-trans-tri-n-butylstannyl-4-(m-chlorophenoxy) 3-triethylsilyloxy-1-butene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16-(m-chlorophenoxy)-17-20-tetranor-5-cis-13-trans prostadiene |
| 441 | 1-trans-tri-n-butylstannyl-4-(m-trifluoromethylphenoxy) 3-triethylsilyloxy-1-butene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16-(m-trifluoromethylphenoxy)-17-20-tetranor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 442 | 1-trans-iodo-5-phenyl 3-triethylsilyloxy-1-pentene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-17-phenyl-18-20-trinor-5-cis-13-trans prostadiene |
| 443 | 1-trans-iodo-4,4-dimethyl-5-phenyl 3-triethylsilyloxy-1-pentene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16,16-dimethyl-17-phenyl-18-20-trinor-5-cis-13-trans prostadiene |
| 444 | 1-trans-iodo-4-cyclopentyl 3-triphenylmethoxy-1-butene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16-cyclopentyl-17-20-tetranor-5-cis-13-trans prostadiene |
| 445 | 1-trans-iodo-4-cyclohexyl 3-triphenylmethoxy-1-butene | 2-[8-methoxy-8-methoxycarbonyl-7-(trimethylsiloxy)-2-cis,7-octadienyl] cyclopent-1-en-1-one | dl-15a-hydroxy-1-(methoxymethoxycarbonylmethyl)-1,9-dioxo-16-cyclohexyl-17-20-tetranor-5-cis-13-trans prostadiene |
| 446 | 1-trans-iodo-4-triphenylmethoxy-1-heptene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-20-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 447 | 1-trans-tri-n-butylstannyl-4-methyl-4-trimethylsilyloxy-1-heptene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-methyl-20-nor-5-cis-13-trans prostadiene |
| 448 | 1-trans-tri-n-butylstannyl-4-ethyl-4-trimethylsilyloxy-1-octene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-ethyl-5-cis-13-trans prostadiene |

| EXAMPLE | VINYL IODIDE | -continued | PRODUCT PROSTAGLANDIN OF THE 11-DEOXY PGE2 SERIES |
|---|---|---|---|
| 449 | 1-trans-tri-n-butylstannyl-5-methyl-4-trimethylsilyloxy-1-heptene | cyclopent-2-en-1-one 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-17-methyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 450 | 1-trans-iodo-5,5-dimethyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-17,17-dimethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 451 | 1-trans-tri-n-butylstannyl-4-vinyl-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-vinyl-20-nor-5-cis-13-trans prostadiene |
| 452 | 1-1-trans-tri-n-butylstannyl-4-cyclopropyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-cyclopropyl-5-cis-13-trans prostadiene |
| 453 | 1-trans-tri-n-butylstannyl-4-trimethylsilylethynyl-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-ethynyl-20-nor-5-cis-13-trans prostadiene |
| 454 | 1-trans-tri-n-butylstannyl-5-methylene-4-triethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-17-methylene-20-nor-5-cis-13-trans prostadiene |
| 455 | 1-trans-tri-n-butylstannyl-4-methyl-5-methylene-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-methyl-17-methylene-20-nor-5-cis-13-trans prostadiene |
| 456 | 1-trans-tri-n-butylstannyl-4-dimethoxymethyl-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-formyl-20-nor-5-cis-13-trans prostadiene |
| 457 | 1-trans-tri-n-butylstannyl-4-fluoromethyl-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-fluoromethyl-20-nor-5-cis-13-trans prostadiene |
| 458 | 1-trans-tri-n-butylstannyl-4-difluoromethyl-4-trimethylsilyloxy-1-heptene | 2[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-difluoromethyl-20-nor-5-cis-13-trans prostadiene |
| 459 | 1-trans-tri-n-butylstannyl-4-trifluoromethyl-4-trimethylsilyloxy-1-heptene | 2[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-trifluoromethyl-20-nor-5-cis-13-trans prostadiene |
| 460 | 1-trans-tri-n-butylstannyl-4-chloromethyl-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-chloromethyl-20-nor-5-cis-13-trans prostadiene |
| 461 | 1-trans-tri-n-butylstannyl-4-trimethylsilyloxymethyl-4-trimethylsilyloxy-1-heptene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 462 | 1-trans-iodo-4-methyl-7-chloro-4-trimethylsilyloxy-1-heptene | 2-[8-methoxy-8-methoxycarbonyl-7-(trimethylsilyloxy)-2-cis,7-octadienyl] cyclopent-2-en-1-one | dl-16a-hydroxy-1-(methoxymethoxycarbonylmethyl)-1,9-dioxo-19-chloro-20-nor-5-cis-13-trans prostadiene |
| 463 | 1-trans-iodo-3-triphenylmethoxy-1-octene | 2[8-methoxy-8-methoxycarbonyl-7-(trimethylsilyloxy)-2-cis,7-octadienyl] cyclopent-2-en-1-one | dl-15a-hydroxy-1-(methoxymethoxycarbonylmethyl)-1,9-dioxo-5-cis-13-trans prostadiene |
| 464 | 1-trans-iodo-3-methyl- | 2-[8-methoxy-8-methoxycarbonyl- | dl-15a-hydroxy-1-(methoxymethoxycarbonylmethyl)-1,9-dioxo-15-methyl- |

| EXAMPLE | VINYL TIN / VINYL IODIDE | CYCLOPENTENONE | PRODUCT PROSTAGLANDIN |
|---|---|---|---|
| 465 | 3-trimethylsilyloxy-1-octene | 7-(trimethylsilyloxy)-2-cis,7-octadienyl] cyclopent-2-en-1-one | 5-cis-13-trans prostadiene |
| | 1-trans-iodo-4,4-dimethyl 3-trimethylsilyloxy-1-octene | 2-[8-methoxy-8-methoxycarbonyl-7-(trimethylsilyloxy)-2-cis,7-octadienyl] cyclopent-2-en-1-one | dl-15a-hydroxy-1-(methoxymethoxycarbonylmethyl)-1,9-dioxo-16,16-dimethyl-5-cis-13-trans prostadiene |
| 466 | 1-trans-iodo-4,4-trimethylene 3-trimethylsilyloxy-1-octene | 2-[8-methoxy-8-methoxycarbonyl-7-(trimethylsilyloxy)-2-cis,7-octadienyl] cyclopent-2-en-1-one | dl-15a-hydroxy-1-(methoxymethoxycarbonylmethyl)-1,9-dioxo-16,16-trimethylene-5-cis-13-trans prostadiene |
| EXAMPLE | VINYL TIN | CYCLOPENTENONE | PRODUCT PROSTAGLANDIN OF THE 11-DEOXY PGE2 SSERIES |
| 467 | 1-trans-tri-n-butylstannyl-3-vinyl-3-trimethylsilyloxy-1-octene | 2-[8-methoxy-8-methoxycarbonyl-7-(trimethylsilyloxy)-2-cis,7-octadienyl] cyclopent-2-en-1-one | dl-15a-hydroxy-1-(methoxymethoxycarbonylmethyl)-1,9-dioxo-15-vinyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 468 | 1-trans-iodo-4-triphenylmethoxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-5-cis-13-trans prostadiene |
| EXAMPLE | VINYL TIN | CYCLOPENTENONE | PRODUCT PROSTAGLANDIN OF THE 11-DEOXY PGE2 SERIES |
| 469 | 1-trans-tri-n-butylstannyl-4-methyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-methyl-5-cis-13-trans prostadiene |
| 470 | 1-trans-tri-n-butylstannyl-5-methyl 4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-17-methyl-5-cis-13-trans prostadiene |
| 471 | 1-trans-tri-n-butylstannyl-4-vinyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-vinyl-5-cis-13-trans prostadiene |
| 472 | 1-trans-tri-n-butylstannyl-4-trimethylsilylethynyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-ethynyl-5-cis-13-trans prostadiene |
| 473 | 1-trans-tri-n-butylstannyl-5-methylene 4-triethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-17-methylene-5-cis-13-trans prostadiene |
| 474 | 1-trans-tri-n-butylstannyl-4-methyl-5-methylene 4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-methyl-17-methylene-5-cis-13-trans prostadiene |
| 475 | 1-trans-tri-n-butylstannyl-4-dimethoxymethyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-formyl-5-cis-13-trans prostadiene |
| 476 | 1-trans-tri-n-butylstannyl-4-fluoromethyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-fluoromethyl-5-cis-13-trans prostadiene |
| 477 | 1-trans-tri-n-butylstannyl-4-difluoromethyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-difluoromethyl-5 cis-13-trans prostadiene |
| 478 | 1-trans-tri-n-butylstannyl-4-trifluoromethmethyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-trifluoromethyl-5-cis-13-trans prostadiene |
| 479 | 1-trans-tri-n-butylstannyl-4-chloromethyl-4-trimethylsilyloxy-1-octene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-chloromethyl-5-cis-13-trans prostadiene |

| EXAMPLE | VINYLIODIDE / VINYL TIN / VINYL IODIDE | CYCLOPENTENONE | PRODUCT PROSTAGLANDIN OF THE 11-DEOXY PGE2 SERIES |
|---|---|---|---|
| 480 | 1-trans-tri-n-butylstannyl-4-trimethylsilyloxymethyl-4-trimethylsilyloxy-1-octene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-hydroxymethyl-5-cis-13-trans prostadiene |
| EXAMPLE | VINYLIODIDE | CYCLOPENTENONE | PRODUCT PROSTAGLANDIN OF THE 11-DEOXY PGE2 SERIES |
| 481 | 1-trans-iodo-3-triphenylmethoxy-1-nonene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-20-methyl-5-cis-13-trans prostadiene |
| 482 | 1-trans-iodo-3-methyl-3-trimethylsilyloxy-1-nonene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-15-methyl-20-methyl-5-cis-13-trans prostadiene |
| 483 | 1-trans-iodo-4,4-dimethyl-3-trimethylsilyloxy-1-nonene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16,16-dimethyl-20-methyl-5-cis-13-trans prostadiene |
| 484 | 1-trans-iodo-4,4-trimethylene-3-trimethylsilyloxy-1-nonene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-16,16-trimethylene-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 485 | 1-trans-tri-n-butylstannyl-3-vinyl-3-trimethylsilyloxy-1-nonene | 2-[8-methoxy-8-methoxycarbonyl-7-(trimethylsiloxy)-2-cis,7-octadienyl] cyclopent-2-en-1-one | dl-15a-hydroxy-1-(methoxymethoxycarbonylmethyl)-1,9-dioxo-15-vinyl-20-methyl-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 486 | 1-trans-iodo-4-triphenylmethoxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-20-methyl-5-cis-13-trans prostadiene |
| EXAMPLE | VINYL TIN | CYCLOPENTENONE | PRODUCT PROSTAGLANDIN OF THE 11-DEOXY PGE2 SERIES |
| 487 | 1-trans-tri-n-butylstannyl-4-methyl-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-methyl-20-methyl-5-cis-13-trans prostadiene |
| 488 | 1-trans-tri-n-butylstannyl-5-methyl-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-17-methyl-20-methyl-5-cis-13-trans prostadiene |
| 489 | 1-trans-tri-n-butylstannyl-4-vinyl-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-vinyl-20-methyl-5-cis-13-trans prostadiene |
| 490 | 1-trans-tri-n-butylstannyl-4-trimethylsilylethynyl-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-ethynyl-20-methyl-5-cis-13-trans prostadiene |
| 491 | 1-trans-tri-n-butylstannyl-5-methylene-4-triethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-17-methylene-20-methyl-5-cis-13-trans prostadiene |
| 492 | 1-trans-tri-n-butylstannyl-4-methyl-5-methylene-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-methyl-17-methylene-20-methyl-5-cis-13-trans prostadiene |
| 493 | 1-trans-tri-n-butylstannyl-4-dimethoxymethyl-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-formyl-20-methyl-5-cis-13-trans prostadiene |
| 494 | 1-trans-tri-n-butylstannyl-4-fluoromethyl-4-trimethylsilyloxy-1-nonene | 2-[8-methoxy-8-methoxycarbonyl-7-(trimethylsiloxy)-2-cis,7-octadienyl] cyclopent-2-en-1-one | dl-16-hydroxy-1-(methoxymethoxycarbonylmethyl)-1,9-dioxo-16-fluoromethyl-20-methyl-5-cis-13-trans prostadiene |

| EXAMPLE | VINYL IODIDE / VINYL TIN | CYCLOPENTENONE | PRODUCT PROSTAGLANDIN |
|---|---|---|---|
| 495 | 1-trans-tri-n-butylstannyl-4-difluoromethyl-4-trimethylsilyloxy-1-nonene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-difluoromethyl-20-methyl-5-cis,13-trans prostadiene |
| 496 | 1-trans-tri-n-butylstannyl-4-trifluoromethyl-4-trimethylsilyloxy-1-nonene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-trifluoromethyl-20-methyl-5-cis,13-trans prostadiene |
| 497 | 1-trans-tri-n-butylstannyl-4-chloromethyl-4-trimethylsilyloxy-1-nonene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-chloromethyl-20-methyl-5-cis,13-trans prostadiene |
| 498 | 1-trans-tri-n-butylstannyl-4-trimethylsilyloxymethyl-4-trimethylsilyloxy-1-nonene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-hydroxymethyl-20-methyl-5-cis,13-trans prostadiene |
| EXAMPLE | VINYL IODIDE | CYCLOPENTENONE | PRODUCT PROSTAGLANDIN OF THE 11-DEOXY PGE2 SERIES |
| 499 | 1-trans-iodo-3-triphenylmethoxy-decene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-20-ethyl-5-cis,13-trans prostadiene |
| 500 | 1-trans-iodo-3-methyl-3-trimethylsilyloxy-1-decene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-15-methyl-20-methyl-5-cis,13-trans prostadiene |
| 501 | 1-trans-iodo-4,4-dimethyl-3-trimethylsilyloxy-1-decene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-16,16-dimethyl-20-ethyl-5-cis,13-trans prostadiene |
| 502 | 1-trans-iodo-4,4-trimethylene-3-trimethylsilyloxy-1-decene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-16,16-trimethylene-20-ethyl-5-cis,13-trans prostadiene |
| EXAMPLE | VINYL TIN | CYCLOPENTENONE | PRODUCT PROSTAGLANDIN OF THE 11-DEOXY PGE2 SERIES |
| 503 | 1-trans-tri-n-butylstannyl-3-vinyl-3-trimethylsilyloxy-1-decene | 2-[8-methoxy-8-methoxycarbonyl-7-(trimethylsiloxy)-2-cis,7-octadienyl]cyclopent-2-en-1-one | dl-15a-hydroxy-1-(methoxymethoxycarbonylmethyl)-1,9-dioxo-15-vinyl-20-ethyl-5-cis,13-trans prostadiene |
| EXAMPLE | VINYL IODIDE | CYCLOPENTENONE | PRODUCT PROSTAGLANDIN OF THE 11-DEOXY PGE2 SERIES |
| 504 | 1-trans-iodo-4-triphenylmethoxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-20-ethyl-5-cis,13-trans prostadiene |
| EXAMPLE | VINYL TIN | CYCLOPENTENONE | PRODUCT PROSTAGLANDIN OF THE 11-DEOXY PGE2 SERIES |
| 505 | 1-trans-tri-n-butylstannyl-4-methyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-methyl-20-ethyl-5-cis,13-trans prostadiene |
| 506 | 1-trans-tri-n-butylstannyl-5-methyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-17-methyl-20-methyl-5-cis,13-trans prostadiene |
| 507 | 1-trans-tri-n-butylstannyl-4-vinyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-vinyl-20-ethyl-5-cis,13-trans prostadiene |
| 508 | 1-trans-tri-n-butylstannyl-4-trimethylsilylethynyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-ethynyl-20-ethyl-5-cis,13-trans prostadiene |
| 509 | 1-trans-tri-n-butylstannyl-5-methylene-4-triethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-17-methylene-20-ethyl-5-cis,13-trans prostadiene |

-continued

| | | | |
|---|---|---|---|
| 510 | 1-trans-tri-n-butylstannyl-4-methyl-5-methylene-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-methyl-17-methylene-20-ethyl-5-cis-13-trans prostadiene |
| 511 | 1-trans-tri-n-butylstannyl-4-dimethoxymethyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-formyl-20-ethyl-5-cis-13-trans prostadiene |
| 512 | 1-trans-tri-n-butylstannyl-4-fluoromethyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-fluoromethyl-20-ethyl-5-cis-13-trans prostadiene |
| 513 | 1-trans-tri-n-butylstannyl-4-difluoromethyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-difluoromethyl-20-ethyl-5-cis-13-trans prostadiene |
| 514 | 1-trans-tri-n-butylstannyl-4-trifluoromethyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-trifluoromethyl-20-ethyl-5-cis-13-trans prostadiene |
| 515 | 1-trans-tri-n-butylstannyl-4-chloromethyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-chloromethyl-20-ethyl-5-cis-13-trans prostadiene |
| 516 | 1-trans-tri-n-butylstannyl-4-trimethylsilyloxymethyl-4-trimethylsilyloxy-1-decene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 517 | 1-trans-iodo-3-triphenylmethoxy-1-heptene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-20-nor-2-homo-5-cis-13-trans prostadiene |
| 518 | 1-trans-iodo-3-methyl-3-trimethylsilyloxy-1-heptene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-methyl-20-nor-2-homo-5-cis-13-trans prostadiene |
| 519 | 1-trans-iodo-4,4-dimethyl-3-trimethylsilyloxy-1-heptene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-dimethyl-20-nor-2-homo-5-cis-13-trans prostadiene |
| 520 | 1-trans-iodo-5,5-dimethyl-3-triphenylmethoxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-17,17-dimethyl-2-homo-5-cis-13-trans prostadiene |
| 521 | 1-trans-iodo-4-methyl-3-triphenylmethoxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16-methyl-2-homo-5-cis-13-trans prostadiene |
| 522 | 1-trans-iodo-4,4-trimethylene-3-trimethylsilyloxy-1-heptene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-trimethylene-20-nor-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 523 | 1-trans-tri-n-butylstannyl-3-vinyl-3-trimethylsilyloxy-1-heptene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-vinyl-20-nor-2-homo-5-cis-13-trans prostadiene |
| 524 | 1-trans-tri-n-butylstannyl-4-phenoxy-3-triethylsilyloxy-1-butene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16-phenoxy-2-homo-17,20-tetranor-5-cis-13-trans prostadiene |
| 525 | 1-trans-tri-n-butylstannyl-4-(p-fluorophenoxy)-3-triethylsilyloxy-1-butene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16-(p-fluorophenoxy)-2-homo-17,20-tetranor-5-cis-13-trans prostadiene |

| | -continued | | |
|---|---|---|---|
| 526 | 1-trans-tri-n-butylstannyl-4-(m-chlorophenoxy)-3-triethylsilyloxy-1-butene | 2-[9-methoxy-9-methoxycarbonyl-8-(trimethylsilyloxy)-2-cis,8-nonadienyl]cyclopent-2-en-1-one | dl-15a-hydroxy-1-(methoxymethoxycarbonylmethyl)-1,9-dioxo-16-(m-chlorophenoxy)-2-homo-17-20-tetranor-5-cis-13-trans prostadiene |
| 527 | 1-trans-tri-n-butylstannyl-4-(m-trifluoromethylphenoxy)-3-triethylsilyloxy-1-butene | 2-[9-methoxy-9-methoxycarbonyl-8-(trimethylsilyloxy)-2-cis,8-nonadienyl]cyclopent-2-en-1-one | dl-15a-hydroxy-1-(methoxymethoxycarbonylmethyl)-1,9-dioxo-16-(m-trifluoromethylphenoxy)-2-homo-17-20-tetranor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 528 | 1-trans-iodo-5-phenyl-3-triethylsilyloxy-1-pentene | 2-[9-methoxy-9-methoxycarbonyl-8-(trimethylsilyloxy)-2-cis,8-nonadienyl]cyclopent-2-en-1-one | dl-15a-hydroxy-1-(methoxymethoxycarbonylmethyl)-1,9-dioxo-17-phenyl-2-homo-18-20-trinor-5-cis-13-trans prostadiene |
| 529 | 1-trans-iodo-4,4-dimethyl-5-phenyl-3-triethylsilyloxy-1-pentene | 2-[9-methoxy-9-methoxycarbonyl-8-(trimethylsilyloxy)-2-cis,8-nonadienyl]cyclopent-2-en-1-one | dl-15a-hydroxy-1-(methoxymethoxycarbonylmethyl)-1,9-dioxo-16,16-dimethyl-17-phenyl-2-homo-18-20-trinor-5-cis-13-trans prostadiene |
| 530 | 1-trans-iodo-4-cyclopentyl-3-triphenylmethoxy-1-butene | 2-[9-methoxy-9-methoxycarbonyl-8-(trimethylsilyloxy)-2-cis,8-nonadienyl]cyclopent-2-en-1-one | dl-15a-hydroxy-1-(methoxymethoxycarbonylmethyl)-1,9-dioxo-16-cyclopentyl-2-homo-17-20-tetranor-5-cis-13-trans prostadiene |
| 531 | 1-trans-iodo-4-cyclohexyl-3-triphenylmethoxy-1-butene | 2-[9-methoxy-9-methoxycarbonyl-8-(trimethylsilyloxy)-2-cis,8-nonadienyl]cyclopent-2-en-1-one | dl-15a-hydroxy-1-(methoxymethoxycarbonylmethyl)-1,9-dioxo-16-cyclohexyl-2-homo-17-20-tetranor-5-cis-13-trans prostadiene |
| 532 | 1-trans-iodo-4-triphenylmethoxy-1-heptene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-20-nor-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 533 | 1-trans-tri-n-butylstannyl-4-methyl-4-trimethylsilyloxy-1-heptene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-16-methyl-20-nor-2-homo-5-cis-13-trans prostadiene |
| 534 | 1-trans-tri-n-butylstannyl-4-ethyl-4-trimethylsilyloxy-1-octene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-16-ethyl-2-homo-5-cis-13-trans prostadiene |
| 535 | 1-trans-tri-n-butylstannyl-5-methyl-4-trimethylsilyloxy-1-heptene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-17-methyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 536 | 1-trans-iodo-5,5-dimethyl-4-trimethylsilyloxy-1-octene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-17,17-dimethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 537 | 1-trans-tri-n-butylstannyl-4-vinyl-4-trimethylsilyloxy-1-heptene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-16-vinyl-20-nor-2-homo-5-cis-13-trans prostadiene |
| 538 | 1-trans-tri-n-butylstannyl-4-cyclopropyl-4-trimethylsilyloxy-1-octene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-16-cyclopropyl-2-homo-5-cis-13-trans prostadiene |
| 539 | 1-trans-tri-n-butylstannyl-4-trimethylsilylethynyl-4-trimethylsilyloxy-1-heptene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-16-ethynyl-20-nor-2-homo-5-cis-13-trans prostadiene |
| 540 | 1-trans-tri-n-butylstannyl-5-methylene-4-triethylsilyloxy-1-heptene | 2-[9-methoxy-9-methoxycarbonyl-8-(trimethylsilyloxy)-2-cis,8-nonadienyl]cyclopent-2-en-1-one | dl-16-hydroxy-1-(methoxymethoxycarbonylmethyl)-1,9-dioxo-17-methylene-20-nor-2-homo-5-cis-13-trans prostadiene |

| EXAMPLE | VINYL TIN | -continued | PRODUCT PROSTAGLANDIN |
|---|---|---|---|
| 541 | 1-trans-tri-n-butylstannyl-4-methyl-5-methylene-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-17-methylene-20-nor-2-homo-5-cis-13-trans prostadiene |
| 542 | 1-trans-tri-n-butylstannyl-4-dimethoxymethyl-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-formyl-20-nor-2-homo-nor-5-cis-13-trans prostadiene |
| 543 | 1-trans-tri-n-butylstannyl-4-fluoromethyl-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-fluoromethyl-20-nor-2-homo-5-cis-13-trans prostadiene |
| 544 | 1-trans-tri-n-butylstannyl-4-difluoromethyl-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-difluoromethyl-20-nor-2-homo-5-cis-13-trans prostadiene |
| 545 | 1-trans-tri-n-butylstannyl-4-trifluoromethyl-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-trifluoromethyl-20-nor-2-homo-5-cis-13-trans prostadiene |
| 546 | 1-trans-tri-n-butylstannyl-4-chloromethyl-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-chloromethyl-20-nor-2-homo-5-cis-13-trans prostadiene |
| 547 | 1-trans-tri-n-butylstannyl-4-trimethylsilyloxymethyl-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-hydroxymethyl-20-nor-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 548 | 1-trans-iodo-4-methyl-7-chloro-4-trimethylsilyloxy-1-heptene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-19-chloro-2-homo-20-nor-5-cis-13-trans prostadiene |
| 549 | 1-trans-iodo-3-triphenylmethoxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-2-homo-5-cis-13-trans prostadiene |
| 550 | 1-trans-iodo-3-methyl-3-trimethylsilyloxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-methyl-2-homo-5-cis-13-trans prostadiene |
| 551 | 1-trans-iodo-4,4-dimethyl-3-trimethylsilyloxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-dimethyl-2-homo-5-cis-13-trans prostadiene |
| 552 | 1-trans-iodo-4,4-trimethylene-3-trimethylsilyloxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-trimethylene-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 553 | 1-trans-tri-n-butylstannyl-3-vinyl-3-trimethylsilyloxy-1-octene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-vinyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 554 | 1-trans-iodo-4-triphenylmethoxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 555 | 1-trans-tri-n-butylstannyl-4-methyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-2-homo-5-cis-13-trans prostadiene |

-continued

| | VINYL TIN | | |
|---|---|---|---|
| 556 | 1-trans-tri-n-butylstannyl-5-methyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-17-methyl-2-homo-5-cis-13-trans prostadiene |
| 557 | 1-trans-tri-n-butylstannyl-4-vinyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-vinyl-2-homo-5-cis-13-trans prostadiene |
| 558 | 1-trans-tri-n-butylstannyl-4-trimethylsilylethynyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-ethynyl-2-homo-5-cis-13-trans prostadiene |
| 559 | 1-trans-tri-n-butylstannyl-5-methylene-4-triethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-17-methylene-2-homo-5-cis-13-trans prostadiene |
| 560 | 1-trans-tri-n-butylstannyl-4-methyl-5-methylene-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-17-methylene-2-homo-5-cis-13-trans prostadiene |
| 561 | 1-trans-tri-n-butylstannyl-4-dimethoxymethyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-formyl-2-homo-5-cis-13-trans prostadiene |
| 562 | 1-trans-tri-n-butylstannyl-4-fluoromethyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-fluoromethyl-2-homo-5-cis-13-trans prostadiene |
| 563 | 1-trans-tri-n-butylstannyl-4-difluoromethyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-difluoromethyl-2-homo-5-cis-13-trans prostadiene |
| 564 | 1-trans-tri-n-butylstannyl-4-trifluoromethyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-trifluoromethyl-2-homo-5-cis-13-trans prostadiene |
| 565 | 1-trans-tri-n-butylstannyl-4-choromethyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-chloromethyl-2-homo-5-cis-13-trans prostadiene |
| 566 | 1-trans-tri-n-butylstannyl-4-trimethylsilyloxymethyl-4-trimethylsilyloxy-1-octene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-hydroxymethyl-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 567 | 1-trans-iodo-3-triphenylmethoxy-1-nonene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-20-methyl-2-homo-5-cis-13-trans prostadiene |
| 568 | 1-trans-iodo-3-methyl-3-trimethylsilyloxy-1-nonene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-methyl-20-methyl-2-homo-5-cis-13-trans prostadiene |
| 569 | 1-trans-iodo-4,4-dimethyl-3-trimethylsilyloxy-1-nonene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-dimethyl-20-methyl-2-homo-5-cis-13-trans prostadiene |
| 570 | 1-trans-iodo-4,4-trimethylene-3-trimethylsilyloxy-1-nonene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-trimethylene-20-methyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 571 | 1-trans-tri-n-butylstannyl-3-vinyl-3-trimethylsilyloxy-1-nonene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-vinyl-20-methyl-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 572 | 1-trans-iodo-4-triphenylmethoxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-20-methyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 573 | 1-trans-tri-n-butylstannyl-4-methyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-methyl-20-methyl-2-homo-5-cis-13-trans prostadiene |
| 574 | 1-trans-tri-n-butylstannyl-5-methyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-17-methyl-20-methyl-2-homo-5-cis-13-trans prostadiene |
| 575 | 1-trans-tri-n-butylstannyl-4-vinyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-vinyl-20-methyl-2-homo-5-cis-13-trans prostadiene |
| 576 | 1-trans-tri-n-butylstannyl-4-methylsilylethynyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-ethynyl-20-methyl-2-homo-5-cis-13-trans prostadiene |
| 577 | 1-trans-tri-n-butylstannyl-5-methylene-4-triethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-17-merthylene-20-methyl-2-homo-5-cis-13-trans prostadiene |
| 578 | 1-trans-tri-n-butylstannyl-4-methyl-5-methylene-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-methyl-17-methylene-20-methyl-2-homo-5-cis-13-trans prostadiene |
| 579 | 1-trans-tri-n-butylstannyl-4-dimethoxymethyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-formyl-20-methyl-2-homo-5-cis-13-trans prostadiene |
| 580 | 1-trans-tri-n-butylstannyl-4-fluoromethyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-fluoromethyl-20-methyl-2-homo-5-cis-13-trans prostadiene |
| 581 | 1-trans-tri-n-butylstannyl-4-difluoromethyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-difluoromethyl-20-methyl-2-homo-5-cis-13-trans prostadiene |
| 582 | 1-trans-tri-n-butylstannyl-4-trifluoromethyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-trifluoromethyl-20-methyl-2-homo-5-cis-13-trans prostadiene |
| 583 | 1-trans-tri-n-butylstannyl-4-chloromethyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-chloromethyl-20-methyl-2-homo-5-cis-13-trans prostadiene |
| 584 | 1-trans-tri-n-butylstannyl-4-trimethylsilyloxymethyl-4-trimethylsilyloxy-1-nonene | 2-[9-methoxy-9-methoxycarbonyl-8-(trimethylsilyloxy)-2-cis,8-nonadienyl] cyclopent-2-en-1-one | dl-16-hydroxy-1-(methoxymethoxycarbonylmethyl)-1,9-dioxo-16-hydroxymethyl-20-methyl-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 585 | 1-trans-iodo-3-triphenylmethoxy-1-decene | 2-[9-methoxy-9-methoxycarbonyl-8-(trimethylsilyloxy)-2-cis,8-nonadienyl] cyclopent-2-en-1-one | dl-15a-hydroxy-1-(methoxymethoxycarbonylmethyl)-1,9-dioxo-20-ethyl-2-homo-5-cis-13-trans prostadiene |
| 586 | 1-trans-iodo-3-methyl-3-trimethylsilyloxy-1-decene | 2-[9-methoxy-9-methoxycarbonyl-8-(trimethylsilyloxy)-2-cis,8-nonadienyl] cyclopent-2-en-1-one | dl-15a-hydroxy-1-(methoxymethoxycarbonylmethyl)-1,9-dioxo-15-methyl-20-ethyl-2-homo-5-cis-13-trans prostadiene |
| 587 | 1-trans-iodo-4,4-dimethyl-3-trimethylsilyloxy-1-decene | 2-[9-methoxy-9-methoxycarbonyl-8-(trimethylsilyloxy)-2-cis,8-nonadienyl] cyclopent-2-en-1-one | dl-15a-hydroxy-1-(methoxymethoxycarbonylmethyl)-1,9-dioxo-16,16-dimethyl-20-ethyl-2-homo-5-cis-13-trans prostadiene |

| | | -continued | |
|---|---|---|---|
| 588 | 1-trans-iodo-4,4-trimethylene-3-trimethylsilyloxy-1-decene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-16,16-trimethylene-20-ethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 589 | 1-trans-tri-n-butylstannyl-3-vinyl-3-trimethylsilyloxy-1-decene | 2-[9-methoxy-9-methoxycarbonyl-8-(trimethylsiloxy)-2-cis,8-nonadienyl]cyclopent-2-en-1-one | dl-15a-hydroxy-1-(methoxymethoxycarbonylmethyl)-1,9-dioxo-15-vinyl-20-ethyl-2-homo-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 590 | 1-trans-iodo-4-triphenylmethoxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-20-ethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 591 | 1-trans-tri-n-butylstannyl-4-methyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-20-ethyl-2-homo-5-cis-13-trans prostadiene |
| 592 | 1-trans-tri-n-butylstannyl-5-methyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-17-methyl-20-ethyl-2-homo-5-cis-13-trans prostadiene |
| 593 | 1-trans-tri-n-butylstannyl-4-vinyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-vinyl-20-ethyl-2-homo-5-cis-13-trans prostadiene |
| 594 | 1-trans-tri-n-butylstannyl-4-trimethylsilylethynyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-ethynyl-20-ethyl-2-homo-5-cis-13-trans prostadiene |
| 595 | 1-trans-tri-n-butylstannyl-5-methylene-4-triethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-17-methylene-20-ethyl-2-homo-5-cis-13-trans prostadiene |
| 596 | 1-trans-tri-n-butylstannyl-4-methyl-5-methylene-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-17-methylene-20-ethyl-2-homo-5-cis-13-trans prostadiene |
| 597 | 1-trans-tri-n-butylstannyl-4-dimethoxymethyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-formyl-20-ethyl-2-homo-5-cis-13-trans prostadiene |
| 598 | 1-trans-tri-n-butylstannyl-4-fluoromethyl-5-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-fluoromethyl-20-ethyl-2-homo-5-cis-13-trans prostadiene |
| 599 | 1-trans-tri-n-butylstannyl-4-difluoromethyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-difluoromethyl-20-ethyl-2-homo-5-cis-13-trans prostadiene |
| 600 | 1-trans-tri-n-butylstannyl-4-trifluoromethyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-trifluoromethyl-20-ethyl-2-homo-5-cis-13-trans prostadiene |
| 601 | 1-trans-tri-n-butylstannyl-4-chloromethyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-chloromethyl-20-ethyl-2-homo-5-cis-13-trans prostadiene |
| 602 | 1-trans-tri-n-butylstannyl-4-trifmethylsiloxymethyl-4-trimethylsilyloxy-1-decene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-hydroxymethyl-20-ethyl-2-homo-5-cis-13-trans prostadiene |
| EXAMPLE | VINYL TIN | CYCLOPENTENONE | PRODUCT PROSTAGLANDIN OF THE PGE1 SERIES |

| Example | Vinyl Tin | Cyclopentenone | Product Prostaglandin |
|---|---|---|---|
| 603 | 1-trans-tri-n-butylstannyl-4-methyl-4-trimethyl-1,7-octadiene | 2-[7-methoxy-7-methoxycarbonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-2-nor-13-trans-19 prostadiene |
| 604 | 1-trans-tri-n-butylstannyl-4-methyl-4-trimethyl-1,7-octadiene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-methyl-13-trans-19 prostadiene |
| 605 | 1-trans-tri-n-butylstannyl-4-methyl-4-trimethyl-1,7-octadiene | 2-[9-methoxy-9-methoxycarbonyl-8-(trimethylsiloxy)-8-nonenyl]-4-trimethylsiloxy cyclopent-2-en-1-one | dl,11a-16-dihydroxy-1-(methoxymethoxycarbonylmethyl)-1,9-dioxo-16-methyl-2-homo-13-trans-19 prostadiene |
| 606 | 1-trans-tri-n-butylstannyl-4-methyl-4-trimethyl-1,7-octadiene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-13-trans-19 prostadiene |

PRODUCT PROSTAGLANDIN OF THE 11-DEOXY PGE1 SERIES

| Example | Vinyl Tin | Cyclopentenone | Product Prostaglandin |
|---|---|---|---|
| 607 | 1-trans-tri-n-butylstannyl-4-methyl-4-trimethyl-1,7-octadiene | 2-[7-methoxy-7-methoxycarbonyl-6-(trimethylsiloxy)-6-heptenyl] cyclopent-2-en-1-one | dl-16-hydroxy-1-(methoxymethoxycarbonylmethyl)-1,9-dioxo-16-methyl-2-nor-13-trans-19 prostadiene |
| 608 | 1-trans-tri-n-butylstannyl-4-methyl-4-trimethyl-1,7-octadiene | 2-[7-methoxy-7-methoxycarbonyl-7-(trimethylsiloxy)-7-octenyl] cyclopent-2-en-1-one | dl-16-hydroxy-1-(methoxymethoxycarbonylmethyl)-1,9-dioxo-16-methyl-13-trans-19 prostadiene |
| 609 | 1-trans-tri-n-butylstannyl-4-methyl-4-trimethyl-1,7-octadiene | 2-[9-methoxy-9-methoxycarbonyl-8-(trimethylsiloxy)-8-nonenyl] cyclopent-2-en-1-one | dl-16-hydroxy-1-(methoxymethoxycarbonylmethyl)-1,9-dioxo-16-methyl-2-homo-13-trans-19 prostadiene |

PRODUCT PROSTAGLANDIN OF THE PGE2 SERIES

| Example | Vinyl Iodide | Cyclopentenone | Product Prostaglandin |
|---|---|---|---|
| 610 | 1-trans-iodo-4-triphenylmethoxy-1,5-heptadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-20-nor-2-nor-5-cis-13-trans-17-trans prostatriene |
| 611 | 1-trans-iodo-4-methyl-4-trimethylsilyloxy-1,5-heptadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-20-nor-2-nor-5-cis-13-trans-17-trans prostatriene |
| 612 | 1-trans-iodo-4-triphenylmethoxy-1,5-octadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-2-nor-5-cis-13-trans-17-trans prostatriene |
| 613 | 1-trans-iodo-4-methyl-4-trimethylsilyloxy-1,5-octadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-2-nor-5-cis-13-trans-17-trans prostatriene |
| 614 | 1-trans-iodo-4-triphenylmethoxy-1,5-nonadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-20-methyl-2-nor-5-cis-13-trans-17-trans prostatriene |
| 615 | 1-trans-iodo-4-methyl-4-trimethylsilyloxy-1,5-nonadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-20-methyl-2-nor-5-cis-13-trans-17-trans prostatriene |
| 616 | 1-trans-iodo-4-triphenylmethoxy-1,5-decadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-20-ethyl-2-nor-5-cis-13-trans-17-trans prostatriene |
| 617 | 1-trans-iodo-4-methyl-4-trimethylsilyloxy-1,5-decadiene | 2-[7-methoxy-7-methoxycarbonyl-6-(trimethylsiloxy)-2-cis,6-heptadienyl]-4-trimethylsiloxy cyclopent-2-en-1-one | dl-11a,16-dihydroxy-1-(methoxymethoxycarbonylmethyl)-1,9-dioxo-16-methyl-20-ethyl-2-nor-5-cis-13-trans-17-trans prostatriene |
| 618 | 1-trans-iodo-4-triphenylmethoxy-1,5-heptadiene | 2-[8-methoxy-8-methoxycarbonyl-7-(trimethylsiloxy)-2-cis,7-octadienyl]-4-trimethylsiloxy cyclopent-2-en-1-one | dl-11a,16-dihydroxy-1-(methoxymethoxycarbonylmethyl)-1,9-dioxo-20-nor-5-cis-13-trans-17-trans prostatriene |
| 619 | 1-trans-iodo-4-methyl- | 2-[8-methoxy-8-methoxycarbonyl- | dl-11a,16-dihydroxy-1-(methoxymethoxycarbonylmethyl)-1,9-dioxo-16-methyl- |

| | | -continued | |
|---|---|---|---|
| | | | |
| 620 | 1-trans-iodo-4-triphenylmethoxy-1,5-heptadiene | 7-(trimethylsilyloxy)-2-cis,7-octadienyl]-4-trimethylsiloxy cyclopent-2-en-1-one | 20-nor-5-cis-13-trans-17-trans prostatriene |
| 621 | 1-trans-iodo-4-triphenylmethoxy-1,5-octadiene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-20-methyl-2-nor-5-cis-13-trans-17-trans prostatriene |
| 621 | 1-trans-iodo-4-trimethylsilyloxy-1,5-octadiene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-5-cis-13-trans-17-trans prostatriene |
| 622 | 1-trans-iodo 4-triphenylmethoxy-1,5-nonadiene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-20-methyl-5-cis-13-trans-17-trans prostatriene |
| 623 | 1-trans-iodo-4-trimethylsilyloxy-1,5-nonadiene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-20-methyl-5-cis-13-trans-17-trans prostatriene |
| 624 | 1-trans-iodo-4-triphenylmethoxy-1,5-decadiene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-20-ethyl-5-cis-13-trans-17-trans prostatriene |
| 625 | 1-trans-iodo-4-trimethylsilyloxy-1,5-decadiene | 2-[8-methoxy-8-methoxycarbonyl-7-(trimethylsilyloxy)-2-cis,7-octadienyl]-4-trimethylsiloxy cyclopent-2-en-1-one | dl-11a,16-dihydroxy-1-(methoxymethoxycarbonylmethyl)-1,9-dioxo-16-methyl-20-ethyl-5-cis-13-trans-17-trans prostatriene |
| 626 | 1-trans-iodo-4-triphenylmethoxy-1,5-heptadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-20-nor-2-homo-5-cis-13-trans-17-trans prostatriene |
| 627 | 1-trans-iodo-4-trimethylsilyloxy-1,5-heptadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-20-nor-2-homo-5-cis-13-trans-17-trans prostatriene |
| 628 | 1-trans-iodo-4-triphenylmethoxy-1,5-octadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-2-homo-5-cis-13-trans-17-trans prostatriene |
| 629 | 1-trans-iodo-4-trimethylsilyloxy-1,5-octadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-2-homo-5-cis-13-trans-17-trans prostatriene |
| 630 | 1-trans-iodo-4-triphenylmethoxy-1,5-nonadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-20-methyl-2-homo-5-cis-13-trans-17-trans prostatriene |
| 631 | 1-trans-iodo-4-trimethylsilyloxy-1,5-nonadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-20-methyl-2-homo-5-cis-13-trans-17-trans prostatriene |
| 632 | 1-trans-iodo-4-triphenylmethoxy-1,5-decadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-20-ethyl-2-homo-5-cis-13-trans-17-trans prostatriene |
| 633 | 1-trans-iodo-4-trimethylsilyloxy-1,5-decadiene | 2-[9-methoxy-9-methoxycarbonyl-8-(trimethylsilyloxy)-2-cis,8-nonadienyl]-4-trimethylsiloxy cyclopent-2-en-1-one | dl-11a,16-dihydroxy-1-(methoxymethoxycarbonylmethyl)-1,9-dioxo-16-methyl-20-ethyl-2-homo-5-cis-13-trans-17-trans prostatriene |
| 634 | 1-trans-iodo-4-triphenylmethoxy-1,5-heptadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-20-nor-5-cis-13-trans-17-trans prostatriene |
| 635 | 1-trans-iodo-4-trimethylsilyloxy-1,5-heptadiene | 2-[8-methoxy-8-methoxycarbonyl-7-(trimethylsilyloxy)-2-cis,7-nonadienyl]4R-trimethylsiloxy cyclopent-2-en-1-one | nat-11a,16-dihydroxy-1-(methoxymethoxycarbonylmethyl)-1,9-dioxo-16-methyl-20-nor-5-cis-13-trans-17-trans prostatriene |
| 636 | 1-trans-iodo-4-triphenylmethoxy-1,5-octadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-5-cis-13-trans-17-trans prostatriene |

-continued

| EXAMPLE | VINYL IODIDE | CYCLOPENTENONE | PRODUCT PROSTAGLANDIN OF THE 11-DEOXY PGE2 SERIES |
|---|---|---|---|
| 637 | 1-trans-iodo-4-methyl-4-trimethylsilyloxy-1,5-octadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-16-methyl-5-cis-13-trans-17-trans prostatriene |
| 638 | 1-trans-iodo-4-triphenylmethoxy-1,5-nonadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-20-methyl-5-cis-13-trans-17-trans prostatriene |
| 639 | 1-trans-iodo-4-methyl-4-trimethylsilyloxy-1,5-nonadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-20-methyl-5-cis-13-trans-17-trans prostatriene |
| 640 | 1-trans-iodo-4-triphenylmethoxy-1,5-decadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-20-ethyl-5-cis-13-trans-17-trans prostatriene |
| 641 | 1-trans-iodo-4-methyl-4-trimethylsilyloxy-1,5-decadiene | 2-[8-methoxy-8-methoxycarbonyl-7-(trimethylsilyloxy)-2-cis,7-octadienyl]-4R-trimethylsiloxy cyclopent-2-en-1-one | nat-11a,16-dihydroxy-1-(methoxymethoxycarbonylmethyl)-1,9-dioxo-20-ethyl-5-cis-13-trans-17-trans prostatriene |
| 642 | 1-trans-iodo-4-triphenylmethoxy-1,5-heptadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-20-nor-2-nor-5-cis-13-trans-17-trans prostatriene |
| 643 | 1-trans-iodo-4-methyl-4-trimethylsilyloxy-1,5-heptadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-20-methyl-2-nor-5-cis-13-trans-17-trans prostatriene |
| 644 | 1-trans-iodo-4-triphenylmethoxy-1,5-octadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-2-nor-5-cis-13-trans-17-trans prostatriene |
| 645 | 1-trans-iodo-4-methyl-4-trimethylsilyloxy-1,5-octadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-16-methyl-2-nor-5-cis-13-trans-17-trans prostatriene |
| 646 | 1-trans-iodo-4-triphenylmethoxy-1,5-nonadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-20-methyl-2-nor-5-cis-13-trans-17-trans prostatriene |
| 647 | 1-trans-iodo-4-methyl-4-trimethylsilyloxy-1,5-nonadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-20-methyl-2-nor-5-cis-13-trans-17-trans prostatriene |
| 648 | 1-trans-iodo-4-triphenylmethoxy-1,5-decadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-20-ethyl-2-nor-5-cis-13-trans-17-trans prostatriene |
| 649 | 1-trans-iodo-methyl-4-trimethylsilyloxy-1,5-decadiene | 2-[7-methoxy-7-methoxycabonyl-6-(trimethylsilyloxy)-2-cis,6-heptadienyl] cyclopent-2-en-1-one | dl-16-hydroxy-1-(methoxymethoxycarbonylmethyl)-1,9-dioxo-20-ethyl-2-nor-5-cis-13-trans-17-trans prostatriene |
| 650 | 1-trans-iodo-4-triphenylmethoxy-1,5-heptadiene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-20-nor-5-cis-13-trans-17-trans prostatriene |
| 651 | 1-trans-iodo-4-methyl-4-trimethylsilyloxy-1,5-heptadiene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-20-nor-5-cis-13-trans-17-trans prostatriene |
| 652 | 1-trans-iodo-4-triphenylmethoxy-1,5-octadiene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-5-cis-13-trans-17-trans prostatriene |
| 653 | 1-trans-iodo-4-methyl-4-trimethylsilyloxy-1,5-octadiene | 2-[8-methoxy-8-methoxycarbonyl-7-(trimethylsilyloxy)-2-cis,7-octadienyl] cyclopent-2-en-1-one | dl-16-hydroxy-1-(methoxymethoxycarbonylmethyl)-1,9-dioxo-16-methyl-5-cis-13-trans-17-trans prostatriene |

| | | -continued | |
|---|---|---|---|
| 654 | 1-trans-iodo-4-triphenylmethoxy-1,5-nonadiene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-20-methyl-5-cis-13-trans-17-trans prostatriene |
| 655 | 1-trans-iodo-4-methyl-4-trimethylsilyloxy-1,5-nonadiene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-methyl-20-methyl-5-cis-13-trans-17-trans prostatriene |
| 656 | 1-trans-iodo-4-triphenylmethoxy-1,5-decadiene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-20-ethyl-5-cis-13-trans-17-trans prostatriene |
| 657 | 1-trans-iodo-4-methyl-4-trimethylsilyloxy-1,5-decadiene | 2-[8-methoxy-8-methoxycarbonyl-7-(trimethylsiloxy)-2-cis,7-octadienyl]cyclopent-2-en-1-one | dl-16-hydroxy-1-(methoxymethoxycarbonylmethyl)-1,9-dioxo-16-methyl-20-ethyl-5-cis-13-trans-17-trans prostatriene |
| 658 | 1-trans-iodo-4-triphenylmethoxy-1,5-heptadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-20-nor-2-homo-5-cis-13-trans-17-trans prostatriene |
| 659 | 1-trans-iodo-4-methyl-4-trimethylsilyloxy-1,5-heptadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-20-nor-2-homo-5-cis-13-trans-17-trans prostatriene |
| 660 | 1-trans-iodo-4-triphenylmethoxy-1,5-octadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-2-homo-5-cis-13-trans-17-trans prostatriene |
| 661 | 1-trans-iodo-4-methyl-4-trimethylsilyloxy-1,5-octadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-2-homo-5-cis-13-trans-17-trans prostatriene |
| 662 | 1-trans-iodo-4-triphenylmethoxy-1,5-nonadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-2-methyl-2-homo-5-cis-13-trans-17-trans prostatriene |
| 663 | 1-trans-iodo-4-methyl-4-trimethylsilyloxy-1,5-nonadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-2-methyl-2-homo-5-cis-13-trans-17-trans prostatriene |
| 664 | 1-trans-iodo-4-triphenylmethoxy-1,5-decadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-2-ethyl-2-homo-5-cis-13-trans-17-trans prostatriene |
| 665 | 1-trans-iodo-4-methyl-4-trimethylsilyloxy-1,5-decadiene | 2-[9-methoxy-9-methoxycarbonyl-8-(trimethylsiloxy)-2-cis,8-nonadienyl]cyclopent-2-en-1-one | dl-16-hydroxy-1-(methoxymethoxycarbonylmethyl)-1,9-dioxo-16-methyl-20-ethyl-2-homo-5-cis-13-trans-17-trans prostatriene |

TABLE XIII

| EXAMPLE | VINYL IODIDE | CYCLOPENTENONE | PRODUCT PROSTAGLANDIN OF THE PGE1 SERIES |
|---|---|---|---|
| 1 | 1-trans-iodo-3-triphenylmethoxy-1-heptene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-20-nor-2-nor-13-trans prostene |
| 2 | 1-trans-iodo-3-methyl-3-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-methyl-20-nor-2-nor-13-trans prostene |
| 3 | 1-trans-iodo-4,4-dimethyl-3-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-dimethyl-20-nor-2-nor-13-trans prostene |
| 4 | 1-trans-iodo-5,5-dimethyl-3-triphenylmethoxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-17,17-dimethyl-2-nor-13-trans prostene |
| 5 | 1-trans-iodo-4-methyl-3-triphenylmethoxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-methyl-2-nor-13-trans prostene |
| 6 | 1-trans-iodo-4,4-trimethylene-3-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-trimethylene-20-nor-2-nor-13-trans prostene |
| 7 | 1-trans-tri-n-butylstannyl-3-vinyl-3-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-vinyl-20-nor-2-nor-13-trans prostene |
| 8 | 1-trans-tri-n-butylstannyl-4-phenoxy-3-triethylsilyloxy-1-butene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-phenoxy-2-nor-17-20-tetranor-13-trans prostene |
| 9 | 1-trans-tri-n-butylstannyl-4-(p-fluorophenoxy)-3-triethylsilyloxy-1-butene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-(p-fluorophenoxy)-2-nor-17-20-tetranor-13-trans prostene |
| 10 | 1-trans-tri-n-butylstannyl-4-(m-chlorophenoxy)-3-triethylsilyloxy-1-butene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-(m-chlorophenoxy)-2-nor-17-20-tetranor-13-trans prostene |
| 11 | 1-trans-tri-n-butylstannyl-4-(m-trifluoromethylphenoxy)-3-triethylsilyloxy-1-butene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-(m-trifluoromethylphenoxy)-2-nor-17-20-tetranor-13-trans prostene |
| 12 | 1-trans-iodo-5-phenyl-3-triethylsilyloxy-1-pentene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-17-phenyl-2-nor-18-20-trinor-13-trans prostene |
| 13 | 1-trans-iodo-4,4-dimethyl-5-phenyl-3-triethylsilyloxy-1-pentene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-dimethyl-17-phenyl-2-nor-18-20-trinor-13-trans prostene |
| 14 | 1-trans-iodo-4-cyclopentyl-3-triphenylmethoxy-1-butene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-cyclopentyl-2-nor-17-20-tetranor-13-trans prostene |
| 15 | 1-trans-iodo-4-cyclohexyl-3-triphenylmethoxy-1-butene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16-cyclohexyl-2-nor-17-20-tetranor-13-trans prostene |
| 16 | 1-trans-iodo-4-triphenylmethoxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-20-nor-2-nor-13-trans prostene |

TABLE XIII-continued

| EXAMPLE | VINYL TIN | CYCLOPENTENONE | PRODUCT PROSTAGLANDIN OF THE PGE1 SERIES |
|---|---|---|---|
| 17 | 1-trans-tri-n-butylstannyl-4-methyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-20-nor-2-nor-13-trans prostene |
| 18 | 1-trans-tri-n-butylstannyl-4-ethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-ethyl-2-nor-13-trans prostene |
| 19 | 1-trans-tri-n-butylstannyl-5-methyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 20 | 1-iodo-5,5-dimethyl 4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17,17-dimethyl-2-nor-13-trans prostene |

| EXAMPLE | VINYL TIN | CYCLOPENTENONE | PRODUCT PROSTAGLANDIN OF THE PGE1 SERIES |
|---|---|---|---|
| 21 | 1-trans-tri-n-butylstannyl-4-vinyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-vinyl-20-nor-2-nor-13-trans prostene |
| 22 | 1-trans-tri-n-butylstannyl-4-cyclopropyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-cyclopropyl-2-nor-13-trans prostene |
| 23 | 1-trans-tri-n-butylstannyl-4-trimethylsilylethynyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-ethynyl-20-nor-2-nor-13-trans prostene |
| 24 | 1-trans-tri-n-butylstannyl-5-methylene 4-triethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methylene-20-nor-2-nor-13-trans prostene |
| 25 | 1-trans-tri-n-butylstannyl-4-methyl-5-methylene 4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-17-methylene-20-nor-2-nor-13-trans prostene |
| 26 | 1-trans-tri-n-butylstannyl-4-dimethoxymethyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-formyl-20-nor-2-nor-13-trans prostene |
| 27 | 1-trans-tri-n-butylstannyl-4-fluoromethyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-fluoromethyl-20-nor-2-nor-13-trans prostene |
| 28 | 1-trans-tri-n-butylstannyl-4-difluoromethyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-difluoromethyl-20-nor-2-nor-13-trans prostene |
| 29 | 1-trans-tri-n-butylstannyl-4-trifluoromethyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-trifluoromethyl-20-nor-2-nor-13-trans prostene |
| 30 | 1-trans-tri-n-butylstannyl-4-chloromethyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-chloromethyl-20-nor-2-nor-13-trans prostene |

TABLE XIII-continued

| EXAMPLE | VINYL IODIDE | CYCLOPENTENONE | PRODUCT PROSTAGLANDIN OF THE PGE1 SERIES |
|---|---|---|---|
| 31 | 1-trans-tri-n-butylstannyl-4-trimethylsilyloxymethyl-4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-hydroxymethyl-20-nor-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 32 | 1-trans-iodo-4-methyl-7-chloro 4-trimethylsilyloxy-1-heptene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-19-chloro-2-nor-20-nor-13-trans prostene |
| 33 | 1-trans-iodo-3-triphenylmethoxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-2-nor-13-trans prostene |
| 34 | 1-trans-iodo-3-methyl-3-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-methyl-2-nor-13-trans prostene |
| 35 | 1-trans-iodo-4,4-dimethyl-3-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-dimethyl-2-nor-13-trans prostene |
| 36 | 1-trans-iodo-4,4-trimethylene-3-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-trimethylene-2-nor-13-trans prostene |

| EXAMPLE | VINYL TIN | CYCLOPENTENONE | PRODUCT PROSTAGLANDIN OF THE PGE1 SERIES |
|---|---|---|---|
| 37 | 1-trans-tri-n-butylstannyl-3-vinyl-3-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-vinyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 38 | 1-trans-iodo-4-triphenylmethoxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-2-nor-13-trans prostene |

| EXAMPLE | VINYL TIN | CYCLOPENTENONE | PRODUCT PROSTAGLANDIN OF THE PGE1 SERIES |
|---|---|---|---|
| 39 | 1-trans-tri-n-butylstannyl-4-methyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-2-nor-13-trans prostene |
| 40 | 1-trans-tri-n-butylstannyl-5-methyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methyl-2-nor-13-trans prostene |
| 41 | 1-trans-tri-n-butylstannyl-4-vinyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-vinyl-2-nor-13-trans prostene |
| 42 | 1-trans-tri-n-butylstannyl-4-trimethylsilylylethynyl-4-trimethylsilyloxy-1-octene | 2-[7-methoxy-7-methoxycabonyl-6-heptenyl]-4-trimethylsiloxy cyclopent-2-en-1-one | dl-11a,16-dihydroxy-1-(methoxymethoxycarbonylmethyl)-1,9-dioxo-16-ethynyl-2-nor-13-trans prostene |
| 43 | 1-trans-tri-n-butylstannyl-5-methylene | 2-[7-methoxy-7-methoxycabonyl- | dl-11a,16-dihydroxy-1-(methoxymethoxycarbonylmethyl)-1,9-dioxo- |

TABLE XIII-continued

| | | | |
|---|---|---|---|
| | | 4-triethylsilyloxy-1-octene | 6-(trimethylsiloxy)-6-heptenyl]-4-trimethylsilyloxy cyclopent-2-en-1-one | 17-methylene-2-nor-13-trans prostene |
| 44 | 1-trans-tri-n-butylstannyl-4-methyl-5-methylene 4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-17-methylene-2-nor-13-trans prostene |
| 45 | 1-trans-tri-n-butylstannyl-4-dimethoxymethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-formyl-2-nor-13-trans prostene |
| 46 | 1-trans-tri-n-butylstannyl-4-fluoromethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-fluoromethyl-2-nor-13-trans prostene |
| 47 | 1-trans-tri-n-butylstannyl-4-difluoromethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-difluoromethyl-2-nor-13-trans prostene |
| 48 | 1-trans-tri-n-butylstannyl-4-trifluoromethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16 trifluoromethyl-2-nor-13-trans prostene |
| 49 | 1-trans-tri-n-butylstannyl-4-chloromethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-chloromethyl-2-nor-13-trans prostene |
| 50 | 1-trans-tri-n-butylstannyl-4-trimethylsilyloxymethyl-4-trimethylsilyloxy-1-octene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-hydroxymethyl-2-nor-13-trans prostene |
| EXAMPLE | VINYL IODIDE | CYCLOPENTENONE | PRODUCT PROSTAGLANDIN OF THE PGE1 SERIES |
| 51 | 1-trans-iodo-3-triphenylmethoxy-1-nonene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-20-methyl-2-nor-13-trans prostene |
| 52 | 1-trans-iodo-3-methyl-3-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-methyl-20-methyl-2-nor-13-trans prostene |
| 53 | 1-trans-iodo-4,4-dimethyl-3-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-dimethyl-20-methyl-2-nor-13-trans prostene |
| 54 | 1-trans-iodo-4,4-trimethylene-3-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-trimethylene-20-methyl-2-nor-13-trans prostene |
| EXAMPLE | VINYL TIN | CYCLOPENTENONE | PRODUCT PROSTAGLANDIN OF THE PGE1 SERIES |
| 55 | 1-trans-tri-n-butylstannyl-3-vinyl-3-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-vinyl-20-methyl-2-nor-13-trans prostene |
| EXAMPLE | VINYL IODIDE | CYCLOPENTENONE | PRODUCT PROSTAGLANDIN OF THE PGE1 SERIES |
| 56 | 1-trans-iodo-4-triphenylmethoxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-20-methyl-2-nor-13-trans prostene |

TABLE XIII-continued

| EX-AMPLE | VINYL TIN | CYCLOPENTENONE | PRODUCT PROSTAGLANDIN OF THE PGE1 SERIES |
|---|---|---|---|
| 57 | 1-trans-tri-n-butylstannyl-4-methyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-20-methyl-2-nor-13-trans prostene |
| 58 | 1-trans-tri-n-butylstannyl-5-methyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methyl-20-methyl-2-nor-13-trans prostene |
| 59 | 1-trans-tri-n-butylstannyl-4-vinyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-vinyl-20-methyl-2-nor-13-trans prostene |
| 60 | 1-trans-tri-n-butylstannyl-4-trimethylsilylethynyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-ethynyl-20-methyl-2-nor-13-trans prostene |
| 61 | 1-trans-tri-n-butylstannyl-5-methylene-4-triethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methylene-20-methyl-2-nor-13-trans prostene |
| 62 | 1-trans-tri-n-butylstannyl-4-methyl-5-methylene-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-17-methylene-20-methyl-2-nor-13-trans prostene |
| 63 | 1-trans-tri-n-butylstannyl-4-dimethoxymethyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-formyl-20-methyl-2-nor-13-trans prostene |
| 64 | 1-trans-tri-n-butylstannyl-4-fluoromethyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-fluoromethyl-20-methyl-2-nor-13-trans prostene |
| 65 | 1-trans-tri-n-butylstannyl-4-difluoromethyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-difluoromethyl-20-methyl-2-nor-13-trans prostene |
| 66 | 1-trans-tri-n-butylstannyl-4-trifluoromethyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-trifluoromethyl-20-methyl-2-nor-13-trans prostene |
| 67 | 1-trans-tri-n-butylstannyl-4-chloromethyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-chloromethyl-20-methyl-2-nor-13-trans prostene |
| 68 | 1-trans-tri-n-butylstannyl-4-trimethlysilyloxymethyl-4-trimethylsilyloxy-1-nonene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-hydroxymethyl-20-methyl-2-nor-13-trans prostene |

| EX-AMPLE | VINYL IODIDE | CYCLOPENTENONE | PRODUCT PROSTAGLANDIN OF THE PGE1 SERIES |
|---|---|---|---|
| 69 | 1-trans-iodo-3-triphenylmethoxy-1-decene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-20-ethyl-2-nor-13-trans prostene |
| 70 | 1-trans-iodo-3-methyl-3-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-methyl-20-ethyl-2-nor-13-trans prostene |
| 71 | 1-trans-iodo-4,4-dimethyl-3-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-16,16-dimethyl-20-ethyl-2-nor-13-trans prostene |
| 72 | 1-trans-iodo-4,4-trimethylene | 2-[7-methoxy-7-methoxycabonyl- | dl-11a,15a-dihydroxy-1-(methoxymethoxycarbonylmethyl)-1,9-dioxo- |

TABLE XIII-continued

| EX-AM-PLE | VINYL TIN | CYCLOPENTENONE | PRODUCT PROSTAGLANDIN OF THE PGE1 SERIES |
|---|---|---|---|
| | 3-trimethylsilyloxy-1-decene | 6-(trimethylsiloxy)-6-heptenyl]-4-trimethylsiloxy cyclopent-2-en-1-one | 16,16-trimethylene-20-ethyl-2-nor-13-trans prostene |
| 73 | 1-trans-tri-n-butylstannyl-3-vinyl-3-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,15a-dihydroxy-1-(methoxymethoxycarbonylmethyl)-1,9-dioxo-15-vinyl-20-ethyl-2-nor-13-trans prostene |

| EX-AM-PLE | VINYL IODIDE | CYCLOPENTENONE | PRODUCT PROSTAGLANDIN OF THE PGE1 SERIES |
|---|---|---|---|
| 74 | 1-trans-iodo-4-triphenylmethoxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-20-ethyl-2-nor-13-trans prostene |

| EX-AM-PLE | VINYL TIN | CYCLOPENTENONE | PRODUCT PROSTAGLANDIN OF THE PGE1 SERIES |
|---|---|---|---|
| 75 | 1-trans-tri-n-butylstannyl-4-methyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-20-ethyl-2-nor-13-trans prostene |
| 76 | 1-trans-tri-n-butylstannyl-5-methyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methyl-20-ethyl-2-nor-13-trans prostene |
| 77 | 1-trans-tri-n-butylstannyl-4-vinyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-vinyl-20-ethyl-2-nor-13-trans prostene |
| 78 | 1-trans-tri-n-butylstannyl-4-trimethylsilylethynyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-ethynyl-20-ethyl-2-nor-13-trans prostene |
| 79 | 1-trans-tri-n-butylstannyl-5-methylene-4-triethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-17-methylene-20-ethyl-2-nor-13-trans prostene |
| 80 | 1-trans-tri-n-butylstannyl-4-methyl-5-methylene-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-methyl-17-methylene-20-ethyl-2-nor-13-trans prostene |
| 81 | 1-trans-tri-n-butylstannyl-4-dimethoxymethyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-formyl-20-ethyl-2-nor-13-trans prostene |
| 82 | 1-trans-tri-n-butylstannyl-4-fluoromethyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-fluoromethyl-20-ethyl-2-nor-13-trans prostene |
| 83 | 1-trans-tri-n-butylstannyl-4-difluoromethyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-difluoromethyl-20-ethyl-2-nor-13-trans prostene |
| 84 | 1-trans-tri-n-butylstannyl-4-trifluoromethyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-trifluoromethyl-20-ethyl-2-nor-13-trans prostene |
| 85 | 1-trans-tri-n-butylstannyl-4-chloromethyl-4-trimethylsilyloxy-1-decene | 2-[7-methoxy-7-methoxycabonyl-6-(trimethylsiloxy)-6-heptenyl]-4-trimethylsiloxy cyclopent-2-en-1-one | dl-11a,16-dihydroxy-1-(methoxymethoxycarbonylmethyl)-1,9-dioxo-16-chloromethyl-20-ethyl-2-nor-13-trans prostene |

TABLE XIII-continued

| EXAMPLE | VINYL IODIDE | CYCLOPENTENONE | PRODUCT PROSTAGLANDIN OF THE PGE1 SERIES |
|---|---|---|---|
| 86 | 1-trans-tri-n-butylstannyl-4-trimethylsilyloxymethyl-4-trimethylsilyloxy-1-decene | 2-[7-methoxy-7-methoxycabonyl-6-(trimethylsilyloxy)-6-heptenyl]-4-trimethylsilyloxy cyclopent-2-en-1-one | dl-11a,16-dihydroxy-1-(methoxymethoxycarbonylmethyl)-1,9-dioxo-16-hydroxymethyl-20-ethyl-2-nor-13-trans prostene |

| EXAMPLE | VINYL IODIDE | CYCLOPENTENONE | PRODUCT PROSTAGLANDIN OF THE PGE1 SERIES |
|---|---|---|---|
| 87 | 1-trans-iodo-3-triphenylmethoxy-1-heptene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-20-nor-13-trans prostene |
| 88 | 1-trans-iodo-3-methyl-3-trimethylsiliyloxy-1-heptene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-15-methyl-20-nor-13-trans prostene |
| 89 | 1-trans-iodo-4,4-dimethyl-3-trimethylsilyloxy-1-heptene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16,16-dimethyl-20-nor-13-trans prostene |
| 90 | 1-trans-iodo-5,5-dimethyl-3-triphenylmethoxy-1-octene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-17,17-dimethyl-13-trans prostene |
| 91 | 1-trans-iodo-4-methyl-3-triphenylmethoxy-1-octene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16-methyl-13-trans prostene |
| 92 | 1-trans-iodo-4,4-trimethylene-3-trimethylsilyloxy-1-heptene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16,16-trimethylene-20-nor-13-trans prostene |

| EXAMPLE | VINYL TIN | CYCLOPENTENONE | PRODUCT PROSTAGLANDIN OF THE PGE1 SERIES |
|---|---|---|---|
| 93 | 1-trans-n-butylstannyl-3-vinyl-3-trimethylsilyloxy-1-heptene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-15-vinyl-20-nor-13-trans prostene |
| 94 | 1-trans-tri-n-butylstannyl-4-phenoxy-3-triethylsilyloxy-1-butene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16-phenoxy-17-20-tetranor-13-trans prostene |
| 95 | 1-trans-tri-n-butylstannyl-4-(p-fluorophenoxy)-3-triethylsilyloxy-1-butene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16-(p-fluorophenoxy)-17-20-tetranor-13-trans prostene |
| 96 | 1-trans-tri-n-butylstannyl-4-(m-chlorophenoxy)-3-triethylsilyloxy-1-butene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16-(m-chlorophenoxy)-17-20-tetranor-13-trans prostene |
| 97 | 1-trans-tri-n-butylstannyl-4-(m-trifluoromethylphenoxy)-3-triethylsilyloxy-1-butene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 98 | 1-iodo-5-phenyl-3-triethylsilyloxy-1-pentene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-17-phenyl-18-20-trinor-13-trans prostene |
| 99 | 1-iodo-4,4-dimethyl-5-phenyl-3-triethylsilyloxy-1-pentene | 2-[8-methoxy-8-methoxycarbonyl-7-octenyl]-4-trimethylsiloxy cyclopent-2-en-1-one | dl-11a,15a-dihydroxy-1-(methoxymethoxycarbonylmethyl)-1,9-dioxo-16,16-dimethyl-17-phenyl-18-20-trinor-13-trans prostene |

TABLE XIII-continued

| EX-AMPLE | VINYL TIN / VINYL IODIDE | CYCLOPENTENONE | PRODUCT PROSTAGLANDIN |
|---|---|---|---|
| 100 | 1-trans-iodo-4-cyclopentyl 3-triphenylmethoxy-1-butene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-16-cyclopentyl-17-20-tetranor-13-trans prostene |
| 101 | 1-trans-iodo-4-cyclohexyl 3-triphenylmethoxy-1-butene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-16-cyclohexyl-17-20-tetranor-13-trans prostene |
| 102 | 1-trans-iodo-4-triphenylmethoxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-20-nor-13-trans prostene |
| EX-AMPLE | VINYL TIN | CYCLOPENTENONE | PRODUCT PROSTAGLANDIN OF THE PGE1 SERIES |
| 103 | 1-trans-tri-n-butylstannyl-4-methyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-methyl-20-nor-13-trans prostene |
| 104 | 1-trans-tri-n-butylstannyl-4-ethyl-4-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-ethyl-13-trans prostene |
| 105 | 1-trans-tri-n-butylstannyl-5-methyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)1,9-dioxo-17-methyl-20-nor-13-trans prostene |
| EX-AMPLE | VINYL IODIDE | CYCLOPENTENONE | PRODUCT PROSTAGLANDIN OF THE PGE1 SERIES |
| 106 | 1-trans-iodo-5,5-dimethyl 4-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-17,17-dimethyl-13-trans prostene |
| EX-AMPLE | VINYL TIN | CYCLOPENTENONE | PRODUCT PROSTAGLANDIN OF THE PGE1 SERIES |
| 107 | 1-trans-tri-n-butylstannyl-4-vinyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-vinyl-20-nor-13-trans prostene |
| 108 | 1-trans-tri-n-butylstannyl-4-cyclopropyl-4-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-cyclopropyl-13-trans prostene |
| 109 | 1-trans-tri-n-butylstannyl-4-trimethylsilylethynyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-ethynyl-20-nor-13-trans prostene |
| 110 | 1-trans-tri-n-butylstannyl-5-methylene 4-triethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-17-methylene-20-nor-13-trans prostene |
| 111 | 1-trans-tri-n-butylstannyl-4-methyl-5-methylene 4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-methyl-17-methylene-20-nor-13-trans prostene |
| 112 | 1-trans-tri-n-butylstannyl-4-dimethoxymethyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-formyl-20-nor-13-trans prostene |
| 113 | 1-trans-tri-n-butylstannyl-4-fluoromethyl- | 2-[8-methoxy-8-methoxycarbonyl- | dl-11a,16-dihydroxy-1-(methoxymethoxycarbonylmethyl)-1,9-dioxo-16-fluoromethyl- |

TABLE XIII-continued

| EX-AMPLE | VINYL IODIDE | CYCLOPENTENONE | PRODUCT PROSTAGLANDIN OF THE PGE1 SERIES |
|---|---|---|---|
| | | 4-trimethylsilyloxy-1-heptene | 20-nor-13-trans prostene |
| 114 | 1-trans-tri-n-butylstannyl-4-difluoromethyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-difluoromethyl-20-nor-13-trans prostene |
| 115 | 1-trans-tri-n-butylstannyl-4-trifluoromethyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-trifluoromethyl-20-nor-13-trans prostene |
| 116 | 1-trans-tri-n-butylstannyl-4-chloromethyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-chloromethyl-20-nor-13-trans prostene |
| 117 | 1-trans-tri-n-butylstannyl-4-trimethylsilyloxymethyl-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-hydroxymethyl-20-nor-13-trans prostene |

| EX-AMPLE | VINYL IODIDE | CYCLOPENTENONE | PRODUCT PROSTAGLANDIN OF THE PGE1 SERIES |
|---|---|---|---|
| 118 | 1-trans-iodo-4-methyl-7-chloro-4-trimethylsilyloxy-1-heptene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-methyl-19-chloro-20-nor-13-trans prostene |
| 119 | 1-iodo-3-triphenylmethoxy-1-octene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-13-trans prostene |
| 120 | 1-trans-iodo-3-methyl-3-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-15-methyl-13-trans prostene |
| 121 | 1-trans-iodo-4,4-dimethyl-3-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-16,16-dimethyl-13-trans prostene |
| 122 | 1-trans-iodo-4,4-trimethylene-3-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-16,16-trimethylene-13-trans prostene |

| EX-AMPLE | VINYL TIN | CYCLOPENTENONE | PRODUCT PROSTAGLANDIN OF THE PGE1 SERIES |
|---|---|---|---|
| 123 | 1-trans-tri-n-butylstannyl-3-vinyl-3-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,15a-dihydroxy-1-(methoxymethoxycarbonylmethyl)-1,9-dioxo-15-vinyl-13-trans prostene |

| EX-AMPLE | VINYL IODIDE | CYCLOPENTENONE | PRODUCT PROSTAGLANDIN OF THE PGE1 SERIES |
|---|---|---|---|
| 124 | 1-iodo-4-triphenylmethoxy-1-octene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-13-trans prostene |

| EX-AMPLE | VINYL TIN | CYCLOPENTENONE | PRODUCT PROSTAGLANDIN OF THE PGE1 SERIES |
|---|---|---|---|
| 125 | 1-trans-tri-n-butylstannyl-4-methyl-4-trimethylsilyloxy-1-octene | 2-[8-methoxy-8-methoxycarbonyl-7-(trimethylsiloxy)-7-octenyl]-4-trimethylsiloxy cyclopent-2-en-1-one | dl-11a,16-dihydroxy-1-(methoxymethoxycarbonylmethyl)-1,9-dioxo-16-methyl-13-trans prostene |

TABLE XIII-continued

| | VINYL IODIDE | CYCLOPENTENONE | PRODUCT |
|---|---|---|---|
| 126 | 1-trans-tri-n-butylstannyl-5-methyl 4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-17-methyl-13-trans prostene |
| 127 | 1-trans-tri-n-butylstannyl-4-vinyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-vinyl-13-trans prostene |
| 128 | 1-trans-tri-n-butylstannyl-4-trimethylsilylethynyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-ethynyl-13-trans prostene |
| 129 | 1-trans-tri-n-butylstannyl-5-methylene 4-triethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-17-methylene-13-trans prostene |
| 130 | 1-trans-tri-n-butylstannyl-4-methyl-5-methylene 4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-methyl-17-methylene-13-trans prostene |
| 131 | 1-trans-tri-n-butylstannyl-4-dimethoxymethyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-formyl-13-trans prostene |
| 132 | 1-trans-tri-n-butylstannyl-4-fluoromethyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-fluoromethyl-13-trans prostene |
| 133 | 1-trans-tri-n-butylstannyl-4-difluoromethyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-difluoromethyl-13-trans prostene |
| 134 | 1-trans-tri-n-butylstannyl-4-trifluoromethyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-trifluoromethyl-13-trans prostene |
| 135 | 1-trans-tri-n-butylstannyl-4-chloromethyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-chloromethyl-13-trans prostene |
| 136 | 1-trans-tri-n-butylstannyl-4-trimethylsilyloxymethyl-4-trimethylsilyloxy-1-octene | 2-[8-methoxy-8-methoxycarbonyl-7-(trimethylsilyloxy)-7-octenyl]-4-trimethylsiloxy cyclopent-2-en-1-one | dl-11a,16-dihydroxy-1-(methoxymethoxycarbonylmethyl)-1,9-dioxo-16-hydroxymethyl-13-trans prostene |

| EXAMPLE | VINYL IODIDE | CYCLOPENTENONE | PRODUCT PROSTAGLANDIN OF THE PGE1 SERIES |
|---|---|---|---|
| 137 | 1-trans-iodo-3-triphenylmethoxy-1-nonene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-20-methyl-13-trans prostene |
| 138 | 1-trans-iodo-3-methyl-3-trimethylsilyloxy-1-nonene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-15-methyl-20-methyl-13-trans prostene |
| 139 | 1-trans-iodo-4,4-dimethyl-3-trimethylsilyloxy-1-nonene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16,16-dimethyl-20-methyl-13-trans prostene |
| 140 | 1-trans-iodo-4,4-trimethylene-3-trimethylsilyloxy-1-nonene | 2-[8-methoxy-8-methoxycarbonyl-7-(trimethylsilyloxy)-7-octenyl]-4-trimethylsiloxy cyclopent-2-en-1-one | dl-11a,15a-dihydroxy-1-(methoxymethoxycarbonylmethyl)-1,9-dioxo-16,16-trimethylene-20-methyl-13-trans prostene |

EXAM-

TABLE XIII-continued

| EXAMPLE | VINYL TIN | CYCLOPENTENONE | PRODUCT PROSTAGLANDIN OF THE PGE1 SERIES |
|---|---|---|---|
| 141 | 1-trans-tri-n-butylstannyl-3-vinyl-3-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,15a-dihydroxy-1-(methoxymethoxycarbonylmethyl)-1,9-dioxo-15-vinyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 142 | 1-trans-iodo-4-triphenylmethoxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-20-methyl-13-trans prostene |

| EXAMPLE | VINYL TIN | CYCLOPENTENONE | PRODUCT PROSTAGLANDIN OF THE PGE1 SERIES |
|---|---|---|---|
| 143 | 1-trans-tri-n-butylstannyl-4-methyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-methyl-20-methyl-13-trans prostene |
| 144 | 1-trans-tri-n-butylstannyl-5-methyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-17-methyl-20-methyl-13-trans prostene |
| 145 | 1-trans-tri-n-butylstannyl-4-vinyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-vinyl-20-methyl-13-trans prostene |
| 146 | 1-trans-tri-n-butylstannyl-4-trimethylsilylethynyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-ethynyl-20-methyl-13-trans prostene |
| 147 | 1-trans-tri-n-butylstannyl-5-methylene-4-triethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-17-methylene-20-methyl-13-trans prostene |
| 148 | 1-trans-tri-n-butylstannyl-4-methyl-5-methylene-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-methyl-17-methylene-20-methyl-13-trans prostene |
| 149 | 1-trans-tri-n-butylstannyl-4-dimethoxymethyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-formyl-20-methyl-13-trans prostene |
| 150 | 1-trans-tri-n-butylstannyl-4-fluoromethyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-fluoromethyl-20-methyl-13-trans prostene |
| 151 | 1-trans-tri-n-butylstannyl-4-difluoromethyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-difluoromethyl-20-methyl-13-trans prostene |
| 152 | 1-trans-tri-n-butylstannyl-4-trifluoromethyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-trifluoromethyl-20-methyl-13-trans prostene |
| 153 | 1-trans-tri-n-butylstannyl-4-chloromethyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-chloromethyl-20-methyl-13-trans prostene |
| 154 | 1-trans-tri-n-butylstannyl-4-trimethylsilyloxymethyl-4-trimethylsilyloxy-1-nonene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-hydroxymethyl-20-methyl-13-trans prostene |

TABLE XIII-continued

| EXAMPLE | VINYL IODIDE | CYCLOPENTENONE | PRODUCT PROSTAGLANDIN OF THE PGE1 SERIES |
|---|---|---|---|
| 155 | 1-trans-iodo-3-triphenylmethoxy-1-decene | 2-[8-methoxy-8-methoxycarbonyl-7-(trimethylsilyloxy)-7-octenyl]-4-trimethylsilyloxy cyclopent-2-en-1-one | dl-11a,15a-dihydroxy-1-(methoxymethoxycarbonylmethyl)-1,9-dioxo-20-ethyl-13-trans prostene |
| 156 | 1-trans-iodo-3-methyl-3-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,15a-dihydroxy-1-(methoxymethoxycarbonylmethyl)-1,9-dioxo-15-methyl-20-ethyl-13-trans prostene |
| 157 | 1-trans-iodo-4,4-dimethyl-3-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,15a-dihydroxy-1-(methoxymethoxycarbonylmethyl)-1,9-dioxo-16,16-dimethyl-20-ethyl-13-trans prostene |
| 158 | 1-trans-iodo-4,4-trimethylene-3-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,15a-dihydroxy-1-(methoxymethoxycarbonylmethyl)-1,9-dioxo-16,16-trimethylene-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 159 | 1-trans-tri-n-butylstannyl-3-vinyl-3-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,15a-dihydroxy-1-(methoxymethoxycarbonylmethyl)-1,9-dioxo-15-vinyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 160 | 1-trans-iodo-4-triphenylmethoxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-20-ethyl-13-trans prostene |

| EXAMPLE | VINYL TIN | CYCLOPENTENONE | PRODUCT PROSTAGLANDIN OF THE PGE1 SERIES |
|---|---|---|---|
| 161 | 1-trans-tri-n-butylstannyl-4-methyl-4-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-methyl-20-ethyl-13-trans prostene |
| 162 | 1-trans-tri-n-butylstannyl-5-methyl-4-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-17-methyl-20-ethyl-13-trans prostene |
| 163 | 1-trans-tri-n-butylstannyl-4-vinyl-4-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-vinyl-20-ethyl-13-trans prostene |
| 164 | 1-trans-tri-n-butylstannyl-4-trimethylsilylethynyl-4-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-ethynyl-20-ethyl-13-trans prostene |
| 165 | 1-trans-tri-n-butylstannyl-5-methylene-4-triethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-17-methylene-20-ethyl-13-trans prostene |
| 166 | 1-trans-tri-n-butylstannyl-4-methyl-5-methylene-4-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-methyl-17-methylene-20-ethyl-13-trans prostene |
| 167 | 1-trans-tri-n-butylstannyl-4-dimethoxymethyl-4-trimethylsilyloxy-1-decene | 2-[8-methoxy-8-methoxycarbonyl-7-(trimethylsilyloxy)-7-octenyl]-4-trimethylsilyloxy cyclopent-2-en-1-one | dl-11a,16-dihydroxy-1-(methoxymethoxycarbonylmethyl)-1,9-dioxo-16-formyl-20-ethyl-13-trans prostene |

TABLE XIII-continued

| | VINYL IODIDE | CYCLOPENTENONE | PRODUCT PROSTAGLANDIN OF THE PGE1 SERIES |
|---|---|---|---|
| 168 | 1-trans-tri-n-butylstannyl-4-fluoromethyl-4-trimethylsilyloxy-1-decene | 2-[8-methoxy-8-methoxycarbonyl-7-(trimethylsiloxy)-7-octenyl]-4-trimethylsilyloxy cyclopent-2-en-1-one | dl-11a,16-dihydroxy-1-(methoxymethoxycarbonylmethyl)-1,9-dioxo-16-fluoromethyl-20-ethyl-13-trans prostene |
| 169 | 1-trans-tri-n-butylstannyl-4-difluoromethyl-4-trimethylsilyloxy-1-decene | 2-[8-methoxy-8-methoxycarbonyl-7-(trimethylsiloxy)-7-octenyl]-4-trimethylsilyloxy cyclopent-2-en-1-one | dl-11a,16-dihydroxy-1-(methoxymethoxycarbonylmethyl)-1,9-dioxo-16-difluoromethyl-20-ethyl-13-trans prostene |
| 170 | 1-trans-tri-n-butylstannyl-4-trifluoromethyl-4-trimethylsilyloxy-1-decene | 2-[8-methoxy-8-methoxycarbonyl-7-(trimethylsiloxy)-7-octenyl]-4-trimethylsilyloxy cyclopent-2-en-1-one | dl-11a,16-dihydroxy-1-(methoxymethoxycarbonylmethyl)-1,9-dioxo-16-trifluoromethyl-20-ethyl-13-trans prostene |
| 171 | 1-trans-tri-n-butylstannyl-4-chloromethyl-4-trimethylsilyloxy-1-decene | 2-[8-methoxy-8-methoxycarbonyl-7-(trimethylsiloxy)-7-octenyl]-4-trimethylsilyloxy cyclopent-2-en-1-one | dl-11a,16-dihydroxy-1-(methoxymethoxycarbonylmethyl)-1,9-dioxo-16-chloromethyl-20-ethyl-13-trans prostene |
| 172 | 1-trans-tri-n-butylstannyl-4-trimethylsilyloxymethyl-4-trimethylsilyloxy-1-decene | 2-[8-methoxy-8-methoxycarbonyl-7-(trimethylsiloxy)-7-octenyl]-4-trimethylsilyloxy cyclopent-2-en-1-one | dl-11a,16-dihydroxy-1-(methoxymethoxycarbonylmethyl)-1,9-dioxo-16-hydroxymethyl-20-ethyl-13-trans prostene |

| EXAMPLE | VINYL IODIDE | CYCLOPENTENONE | PRODUCT PROSTAGLANDIN OF THE PGE1 SERIES |
|---|---|---|---|
| 173 | 1-trans-iodo-3-triphenylmethoxy-1-heptene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-20-nor-2-homo-13-trans prostene |
| 174 | 1-trans-iodo-3-methyl-3-trimethylsilyloxy-1-heptene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-15-methyl-20-nor-2-homo-13-trans prostene |
| 175 | 1-trans-iodo-4,4-dimethyl-3-trimethylsilyloxy-1-heptene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-16,16-dimethyl-20-nor-2-homo-13-trans prostene |
| 176 | 1-trans-iodo-5,5-dimethyl-3-triphenylmethoxy-1-octene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-17,17-dimethyl-2-homo-13-trans prostene |
| 177 | 1-trans-iodo-4-methyl-3-triphenylmethoxy-1-octene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-16-methyl-2-homo-13-trans prostene |
| 178 | 1-trans-iodo-4,4-trimethylene-3-trimethylsilyloxy-1-heptene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-16,16-trimethylene-20-nor-2-homo-13-trans prostene |

| EXAMPLE | VINYL TIN | CYCLOPENTENONE | PRODUCT PROSTAGLANDIN OF THE PGE1 SERIES |
|---|---|---|---|
| 179 | 1-trans-tri-n-butylstannyl-3-vinyl-3-trimethylsilyloxy-1-heptene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-15-vinyl-20-nor-2-homo-13-trans prostene |
| 180 | 1-trans-tri-n-butylstannyl-4-phenoxy-3-triethylsilyloxy-1-butene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-16-phenoxy-2-homo-17,20-tetranor-13-trans prostene |
| 181 | 1-trans-tri-n-butylstannyl-4-(p-fluorophenoxy)-3-triethylsilyloxy-1-butene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-16-(p-fluorophenoxy)-2-homo-17,20-tetranor-13-trans prostene |
| 182 | 1-trans-tri-n-butylstannyl-4-(m-chlorophenoxy)-3-triethylsilyloxy-1-butene | 2-[9-methoxy-9-methoxycarbonyl-8-(trimethylsiloxy)-8-nonenyl]-4-trimethylsilyloxy cyclopent-2-en-1-one | dl-11a,15a-dihydroxy-1-(methoxymethoxycarbonylmethyl)-1,9-dioxo-16-(m-chlorophenoxy)-2-homo-17,20-tetranor-13-trans prostene |

TABLE XIII-continued

| EX-AM-PLE | VINYL IODIDE | CYCLOPENTENONE | PRODUCT PROSTAGLANDIN OF THE PGE1 SERIES |
|---|---|---|---|
| 183 | 1-trans-tri-n-butylstannyl-4-(m-trifluoromethylphenoxy)-3-triethylsilyloxy-1-butene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16-(m-trifluoromethylphenoxy)-2-homo-17-20-tetranor-13-trans prostene |

| EX-AM-PLE | VINYL IODIDE | CYCLOPENTENONE | PRODUCT PROSTAGLANDIN OF THE PGE1 SERIES |
|---|---|---|---|
| 184 | 1-trans-iodo-5-phenyl-3-triethylsilyloxy-1-pentene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-17-phenyl-2-homo-18-20-trinor-13-trans prostene |
| 185 | 1-trans-iodo-4,4-dimethyl-5-phenyl-3-triethylsilyloxy-1-pentene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16,16-dimethyl-17-phenyl-2-homo-18-20-trinor-13-trans prostene |
| 186 | 1-trans-iodo-4-cyclopentyl-3-triphenylmethoxy-1-butene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16-cyclopentyl-2-homo-17-20-tetranor-13-trans prostene |
| 187 | 1-trans-iodo-4-cyclohexyl-3-triphenylmethoxy-1-butene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16-cyclohexyl-2-homo-17-20-tetranor-13-trans prostene |
| 188 | 1-trans-iodo-4-triphenylmethoxy-1-heptene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-20-nor-2-homo-13-trans prostene |

| EX-AM-PLE | VINYL TIN | CYCLOPENTENONE | PRODUCT PROSTAGLANDIN OF THE PGE1 SERIES |
|---|---|---|---|
| 189 | 1-trans-tri-n-butylstannyl-4-methyl-4-trimethylsilyloxy-1-heptene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-20-nor-2-homo-13-trans prostene |
| 190 | 1-trans-tri-n-butylstannyl-4-ethyl-4-trimethylsilyloxy-1-octene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-ethyl-2-homo-13-trans prostene |
| 191 | 1-trans-tri-n-butylstannyl-5-methyl-4-trimethylsilyloxy-1-heptene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-17-methyl-20-nor-2-homo-13-trans prostene |

| EX-AM-PLE | VINYL IODIDE | CYCLOPENTENONE | PRODUCT PROSTAGLANDIN OF THE PGE1 SERIES |
|---|---|---|---|
| 192 | 1-trans-iodo-5,5-dimethyl-4-trimethylsilyloxy-1-octene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-17,17-dimethyl-2-homo-13-trans prostene |

| EX-AM-PLE | VINYL TIN | CYCLOPENTENONE | PRODUCT PROSTAGLANDIN OF THE PGE1 SERIES |
|---|---|---|---|
| 193 | 1-trans-tri-n-butylstannyl-4-vinyl-4-trimethylsilyloxy-1-heptene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-vinyl-20-nor-2-homo-13-trans prostene |
| 194 | 1-trans-tri-n-butylstannyl-4-cyclopropyl-4-trimethylsilyloxy-1-octene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-cyclopropyl-2-homo-13-trans prostene |
| 195 | 1-trans-tri-n-butylstannyl-4-trimethylsilylethynyl- | 2-[9-methoxy-9-methoxycarbonyl- | dl-11a,16-dihydroxy-1-(methoxymethoxycarbonylmethyl)-1,9-dioxo-16-ethynyl- |

TABLE XIII-continued

| EXAMPLE | VINYL IODIDE | CYCLOPENTENONE | PRODUCT PROSTAGLANDIN OF THE PGE1 SERIES |
|---|---|---|---|
| | 4-trimethylsilyloxy-1-heptene | 8-(trimethylsilyloxy)-8-nonenyl]-4-trimethylsilyloxy cyclopent-2-en-1-one | 20-nor-2-homo-13-trans prostene |
| 196 | 1-trans-tri-n-butylstannyl-5-methylene-4-triethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-17-methylene-20-nor-2-homo-13-trans prostene |
| 197 | 1-trans-tri-n-butylstannyl-4-methyl-5-methylene-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-methyl-17-methylene-20-nor-2-homo-13-trans prostene |
| 198 | 1-trans-tri-n-butylstannyl-4-dimethoxymethyl-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-formyl-20-nor-2-homo-13-trans prostene |
| 199 | 1-trans-tri-n-butylstannyl-4-fluoromethyl-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-fluoromethyl-20-nor-2-homo-13-trans prostene |
| 200 | 1-trans-tri-n-butylstannyl-4-difluoromethyl-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-difluoromethyl-20-nor-2-homo-13-trans prostene |
| 201 | 1-trans-tri-n-butylstannyl-4-trifluoromethyl-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-trifluoromethyl-20-nor-2-homo-13-trans prostene |
| 202 | 1-trans-tri-n-butylstannyl-4-chloromethyl-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-chloromethyl-20-nor-2-homo-13-trans-prostene |
| 203 | 1-trans-tri-n-butylstannyl-4-trimethylsilyloxymethyl-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-hydroxymethyl-20-nor-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 204 | 1-trans-iodo-4-methyl-7-chloro-4-trimethylsilyloxy-1-heptene | 2-[9-methoxy-9-methoxycarbonyl-8-(trimethylsilyoxy)-8-nonenyl]-4-trimethylsilyloxy cyclopent-2-en-1-one | dl-11a,16-dihydroxy-1-(methoxymethoxycarbonylmethyl)-1,9-dioxo-16-methyl-19-chloro-2-homo-20-nor-13-trans prostene |
| 205 | 1-trans-iodo-3-triphenylmethoxy-1-octene | 2-[9-methoxy-9-methoxycarbonyl-8-(trimethylsilyoxy)-8-nonenyl]-4-trimethylsilyloxy cyclopent-2-en-1-one | dl-11a,15a-dihydroxy-1-(methoxymethoxycarbonylmethyl)-1,9-dioxo-2-homo-13-trans prostene |
| 206 | 1-trans-iodo-3-methyl-3-trimethylsilyloxy-1-octene | 2-[9-methoxy-9-methoxycarbonyl-8-(trimethylsilyoxy)-8-nonenyl]-4-trimethylsilyloxy cyclopent-2-en-1-one | dl-11a,15a-dihydroxy-1-(methoxymethoxycarbonylmethyl)-1,9-dioxo-15-methyl-2-homo-13-trans prostene |
| 207 | 1-trans-iodo-4,4-dimethyl-3-trimethylsilyloxy-1-octene | 2-[9-methoxy-9-methoxycarbonyl-8-(trimethylsilyoxy)-8-nonenyl]-4-trimethylsilyloxy cyclopent-2-en-1-one | dl-11a,15a-dihydroxy-1-(methoxymethoxycarbonylmethyl)-1,9-dioxo-16,16-dimethyl-2-homo-13-trans prostene |
| 208 | 1-trans-iodo-4,4-trimethylene-3-trimethylsilyloxy-1-octene | 2-[9-methoxy-9-methoxycarbonyl-8-(trimethylsilyoxy)-8-nonenyl]-4-trimethylsilyloxy cyclopent-2-en-1-one | dl-11a,15a-dihydroxy-1-(methoxymethoxycarbonylmethyl)-1,9-dioxo-16,16-trimethylene-2-homo-13-trans prostene |

| EXAMPLE | VINYL TIN | CYCLOPENTENONE | PRODUCT PROSTAGLANDIN OF THE PGE1 SERIES |
|---|---|---|---|
| 209 | 1-trans-tri-n-butylstannyl-3-vinyl-3-trimethylsilyloxy-1-octene | 2-[9-methoxy-9-methoxycarbonyl-8-(trimethylsilyoxy)-8-nonenyl]-4-trimethylsilyloxy cyclopent-2-en-1-one | dl-11a,15a-dihydroxy-1-(methoxymethoxycarbonylmethyl)-1,9-dioxo-15-vinyl-2-homo-13-trans prostene |

TABLE XIII-continued

| EXAMPLE | VINYL IODIDE | CYCLOPENTENONE | PRODUCT PROSTAGLANDIN OF THE PGE1 SERIES |
|---|---|---|---|
| 210 | 1-trans-iodo-4-triphenylmethoxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-2-homo-13-trans prostene |

| EXAMPLE | VINYL TIN | CYCLOPENTENONE | PRODUCT PROSTAGLANDIN OF THE PGE1 SERIES |
|---|---|---|---|
| 211 | 1-trans-tri-n-butylstannyl-4-methyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-2-homo-13-trans prostene |
| 212 | 1-trans-tri-n-butylstannyl-5-methyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-17-methyl-2-homo-13-trans prostene |
| 213 | 1-trans-tri-n-butylstannyl-4-vinyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-vinyl-2-homo-13-trans prostene |
| 214 | 1-trans-tri-n-butylstannyl-4-trimethylsilylethynyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-ethynyl-2-homo-13-trans prostene |
| 215 | 1-trans-tri-n-butylstannyl-5-methylene-4-triethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-17-methylene-2-homo-13-trans prostene |
| 216 | 1-trans-tri-n-butylstannyl-4-methyl-5-methylene-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-17-methylene-2-homo-13-trans prostene |
| 217 | 1-trans-tri-n-butylstannyl-4-dimethoxymethyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-formyl-2-homo-13-trans prostene |
| 218 | 1-trans-tri-n-butylstannyl-4-fluoromethyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-fluoromethyl-2-homo-13-trans prostene |
| 219 | 1-trans-tri-n-butylstannyl-4-difluoromethyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-difluoromethyl-2-homo-13-trans prostene |
| 220 | 1-trans-tri-n-butylstannyl-4-trifluoromethyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-trifluoromethyl-2-homo-13-trans prostene |
| 221 | 1-trans-tri-n-butylstannyl-4-chloromethyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-chloromethyl-2-homo-13-trans prostene |
| 222 | 1-trans-tri-n-butylstannyl-4-trimethylsilyloxymethyl-4-trimethylsilyloxy-1-octene | 2-[9-methoxy-9-methoxycarbonyl-8-(trimethylsilyloxy)-8-nonenyl]-4-trimethylsiloxy cyclopent-2-en-1-one | dl-11a,16-dihydroxy-1-(methoxymethoxycarbonylmethyl)-1,9-dioxo-16-hydroxymethyl-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 223 | 1-trans-iodo-3-triphenylmethoxy-1-nonene | 2-[9-methoxy-9-methoxycarbonyl-8-(trimethylsilyloxy)-8-nonenyl]-4-trimethylsiloxy cyclopent-2-en-1-one | dl-11a,15a-dihydroxy-1-(methoxymethoxycarbonylmethyl)-1,9-dioxo-20-methyl-2-homo-13-trans prostene |
| 224 | 1-trans-iodo-3-methyl- | 2-[9-methoxy-9-methoxycarbonyl- | dl-11a,15a-dihydroxy-1-(methoxymethoxycarbonylmethyl)-1,9-dioxo-15-methyl- |

TABLE XIII-continued

| EXAMPLE | VINYL TIN / VINYL IODIDE | CYCLOPENTENONE | PRODUCT PROSTAGLANDIN OF THE PGE1 SERIES |
|---|---|---|---|
| | 3-trimethylsilyloxy-1-nonene | 8-(trimethylsiloxy)-8-nonenyl]-4-trimethylsiloxy cyclopent-2-en-1-one | 20-methyl-2-homo-13-trans prostene |
| 225 | 1-trans-iodo-4,4-dimethyl-3-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16,16-dimethyl-20-methyl-2-homo-13-trans prostene |
| 226 | 1-trans-iodo-4,4-trimethylene-3-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16,16-trimethylene-20-methyl-2-homo-13-trans prostene |

| EXAMPLE | VINYL TIN | CYCLOPENTENONE | PRODUCT PROSTAGLANDIN OF THE PGE1 SERIES |
|---|---|---|---|
| 227 | 1-trans-tri-n-butylstannyl-3-vinyl-3-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-15-vinyl-20-methyl-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 228 | 1-trans-iodo-4-triphenylmethoxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-20-methyl-2-homo-13-trans prostene |

| EXAMPLE | VINYL TIN | CYCLOPENTENONE | PRODUCT PROSTAGLANDIN OF THE PGE1 SERIES |
|---|---|---|---|
| 229 | 1-trans-tri-n-butylstannyl-4-methyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-20-methyl-2-homo-13-trans prostene |
| 230 | 1-trans-tri-n-butylstannyl-5-methyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-17-methyl-20-methyl-2-homo-13-trans prostene |
| 231 | 1-trans-tri-n-butylstannyl-4-vinyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-vinyl-20-methyl-2-homo-13-trans prostene |
| 232 | 1-trans-tri-n-butylstannyl-4-trimethylsilylethynyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-ethynyl-20-methyl-2-homo-13-trans prostene |
| 233 | 1-trans-tri-n-butylstannyl-5-methylene-4-triethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-17-methylene-20-methyl-2-homo-13-trans prostene |
| 234 | 1-trans-tri-n-butylstannyl-4-methyl-5-methylene-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-17-methylene-20-methyl-2-homo-13-trans prostene |
| 235 | 1-trans-tri-n-butylstannyl-4-dimethoxymethyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-formyl-20-methyl-2-homo-13-trans prostene |
| 236 | 1-trans-tri-n-butylstannyl-4-fluoromethyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-fluoromethyl-20-methyl-2-homo-13-trans prostene |
| 237 | 1-trans-tri-n-butylstannyl-4-difluoromethyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-difluoromethyl-20-methyl-2-homo-13-trans prostene |

TABLE XIII-continued

| EX-AM-PLE | VINYL IODIDE / VINYL TIN | CYCLOPENTENONE | PRODUCT PROSTAGLANDIN OF THE PGE1 SERIES |
|---|---|---|---|
| 238 | 1-trans-tri-n-butylstannyl-4-trifluoromethyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-trifluoromethyl-20-methyl-2-homo-13-trans prostene |
| 239 | 1-trans-tri-n-butylstannyl-4-chloromethyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-chloromethyl-20-methyl-2-homo-13-trans prostene |
| 240 | 1-trans-tri-n-butylstannyl-4-trimethylsilyloxymethyl-4-trimethylsilyloxy-1-nonene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-hydroxymethyl-20-methyl-2-homo-13-trans prostene |

| EX-AM-PLE | VINYL IODIDE | CYCLOPENTENONE | PRODUCT PROSTAGLANDIN OF THE PGE1 SERIES |
|---|---|---|---|
| 241 | 1-trans-iodo-3-triphenylmethoxy-1-decene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-20-ethyl-2-homo-13-trans prostene |
| 242 | 1-trans-iodo-3-methyl-3-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-15-methyl-20-ethyl-2-homo-13-trans prostene |
| 243 | 1-trans-iodo-4,4-dimethyl-3-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16,16-dimethyl-20-ethyl-2-homo-13-trans prostene |
| 244 | 1-trans-iodo-4,4-trimethylene-3-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-16,16-trimethylene-20-ethyl-2-homo-13-trans prostene |

| EX-AM-PLE | VINYL TIN | CYCLOPENTENONE | PRODUCT PROSTAGLANDIN OF THE PGE1 SERIES |
|---|---|---|---|
| 245 | 1-trans-tri-n-butylstannyl-3-vinyl-3-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,15a-dihydroxy-1-(methoxymethoxycarbonylmethyl)-1,9-dioxo-15-vinyl-20-ethyl-2-homo-13-trans prostene |

| EX-AM-PLE | VINYL IODIDE | CYCLOPENTENONE | PRODUCT PROSTAGLANDIN OF THE PGE1 SERIES |
|---|---|---|---|
| 246 | 1-trans-iodo-4-triphenylmethoxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-20-ethyl-2-homo-13-trans prostene |

| EX-AM-PLE | VINYL TIN | CYCLOPENTENONE | PRODUCT PROSTAGLANDIN OF THE PGE1 SERIES |
|---|---|---|---|
| 247 | 1-trans-tri-n-butylstannyl-4-methyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-20-ethyl-2-homo-13-trans prostene |
| 248 | 1-trans-tri-n-butylstannyl-5-methyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-17-methyl-20-ethyl-2-homo-13-trans prostene |
| 249 | 1-trans-tri-n-butylstannyl-4-vinyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-vinyl-20-ethyl-2-homo-13-trans prostene |
| 250 | 1-trans-tri-n-butylstannyl-4-trimethylsilylethynyl- | 2-[9-methoxy-9-methoxycarbonyl- | dl-11a,16-dihydroxy-1-(methoxymethoxycarbonylmethyl)-1,9-dioxo-16-ethynyl- |

TABLE XIII-continued

| | VINYL IODIDE | CYCLOPENTENONE | PRODUCT PROSTAGLANDIN OF THE PGE1 SERIES |
|---|---|---|---|
| | 4-trimethylsilyloxy-1-decene | 8-(trimethylsilyloxy)-8-nonenyl]-4-trimethylsiloxy cyclopent-2-en-1-one | 20-ethyl-2-homo-13-trans prostene |
| 251 | 1-trans-tri-n-butylstannyl-5-methylene 4-triethylsilyloxy-1-decene | 2-[9-methoxy-9-methoxycarbonyl-8-(trimethylsiloxy)-8-nonenyl] -4-trimethylsiloxy cyclopent-2-en-1-one | dl-11a,16-dihydroxy-1-(methoxymethoxycarbonylmethyl)-1,9-dioxo-17-methylene-20-ethyl-2-homo-13-trans prostene |
| 252 | 1-trans-tri-n-butylstannyl-4-methyl-5-methylene 4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-methyl-17-methylene-20-ethyl-2-homo-13-trans prostene |
| 253 | 1-trans-tri-n-butylstannyl-4-methyl-4-dimethoxymethyl 4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-formyl-20-ethyl-2-homo-13-trans prostene |
| 254 | 1-trans-tri-n-butylstannyl-4-fluoromethyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-fluoromethyl-20-ethyl-2-homo-13-trans prostene |
| 255 | 1-trans-tri-n-butylstannyl-4-difluoromethyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-difluoromethyl-20-ethyl-2-homo-13-trans prostene |
| 256 | 1-trans-tri-n-butylstannyl-4-trifluoromethyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-trifluoromethyl-20-ethyl-2-homo-13-trans prostene |
| 257 | 1-trans-tri-n-butylstannyl-4-chloromethyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-chloromethyl-20-ethyl-2-homo-13-trans prostene |
| 258 | 1-trans-tri-n-butylstannyl-4-trimethylsilyloxymethyl-4-trimethylsilyloxy-1-decene | 2-[9-methoxy-9-methoxycarbonyl-8-(trimethylsiloxy)-8-nonenyl]-4-trimethylsiloxy cyclopent-2-en-1-one | dl-11a,16-dihydroxy-1-(methoxymethoxycarbonylmethyl)-1,9-dioxo-16-hydroxymethyl-20-ethyl-2-homo-13-trans prostene |

| EXAMPLE | VINYL IODIDE | CYCLOPENTENONE | PRODUCT PROSTAGLANDIN OF THE PGE1 SERIES |
|---|---|---|---|
| 259 | 1-trans-iodo-3-triphenylmethoxy-1-heptene | 2-[8-methoxy-8-methoxycarbonyl-7-(trimethylsilyoxy)-7-octenyl]-4R-trimethylsiloxy cyclopent-2-en-1-one | nat-11a,15a-dihydroxy-1-(methoxymethoxycarbonylmethyl)-1,9-dioxo-20-nor-13-trans prostene |
| 260 | 1-trans-iodo-3-methyl-3-trimethylsilyloxy-1-heptene | 2-[8-methoxy-8-methoxycarbonyl-7-(trimethylsilyoxy)-7-octenyl]-4R-trimethylsiloxy cyclopent-2-en-1-one | nat-11a,15a-dihydroxy-1-(methoxymethoxycarbonylmethyl)-1,9-dioxo-15-methyl-20-nor-13-trans prostene |
| 261 | 1-trans-iodo-4,4-dimethyl-3-trimethylsilyloxy-1-heptene | 2-[8-methoxy-8-methoxycarbonyl-7-(trimethylsilyoxy)-7-octenyl]-4R-trimethylsiloxy cyclopent-2-en-1-one | nat-11a,15a-dihydroxy-1-(methoxymethoxycarbonylmethyl)-1,9-dioxo-16,16-dimethyl-20-nor-13-trans prostene |
| 262 | 1-trans-iodo-5,5-dimethyl-3-triphenylmethoxy-1-octene | 2-[8-methoxy-8-methoxycarbonyl-7-(trimethylsilyoxy)-7-octenyl]-4R-trimethylsiloxy cyclopent-2-en-1-one | nat-11a,15a-dihydroxy-1-(methoxymethoxycarbonylmethyl)-1,9-dioxo-17,17-dimethyl-13-trans prostene |
| 263 | 1-trans-iodo-4-methyl-3-triphenylmethoxy-1-octene | 2-[8-methoxy-8-methoxycarbonyl-7-(trimethylsilyoxy)-7-octenyl]-4R-trimethylsiloxy cyclopent-2-en-1-one | nat-11a,15a-dihydroxy-1-(methoxymethoxycarbonylmethyl)-1,9-dioxo-16-methyl-13-trans prostene |
| 264 | 1-trans-iodo-4,4-trimethylene-3-trimethylsilyloxy-1-heptene | 2-[8-methoxy-8-methoxycarbonyl-7-(trimethylsilyoxy)-7-octenyl]-4R-trimethylsiloxy cyclopent-2-en-1-one | nat-11a,15a-dihydroxy-1-(methoxymethoxycarbonylmethyl)-1,9-dioxo-16,16-trimethylene-20-nor-13-trans prostene |

| EXAMPLE | VINYL TIN | CYCLOPENTENONE | PRODUCT PROSTAGLANDIN OF THE PGE1 SERIES |
|---|---|---|---|
| 265 | 1-trans-tri-n-butylstannyl-3-vinyl- | 2-[8-methoxy-8-methoxycarbonyl- | nat-11a,15a-dihydroxy-1-(methoxymethoxycarbonylmethyl)-1,9-dioxo-15-vinyl- |

TABLE XIII-continued

| EXAMPLE | VINYL IODIDE | CYCLOPENTENONE | PRODUCT PROSTAGLANDIN OF THE PGE1 SERIES |
|---|---|---|---|
| 266 | 1-trans-tri-n-butylstannyl-4-phenoxy-3-trimethylsilyloxy-1-butene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16-phenoxy-17-20-tetranor-13-trans prostene |
| 267 | 1-trans-tri-n-butylstannyl-4-(p-fluorophenoxy)-3-triethylsilyloxy-1-butene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16-(p-fluorophenoxy)-17-20-tetranor-13-trans prostene |
| 268 | 1-trans-tri-n-butylstannyl-4-(m-chlorophenoxy)-3-triethylsilyloxy-1-butene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16-(m-chlorophenoxy)-17-20-tetranor-13-trans prostene |
| 269 | 1-trans-tri-n-butylstannyl-4-(m-trifluoromethylphenoxy)-3-triethylsilyloxy-1-butene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE PGE1 SERIES |
|---|---|---|---|
| 270 | 1-trans-iodo-5-phenyl-3-triethylsilyloxy-1-pentene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-17-phenyl-18-20-trinor-13-trans prostene |
| 271 | 1-trans-iodo-4,4-dimethyl-5-phenyl-3-triethylsilyloxy-1-pentene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16,16-dimethyl-17-phenyl-18-20-trinor-13-trans prostene |
| 272 | 1-trans-iodo-4-cyclopentyl-3-triphenylmethoxy-1-butene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16-cyclopentyl-17-20-tetranor-13-trans prostene |
| 273 | 1-trans-iodo-4-cyclohexyl-3-triphenylmethoxy-1-butene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-16-cyclohexyl-17-20-tetranor-13-trans prostene |
| 274 | 1-trans-iodo-4-triphenylmethoxy-1-heptene | 2-[8-methoxy-8-methoxycarbonyl-7-(trimethylsilyloxy)-7-octenyl]-4R-trimethylsiloxy cyclopent-2-en-1-one | nat-11a,15a-dihydroxy-1-(methoxymethoxycarbonylmethyl)-1,9-dioxo-20-nor-13-trans prostene |

| EXAMPLE | VINYL TIN | CYCLOPENTENONE | PRODUCT PROSTAGLANDIN OF THE PGE1 SERIES |
|---|---|---|---|
| 275 | 1-trans-tri-n-butylstannyl-4-methyl-4-trimethylsilyloxy-1-heptene | 2-[8-methoxy-8-methoxycarbonyl-7-(trimethylsilyloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-20-nor-13-trans prostene |
| 276 | 1-trans-tri-n-butylstannyl-4-ethyl-4-trimethylsilyloxy-1-octene | 2-[8-methoxy-8-methoxycarbonyl-7-(trimethylsilyloxy)-7-octenyl]-4R-trimethylsiloxy cyclopent-2-en-1-one | nat-11a,16-dihydroxy-1-(methoxymethoxycarbonylmethyl)-1,9-dioxo-16-ethyl-13-trans prostene |
| 277 | 1-trans-tri-n-butylstannyl-5-methyl-4-trimethylsilyloxy-1-heptene | 2-[8-methoxy-8-methoxycarbonyl-7-(trimethylsilyloxy)-7-octenyl]-4R-trimethylsiloxy cyclopent-2-en-1-one | nat-11a,16-dihydroxy-1-(methoxymethoxycarbonylmethyl)-1,9-dioxo-17-methyl-20-nor-13-trans prostene |

| EXAMPLE | VINYL IODIDE | CYCLOPENTENONE | PRODUCT PROSTAGLANDIN OF THE PGE1 SERIES |
|---|---|---|---|
| 278 | 1-trans-iodo-5,5-dimethyl-4-trimethylsilyloxy-1-octene | 2-[8-methoxy-8-methoxycarbonyl-7-(trimethylsilyloxy)-7-octenyl]-4R-trimethylsiloxy cyclopent-2-en-1-one | nat-11a,16-dihydroxy-1-(methoxymethoxycarbonylmethyl)-1,9-dioxo-17,17-dimethyl-13-trans prostene |

TABLE XIII-continued

| EXAMPLE | VINYL TIN | CYCLOPENTENONE | PRODUCT PROSTAGLANDIN OF THE PGE1 SERIES |
|---|---|---|---|
| 279 | 1-trans-tri-n-butylstannyl-4-vinyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-vinyl-20-nor-13-trans prostene |
| 280 | 1-trans-tri-n-butylstannyl-4-cyclopropyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-cyclopropyl-13-trans prostene |
| 281 | 1-trans-tri-n-butylstannyl-4-trimethylsilylethynyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-ethynyl-20-nor-13-trans prostene |
| 282 | 1-trans-tri-n-butylstannyl-5-methylene-4-triethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-17-methylene-20-nor-13-trans prostene |
| 283 | 1-trans-tri-n-butylstannyl-4-methyl-5-methylene-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-17-methylene-20-nor-13-trans prostene |
| 284 | 1-trans-tri-n-butylstannyl-4-dimethoxymethyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-formyl-20-nor-13-trans prostene |
| 285 | 1-trans-tri-n-butylstannyl-4-fluoromethyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-fluoromethyl-20-nor-13-trans prostene |
| 286 | 1-trans-tri-n-butylstannyl-4-difluoromethyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-difluoromethyl-20-nor-13-trans prostene |
| 287 | 1-trans-tri-n-butylstannyl-4-trifluoromethyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-trifluoromethyl-20-nor-13-trans prostene |
| 288 | 1-trans-tri-n-butylstannyl-4-chloromethyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-chloromethyl-20-nor-13-trans prostene |
| 289 | 1-trans-tri-n-butylstannyl-4-trimethylsilyloxymethyl-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-hydroxymethyl-20-nor-13-trans prostene |

| EXAMPLE | VINYL IODIDE | CYCLOPENTENONE | PRODUCT PROSTAGLANDIN OF THE PGE1 SERIES |
|---|---|---|---|
| 290 | 1-trans-iodo-4-methyl-7-chloro-4-trimethylsilyloxy-1-heptene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-19-chloro-20-nor-13-trans prostene |
| 291 | 1-trans-iodo-3-triphenylmethoxy-1-octene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-13-trans prostene |
| 292 | 1-trans-iodo-3-methyl-3-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-15-methyl-13-trans prostene |
| 293 | 1-trans-iodo-4,4-dimethyl-3-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-16,16-dimethyl-13-trans prostene |
| 294 | 1-trans-iodo-4,4-trimethylene- | 2-[8-methoxy-8-methoxycarbonyl- | nat-11a,15a-dihydroxy-1-(methoxymethoxycarbonylmethyl)-1,9-dioxo- |

TABLE XIII-continued

| EX-AM-PLE | VINYL TIN | CYCLOPENTENONE | PRODUCT PROSTAGLANDIN OF THE PGE1 SERIES |
|---|---|---|---|
| | 3-trimethylsilyloxy-1-octene | 7-(trimethylsilyloxy)-7-octenyl]-4R-trimethylsiloxy cyclopent-2-en-1-one | 16,16-trimethylene-13-trans prostene |
| 295 | 1-trans-tri-n-butylstannyl-3-vinyl-3-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-15-vinyl-13-trans prostene |

| EX-AM-PLE | VINYL IODIDE | CYCLOPENTENONE | PRODUCT PROSTAGLANDIN OF THE PGE1 SERIES |
|---|---|---|---|
| 296 | 1-trans-iodo-4-triphenylmethoxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-13-trans prostene |

| EX-AM-PLE | VINYL TIN | CYCLOPENTENONE | PRODUCT PROSTAGLANDIN OF THE PGE1 SERIES |
|---|---|---|---|
| 297 | 1-trans-tri-n-butylstannyl-4-methyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-13-trans prostene |
| 298 | 1-trans-tri-n-butylstannyl-5-methyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-17-methyl-13-trans prostene |
| 299 | 1-trans-tri-n-butylstannyl-4-vinyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-vinyl-13-trans prostene |
| 300 | 1-trans-tri-n-butylstannyl-4-trimethylsilyethynyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-ethynyl-13-trans prostene |
| 301 | 1-trans-tri-n-butylstannyl-5-methylene-4-triethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-17-methylene-13-trans prostene |
| 302 | 1-trans-tri-n-butylstannyl-4-methyl-5-methylene-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-17-methylene-13-trans prostene |
| 303 | 1-trans-tri-n-butylstannyl-4-dimethoxymethyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-formyl-13-trans prostene |
| 304 | 1-trans-tri-n-butylstannyl-4-fluoromethyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-fluoromethyl-13-trans prostene |
| 305 | 1-trans-tri-n-butylstannyl-4-difluoromethyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-difluoromethyl-13-trans prostene |
| 306 | 1-trans-tri-n-butylstannyl-4-trifluoromethyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-trifluoromethyl-13-trans prostene |
| 307 | 1-trans-tri-n-butylstannyl-4-chloromethyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-chloromethyl-13-trans prostene |

TABLE XIII-continued

| EXAMPLE | VINYL IODIDE | CYCLOPENTENONE | PRODUCT PROSTAGLANDIN OF THE PGE1 SERIES |
|---|---|---|---|
| 308 | 1-trans-tri-n-butylstannyl-4-trimethylsilyloxymethyl-4-trimethylsilyloxy-1-octene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-,16-hydroxymethyl-13-trans prostene |

| EXAMPLE | VINYL IODIDE | CYCLOPENTENONE | PRODUCT PROSTAGLANDIN OF THE PGE1 SERIES |
|---|---|---|---|
| 309 | 1-trans-iodo-3-triphenylmethoxy-1-nonene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-20-methyl-13-trans prostene |
| 310 | 1-trans-iodo-3-methyl-3-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-15-methyl-20-methyl-13-trans prostene |
| 311 | 1-trans-iodo-4,4-dimethyl-3-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-16,16-dimethyl-20-methyl-13-trans prostene |
| 312 | 1-trans-iodo-4,4-trimethylene-3-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-16,16-trimethylene-20-methyl-13-trans prostene |

| EXAMPLE | VINYL TIN | CYCLOPENTENONE | PRODUCT PROSTAGLANDIN OF THE PGE1 SERIES |
|---|---|---|---|
| 313 | 1-trans-tri-n-butylstannyl-3-vinyl-3-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-15-vinyl-20-methyl-13-trans prostene |

| EXAMPLE | VINYL IODIDE | CYCLOPENTENONE | PRODUCT PROSTAGLANDIN OF THE PGE1 SERIES |
|---|---|---|---|
| 314 | 1-trans-iodo-4-triphenylmethoxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-20-methyl-13-trans prostene |

| EXAMPLE | VINYL TIN | CYCLOPENTENONE | PRODUCT PROSTAGLANDIN OF THE PGE1 SERIES |
|---|---|---|---|
| 315 | 1-trans-tri-n-butylstannyl-4-methyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-methyl-20-methyl-13-trans prostene |
| 316 | 1-trans-tri-n-butylstannyl-5-methyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-17-methyl-20-methyl-13-trans prostene |
| 317 | 1-trans-tri-n-butylstannyl-4-vinyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-vinyl-20-methyl-13-trans prostene |
| 318 | 1-trans-tri-n-butylstannyl-4-trimethylsilylethynyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-ethynyl-20-methyl-13-trans prostene |
| 319 | 1-trans-tri-n-butylstannyl-5-methylene-4-triethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-17-methylene-20-methyl-13-trans prostene |
| 320 | 1-trans-tri-n-butylstannyl-4-methyl-5-methylene | 2-[8-methoxy-8-methoxycarbonyl- | nat-11a,16-dihydroxy-1-(methoxymethoxycarbonylmethyl)-1,9-dioxo-16-methyl- |

TABLE XIII-continued

| | | | |
|---|---|---|---|
| | | 4-trimethylsilyloxy-1-nonene | 7-(trimethylsiloxy)-7-octenyl]-4R-trimethylsiloxy cyclopent-2-en-1-one | 17-methylene-20-methyl-13-trans prostene |
| 321 | 1-trans-tri-n-butylstannyl-4-dimethoxymethyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-formyl-20-methyl-13-trans prostene |
| 322 | 1-trans-tri-n-butylstannyl-4-fluoromethyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-fluoromethyl-20-methyl-13-trans prostene |
| 323 | 1-trans-tri-n-butylstannyl-4-difluoromethyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-difluoromethyl-20-methyl-13-trans prostene |
| 324 | 1-trans-tri-n-butylstannyl-4-trifluoromethyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-trifluoromethyl-20-methyl-13-trans prostene |
| 325 | 1-trans-tri-n-butylstannyl-4-chloromethyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-chloromethyl-20-methyl-13-trans prostene |
| 326 | 1-trans-tri-n-butylstannyl-4-trimethylsilyloxymethyl-4-trimethylsilyloxy-1-nonene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-16-hydroxymethyl-20-methyl-13-trans prostene |
| EXAMPLE | VINYL IODIDE | CYCLOPENTENONE | PRODUCT PROSTAGLANDIN OF THE PGE1 SERIES |
| 327 | 1-trans-iodo-3-triphenylmethoxy-1-decene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-20-ethyl-13-trans prostene |
| 328 | 1-trans-iodo-3-methyl-3-trimethylsilyloxy-1-decene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-15-methyl-20-ethyl-13-trans prostene |
| 329 | 1-trans-iodo-4,4-dimethyl-3-trimethylsilyloxy-1-decene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-16,16-dimethyl-20-ethyl-13-trans prostene |
| 330 | 1-trans-iodo-4,4-trimethylene-3-trimethylsilyloxy-1-decene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-16,16-trimethylene-20-ethyl-13-trans prostene |
| EXAMPLE | VINYL TIN | CYCLOPENTENONE | PRODUCT PROSTAGLANDIN OF THE PGE1 SERIES |
| 331 | 1-trans-tri-n-butylstannyl-3-vinyl-3-trimethylsilyloxy-1-decene | 2-[8-methoxy-8-methoxycarbonyl-7-(trimethylsiloxy)-7-octenyl]-4R-trimethylsiloxy cyclopent-2-en-1-one | nat-11a,15a-dihydroxy-1-(methoxymethoxycarbonylmethyl)-1,9-dioxo-15-vinyl-20-ethyl-13-trans prostene |
| EXAMPLE | VINYL IODIDE | CYCLOPENTENONE | PRODUCT PROSTAGLANDIN OF THE PGE1 SERIES |
| 332 | 1-trans-iodo-4-triphenylmethoxy-1-decene | 2-[8-methoxy-8-methoxycarbonyl-7-(trimethylsiloxy)-7-octenyl]-4R-trimethylsiloxy cyclopent-2-en-1-one | nat-11a,16-dihydroxy-1-(methoxymethoxycarbonylmethyl)-1,9-dioxo-20-ethyl-13-trans prostene |
| EXAM- | | | |

TABLE XIII-continued

| EXAMPLE | VINYL TIN | CYCLOPENTENONE | PRODUCT PROSTAGLANDIN OF THE PGE1 SERIES |
|---|---|---|---|
| 333 | 1-trans-tri-n-butylstannyl-4-methyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-methyl-20-ethyl-13-trans prostene |
| 334 | 1-trans-tri-n-butylstannyl-5-methyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-17-methyl-20-ethyl-13-trans prostene |
| 335 | 1-trans-tri-n-butylstannyl-4-vinyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-vinyl-20-ethyl-13-trans prostene |
| 336 | 1-trans-tri-n-butylstannyl-4-trimethylsilyethynyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-ethynyl-20-ethyl-13-trans prostene |
| 337 | 1-trans-tri-n-butylstannyl-5-methylene-4-triethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-17-methylene-20-ethyl-13-trans prostene |
| 338 | 1-trans-tri-n-butylstannyl-4-methyl-5-methylene-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-methyl-17-methylene-20-ethyl-13-trans prostene |
| 339 | 1-trans-tri-n-butylstannyl-4-dimethoxymethyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-formyl-20-ethyl-13-trans prostene |
| 340 | 1-trans-tri-n-butylstannyl-4-fluoromethyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-fluoromethyl-20-ethyl-13-trans prostene |
| 341 | 1-trans-tri-n-butylstannyl-4-difluoromethyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-difluoromethyl-20-ethyl-13-trans prostene |
| 342 | 1-trans-tri-n-butylstannyl-4-trifluoromethyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-trifluoromethyl-20-ethyl-13-trans prostene |
| 343 | 1-trans-tri-n-butylstannyl-4-chloromethyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-chloromethyl-20-ethyl-13-trans prostene |
| 344 | 1-trans-tri-n-butylstannyl-4-trimethylsilyloxymethyl-4-trimethylsilyloxy-1-decene | 2-[8-methoxy-8-methoxycarbonyl-7-(trimethylsilyloxy)-7-octenyl]-4R-trimethylsilyloxy cyclopent-2-en-1-one | nat-11a,16-dihydroxy-1-(methoxymethoxycarbonylmethyl)-1,9-dioxo-16-hydroxymethyl-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 345 | 1-trans-iodo-3-triphenylmethoxy-1-heptene | 2-[7-methoxy-7-methoxycabonyl-6-(trimethylsilyoxy)-6-heptenyl] cyclopent-2-en-1-one | dl-15a-hydroxy-1-(methoxymethoxycarbonylmethyl)-1,9-dioxo-20-nor-2-nor-13-trans prostene |
| 346 | 1-trans-iodo-3-methyl-3-trimethylsilyloxy-1-heptene | 2-[7-methoxy-7-methoxycarbonyl-6-(trimethylsilyoxy)-6-heptenyl] cyclopent-2-en-1-one | dl-15a-hydroxy-1-(methoxymethoxycarbonylmethyl)-1,9-dioxo-15-methyl-20-nor-2-nor-13-trans prostene |
| 347 | 1-trans-iodo-4,4-dimethyl-3-trimethylsilyloxy-1-heptene | 2-[7-methoxy-7-methoxycabonyl-6-(trimethylsilyoxy)-6-heptenyl] cyclopent-2-en-1-one | dl-15a-hydroxy-1-(methoxymethoxycarbonylmethyl)-1,9-dioxo-16,16-dimethyl-20-nor-2-nor-13-trans prostene |
| 348 | 1-trans-iodo-5,5-dimethyl-3-triphenylmethoxy-1-octene | 2-[7-methoxy-7-methoxycabonyl-6-(trimethylsilyoxy)-6-heptenyl] cyclopent-2-en-1-one | dl-15a-hydroxy-1-(methoxymethoxycarbonylmethyl)-1,9-dioxo-17,17-dimethyl-2-nor-13-trans prostene |

TABLE XIII-continued

| EXAMPLE | VINYL TIN | CYCLOPENTENONE | PRODUCT PROSTAGLANDIN OF THE 11-DEOXY PGE1 SERIES |
|---|---|---|---|
| 349 | 1-trans-iodo-4-methyl-3-triphenylmethoxy-1-octene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-methyl-2-nor-13-trans prostene |
| 350 | 1-trans-iodo-4,4-trimethylene-3-trimethylsilyloxy-1-heptene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16,16-trimethylene-20-nor-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 351 | 1-trans-tri-n-butylstannyl-3-vinyl-3-trimethylsilyloxy-1-heptene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-15-vinyl-20-nor-2-nor-13-trans prostene |
| 352 | 1-trans-tri-n-butylstannyl-4-phenoxy-3-triethylsilyloxy-1-butene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-phenoxy-2-nor-17-20-tetranor-13-trans prostene |
| 353 | 1-trans-tri-n-butylstannyl-4-(p-fluorophenoxy)-3-triethylsilyloxy-1-butene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-(p-fluorophenoxy)-2-nor-17-20-tetranor-13-trans prostene |
| 354 | 1-trans-tri-n-butylstannyl-4-(m-chlorophenoxy)-3-triethylsilyloxy-1-butene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-(m-chlorophenoxy)-2-nor-17-20-tetranor-13-trans prostene |
| 355 | 1-trans-tri-n-butylstannyl-4-(m-trifluoromethylphenoxy)-3-triethylsilyloxy-1-butene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-(m-trifluoromethylphenoxy)-2-nor-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 356 | 1-trans-iodo-5-phenyl-3-triethylsilyloxy-1-pentene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-17-phenyl-2-nor-18-20-trinor-13-trans prostene |
| 357 | 1-trans-iodo-4,4-dimethyl-5-phenyl-3-triethylsilyloxy-1-pentene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16,16-dimethyl-17-phenyl-2-nor-18-20-trinor-13-trans prostene |
| 358 | 1-trans-iodo-4-cyclopentyl-3-triphenylmethoxy-1-butene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-cyclopentyl-2-nor-17-20-tetranor-13-trans prostene |
| 359 | 1-trans-iodo-4-cyclohexyl-3-triphenylmethoxy-1-butene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16-cyclohexyl-2-nor-17-20-tetranor-13-trans prostene |
| 360 | 1-trans-iodo-4-triphenylmethoxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-20-nor-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 361 | 1-trans-tri-n-butylstannyl-4-methyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-20-nor-2-nor-13-trans prostene |
| 362 | 1-trans-tri-n-butylstannyl-4-ethyl- | 2-[7-methoxy-7-methoxycabonyl- | dl-16-hydroxy-1-(methoxymethoxycarbonylmethyl)-1,9-dioxo-16-ethyl- |

TABLE XIII-continued

| EXAMPLE | VINYL IODIDE | CYCLOPENTENONE | PRODUCT PROSTAGLANDIN OF THE 11-DEOXY PGE1 SERIES |
|---|---|---|---|
| | 4-trimethylsilyloxy-1-octene | 6-(trimethylsiloxy)-6-heptenyl]cyclopent-2-en-1-one | 2-nor-13-trans prostene |
| 363 | 1-trans-tri-n-butylstannyl-5-methyl-4-trimethylsilyloxy-1-heptene | 2-[7-methoxy-7-methoxycabonyl-6-(trimethylsiloxy)-6-heptenyl]cyclopent-2-en-1-one. | dl-16-hydroxy-1-(methoxymethoxycarbonylmethyl)-1,9-dioxo-17-methyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 364 | 1-iodo-5,5-dimethyl 4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17,17-dimethyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 365 | 1-trans-tri-n-butylstannyl-4-vinyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-vinyl-20-nor-2-nor-13-trans prostene |
| 366 | 1-trans-tri-n-butylstannyl-4-cyclopropyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-cyclopropyl-2-nor-2-nor-13-trans prostene |
| 367 | 1-trans-tri-n-butylstannyl-4-trimethylsilylethynyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-ethynyl-20-nor-2-nor-13-trans prostene |
| 368 | 1-trans-tri-n-butylstannyl-5-methylene 4-triethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methylene-20-nor-2-nor-13-trans prostene |
| 369 | 1-trans-tri-n-butylstannyl-4-methyl-5-methylene 4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-17-methylene-20-nor-2-nor-13-trans prostene |
| 370 | 1-trans-tri-n-butylstannyl-4-dimethoxymethyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-formyl-20-nor-2-nor-13-trans prostene |
| 371 | 1-trans-tri-n-butylstannyl-4-fluoromethyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-fluoromethyl-20-nor-2-nor-13-trans prostene |
| 372 | 1-trans-tri-n-butylstannyl-4-difluoromethyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-difluoromethyl-20-nor-2-nor-13-trans prostene |
| 373 | 1-trans-tri-n-butylstannyl-4-trifluoromethyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-trifluoromethyl-20-nor-2-nor-13-trans prostene |
| 374 | 1-trans-tri-n-butylstannyl-4-chloromethyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-chloromethyl-20-nor-2-nor-13-trans prostene |
| 375 | 1-trans-tri-n-butylstannyl-4-trimethylsilyloxymethyl-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-hydroxymethyl-20-nor-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|

TABLE XIII-continued

| | | | |
|---|---|---|---|
| 376 | 1-trans-iodo-4-methyl-7-chloro-4-trimethylsilyloxy-1-heptene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-19-chloro-2-nor-20-nor-13-trans prostene |
| 377 | 1-trans-iodo-3-triphenylmethoxy-1-octene | 2-[7-methoxy-7-methoxycarbonyl-6-(trimethylsiloxy)-6-heptenyl]cyclopent-2-en-1-one | dl-15a-hydroxy-1-(methoxymethoxycarbonylmethyl)-1,9-dioxo-2-nor-13-trans prostene |
| 378 | 1-trans-iodo-3-methyl-3-trimethylsilyloxy-1-octene | 2-[7-methoxy-7-methoxycarbonyl-6-(trimethylsiloxy)-6-heptenyl]cyclopent-2-en-1-one | dl-15a-hydroxy-1-(methoxymethoxycarbonylmethyl)-1,9-dioxo-15-methyl-2-nor-13-trans prostene |
| 379 | 1-trans-iodo-4,4-dimethyl-3-trimethylsilyloxy-1-octene | 2-[7-methoxy-7-methoxycarbonyl-6-(trimethylsiloxy)-6-heptenyl]cyclopent-2-en-1-one | dl-15a-hydroxy-1-(methoxymethoxycarbonylmethyl)-1,9-dioxo-16,16-dimethyl-2-nor-13-trans prostene |
| 380 | 1-trans-iodo-4,4-trimethylene-3-trimethylsilyloxy-1-octene | 2-[7-methoxy-7-methoxycarbonyl-6-(trimethylsiloxy)-6-heptenyl]cyclopent-2-en-1-one | dl-15a-hydroxy-1-(methoxymethoxycarbonylmethyl)-1,9-dioxo-16,16-trimethylene-2-nor-13-trans prostene |
| EXAMPLE | VINYL TIN | CYCLOPENTENONE | PRODUCT PROSTAGLANDIN OF THE 11-DEOXY PGE1 SERIES |
| 381 | 1-trans-tri-n-butylstannyl-3-vinyl-3-trimethylsilyloxy-1-octene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-15-vinyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 382 | 1-trans-iodo-4-triphenylmethoxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-2-nor-13-trans prostene |
| EXAMPLE | VINYL TIN | CYCLOPENTENONE | PRODUCT PROSTAGLANDIN OF THE 11-DEOXY PGE1 SERIES |
| 383 | 1-trans-tri-n-butylstannyl-4-methyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-2-nor-13-trans prostene |
| 384 | 1-trans-tri-n-butylstannyl-5-methyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methyl-2-nor-13-trans prostene |
| 385 | 1-trans-tri-n-butylstannyl-4-vinyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-vinyl-2-nor-13-trans prostene |
| 386 | 1-trans-tri-n-butylstannyl-4-trimethylsilylethynyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-ethynyl-2-nor-13-trans prostene |
| 387 | 1-trans-tri-n-butylstannyl-5-methylene-4-triethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methylene-2-nor-13-trans prostene |
| 388 | 1-trans-tri-n-butylstannyl-4-methyl-5-methylene-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-17-methylene-2-nor-13-trans prostene |
| 389 | 1-trans-tri-n-butylstannyl-4-dimethoxymethyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-formyl-2-nor-13-trans prostene |

TABLE XIII-continued

| EXAMPLE | VINYL IODIDE | CYCLOPENTENONE | PRODUCT PROSTAGLANDIN OF THE 11-DEOXY PGE1 SERIES |
|---|---|---|---|
| 390 | 1-trans-tri-n-butylstannyl-4-fluoromethyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-fluoromethyl-2-nor-13-trans prostene |
| 391 | 1-trans-tri-n-butylstannyl-4-difluoromethyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-difluoromethyl-2-nor-13-trans prostene |
| 392 | 1-trans-tri-n-butylstannyl-4-trifluoromethyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-trifluoromethyl-2-nor-13-trans prostene |
| 393 | 1-trans-tri-n-butylstannyl-4-chloromethyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-chloromethyl-2-nor-13-trans prostene |
| 394 | 1-trans-tri-n-butylstannyl-4-trimethylsilyloxymethyl-4-trimethylsilyloxy-1-octene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-hydroxymethyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 395 | 1-trans-iodo-3-triphenylmethoxy-1-nonene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-20-methyl-2-nor-13-trans prostene |
| 396 | 1-trans-iodo-3-methyl-3-trimethylmethoxy-1-nonene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-15-methyl-20-methyl-2-nor-13-trans prostene |
| 397 | 1-trans-iodo-4,4-dimethyl-3-trimethylmethoxy-1-nonene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16,16-dimethyl-20-methyl-2-nor-13-trans prostene |
| 398 | 1-trans-iodo-4,4-trimethylene-3-trimethylmethoxy-1-nonene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16,16-trimethylene-20-methyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 399 | 1-trans-tri-n-butylstannyl-3-vinyl-3-trimethylsilyloxy-1-nonene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-15-vinyl-20-methyl-2-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 400 | 1-trans-iodo-4-triphenylmethoxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-20-methyl-2-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 401 | 1-trans-tri-n-butylstannyl-4-methyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-20-methyl-2-nor-13-trans prostene |

TABLE XIII-continued

| EXAMPLE | | CYCLOPENTENONE | |
|---|---|---|---|
| 402 | 1-trans-tri-n-butylstannyl-5-methyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methyl-20-methyl-2-nor-13-trans prostene |
| 403 | 1-trans-tri-n-butylstannyl-4-vinyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-vinyl-20-methyl-2-nor-13-trans prostene |
| 404 | 1-trans-tri-n-butylstannyl-4-trimethylsilylethynyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-ethynyl-20-methyl-2-nor-13-trans prostene |
| 405 | 1-trans-tri-n-butylstannyl-5-methylene-4-triethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methylene-20-methyl-2-nor-13-trans prostene |
| 406 | 1-trans-tri-n-butylstannyl-4-methyl-5-methylene-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-17-methylene-20-methyl-2-nor-13-trans prostene |
| 407 | 1-trans-tri-n-butylstannyl-4-dimethoxymethyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-formyl-20-methyl-2-nor-13-trans prostene |
| 408 | 1-trans-tri-n-butylstannyl-4-fluoromethyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-fluoromethyl-20-methyl-2-nor-13-trans prostene |
| 409 | 1-trans-tri-n-butylstannyl-4-difluoromethyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-difluoromethyl-20-methyl-2-nor-13-trans prostene |
| 410 | 1-trans-tri-n-butylstannyl-4-trifluoromethyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-trifluoromethyl-20-methyl-2-nor-13-trans prostene |
| 411 | 1-trans-tri-n-butylstannyl-4-chloromethyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-chloromethyl-20-methyl-2-nor-13-trans prostene |
| 412 | 1-trans-tri-n-butylstannyl-4-trimethylsilyloxymethyl-4-trimethylsilyloxy-1-nonene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-hydroxymethyl-20-methyl-2-nor-13-trans prostene |
| EXAMPLE | VINYL IODIDE | CYCLOPENTENONE | PRODUCT PROSTAGLANDIN OF THE 11-DEOXY PGE1 SERIES |
| 413 | 1-iodo-3-triphenylmethoxy-1-decene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-20-ethyl-2-nor-13-trans prostene |
| 414 | 1-iodo-3-methyl-3-trimethylsilyloxy-1-decene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-15-methyl-20-ethyl-2-nor-13-trans prostene |
| 415 | 1-iodo-4,4-dimethyl-3-trimethylsilyloxy-1-decene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16,16-dimethyl-20-ethyl-2-nor-13-trans prostene |
| 416 | 1-iodo-4,4-trimethylene-3-trimethylsilyloxy-1-decene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-16,16-trimethylene-20-ethyl-2-nor-13-trans prostene |
| EXAMPLE | VINYL TIN | CYCLOPENTENONE | PRODUCT PROSTAGLANDIN OF THE 11-DEOXY PGE1 SERIES |

TABLE XIII-continued

| EX-AMPLE | VINYL IODIDE | CYCLOPENTENONE | PRODUCT PROSTAGLANDIN OF THE 11-DEOXY PGE1 SERIES |
|---|---|---|---|
| 417 | 1-trans-tri-n-butylstannyl-3-vinyl-3-trimethylsilyloxy-1-decene | 2-[7-methoxy-7-methoxycabonyl-6-(trimethylsiloxy)-6-heptenyl]cyclopent-2-en-1-one | dl-15a-hydroxy-1-(methoxymethoxycarbonylmethyl)-1,9-dioxo-15-vinyl-20-ethyl-2-nor-13-trans prostene |
| 418 | 1-trans-iodo-4-triphenylmethoxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-20-ethyl-2-nor-13-trans prostene |

| EX-AMPLE | VINYL TIN | CYCLOPENTENONE | PRODUCT PROSTAGLANDIN OF THE 11-DEOXY PGE1 SERIES |
|---|---|---|---|
| 419 | 1-trans-tri-n-butylstannyl-4-methyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-20-ethyl-2-nor-13-trans prostene |
| 420 | 1-trans-tri-n-butylstannyl-5-methyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methyl-20-ethyl-2-nor-13-trans prostene |
| 421 | 1-trans-tri-n-butylstannyl-4-vinyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-vinyl-20-ethyl-2-nor-13-trans prostene |
| 422 | 1-trans-tri-n-butylstannyl-4-trimethylsilyethynyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-ethynyl-20-ethyl-2-nor-13-trans prostene |
| 423 | 1-trans-tri-n-butylstannyl-5-methylene-4-triethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-17-methylene-20-ethyl-2-nor-13-trans prostene |
| 424 | 1-trans-tri-n-butylstannyl-4-methyl-5-methylene-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-methyl-17-methylene-20-ethyl-2-nor-13-trans prostene |
| 425 | 1-trans-tri-n-butylstannyl-4-dimethoxymethyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-formyl-20-ethyl-2-nor-13-trans prostene |
| 426 | 1-trans-tri-n-butylstannyl-4-fluoromethyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-fluoromethyl-20-ethyl-2-nor-13-trans prostene |
| 427 | 1-trans-tri-n-butylstannyl-4-difluoromethyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-difluoromethyl-20-ethyl-2-nor-13-trans prostene |
| 428 | 1-trans-tri-n-butylstannyl-4-trifluoromethyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-trifluoromethyl-20-ethyl-2-nor-13-trans prostene |
| 429 | 1-trans-tri-n-butylstannyl-4-chloromethyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-chloromethyl-20-ethyl-2-nor-13-trans prostene |
| 430 | 1-trans-tri-n-butylstannyl-4-trimethylsilyloxymethyl-4-trimethylsilyloxy-1-decene | 2-[7-methoxy-7-methoxycabonyl-6-(trimethylsiloxy)-6-heptenyl]cyclopent-2-en-1-one | dl-16-hydroxy-1-(methoxymethoxycarbonylmethyl)-1,9-dioxo-16-hydroxymethyl-20-ethyl-2-nor-13-trans prostene |

TABLE XIII-continued

| EXAMPLE | VINYL IODIDE | CYCLOPENTENONE | PRODUCT PROSTAGLANDIN OF THE 11-DEOXY PGE1 SERIES |
|---|---|---|---|
| 431 | 1-trans-iodo-3-triphenylmethoxy-1-heptene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-20-nor-13-trans prostene |
| 432 | 1-trans-iodo-3-methyl-3-trimethylsilyloxy-1-heptene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-methyl-20-nor-13-trans prostene |
| 433 | 1-trans-iodo-4,4-dimethyl-3-trimethylsilyloxy-1-heptene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-dimethyl-20-nor-13-trans prostene |
| 434 | 1-trans-iodo-5,5-dimethyl-3-triphenylmethoxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-17,17-dimethyl-13-trans prostene |
| 435 | 1-trans-iodo-4-methyl-3-triphenylmethoxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-methyl-13-trans prostene |
| 436 | 1-trans-iodo-4,4-trimethylene-3-trimethylsilyloxy-1-heptene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-trimethylene-20-nor-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 437 | 1-trans-tri-n-butylstannyl-3-vinyl-3-trimethylsilyloxy-1-heptene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-vinyl-20-nor-13-trans prostene |
| 438 | 1-trans-tri-n-butylstannyl-4-phenoxy-3-triethylsilyloxy-1-butene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-phenoxy-17-20-tetranor-13-trans prostene |
| 439 | 1-trans-tri-n-butylstannyl-4-(p-fluorophenoxy)-3-triethylsilyloxy-1-butene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-(p-fluorophenoxy)-17-20-tetranor-13-trans prostene |
| 440 | 1-trans-tri-n-butylstannyl-4-(m-chlorophenoxy)-3-triethylsilyloxy-1-butene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-(m-chlorophenoxy)-17-20-tetranor-13-trans prostene |
| 441 | 1-trans-tri-n-butylstannyl-4-(m-trifluoromethylphenoxy)-3-triethylsilyloxy-1-butene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-(m-trifluoromethylphenoxy)-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 442 | 1-trans-iodo-5-phenyl-3-triethylsilyloxy-1-pentene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-17-phenyl-18-20-trinor-13-trans prostene |
| 443 | 1-trans-iodo-4,4-dimethyl-5-phenyl-3-triethylsilyloxy-1-pentene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-dimethyl-17-phenyl-18-20-trinor-13-trans prostene |
| 444 | 1-trans-iodo-4-cyclopentyl-3-triphenylmethoxy-1-butene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-cyclopentyl-17-20-tetranor-13-trans prostene |
| 445 | 1-trans-iodo-4-cyclohexyl-3-triphenylmethoxy-1-butene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16-cyclohexyl-17-20-tetranor-13-trans prostene |

TABLE XIII-continued

| EX-AMPLE | VINYL IODIDE / VINYL TIN | CYCLOPENTENONE | PRODUCT PROSTAGLANDIN OF THE 11-DEOXY PGE1 SERIES |
|---|---|---|---|
| 446 | 1-trans-iodo-4-triphenylmethoxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-20-nor-13-trans prostene |

| EX-AMPLE | VINYL TIN | CYCLOPENTENONE | PRODUCT PROSTAGLANDIN OF THE 11-DEOXY PGE1 SERIES |
|---|---|---|---|
| 447 | 1-trans-tri-n-butylstannyl-4-methyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-methyl-20-nor-13-trans prostene |
| 448 | 1-trans-tri-n-butylstannyl-4-ethyl-4-trimethylsilyloxy-1-octene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-ethyl-13-trans prostene |
| 449 | 1-trans-tri-n-butylstannyl-5-methyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-17-methyl-20-nor-13-trans prostene |

| EX-AMPLE | VINYL IODIDE | CYCLOPENTENONE | PRODUCT PROSTAGLANDIN OF THE 11-DEOXY PGE1 SERIES |
|---|---|---|---|
| 450 | 1-trans-iodo-5,5-dimethyl-4-trimethylsilyloxy-1-octene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-17,17-dimethyl-13-trans prostene |

| EX-AMPLE | VINYL TIN | CYCLOPENTENONE | PRODUCT PROSTAGLANDIN OF THE 11-DEOXY PGE1 SERIES |
|---|---|---|---|
| 451 | 1-trans-tri-n-butylstannyl-4-vinyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-vinyl-20-nor-13-trans prostene |
| 452 | 1-trans-tri-n-butylstannyl-4-cyclopropyl-4-trimethylsilyloxy-1-octene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-cyclopropyl-13-trans prostene |
| 453 | 1-trans-tri-n-butylstannyl-4-trimethylsilylethynyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-ethynyl-20-nor-13-trans prostene |
| 454 | 1-trans-tri-n-butylstannyl-5-methyl-4-triethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-17-methylene-20-nor-13-trans prostene |
| 455 | 1-trans-tri-n-butylstannyl-4-methyl-5-methylene-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-methyl-17-methylene-20-nor-13-trans prostene |
| 456 | 1-trans-tri-n-butylstannyl-4-dimethoxymethyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-formyl-20-nor-13-trans prostene |
| 457 | 1-trans-tri-n-butylstannyl-4-fluoromethyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-fluoromethyl-20-nor-13-trans prostene |
| 458 | 1-trans-tri-n-butylstannyl-4-difluoromethyl-4-trimethylsilyloxy-1-heptene | 2-[8-methoxy-8-methoxycarbonyl-7-(trimethylsilyloxy)-7-octenyl]cyclopent-2-en-1-one | dl-16-hydroxy-1-(methoxymethoxycarbonylmethyl)-1,9-dioxo-16-difluoromethyl-20-nor-13-trans prostene |
| 459 | 1-trans-tri-n-butylstannyl-4-trifluoromethyl- | 2-[8-methoxy-8-methoxycarbonyl- | dl-16-hydroxy-1-(methoxymethoxycarbonylmethyl)-1,9-dioxo-16-trifluoromethyl- |

TABLE XIII-continued

| EXAMPLE | VINYL IODIDE / VINYL TIN | CYCLOPENTENONE | PRODUCT PROSTAGLANDIN OF THE 11-DEOXY PGE1 SERIES |
|---|---|---|---|
| | 4-trimethylsilyloxy-1-heptene | 7-(trimethylsiloxy)-7-octenyl]cyclopent-2-en-1-one | 20-nor-13-trans prostene |
| 460 | 1-trans-tri-n-butylstannyl-4-chloromethyl-4-trimethylsilyloxy-1-heptene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-chloromethyl-20-nor-13-trans prostene |
| 461 | 1-trans-tri-n-butylstannyl-4-trimethylsilyloxymethyl-4-trimethylsilyloxy-1-heptene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-hydroxymethyl-20-nor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 462 | 1-trans-iodo-4-methyl-7-chloro-4-trimethylsilyloxy-1-heptene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-methyl-19-chloro-20-nor-13-trans prostene |
| 463 | 1-trans-iodo-3-triphenylmethoxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-13-trans prostene |
| 464 | 1-trans-iodo-3-methyl-3-trimethylsilyloxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-methyl-13-trans prostene |
| 465 | 1-trans-iodo-4,4-dimethyl-3-trimethylsilyloxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-dimethyl-13-trans prostene |
| 466 | 1-trans-iodo-4,4-trimethylene-3-trimethylsilyloxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-trimethylene-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 467 | 1-trans-tri-n-butylstannyl-3-vinyl-3-trimethylsilyloxy-1-octene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-vinyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 468 | 1-trans-iodo-4-triphenylmethoxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 469 | 1-trans-tri-n-butylstannyl-4-methyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-methyl-13-trans prostene |
| 470 | 1-trans-tri-n-butylstannyl-5-methyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-17-methyl-13-trans prostene |
| 471 | 1-trans-tri-n-butylstannyl-4-vinyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonyl)-1,9-dioxo-16-vinyl-13-trans prostene |

TABLE XIII-continued

| EXAMPLE | | | |
|---|---|---|---|
| 472 | 1-trans-tri-n-butylstannyl-4-trimethylsilylethynyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-ethynyl-13-trans prostene |
| 473 | 1-trans-tri-n-butylstannyl-5-methylene-4-triethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-17-methylene-13-trans prostene |
| 474 | 1-trans-tri-n-butylstannyl-4-methyl-5-methylene-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-methyl-17-methylene-13-trans prostene |
| 475 | 1-trans-tri-n-butylstannyl-4-dimethoxymethyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-formyl-13-trans prostene |
| 476 | 1-trans-tri-n-butylstannyl-4-fluoromethyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-fluoromethyl-13-trans prostene |
| 477 | 1-trans-tri-n-butylstannyl-4-difluoromethyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-difluoromethyl-13-trans prostene |
| 478 | 1-trans-tri-n-butylstannyl-4-trifluoromethyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-trifluoromethyl-13-trans prostene |
| 479 | 1-trans-tri-n-butylstannyl-4-chloromethyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-chloromethyl-13-trans prostene |
| 480 | 1-trans-tri-n-butylstannyl-4-trimethylsilyloxymethyl-4-trimethylsilyloxy-1-octene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-hydroxymethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 481 | 1-trans-iodo-3-triphenylmethoxy-1-nonene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-20-methyl-13-trans prostene |
| 482 | 1-trans-iodo-3-methyl-3-trimethylsilyloxy-1-nonene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-methyl-20-methyl-13-trans prostene |
| 483 | 1-trans-iodo-4,4-dimethyl-3-trimethylsilyloxy-1-nonene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-dimethyl-20-methyl-13-trans prostene |
| 484 | 1-trans-iodo-4,4-trimethylene-3-trimethylsilyloxy-1-nonene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-16,16-trimethylene-20-methyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 485 | 1-trans-tri-n-butylstannyl-3-vinyl-3-trimethylsilyloxy-1-nonene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-vinyl-20-methyl-13-trans prostene |

TABLE XIII-continued

| EXAMPLE | VINYL IODIDE | CYCLOPENTENONE | PRODUCT PROSTAGLANDIN OF THE 11-DEOXY PGE1 SERIES |
|---|---|---|---|
| 486 | 1-trans-iodo-4-triphenylmethoxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-20-methyl-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 487 | 1-trans-tri-n-butylstannyl-4-methyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-methyl-20-methyl-13-trans prostene |
| 488 | 1-trans-tri-n-butylstannyl-4-methyl-5-methyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-17-methyl-20-methyl-13-trans prostene |
| 489 | 1-trans-tri-n-butylstannyl-4-vinyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-vinyl-20-methyl-13-trans prostene |
| 490 | 1-trans-tri-n-butylstannyl-4-trimethylsilylethynyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-ethynyl-20-methyl-13-trans prostene |
| 491 | 1-trans-tri-n-butylstannyl-5-methylene-4-triethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-17-methylene-20-methyl-13-trans prostene |
| 492 | 1-trans-tri-n-butylstannyl-4-methyl-5-methylene-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-methyl-17-methylene-20-methyl-13-trans prostene |
| 493 | 1-trans-tri-n-butylstannyl-4-dimethoxymethyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-formyl-20-methyl-13-trans prostene |
| 494 | 1-trans-tri-n-butylstannyl-4-fluoromethyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-fluoromethyl-20-methyl-13-trans prostene |
| 495 | 1-trans-tri-n-butylstannyl-4-difluoromethyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-difluoromethyl-20-methyl-13-trans prostene |
| 496 | 1-trans-tri-n-butylstannyl-4-trifluoromethyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-trifluoromethyl-20-methyl-13-trans prostene |
| 497 | 1-trans-tri-n-butylstannyl-4-chloromethyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-chloromethyl-20-methyl-13-trans prostene |
| 498 | 1-trans-tri-n-butylstannyl-4-trimethylsilyloxymethyl-4-trimethylsilyloxy-1-nonene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-hydroxymethyl-20-methyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 499 | 1-trans-iodo-3-triphenylmethoxy-1-decene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-20-ethyl-13-trans prostene |
| 500 | 1-trans-iodo-3-methyl-3-trimethylsilyloxy-1-decene | 2-[8-methoxy-8-methoxycarbonyl-7-(trimethylsiloxy)-7-octenyl]cyclopent-2-en-1-one | dl-15a-hydroxy-1-(methoxymethoxycarbonylmethyl)-1,9-dioxo-15-methyl-20-ethyl-13-trans prostene |

TABLE XIII-continued

| EXAMPLE | VINYL TIN / VINYL IODIDE | CYCLOPENTENONE | PRODUCT PROSTAGLANDIN |
|---|---|---|---|
| 501 | 1-trans-iodo-4,4-dimethyl 3-trimethylsilyloxy-1-decene | 2-[8-methoxy-8-methoxycarbonyl-7-(trimethylsiloxy)-7-octenyl] cyclopent-2-en-1-one | dl-15a-hydroxy-1-(methoxymethoxycarbonylmethyl)-1,9-dioxo-16,16-dimethyl-20-ethyl-13-trans prostene |
| 502 | 1-trans-iodo-4,4-trimethylene 3-trimethylsilyloxy-1-decene | 2-[8-methoxy-8-methoxycarbonyl-7-(trimethylsiloxy)-7-octenyl] cyclopent-2-en-1-one | dl-15a-hydroxy-1-(methoxymethoxycarbonylmethyl)-1,9-dioxo-16,16-trimethylene-20-ethyl-13-trans prostene |

PRODUCT PROSTAGLANDIN OF THE 11-DEOXY PGE1 SERIES

| EXAMPLE | VINYL TIN | CYCLOPENTENONE | PRODUCT PROSTAGLANDIN |
|---|---|---|---|
| 503 | 1-trans-tri-n-butylstannyl-3-vinyl-3-trimethylsilyloxy-1-decene | 2-[8-methoxy-8-methoxycarbonyl-7-(trimethylsiloxy)-7-octenyl] cyclopent-2-en-1-one | dl-15a-hydroxy-1-(methoxymethoxycarbonylmethyl)-1,9-dioxo-15-vinyl-20-ethyl-13-trans prostene |

PRODUCT PROSTAGLANDIN OF THE 11-DEOXY PGE1 SERIES

| EXAMPLE | VINYL IODIDE | CYCLOPENTENONE | PRODUCT PROSTAGLANDIN |
|---|---|---|---|
| 504 | 1-trans-iodo-4-triphenylmethoxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-20-ethyl-13-trans prostene |

PRODUCT PROSTAGLANDIN OF THE 11-DEOXY PGE1 SERIES

| EXAMPLE | VINYL TIN | CYCLOPENTENONE | PRODUCT PROSTAGLANDIN |
|---|---|---|---|
| 505 | 1-trans-tri-n-butylstannyl-4-methyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-methyl-20-ethyl-13-trans prostene |
| 506 | 1-trans-tri-n-butylstannyl-5-methyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-17-methyl-20-ethyl-13-trans prostene |
| 507 | 1-trans-tri-n-butylstannyl-4-vinyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-vinyl-20-ethyl-13-trans prostene |
| 508 | 1-trans-tri-n-butylstannyl-4-trimethylsilylethynyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-ethynyl-20-ethyl-13-trans prostene |
| 509 | 1-trans-tri-n-butylstannyl-5-methylene-4-triethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-17-methylene-20-ethyl-13-trans prostene |
| 510 | 1-trans-tri-n-butylstannyl-4-methyl-5-methylene 4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-methyl-17-methylene-20-ethyl-13-trans prostene |
| 511 | 1-trans-tri-n-butylstannyl-4-dimethoxymethyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-formyl-20-ethyl-13-trans prostene |
| 512 | 1-trans-tri-n-butylstannyl-4-fluoromethyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-fluoromethyl-20-ethyl-13-trans prostene |
| 513 | 1-trans-tri-n-butylstannyl-4-difluoromethyl-4-trimethylsilyloxy-1-decene | 2-[8-methoxy-8-methoxycarbonyl-7-(trimethylsiloxy)-7-octenyl] cyclopent-2-en-1-one | dl-16-hydroxy-1-(methoxymethoxycarbonylmethyl)-1,9-dioxo-16-difluoromethyl-20-ethyl-13-trans prostene |
| 514 | 1-trans-tri-n-butylstannyl-4-trifluoromethyl- | 2-[8-methoxy-8-methoxycarbonyl- | dl-16-hydroxy-1-(methoxymethoxycarbonylmethyl)-1,9-dioxo-16-trifluoromethyl- |

TABLE XIII-continued

| EXAMPLE | VINYL IODIDE | CYCLOPENTENONE | PRODUCT PROSTAGLANDIN OF THE 11-DEOXY PGE1 SERIES |
|---|---|---|---|
| | 4-trimethylsilyloxy-1-decene | 7-(trimethylsiloxy)-7-octenyl]cyclopent-2-en-1-one | 20-ethyl-13-trans prostene |
| 515 | 1-trans-tri-n-butylstannyl-4-chloromethyl-4-trimethylsilyloxy-1-decene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-chloromethyl-20-ethyl-13-trans prostene |
| 516 | 1-trans-tri-n-butylstannyl-4-trimethylsilyloxymethyl-4-trimethylsilyloxy-1-decene | 2-[8-methoxy-8-methoxycarbonyl-7-(trimethylsiloxy)-7-octenyl]cyclopent-2-en-1-one | dl-16-hydroxy-1-(methoxymethoxycarbonylmethyl)-1,9-dioxo-16-hydroxymethyl-20-ethyl-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 517 | 1-trans-iodo-3-triphenylmethoxy-1-heptene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-20-nor-2-homo-13-trans prostene |
| 518 | 1-trans-iodo-3-methyl-3-trimethylsilyloxy-1-heptene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-15-methyl-20-nor-2-homo-13-trans prostene |
| 519 | 1-trans-iodo-4,4-dimethyl-3-trimethylsilyloxy-1-heptene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16,16-dimethyl-20-nor-2-homo-13-trans prostene |
| 520 | 1-trans-iodo-5,5-dimethyl-3-triphenylmethoxy-1-octene | 2-[9-methoxy-9-methoxycarbonyl-8-(trimethylsiloxy)-8-nonenyl]cyclopent-2-en-1-one | dl-15a-hydroxy-1-(meythoxymethoxycarbonylmethyl)-1,9-dioxo-17,17-dimethyl-2-homo-13-trans prostene |
| 521 | 1-trans-iodo-4-methyl-3-triphenylmethoxy-1-octene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16-methyl-2-homo-13-trans prostene |
| 522 | 1-trans-iodo-4,4-trimethylene-3-trimethylsilyloxy-1-heptene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16,16-trimethylene-20-nor-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 523 | 1-trans-tri-n-butylstannyl-3-vinyl-3-trimethylsilyloxy-1-heptene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-15-vinyl-20-nor-2-homo-13-trans prostene |
| 524 | 1-trans-tri-n-butylstannyl-4-phenoxy-3-triethylsilyloxy-1-butene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16-phenoxy-2-homo-17-20-tetranor-13-trans prostene |
| 525 | 1-trans-tri-n-butylstannyl-4-(p-fluorophenoxy)-3-triethylsilyloxy-1-butene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16-(p-fluorophenoxy)-2-homo-17-20-tetranor-13-trans prostene |
| 526 | 1-trans-tri-n-butylstannyl-4-(m-chlorophenoxy)-3-triethylsilyloxy-1-butene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16-(m-chlorophenoxy)-2-homo-17-20-tetranor-13-trans prostene |
| 527 | 1-trans-tri-n-butylstannyl-4-(m-trifluoromethylphenoxy)-3-triethylsilyloxy-1-butene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16-(m-trifluoromethylphenoxy)-2-homo-17-20-tetranor-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|

TABLE XIII-continued

| EXAMPLE | VINYL IODIDE | CYCLOPENTENONE | PRODUCT PROSTAGLANDIN |
|---|---|---|---|
| 528 | 1-trans-iodo-5-phenyl-3-triethylsilyloxy-1-pentene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-17-phenyl-2-homo-18-20-trinor-13-trans prostene |
| 529 | 1-trans-iodo-4,4-dimethyl-5-phenyl-3-triethylsilyloxy-1-pentene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-16,16-dimethyl-17-phenyl-2-homo-18-20-trinor-13-trans prostene |
| 530 | 1-trans-iodo-4-cyclopentyl-3-triphenylmethoxy-1-butene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-16-cyclopentyl-2-homo-17-20-tetranor-13-trans prostene |
| 531 | 1-trans-iodo-4-cyclohexyl-3-triphenylmethoxy-1-butene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-16-cyclohexyl-2-homo-17-20-tetranor-13-trans prostene |
| 532 | 1-trans-iodo-4-triphenylmethoxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-20-nor-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 533 | 1-trans-tri-n-butylstannyl-4-methyl-4-trimethylsilyloxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-methyl-20-nor-2-homo-13-trans prostene |
| 534 | 1-trans-tri-n-butylstannyl-4-ethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-ethyl-2-homo-13-trans prostene |
| 535 | 1-trans-tri-n-butylstannyl-5-methyl-4-trimethylsilyloxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-17-methyl-20-nor-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 536 | 1-trans-iodo-5,5-dimethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-17,17-dimethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 537 | 1-trans-tri-n-butylstannyl-4-vinyl-4-trimethylsilyloxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-vinyl-20-nor-2-homo-13-trans prostene |
| 538 | 1-trans-tri-n-butylstannyl-4-cyclopropyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-cyclopropyl-2-homo-13-trans prostene |
| 539 | 1-trans-tri-n-butylstannyl-4-trimethylsilylethynyl-4-trimethylsilyloxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-ethynyl-20-nor-2-homo-13-trans prostene |
| 540 | 1-trans-tri-n-butylstannyl-5-methylene-4-triethylsilyloxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-17-methylene-20-nor-2-homo-13-trans prostene |
| 541 | 1-trans-tri-n-butylstannyl-4-methyl-5-methylene-4-trimethylsilyloxy-1-heptene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-methyl-17-methylene-20-nor-2-homo-13-trans prostene |

TABLE XIII-continued

| | CYCLOPENTENONE | VINYL IODIDE | PRODUCT PROSTAGLANDIN |
|---|---|---|---|
| 542 | 2-[9-methoxy-9-methoxycarbonyl-8-(trimethylsiloxy)-8-nonenyl]cyclopent-2-en-1-one | 1-trans-tri-n-butylstannyl-4-dimethoxymethyl-4-trimethylsilyloxy-1-heptene | dl-16-hydroxy-1-(methoxymethoxycarbonylmethyl)-1,9-dioxo-16-formyl-20-nor-2-homo-13-trans prostene |
| 543 | 2-[9-methoxy-9-methoxycarbonyl-8-(trimethylsiloxy)-8-nonenyl]cyclopent-2-en-1-one | 1-trans-tri-n-butylstannyl-4-fluoromethyl-4-trimethylsilyloxy-1-heptene | dl-16-hydroxy-1-(methoxymethoxycarbonylmethyl)-1,9-dioxo-16-fluoromethyl-20-nor-2-homo-13-trans prostene |
| 544 | 2-[9-methoxy-9-methoxycarbonyl-8-(trimethylsiloxy)-8-nonenyl]cyclopent-2-en-1-one | 1-trans-tri-n-butylstannyl-4-difluoromethyl-4-trimethylsilyloxy-1-heptene | dl-16-hydroxy-1-(methoxymethoxycarbonylmethyl)-1,9-dioxo-16-difluoromethyl-20-nor-2-homo-13-trans prostene |
| 545 | 2-[9-methoxy-9-methoxycarbonyl-8-(trimethylsiloxy)-8-nonenyl]cyclopent-2-en-1-one | 1-trans-tri-n-butylstannyl-4-trifluoromethyl-4-trimethylsilyloxy-1-heptene | dl-16-hydroxy-1-(methoxymethoxycarbonylmethyl)-1,9-dioxo-16-trifluoromethyl-20-nor-2-homo-13-trans prostene |
| 546 | 2-[9-methoxy-9-methoxycarbonyl-8-(trimethylsiloxy)-8-nonenyl]cyclopent-2-en-1-one | 1-trans-tri-n-butylstannyl-4-chloromethyl-4-trimethylsilyloxy-1-heptene | dl-16-hydroxy-1-(methoxymethoxycarbonylmethyl)-1,9-dioxo-16-chloromethyl-20-nor-2-homo-13-trans prostene |
| 547 | 2-[9-methoxy-9-methoxycarbonyl-8-(trimethylsiloxy)-8-nonenyl]cyclopent-2-en-1-one | 1-trans-tri-n-butylstannyl-4-trimethylsilyloxymethyl-4-trimethylsilyloxy-1-heptene | dl-16-hydroxy-1-(methoxymethoxycarbonylmethyl)-1,9-dioxo-16-hydroxymethyl-20-nor-2-homo-13-trans prostene |

| EXAMPLE | CYCLOPENTENONE | VINYL IODIDE | PRODUCT PROSTAGLANDIN OF THE 11-DEOXY PGE1 SERIES |
|---|---|---|---|
| 548 | 2-[9-methoxy-9-methoxycarbonyl-8-(trimethylsiloxy)-8-nonenyl]cyclopent-2-en-1-one | 1-iodo-4-methyl-7-chloro-4-trimethylsilyloxy-1-heptene | dl-16-hydroxy-1-(methoxymethoxycarbonylmethyl)-1,9-dioxo-methyl-19-chloro-2-homo-20-nor-13-trans prostene |
| 549 | 2-[9-methoxy-9-methoxycarbonyl-8-(trimethylsiloxy)-8-nonenyl]cyclopent-2-en-1-one | 1-trans-iodo-3-triphenylmethoxy-1-octene | dl-15a-hydroxy-1-(methoxymethoxycarbonylmethyl)-1,9-dioxo-2-homo-13-trans prostene |
| 550 | 2-[9-methoxy-9-methoxycarbonyl-8-(trimethylsiloxy)-8-nonenyl]cyclopent-2-en-1-one | 1-trans-iodo-3-methyl-3-trimethylsilyloxy-1-octene | dl-15a-hydroxy-1-(methoxymethoxycarbonylmethyl)-1,9-dioxo-15-methyl-2-homo-13-trans prostene |
| 551 | 2-[9-methoxy-9-methoxycarbonyl-8-(trimethylsiloxy)-8-nonenyl]cyclopent-2-en-1-one | 1-trans-iodo-4,4-dimethyl-3-trimethylsilyloxy-1-octene | dl-15a-hydroxy-1-(methoxymethoxycarbonylmethyl)-1,9-dioxo-16,16-dimethyl-2-homo-13-trans prostene |
| 552 | 2-[9-methoxy-9-methoxycarbonyl-8-(trimethylsiloxy)-8-nonenyl]cyclopent-2-en-1-one | 1-trans-iodo-4,4-trimethylene-3-trimethylsilyloxy-1-octene | dl-15a-hydroxy-1-(methoxymethoxycarbonylmethyl)-1,9-dioxo-16,16-trimethylene-2-homo-13-trans prostene |

| EXAMPLE | CYCLOPENTENONE | VINYL TIN | PRODUCT PROSTAGLANDIN OF THE 11-DEOXY PGE1 SERIES |
|---|---|---|---|
| 553 | 2-[9-methoxy-9-methoxycarbonyl-8-(trimethylsiloxy)-8-nonenyl]cyclopent-2-en-1-one | 1-trans-tri-n-butylstannyl-3-vinyl-3-trimethylsilyloxy-1-octene | dl-15a-hydroxy-1-(methoxymethoxycarbonylmethyl)-1,9-dioxo-15-vinyl-2-homo-13-trans prostene |

| EXAMPLE | CYCLOPENTENONE | VINYL IODIDE | PRODUCT PROSTAGLANDIN OF THE 11-DEOXY PGE1 SERIES |
|---|---|---|---|
| 554 | 2-[9-methoxy-9-methoxycarbonyl-8-(trimethylsiloxy)-8-nonenyl]cyclopent-2-en-1-one | 1-trans-iodo-4-triphenylmethoxy-1-octene | dl-16-hydroxy-1-(methoxymethoxycarbonylmethyl)-1,9-dioxo-2-homo-13-trans prostene |

TABLE XIII-continued

| EXAMPLE | VINYL TIN | CYCLOPENTENONE | PRODUCT PROSTAGLANDIN OF THE 11-DEOXY PGE1 SERIES |
|---|---|---|---|
| 555 | 1-trans-tri-n-butylstannyl-4-methyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-methyl-2-homo-13-trans prostene |
| 556 | 1-trans-tri-n-butylstannyl-4-methyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-17-methyl-2-homo-13-trans prostene |
| 557 | 1-trans-tri-n-butylstannyl-4-vinyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-vinyl-2-homo-13-trans prostene |
| 558 | 1-trans-tri-n-butylstannyl-4-trimethylsilylethynyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-ethynyl-2-homo-13-trans prostene |
| 559 | 1-trans-tri-n-butylstannyl-5-methylene-4-triethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-17-methylene-2-homo-13-trans prostene |
| 560 | 1-trans-tri-n-butylstannyl-4-methyl-5-methylene-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-methyl-17-methylene-2-homo-13-trans prostene |
| 561 | 1-trans-tri-n-butylstannyl-4-dimethoxymethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-formyl-2-homo-13-trans prostene |
| 562 | 1-trans-tri-n-butylstannyl-4-fluoromethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-fluoromethyl-2-homo-13-trans prostene |
| 563 | 1-trans-tri-n-butylstannyl-4-difluoromethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-difluoromethyl-2-homo-13-trans prostene |
| 564 | 1-trans-tri-n-butylstannyl-4-trifluoromethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-trifluoromethyl-2-homo-13-trans prostene |
| 565 | 1-trans-tri-n-butylstannyl-4-chloromethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-chloromethyl-2-homo-13-trans prostene |
| 566 | 1-trans-tri-n-butylstannyl-4-trimethylsilyloxymethyl-4-trimethylsilyloxy-1-octene | 2-[9-methoxy-9-methoxycarbonyl-8-(trimethylsilyloxy)-8-nonenyl]cyclopent-2-en-1-one | dl-16-hydroxy-1-(methoxymethoxycarbonylmethyl)-1,9-dioxo-16-hydroxymethyl-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 567 | 1-trans-iodo-3-triphenylmethoxy-1-nonene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-20-methyl-2-homo-13-trans prostene |
| 568 | 1-trans-iodo-3-methyl-3-trimethylsilyloxy-1-nonene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-15-methyl-20-methyl-2-homo-13-trans prostene |
| 569 | 1-trans-iodo-4,4-dimethyl-3-trimethylsilyloxy-1-nonene | 2-[9-methoxy-9-methoxycarbonyl-8-(trimethylsilyloxy)-8-nonenyl]cyclopent-2-en-1-one | dl-15a-hydroxy-1-(methoxymethoxycarbonylmethyl)-1,9-dioxo-16,16-dimethyl-20-methyl-2-homo-13-trans prostene |
| 570 | 1-trans-iodo-4,4-trimethylene | 2-[9-methoxy-9-methoxycarbonyl- | dl-15a-hydroxy-1-(methoxymethoxycarbonylmethyl)-1,9-dioxo- |

TABLE XIII-continued

| EX-AM-PLE | VINYL TIN | CYCLOPENTENONE | PRODUCT PROSTAGLANDIN OF THE 11-DEOXY PGE1 SERIES |
|---|---|---|---|
| | 3-trimethylsilyloxy-1-nonene | 8-(trimethylsilyloxy)-cyclopent-2-en-1-one | 16,16-trimethylene-20-methyl-2-homo-13-trans prostene |

| EX-AM-PLE | VINYL TIN | CYCLOPENTENONE | PRODUCT PROSTAGLANDIN OF THE 11-DEOXY PGE1 SERIES |
|---|---|---|---|
| 571 | 1-trans-tri-n-butylstannyl-3-vinyl-3-trimethylsilyloxy-1-nonene | 2-[9-methoxy-9-methoxycarbonyl]-8-(trimethylsilyloxy)-8-nonenyl]cyclopent-2-en-1-one | dl-15a-hydroxy-1-(methoxymethoxycarbonylmethyl)-1,9-dioxo-15-vinyl-20-methyl-2-homo-13-trans prostene |

| EX-AM-PLE | VINYL IODIDE | CYCLOPENTENONE | PRODUCT PROSTAGLANDIN OF THE 11-DEOXY PGE1 SERIES |
|---|---|---|---|
| 572 | 1-trans-iodo-4-triphenylmethoxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-20-methyl-2-homo-13-trans prostene |

| EX-AM-PLE | VINYL TIN | CYCLOPENTENONE | PRODUCT PROSTAGLANDIN OF THE 11-DEOXY PGE1 SERIES |
|---|---|---|---|
| 573 | 1-trans-tri-n-butylstannyl-4-methyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-methyl-20-methyl-2-homo-13-trans prostene |
| 574 | 1-trans-tri-n-butylstannyl-4-methyl-5-methyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-17-methyl-20-methyl-2-homo-13-trans prostene |
| 575 | 1-trans-tri-n-butylstannyl-4-vinyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-vinyl-20-methyl-2-homo-13-trans prostene |
| 576 | 1-trans-tri-n-butylstannyl-4-trimethylsilylethynyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-ethynyl-20-methyl-2-homo-13-trans prostene |
| 577 | 1-trans-tri-n-butylstannyl-4-methyl-5-methylene-4-triethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-17-methylene-20-methyl-2-homo-13-trans prostene |
| 578 | 1-trans-tri-n-butylstannyl-4-methyl-5-methylene-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-methyl-17-methylene-20-methyl-2-homo-13-trans prostene |
| 579 | 1-trans-tri-n-butylstannyl-4-dimethoxymethyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-formyl-20-methyl-2-homo-13-trans prostene |
| 580 | 1-trans-tri-n-butylstannyl-4-fluoromethyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-fluoromethyl-20-methyl-2-homo-13-trans prostene |
| 581 | 1-trans-tri-n-butylstannyl-4-difluoromethyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-difluoromethyl-20-methyl-2-homo-13-trans prostene |
| 582 | 1-trans-tri-n-butylstannyl-4-trifluoromethyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxycarbonylmethyl)-1,9-dioxo-16-trifluoromethyl-20-methyl-2-homo-13-trans prostene |
| 583 | 1-trans-tri-n-butylstannyl-4-chloromethyl-4-trimethylsilyloxy-1-nonene | 2-[9-methoxy-9-methoxycarbonyl]-8-(trimethylsilyloxy)-8-nonenyl]cyclopent-2-en-1-one | dl-16-hydroxy-1-(methoxymethoxymethyl)-1,9-dioxo-16-chloromethyl-20-methyl-2-homo-13-trans prostene |

TABLE XIII-continued

| EXAMPLE | VINYL IODIDE | CYCLOPENTENONE | PRODUCT PROSTAGLANDIN OF THE 11-DEOXY PGE1 SERIES |
|---|---|---|---|
| 584 | 1-trans-tri-n-butylstannyl-4-trimethylsilyloxymethyl-4-trimethylsilyloxy-1-nonene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-hydroxymethyl-20-methyl-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 585 | 1-trans-iodo-3-triphenylmethoxy-1-decene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-20-ethyl-2-homo-13-trans prostene |
| 586 | 1-trans-iodo-3-methyl-3-trimethylsilyloxy-1-decene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-15-methyl-20-ethyl-2-homo-13-trans prostene |
| 587 | 1-trans-iodo-4,4-dimethyl-3-trimethylsilyloxy-1-decene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16,16-dimethyl-20-ethyl-2-homo-13-trans prostene |
| 588 | 1-trans-iodo-4,4-trimethylene-3-trimethylsilyloxy-1-decene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-16,16-trimethylene-20-ethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 589 | 1-trans-tri-n-butylstannyl-3-vinyl-3-trimethylsilyloxy-1-decene | 2-[9-methoxy-9-methoxycarbonyl-8-(trimethylsiloxy)-8-nonenyl]cyclopent-2-en-1-one | dl-15a-hydroxy-1-(methoxymethoxycarbonylmethyl)-1,9-dioxo-15-vinyl-20-ethyl-2-homo-13-trans prostene |

| EXAMPLE | VINYL IODIDE | CYCLOPENTENONE | PRODUCT PROSTAGLANDIN OF THE 11-DEOXY PGE1 SERIES |
|---|---|---|---|
| 590 | 1-trans-iodo-4-triphenylmethoxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-20-ethyl-2-homo-13-trans prostene |

| EXAMPLE | VINYL TIN | CYCLOPENTENONE | PRODUCT PROSTAGLANDIN OF THE 11-DEOXY PGE1 SERIES |
|---|---|---|---|
| 591 | 1-trans-tri-n-butylstannyl-4-methyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-methyl-20-ethyl-2-homo-13-trans prostene |
| 592 | 1-trans-tri-n-butylstannyl-4-methyl-5-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-17-methyl-20-ethyl-2-homo-13-trans prostene |
| 593 | 1-trans-tri-n-butylstannyl-4-vinyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-vinyl-20-ethyl-2-homo-13-trans prostene |
| 594 | 1-trans-tri-n-butylstannyl-4-trimethylsilylethynyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-ethynyl-20-ethyl-2-homo-13-trans prostene |
| 595 | 1-trans-tri-n-butylstannyl-5-methylene-4-triethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-17-methylene-20-ethyl-2-homo-13-trans prostene |
| 596 | 1-trans-tri-n-butylstannyl-4-methyl-5-methylene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-methyl- |

TABLE XIII-continued

| | | | |
|---|---|---|---|
| | 4-trimethylsilyloxy-1-decene | 8-(trimethylsiloxy)-8-nonenyl]cyclopent-2-en-1-one | 17-methylene-20-ethyl-2-homo-13-trans prostene |
| 597 | 1-trans-tri-n-butylstannyl-4-dimethoxymethyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-formyl-20-ethyl-2-homo-13-trans prostene |
| 598 | 1-trans-tri-n-butylstannyl-4-fluoromethyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-fluoromethyl-20-ethyl-2-homo-13-trans prostene |
| 599 | 1-trans-tri-n-butylstannyl-4-difluoromethyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-difluoromethyl-20-ethyl-2-homo-13-trans prostene |
| 600 | 1-trans-tri-n-butylstannyl-4-trifluoromethyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-trifluoromethyl-20-ethyl-2-homo-13-trans prostene |
| 601 | 1-trans-tri-n-butylstannyl-4-chloromethyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-chloromethyl-20-ethyl-2-homo-13-trans prostene |
| 602 | 1-trans-tri-n-butylstannyl-4-trimethylsilyloxymethyl-4-trimethylsilyloxy-1-decene | 2-[9-methoxy-9-methoxycarbonyl-8-(trimethylsiloxy)-8-nonenyl]cyclopent-2-en-1-one | dl-16-hydroxy-1-(methoxymethoxycarbonylmethyl)-1,9-dioxo-16-hydroxymethyl-20-ethyl-2-homo-13-trans prostene |

TABLE XIV

| Example | Cyclopentenone: | Vinyliodide: | Product: |
|---|---|---|---|
| 1 | 2-[6-methylthioacetylhexyl]-4-trimethylsilyloxy-cyclopent-2-en-1-one. | 1-trans-iodo-4-methyl-4-trimethylsilyloxy-1,5-octadiene. | 11α,16-dihydroxy-1-methylthiamethyl-1,9-dioxo-16-methyl-13-trans-17-trans-prostadiene. |
| 2 | 2-[6-methylthioacetylhex-2-cis-enyl]-4-trimethylsilyloxy-cyclopent-2-en-1-one. | 1-trans-iodo-4-methyl-4-trimethylsilyloxy-1,5-octadiene. | 11α,16-dihydroxy-1-methylthiamethyl-1,9-dioxo-16-methyl-5-cis-13-trans-17-trans-prostatriene. |
| 3 | 2-[6-phenoxyacetylhexyl]-4-trimethylsilyloxy-cyclopent-2-en-1-one. | 1-trans-1-iodo-4-methyl-4-trimethylsilyloxy-5-octadiene. | 11α,16-dihydroxy-1-phenoxymethyl-1,9-dioxo-16-methyl-13-trans-17-trans-prostadiene. |
| 4 | 2-[6-phenoxyacetylhex-2-cis-enyl]-4-trimethylsilyloxy-cyclopent-2-en-1-one. | 1-trans-1-iodo-4-methyl-4-trimethylsilyloxy-5-octadiene. | 11α,16-dihydroxy-1-phenoxymethyl-1,9-dioxo-16-methyl-5-cis-13-trans-17-trans-prostatriene. |
| 5 | 2-[8-methoxy-8-methoxycarbonyl-7-(trimethylsilyloxy)-7-octenyl]-4-trimethylsilyloxy-cyclopent-2-en-1-one. | 1-trans-iodo-4-methyl-4-trimethylsilyloxy-1,5-octadiene. | 11α,16-dihydroxy-1-methoxymethoxycarbonylmethyl-1,9-dioxo-16-methyl-13-trans-17-trans-prostadiene. |
| 6 | 2-[8-methoxy-8-methoxycarbonyl-7-(trimethylsilyloxy)-2-cis,7-octadienyl]-4-trimethylsilyloxy-cyclopent-2-en-1-one. | 1-trans-1-iodo-4-methyl-4-trimethylsilyloxy-5-octadiene. | 11α,16-dihydroxy-1-methoxymethoxycarbonylmethyl-1,9-dioxo-16-methyl-5-cis-13-trans-17-trans-prostatriene. |

| Example | Cyclopentenone: | Vinylstannane: | Product: |
|---|---|---|---|
| 7 | 2-[6-methylthioacetylhexyl]-4-trimethylsilyloxy-cyclopent-2-en-1-one. | 1-trans-tri-n-butylstannyl-4-methyl-4-trimethylsilyloxy-1,7-octadiene. | 11α,16-dihydroxy-1-methylthiamethyl-1,9-dioxo-16-methyl-13-trans-19-trans-prostatriene. |
| 8 | 2-[6-methylthioacetylhex-2-cis-enyl]-4-trimethylsilyloxy-cyclopent-2-en-1-one. | 1-trans-tri-n-butylstannyl-4-methyl-4-trimethylsilyloxy-1,7-octadiene. | 11α,16-dihydroxy-1-methylthiamethyl-1,9-dioxo-16-methyl-5-cis-13-trans-19-trans-prostatriene. |
| 9 | 2-[6-phenoxyacetylhexyl]-4-trimethylsilyloxy-cyclopent-2-en-1-one. | 1-tri-n-butylstannyl-4-methyl-4-trimethylsilyloxy-1,7-octadiene. | 11α,16-dihydroxy-1-phenoxymethyl-1,9-dioxo-16-methyl-13-trans-19-trans-prostatriene. |
| 10 | 2-[6-phenoxyacetylhex-2-cis-enyl]-4-trimethylsilyloxy-cyclopent-2-en-1-one. | 1-tri-n-butylstannyl-4-methyl-4-trimethylsilyloxy-1,7-octadiene. | 11α,16-dihydroxy-1-phenoxymethyl-1,9-dioxo-16-methyl-5-cis-13-trans-19-trans-prostatriene. |
| 11 | 2-[8-methoxy-8-methoxycarbonyl-7-(trimethylsilyloxy)-7-octenyl]-4-trimethylsilyloxy-cyclopent-2-en-1-one. | 1-tri-n-butylstannyl-4-methyl-4-trimethylsilyloxy-1,7-octadiene. | 11α,16-dihydroxy-1-methoxymethoxycarbonylmethyl-1,9-dioxo-16-methyl-13-trans-19-trans-prostatriene. |
| 12 | 2-[8-methoxy-8-methoxycarbonyl-7-(trimethylsilyloxy)-2-cis,7-octadienyl]-4-trimethylsilyloxy-cyclopent-2-en-1-one. | 1-trans-1-tri-n-butylstannyl-4-methyl-4-trimethylsilyloxy-1,5-octadiene. | 11α,16-dihydroxy-1-methoxymethoxycarbonylmethyl-1,9-dioxo-16-methyl-5-cis-13-trans-19-trans-prostatriene. |
| 13 | 2-[6-methylthioacetylhexyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-methylthiamethyl-1,9-dioxo-16-methyl-19-chloro-20-nor-13-trans-prostene. |
| 14 | 2-[6-methylthioacetylhex-2-cis-enyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-methylthiamethyl-1,9-dioxo-16-methyl-19-chloro-20-nor-5-cis-13-trans-prostadiene. |
| 15 | 2-[6-phenoxyacetylhexyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-phenoxymethyl-1,9-dioxo-20-nor-13-trans-prostene. |
| 16 | 2-[6-phenoxyacetylhex-2-cis-enyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-phenoxymethyl-1,9-dioxo-20-nor-5-cis-13-trans-prostadiene. |

| Example | Cyclopentenone: | Vinyliodide: | Product: |
|---|---|---|---|
| 17 | 2-[6-methoxyacetylhexyl]-4-trimethylsilyloxy-cyclopent-2-en-1-one. | 1-trans-1-tri-n-butylstannyl-7-chloro-4-methyl-4-trimethylsilyloxy-1-heptene. | 11α,16-dihydroxy-1-methoxymethyl-1,9-dioxo-16-methyl-19-chloro-20-nor-13-trans-prostene. |

| Example | Cyclopentenone: | Vinylstannane: | Product: |
|---|---|---|---|
| 18 | 2-[6-methoxyacetylhex-2-cis-enyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-methoxymethyl-1,9-dioxo-16-methyl-19-chloro-20-nor-5-cis-13-trans-prostadiene. |
| 19 | 2-[8-methoxy-8-methoxycarbonyl-7-(trimethylsilyloxy)-7-octenyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-methoxymethoxycarbonylmethyl-1,9-dioxo-16-methyl-19-chloro-20-nor-13-trans-prostene. |
| 20 | 2-[8-methoxy-8-methoxycarbonyl-7-(trimethylsilyloxy)-2-cis,7-octadienyl]-4-trimethylsilyloxy-cyclopent-2-en-1-one. | 1-tri-n-butylstannyl-7-chloro-4-methyl-4-trimethylsilyloxy-1-heptene. | 11α,16-dihydroxy-1-methoxymethoxycarbonylmethyl-1,9-dioxo-16-methyl-19-chloro-20-nor-5-cis-13-trans-prostadiene. |

| Example | Cyclopentenone: | Vinyliodide: | Product: |
|---|---|---|---|
| 21 | 2-[6-methylthioacetylhexyl]-4-trimethylsilyloxy- | 1-trans-iodo-4-propadienyl-4-trimethylsilyloxy- | 11α,16-dihydroxy-1-methylthiamethyl-1,9-dioxo-16- |

TABLE XIV-continued

| | Cyclopentenone: | 1-octene. | allenyl-13-trans-prostene. |
|---|---|---|---|
| 22 | 2-[6-methylthiaacetylhexyl-2-cis-enyl]-4-trimethylsilyloxy-cyclopent-2-en-1-one. | 1-trans-iodo-4-propadienyl-4-trimethylsilyloxy-1-octene. | 11α,16-dihydroxy-1-methylthiamethyl-1,9-dioxo-16-allenyl-5-cis-13-trans-prostadiene. |
| 23 | 2-[6-phenoxyacetylhexyl-4-trimethylsilyloxy-cyclopent-2-en-1-one. | 1-trans-1-iodo-4-propadienyl-4-trimethylsilyloxy-1-octene. | 11α,16-dihydroxy-1-phenoxymethyl-1,9-dioxo-16-allenyl-13-trans-prostene. |
| 24 | 2-[6-phenoxyacetylhex-2-cis-enyl]-4-trimethylsilyloxy-cyclopent-2-en-1-one. | 1-trans-1-iodo-4-propadienyl-4-trimethylsilyloxy-1-octene. | 11α,16-dihydroxy-1-phenoxymethyl-1,9-dioxo-16-allenyl-5-cis-13-trans-prostene. |
| 25 | 2-[8-methoxy-8-methoxycarbonyl-7-(trimethylsilyloxy)-7-octenyl]-4-trimethylsilyloxy-cyclopent-2-en-1-one. | 1-trans-1-iodo-4-propadienyl-4-trimethylsilyloxy-1-octene. | 11α,16-dihydroxy-1-methoxymethoxycarbonylmethyl-1,9-dioxo-16-allenyl-13-trans-prostene. |
| 26 | 2-[8-methoxy-8-methoxycarbonyl]-4-trimethylsilyloxy)-2-cis,7-octadienyl]-4-trimethylsilyloxy-cyclopent-2-en-1-one. | 1-trans-1-iodo-4-propadienyl-4-trimethylsilyloxy-1-octene. | 11α,16-dihydroxy-1-methoxymethoxycarbonylmethyl-1,9-dioxo-16-allenyl-5-cis-13-trans-prostadiene. |
| 27 | 2-[6-methoxyacetylhexyl]-4-trimethylsilyloxy-cyclopent-2-en-1-one. | 1-trans-1-iodo-4-propadienyl-4-trimethylsilyloxy-1-octene. | 11α,16-dihydroxy-1-methoxymethyl-1,9-dioxo-16-allenyl-13-trans-prostene. |
| 28 | 2-[6-methoxyacetylhex-2-cis-enyl]-4-trimethylsilyloxy-cyclopent-2-en-1-one. | 1-trans-1-iodo-4-propadienyl-4-trimethylsilyloxy-1-octene. | 11α,16-dihydroxy-1-methoxymethyl-1,9-dioxo-16-allenyl-5-cis-13-trans-prostadiene. |

| Example | Cyclopentenone: | Vinylstannane: | Product: |
|---|---|---|---|
| 29 | 2-[6-methylthiaacetylhexyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-methylthiamethyl-4-methyl-19-oxa-5-cis-13-trans-prostene. |
| 30 | 2-[6-methylthiaacetylhex-2-cis-enyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-methylthiamethyl-16-methyl-19-oxa-5-cis-13-trans-prostadiene. |
| 31 | 2-[6-phenoxyacetylhexyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-phenoxymethyl-1,9-dioxo-methyl-19-oxa-5-cis-13-trans-prostene. |
| 32 | 2-[6-phenoxyacetylhex-2-cis-enyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-phenoxymethyl-1,9-dioxo-methyl-19-oxa-5-cis-13-trans-prostadiene. |
| 33 | 2-[8-methoxy-8-methoxycarbonyl-7-(trimethylsilyloxy)-7-octenyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-methoxymethoxycarbonylmethyl-1,9-dioxo-16-methyl-19-oxa-13-trans-prostene. |
| 34 | 2-[8-methoxy-8-methoxycarbonyl-7-(trimethylsilyloxy)-2-cis,7-octadienyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-methoxymethoxycarbonylmethyl-1,9-dioxo-16-methyl-19-oxa-5-cis-13-trans-prostadiene. |
| 35 | 2-[6-methoxyacetylhexyl]-4-trimethylsilyloxy-cyclopent-2-en-1-one. | 1-trans-1-tri-n-butylstannyl-4-methyl-4-trimethylsilyloxy-7-oxa-1-octene. | 11α,16-dihydroxy-1-methoxymethyl-1,9-dioxo-16-methyl-19-oxa-13-trans-prostene. |
| 36 | 2-[6-methoxyacetylhex-2-cis-enyl]-4-trimethylsilyloxy-cyclopent-2-en-1-one. | 1-trans-1-tri-n-butylstannyl-7-chloro-4-methyl-4-trimethylsilyloxy-7-oxa-1-octene. | 11α,16-dihydroxy-1-methoxymethyl-1,9-dioxo-16-methyl-19-oxa-5-cis-13-trans-prostadiene. |

Example 37

In accordance with the procedure of Examples 29-36, if the vinylstannane 1-trans-1-tri-n-butylstannyl-4-methyl-4-trimethylsilyloxy-7-sulfa-1-octene is employed in place of the listed 7-oxa vinylstannane, the corresponding 19-thia prostaglandin to the listed 19-oxa prostaglandin will be produced.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

I claim:

1. An optically active compound of the formula:

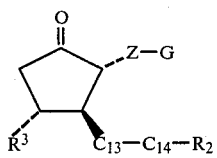

wherein Z is —(CH$_2$)$_g$—or

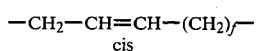

wherein g is an integer from 5 to 7 inclusive, and f is an integer from 2 to 4, inclusive; C$_{13}$–C$_{14}$ is ethylene or trans-vinylene; R$_3$ is hydrogen or hydroxyl; G is selected from the group consisting of:

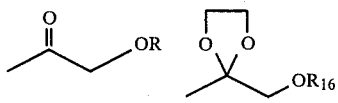

wherein R is C$_1$–C$_6$ alkyl, phenyl or phenyl substituted with one or more substituents selected from the group consisting of C$_1$–C$_4$ alkyl, —OR$_{15}$, —SR$_{15}$, Fl or Cl wherein R$_{15}$ is C$_1$–C$_4$ alkyl; R$_{16}$ is C$_1$ to C$_6$ alkyl; R$_2$ is selected from the group consisting of:

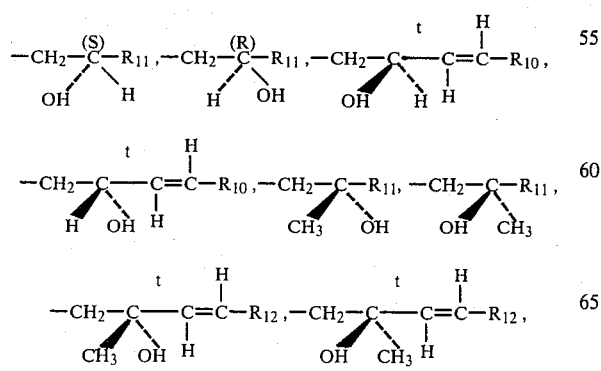

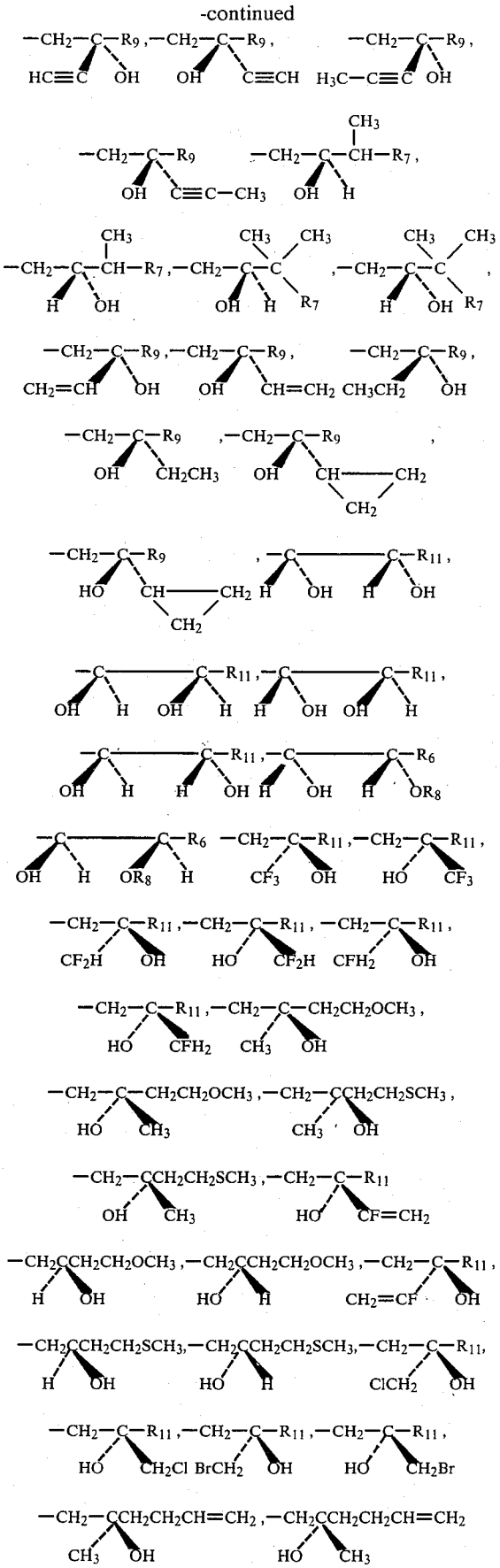

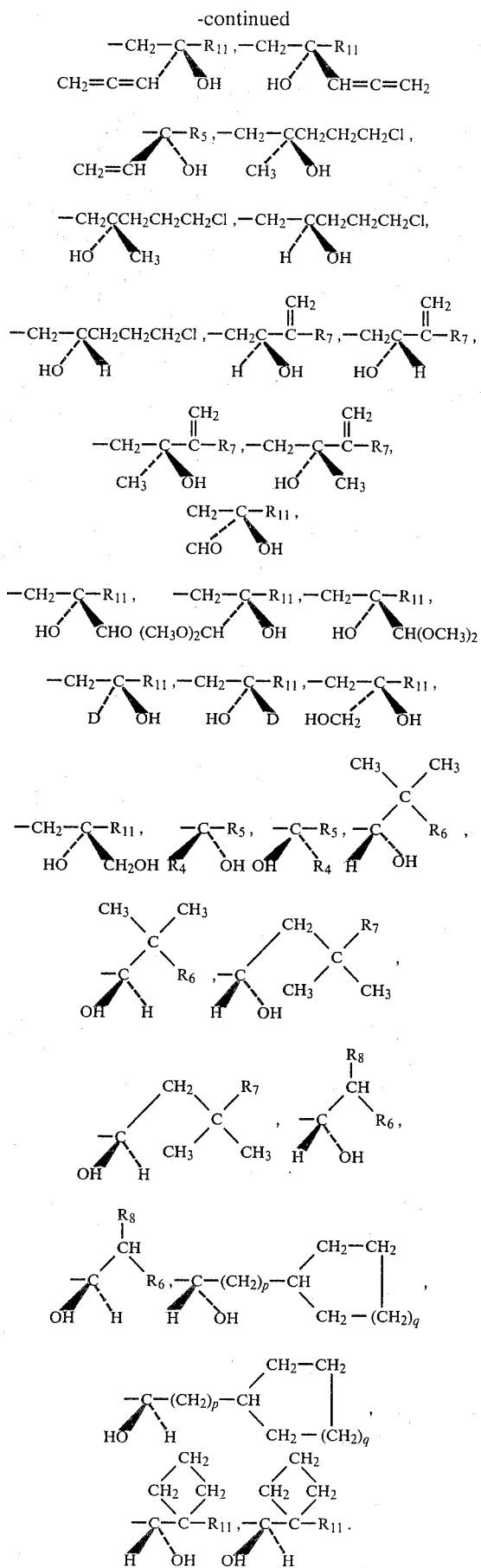

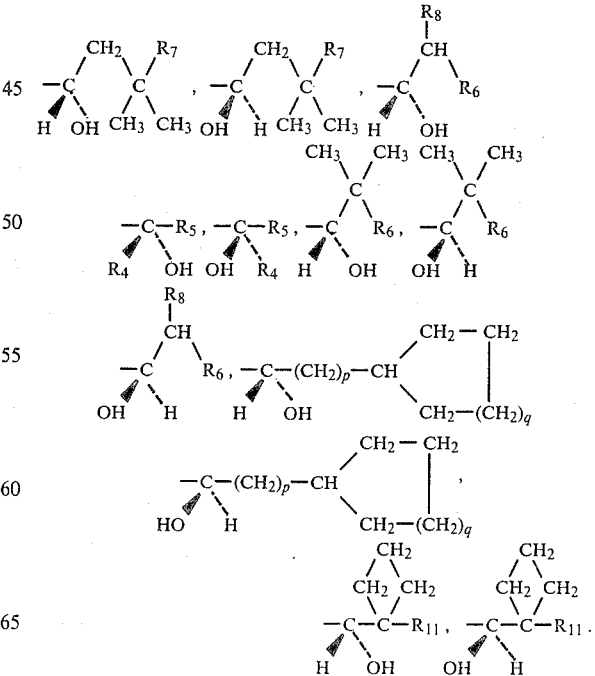

-continued wherein $R_4$ is hydrogen or methyl; $R_5$ is selected from the group consisting of $C_4$-$C_7$ alkyl; $R_6$ is selected from the group consisting of $C_3$-$C_6$ alkyl; $R_7$ is selected from the group consisting of $C_2$-$C_4$ alkyl; $R_8$ is selected from the group consisting of $C_1$-$C_2$ alkyl; $R_9$ is selected from the group consisting of $C_3$-$C_6$ alkyl; $R_{10}$ is selected from the group consisting of $C_1$-$C_4$ alkyl; $R_{11}$ is selected from the group consisting of $C_3$-$C_7$ alkyl; $R_{12}$ is selected from the group consisting of $C_1$-$C_4$ alkyl; p is an integer from 0 to 3; q is 1 or 2; G' is —O— or —CH$_2$—; and t is hydrogen, chloro, fluoro, dichloro, trifluoremethyl or methoxy.

2. The compound according to claim 1 wherein R and $R_{16}$ are methyl groups.

3. The compound according to claim 2 wherein Z is $$-CH_2-CH=CH-(CH_2)_6-$$
cis and $C_{13}$-$C_{14}$ is trans-vinylene.

4. The compound according to claim 2 wherein Z is —(CH$_2$)$_6$— and $C_{13}$-$C_{14}$ is trans-vinylene.

5. The compound according to claim 3 wherein $R_3$ is an hydroxyl group.

6. The compound according to claim 3 wherein $R_3$ is hydrogen.

7. The compound according to claim 4 wherein $R_3$ is hydroxyl.

8. The compound according to claim 4 wherein $R_3$ is hydrogen.

9. The compound according to claims 3 or 4 wherein $R_2$ is selected from the group consisting of

10. The compound according to claims 3 or 4 wherein $R_2$ is selected from the group consisting of:

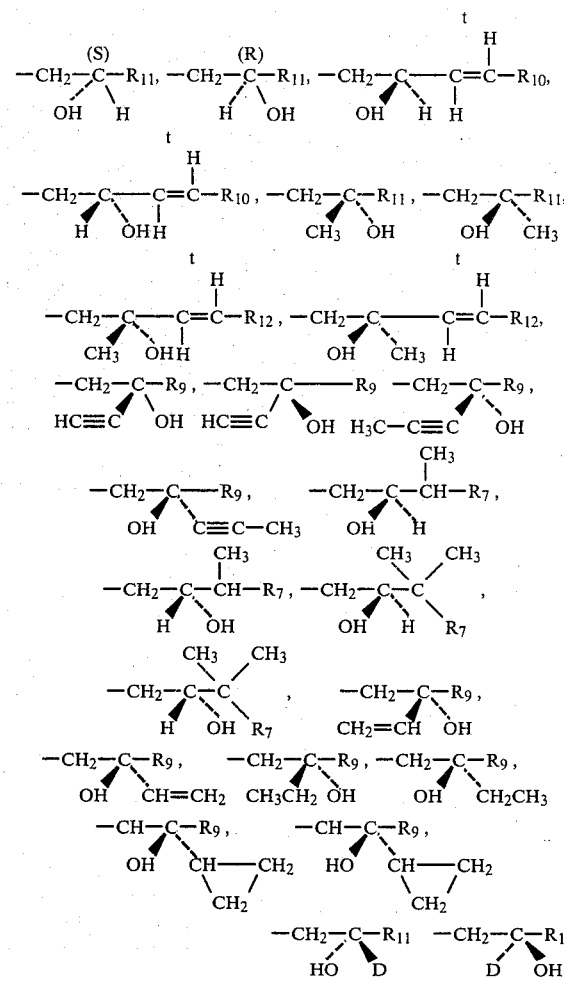

11. The compound according to claims 3 or 4 wherein $R_2$ is selected from the group consisting of:

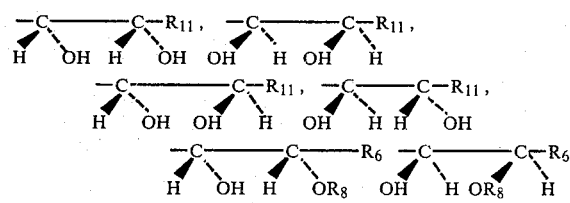

12. The compound according to claims 3 or 4 wherein $R_2$ is selected from the group consisting of:

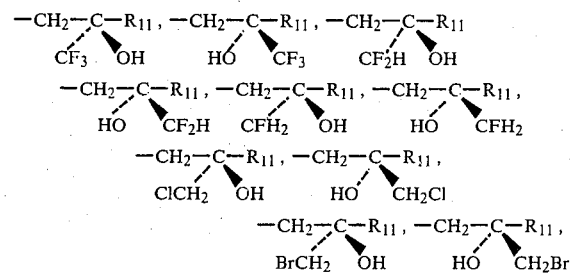

13. The compound according to claims 3 or 4 wherein $R_2$ is selected from the group consisting of:

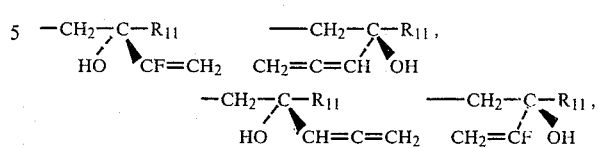

14. The compound according to claims 3 or 4 wherein $R_2$ is selected from the group consisting of:

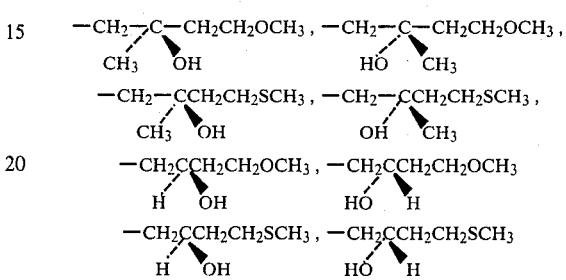

15. The compound according to claims 3 or 4 wherein $R_2$ is selected from the group consisting of:

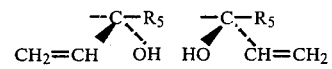

16. The compound according to claims 3 or 4 wherein $R_2$ is selected from the group consisting of:

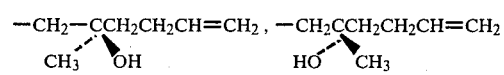

17. The compound according to claims 3 or 4 wherein $R_2$ is selected from the group consisting of:

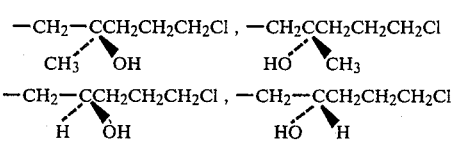

18. The compound according to claims 3 or 4 wherein $R_2$ is selected from the group consisting of:

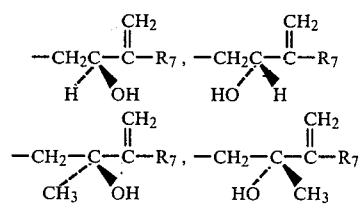

19. The compound according to claims 3 or 4 wherein $R_2$ is selected from the group consisting of:

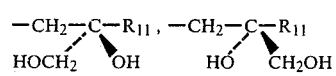

-continued

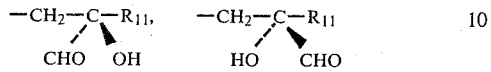

20. The compound according to claims 3 or 4 wherein $R_2$ is selected from the group consisting of:

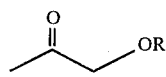

21. The compound according to claims 3 or 4 wherein $R_2$ is selected from the group consisting of:

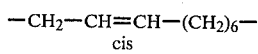

22. The compound according to claim 1 wherein G is:

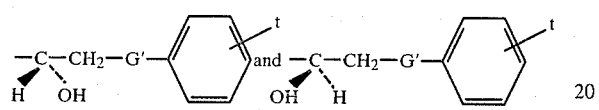

wherein R is a phenyl group.

23. The compound according to claim 22 wherein Z is $$-CH_2-CH=CH-(CH_2)_6-$$
cis and $C_{13}-C_{14}$ is trans-vinylene.

24. The compound according to claim 22 wherein Z is $-(CH_2)_6-$ and $C_{13}-C_{14}$ is trans-vinylene.

25. The compound according to claim 23 wherein $R_3$ is an hydroxyl group.

26. The compound according to claim 23 wherein $R_3$ is hydrogen.

27. The compound according to claim 24 wherein $R_3$ is hydroxyl.

28. The compound according to claim 24 wherein $R_3$ is hydrogen.

29. The compound according to claims 23 or 24 wherein $R_2$ is selected from the group consisting of:

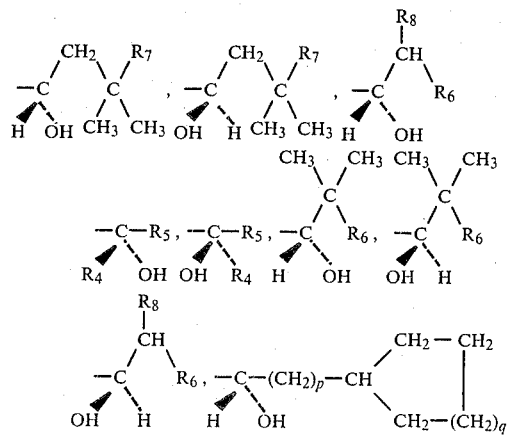

-continued

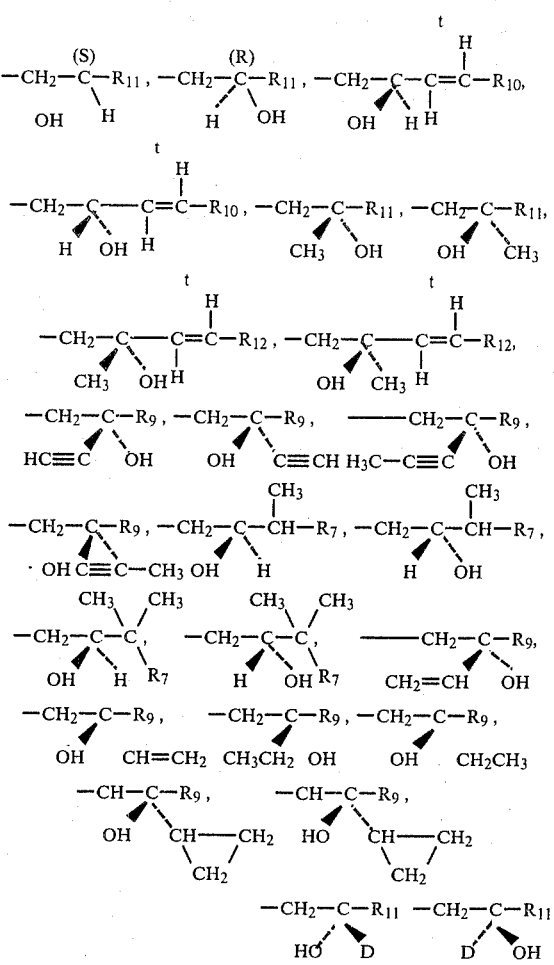

30. The compound according to claims 23 or 24 wherein $R_2$ is selected from the group consisting of:

31. The compound according to claims 23 or 24 wherein $R_2$ is selected from the group consisting of:

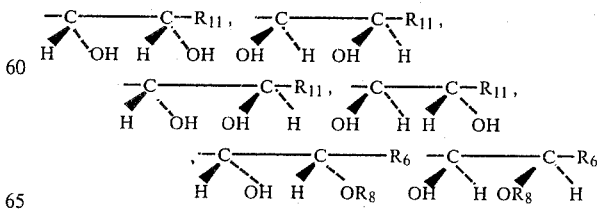

32. The compound according to claims 23 or 24 wherein $R_2$ is selected from the group consisting of:

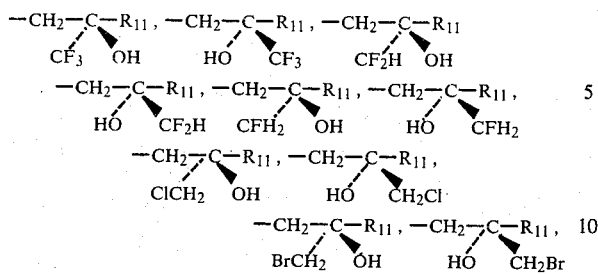

33. The compound according to claims 23 or 24 wherein $R_2$ is selected from the group consisting of:

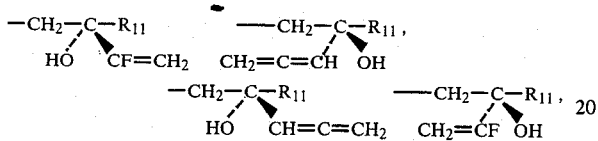

34. The compound according to claims 23 or 24 wherein $R_2$ is selected from the group consisting of:

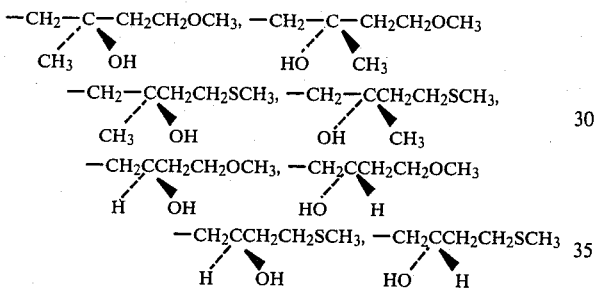

35. The compound according to claims 23 or 24 wherein $R_2$ is selected from the group consisting of:

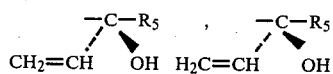

36. The compound according to claims 23 or 24 wherein $R_2$ is selected from the group consisting of:

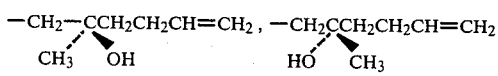

37. The compound according to claims 23 or 24 wherein $R_2$ is selected from the group consisting of:

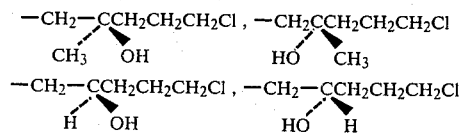

38. The compound according to claims 23 or 24 wherein $R_2$ is selected from the group consisting of:

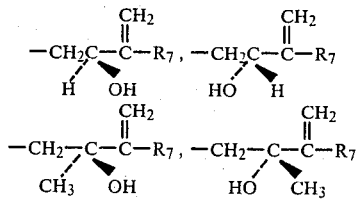

39. The compound according to claims 23 or 24 wherein $R_2$ is selected from the group consisting of:

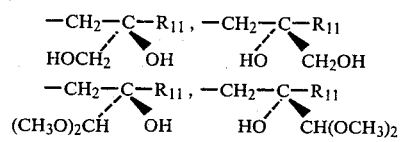

40. The compound according to claims 23 or 24 wherein $R_2$ is selected from the group consisting of:

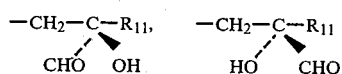

41. The compound according to claims 23 or 24 wherein $R_2$ is selected from the group consisting of:

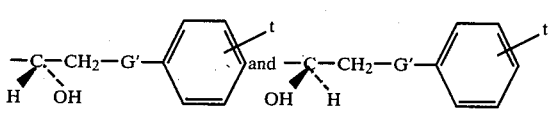

42. The racemic compound according to claim 10, 1,9-dioxo-11α,15α-dihydroxy-1-methoxymethyl-15-vinyl-13-trans-prostene, and the optically active compound of this formula.

43. The racemic compound according to claim 30, 1,9-dioxo-11α,16-dihydroxy-1-phenoxymethyl-16-methyl-13-trans-prostene, and the optically active compound of this formula having a 16α- or 16β-hydroxy substituent.

44. The racemic compound according to claim 10, 1,9-dioxo-11α,16-dihydroxy-1-methoxymethyl-16-vinyl-13-trans-prostene, and the optically active compound of this formula having a 16α- or 16β-hydroxy substituent.

45. The racemic compound according to claim 10, 1,9-dioxo-11α,16-dihydroxy-1-methoxymethyl-16-methyl-13-trans-prostene, and the optically active compound of this formula having a 16α- or 16β- hydroxy substituent.

46. The racemic compound according to claim 10, 1,9-dioxo-11α,16-dihydroxy-1-methoxymethyl-16-methyl-5-cis-13-trans-prostadiene, and the optically active compound of this formula having a 16α- or 16β-hydroxy substituent.

47. The optically active compound according to claim 45, 1,9-dioxo-11α,16α-dihydroxy-1-(methoxymethyl)-16-methyl-13-trans-prostene.

* * * * *